US012522571B2

(12) United States Patent
Veiseh et al.

(10) Patent No.: US 12,522,571 B2
(45) Date of Patent: Jan. 13, 2026

(54) COMPOUNDS, DEVICES, AND USES THEREOF

(71) Applicant: SIGILON THERAPEUTICS, INC., Cambridge, MA (US)

(72) Inventors: Omid Veiseh, Bellaire, TX (US); Richard Heidebrecht, Somerville, MA (US); Paul Kevin Wotton, Boston, MA (US); Matthias Alexander Oberli, Cambridge, MA (US); Robert James Miller, East Bridgewater, MA (US)

(73) Assignee: SIGILON THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 18/529,334

(22) Filed: Dec. 5, 2023

(65) Prior Publication Data

US 2024/0279187 A1 Aug. 22, 2024

Related U.S. Application Data

(62) Division of application No. 16/339,285, filed as application No. PCT/US2017/055001 on Oct. 3, 2017, now Pat. No. 11,945,786.

(Continued)

(51) Int. Cl.

| | |
|---|---|
| ***C07D 401/04*** | (2006.01) |
| ***A61K 9/00*** | (2006.01) |
| ***A61K 31/4192*** | (2006.01) |
| ***A61K 31/54*** | (2006.01) |
| ***A61K 31/541*** | (2006.01) |
| ***A61K 31/695*** | (2006.01) |
| ***A61K 31/7056*** | (2006.01) |
| ***A61K 35/30*** | (2015.01) |
| ***A61K 38/47*** | (2006.01) |
| ***A61K 39/395*** | (2006.01) |
| ***A61P 3/00*** | (2006.01) |
| ***A61P 7/02*** | (2006.01) |
| ***A61P 7/04*** | (2006.01) |
| ***A61P 37/00*** | (2006.01) |
| ***A61P 37/04*** | (2006.01) |
| ***A61P 37/06*** | (2006.01) |
| ***A61P 43/00*** | (2006.01) |
| ***C07D 249/04*** | (2006.01) |
| ***C07D 249/06*** | (2006.01) |
| ***C07D 295/088*** | (2006.01) |
| ***C07D 401/06*** | (2006.01) |
| ***C07D 401/10*** | (2006.01) |
| ***C07D 401/12*** | (2006.01) |

(Continued)

(52) U.S. Cl.

CPC .......... *C07D 249/04* (2013.01); *A61K 9/0019* (2013.01); *A61K 31/4192* (2013.01); *A61K 31/54* (2013.01); *A61K 31/541* (2013.01); *A61K 31/695* (2013.01); *A61K 31/7056* (2013.01); *A61K 35/30* (2013.01); *A61K 38/47* (2013.01); *A61K 39/3955* (2013.01); *A61P 37/04* (2018.01); *A61P 37/06* (2018.01); *C07D 295/088* (2013.01); *C07D 403/12* (2013.01); *C07D 405/12* (2013.01); *C07D 405/14* (2013.01); *C07D 409/04* (2013.01); *C07F 7/1804* (2013.01); *C07F 7/1892* (2013.01); *C07H 15/26* (2013.01); *C07K 16/22* (2013.01); *C12N 9/2465* (2013.01); *C12Y 302/01022* (2013.01)

(58) Field of Classification Search

CPC .. C07D 401/04; C07D 401/06; C07D 401/10; C07D 401/12; C07D 401/14; C07D 403/04; C07D 403/06; C07D 403/12; C07D 405/04; C07D 405/06; C07D 405/12; C07D 405/14; C07D 407/04; C07D 407/12; C07D 409/04; C07D 409/06; C07D 409/14; C07D 413/04; C07D 413/06; C07D 413/12; C07D 417/06; C07D 417/14; C07D 471/04; C07D 471/10; C07D 487/04; C07D 491/107; C07D 498/10; C07D 249/04; C07D 249/06; C07D 295/088; A61K 9/0019; A61K 9/0024; A61K 31/4192; A61K 31/54; A61K 31/541; A61K 31/695; A61K 31/7056; A61K 31/5545; A61K 35/30; A61K 38/47; A61K 39/3955; A61P 3/00; A61P 7/02; A61P 7/04; A61P 37/00; A61P 37/04; A61P 37/06; A61P 43/00

See application file for complete search history.

(56) References Cited

U.S. PATENT DOCUMENTS 7,799,524 B2 9/2010 Kindermann et al.
9,500,653 B2 11/2016 Crews et al.

FOREIGN PATENT DOCUMENTS

CN 104072478 A 10/2014
CN 104844533 A 8/2015

(Continued)

OTHER PUBLICATIONS

Xiang et al., "Discovery of novel sphingosine kinase-1 inhibitors. Part 2" Bioorganic & Medicinal Chemistry Letters, 2010, vol. 20, pp. 4550-4554.

(Continued)

*Primary Examiner* — Brenda L Coleman
(74) *Attorney, Agent, or Firm* — Lando & Anastasi, LLP

(57) ABSTRACT

The present invention provides compounds, e.g., compounds of Formula (I) and pharmaceutically acceptable salts, solvates, hydrates, tautomers, stereoisomers, isotopically labeled derivatives, and compositions thereof. Also provided are implantable elements (e.g., devices and mate- (Continued)

rials) comprising the same, as well as methods of use thereof, e.g., for treating or preventing a disease, disorder, or condition.

12 Claims, 326 Drawing Sheets

Related U.S. Application Data

(60) Provisional application No. 62/436,832, filed on Dec. 20, 2016, provisional application No. 62/403,554, filed on Oct. 3, 2016, provisional application No. 62/403,556, filed on Oct. 3, 2016, provisional application No. 62/403,548, filed on Oct. 3, 2016, provisional application No. 62/403,543, filed on Oct. 3, 2016, provisional application No. 62/403,538, filed on Oct. 3, 2016, provisional application No. 62/403,559, filed on Oct. 3, 2016, provisional application No. 62/403,532, filed on Oct. 3, 2016.

(51) Int. Cl.

| | |
|---|---|
| ***C07D 401/14*** | (2006.01) |
| ***C07D 403/04*** | (2006.01) |
| ***C07D 403/06*** | (2006.01) |
| ***C07D 403/12*** | (2006.01) |
| ***C07D 405/04*** | (2006.01) |
| ***C07D 405/06*** | (2006.01) |
| ***C07D 405/12*** | (2006.01) |
| ***C07D 405/14*** | (2006.01) |
| ***C07D 407/04*** | (2006.01) |
| ***C07D 407/12*** | (2006.01) |
| ***C07D 409/04*** | (2006.01) |
| ***C07D 409/06*** | (2006.01) |
| ***C07D 409/14*** | (2006.01) |
| ***C07D 413/04*** | (2006.01) |
| ***C07D 413/06*** | (2006.01) |
| ***C07D 413/12*** | (2006.01) |
| ***C07D 417/06*** | (2006.01) |
| ***C07D 417/14*** | (2006.01) |
| ***C07D 471/04*** | (2006.01) |
| ***C07D 471/10*** | (2006.01) |
| ***C07D 487/04*** | (2006.01) |
| ***C07D 491/107*** | (2006.01) |
| ***C07D 498/10*** | (2006.01) |
| ***C07F 7/18*** | (2006.01) |
| ***C07H 15/26*** | (2006.01) |
| ***C07K 16/22*** | (2006.01) |
| ***C12N 9/40*** | (2006.01) |

(56) References Cited

FOREIGN PATENT DOCUMENTS

| | | | |
|---|---|---|---|
| JP | 2004-532234 | A | 10/2004 |
| JP | 5725475 | B2 | 5/2015 |
| JP | 2016-516020 | A | 6/2016 |
| JP | 2016-517879 | A | 6/2016 |
| WO | 2007/058646 | A1 | 5/2007 |
| WO | 2008/021388 | A1 | 2/2008 |
| WO | 2008/036308 | A2 | 3/2008 |
| WO | 2010/033701 | A2 | 3/2010 |
| WO | 2012/167223 | A1 | 12/2012 |
| WO | 2015/138895 | A1 | 9/2015 |
| WO | 2016/019391 | A1 | 2/2016 |
| WO | 2016/187225 | A1 | 11/2016 |
| WO | 2017/075630 | A1 | 5/2017 |
| WO | 2017/075631 | A1 | 5/2017 |
| WO | 2018/067615 | A1 | 4/2018 |
| WO | 2019/067766 | A1 | 4/2019 |

OTHER PUBLICATIONS

Carvalho et al., "'Click Chemistry' synthesis of a library of 1,2,3-triazole-substituted galactose derivatives and their evaluation against Trypanosoma cruzi and its cell surface trans-sialidase," Bioorganic & Medicinal Chemistry, vol. 18, No. 7, pp. 2412-2427, (2010).

Corbel et al., "Identification of potential cellular targets of aloisine A by affinity chromatography," Bioorganic & Medicinal Chemistry, vol. 17, No. 15, pp. 5572-5582, (2009).

Struthers et al., "'Click-to-Chelate': Design and Incorporation of Triazole-containing Metal-chelating Systems into Biomolecules of Diagnostic and Therapeutic Interest," Chemistry—A European Journal, vol. 14, No. 20, pp. 6173-6183, (2008).

International Search Report and Written Opinion for PCT/US2017/055001 mailed Nov. 27, 2017.

Arunrungvichian et al., "Selectivity optimization of substituted 1,2,3-Triazoles as a7 nicotinic acetylcholine receptor agonists" ACS Chemical Neuroscience, vol. 6, No. 8, 2015, pp. 1317-1330.

RN: 1545351-08-3, Database Registry [Online], Retrieved from STN, Feb. 16, 2014.

Panda et al., "A nucleus-imaging probe that selectively stabilizes a minor conformation of c-MYC G-quadruplex and Down-regulates c-MYC Transcription in Human Cancer Cells" Scienctific Reports, 2015, vol. 5, pp. 1-16.

Bremond et al., "Formation of liquid-core capsules having a thin hydrogel membrane: liquid pearls" Soft Matter, 2010, vol. 6, No. 11, pp. 2484-2488.

Veiseh et al., "Size- and shape-dependent foreign body immune response to materials implanted in rodents and non-human primates" Nature Materials, 2015, vol. 14, pp. 643-652.

Lee et al., "Size and shape of calcium alginate beads produced by extrusion dripping" Chemical Engineering and Technology, 2013, vol. 36, No. 10, pp. 1627-1642.

Vegas et al., "Combinatorial hydrogel library enables identification of materials that mitigate the foreign body response in primates" Nature Biotechnology, 2016, vol. 34, No. 3, pp. 345-352.

International Search Report and Written Opinion for Application No. PCT/US2019/020248 mailed Jun. 26, 2019.

International Search Report and Written Opinion for Application No. PCT/US2019/020405 mailed Jul. 15, 2019.

Renfrew et al., "Adding diversity to ruthenium(II)-arene anticancer (RAPTA) compounds via click chemistry: The influence of hydrophobic chains" Journal of Organometallic Chemistry, 2011, vol. 696, No. 3, pp. 772-779.

Sun et al., "Recyclable Cu(I)/melanin dots for cycloaddition, bioconjugation and cell labelling" Chemical Science, 2016, vol. 7, No. 9, pp. 5888-5892.

Seerden et al., "Syntheses and structure—activity relationships for some triazolyl p38a MAPK inhibitors" Bioorganic & Medicinal Chemistry Letters, 2014, vol. 24, No. 5, pp. 1352-1357.

Germeroth et al., "Triazole biotin: a tight-binding biotinidase-resistant conjugate" Organic & Biomolecular Chemistry, 2013, vol. 11, No. 44, pp. 7700-7704.

Agalave et al., "Click chemistry: 1,2,3-Triazoles as Pharmacophores" Chem. Asian J., 2011, vol. 6, pp. 2696-2718.

Feldman et al., "One-pot synthesis of 1,4-Disubstituted 1,2,3-Triazoles from in situ generated azides" Organic Letters, 2004, vol. 6, No. 22, pp. 3897-3899.

Kim et al., "Synthesis and biological evaluation of phenyl-1H-1,2,3-triazole derivatives as anti-inflammatory agents" Bioorganic Chemistry, Jan. 2015, vol. 59, pp. 1-11.

Gonzaga et al., "1-Phenyl-1H- and 2-phenyl-2H-1,2,3-triazol derivatives: Design, synthesis and inhibitory effect on alpha-glycosidases" European Journal of Medicinal Chemistry, Jan. 2014, vol. 74, pp. 461-476.

| Compound No. | Structure | Compound No. | Structure |
|---|---|---|---|
| 100 |  | 108 |  |
| 101 |  | 109 |  |
| 102 |  | 110 |  |
| 103 |  | 111 |  |
| 104 |  | 112 |  |

| | | | |
|---|---|---|---|
| 105 |  | 113 |  |
| 106 |  | 114 |  |
| 107 |  | 115 |  |
| 116 |  | 124 |  |
| 117 |  | 125 |  |

| | | | |
|---|---|---|---|
| 118 |  | 126 |  |
| 119 |  | 127 |  |
| 120 |  | 128 |  |
| 121 |  | 129 |  |
| 122 |  | 130 |  |

| | | | |
|---|---|---|---|
| 123 |  | 131 |  |
| 132 |  | 139 |  |
| 133 |  | 140 |  |
| 134 |  | 141 |  |
| 135 |  | 142 |  |

| | | | |
|---|---|---|---|
| 136 |  | 143 |  |
| 137 |  | 144 |  |
| 138 |  | 145 |  |
| 146 |  | 154 |  |

| | | | |
|---|---|---|---|
| 147 |  | 155 |  |
| 148 |  | 156 |  |
| 149 |  | 157 |  |
| 150 |  | 158 |  |

| | | | |
|---|---|---|---|
| 151 |  | 159 |  |
| 152 |  | 160 |  |
| 153 |  | 161 |  |
| 162 |  | 169 |  |
| 163 |  | 170 |  |
| 164 |  | 171 |  |

| | | | |
|---|---|---|---|
| 165 |  | 172 |  |
| 166 |  | 173 |  |
| 167 |  | 174 |  |

| | | | |
|---|---|---|---|
| 168 |  | 175 |  |
| 176 |  | 184 |  |
| 177 |  | 185 |  |
| 178 |  | 186 |  |

| | | | |
|---|---|---|---|
| 179 |  | 187 |  |

| | | | |
|---|---|---|---|
| 180 |  | 188 |  |
| 181 |  | 189 |  |
| 182 |  | 190 |  |
| 183 |  | 191 |  |

| | | | |
|---|---|---|---|
| 192 |  | 201 |  |
| 193 |  | 202 |  |
| 194 |  | 203 |  |
| 195 |  | 204 |  |

| | | | |
|---|---|---|---|
| 196 |  | 205 |  |
| 197 |  | 206 |  |

| | | | |
|---|---|---|---|
| 198 |  | 207 |  |
| 199 |  | 208 |  |

| | | | |
|---|---|---|---|
| 200 |  | 209 |  |
| 210 |  | 218 |  |
| 211 |  | 219 |  |

| | | | |
|---|---|---|---|
| 212 |  | 220 |  |
| 213 |  | 221 |  |
| 214 |  | 222 |  |
| 215 |  | 223 |  |
| 216 |  | 224 |  |

| | | | |
|---|---|---|---|
| 217 |  | 225 |  |
| 226 |  | 234 |  |
| 227 |  | 235 |  |
| 228 |  | 236 |  |
| 229 |  | 237 |  |

| | | | |
|---|---|---|---|
| 230 |  | 238 |  |
| 231 |  | 239 |  |
| 232 |  | 240 |  |
| 233 |  | 241 |  |
| 242 |  | 250 |  |

| | | | |
|---|---|---|---|
| 243 |  | 251 |  |
| 244 |  | 252 |  |
| 245 |  | 253 |  |
| 246 |  | 254 |  |
| 247 |  | 255 |  |

| | | | |
|---|---|---|---|
| 248 |  | 256 |  |
| 249 |  | 257 |  |
| 258 |  | 267 |  |
| 259 |  | 268 |  |
| 260 |  | 269 |  |

| | | | |
|---|---|---|---|
| 261 |  | 270 |  |
| 262 |  | 271 |  |
| 263 |  | 272 |  |
| 264 |  | 273 |  |
| 265 |  | 274 |  |

| | | | |
|---|---|---|---|
| 266 |  | 275 |  |

| | | | |
|---|---|---|---|
| 276 |  | 285 |  |
| 277 |  | 286 |  |

| | | | |
|---|---|---|---|
| 278 |  | 287 |  |
| 279 |  | 288 |  |

| | | | |
|---|---|---|---|
| 280 |  | 289 |  |
| 281 |  | 290 |  |
| 282 |  | 291 |  |
| 283 |  | 292 |  |
| 284 |  | 293 |  |
| 294 |  | 303 |  |

| | | | |
|---|---|---|---|
| 295 |  | 304 |  |
| 296 |  | 305 |  |
| 297 |  | 306 |  |
| 298 |  | 307 |  |
| 299 |  | 308 |  |

| | | | |
|---|---|---|---|
| 300 |  | 309 |  |
| 301 |  | 310 |  |
| 302 |  | 311 |  |
| 312 |  | 321 |  |
| 313 |  | 322 |  |
| 314 |  | 323 |  |

| | | | |
|---|---|---|---|
| 315 |  | 324 |  |
| 316 |  | 325 |  |
| 317 |  | 326 |  |
| 318 |  | 327 |  |
| 319 |  | 328 |  |

| | | | |
|---|---|---|---|
| 320 |  | 329 |  |
| 330 |  | 339 |  |
| 331 |  | 340 |  |
| 332 |  | 341 |  |
| 333 |  | 342 |  |
| 334 |  | 343 |  |
| 335 |  | 344 |  |

| | | | |
|---|---|---|---|
| 336 |  | 345 |  |
| 337 |  | 346 |  |
| 338 |  | 347 |  |

| | | | |
|---|---|---|---|
| 348 |  | 356 |  |
| 349 |  | 357 |  |
| 350 |  | 358 |  |

| | | | |
|---|---|---|---|
| 351 |  | 359 |  |
| 352 |  | 360 |  |
| 353 |  | 361 |  |
| 354 |  | 362 |  |
| 355 |  | 363 |  |

| | | | |
|---|---|---|---|
| 364 |  | 372 |  |
| 365 |  | 373 |  |
| 366 |  | 374 |  |
| 367 |  | 375 |  |
| 368 |  | 376 |  |

| | | | |
|---|---|---|---|
| 369 |  | 377 |  |
| 370 |  | 378 |  |
| 371 |  | 379 |  |
| 380 |  | 387 |  |
| 381 |  | 388 |  |

| | | | |
|---|---|---|---|
| 382 |  | 389 |  |
| 383 |  | 390 |  |
| 384 |  | 391 |  |
| 385 |  | 392 |  |
| 386 |  | 393 |  |

| | | | |
|---|---|---|---|
| 394 |  | 401 |  |
| 395 |  | 402 |  |
| 396 |  | 403 |  |
| 397 |  | 404 |  |

| | | | |
|---|---|---|---|
| 398 |  | 405 |  |
| 399 |  | 406 |  |
| 400 |  | 407 |  |
| 408 |  | 415 |  |
| 409 |  | 416 |  |

| | | | |
|---|---|---|---|
| 410 |  | 417 |  |
| 411 |  | 418 |  |
| 412 |  | 419 |  |
| 413 |  | 420 |  |

| | | | |
|---|---|---|---|
| 414 |  | 421 |  |
| 422 |  | 429 |  |
| 423 |  | 430 |  |
| 424 |  | 431 |  |

| | | | |
|---|---|---|---|
| 425 |  | 432 |  |
| 426 |  | 433 |  |
| 427 |  | 434 |  |

| | | | |
|---|---|---|---|
| 428 |  | 435 |  |
| 436 |  | 444 |  |
| 437 |  | 445 |  |

| | | | |
|---|---|---|---|
| 438 |  | 446 |  |
| 439 |  | 447 |  |
| 440 |  | 448 |  |
| 441 |  | 449 |  |
| 442 |  | 450 |  |
| 443 |  | 451 |  |

| | | | |
|---|---|---|---|
| 452 |  | 459 |  |
| 453 |  | 460 |  |
| 454 |  | 461 |  |

| | | | |
|---|---|---|---|
| 455 |  | 462 |  |
| 456 |  | 463 |  |
| 457 |  | 464 |  |
| 458 |  | 465 |  |

| | | | |
|---|---|---|---|
| 466 |  | 474 |  |
| 467 |  | 475 |  |
| 468 |  | 476 |  |
| 469 |  | 477 |  |
| 470 |  | 478 |  |
| 471 |  | 479 |  |

| | | | |
|---|---|---|---|
| 472 |  | 480 |  |
| 473 |  | 481 |  |
| 482 |  | 490 |  |
| 483 |  | 491 |  |
| 484 |  | 492 |  |
| 485 |  | 493 |  |

| | | | |
|---|---|---|---|
| 486 |  | 494 |  |
| 487 |  | 495 |  |
| 488 |  | 496 |  |
| 489 |  | 497 |  |
| 498 |  | 506 |  |
| 499 |  | 507 |  |

| | | | |
|---|---|---|---|
| 500 |  | 508 |  |
| 501 |  | 509 |  |
| 502 |  | 510 |  |
| 503 |  | 511 |  |
| 504 |  | 512 |  |
| 505 |  | 513 |  |

| | | | |
|---|---|---|---|
| 514 |  | 521 |  |
| 515 |  | 522 |  |
| 516 |  | 523 |  |
| 517 |  | 524 |  |
| 518 |  | 525 |  |
| 519 |  | 526 |  |

| | | | |
|---|---|---|---|
| 520 |  | 527 |  |

| | | | |
|---|---|---|---|
| 528 |  | 533 |  |
| 529 |  | 534 |  |

| | | | |
|---|---|---|---|
| 530 |  | 535 |  |
| 531 |  | 536 |  |

| | | | |
|---|---|---|---|
| 532 |  | 537 |  |
| 538 |  | 546 |  |
| 539 |  | 547 |  |
| 540 |  | 548 |  |

| | | | |
|---|---|---|---|
| 541 |  | 549 |  |
| 542 |  | 550 |  |
| 543 |  | 551 |  |
| 544 |  | 552 |  |
| 545 |  | 553 |  |

| | | | |
|---|---|---|---|
| 554 |  | 562 |  |
| 555 |  | 563 |  |
| 556 |  | 564 |  |
| 557 |  | 565 |  |
| 558 |  | 566 |  |
| 559 |  | 567 |  |

| | | | |
|---|---|---|---|
| 560 |  | 568 |  |
| 561 |  | 569 |  |
| 570 |  | 578 |  |
| 571 |  | 579 |  |
| 572 |  | 580 |  |
| 573 |  | 581 |  |

| | | | |
|---|---|---|---|
| 574 |  | 582 |  |
| 575 |  | 583 |  |
| 576 |  | 584 |  |
| 577 |  | 585 |  |
| 586 |  | 592 |  |
| 587 |  | 593 |  |

FIG. 1AAA
| | | | |
|---|---|---|---|
| 588 | 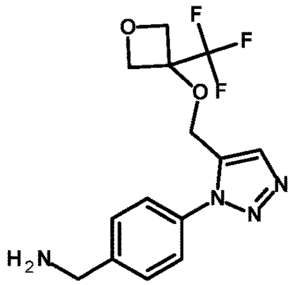 | 594 | 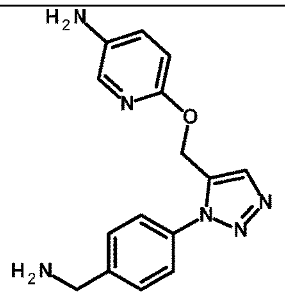 |
| 589 | 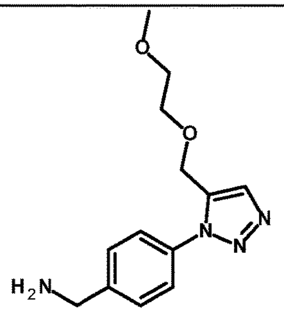 | 595 | 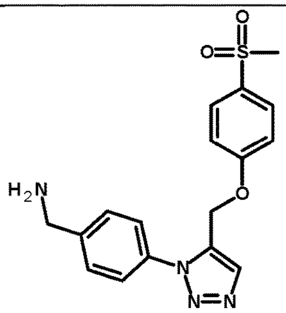 |
| 590 | 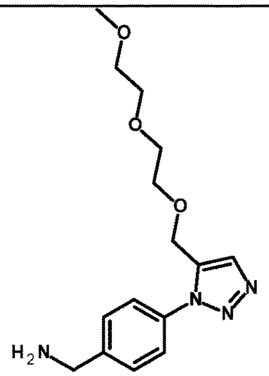 | 596 | 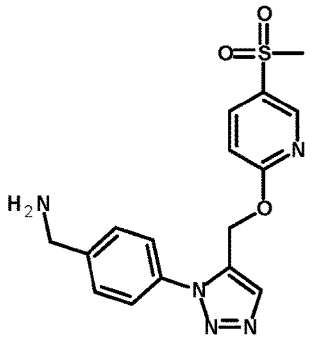 |
| 591 | 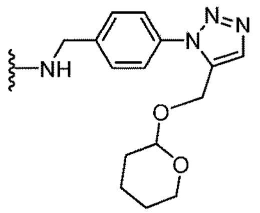 | 597 | 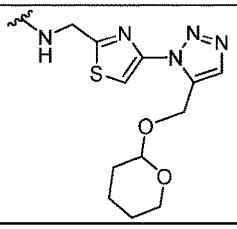 |

| | | | |
|---|---|---|---|
| 598 |  | 604 |  |
| 599 |  | 605 |  |
| 600 |  | 606 |  |
| 601 |  | 607 |  |
| 602 |  | 608 |  |

| | | | |
|---|---|---|---|
| 603 |  | 609 |  |
| 610 |  | 617 |  |
| 611 |  | 618 |  |
| 612 |  | 619 |  |

| | | | |
|---|---|---|---|
| 613 |  | 620 |  |
| 614 |  | 621 |  |
| 615 |  | 622 |  |
| 616 |  | 623 |  |
| 624 |  | 631 |  |

| | | | |
|---|---|---|---|
| 625 |  | 632 |  |
| 626 |  | 633 |  |
| 627 |  | 634 |  |
| 628 |  | 635 |  |
| 629 |  | 636 |  |

| | | | |
|---|---|---|---|
| 630 |  | 637 |  |
| 638 |  | 645 |  |
| 639 |  | 646 |  |
| 640 |  | 647 |  |

| | | | |
|---|---|---|---|
| 641 |  | 648 |  |
| 642 |  | 649 |  |
| 643 |  | 650 |  |
| 644 |  | 651 |  |
| 652 |  | 659 |  |

| | | | |
|---|---|---|---|
| 653 |  | 660 |  |
| 654 |  | 661 |  |
| 655 |  | 662 |  |
| 656 |  | 663 |  |

| | | | |
|---|---|---|---|
| 657 |  | 664 |  |
| 658 |  | 665 |  |
| 666 |  | 673 |  |
| 667 |  | 674 |  |

| | | | |
|---|---|---|---|
| 668 |  | 675 |  |
| 669 |  | 676 |  |

| | | | |
|---|---|---|---|
| 670 |  | 677 |  |
| 671 |  | 678 |  |
| 672 |  | 679 |  |
| 680 |  | 689 |  |

| | | | |
|---|---|---|---|
| 681 |  | 690 |  |
| 682 |  | 691 |  |
| 683 |  | 692 |  |
| 684 |  | 693 |  |
| 685 |  | 694 |  |
| 686 |  | 695 |  |

| | | | |
|---|---|---|---|
| 687 |  | 696 |  |
| 688 |  | 697 |  |
| 698 |  | 706 |  |
| 699 |  | 707 |  |

| | | | |
|---|---|---|---|
| 700 |  | 708 |  |
| 701 |  | 709 |  |
| 702 |  | 710 |  |
| 703 |  | 711 |  |

| | | | |
|---|---|---|---|
| 704 |  | 712 |  |
| 705 |  | 713 |  |
| 714 |  | 723 |  |
| 715 |  | 724 |  |
| 716 |  | 725 |  |
| 717 |  | 726 |  |

| | | | |
|---|---|---|---|
| 718 |  | 727 |  |
| 719 |  | 728 |  |
| 720 |  | 729 |  |
| 721 |  | 730 |  |
| 722 |  | 731 |  |
| 732 |  | 741 |  |

| | | | |
|---|---|---|---|
| 733 |  | 742 |  |
| 734 |  | 743 |  |
| 735 |  | 744 |  |
| 736 |  | 745 |  |
| 737 |  | 746 |  |
| 738 |  | 747 |  |

| | | | |
|---|---|---|---|
| 739 |  | 748 |  |
| 740 |  | 749 |  |
| 750 |  | 759 |  |
| 751 |  | 760 |  |
| 752 |  | 761 |  |
| 753 |  | 762 |  |
| 754 |  | 763 |  |

| | | | |
|---|---|---|---|
| 755 |  | 764 |  |
| 756 |  | 765 |  |
| 757 |  | 766 |  |
| 758 |  | 767 |  |
| 768 |  | 778 |  |
| 769 |  | 779 |  |
| 770 |  | 780 |  |

| | | | |
|---|---|---|---|
| 771 |  | 781 |  |
| 772 |  | 782 |  |
| 773 |  | 783 |  |
| 774 |  | 784 |  |
| 775 |  | 785 |  |
| 776 |  | 786 |  |
| 777 |  | 787 |  |

| | | | |
|---|---|---|---|
| 788 |  | 798 |  |
| 789 |  | 799 |  |
| 790 |  | 800 |  |
| 791 |  | 801 |  |
| 792 |  | 802 |  |
| 793 |  | 803 |  |
| 794 |  | 804 |  |

| | | | |
|---|---|---|---|
| 795 |  | 805 |  |
| 796 |  | 806 |  |
| 797 |  | 807 |  |
| 808 |  | 818 |  |

| | | | |
|---|---|---|---|
| 809 |  | 819 |  |
| 810 |  | 820 |  |
| 811 |  | 821 |  |
| 812 |  | 822 |  |
| 813 |  | 823 |  |

| | | | |
|---|---|---|---|
| 814 |  | 824 |  |
| 815 |  | 825 |  |
| 816 |  | 826 |  |
| 817 |  | 827 |  |
| 828 |  | 835 |  |
| 829 |  | 836 |  |

| | | | |
|---|---|---|---|
| 830 |  | 837 |  |
| 831 |  | 838 |  |

| | | | |
|---|---|---|---|
| 832 |  | 839 |  |
| 833 |  | 840 |  |
| 834 |  | 841 |  |

| | | | |
|---|---|---|---|
| 842 |  | 848 |  |
| 843 |  | 849 |  |
| 844 |  | 850 |  |
| 845 |  | 851 |  |

| | | | |
|---|---|---|---|
| 846 |  | 852 |  |
| 847 |  | 853 |  |
| 854 |  | 860 |  |
| 855 |  | 861 |  |

| | | | |
|---|---|---|---|
| 856 |  | 862 |  |
| 857 |  | 863 |  |
| 858 |  | 864 |  |
| 859 |  | 865 |  |

| | | | |
|---|---|---|---|
| 866 |  | 872 |  |
| 867 |  | 873 |  |
| 868 |  | 874 |  |

| | | | |
|---|---|---|---|
| 869 |  | 875 |  |
| 870 |  | 876 |  |
| 871 |  | 877 |  |
| 878 |  | 883 |  |

| | | | |
|---|---|---|---|
| 879 |  | 884 |  |
| 880 |  | 885 |  |
| 881 |  | 886 |  |
| 882 |  | 887 |  |

| | | | |
|---|---|---|---|
| 888 |  | 893 |  |
| 889 |  | 894 |  |
| 890 |  | 895 |  |

| | | | |
|---|---|---|---|
| 891 |  | 896 |  |
| 892 |  | 897 |  |
| 898 |  | 903 |  |
| 899 |  | 904 |  |

| | | | |
|---|---|---|---|
| 900 |  | 905 |  |
| 901 |  | 906 |  |
| 902 |  | 907 |  |

| | | | |
|---|---|---|---|
| 908 |  | 913 |  |
| 909 |  | 914 |  |
| 910 |  | 915 |  |
| 911 |  | 916 |  |

| | | | |
|---|---|---|---|
| 912 |  | 917 |  |
| 918 |  | 925 |  |
| 919 |  | | |

| | | | |
|---|---|---|---|
| 920 |  | 926 |  |

| | | | |
|---|---|---|---|
| 921 |  | 927 |  |
| 922 |  | 928 |  |
| 923 |  | 929 |  |
| 924 |  | 930 |  |
| 931 |  | 937 |  |

| | | | |
|---|---|---|---|
| 932 |  | 938 |  |
| 933 |  | 939 |  |
| 934 |  | 940 |  |

| | | | |
|---|---|---|---|
| 935 |  | 941 |  |
| 936 |  | 942 |  |
| 943 |  | 949 |  |

| | | | |
|---|---|---|---|
| 944 |  | 950 |  |
| 945 |  | 951 |  |
| 946 |  | 952 |  |
| 947 |  | 953 |  |

| | | | |
|---|---|---|---|
| 948 |  | 954 |  |
| 955 |  | 962 |  |
| 956 |  | 963 |  |
| 957 |  | 964 |  |
| 958 |  | 965 |  |
| 959 |  | 966 |  |

| | | | |
|---|---|---|---|
| 960 |  | 967 |  |
| 961 |  | 968 |  |
| 969 |  | 977 |  |
| 970 |  | 978 |  |
| 971 |  | 079 |  |
| 972 |  | 980 |  |

| | | | |
|---|---|---|---|
| 973 |  | 981 |  |
| 974 |  | 982 |  |
| 975 |  | 983 |  |
| 976 |  | 984 |  |
| 985 |  | 993 |  |
| 986 |  | 994 |  |

| | | | |
|---|---|---|---|
| 987 |  | 995 |  |
| 988 |  | 996 |  |
| 989 |  | 997 |  |
| 990 |  | 998 |  |
| 991 |  | 999 |  |
| 992 |  | 1000 |  |

| | | | |
|---|---|---|---|
| 1001 |  | 1008 |  |
| 1002 |  | 1009 |  |
| 1003 |  | 1010 |  |
| 1004 |  | 1011 |  |
| 1005 |  | 1012 |  |
| 1006 |  | 1013 |  |

| | | | |
|---|---|---|---|
| 1007 |  | 1014 |  |

| | | | |
|---|---|---|---|
| 1015 |  | 1023 |  |
| 1016 |  | 1024 |  |
| 1017 |  | 1025 |  |
| 1018 |  | 1026 |  |

| | | | |
|---|---|---|---|
| 1019 |  | 1027 |  |
| 1020 |  | 1028 |  |
| 1021 |  | 1029 |  |
| 1022 |  | 1030 |  |
| 1031 |  | 1038 |  |

| | | | |
|---|---|---|---|
| 1032 |  | 1039 |  |
| 1033 |  | 1040 |  |
| 1034 |  | 1041 |  |
| 1035 |  | 1042 |  |
| 1036 |  | 1043 |  |

| | | | |
|---|---|---|---|
| 1037 |  | 1044 |  |
| 1045 |  | 1052 |  |
| 1046 |  | 1053 |  |
| 1047 |  | 1054 |  |

| | | | |
|---|---|---|---|
| 1048 |  | 1055 |  |
| 1049 |  | 1056 |  |
| 1050 |  | 1057 |  |
| 1051 |  | 1058 |  |

| | | | |
|---|---|---|---|
| 1059 |  | 1064 |  |
| 1060 |  | 1065 |  |
| 1061 |  | 1066 |  |
| 1062 |  | 1067 |  |

| | | | |
|---|---|---|---|
| 1063 |  | 1068 |  |
| 1069 |  | 1073 |  |
| 1070 |  | 1074 |  |
| 1071 |  | 1075 |  |

| | | | |
|---|---|---|---|
| 1072 |  | 1076 |  |

| | | | |
|---|---|---|---|
| 1077 |  | 1085 |  |
| 1078 |  | 1086 |  |
| 1079 |  | 1087 |  |
| 1080 |  | 1088 |  |
| 1081 |  | 1089 |  |
| 1082 |  | 1090 |  |

| | | | |
|---|---|---|---|
| 1083 |  | 1091 |  |
| 1084 |  | 1092 |  |
| 1093 |  | 1098 |  |

| | | | |
|---|---|---|---|
| 1094 |  | 1099 |  |
| 1095 |  | 1100 |  |
| 1096 |  | 1101 |  |

| | | | |
|---|---|---|---|
| 1097 |  | 1102 |  |
| 1103 |  | 1108 |  |
| 1104 |  | 1109 |  |

| | | | |
|---|---|---|---|
| 1105 |  | 1110 |  |
| 1106 |  | 1111 |  |
| 1107 |  | 1112 |  |

| | | | |
|---|---|---|---|
| 1113 |  | 1119 |  |
| 1114 |  | 1120 |  |
| 1115 |  | 1121 |  |
| 1116 |  | 1122 |  |
| 1117 |  | 1123 |  |

| | | | |
|---|---|---|---|
| 1118 |  | 1124 |  |
| 1125 |  | 1136 |  |
| 1126 |  | 1137 |  |
| 1127 |  | 1138 |  |
| 1128 |  | 1139 |  |

| | | | |
|---|---|---|---|
| 1129 |  | 1140 |  |
| 1130 |  | 1141 |  |
| 1131 |  | 1142 |  |
| 1132 |  | 1143 |  |
| 1133 |  | 1144 |  |
| 1134 |  | 1145 |  |
| 1135 |  | 1146 |  |
| 1147 |  | 1156 |  |
| 1148 |  | 1157 |  |
| 1149 |  | 1158 |  |
| 1150 |  | 1159 |  |

| | | | |
|---|---|---|---|
| 1151 |  | 1160 |  |
| 1152 |  | 1161 |  |
| 1153 |  | 1162 |  |
| 1154 |  | 1163 |  |
| 1155 |  | 1164 |  |
| 1165 |  | 1170 |  |

| | | | |
|---|---|---|---|
| 1166 |  | 1171 |  |
| 1167 |  | 1172 |  |
| 1168 |  | 1173 |  |

| | | | |
|---|---|---|---|
| 1169 |  | 1174 |  |
| 1175 |  | 1182 |  |
| 1176 |  | 1183 |  |
| 1177 |  | 1184 |  |
| 1178 |  | 1185 |  |

| | | | |
|---|---|---|---|
| 1179 |  | 1186 |  |
| 1180 |  | 1187 |  |
| 1181 |  | 1188 |  |
| 1189 |  | 1194 |  |
| 1190 |  | 1195 |  |

| | | | |
|---|---|---|---|
| 1191 |  | 1196 |  |
| 1192 |  | 1197 |  |
| 1193 |  | 1198 |  |

| | | | |
|---|---|---|---|
| 1199 |  | 1204 |  |
| 1200 |  | 1205 |  |
| 1201 |  | 1206 |  |

| | | | |
|---|---|---|---|
| 1202 |  | 1207 |  |
| 1203 |  | 1208 |  |
| 1209 |  | 1213 |  |

| | | | |
|---|---|---|---|
| 1210 |  | 1214 |  |
| 1211 |  | 1215 |  |
| 1212 |  | 1216 |  |
| 1217 |  | 1221 |  |

| | | | |
|---|---|---|---|
| 1218 |  | 1222 |  |
| 1219 |  | 1223 |  |
| 1220 |  | 1224 |  |

| | | | |
|---|---|---|---|
| 1225 |  | 1230 |  |
| 1226 |  | 1231 |  |
| 1227 |  | 1232 |  |

| | | | |
|---|---|---|---|
| 1228 |  | 1233 |  |
| 1229 |  | 1234 |  |

| | | | |
|---|---|---|---|
| 1235 |  | 1239 |  |
| 1236 |  | 1240 |  |
| 1237 |  | 1241 |  |

| | | | |
|---|---|---|---|
| 1238 |  | 1242 |  |
| 1243 |  | 1250 |  |
| 1244 |  | 1251 |  |

| | | | |
|---|---|---|---|
| 1245 |  | 1252 |  |
| 1246 |  | 1253 |  |

| | | | |
|---|---|---|---|
| 1247 |  | 1254 |  |
| 1248 |  | 1255 |  |
| 1249 |  | 1256 |  |
| 1257 |  | 1265 |  |
| 1258 |  | 1266 |  |
| 1259 |  | 1267 |  |
| 1260 |  | 1268 |  |

| | | | |
|---|---|---|---|
| 1261 |  | 1269 |  |
| 1262 |  | 1270 |  |
| 1263 |  | 1271 |  |
| 1264 |  | 1272 |  |
| 1273 |  | 1280 |  |
| 1274 |  | 1281 |  |

| | | | |
|---|---|---|---|
| 1275 |  | 1282 |  |
| 1276 |  | 1283 |  |
| 1277 |  | 1284 |  |
| 1278 |  | 1285 |  |
| 1279 |  | 1286 |  |
| 1287 |  | 1295 |  |

| | | | |
|---|---|---|---|
| 1288 |  | 1296 |  |
| 1289 |  | 1297 |  |
| 1290 |  | 1298 |  |
| 1291 |  | 1299 |  |
| 1292 |  | 1300 |  |
| 1293 |  | 1301 |  |

| | | | |
|---|---|---|---|
| 1294 |  | 1302 |  |
| 1303 |  | 1311 |  |
| 1304 |  | 1312 |  |
| 1305 |  | 1313 |  |
| 1306 |  | 1314 |  |
| 1307 |  | 1315 |  |
| 1308 |  | 1316 |  |

| | | | |
|---|---|---|---|
| 1309 |  | 1317 |  |
| 1310 |  | 1318 |  |
| 1319 |  | 1327 |  |
| 1320 |  | 1328 |  |
| 1321 |  | 1329 |  |
| 1322 |  | 1330 |  |
| 1323 |  | 1331 |  |

| | | | |
|---|---|---|---|
| 1324 |  | 1332 |  |
| 1325 |  | 1333 |  |
| 1326 |  | 1334 |  |
| 1335 |  | 1344 |  |
| 1336 |  | 1345 |  |
| 1337 |  | 1346 |  |

| | | | |
|---|---|---|---|
| 1338 |  | 1347 |  |
| 1339 |  | 1348 |  |
| 1340 |  | 1349 |  |
| 1341 |  | 1350 |  |
| 1342 |  | 1351 |  |
| 1343 |  | 1352 |  |
| 1353 |  | 1365 |  |

| | | | |
|---|---|---|---|
| 1354 |  | 1366 |  |
| 1355 |  | 1367 |  |
| 1356 |  | 1368 |  |
| 1357 |  | 1369 |  |
| 1358 |  | 1370 |  |
| 1359 |  | 1371 |  |
| 1360 |  | 1372 |  |
| 1361 |  | 1373 |  |
| 1362 |  | 1374 |  |

| | | | |
|---|---|---|---|
| 1363 |  | 1375 |  |
| 1364 |  | 1376 |  |
| 1377 |  | 1385 |  |
| 1378 |  | 1386 |  |
| 1379 |  | 1387 |  |
| 1380 |  | 1388 |  |
| 1381 |  | 1389 |  |

| | | | |
|---|---|---|---|
| 1382 |  | 1390 |  |
| 1383 |  | 1391 |  |
| 1384 |  | 1392 |  |
| 1393 |  | 1401 |  |
| 1394 |  | 1402 |  |
| 1395 |  | 1403 |  |
| 1396 |  | 1404 |  |

| | | | |
|---|---|---|---|
| 1397 |  | 1405 |  |
| 1398 |  | 1406 |  |
| 1399 |  | 1407 |  |
| 1400 |  | 1408 |  |
| 1409 |  | 1416 |  |
| 1410 |  | 1417 |  |

| | | | |
|---|---|---|---|
| 1411 |  | 1418 |  |
| 1412 |  | 1419 |  |
| 1413 |  | 1420 |  |
| 1414 |  | 1421 |  |
| 1415 |  | 1422 |  |
| 1423 |  | 1432 |  |

| | | | |
|---|---|---|---|
| 1424 |  | 1433 |  |
| 1425 |  | 1434 |  |
| 1426 |  | 1435 |  |

| | | | |
|---|---|---|---|
| 1427 |  | 1436 |  |
| 1428 |  | 1437 |  |
| 1429 |  | 1438 |  |
| 1430 |  | 1439 |  |
| 1431 |  | 1440 |  |

| | | | |
|---|---|---|---|
| 1441 |  | 1451 |  |
| 1442 |  | 1452 |  |
| 1443 |  | 1453 |  |
| 1444 |  | 1454 |  |
| 1445 |  | 1455 |  |

| | | | |
|---|---|---|---|
| 1446 |  | 1456 |  |
| 1447 |  | 1457 |  |
| 1448 |  | 1458 |  |
| 1449 |  | 1459 |  |
| 1450 |  | 1460 |  |
| 1461 |  | 1472 |  |
| 1462 |  | 1473 |  |
| 1463 |  | 1474 |  |
| 1464 |  | 1475 |  |

| | | | |
|---|---|---|---|
| 1465 |  | 1476 |  |
| 1466 |  | 1477 |  |
| 1467 |  | 1478 |  |
| 1468 |  | 1479 |  |
| 1469 |  | 1480 |  |
| 1470 |  | 1481 |  |
| 1471 |  | 1482 |  |
| 1483 |  | 1493 |  |

| | | | |
|---|---|---|---|
| 1484 |  | 1494 |  |
| 1485 |  | 1495 |  |
| 1486 |  | 1496 |  |
| 1487 |  | 1497 |  |
| 1488 |  | 1498 |  |
| 1489 |  | 1499 |  |
| 1490 |  | 1500 |  |
| 1491 |  | 1501 |  |

| | | | |
|---|---|---|---|
| 1492 |  | 1502 |  |
| 1503 |  | 1513 |  |
| 1504 |  | 1514 |  |
| 1505 |  | 1515 |  |
| 1506 |  | 1516 |  |
| 1507 |  | 1517 |  |
| 1508 |  | 1518 |  |
| 1509 |  | 1519 |  |

| | | | |
|---|---|---|---|
| 1510 |  | 1520 |  |
| 1511 |  | 1521 |  |
| 1512 |  | 1522 |  |
| 1523 |  | 1533 |  |
| 1524 |  | 1534 |  |
| 1525 |  | 1535 |  |
| 1526 |  | 1536 |  |
| 1527 |  | 1537 |  |

| | | | |
|---|---|---|---|
| 1528 |  | 1538 |  |
| 1529 |  | 1539 |  |
| 1530 |  | 1540 |  |
| 1531 |  | 1541 |  |

| | | | |
|---|---|---|---|
| 1532 |  | 1542 |  |

| | | | |
|---|---|---|---|
| 1543 |  | 1550 |  |
| 1544 |  | 1551 |  |
| 1545 |  | 1552 |  |
| 1546 |  | 1553 |  |
| 1547 |  | 1554 |  |
| 1548 |  | 1555 |  |

| | | | |
|---|---|---|---|
| 1549 |  | 1556 |  |
| 1557 |  | 1561 |  |
| 1558 |  | 1562 |  |
| 1559 |  | 1563 |  |

| | | | |
|---|---|---|---|
| 1560 |  | 1564 |  |
| 1565 |  | 1569 |  |
| 1566 |  | 1570 |  |
| 1567 |  | 1571 |  |

| | | | |
|---|---|---|---|
| 1568 |  | 1572 |  |
| 1573 |  | 1578 |  |
| 1574 |  | 1579 |  |
| 1575 |  | 1580 |  |

| | | | |
|---|---|---|---|
| 1576 |  | 1581 |  |
| 1577 |  | 1582 |  |
| 1583 |  | 1589 |  |
| 1584 |  | 1590 |  |
| 1585 |  | 1591 |  |
| 1586 |  | 1592 |  |

| | | | |
|---|---|---|---|
| 1587 |  | 1593 |  |
| 1588 |  | 1594 |  |
| 1595 |  | 1603 |  |
| 1596 |  | 1604 |  |
| 1597 |  | 1605 |  |

| | | | |
|---|---|---|---|
| 1598 |  | 1606 |  |
| 1599 |  | 1607 |  |
| 1600 |  | 1608 |  |
| 1601 |  | 1609 |  |
| 1602 |  | 1610 |  |
| 1611 |  | 1619 |  |
| 1612 |  | 1620 |  |
| 1613 |  | 1621 |  |

| | | | |
|---|---|---|---|
| 1614 |  | 1622 |  |
| 1615 |  | 1623 |  |
| 1616 |  | 1624 |  |
| 1617 |  | 1625 |  |
| 1618 |  | 1626 |  |
| 1627 |  | 1632 |  |

| | | | |
|---|---|---|---|
| 1628 |  | 1633 |  |
| 1629 |  | 1634 |  |
| 1630 |  | 1635 |  |
| 1631 |  | 1636 |  |

| | | | |
|---|---|---|---|
| 1637 |  | 1642 |  |
| 1638 |  | 1643 |  |
| 1639 |  | 1644 |  |
| 1640 |  | 1645 |  |
| 1641 |  | 1646 |  |

FIG. 3AAA
| | | | |
|---|---|---|---|
| 1647 | 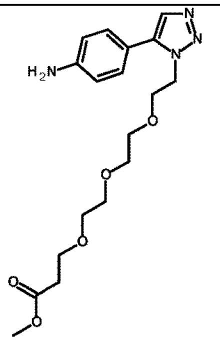 | 1654 | 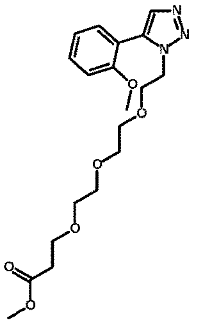 |
| 1648 | 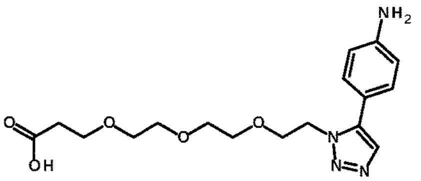 | 1655 | 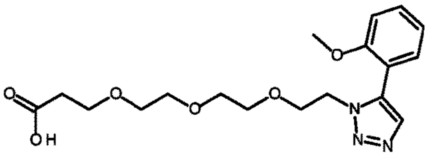 |
| 1649 | 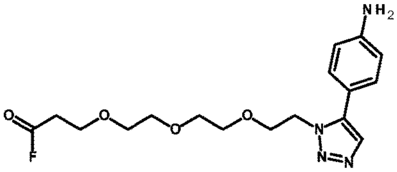 | 1656 | 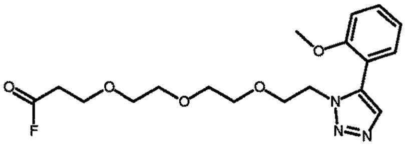 |
| 1650 | 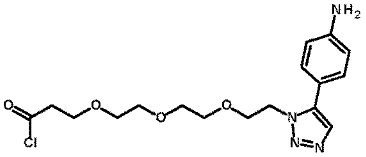 | 1657 | 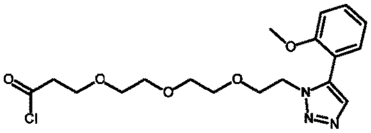 |
| 1651 | 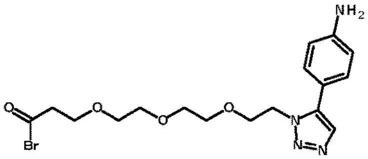 | 1658 | 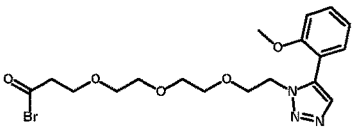 |
| 1652 | 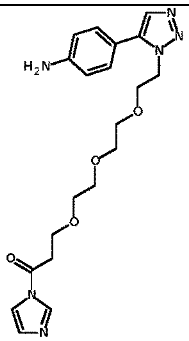 | 1659 | 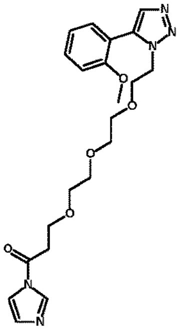 |

FIG. 3BBB
| | | | |
|---|---|---|---|
| 1653 | 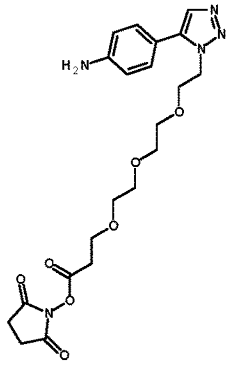 | 1660 | 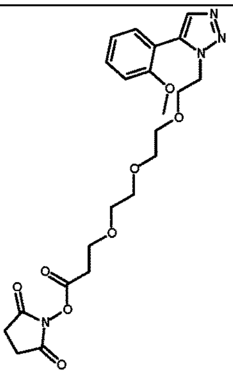 |
| 1661 | 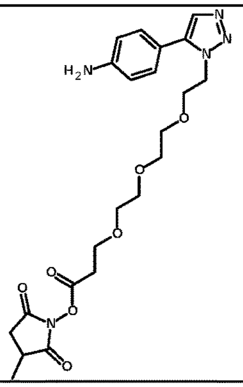 | 1667 | 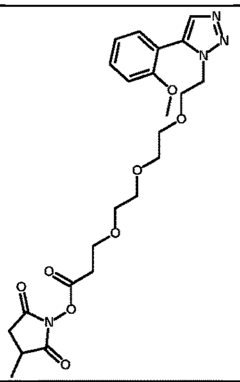 |
| 1662 | 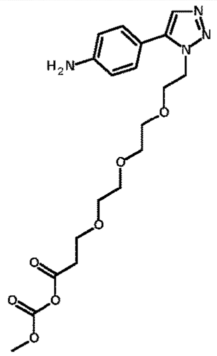 | 1668 | 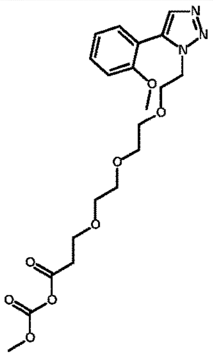 |
| 1663 | 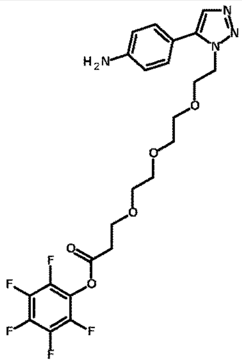 | 1669 | 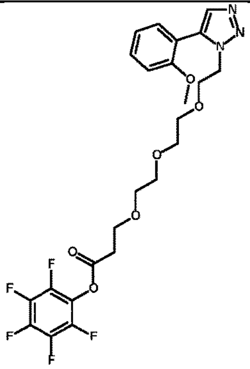 |

FIG. 3CCC
| | | | |
|---|---|---|---|
| 1664 | 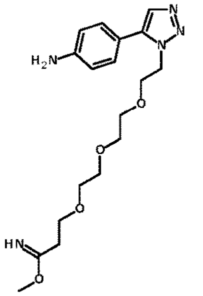 | 1670 | 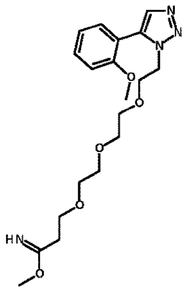 |
| 1665 | 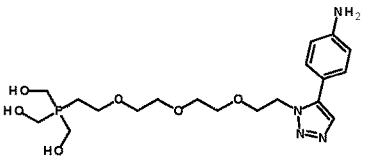 | 1671 | 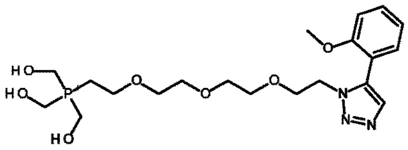 |
| 1666 | 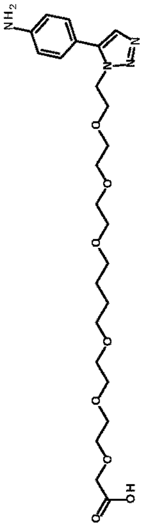 | 1672 | 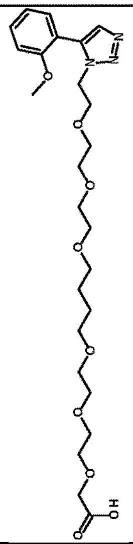 |
| 1673 | 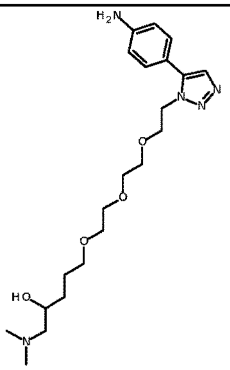 | 1678 | 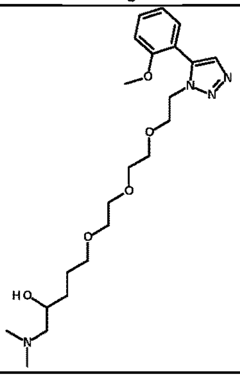 |

FIG. 3DDD
| | | | |
|---|---|---|---|
| 1674 | 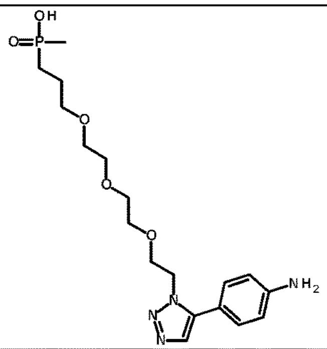 | 1679 | 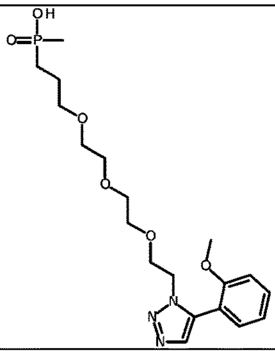 |
| 1675 | 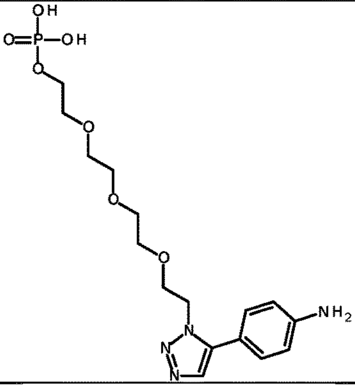 | 1680 | 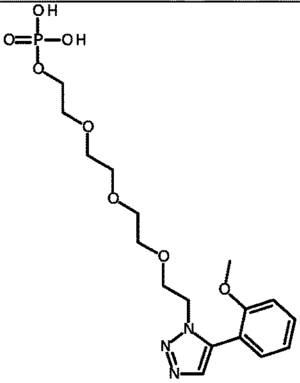 |
| 1676 | 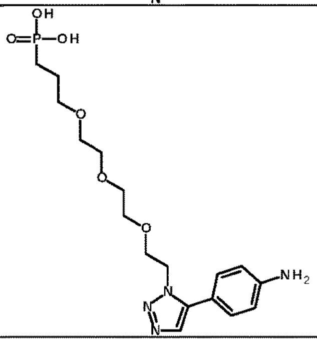 | 1681 | 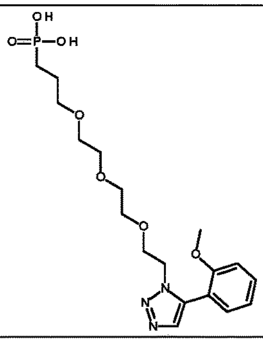 |
| 1677 | 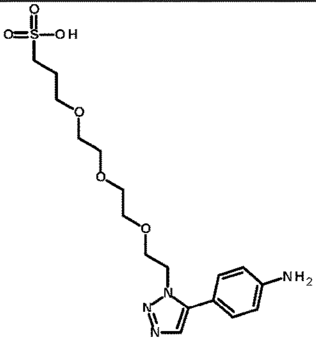 | 1682 | 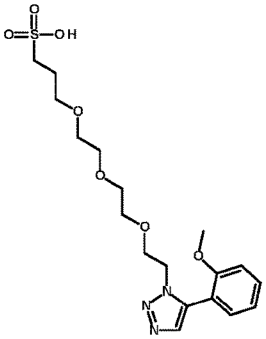 |
| 1683 | 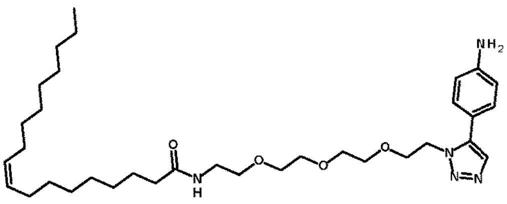 | 1688 | 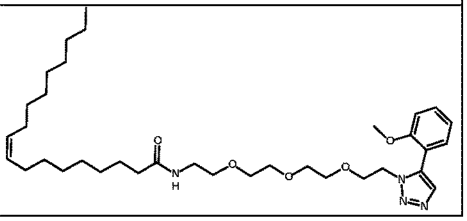 |

FIG. 3EEE
| | | | |
|---|---|---|---|
| 1684 | 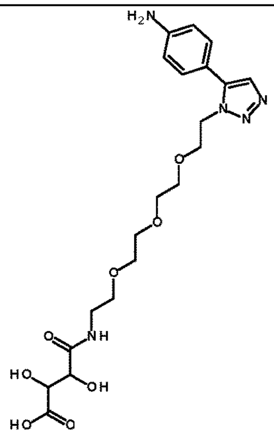 | 1689 | 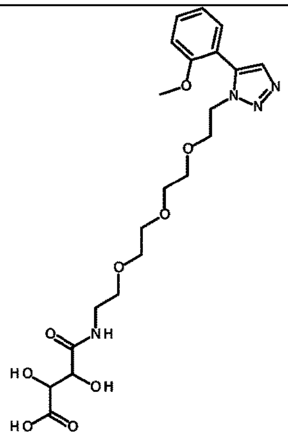 |
| 1685 | 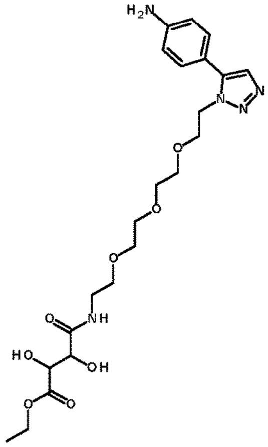 | 1690 | 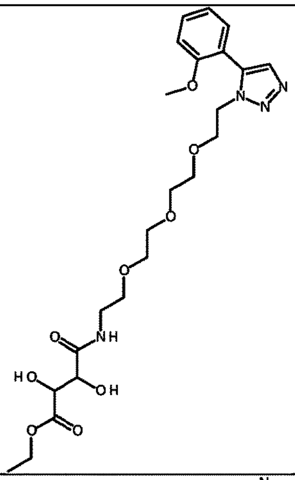 |
| 1686 | 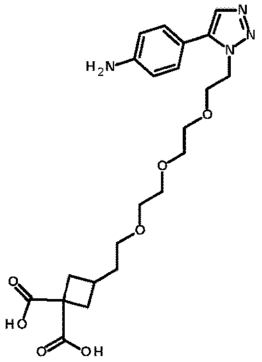 | 1691 | 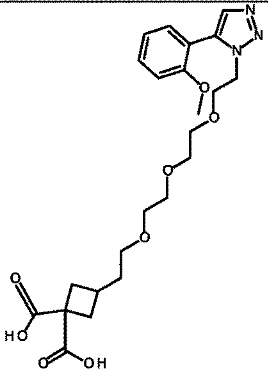 |

FIG. 3FFF
| | | | |
|---|---|---|---|
| 1687 | 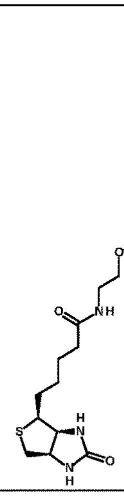 | 1692 | 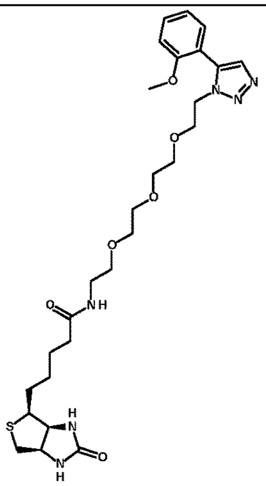 |
| 1693 | 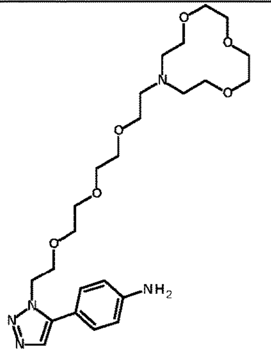 | 1698 | 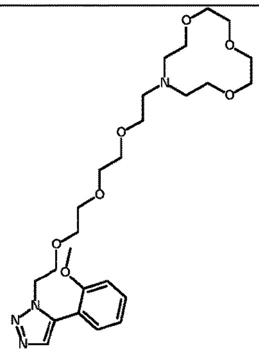 |
| 1694 | 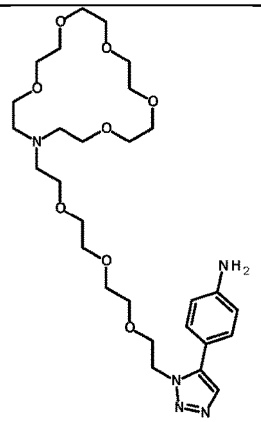 | 1699 | 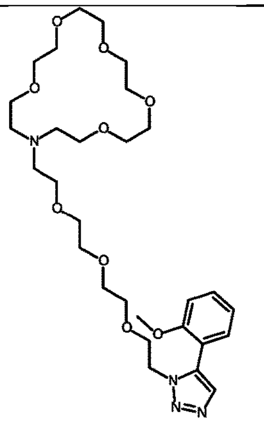 |
| 1695 | 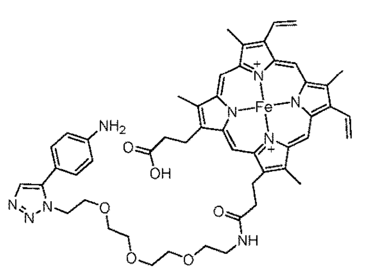 | 1700 | 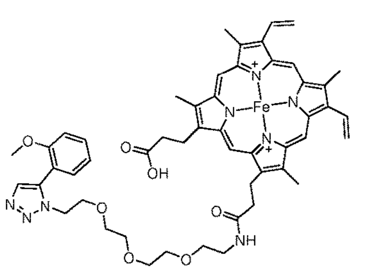 |

FIG. 3GGG
| | | | |
|---|---|---|---|
| 1696 | 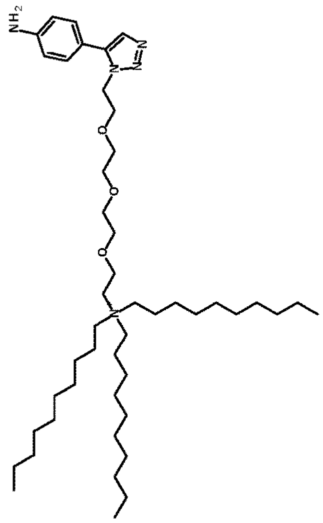 | 1701 | 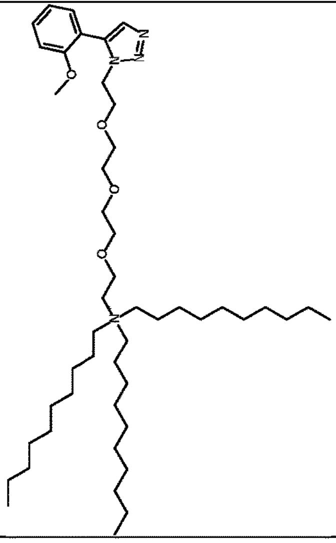 |
| 1697 | 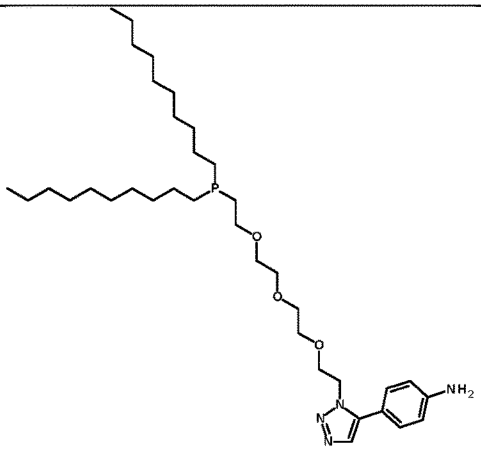 | 1702 | 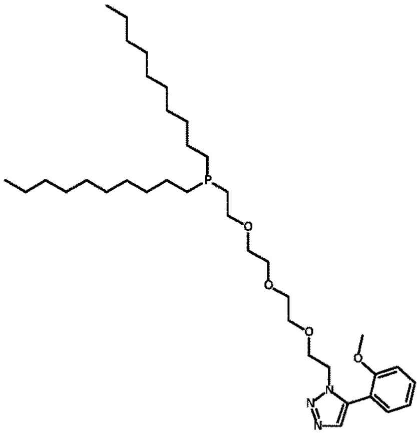 |
| 1703 | 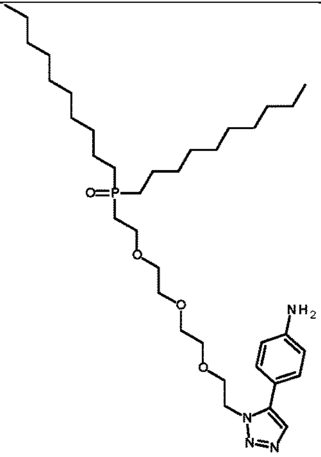 | 1708 | 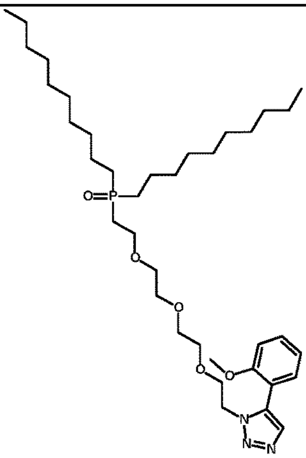 |
| 1704 | 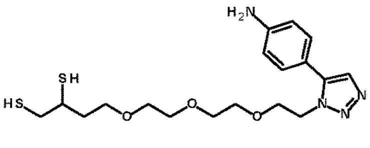 | 1709 | 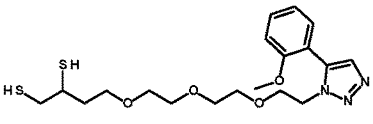 |

FIG. 3HHH
| | | | |
|---|---|---|---|
| 1705 | 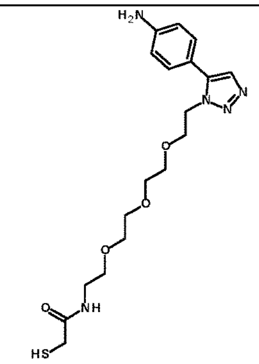 | 1710 | 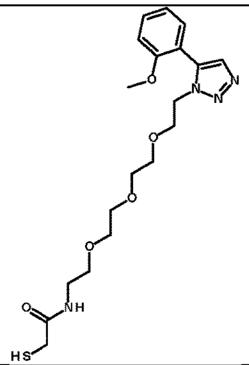 |
| 1706 | 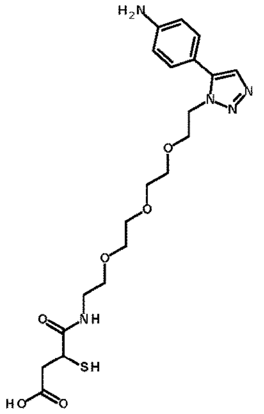 | 1711 | 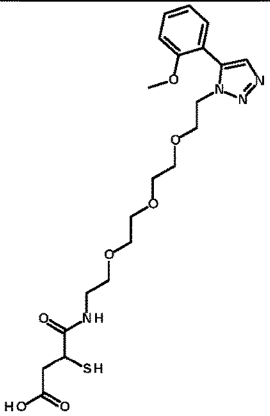 |
| 1707 | 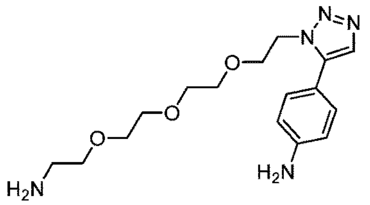 | 1712 | 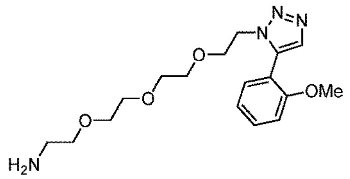 |
| | | | |
|---|---|---|---|
| 1713 | 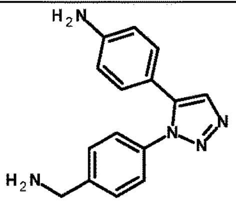 | 1722 | 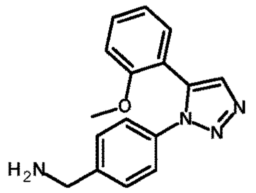 |
| 1714 | 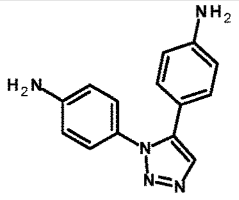 | 1723 | 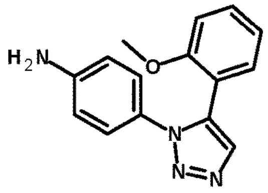 |

FIG. 3III
| | | | |
|---|---|---|---|
| 1715 | 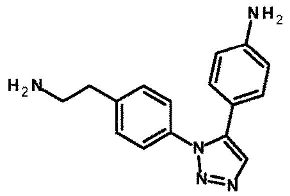 | 1724 | 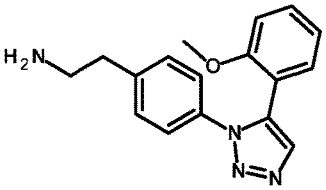 |
| 1716 | 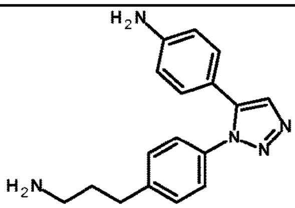 | 1725 | 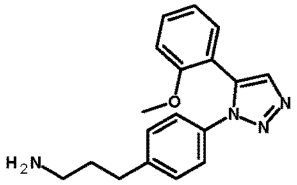 |
| 1717 | 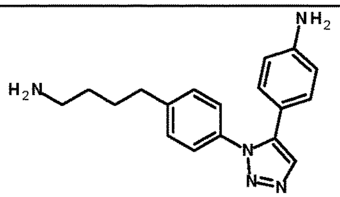 | 1726 | 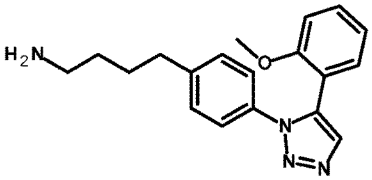 |
| 1718 | 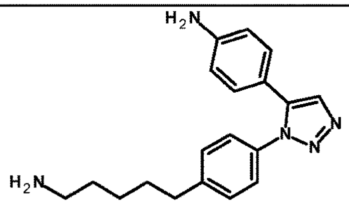 | 1727 | 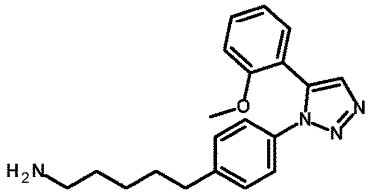 |
| 1719 | 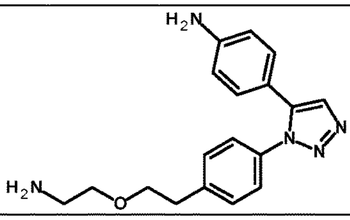 | 1728 | 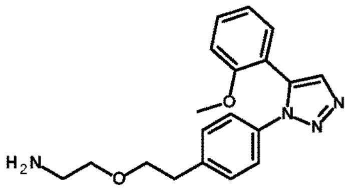 |
| 1720 | 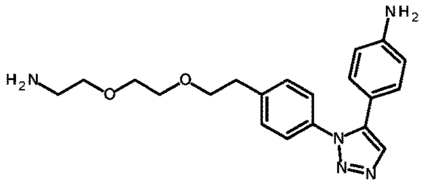 | 1729 | 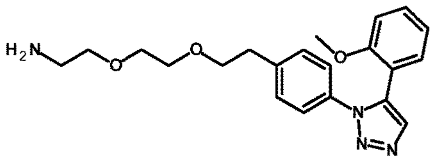 |
| 1721 | 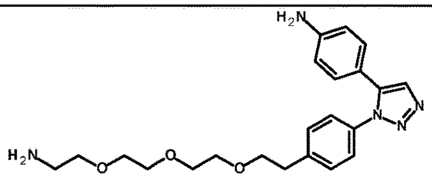 | 1730 | 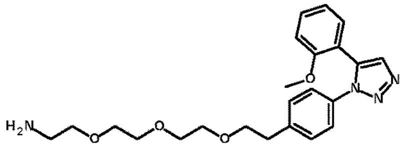 |
| 1731 | 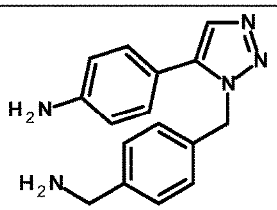 | 1739 | 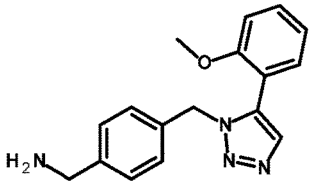 |

FIG. 3JJJ
| | | | |
|---|---|---|---|
| 1732 | 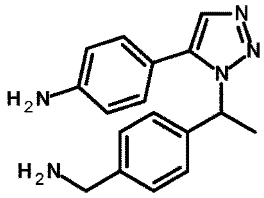 | 1740 | 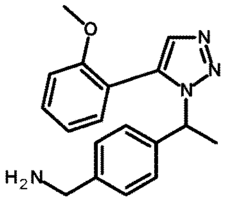 |
| 1733 | 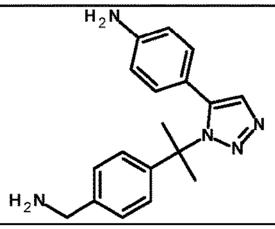 | 1741 | 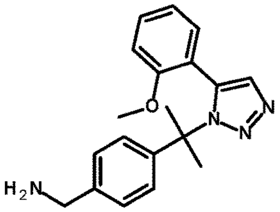 |
| 1734 | 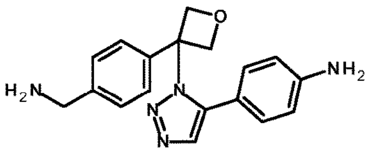 | 1742 | 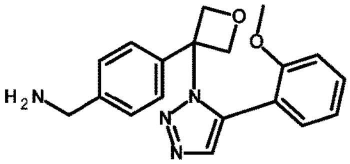 |
| 1735 | 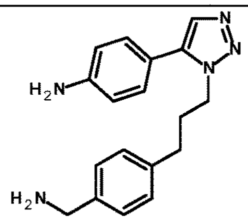 | 1743 | 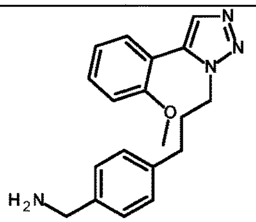 |
| 1736 | 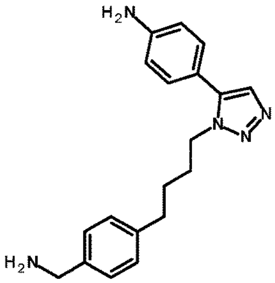 | 1744 | 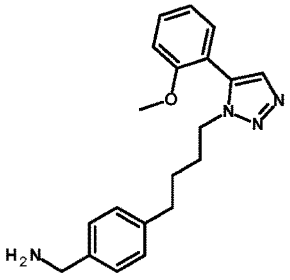 |
| 1737 | 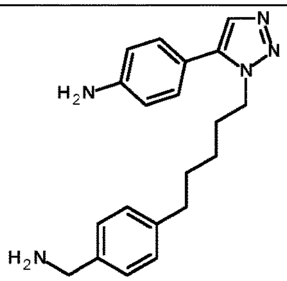 | 1745 | 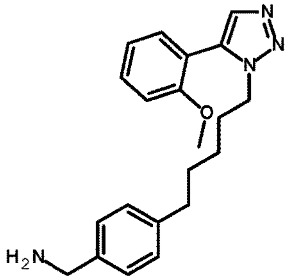 |

FIG. 3KKK
| | | | |
|---|---|---|---|
| 1738 | 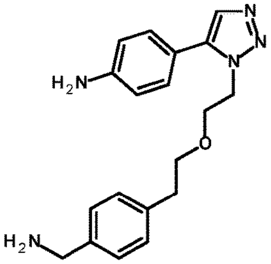 | 1746 | 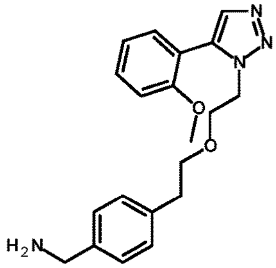 |
| 1747 | 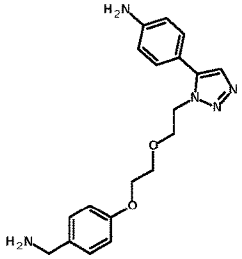 | 1755 | 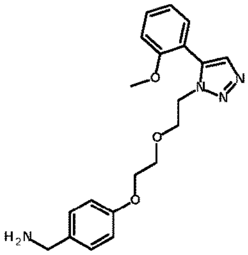 |
| 1748 | 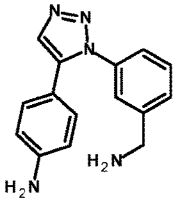 | 1756 | 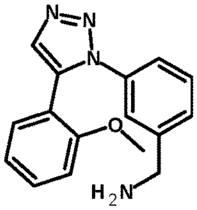 |
| 1749 | 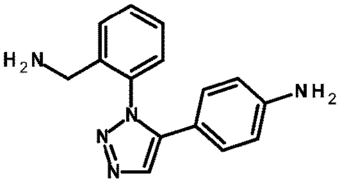 | 1757 | 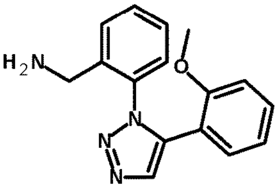 |
| 1750 | 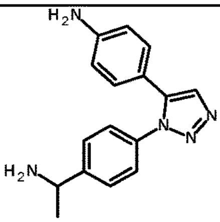 | 1758 | 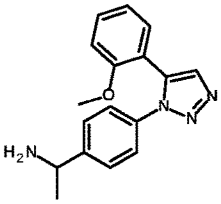 |
| 1751 | 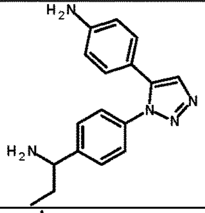 | 1759 | 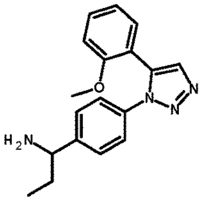 |
| 1752 | 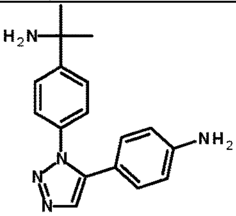 | 1760 | 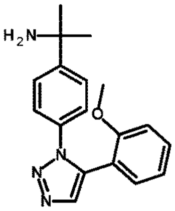 |

FIG. 3LLL
| | | | |
|---|---|---|---|
| 1753 | 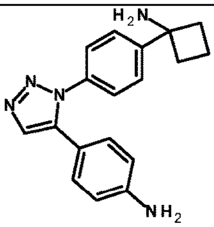 | 1761 | 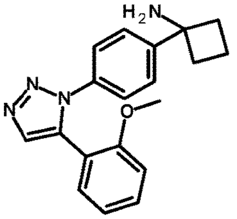 |
| 1754 | 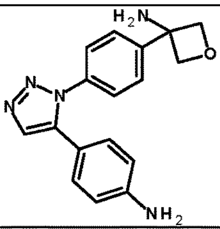 | 1762 | 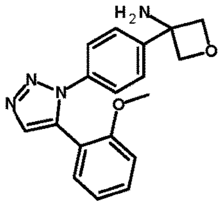 |
| 1763 | 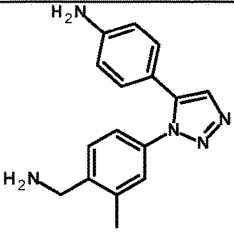 | 1771 | 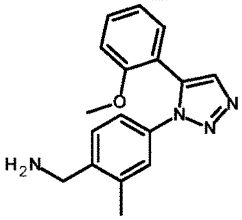 |
| 1764 | 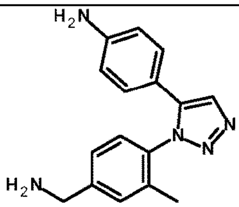 | 1772 | 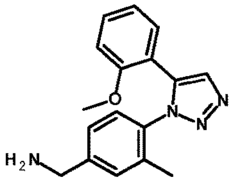 |
| 1765 | 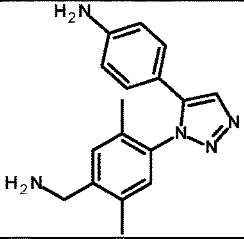 | 1773 | 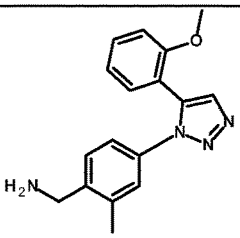 |
| 1766 | 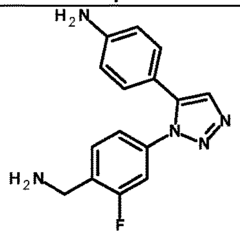 | 1774 | 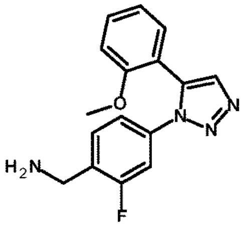 |
| 1767 | 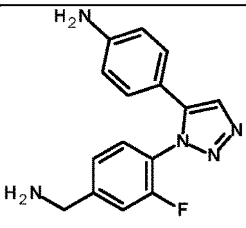 | 1775 | 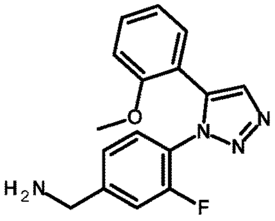 |

FIG. 3MMM
| | | | |
|---|---|---|---|
| 1768 | 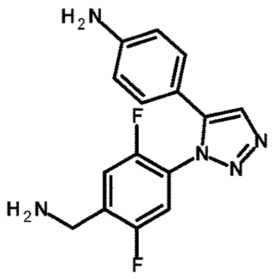 | 1776 | 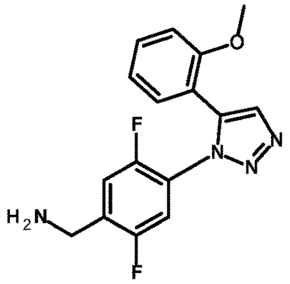 |
| 1769 | 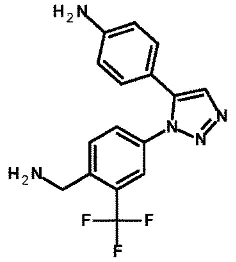 | 1777 | 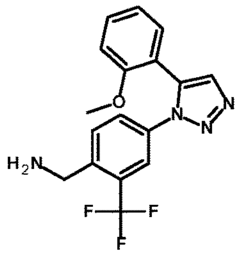 |
| 1770 | 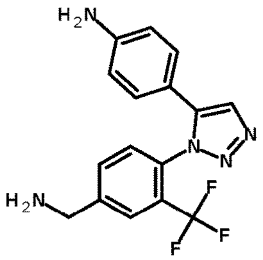 | 1778 | 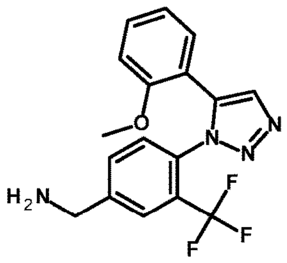 |
| 1779 | 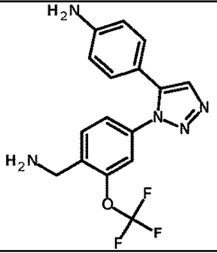 | 1786 | 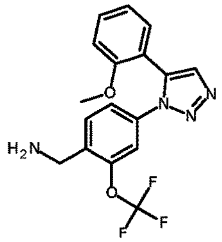 |
| 1780 | 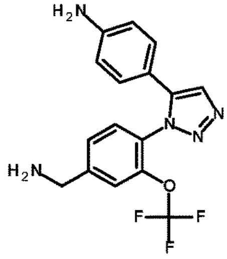 | 1787 | 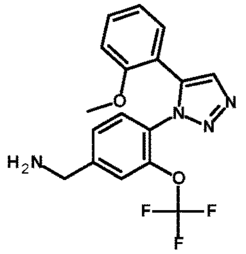 |
| 1781 | 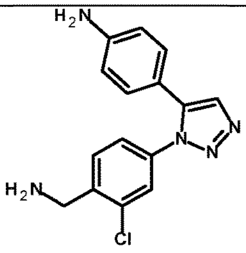 | 1787 | 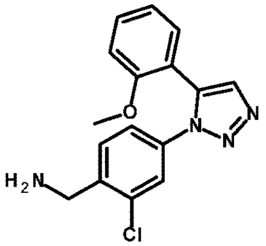 |

FIG. 3NNN
| | | | |
|---|---|---|---|
| 1782 | 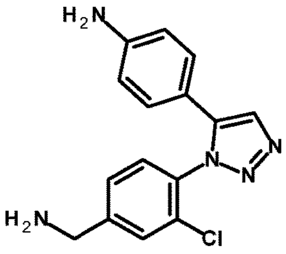 | 1788 | 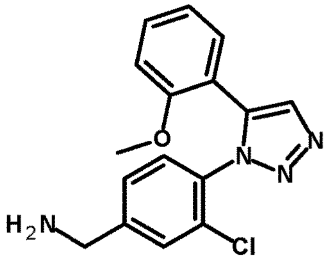 |
| 1783 | 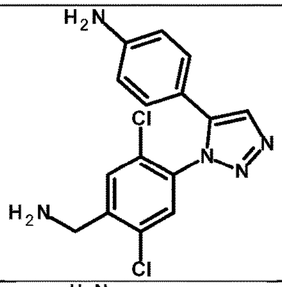 | 1789 | 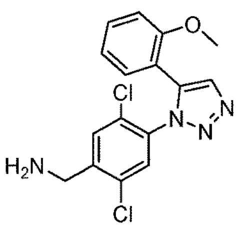 |
| 1784 | 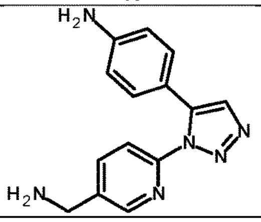 | 1790 | 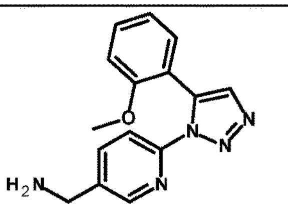 |
| 1785 | 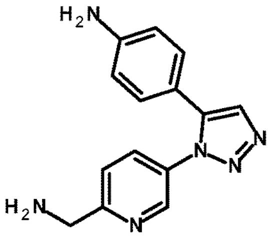 | 1791 | 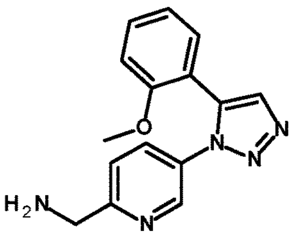 |
| 1792 | 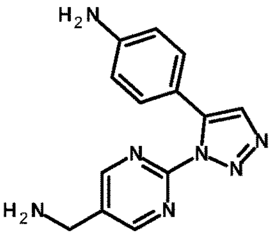 | 1800 | 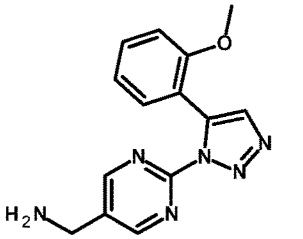 |
| 1793 | 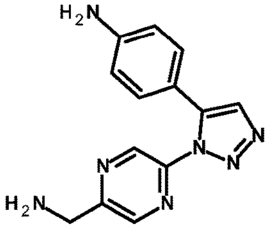 | 1801 | 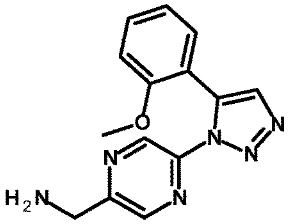 |

FIG. 3OOO
| | | | |
|---|---|---|---|
| 1794 | 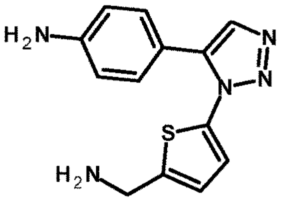 | 1802 | 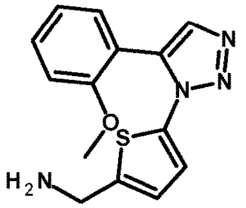 |
| 1795 | 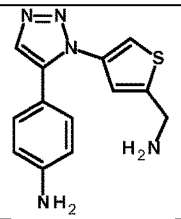 | 1803 | 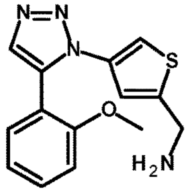 |
| 1796 | 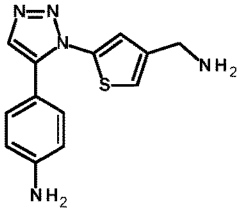 | 1804 | 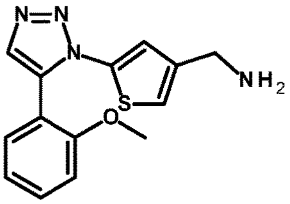 |
| 1797 | 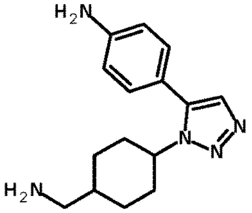 | 1805 | 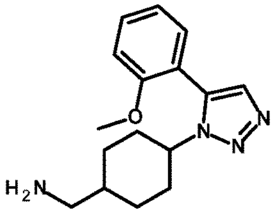 |
| 1798 | 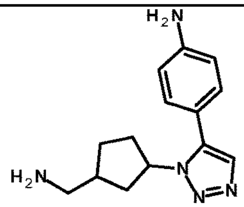 | 1806 | 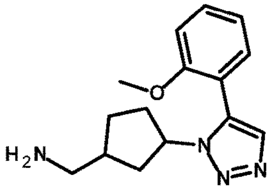 |
| 1799 | 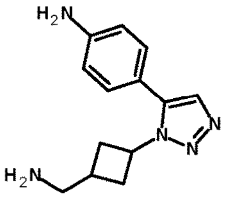 | 1807 | 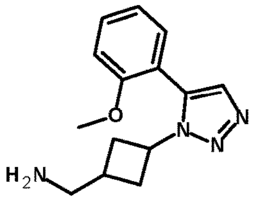 |
| 1808 | 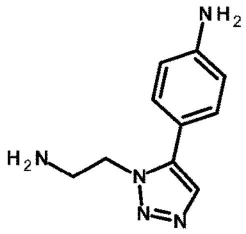 | 1817 | 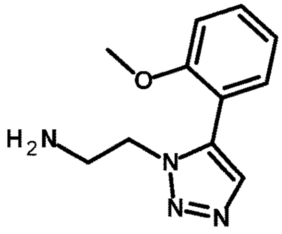 |

FIG. 3PPP
| | | | |
|---|---|---|---|
| 1809 | 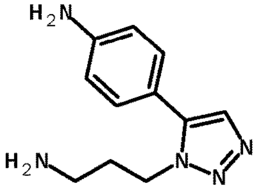 | 1818 | 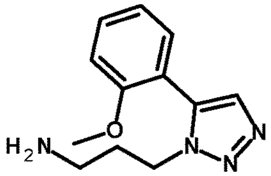 |
| 1810 | 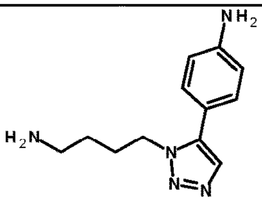 | 1819 | 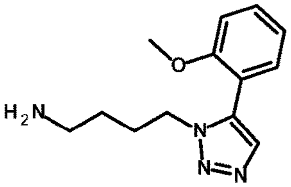 |
| 1811 | 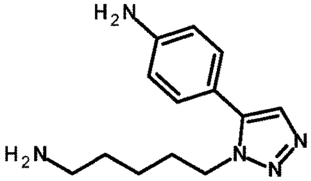 | 1820 | 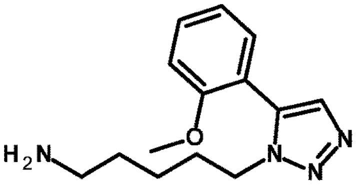 |
| 1812 | 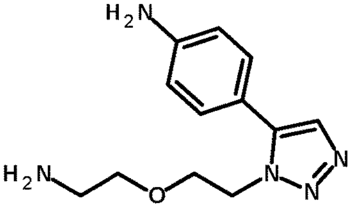 | 1821 | 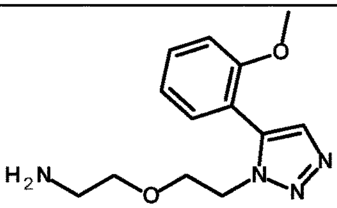 |
| 1813 | 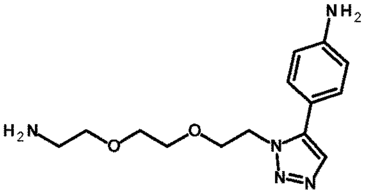 | 1822 | 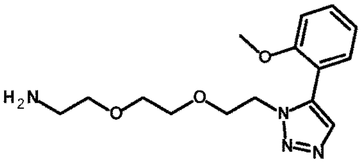 |
| 1814 | 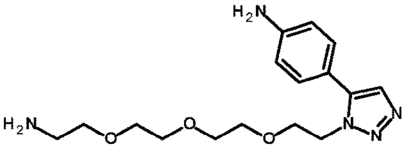 | 1823 | 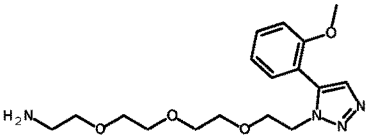 |
| 1815 | 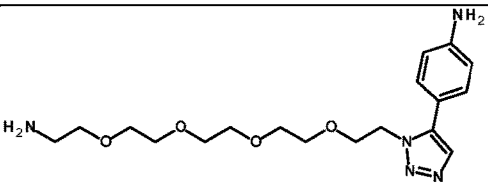 | 1824 | 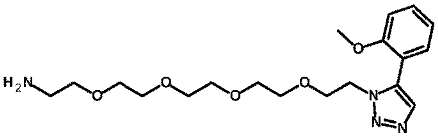 |
| 1816 | 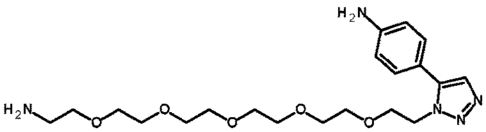 | 1825 | 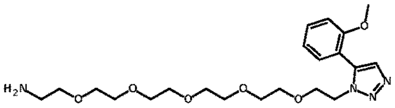 |

FIG. 3QQQ
| | | | |
|---|---|---|---|
| 1826 | 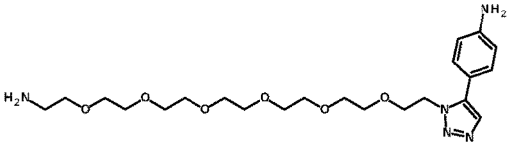 | 1837 | 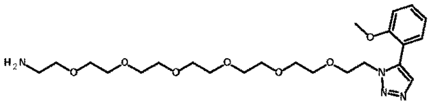 |
| 1827 | 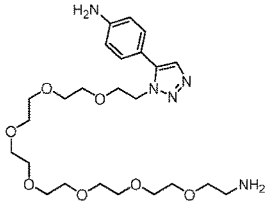 | 1838 | 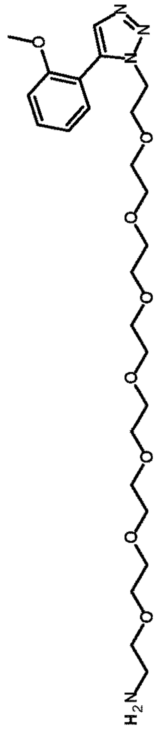 |
| 1828 | 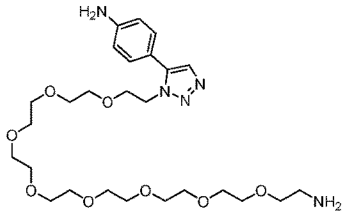 | 1839 | 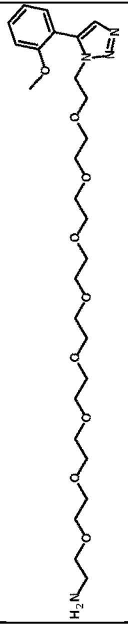 |

FIG. 3RRR
| | | | |
|---|---|---|---|
| 1829 | 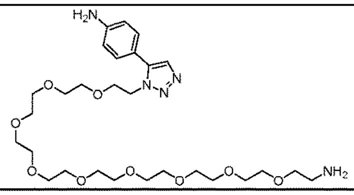 | 1840 | 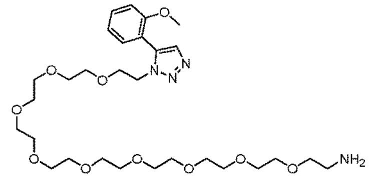 |
| 1830 | 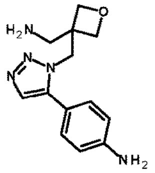 | 1841 | 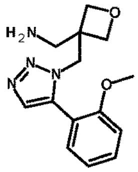 |
| 1831 | 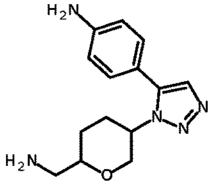 | 1842 | 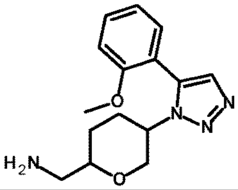 |
| 1832 | 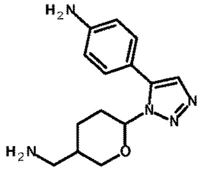 | 1843 | 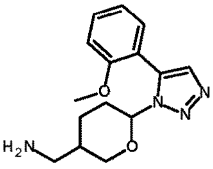 |
| 1833 | 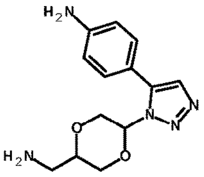 | 1844 | 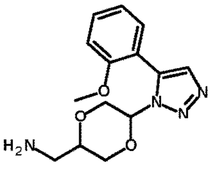 |
| 1834 | 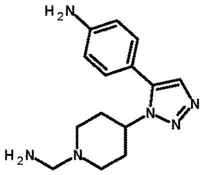 | 1845 | 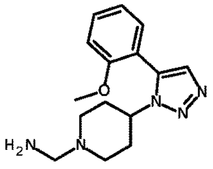 |
| 1835 | 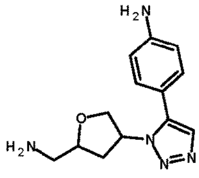 | 1846 | 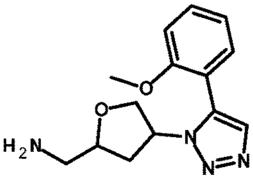 |
| 1836 | 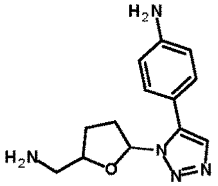 | 1847 | 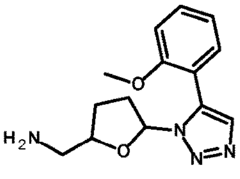 |

FIG. 3SSS
| | | | |
|---|---|---|---|
| 1848 | 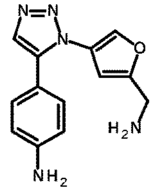 | 1857 | 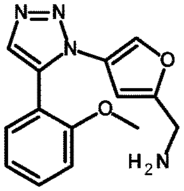 |
| 1849 | 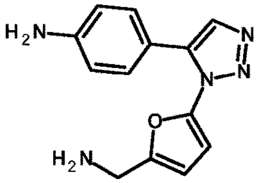 | 1858 | 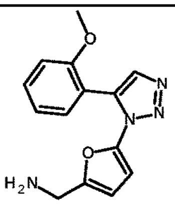 |
| 1850 | 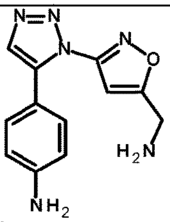 | 1859 | 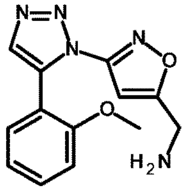 |
| 1851 | 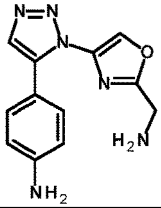 | 1860 | 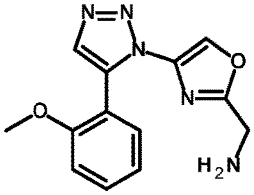 |
| 1852 | 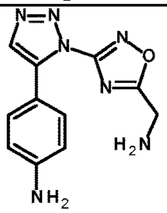 | 1861 | 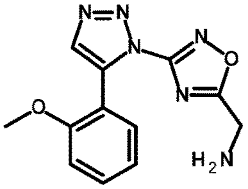 |
| 1853 | 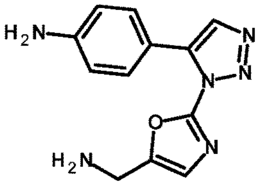 | 1862 | 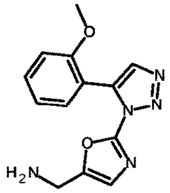 |
| 1854 | 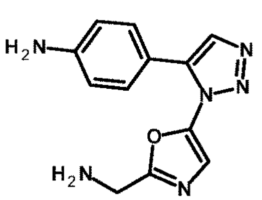 | 1863 | 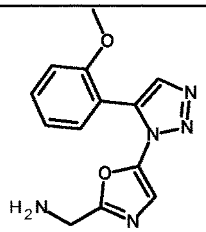 |

FIG. 3TTT
| | | | |
|---|---|---|---|
| 1855 | 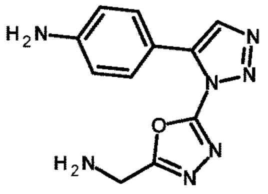 | 1864 | 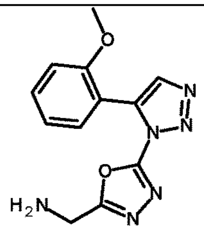 |
| 1856 | 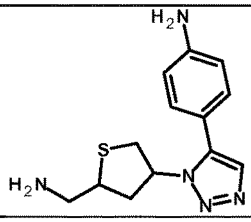 | 1865 | 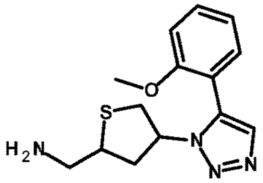 |
| 1866 | 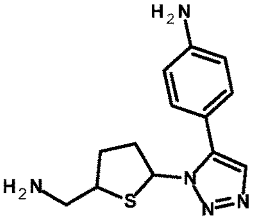 | 1875 | 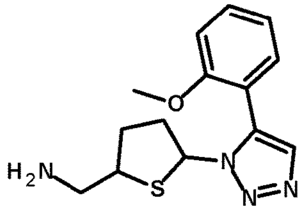 |
| 1867 | 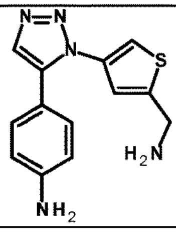 | 1876 | 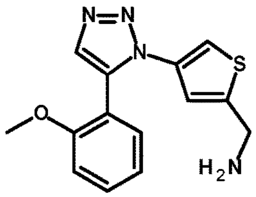 |
| 1868 | 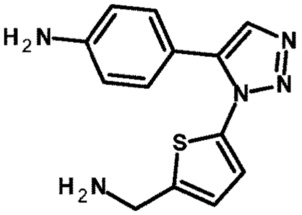 | 1877 | 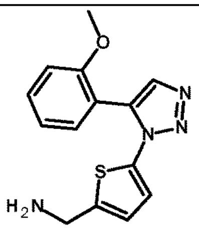 |
| 1869 | 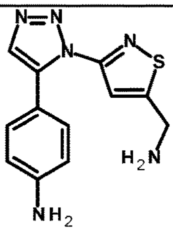 | 1878 | 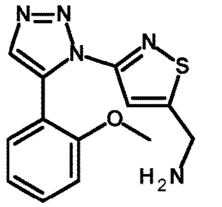 |
| 1870 | 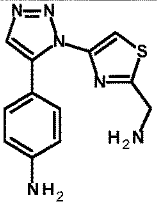 | 1879 | 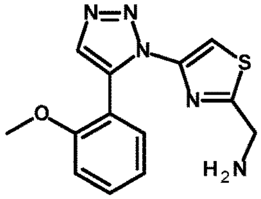 |

FIG. 3UUU
| | | | |
|---|---|---|---|
| 1871 | 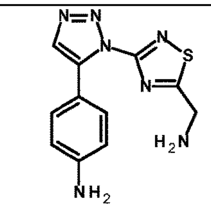 | 1880 | 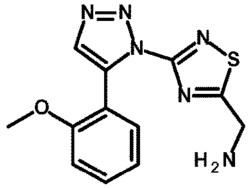 |
| 1872 | 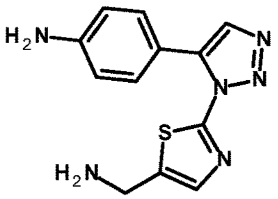 | 1881 | 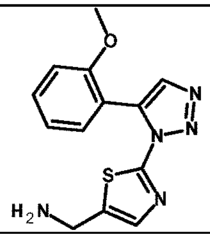 |
| 1873 | 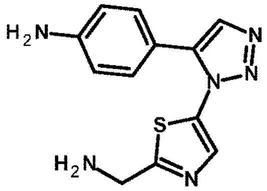 | 1882 | 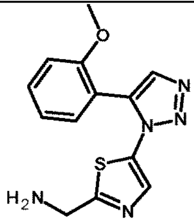 |
| 1874 | 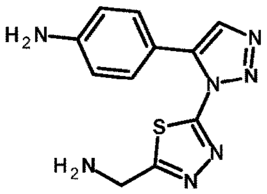 | 1883 | 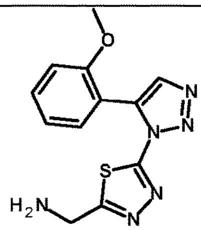 |
| 1884 | 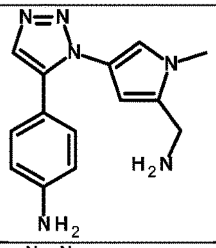 | 1893 | 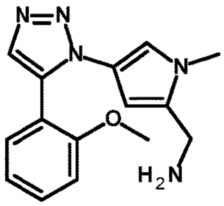 |
| 1885 | 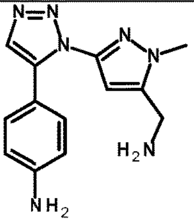 | 1894 | 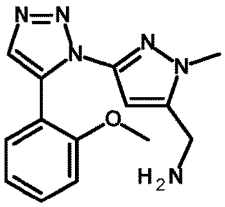 |
| 1886 | 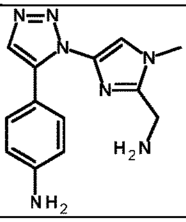 | 1895 | 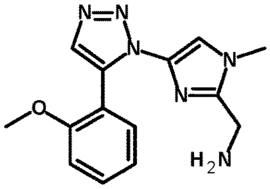 |

FIG. 3VVV
| | | | |
|---|---|---|---|
| 1887 | 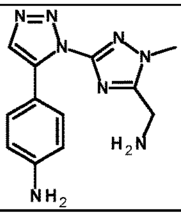 | 1896 | 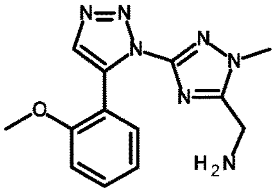 |
| 1888 | 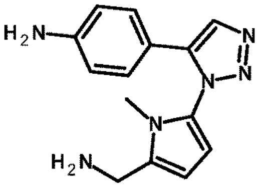 | 1897 | 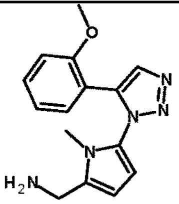 |
| 1889 | 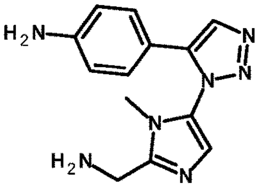 | 1898 | 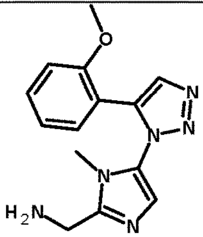 |
| 1890 | 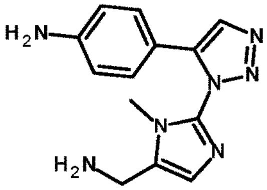 | 1899 | 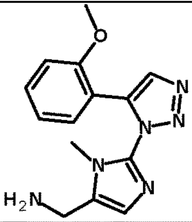 |
| 1891 | 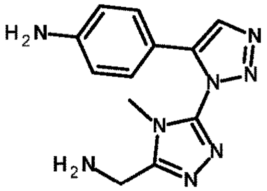 | 1900 | 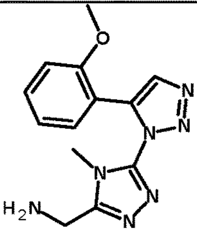 |
| 1892 | 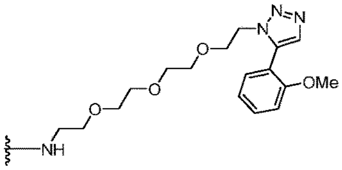 | 1901 | 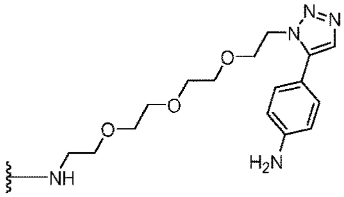 |
| | | | |
|---|---|---|---|
| 1902 | 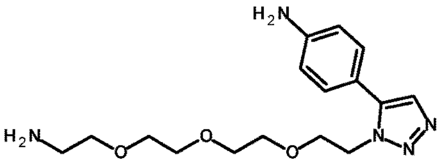 | 1909 | 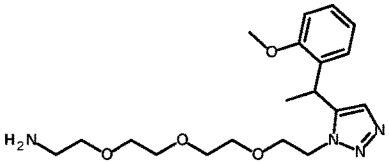 |

FIG. 3WWW
| | | | |
|---|---|---|---|
| 1903 | 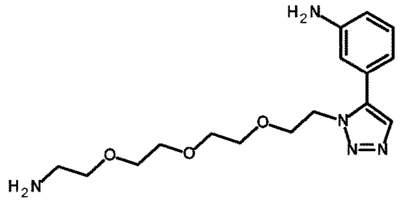 | 1910 | 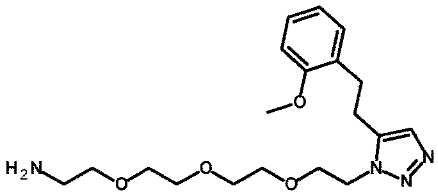 |
| 1904 | 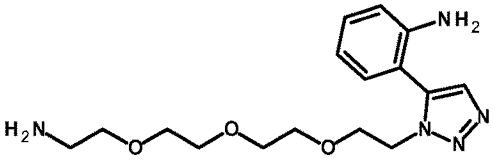 | 1911 | 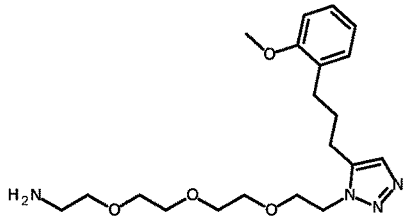 |
| 1905 | 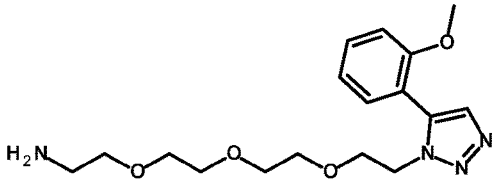 | 1912 | 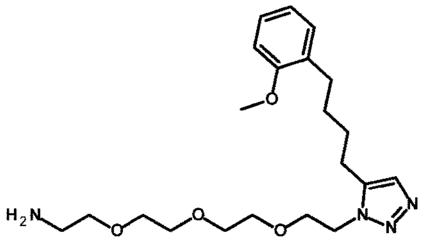 |
| 1906 | 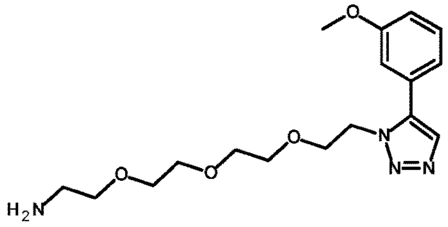 | 1913 | 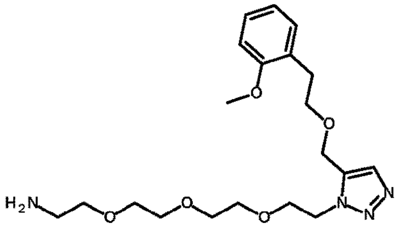 |
| 1907 | 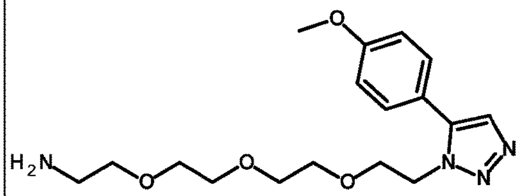 | 1914 | 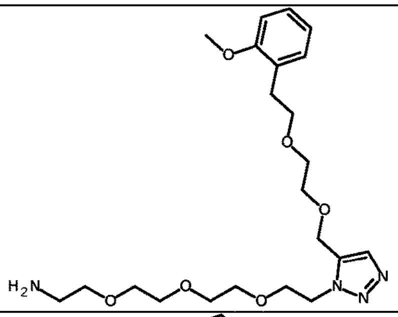 |
| 1908 | 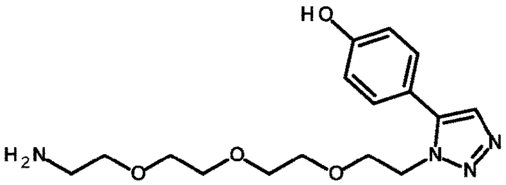 | 1915 | 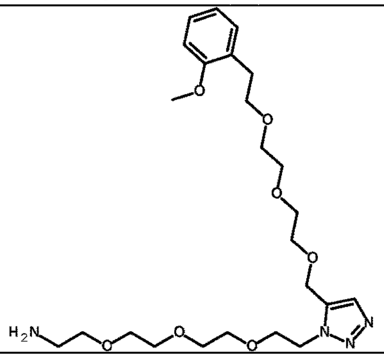 |

FIG. 3XXX
| | | | |
|---|---|---|---|
| 1916 | 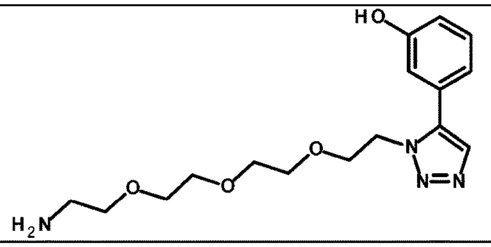 | 1924 | 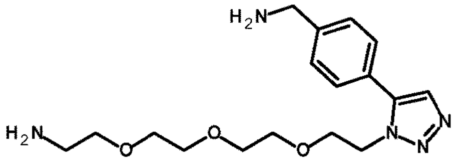 |
| 1917 | 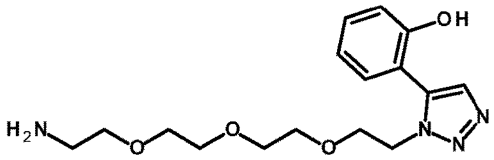 | 1925 | 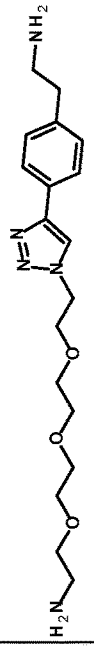 |
| 1918 | 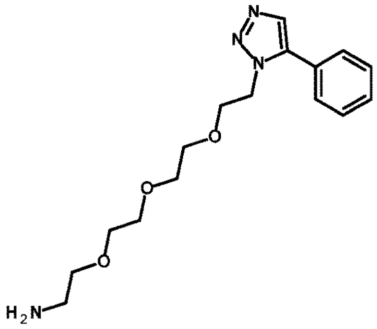 | 1926 | 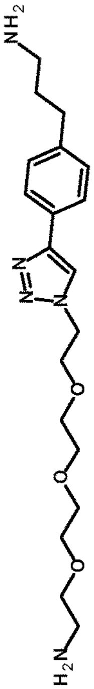 |

FIG. 3YYY
| | | | |
|---|---|---|---|
| 1919 | 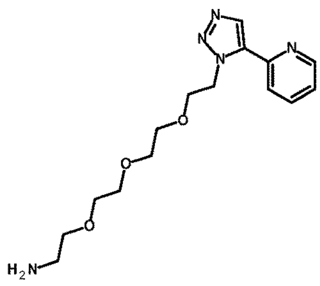 | 1927 | 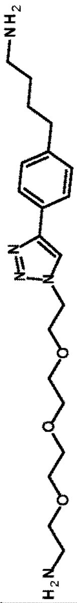 |
| 1920 | 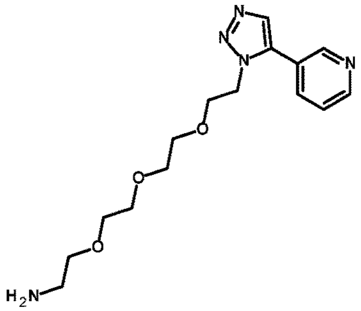 | 1928 | 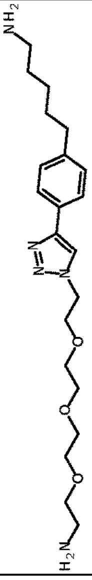 |

FIG. 3ZZZ
| | | | |
|---|---|---|---|
| 1921 | 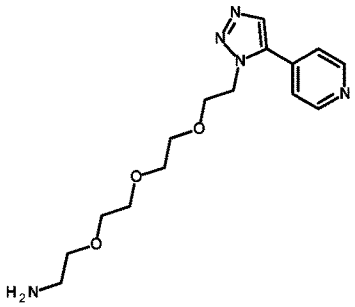 | 1929 | 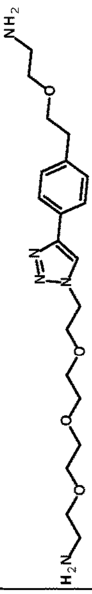 |
| 1922 | 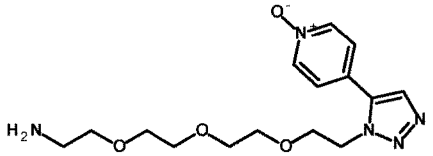 | 1930 | 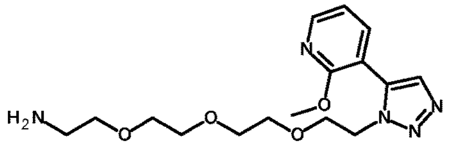 |
| 1923 | 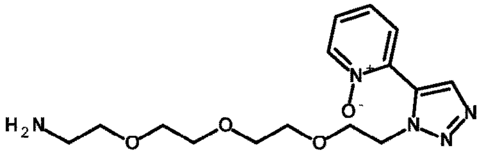 | 1931 | 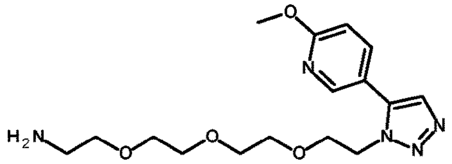 |
| 1932 | 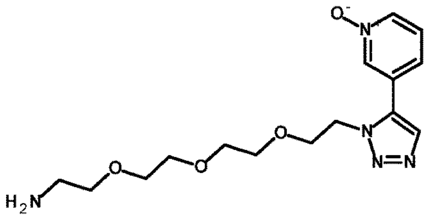 | 1940 | 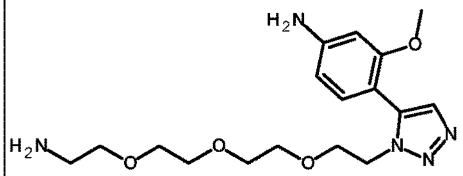 |
| 1933 | 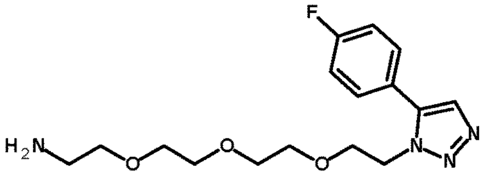 | 1941 | 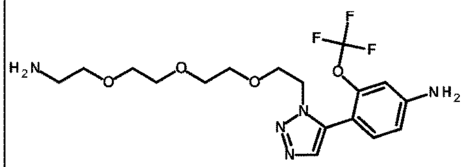 |
| 1934 | 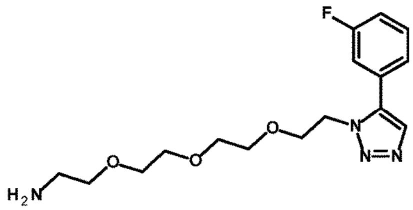 | 1942 | 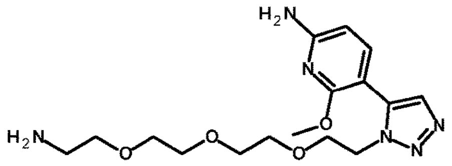 |

FIG. 3AAAA
| | | | |
|---|---|---|---|
| 1935 | 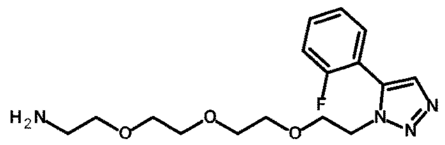 | 1943 | 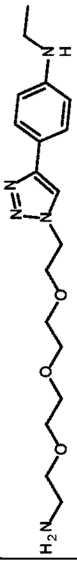 |
| 1936 | 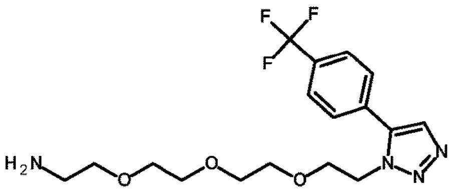 | 1944 | 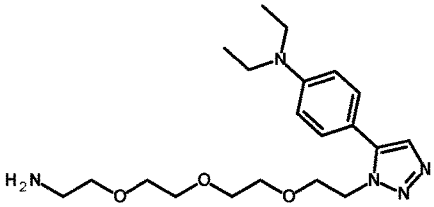 |
| 1937 | 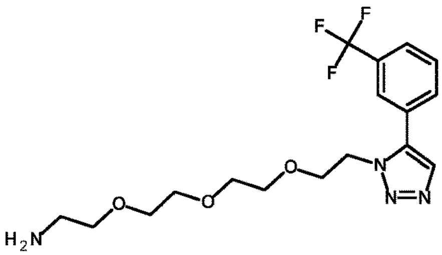 | 1945 | 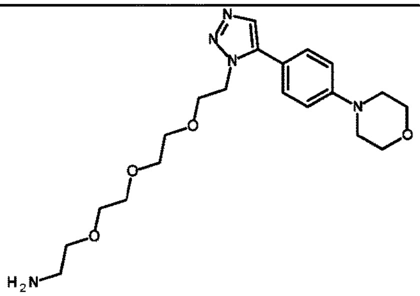 |
| 1938 | 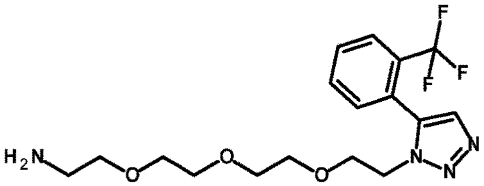 | 1946 | 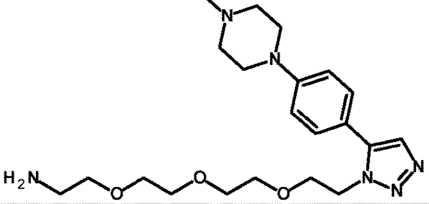 |
| 1939 | 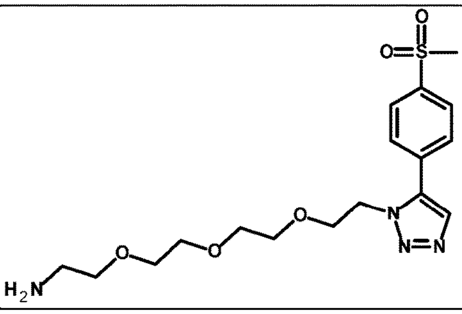 | 1947 | 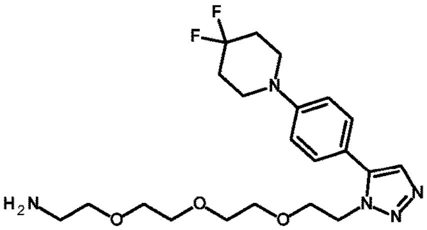 |

FIG. 3BBBB
| | | | |
|---|---|---|---|
| 1948 | 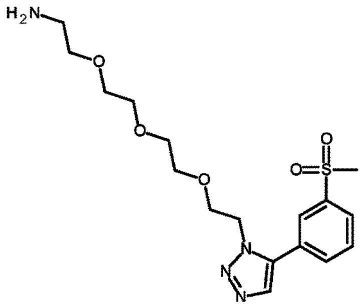 | 1955 | 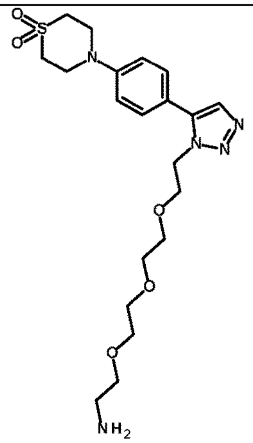 |
| 1949 | 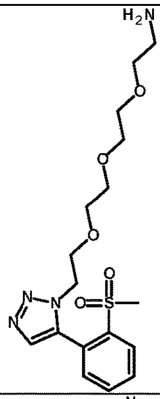 | 1956 | 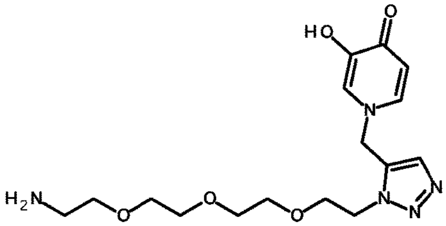 |
| 1950 | 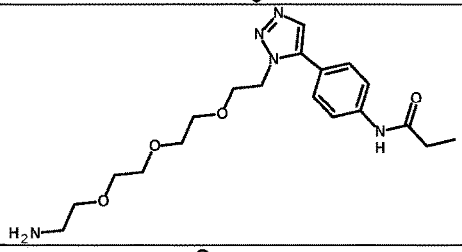 | 1957 | 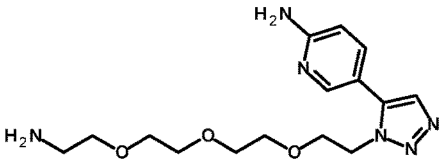 |
| 1951 | 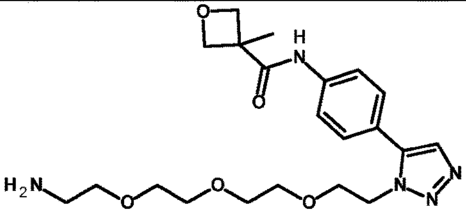 | 1958 | 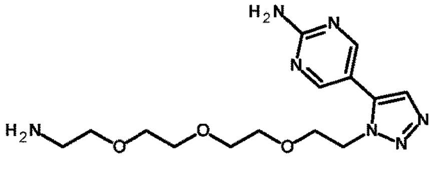 |
| 1952 | 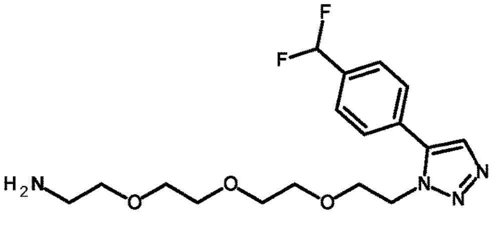 | 1959 | 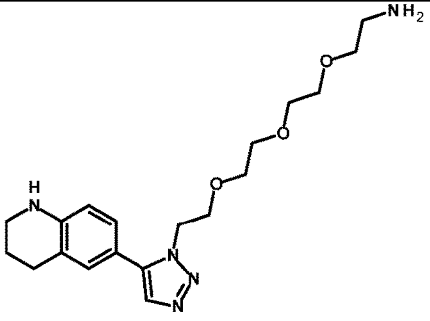 |

FIG. 3CCCC
| | | | |
|---|---|---|---|
| 1953 | 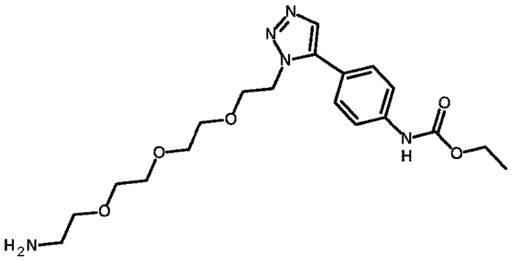 | 1960 | 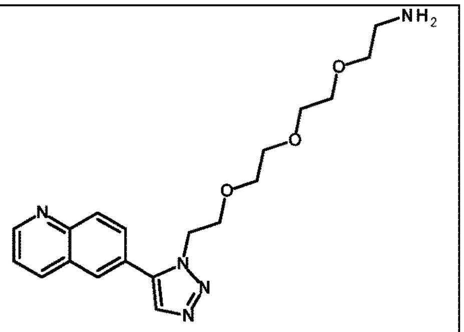 |
| 1954 | 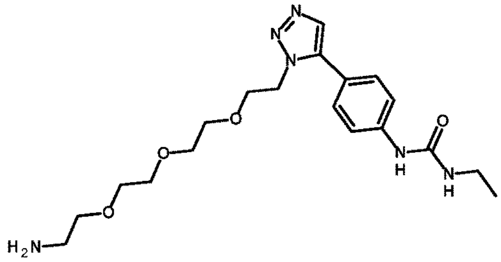 | 1961 | 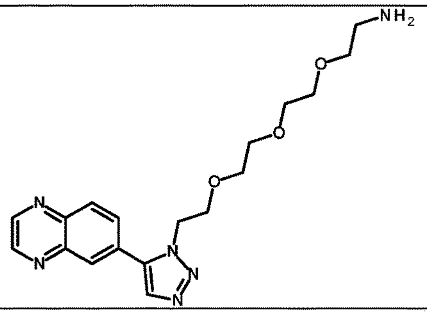 |
| 1962 | 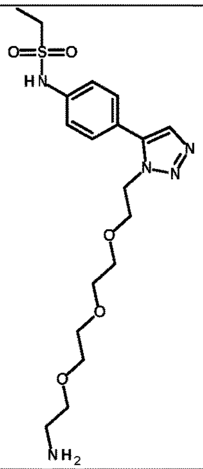 | 1968 | 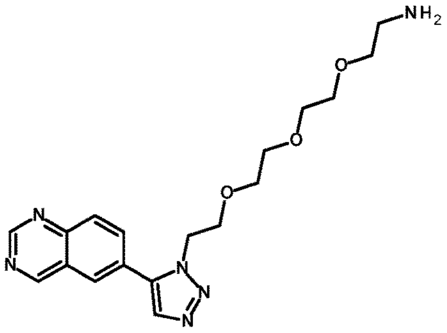 |
| 1963 | 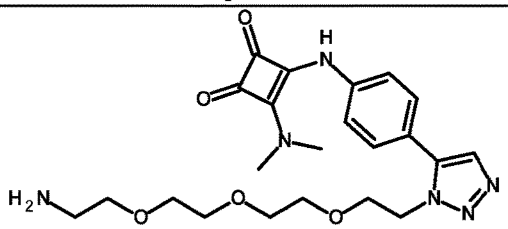 | 1969 | 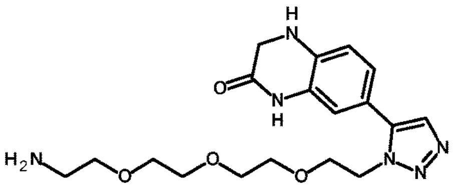 |
| 1964 | 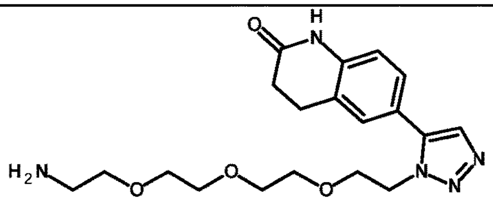 | 1970 | 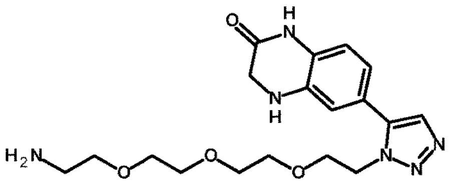 |

FIG. 3DDDD
| | | | |
|---|---|---|---|
| 1965 | 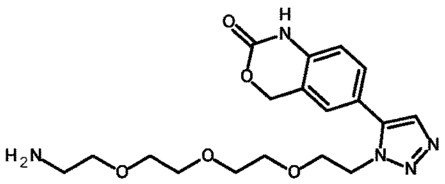 | 1971 | 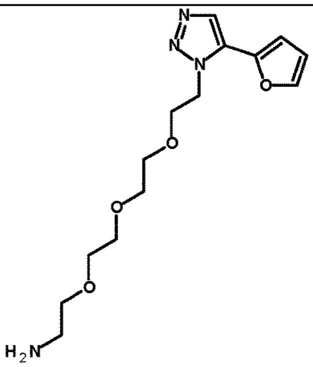 |
| 1966 | 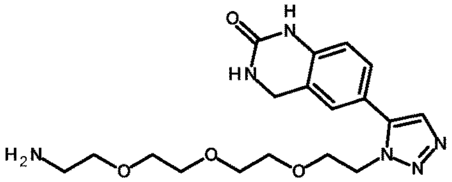 | 1972 | 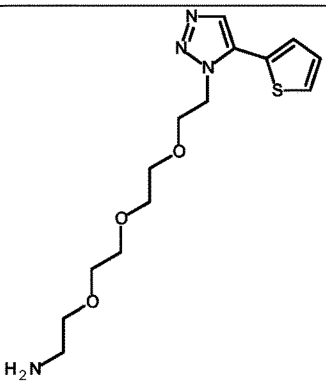 |
| 1967 | 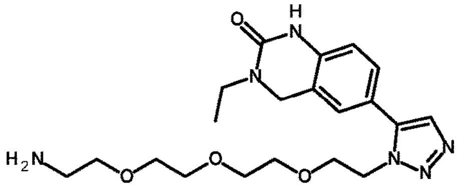 | 1973 | 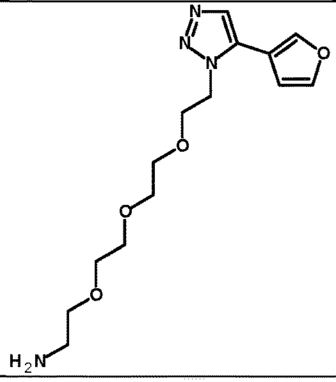 |
| 1974 | 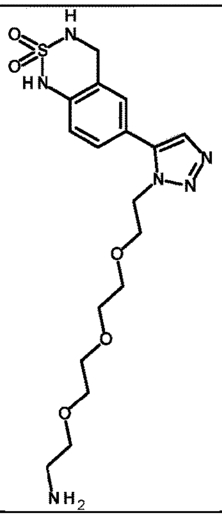 | 1980 | 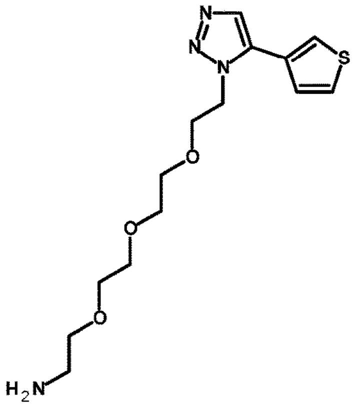 |

FIG. 3EEEE
| | | | |
|---|---|---|---|
| 1975 | 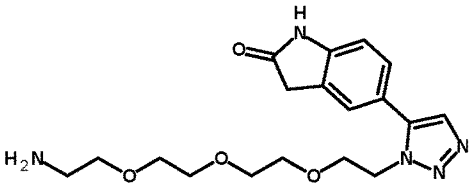 | 1981 | 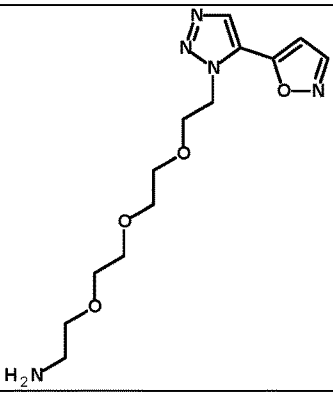 |
| 1976 | 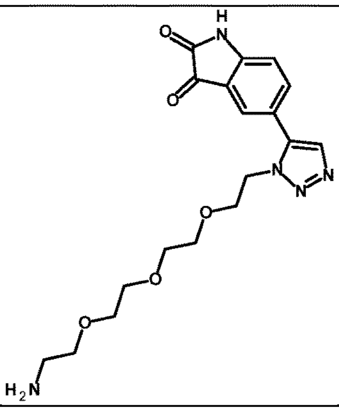 | 1982 | 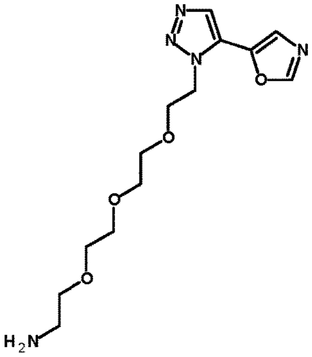 |
| 1977 | 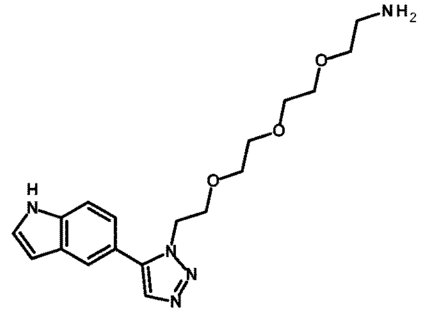 | 1983 | 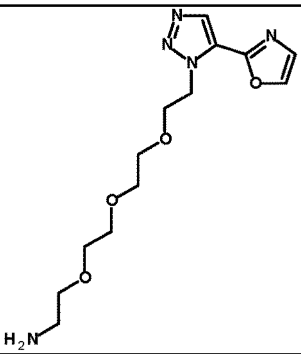 |
| 1978 | 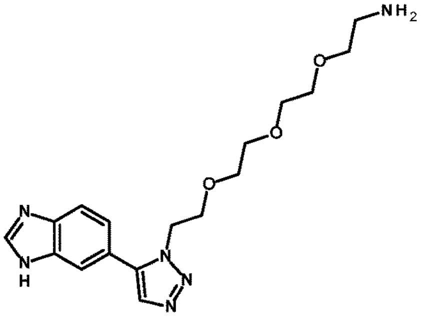 | 1984 | 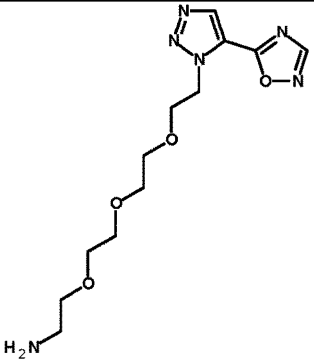 |

FIG. 3FFFF
| | | | |
|---|---|---|---|
| 1979 | 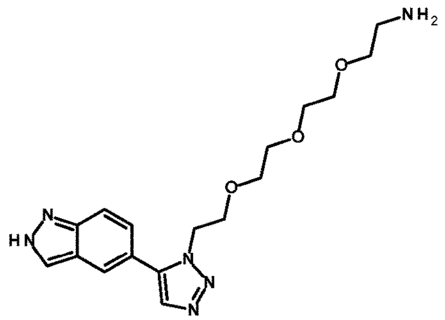 | 1985 | 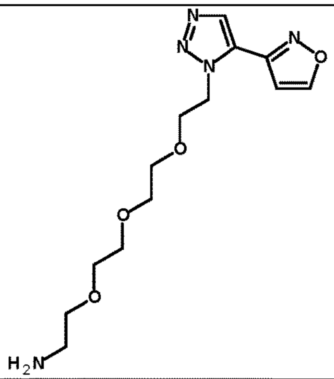 |
| 1986 | 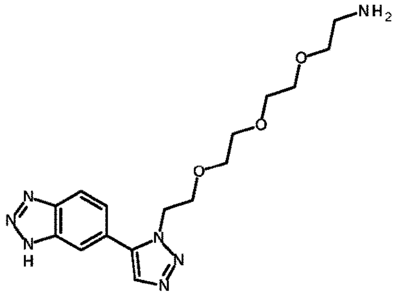 | 1992 | 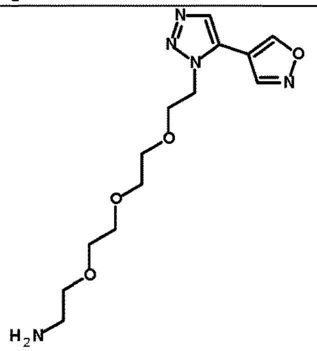 |
| 1987 | 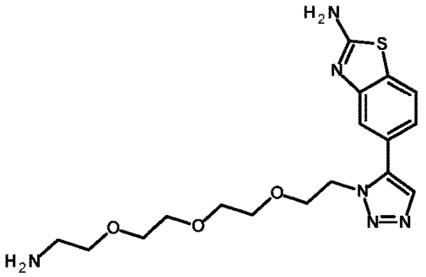 | 1993 | 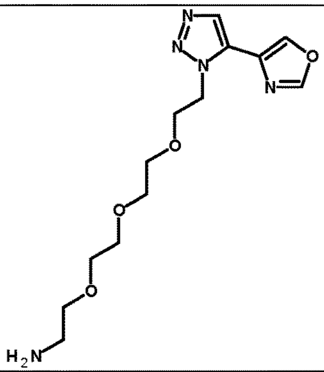 |
| 1988 | 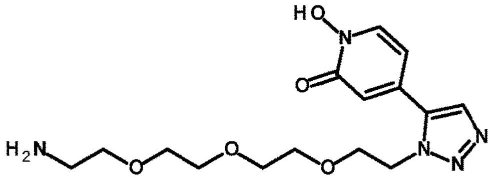 | 1994 | 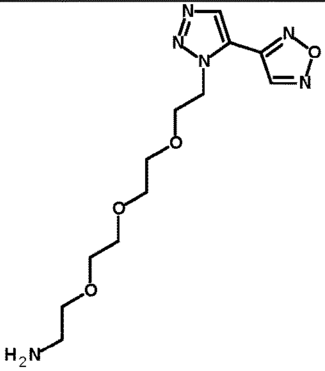 |

FIG. 3GGGG
| | | | |
|---|---|---|---|
| 1989 | 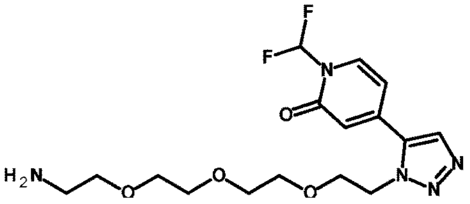 | 1995 | 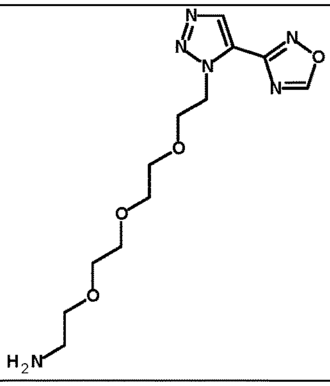 |
| 1990 | 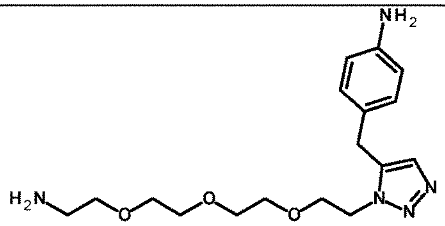 | 1996 | 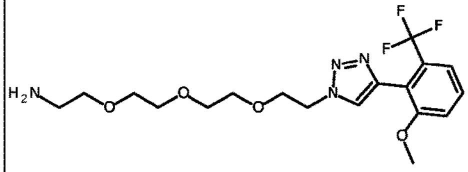 |
| 1991 | 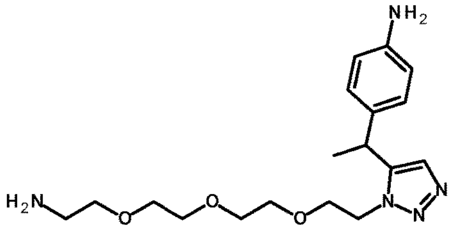 | 1997 | 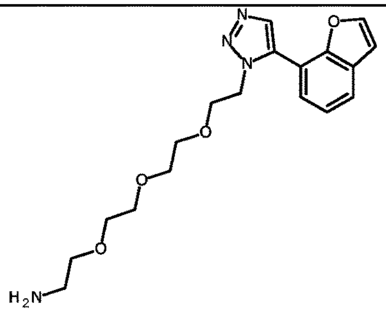 |
| 1998 | 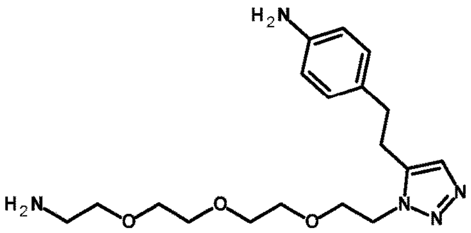 | 2004 | 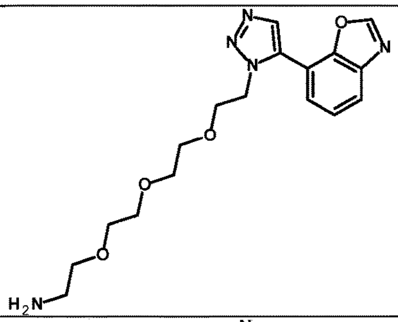 |
| 1999 | 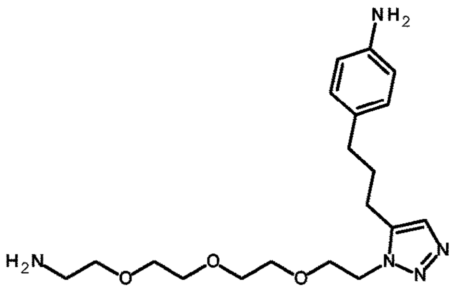 | 2005 | 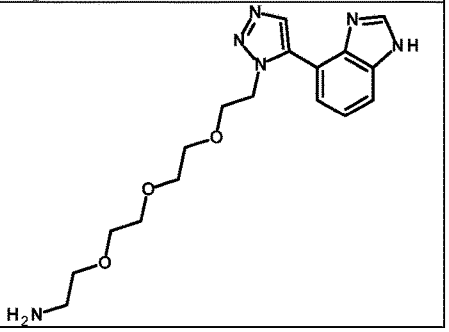 |

FIG. 3HHHH
| | | | |
|---|---|---|---|
| 2000 | 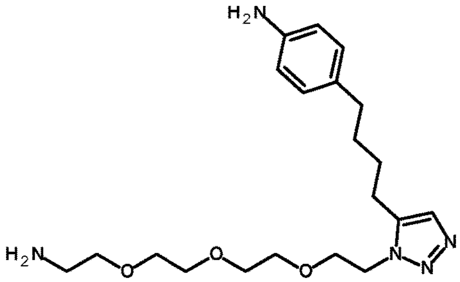 | 2006 | 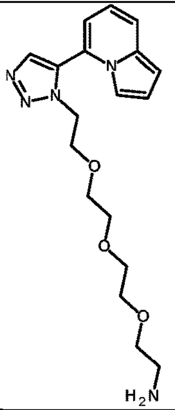 |
| 2001 | 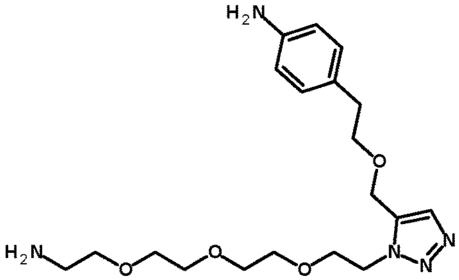 | 2007 | 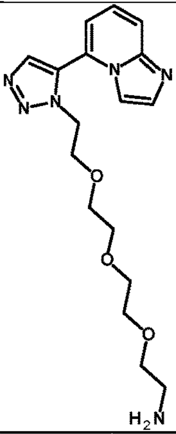 |
| 2002 | 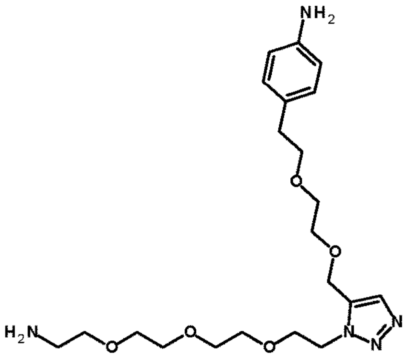 | 2008 | 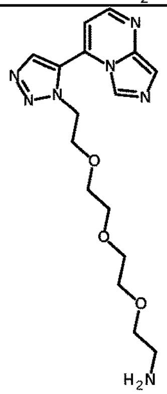 |
| 2003 | 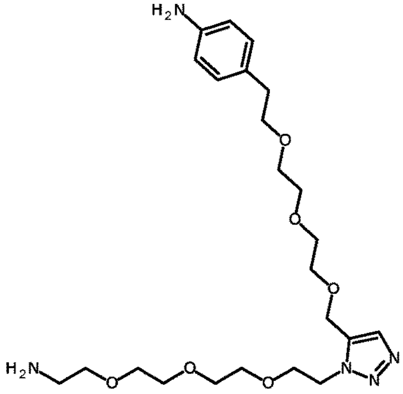 | 2009 | 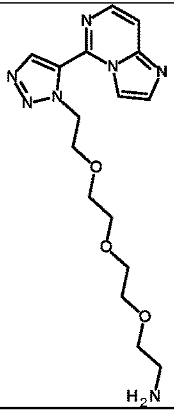 |

FIG. 3IIII
| | | | |
|---|---|---|---|
| 2010 | 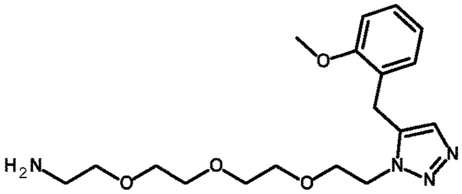 | 2011 | 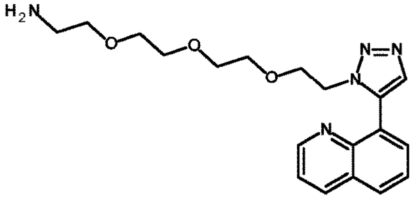 |

| | | | |
|---|---|---|---|
| 2012 |  | 2020 |  |
| 2013 |  | 2021 |  |
| 2014 |  | 2022 |  |
| 2015 |  | 2023 |  |
| 2016 |  | 2024 |  |
| 2017 |  | 2025 |  |

| | | | |
|---|---|---|---|
| 2018 |  | 2026 |  |
| 2019 |  | 2027 |  |
| 2028 |  | 2036 |  |
| 2029 |  | 2037 |  |
| 2030 |  | 2038 |  |
| 2031 |  | 2039 |  |

| | | | |
|---|---|---|---|
| 2032 |  | 2040 |  |
| 2033 |  | 2041 |  |
| 2034 |  | 2042 |  |
| 2035 |  | 2043 |  |
| 2044 |  | 2052 |  |
| 2045 |  | 2053 |  |

| | | | |
|---|---|---|---|
| 2046 |  | 2054 |  |
| 2047 |  | 2055 |  |
| 2048 |  | 2056 |  |
| 2049 |  | 2057 |  |
| 2050 |  | 2058 |  |
| 2051 |  | 2059 |  |

| | | | |
|---|---|---|---|
| 2060 |  | 2068 |  |
| 2061 |  | 2069 |  |
| 2062 |  | 2070 |  |
| 2063 |  | 2071 |  |
| 2064 |  | 2072 |  |

| | | | |
|---|---|---|---|
| 2065 |  | 2073 |  |
| 2066 |  | 2074 |  |
| 2067 |  | 2075 |  |
| 2076 |  | 2085 |  |
| 2077 |  | 2086 |  |
| 2078 |  | 2087 |  |

| | | | |
|---|---|---|---|
| 2079 |  | 2088 |  |
| 2080 |  | 2089 |  |
| 2081 |  | 2090 |  |

| | | | |
|---|---|---|---|
| 2082 |  | 2091 |  |
| 2083 |  | 2092 |  |
| 2084 |  | 2093 |  |
| 2094 |  | 2103 |  |

| | | | |
|---|---|---|---|
| 2095 |  | 2104 |  |

| | | | |
|---|---|---|---|
| 2096 |  | 2105 |  |
| 2097 |  | 2106 |  |
| 2098 |  | 2107 |  |
| 2099 |  | 2108 |  |
| 2100 |  | 2109 |  |
| 2101 |  | 2110 |  |

| | | | |
|---|---|---|---|
| 2102 |  | 2111 |  |
| 2112 |  | 2121 |  |

| | | | |
|---|---|---|---|
| 2113 |  | 2122 |  |
| 2114 |  | 2123 |  |
| 2115 |  | 2124 |  |
| 2116 |  | 2125 |  |
| 2117 |  | 2126 |  |

| | | | |
|---|---|---|---|
| 2118 |  | 2127 |  |
| 2119 |  | 2128 |  |
| 2120 |  | 2129 |  |
| 2130 |  | 2138 |  |
| 2131 |  | 2139 |  |
| 2132 |  | 2140 |  |
| 2133 |  | 2141 |  |

| | | | |
|---|---|---|---|
| 2134 |  | 2142 |  |
| 2135 |  | 2143 |  |
| 2136 |  | 2144 |  |
| 2137 |  | 2145 |  |
| 2146 |  | 2154 |  |
| 2147 |  | 2155 |  |

| | | | |
|---|---|---|---|
| 2148 |  | 2156 |  |
| 2149 |  | 2157 |  |
| 2150 |  | 2158 |  |
| 2151 |  | 2159 |  |
| 2152 |  | 2160 |  |
| 2153 |  | 2166 |  |

| | | | |
|---|---|---|---|
| 2167 |  | 2175 |  |
| 2168 |  | 2176 |  |
| 2169 |  | 2177 |  |
| 2170 |  | 2178 |  |
| 2171 |  | 2179 |  |
| 2172 |  | 2180 |  |

| | | | |
|---|---|---|---|
| 2173 |  | 2181 |  |
| 2174 |  | 2182 |  |
| 2183 |  | 2191 |  |
| 2184 |  | 2192 |  |
| 2185 |  | 2193 |  |
| 2186 |  | 2194 |  |

| | | | |
|---|---|---|---|
| 2187 |  | 2195 |  |

| | | | |
|---|---|---|---|
| 2188 |  | 2196 |  |
| 2189 |  | 2197 |  |
| 2190 |  | 2198 |  |
| 2199 |  | 2207 |  |
| 2200 |  | 2208 |  |
| 2201 |  | 2209 |  |

| | | | |
|---|---|---|---|
| 2202 |  | 2210 |  |
| 2203 |  | 2211 |  |
| 2204 |  | 2212 |  |
| 2205 |  | 2213 |  |
| 2206 |  | 2214 |  |
| 2215 |  | 2223 |  |

| | | | |
|---|---|---|---|
| 2216 |  | 2224 |  |
| 2217 |  | 2225 |  |
| 2218 |  | 2226 |  |
| 2219 |  | 2227 |  |
| 2220 |  | 2228 |  |
| 2221 |  | 2229 |  |

| | | | |
|---|---|---|---|
| 2222 |  | 2230 |  |
| 2231 |  | 2240 |  |
| 2232 |  | 2241 |  |
| 2233 |  | 2242 |  |
| 2234 |  | 2243 |  |
| 2235 |  | 2244 |  |
| 2236 |  | 2245 |  |

| | | | |
|---|---|---|---|
| 2237 |  | 2246 |  |
| 2238 |  | 2247 |  |
| 2239 |  | 2248 |  |
| 2249 |  | 2258 |  |
| 2250 |  | 2259 |  |
| 2251 |  | 2260 |  |
| 2252 |  | 2261 |  |
| 2253 |  | 2262 |  |

| | | | |
|---|---|---|---|
| 2254 |  | 2263 |  |
| 2255 |  | 2264 |  |
| 2256 |  | 2265 |  |
| 2257 |  | 2266 |  |
| 2267 |  | 2276 |  |
| 2268 |  | 2277 |  |
| 2269 |  | 2278 |  |

| | | | |
|---|---|---|---|
| 2270 |  | 2279 |  |
| 2271 |  | 2280 |  |
| 2272 |  | 2281 |  |
| 2273 |  | 2282 |  |
| 2274 |  | 2283 |  |
| 2275 |  | 2284 |  |
| 2285 |  | 2293 |  |

| | | | |
|---|---|---|---|
| 2286 |  | 2294 |  |
| 2287 |  | 2295 |  |
| 2288 |  | 2296 |  |
| 2289 |  | 2297 |  |
| 2290 |  | 2298 |  |
| 2291 |  | 2299 |  |

| | | | |
|---|---|---|---|
| 2292 |  | 2300 |  |
| 2301 |  | 2309 |  |
| 2302 |  | 2310 |  |
| 2303 |  | 2311 |  |
| 2304 |  | 2312 |  |
| 2305 |  | 2313 |  |

| | | | |
|---|---|---|---|
| 2306 |  | 2314 |  |
| 2307 |  | 2315 |  |
| 2308 |  | 2316 |  |
| 2317 |  | 2325 |  |
| 2318 |  | 2326 |  |

| | | | |
|---|---|---|---|
| 2319 |  | 2327 |  |
| 2320 |  | 2328 |  |
| 2321 |  | 2329 |  |
| 2322 |  | 2330 |  |
| 2323 |  | 2331 |  |
| 2324 |  | 2332 |  |

| | | | |
|---|---|---|---|
| 2333 |  | 2341 |  |
| 2334 |  | 2342 |  |
| 2335 |  | 2343 |  |
| 2336 |  | 2344 |  |
| 2337 |  | 2345 |  |
| 2338 |  | 2346 |  |

| | | | |
|---|---|---|---|
| 2339 |  | 2347 |  |
| 2340 |  | 2348 |  |
| 2349 |  | 2356 |  |
| 2350 |  | 2357 |  |
| 2351 |  | 2358 |  |

| | | | |
|---|---|---|---|
| 2352 |  | 2359 |  |
| 2353 |  | 2360 |  |
| 2354 |  | 2361 |  |
| 2355 |  | 2362 |  |
| 2363 |  | 2370 |  |

| | | | |
|---|---|---|---|
| 2364 |  | 2371 |  |
| 2365 |  | 2372 |  |
| 2366 |  | 2373 |  |
| 2367 |  | 2374 |  |
| 2368 |  | 2375 |  |
| 2369 |  | | |

| | | | |
|---|---|---|---|
| 2376 |  | 2384 |  |
| 2377 |  | 2385 |  |
| 2378 |  | 2386 |  |
| 2379 |  | 2387 |  |
| 2380 |  | 2388 |  |
| 2381 |  | 2389 |  |

| | | | |
|---|---|---|---|
| 2382 |  | 2390 |  |
| 2383 |  | 2391 |  |
| 2392 |  | 2400 |  |
| 2393 |  | 2401 |  |

| | | | |
|---|---|---|---|
| 2394 |  | 2402 |  |
| 2395 |  | 2403 |  |
| 2396 |  | 2404 |  |

| | | | |
|---|---|---|---|
| 2397 |  | 2405 |  |
| 2398 |  | 2406 |  |
| 2399 |  | 2407 |  |
| 2408 |  | 2416 |  |
| 2409 |  | 2417 |  |
| 2410 |  | 2418 |  |

| | | | |
|---|---|---|---|
| 2411 |  | 2419 |  |
| 2412 |  | 2420 |  |
| 2413 |  | 2421 |  |
| 2414 |  | 2422 |  |
| 2415 |  | 2423 |  |
| 2424 |  | 2432 |  |

| | | | |
|---|---|---|---|
| 2425 |  | 2433 |  |
| 2426 |  | 2434 |  |
| 2427 |  | 2435 |  |
| 2428 |  | 2436 |  |
| 2429 |  | 2437 |  |
| 2430 |  | 2438 |  |

| | | | |
|---|---|---|---|
| 2431 |  | 2439 |  |
| 2440 |  | 2448 |  |
| 2441 |  | 2449 |  |
| 2442 |  | 2450 |  |
| 2443 |  | 2451 |  |
| 2444 |  | 2452 |  |

| | | | |
|---|---|---|---|
| 2445 |  | 2453 |  |
| 2446 |  | 2454 |  |
| 2447 |  | 2455 |  |
| 2456 |  | 2464 |  |
| 2457 |  | 2465 |  |
| 2458 |  | 2465 |  |

| | | | |
|---|---|---|---|
| 2459 |  | 2467 |  |
| 2460 |  | 2468 |  |
| 2461 |  | 2469 |  |
| 2462 |  | | |

| | | | |
|---|---|---|---|
| 2463 |  | 2470 |  |
| 2471 |  | 2479 |  |

| | | | |
|---|---|---|---|
| 2472 |  | 2480 |  |
| 2473 |  | 2481 |  |
| 2474 |  | 2482 |  |
| 2475 |  | 2483 |  |
| 2476 |  | 2484 |  |
| 2477 |  | 2485 |  |

| | | | |
|---|---|---|---|
| 2478 |  | 2486 |  |
| 2487 |  | 2494 |  |
| 2488 |  | 2495 |  |
| 2489 |  | 2496 |  |

| | | | |
|---|---|---|---|
| 2490 |  | 2497 |  |
| 2491 |  | 2498 |  |
| 2492 |  | 2499 |  |
| 2493 |  | 2500 |  |
| 2501 |  | 2509 |  |
| 2502 |  | 2510 |  |

| | | | |
|---|---|---|---|
| 2503 |  | 2511 |  |
| 2504 |  | 2512 |  |
| 2505 |  | 2513 |  |
| 2506 |  | 2514 |  |
| 2507 |  | 2515 |  |
| 2508 |  | 2516 |  |

| | | | |
|---|---|---|---|
| 2517 |  | 2525 |  |
| 2518 |  | 2526 |  |
| 2519 |  | 2527 |  |
| 2520 |  | 2528 |  |
| 2521 |  | 2529 |  |
| 2522 |  | 2530 |  |

| | | | |
|---|---|---|---|
| 2523 |  | 2531 |  |
| 2524 |  | 2532 |  |
| 2533 |  | 2541 |  |
| 2534 |  | 2542 |  |
| 2535 |  | 2543 |  |
| 2536 |  | 2544 |  |

| | | | |
|---|---|---|---|
| 2537 |  | 2545 |  |
| 2538 |  | 2546 |  |
| 2539 |  | 2547 |  |
| 2540 |  | 2548 |  |
| 2549 |  | 2554 |  |
| 2550 |  | 2555 |  |

| | | | |
|---|---|---|---|
| 2551 |  | 2556 |  |
| 2552 |  | 2557 |  |
| 2553 |  | 2558 |  |

| | | | |
|---|---|---|---|
| 2559 |  | 2567 |  |
| 2560 |  | 2568 |  |
| 2561 |  | 2569 |  |
| 2562 |  | 2570 |  |
| 2563 |  | 2571 |  |
| 2564 |  | 2572 |  |

| | | | |
|---|---|---|---|
| 2565 |  | 2573 |  |
| 2566 |  | 2574 |  |
| 2575 |  | 2581 |  |

| | | | |
|---|---|---|---|
| 2576 |  | 2582 |  |
| 2577 |  | 2583 |  |
| 2578 |  | 2584 |  |

| | | | |
|---|---|---|---|
| 2579 |  | 2585 |  |
| 2580 |  | 2586 |  |
| 2587 |  | 2592 |  |
| 2588 |  | 2593 |  |

| | | | |
|---|---|---|---|
| 2589 |  | 2594 |  |
| 2590 |  | 2595 |  |
| 2591 |  | 2596 |  |

| | | | |
|---|---|---|---|
| 2597 |  | 2603 |  |
| 2598 |  | 2604 |  |
| 2599 |  | 2605 |  |
| 2600 |  | 2606 |  |
| 2601 |  | 2607 |  |
| 2602 |  | 2608 |  |

| | | | |
|---|---|---|---|
| 2609 |  | 2614 |  |
| 2610 |  | 2615 |  |
| 2611 |  | 2616 |  |
| 2612 |  | 2617 |  |

| | | | |
|---|---|---|---|
| 2613 |  | 2618 |  |

| | | | |
|---|---|---|---|
| 2619 |  | 2626 |  |
| 2620 |  | 2627 |  |
| 2621 |  | 2628 |  |

| | | | |
|---|---|---|---|
| 2622 |  | 2629 |  |
| 2623 |  | 2630 |  |
| 2624 |  | 2631 |  |
| 2625 |  | 2632 |  |

| | | | |
|---|---|---|---|
| 2633 |  | 2639 |  |
| 2634 |  | 2640 |  |
| 2635 |  | 2641 |  |

| | | | |
|---|---|---|---|
| 2636 |  | 2642 |  |
| 2637 |  | 2643 |  |
| 2638 |  | 2644 |  |

| | | | |
|---|---|---|---|
| 2645 |  | 2652 |  |
| 2646 |  | 2653 |  |

| | | | |
|---|---|---|---|
| 2647 |  | 2654 |  |
| 2648 |  | 2655 |  |
| 2649 |  | 2656 |  |
| 2650 |  | 2657 |  |
| 2651 |  | 2658 |  |
| 2659 |  | 2666 |  |

| | | | |
|---|---|---|---|
| 2660 |  | 2667 |  |
| 2661 |  | 2668 |  |
| 2662 |  | 2669 |  |
| 2663 |  | 2670 |  |
| 2664 |  | 2671 |  |
| 2665 |  | 2672 |  |

| | | | |
|---|---|---|---|
| 2673 |  | 2680 |  |
| 2674 |  | 2681 |  |
| 2675 |  | 2682 |  |
| 2676 |  | 2683 |  |
| 2677 |  | 2684 |  |

| | | | |
|---|---|---|---|
| 2678 |  | 2685 |  |
| 2679 |  | 2686 |  |
| 2687 |  | 2694 |  |
| 2688 |  | 2695 |  |
| 2689 |  | 2696 |  |

| | | | |
|---|---|---|---|
| 2690 |  | 2697 |  |
| 2691 |  | 2698 |  |
| 2692 |  | 2699 |  |
| 2693 |  | 2700 |  |
| 2701 |  | 2708 |  |
| 2702 |  | 2709 |  |

| | | | |
|---|---|---|---|
| 2703 |  | 2710 |  |
| 2704 |  | 2711 |  |
| 2705 |  | 2712 |  |
| 2706 |  | 2713 |  |
| 2707 |  | 2714 |  |
| 2715 |  | 2722 |  |

| | | | |
|---|---|---|---|
| 2716 |  | 2723 |  |
| 2717 |  | 2724 |  |
| 2718 |  | 2725 |  |
| 2719 |  | 2726 |  |
| 2720 |  | 2727 |  |
| 2721 |  | 2728 |  |

| | | | |
|---|---|---|---|
| 2729 |  | 2737 |  |
| 2730 |  | 2738 |  |
| 2731 |  | 2739 |  |
| 2732 |  | 2740 |  |
| 2733 |  | 2741 |  |
| 2734 |  | 2742 |  |
| 2735 |  | 2743 |  |

| | | | |
|---|---|---|---|
| 2736 |  | 2744 |  |
| 2745 |  | 2753 |  |
| 2746 |  | 2754 |  |

| | | | |
|---|---|---|---|
| 2747 |  | 2755 |  |
| 2748 |  | 2756 |  |
| 2749 |  | 2757 |  |
| 2750 |  | 2758 |  |
| 2751 |  | 2759 |  |
| 2752 |  | 2760 |  |

| | | | |
|---|---|---|---|
| 2761 |  | 2770 |  |
| 2762 |  | 2771 |  |
| 2763 |  | 2772 |  |
| 2764 |  | 2773 |  |
| 2765 |  | 2774 |  |

| | | | |
|---|---|---|---|
| 2766 |  | 2775 |  |
| 2767 |  | 2776 |  |
| 2768 |  | 2777 |  |
| 2769 |  | 2778 |  |

| | | | |
|---|---|---|---|
| 2779 |  | 2786 |  |
| 2780 |  | 2787 |  |
| 2781 |  | 2788 |  |

| | | | |
|---|---|---|---|
| 2782 |  | 2789 |  |
| 2783 |  | 2790 |  |
| 2784 |  | 2791 |  |
| 2785 |  | 2792 |  |
| 2793 |  | 2800 |  |

| | | | |
|---|---|---|---|
| 2794 |  | 2801 |  |
| 2795 |  | 2802 |  |
| 2796 |  | 2803 |  |

| | | | |
|---|---|---|---|
| 2797 |  | 2804 |  |

| | | | |
|---|---|---|---|
| 2798 |  | 2805 |  |
| 2799 |  | 2806 |  |
| 2807 |  | 2813 |  |
| 2808 |  | 2814 |  |

| | | | |
|---|---|---|---|
| 2809 |  | 2815 |  |
| 2810 |  | 2816 |  |
| 2811 |  | 2817 |  |
| 2812 |  | 2818 |  |

| | | | |
|---|---|---|---|
| 2819 |  | 2827 |  |
| 2820 |  | 2828 |  |
| 2821 |  | 2829 |  |
| 2822 |  | 2830 |  |
| 2823 |  | 2831 |  |

| | | | |
|---|---|---|---|
| 2824 |  | 2832 |  |
| 2825 |  | 2833 |  |
| 2826 |  | 2834 |  |
| 2835 |  | 2843 |  |
| 2836 |  | 2844 |  |
| 2837 |  | 2845 |  |

| | | | |
|---|---|---|---|
| 2838 |  | 2846 |  |
| 2839 |  | 2847 |  |
| 2840 |  | 2848 |  |
| 2841 |  | 2849 |  |

| | | | |
|---|---|---|---|
| 2842 |  | 2850 |  |
| 2851 |  | 2859 |  |
| 2852 |  | 2860 |  |
| 2853 |  | 2861 |  |
| 2854 |  | 2862 |  |
| 2855 |  | 2863 |  |

| | | | |
|---|---|---|---|
| 2856 |  | 2864 |  |
| 2857 |  | 2865 |  |
| 2858 |  | 2866 |  |
| 2867 |  | 2874 |  |
| 2868 |  | 2875 |  |

| | | | |
|---|---|---|---|
| 2869 |  | 2876 |  |
| 2870 |  | 2877 |  |
| 2871 |  | 2878 |  |
| 2872 |  | 2879 |  |

| | | | |
|---|---|---|---|
| 2873 |  | 2880 |  |
| 2881 |  | 2888 |  |
| 2882 |  | 2889 |  |
| 2883 |  | 2890 |  |
| 2884 |  | 2891 |  |

| | | | |
|---|---|---|---|
| 2885 |  | 2892 |  |
| 2886 |  | 2893 |  |
| 2887 |  | 2894 |  |
| 2895 |  | 2903 |  |
| 2896 |  | 2904 |  |
| 2897 |  | 2905 |  |

| | | | |
|---|---|---|---|
| 2898 |  | 2906 |  |
| 2899 |  | 2907 |  |
| 2900 |  | 2908 |  |
| 2901 |  | 2909 |  |
| 2902 |  | 2910 |  |
| 2911 |  | 2919 |  |

| | | | |
|---|---|---|---|
| 2912 |  | 2920 |  |
| 2913 |  | 2921 |  |
| 2914 |  | 2922 |  |
| 2915 |  | 2923 |  |
| 2916 |  | 2924 |  |
| 2917 |  | 2925 |  |

| | | | |
|---|---|---|---|
| 2918 |  | 2926 |  |
| 2927 |  | 2935 |  |
| 2928 |  | 2936 |  |
| 2929 |  | 2937 |  |
| 2930 |  | 2938 |  |
| 2931 |  | 2939 |  |

| | | | |
|---|---|---|---|
| 2932 |  | 2940 |  |
| 2933 |  | 2941 |  |
| 2934 |  | 2942 |  |
| 2943 |  | 2951 |  |
| 2944 |  | 2952 |  |
| 2945 |  | 2953 |  |

| | | | |
|---|---|---|---|
| 2946 |  | 2954 |  |
| 2947 |  | 2955 |  |
| 2948 |  | 2956 |  |
| 2949 |  | 2957 |  |
| 2950 |  | 2958 |  |
| 2959 |  | 2967 |  |

| | | | |
|---|---|---|---|
| 2960 |  | 2968 |  |
| 2961 |  | 2969 |  |
| 2962 |  | 2970 |  |
| 2963 |  | 2971 |  |
| 2964 |  | 2972 |  |
| 2965 |  | 2973 |  |

| | | | |
|---|---|---|---|
| 2966 |  | 2974 |  |
| 2975 |  | 2983 |  |
| 2976 |  | 2984 |  |
| 2977 |  | | |

| | | | |
|---|---|---|---|
| 2978 |  | 2985 |  |
| 2979 |  | 2986 |  |

| | | | |
|---|---|---|---|
| 2980 |  | 2987 |  |
| 2981 |  | 2988 |  |
| 2982 |  | 2989 |  |
| 2990 |  | 2998 |  |
| 2991 |  | 2999 |  |

| | | | |
|---|---|---|---|
| 2992 |  | 3000 |  |
| 2993 |  | 3001 |  |
| 2994 |  | 3002 |  |
| 2995 |  | 3003 |  |
| 2996 |  | 3004 |  |
| 2997 |  | 3005 |  |

| | | | |
|---|---|---|---|
| 3006 |  | 3012 |  |
| 3007 |  | 3013 |  |
| 3008 |  | 3014 |  |
| 3009 |  | 3015 |  |
| 3010 |  | 3016 |  |

| | | | |
|---|---|---|---|
| 3011 |  | 3017 |  |
| 3018 |  | 3025 |  |
| 3019 |  | 3026 |  |
| 3020 |  | 3027 |  |

| | | | |
|---|---|---|---|
| 3021 |  | 3028 |  |
| 3022 |  | 3029 |  |
| 3023 |  | 3030 |  |
| 3024 |  | 3031 |  |

| | | | |
|---|---|---|---|
| 3032 |  | 3035 |  |
| 3033 |  | 3036 |  |
| 3034 |  | | |

| | |
|---|---|
| 3037 |  |
| 3038 |  |
| 3039 |  |
| 3040 |  |
| 3041 |  |
| 3042 |  |
| 3043 |  |
| 3044 |  |
| 3045 |  |

| | |
|---|---|
| 3046 |  |
| 3047 |  |
| 3048 |  |
| 3049 |  |
| 3050 |  |
| 3051 |  |
| 3052 |  |
| 3053 |  |
| 3054 |  |
| 3055 |  |
| 3056 |  |
| 3057 |  |

| | |
|---|---|
| 3058 |  |
| 3059 |  |
| 3060 |  |
| 3061 |  |
| 3062 |  |
| 3063 |  |
| 3064 |  |
| 3065 |  |
| 3066 |  |
| 3067 |  |

| | |
|---|---|
| 3068 |  |
| 3069 |  |
| 3070 |  |
| 3071 |  |
| 3072 |  |
| 3073 |  |
| 3074 |  |
| 3075 |  |
| 3076 |  |

| | |
|---|---|
| 3077 |  |
| 3078 |  |
| 3079 |  |
| 3080 |  |
| 3081 |  |
| 3082 |  |
| 3083 |  |
| 3084 |  |
| 3085 |  |
| 3086 |  |

| | |
|---|---|
| 3087 |  |
| 3088 |  |
| 3089 |  |
| 3090 |  |
| 3091 |  |
| 3092 |  |
| 3093 |  |
| 3094 |  |
| 3095 |  |
| 3096 |  |
| 3097 |  |

| | |
|---|---|
| 3098 |  |
| 3099 |  |
| 3100 |  |
| 3101 |  |
| 3102 |  |
| 3103 |  |
| 3104 |  |
| 3105 |  |
| 3106 |  |
| 3107 |  |

| | |
|---|---|
| 3108 |  |
| 3109 |  |
| 3110 |  |
| 3111 |  |
| 3112 |  |
| 3113 |  |
| 3114 |  |
| 3115 |  |
| 3116 |  |
| 3117 |  |
| 3118 |  |

| | |
|---|---|
| 3119 |  |
| 3120 |  |
| 3121 |  |
| 3122 |  |
| 3123 |  |
| 3124 |  |
| 3125 |  |
| 3126 |  |
| 3127 |  |
| 3128 |  |

| | |
|---|---|
| 3129 |  |
| 3130 |  |
| 3131 |  |
| 3132 |  |
| 3133 |  |
| 3134 |  |
| 3135 |  |
| 3136 |  |
| 3137 |  |

| | |
|---|---|
| 3138 |  |
| 3139 |  |
| 3140 |  |
| 3141 |  |
| 3142 |  |
| 3143 |  |
| 3144 |  |
| 3145 |  |
| 3146 |  |
| 3147 |  |

| | |
|---|---|
| 3148 |  |
| 3149 |  |
| 3150 |  |
| 3151 |  |
| 3152 |  |
| 3153 |  |
| 3154 |  |
| 3155 |  |
| 3156 |  |
| 3157 |  |

| | |
|---|---|
| 3158 |  |
| 3159 |  |
| 3160 |  |
| 3161 |  |
| 3162 |  |
| 3163 |  |
| 3164 |  |
| 3165 |  |
| 3166 |  |

| | |
|---|---|
| 3167 |  |
| 3168 |  |
| 3169 |  |
| 3170 |  |
| 3171 |  |
| 3172 |  |
| 3173 |  |
| 3174 |  |
| 3175 |  |
| 3176 |  |
| 3177 |  |
| 3178 |  |

| | |
|---|---|
| 3179 |  |
| 3180 |  |
| 3181 |  |
| 3182 |  |
| 3183 |  |
| 3184 |  |
| 3185 |  |
| 3186 |  |
| 3187 |  |
| 3188 |  |
| 3189 |  |
| 3190 |  |
| 3191 |  |
| 3192 |  |

| | |
|---|---|
| 3193 |  |
| 3194 |  |
| 3195 |  |
| 3196 |  |
| 3197 |  |
| 3198 |  |
| 3199 |  |
| 3200 |  |
| 3201 |  |
| 3202 |  |
| 3203 |  |
| 3204 |  |

| | |
|---|---|
| 3205 |  |
| 3206 |  |
| 3207 |  |
| 3208 |  |
| 3209 |  |
| 3210 |  |
| 3211 |  |
| 3212 |  |
| 3213 |  |
| 3214 |  |
| 3215 |  |
| 3216 |  |
| 3217 |  |
| 3218 |  |
| 3219 |  |
| 3220 |  |

| | |
|---|---|
| 3221 |  |
| 3222 |  |
| 3223 |  |
| 3224 |  |
| 3225 |  |
| 3226 |  |
| 3227 |  |
| 3228 |  |
| 3229 |  |
| 3230 |  |
| 3231 |  |
| 3232 |  |
| 3233 |  |
| 3234 |  |
| 3235 |  |
| 3236 |  |
| 3237 |  |

| | |
|---|---|
| 3238 |  |
| 3239 |  |
| 3240 |  |
| 3241 |  |
| 3242 |  |
| 3243 |  |
| 3244 |  |
| 3245 |  |
| 3246 |  |
| 3247 |  |
| 3248 |  |
| 3249 |  |
| 3250 |  |
| 3251 |  |

| | |
|---|---|
| 3252 |  |
| 3253 |  |
| 3254 |  |
| 3255 |  |
| 3256 |  |
| 3257 |  |
| 3258 |  |
| 3259 |  |
| 3260 |  |
| 3261 |  |
| 3262 |  |
| 3263 |  |
| 3264 |  |

| | |
|---|---|
| 3265 |  |
| 3266 |  |
| 3267 |  |
| 3268 |  |
| 3270 |  |
| 3271 |  |
| 3272 |  |
| 3273 |  |
| 3274 |  |
| 3275 |  |

| | |
|---|---|
| 3276 |  |
| 3277 |  |
| 3278 |  |
| 3279 |  |
| 3280 |  |
| 3281 |  |
| 3282 |  |
| 3283 |  |
| 3284 |  |
| 3285 |  |

| | |
|---|---|
| 3286 |  |
| 3287 |  |
| 3288 |  |
| 3290 |  |
| 3292 |  |
| 3293 |  |
| 3294 |  |
| 3295 |  |
| 3296 |  |
| 3297 |  |
| 3298 |  |
| 3299 |  |

| | |
|---|---|
| 3300 |  |
| 3301 |  |
| 3302 |  |
| 3303 |  |
| 3304 |  |
| 3305 |  |
| 3306 |  |
| 3307 |  |
| 3308 |  |
| 3309 |  |

| | |
|---|---|
| 3310 |  |
| 3311 |  |
| 3312 |  |
| 3313 |  |
| 3315 |  |
| 3316 |  |
| 3317 |  |
| 3318 |  |

| | |
|---|---|
| 3319 |  |
| 3320 |  |
| 3321 |  |
| 3322 |  |
| 3323 |  |
| 3324 |  |
| 3325 |  |

| | |
|---|---|
| 3326 |  |
| 3327 |  |
| 3328 |  |
| 3329 |  |
| 3330 |  |
| 3331 |  |
| 3332 |  |
| 3333 |  |
| 3334 |  |

| | |
|---|---|
| 3335 |  |
| 3336 |  |
| 3337 |  |
| 3338 |  |
| 3339 |  |
| 3340 |  |
| 3341 |  |
| 3342 |  |
| 3343 |  |

| | |
|---|---|
| 3344 |  |
| 3345 |  |
| 3346 |  |
| 3347 |  |
| 3348 |  |
| 3349 |  |
| 3350 |  |
| 3351 |  |
| 3352 |  |
| 3353 |  |
| 3354 |  |

| | |
|---|---|
| 3355 |  |
| 3356 |  |
| 3357 |  |
| 3358 |  |
| 3359 |  |
| 3360 |  |
| 3361 |  |
| 3362 |  |
| 3363 |  |

| | |
|---|---|
| 3364 |  |
| 3365 |  |
| 3366 |  |
| 3367 |  |
| 3368 |  |
| 3369 |  |
| 3370 |  |
| 3371 |  |
| 3372 |  |

| | |
|---|---|
| 3373 |  |
| 3374 |  |
| 3375 |  |
| 3376 |  |
| 3377 |  |
| 3378 |  |
| 3379 |  |
| 3380 |  |
| 3381 |  |

| | |
|---|---|
| 3382 |  |
| 3383 |  |
| 3384 |  |
| 3385 |  |
| 3386 |  |
| 3387 |  |
| 3388 |  |
| 3389 |  |
| 3390 |  |

| | |
|---|---|
| 3391 |  |
| 3392 |  |
| 3393 |  |
| 3394 |  |
| 3395 |  |
| 3397 |  |
| 3398 |  |
| 3399 |  |
| 3400 |  |
| 3401 |  |

| | |
|---|---|
| 3402 |  |
| 3403 |  |
| 3404 |  |
| 3405 |  |
| 3406 |  |
| 3407 |  |
| 3408 |  |
| 3409 |  |
| 3410 |  |
| 3411 |  |
| 3412 |  |
| 3413 |  |

| | |
|---|---|
| 3414 |  |
| 3415 |  |
| 3416 |  |
| 3417 |  |
| 3418 |  |
| 3419 |  |
| 3420 |  |
| 3421 |  |
| 3422 |  |
| 3423 |  |
| 3424 |  |
| 3425 |  |

| | |
|---|---|
| 3426 |  |
| 3427 |  |
| 3428 |  |
| 3429 |  |
| 3430 |  |
| 3431 |  |

COMPOUNDS, DEVICES, AND USES THEREOF

CROSS REFERENCE TO RELATED APPLICATIONS

This application is a divisional of U.S. application Ser. No. 16/339,285, filed Apr. 3, 2019, which is a U.S. national phase application and claims the benefit of priority under 35 U.S.C § 371 of International Application No. PCT/US2017/055001, filed Oct. 3, 2017, which claims benefit of U.S. Provisional Application No. 62/403,559, filed Oct. 3, 2016, U.S. Provisional Application No. 62/403,532, filed Oct. 3, 2016, U.S. Provisional Application No. 62/403,548, filed Oct. 3, 2016, U.S. Provisional Application No. 62/403,538, filed Oct. 3, 2016, U.S. Provisional Application No. 62/403,543, filed Oct. 3, 2016, U.S. Provisional Application No. 62/403,554, filed Oct. 3, 2016, U.S. Provisional Application No. 62/403,556, filed Oct. 3, 2016, and U.S. Provisional Application No. 62/436,832, filed Dec. 20, 2016. The entire contents of each of the foregoing applications are hereby incorporated by reference.

BACKGROUND OF THE INVENTION

The function of implanted devices depends in large part on the biological immune response pathway of the recipient (Anderson et al., *Semin. Immunol.* 20:86-100 (2008); Langer, *Adv. Mater.* 21:3235-3236 (2009)). Modulation of the immune response may impart a beneficial effect on the fidelity and function of these devices. As such, there is a need in the art for new compounds, compositions, and devices that achieve this goal.

SUMMARY OF THE INVENTION

Described herein are compounds (e.g., compounds of Formula (I)), compositions and implantable elements (e.g., devices and materials) comprising the same, as well as methods of use thereof. In particular, the compounds (e.g., compounds of Formula (I)) and related compositions, and implantable elements may be used in methods for the prevention and treatment of a disease, disorder or condition in a subject. In some embodiments, the compounds (e.g., compounds of Formula (I)), and pharmaceutically acceptable salts, solvates, hydrates, tautomers, stereoisomers, isotopically labeled derivatives, and compositions thereof and implantable elements comprising the same, are capable of modulating the immune response in a subject, e.g., upregulating or downregulating the immune response in a subject.

In one aspect, the present invention features a compound of Formula (I):

$$A\text{-}L^1\text{-}M\text{-}L^2\text{-}P\text{-}L^3\text{-}Z, \qquad (I)$$

or a salt thereof, wherein A is selected from A1 or A2, wherein A1 is hydrogen, alkyl, alkenyl, alkynyl, heteroalkyl, cycloalkyl, heterocyclyl, aryl, heteroaryl, $—OR^A$, $—C(O)OR^A$, $—C(O)R^B$, $—OC(O)R^B$, $—N(R^C)(R^D)$, $—N(R^C)C(O)R^B$, $—C(O)N(R^C)(R^D)$, $—N_3$, —NC, —CN, —NCO, —NCS, $—N(R^C)N(R^D)_2$, $—NCNR^C$, $—C(=N(R^C)(R^D))OR^A$, $—SR^E$, $—S(O)_xR^E$, $—OS(O)_xR^E$, $—N(R^C)S(O)_xR^E$, $—S(O)_xN(R^C)(R^D)$, $—P(R^F)_y$, $—Si(OR^A)_3$, $—Si(R^G)(OR^A)_2$, $—B(OR^A)_2$, or a metal, wherein each alkyl, alkenyl, alkynyl, heteroalkyl, cycloalkyl, heterocyclyl, aryl, heteroaryl is optionally substituted with one or more $R^1$; A2 is alkyl, alkenyl, alkynyl, heteroalkyl, cycloalkyl, heterocyclyl, aryl, heteroaryl, —O—, —C(O)O—, —C(O)—, —OC(O)—, $—N(R^C)—$, $—N(R^C)C(O)—$, $—C(O)N(R^C)—$, $—N(R^C)N(R^D)—$, —NCN—, $—C(=N(R^C)(R^D))O—$, —S—, $—S(O)_x—$, $—OS(O)_x—$, $—N(R^C)S(O)_x$, $—S(O)_xN(R^C)—$, $—P(R^F)_y—$, $—Si(OR^A)_2—$, $—Si(R^G)(OR^A)$, $—B(OR^A)$, or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted by one or more $R^1$; each $L^1$, $L^2$, and $L^3$ is independently a bond, alkyl, alkenyl, alkynyl, or heteroalkyl, wherein each alkyl, alkenyl, alkynyl, and heteroalkyl is optionally substituted by 1-5 $R^2$; M is alkyl, alkenyl, alkynyl, heteroalkyl, cycloalkyl, heterocyclyl, aryl, or heteroaryl, each of which is optionally substituted by one or more $R^3$; P is cycloalkyl, heterocyclyl, aryl, or heteroaryl, each of which is optionally substituted by one or more $R^4$; Z is alkyl, alkenyl, alkynyl, heteroalkyl, cycloalkyl, heterocyclyl, aryl, or heteroaryl, each of which is optionally substituted by one or more $R^5$; each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with one or more $R^6$, or $R^C$ and $R^D$, taken together with the nitrogen atom to which they are attached, form a ring (e.g., a 5-7 membered ring), optionally substituted with one or more $R^6$, each $R^1$, $R^2$, $R^3$, $R^4$, $R^5$, and $R^6$ is independently alkyl, alkenyl, alkynyl, heteroalkyl, halogen, cyano, azido, oxo, $—OR^{A1}$, $—C(O)OR^{A1}$, $—C(O)R^{B1}$, $—OC(O)R^{B1}$, $—N(R^{C1})(R^{D1})$, $—N(R^{C1})C(O)R^{B1}$, $—C(O)N(R^{C1})$, $SR^{E1}$, $—S(O)_xR^E$, $—OS(O)_xR^E$, $—N(R^C)S(O)_xR^E$, $—S(O)_xN(R^C)(R^D)$, $—P(R^F)_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$; each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$; each $R^7$ is independently alkyl, alkenyl, alkynyl, heteroalkyl, halogen, cyano, oxo, hydroxyl, cycloalkyl, or heterocyclyl; x is 1 or 2; and y is 2, 3, or 4.

In some embodiments, A is A1. In some embodiments, A1 is hydrogen, alkyl, alkenyl, alkynyl, heteroalkyl, cycloalkyl, heterocyclyl, aryl, heteroaryl, $—OR^A$, $—C(O)OR^A$, $—C(O)R^B$, $—OC(O)R^B$, or $—N(R^C)(R^D)$. In some embodiments, A1 is $—N(R^C)(R^D)$ (e.g., $NH_2$). In some embodiments, A1 is $NH_2$ or $NHC(O)C(CH_2)CH_3$.

In some embodiments, A is A2. In some embodiments, A2 is alkyl, heteroalkyl, cycloalkyl, heterocyclyl, aryl, heteroaryl, —O—, —C(O)O—, —C(O)—, —OC(O)—, $—N(R^C)—$, $—N(R^C)C(O)—$, $—C(O)N(R^C)—$, $—Si(OR^A)_2—$, $—Si(R^G)(OR^A)—$, or $—B(OR^A)—$. In some embodiments, A2 is $—N(R^C)—$ (e.g., NH—). In some embodiments, A2 is NH— or $NH(C(O)C(CH_3)CH_2—$. In some embodiments, the compound comprises A2, and, e.g., is covalently attached to an implantable element, e.g., a device. In some embodiments, A2 is attached directly to a device. In some embodiments, A2 is attached to a device by an attachment group (e.g., an attachment group described herein). In some embodiments, the device is attached, e.g., covalently, to the attachment group, and A2 is attached, e.g., covalently to the attachment group.

In some embodiments, each of $L^1$, $L^2$, and $L^3$ is independently a bond, alkyl, or heteroalkyl. In some embodiments, $L^1$ is a bond, alkyl, or heteroalkyl. In some embodiments, $L^1$ is $C_1$-$C_6$ alkyl (e.g., $—CH_2—$ or $—CH_2CH_2—$). In some embodiments, $L^2$ is a bond. In some embodiments, $L^3$ is a bond, alkyl, or heteroalkyl. In some embodiments, $L^3$ is $C_1$-$C_6$ alkyl (e.g., —$CH_2$—) or heteroalkyl (e.g., —$CH_2O$—).

In some embodiments, M is heteroalkyl, aryl, or heteroaryl. In some embodiments, M is heteroalkyl. In some embodiments, M is (—$OCH_2CH_2$—)z, wherein z is an integer selected from 1 to 10. In some embodiments, M is aryl (e.g., phenyl).

In some embodiments, P is a tricyclic, bicyclic, or monocyclic heteroaryl. In some embodiments, P is a nitrogen-containing heteroaryl. In some embodiments, P is a 5-membered nitrogen-containing heteroaryl (e.g., tetrazolyl, imidazolyl, pyrazolyl, or triazolyl, pyrrolyl, oxazolyl, or thiazolyl). In some embodiments, P is triazolyl (e.g., 1,2,3-triazolyl or 1,2,4-triazolyl). In some embodiments, P is selected from

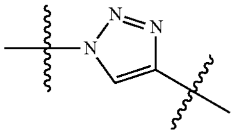

and

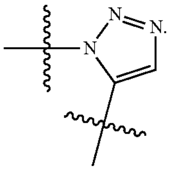

In some embodiments, P is

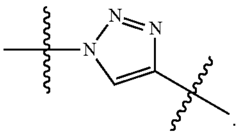 [SMILES: *c1cn(*)nn1]

In some embodiments, Z is alkyl, heterocyclyl, or aryl, each of which is optionally substituted by one or more $R^5$. In some embodiments, Z is heterocyclyl (e.g., 6-membered heterocyclyl). In some embodiments, Z is a nitrogen-containing heterocyclyl, an oxygen-containing heterocyclyl, or a sulfur-containing heterocyclyl (e.g., tetrahydropyranyl or thiomorpholinyl-1,1-dioxide). In some embodiments, Z is oxetanyl, tetrahydrofuranyl, tetrahydropyranyl, thiomorpholinyl-1,1-dioxide, piperidinyl, piperazinyl, or pyrrolidinyl.

In some embodiments, Z is aryl (e.g., phenyl). In some embodiments, Z is monosubstituted phenyl (e.g., with 1 $R^5$). In some embodiments, Z is monosubstituted phenyl, wherein the 1 $R^5$ an amine-containing group (e.g., $NH_2$). In some embodiments, Z is monosubstituted phenyl, wherein the 1 $R^5$ is an oxygen-containing group (e.g., $OCH_3$). In some embodiments, the 1 $R^5$ is in the ortho position or the para position.

In some embodiments, Z is alkyl (e.g., $C_1$-$C_{12}$ alkyl). In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1})(R^{D1})$. In some embodiments, Z is $C_1$-$C_8$ alkyl substituted with 1 $R^5$, wherein $R^5$ is —OH or —C(O)OH.

In some embodiments, Z is heteroalkyl (e.g., $C_1$-$C_{12}$ heteroalkyl). In some embodiments, Z is an oxygen-containing heteroalkyl or a nitrogen-containing heteroalkyl. In some embodiments, Z is (—OCH2CH2-)z$OCH_3$, wherein z is an integer selected from 1 to 10 (e.g., z is 1, 2, 3, 4, 5, 6, 7, 8, 9, or 10).

In some embodiments, the compound of Formula (I) is a compound of Formula (II):

Formula (II)

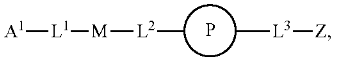

or a salt thereof, wherein A1 is hydrogen, alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, —$N(R^C)(R^D)$, —$N(R^C)C(O)R^B$, —$C(O)N(R^C)(R^D)$, —$N_3$, —NC, —CN, —NCO, —NCS, —$N(R^C)N(R^D)_2$, —$NCN(R^C)$, —$C(=N(R^C)(R^D))OR^A$, —$SR^E$, —$S(O)_xR^E$, —$OS(O)_xR^E$, —$N(R^C)S(O)_xR^E$, —$S(O)_xN(R^C)(R^D)$, —$P(R^F)$, —$Si(OR^A)_3$, —$Si(R^G)(OR^A)_2$, —$B(OR^A)_2$, or a metal, wherein each alkyl, alkenyl, alkynyl, heteroalkyl, cycloalkyl, heterocyclyl, aryl, and heteroaryl is optionally substituted by one or more $R^1$; each of $L^1$ and $L^3$ is independently a bond, alkyl, or heteroalkyl, wherein each alkyl and heteroalkyl is optionally substituted by one or more $R^2$; $L^2$ is a bond; M is alkyl, heteroalkyl, cycloalkyl, heterocyclyl, aryl, or heteroaryl, each of which is optionally substituted by one or more $R^3$; P is heteroaryl optionally substituted by one or more $R^4$; Z is alkyl, alkenyl, alkynyl, heteroalkyl, cycloalkyl, heterocyclyl, aryl, or heteroaryl, each of which is optionally substituted by one or more $R^5$; each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$; or $R^C$ and $R^D$, taken together with the nitrogen atom to which they are attached, form a ring (e.g., a 5-7 membered ring), optionally substituted with one or more $R^6$; each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, $S(O)_xR^{E1}$, —$OS(O)_xR^{E1}$, —$N(R^{C1})S(O)_xR^{E1}$, —$S(O)_xN(R^{C1})(R^{D1})$, —$P(R^{F1})_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$; each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$; each $R^7$ is independently alkyl, alkenyl, alkynyl, heteroalkyl, halogen, cyano, oxo, hydroxyl, cycloalkyl, or heterocyclyl; x is 1 or 2; and y is 2, 3, or 4.

In some embodiments, A1 is hydrogen, alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, or —$N(R^C)(R^D)$. In some embodiments, A1 is —$N(R^C)(R^D)$ (e.g., $NH_2$). In some embodiments, A1 is $NH_2$ or $NHC(O)C(CH_2)CH_3$.

In some embodiments, each $L^1$, $L^2$, and $L^3$ is independently a bond, alkyl, or heteroalkyl. In some embodiments, $L^1$ is a bond, alkyl, or heteroalkyl. In some embodiments, $L^1$ is $C_1$-$C_6$ alkyl (e.g., —$CH_2$— or —$CH_2CH_2$—). In some embodiments, $L^2$ is a bond. In some embodiments, $L^3$ is a bond, alkyl, or heteroalkyl. In some embodiments, $L^3$ is $C_1$-$C_6$ alkyl (e.g., —$CH_2$—) or heteroalkyl (e.g., —$CH_2O$—).

In some embodiments, M is heteroalkyl, aryl, or heteroaryl. In some embodiments, M is heteroalkyl. In some embodiments, M is (—$OCH_2CH_2$—)z, wherein z is an integer selected from 1 to 10. In some embodiments, M is aryl (e.g., phenyl).

In some embodiments, P is a tricyclic, bicyclic, or monocyclic heteroaryl. In some embodiments, P is a nitrogen-containing heteroaryl. In some embodiments, P is a 5-membered nitrogen-containing heteroaryl (e.g., tetrazolyl, imidazolyl, pyrazolyl, or triazolyl, pyrrolyl, oxazolyl, or thiazolyl). In some embodiments, P is triazolyl (e.g., 1,2,3-triazolyl or 1,2,4-triazolyl). In some embodiments, P is selected from

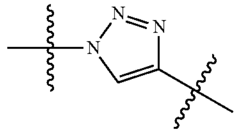

and

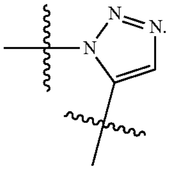

In some embodiments, P is

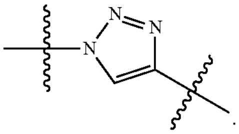 [SMILES: *c1cn(*)nn1]

In some embodiments, Z is alkyl, heterocyclyl, or aryl, each of which is optionally substituted by one or more $R^5$. In some embodiments, Z is heterocyclyl (e.g., 6-membered heterocyclyl). In some embodiments, Z is a nitrogen-containing heterocyclyl, an oxygen-containing heterocyclyl, or a sulfur-containing heterocyclyl (e.g., tetrahydropyranyl or thiomorpholinyl-1,1-dioxide). In some embodiments, Z is oxetanyl, tetrahydrofuranyl, tetrahydropyranyl, thiomorpholinyl-1,1-dioxide, piperidinyl, piperazinyl, or pyrrolidinyl.

In some embodiments, Z is aryl (e.g., phenyl). In some embodiments, Z is monosubstituted phenyl (e.g., with 1 $R^5$). In some embodiments, Z is monosubstituted phenyl, wherein the 1 $R^5$ an amine-containing group (e.g., $NH_2$). In some embodiments, Z is monosubstituted phenyl, wherein the 1 $R^5$ is an oxygen-containing group (e.g., $OCH_3$). In some embodiments, the 1 $R^5$ is in the ortho position or the para position.

In some embodiments, Z is alkyl (e.g., $C_1$-$C_{12}$ alkyl). In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1})(R^{D1})$. In some embodiments, Z is $C_1$-$C_8$ alkyl substituted with 1 $R^5$, wherein $R^5$ is —OH or —C(O)OH.

In some embodiments, Z is heteroalkyl (e.g., $C_1$-$C_{12}$ heteroalkyl). In some embodiments, Z is an oxygen-containing heteroalkyl or a nitrogen-containing heteroalkyl. In some embodiments, Z is (—OCH2CH2-)z$OCH_3$, wherein z is an integer selected from 1 to 10 (e.g., z is 1, 2, 3, 4, 5, 6, 7, 8, 9, or 10).

In some embodiments, the compound of Formula (II) is a compound of Formula (II-c):

Formula (II-c)

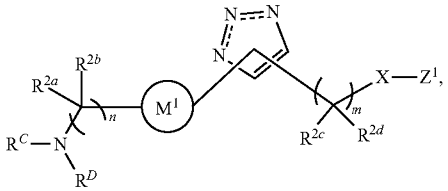

or a salt thereof, wherein Ring $M^1$ is cycloalkyl, heterocyclyl, aryl, or heteroaryl, each of which is optionally substituted with 1-5 $R^3$; $Z^1$ is alkyl, alkenyl, alkynyl, heteroalkyl, cycloalkyl, heterocyclyl, aryl, or heteroaryl, each of which is optionally substituted by one or more $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; or $R^C$ and $R^D$, taken together with the nitrogen atom to which they are attached, form a ring (e.g., a 5-7 membered ring), optionally substituted with 1-6 $R^6$; each of $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, heteroaryl; each of $R^{10}$ and $R^{11}$ is independently hydrogen, alkyl, alkenyl, alkynyl, heteroalkyl, halogen, —$C(O)R^{B1}$, —$N(R^{C1})C(O)R^{B1}$, —$C(O)N(R^{C1})$, $SR^{E1}$, $S(O)_x$, cycloalkyl, or heterocyclyl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 0, 1, 2, 3, 4, 5, or 6; and x is 1 or 2.

In some embodiments, Ring $M^1$ is aryl, or heteroaryl. In some embodiments, M is aryl (e.g., phenyl).

In some embodiments, P is selected from

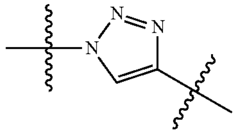

and

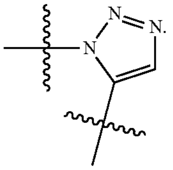

In some embodiments, P is

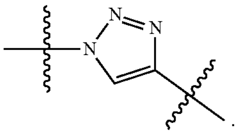 [SMILES: *c1cn(*)nn1]

In some embodiments, Ring $Z^1$ is heterocyclyl (e.g., 6-membered heterocyclyl). In some embodiments, Ring $Z^1$ is a nitrogen-containing heterocyclyl, an oxygen-containing heterocyclyl, or a sulfur-containing heterocyclyl (e.g., tetrahydropyranyl or phthalic anhydridyl). In some embodiments, Z is oxetanyl, tetrahydrofuranyl, tetrahydropyranyl, thiomorpholinyl-1,1-dioxide, piperidinyl, piperazinyl, or pyrrolidinyl.

In some embodiments, the compound of Formula (II) is a compound of Formula (II-k):

Formula (II-k)

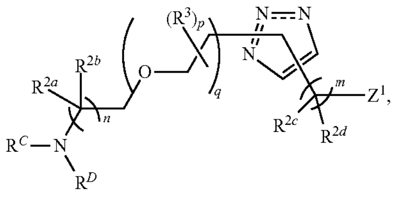

or a salt thereof, wherein $Z^1$ is alkyl, alkenyl, alkynyl, heteroalkyl, cycloalkyl, heterocyclyl, aryl, or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; or $R^C$ and $R^D$, taken together with the nitrogen atom to which they are attached, form a ring (e.g., a 5-7 membered ring), optionally substituted with 1-6 $R^6$; each of $R^3$, $R^5$, and $R^6$ is independently alkyl, alkenyl, alkynyl, heteroalkyl, halogen, cyano, azido, oxo, $—OR^{A1}$, $—C(O)OR^{A1}$, $—C(O)R^{B1}$, $—OC(O)R^{B1}$, $—N(R^{C1})(R^{D1})$, $—N(R^{C1})C(O)R^{B1}$, $—C(O)N(R^{C1})$, $SR^{E1}$, cycloalkyl, heterocyclyl, aryl, heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; m and n are each independently 0, 1, 2, 3, 4, 5, or 6; p is 0, 1, 2, 3, or 4; and q is an integer from 0 to 25.

In some embodiments, the triazolyl is selected from

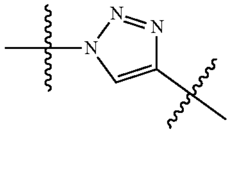

and

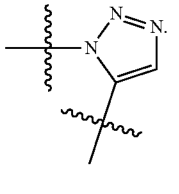

In some embodiments, the triazolyl is

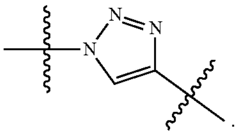 [SMILES: *c1cn(*)nn1]

In some embodiments, $Z^1$ is alkyl, heterocyclyl, or aryl, each of which is optionally substituted by one or more $R^5$. In some embodiments, $Z^1$ is heterocyclyl (e.g., 6-membered heterocyclyl). In some embodiments, $Z^1$ is a nitrogen-containing heterocyclyl or a sulfur-containing heterocyclyl (e.g., thiomorpholinyl-1,1-dioxide). In some embodiments, $Z^1$ is oxetanyl, tetrahydrofuranyl, tetrahydropyranyl, thiomorpholinyl-1,1-dioxide, piperidinyl, piperazinyl, or pyrrolidinyl.

In some embodiments, $Z^1$ is aryl (e.g., phenyl). In some embodiments, Z is monosubstituted phenyl (e.g., with 1 $R^5$). In some embodiments, $Z^1$ is monosubstituted phenyl, wherein the 1 $R^5$ an amine-containing group (e.g., $NH_2$). In some embodiments, Z is monosubstituted phenyl, wherein the 1 $R^5$ is an oxygen-containing group (e.g., $OCH_3$). In some embodiments, the 1 $R^5$ is in the ortho position or the para position.

In some embodiments, Z is alkyl (e.g., $C_1$-$C_{12}$ alkyl). In some embodiments, Z is $C_1$-$C_8$ alkyl substituted with 1 $R^5$, wherein $R^5$ is alkyl, heteroalkyl, halogen, oxo, $—OR^{A1}$, $—C(O)OR^{A1}$, $—C(O)R^{B1}$, $—OC(O)R^{B1}$, or $—N(R^{C1})(R^{D1})$. In some embodiments, Z is $C_1$-$C_8$ alkyl substituted with 1 $R^5$, wherein $R^5$ is —OH or —C(O)OH.

In some embodiments, the compound of Formula (I) is a compound of Formula (III):

Formula (III)

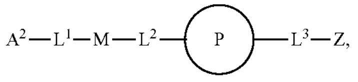

or a salt thereof, wherein A2 is alkyl, alkenyl, alkynyl, heteroalkyl, cycloalkyl, heterocyclyl, aryl, heteroaryl, —O—, —C(O)O—, —C(O)—, —OC(O)—, $—N(R^C)—$, $—N(R^C)C(O)—$, $—C(O)N(R^C)—$, $—N(R^C)N(R^D)—$, —NCN—, $—C(=N(R^C)(R^D))O—$, —S—, $—S(O)_x—$, $—OS(O)_x—$, $—N(R^C)S(O)_x$, $—S(O)_xN(R^C)—$, $—P(R^F)_y—$, $—Si(OR^A)_2—$, $—Si(R^G)(OR^A)—$, $—B(OR^A)$, or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted by one or more $R^1$; each of $L^1$ and $L^3$ is independently a bond, alkyl, or heteroalkyl, wherein each alkyl and heteroalkyl is optionally substituted by one or more $R^2$; $L^2$ is a bond; M is alkyl, heteroalkyl, cycloalkyl, heterocyclyl, aryl, or heteroaryl, each of which is optionally substituted by one or more $R^3$; P is heteroaryl optionally substituted by one or more $R^4$; Z is alkyl, alkenyl, alkynyl, heteroalkyl, cycloalkyl, heterocyclyl, aryl, or heteroaryl, each of which is optionally substituted by one or more $R^5$; each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$; or $R^C$ and $R^D$, taken together with the nitrogen atom to which they are attached, form a ring (e.g., a 5-7 membered ring), optionally substituted with one or more $R^6$; each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, $S(O)_xR^{E1}$, —$OS(O)_xR^{E1}$, —$N(R^{C1})S(O)_xR^{E1}$, —$S(O)_xN(R^{C1})(R^{D1})$, —$P(R^{F1})_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$; each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$; each $R^7$ is independently alkyl, alkenyl, alkynyl, heteroalkyl, halogen, cyano, oxo, hydroxyl, cycloalkyl, or heterocyclyl; x is 1 or 2; and y is 2, 3, or 4. The compound of any one of the preceding claims, wherein the compound (e.g., the compound of Formula (I) or Formula (II)) is disposed on a surface, e.g., an inner or outer surface, of a device.

In some embodiments, the compound (e.g., the compound of Formula (I) or Formula (II)) is disposed on a surface, e.g., an inner or outer surface, of a device.

In some embodiments, A2 is alkyl, heteroalkyl, cycloalkyl, heterocyclyl, aryl, heteroaryl, —O—, —C(O)O—, —C(O)—, —OC(O)—, —$N(R^C)$—, —$N(R^C)C(O)$—, —$C(O)N(R^C)$—, —$Si(OR^A)_2$—, —$Si(R^G)(OR^A)$—, or —$B(OR^A)$—. In some embodiments, A2 is —$N(R^C)$— (e.g., NH—). In some embodiments, A2 is NH— or $NH(C(O)C(CH_3)CH_2$—. In some embodiments, the compound comprises A2, and, e.g., is covalently attached to a device. In some embodiments, A2 is attached directly to the device. In some embodiments, A2 is attached to the device by an attachment group (e.g., an attachment group described herein). In some embodiments, the device is attached, e.g., covalently, to the attachment group, and A2 is attached, e.g., covalently to the attachment group.

In some embodiments, each of $L^1$, $L^2$, and $L^3$ is independently a bond, alkyl, or heteroalkyl. In some embodiments, $L^1$ is a bond, alkyl, or heteroalkyl. In some embodiments, $L^1$ is $C_1$-$C_6$ alkyl (e.g., —$CH_2$— or —$CH_2CH_2$—). In some embodiments, $L^2$ is a bond. In some embodiments, $L^3$ is a bond, alkyl, or heteroalkyl. In some embodiments, $L^3$ is $C_1$-$C_6$ alkyl (e.g., —$CH_2$—) or heteroalkyl (e.g., —$CH_2O$—).

In some embodiments, M is heteroalkyl, aryl, or heteroaryl. In some embodiments, M is heteroalkyl. In some embodiments, M is (—$OCH_2CH_2$-)z, wherein z is an integer selected from 1 to 10. In some embodiments, M is aryl (e.g., phenyl).

In some embodiments, P is a tricyclic, bicyclic, or monocyclic heteroaryl. In some embodiments, P is a nitrogen-containing heteroaryl. In some embodiments, P is a 5-membered nitrogen-containing heteroaryl (e.g., tetrazolyl, imidazolyl, pyrazolyl, or triazolyl, pyrrolyl, oxazolyl, or thiazolyl). In some embodiments, P is triazolyl (e.g., 1,2,3-triazolyl or 1,2,4-triazolyl). In some embodiments, P is selected from

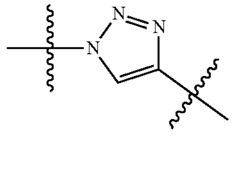

and

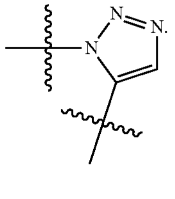

In some embodiments, P is

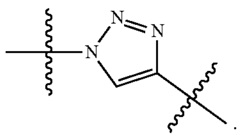 [SMILES: *c1cn(*)nn1]

In some embodiments, Z is alkyl, heterocyclyl, or aryl, each of which is optionally substituted by one or more $R^5$. In some embodiments, Z is heterocyclyl (e.g., 6-membered heterocyclyl). In some embodiments, Z is a nitrogen-containing heterocyclyl, an oxygen-containing heterocyclyl, or a sulfur-containing heterocyclyl (e.g., tetrahydropyranyl or thiomorpholinyl-1,1-dioxide). In some embodiments, Z is oxetanyl, tetrahydrofuranyl, tetrahydropyranyl, thiomorpholinyl-1,1-dioxide, piperidinyl, piperazinyl, or pyrrolidinyl.

In some embodiments, Z is aryl (e.g., phenyl). In some embodiments, Z is monosubstituted phenyl (e.g., with 1 $R^5$). In some embodiments, Z is monosubstituted phenyl, wherein the 1 $R^5$ an amine-containing group (e.g., $NH_2$). In some embodiments, Z is monosubstituted phenyl, wherein the 1 $R^5$ is an oxygen-containing group (e.g., $OCH_3$). In some embodiments, the 1 $R^5$ is in the ortho position or the para position.

In some embodiments, Z is alkyl (e.g., $C_1$-$C_{12}$ alkyl). In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1})(R^{D1})$. In some embodiments, Z is $C_1$-$C_8$ alkyl substituted with 1 $R^5$, wherein $R^5$ is —OH or —C(O)OH.

In some embodiments, Z is heteroalkyl (e.g., $C_1$-$C_{12}$ heteroalkyl). In some embodiments, Z is an oxygen-containing heteroalkyl or a nitrogen-containing heteroalkyl. In some embodiments, Z is (—OCH2CH2-)z$OCH_3$, wherein z is an integer selected from 1 to 10 (e.g., z is 1, 2, 3, 4, 5, 6, 7, 8, 9, or 10).

In some embodiments, the compound described herein is selected from a compound depicted in any one of FIGS. 1A-6KK, or a pharmaceutically acceptable salt thereof. In some embodiments, the compound of Formula (I) is selected from a compound depicted in any one of FIGS. 1A-6KK, or a pharmaceutically acceptable salt thereof. In some embodiments, the compound of Formula (I) is selected from a compound depicted in any one of FIGS. 1A-6KK and associated with an implantable element (e.g., a device or material) described herein. In some embodiments, the compound of Formula (I) is covalently bound to an implantable element (e.g., a device or material) through an attachment group (e.g., an attachment group described herein).

In some embodiments, the present invention features a pharmaceutical composition comprising a compound described herein (e.g., a compound of Formula (I)) and a pharmaceutically acceptable excipient.

In one aspect, the present invention features a method of treating a disease, disorder, or condition, or a method of modulating an immune response in a subject, e.g., at a site in the subject, e.g., the site of an implanted cell or device, comprising providing to the subject, e.g., at the site, a compound of Formula (I):

$$A\text{-}L^1\text{-}M\text{-}L^2\text{-}P\text{-}L^3\text{-}Z \qquad (I)$$

wherein A is A1 or A2; A1 is hydrogen, alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, —N($R^C$)($R^D$), —N($R^C$)C(O)$R^B$, —C(O)N($R^C$)($R^D$), —$N_3$, —NC, —CN, —NCO, —NCS, —N($R^C$)N($R^D$)$_2$, —NCN$R^C$, —C(═N($R^C$)($R^D$))O$R^A$, —S$R^E$, —S(O)$_x$$R^E$, —OS(O)$_x$$R^E$, —N($R^C$)S(O)$_x$$R^E$, —S(O)$_x$N($R^C$)($R^D$), —P($R^F$)$_y$, —Si(O$R^A$)$_3$, —Si($R^G$)(O$R^A$)$_2$, —B(O$R^A$)$_2$, or a metal, wherein each alkyl, alkenyl, alkynyl, heteroalkyl, cycloalkyl, heterocyclyl, aryl, heteroaryl is optionally substituted with one or more $R^1$; A2 is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, —NCN—, —C(═N($R^C$)($R^D$))O—, —S—, —S(O)$_x$—, —OS(O)$_x$, —N($R^C$)S(O)$_x$—, —S(O)$_x$N($R^C$)—, —P($R^F$)$_y$—, —Si(O$R^A$)$_2$—, —Si($R^G$)(O$R^A$)—, —B(O$R^A$), or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted by one or more $R^1$; each of $L^1$, $L^2$, and $L^3$ is independently a bond, alkyl, alkenyl, alkynyl, or heteroalkyl, wherein each alkyl, alkenyl, alkynyl, and heteroalkyl is optionally substituted by 1-5 $R^2$; M is alkyl, alkenyl, alkynyl, heteroalkyl, cycloalkyl, heterocyclyl, aryl, or heteroaryl, each of which is optionally substituted by one or more $R^3$; P is cycloalkyl, heterocyclyl, aryl, or heteroaryl, each of which is optionally substituted by one or more $R^4$; Z is alkyl, alkenyl, alkynyl, heteroalkyl, cycloalkyl, heterocyclyl, aryl, or heteroaryl, each of which is optionally substituted by one or more $R^5$; each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with one or more $R^6$, or $R^C$ and $R^D$, taken together with the nitrogen atom to which they are attached, form a ring (e.g., a 5-7 membered ring), optionally substituted with one or more $R^6$, each $R^1$, $R^2$, $R^3$, $R^4$, $R^5$, and $R^6$ is independently alkyl, alkenyl, alkynyl, heteroalkyl, halogen, cyano, azido, oxo, —O$R^{A1}$, —C(O)O$R^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), S$R^{E1}$, —S(O)$_x$$R^E$, —OS(O)$_x$$R^E$, —N($R^C$)S(O)$_x$$R^E$, —S(O)$_x$N($R^C$)($R^D$), —P($R^F$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$; each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$; each $R^7$ is independently alkyl, alkenyl, alkynyl, heteroalkyl, halogen, cyano, oxo, hydroxyl, cycloalkyl, or heterocyclyl; x is 1 or 2; and y is 2, 3, or 4, to thereby treat the subject or modulate the immune response of the subject.

In some embodiments, providing comprises providing an implantable element, e.g., a device or material described herein, to the subject. In some embodiments, providing comprises providing a device, e.g., a device described herein, to the subject. In some embodiments, providing comprises administering the compound systemically, or locally.

In some embodiments, the method comprises treating a subject, e.g., for a disorder or condition, e.g., a condition characterized by unwanted immune response. In some embodiments, the method comprises treating a subject, e.g., for a disorder or condition, e.g., a condition characterized by an inadequate immune response.

In some embodiments, the method comprises providing a compound of Formula (I) or a pharmaceutically acceptable salt or composition thereof, e.g., to downregulate an immune response. In some embodiments, the method comprises providing a compound of Formula (I) or a pharmaceutically acceptable salt or composition thereof, e.g., to upregulate an immune response.

In some embodiments, the method comprises reducing an unwanted reaction to an implanted device or cell, e.g., reducing fibrosis or, inflammation at, or inactivation of, the implanted device or cell. In some embodiments, the device comprises a cell, e.g., a recombinant cell, which provides a substance, e.g., a therapeutic agent.

In some embodiments, A is A1. In some embodiments, A1 is hydrogen, alkyl, alkenyl, alkynyl, heteroalkyl, cycloalkyl, heterocyclyl, aryl, heteroaryl, —O$R^A$, —C(O)O$R^A$, —C(O)$R^B$, —OC(O)$R^B$, or —N($R^C$)($R^D$). In some embodiments, A1 is —N($R^C$)($R^D$) (e.g., $NH_2$). In some embodiments, A1 is $NH_2$ or NHC(O)C($CH_2$)$CH_3$.

In some embodiments, A is A2. In some embodiments, A2 is alkyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —Si(O$R^A$)$_2$—, —Si($R^G$)(O$R^A$)—, or —B(O$R^A$)—. In some embodiments, A2 is —N($R^C$)— (e.g., NH—). In some embodiments, A2 is NH— or NH(C(O)C($CH_3$)$CH_2$—. In some embodiments, the compound comprises A2, and, e.g., is covalently attached to a device. In some embodiments, A2 is attached directly to the device. In some embodiments, A2 is attached to the device by an attachment group (e.g., an attachment group described herein). In some embodiments, the device is attached, e.g., covalently, to the attachment group, and A2 is attached, e.g., covalently to the attachment group.

In some embodiments, each $L^1$, $L^2$, and $L^3$ is independently a bond, alkyl, or heteroalkyl. In some embodiments, $L^1$ is a bond, alkyl, or heteroalkyl. In some embodiments, $L^1$ is $C_1$-$C_6$ alkyl (e.g., —$CH_2$— or —$CH_2CH_2$—). In some embodiments, $L^2$ is a bond. In some embodiments, $L^3$ is a bond, alkyl, or heteroalkyl. In some embodiments, $L^3$ is $C_1$-$C_6$ alkyl (e.g., —$CH_2$—) or heteroalkyl (e.g., —$CH_2O$—).

In some embodiments, M is heteroalkyl, aryl, or heteroaryl. In some embodiments, M is heteroalkyl. In some embodiments, M is (—$OCH_2CH_2$-)z, wherein z is an integer selected from 1 to 10. In some embodiments, M is aryl (e.g., phenyl).

In some embodiments, P is a tricyclic, bicyclic, or monocyclic heteroaryl. In some embodiments, P is a nitrogen-containing heteroaryl. In some embodiments, P is a 5-membered nitrogen-containing heteroaryl (e.g., tetrazolyl, imidazolyl, pyrazolyl, or triazolyl, pyrrolyl, oxazolyl, or thiazolyl). In some embodiments, P is triazolyl (e.g., 1,2,3-triazolyl or 1,2,4-triazolyl). In some embodiments, P is selected from

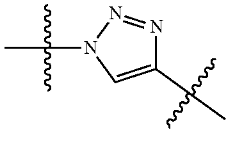

and

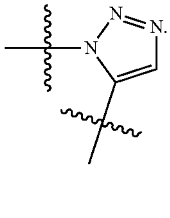

.

In some embodiments, P is

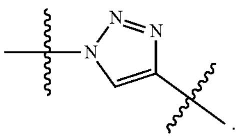 [SMILES: *c1cn(*)nn1]

In some embodiments, Z is alkyl, heterocyclyl, or aryl, each of which is optionally substituted by one or more $R^5$. In some embodiments, Z is heterocyclyl (e.g., 6-membered heterocyclyl). In some embodiments, Z is a nitrogen-containing heterocyclyl, an oxygen-containing heterocyclyl, or a sulfur-containing heterocyclyl (e.g., tetrahydropyranyl or thiomorpholinyl-1,1-dioxide). In some embodiments, Z is oxetanyl, tetrahydrofuranyl, tetrahydropyranyl, thiomorpholinyl-1,1-dioxide, piperidinyl, piperazinyl, or pyrrolidinyl.

In some embodiments, Z is aryl (e.g., phenyl). In some embodiments, Z is monosubstituted phenyl (e.g., with 1 $R^5$). In some embodiments, Z is monosubstituted phenyl, wherein the 1 $R^5$ an amine-containing group (e.g., $NH_2$). In some embodiments, Z is monosubstituted phenyl, wherein the 1 $R^5$ is an oxygen-containing group (e.g., $OCH_3$). In some embodiments, the 1 $R^5$ is in the ortho position or the para position.

In some embodiments, Z is alkyl (e.g., $C_1$-$C_{12}$ alkyl). In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1})(R^{D1})$. In some embodiments, Z is $C_1$-$C_8$ alkyl substituted with 1 $R^5$, wherein $R^5$ is —OH or —C(O)OH.

In some embodiments, Z is heteroalkyl (e.g., $C_1$-$C_{12}$ heteroalkyl). In some embodiments, Z is an oxygen-containing heteroalkyl or a nitrogen-containing heteroalkyl. In some embodiments, Z is (—OCH2CH2-)z$OCH_3$, wherein z is an integer selected from 1 to 10 (e.g., z is 1, 2, 3, 4, 5, 6, 7, 8, 9, or 10).

In another aspect, the present invention features an implantable element (e.g., a device or material). In some embodiments, the implantable element is a device or material comprising a compound of Formula (I):

$$A\text{-}L^1\text{-}M\text{-}L^2\text{-}P\text{-}L^3\text{-}Z, \quad (I)$$

wherein A is A1 or A2; A1 is hydrogen, alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, —$N(R^C)(R^D)$, —$N(R^C)C(O)R^B$, —$C(O)N(R^C)(R^D)$, —$N_3$, —NC, —CN, —NCO, —NCS, —$N(R^C)N(R^D)_2$, —$NCNR^C$, —$C(=N(R^C)(R^D))OR^A$, —$SR^E$, —$S(O)_xR^E$, —$OS(O)_xR^E$, —$N(R^C)S(O)_xR^E$, —$S(O)_xN(R^C)(R^D)$, —$P(R^F)_y$, —$Si(OR^A)_3$, —$Si(R^G)(OR^A)_2$, —$B(OR^A)_2$, or a metal, wherein each alkyl, alkenyl, alkynyl, heteroalkyl, cycloalkyl, heterocyclyl, aryl, heteroaryl is optionally substituted with one or more $R^1$; A2 is alkyl, alkenyl, alkynyl, heteroalkyl, cycloalkyl, heterocyclyl, aryl, heteroaryl, —O—, —C(O)O—, —C(O)—, —OC(O)—, —$N(R^C)$—, —$N(R^C)C(O)$—, —$C(O)N(R^C)$—, —$N(R^C)N(R^D)$—, —NCN—, —$C(=N(R^C)(R^D))O$—, —S—, —$S(O)_x$—, —$OS(O)_x$, —$N(R^C)S(O)_x$—, —$S(O)_xN(R^C)$—, —$P(R^F)$, —$Si(OR^A)_2$—, —$Si(R^G)(OR^A)$, —$B(OR^A)$, or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted by one or more $R^1$; each $L^1$, $L^2$, and $L^3$ is independently a bond, alkyl, alkenyl, alkynyl, or heteroalkyl, wherein each alkyl, alkenyl, alkynyl, and heteroalkyl is optionally substituted by 1-5 $R^2$; M is alkyl, alkenyl, alkynyl, heteroalkyl, cycloalkyl, heterocyclyl, aryl, or heteroaryl, each of which is optionally substituted by one or more $R^3$; P is cycloalkyl, heterocyclyl, aryl, or heteroaryl, each of which is optionally substituted by one or more $R^4$; Z is alkyl, alkenyl, alkynyl, heteroalkyl, cycloalkyl, heterocyclyl, aryl, or heteroaryl, each of which is optionally substituted by one or more $R^5$; each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with one or more $R^6$, or $R^C$ and $R^D$, taken together with the nitrogen atom to which they are attached, form a ring (e.g., a 5-7 membered ring), optionally substituted with one or more $R^6$, each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, —$S(O)_xR^E$, —$OS(O)_xR^E$, —$N(R^C)S(O)_xR^E$, —$S(O)_xN(R^C)(R^D)$, —$P(R^F)_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$; each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$; each $R^7$ is independently alkyl, alkenyl, alkynyl, heteroalkyl, halogen, cyano, oxo, hydroxyl, cycloalkyl, or heterocyclyl; x is 1 or 2; and y is 2, 3, or 4.

In some embodiments, the compound is disposed on a surface, e.g., an inner or outer surface, of the implantable element (e.g., a device or material). In some embodiments, the implantable element is a device. In some embodiments, the compound is disposed on a surface, e.g., an inner or outer surface, of the device. In some embodiments, the compound is distributed evenly across the surface. In some embodiments, the compound is distributed unevenly across the surface.

In some embodiments, the implantable element (e.g., a device or material) is administered or provided to a subject for the treatment of a disease, disorder, or condition. In some embodiments, the implantable element is a device. In some embodiments, the device is administered or provided to a subject for the treatment of a disease, disorder, or condition. In some embodiments, the disease, disorder or condition is a neurodegenerative disease, diabetes, a heart disease, an autoimmune disease, a cancer, a liver disease, a lysosomal storage disease, a blood clotting disorder or a coagulation disorder, an orthopedic conditions, an amino acid metabolism disorder.

In some embodiments, the disease, disorder or condition is a neurodegenerative disease, such as Alzheimer's disease, Huntington's disease, Parkinson's disease (PD) amyotrophic lateral sclerosis (ALS), multiple sclerosis (MS) and cerebral palsy (CP), dentatorubro-pallidoluysian atrophy (DRPLA), neuronal intranuclear hyaline inclusion disease (NIHID), dementia with Lewy bodies, Down's syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Jakob-Creutzfeldt disease, Niemann-Pick disease type 3, progressive supranuclear palsy, subacute sclerosing panencephalitis, spinocerebellar ataxias, Pick's disease, and dentatorubral-pallidoluysian atrophy.

In some embodiments, the disease, disorder or condition is a lysosomal storage disease, such as Exemplary lysosomal storage diseases include Gaucher disease (e.g., Type I, Type II, Type III), Tay-Sachs disease, Fabry disease, Farber disease, Hurler syndrome, Hunter syndrome, lysosomal acid lipase deficiency, Niemann-Pick disease, Salla disease, Sanfilippo syndrome, multiple sulfatase deficiency, Maroteaux-Lamy syndrome, metachromatic leukodystrophy, Krabbe disease, Scheie syndrome, Hurler-Scheie syndrome, Sly syndrome, hyaluronidase deficiency, Pompe disease, Danon disease, gangliosidosis, or Morquio syndrome.

In some embodiments, the disease, disorder or condition is a blood clotting disorder or coagulation disorder, such as hemophilia (e.g., hemophilia A or hemophilia B), Von Willebrand disease, thrombocytopenia, uremia, Bernard-Soulier syndrome, Factor XII deficiency, vitamin K deficiency, or congenital afibrinogenimia).

In some embodiments, the disease, disorder, or condition is an amino acid metabolism disorder, e.g., phenylketonuria, tyrosinemia (e.g., Type 1 or Type 2), alkaptonuria, homocystinuria, hyperhomocysteinemia, maple syrup urine disease.

In some embodiments, the disease, disorder, or condition is a fatty acid metabolism disorder, e.g., hyperlipidemia, hypercholesterolemia, galactosemia.

In some embodiments, a first portion of the surface of the device comprises a compound of Formula (I) that modulates, e.g., down regulates or upregulates, an immune response and a second portion of the device lacks the compound, or has substantially lower density of the compound. In some embodiments, a first portion of the surface of the device comprises a compound of Formula I that modulates, e.g., down regulates, an immune response and a second portion of the surface comprises a second compound of Formula I, e.g., that upregulates the immune response, second portion of the device lacks the compound, or has substantially lower density of the compound.

In some embodiments, the device comprises a cell, e.g., a recombinant cell, which provides a substance, e.g., a therapeutic agent. In some embodiments, the substance comprises a polypeptide. In some embodiments, the polypeptide is a replacement therapy or a replacement protein (e.g., a clotting factor, an enzyme, or an antibody).

In some embodiments, the disorder is diabetes and the substance (e.g., therapeutic agent) is insulin. In some embodiments, the disorder is a blood clotting disorder (e.g., hemophilia) and the substance (e.g., therapeutic agent) is a blood clotting factor (e.g., Factor VIII or Factor IX). In some embodiments, the disorder is a lysosomal storage disorder (e.g., Fabry Disease, Gaucher Disease, Pompe Disease, or MPS I) and the substance (e.g., therapeutic agent) is an enzyme (e.g., alpha-galactosidase, alpha-glucosidase, or a glucocerebrodisase). In some embodiments, the disorder is a neurodegenerative disease, and the substance is a hormone or neurotransmitter, or an analog, precursor, or derivative thereof.

In some embodiments, A is A1. In some embodiments, A1 is hydrogen, alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, or —$N(R^C)(R^D)$. In some embodiments, A1 is —$N(R^C)(R^D)$ (e.g., $NH_2$). In some embodiments, A1 is $NH_2$ or $NHC(O)C(CH_2)CH_3$.

In some embodiments, A is A2. In some embodiments, A2 is alkyl, heteroalkyl, cycloalkyl, heterocyclyl, aryl, heteroaryl, —O—, —C(O)O—, —C(O)—, —OC(O)—, —$N(R^C)$—, —$N(R^C)C(O)$—, —$C(O)N(R^C)$—, —$Si(OR^A)_2$—, —$Si(R^G)(OR^A)$—, or —$B(OR^A)$—. In some embodiments, A2 is —$N(R^C)$— (e.g., NH—). In some embodiments, A2 is NH— or $NH(C(O)C(CH_3)CH_2$—. In some embodiments, the compound comprises A2, and, e.g., is covalently attached to a device. In some embodiments, A2 is attached directly to the device. In some embodiments, A2 is attached to the device by an attachment group (e.g., an attachment group described herein). In some embodiments, the device is attached, e.g., covalently, to the attachment group, and A2 is attached, e.g., covalently to the attachment group.

In some embodiments, each of $L^1$, $L^2$, and $L^3$ is independently a bond, alkyl, or heteroalkyl. In some embodiments, $L^1$ is a bond, alkyl, or heteroalkyl. In some embodiments, $L^1$ is $C_1$-$C_6$ alkyl (e.g., —$CH_2$— or —$CH_2CH_2$—). In some embodiments, $L^2$ is a bond. In some embodiments, $L^3$ is a bond, alkyl, or heteroalkyl. In some embodiments, $L^3$ is $C_1$-$C_6$ alkyl (e.g., —$CH_2$—) or heteroalkyl (e.g., —$CH_2O$—).

In some embodiments, M is heteroalkyl, aryl, or heteroaryl. In some embodiments, M is heteroalkyl. In some embodiments, M is (—$OCH_2CH_2$-)z, wherein z is an integer selected from 1 to 10. In some embodiments, M is aryl (e.g., phenyl).

In some embodiments, P is a tricyclic, bicyclic, or monocyclic heteroaryl. In some embodiments, P is a nitrogen-containing heteroaryl. In some embodiments, P is a 5-membered nitrogen-containing heteroaryl (e.g., tetrazolyl, imidazolyl, pyrazolyl, or triazolyl, pyrrolyl, oxazolyl, or thiazolyl). In some embodiments, P is triazolyl (e.g., 1,2,3-triazolyl or 1,2,4-triazolyl). In some embodiments, P is selected from

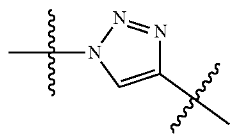

and

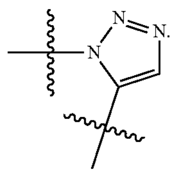

In some embodiments, P is

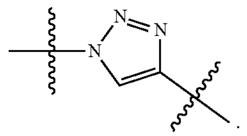 [SMILES: *c1cn(*)nn1]

In some embodiments, Z is alkyl, heterocyclyl, or aryl, each of which is optionally substituted by one or more $R^5$. In some embodiments, Z is heterocyclyl (e.g., 6-membered heterocyclyl). In some embodiments, Z is a nitrogen-containing heterocyclyl, an oxygen-containing heterocyclyl, or a sulfur-containing heterocyclyl (e.g., tetrahydropyranyl or thiomorpholinyl-1,1-dioxide). In some embodiments, Z is oxetanyl, tetrahydrofuranyl, tetrahydropyranyl, thiomorpholinyl-1,1-dioxide, piperidinyl, piperazinyl, or pyrrolidinyl.

In some embodiments, Z is aryl (e.g., phenyl). In some embodiments, Z is monosubstituted phenyl (e.g., with 1 $R^5$). In some embodiments, Z is monosubstituted phenyl, wherein the 1 $R^5$ an amine-containing group (e.g., $NH_2$). In some embodiments, Z is monosubstituted phenyl, wherein the 1 $R^5$ is an oxygen-containing group (e.g., $OCH_3$). In some embodiments, the 1 $R^5$ is in the ortho position or the para position.

In some embodiments, Z is alkyl (e.g., $C_1$-$C_{12}$ alkyl). In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1})(R^{D1})$. In some embodiments, Z is $C_1$-$C_8$ alkyl substituted with 1 $R^5$, wherein $R^5$ is —OH or —C(O)OH.

In some embodiments, Z is heteroalkyl (e.g., $C_1$-$C_{12}$ heteroalkyl). In some embodiments, Z is an oxygen-containing heteroalkyl or a nitrogen-containing heteroalkyl. In some embodiments, Z is (—OCH2CH2-)z$OCH_3$, wherein z is an integer selected from 1 to 10 (e.g., z is 1, 2, 3, 4, 5, 6, 7, 8, 9, or 10).

In another aspect, the present invention features a method of making a device comprising Formula (I):

$$A\text{-}L^1\text{-}M\text{-}L^2\text{-}P\text{-}L^3\text{-}Z \quad (I)$$

wherein A is A1 or A2; A1 is hydrogen, alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, —$N(R^C)(R^D)$, —$N(R^C)C(O)R^B$, —$C(O)N(R^C)(R^D)$, —$N_3$, —NC, —CN, —NCO, —NCS, —$N(R^C)N(R^D)_2$, —$NCNR^C$, —$C(=N(R^C)(R^D))OR^A$, —$SR^E$, —$S(O)_xR^E$, —$OS(O)_xR^E$, —$N(R^C)S(O)_xR^E$, —$S(O)_xN(R^C)(R^D)$, —$P(R^F)_y$, —$Si(OR^A)_3$, —$Si(R^G)(OR^A)_2$, —$B(OR^A)_2$, or a metal, wherein each alkyl, alkenyl, alkynyl, heteroalkyl, cycloalkyl, heterocyclyl, aryl, heteroaryl is optionally substituted with one or more $R^1$; A2 is alkyl, alkenyl, alkynyl, heteroalkyl, cycloalkyl, heterocyclyl, aryl, heteroaryl, —O—, —C(O)O—, —C(O)—, —OC(O)—, —$N(R^C)$—, —$N(R^C)C(O)$—, —$C(O)N(R^C)$—, —$N(R^C)N(R^D)$—, —NCN—, —$C(=N(R^C)(R^D))O$—, —S—, —$S(O)_x$—, —$OS(O)_x$, —$N(R^C)S(O)_x$—, —$S(O)_xN(R^C)$—, —$P(R^F)$, —$Si(OR^A)_2$—, —$Si(R^G)(OR^A)$—, —$B(OR^A)$, or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted by one or more $R^1$; each $L^1$, $L^2$, and $L^3$ is independently a bond, alkyl, alkenyl, alkynyl, or heteroalkyl, wherein each alkyl, alkenyl, alkynyl, and heteroalkyl is optionally substituted by 1-5 $R^2$; M is alkyl, alkenyl, alkynyl, heteroalkyl, cycloalkyl, heterocyclyl, aryl, or heteroaryl, each of which is optionally substituted by one or more $R^3$; P is cycloalkyl, heterocyclyl, aryl, or heteroaryl, each of which is optionally substituted by one or more $R^4$; Z is alkyl, alkenyl, alkynyl, heteroalkyl, cycloalkyl, heterocyclyl, aryl, or heteroaryl, each of which is optionally substituted by one or more $R^5$; each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with one or more $R^6$, or $R^C$ and $R^D$, taken together with the nitrogen atom to which they are attached, form a ring (e.g., a 5-7 membered ring), optionally substituted with one or more $R^6$, each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, —$S(O)_xR^E$, —$OS(O)_xR^E$, —$N(R^C)S(O)_xR^E$, —$S(O)_xN(R^C)(R^D)$, —$P(R^F)_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$; each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$; each $R^7$ is independently alkyl, alkenyl, alkynyl, heteroalkyl, halogen, cyano, oxo, hydroxyl, cycloalkyl, or heterocyclyl; x is 1 or 2; and y is 2, 3, or 4, wherein the compound of Formula (I) is associated with the device (e.g., through an attachment group).

In some embodiments, A is A1. In some embodiments, A1 is hydrogen, alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, or —$N(R^C)(R^D)$. In some embodiments, A1 is —$N(R^C)(R^D)$ (e.g., $NH_2$). In some embodiments, A1 is $NH_2$ or $NHC(O)C(CH_2)CH_3$.

In some embodiments, A is A2. In some embodiments, A2 is alkyl, heteroalkyl, cycloalkyl, heterocyclyl, aryl, heteroaryl, —O—, —C(O)O—, —C(O)—, —OC(O)—, —$N(R^C)$—, —$N(R^C)C(O)$—, —$C(O)N(R^C)$—, —$Si(OR^A)_2$—, —$Si(R^G)(OR^A)$—, or —$B(OR^A)$—. In some embodiments, A2 is —$N(R^C)$— (e.g., NH—). In some embodiments, A2 is NH— or $NH(C(O)C(CH_3)CH_2$—. In some embodiments, the compound comprises A2, and, e.g., is covalently attached to a device. In some embodiments, A2 is attached directly to the device. In some embodiments, A2 is attached to the device by an attachment group (e.g., an attachment group described herein). In some embodiments, the device is attached, e.g., covalently, to the attachment group, and A2 is attached, e.g., covalently to the attachment group.

In some embodiments, each $L^1$, $L^2$, and $L^3$ is independently a bond, alkyl, or heteroalkyl. In some embodiments, $L^1$ is a bond, alkyl, or heteroalkyl. In some embodiments, $L^1$ is $C_1$-$C_6$ alkyl (e.g., —$CH_2$— or —$CH_2CH_2$—). In some embodiments, $L^2$ is a bond. In some embodiments, $L^3$ is a bond, alkyl, or heteroalkyl. In some embodiments, $L^3$ is $C_1$-$C_6$ alkyl (e.g., —$CH_2$—) or heteroalkyl (e.g., —$CH_2O$—).

In some embodiments, M is heteroalkyl, aryl, or heteroaryl. In some embodiments, M is heteroalkyl. In some embodiments, M is (—$OCH_2CH_2$-)z, wherein z is an integer selected from 1 to 10. In some embodiments, M is aryl (e.g., phenyl).

In some embodiments, P is a tricyclic, bicyclic, or monocyclic heteroaryl. In some embodiments, P is a nitrogen-containing heteroaryl. In some embodiments, P is a 5-membered nitrogen-containing heteroaryl (e.g., tetrazolyl, imidazolyl, pyrazolyl, or triazolyl, pyrrolyl, oxazolyl, or thiazolyl). In some embodiments, P is triazolyl (e.g., 1,2,3-triazolyl or 1,2,4-triazolyl). In some embodiments, P is selected from

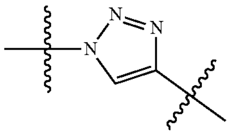

and

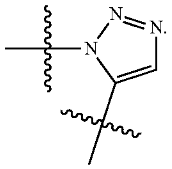

In some embodiments, P is

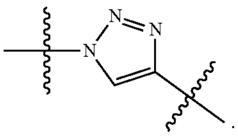 [SMILES: *c1cn(*)nn1]

In some embodiments, Z is alkyl, heterocyclyl, or aryl, each of which is optionally substituted by one or more $R^5$. In some embodiments, Z is heterocyclyl (e.g., 6-membered heterocyclyl). In some embodiments, Z is a nitrogen-containing heterocyclyl, an oxygen-containing heterocyclyl, or a sulfur-containing heterocyclyl (e.g., tetrahydropyranyl or thiomorpholinyl-1,1-dioxide). In some embodiments, Z is oxetanyl, tetrahydrofuranyl, tetrahydropyranyl, thiomorpholinyl-1,1-dioxide, piperidinyl, piperazinyl, or pyrrolidinyl.

In some embodiments, Z is aryl (e.g., phenyl). In some embodiments, Z is monosubstituted phenyl (e.g., with 1 $R^5$). In some embodiments, Z is monosubstituted phenyl, wherein the 1 $R^5$ an amine-containing group (e.g., $NH_2$). In some embodiments, Z is monosubstituted phenyl, wherein the 1 $R^5$ is an oxygen-containing group (e.g., $OCH_3$). In some embodiments, the 1 $R^5$ is in the ortho position or the para position.

In some embodiments, Z is alkyl (e.g., $C_1$-$C_{12}$ alkyl). In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1})(R^{D1})$. In some embodiments, Z is $C_1$-$C_8$ alkyl substituted with 1 $R^5$, wherein $R^5$ is —OH or —C(O)OH.

In some embodiments, Z is heteroalkyl (e.g., $C_1$-$C_{12}$ heteroalkyl). In some embodiments, Z is an oxygen-containing heteroalkyl or a nitrogen-containing heteroalkyl. In some embodiments, Z is (—OCH2CH2-)z$OCH_3$, wherein z is an integer selected from 1 to 10 (e.g., z is 1, 2, 3, 4, 5, 6, 7, 8, 9, or 10).

In any and all aspects of the present invention, in some embodiments, the compound, composition, or implantable element (e.g., device or material) described herein is a composition, or implantable element (e.g., device or material) other than a compound, composition, or implantable element (e.g., device or material) described in WO2012/112982, WO2012/167223, WO2014/153126, WO2016/187225, WO2016/019391, WO2017/075630, WO 2017/075631, and US 2016-0030359. In some embodiments, the compound of Formula (I) or device comprising the same is a compound or device other than a compound or device described in WO2012/112982, WO2012/167223, WO2014/153126, WO2016/187225, WO2016/019391, WO2017/075630, WO 2017/075631, and US 2016-0030359. In some embodiments, the device comprises a material other than a material described in WO2012/112982, WO2012/167223, WO2014/153126, WO2016/187225, WO2016/019391, WO2017/075630, WO 2017/075631, and US 2016-0030359. In some embodiments, the device is attached to a compound of Formula (I) through an attachment group other than an attachment group described in WO2012/112982, WO2012/167223, WO2014/153126, WO2016/187225, WO2016/019391, WO2017/075630, WO 2017/075631, and US 2016-0030359.

The details of one or more embodiments of the invention are set forth herein. Other features, objects, and advantages of the invention will be apparent from the Detailed Description, the Figures, the Examples, and the Claims.

DETAILED DESCRIPTION

Figure 1A:
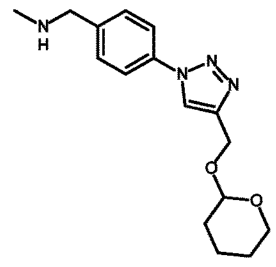
FIGS. 1A-6KK are tables of exemplary compounds, e.g., compounds of Formula (I). Several species labeled Compounds 3271 through 3431 in FIGS. 1A-6KK are duplicates of Compounds 100 through 3270 described herein.

The present invention provides compounds, e.g., compounds of Formula (I), and compositions and implantable elements (e.g., devices and materials) comprising the same, as well as methods of use thereof. In particular, the compounds of Formula (I) and compositions and devices comprising said compounds may be used in methods for the prevention and treatment of a disease, disorder or condition in a subject. In some embodiments, the compounds of Formula (I), and pharmaceutically acceptable salts, solvates, hydrates, tautomers, stereoisomers, isotopically labeled derivatives, and compositions and devices thereof, are capable of modulating the immune response in a subject, e.g., upregulating or downregulating the immune response in a subject.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_8$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The following terms are intended to have the meanings presented therewith below and are useful in understanding the description and intended scope of the present invention.

As used herein, "alkyl" refers to a radical of a straight-chain or branched saturated hydrocarbon group having from 1 to 24 carbon atoms ("$C_1$-$C_{24}$ alkyl"). In some embodiments, an alkyl group has 1 to 12 carbon atoms ("$C_1$-$C_{12}$ alkyl"). In some embodiments, an alkyl group has 1 to 8 carbon atoms ("$C_1$-$C_8$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_8$ alkyl"). In some embodiments, an alkyl group has 1 to 4 carbon atoms ("$C_1$-$C_4$alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). In some embodiments, an alkyl group has 2 to 6 carbon atoms ("$C_2$-$C_6$alkyl"). Examples of $C_1$-$C_6$alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-6}$ alkyl.

As used herein, "alkenyl" refers to a radical of a straight-chain or branched hydrocarbon group having from 2 to 24 carbon atoms, one or more carbon-carbon double bonds, and no triple bonds ("$C_2$-$C_{24}$ alkenyl"). In some embodiments, an alkenyl group has 2 to 10 carbon atoms ("$C_2$-$C_{10}$ alkenyl"). In some embodiments, an alkenyl group has 2 to 8 carbon atoms ("$C_2$-$C_8$ alkenyl"). In some embodiments, an alkenyl group has 2 to 6 carbon atoms ("$C_2$-$C_6$ alkenyl"). In some embodiments, an alkenyl group has 2 to 5 carbon atoms ("$C_2$-$C_5$ alkenyl"). In some embodiments, an alkenyl group has 2 to 4 carbon atoms ("$C_2$-$C_4$ alkenyl"). In some embodiments, an alkenyl group has 2 to 3 carbon atoms ("$C_2$-$C_3$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-6}$ alkenyl.

As used herein, the term "alkynyl" refers to a radical of a straight-chain or branched hydrocarbon group having from 2 to 24 carbon atoms, one or more carbon-carbon triple bonds ("$C_2$-$C_{24}$ alkenyl"). In some embodiments, an alkynyl group has 2 to 10 carbon atoms ("$C_2$-$C_{10}$ alkynyl"). In some embodiments, an alkynyl group has 2 to 8 carbon atoms ("$C_2$-$C_8$ alkynyl"). In some embodiments, an alkynyl group has 2 to 6 carbon atoms ("$C_2$-$C_6$ alkynyl"). In some embodiments, an alkynyl group has 2 to 5 carbon atoms ("$C_2$-$C_5$ alkynyl"). In some embodiments, an alkynyl group has 2 to 4 carbon atoms ("$C_2$-$C_4$ alkynyl"). In some embodiments, an alkynyl group has 2 to 3 carbon atoms ("$C_2$-$C_3$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally substituted, i.e., unsubstituted (an "unsubstituted alkynyl") or substituted (a "substituted alkynyl") with one or more substituents e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-6}$ alkynyl.

As used herein, the term "heteroalkyl," refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any position of the heteroalkyl group. Exemplary heteroalkyl groups include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH═CHO—$CH_3$, —$Si(CH_3)_3$, —$CH_2$—CH═N—$OCH_3$, —CH═CH—N($CH_3$)—$CH_3$, —O—$CH_3$, and —O—$CH_2$—$CH_3$. Up to two or three heteroatoms may be consecutive, such as, for example, —$CH_2$—NH—$OCH_3$ and —$CH_2$—O—$Si(CH_3)_3$. Where "heteroalkyl" is recited, followed by recitations of specific heteroalkyl groups, such as —$CH_2O$, —$NR^CR^D$, or the like, it will be understood that the terms heteroalkyl and —$CH_2O$ or —$NR^CR^D$ are not redundant or mutually exclusive. Rather, the specific heteroalkyl groups are recited to add clarity. Thus, the term "heteroalkyl" should not be interpreted herein as excluding specific heteroalkyl groups, such as —$CH_2O$, —$NR^CR^D$, or the like.

The terms "alkylene," "alkenylene," "alkynylene," or "heteroalkylene," alone or as part of another substituent, mean, unless otherwise stated, a divalent radical derived from an alkyl, alkenyl, alkynyl, or heteroalkyl, respectively. The term "alkenylene," by itself or as part of another substituent, means, unless otherwise stated, a divalent radical derived from an alkene. An alkylene, alkenylene, alkynylene, or heteroalkylene group may be described as, e.g., a $C_1$-$C_6$-membered alkylene, $C_1$-$C_6$-membered alkenylene, $C_1$-$C_6$-membered alkynylene, or $C_1$-$C_6$-membered heteroalkylene, wherein the term "membered" refers to the non-hydrogen atoms within the moiety. In the case of heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— may represent both —$C(O)_2R'$— and —$R'C(O)_2$—.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents. In certain embodiments, the aryl group is unsubstituted $C_6$-$C_{14}$ aryl. In certain embodiments, the aryl group is substituted $C_6$-$C_{14}$ aryl.

As used herein, "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl.

Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Other exemplary heteroaryl groups include heme and heme derivatives.

As used herein, the terms "arylene" and "heteroarylene," alone or as part of another substituent, mean a divalent radical derived from an aryl and heteroaryl, respectively.

As used herein, "cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$cycloalkyl"). In some embodiments, a cycloalkyl group has 3 to 6 ring carbon atoms ("$C_3$-$C_6$ cycloalkyl"). In some embodiments, a cycloalkyl group has 3 to 6 ring carbon atoms ("$C_3$-$C_6$ cycloalkyl"). In some embodiments, a cycloalkyl group has 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_5$), cubanyl ($C_8$), bicyclo[1.1.1]pentanyl ($C_5$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is a substituted $C_3$-$C_{10}$ cycloalkyl.

"Heterocyclyl" as used herein refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Amino" as used herein refers to the radical —$NR^{70}R^{71}$, wherein $R^{70}$ and $R^{71}$ are each independently hydrogen, $C_1$-$C_8$ alkyl, $C_3$-$C_{10}$ cycloalkyl, $C_4$-$C_{10}$ heterocyclyl, $C_6$-$C_{10}$ aryl, and $C_5$-$C_{10}$ heteroaryl. In some embodiments, amino refers to $NH_2$.

"Cyano" refers to the radical —CN.

As used herein, "halo" or "halogen," independently or as part of another substituent, mean, unless otherwise stated, a fluorine (F), chlorine (Cl), bromine (Br), or iodine (I) atom.

"Hydroxy" refers to the radical —OH.

Alkyl, alkenyl, alkynyl, heteroalkyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; and the like.

The term "pharmaceutically acceptable salt" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al, *Journal of Pharmaceutical Science* 66: 1-19 (1977)). Certain specific compounds of the present invention contain both basic and acidic functionalities that allow the compounds to be converted into either base or acid addition salts. These salts may be prepared by methods known to those skilled in the art. Other pharmaceutically acceptable carriers known to those of skill in the art are suitable for the present invention.

In addition to salt forms, the present invention provides compounds in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) may be prepared, e.g., in crystalline form, and may be solvated. Suitable solvates include pharmaceutically acceptable solvates and further include both stoichiometric solvates and non-stoichiometric solvates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R·x $H_2O$, wherein R is the compound and wherein x is a number greater than 0.

The term "tautomer" as used herein refers to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Tautomeric forms may be relevant to the attainment of the optimal chemical reactivity and biological activity of a compound of interest.

Other Definitions

The following definitions are more general terms used throughout the present application.

"Acquire" or "acquiring" as used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing an analytical method or protocol) to obtain the value or physical entity. "Indirectly acquiring" refers to receiving the value or physical entity from another party or source (e.g., a third party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., fluorescence microscope to acquire fluorescence microscopy data or nuclear magnetic resonance (NMR) instrument to acquire an NMR spectrum. The terms "administer," "administering," or "administration," as used herein refers to implanting, absorbing, ingesting, injecting, or otherwise introducing an inventive compound (e.g., a compound described herein, e.g., a compound of Formula (I)), or a composition or implantable element comprising the same, e.g., to a subject.

"Cell," as used herein, refers to an engineered cell or a cell that is not engineered.

An "effective amount," e.g., of a compound of Formula (I) or a composition or implantable element comprising the same, refers to an amount sufficient to elicit a desired biological response, e.g., to treat a disease, disorder, or condition. As will be appreciated by those of ordinary skill in this art, the effective amount may vary depending on such factors as the desired biological endpoint, the pharmacokinetics of the compound, composition or device, the condition being treated, the mode of administration, and the age and health of the subject. An effective amount encompasses therapeutic and prophylactic treatment. For example, to treat a fibrotic condition, an effective amount of a compound may reduce the fibrosis or stop the growth or spread of fibrotic tissue.

An "endogenous nucleic acid" as used herein, is a nucleic acid that occurs naturally in a subject cell.

An "endogenous polypeptide," as used herein, is a n polypeptide that occurs naturally in a subject cell.

"Engineered cell," as used herein, is a cell having a non-naturally occurring alteration, and typically comprises a nucleic acid sequence (e.g., DNA or RNA) or a polypeptide not present (or present at a different level than) in an otherwise similar cell under similar conditions that is not engineered (an exogenous nucleic acid sequence). In an embodiment, an engineered cell comprises an exogenous nucleic acid (e.g., a vector or an altered chromosomal sequence). In an embodiment, an engineered cell comprises an exogenous polypeptide. In an embodiment, an engineered cell comprises an exogenous nucleic acid sequence, e.g., a sequence, e.g., DNA or RNA, not present in a similar cell that is not engineered. In an embodiment, the exogenous nucleic acid sequence is chromosomal, e.g., the exogenous nucleic acid sequence is an exogenous sequence disposed in endogenous chromosomal sequence. In an embodiment, the exogenous nucleic acid sequence is chromosomal or extra chromosomal, e.g., a non-integrated vector. In an embodiment, the exogenous nucleic acid sequence comprises an RNA sequence, e.g., an mRNA. In an embodiment, the exogenous nucleic acid sequence comprises a chromosomal or extra-chromosomal exogenous nucleic acid sequence that comprises a sequence which is expressed as RNA, e.g., mRNA or a regulatory RNA. In an embodiment, the exogenous nucleic acid sequence comprises a chromosomal or extra-chromosomal nucleic acid sequence that comprises a sequence which encodes a polypeptide or which is expressed as a polypeptide. In an embodiment, the exogenous nucleic acid sequence comprises a first chromosomal or extra-chromosomal exogenous nucleic acid sequence that modulates the conformation or expression of a second nucleic acid sequence, wherein the second amino acid sequence can be exogenous or endogenous. For example, an engineered cell can comprise an exogenous nucleic acid that controls the expression of an endogenous sequence. In an embodiment, an engineered cell comprises a polypeptide present at a level or distribution which differs from the level found in a similar cell that has not been engineered. For example, an engineered cell may comprise an exogenous nucleic acid sequence comprising a chromosomal or extra-chromosomal exogenous nucleic acid sequence that comprises a sequence which is expressed as RNA, e.g., mRNA or a regulatory RNA. In an embodiment, an engineered cell comprises an exogenous nucleic acid sequence that comprises a chromosomal or extra-chromosomal nucleic acid sequence that comprises a sequence which encodes a polypeptide or which is expressed as a polypeptide. In an embodiment, an engineered cell comprises an exogenous nucleic acid sequence that modulates the conformation or expression of an endogenous sequence.

The term "immunomodulator" as used herein refers to a compound, composition, material, or device capable of modifying an immune response, a function of the immune system, or a component thereof. In some embodiments, an immunomodulator upregulates or downregulates an immune response or a component thereof. In some embodiments, an immunomodulator is tunable over a spectrum. An immunomodulator may modulate (e.g., increase or decrease) in a subject one or more of: inflammation, cytokine production, complement cascade, leukocyte production or response, lymphocyte production or response, antibody production or response, fibrosis, growth factor production or response (e.g., TGF-b, CTGF, PDGF production or response), or a molecular marker of immune response, e.g., the level of TNF-α, IL-13, IL-6, G-CSF, GM-CSF, IL-4, CCL2, or CCL4, as measured, e.g., by ELISA, e.g., at the site of an implanted device or cell.

An "implantable element" as used herein, comprises a cell, e.g., a plurality of cells, e.g., a cluster of cells, wherein the cell or active cells are entirely or partially disposed within an enclosing component (which enclosing component is other than a cell), e.g., the enclosing component comprises a non-cellular component. The term "implantable element" comprises a device or material described herein. In an embodiment, the implantable element inhibits an immune attack, or the effect of the immune attack, on the enclosed cell or cells. In an embodiment, the implantable element comprises a semipermeable membrane or a semipermeable polymer matrix or coating. Typically, the implantable element allows passage of small molecules, e.g., nutrients and waste products. Typically, the implantable element allows passage of a product (e.g., a therapeutic polypeptide) released by a cell disposed within the enclosing component. In an embodiment, placement within an implantable element minimizes an effect of a host response (e.g., an immune response, e.g., a fibrotic response) directed at the implantable element, e.g., against a cell within an implantable element, e.g., as compared with a similar cell that is not disposed in an implantable element. In an embodiment, the implantable element comprises a moiety, e.g., a moiety described herein, that minimizes an effect of an immune response, e.g., a fibrotic response, of the subject directed at the implantable element, e.g., against the enclosing component or a cell within the implantable element, e.g., as compared with a similar implantable element lacking the moiety. In some embodiments, said moiety is a compound, e.g., a compound described herein (e.g., a compound of Formula (I)). In some embodiments, the implantable element (e.g., a device or material) is associated (e.g., directly associated) with a compound described herein, e.g., a compound of Formula (I).

"Polypeptide", as used herein, refers to a polymer comprising amino acid residues linked through peptide bonds and having at least two, and in embodiments, at least 10, 100, or 200 amino acid residues.

"Prevention," "prevent," and "preventing" as used herein refers to a treatment that comprises administering or applying a therapy, e.g., administering a compound described herein (e.g., a compound of Formula (I)) or a composition or implantable element (e.g., a device or material) comprising a compound described herein (e.g., a compound of Formula (I), prior to the onset of a disease, disorder, or condition in order to preclude the physical manifestation of said disease, disorder, or condition. In some embodiments, "prevention," "prevent," and "preventing" require that signs or symptoms of the disease, disorder, or condition have not yet developed or have not yet been observed. In some embodiments, treatment comprises prevention and in other embodiments it does not.

A "replacement therapy" or "replacement protein" is a therapeutic protein or functional fragment thereof that replaces or augments a protein that is diminished, present in insufficient quantity, altered (e.g., mutated) or lacking in a subject having a disease or condition related to the diminished, altered or lacking protein. Examples are certain blood clotting factors in certain blood clotting disorders or certain lysosomal enzymes in certain lysosomal storage diseases. In an embodiment, a replacement therapy or replacement protein provides the function of an endogenous protein. In an embodiment, a or replacement therapy or replacement protein has the same amino acid sequence of a naturally occurring variant, e.g., a wildtype allele or an allele not associated with a disorder, of the replaced protein. In an embodiment, or replacement therapy or a replacement protein differs in amino acid sequence from a naturally occurring variant, e.g, a wildtype allele or an allele not associated with a disorder, e.g, the allele carried by a subject, at no more than about 1, 2, 3, 4, 5, 10, 15 or 20% of the amino acid residues.

The term "subject" as used herein refers to the recipient of the compound, composition, device, or method of use thereof, e.g., as described herein. The subject may include a human (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

As used herein, the terms "treatment," "treat," and "treating" refer to reversing, alleviating, delaying the onset of, or inhibiting the progress of one or more of a symptom, manifestation, or underlying cause of a disease, disorder, or condition. (e.g., as described herein), e.g., by administering or applying a therapy, e.g., administering a compound described herein (e.g., a compound of Formula (I)) or a composition or implantable element (e.g., a device or material) comprising a compound described herein (e.g., a compound of Formula (I). In an embodiment, treating comprises reducing, reversing, alleviating, delaying the onset of, or inhibiting the progress of a symptom of a disease, disorder, or condition. In an embodiment, treating comprises reducing, reversing, alleviating, delaying the onset of, or inhibiting the progress of a manifestation of a disease, disorder, or condition. In an embodiment, treating comprises reducing, reversing, alleviating, reducing, or delaying the onset of, an underlying cause of a disease, disorder, or condition. In some embodiments, "treatment," "treat," and "treating" require that signs or symptoms of the disease, disorder, or condition have developed or have been observed. In other embodiments, treatment may be administered in the absence of signs or symptoms of the disease or condition, e.g., in preventive treatment. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence. Treatment may also be continued after symptoms have resolved, for example, to delay or prevent recurrence. In some embodiments, treatment comprises prevention and in other embodiments it does not.

Compounds

The present invention features a compound of Formula (I):

$$A\text{-}L^1\text{-}M\text{-}L^2\text{-}P\text{-}L^3\text{-}Z \qquad (I)$$

or a salt, solvate, hydrate, tautomer, stereoisomer, or isotopically labeled derivative thereof, wherein:

A is selected from A1 or A2, wherein:

A1 is hydrogen, alkyl, alkenyl, alkynyl, heteroalkyl, cycloalkyl, heterocyclyl, aryl, heteroaryl, $-OR^A$, $-C(O)OR^A$, $-C(O)R^B$, $-OC(O)R^B$, $-N(R^C)(R^D)$, $-N(R^C)C(O)R^B$, $-C(O)N(R^C)(R^D)$, $-N_3$, $-NC$, $-CN$, $-NCO$, $-NCS$, $-N(R^C)N(R^D)_2$, $-NCN(R^C)$, $-C(=N(R^C)(R^D))OR^A$, $-SR^E$, $-S(O)_xR^E$, $-OS(O)_xR^E$, $-N(R^C)S(O)_xR^E$, $-S(O)_x N(R^C)(R^D)$, $-P(R^F)_y$, $-Si(OR^A)_3$, $-Si(R^G)(OR^A)_2$, $-B(OR^A)_2$, or a metal, wherein each alkyl, alkenyl, alkynyl, heteroalkyl, cycloalkyl, heterocyclyl, aryl, and heteroaryl is optionally substituted by one or more $R^1$;

A2 is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, —NCN—, —C(═N($R^C$)($R^D$))O—, —S—, —S(O)$_x$—, —OS(O)$_x$—, —N($R^C$)S(O)$_x$—, —S(O)$_x$N($R^C$)—, —P($R^F$)$_y$—, —Si($OR^A$)$_2$—, —Si($R^G$)($OR^A$)—, —B($OR^A$)—, or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted by one or more $R^1$;

each $L^1$, $L^2$, and $L^3$ is independently a bond, alkyl, alkenyl, alkynyl, or heteroalkyl, wherein each alkyl, alkenyl, alkynyl, and heteroalkyl is optionally substituted by one or more $R^2$.

M is alkyl, alkenyl, alkynyl, heteroalkyl, cycloalkyl, heterocyclyl, aryl, or heteroaryl, each of which is optionally substituted by one or more $R^3$;

P is cycloalkyl, heterocyclyl, aryl, or heteroaryl, each of which is optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$, or $R^C$ and $R^D$, taken together with the nitrogen atom to which they are attached, form a ring (e.g., a 5-7 membered ring), optionally substituted with one or more $R^6$, or one or both of $R^C$ and $R^D$ is bound to an atom within L or M or one of the substituents of L or M to form a ring optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, S(O)$_x R^{E1}$, —OS(O)$_x R^{E1}$, —N($R^{C1}$)S(O)$_x R^{E1}$, —S(O)$_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

As generally described herein, A is selected from A1 and A2. In some embodiments, A is A1. In some embodiments, A1 is hydrogen, alkyl, alkenyl, alkynyl, heteroalkyl, cycloalkyl, heterocyclyl, aryl, heteroaryl, —$OR^A$, —C(O)$OR^A$, —C(O)$R^B$, —OC(O)$R^B$, —N($R^C$)($R^D$), —N($R^C$)C(O)$R^B$, —C(O)N($R^C$), —$N_3$, —NC, —CN, —NCO, —NCS, —N($R^C$)N($R^D$)$_2$, —NCN($R^C$), —C(═N($R^C$)($R^D$))$OR^A$, —$SR^E$, —S(O)$_x R^E$, —OS(O)$_x R^E$, —P($R^F$)$_y$, —Si($OR^A$)$_3$, —Si($R^G$)($OR^A$)$_2$, —B($OR^A$)$_2$, or a metal, wherein each alkyl, alkenyl, alkynyl, heteroalkyl, cycloalkyl, heterocyclyl, aryl, heteroaryl is optionally substituted with one or more $R^1$.

In some embodiments, A1 is hydrogen. In some embodiments, A1 is alkyl, alkenyl, alkynyl, or heteroalkyl (e.g., $C_1$-$C_{12}$ alkyl, $C_2$-$C_{12}$ alkenyl, $C_2$-$C_{12}$ alkynyl, or $C_1$-$C_{12}$ heteroalkyl). In some embodiments, A1 is unsubstituted alkyl, unsubstituted alkenyl, unsubstituted alkynyl, or unsubstituted heteroalkyl. In some embodiments, A1 is substituted alkyl, substituted alkenyl, substituted alkynyl, or substituted heteroalkyl, each of which is substituted with one or more $R^1$.

In some embodiments, A1 is methyl, ethyl, propyl, butyl, pentyl, or hexyl. In some embodiments, A1 is unsubstituted methyl, unsubstituted ethyl, unsubstituted propyl, unsubstituted butyl, unsubstituted pentyl, or unsubstituted hexyl. In some embodiments, A1 is substituted methyl, substituted ethyl, substituted propyl, substituted butyl, substituted pentyl, or substituted hexyl, each of which is substituted with one or more $R^1$.

In some embodiments, A1 is —$OR^A$, wherein $R^A$ is hydrogen, alkyl, or alkenyl. In some embodiments, A1 is —OH, —$OCH_3$, or —$OCH_2CH_3$, or —$OCH_2CH$═$CH_2$.

In some embodiments, A1 is —C(O)$R^B$, wherein $R^A$ is hydrogen, alkyl (e.g., methyl or ethyl), halogen or azido. In some embodiments, A1 is —C(O)$R^B$, wherein $R^A$ is hydrogen or alkyl (e.g., methyl or ethyl).

In some embodiments, A1 is —OC(O)$R^B$, wherein $R^B$ is alkyl, alkenyl, or alkynyl. In some embodiments, A1 is —OC(O)$R^B$, wherein $R^A$ is ethenyl (e.g., —CH═$CH_2$). In some embodiments, A1 is —OC(O)$R^B$, wherein $R^B$ is methyl (e.g, halomethyl).

In some embodiments, A1 is —C(O)$OR^A$, wherein $R^A$ is hydrogen, alkyl, alkenyl, alkynyl, C(O)$OR^{A1}$, heterocyclyl, or aryl. In some embodiments, A1 is —C(O)$OR^A$, wherein $R^A$ is succinimidyl or phenyl (e.g., 2,3,4,5,6-pentafluorophenyl). In some embodiments, A1 is —N($R^C$)C(O)$R^B$, wherein $R^C$ is hydrogen or methyl and $R^B$ is alkyl (e.g., haloalkyl) or alkenyl (e.g., ethenyl).

In some embodiments, A1 is —N($R^C$)($R^D$). In some embodiments, A1 is —N($R^C$)($R^D$), wherein one of $R^C$ or $R^D$ is hydrogen. In some embodiments, A1 is —N($R^C$)($R^D$), wherein one of $R^C$ or $R^D$ is hydrogen and the other of $R^C$ or $R^D$ is alkyl. In some embodiments, A1 is —$NH_2$. In some embodiments, A1 is $NH_2$ or NHC(O)C($CH_2$)$CH_3$. In some embodiments, A is —N($R^C$)($R^D$), wherein $R^C$ and $R^D$ are taken together with the nitrogen atom to which they are attached to form a ring (e.g., a 5-7 membered ring).

In some embodiments, A1 is —NCO. In some embodiments, A is —NCS. In some embodiments, A1 is —NC. In some embodiments, A1 is —$N_3$.

In some embodiments, A1 is —S(O)$_x R^E$, (e.g., wherein x is 2 and $R^E$ is alkyl, alkenyl, or halogen). In some embodiments, A1 is —S(O)$_2$(CH═$CH_2$). In some embodiments, A1 is —OS(O)$_x R^E$, (e.g., wherein x is 2 and $R^E$ is aryl).

In some embodiments, A1 is —Si($OR^A$)$_3$ (e.g., —Si(OH)$_3$, —Si(OMe)$_3$, or —Si(OEt)$_3$). In some embodiments, A1 is —Si($R^G$)($OR^A$)$_2$ (e.g., —Si(OH)$_2$(alkyl)). In some embodiments, A1 is —B($OR^A$)$_2$ (e.g., —B(OH)$_2$). In some embodiments, A1 is —P($R^F$)$_y$ (e.g., —P($CH_2OH$)$_3$)$^+$).

In some embodiments, A1 is cycloalkyl (e.g., a 3-membered cycloalkyl, 4-membered cycloalkyl, 5-membered cycloalkyl, 6-membered cycloalkyl). In some embodiments, A1 is heterocyclyl (e.g., a 3-membered heterocyclyl, 4-membered heterocyclyl, 5-membered heterocyclyl, 6-membered heterocyclyl). In some embodiments, A1 is a nitrogen-containing heterocyclyl (e.g., a 3-membered nitrogen-containing heterocyclyl, 4-membered nitrogen-containing heterocyclyl, 5-membered nitrogen-containing heterocyclyl, 6-membered nitrogen-containing heterocyclyl). In some embodiments, A1 is a 5-membered nitrogen-containing heterocyclyl (e.g., maleimidyl). In some embodiments, A1 is an oxygen-containing heterocyclyl (e.g., a 3-membered oxygen-containing heterocyclyl, 4-membered oxygen-containing heterocyclyl, 5-membered oxygen-containing heterocyclyl, 6-membered oxygen-containing heterocyclyl). In some embodiments, A1 is a 3-membered oxygen-containing heterocyclyl (e.g., oxiranyl).

In some embodiments, A1 is aryl (e.g., phenyl). In some embodiments, A1 is phenyl substituted with 1-2 $R^1$ (e.g., —$OR^A$ or —$B(OR^A)_2$). In some embodiments, A1 is phenyl substituted with —$OR^A$ (e.g., OH) or —$B(OR^A)_2$ (e.g., —$B(OH)_2$).

In some embodiments, A1 is heteroaryl (e.g., 5-membered heteroaryl, 6-membered heteroaryl). In some embodiments, A1 is a nitrogen-containing heteroaryl (e.g., 5-membered nitrogen-containing heteroaryl, 6-membered nitrogen-containing heteroaryl). In some embodiments, A1 is a 6-membered nitrogen-containing heteroaryl (e.g., imidazolyl).

In some embodiments, A1 is a metal (e.g., Fe, Ti, Au, Ni, Ca) or a metal alloy or mixture (e.g., stainless steel, alumina, Ni—Ti).

In some embodiments, A1 is selected from:

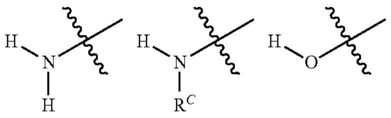

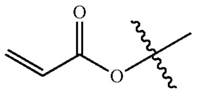 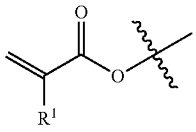

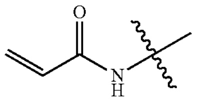 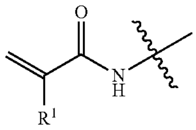

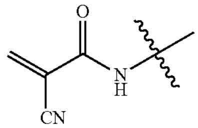 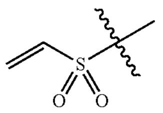

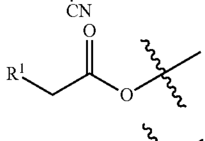 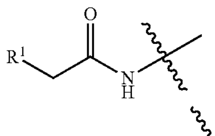

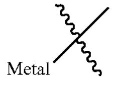 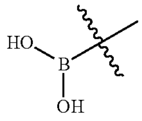 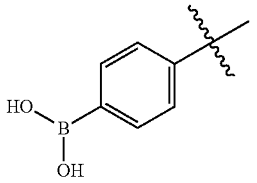

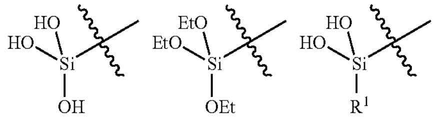

-continued

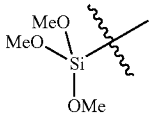 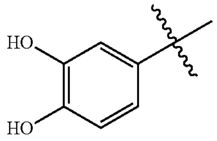 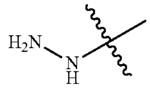

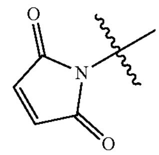 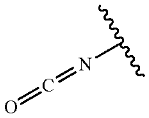 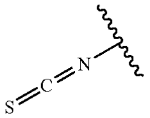

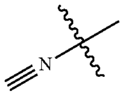 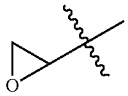

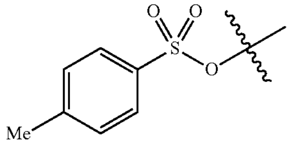

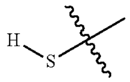 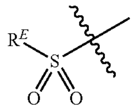 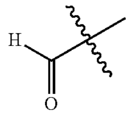

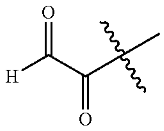 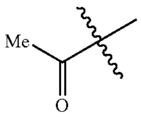 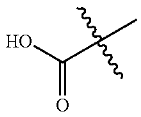

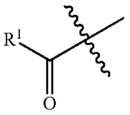 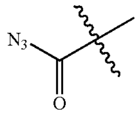 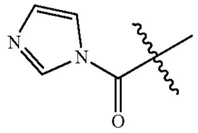

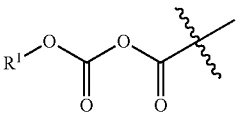 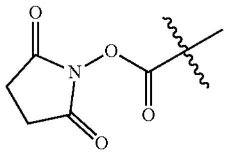

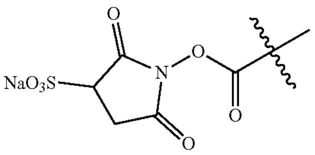

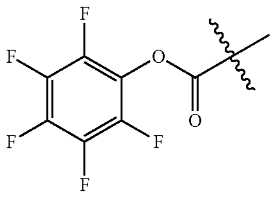 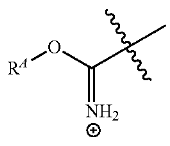

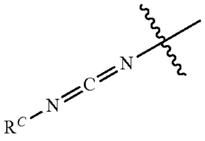 and 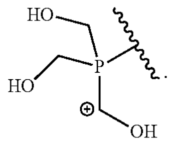

In some embodiments, A1 is selected from:

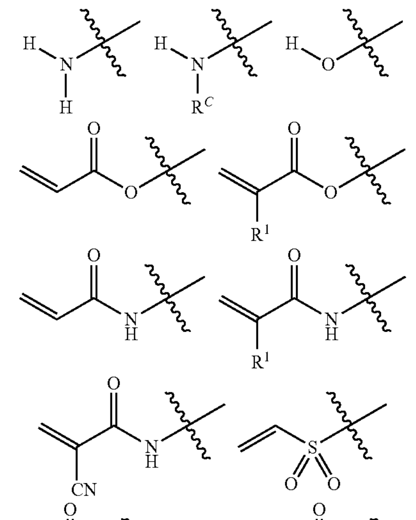

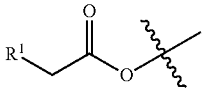

and

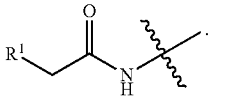

In some embodiments, A1 is selected from:

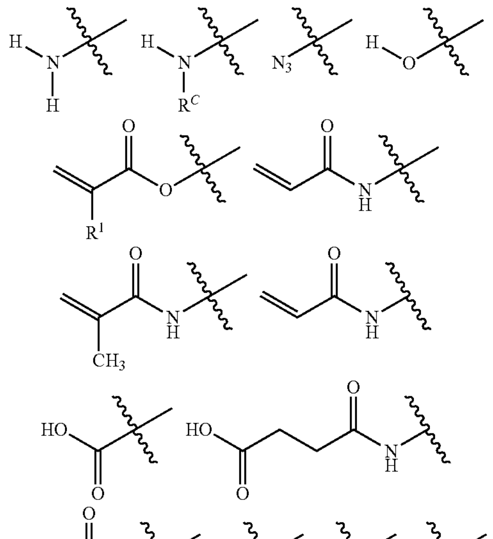

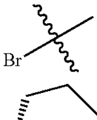

and

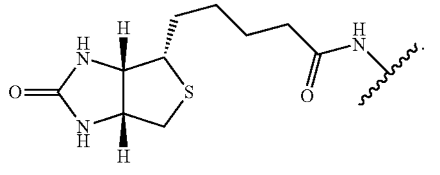

In some embodiments, "〰" refers to the connection between A1 and $L^1$.

In some embodiments, A is A2. In some embodiments, A2 is alkyl, alkenyl, alkynyl, heteroalkyl, cycloalkyl, heterocyclyl, aryl, heteroaryl, —O—, —C(O)O—, —C(O)—, —OC(O)—, —$N(R^C)$—, —$N(R^C)C(O)$—, —$C(O)N(R^C)$—, —$N(R^C)N(R^D)$—, —NCN—, —$C(=N(R^C)(R^D))O$—, —S—, —$S(O)_x$—, —$OS(O)_x$—, —$P(R^F)_y$—, —$Si(OR^A)_2$—, —$Si(R^G)(OR^A)$, —$B(OR^A)$—, or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted with one or more $R^1$.

In some embodiments, A2 is O. In some embodiments, A2 is —C(O)O—. In some embodiments, A2 is —C(O)—. In some embodiments, A2 is —OC(O)—. In some embodiments, A2 is S.

In some embodiments, A2 is alkyl, alkenyl, alkynyl, or heteroalkyl (e.g., $C_1$-$C_{12}$ alkyl, $C_2$-$C_{12}$ alkenyl, $C_2$-$C_{12}$ alkynyl, or $C_1$-$C_{12}$ heteroalkyl). In some embodiments, A2 is unsubstituted alkyl, unsubstituted alkenyl, unsubstituted alkynyl, or unsubstituted heteroalkyl. In some embodiments, A2 is substituted alkyl, substituted alkenyl, substituted alkynyl, or substituted heteroalkyl, each of which is substituted with one or more $R^1$.

In some embodiments, A2 is methyl, ethyl, propyl, butyl, pentyl, or hexyl. In some embodiments, A2 is unsubstituted methyl, unsubstituted ethyl, unsubstituted propyl, unsubstituted butyl, unsubstituted pentyl, or unsubstituted hexyl. In some embodiments, A2 is substituted methyl, substituted ethyl, substituted propyl, substituted butyl, substituted pentyl, or substituted hexyl, each of which is substituted with one or more $R^1$.

In some embodiments, A2 is —$N(R^C)$—. In some embodiments, A2 is —$N(R^C)$—, wherein $R^C$ is hydrogen or alkyl. In some embodiments, A2 is —NH—. In some embodiments, A2 is NH— or $NH(C(O)C(CH_3)CH_2$—.

In some embodiments, A2 is —$S(O)_x$— or —$OS(O)_x$— (e.g., wherein x is 2).

In some embodiments, A2 is —$Si(OR^A)_2$— (e.g., —$Si(OH)_2$—, —$Si(OCH_3)_2$—, or —$Si(OCH_2CH_3)_2$—).

In some embodiments, A2 is cycloalkyl (e.g., a 3-membered cycloalkyl, 4-membered cycloalkyl, 5-membered cycloalkyl, 6-membered cycloalkyl). In some embodiments, A2 is heterocyclyl (e.g., a 3-membered heterocyclyl, 4-membered heterocyclyl, 5-membered heterocyclyl, 6-membered heterocyclyl). In some embodiments, A2 is a nitrogen-containing heterocyclyl (e.g., a 3-membered nitrogen-containing heterocyclyl, 4-membered nitrogen-containing heterocyclyl, 5-membered nitrogen-containing heterocyclyl, 6-membered nitrogen-containing heterocyclyl). In some embodiments, A2 is a 5-membered nitrogen-containing heterocyclyl. In some embodiments, A2 is an oxygen-containing heterocyclyl (e.g., a 3-membered oxygen-containing heterocyclyl, 4-membered oxygen-containing heterocyclyl, 5-membered oxygen-containing heterocyclyl, 6-membered oxygen-containing heterocyclyl). In some embodiments, A2 is a 3-membered oxygen-containing heterocyclyl (e.g., oxiranyl).

In some embodiments, A2 is aryl (e.g., phenyl). In some embodiments, A2 is phenyl substituted with 1-2 $R^1$ (e.g., —$OR^A$ or —$B(OR^A)_2$). In some embodiments, A2 is phenyl substituted with —$OR^A$ (e.g., OH) or —$B(OR^A)_2$ (e.g., —$B(OH)_2$).

In some embodiments, A2 is heteroaryl (e.g., 5-membered heteroaryl, 6-membered heteroaryl). In some embodiments, A2 is a nitrogen-containing heteroaryl (e.g., 5-membered nitrogen-containing heteroaryl, 6-membered nitrogen-containing heteroaryl). In some embodiments, A2 is a 6-membered nitrogen-containing heteroaryl (e.g., imidazolyl).

In some embodiments, A2 is a metal (e.g., Fe, Ti, Au, Ni, Ca) or a metal alloy or mixture (e.g., stainless steel, alumina, Ni—Ti).

In some embodiments, A2 is selected from:

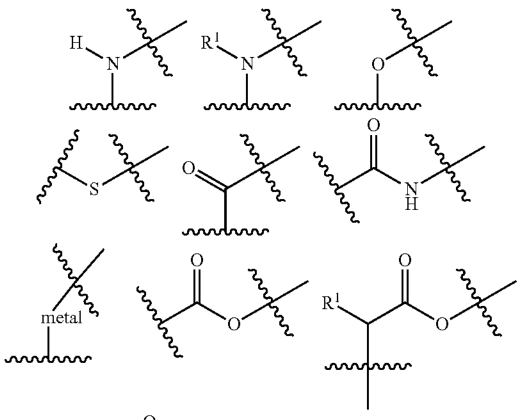

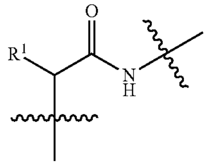

and

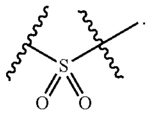

In some embodiments, "" refers to the connections between A2 and $L^1$ and an attachment group (e.g., as described herein).

In some embodiments, at least one of $L^1$, $L^2$, and $L^3$ is a bond. In some embodiments, at least two of $L^1$, $L^2$, and $L^3$ is a bond. In some embodiments, each of $L^1$, $L^2$, and $L^3$ is a bond.

In some embodiments, at least one of $L^1$, $L^2$, and $L^3$ is alkyl. In some embodiments, at least two of $L^1$, $L^2$, and $L^3$ is alkyl. In some embodiments, each of $L^1$, $L^2$, and $L^3$ is alkyl. In some embodiments, alkyl is an unsubstituted alkyl. In some embodiments, alkyl is a substituted alkyl (e.g., alkyl substituted with one or more $R^2$, wherein $R^2$ is as described herein).

In some embodiments, alkyl is a $C_1$-$C_{12}$ alkyl. In some embodiments, alkyl is a $C_1$-$C_8$ alkyl. In some embodiments, alkyl is a $C_1$-$C_4$ alkyl. In some embodiments, alkyl is a $C_1$ alkyl (e.g., unsubstituted $C_1$ alkyl, substituted $C_1$ alkyl (e.g., —$C(R^2)_2$) wherein $R^2$ is as described herein (e.g., each $R^2$ is independently selected from the group: hydrogen, alkyl, aryl, oxo, and heteroaryl; or two $R^2$ together with the atom to which they are attached form a ring). In some embodiments, alkyl is a $C_2$ alkyl (e.g., unsubstituted $C_2$ alkyl, substituted $C_2$ alkyl). In some embodiments, alkyl is a $C_3$ alkyl (e.g., unsubstituted $C_3$ alkyl, substituted $C_3$ alkyl). In some embodiments, alkyl is a $C_4$ alkyl (e.g., unsubstituted $C_4$ alkyl, substituted $C_4$ alkyl).

In some embodiments, alkyl is substituted, for example by at least one $R^2$ group. In some embodiments, each $R^2$ is independently selected from the group of hydrogen, alkyl, aryl, oxo, and heteroaryl. In some embodiments, two $R^A$ groups together with the atom to which they are attached form a ring. In some embodiments, one $R^2$ group together with an atom of M, P, or Z (e.g., M, P, or Z as described herein) form a ring.

In some embodiments, at least one of $L^1$, $L^2$, and $L^3$ is heteroalkyl. In some embodiments, at least two of $L^1$, $L^2$, and $L^3$ is heteroalkyl. In some embodiments, each of $L^1$, $L^2$, and $L^3$ is heteroalkyl. In some embodiments, heteroalkyl is a $C_1$-$C_{12}$ heteroalkyl. In some embodiments, heteroalkyl is a $C_1$-$C_8$ heteroalkyl. In some embodiments, heteroalkyl is a $C_1$-$C_4$ heteroalkyl.

In some embodiments, heteroalkyl is an unsubstituted heteroalkyl. In some embodiments, heteroalkyl is a substituted heteroalkyl (e.g., heteroalkyl substituted with one or more $R^2$ groups, wherein $R^2$ is as described herein). In some embodiments, $R^2$ is hydrogen, alkyl, aryl, or heteroaryl. In some embodiments, the substituted heteroalkyl comprises a carbonyl group (e.g., an amide, ester, or keto). In some embodiments, one $R^2$ group together with an atom of M, P, or Z (e.g., M, P, or Z as described herein) form a ring.

In some embodiments, the heteroalkyl comprises 1 or more heteroatoms. In some embodiments, the heteroalkyl comprises an oxygen, sulfur, nitrogen, boron, silicon, or phosphorus atom. In some embodiments, the heteroalkyl comprises an oxygen, sulfur, or nitrogen atom. In some embodiments, the heteroalkyl comprises an oxygen atom. In some embodiments, the heteroalkyl is —$C(R^2)O$, wherein $R^2$ is as described herein). In some embodiments, the heteroalkyl is —$CH_2O$.

In some embodiments, heteroalkyl comprises a polyethylene glycol (PEG) group. For example in some embodiments, heteroalkyl is —$(CH_2)_m$—$(OCH_2CH_2)_n$—), wherein each of m and n is an integer independently selected from 0 to 100 (e.g., 0 to 75, 0 to 50, 0 to 20, 0 to 10, or 0 to 5).

In some embodiments, at least one of $L^1$, $L^2$, or $L^3$ is independently a heteroalkyl selected from:

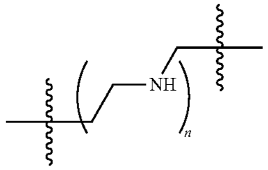

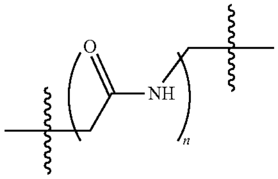

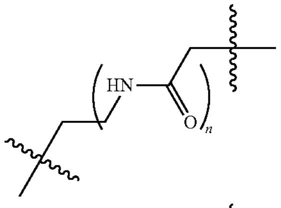

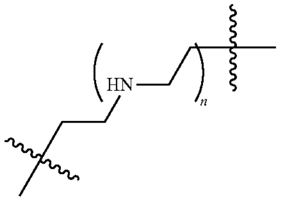

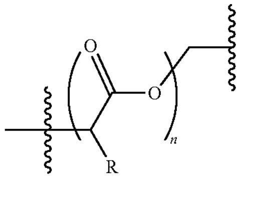

-continued
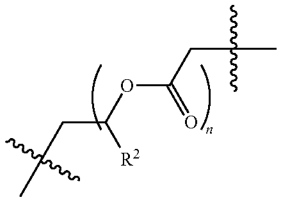
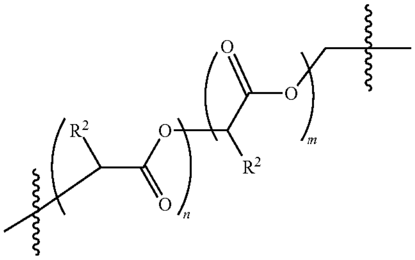
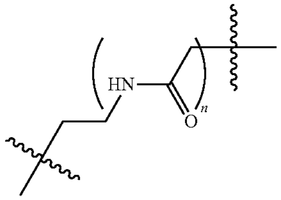
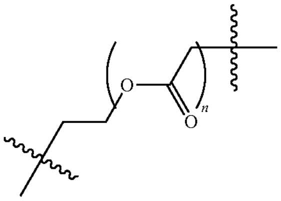
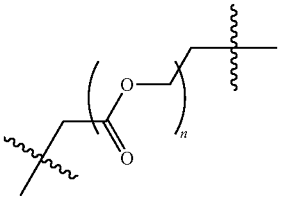
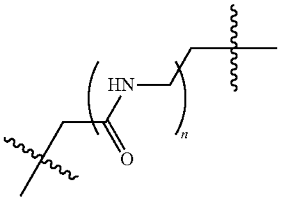
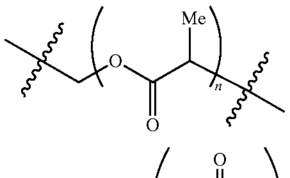
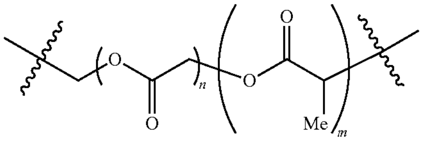
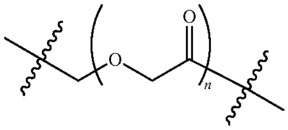
and
-continued
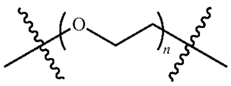
wherein each of m and n is independently an integer selected from 0 to 100 (e.g., 0 to 75, 0 to 50, 0 to 20, 0 to 10, or 0 to 5.
In some embodiments, each of $L^1$, $L^2$, or $L^3$ is independently a heteroalkyl selected from:
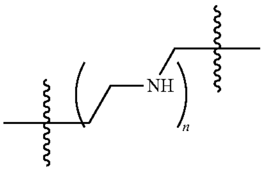
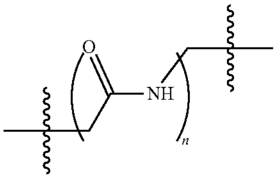
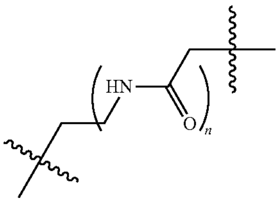
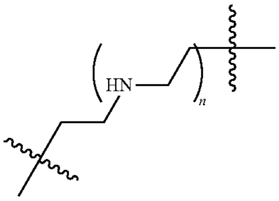
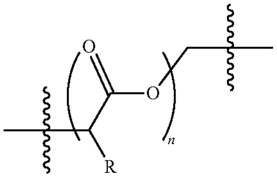
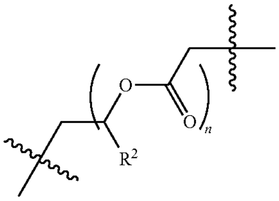
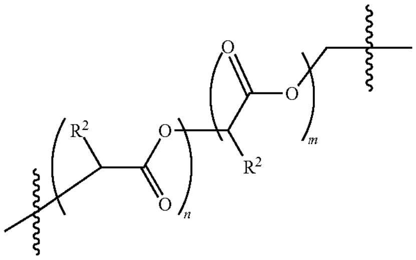

-continued

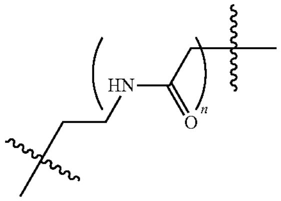

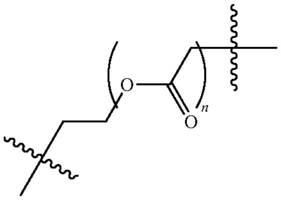

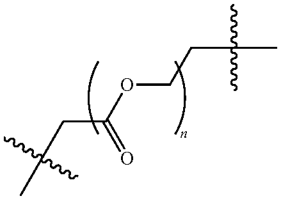

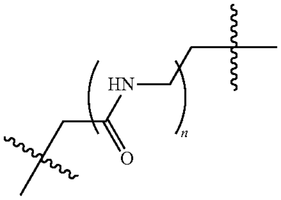

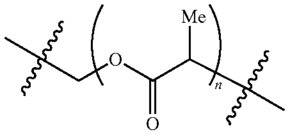

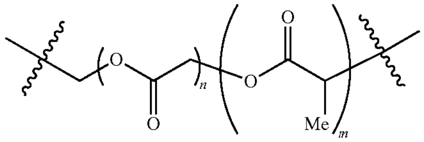

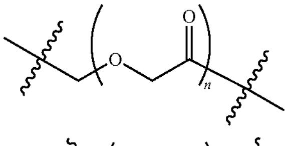

and

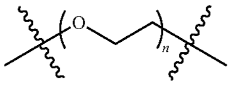

wherein each of m and n is independently an integer selected from 0 to 100 (e.g., 0 to 75, 0 to 50, 0 to 20, 0 to 10, or 0 to 5.

In some embodiments, each of $L^1$, $L^2$, or $L^3$ is independently a heteroalkyl selected from:

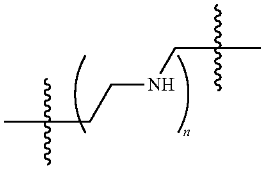

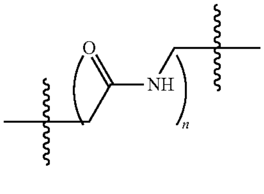

-continued

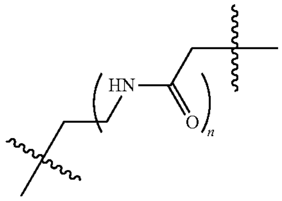

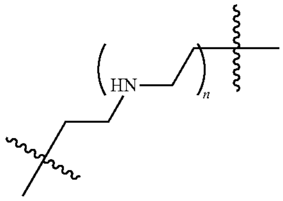

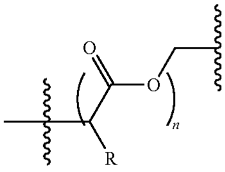

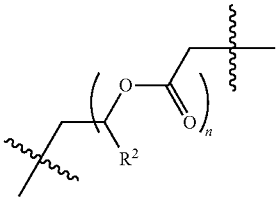

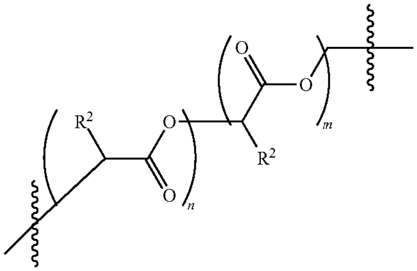

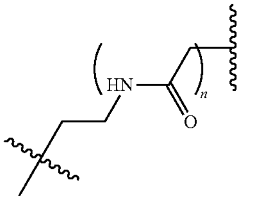

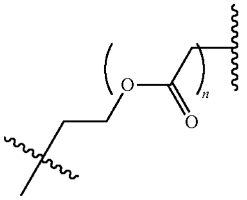

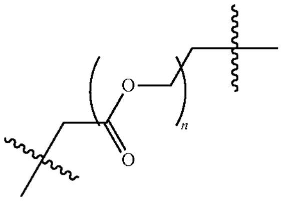

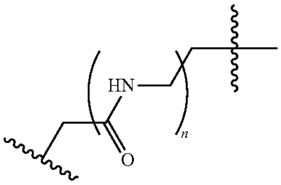

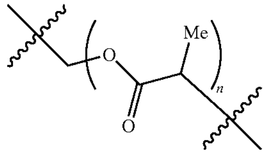

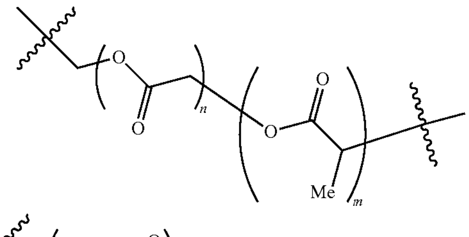

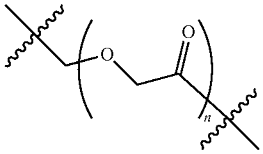

and

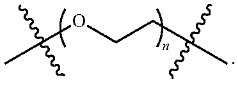

.

In some embodiments, "~" refers to the connections between each of $L^1$, $L^2$, and $L^3$ and A, M, P, or Z.

In some embodiments, at least one of $L^1$, $L^2$, and $L^3$ is heteroalkyl. In some embodiments, the heteroalkyl comprises a positive charge (e.g., a quaternary amine). In some embodiments, the heteroalkyl comprises a negative charge (e.g., a carboxylate, sulfonate, or phosphinate). In some embodiments, the heteroalkyl is a zwitterion (e.g., a neutral molecule comprising both a positive and negative charge). In some embodiments, the heteroalkyl comprises a quaternary amine and a carboxylate.

In some embodiments, each of $L^1$, $L^2$, or $L^3$ is independently a zwitterionic heteroalkyl selected from:

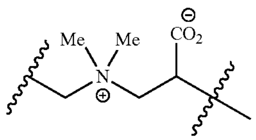

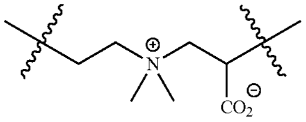

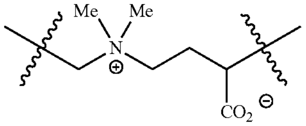

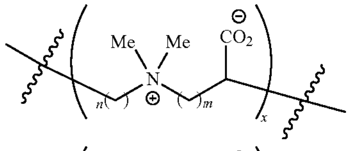

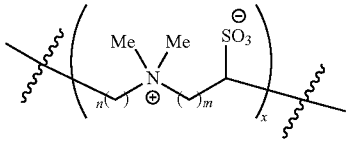

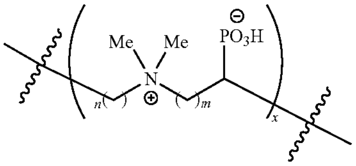

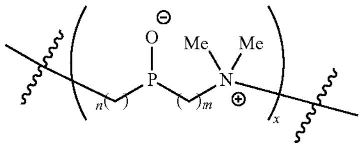

wherein each of x, m and n is independently an integer selected from 0 to 100 (e.g., 0 to 75, 0 to 50, 0 to 20, 0 to 10, or 0 to 5).

In some embodiments, at least one of $L^1$, $L^2$, or $L^3$ is independently substituted with $R^2$. In some embodiments, $R^2$ is oxo, halo, or alkyl (e.g., wherein alkyl may be optionally substituted by $R^7$). In some embodiments, at least one of $L^1$, $L^2$, or $L^3$ is not independently substituted with $R^2$. In some embodiments, $R^2$ is oxo, halo, or alkyl (e.g., wherein alkyl may be optionally substituted by $R^7$). In some embodiments, $L^1$ is not substituted with $R^2$ (e.g., oxo, halo, or alkyl (e.g., wherein alkyl may be optionally substituted by $R^7$). In some embodiments, $L^2$ is not substituted with $R^2$ (e.g., oxo, halo, or alkyl (e.g., wherein alkyl may be optionally substituted by $R^7$). In some embodiments, $L^3$ is not substituted with $R^2$ (e.g., oxo, halo, or alkyl (e.g., wherein alkyl may be optionally substituted by $R^7$).

As generally described herein, M refers to an alkyl, heteroalkyl, cycloalkyl, heterocyclyl, aryl, or heteroaryl, each of which is optionally substituted with one or more $R^3$.

In some embodiments, M is alkyl. In some embodiments, M is unsubstituted alkyl. In some embodiments, M is substituted alkyl (e.g., alkyl substituted with one or more $R^3$ groups, wherein $R^3$ is as described herein).

In some embodiments, M is $C_1$-$C_{12}$ alkyl. In some embodiments, M is $C_1$-$C_8$ alkyl. In some embodiments, M is a $C_1$-$C_4$ alkyl. In some embodiments, M is $C_1$ alkyl (e.g., unsubstituted $C_1$ alkyl, substituted $C_1$ alkyl (e.g., —$C(R^3)_2$) wherein $R^3$ is as described herein (e.g., each $R^3$ is independently selected from alkyl, aryl, halogen, oxo, and heteroaryl; or two $R^3$ together with the atom to which they are attached form a ring). In some embodiments, M is $C_2$ alkyl (e.g., unsubstituted $C_2$ alkyl, substituted $C_2$ alkyl). In some embodiments, M is $C_3$ alkyl (e.g., unsubstituted $C_3$ alkyl, substituted $C_3$ alkyl). In some embodiments, M is $C_4$ alkyl (e.g., unsubstituted $C_4$ alkyl, substituted $C_4$ alkyl).

In some embodiments, M is substituted by one or more $R^3$. In some embodiments, each $R^3$ is independently alkyl, halogen, oxo, cycloalkyl, heterocyclyl, aryl, and heteroaryl. In some embodiments, one $R^3$ group together with an atom of M, P, or Z (e.g., M, P, or Z as described herein) forms a ring.

In some embodiments, M is $C_1$-$C_{12}$ heteroalkyl. In some embodiments, M is $C_1$-$C_5$ heteroalkyl. In some embodiments, M is a $C_1$-$C_4$ heteroalkyl. In some embodiments, heteroalkyl is unsubstituted or substituted by one or more $R^3$. In some embodiments, each $R^3$ is independently selected from alkyl, halogen, aryl, oxo, and heteroaryl; or two $R^3$ together with the atom to which they are attached form a ring. In some embodiments, M is $C_3$ heteroalkyl (e.g., unsubstituted $C_3$ heteroalkyl, substituted $C_3$ heteroalkyl). In some embodiments, M is $C_4$ heteroalkyl (e.g., unsubstituted $C_4$ heteroalkyl, substituted $C_4$ heteroalkyl). In some embodiments, M is $C_5$ heteroalkyl (e.g., unsubstituted $C_5$ heteroalkyl, substituted $C_5$ heteroalkyl). In some embodiments, M is $C_6$ heteroalkyl (e.g., unsubstituted $C_6$ heteroalkyl, substituted $C_6$ heteroalkyl).

In some embodiments, the heteroalkyl comprises 1 or more heteroatoms. In some embodiments, the heteroalkyl comprises an oxygen, sulfur, nitrogen, boron, silicon, or phosphorus atom. In some embodiments, the heteroalkyl comprises an oxygen, sulfur, or nitrogen atom. In some embodiments, the heteroalkyl comprises an oxygen atom. In some embodiments, heteroalkyl comprises a polyethylene glycol (PEG) group. For example in some embodiments, heteroalkyl is $-(CH_2)_m-(OCH_2CH_2)_n-$) wherein each m and n is an integer independently selected from 0 to 100 (e.g., 0 to 75, 0 to 50, 0 to 20, 0 to 10, or 0 to 5). In some embodiments, M is a heteroalkyl selected from:

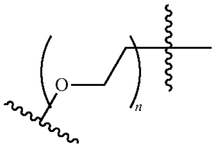

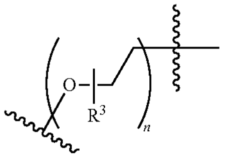

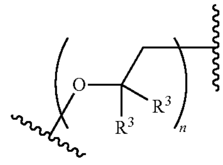

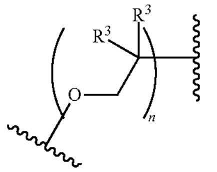

-continued

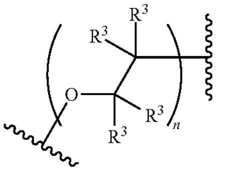

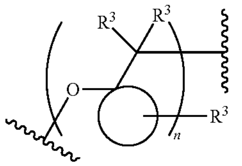

spiro

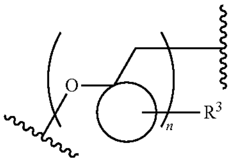

and spiro

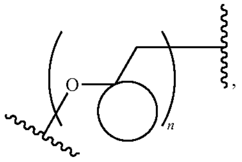

spiro wherein each n is an integer independently selected from 0 to 100 (e.g., 0 to 75, 0 to 50, 0 to 20, 0 to 10, or 0 to 5) and each $R^3$ is independently described herein.

In some embodiments, "" refers to the connections between M and $L^1$ and $L^2$.

In some embodiments, M is:

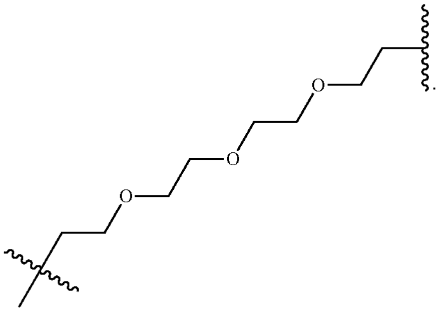 [SMILES: *CCOCCOCCOCC*]

In some embodiments, M is cycloalkyl, heterocyclyl, aryl, or heteroaryl. In some embodiments, M is unsubstituted cycloalkyl, unsubstituted heterocyclyl, unsubstituted aryl, or unsubstituted heteroaryl. In some embodiments, M is substituted cycloalkyl, unsubstituted heterocyclyl, unsubstituted aryl, or unsubstituted heteroaryl (e.g., substituted with one or more $R^3$, wherein $R^3$ is as described herein). In some embodiments, M is a 3 to 12-membered ring. In some embodiments, M is a 3 to 7-membered ring. In some embodiments, M is a 5-membered ring. In some embodiments, M is a 5-membered ring.

In some embodiments, M is aryl (e.g., phenyl). In some embodiments, M is phenyl optionally substituted by 1-4 $R^3$. In some embodiments, $R^3$ is halo or alkyl (e.g., wherein alkyl is optionally substituted by $R^7$). In some embodiments, M is selected from:

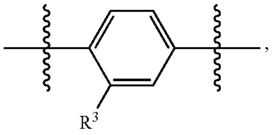

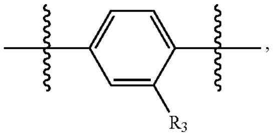

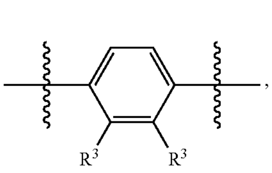

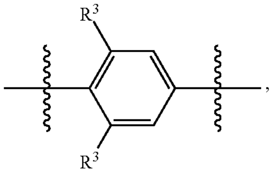

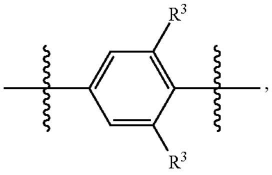

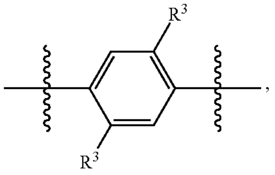

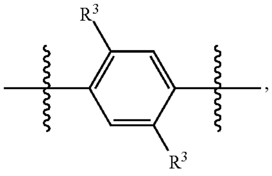

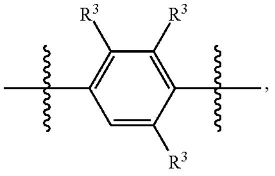

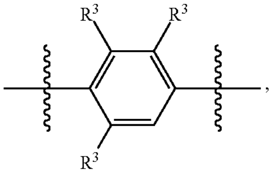

and

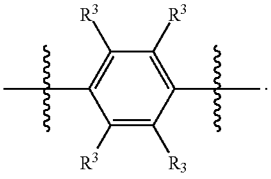

In some embodiments, M is selected from:

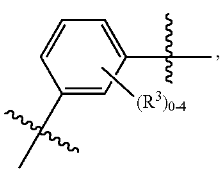

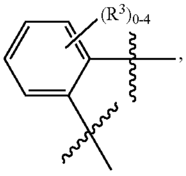

and

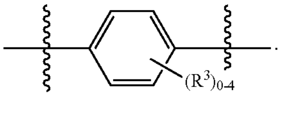

In some embodiments, M is cycloalkyl. In some embodiments, M is selected from:

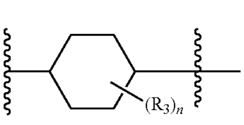

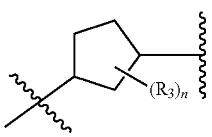

and

-continued

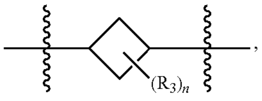, wherein each n is an integer independently selected from 0 to 10 and each $R^3$ is independently described herein.

In some embodiments, M is heterocyclyl. In some embodiments, heterocyclyl comprises an oxygen, sulfur, nitrogen, boron, silicon, or phosphorus atom. In some embodiments, heterocyclyl comprises an oxygen, sulfur, or nitrogen atom. In some embodiments, M is an oxygen-containing heterocyclyl). In some embodiments, M is oxiranyl, dioxiranyl, oxetanyl, dioxetanyl, tetrahydrofuranyl, dioxolanyl, oxanyl, dioxanyl, trioxanyl, or oxepanyl. In some embodiments, M is selected from:

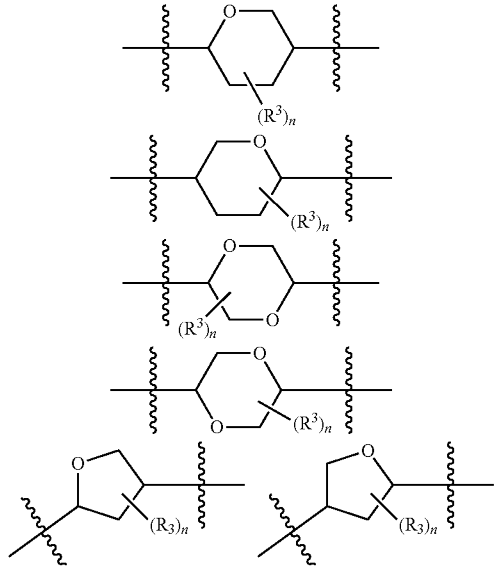

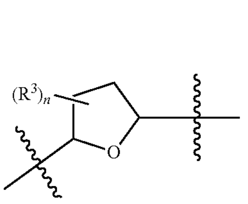 and 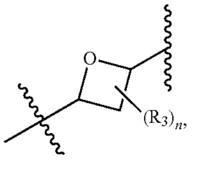

wherein each n is an integer independently selected from 0 to 10 and each $R^3$ is independently described herein.

In some embodiments, M is:

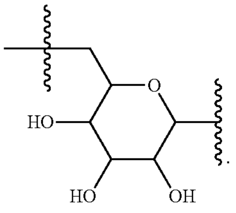 [SMILES: *CC1OC(*)C(O)C(O)C1O].

In some embodiments, M is nitrogen-containing heterocyclyl. In some embodiments, M is aziridinyl, azetidinyl, diazetidinyl, pyrrolidinyl, imidazolyl, oxazolidinyl, isoxazolidinyl, piperazolidinyl, piperazinyl, piperidinyl, or homopiperazinyl. In some embodiments, M is selected from:

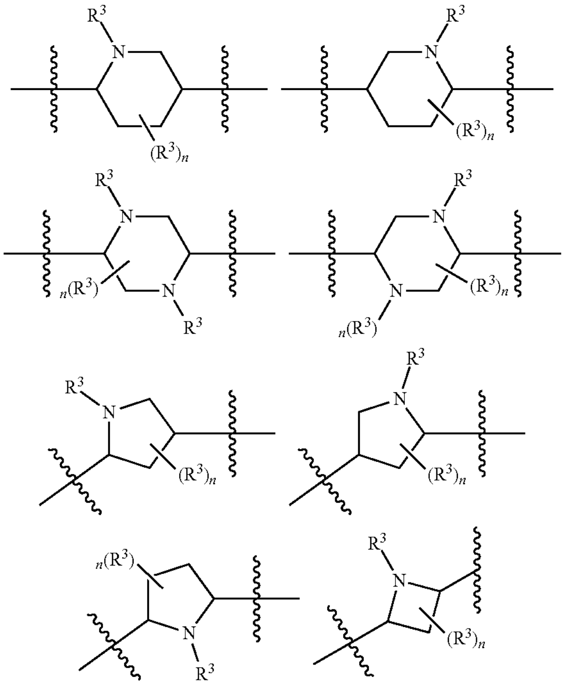

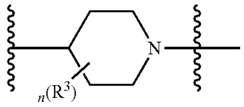 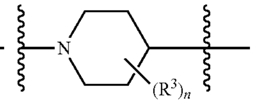 and

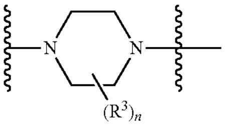, wherein each n is an integer independently selected from 0 to 10 and each $R^3$ is independently described herein.

In some embodiments, M is heteroaryl. In some embodiments, M is furanyl, pyrrolyl, thiofuranyl, oxazolyl, isoxazolyl, oxaziridinyl, thiadiazolyl, triazolyl, tetrazolyl, pyridyl, pyrazinyl, or pyrimidinyl. In some embodiments, M is selected from:

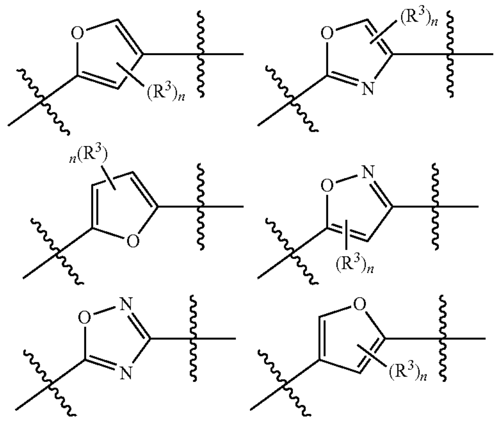

-continued

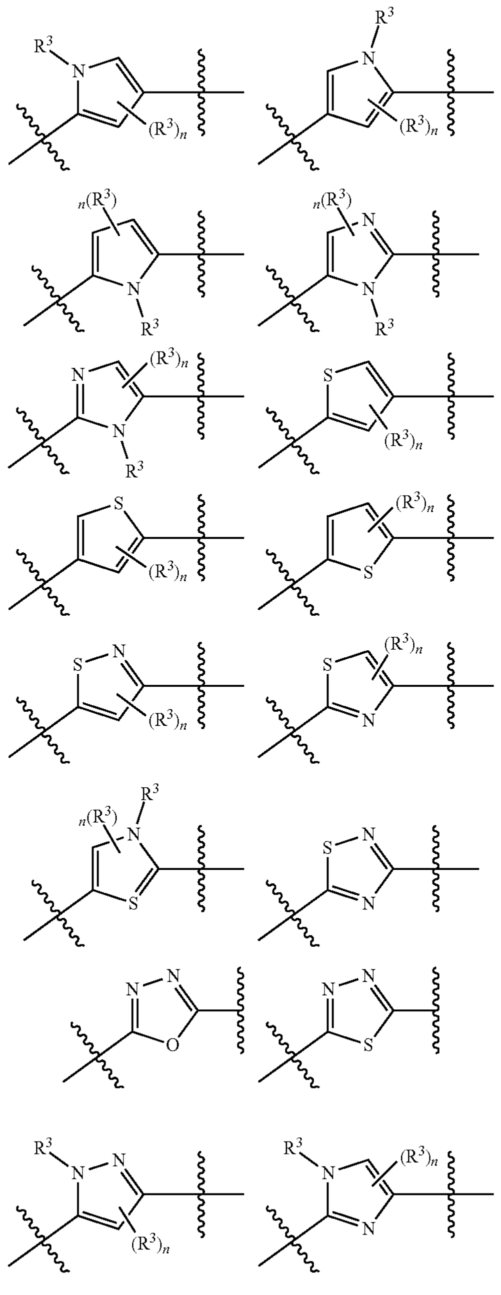

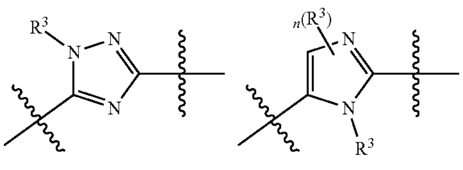

and

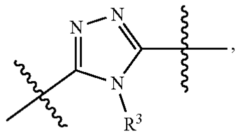

, wherein each n is an integer independently selected from 0 to 10 and each $R^3$ is independently described herein.

In some embodiments, M is selected from:

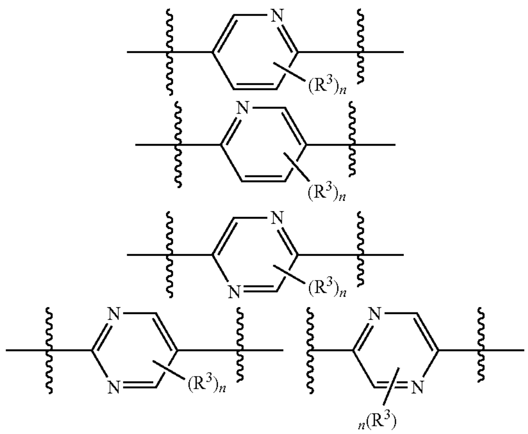

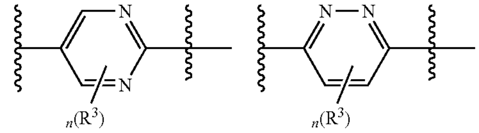

and

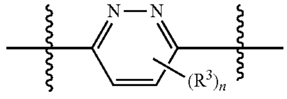

, wherein each n is an integer independently selected from 0 to 10 and each $R^3$ is independently described herein.

As generally described herein, P refers to alkyl, heteroalkyl, cycloalkyl, heterocyclyl, aryl, or heteroaryl, each of which is optionally substituted with one or more $R^4$.

In some embodiments, P refers to a ring. In some embodiments, the ring is a 3 to 12-membered ring. In some embodiments, P is a cycloalkyl, heterocyclyl, aryl, or heteroaryl ring. In some embodiments, P is a 3 to 12-membered ring. In some embodiments, P is a 3 to 7-membered ring. In some embodiments, P is a 5-membered ring.

In some embodiments, P is cycloalkyl. In some embodiments, P is unsubstituted cycloalkyl or substituted cycloalkyl (e.g., substituted by one or more $R^4$). In some embodiments, P is a 4-membered cycloalkyl, 5-membered cycloalkyl, 6-membered cycloalkyl, 7-membered cycloalkyl, or 8-membered cycloalkyl. In some embodiments, P is trans-cyclooctene.

In some embodiments, P is heterocyclyl. In some embodiments, P is unsubstituted heterocyclyl or substituted heterocyclyl (e.g., substituted by one or more $R^4$). In some embodiments, P is a heterocyclyl comprising an oxygen, sulfur, nitrogen, boron, silicon, or phosphorus atom. In some embodiments, P is a heterocyclyl comprising an oxygen, sulfur, or nitrogen atom. In some embodiments, P is a 4-membered heterocyclyl, 5-membered heterocyclyl, 6-membered heterocyclyl, 7-membered heterocyclyl, or 8-membered heterocyclyl.

In some embodiments, P is aryl. In some embodiments, P is unsubstituted aryl or substituted aryl (e.g., substituted by one or more $R^4$). In some embodiments, P is 6-membered aryl (e.g., phenyl). In some embodiments, P is aryl substituted by 1-5 $R^4$. In some embodiments, P is a fused aryl ring (e.g., dibenzocyclooctyne).

In some embodiments, P is heteroaryl. In some embodiments, P is unsubstituted heteroaryl or substituted heteroaryl (e.g., substituted by one or more $R^4$). In some embodiments, P is a 3 to 12-membered heteroaryl ring. In some embodiments, P is a 3 to 7-membered heteroaryl ring. In some embodiments, P is heteroaryl comprising a nitrogen, oxygen, or sulfur atom. In some embodiments, P is a nitrogen-containing heteroaryl. In some embodiments, P is tetrazolyl, imidazolyl, pyrazolyl, or pyrrolyl.

In some embodiments, P is a 6-membered heteroaryl (e.g., P comprises tetrazine). In some embodiments, P is a 5-membered heteroaryl.

Exemplary heteroaryls include:

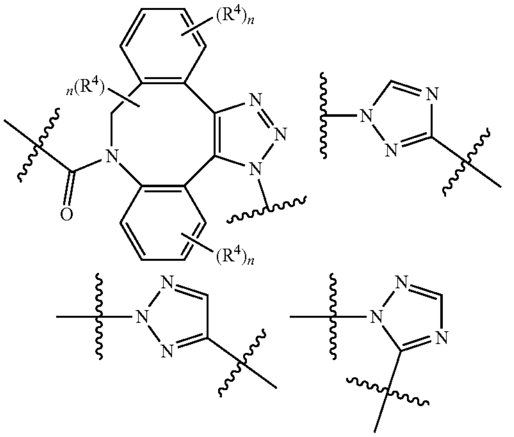

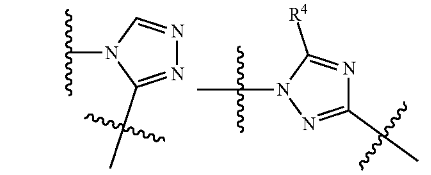

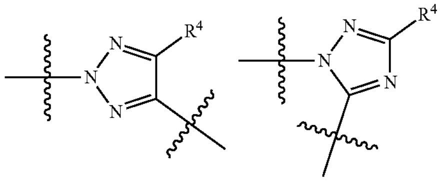

and

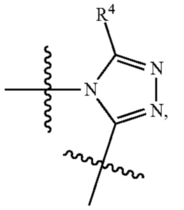

wherein wherein each n is an integer independently selected from 0 to 10 and each $R^4$ is independently described herein.

In some embodiments, the heteroaryl is a tetrazole, e.g., a tetrazole represented by

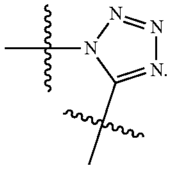

In some embodiments, the heteroaryl is an imidazole or pyrazole, e.g., an imidazole or pyrazole represented by:

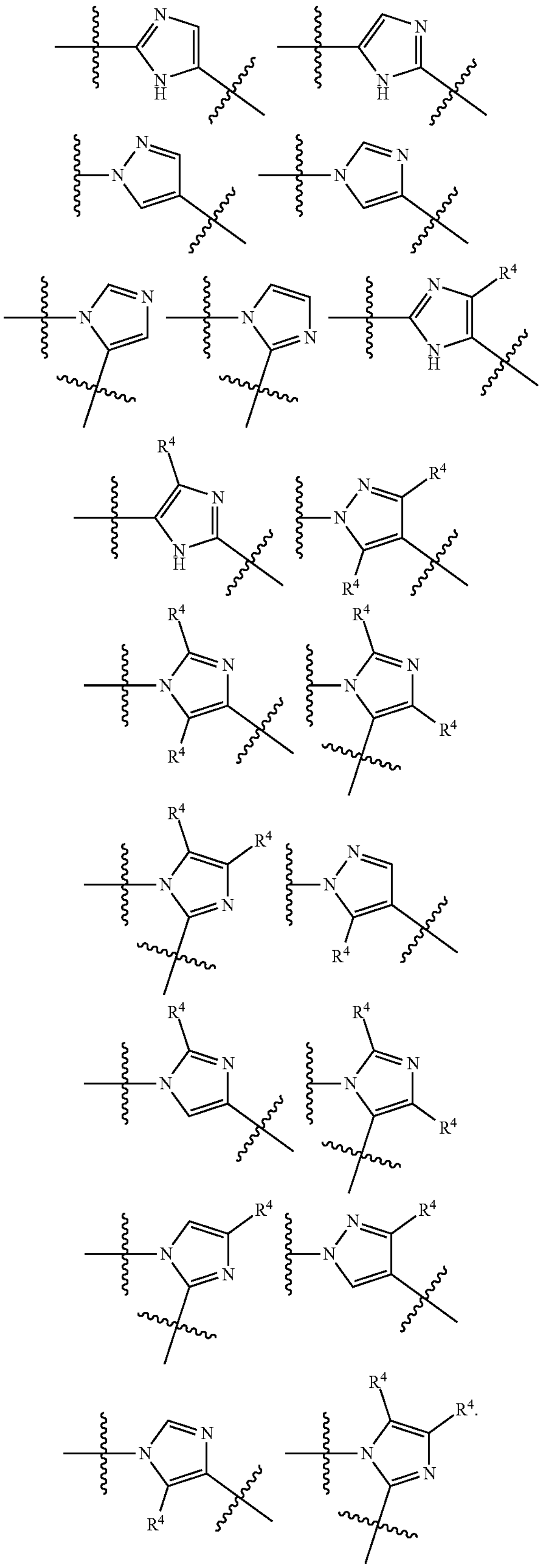

In some embodiments, the heteroaryl is selected from the group:

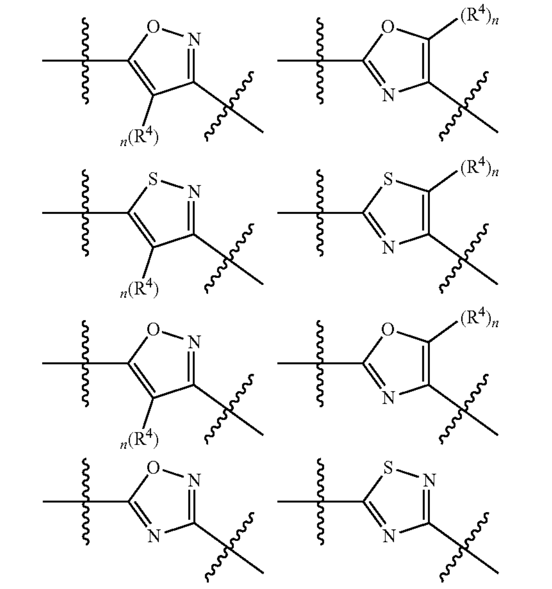

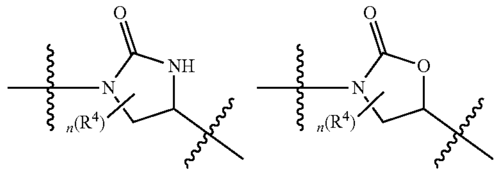

and

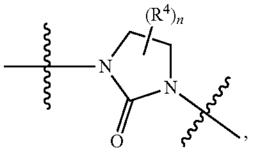

wherein each n is an integer independently selected from 0 to 5 and each $R^4$ is independently described herein.

In some embodiments, the heteroaryl is pyrrole. For example, the heteroaryl is a pyrrole, e.g., a pyrrole represented by

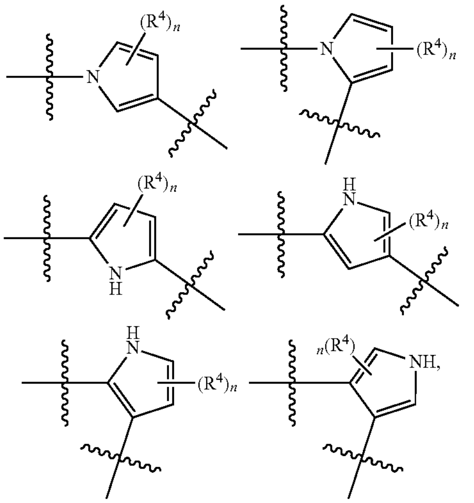

wherein each n is an integer independently selected from 0 to 5 and each $R^4$ is independently described herein.

In some embodiments, the heteroaryl is a fused heteroaryl. Exemplary fused heteroaryls include:

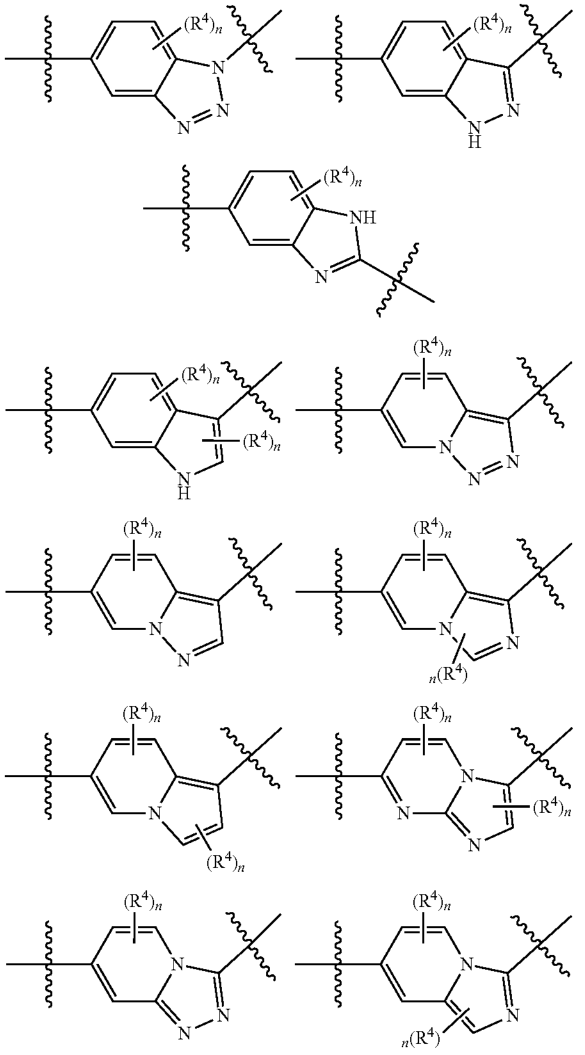

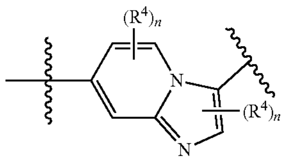

and

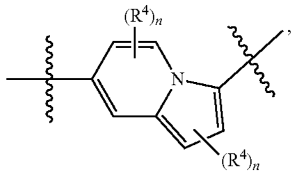

wherein each n is an integer independently selected from 0 to 5 and each $R^4$ is independently described herein.

In some embodiments, P is a triazole (e.g., a 1,2,3-triazole or 1,2,4-triazole). In some embodiments, P is a triazole of the formula (P-2):

(P-2)

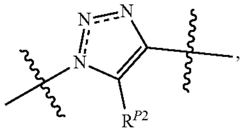

wherein: $R^{P2}$ is hydrogen, halogen, cyano, nitro, alkyl, alkenyl, alkynyl, carbocyclyl, heterocyclyl, aryl, heteroaryl, $—OR^{P20}$, $—SR^{P20}$, $—N(R^{P20})_2$, $—OC(═O)R^{P20}$, $—OC(═O)OR^{P20}$, $—OC(═O)SR^{P20}$, $—OC(═O)N(R^{P20})_2$, $—SC(═O)R^{P21}$, $—SC(═O)OR^{P20}$, $—SC(═O)SR^{P20}$, $—SC(═O)N(R^{P20})_2$, $—NHC(═O)R^{P20}$, $—NHC(═O)OR^{P20}$, $—NHC(═O)SR^{P20}$, $—NHC(═O)N(R^{P20})_2$, $—OS(═O)_2R^{P21}$, $—OS(═O)_2OR^{P20}$, $—S—S(═O)_2R^{P21}$, $—S—S(═O)_2OR^{P20}$, $—S(═O)R^{P21}$, $—SO_2R^{P21}$, or $—S(═O)_2OR^{P20}$, wherein each instance of $R^{P20}$ is independently hydrogen, alkyl, alkenyl, alkynyl, carbocyclyl, heterocyclyl, aryl, heteroaryl, or two $R^{P20}$ groups are joined to form an heterocyclic or heteroaryl ring; and $R^{P21}$ is alkyl, alkenyl, alkynyl, carbocyclyl, heterocyclyl, aryl, or heteroaryl; and ═ represents a single or double bond, wherein one ═ is a double bond, and the other ═ is a single bond.

In some embodiments, P is a triazole of the formula (P-3):

(P-3)

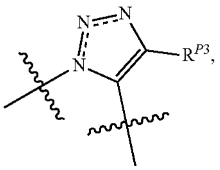

wherein: $R^{P3}$ is hydrogen, halogen, cyano, nitro, alkyl, alkenyl, alkynyl, carbocyclyl, heterocyclyl, aryl, heteroaryl, $—OR^{P20}$, $—SR^{P20}$, $—N(R^{P20})_2$, $—OC(═O)R^{P20}$, $—OC(═O)OR^{P20}$, $—OC(═O)SR^{P20}$, $—OC(═O)N(R^{P20})_2$, $—SC(═O)R^{P21}$, $—SC(═O)OR^{P20}$, $—SC(═O)SR^{P20}$, $—SC(═O)N(R^{P20})_2$, $—NHC(═O)R^{P20}$, $—NHC(═O)OR^{P20}$, $—NHC(═O)SR^{P20}$, $—NHC(═O)N(R^{P20})_2$, $—OS(═O)_2R^{P21}$, $—OS(═O)_2OR^{P20}$, $—S—S(═O)_2R^{P21}$, $—S—S(═O)_2OR^{P20}$, $—S(═O)R^{P21}$, $—SO_2R^{P21}$, or $—S(═O)_2OR^{P20}$, wherein each instance of $R^{P20}$ is independently hydrogen, alkyl, alkenyl, alkynyl, carbocyclyl, heterocyclyl, aryl, heteroaryl, or two $R^{P20}$ groups are joined to form an heterocyclic or heteroaryl ring; and $R^{P21}$ is alkyl alkenyl, alkynyl, carbocyclyl, heterocyclyl, aryl, or heteroaryl; and ═ represents a single or double bond, wherein one ═ is a double bond, and the other ═ is a single bond.

Exemplary triazoles include:

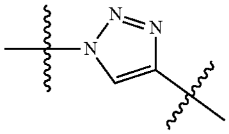
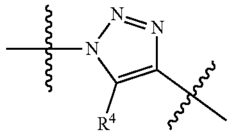
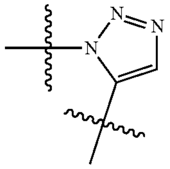
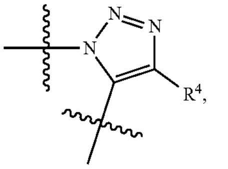

wherein $R^4$ is as described herein. In some embodiments, P is a triazole and $R^4$ is alkyl, aryl or heteroaryl, or $R^4$ together with an atom of $L^2$ or $L^3$ (e.g., $L^2$ and $L^3$ as described herein) form a ring. In some embodiments, P is an unsubstituted triazole.

As generally described herein, Z refers to alkyl, alkenyl, alkynyl, heteroalkyl, cycloalkyl, heterocyclyl, aryl, or heteroaryl, each of which is optionally substituted by one or more $R^5$.

In some embodiments, Z is alkyl, alkenyl, alkynyl, or heteroalkyl (e.g., $C_1$-$C_{12}$ alkyl, $C_2$-$C_{12}$ alkenyl, $C_2$-$C_{12}$ alkynyl, or $C_1$-$C_{12}$ heteroalkyl). In some embodiments, Z is unsubstituted alkyl, unsubstituted alkenyl, unsubstituted alkynyl, or unsubstituted heteroalkyl. In some embodiments, Z is substituted alkyl, substituted alkenyl, substituted alkynyl, or substituted heteroalkyl, each of which is substituted with one or more $R^5$.

In some embodiments, Z is methyl, ethyl, propyl, butyl, pentyl, or hexyl. In some embodiments, Z is unsubstituted methyl, unsubstituted ethyl, unsubstituted propyl, unsubstituted butyl, unsubstituted pentyl, or unsubstituted hexyl. In some embodiments, Z is substituted methyl, substituted ethyl, substituted propyl, substituted butyl, substituted pentyl, or substituted hexyl, each of which is substituted with one or more $R^5$.

In some embodiments, Z is heteroalkyl (e.g., unsubstituted heteroalkyl, substituted heteroalkyl). In some embodiments, the heteroalkyl comprises 1 or more heteroatoms (e.g., oxygen, sulfur, nitrogen, boron, silicon, phosphorus). In some embodiments, heteroalkyl is an unsubstituted heteroalkyl. In some embodiments, heteroalkyl is a substituted heteroalkyl (e.g., heteroalkyl substituted with one or more $R^A$ groups, wherein $R^A$ is as described herein.

In some embodiments, heteroalkyl is a $C_1$-$C_{12}$ heteroalkyl. In some embodiments, heteroalkyl is a $C_1$-$C_8$ heteroalkyl. In some embodiments, heteroalkyl is a $C_1$-$C_4$ heteroalkyl.

In some embodiments, the heteroalkyl comprises 1 or more heteroatoms. In some embodiments, the heteroalkyl comprises an oxygen, sulfur, nitrogen, boron, silicon, or phosphorus atom. In some embodiments, the heteroalkyl comprises an oxygen, sulfur, or nitrogen atom. In some embodiments, the heteroalkyl comprises a sulfur atom. In some embodiments, the heteroalkyl comprises a nitrogen atom. In some embodiments, the heteroalkyl comprises a secondary amine. In some embodiments, the heteroalkyl comprises a tertiary amine.

In some embodiments, Z is an oxygen-containing heteroalkyl or a nitrogen-containing heteroalkyl.

In some embodiments, Z is a heteroalkyl of the formula $—OR^A$, wherein $R^A$ is hydrogen, alkyl, or alkenyl. In some embodiments, Z is $—OH$, $—OCH_3$, or $—OCH_2CH_3$, $—OCH_2CF_3$, or $—OCH_2CH═CH_2$.

In some embodiments, Z is selected from:

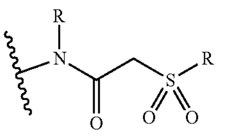
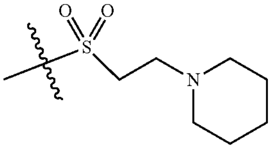
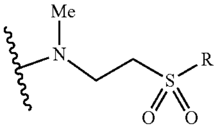
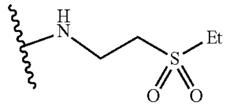

-continued

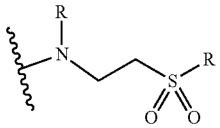

In some embodiments, Z is

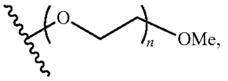

wherein n is an integer selected from 0 to 50. In some embodiments, n is an integer selected from 1 to 10 (e.g., n is 1, 2, 3, 4, 5, 6, 7, 8, 9, or 10). In some embodiments, n is an integer selected from 1, 2, 3, 4, or 5. In some embodiments, n is 1. In some embodiments, n is 2. In some embodiments, n is 3. In some embodiments, n is 4. In some embodiments, n is 5.

In some embodiments, Z is (—OCH2CH2-)zOCH$_3$, wherein z is an integer selected from 1 to 10 (e.g., z is 1, 2, 3, 4, 5, 6, 7, 8, 9, or 10). In some embodiments, z is 1. In some embodiments, z is 2. In some embodiments, z is 3. In some embodiments, z is 4. In some embodiments, z is 5. In some embodiments, z is 6. In some embodiments, z is 7. In some embodiments, z is 8. In some embodiments, z is 9. In some embodiments, z is 10.

Exemplary alkyls and heteroalkyls include:

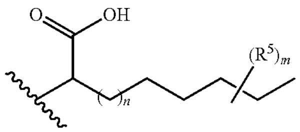

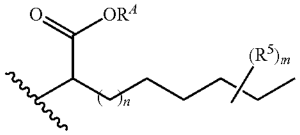

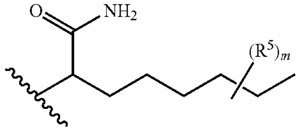

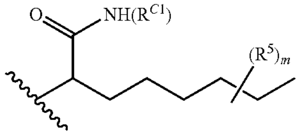

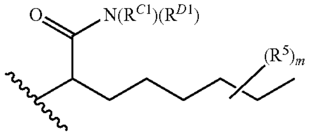

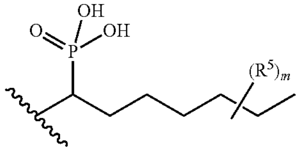

-continued

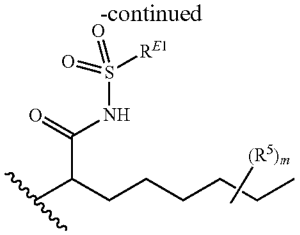

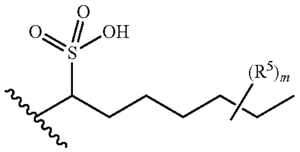

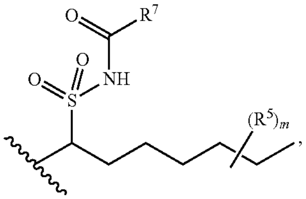

wherein each of m and n is independently an integer selected from 0 to 50.

In some embodiments, the heteroalkyl is a zwitterion (e.g., the heteroalkyl is a neutral molecule comprising both a positive and negative charge). In some embodiments, the heteroalkyl comprises a positive charge (e.g., a quaternary amine). In some embodiments, the heteroalkyl comprises a negative charge (e.g., a carboxylate, sulfonate, or phosphinate). In some embodiments, the heteroalkyl comprises a quaternary amine and a carboxylate. Exemplary zwitterionic heteroalkyl groups include, but are not limited to:

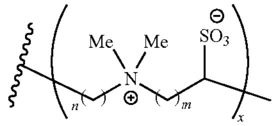

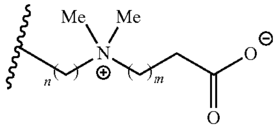

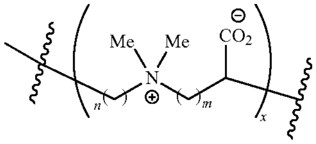

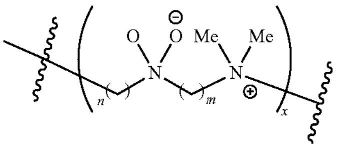

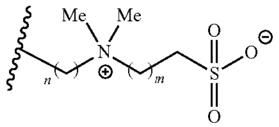

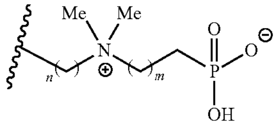

-continued

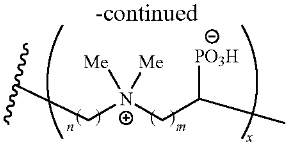

In some embodiments, Z is silyl (e.g., a silicon-containing group of the formula —$Si(R^G)_3$) wherein $R^G$ is as described herein. Exemplary silyls include:

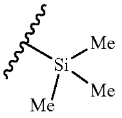
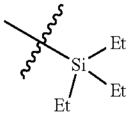
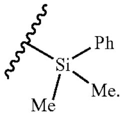

In some embodiments, Z is cycloalkyl (e.g., a 3-membered cycloalkyl, 4-membered cycloalkyl, 5-membered cycloalkyl, 6-membered cycloalkyl), optionally substituted with one or more $R^5$. Exemplary cycloalkyl include:

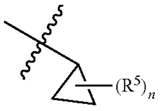
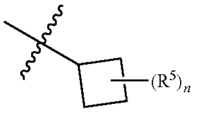
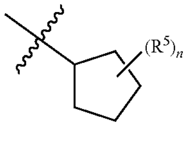
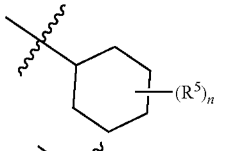
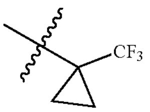
and
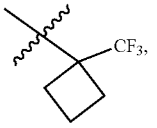

wherein each n is independently an integer selected from 0 to 20 and $R^5$ is as described herein.

In some embodiments, Z is heterocyclyl (e.g., a 3-membered heterocyclyl, 4-membered heterocyclyl, 5-membered heterocyclyl, 6-membered heterocyclyl). In some embodiments, heterocyclyl comprises an oxygen, sulfur, nitrogen, boron, silicon, or phosphorus atom. In some embodiments, heterocyclyl comprises an oxygen, sulfur, or nitrogen atom. In some embodiments, Z is a nitrogen-containing heterocyclyl (e.g., a 3-membered nitrogen-containing heterocyclyl, 4-membered nitrogen-containing heterocyclyl, 5-membered nitrogen-containing heterocyclyl, 6-membered nitrogen-containing heterocyclyl). In some embodiments, Z is a 5-membered nitrogen-containing heterocyclyl. In some embodiments, Z is a 6-membered nitrogen-containing heterocyclyl. In some embodiments, Z is an oxygen-containing heterocyclyl (e.g., a 3-membered oxygen-containing heterocyclyl, 4-membered oxygen-containing heterocyclyl, 5-membered oxygen-containing heterocyclyl, 6-membered oxygen-containing heterocyclyl). In some embodiments, Z is a 5-membered oxygen-containing heterocyclyl (e.g., tetrahydrofuranyl). In some embodiments, Z is a 6-membered oxygen-containing heterocyclyl (e.g., tetrahydropyranyl). In some embodiments, Z is a 5-membered sulfur-containing heterocyclyl. In some embodiments, Z is a 6-membered sulfur-containing heterocyclyl.

In some embodiments, Z is an oxygen-containing heterocyclyl. In some embodiments, Z is oxiranyl, oxetanyl, tetrahydrofuranyl, or tetrahydropyranyl. In some embodiments, Z is oxiranyl. In some embodiments, Z is oxetanyl. In some embodiments, Z is tetrahydrofuranyl. In some embodiments, Z is tetrahydropyranyl.

Exemplary oxygen-containing heterocyclyls include:

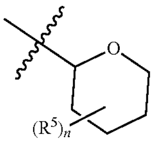
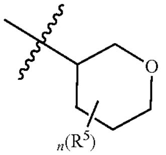
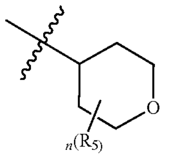
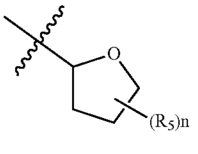
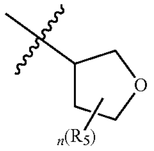
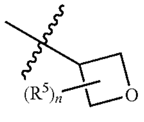
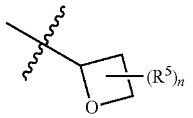
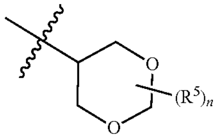
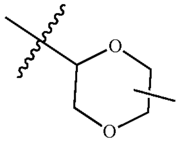
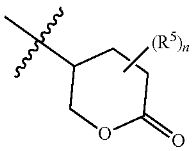
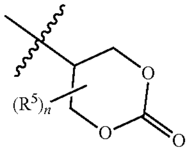
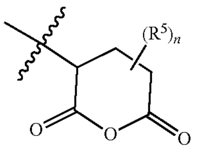
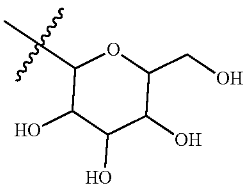
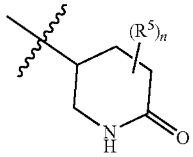
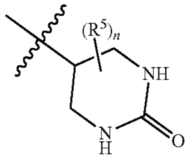
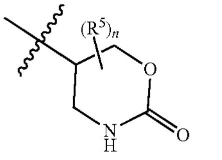
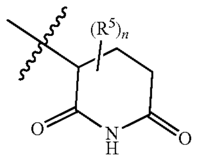
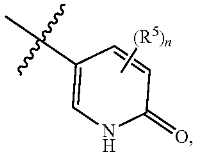

wherein each n is independently an integer selected from 0 to 20 and $R^5$ is as described herein.

In some embodiments, Z is nitrogen-containing heterocyclyl. In some embodiments, Z is aziridinyl, azetidinyl, diazetidinyl, pyrrolidinyl, imidazolyl, oxazolidinyl, isoxazolidinyl, piperazolidinyl, piperazinyl, piperidinyl, or homopiperazinyl. In some embodiments, Z is selected from:

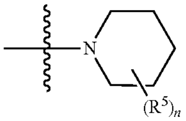
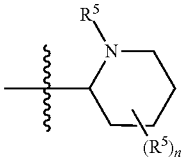
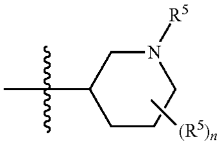
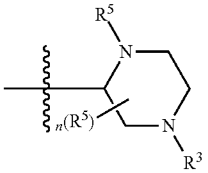
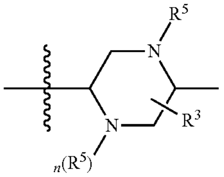
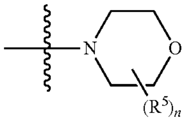
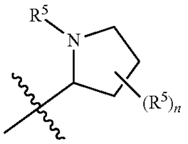
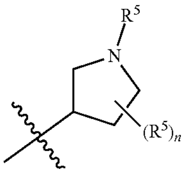
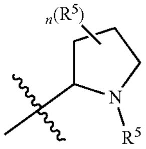
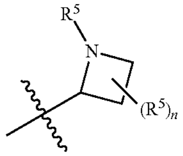
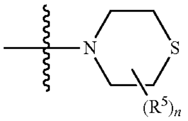
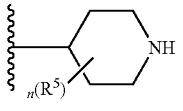
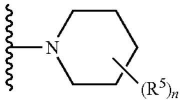
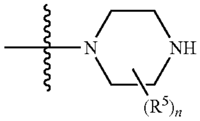
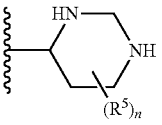
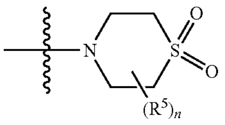
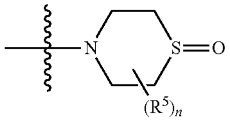
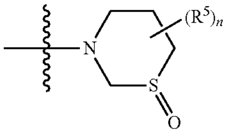 and

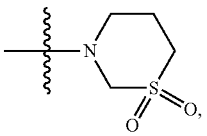

wherein each n is an integer independently selected from 0 to 10 and each $R^5$ is independently described herein.

In some embodiments, Z is selected from

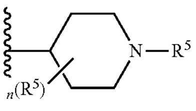
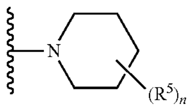

-continued

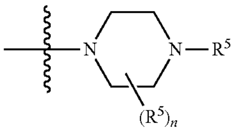 and

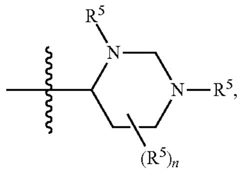

wherein n is an integer independently selected from 0 to 10 and each $R^5$ is independently described herein. In some embodiments, $R^5$ is alkyl (e.g., methyl, ethyl, isopropyl, or propyl).

In some embodiments, Z is a heterocyclyl of the formula (Z-1):

(Z-1)

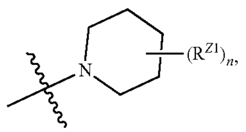

wherein each $R^{Z1}$ is independently selected from alkyl, heteroalkyl, aryl, heteroaryl, cycloalkyl, heterocyclyl, halogen, cyano, —$OR^A$, —$C(O)R^A$, —$C(O)N(R^B)(R^C)$, —$C(O)OR^A$, —$S(O)_{2-x}R^A$; or two $R^{Z1}$ groups together with the atom to which they are attached form an oxo group or a ring.

In some embodiments, n is 1. In some embodiments, Z is selected from:

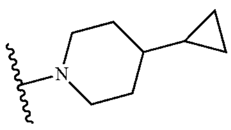
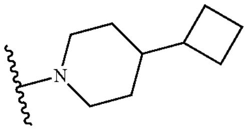
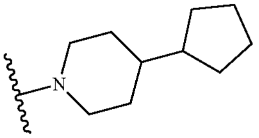
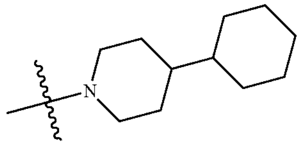
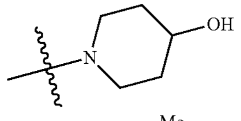
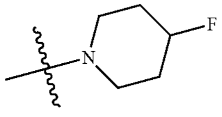
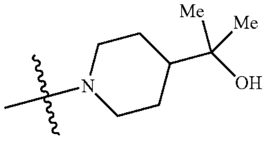
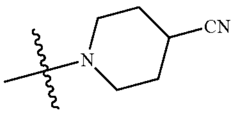
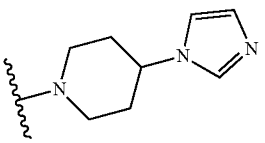
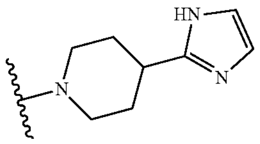

-continued

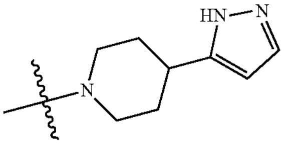
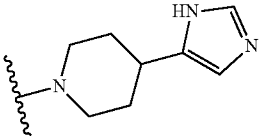
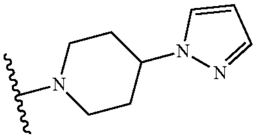
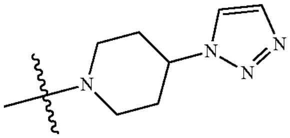
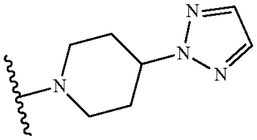
and
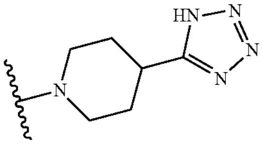

In some embodiments, n is 2. In some embodiments, n is 2 and two $R^{Z1}$ groups together with the atom to which they are attached form an oxo. In some embodiments, Z is selected from:

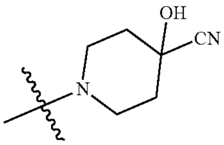
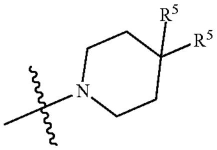
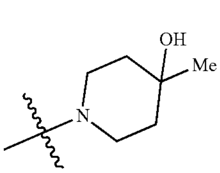
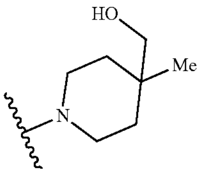
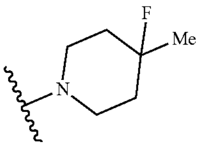
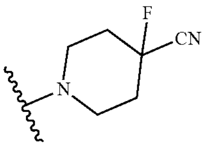
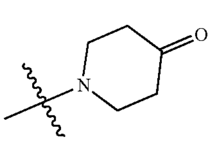
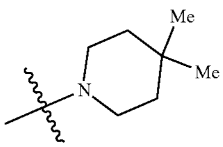
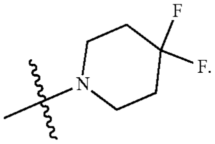

In some embodiments, two $R^{Z1}$ groups together with the carbon atom to which they are attached form a ring. In some embodiments, the heterocyclyl of formula (Z-1) is selected from a heterocyclyl of formula (Z-1-i):

(Z-1-i)

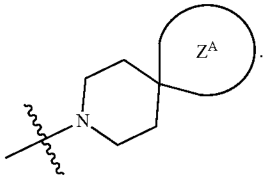

wherein Ring $Z^A$ is a 4-, 5-, 6-, or 7-membered ring. In some embodiments, the heterocyclyl of formula (Z-1-i) is:

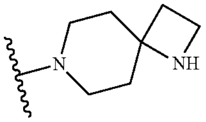
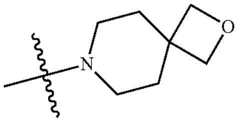
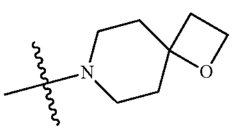
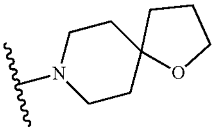
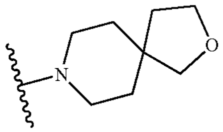
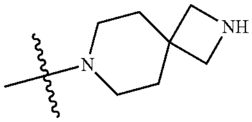
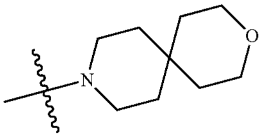
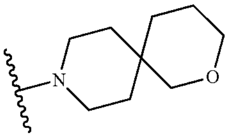
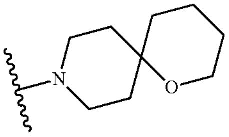
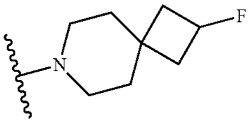
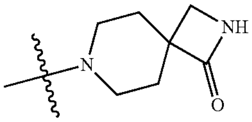
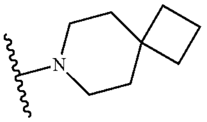
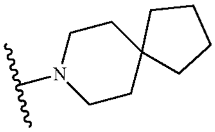
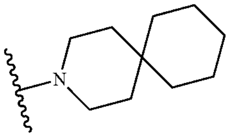
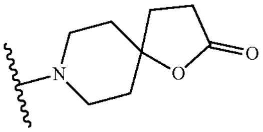
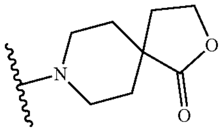
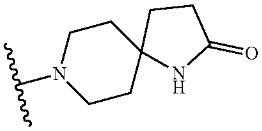
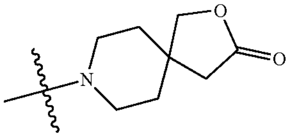
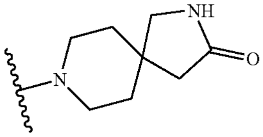

-continued

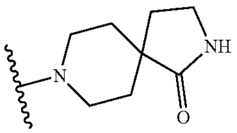 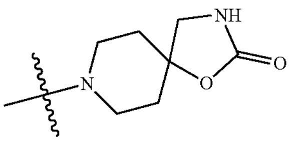

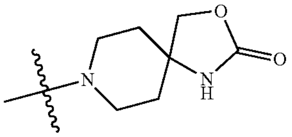 and

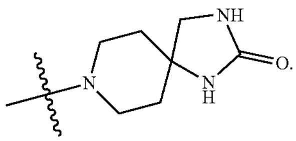

In some embodiments, Z is aryl. In some embodiments, Z is phenyl. In some embodiments, Z is phenyl optionally substituted by 1-4 $R^5$. In some embodiments, Z is selected from:

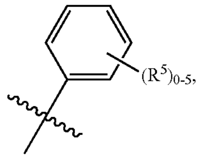 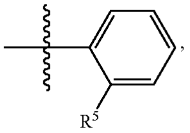

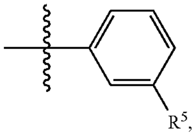 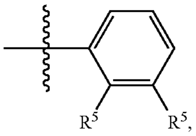

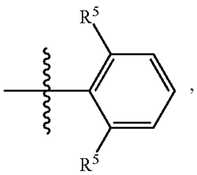 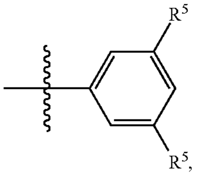

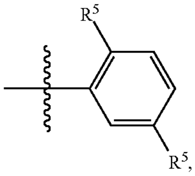

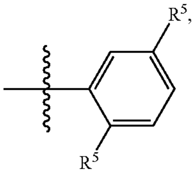

-continued

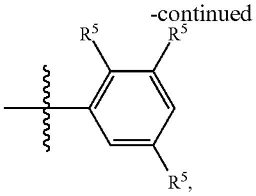 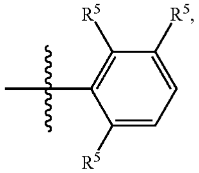

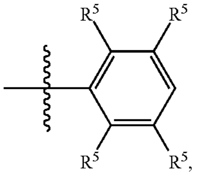 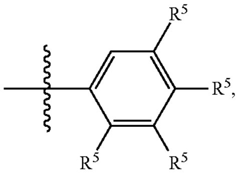

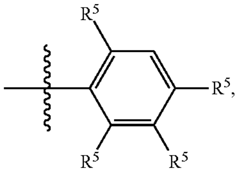 and 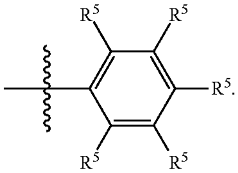

Exemplary aryl groups include:

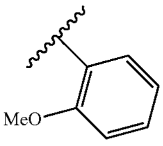 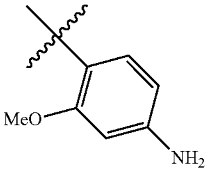 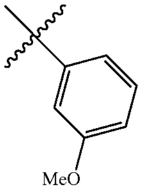

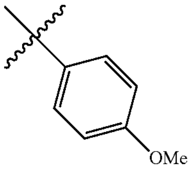 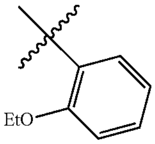 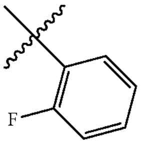

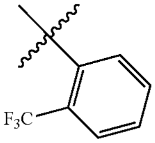 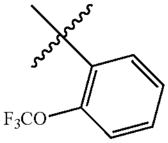 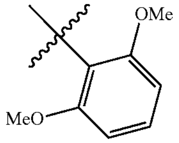

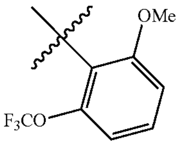 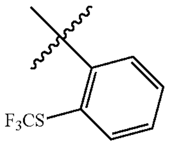 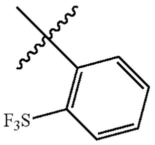

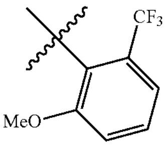 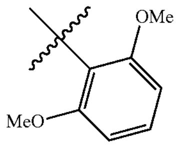

In some embodiments, Z is a substituted aryl group, substituted with two $R^5$ groups. In some embodiments, the two $R^5$ groups together with the atom to which they are attached form a ring (e.g., a fused ring). In some embodiments, the substituted aryl group is:

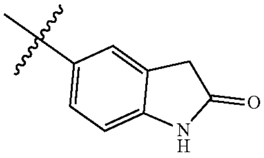

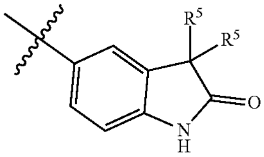

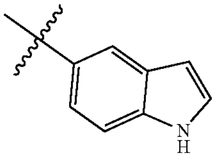

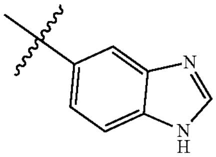

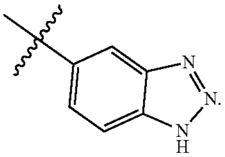

In some embodiments, the substituted aryl group is:

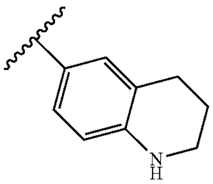

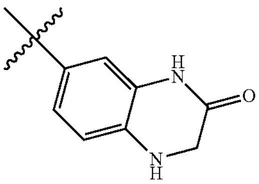

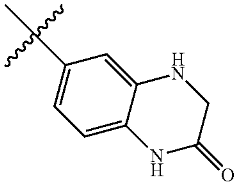

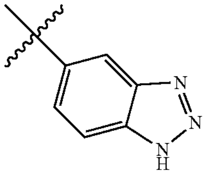

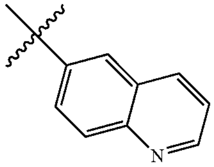

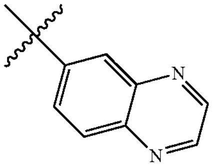

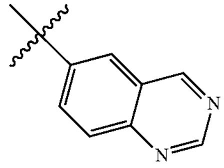

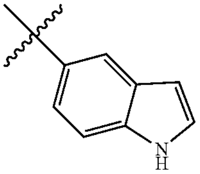

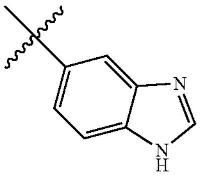

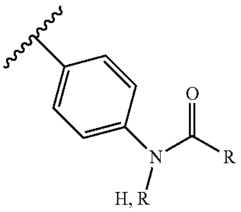

-continued

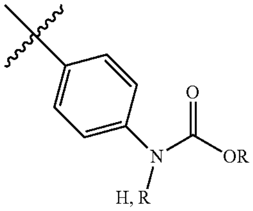

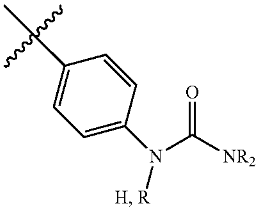

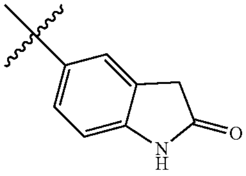

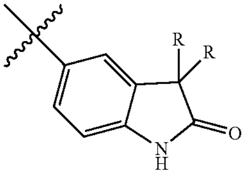

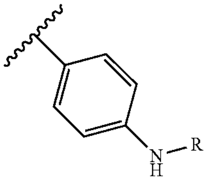

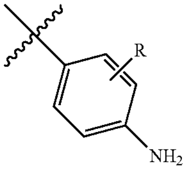

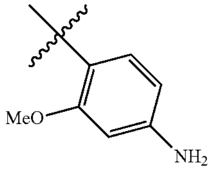

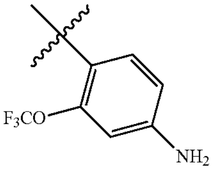

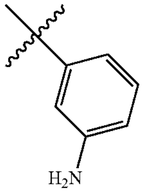

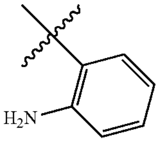

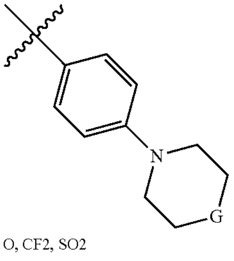

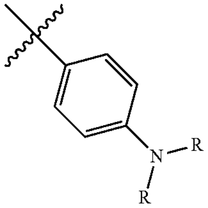

G = CH2, O, CF2, SO2

In some embodiments, Z is heteroaryl. In some embodiments, Z is unsubstituted heteroaryl or substituted heteroaryl (e.g., with one or more $R^5$). In some embodiments, the heteroaryl is a 3 to 7-membered heteroaryl. In some embodiments, the heteroaryl is a 5- or 6-membered heteroaryl. In some embodiments, the heteroaryl is a nitrogen, oxygen, or sulfur containing heteroaryl. In some embodiments, the heteroaryl is a nitrogen-containing heteroaryl. In some embodiments, the heteroaryl is an oxygen-containing heteroaryl. In some embodiments, the heteroaryl is a sulfur-containing heteroaryl. In some embodiments, the heteroaryl comprises at least one nitrogen. In some embodiments, the heteroaryl comprises at least one oxygen. In some embodiments, the heteroaryl comprises at least one sulfur.

In some embodiments, the heteroaryl is a 5-membered heteroaryl. In some embodiments, Z is furanyl, pyrrolyl, thiofuranyl, oxazolyl, isoxazolyl, oxaziridinyl, thiadiazolyl, triazolyl, tetrazolyl, pyridyl, pyrazinyl, or pyrimidinyl. In some embodiments, Z is selected from:

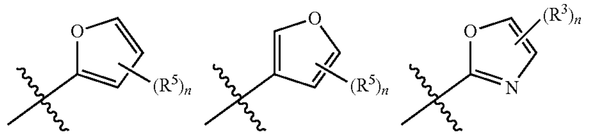
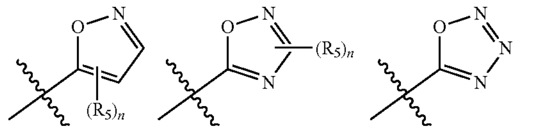
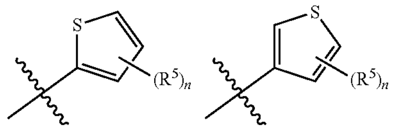
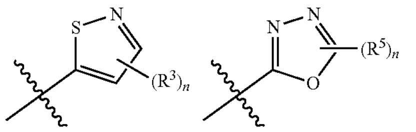
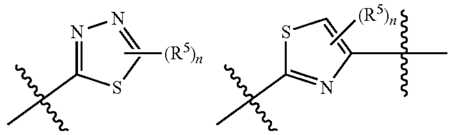
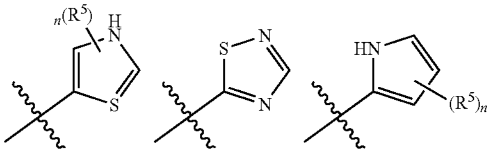
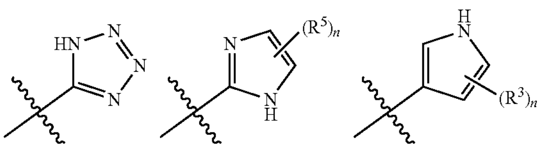
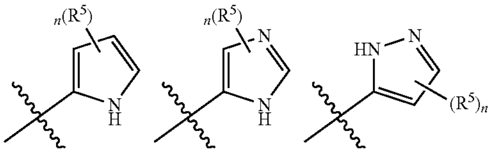
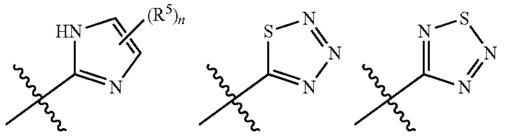
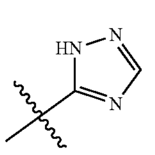

and

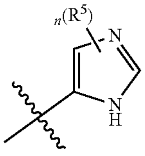

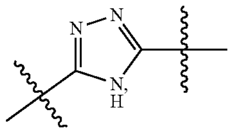

, wherein each n is an integer independently selected from 0 to 10 and each $R^5$ is independently described herein.

In some embodiments, Z is selected from:

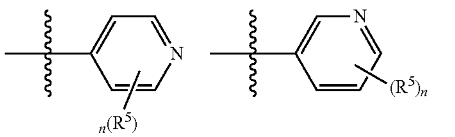
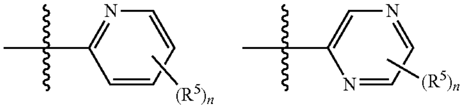
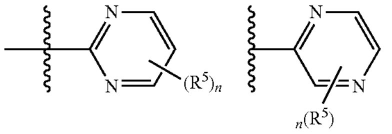
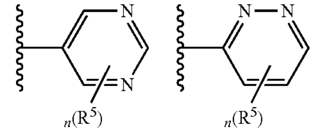

and

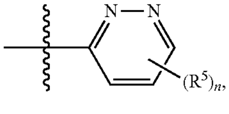

wherein each n is an integer independently selected from 0 to 10 and each $R^5$ is independently described herein.

In some embodiments, Z is selected from:

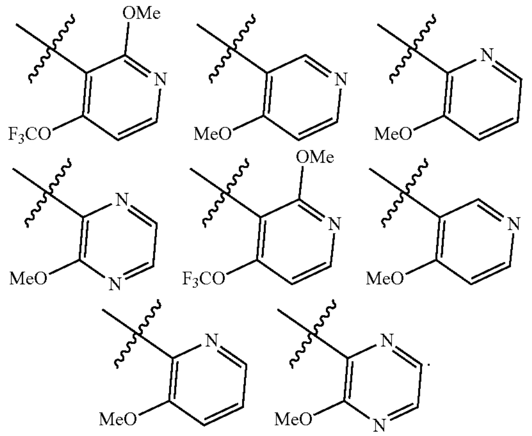

In some embodiments, Z is a heteroaryl substituted with at least one $R^5$. In some embodiments, one $R^5$ together with a substitutent (e.g., $R^2$) of $L^3$ form a ring. In some embodiments, $-L^3-Z$ is:

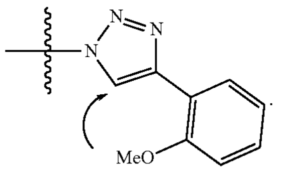 [SMILES: *n1cc(-c2ccccc2OC)nn1]

Figure 1A:
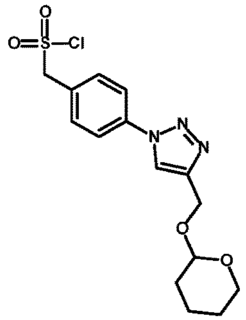
Figure 1A:
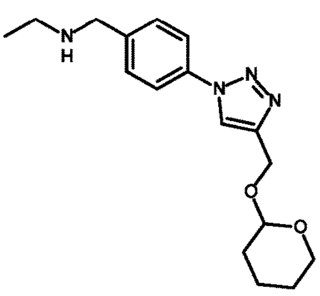
Figure 1A:
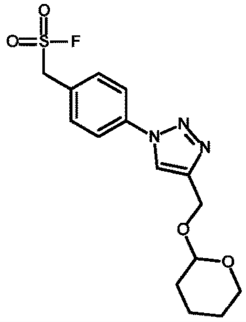
Figure 1A:
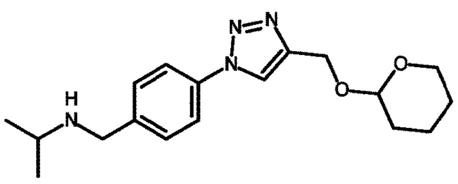
Figure 1A:
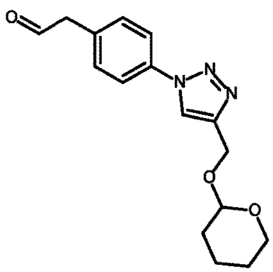
Figure 1A:
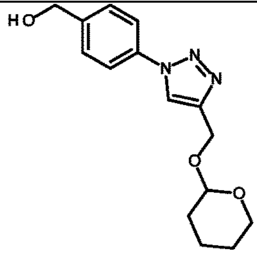
Figure 1A:
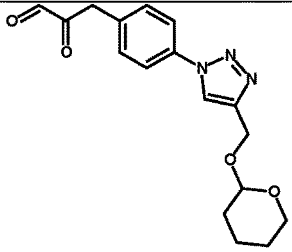
Figure 1A:
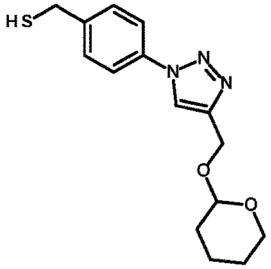
Figure 1A:
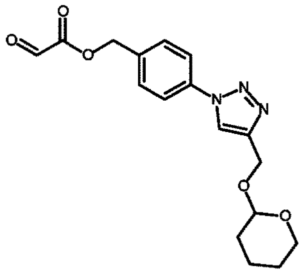
Figure 1B:
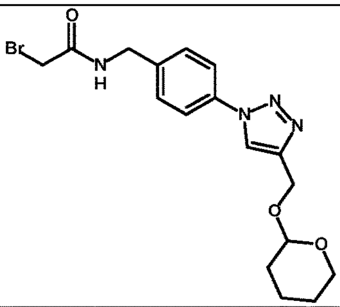
Figure 1B:
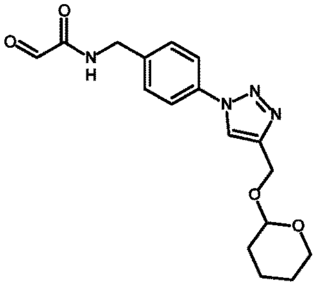
Figure 1B:
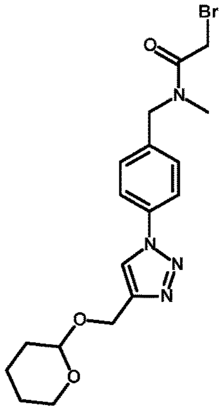
Figure 1B:
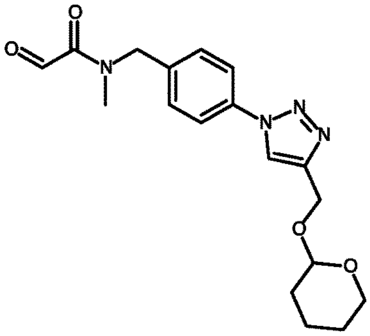
Figure 1B:
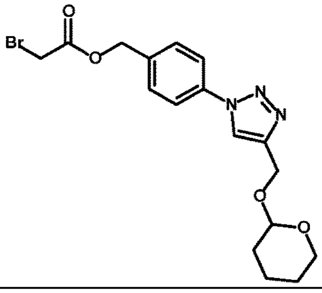
Figure 1B:
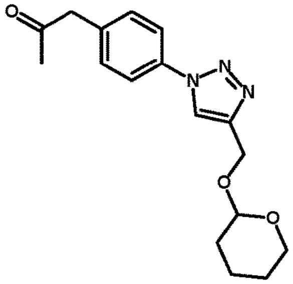
Figure 1B:
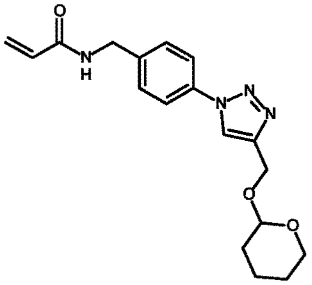
Figure 1B:
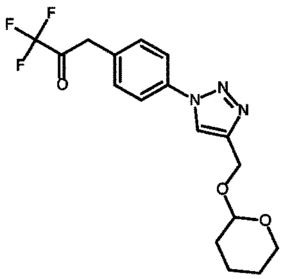
Figure 1B:
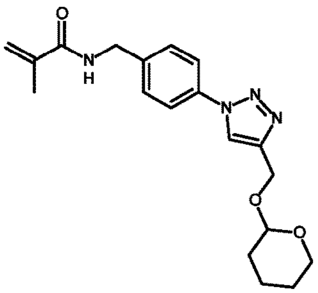
Figure 1B:
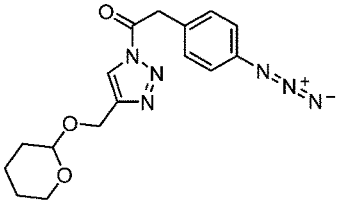
Figure 1C:
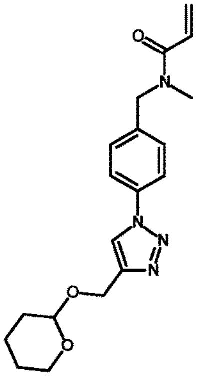
Figure 1C:
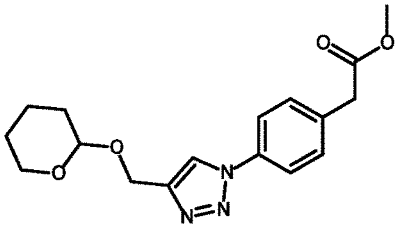
Figure 1C:
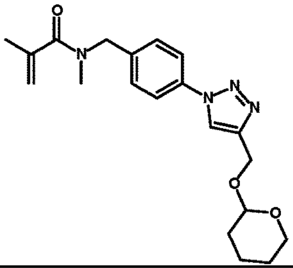
Figure 1C:
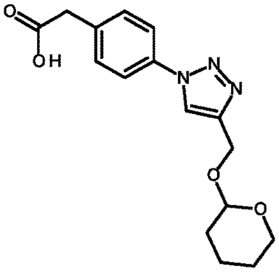
Figure 1C:
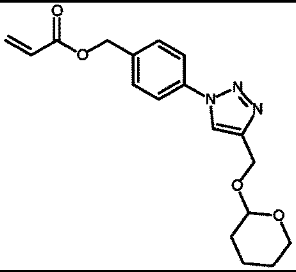
Figure 1C:
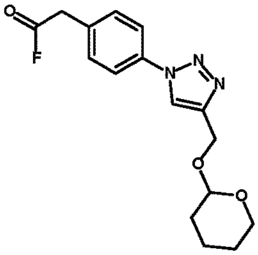
Figure 1C:
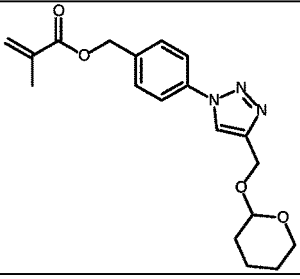
Figure 1C:
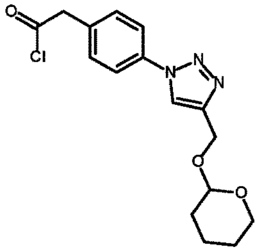
Figure 1C:
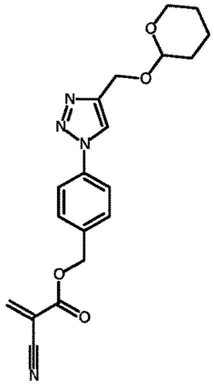
Figure 1C:
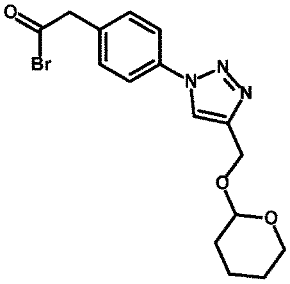
Figure 1D:
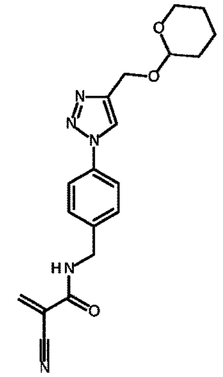
Figure 1D:
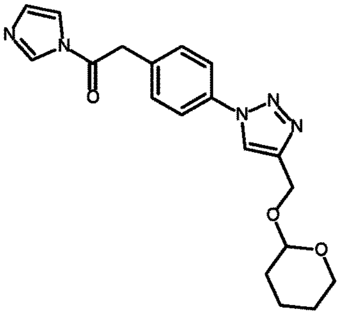
Figure 1D:
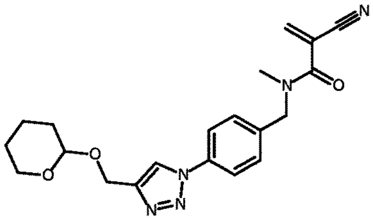
Figure 1D:
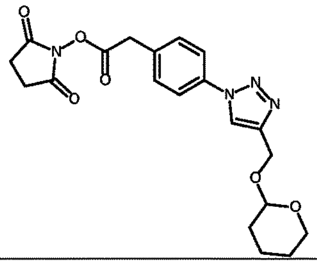
Figure 1D:
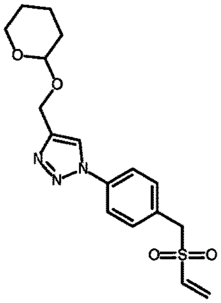
Figure 1D:
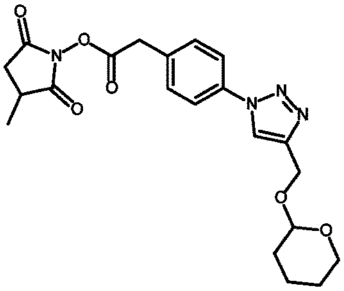
Figure 1D:
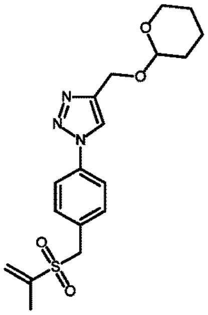
Figure 1D:
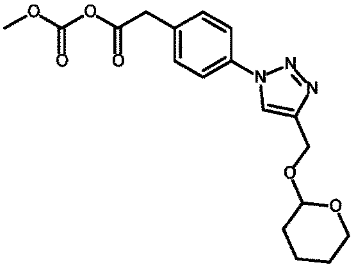
Figure 1D:
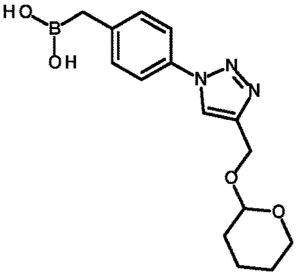
Figure 1D:
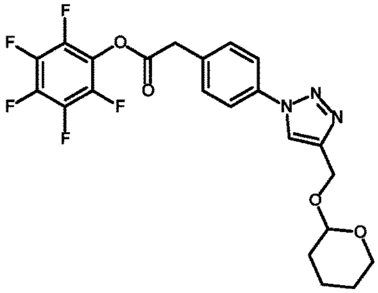
Figure 1E:
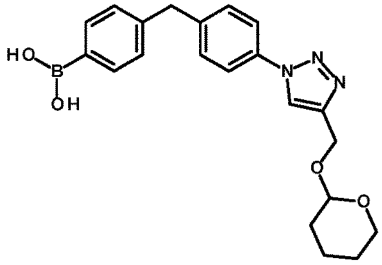
Figure 1E:
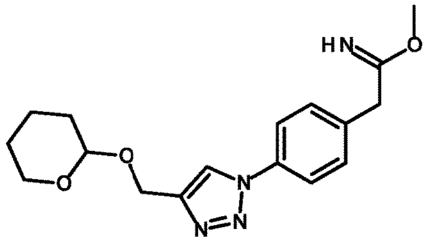
Figure 1E:
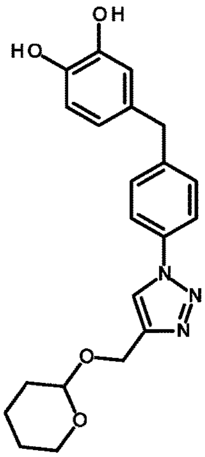
Figure 1E:
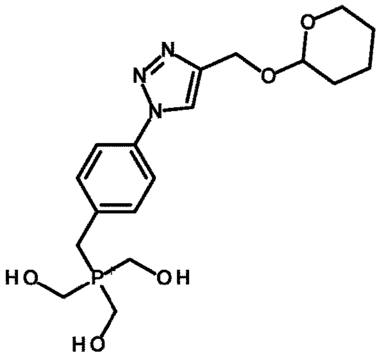
Figure 1E:
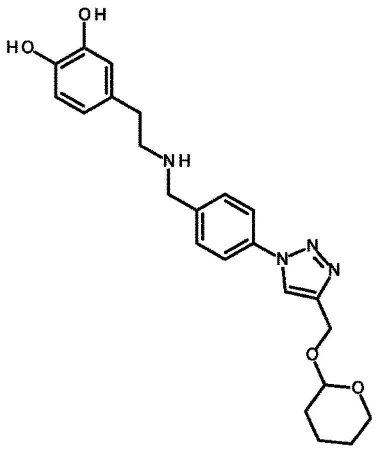
Figure 1E:
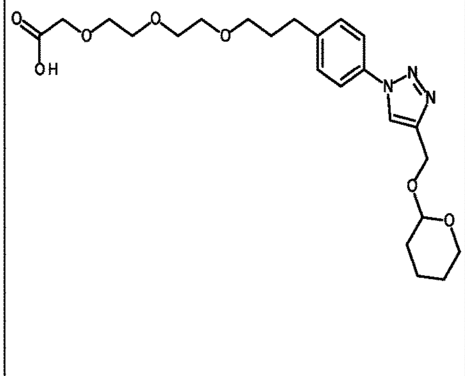
Figure 1E:
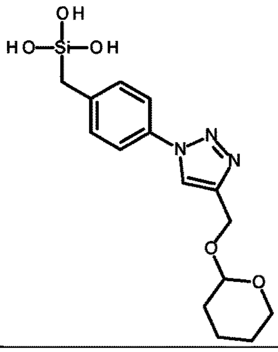
Figure 1E:
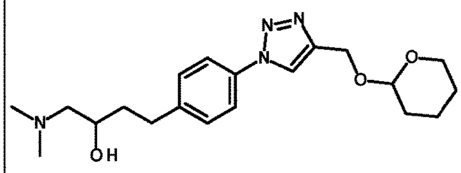
Figure 1F:
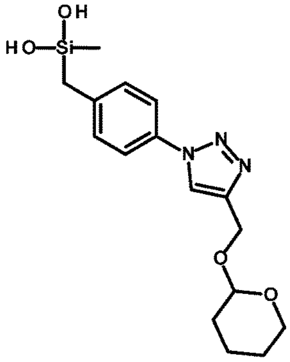
Figure 1F:
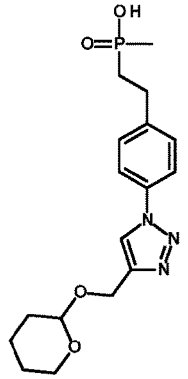
Figure 1F:
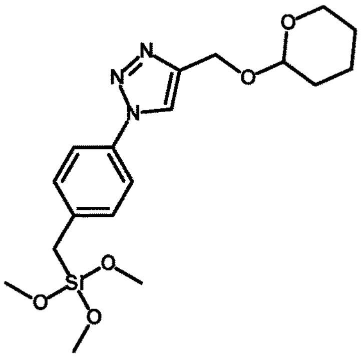
Figure 1F:
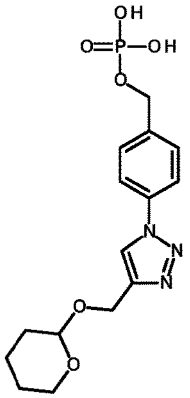
Figure 1F:
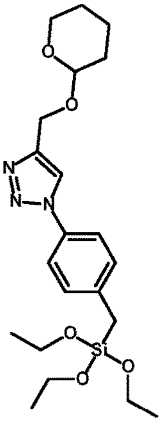
Figure 1F:
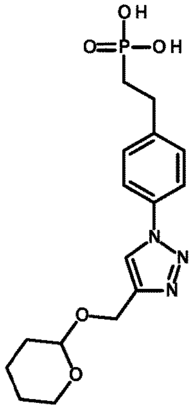
Figure 1F:
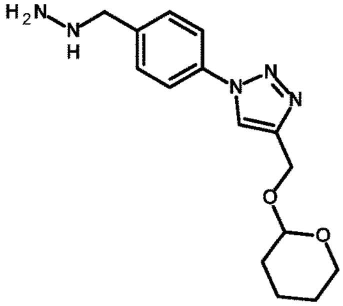
Figure 1F:
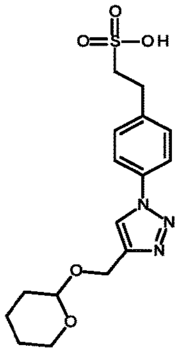
Figure 1G:
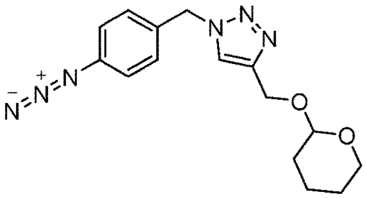
Figure 1G:
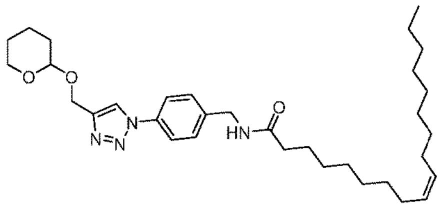
Figure 1G:
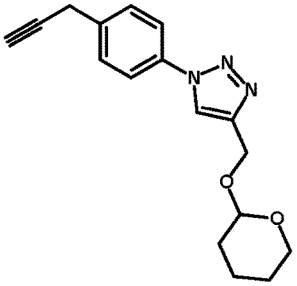
Figure 1G:
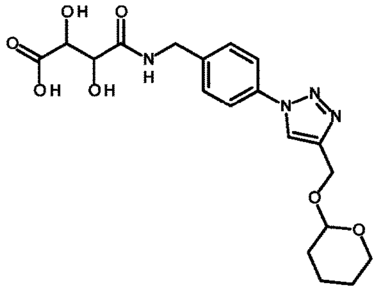
Figure 1G:
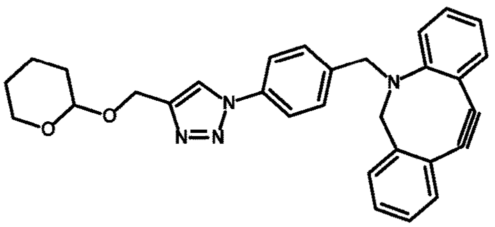
Figure 1G:
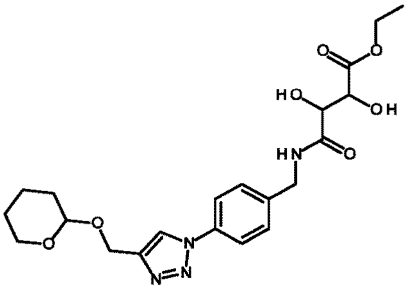
Figure 1G:
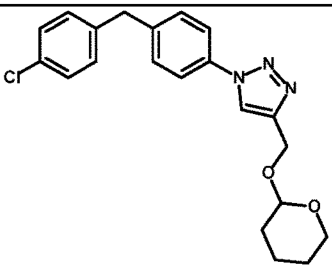
Figure 1G:
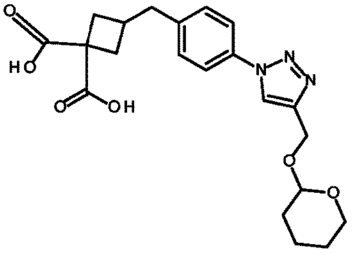
Figure 1G:
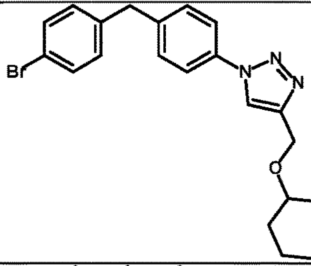
Figure 1G:
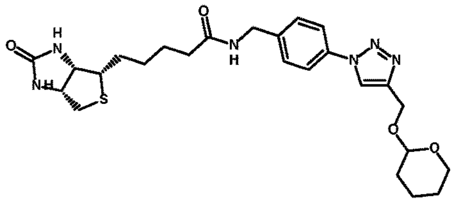
Figure 1G:
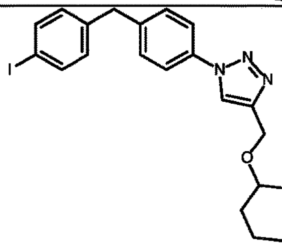
Figure 1G:
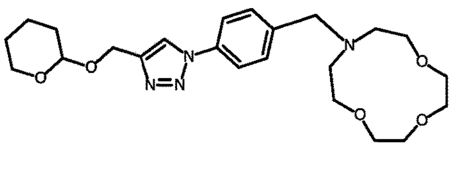
Figure 1H:
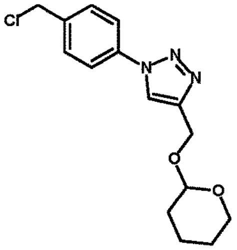
Figure 1H:
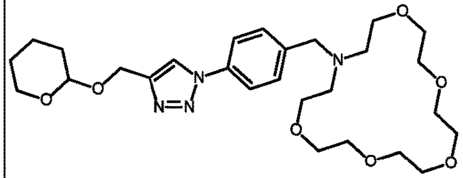
Figure 1H:
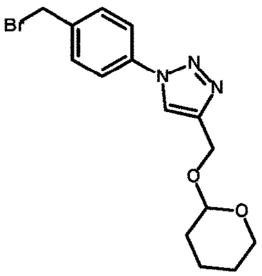
Figure 1H:
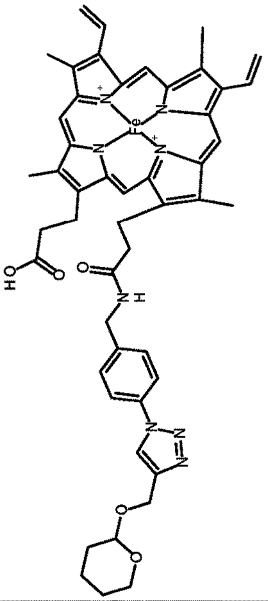
Figure 1H:
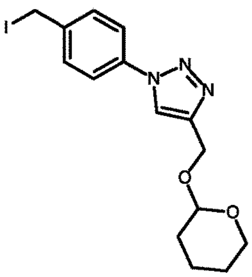
Figure 1H:
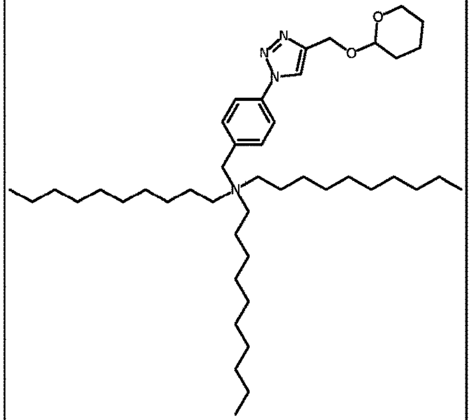
Figure 1I:
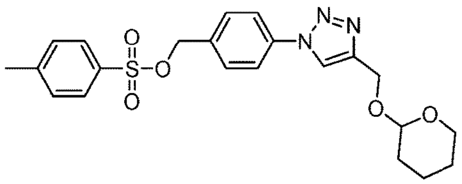
Figure 1I:
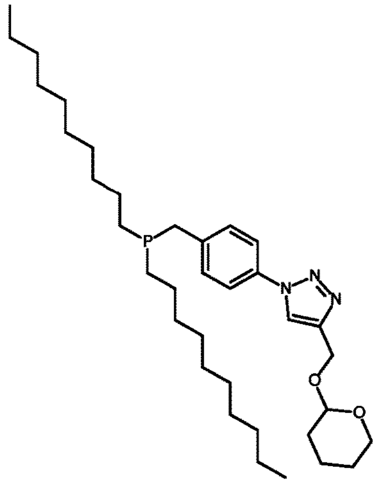
Figure 1I:
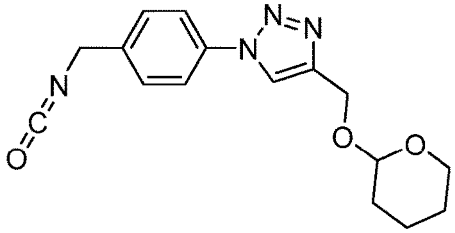
Figure 1I:
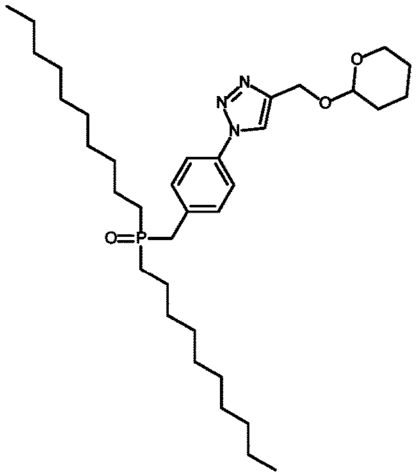
Figure 1I:
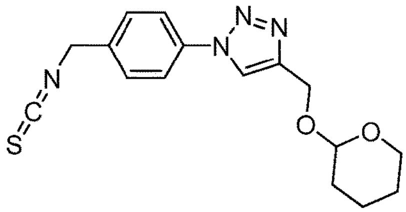
Figure 1I:
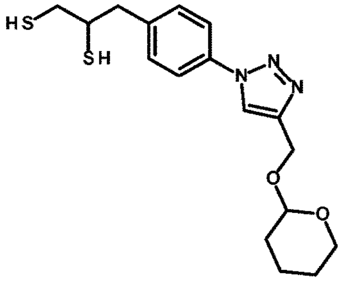
Figure 1I:
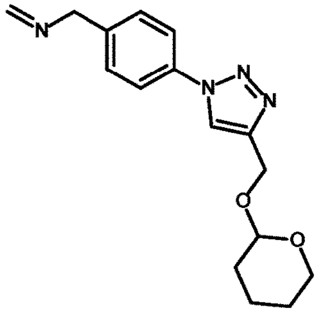
Figure 1I:
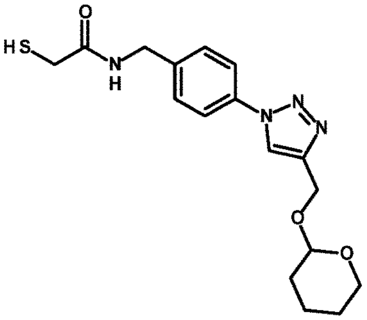
Figure 1J:
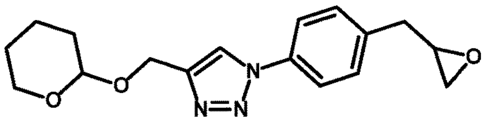
Figure 1J:
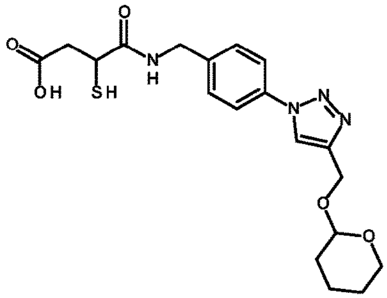
Figure 1J:
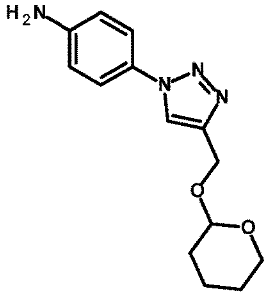
Figure 1J:
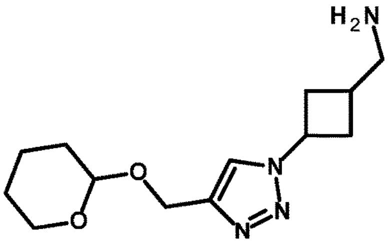
Figure 1J:
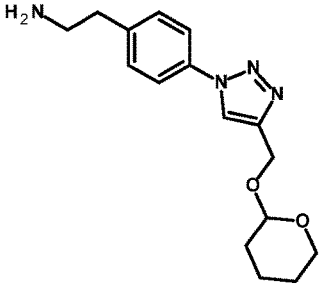
Figure 1J:
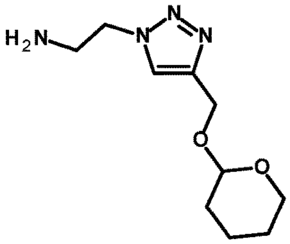
Figure 1J:
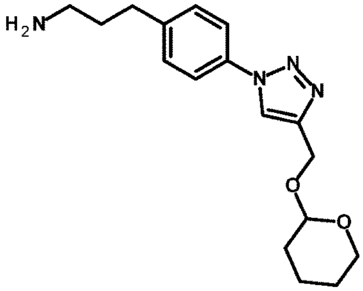
Figure 1J:
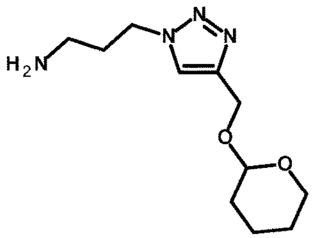
Figure 1J:
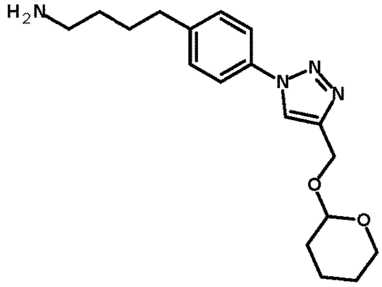
Figure 1J:
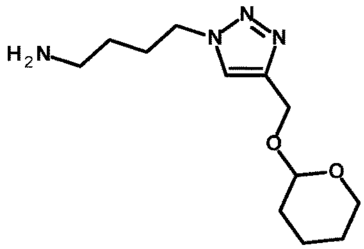
Figure 1K:
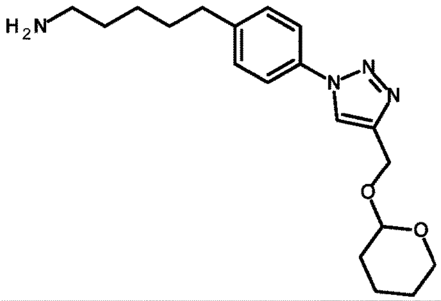
Figure 1K:
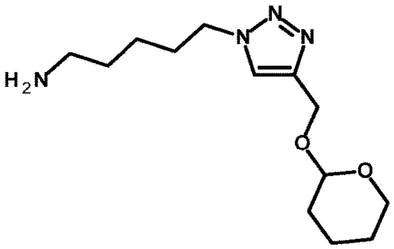
Figure 1K:
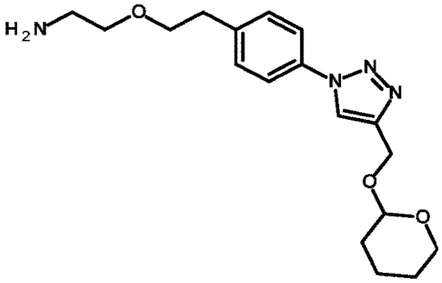
Figure 1K:
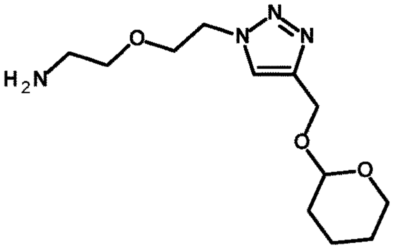
Figure 1K:
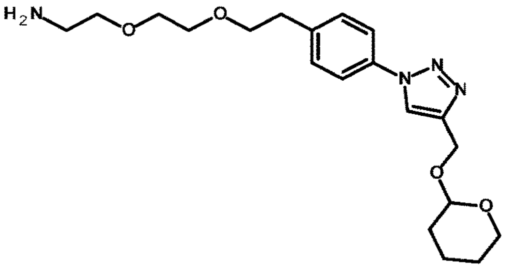
Figure 1K:
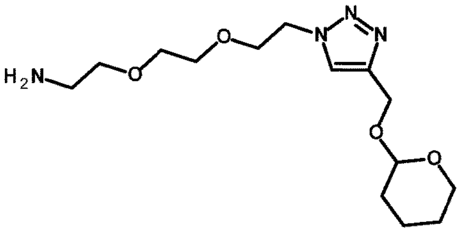
Figure 1K:
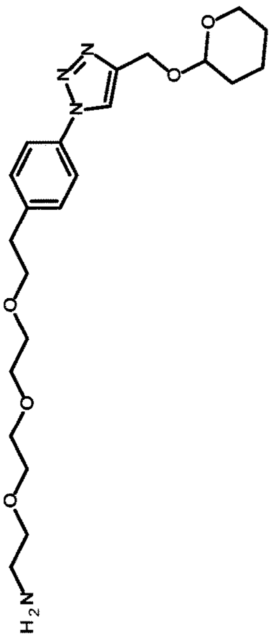
Figure 1K:
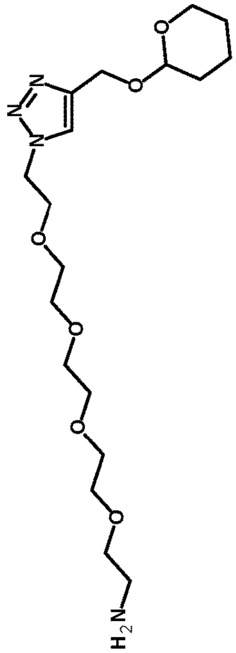
Figure 1L:
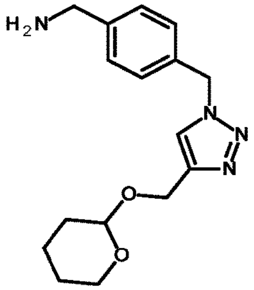
Figure 1L:
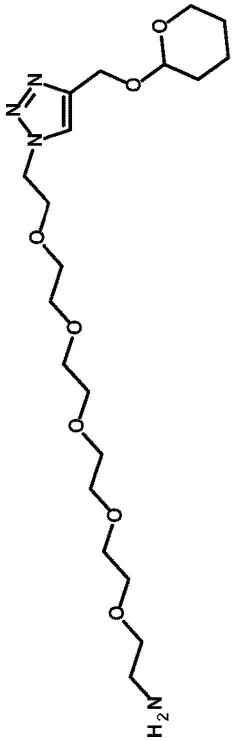
Figure 1L:
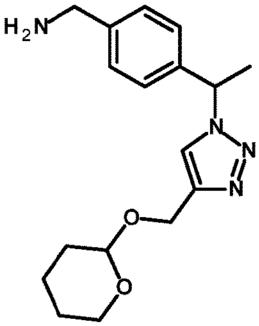
Figure 1L:
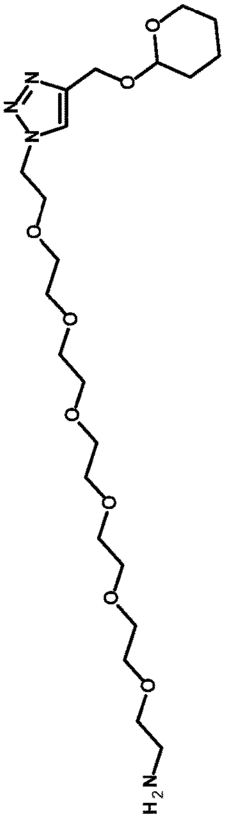
Figure 1M:
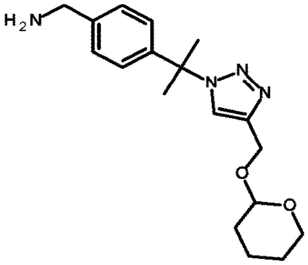
Figure 1M:
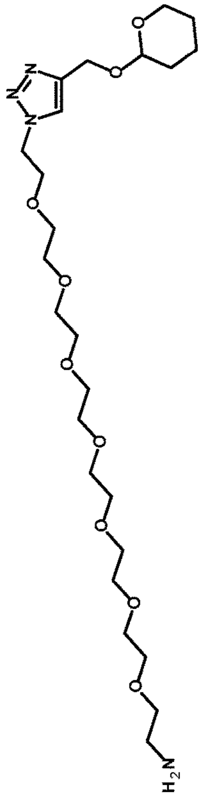
Figure 1M:
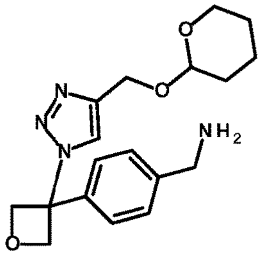
Figure 1M:
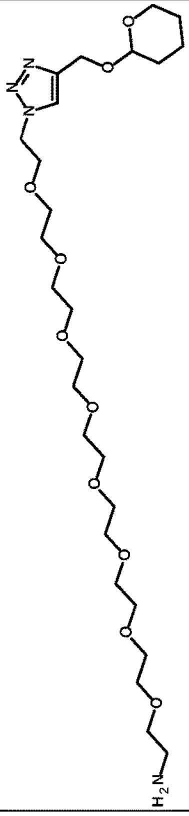
Figure 1N:
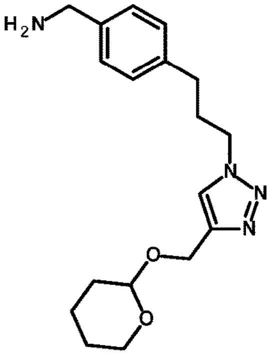
Figure 1N:
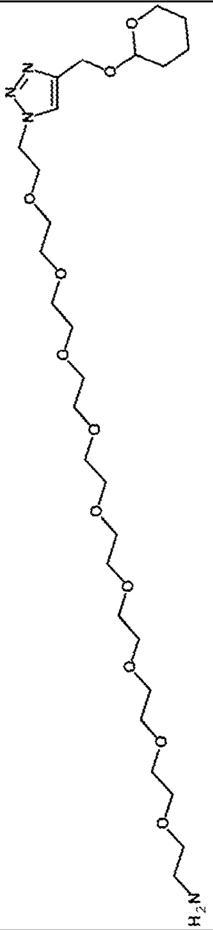
Figure 1N:
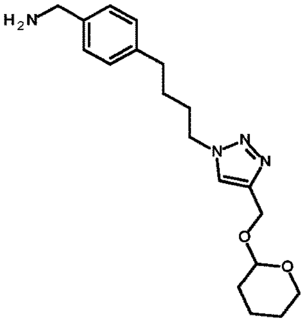
Figure 1N:
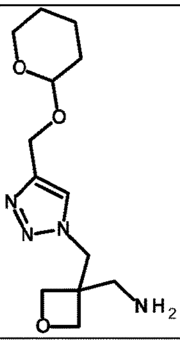
Figure 1N:
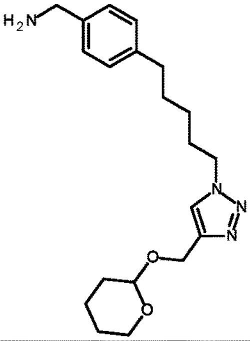
Figure 1N:
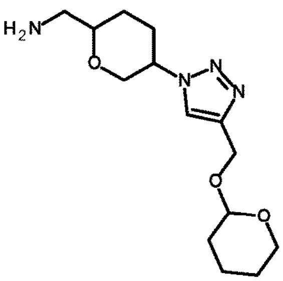
Figure 1O:
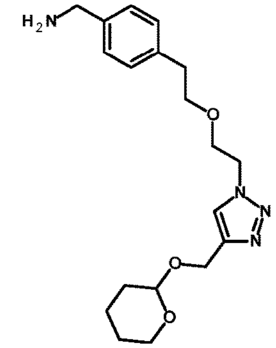
Figure 1O:
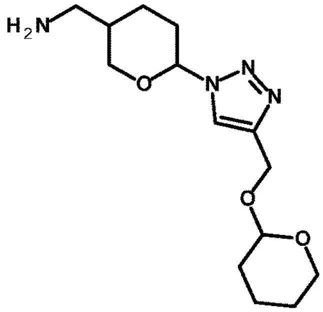
Figure 1O:
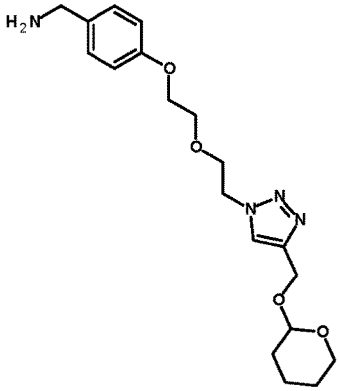
Figure 1O:
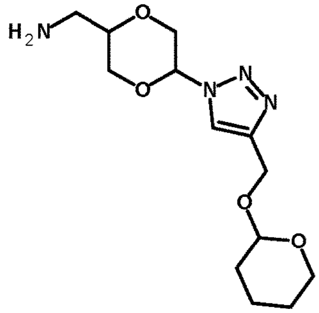
Figure 1O:
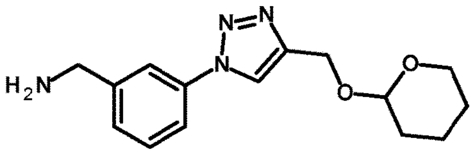
Figure 1O:
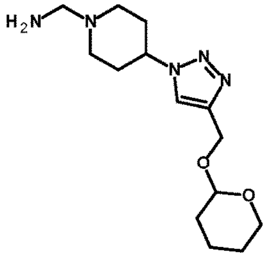
Figure 1O:
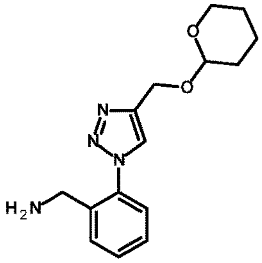
Figure 1O:
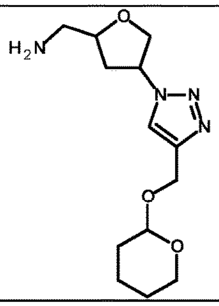
Figure 1O:
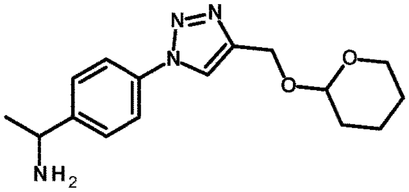
Figure 1O:
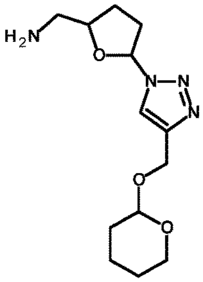
Figure 1P:
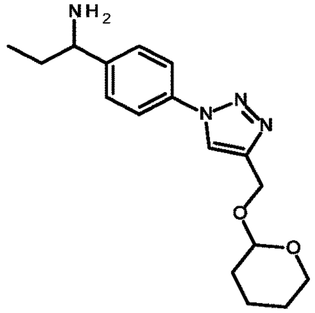
Figure 1P:
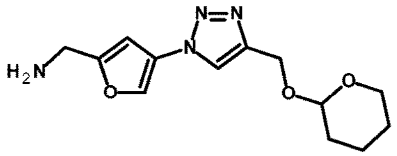
Figure 1P:
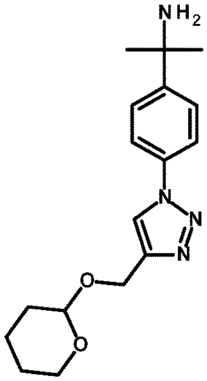
Figure 1P:
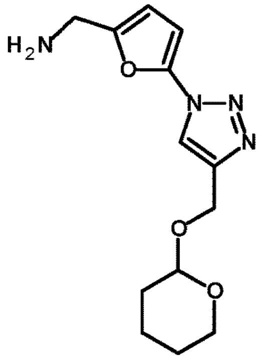
Figure 1P:
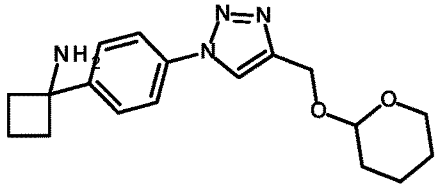
Figure 1P:
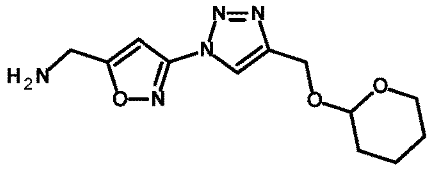
Figure 1P:
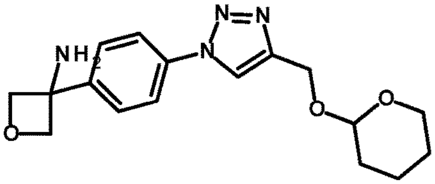
Figure 1P:
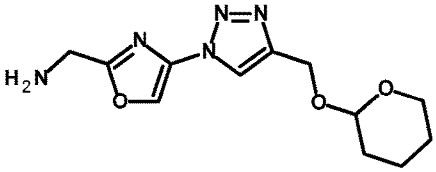
Figure 1P:
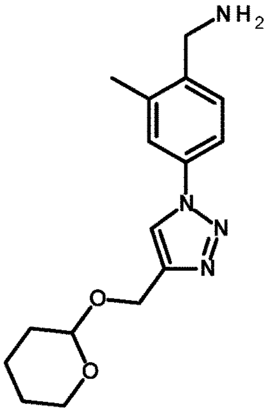
Figure 1P:
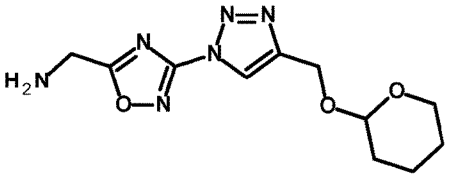
Figure 1Q:
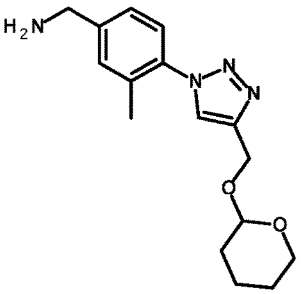
Figure 1Q:
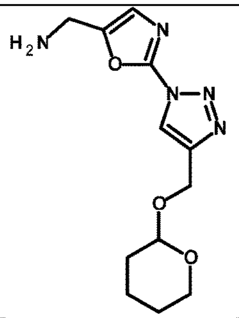
Figure 1Q:
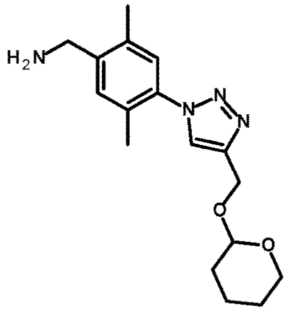
Figure 1Q:
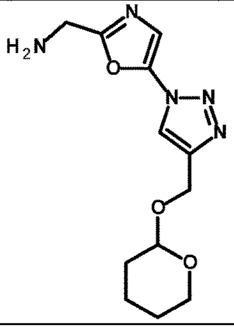
Figure 1Q:
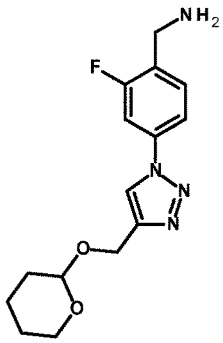
Figure 1Q:
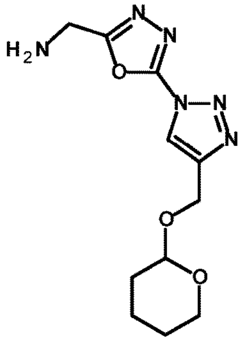
Figure 1Q:
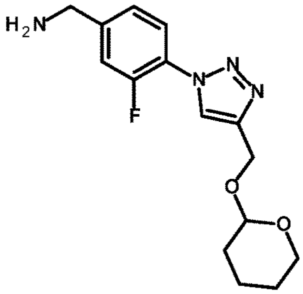
Figure 1Q:
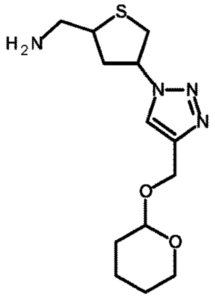
Figure 1Q:
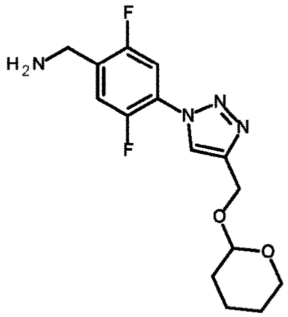
Figure 1Q:
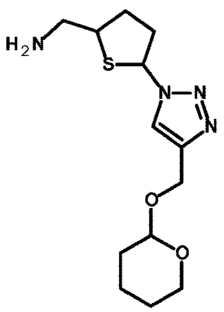
Figure 1R:
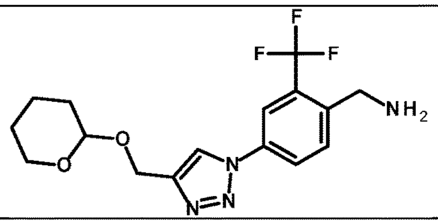
Figure 1R:
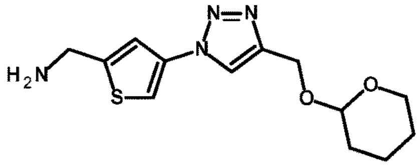
Figure 1R:
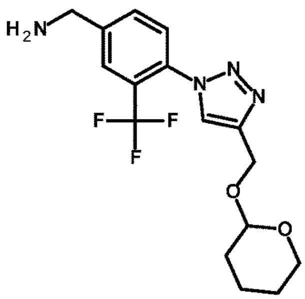
Figure 1R:
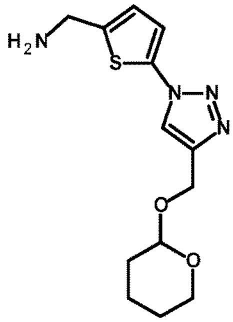
Figure 1R:
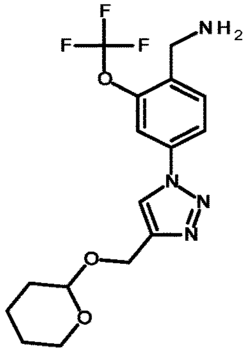
Figure 1R:
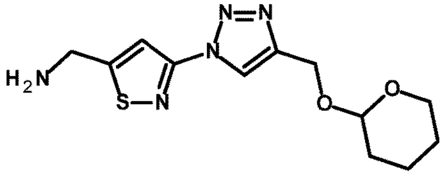
Figure 1R:
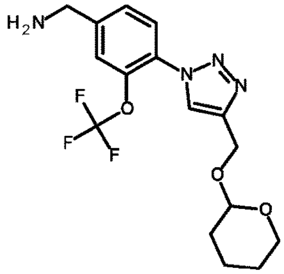
Figure 1R:
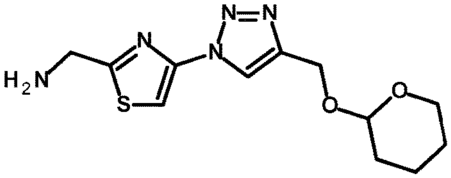
Figure 1R:
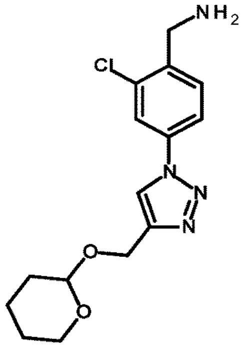
Figure 1R:
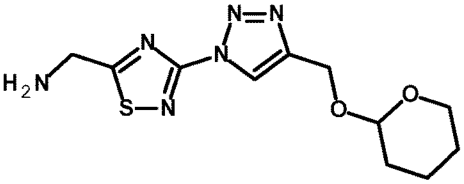
Figure 1S:
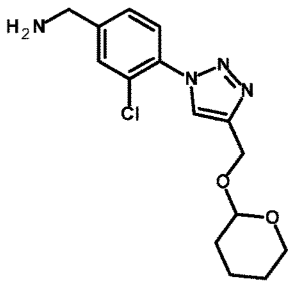
Figure 1S:
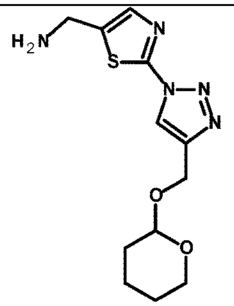
Figure 1S:
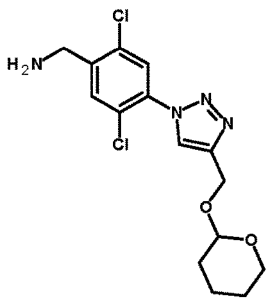
Figure 1S:
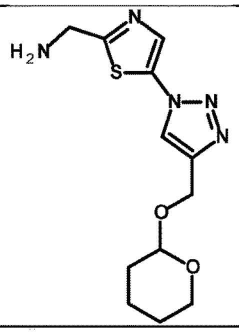
Figure 1S:
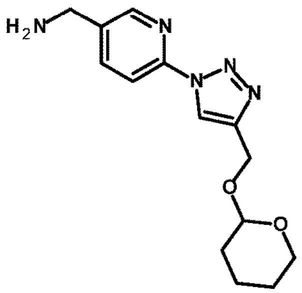
Figure 1S:
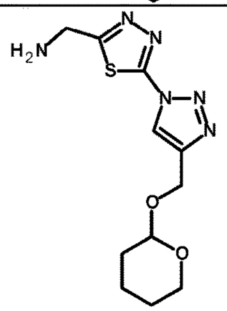
Figure 1S:
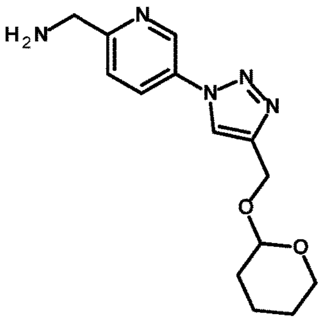
Figure 1S:
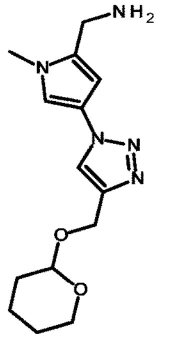
Figure 1S:
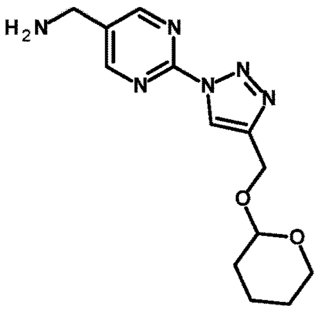
Figure 1S:
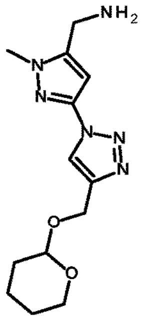
Figure 1T:
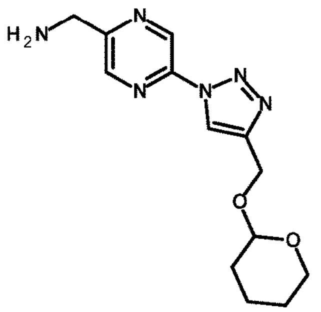
Figure 1T:
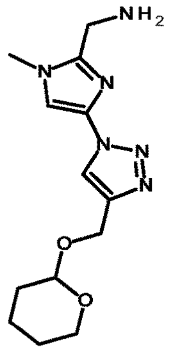
Figure 1T:
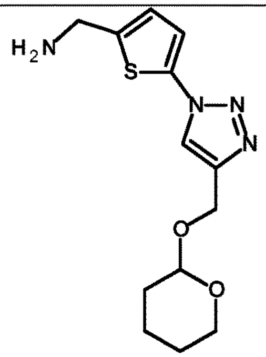
Figure 1T:
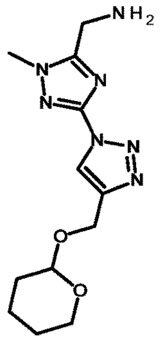
Figure 1T:
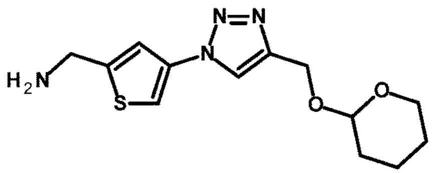
Figure 1T:
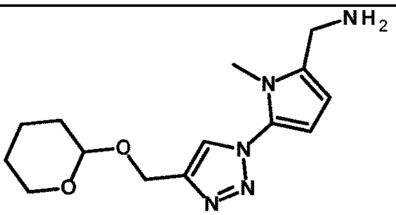
Figure 1T:
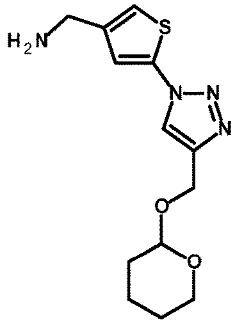
Figure 1T:
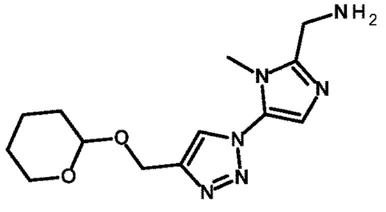
Figure 1T:
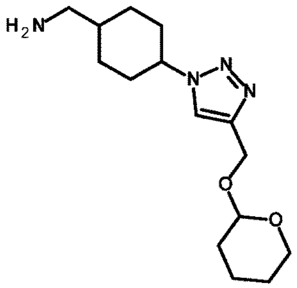
Figure 1T:
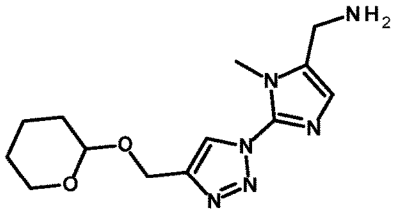
Figure 1U:
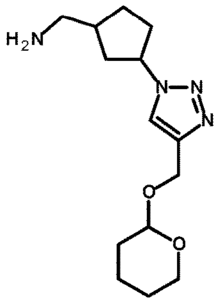
Figure 1U:
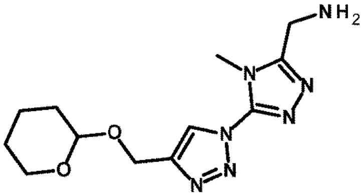
Figure 1U:
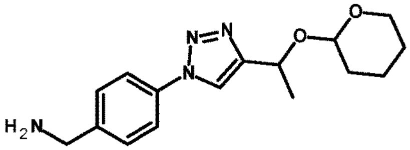
Figure 1U:
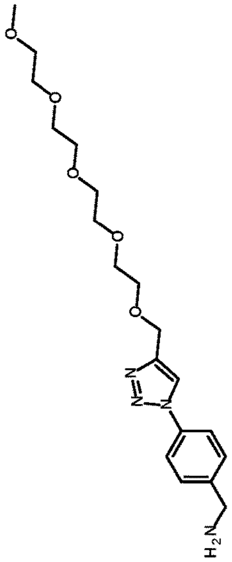
Figure 1U:
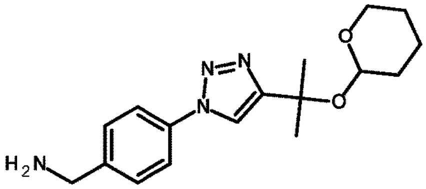
Figure 1U:
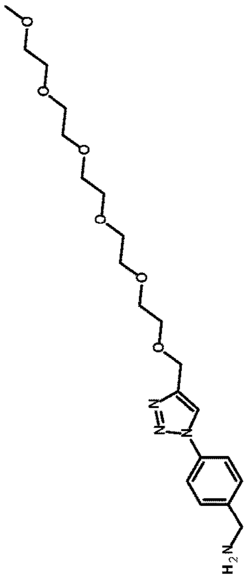
Figure 1V:
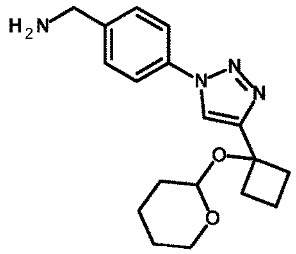
Figure 1V:
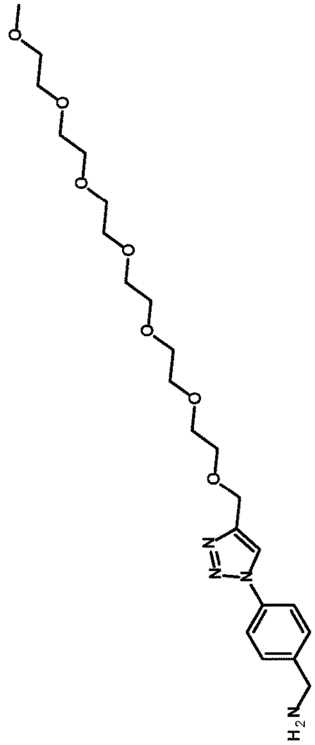
Figure 1V:
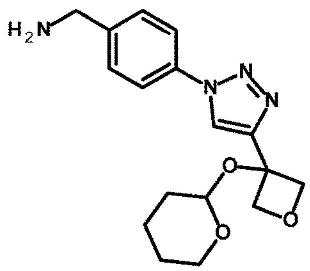
Figure 1V:
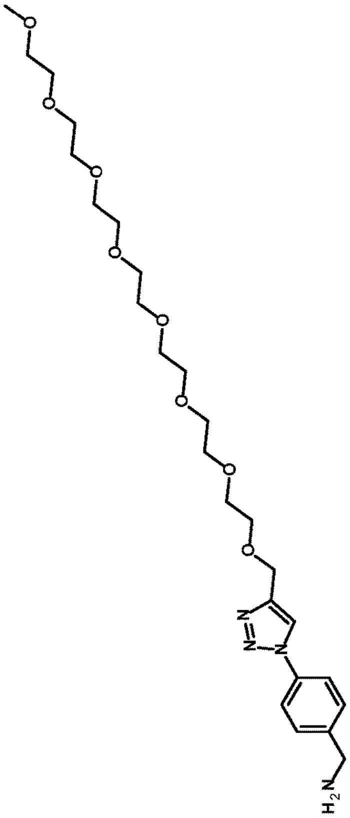
Figure 1W:
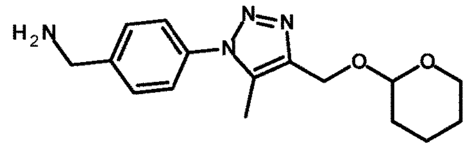
Figure 1W:
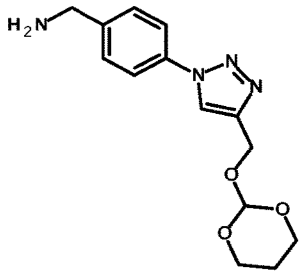
Figure 1W:
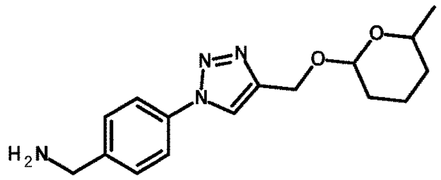
Figure 1W:
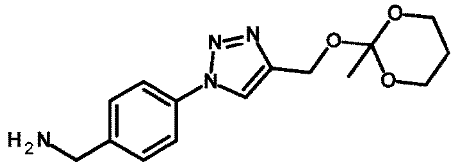
Figure 1W:
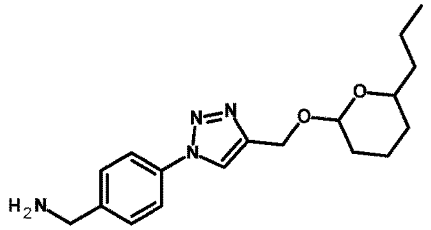
Figure 1W:
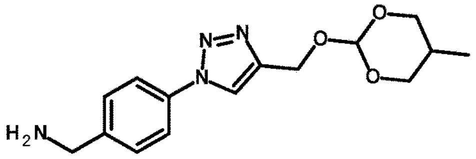
Figure 1W:
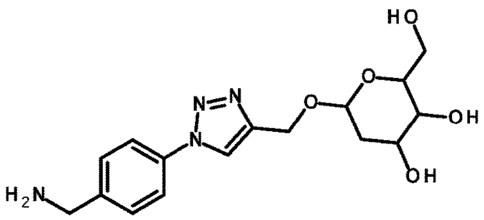
Figure 1W:
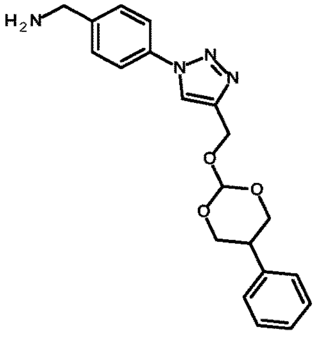
Figure 1W:
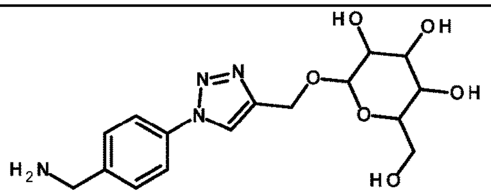
Figure 1W:
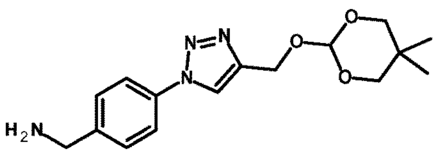
Figure 1W:
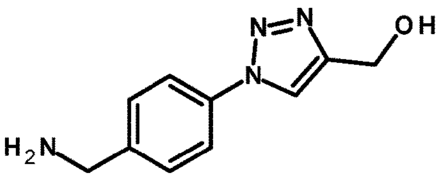
Figure 1W:
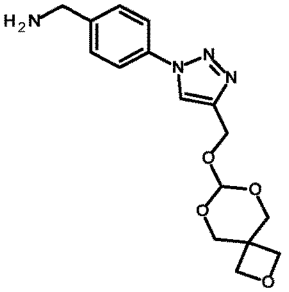
Figure 1X:
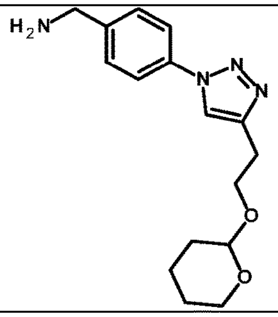
Figure 1X:
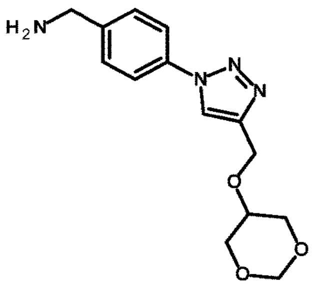
Figure 1X:
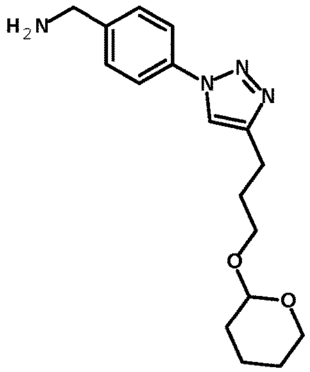
Figure 1X:
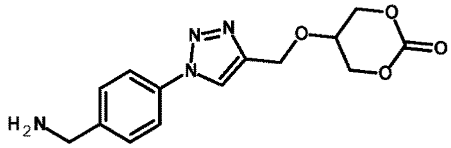
Figure 1X:
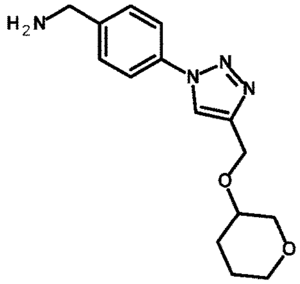
Figure 1X:
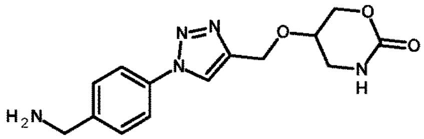
Figure 1X:
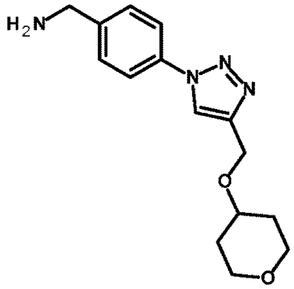
Figure 1X:
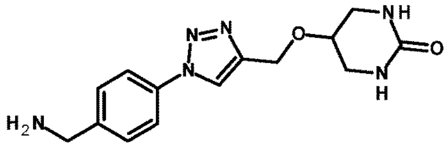
Figure 1X:
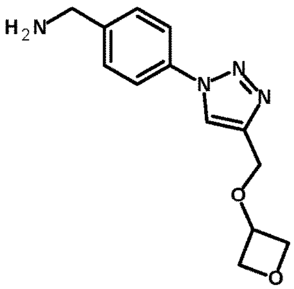
Figure 1X:
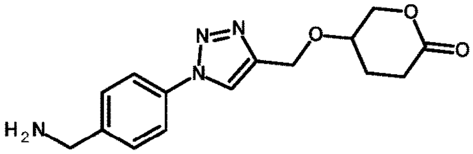
Figure 1Y:
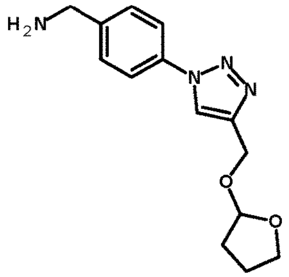
Figure 1Y:
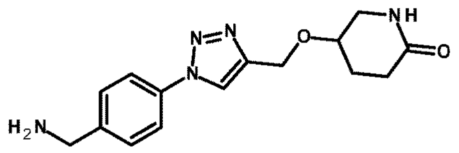
Figure 1Y:
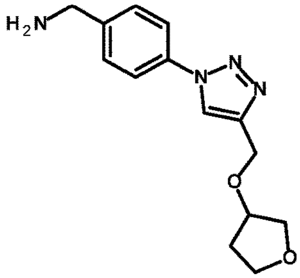
Figure 1Y:
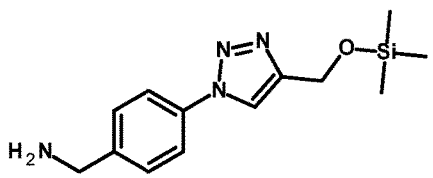
Figure 1Y:
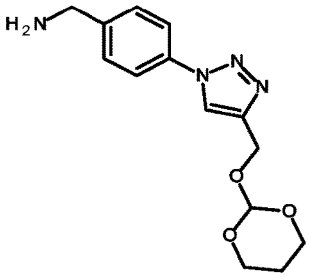
Figure 1Y:
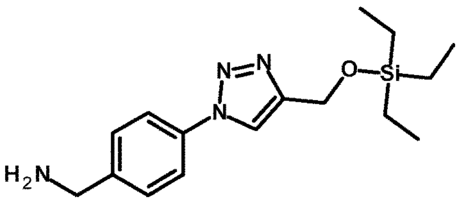
Figure 1Y:
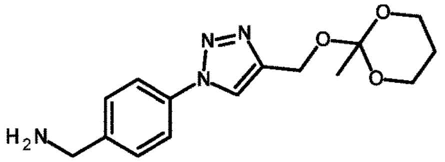
Figure 1Y:
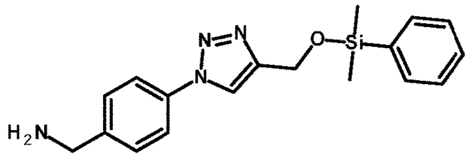
Figure 1Y:
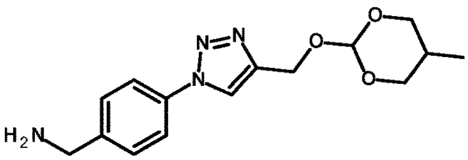
Figure 1Y:
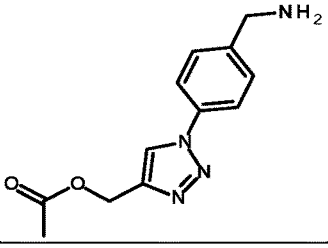
Figure 1Y:
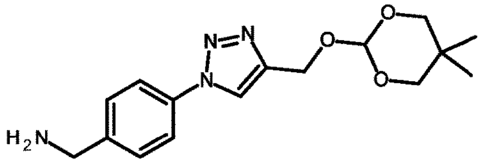
Figure 1Y:
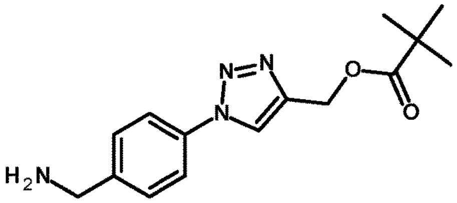
Figure 1Z:
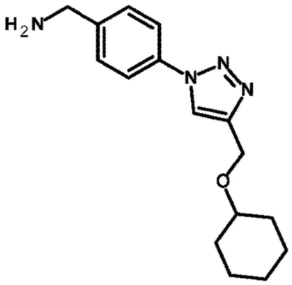
Figure 1Z:
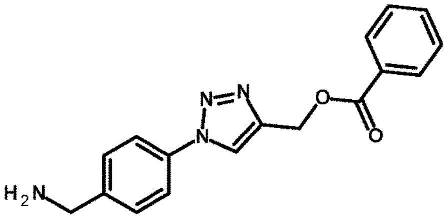
Figure 1Z:
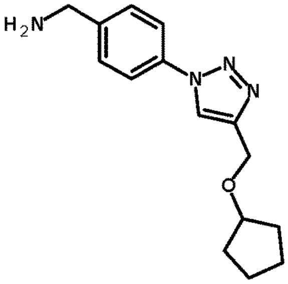
Figure 1Z:
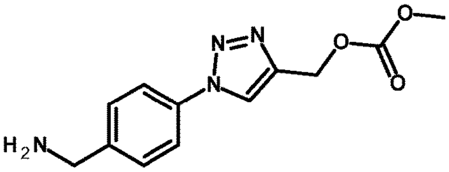
Figure 1Z:
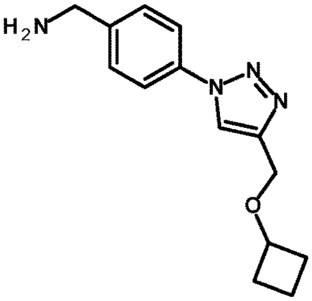
Figure 1Z:
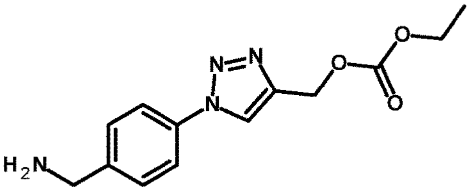
Figure 1Z:
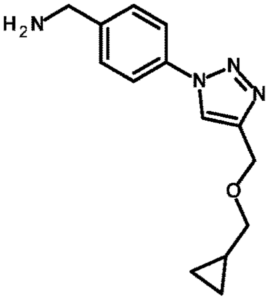
Figure 1Z:
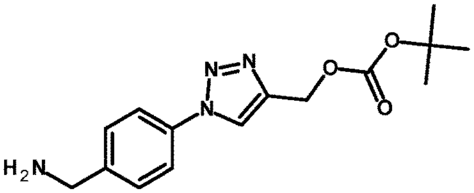
Figure 1Z:
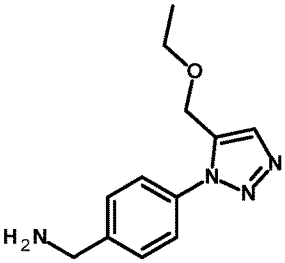
Figure 1Z:
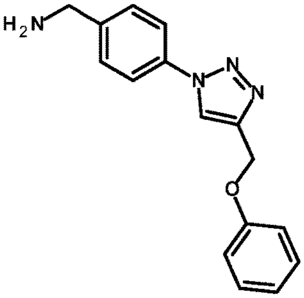
Figure 1A:
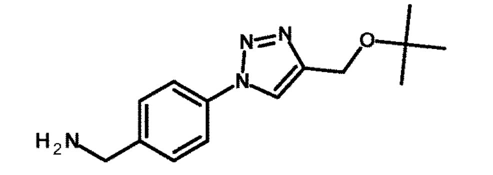
Figure 1A:
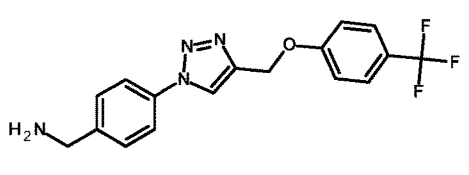
Figure 1A:
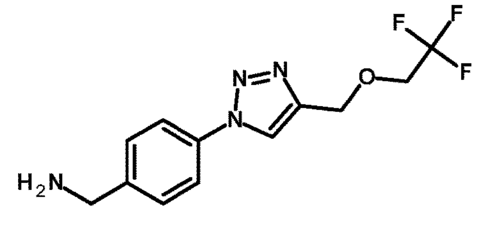
Figure 1A:
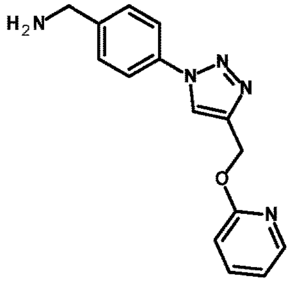
Figure 1A:
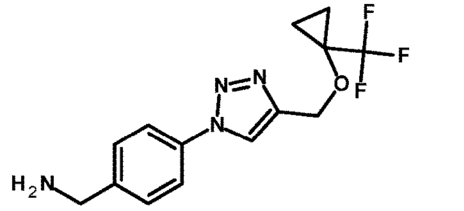
Figure 1A:
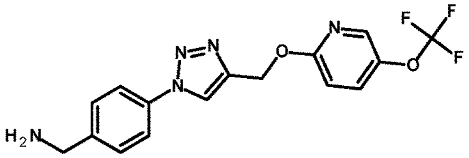
Figure 1A:
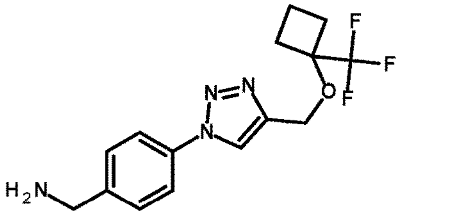
Figure 1A:
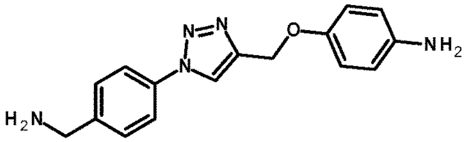
Figure 1A:
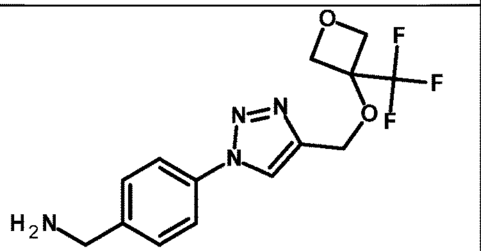
Figure 1A:
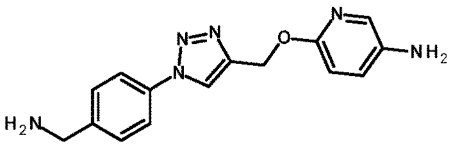
Figure 1A:
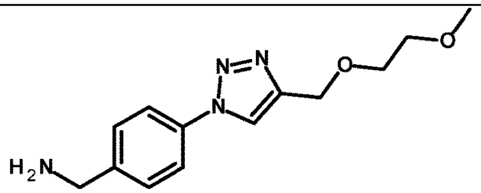
Figure 1A:
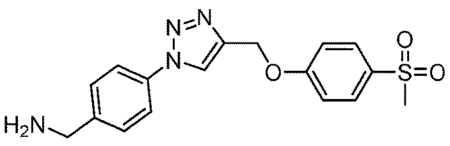
Figure 1A:
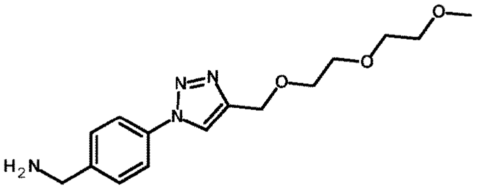
Figure 1A:
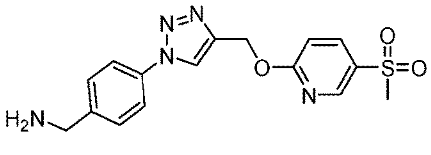
Figure 1B:
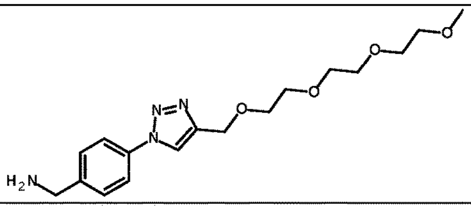
Figure 1B:
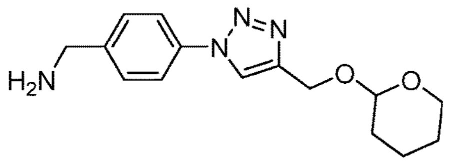
Figure 1B:
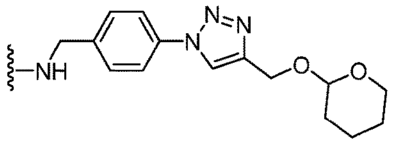
Figure 1B:
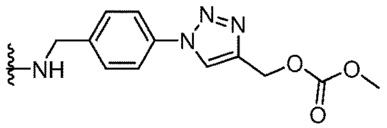
Figure 1B:
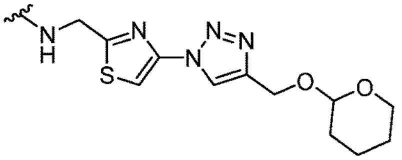
Figure 1B:
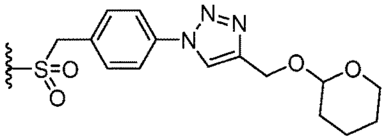
Figure 1B:
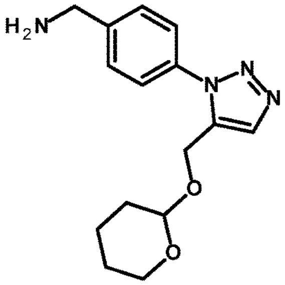
Figure 1B:
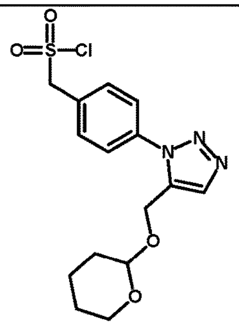
Figure 1B:
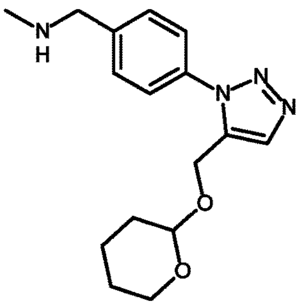
Figure 1B:
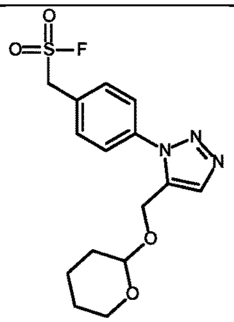
Figure 1B:
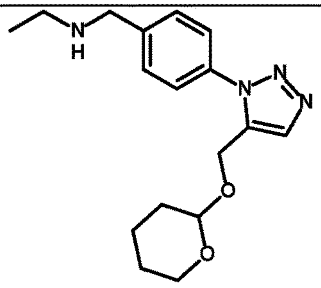
Figure 1B:
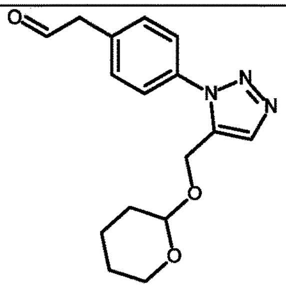
Figure 1C:
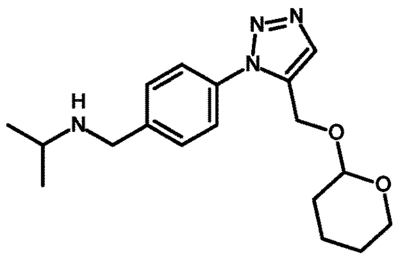
Figure 1C:
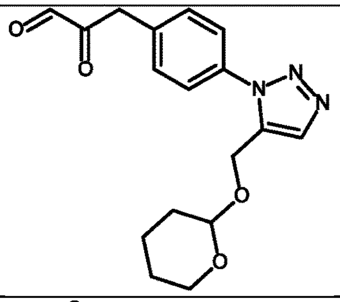
Figure 1C:
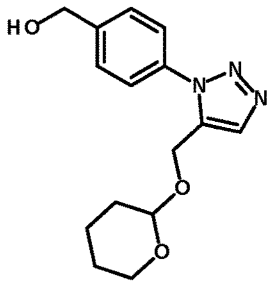
Figure 1C:
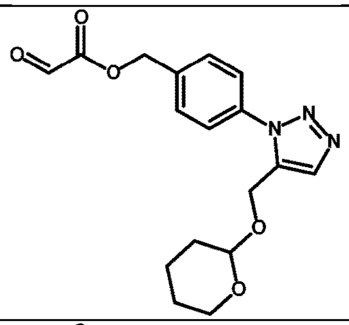
Figure 1C:
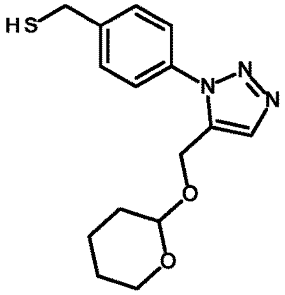
Figure 1C:
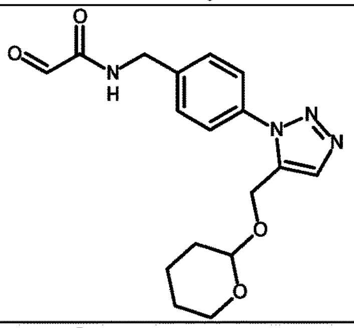
Figure 1C:
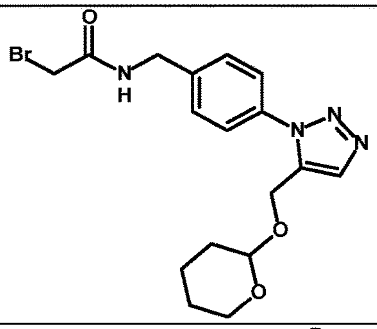
Figure 1C:
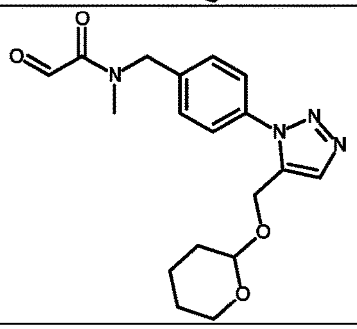
Figure 1C:
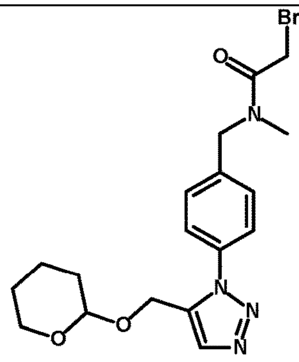
Figure 1C:
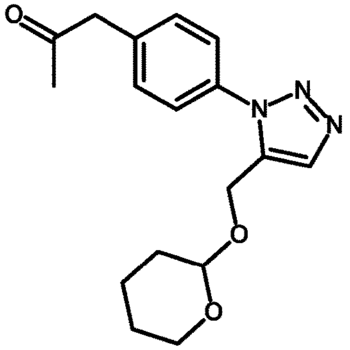
Figure 1D:
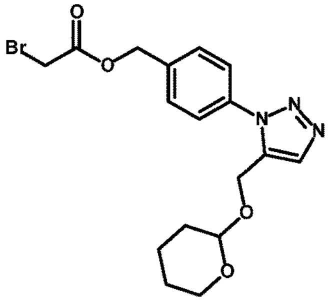
Figure 1D:
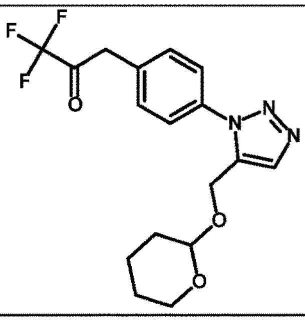
Figure 1D:
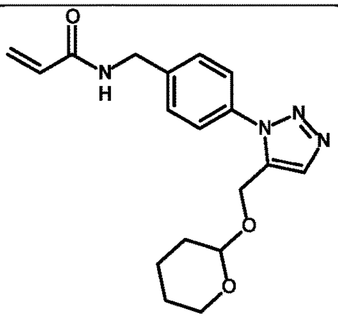
Figure 1D:
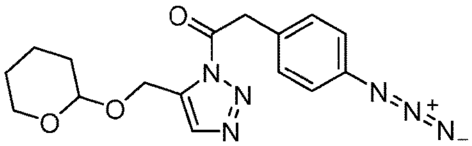
Figure 1D:
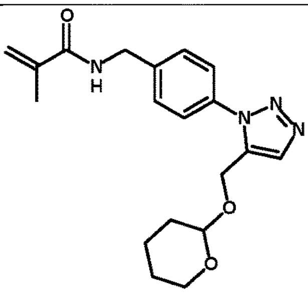
Figure 1D:
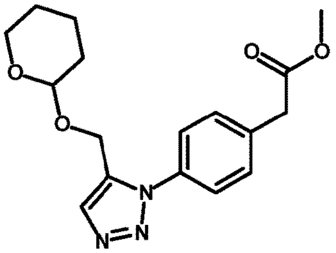
Figure 1D:
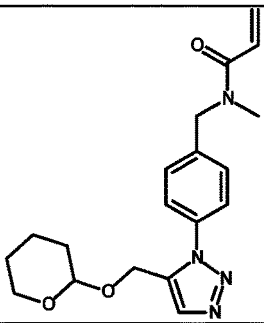
Figure 1D:
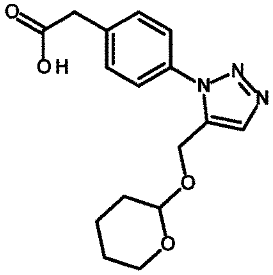
Figure 1D:
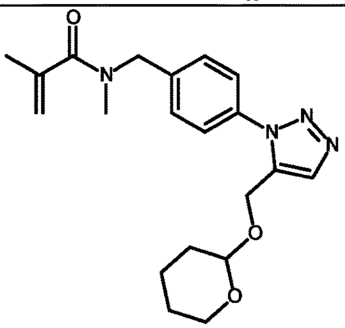
Figure 1D:
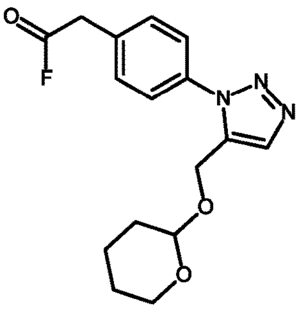
Figure 1E:
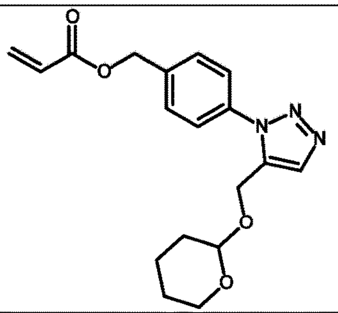
Figure 1E:
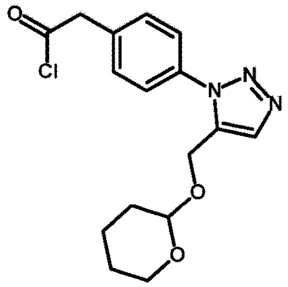
Figure 1E:
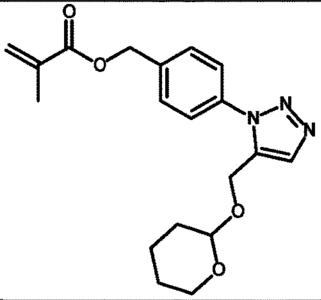
Figure 1E:
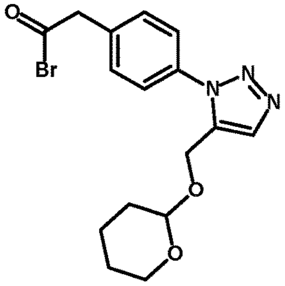
Figure 1E:
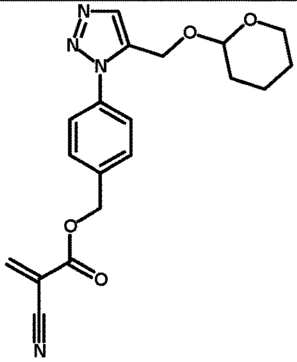
Figure 1E:
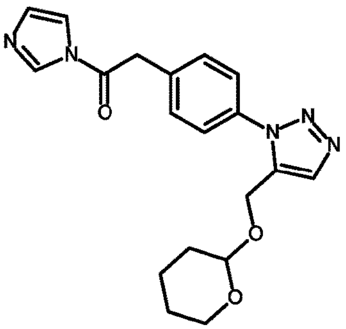
Figure 1E:
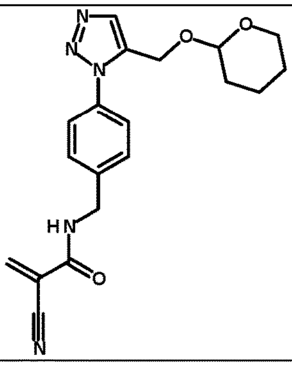
Figure 1E:
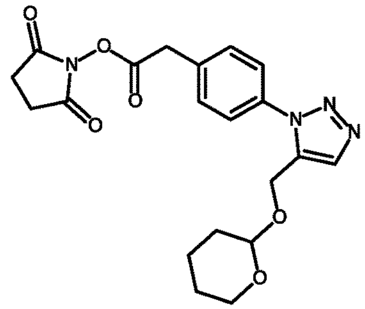
Figure 1E:
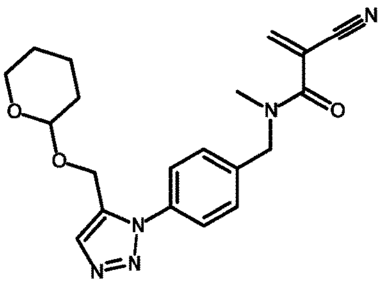
Figure 1E:
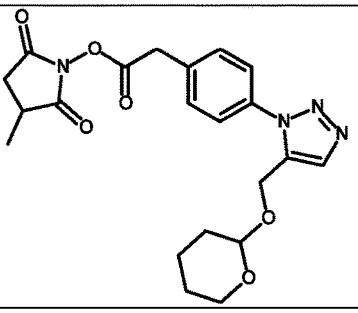
Figure 1F:
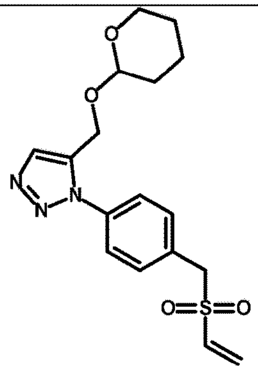
Figure 1F:
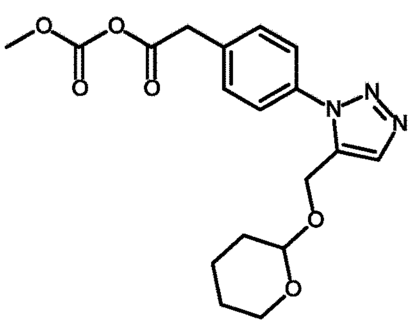
Figure 1F:
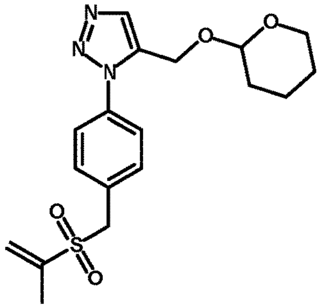
Figure 1F:
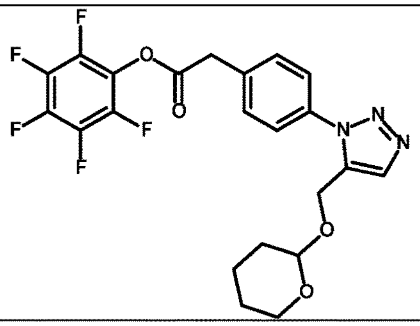
Figure 1F:
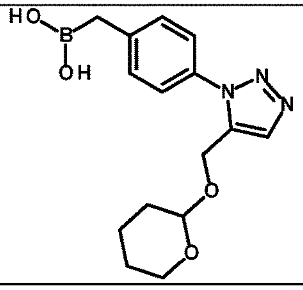
Figure 1F:
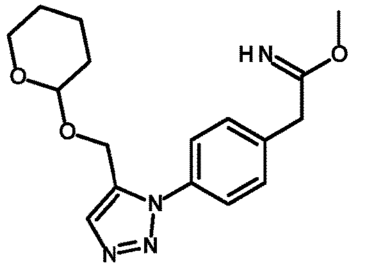
Figure 1F:
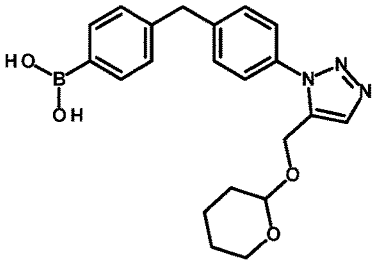
Figure 1F:
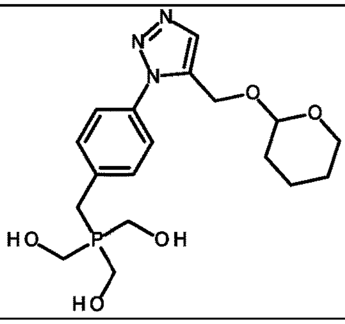
Figure 1F:
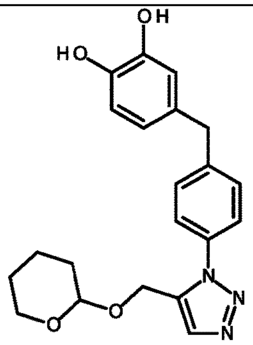
Figure 1F:
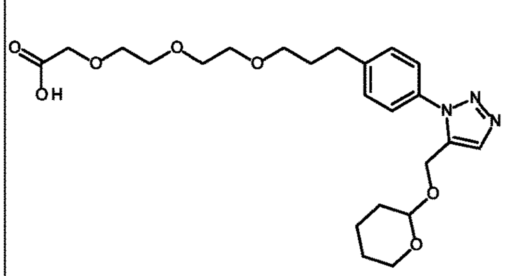
Figure 1G:
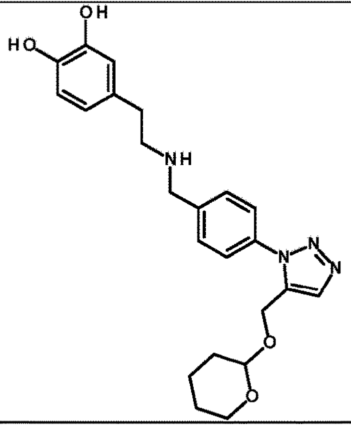
Figure 1G:
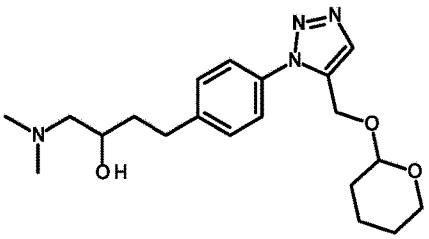
Figure 1G:
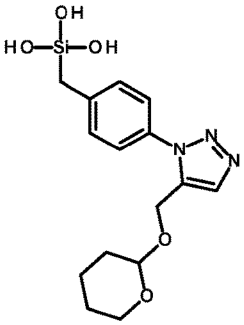
Figure 1G:
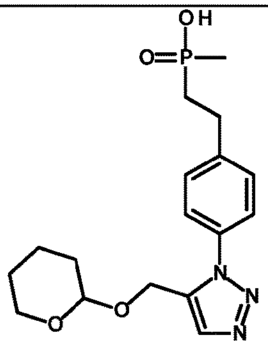
Figure 1G:
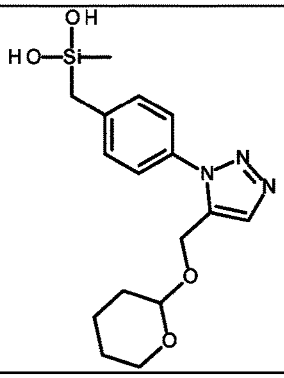
Figure 1G:
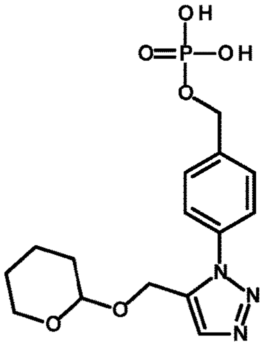
Figure 1G:
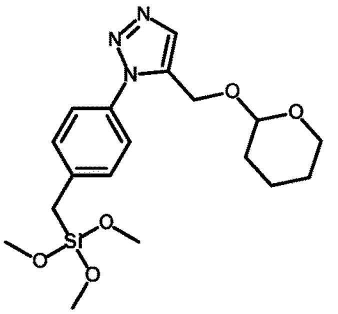
Figure 1G:
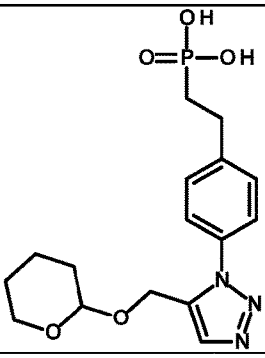
Figure 1H:
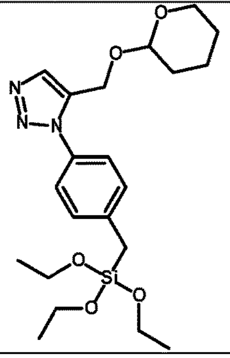
Figure 1H:
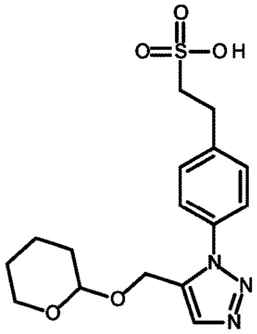
Figure 1H:
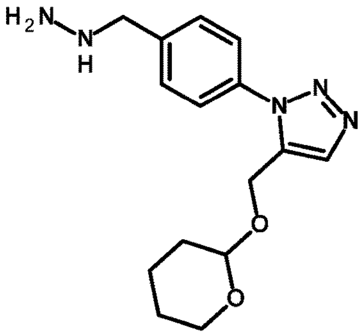
Figure 1H:
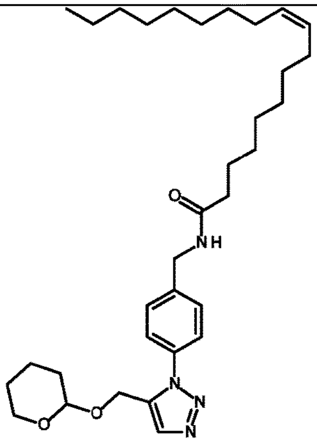
Figure 1H:
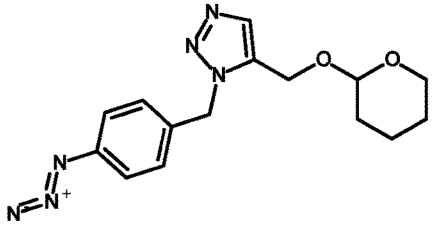
Figure 1H:
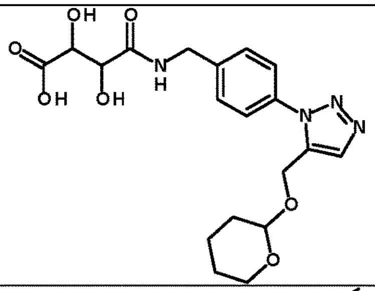
Figure 1H:
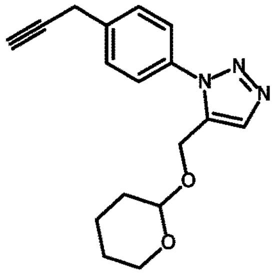
Figure 1H:
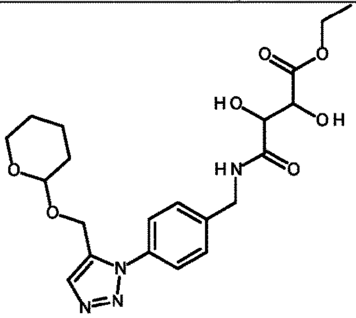
Figure 1H:
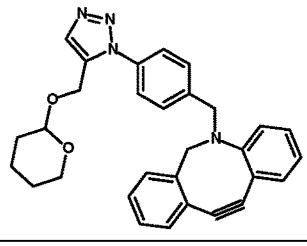
Figure 1H:
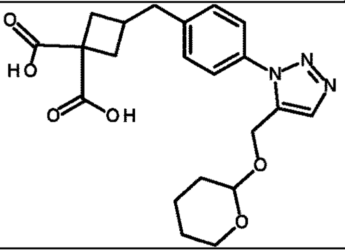
Figure 1I:
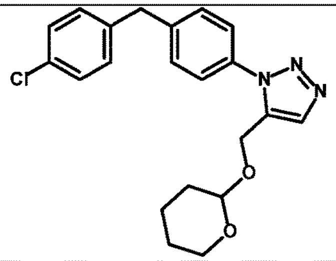
Figure 1I:
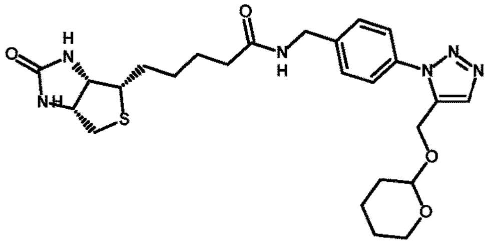
Figure 1I:
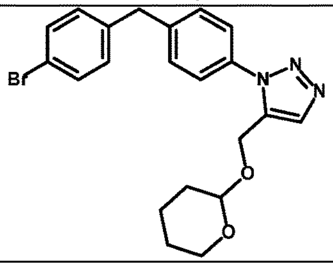
Figure 1I:
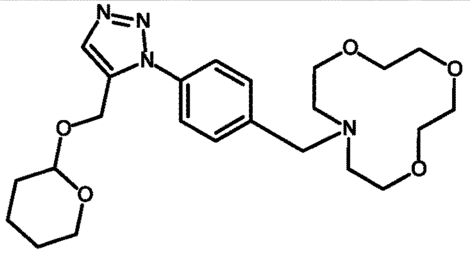
Figure 1I:
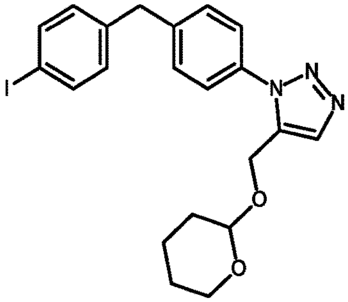
Figure 1I:
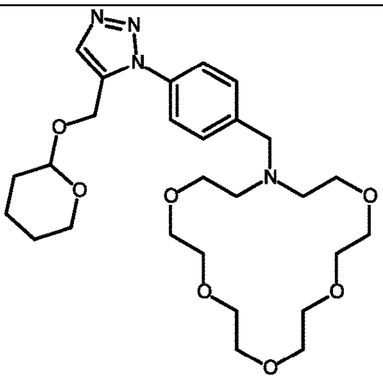
Figure 1I:
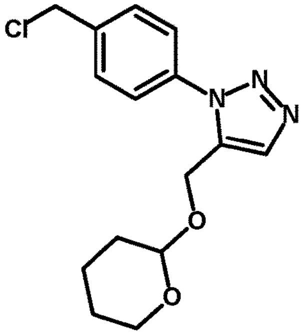
Figure 1I:
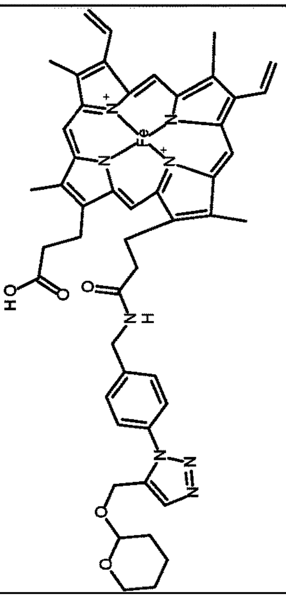
Figure 1J:
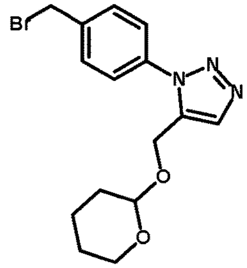
Figure 1J:
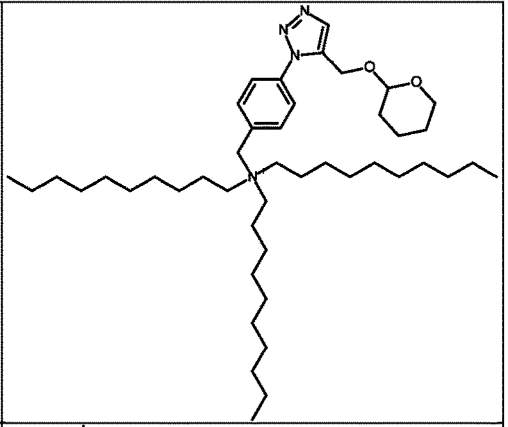
Figure 1J:
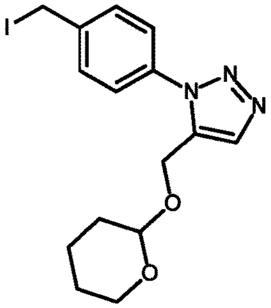
Figure 1J:
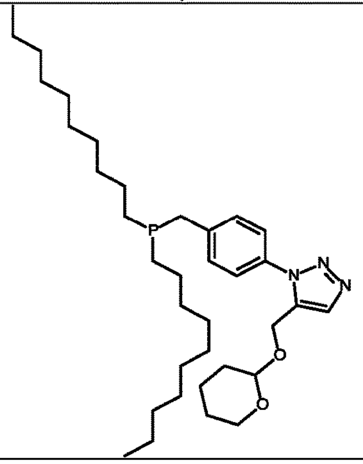
Figure 1J:
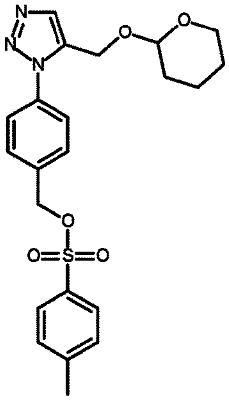
Figure 1J:
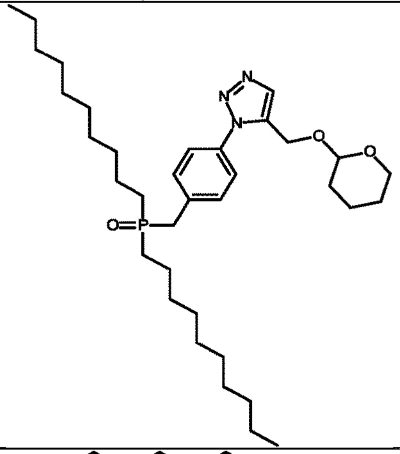
Figure 1J:
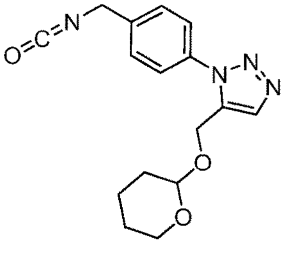
Figure 1J:
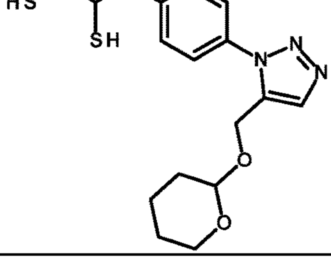
Figure 1K:
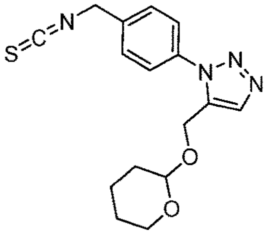
Figure 1K:
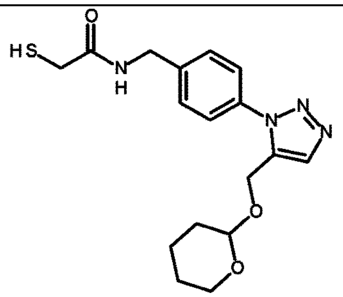
Figure 1K:
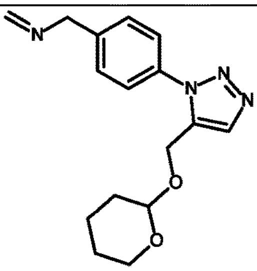
Figure 1K:
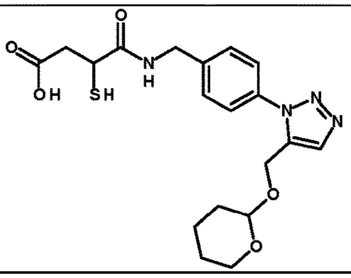
Figure 1K:
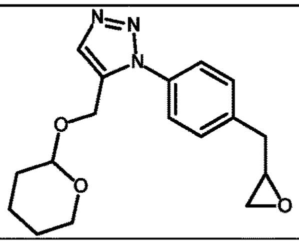
Figure 1K:
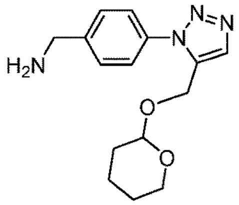
Figure 1K:
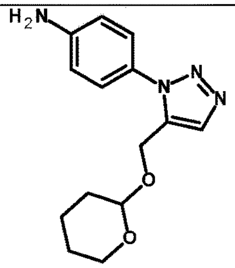
Figure 1K:
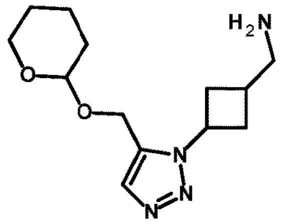
Figure 1K:
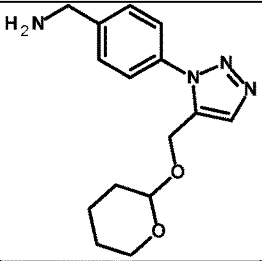
Figure 1K:
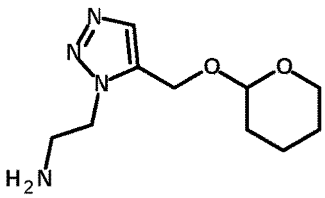
Figure 1K:
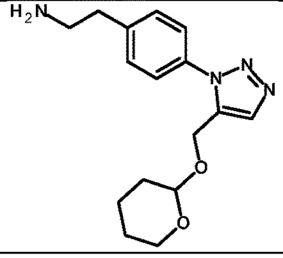
Figure 1K:
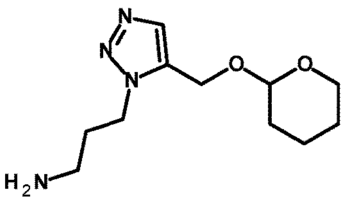
Figure 1L:
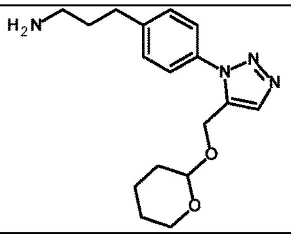
Figure 1L:
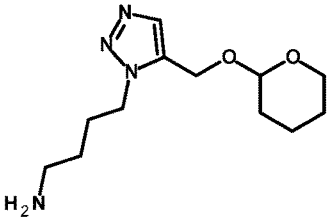
Figure 1L:
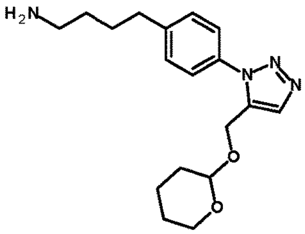
Figure 1L:
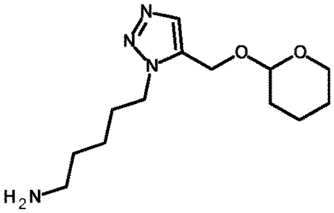
Figure 1L:
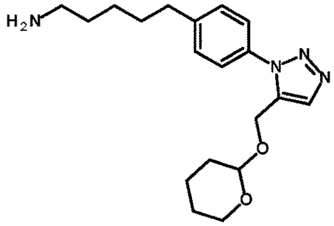
Figure 1L:
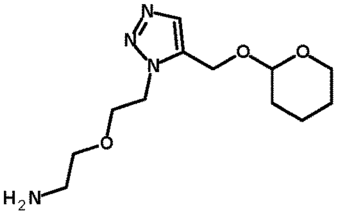
Figure 1L:
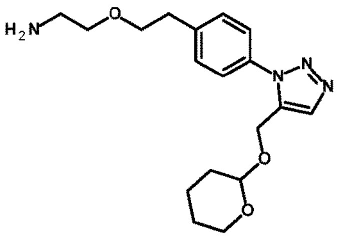
Figure 1L:
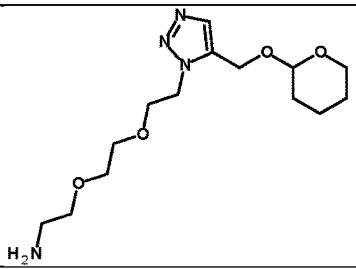
Figure 1L:
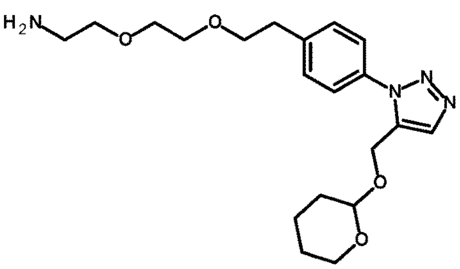
Figure 1L:
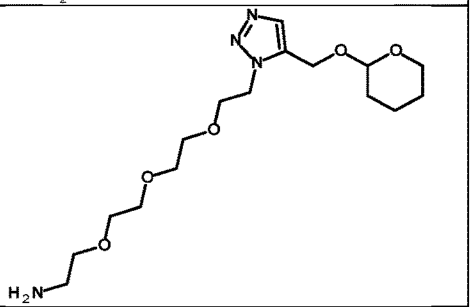
Figure 1L:
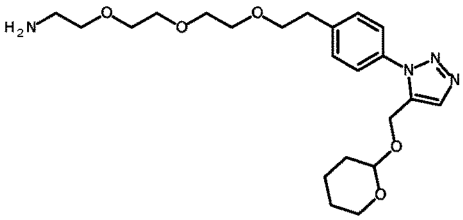
Figure 1L:
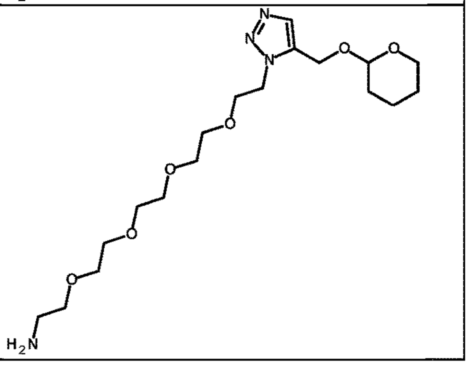
Figure 1M:
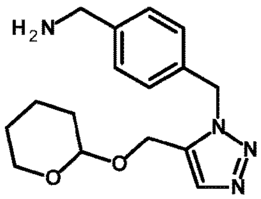
Figure 1M:
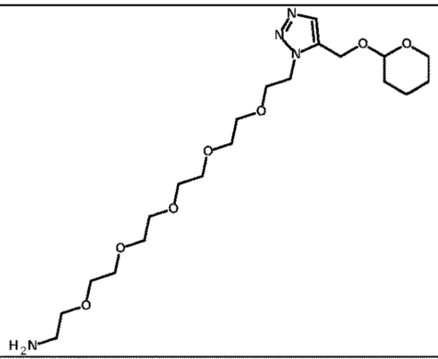
Figure 1M:
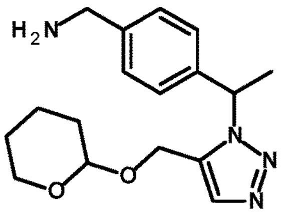
Figure 1M:
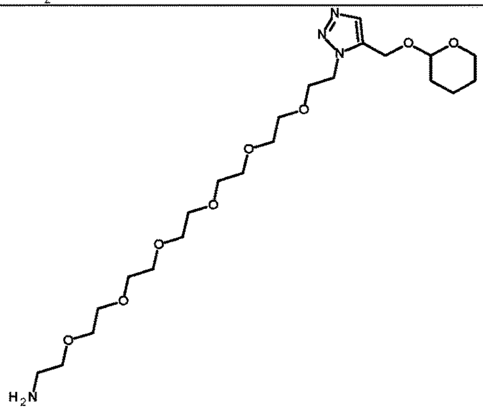
Figure 1M:
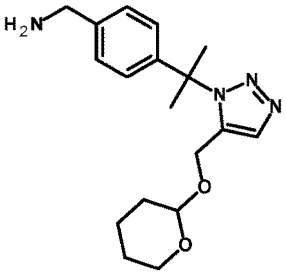
Figure 1M:
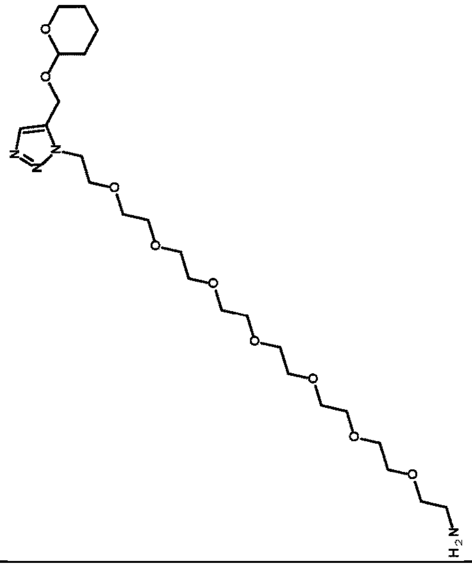
Figure 1N:
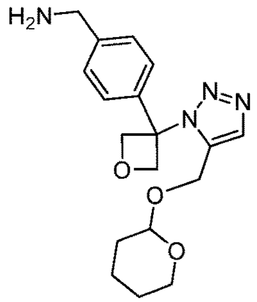
Figure 1N:
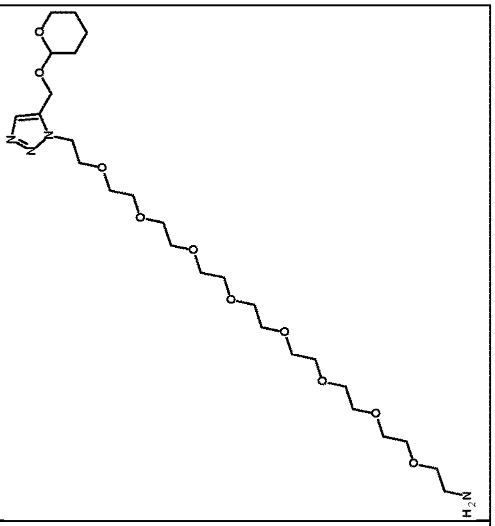
Figure 1N:
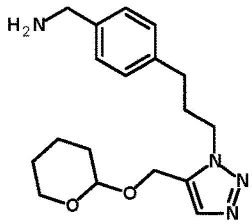
Figure 1N:
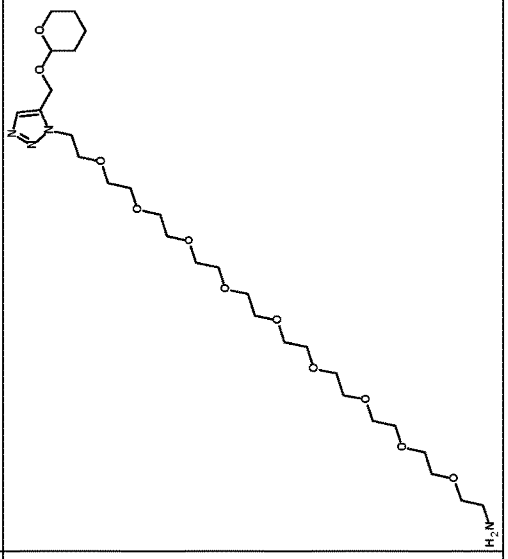
Figure 1N:
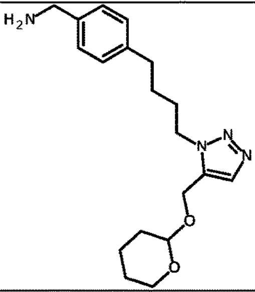
Figure 1N:
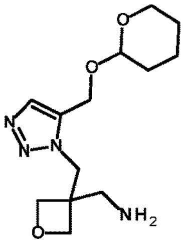
Figure 1N:
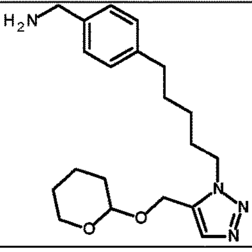
Figure 1N:
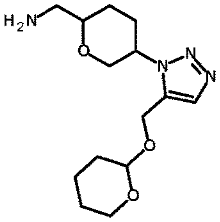
Figure 1O:
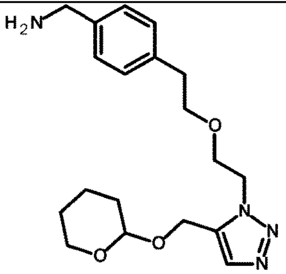
Figure 1O:
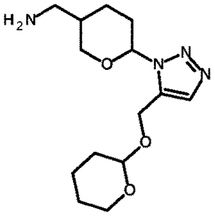
Figure 1O:
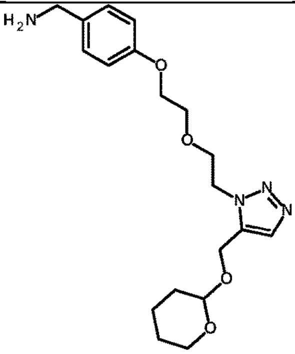
Figure 1O:
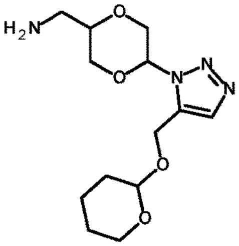
Figure 1O:
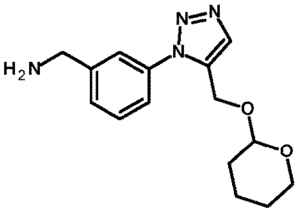
Figure 1O:
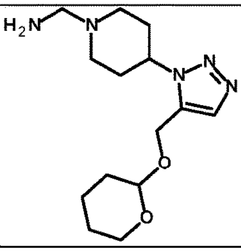
Figure 1O:
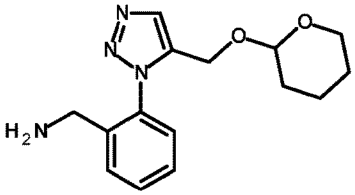
Figure 1O:
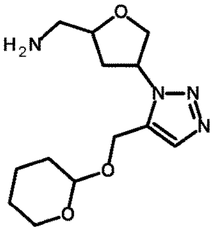
Figure 1O:
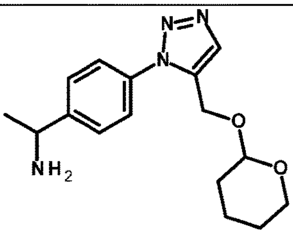
Figure 1O:
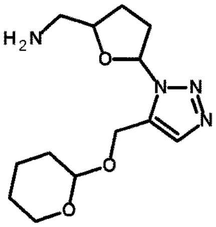
Figure 1O:
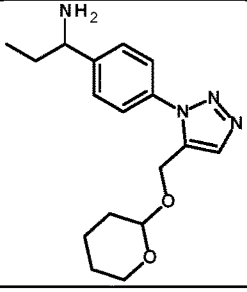
Figure 1O:
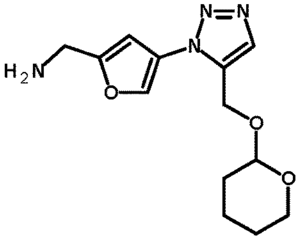
Figure 1P:
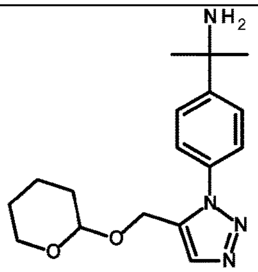
Figure 1P:
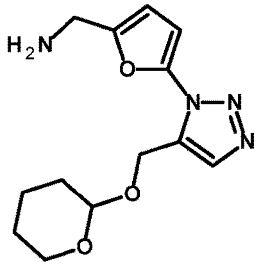
Figure 1P:
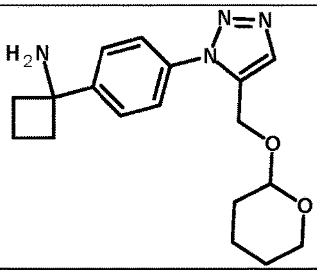
Figure 1P:
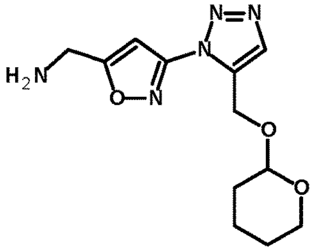
Figure 1P:
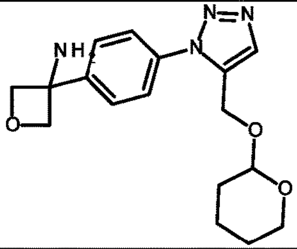
Figure 1P:
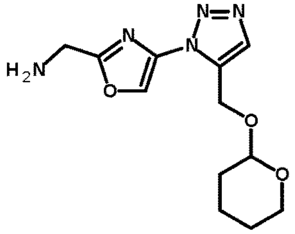
Figure 1P:
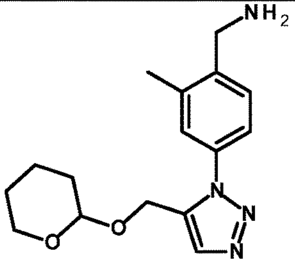
Figure 1P:
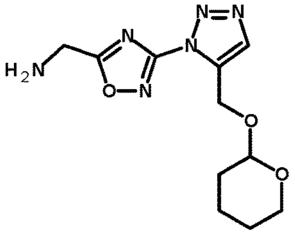
Figure 1P:
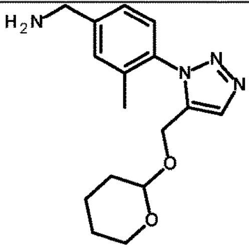
Figure 1P:
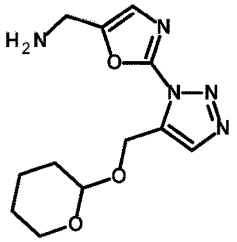
Figure 1P:
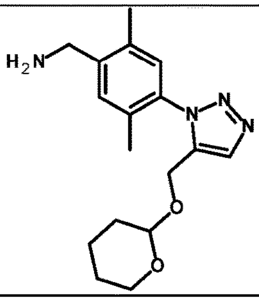
Figure 1P:
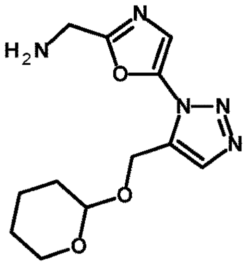
Figure 1Q:
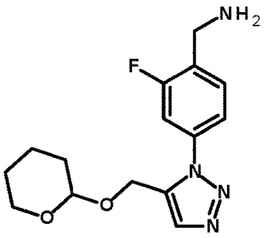
Figure 1Q:
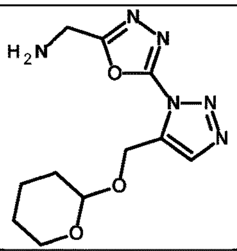
Figure 1Q:
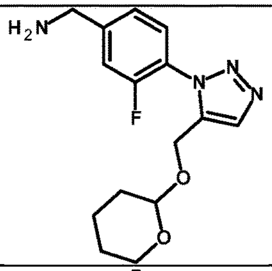
Figure 1Q:
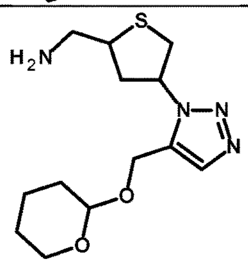
Figure 1Q:
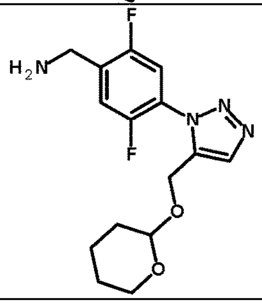
Figure 1Q:
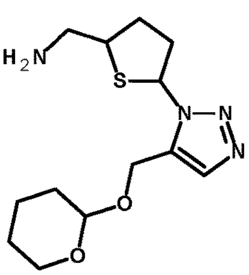
Figure 1Q:
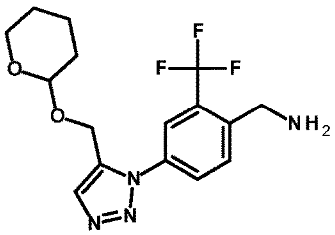
Figure 1Q:
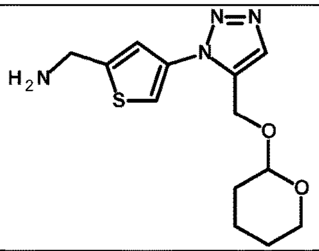
Figure 1Q:
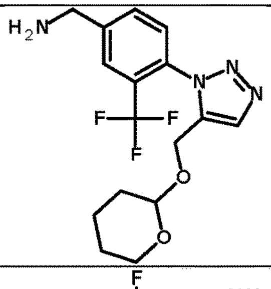
Figure 1Q:
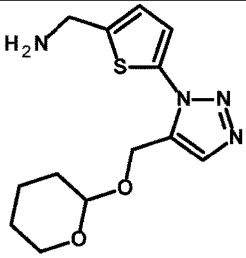
Figure 1Q:
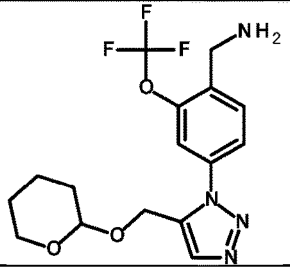
Figure 1Q:
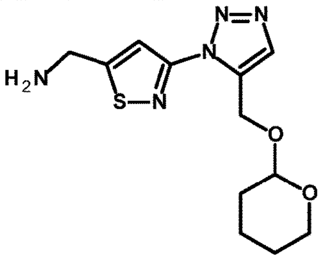
Figure 1R:
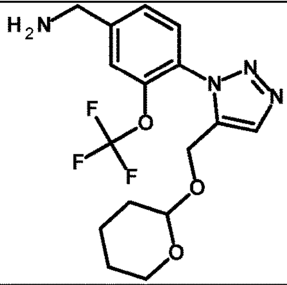
Figure 1R:
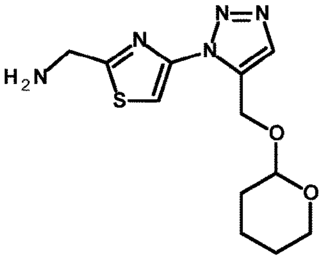
Figure 1R:
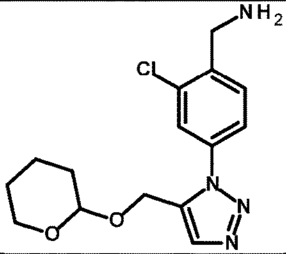
Figure 1R:
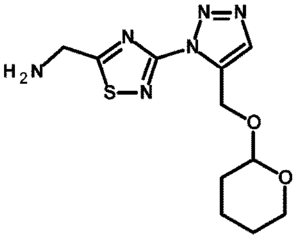
Figure 1R:
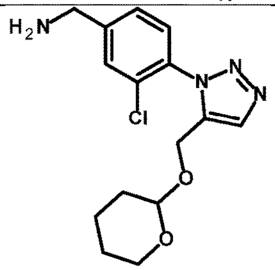
Figure 1R:
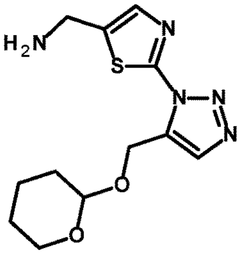
Figure 1R:
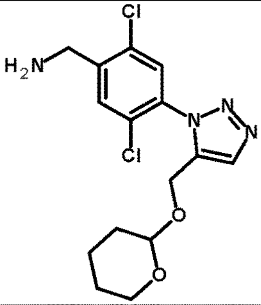
Figure 1R:
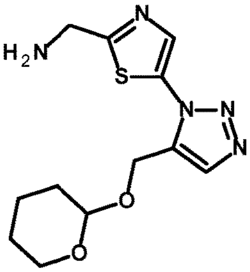
Figure 1R:
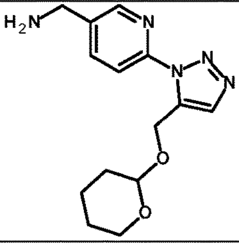
Figure 1R:
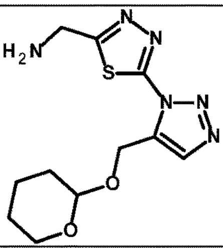
Figure 1R:
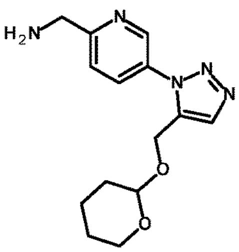
Figure 1R:
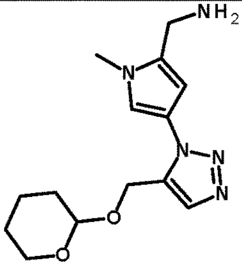
Figure 1S:
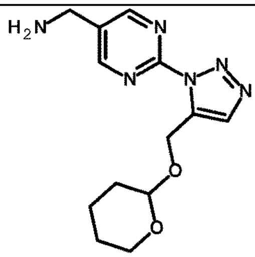
Figure 1S:
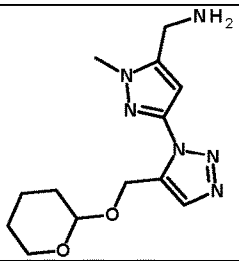
Figure 1S:
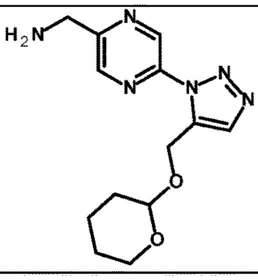
Figure 1S:
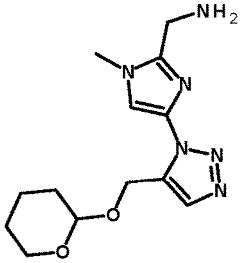
Figure 1S:
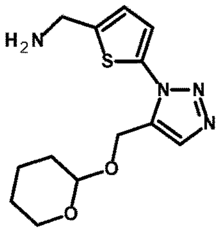
Figure 1S:
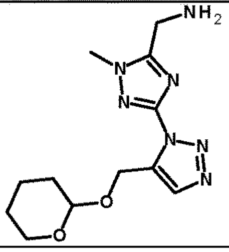
Figure 1S:
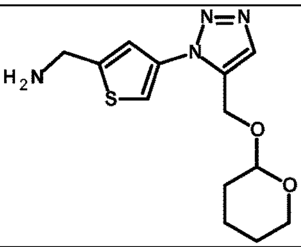
Figure 1S:
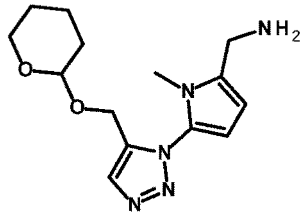
Figure 1S:
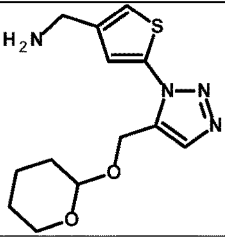
Figure 1S:
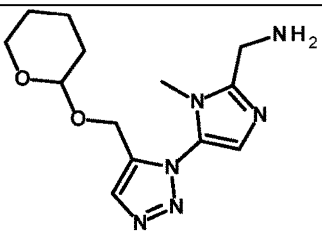
Figure 1S:
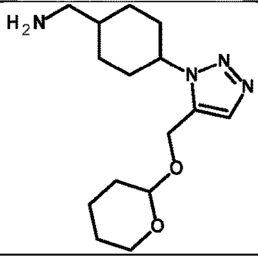
Figure 1S:
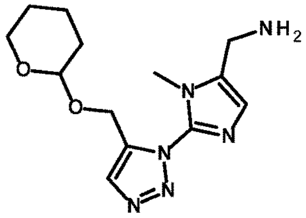
Figure 1T:
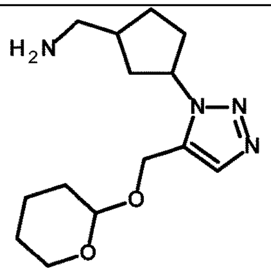
Figure 1T:
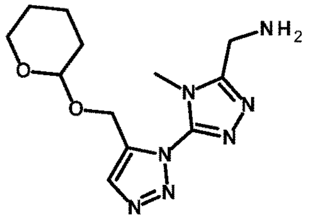
Figure 1T:
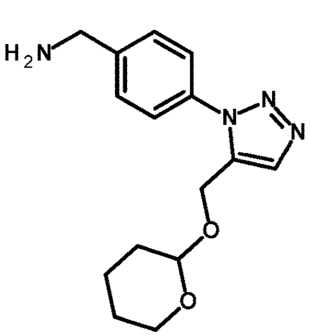
Figure 1T:
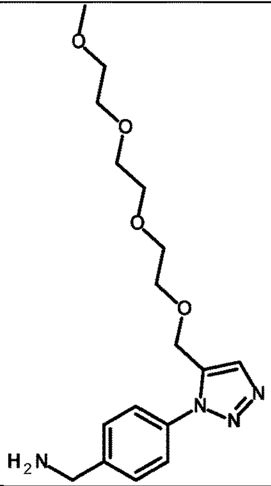
Figure 1T:
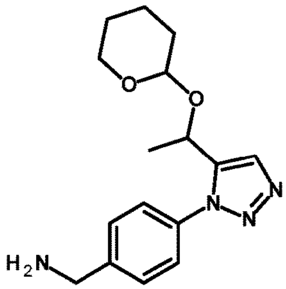
Figure 1T:
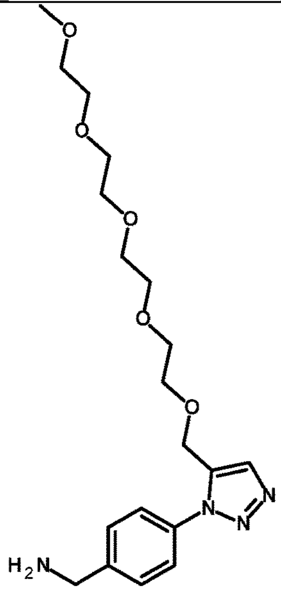
Figure 1U:
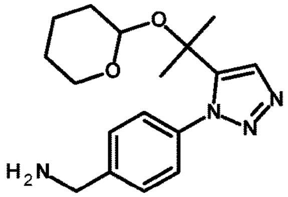
Figure 1U:
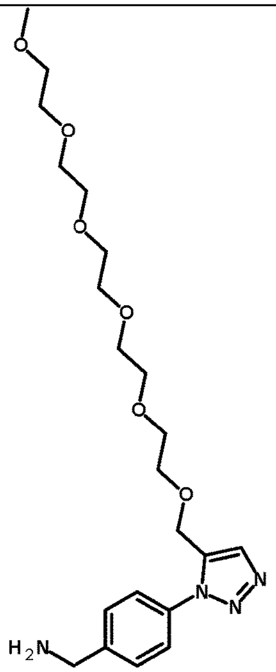
Figure 1U:
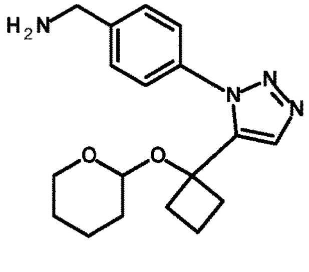
Figure 1U:
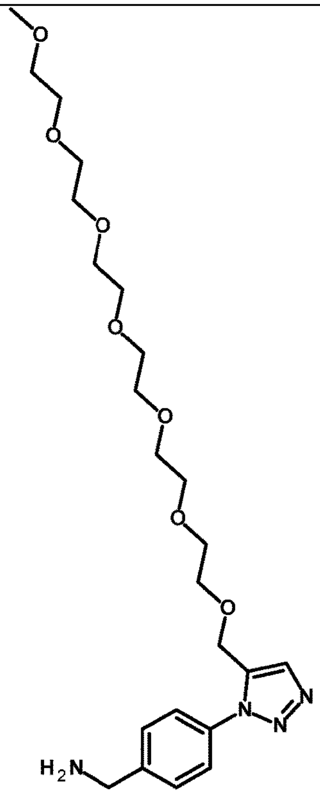
Figure 1V:
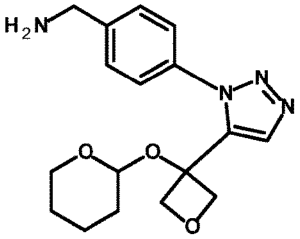
Figure 1V:
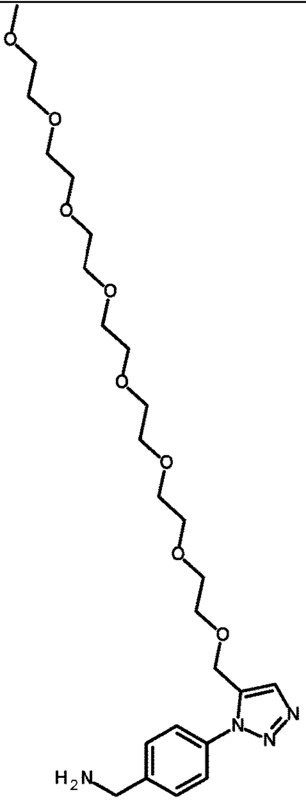
Figure 1V:
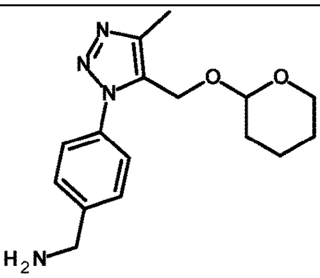
Figure 1V:
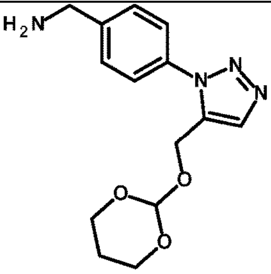
Figure 1V:
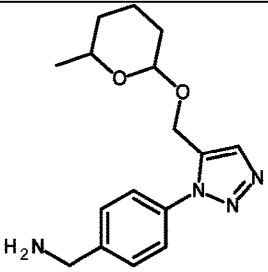
Figure 1V:
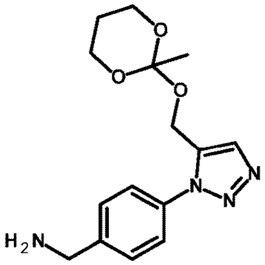
Figure 1V:
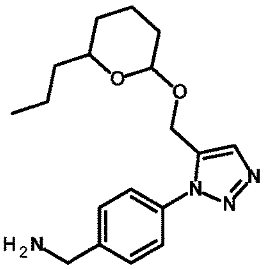
Figure 1V:
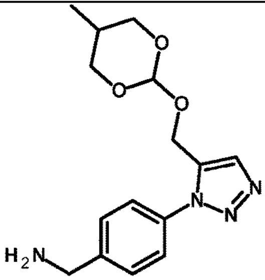
Figure 1W:
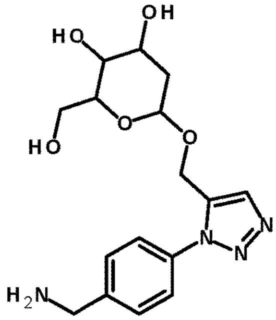
Figure 1W:
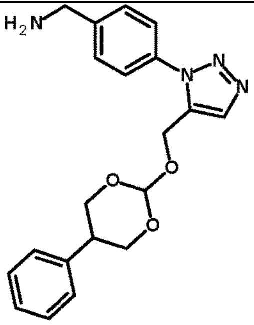
Figure 1W:
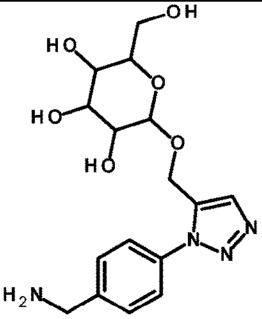
Figure 1W:
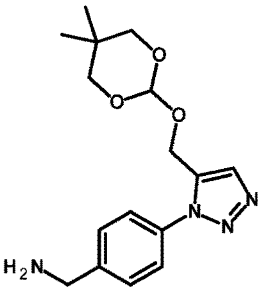
Figure 1W:
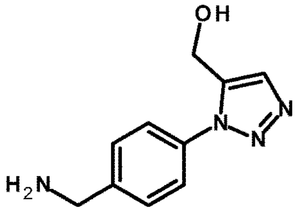
Figure 1W:
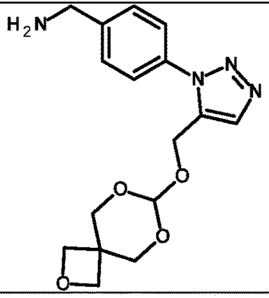
Figure 1W:
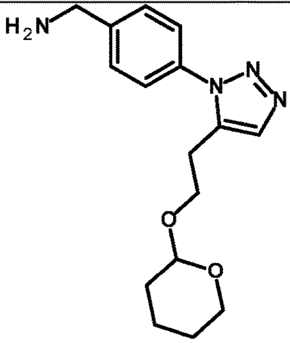
Figure 1W:
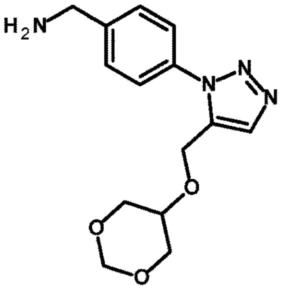
Figure 1W:
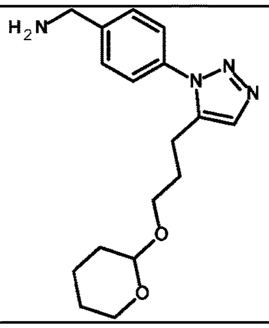
Figure 1W:
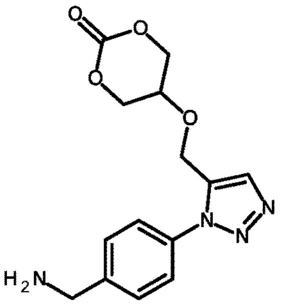
Figure 1X:
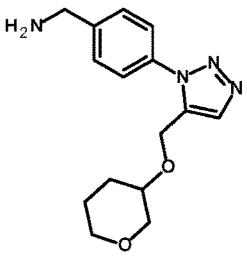
Figure 1X:
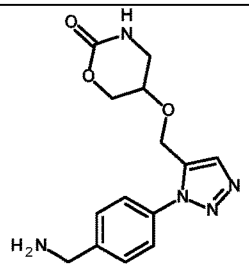
Figure 1X:
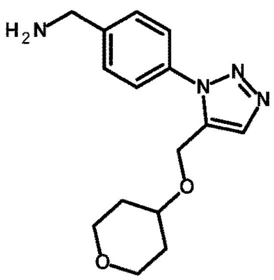
Figure 1X:
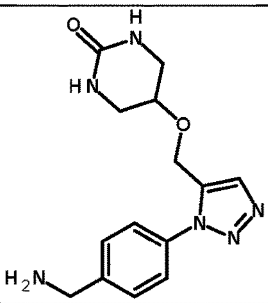
Figure 1X:
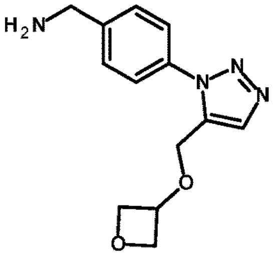
Figure 1X:
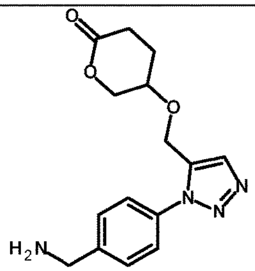
Figure 1X:
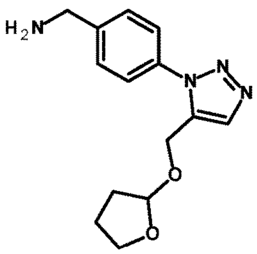
Figure 1X:
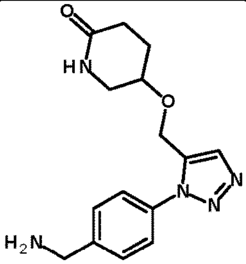
Figure 1X:
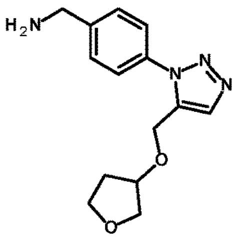
Figure 1X:
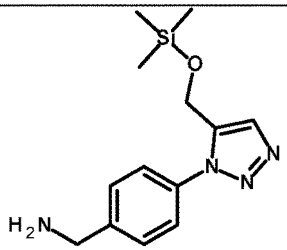
Figure 1X:
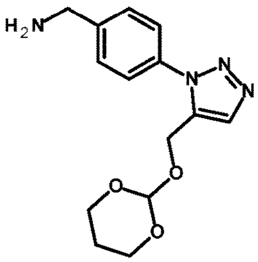
Figure 1X:
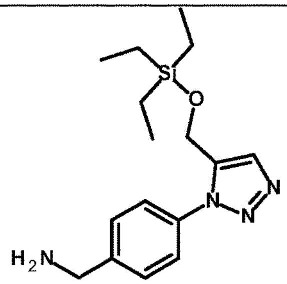
Figure 1Y:
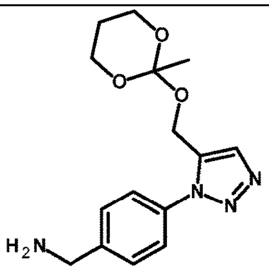
Figure 1Y:
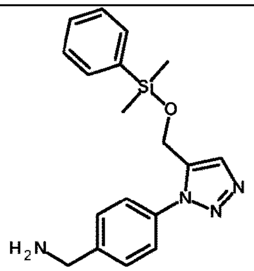
Figure 1Y:
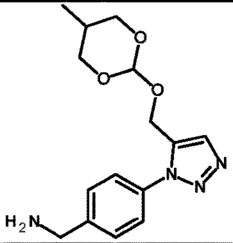
Figure 1Y:
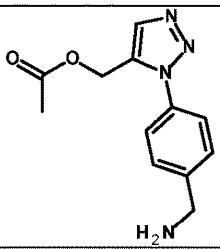
Figure 1Y:
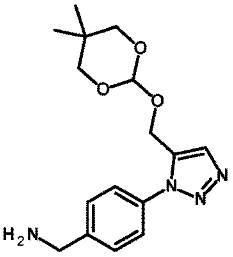
Figure 1Y:
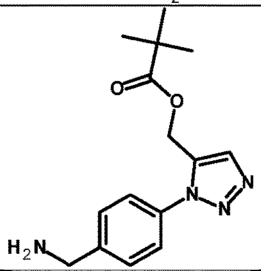
Figure 1Y:
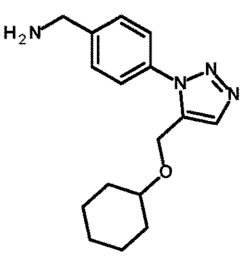
Figure 1Y:
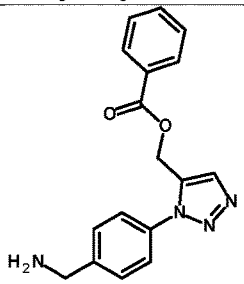
Figure 1Y:
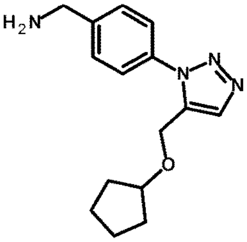
Figure 1Y:
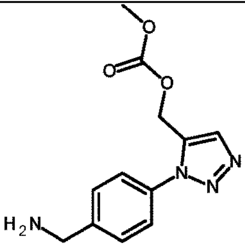
Figure 1Y:
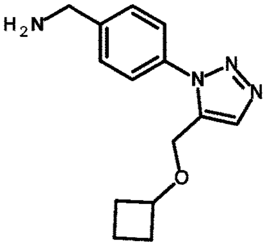
Figure 1Y:
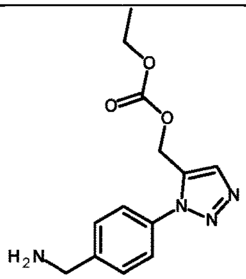
Figure 1Z:
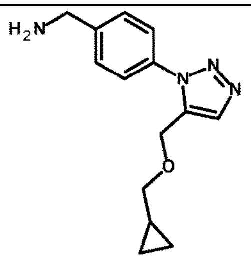
Figure 1Z:
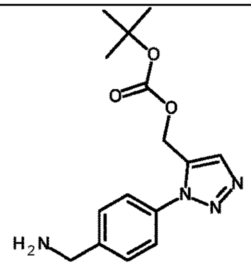
Figure 1Z:
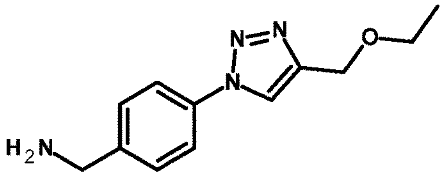
Figure 1Z:
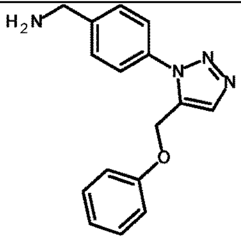
Figure 1Z:
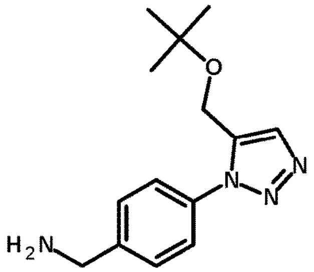
Figure 1Z:
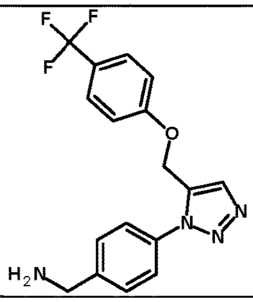
Figure 1Z:
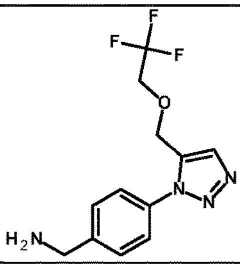
Figure 1Z:
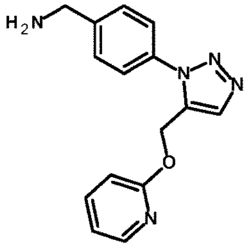
Figure 1Z:
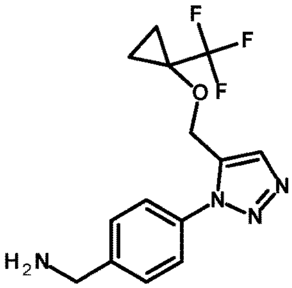
Figure 1Z:
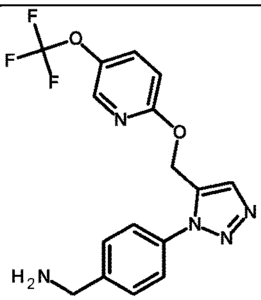
Figure 1Z:
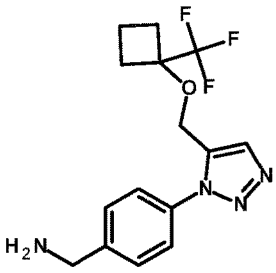
Figure 1Z:
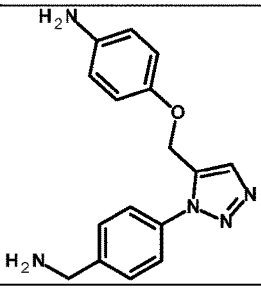
Figure 2A:
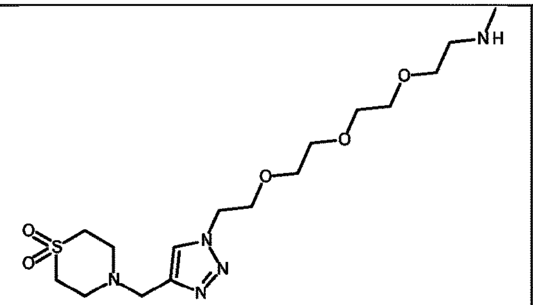
Figure 2A:
Figure 2A:
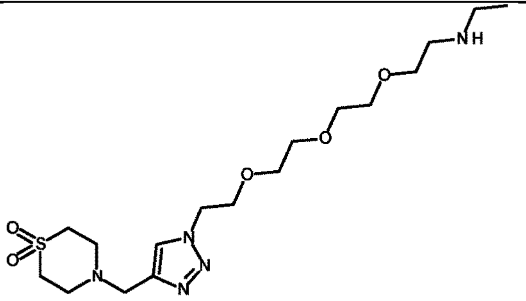
Figure 2A:
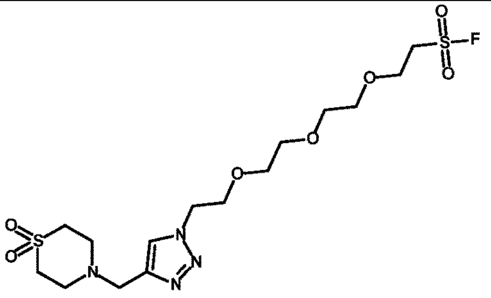
Figure 2A:
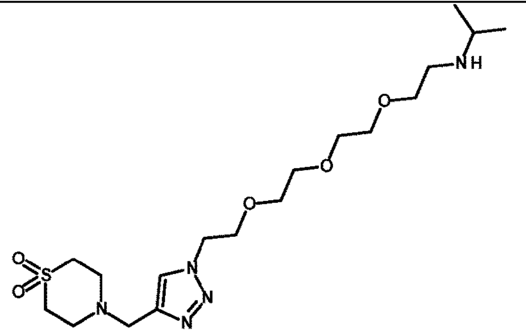
Figure 2A:
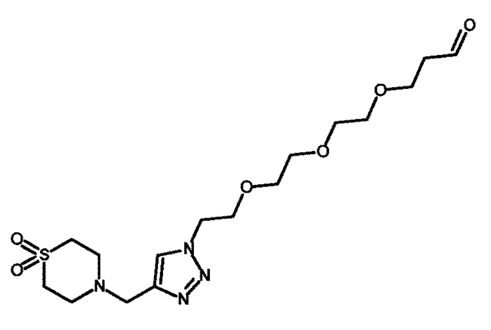
Figure 2A:
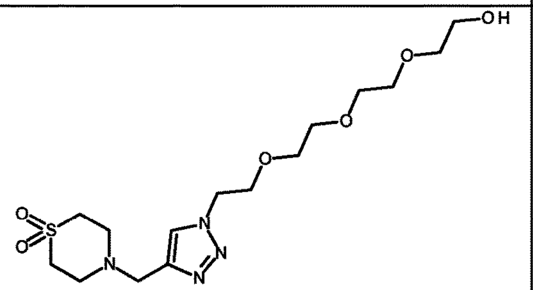
Figure 2A:
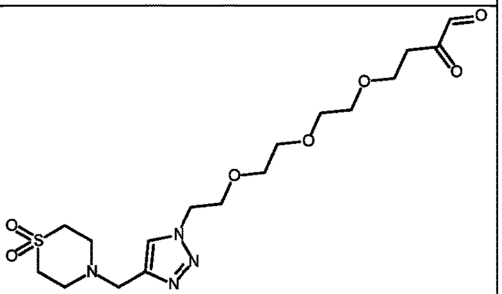
Figure 2A:
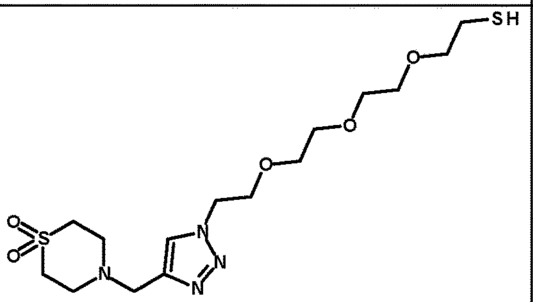
Figure 2A:
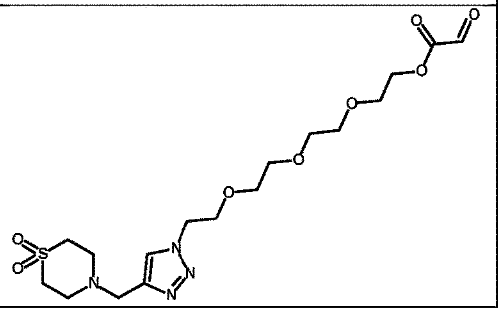
Figure 2B:
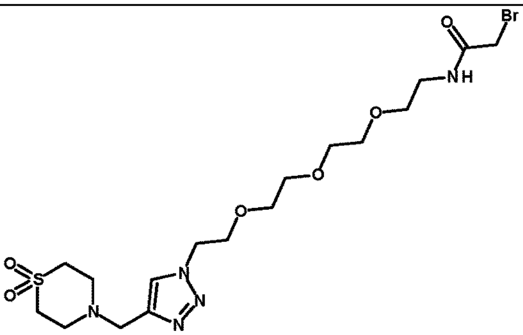
Figure 2B:
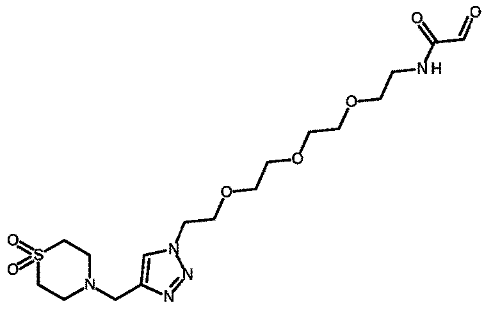
Figure 2B:
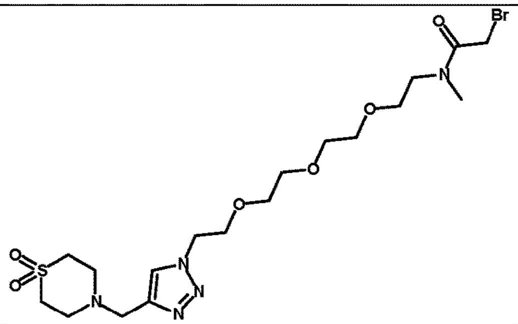
Figure 2B:
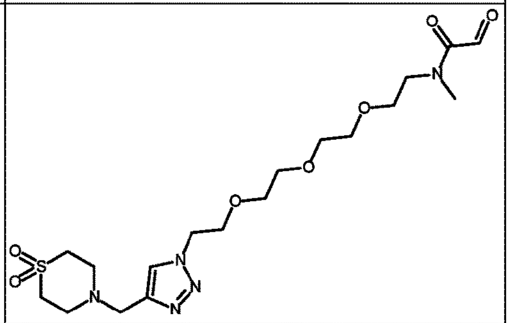
Figure 2B:
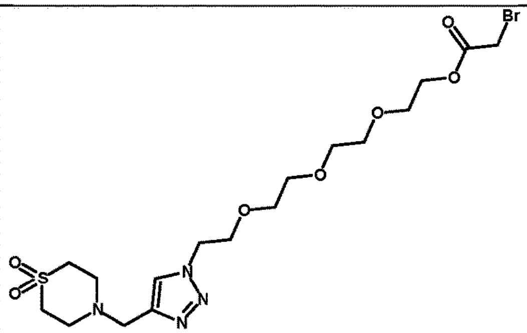
Figure 2B:
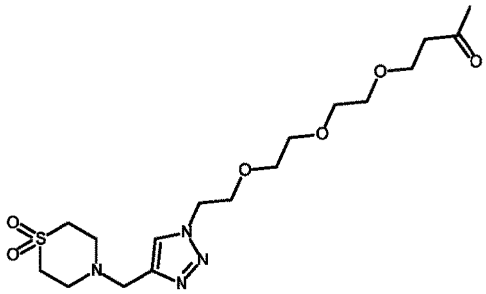
Figure 2B:
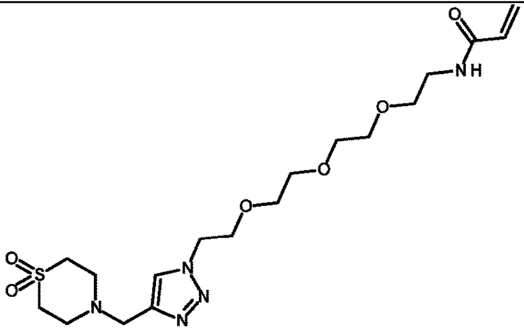
Figure 2B:
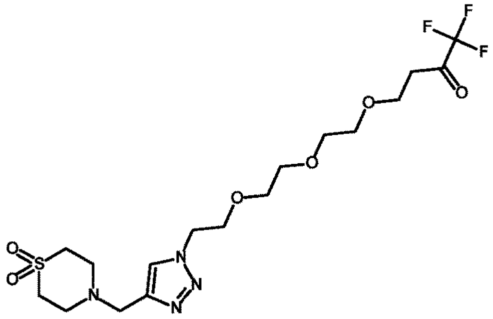
Figure 2C:
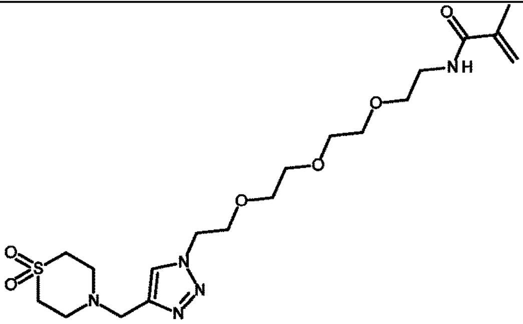
Figure 2C:
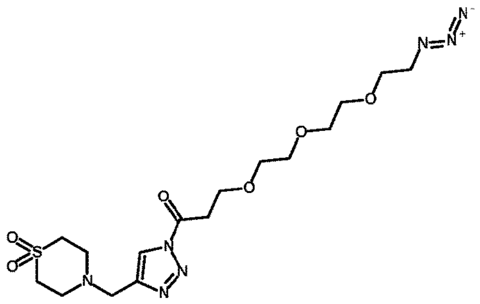
Figure 2C:
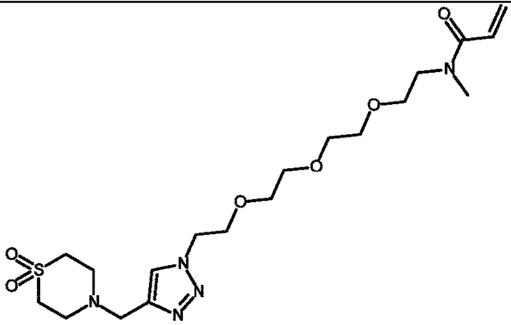
Figure 2C:
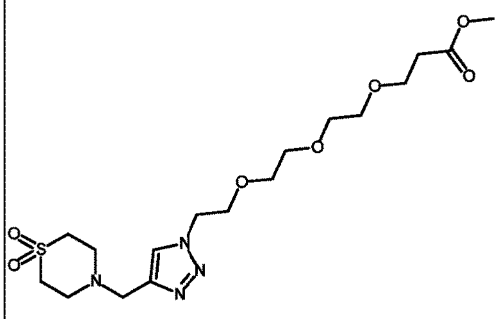
Figure 2C:
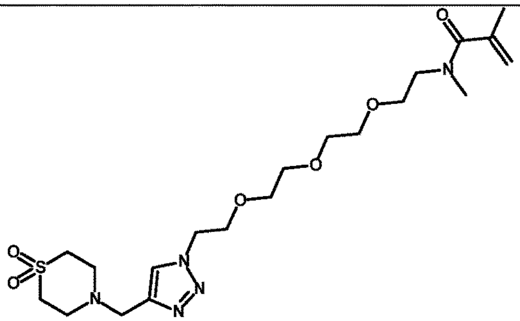
Figure 2C:
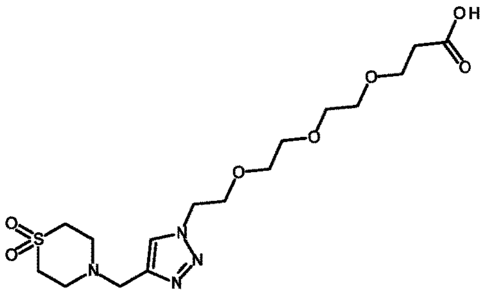
Figure 2C:
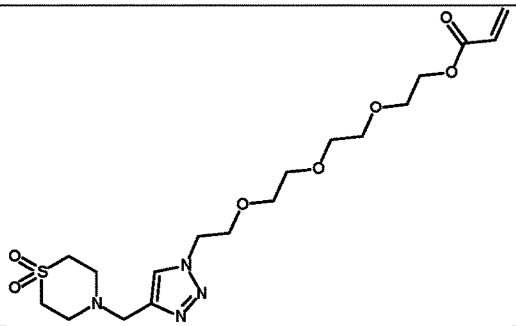
Figure 2C:
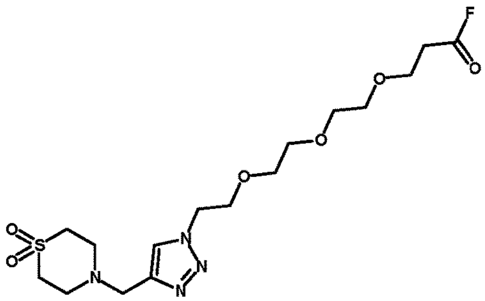
Figure 2C:
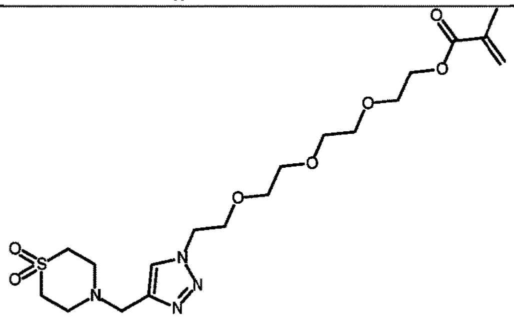
Figure 2C:
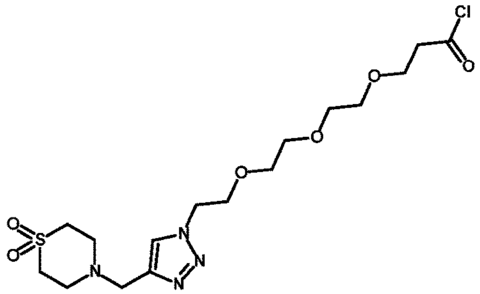
Figure 2D:
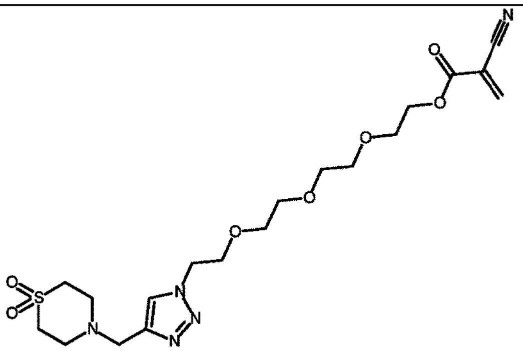
Figure 2D:
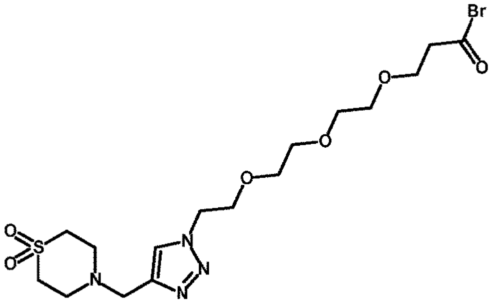
Figure 2D:
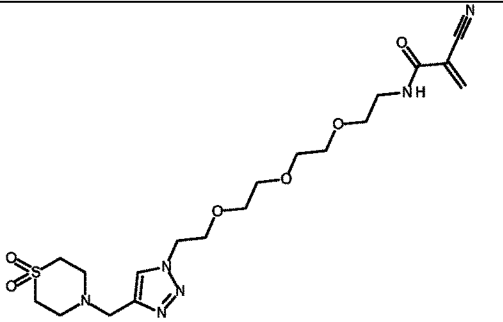
Figure 2D:
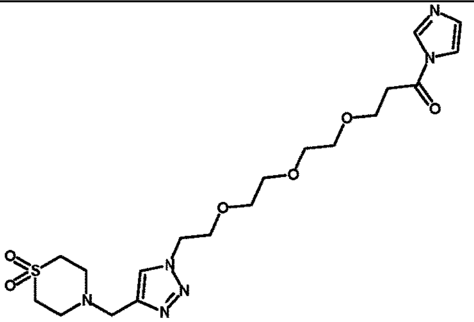
Figure 2D:
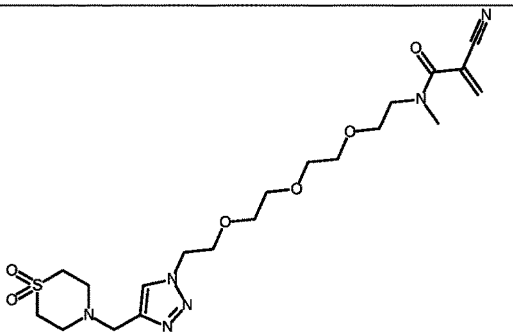
Figure 2D:
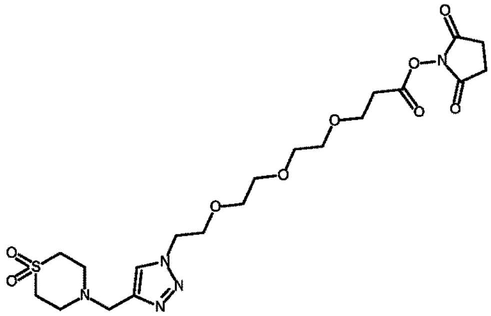
Figure 2D:
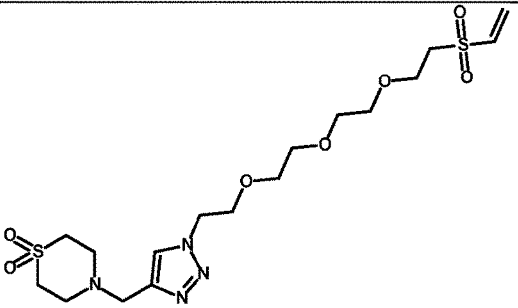
Figure 2D:
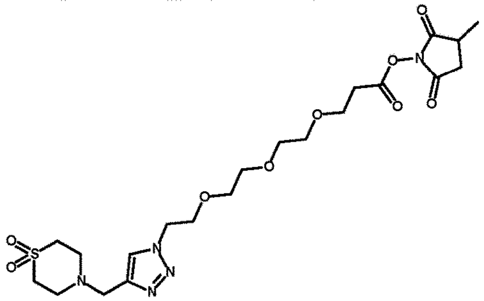
Figure 2D:
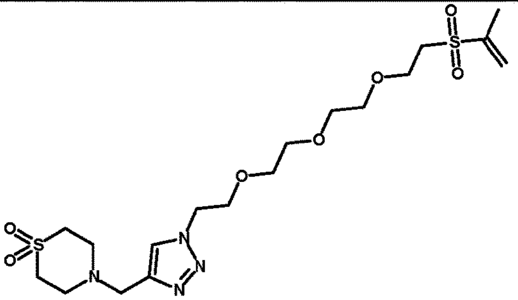
Figure 2D:
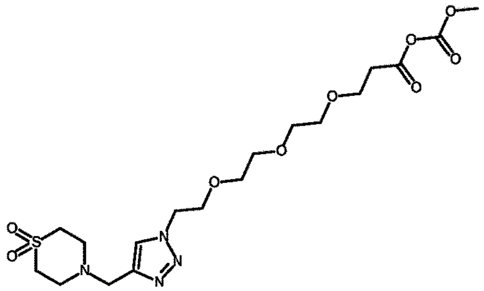
Figure 2E:
Figure 2E:
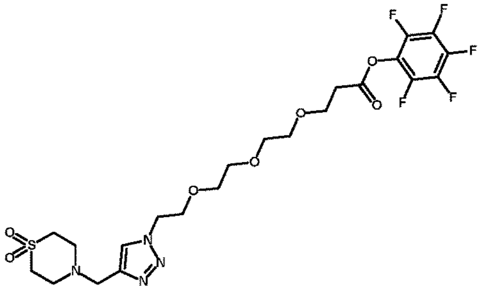
Figure 2E:
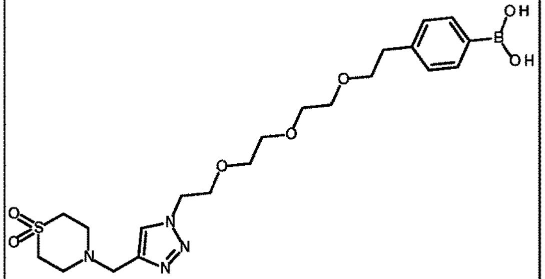
Figure 2E:
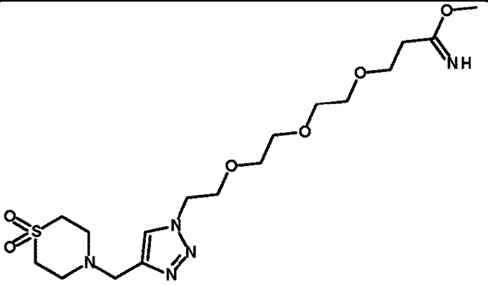
Figure 2E:
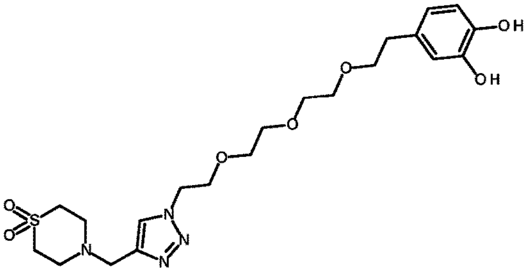
Figure 2E:
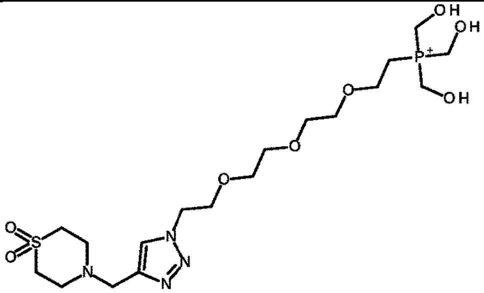
Figure 2E:
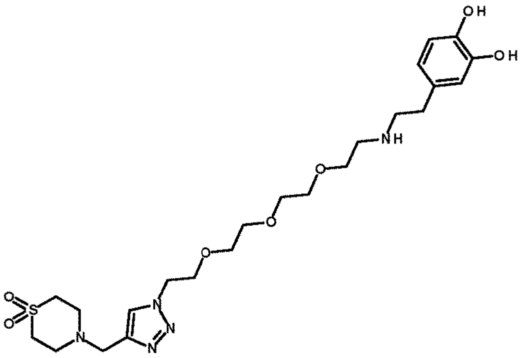
Figure 2E:
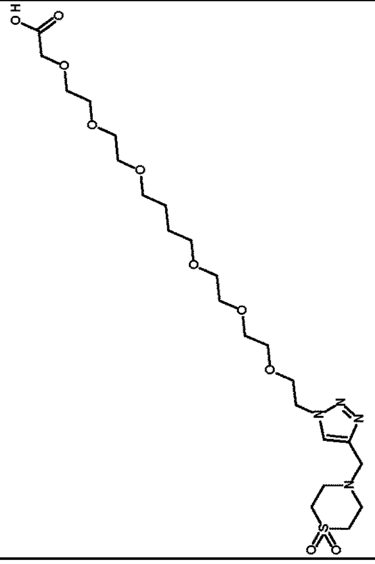
Figure 2F:
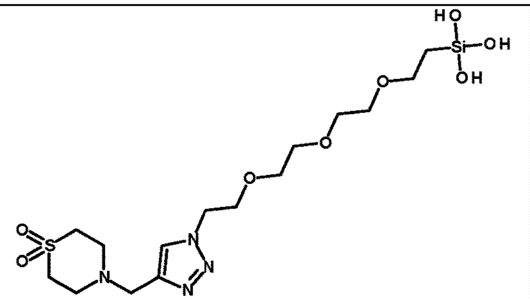
Figure 2F:
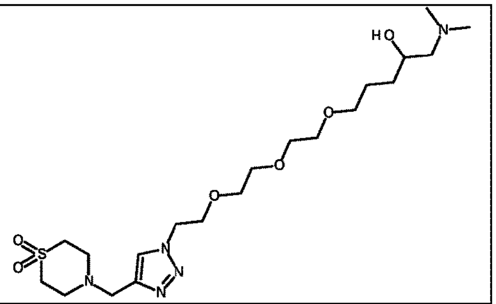
Figure 2F:
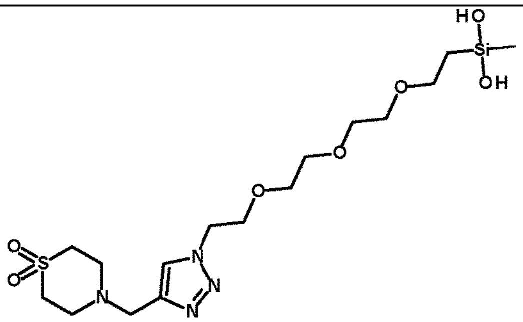
Figure 2F:
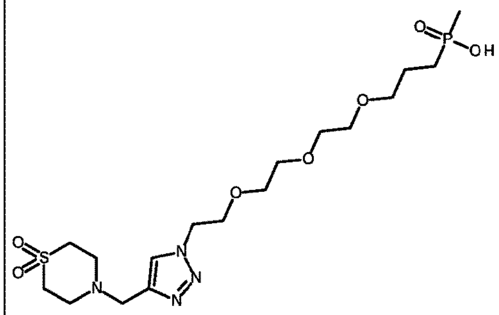
Figure 2F:
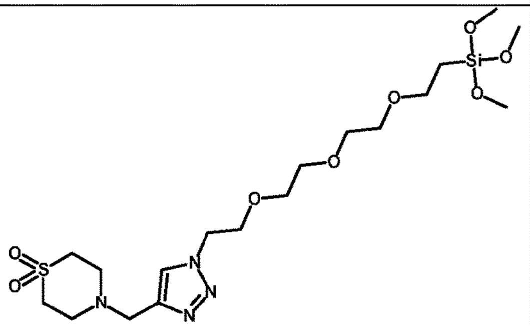
Figure 2F:
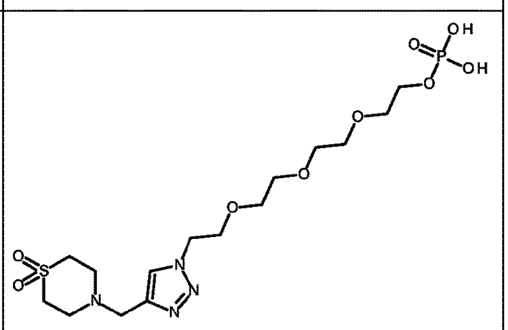
Figure 2F:
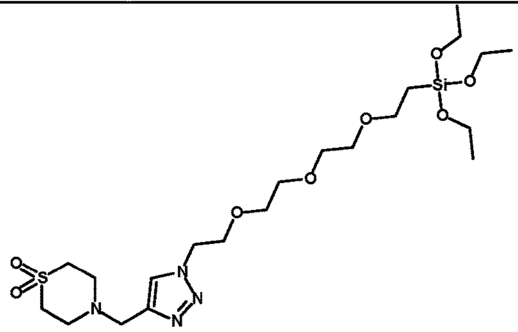
Figure 2F:
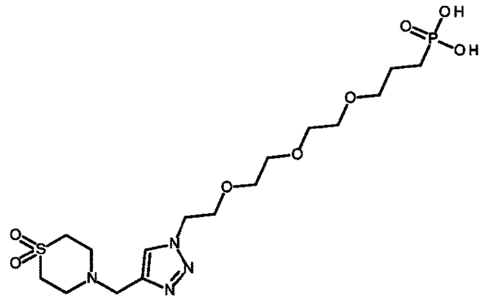
Figure 2F:
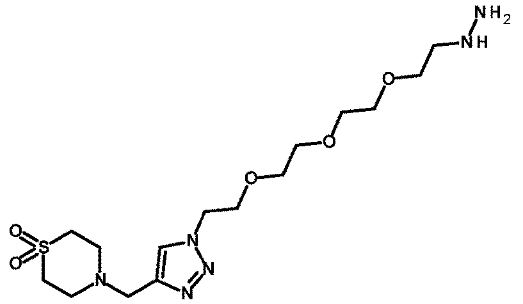
Figure 2F:
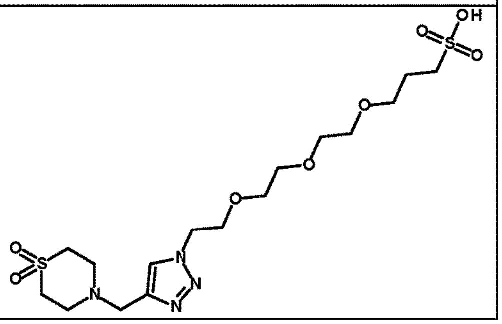
Figure 2G:
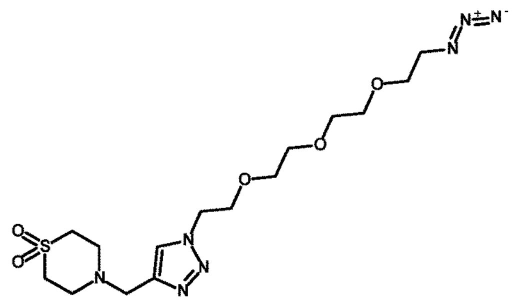
Figure 2G:
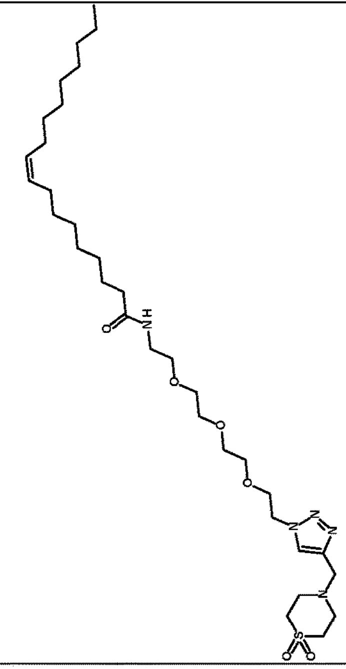
Figure 2G:
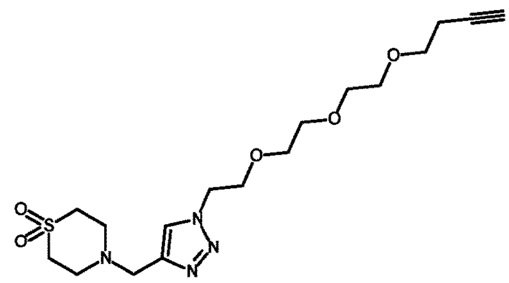
Figure 2G:
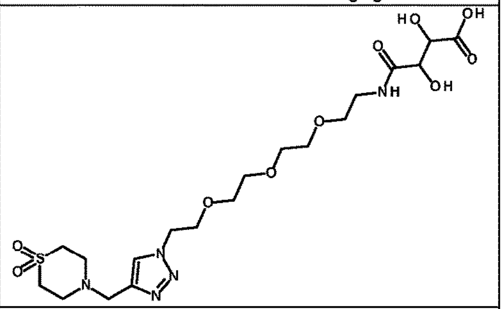
Figure 2G:
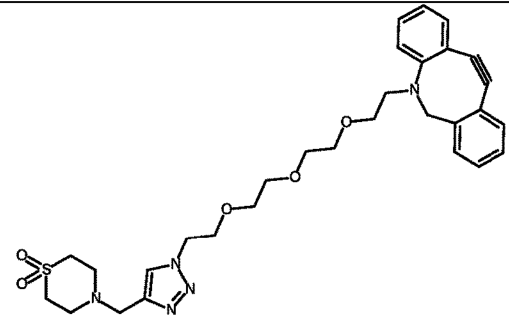
Figure 2G:
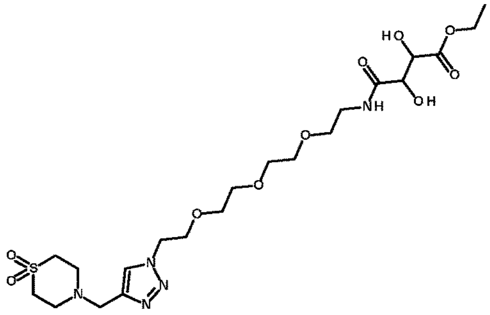
Figure 2G:
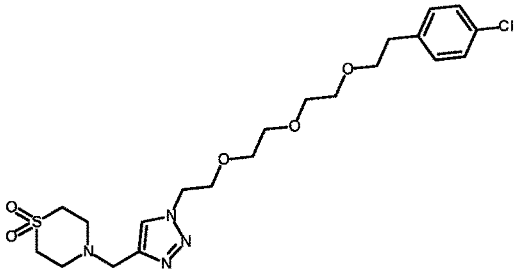
Figure 2G:
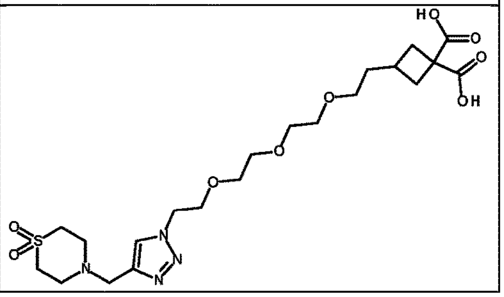
Figure 2H:
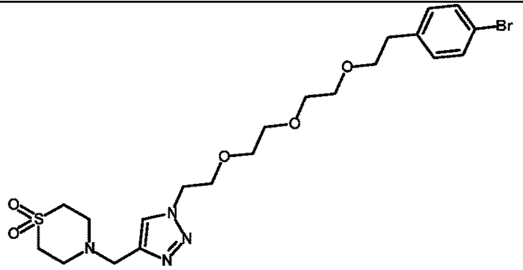
Figure 2H:
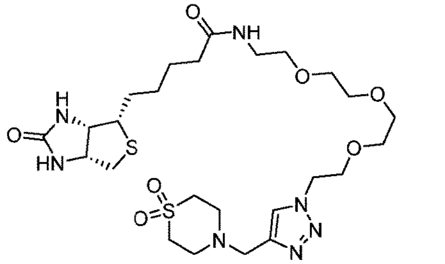
Figure 2H:
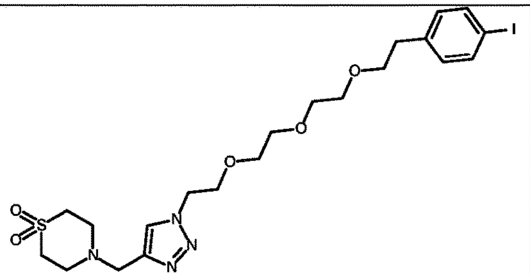
Figure 2H:
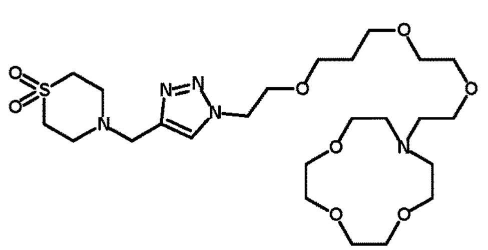
Figure 2H:
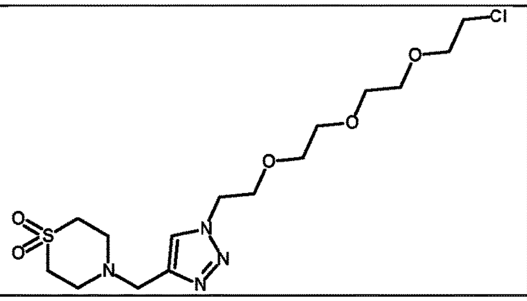
Figure 2H:
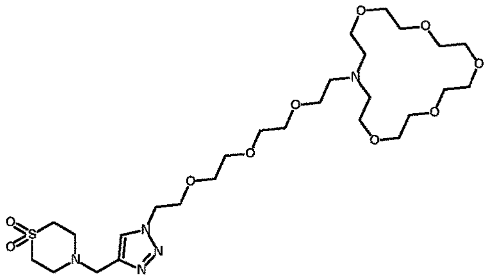
Figure 2H:
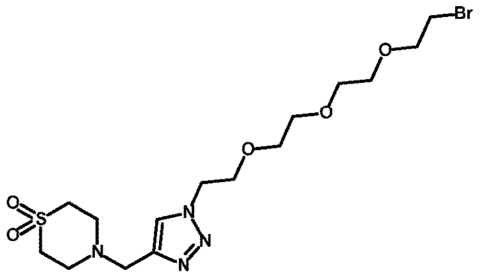
Figure 2H:
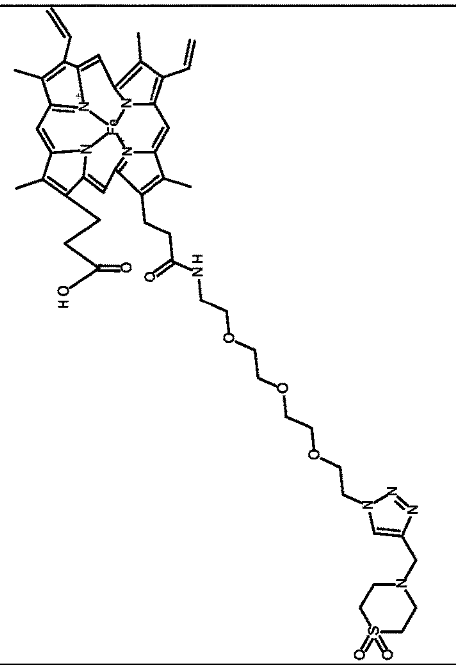
Figure 2I:
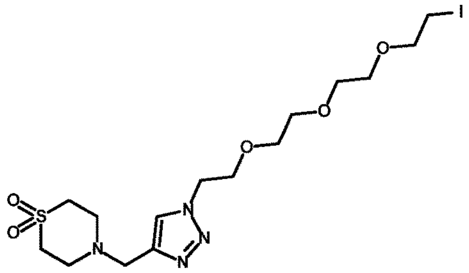
Figure 2I:
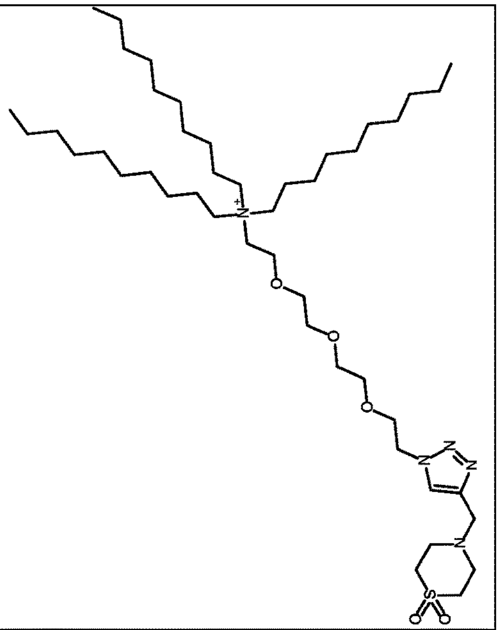
Figure 2I:
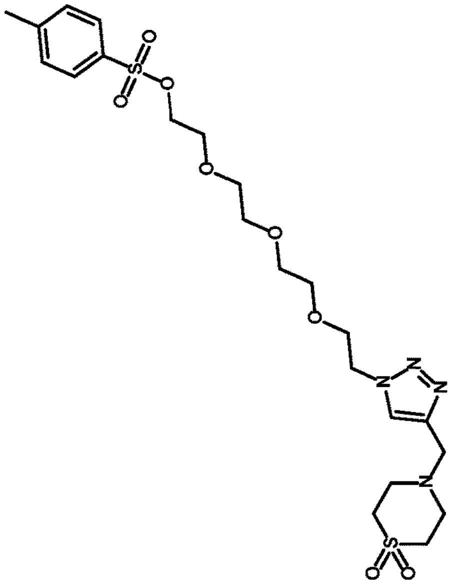
Figure 2I:
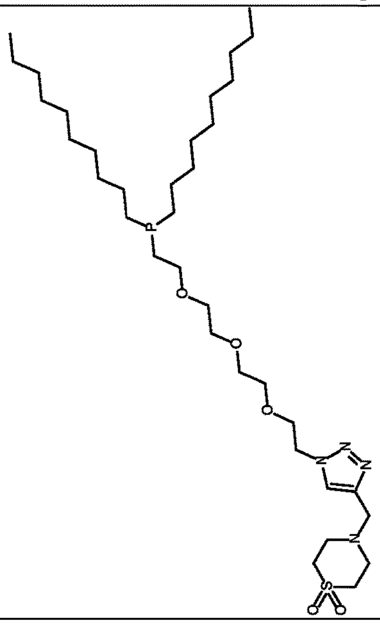
Figure 2J:
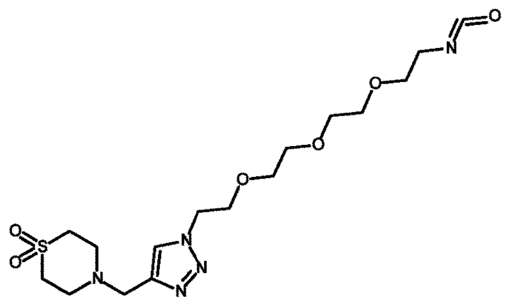
Figure 2J:
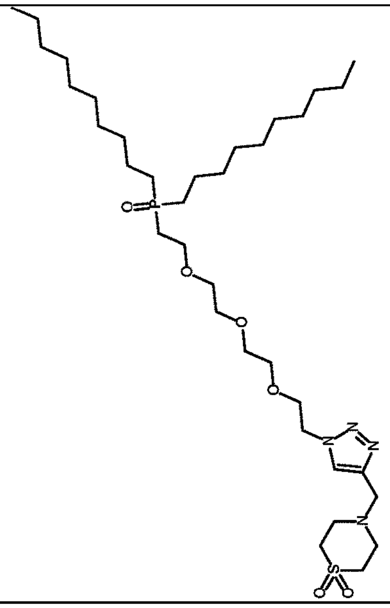
Figure 2J:
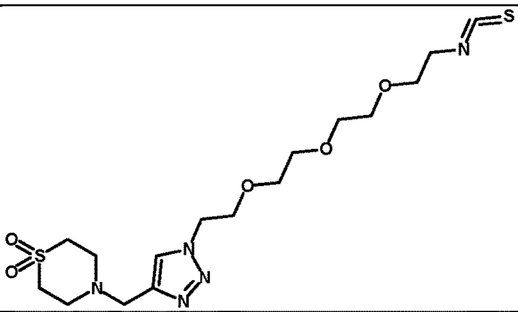
Figure 2J:
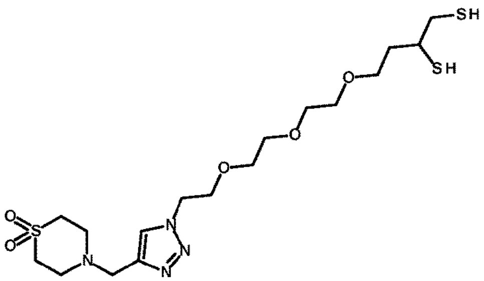
Figure 2J:
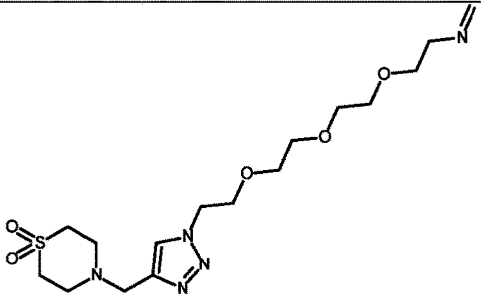
Figure 2J:
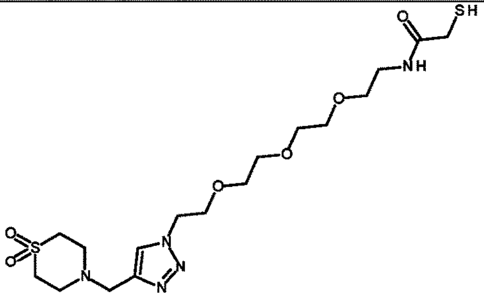
Figure 2J:
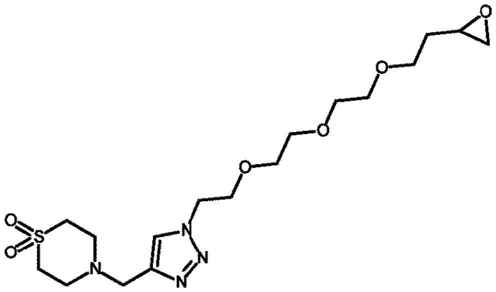
Figure 2J:
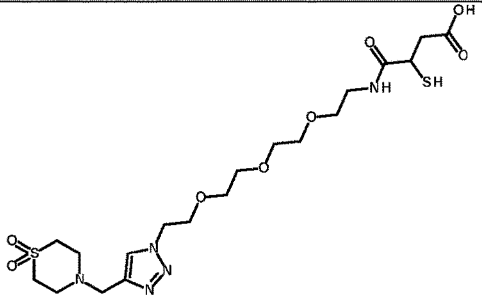
Figure 2K:
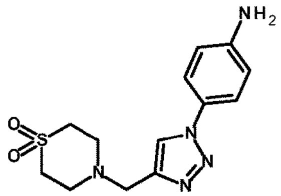
Figure 2K:
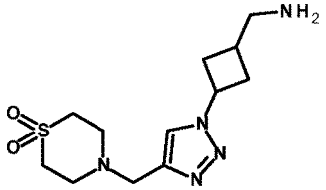
Figure 2K:
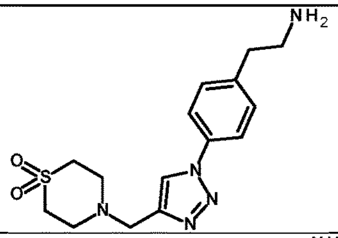
Figure 2K:
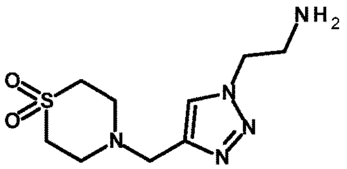
Figure 2K:
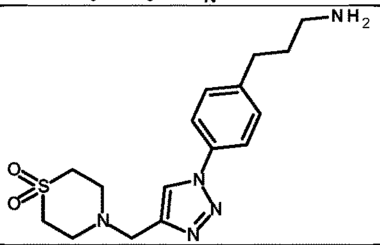
Figure 2K:
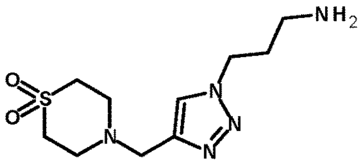
Figure 2K:
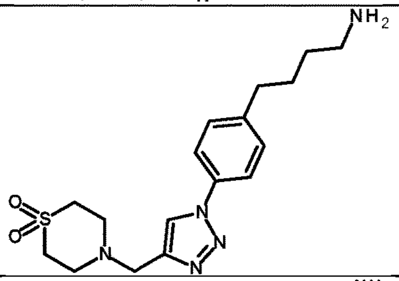
Figure 2K:
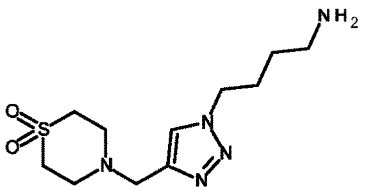
Figure 2K:
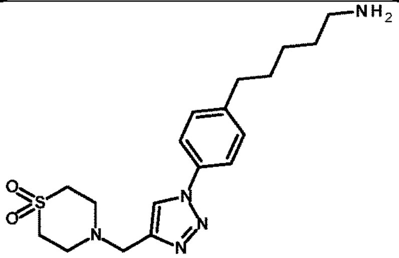
Figure 2K:
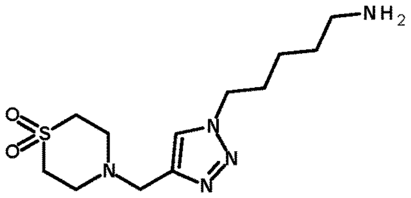
Figure 2K:
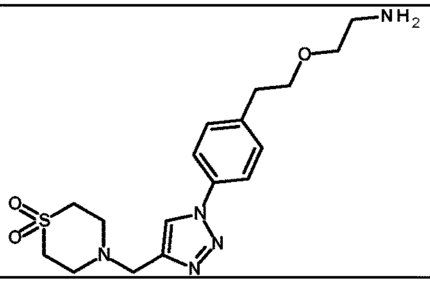
Figure 2K:
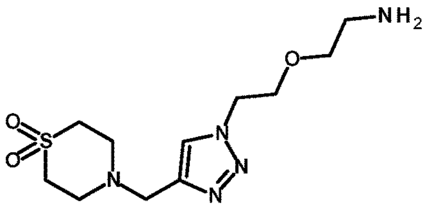
Figure 2L:
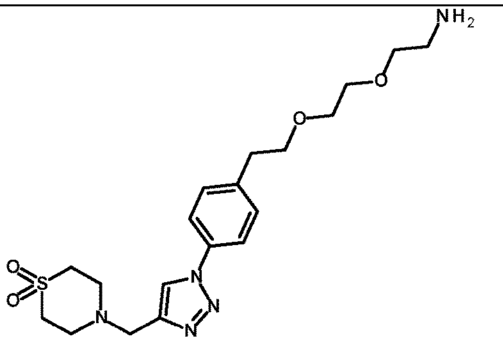
Figure 2L:
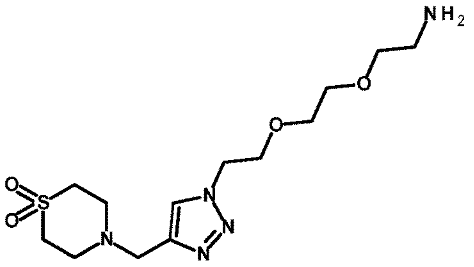
Figure 2L:
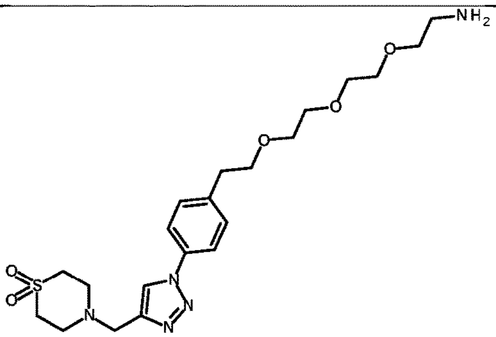
Figure 2L:
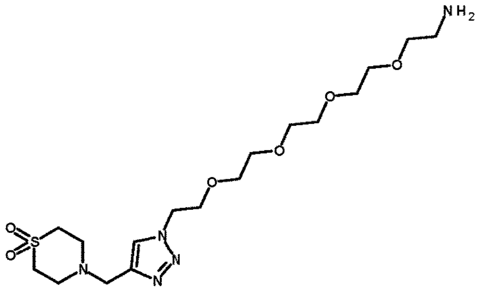
Figure 2L:
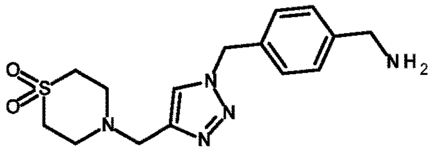
Figure 2L:
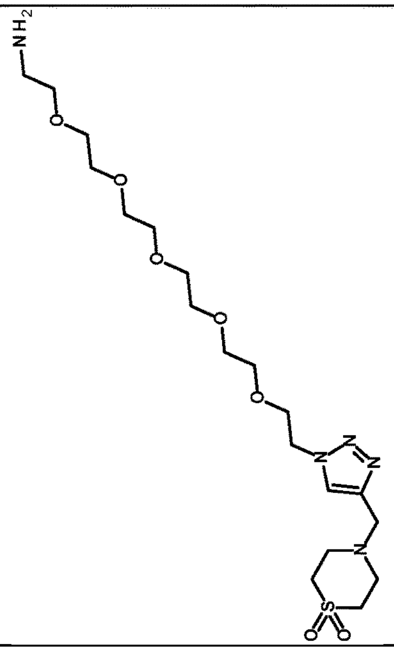
Figure 2L:
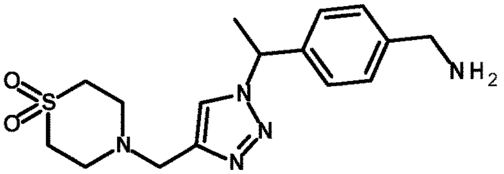
Figure 2L:
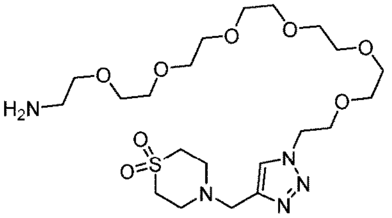
Figure 2M:
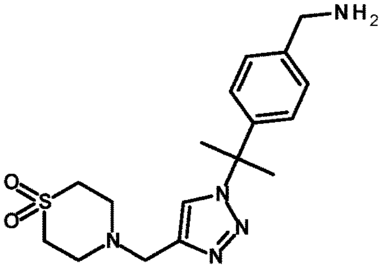
Figure 2M:
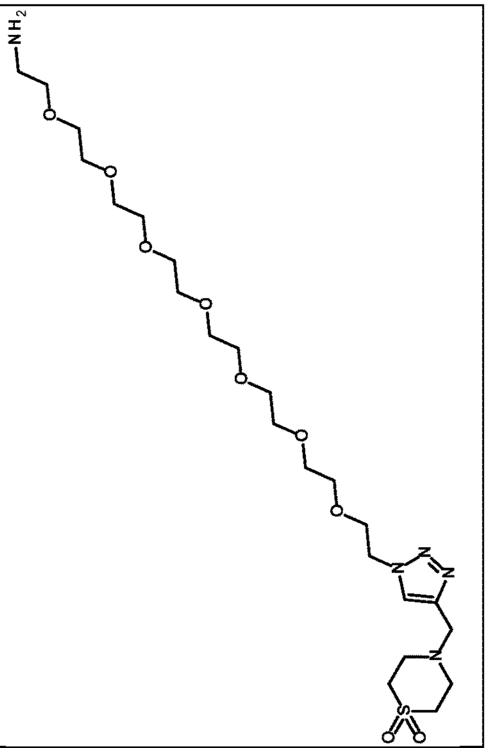
Figure 2M:
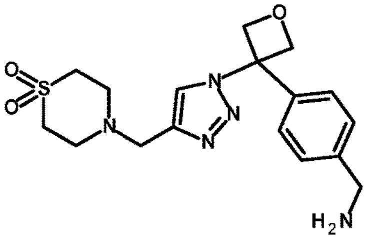
Figure 2M:
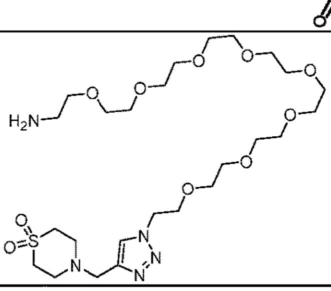
Figure 2M:
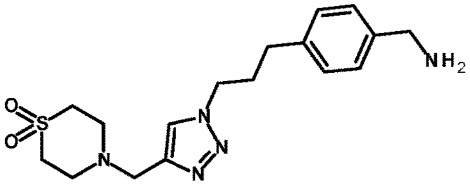
Figure 2M:
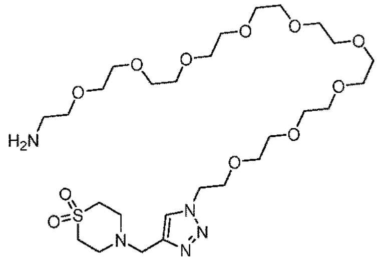
Figure 2M:
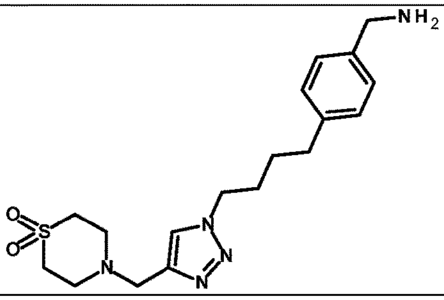
Figure 2M:
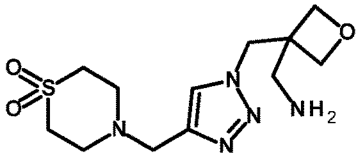
Figure 2N:
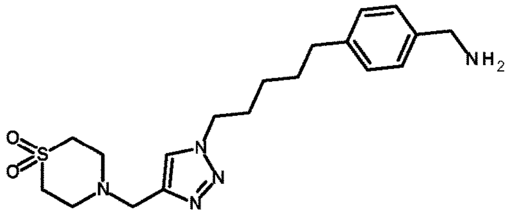
Figure 2N:
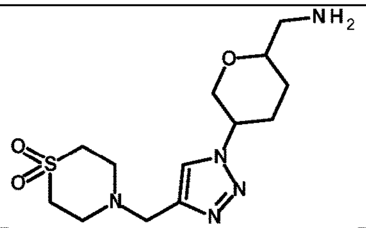
Figure 2N:
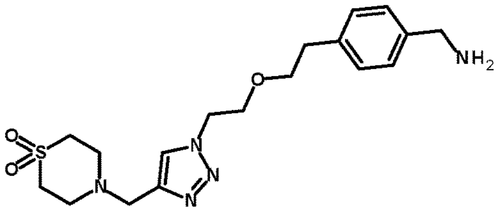
Figure 2N:
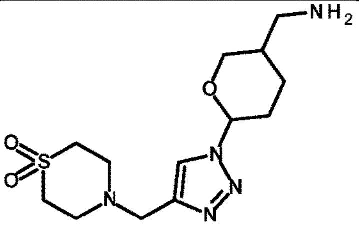
Figure 2N:
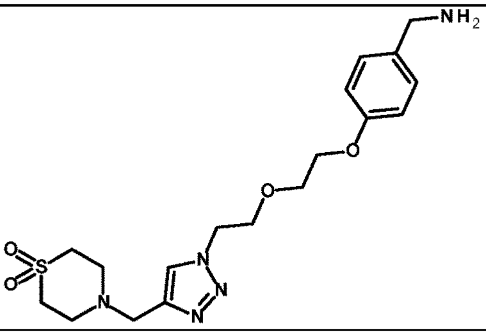
Figure 2N:
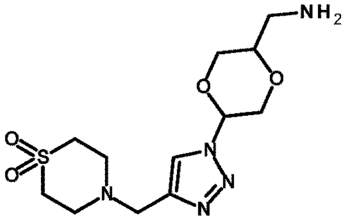
Figure 2N:
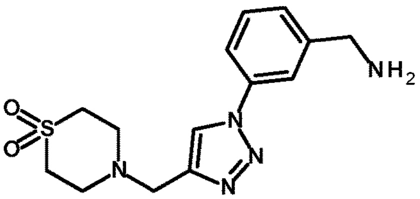
Figure 2N:
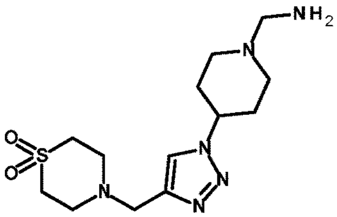
Figure 2N:
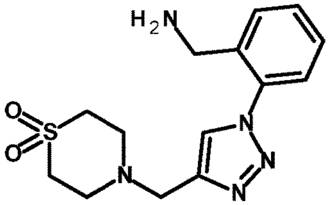
Figure 2N:
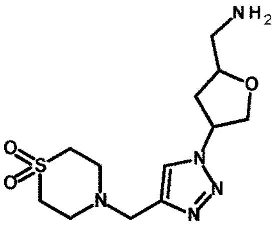
Figure 2N:
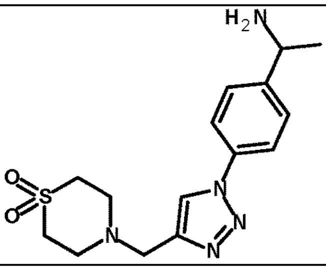
Figure 2N:
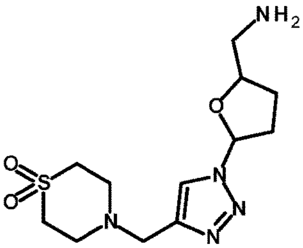
Figure 2O:
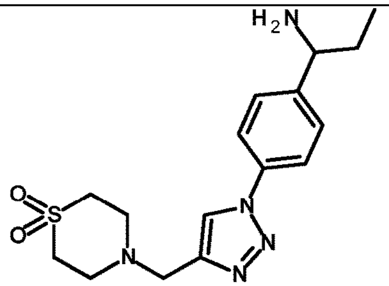
Figure 2O:
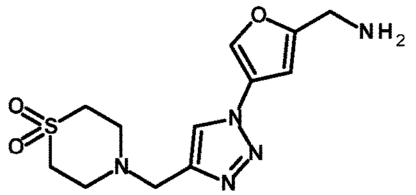
Figure 2O:
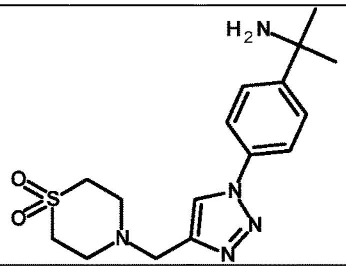
Figure 2O:
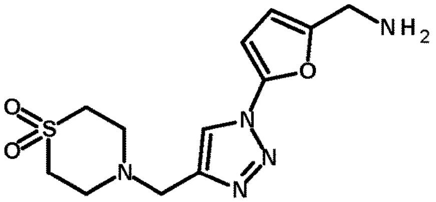
Figure 2O:
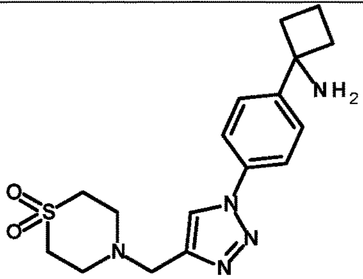
Figure 2O:
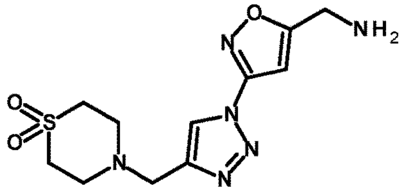
Figure 2O:
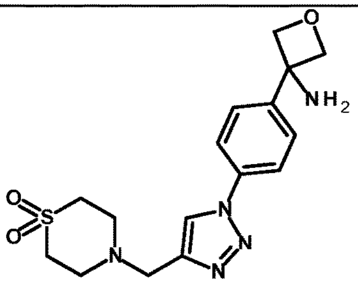
Figure 2O:
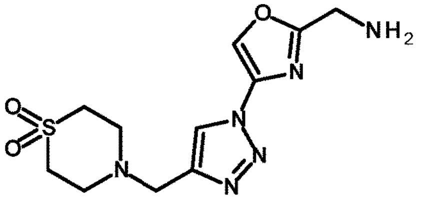
Figure 2O:
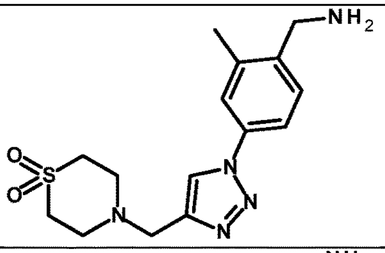
Figure 2O:
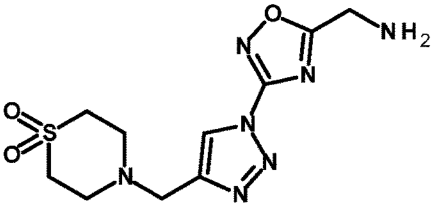
Figure 2O:
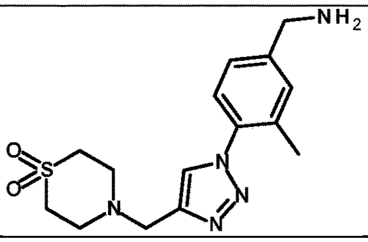
Figure 2O:
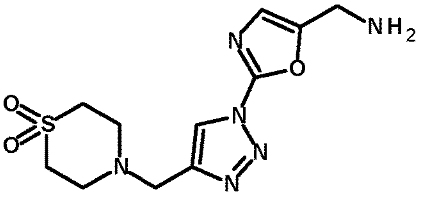
Figure 2P:
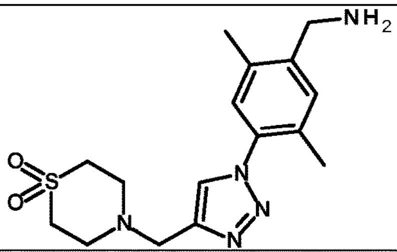
Figure 2P:
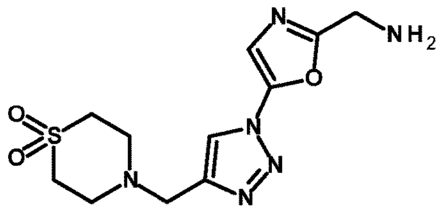
Figure 2P:
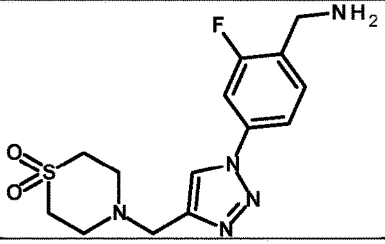
Figure 2P:
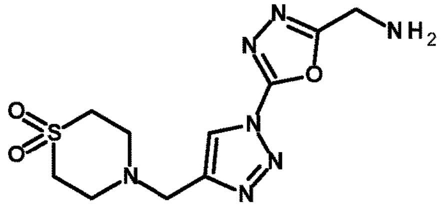
Figure 2P:
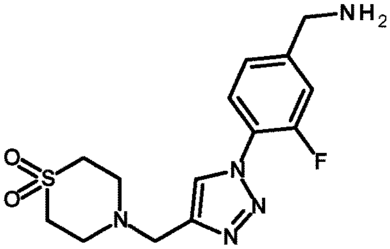
Figure 2P:
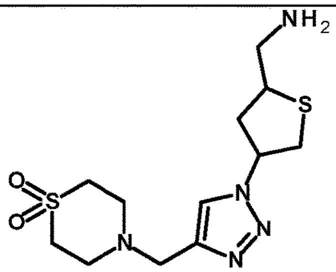
Figure 2P:
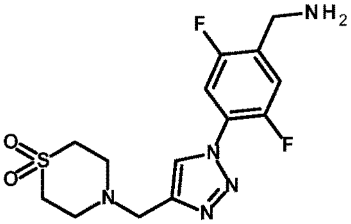
Figure 2P:
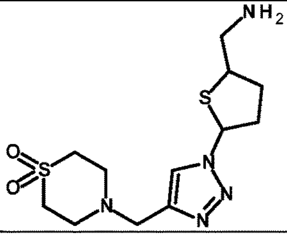
Figure 2P:
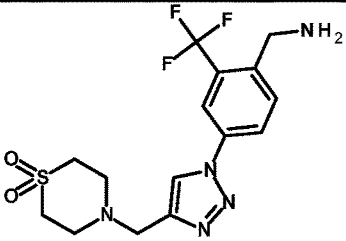
Figure 2P:
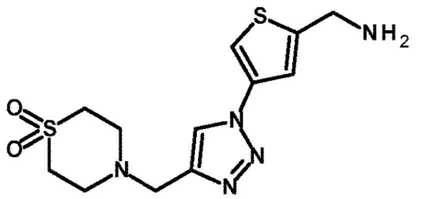
Figure 2P:
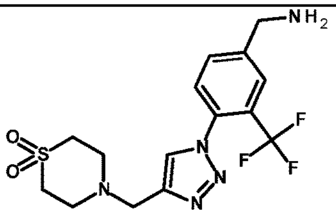
Figure 2P:
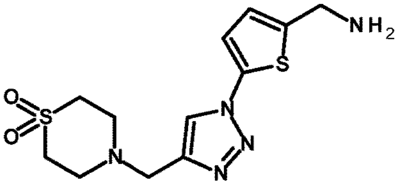
Figure 2Q:
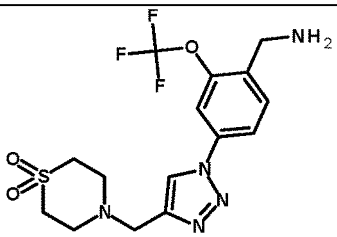
Figure 2Q:
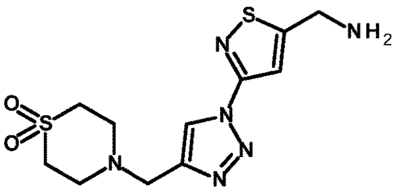
Figure 2Q:
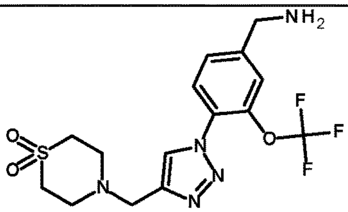
Figure 2Q:
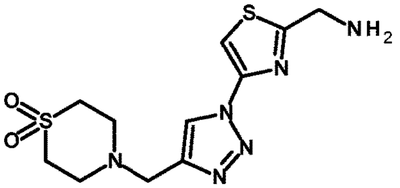
Figure 2Q:
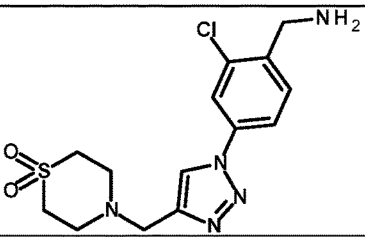
Figure 2Q:
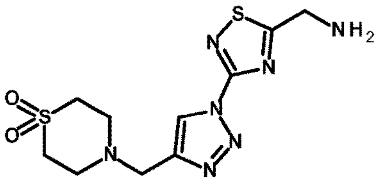
Figure 2Q:
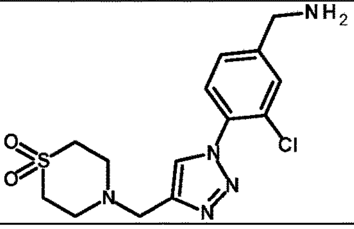
Figure 2Q:
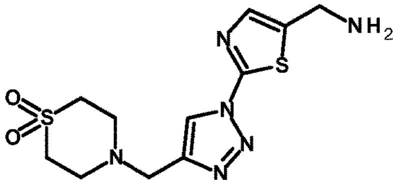
Figure 2Q:
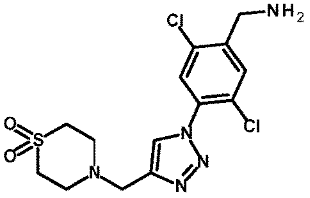
Figure 2Q:
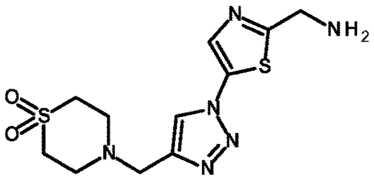
Figure 2Q:
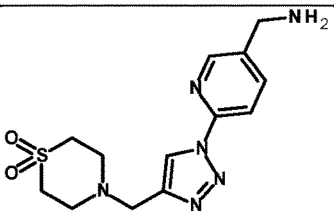
Figure 2Q:
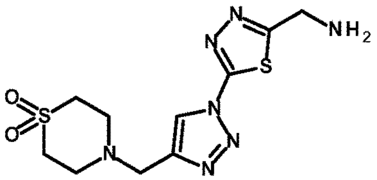
Figure 2Q:
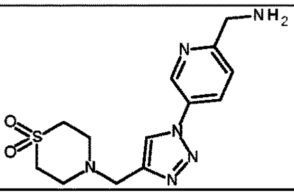
Figure 2Q:
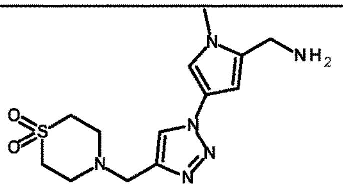
Figure 2R:
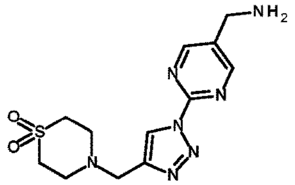
Figure 2R:
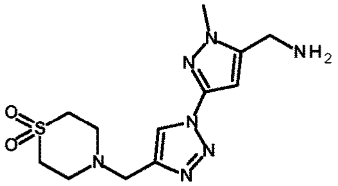
Figure 2R:
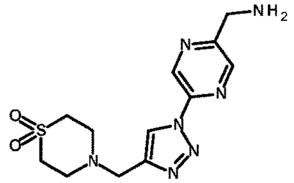
Figure 2R:
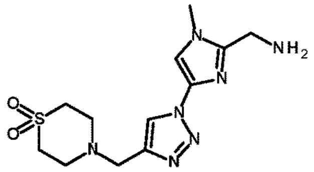
Figure 2R:
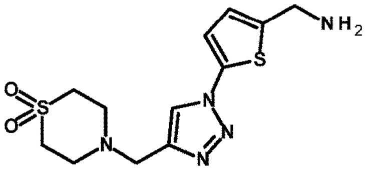
Figure 2R:
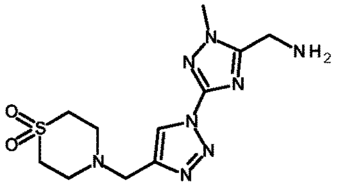
Figure 2R:
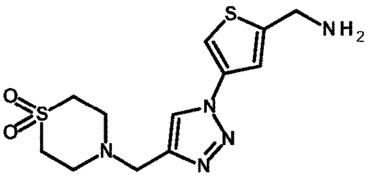
Figure 2R:
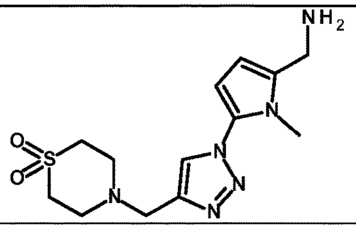
Figure 2R:
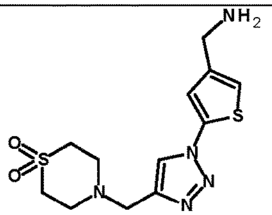
Figure 2R:
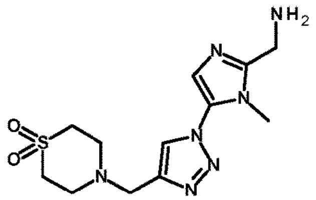
Figure 2R:
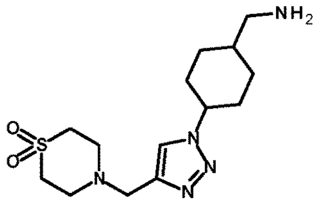
Figure 2R:
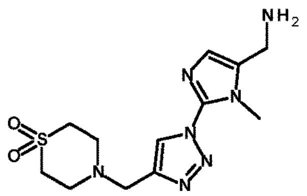
Figure 2R:
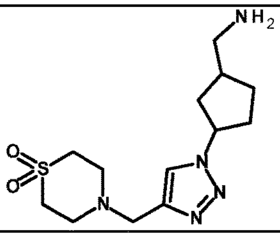
Figure 2R:
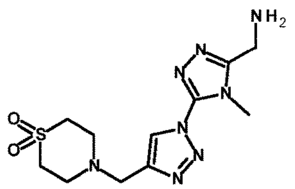
Figure 2S:
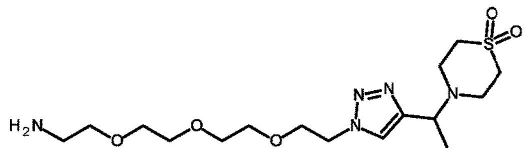
Figure 2S:
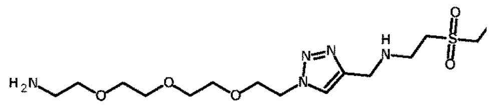
Figure 2S:
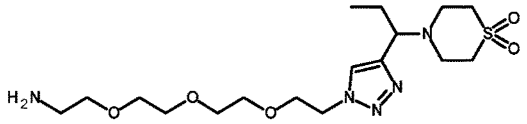
Figure 2S:
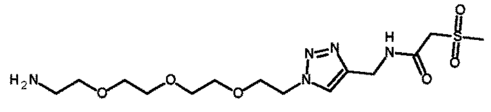
Figure 2S:
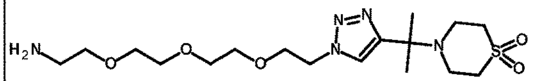
Figure 2S:
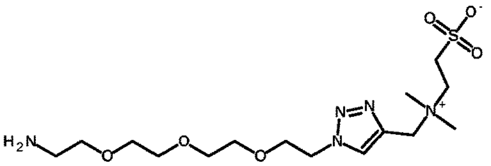
Figure 2S:
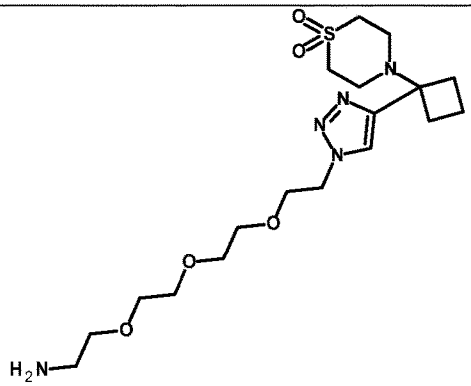
Figure 2S:
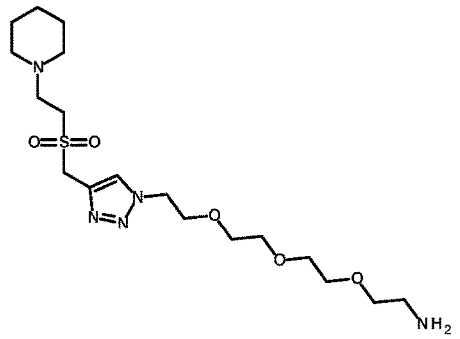
Figure 2S:
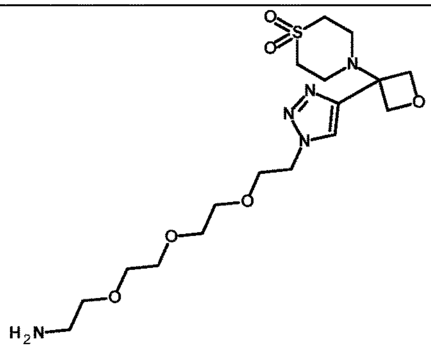
Figure 2S:
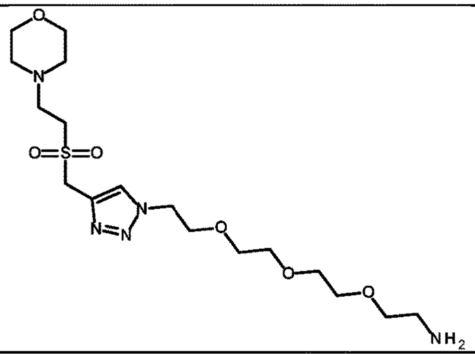
Figure 2S:
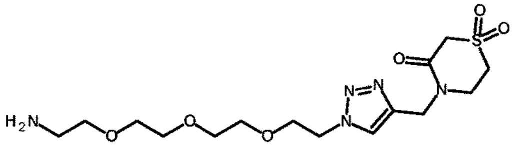
Figure 2S:
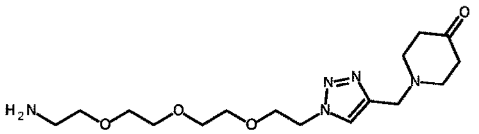
Figure 2S:
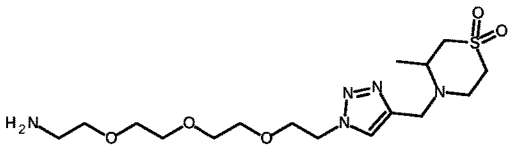
Figure 2S:
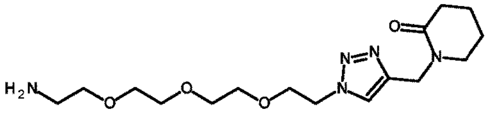
Figure 2T:
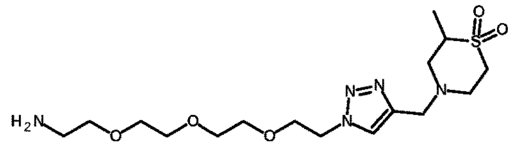
Figure 2T:
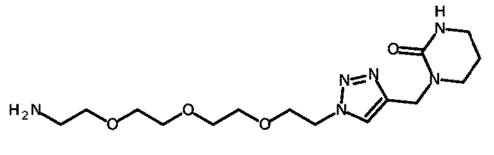
Figure 2T:
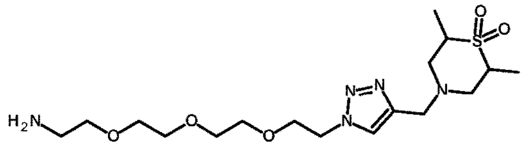
Figure 2T:
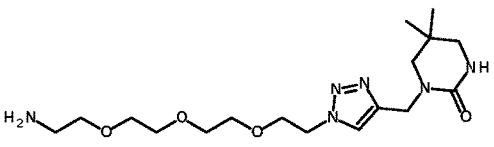
Figure 2T:
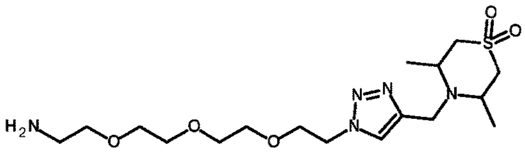
Figure 2T:
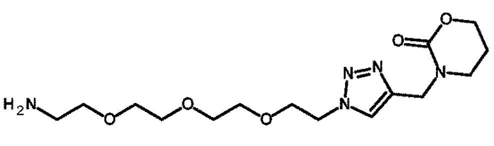
Figure 2T:
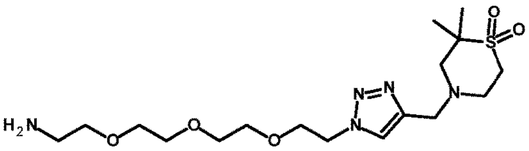
Figure 2T:
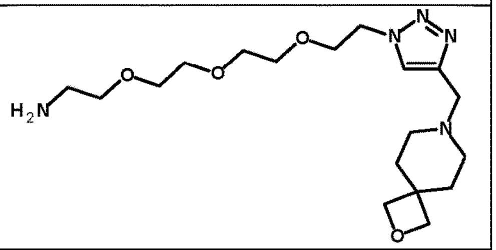
Figure 2T:
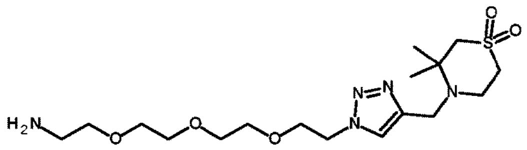
Figure 2T:
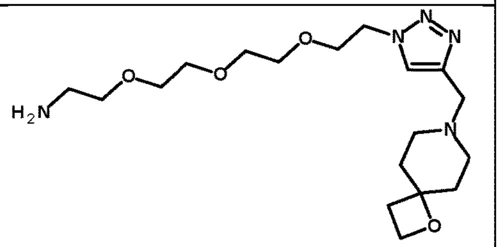
Figure 2T:
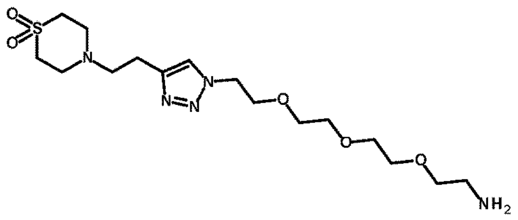
Figure 2T:
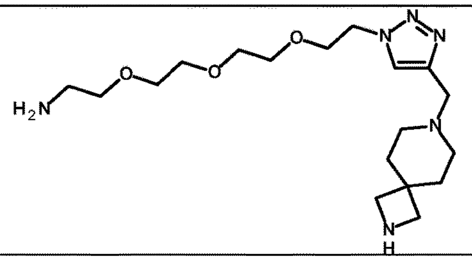
Figure 2T:
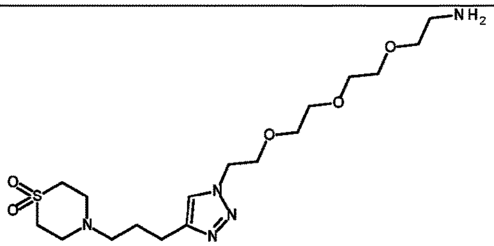
Figure 2T:
Figure 2U:
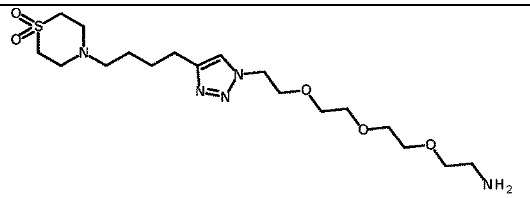
Figure 2U:
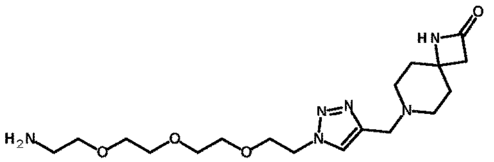
Figure 2U:
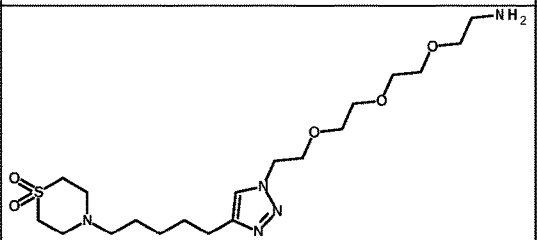
Figure 2U:
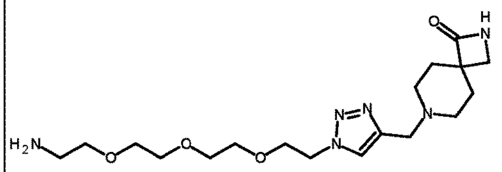
Figure 2U:
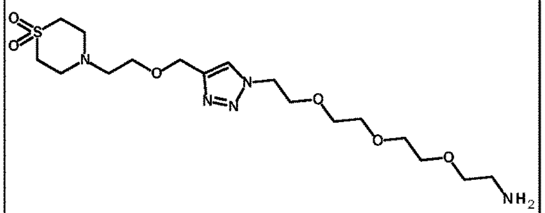
Figure 2U:
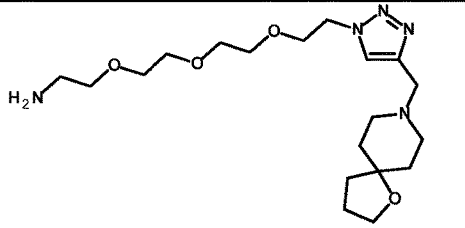
Figure 2U:
Figure 2U:
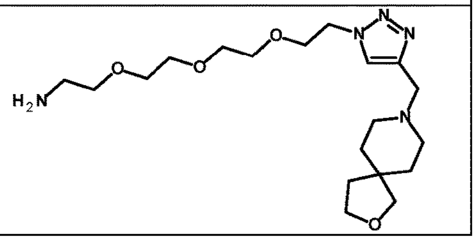
Figure 2V:
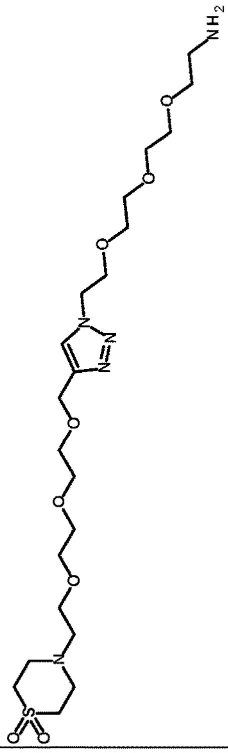
Figure 2V:
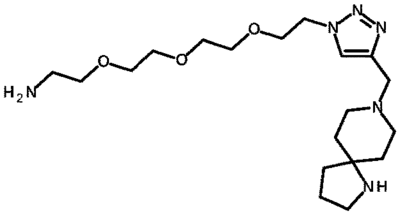
Figure 2V:
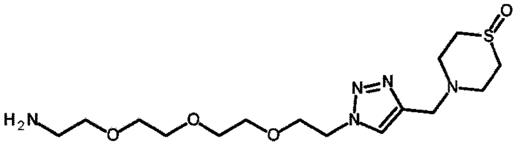
Figure 2V:
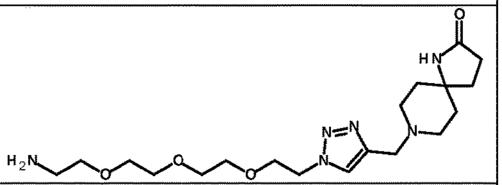
Figure 2V:
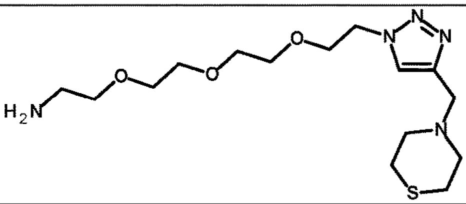
Figure 2V:
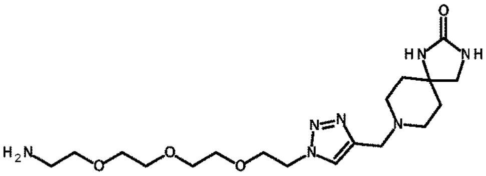
Figure 2V:
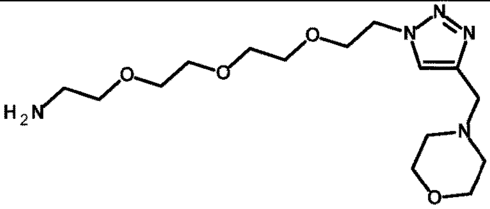
Figure 2V:
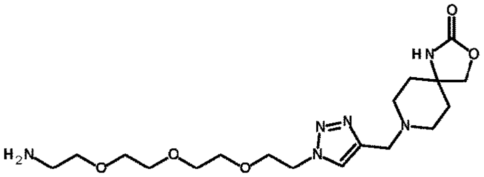
Figure 2V:
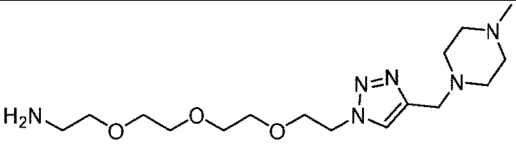
Figure 2V:
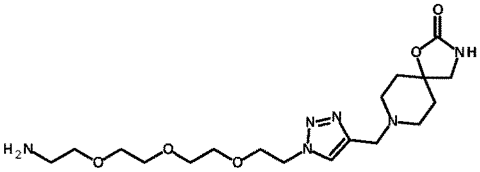
Figure 2W:
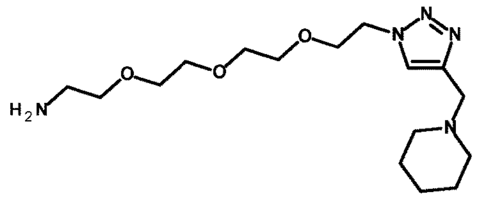
Figure 2W:
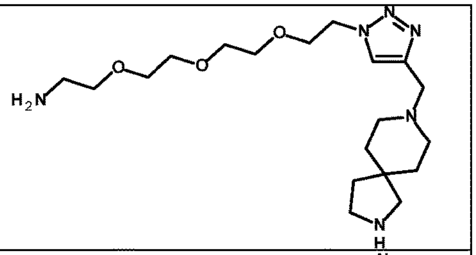
Figure 2W:
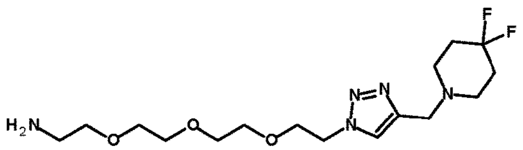
Figure 2W:
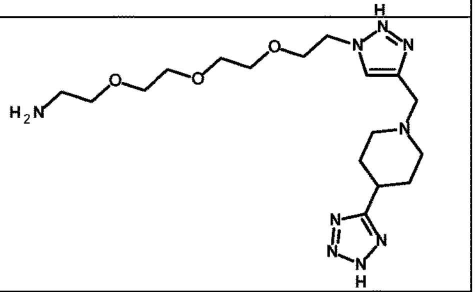
Figure 2W:
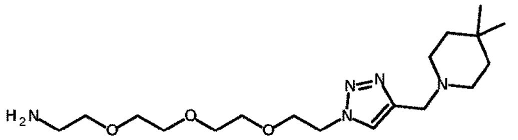
Figure 2W:
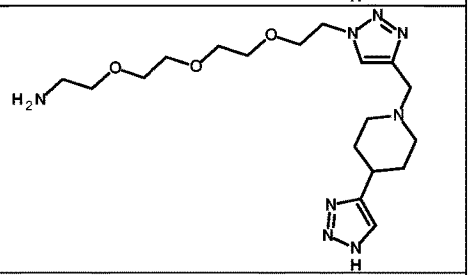
Figure 2W:
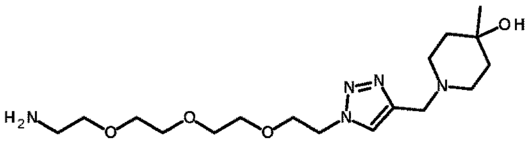
Figure 2W:
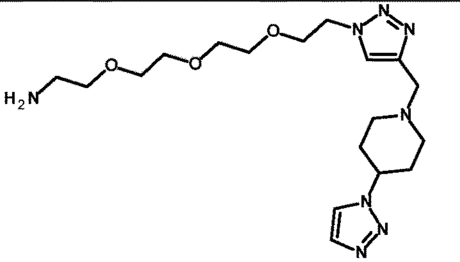
Figure 2W:
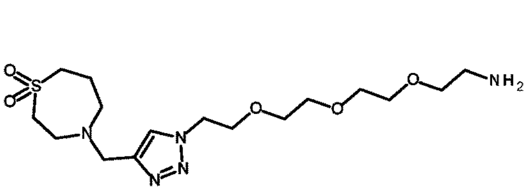
Figure 2W:
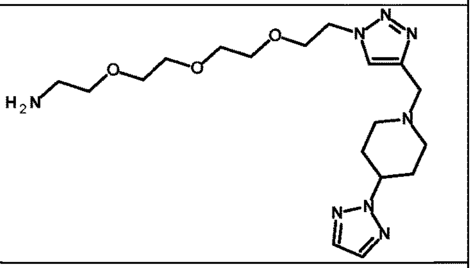
Figure 2W:
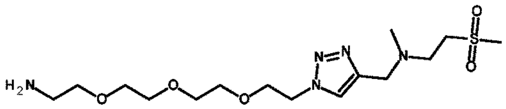
Figure 2W:
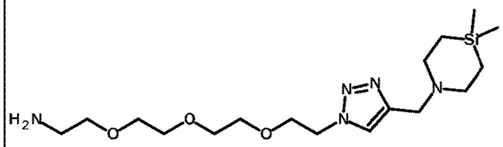
Figure 2X:
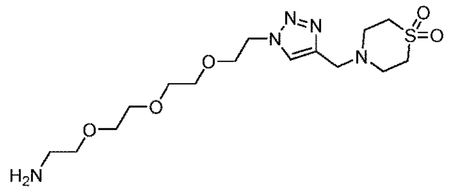
Figure 2X:
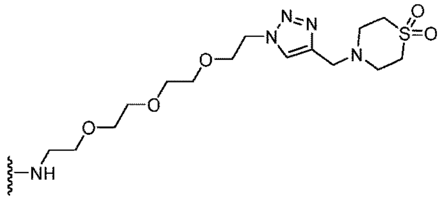
Figure 2X:
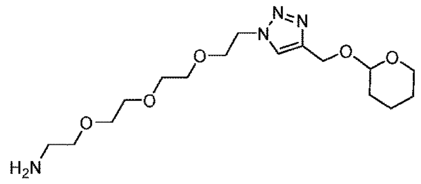
Figure 2X:
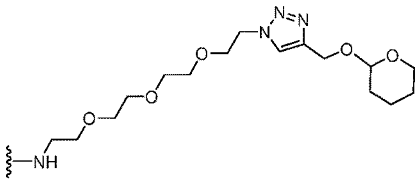
Figure 2X:
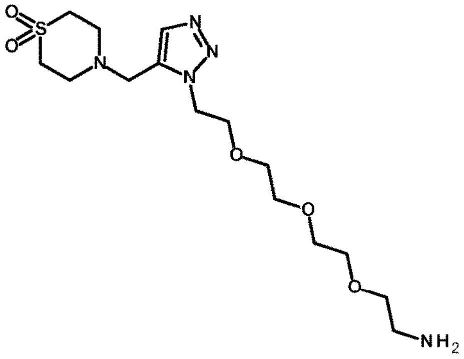
Figure 2X:
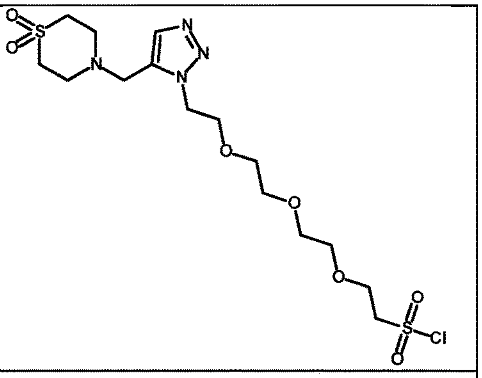
Figure 2X:
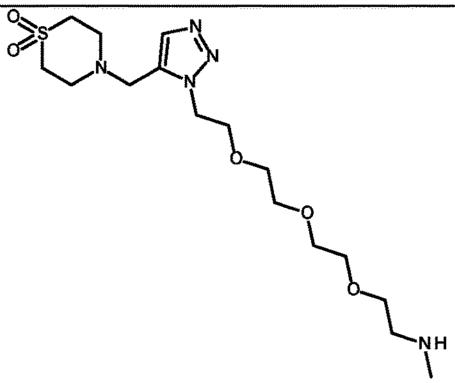
Figure 2X:
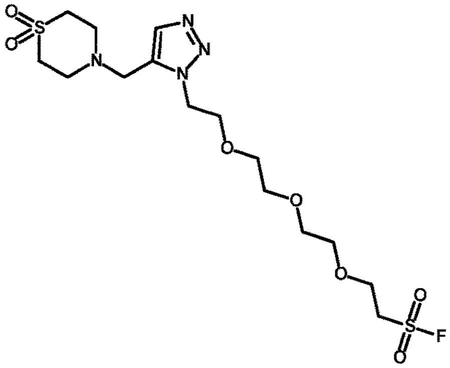
Figure 2X:
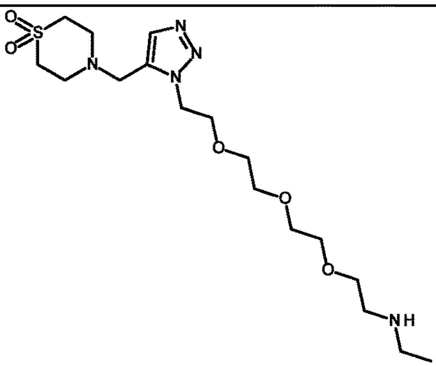
Figure 2X:
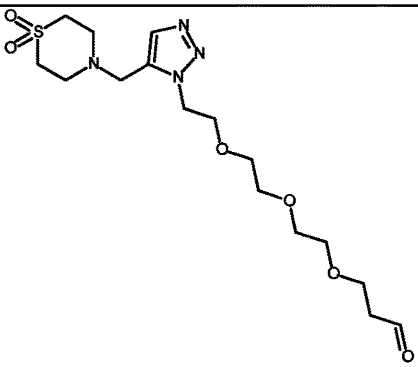
Figure 2Y:
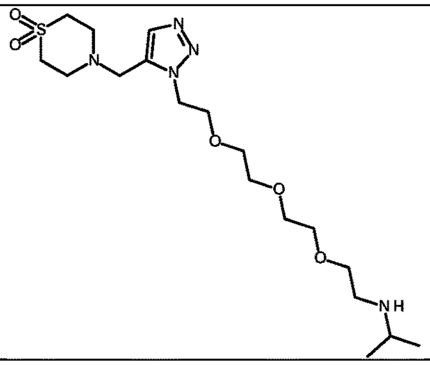
Figure 2Y:
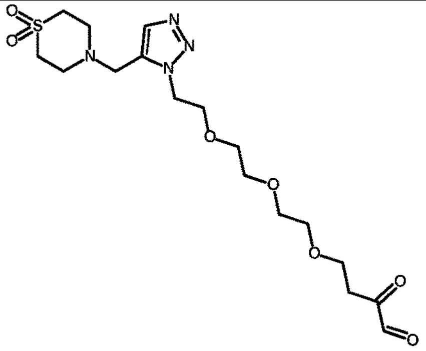
Figure 2Y:
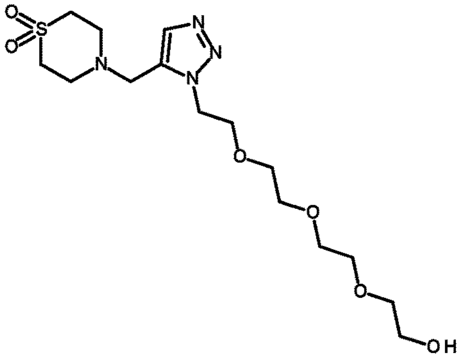
Figure 2Y:
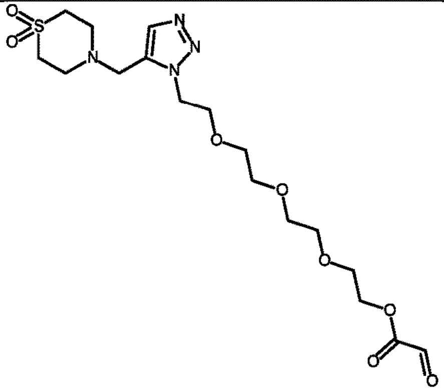
Figure 2Y:
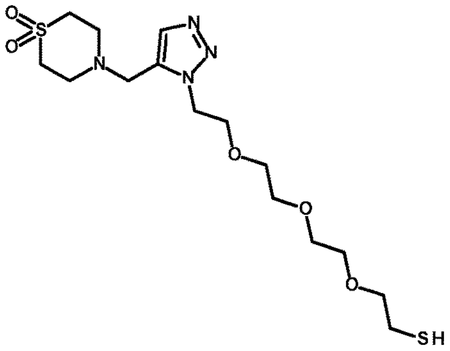
Figure 2Y:
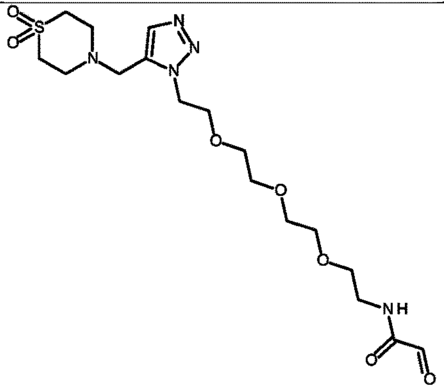
Figure 2Y:
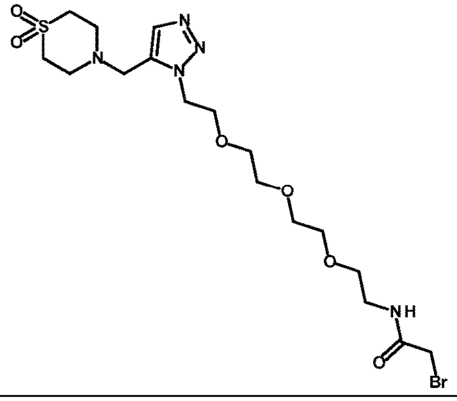
Figure 2Y:
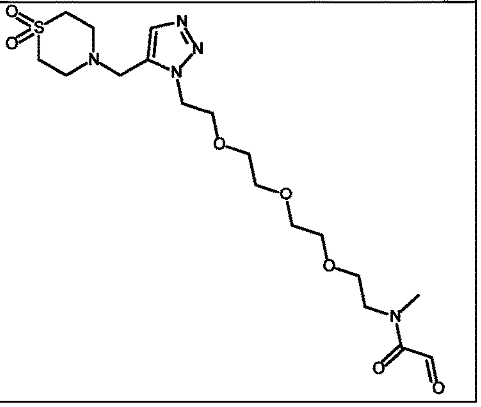
Figure 2Z:
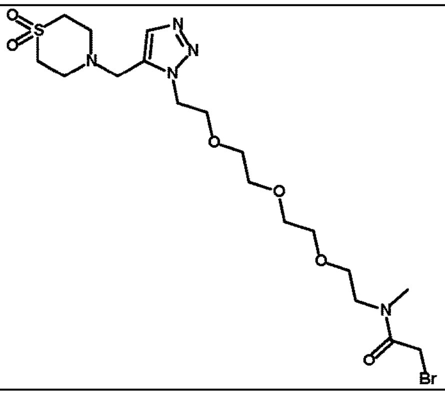
Figure 2Z:
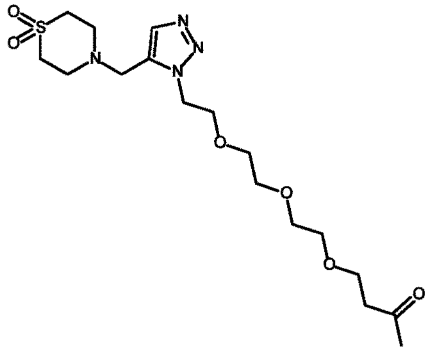
Figure 2Z:
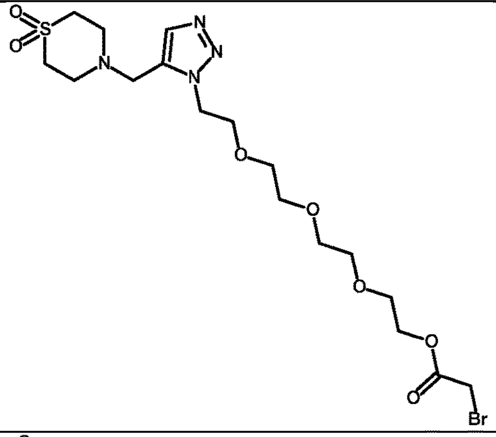
Figure 2Z:
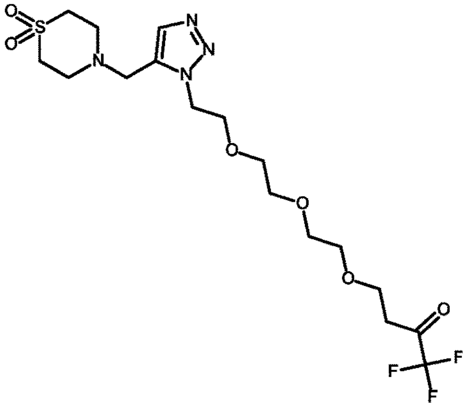
Figure 2Z:
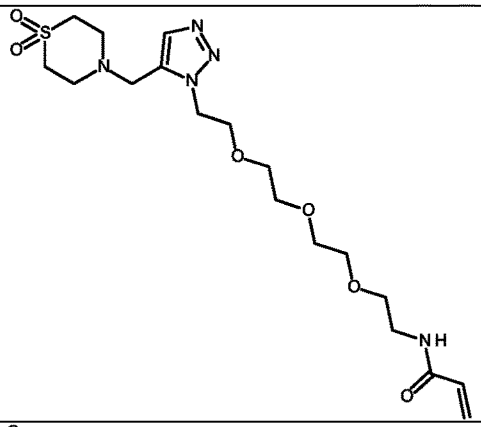
Figure 2Z:
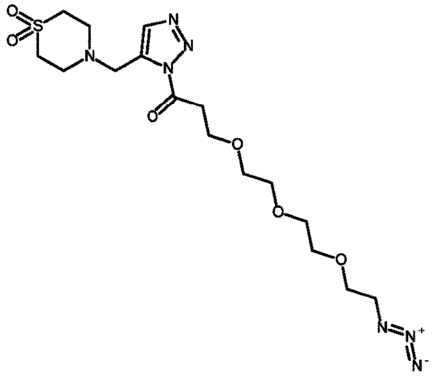
Figure 2Z:
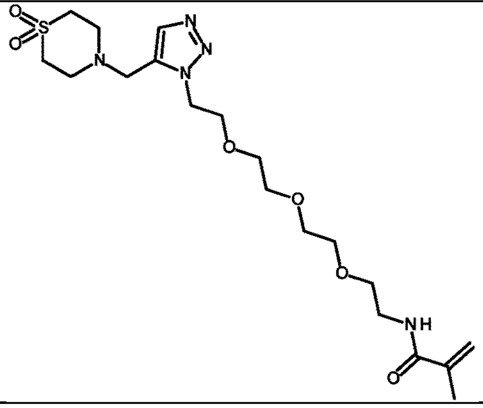
Figure 2Z:
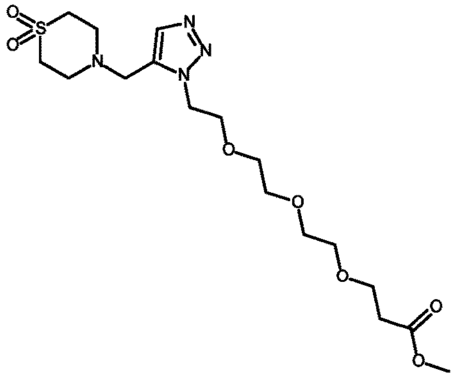
Figure 2A:
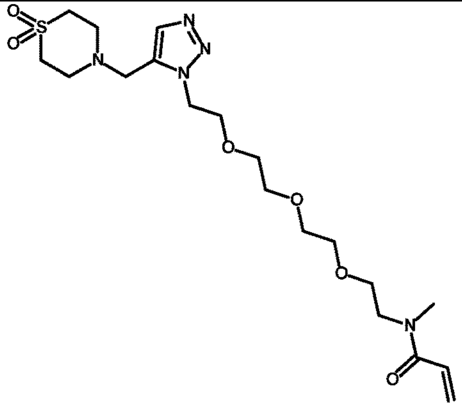
Figure 2A:
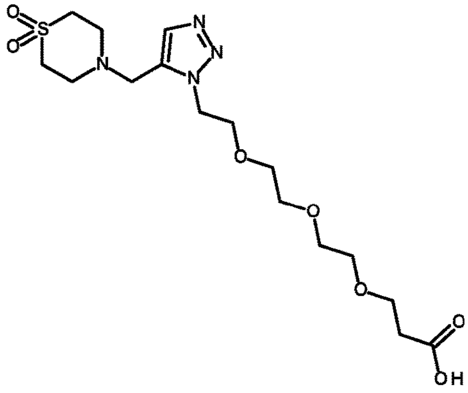
Figure 2A:
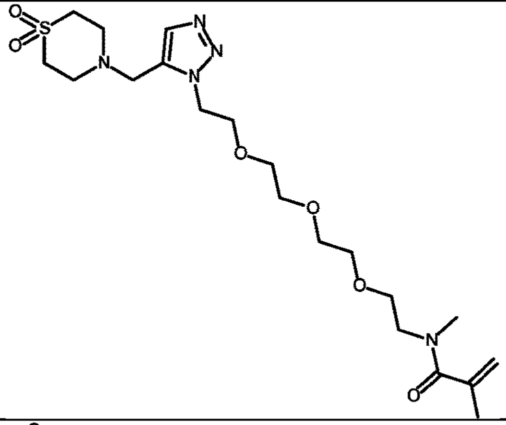
Figure 2A:
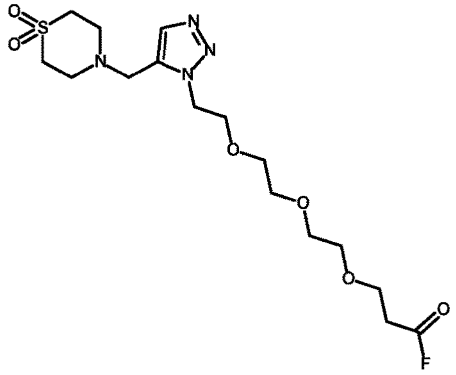
Figure 2A:
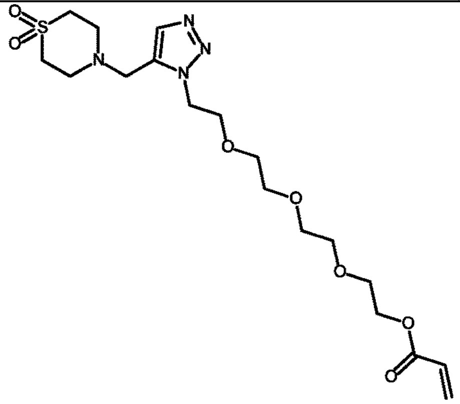
Figure 2A:
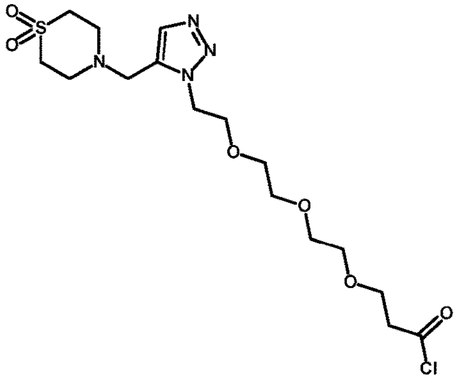
Figure 2A:
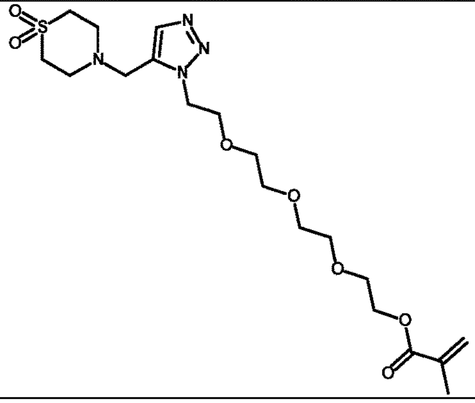
Figure 2A:
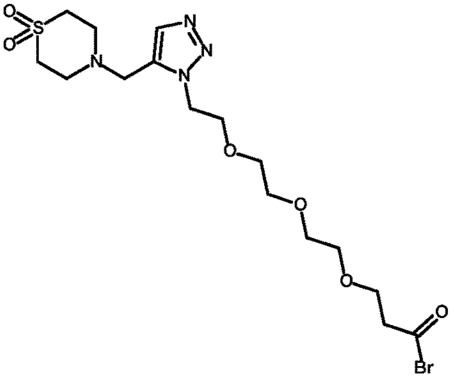
Figure 2B:
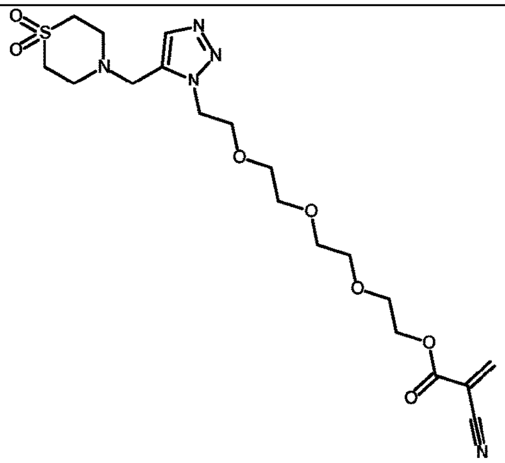
Figure 2B:
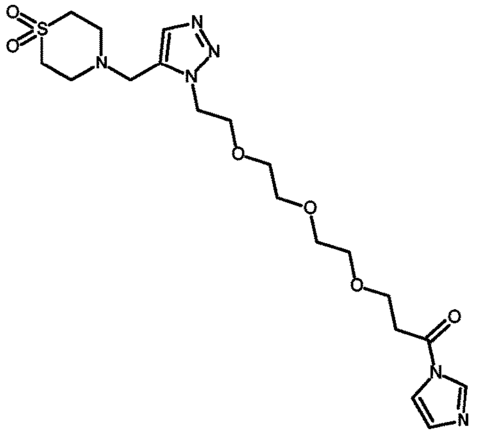
Figure 2B:
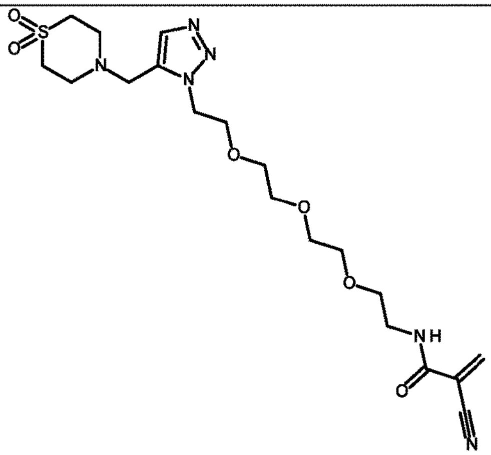
Figure 2B:
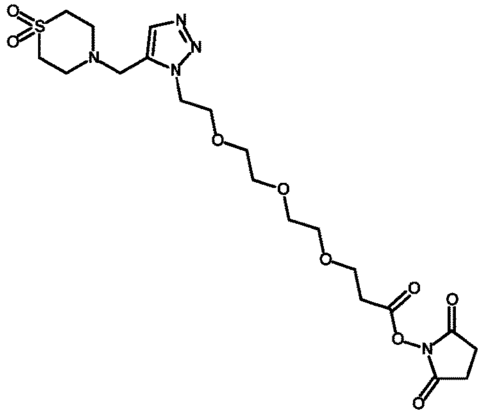
Figure 2B:
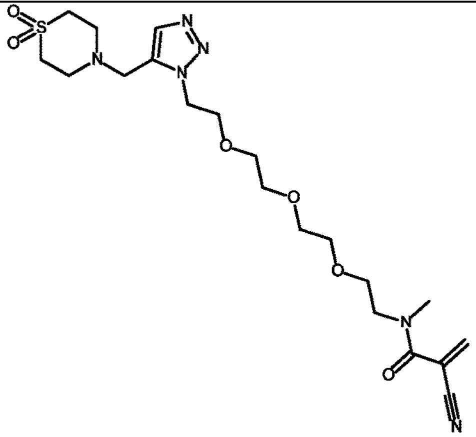
Figure 2B:
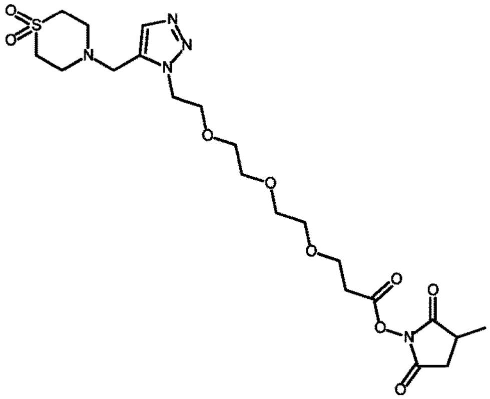
Figure 2C:
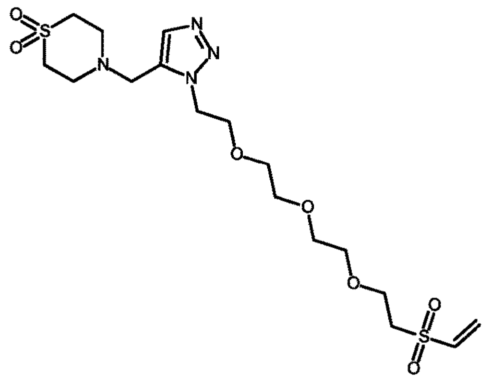
Figure 2C:
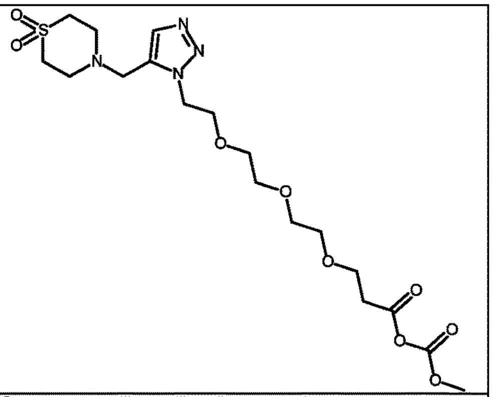
Figure 2C:
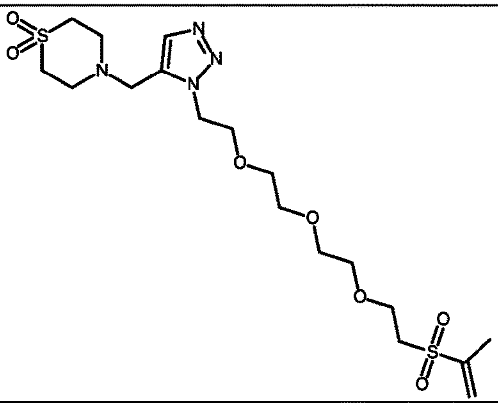
Figure 2C:
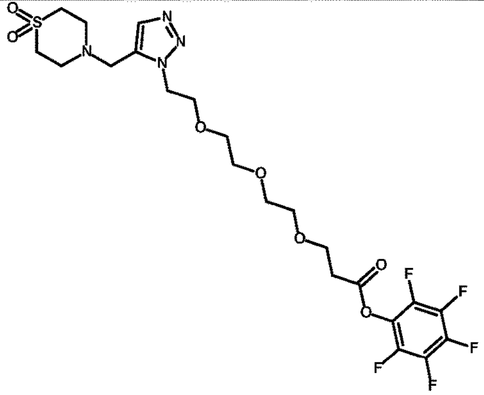
Figure 2C:
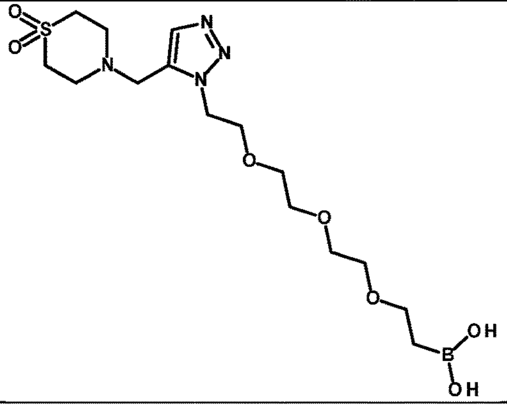
Figure 2C:
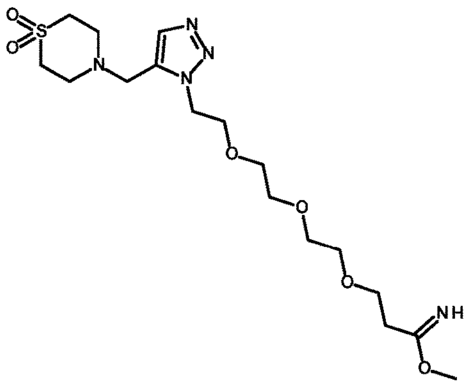
Figure 2C:
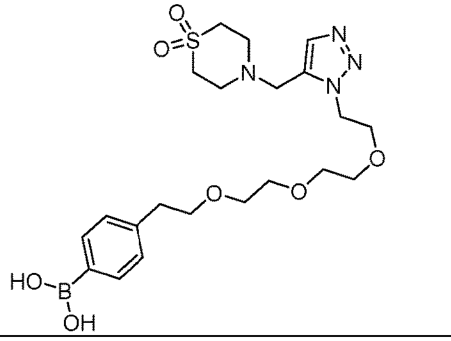
Figure 2C:
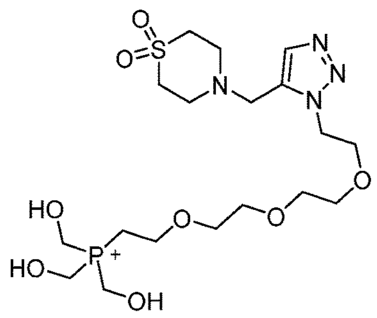
Figure 2D:
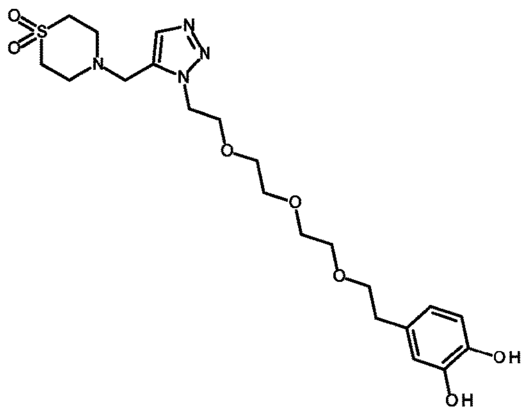
Figure 2D:
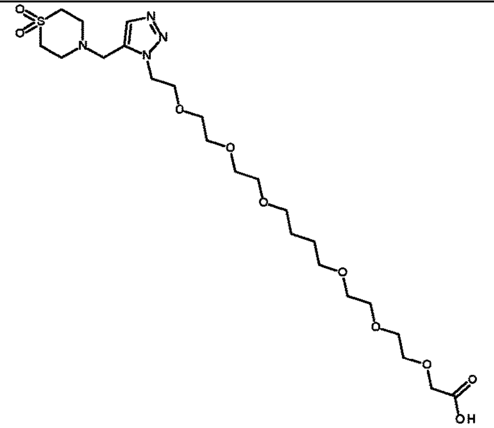
Figure 2D:
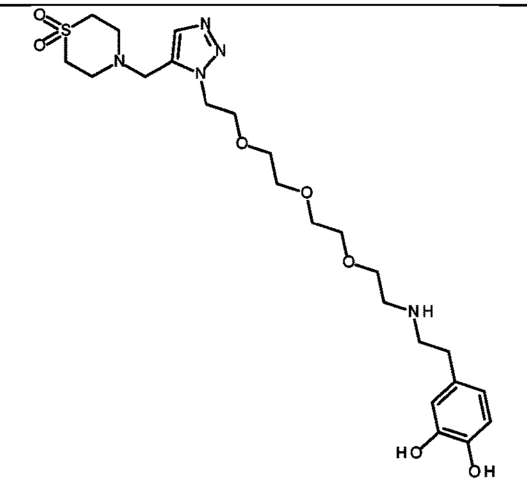
Figure 2D:
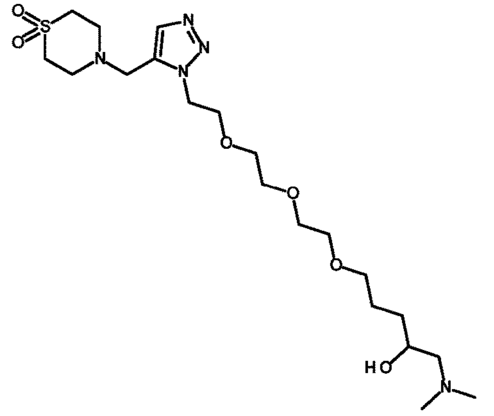
Figure 2D:
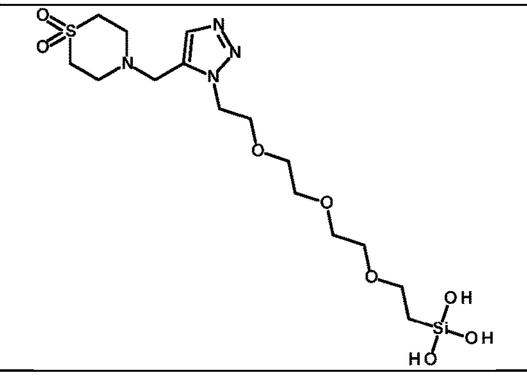
Figure 2D:
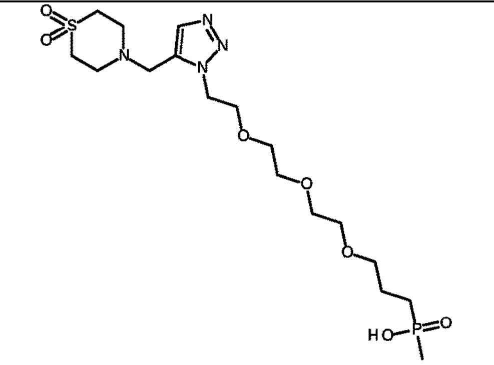
Figure 2D:
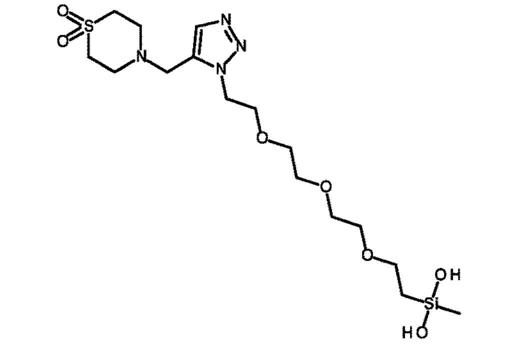
Figure 2D:
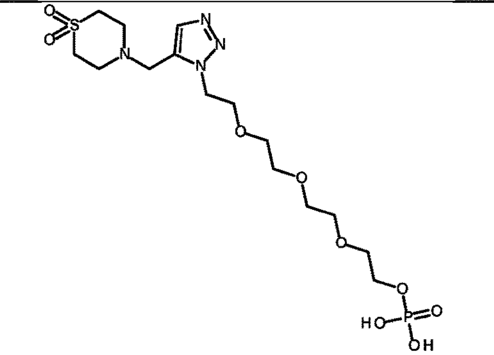
Figure 2E:
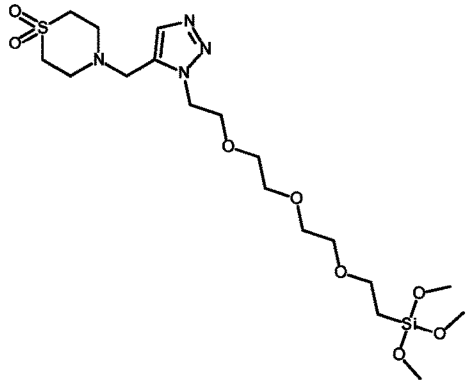
Figure 2E:
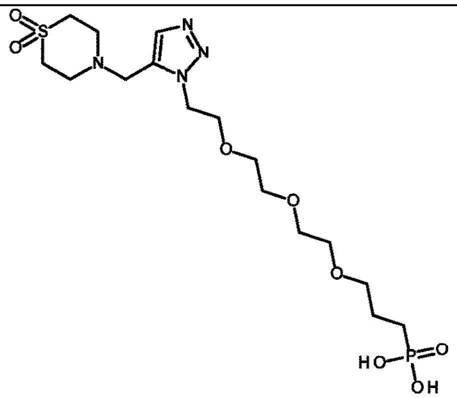
Figure 2E:
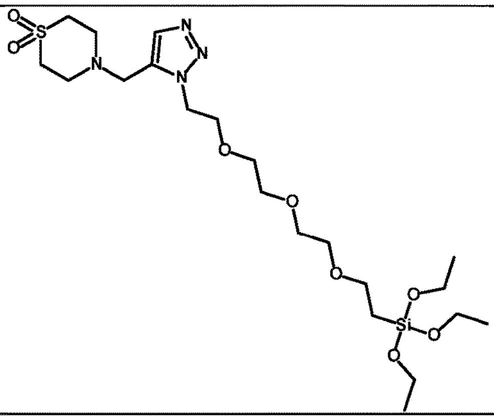
Figure 2E:
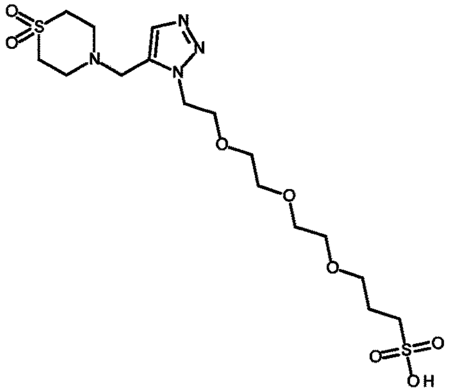
Figure 2E:
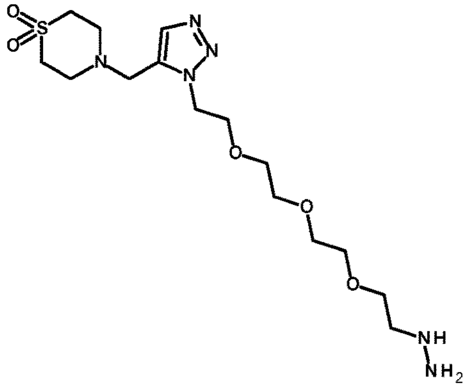
Figure 2E:
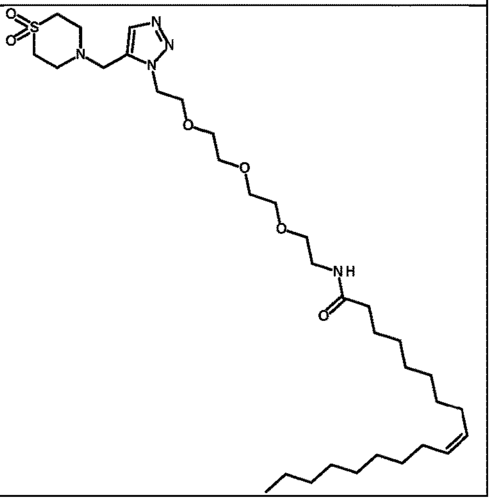
Figure 2F:
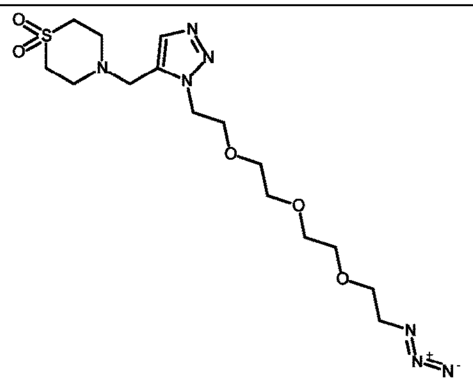
Figure 2F:
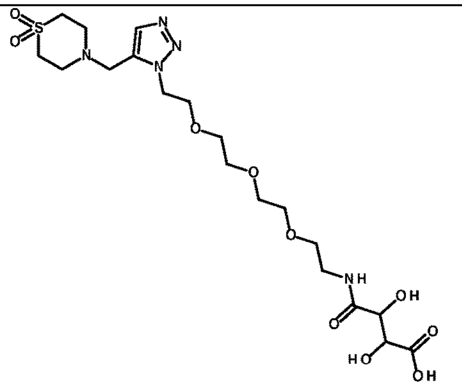
Figure 2F:
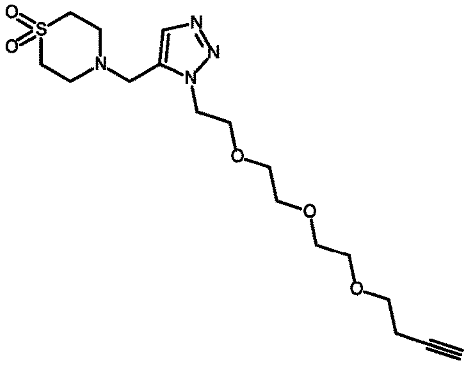
Figure 2F:
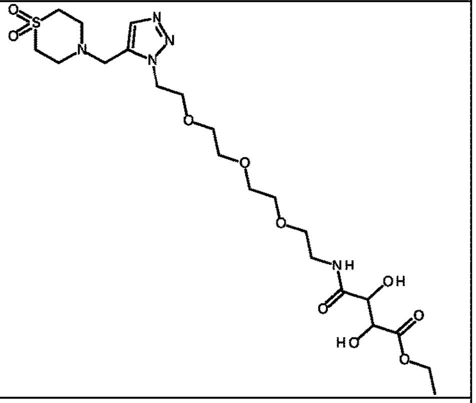
Figure 2F:
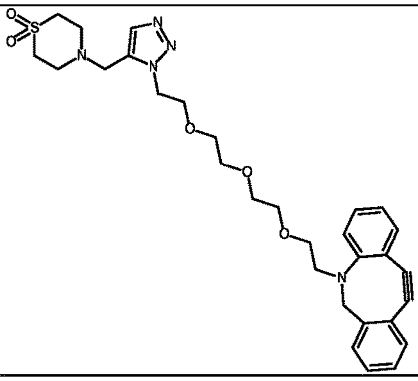
Figure 2F:
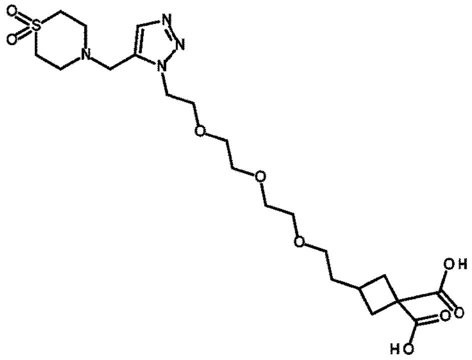
Figure 2F:
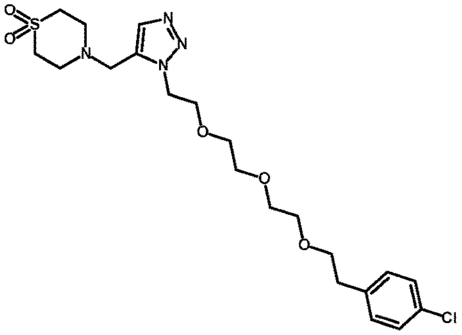
Figure 2F:
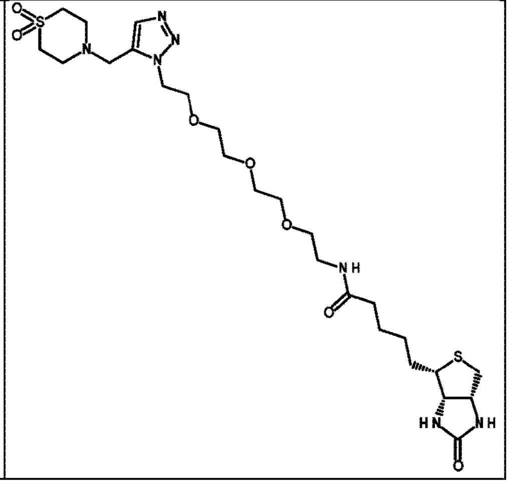
Figure 2G:
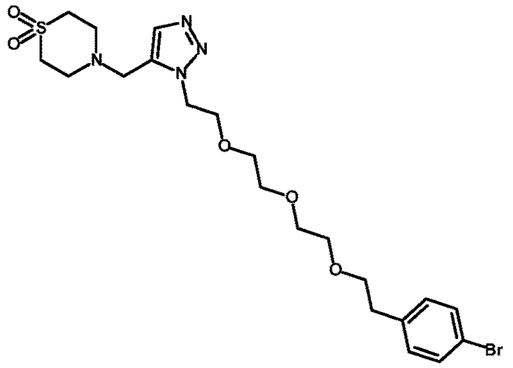
Figure 2G:
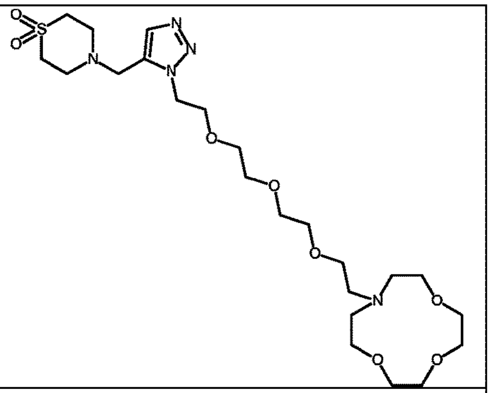
Figure 2G:
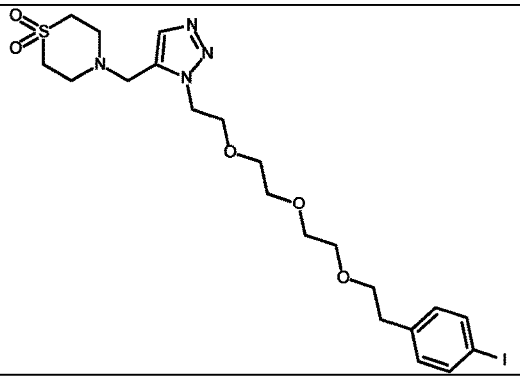
Figure 2G:
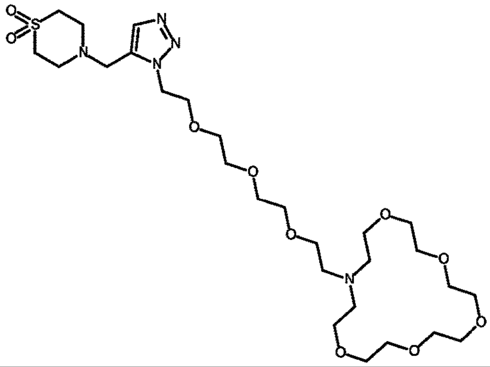
Figure 2G:
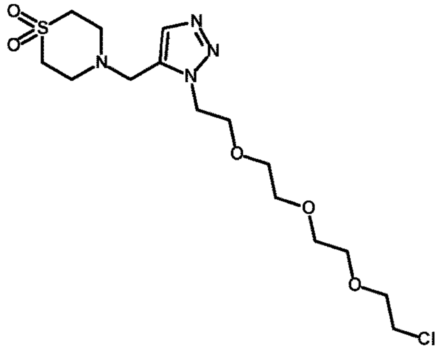
Figure 2G:
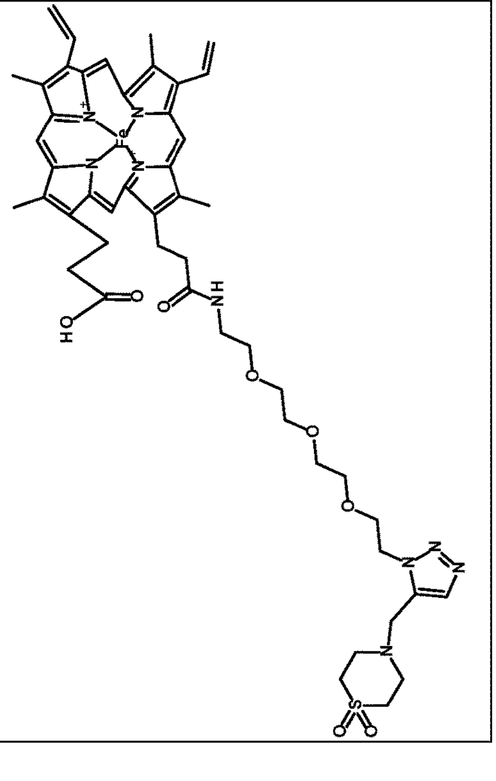
Figure 2H:
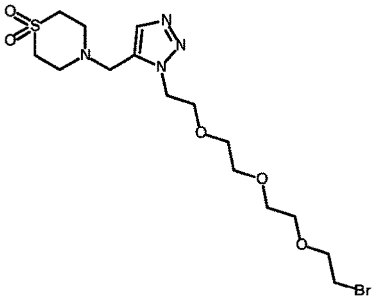
Figure 2H:
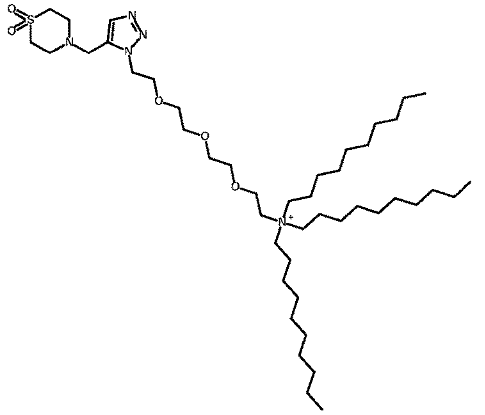
Figure 2H:
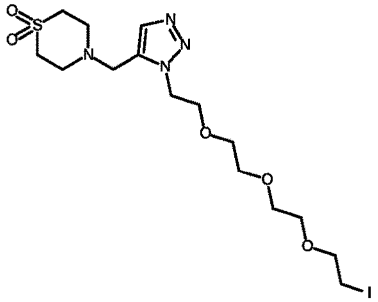
Figure 2H:
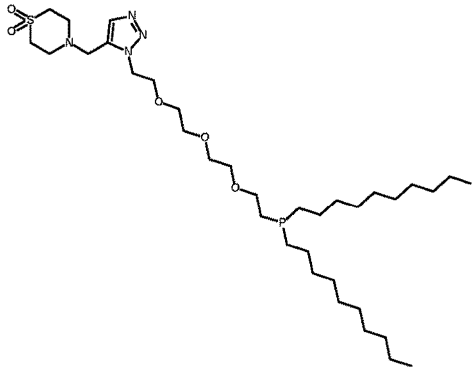
Figure 2H:
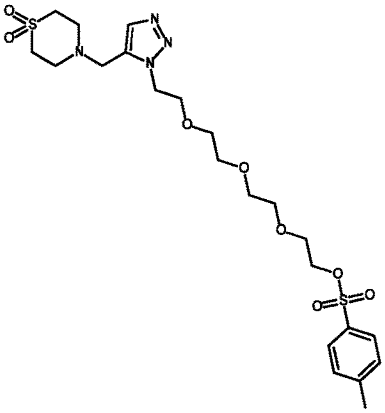
Figure 2H:
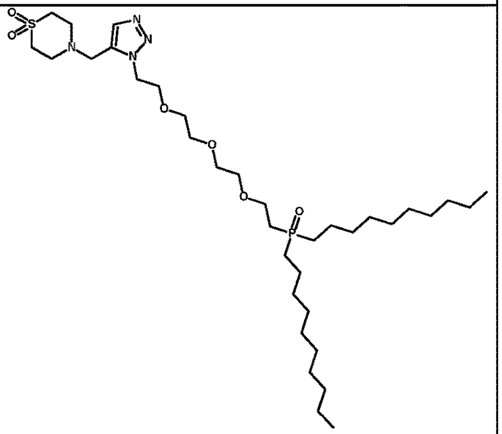
Figure 2H:
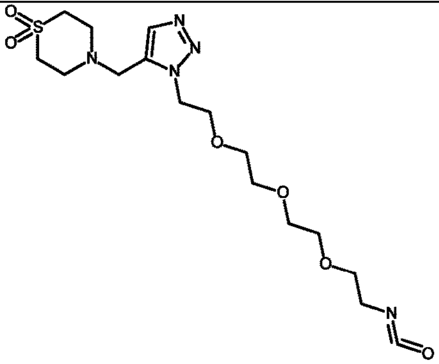
Figure 2H:
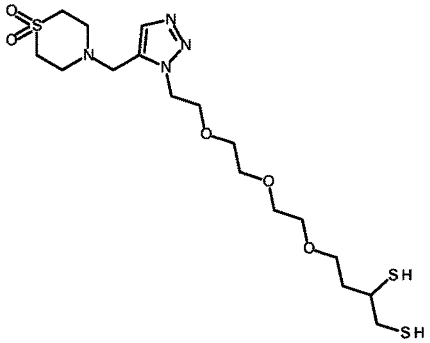
Figure 2I:
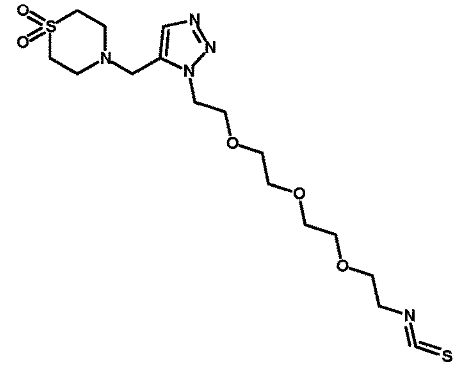
Figure 2I:
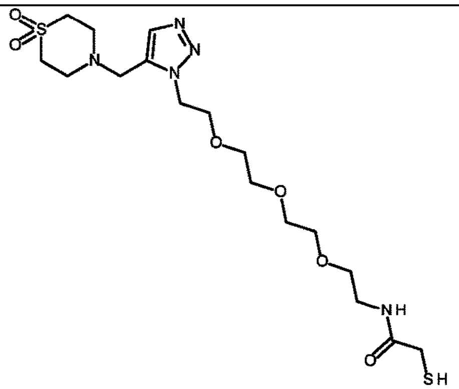
Figure 2I:
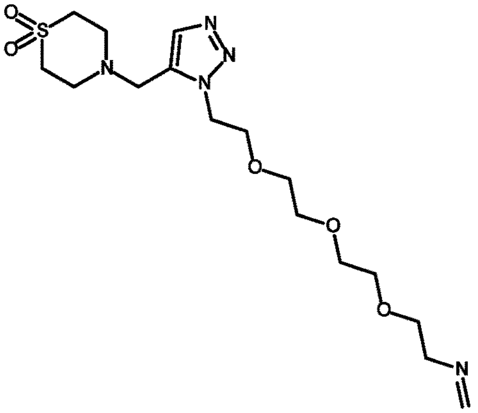
Figure 2I:
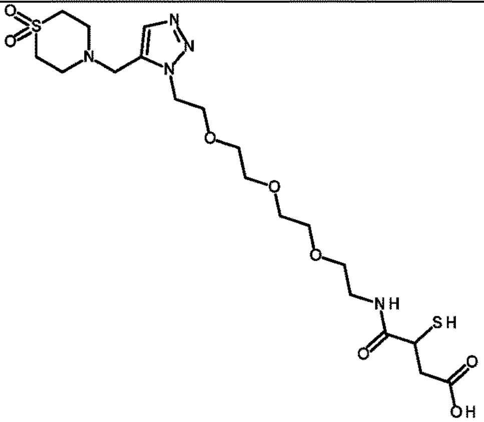
Figure 2I:
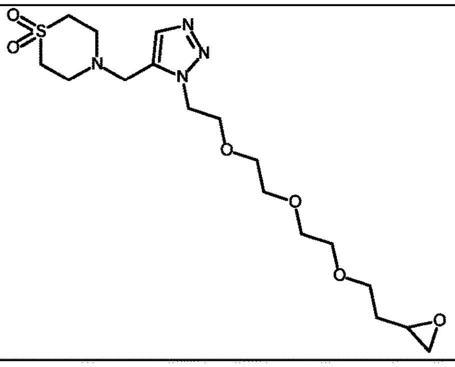
Figure 2I:
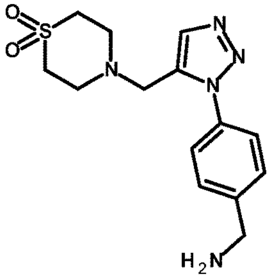
Figure 2I:
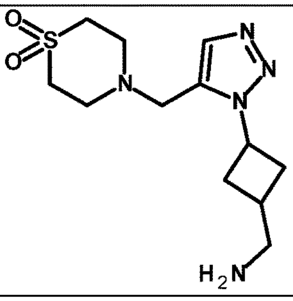
Figure 2J:
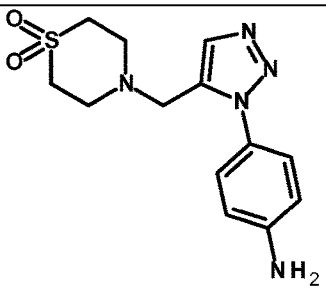
Figure 2J:
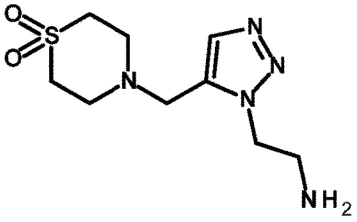
Figure 2J:
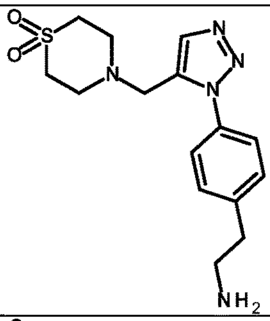
Figure 2J:
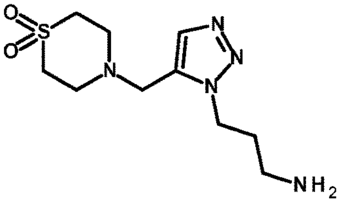
Figure 2J:
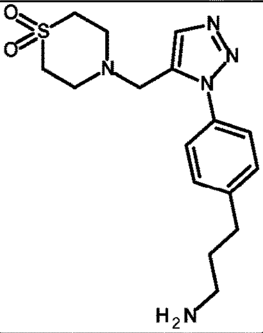
Figure 2J:
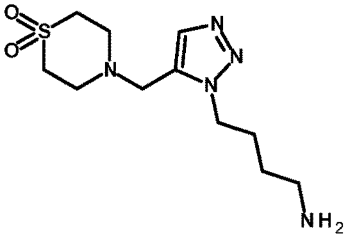
Figure 2J:
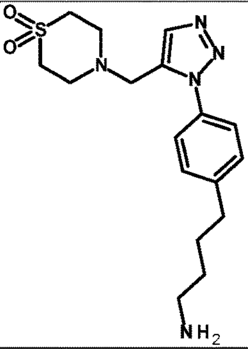
Figure 2J:
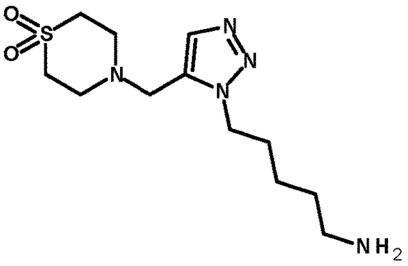
Figure 2J:
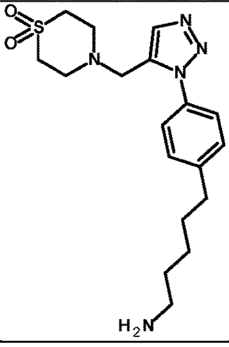
Figure 2J:
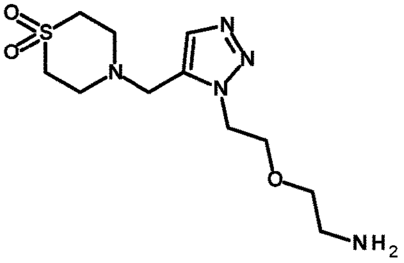
Figure 2K:
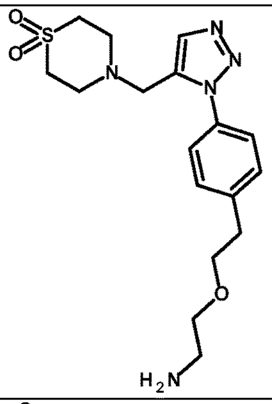
Figure 2K:
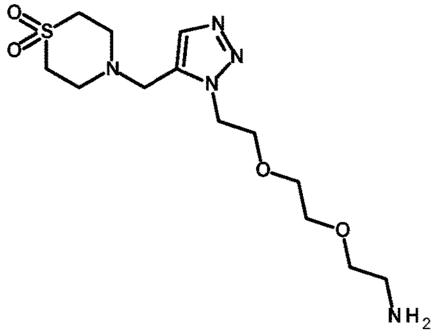
Figure 2K:
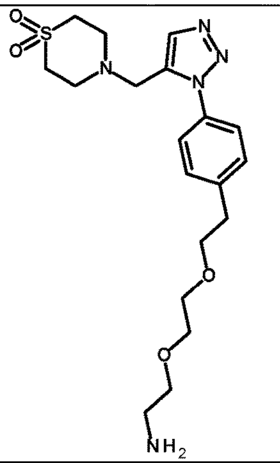
Figure 2K:
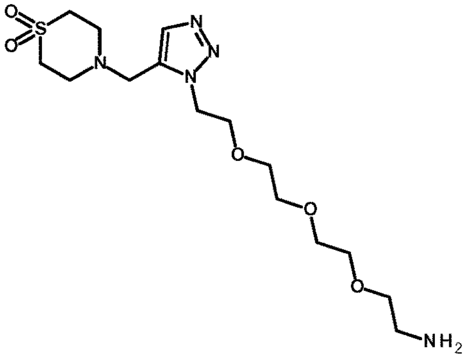
Figure 2K:
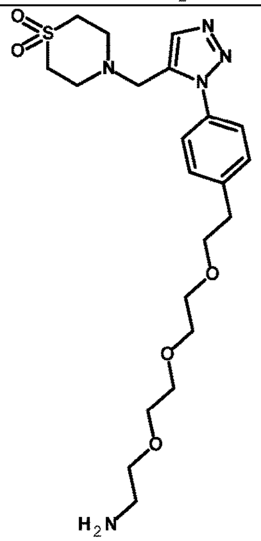
Figure 2K:
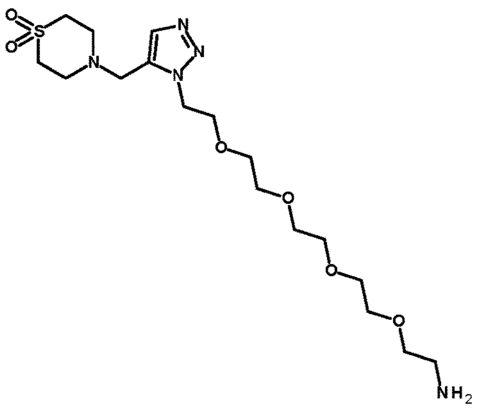
Figure 2L:
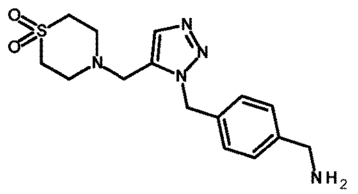
Figure 2L:
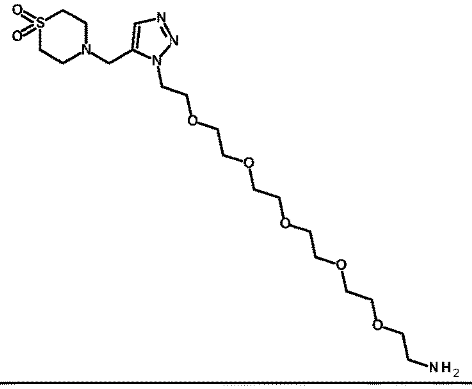
Figure 2L:
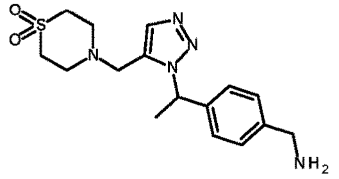
Figure 2L:
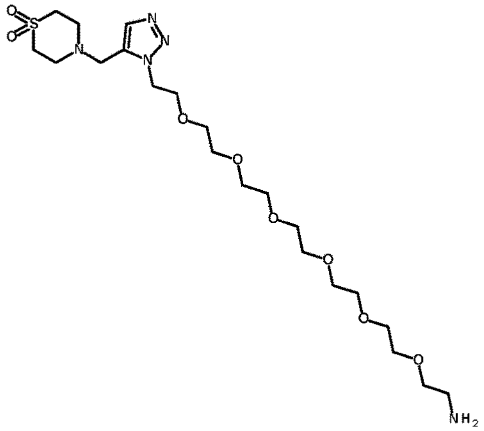
Figure 2L:
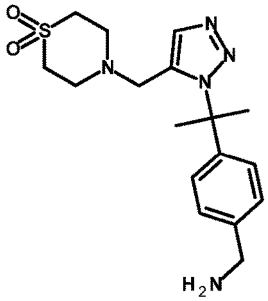
Figure 2L:
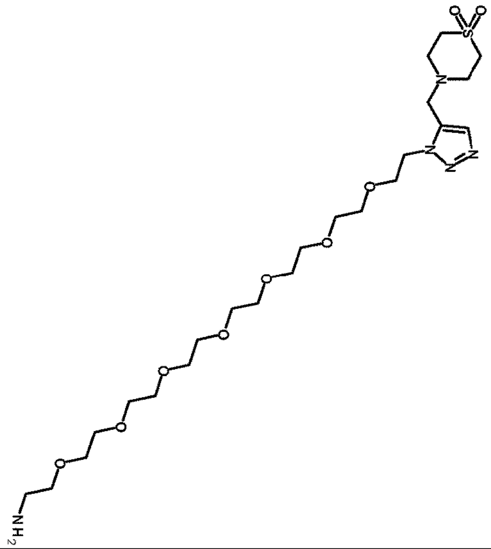
Figure 2M:
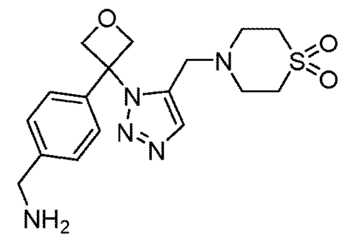
Figure 2M:
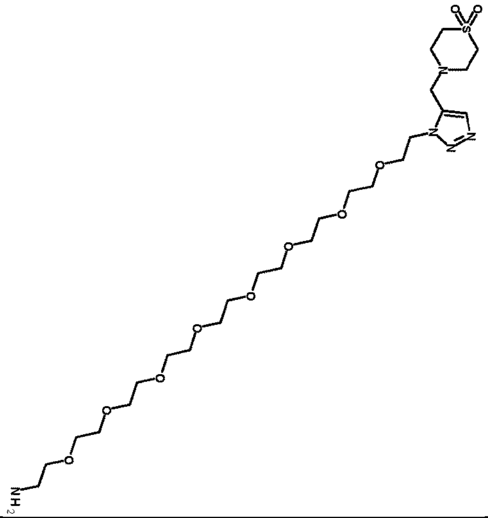
Figure 2M:
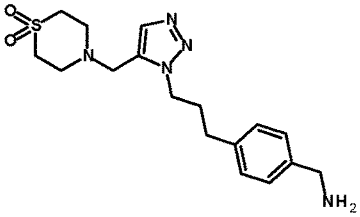
Figure 2M:
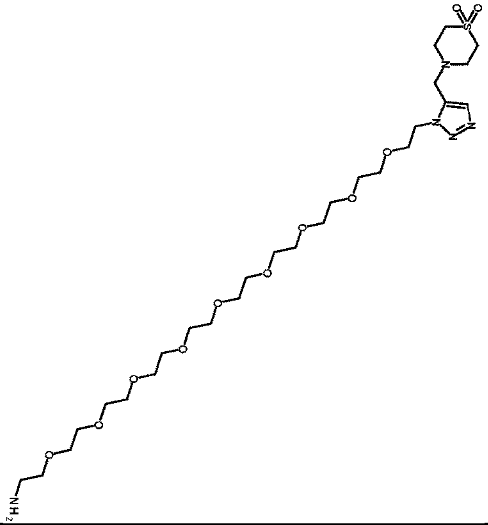
Figure 2M:
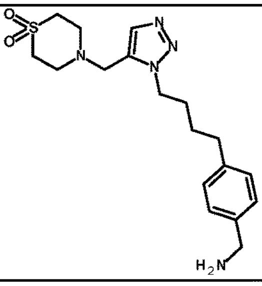
Figure 2M:
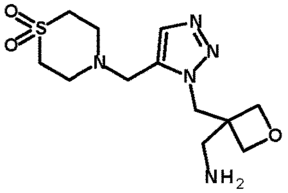
Figure 2M:
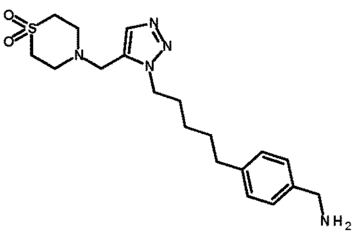
Figure 2M:
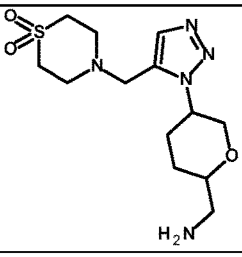
Figure 2N:
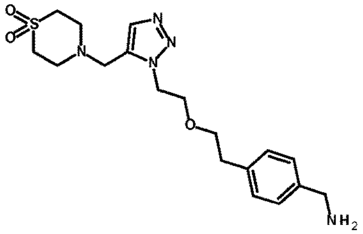
Figure 2N:
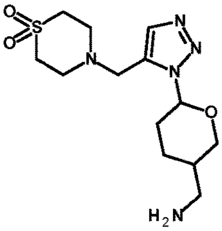
Figure 2N:
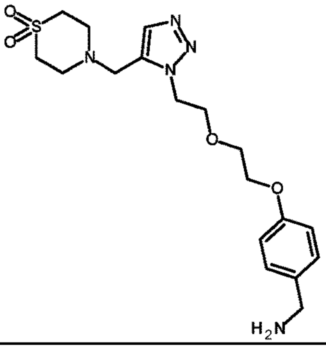
Figure 2N:
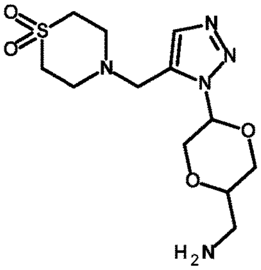
Figure 2N:
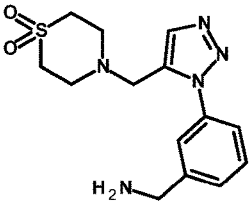
Figure 2N:
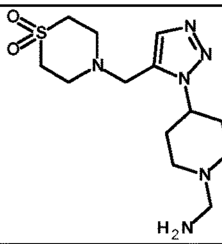
Figure 2N:
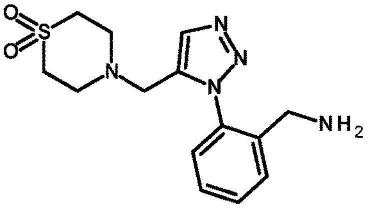
Figure 2N:
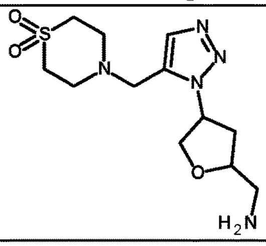
Figure 2N:
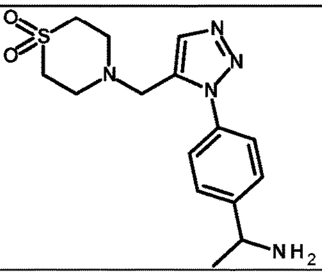
Figure 2N:
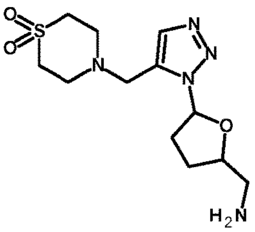
Figure 2N:
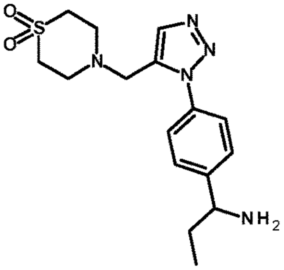
Figure 2N:
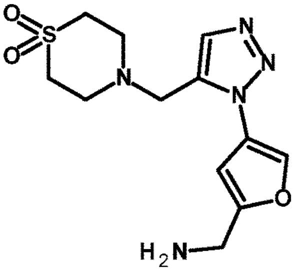
Figure 2O:
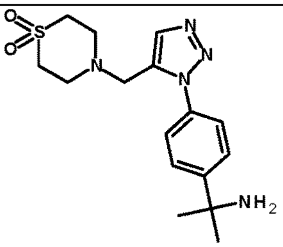
Figure 2O:
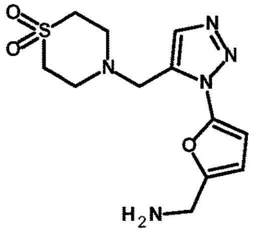
Figure 2O:
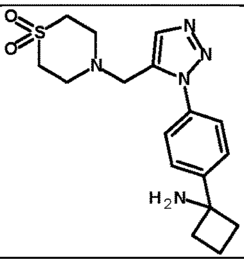
Figure 2O:
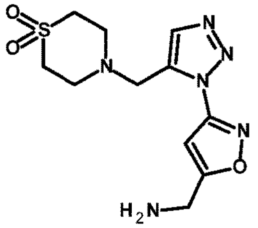
Figure 2O:
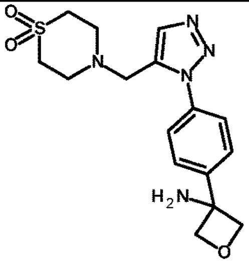
Figure 2O:
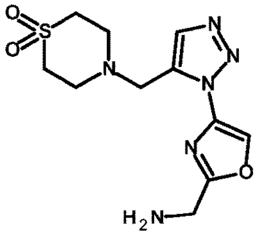
Figure 2O:
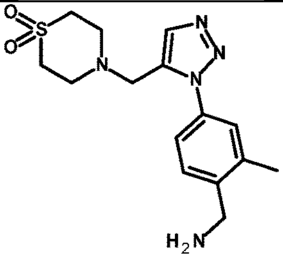
Figure 2O:
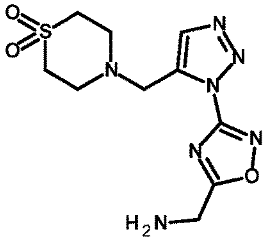
Figure 2O:
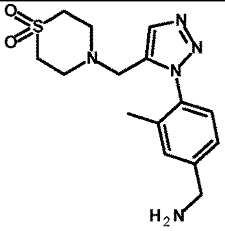
Figure 2O:
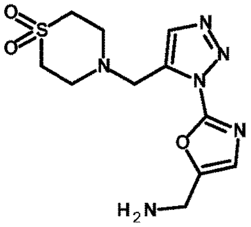
Figure 2O:
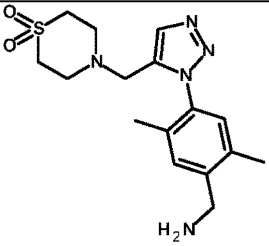
Figure 2O:
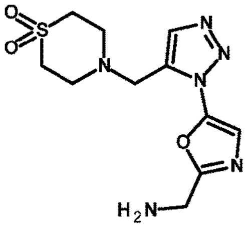
Figure 2P:
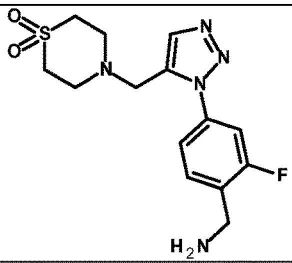
Figure 2P:
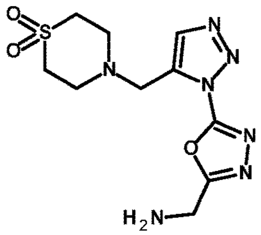
Figure 2P:
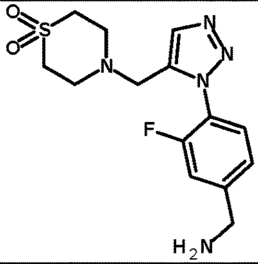
Figure 2P:
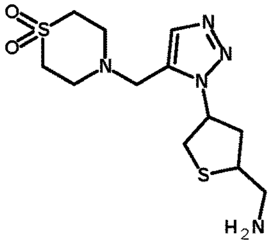
Figure 2P:
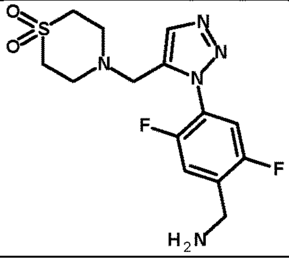
Figure 2P:
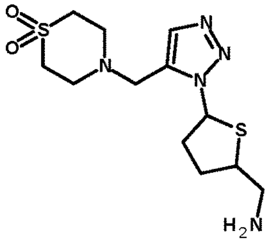
Figure 2P:
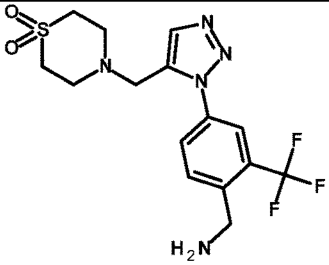
Figure 2P:
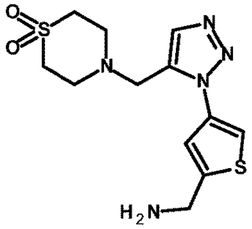
Figure 2P:
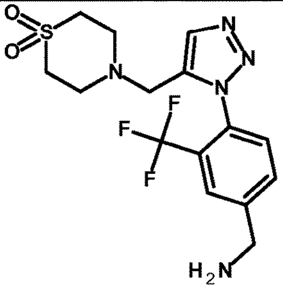
Figure 2P:
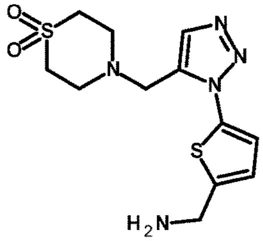
Figure 2P:
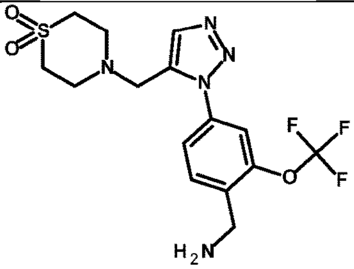
Figure 2P:
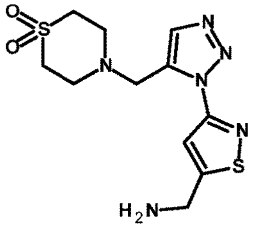
Figure 2Q:
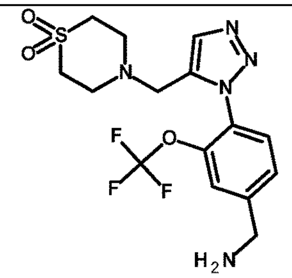
Figure 2Q:
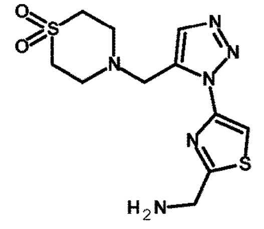
Figure 2Q:
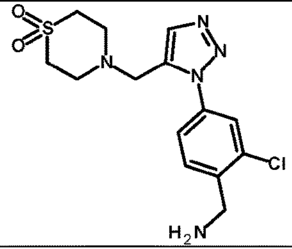
Figure 2Q:
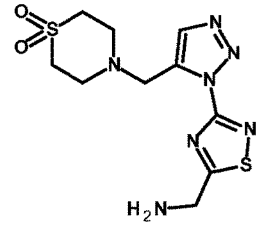
Figure 2Q:
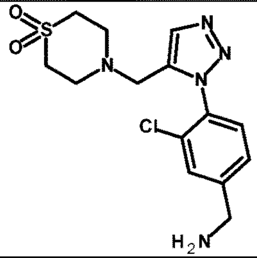
Figure 2Q:
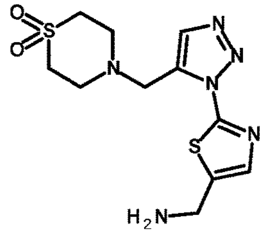
Figure 2Q:
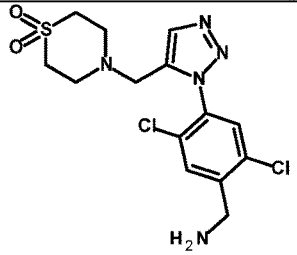
Figure 2Q:
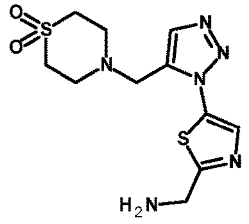
Figure 2Q:
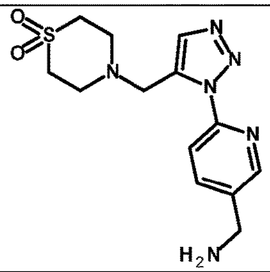
Figure 2Q:
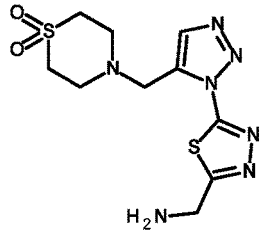
Figure 2Q:
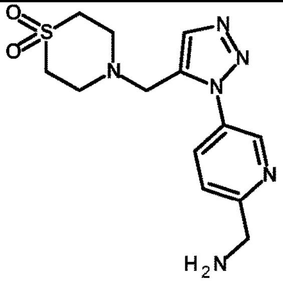
Figure 2Q:
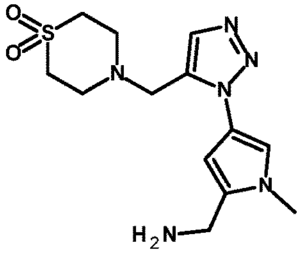
Figure 2R:
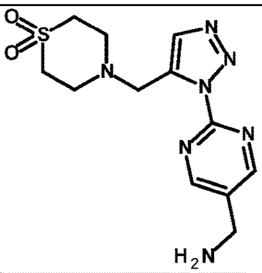
Figure 2R:
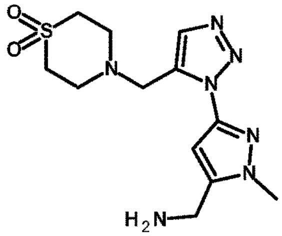
Figure 2R:
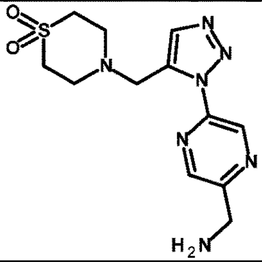
Figure 2R:
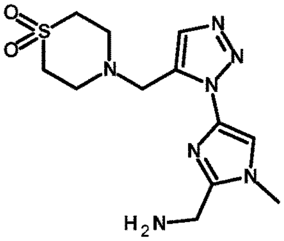
Figure 2R:
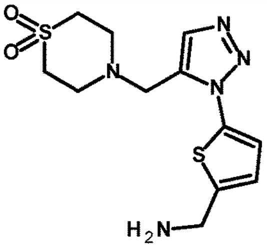
Figure 2R:
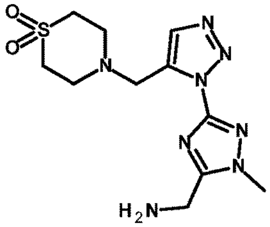
Figure 2R:
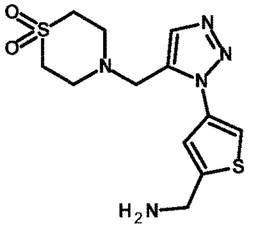
Figure 2R:
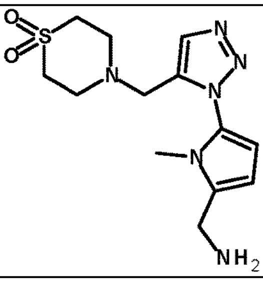
Figure 2R:
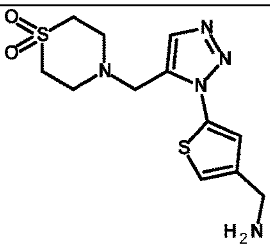
Figure 2R:
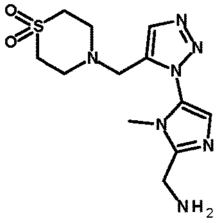
Figure 2R:
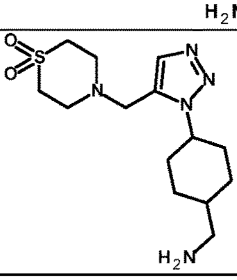
Figure 2R:
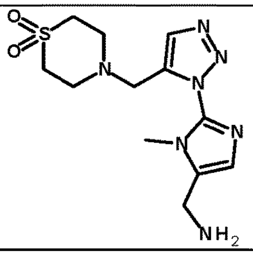
Figure 2S:
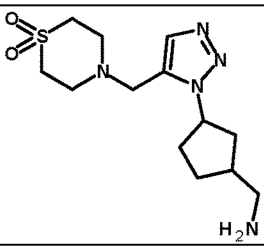
Figure 2S:
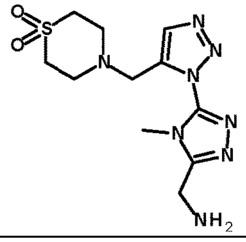
Figure 2S:
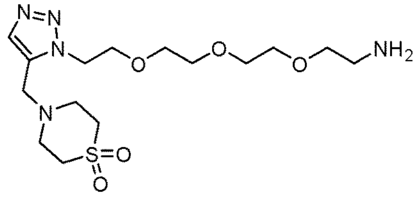
Figure 2S:
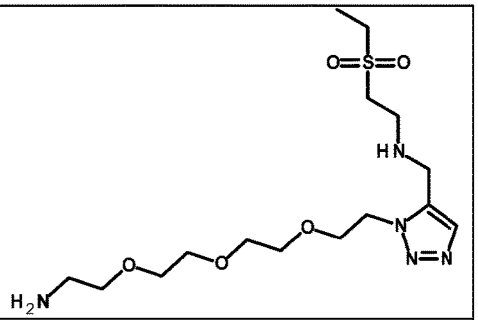
Figure 2S:
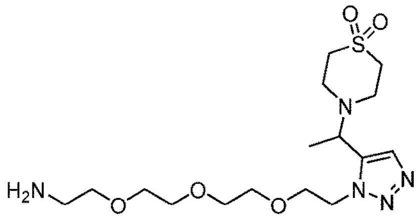
Figure 2S:
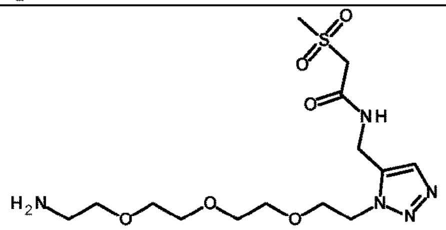
Figure 2S:
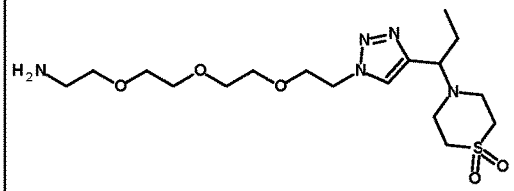
Figure 2S:
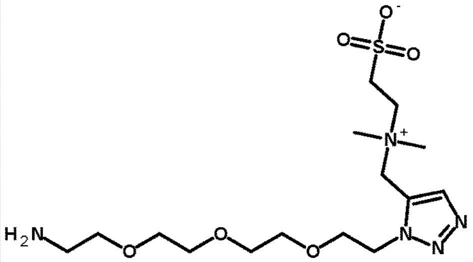
Figure 2S:
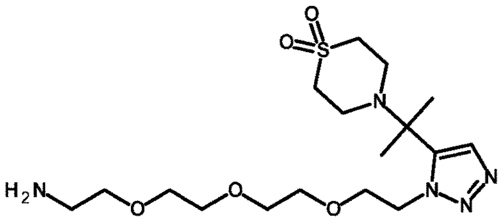
Figure 2S:
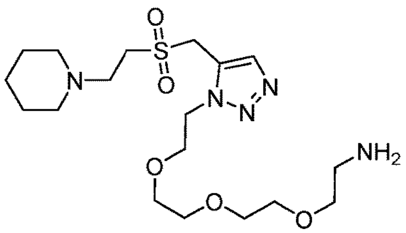
Figure 2T:
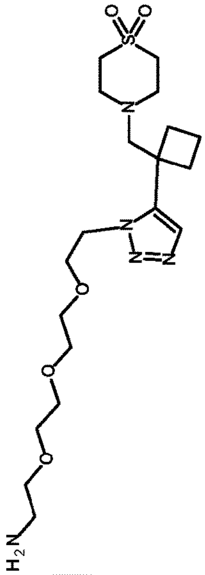
Figure 2T:
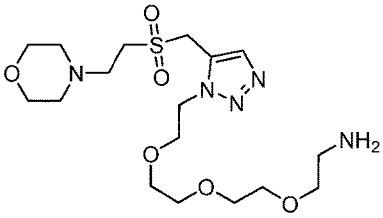
Figure 2T:
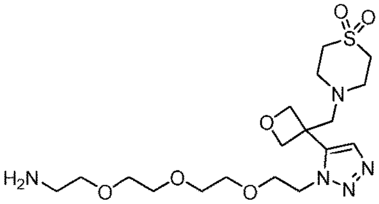
Figure 2T:
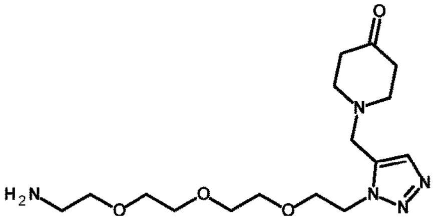
Figure 2T:
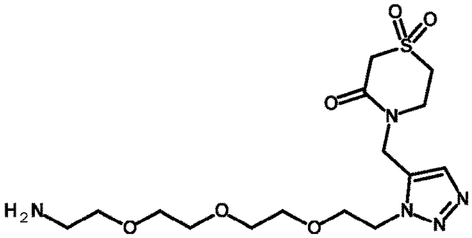
Figure 2T:
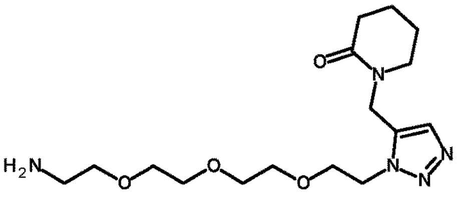
Figure 2T:
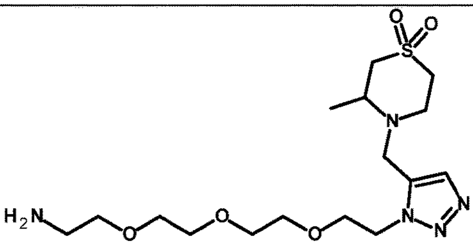
Figure 2T:
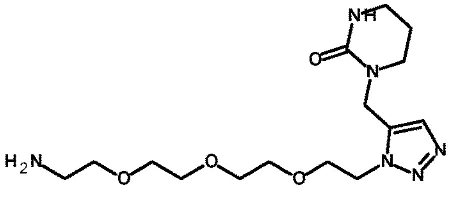
Figure 2T:
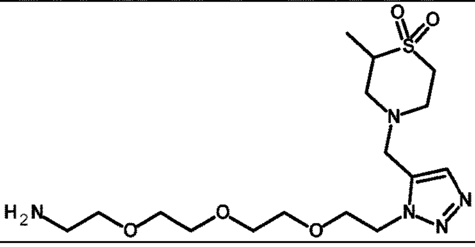
Figure 2T:
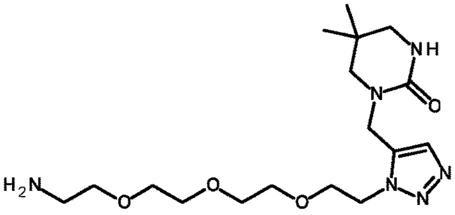
Figure 2U:
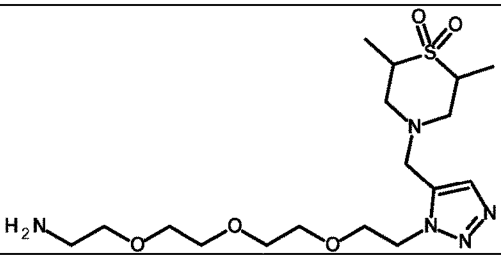
Figure 2U:
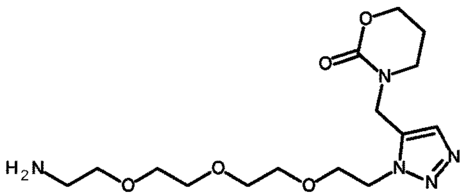
Figure 2U:
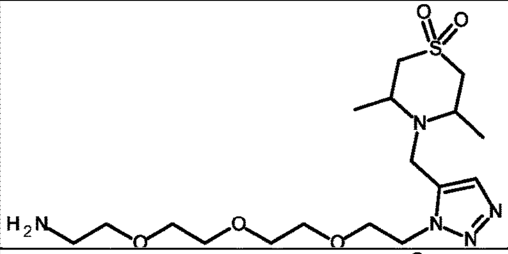
Figure 2U:
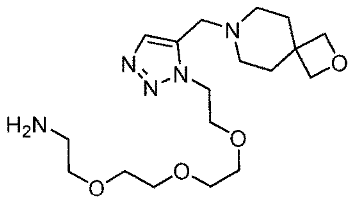
Figure 2U:
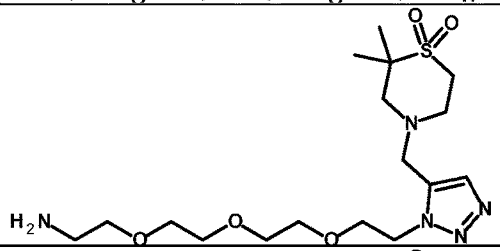
Figure 2U:
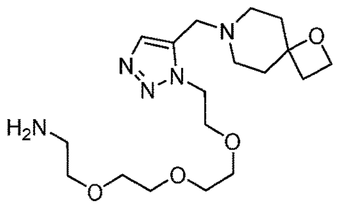
Figure 2U:
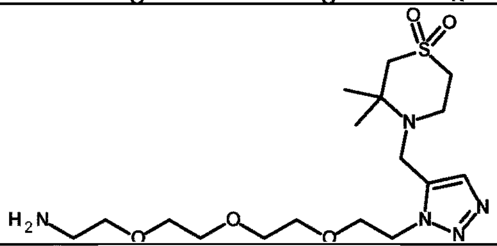
Figure 2U:
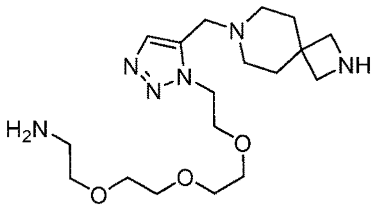
Figure 2U:
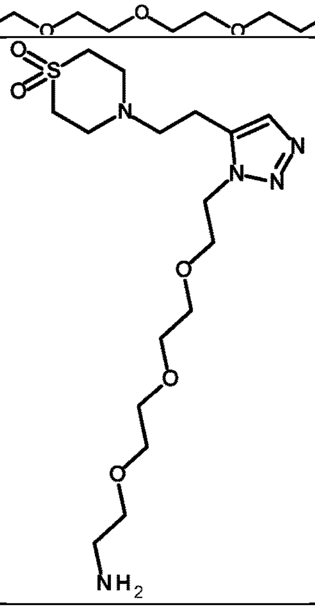
Figure 2U:
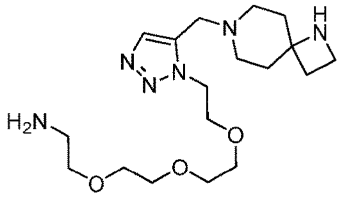
Figure 2V:
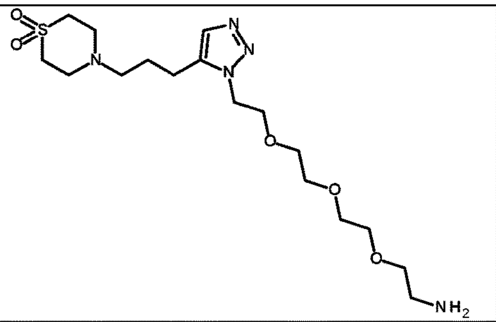
Figure 2V:
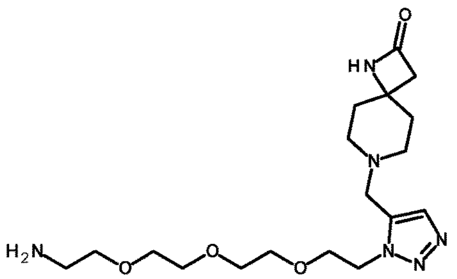
Figure 2V:
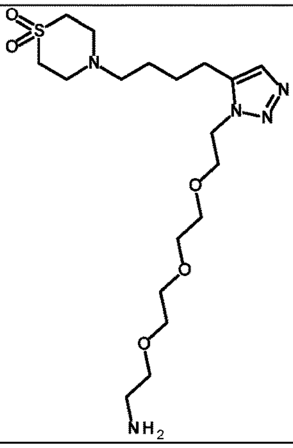
Figure 2V:
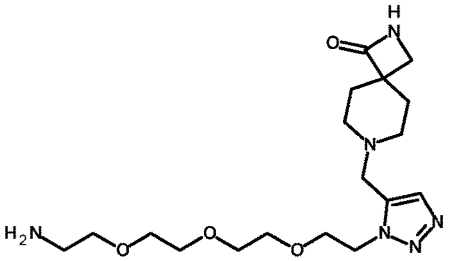
Figure 2V:
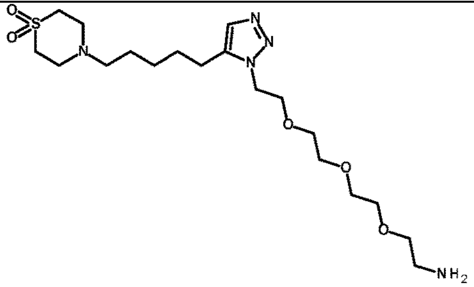
Figure 2V:
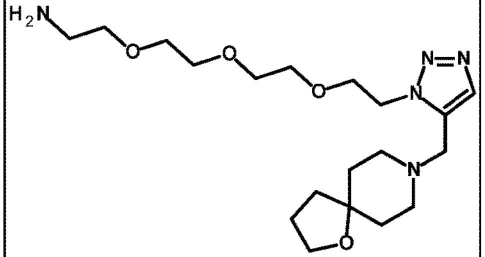
Figure 2V:
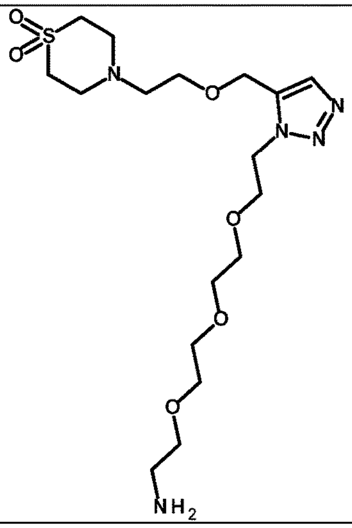
Figure 2V:
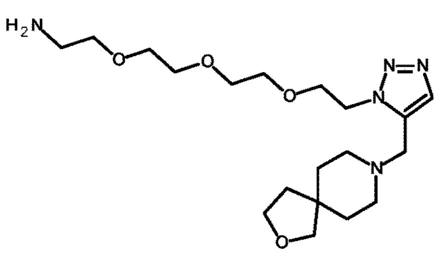
Figure 2W:
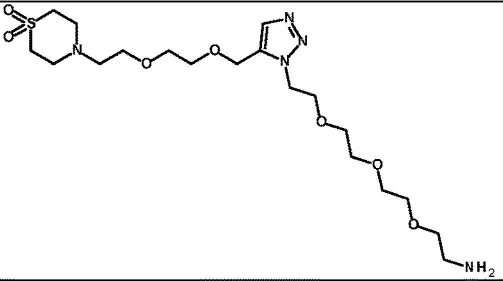
Figure 2W:
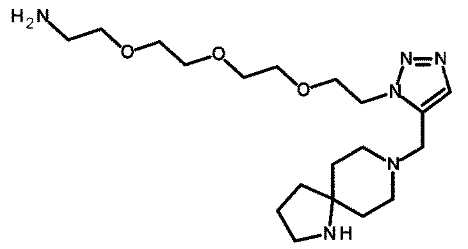
Figure 2W:
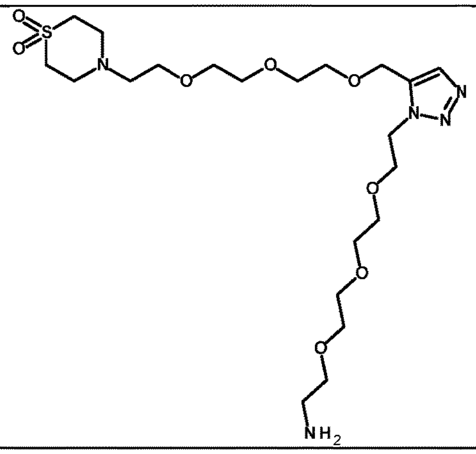
Figure 2W:
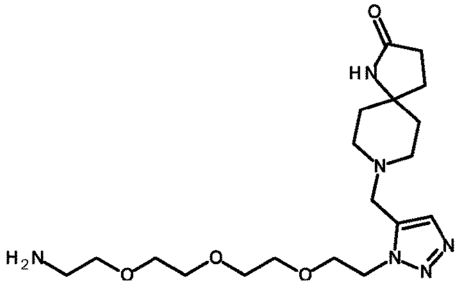
Figure 2W:
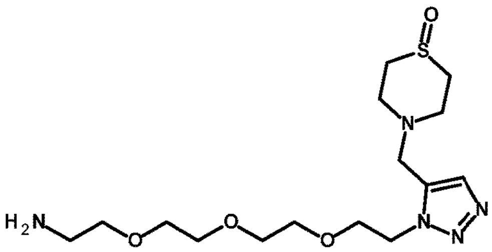
Figure 2W:
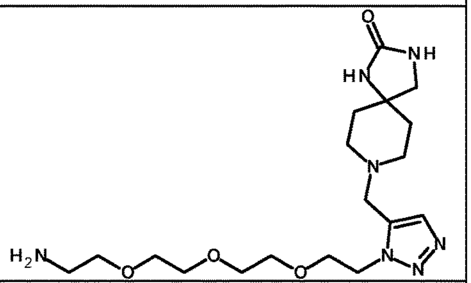
Figure 2W:
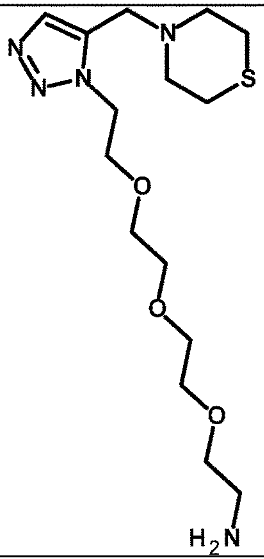
Figure 2W:
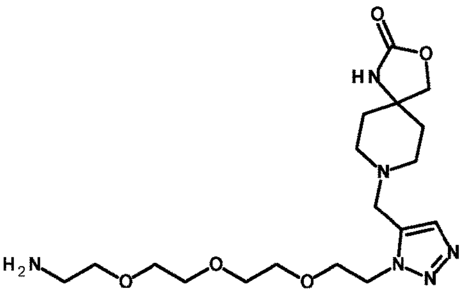
Figure 2X:
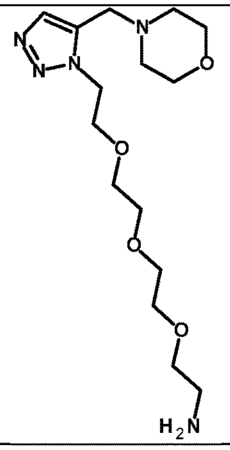
Figure 2X:
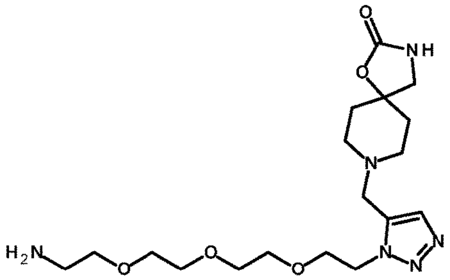
Figure 2X:
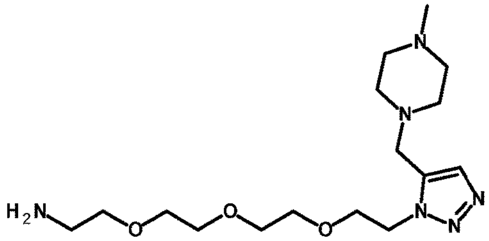
Figure 2X:
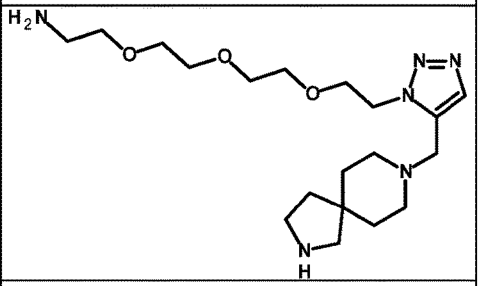
Figure 2X:
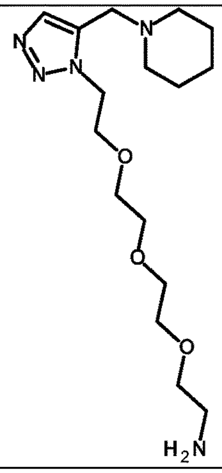
Figure 2X:
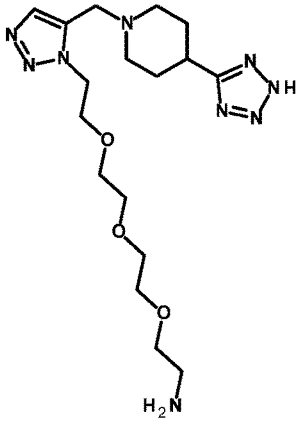
Figure 2X:
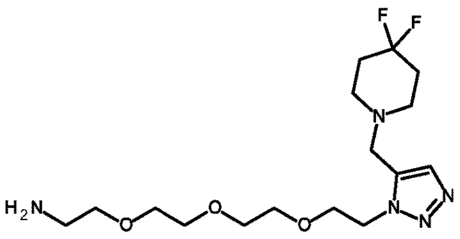
Figure 2X:
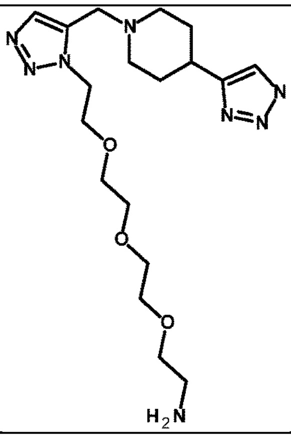
Figure 2Y:
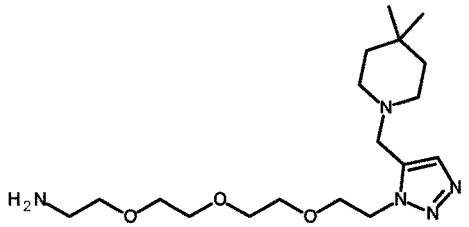
Figure 2Y:
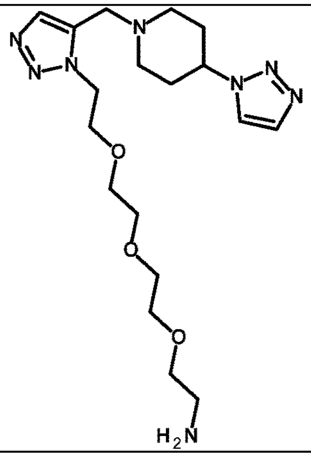
Figure 2Y:
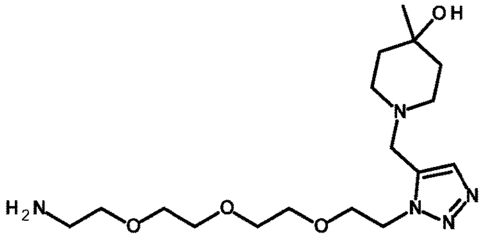
Figure 2Y:
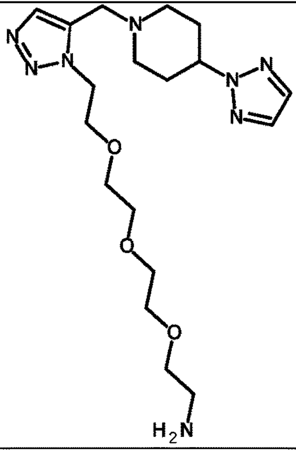
Figure 2Y:
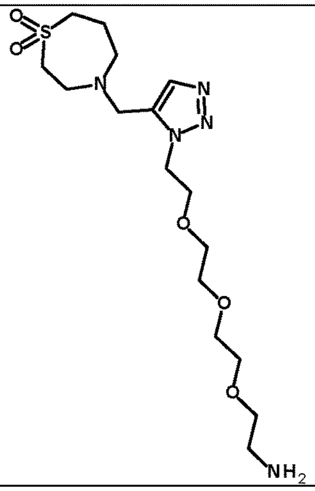
Figure 2Y:
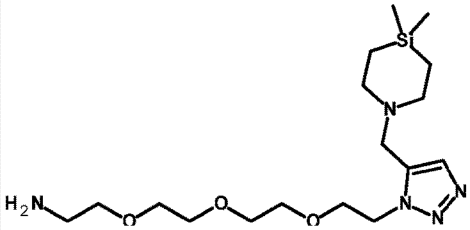
Figure 2Y:
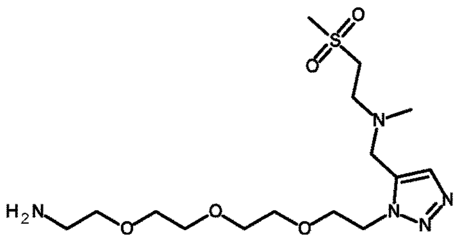
Figure 2Y:
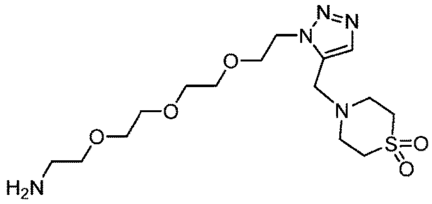
Figure 2Z:
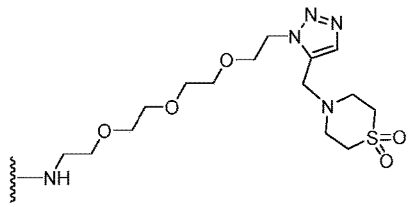
Figure 2Z:
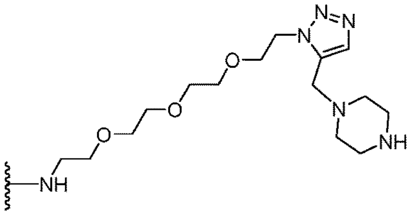
Figure 3A:
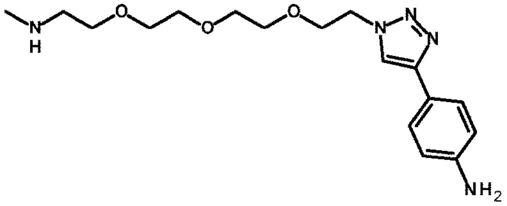
Figure 3A:
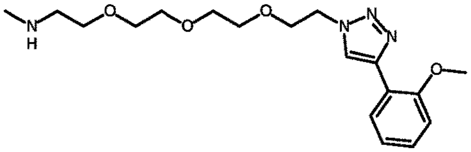
Figure 3A:
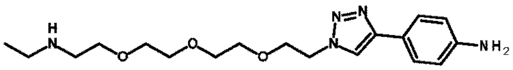
Figure 3A:
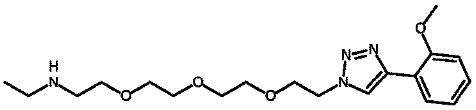
Figure 3A:
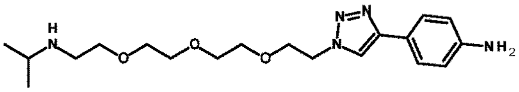
Figure 3A:
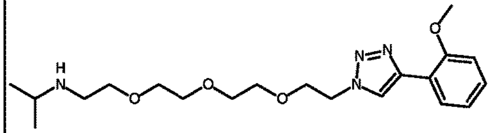
Figure 3A:
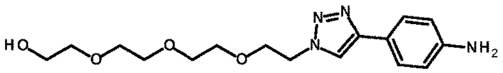
Figure 3A:
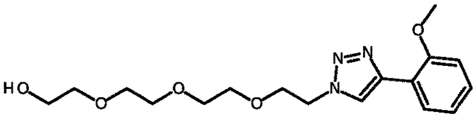
Figure 3A:
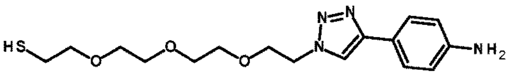
Figure 3A:
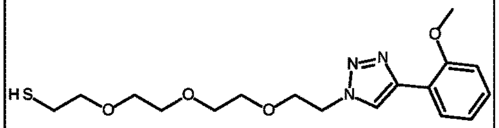
Figure 3A:
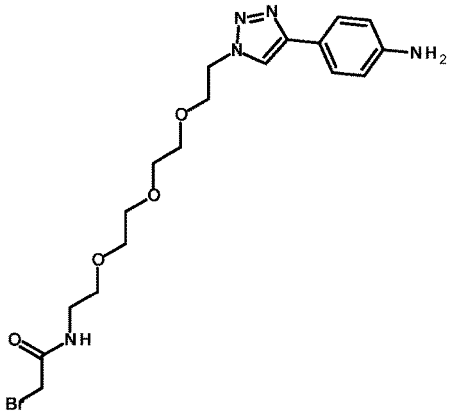
Figure 3A:
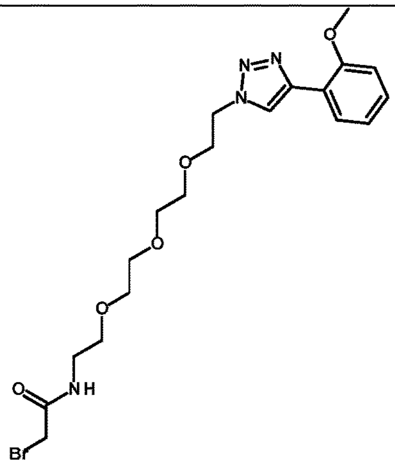
Figure 3B:
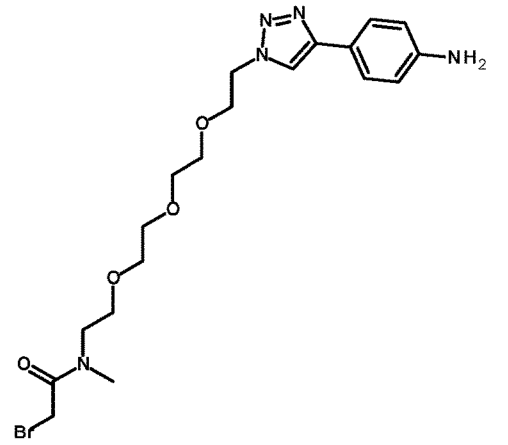
Figure 3B:
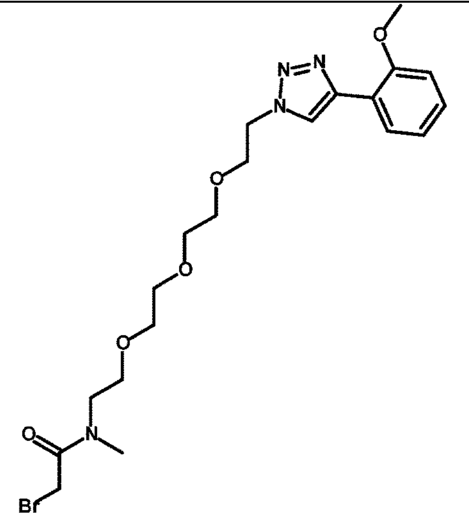
Figure 3B:
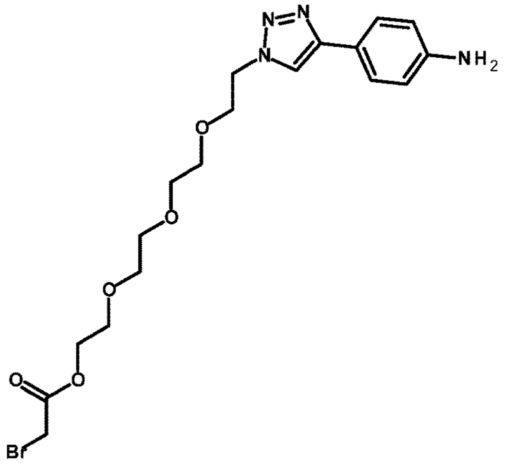
Figure 3B:
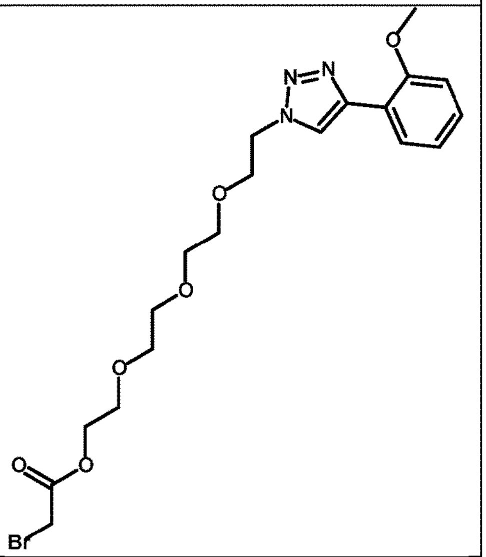
Figure 3B:
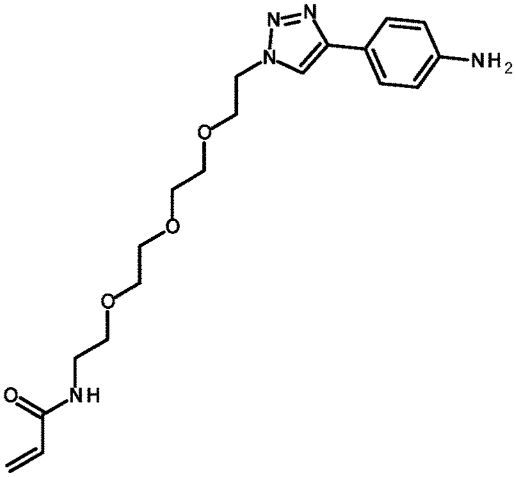
Figure 3B:
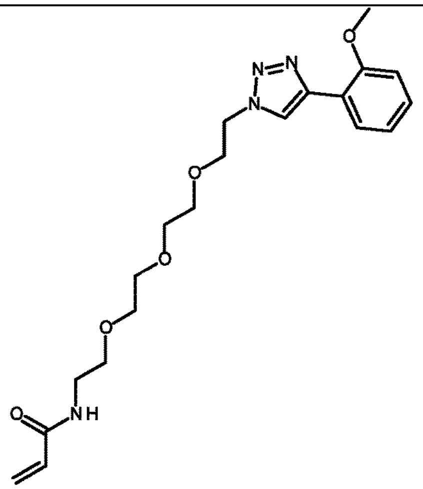
Figure 3C:
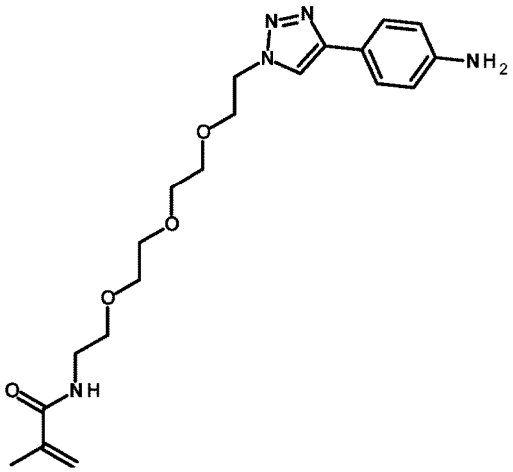
Figure 3C:
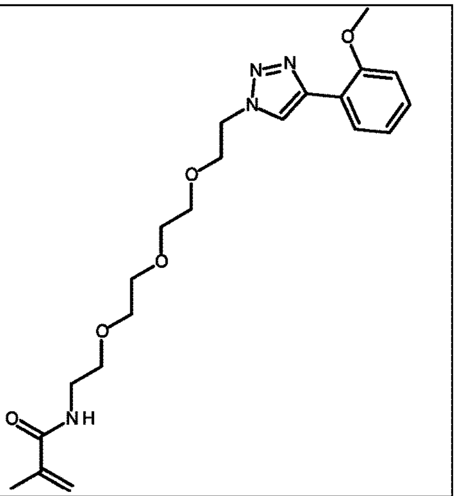
Figure 3C:
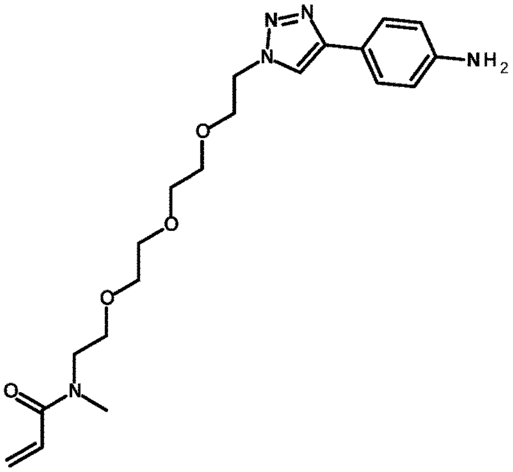
Figure 3C:
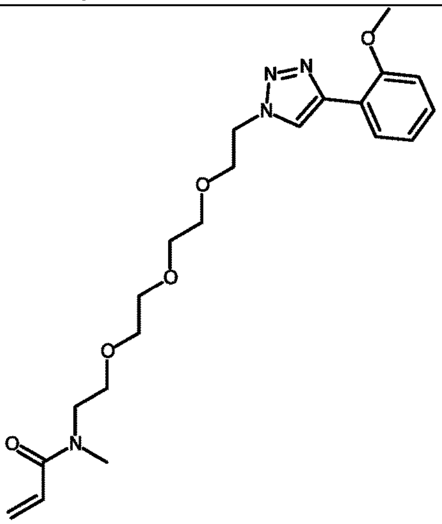
Figure 3C:
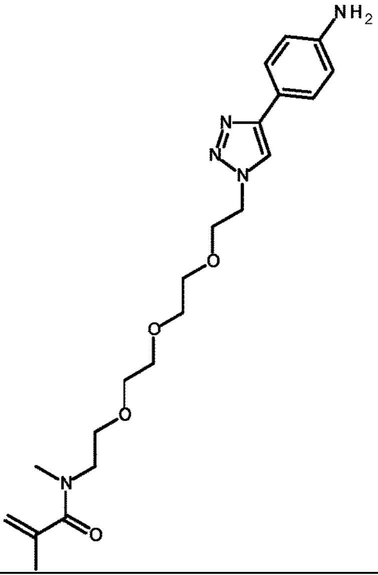
Figure 3C:
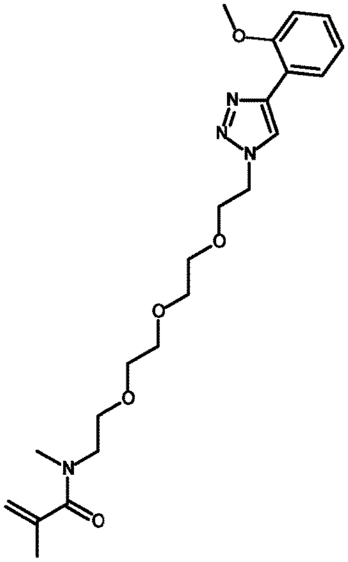
Figure 3D:
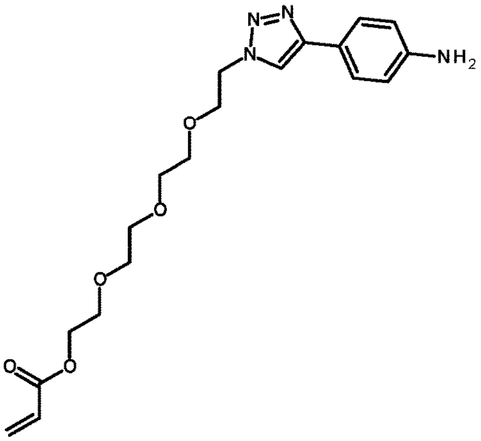
Figure 3D:
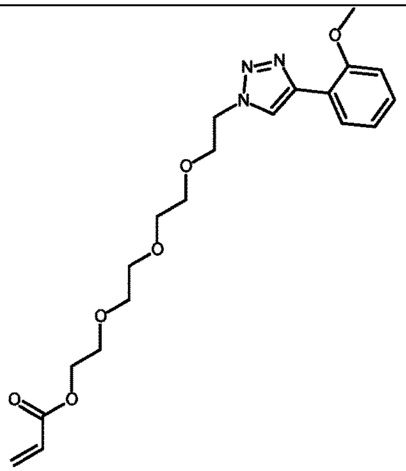
Figure 3D:
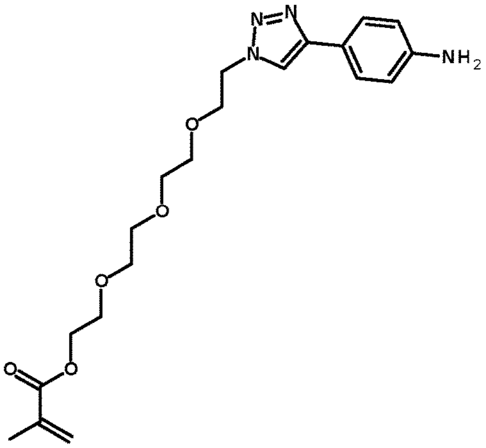
Figure 3D:
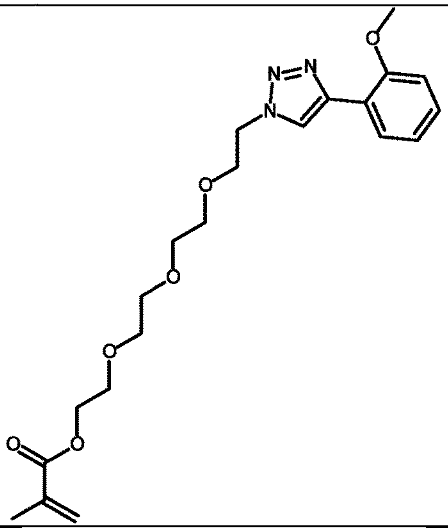
Figure 3D:
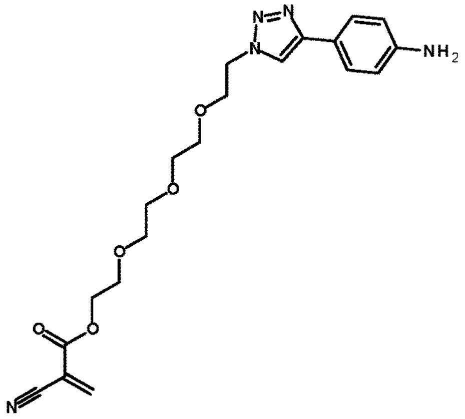
Figure 3D:
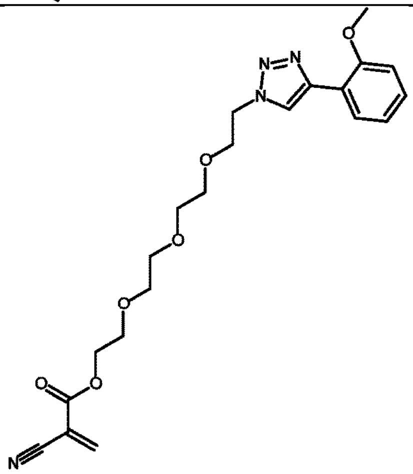
Figure 3E:
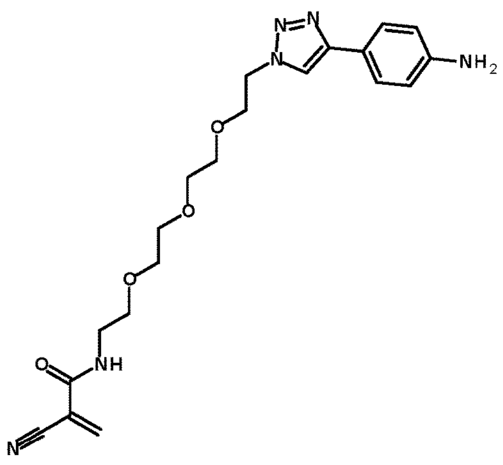
Figure 3E:
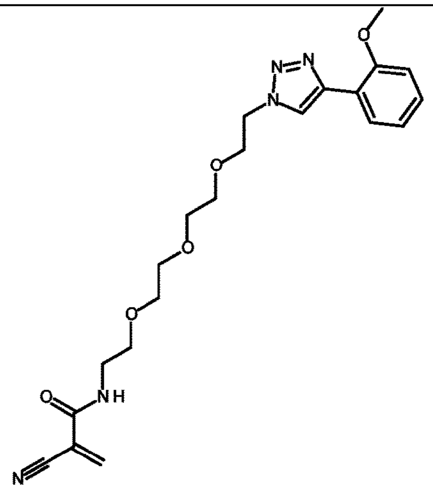
Figure 3E:
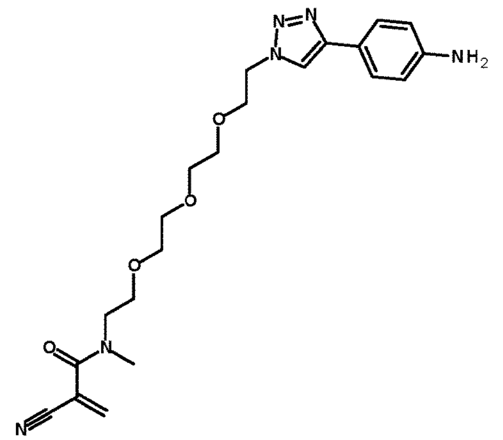
Figure 3E:
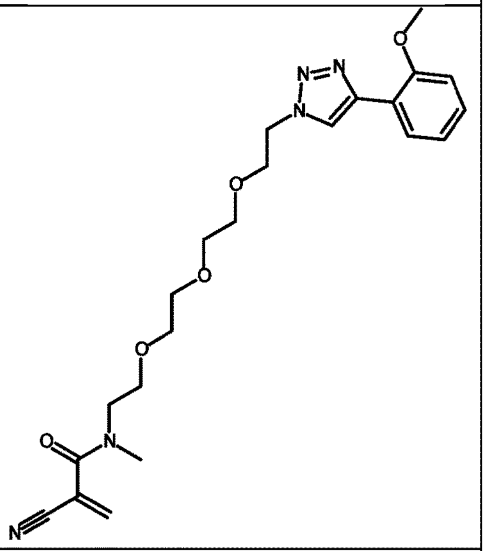
Figure 3E:
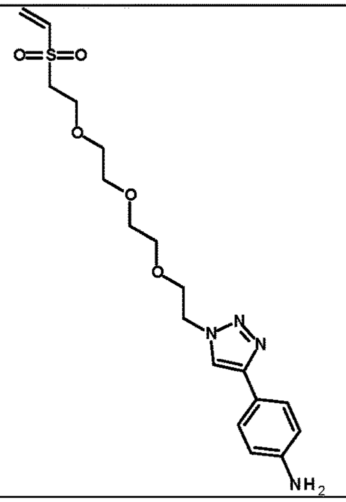
Figure 3E:
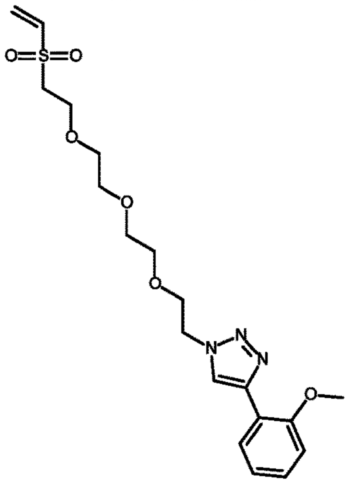
Figure 3F:
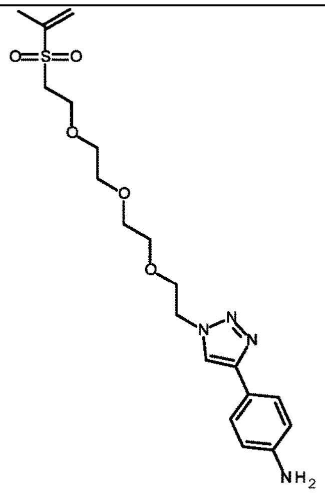
Figure 3F:
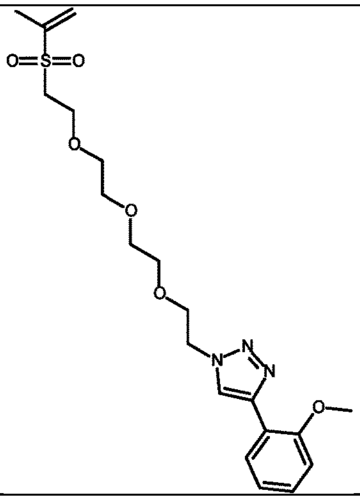
Figure 3F:
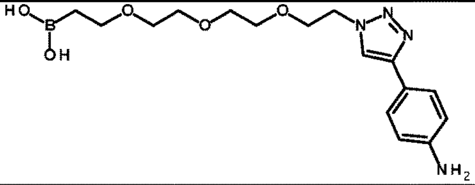
Figure 3F:
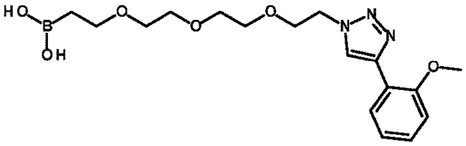
Figure 3F:
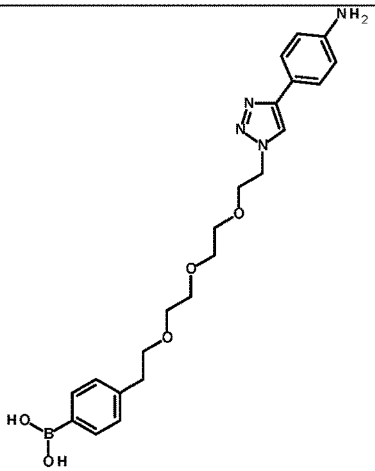
Figure 3F:
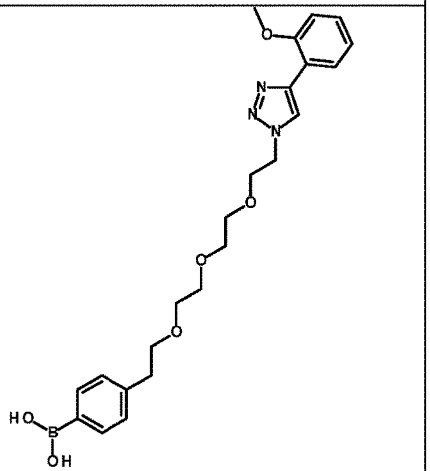
Figure 3F:
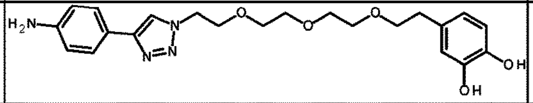
Figure 3F:
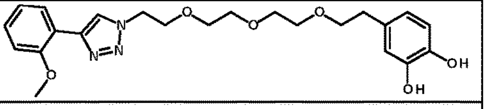
Figure 3F:
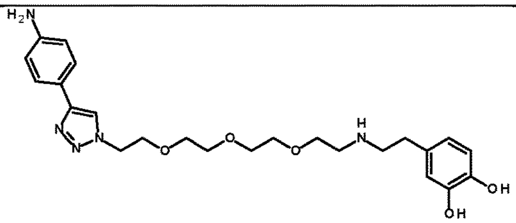
Figure 3F:
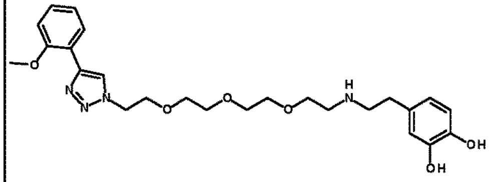
Figure 3G:
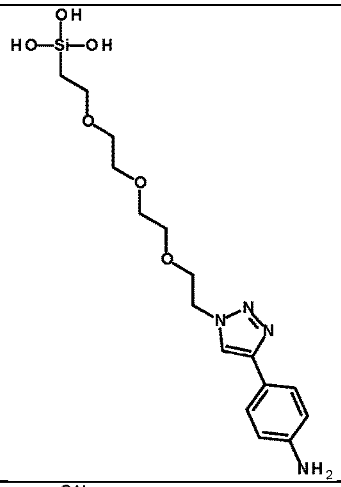
Figure 3G:
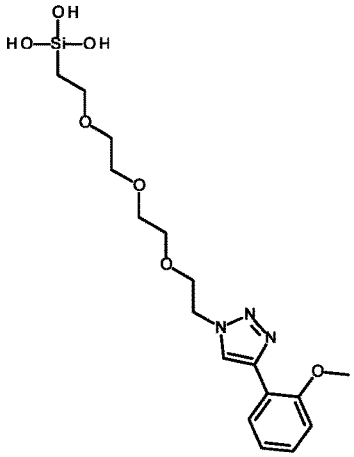
Figure 3G:
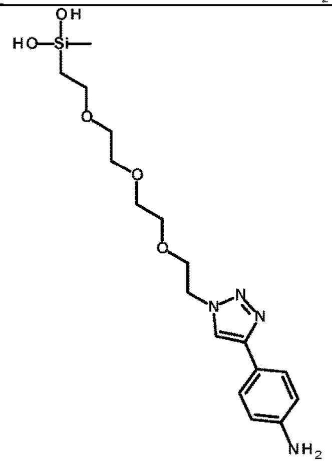
Figure 3G:
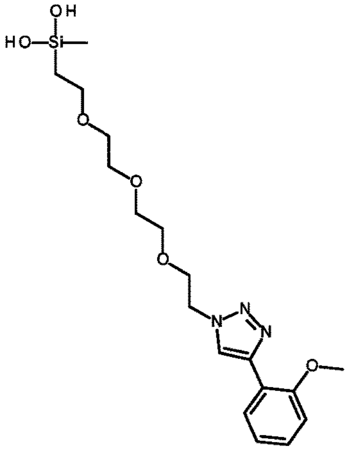
Figure 3G:
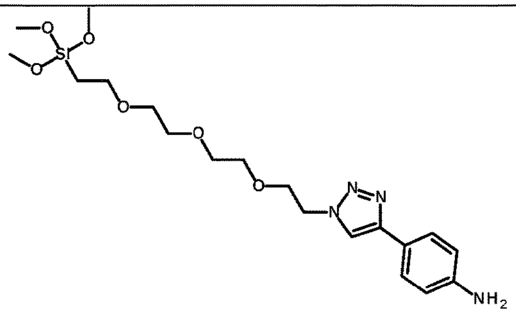
Figure 3G:
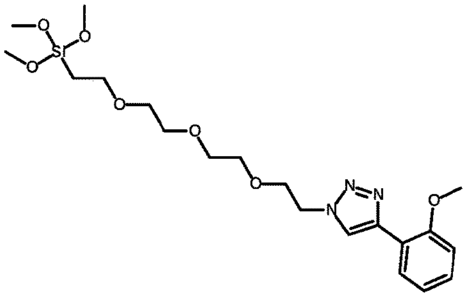
Figure 3G:
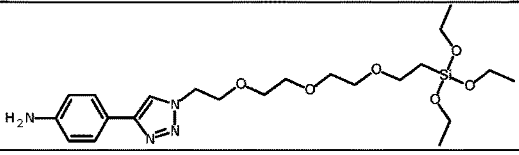
Figure 3G:
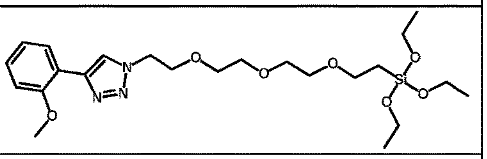
Figure 3G:
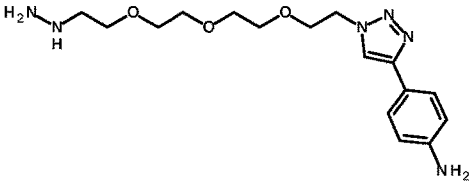
Figure 3G:
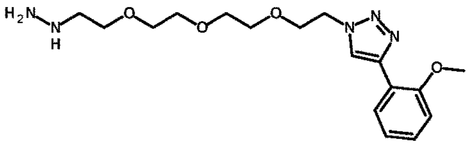
Figure 3H:
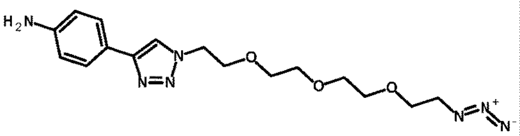
Figure 3H:
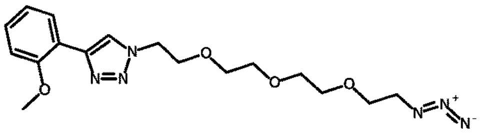
Figure 3H:
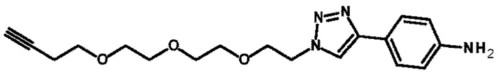
Figure 3H:
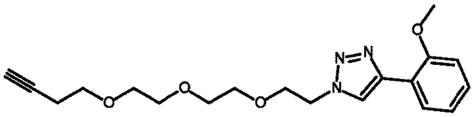
Figure 3H:
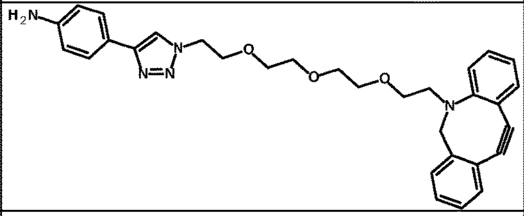
Figure 3H:
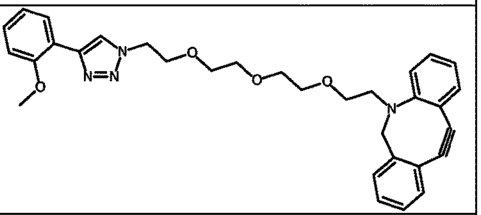
Figure 3H:
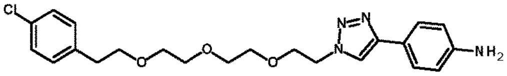
Figure 3H:
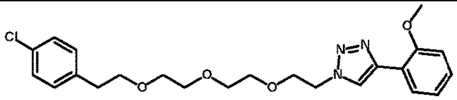
Figure 3H:
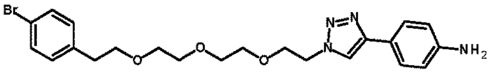
Figure 3H:
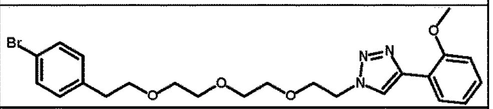
Figure 3H:
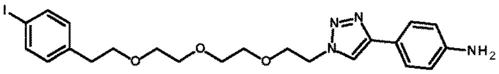
Figure 3H:
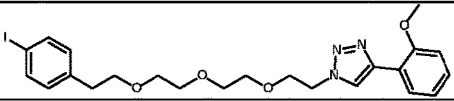
Figure 3H:
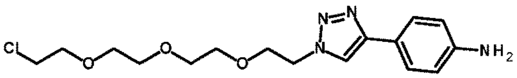
Figure 3H:
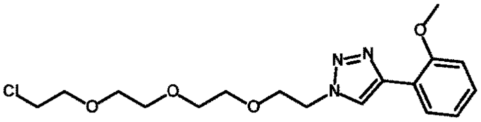
Figure 3H:
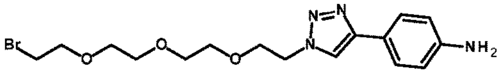
Figure 3H:
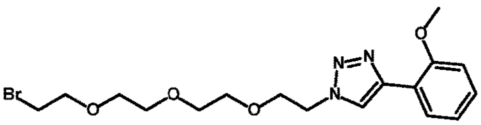
Figure 3H:
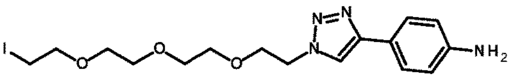
Figure 3H:
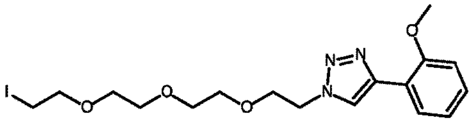
Figure 3H:
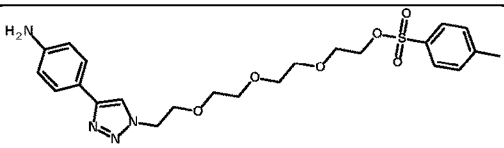
Figure 3H:
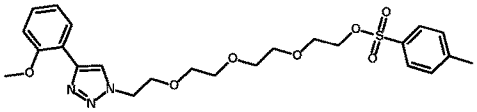
Figure 3H:
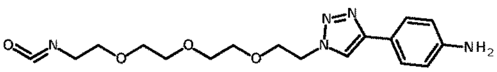
Figure 3H:
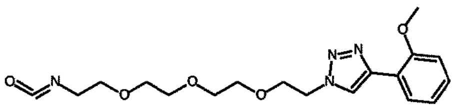
Figure 3I:
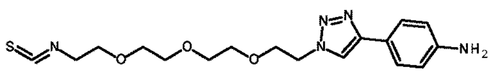
Figure 3I:
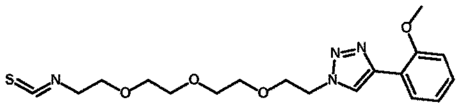
Figure 3I:
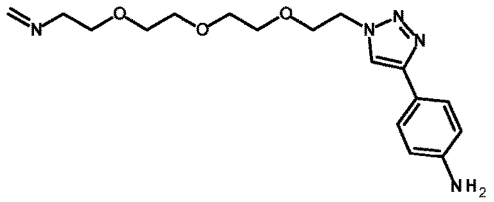
Figure 3I:
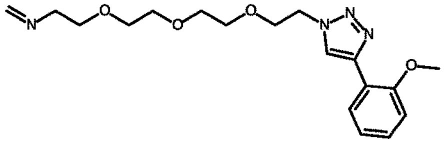
Figure 3I:
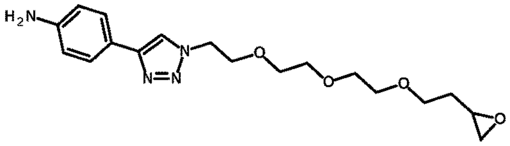
Figure 3I:
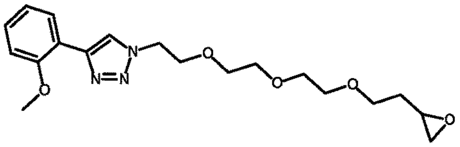
Figure 3I:
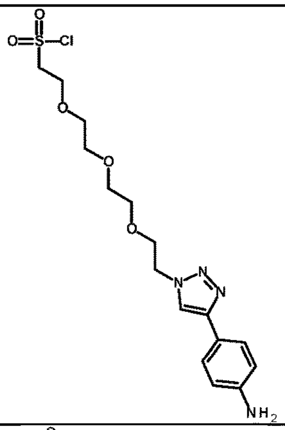
Figure 3I:
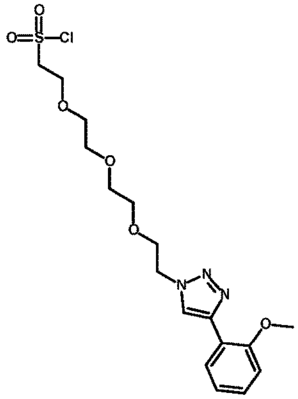
Figure 3I:
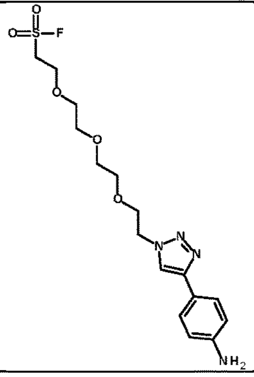
Figure 3I:
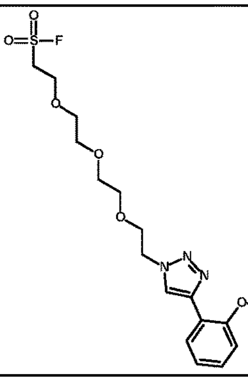
Figure 3I:
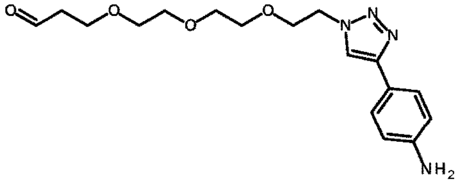
Figure 3I:
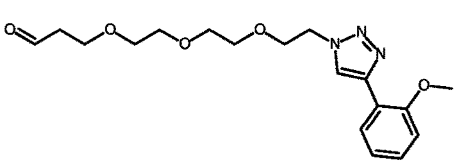
Figure 3J:
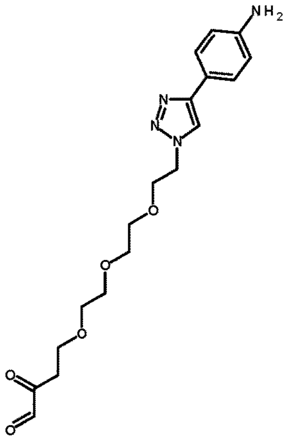
Figure 3J:
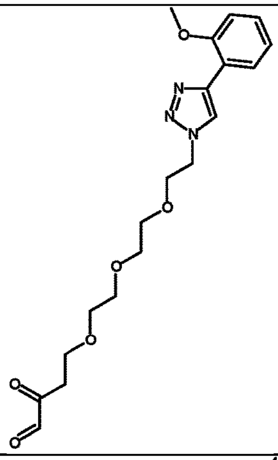
Figure 3J:
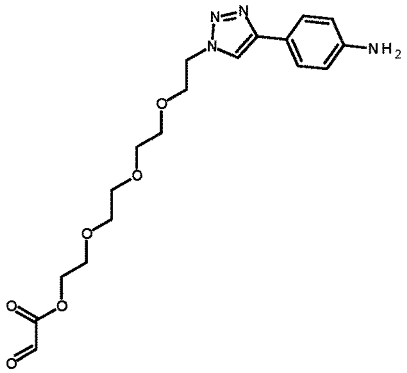
Figure 3J:
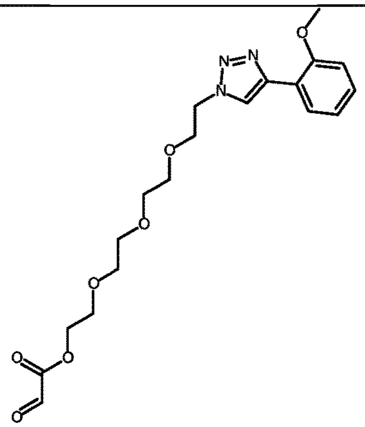
Figure 3J:
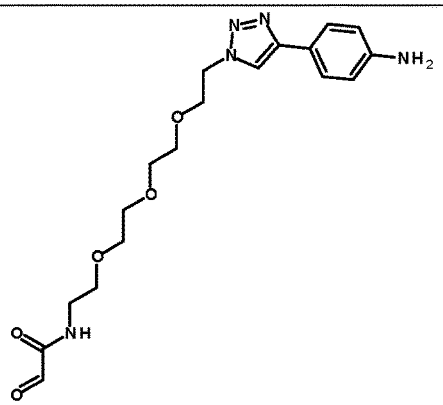
Figure 3J:
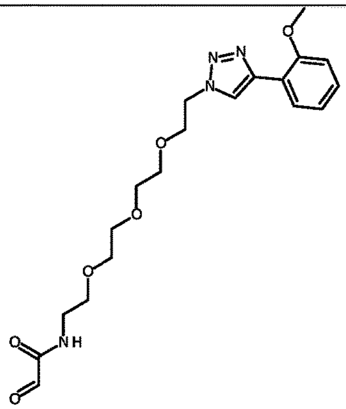
Figure 3K:
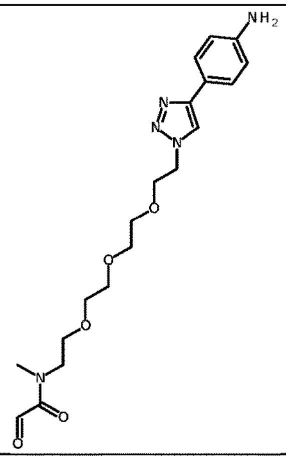
Figure 3K:
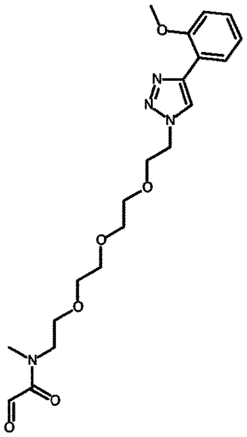
Figure 3K:
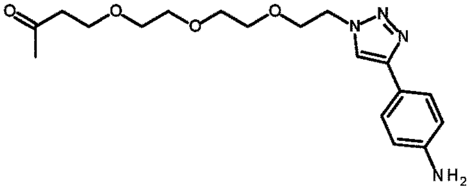
Figure 3K:
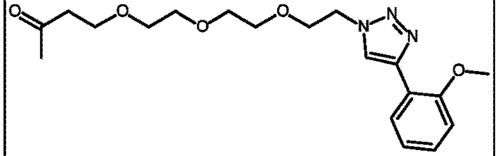
Figure 3K:
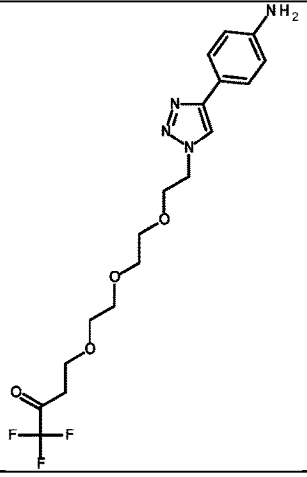
Figure 3K:
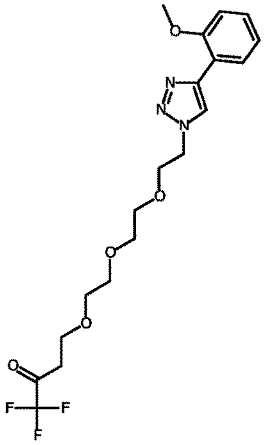
Figure 3K:
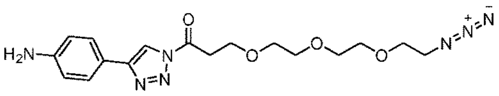
Figure 3K:
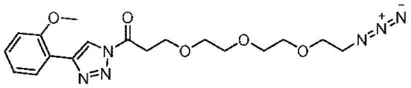
Figure 3K:
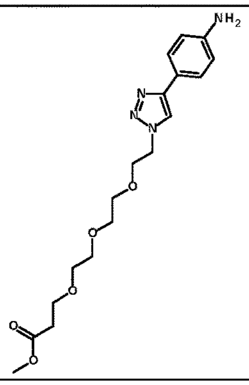
Figure 3K:
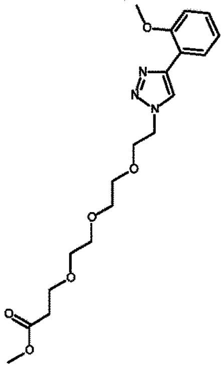
Figure 3L:
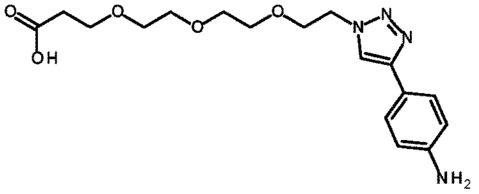
Figure 3L:
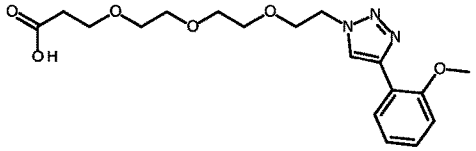
Figure 3L:
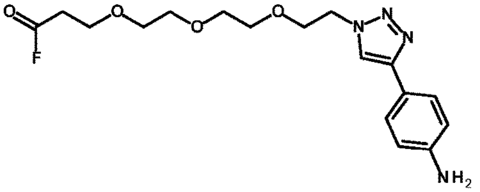
Figure 3L:
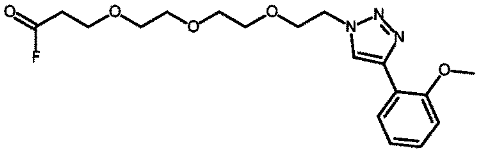
Figure 3L:
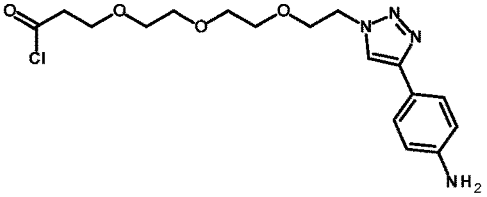
Figure 3L:
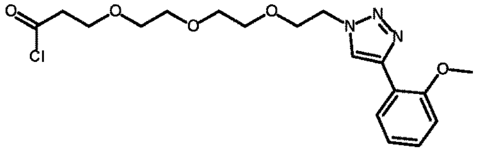
Figure 3L:
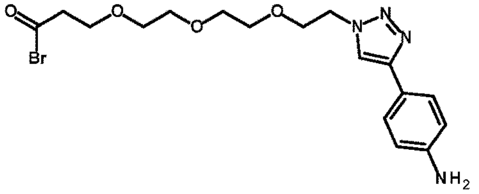
Figure 3L:
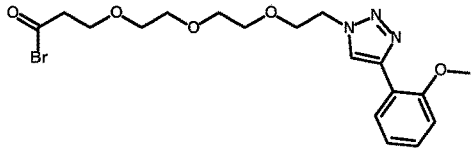
Figure 3L:
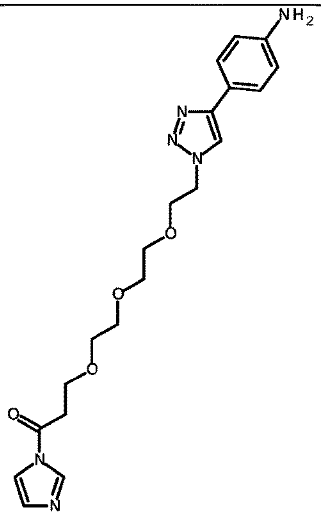
Figure 3L:
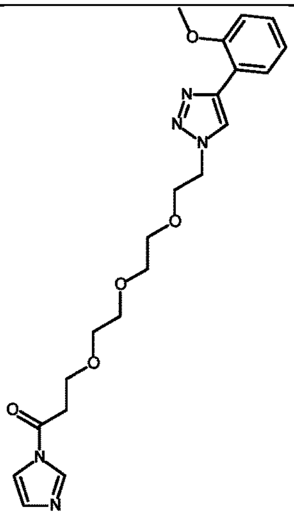
Figure 3M:
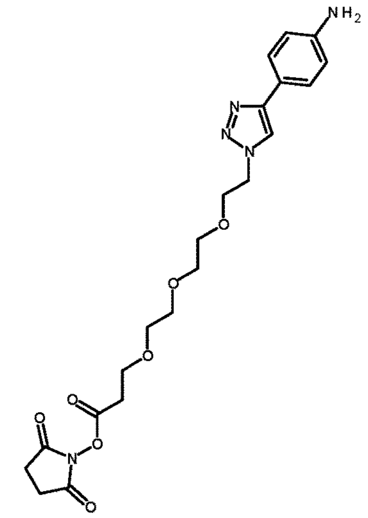
Figure 3M:
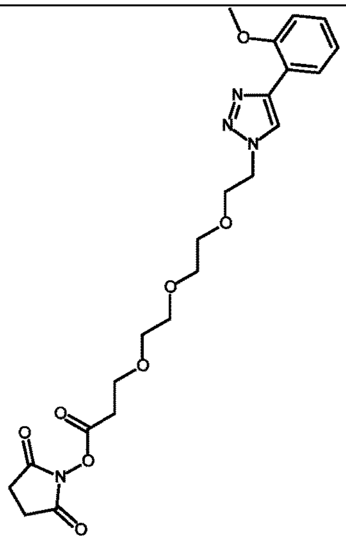
Figure 3M:
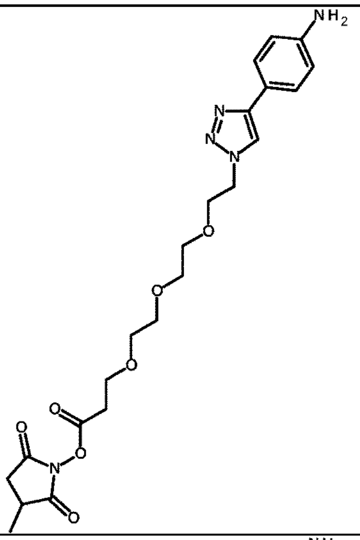
Figure 3M:
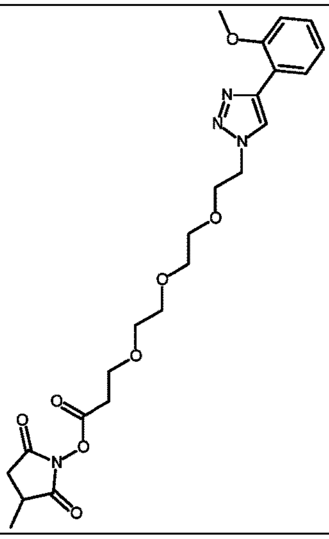
Figure 3M:
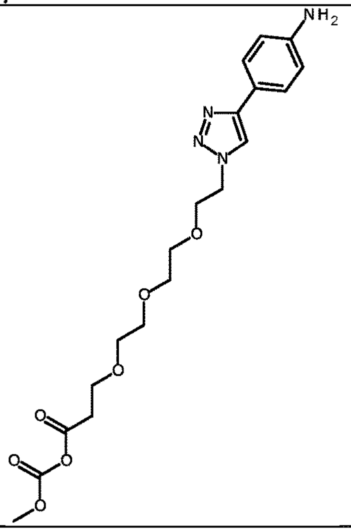
Figure 3M:
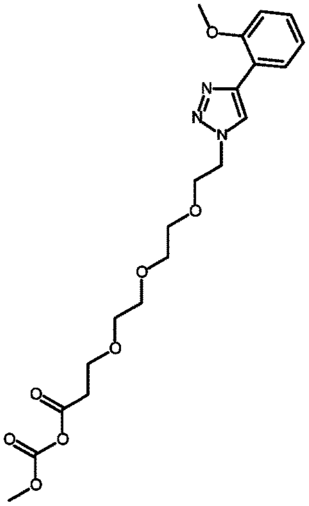
Figure 3N:
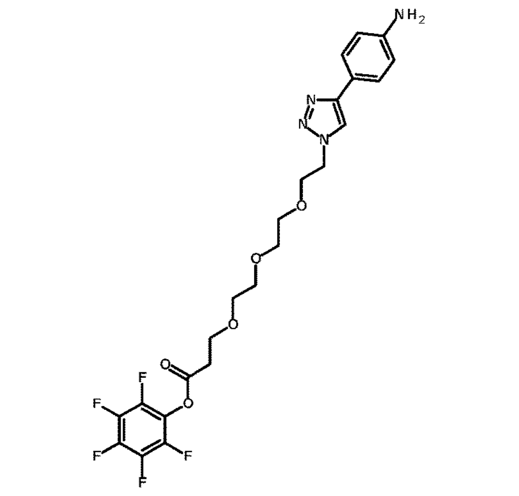
Figure 3N:
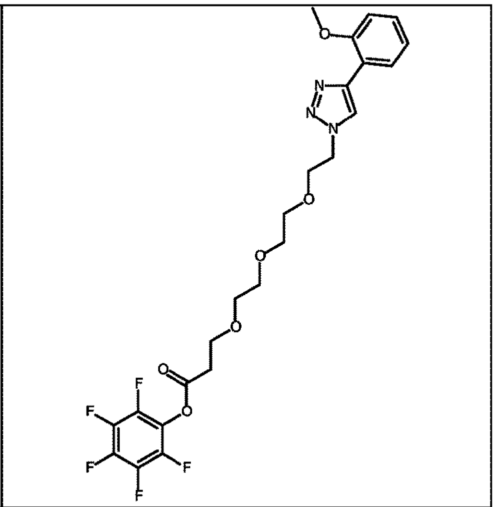
Figure 3N:
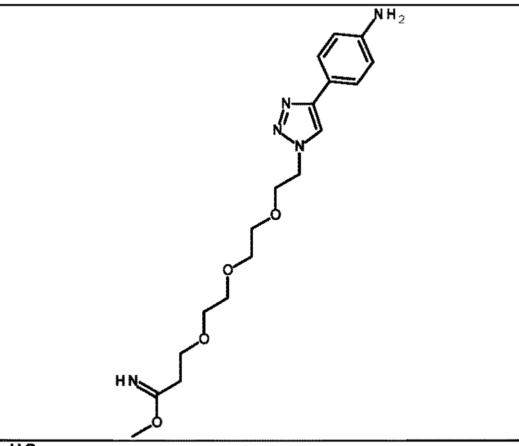
Figure 3N:
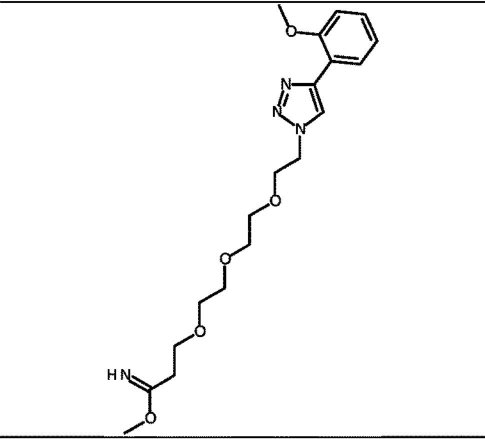
Figure 3N:
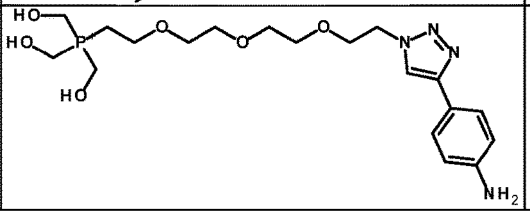
Figure 3N:
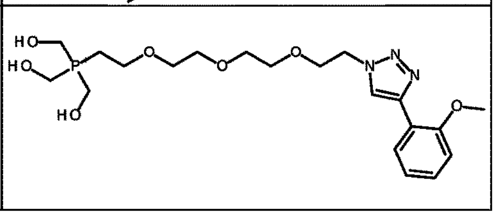
Figure 3O:
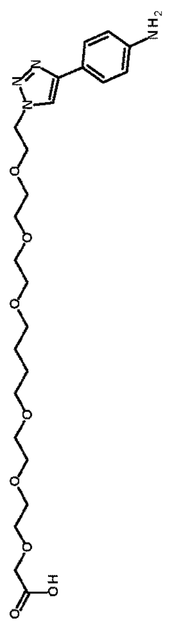
Figure 3O:
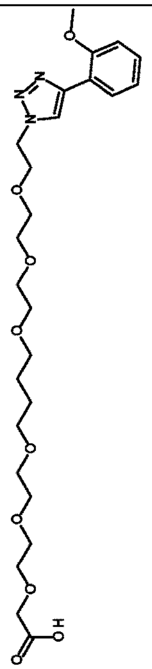
Figure 3O:
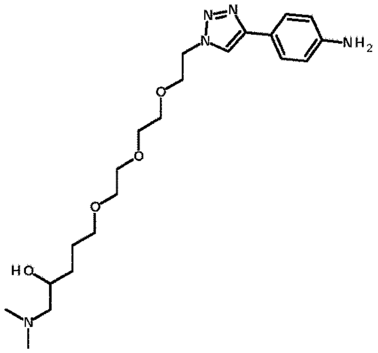
Figure 3O:
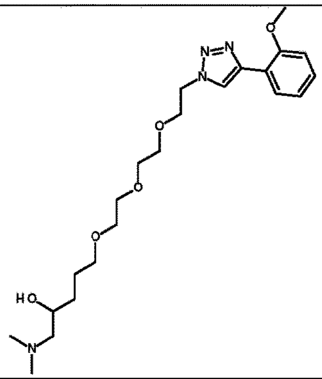
Figure 3O:
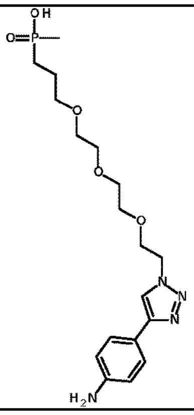
Figure 3O:
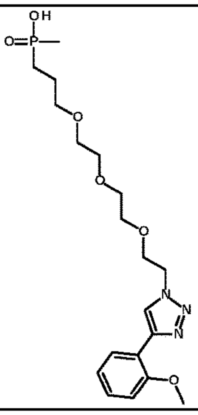
Figure 3P:
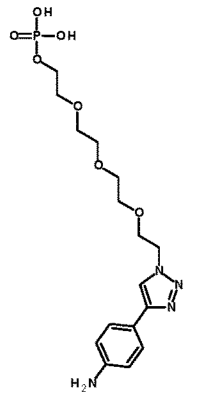
Figure 3P:
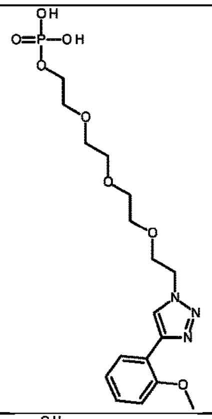
Figure 3P:
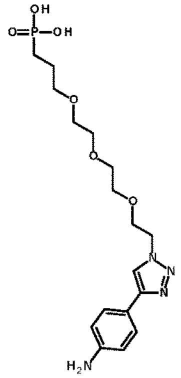
Figure 3P:
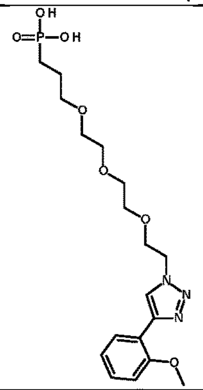
Figure 3P:
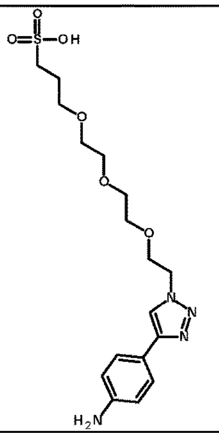
Figure 3P:
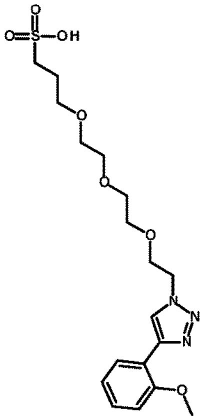
Figure 3P:
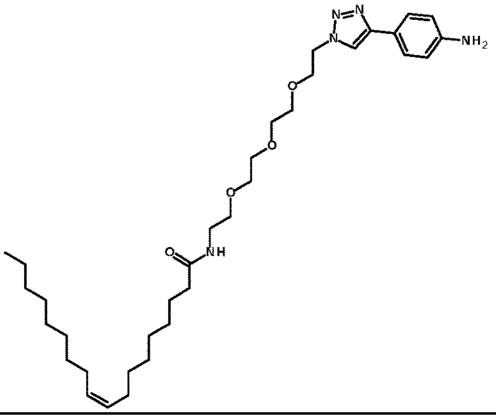
Figure 3P:
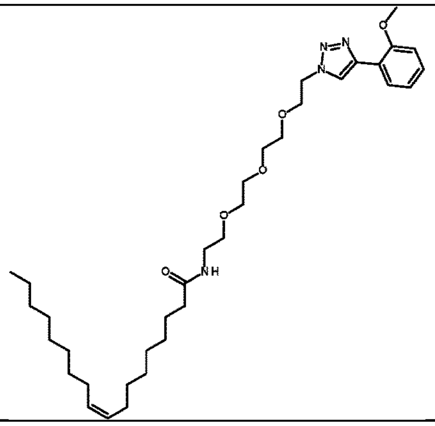
Figure 3Q:
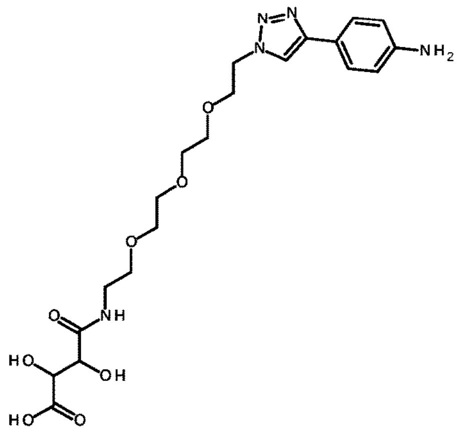
Figure 3Q:
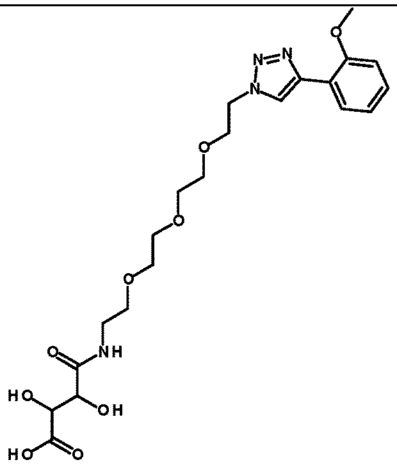
Figure 3Q:
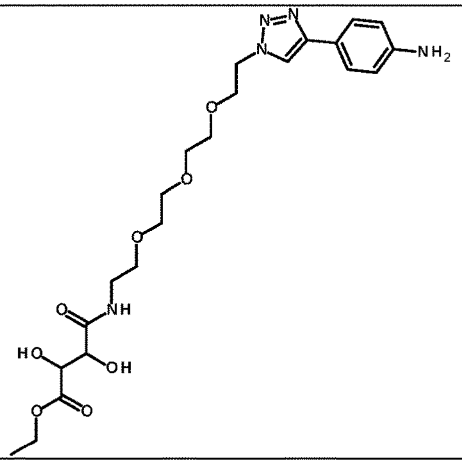
Figure 3Q:
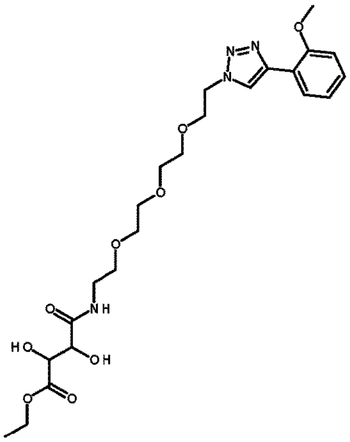
Figure 3Q:
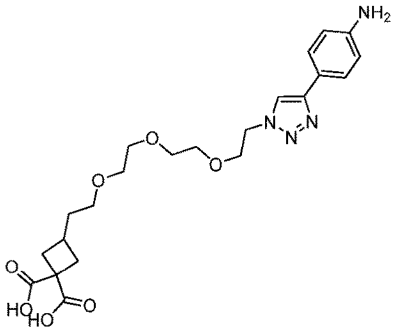
Figure 3Q:
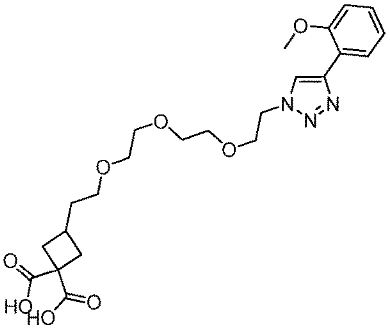
Figure 3R:
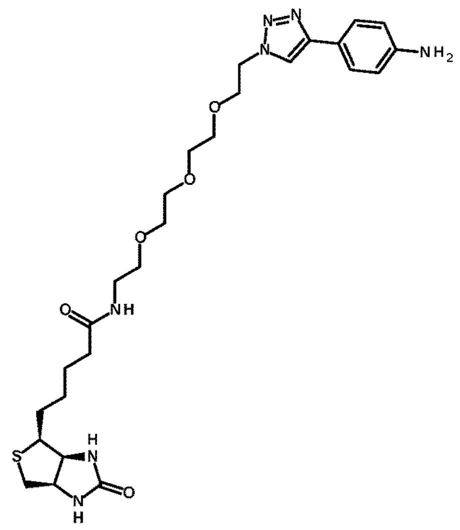
Figure 3R:
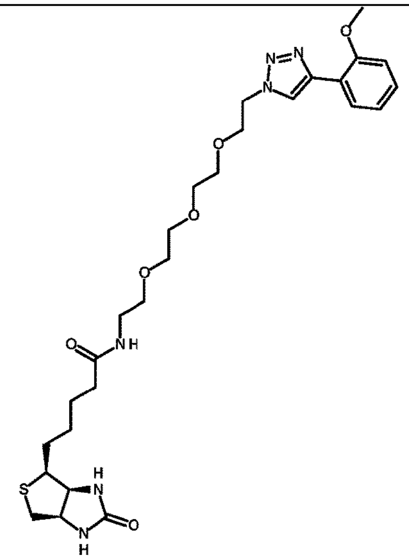
Figure 3R:
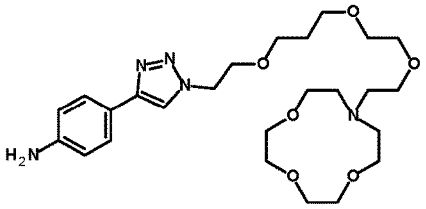
Figure 3R:
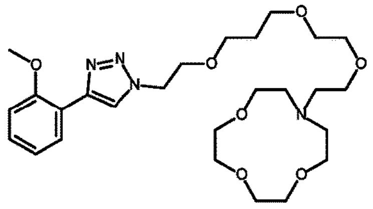
Figure 3R:
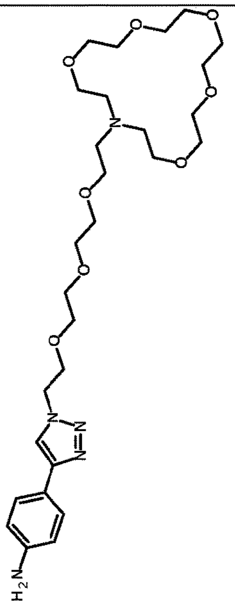
Figure 3R:
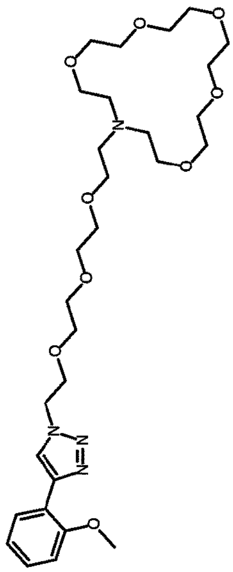
Figure 3S:
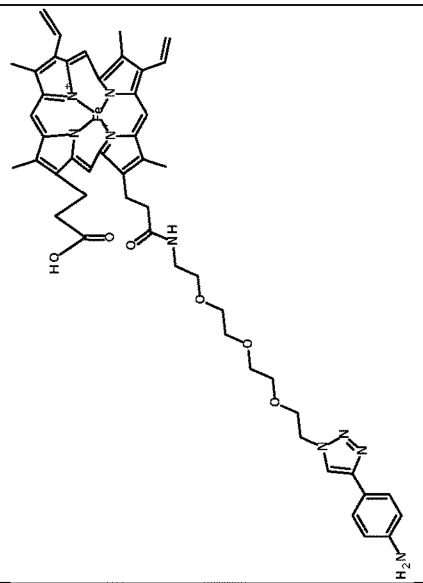
Figure 3S:
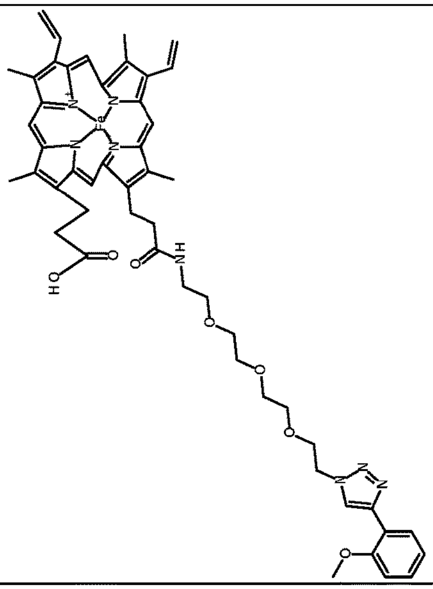
Figure 3S:
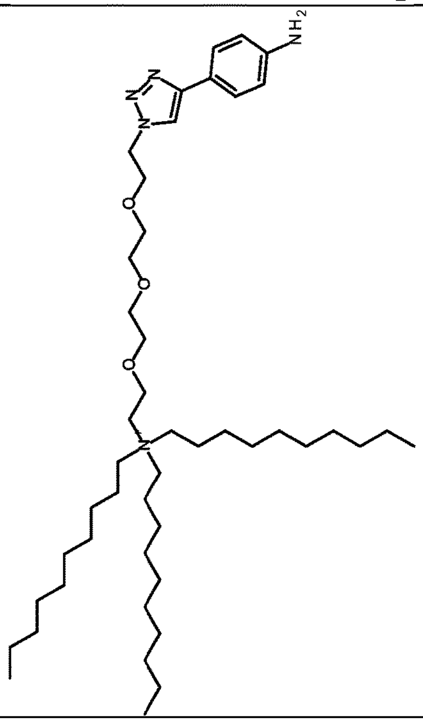
Figure 3S:
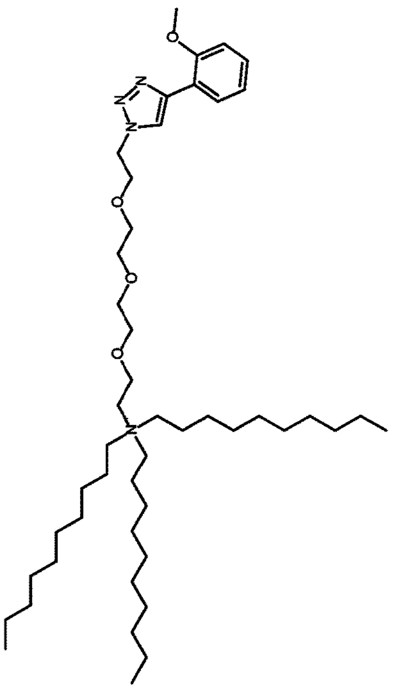
Figure 3T:
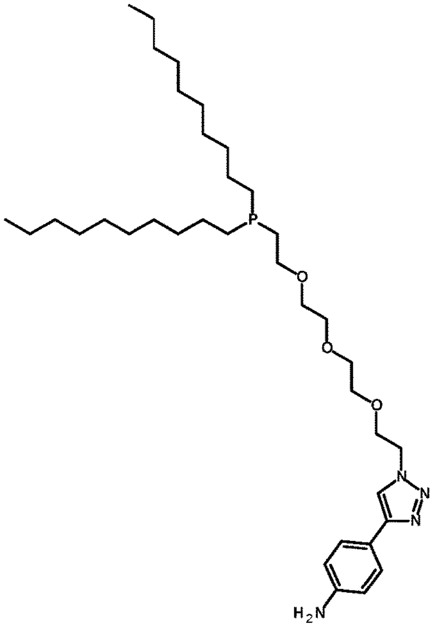
Figure 3T:
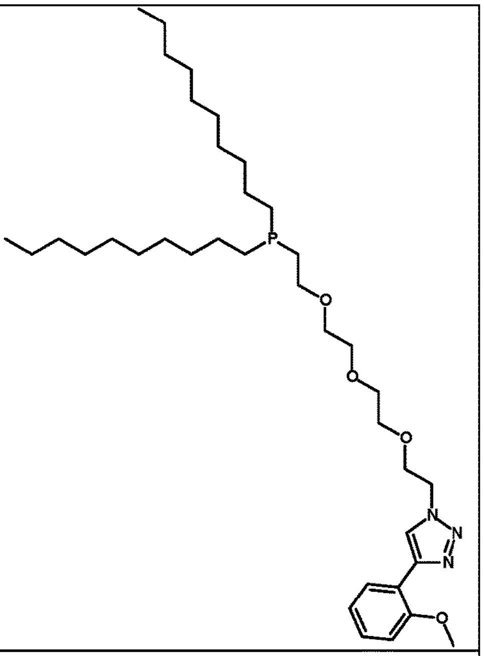
Figure 3T:
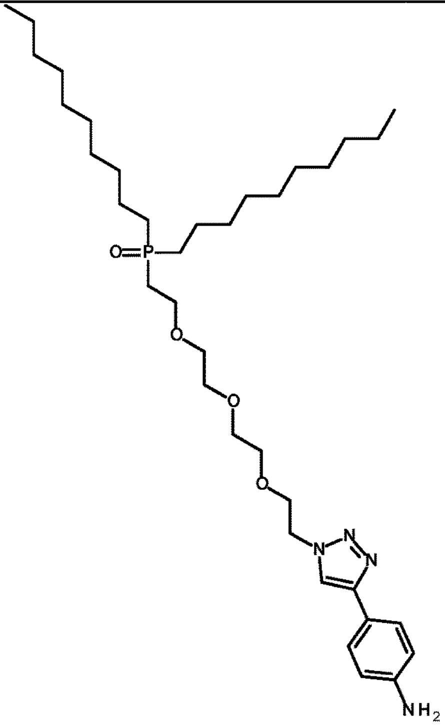
Figure 3T:
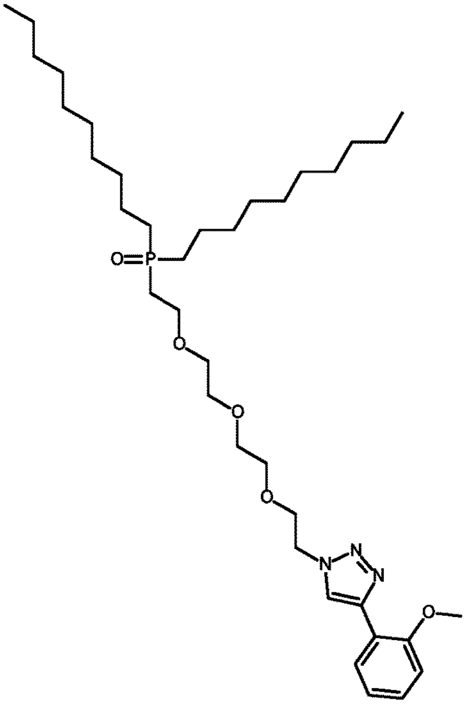
Figure 3T:
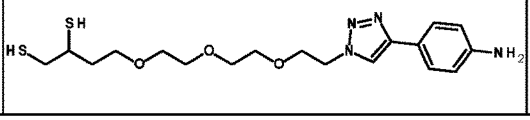
Figure 3T:
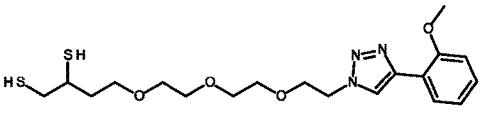
Figure 3U:
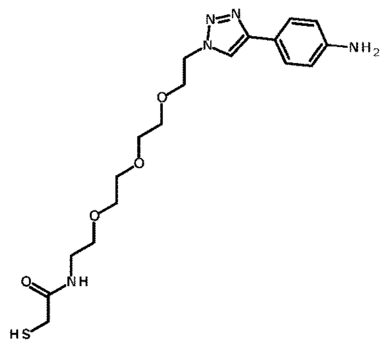
Figure 3U:
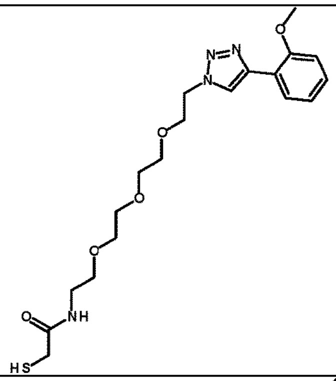
Figure 3U:
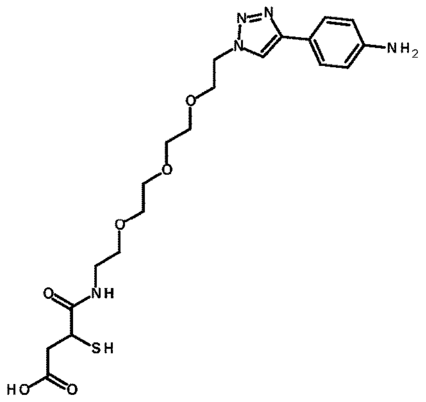
Figure 3U:
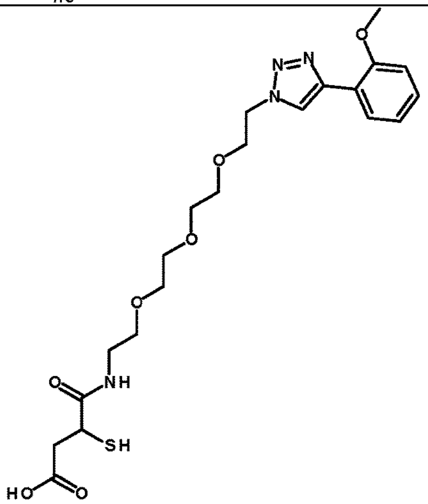
Figure 3U:
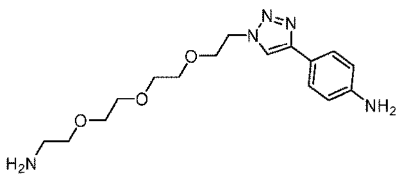
Figure 3U:
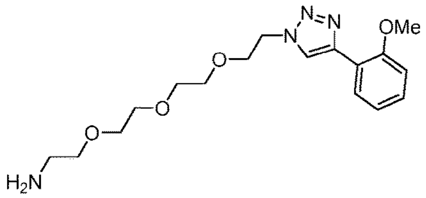
Figure 3U:
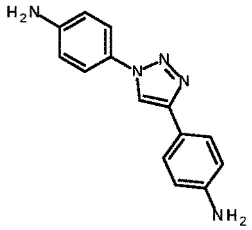
Figure 3U:
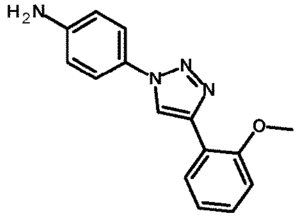
Figure 3U:
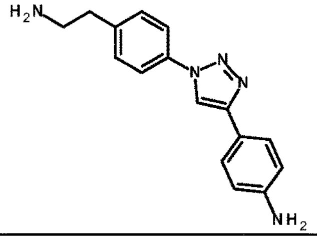
Figure 3U:
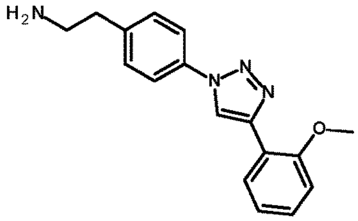
Figure 3V:
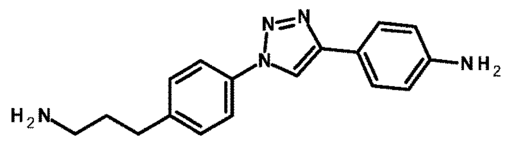
Figure 3V:
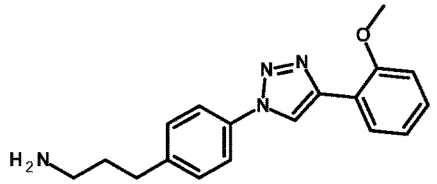
Figure 3V:
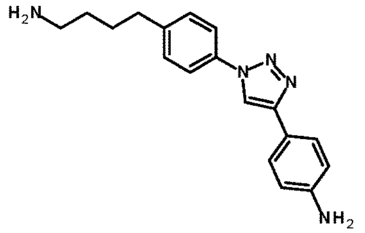
Figure 3V:
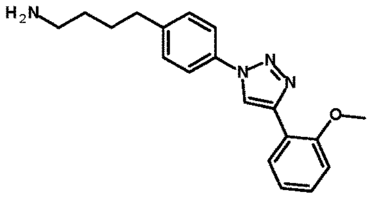
Figure 3V:
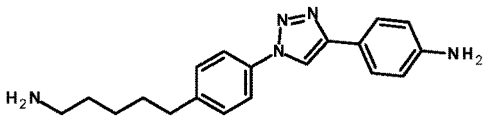
Figure 3V:
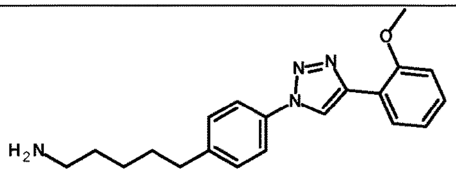
Figure 3V:
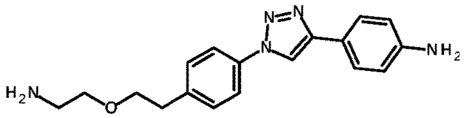
Figure 3V:
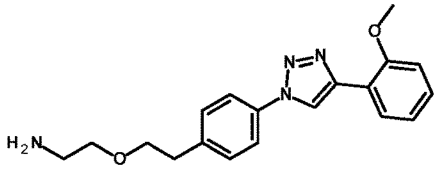
Figure 3V:
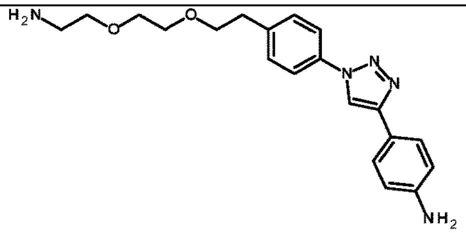
Figure 3V:
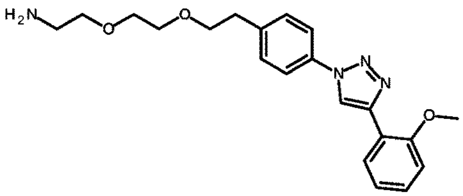
Figure 3V:
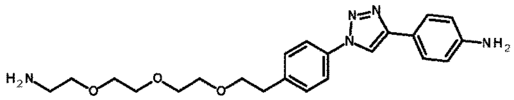
Figure 3V:
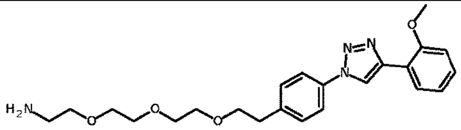
Figure 3V:
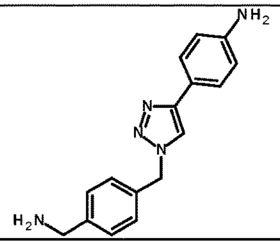
Figure 3V:
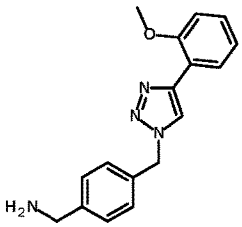
Figure 3W:
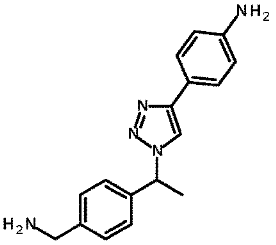
Figure 3W:
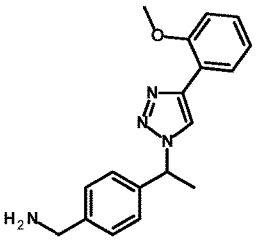
Figure 3W:
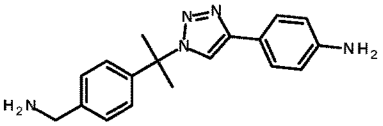
Figure 3W:
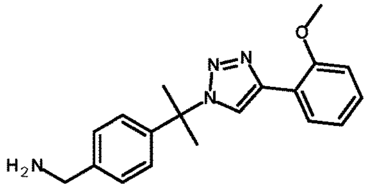
Figure 3W:
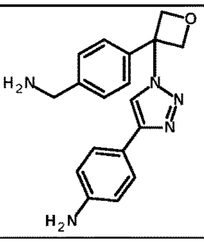
Figure 3W:
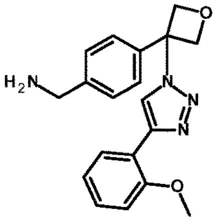
Figure 3W:
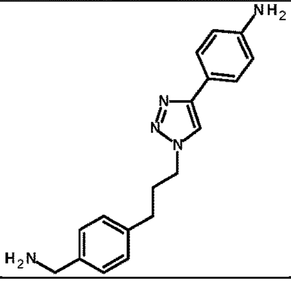
Figure 3W:
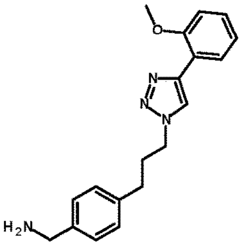
Figure 3W:
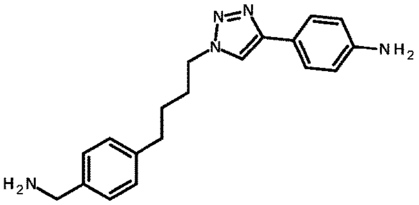
Figure 3W:
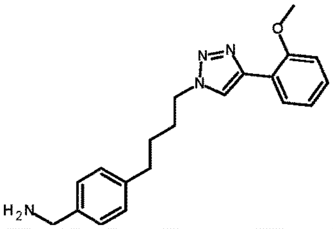
Figure 3W:
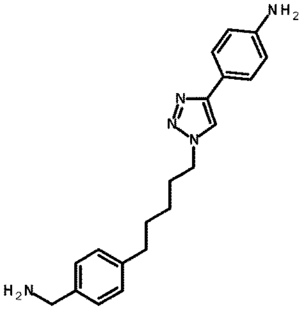
Figure 3W:
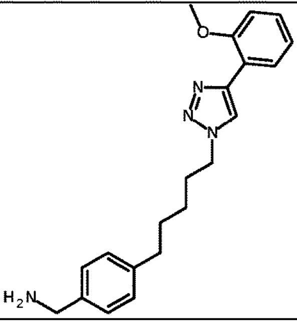
Figure 3X:
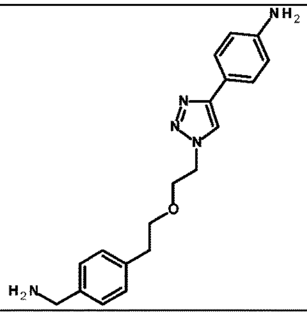
Figure 3X:
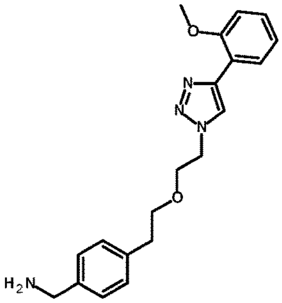
Figure 3X:
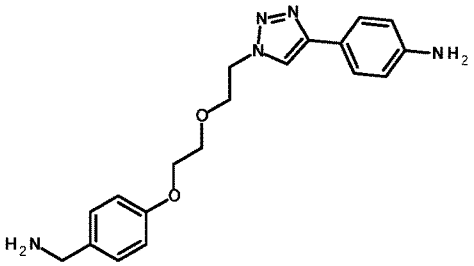
Figure 3X:
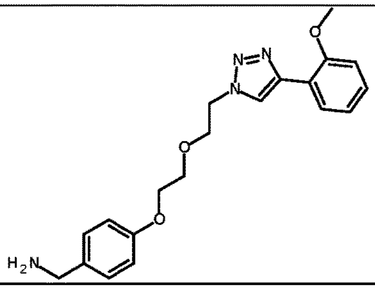
Figure 3X:
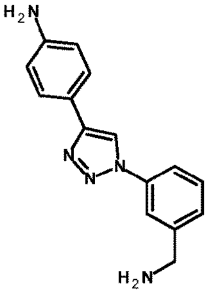
Figure 3X:
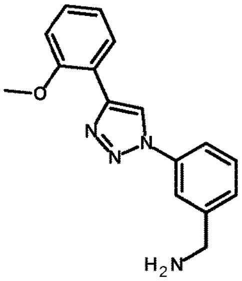
Figure 3X:
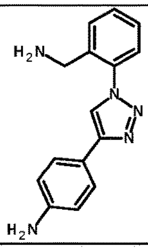
Figure 3X:
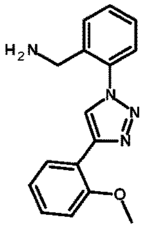
Figure 3X:
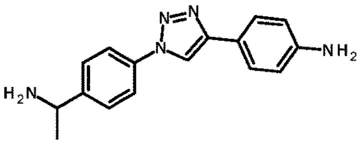
Figure 3X:
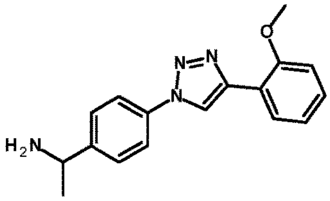
Figure 3X:
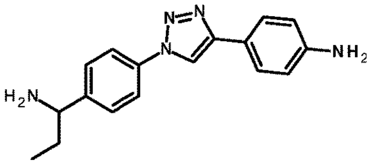
Figure 3X:
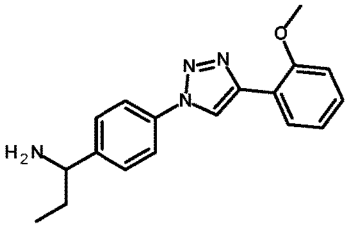
Figure 3Y:
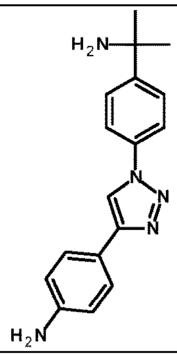
Figure 3Y:
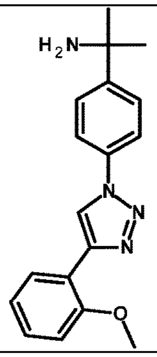
Figure 3Y:
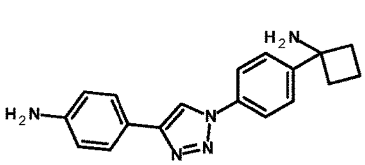
Figure 3Y:
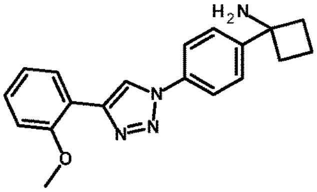
Figure 3Y:
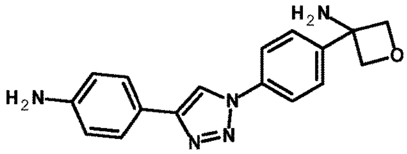
Figure 3Y:
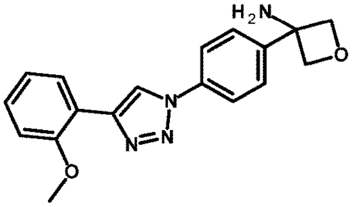
Figure 3Y:
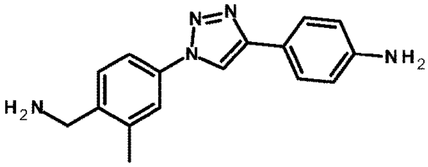
Figure 3Y:
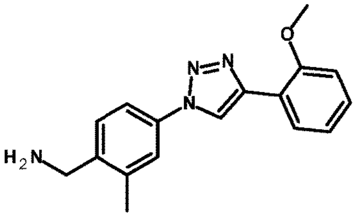
Figure 3Y:
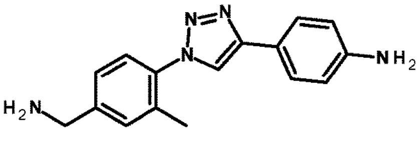
Figure 3Y:
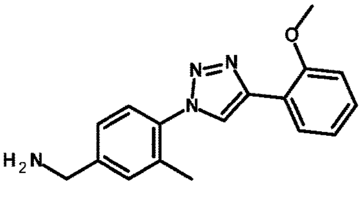
Figure 3Y:
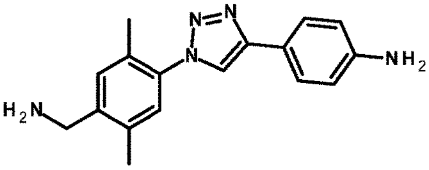
Figure 3Y:
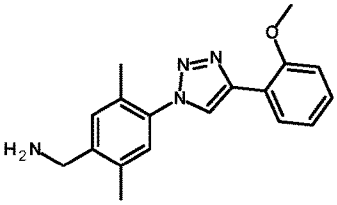
Figure 3Z:
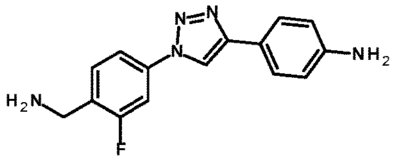
Figure 3Z:
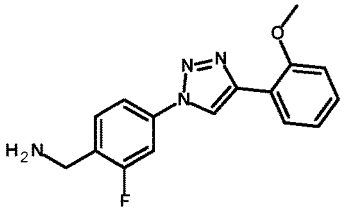
Figure 3Z:
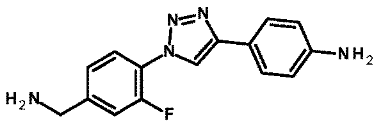
Figure 3Z:
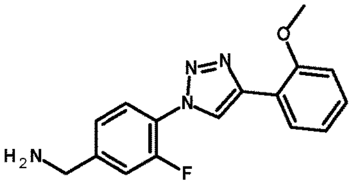
Figure 3Z:
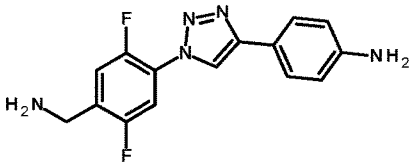
Figure 3Z:
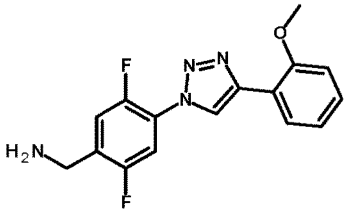
Figure 3Z:
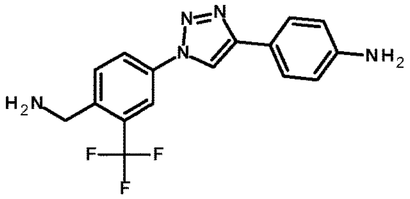
Figure 3Z:
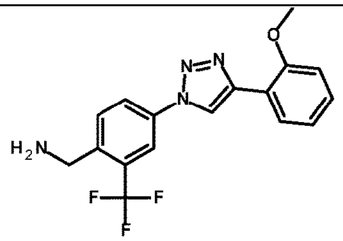
Figure 3Z:
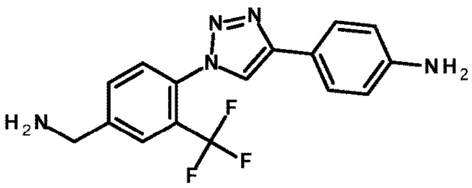
Figure 3Z:
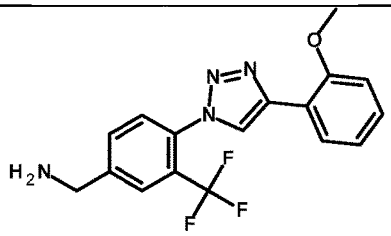
Figure 3Z:
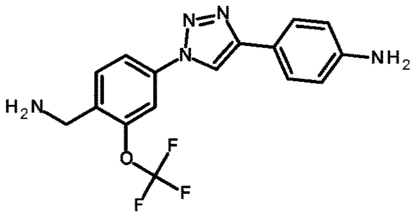
Figure 3Z:
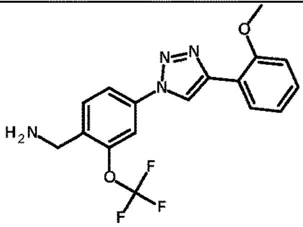
Figure 3Z:
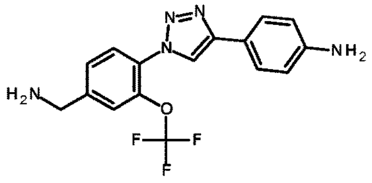
Figure 3Z:
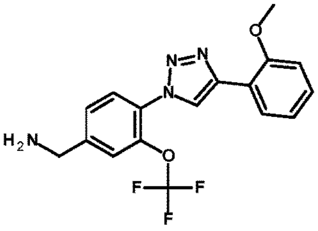
Figure 3A:
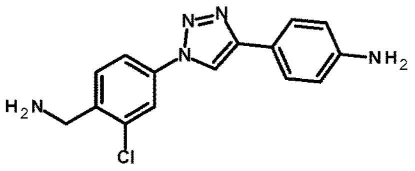
Figure 3A:
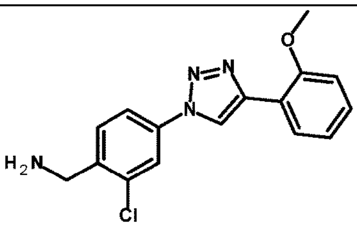
Figure 3A:
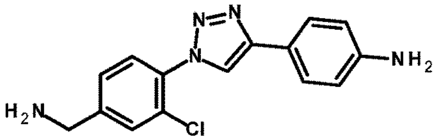
Figure 3A:
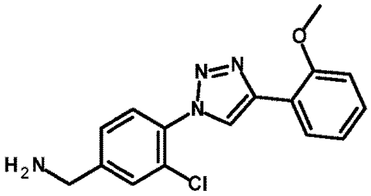
Figure 3A:
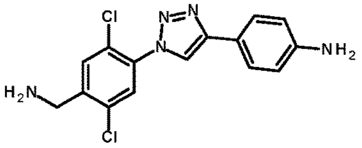
Figure 3A:
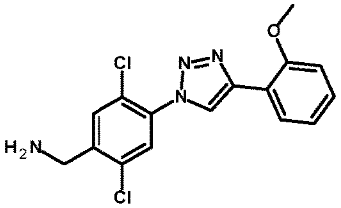
Figure 3A:
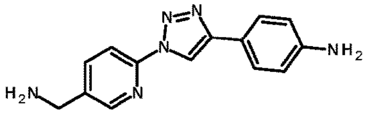
Figure 3A:
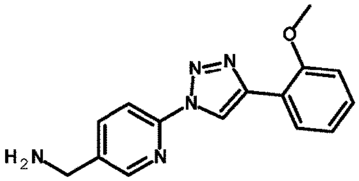
Figure 3A:
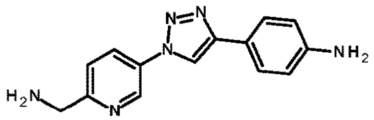
Figure 3A:
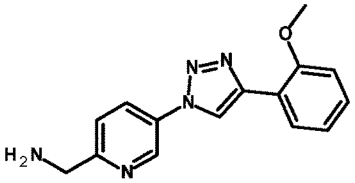
Figure 3A:
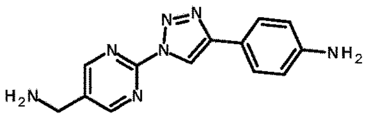
Figure 3A:
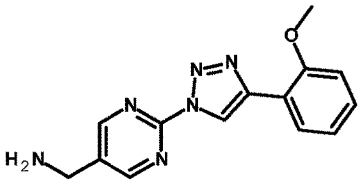
Figure 3A:
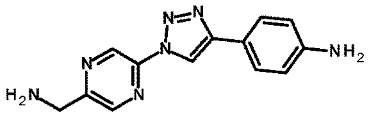
Figure 3A:
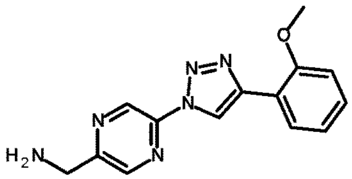
Figure 3B:
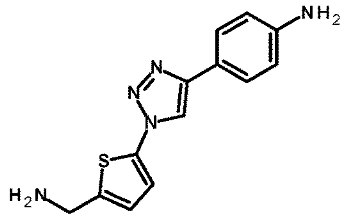
Figure 3B:
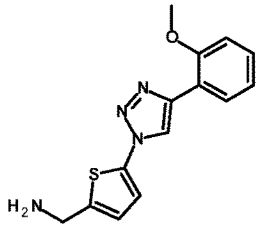
Figure 3B:
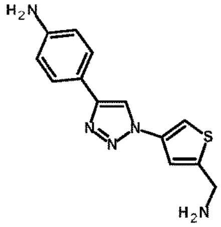
Figure 3B:
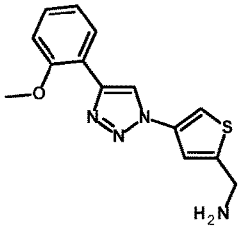
Figure 3B:
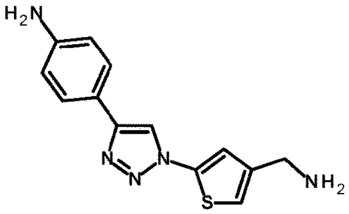
Figure 3B:
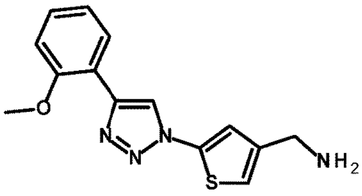
Figure 3B:
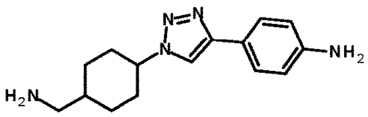
Figure 3B:
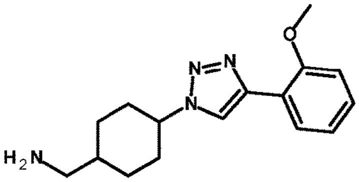
Figure 3B:
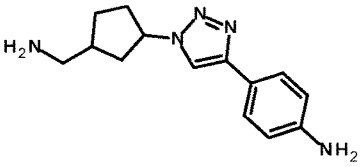
Figure 3B:
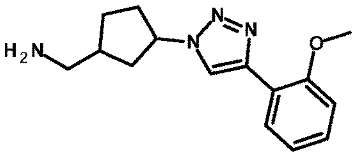
Figure 3B:
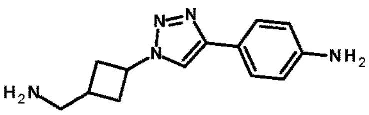
Figure 3B:
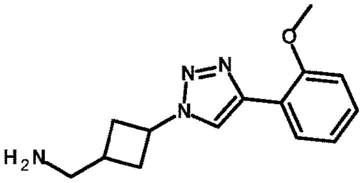
Figure 3C:
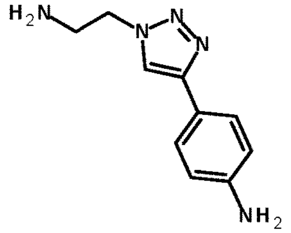
Figure 3C:
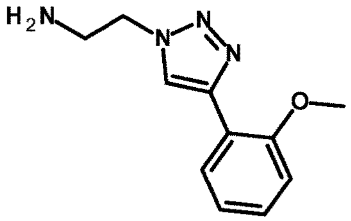
Figure 3C:
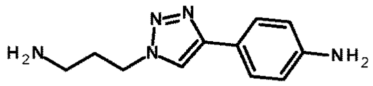
Figure 3C:
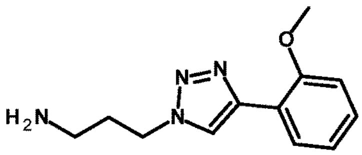
Figure 3C:
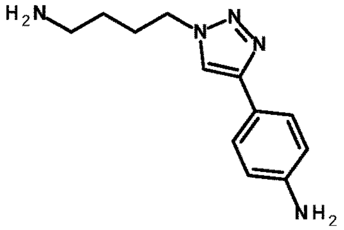
Figure 3C:
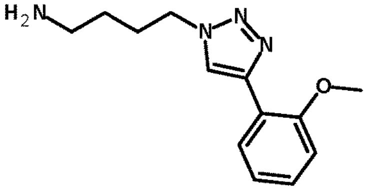
Figure 3C:
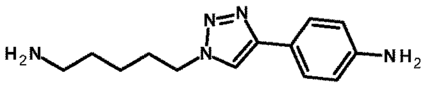
Figure 3C:
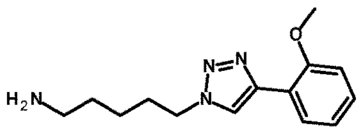
Figure 3C:
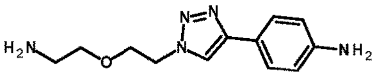
Figure 3C:
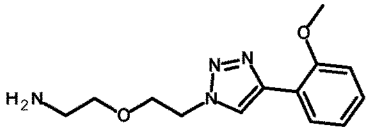
Figure 3C:
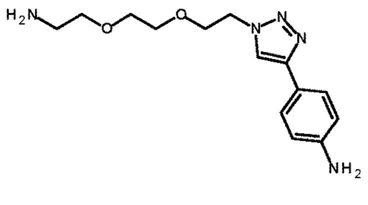
Figure 3C:
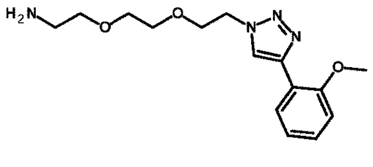
Figure 3C:
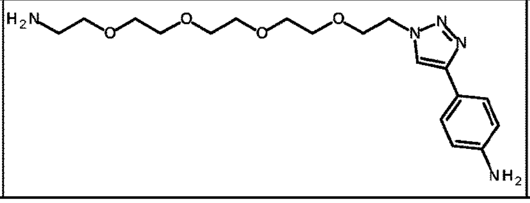
Figure 3C:
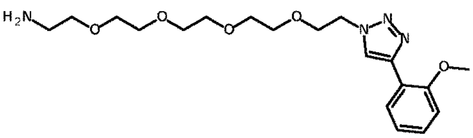
Figure 3D:
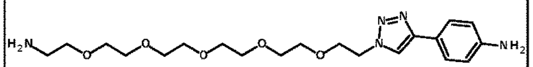
Figure 3D:
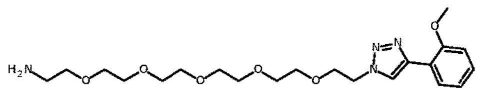
Figure 3D:
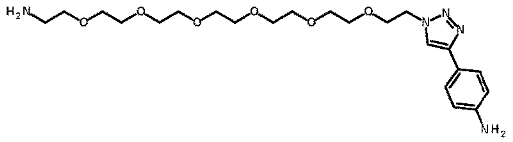
Figure 3D:
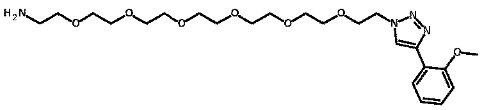
Figure 3D:
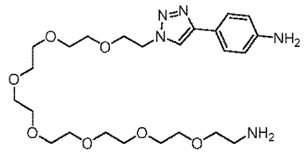
Figure 3D:
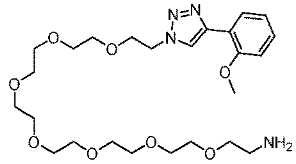
Figure 3D:
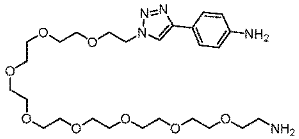
Figure 3D:
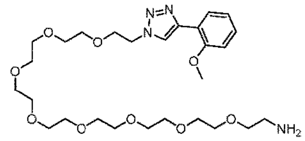
Figure 3D:
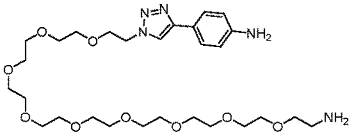
Figure 3D:
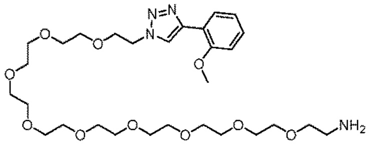
Figure 3D:
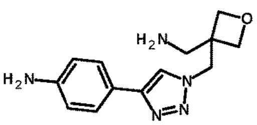
Figure 3D:
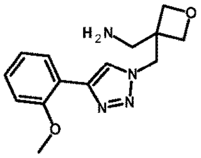
Figure 3D:
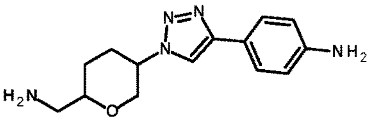
Figure 3D:
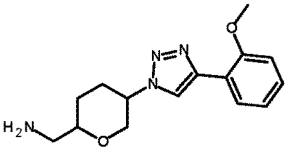
Figure 3D:
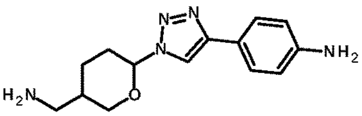
Figure 3D:
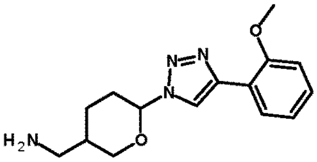
Figure 3D:
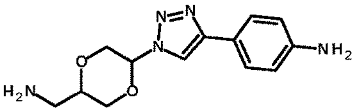
Figure 3D:
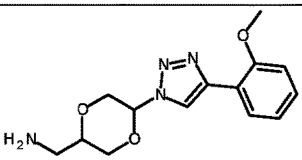
Figure 3E:
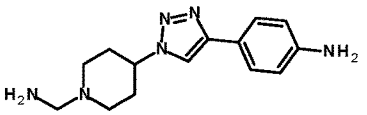
Figure 3E:
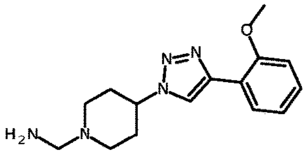
Figure 3E:
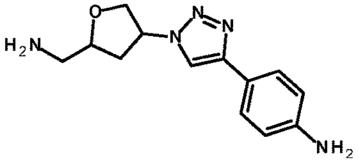
Figure 3E:
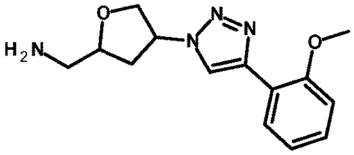
Figure 3E:
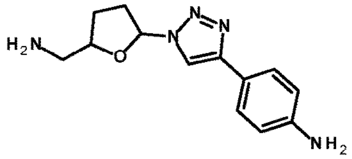
Figure 3E:
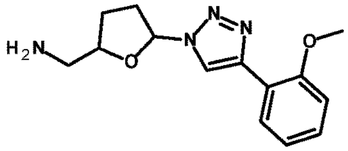
Figure 3E:
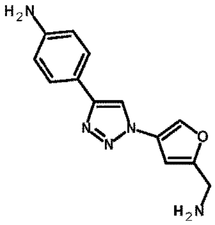
Figure 3E:
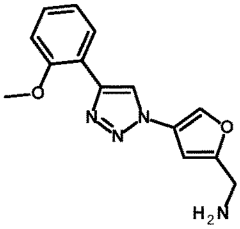
Figure 3E:
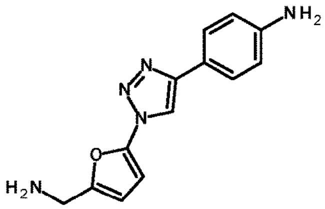
Figure 3E:
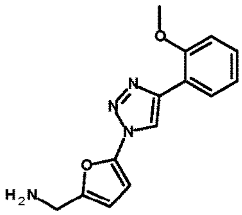
Figure 3E:
Figure 3E:
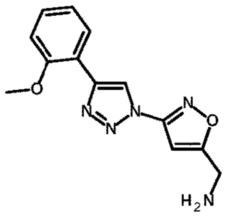
Figure 3E:
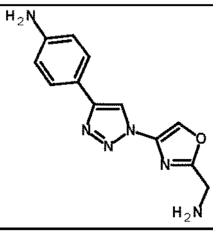
Figure 3E:
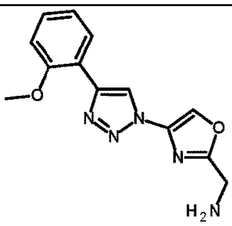
Figure 3F:
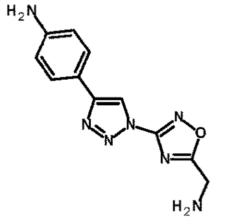
Figure 3F:
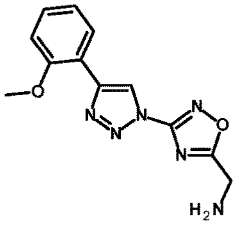
Figure 3F:
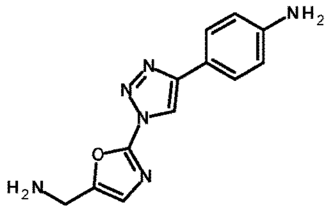
Figure 3F:
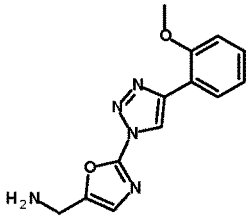
Figure 3F:
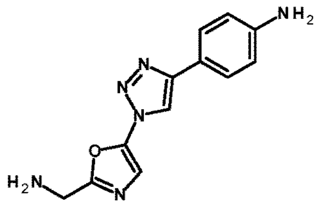
Figure 3F:
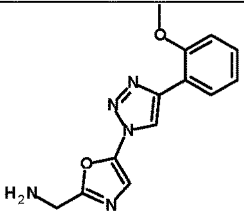
Figure 3F:
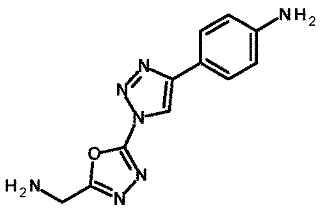
Figure 3F:
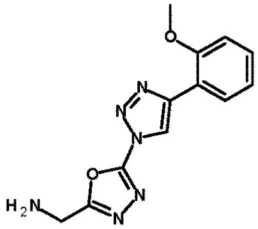
Figure 3F:
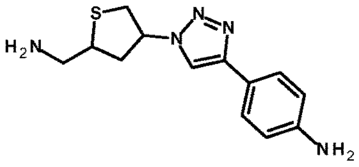
Figure 3F:
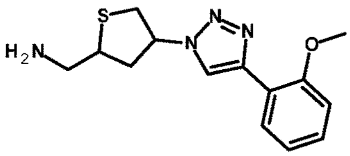
Figure 3F:
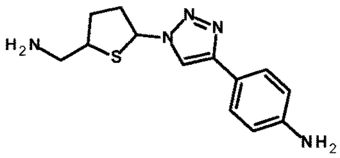
Figure 3F:
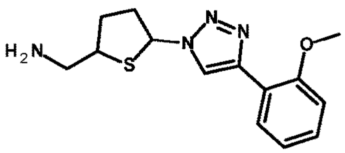
Figure 3F:
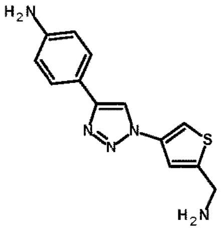
Figure 3F:
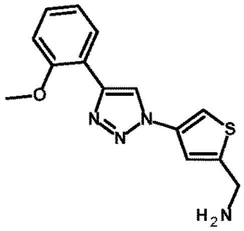
Figure 3G:
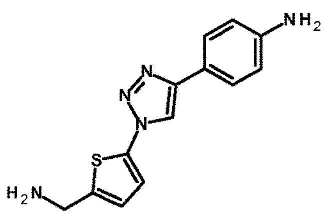
Figure 3G:
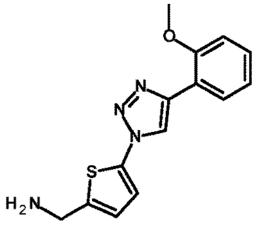
Figure 3G:
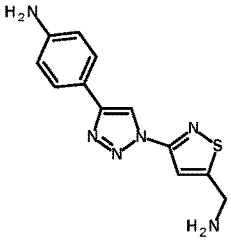
Figure 3G:
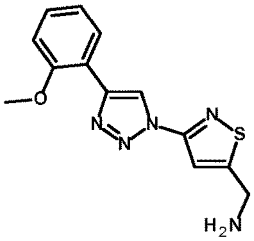
Figure 3G:
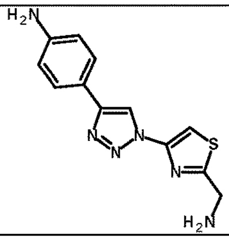
Figure 3G:
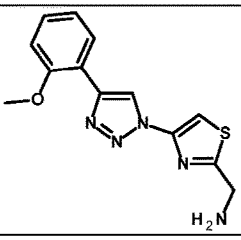
Figure 3G:
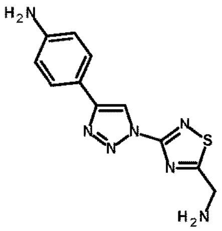
Figure 3G:
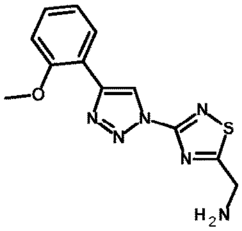
Figure 3G:
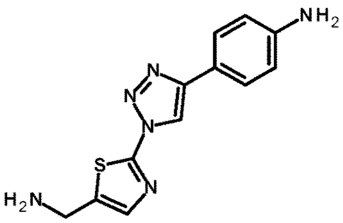
Figure 3G:
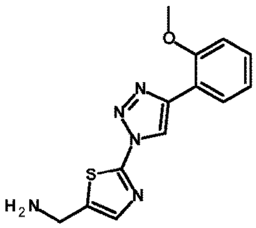
Figure 3G:
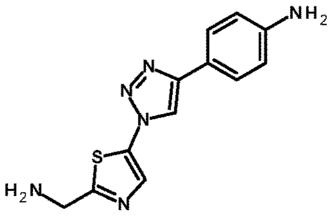
Figure 3G:
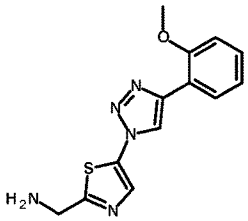
Figure 3H:
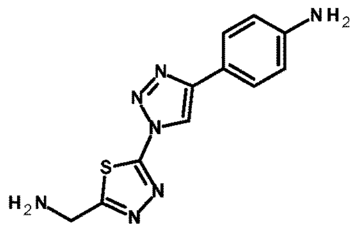
Figure 3H:
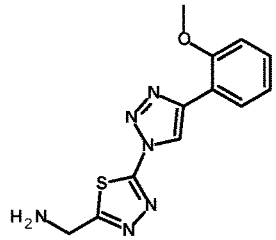
Figure 3H:
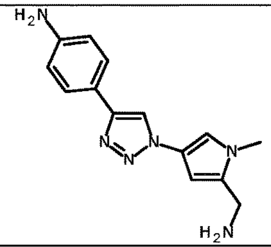
Figure 3H:
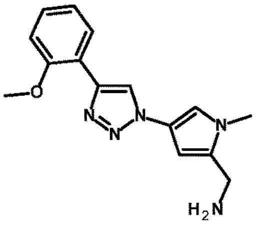
Figure 3H:
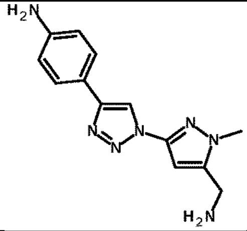
Figure 3H:
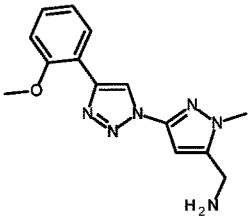
Figure 3H:
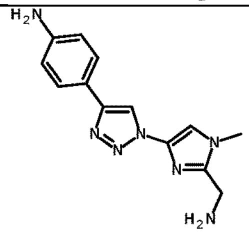
Figure 3H:
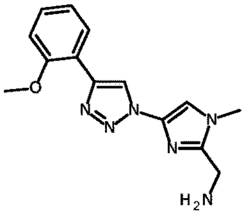
Figure 3H:
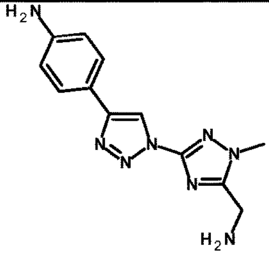
Figure 3H:
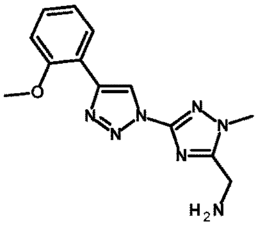
Figure 3H:
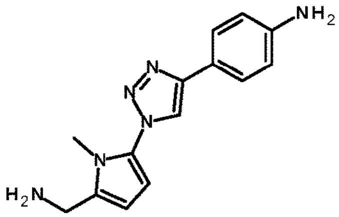
Figure 3H:
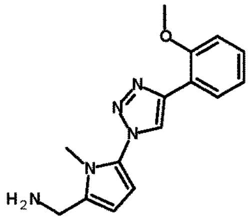
Figure 3I:
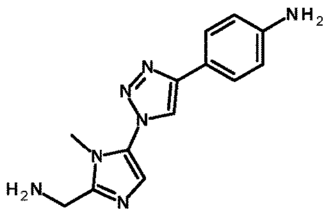
Figure 3I:
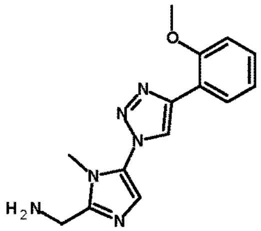
Figure 3I:
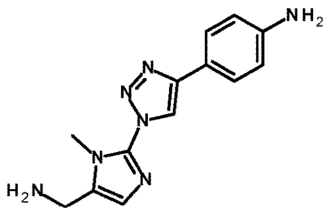
Figure 3I:
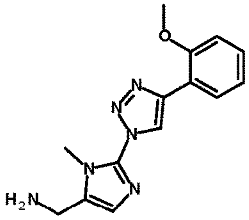
Figure 3I:
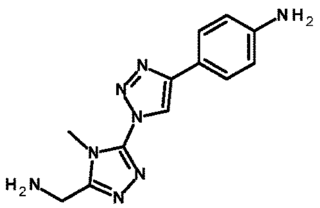
Figure 3I:
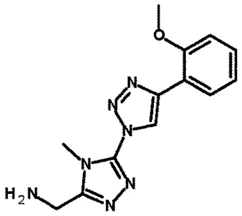
Figure 3I:
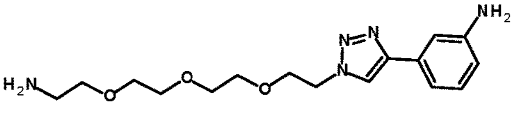
Figure 3I:
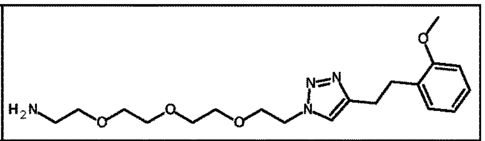
Figure 3I:
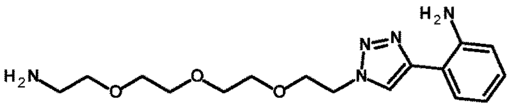
Figure 3I:
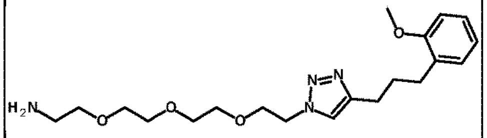
Figure 3I:
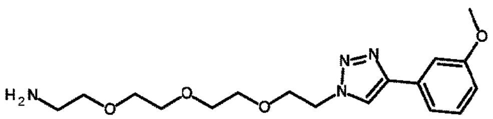
Figure 3I:
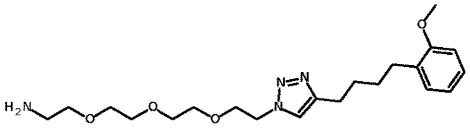
Figure 3I:
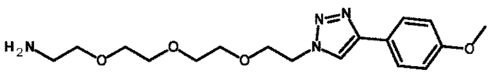
Figure 3I:
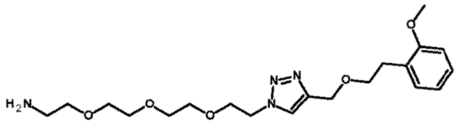
Figure 3I:
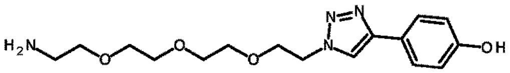
Figure 3I:
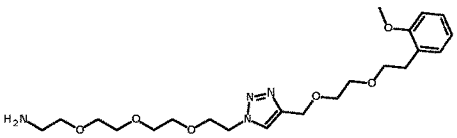
Figure 3J:
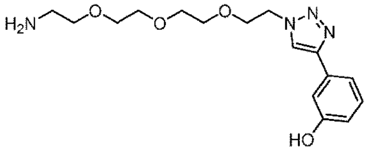
Figure 3J:
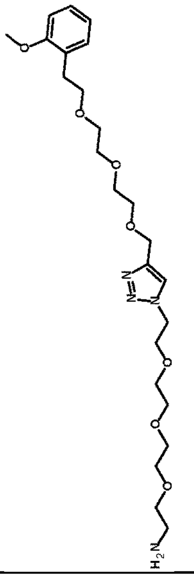
Figure 3J:
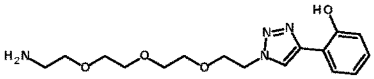
Figure 3J:
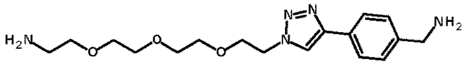
Figure 3J:
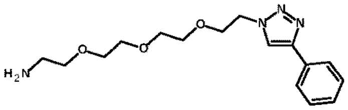
Figure 3J:
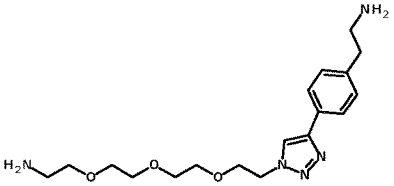
Figure 3J:
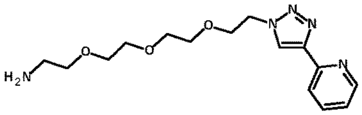
Figure 3J:
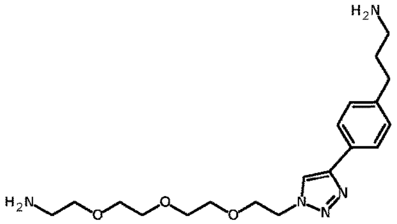
Figure 3J:
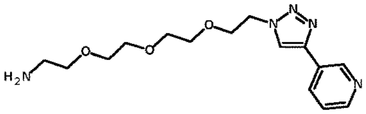
Figure 3J:
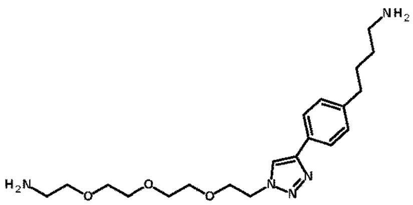
Figure 3K:
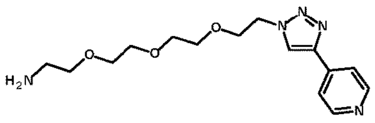
Figure 3K:
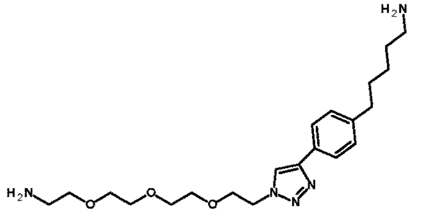
Figure 3K:
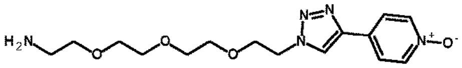
Figure 3K:
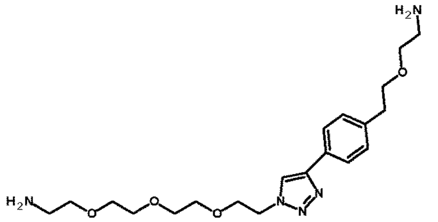
Figure 3K:
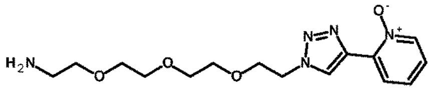
Figure 3K:
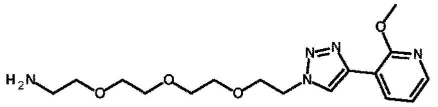
Figure 3K:
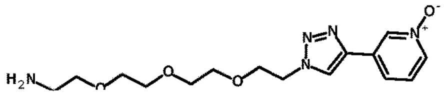
Figure 3K:
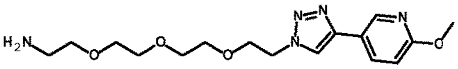
Figure 3K:
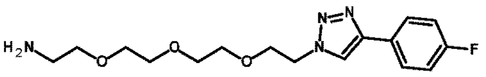
Figure 3K:
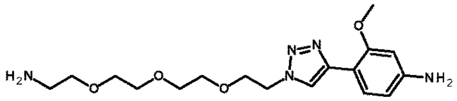
Figure 3K:
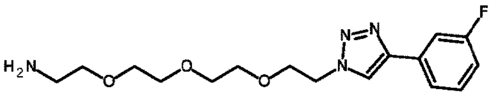
Figure 3K:
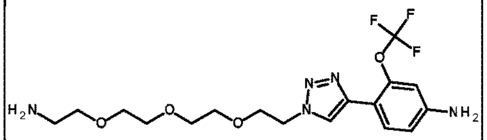
Figure 3K:
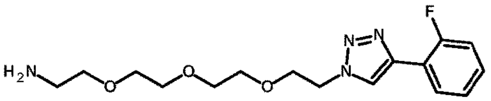
Figure 3K:
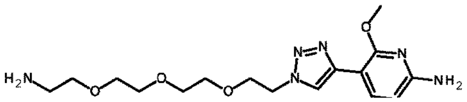
Figure 3K:
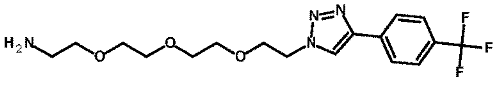
Figure 3K:
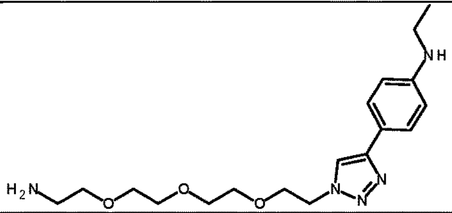
Figure 3K:
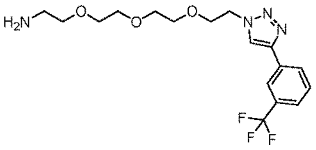
Figure 3K:
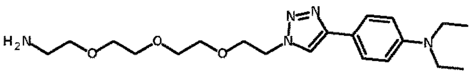
Figure 3L:
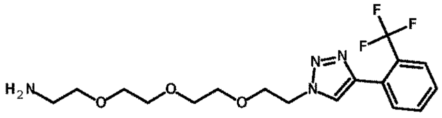
Figure 3L:
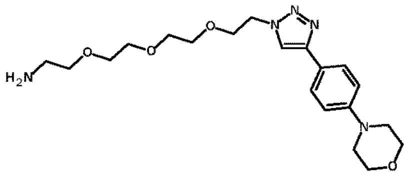
Figure 3L:
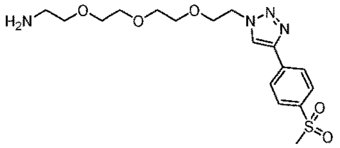
Figure 3L:
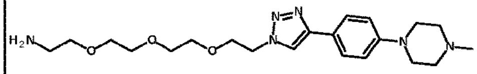
Figure 3L:
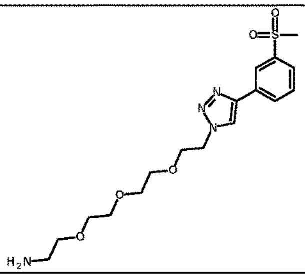
Figure 3L:
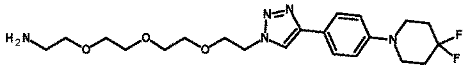
Figure 3L:
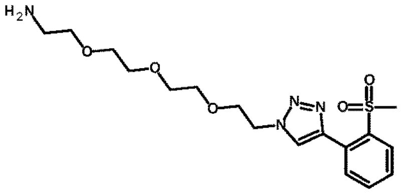
Figure 3L:
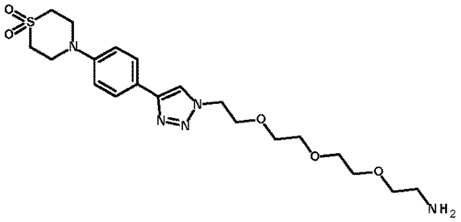
Figure 3L:
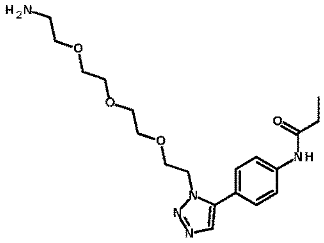
Figure 3L:
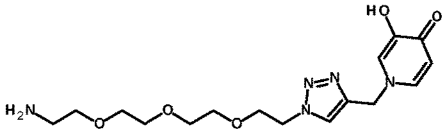
Figure 3L:
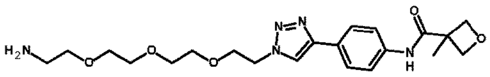
Figure 3L:
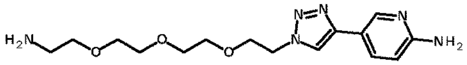
Figure 3L:
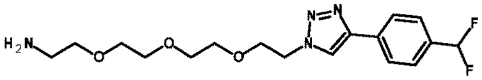
Figure 3L:
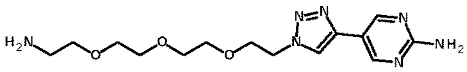
Figure 3L:
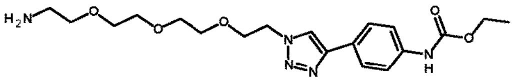
Figure 3L:
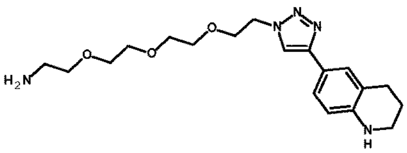
Figure 3M:
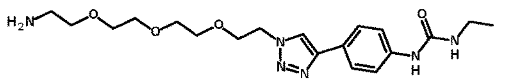
Figure 3M:
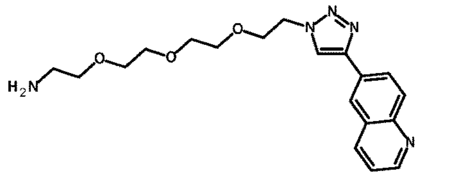
Figure 3M:
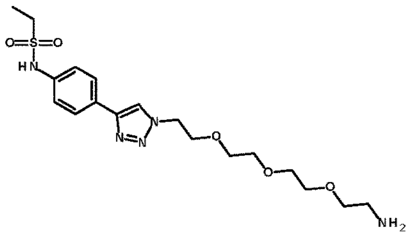
Figure 3M:
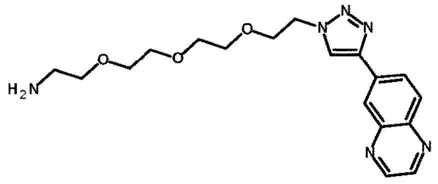
Figure 3M:
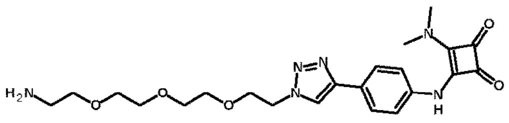
Figure 3M:
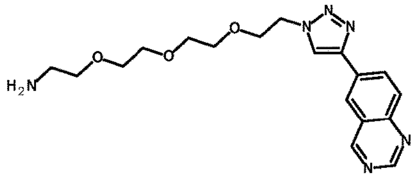
Figure 3M:
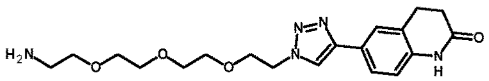
Figure 3M:
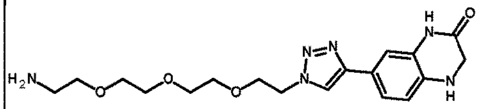
Figure 3M:
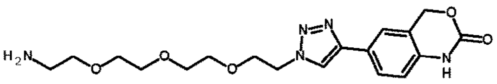
Figure 3M:
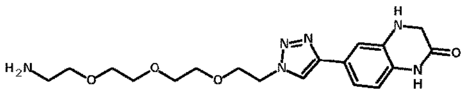
Figure 3M:
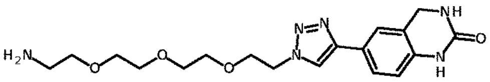
Figure 3M:
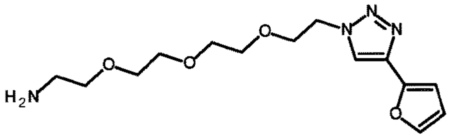
Figure 3M:
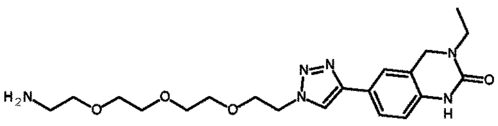
Figure 3M:
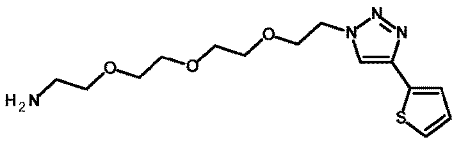
Figure 3M:
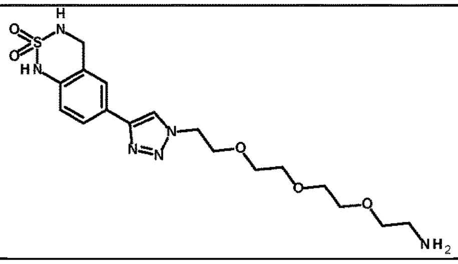
Figure 3M:
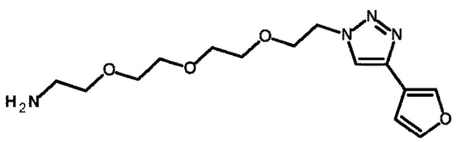
Figure 3N:
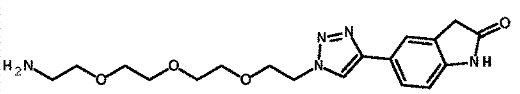
Figure 3N:
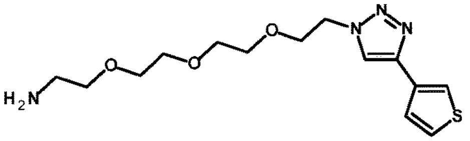
Figure 3N:
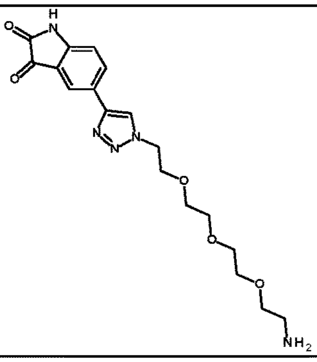
Figure 3N:
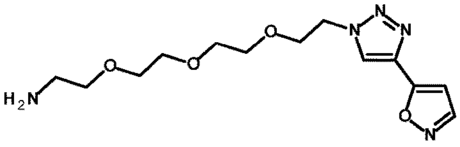
Figure 3N:
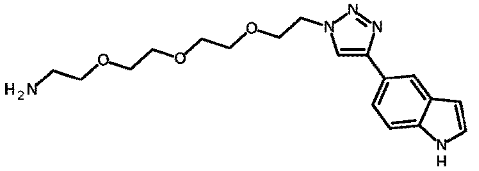
Figure 3N:
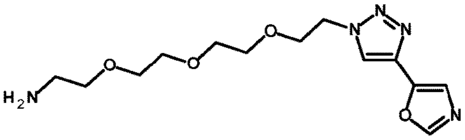
Figure 3N:
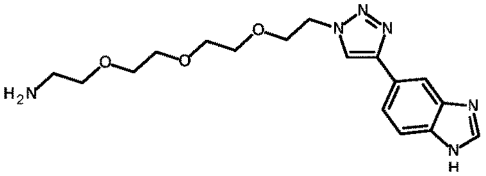
Figure 3N:
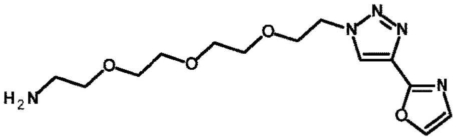
Figure 3N:
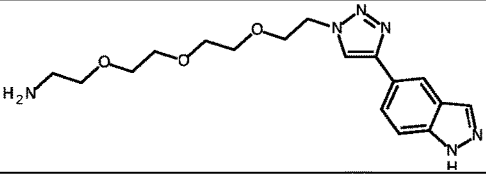
Figure 3N:
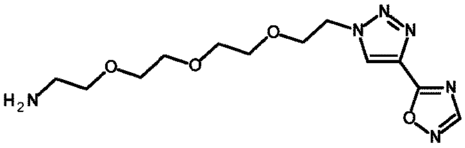
Figure 3N:
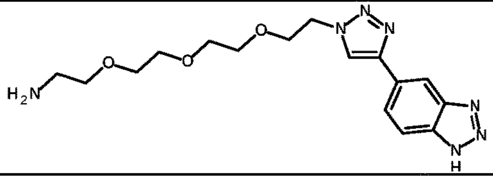
Figure 3N:
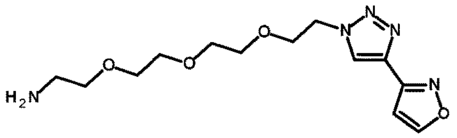
Figure 3N:
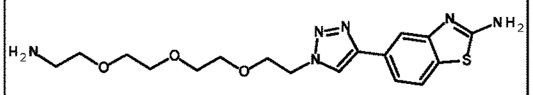
Figure 3N:
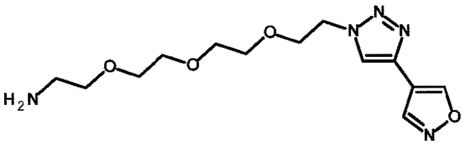
Figure 3N:
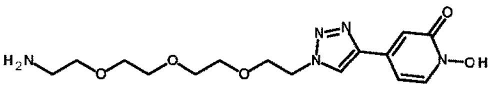
Figure 3N:
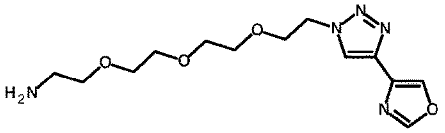
Figure 3O:
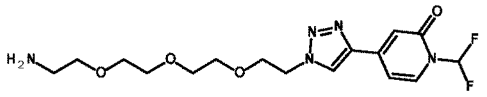
Figure 3O:
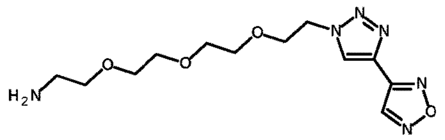
Figure 3O:
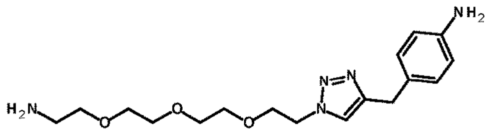
Figure 3O:
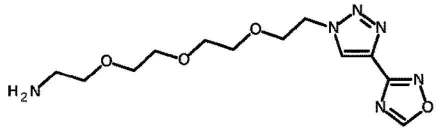
Figure 3O:
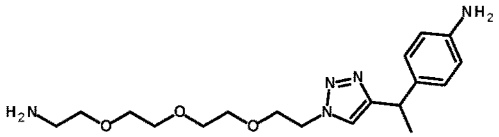
Figure 3O:
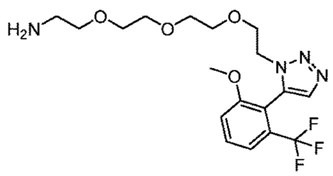
Figure 3O:
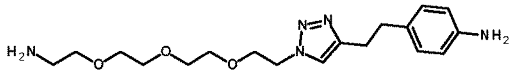
Figure 3O:
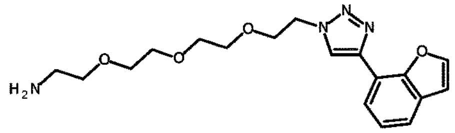
Figure 3O:
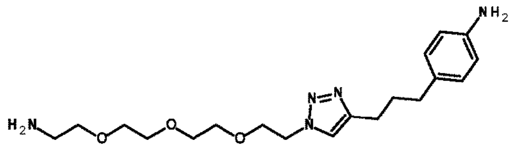
Figure 3O:
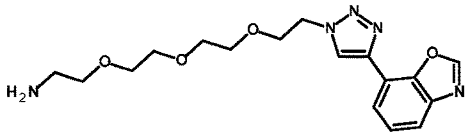
Figure 3O:
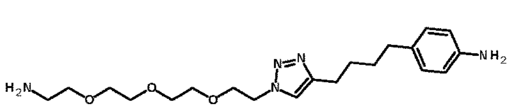
Figure 3O:
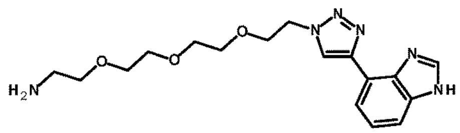
Figure 3O:
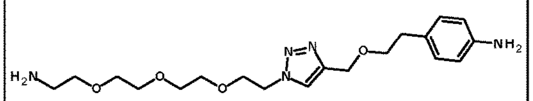
Figure 3O:
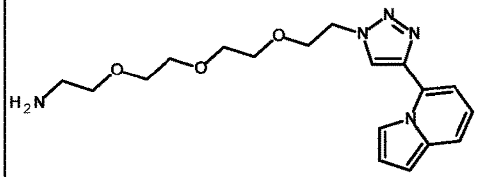
Figure 3O:
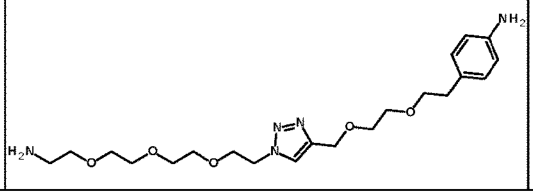
Figure 3O:
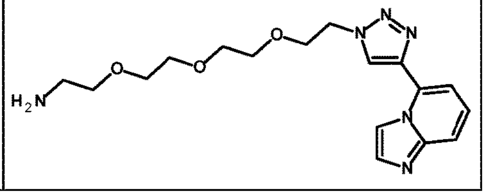
Figure 3P:
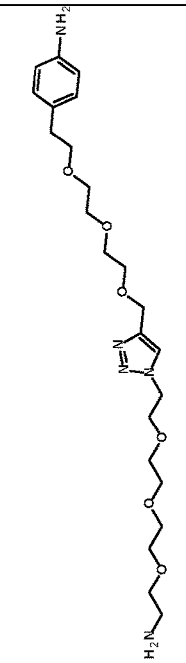
Figure 3P:
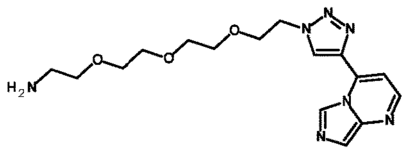
Figure 3P:
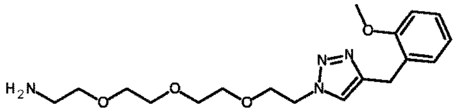
Figure 3P:
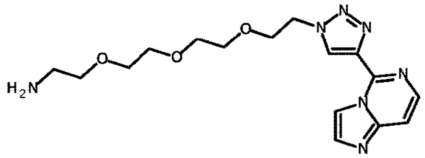
Figure 3P:
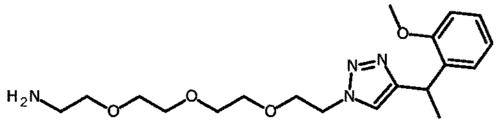
Figure 3P:
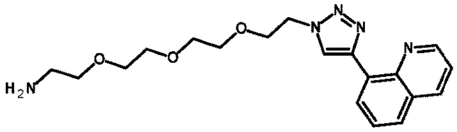
Figure 3P:
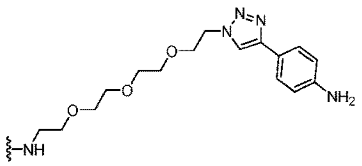
Figure 3P:
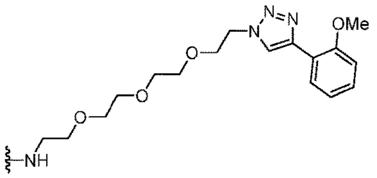
Figure 3P:
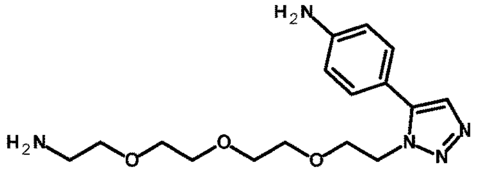
Figure 3P:
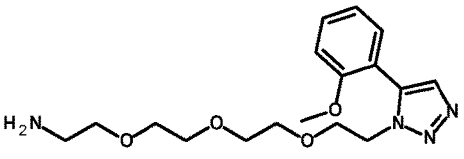
Figure 3Q:
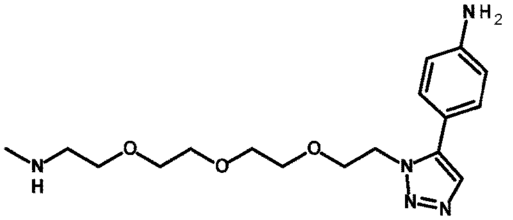
Figure 3Q:
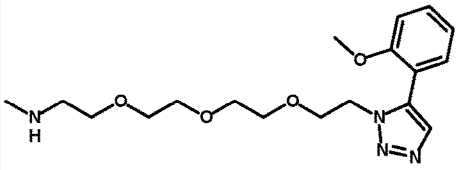
Figure 3Q:
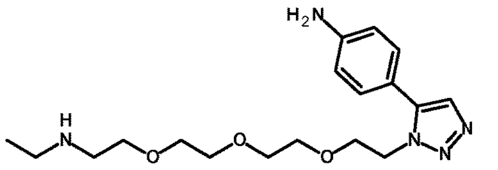
Figure 3Q:
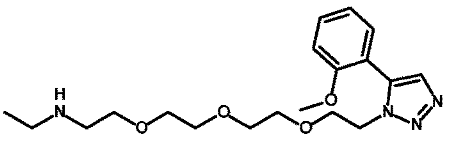
Figure 3Q:
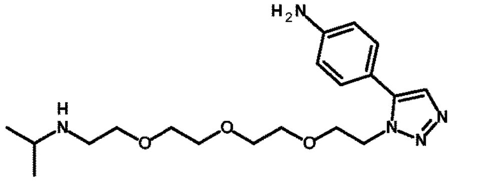
Figure 3Q:
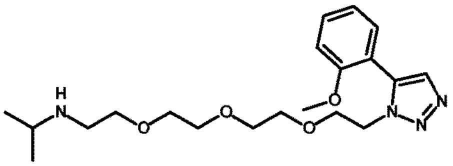
Figure 3Q:
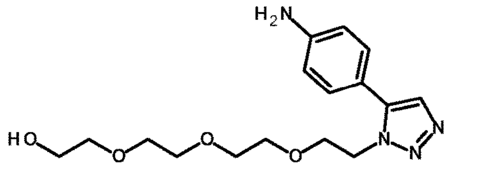
Figure 3Q:
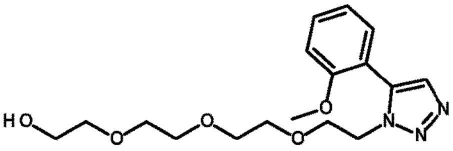
Figure 3Q:
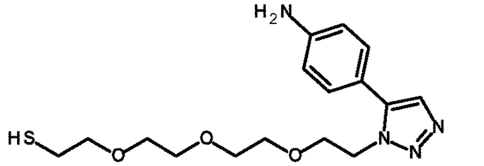
Figure 3Q:
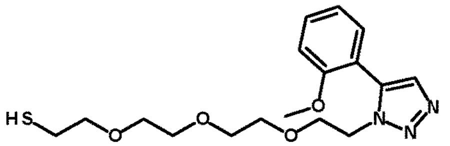
Figure 3Q:
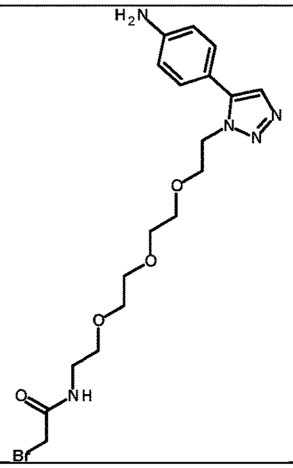
Figure 3Q:
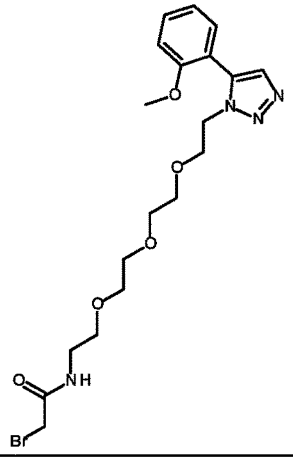
Figure 3R:
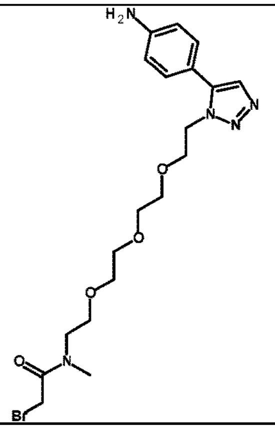
Figure 3R:
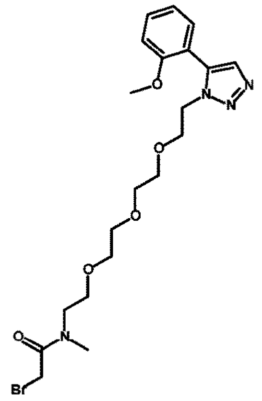
Figure 3R:
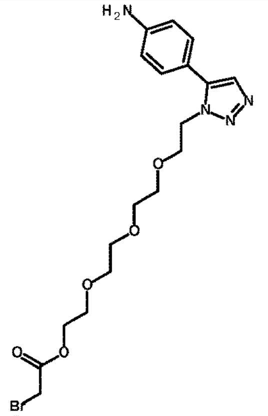
Figure 3R:
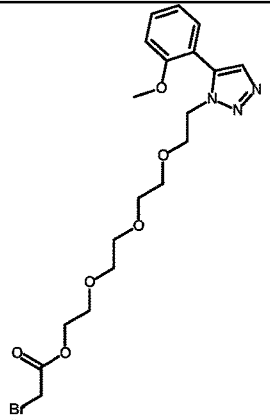
Figure 3R:
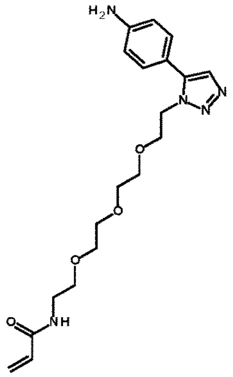
Figure 3R:
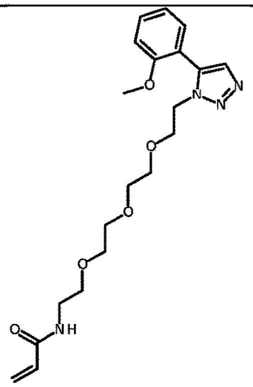
Figure 3R:
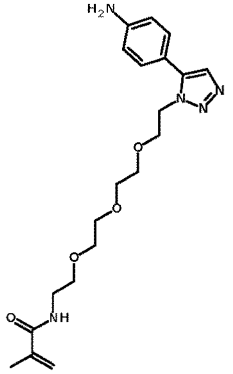
Figure 3R:
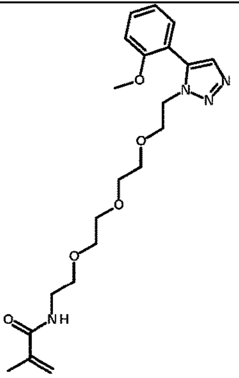
Figure 3S:
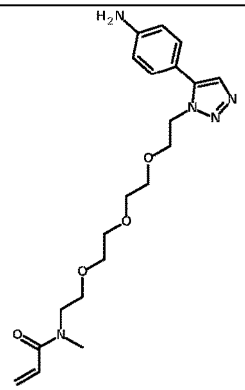
Figure 3S:
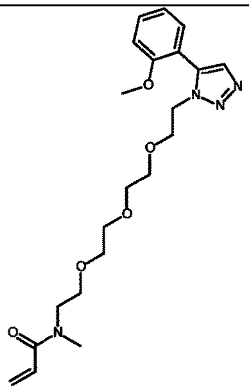
Figure 3S:
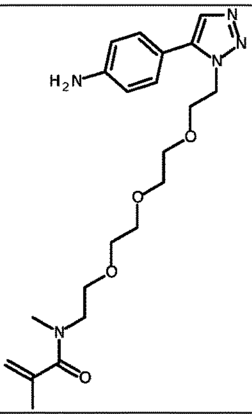
Figure 3S:
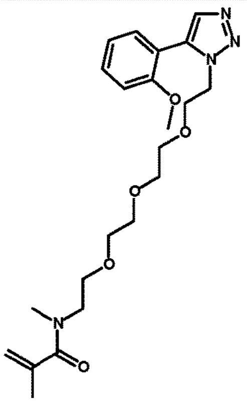
Figure 3S:
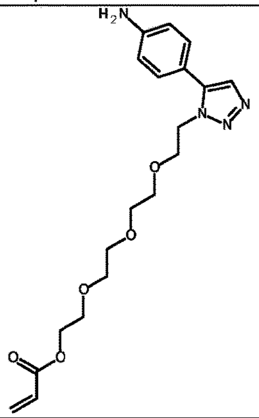
Figure 3S:
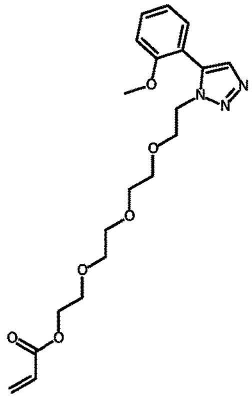
Figure 3S:
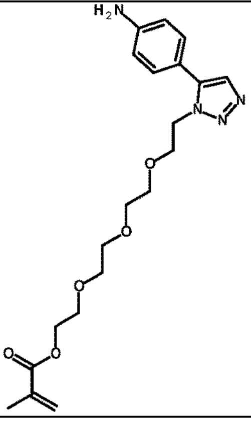
Figure 3S:
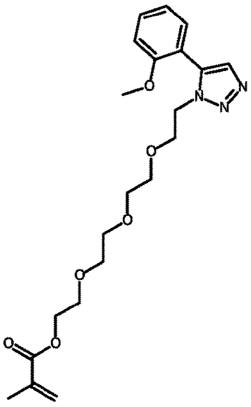
Figure 3T:
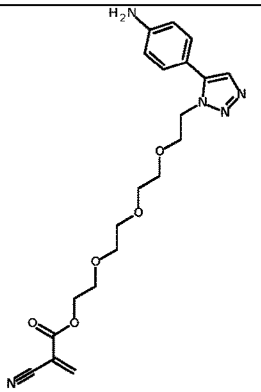
Figure 3T:
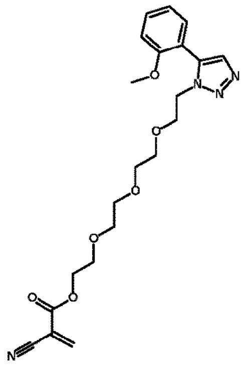
Figure 3T:
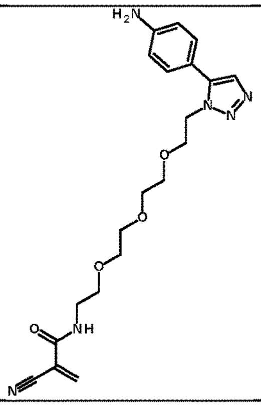
Figure 3T:
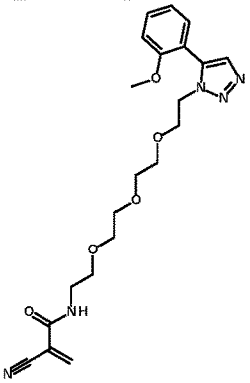
Figure 3T:
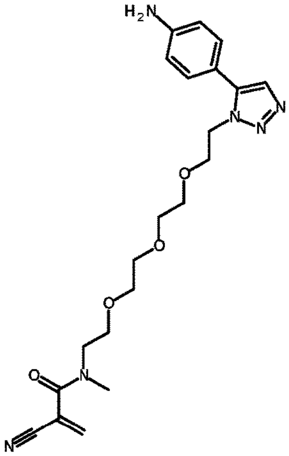
Figure 3T:
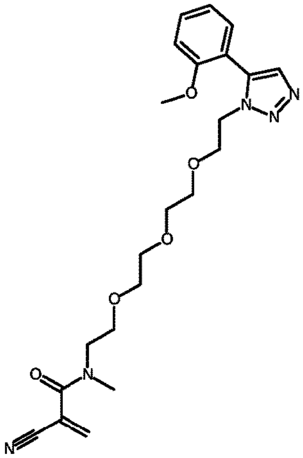
Figure 3T:
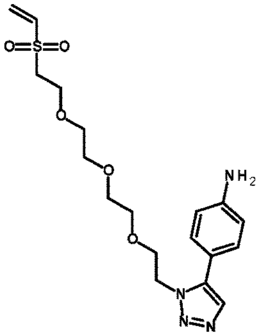
Figure 3T:
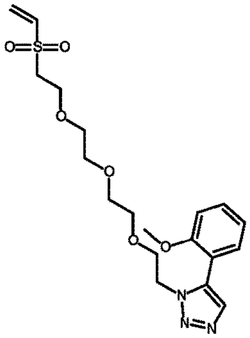
Figure 3U:
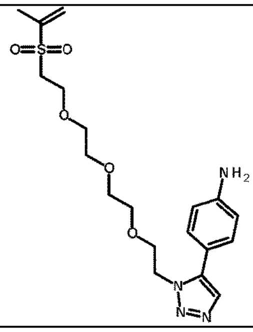
Figure 3U:
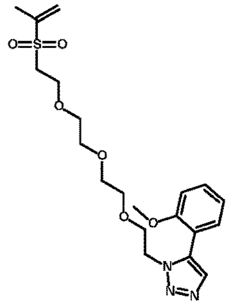
Figure 3U:
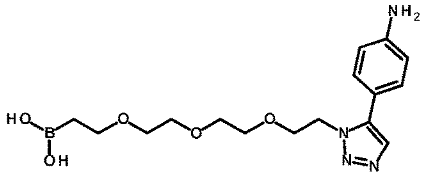
Figure 3U:
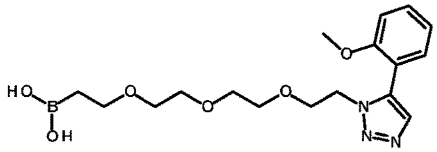
Figure 3U:
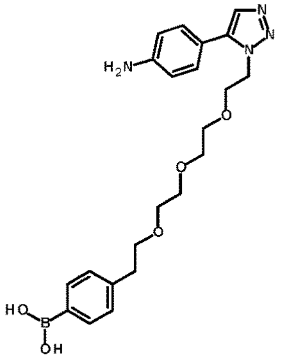
Figure 3U:
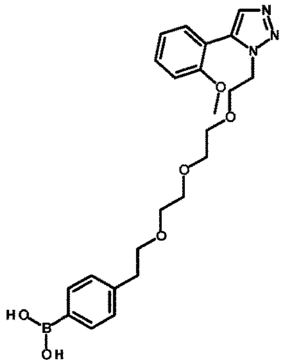
Figure 3U:
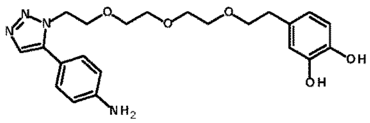
Figure 3U:
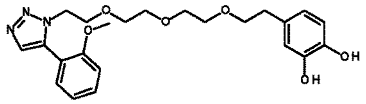
Figure 3U:
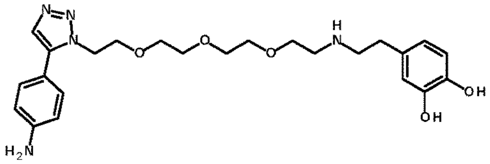
Figure 3U:
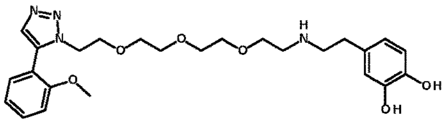
Figure 3U:
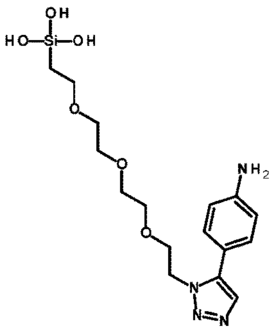
Figure 3U:
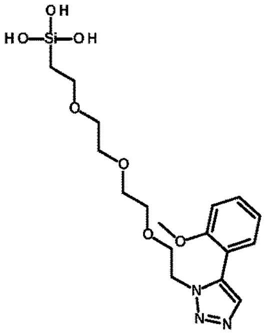
Figure 3V:
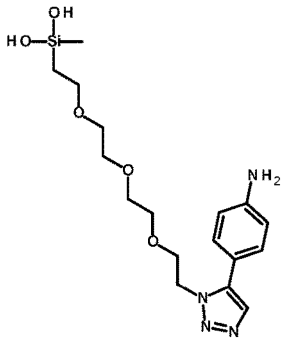
Figure 3V:
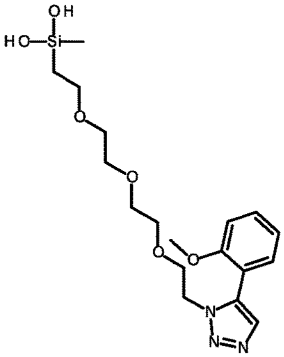
Figure 3V:
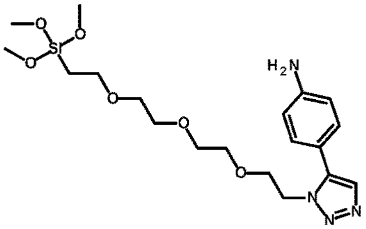
Figure 3V:
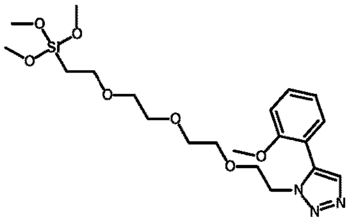
Figure 3V:
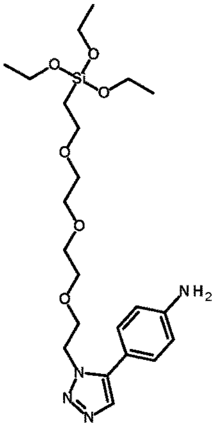
Figure 3V:
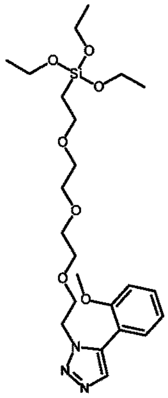
Figure 3V:
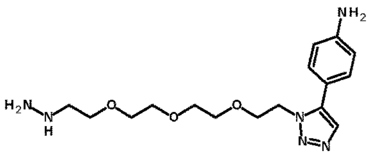
Figure 3V:
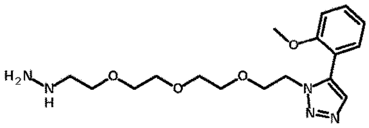
Figure 3V:
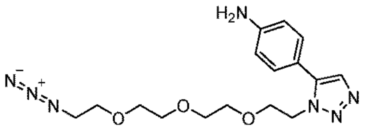
Figure 3V:
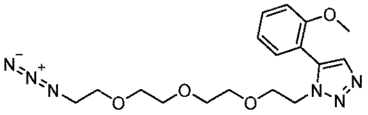
Figure 3W:
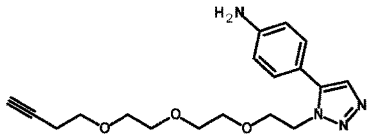
Figure 3W:
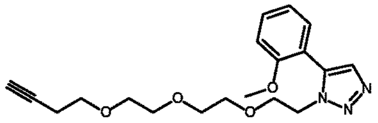
Figure 3W:
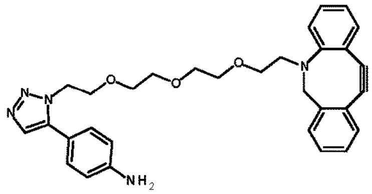
Figure 3W:
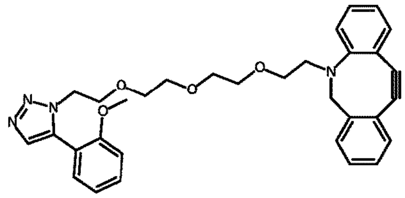
Figure 3W:
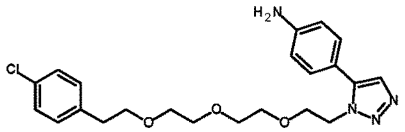
Figure 3W:
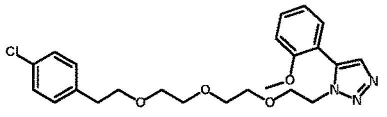
Figure 3W:
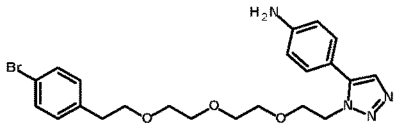
Figure 3W:
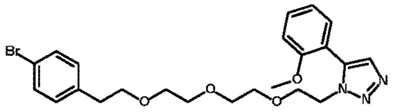
Figure 3W:
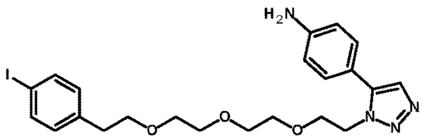
Figure 3W:
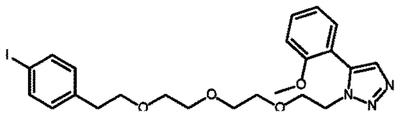
Figure 3W:
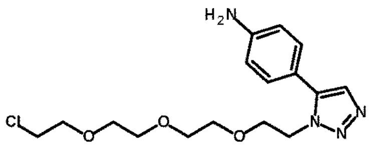
Figure 3W:
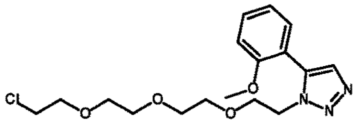
Figure 3W:
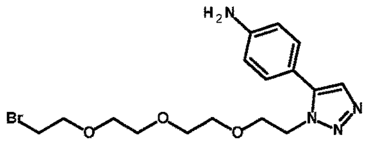
Figure 3W:
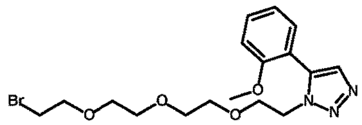
Figure 3W:
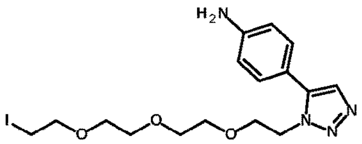
Figure 3W:
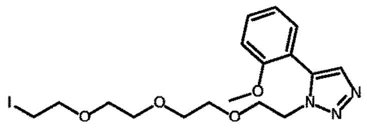
Figure 3X:
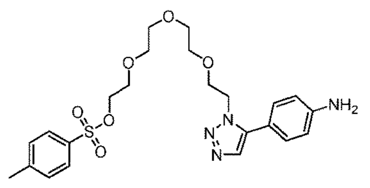
Figure 3X:
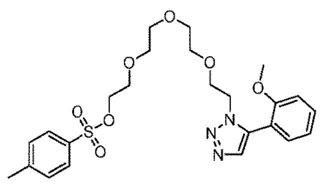
Figure 3X:
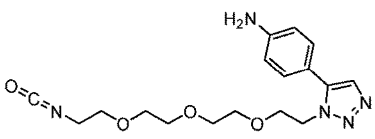
Figure 3X:
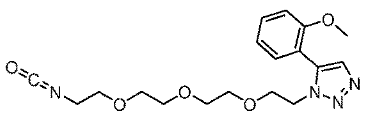
Figure 3X:
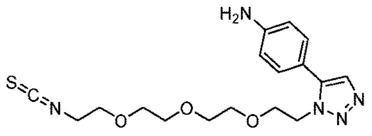
Figure 3X:
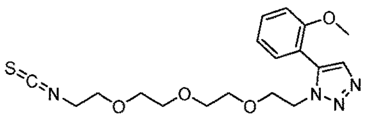
Figure 3X:
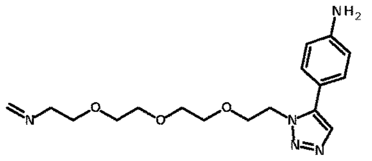
Figure 3X:
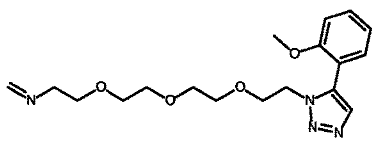
Figure 3X:
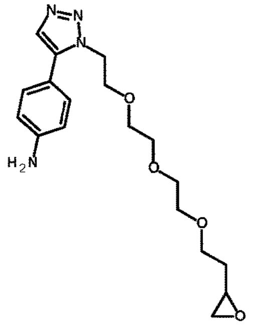
Figure 3X:
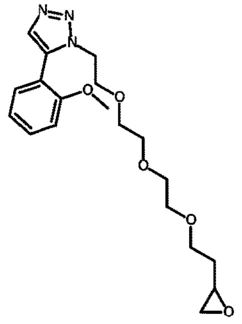
Figure 3X:
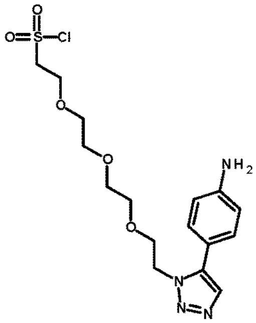
Figure 3X:
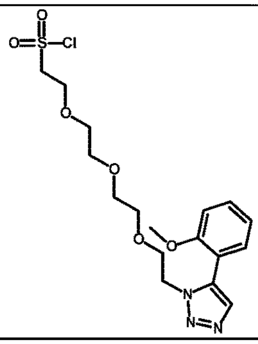
Figure 3Y:
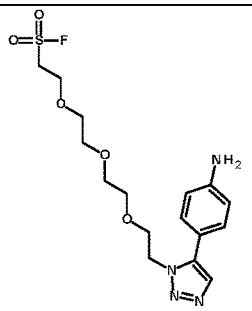
Figure 3Y:
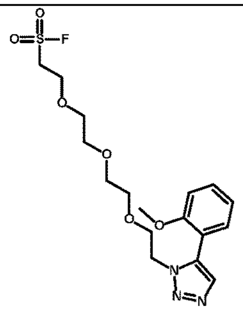
Figure 3Y:
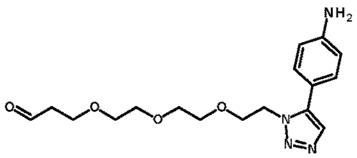
Figure 3Y:
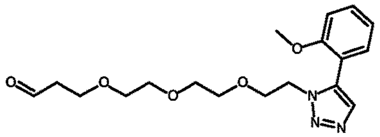
Figure 3Y:
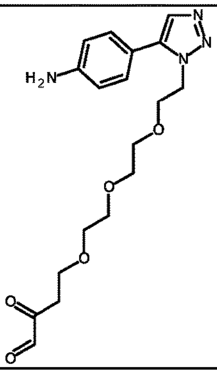
Figure 3Y:
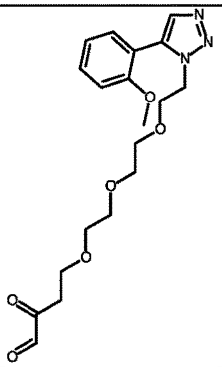
Figure 3Y:
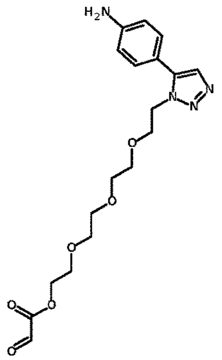
Figure 3Y:
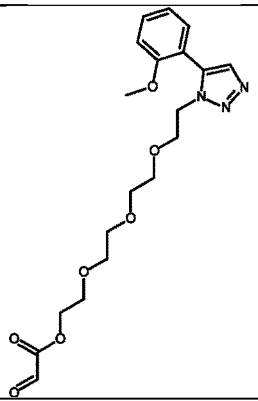
Figure 3Z:
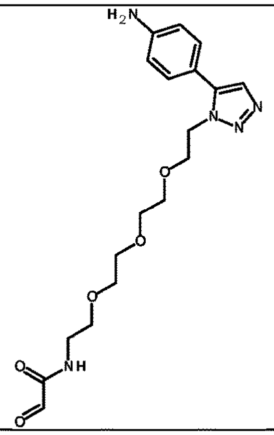
Figure 3Z:
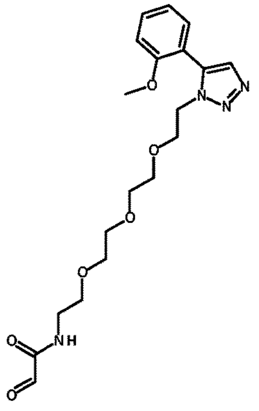
Figure 3Z:
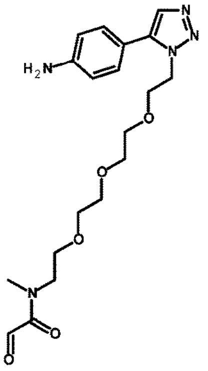
Figure 3Z:
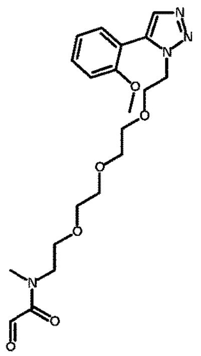
Figure 3Z:
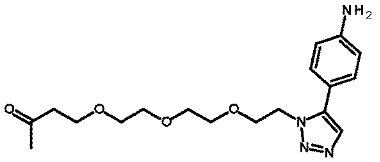
Figure 3Z:
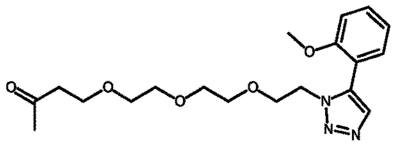
Figure 3Z:
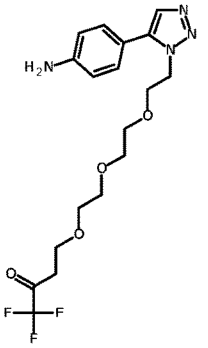
Figure 3Z:
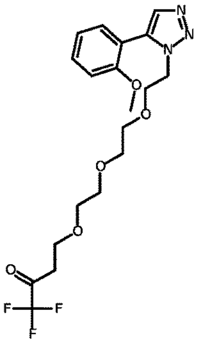
Figure 3Z:
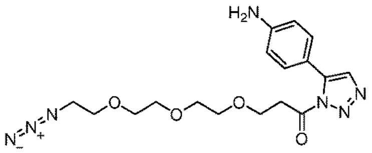
Figure 3Z:
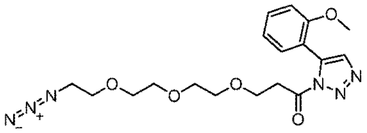
Figure 4A:
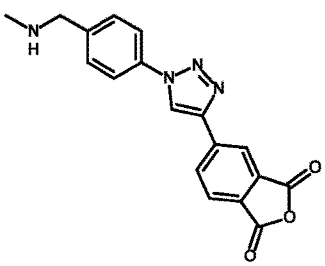
Figure 4A:
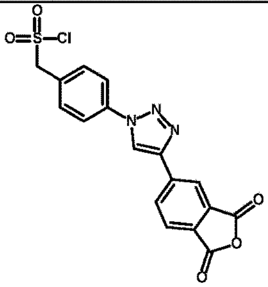
Figure 4A:
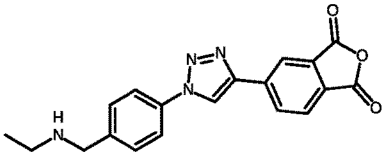
Figure 4A:
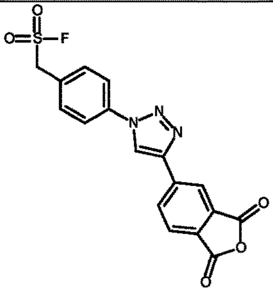
Figure 4A:
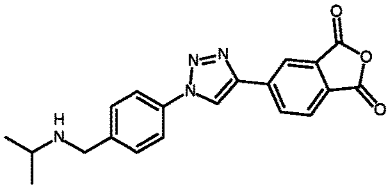
Figure 4A:
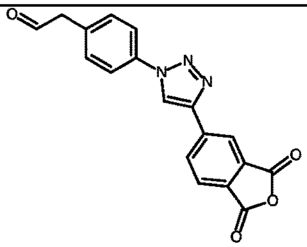
Figure 4A:
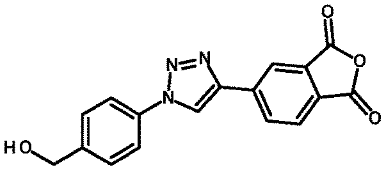
Figure 4A:
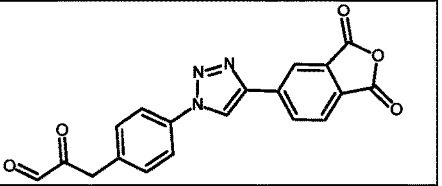
Figure 4A:
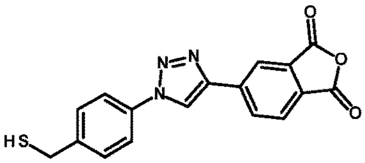
Figure 4A:
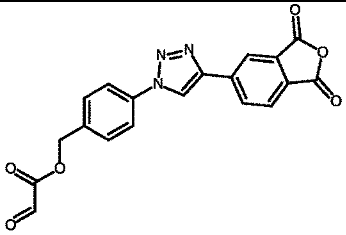
Figure 4A:
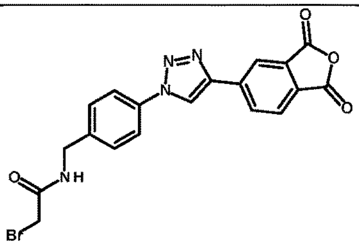
Figure 4A:
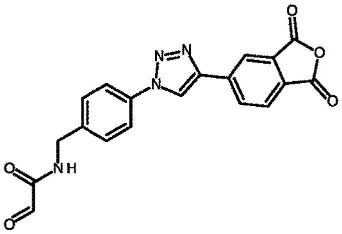
Figure 4B:
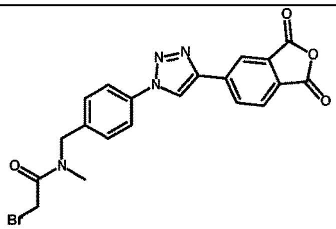
Figure 4B:
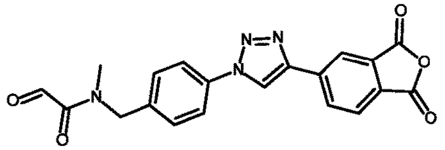
Figure 4B:
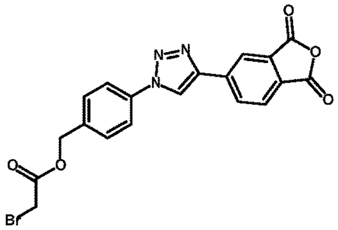
Figure 4B:
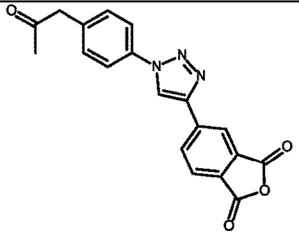
Figure 4B:
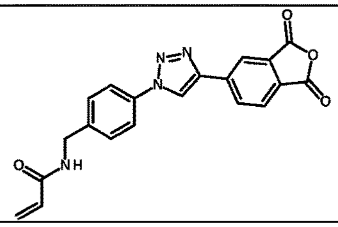
Figure 4B:
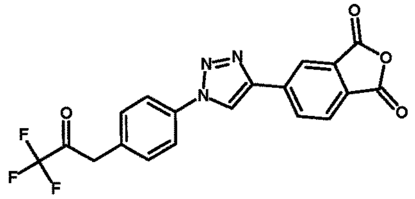
Figure 4B:
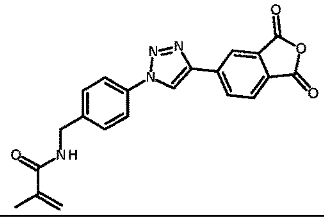
Figure 4B:
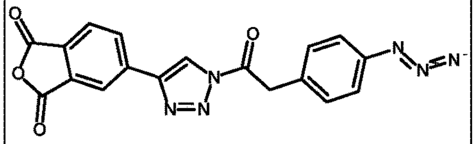
Figure 4B:
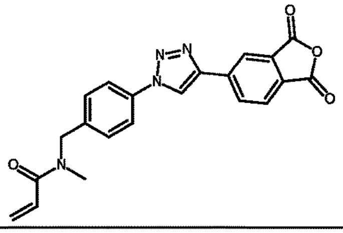
Figure 4B:
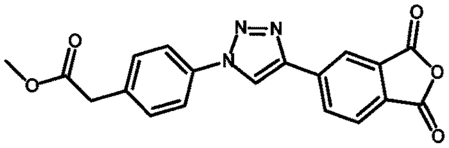
Figure 4B:
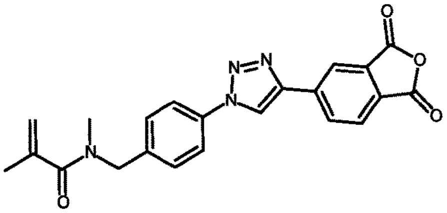
Figure 4B:
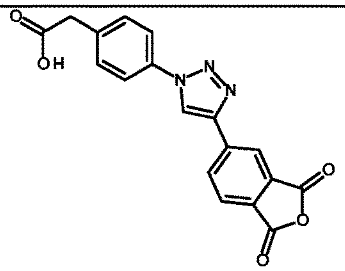
Figure 4C:
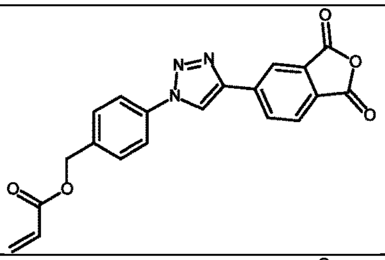
Figure 4C:
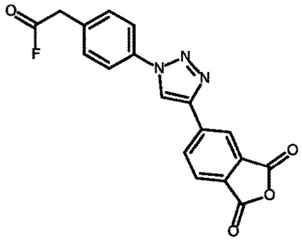
Figure 4C:
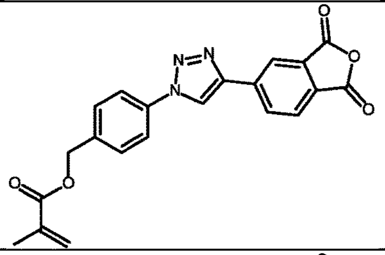
Figure 4C:
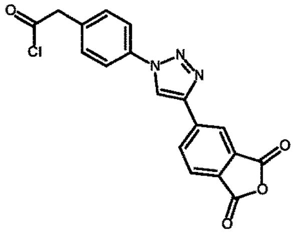
Figure 4C:
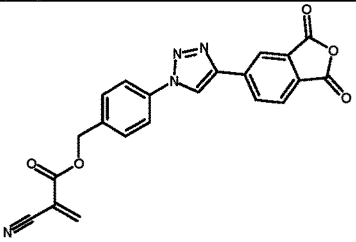
Figure 4C:
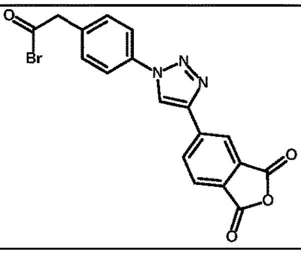
Figure 4C:
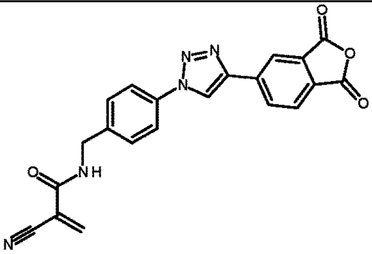
Figure 4C:
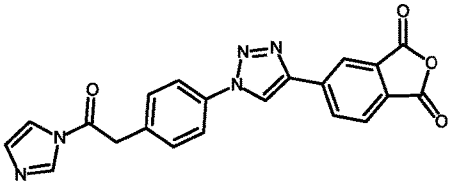
Figure 4C:
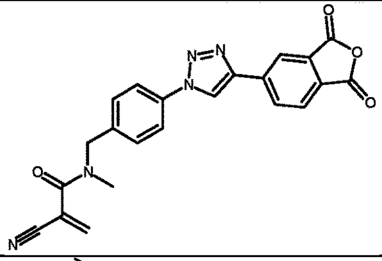
Figure 4C:
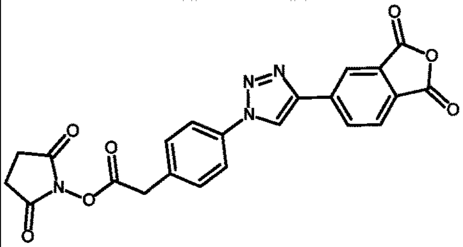
Figure 4C:
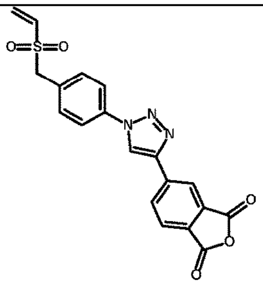
Figure 4C:
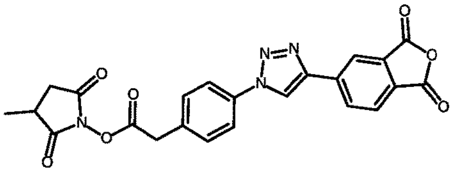
Figure 4D:
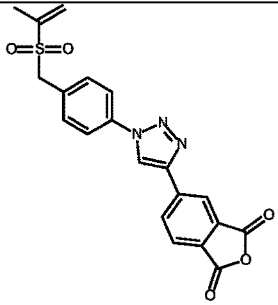
Figure 4D:
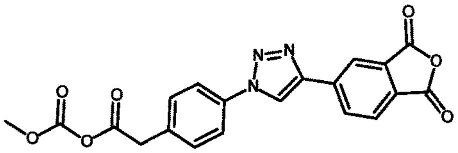
Figure 4D:
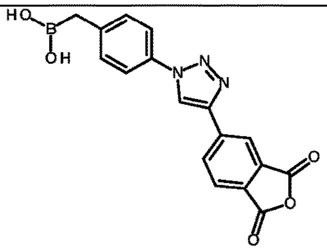
Figure 4D:
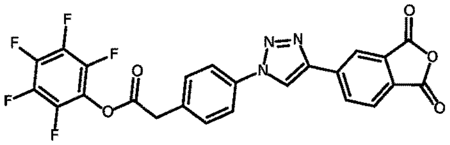
Figure 4D:
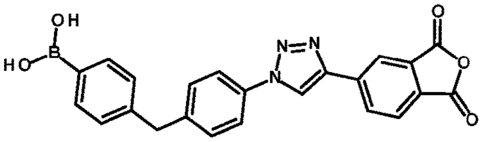
Figure 4D:
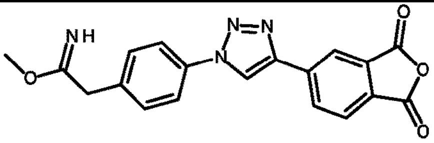
Figure 4D:
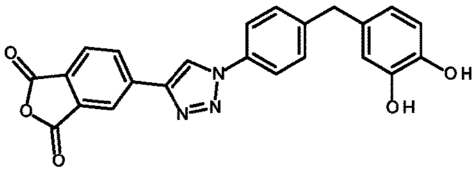
Figure 4D:
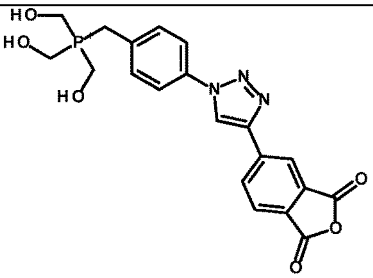
Figure 4D:
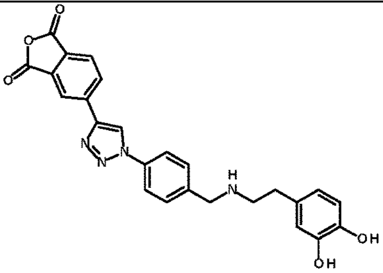
Figure 4D:
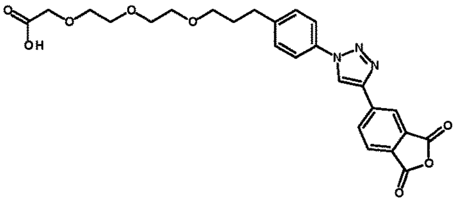
Figure 4D:
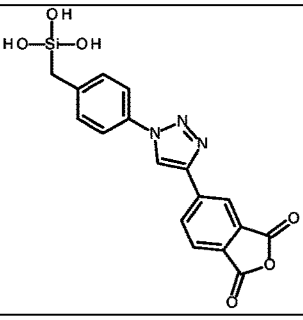
Figure 4D:
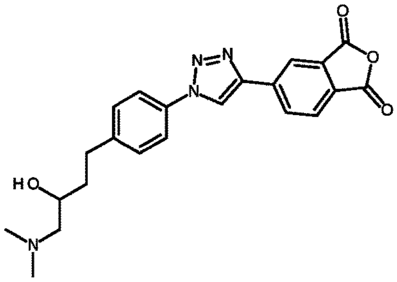
Figure 4E:
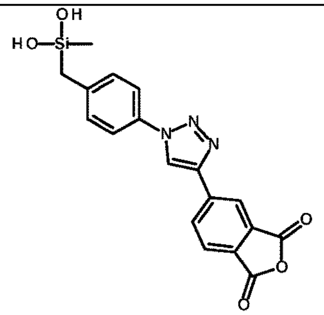
Figure 4E:
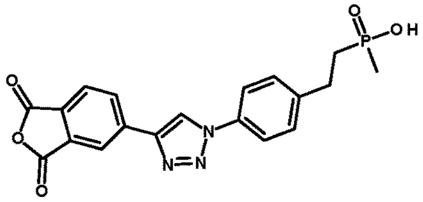
Figure 4E:
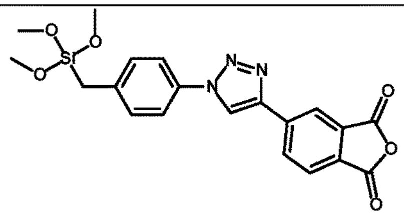
Figure 4E:
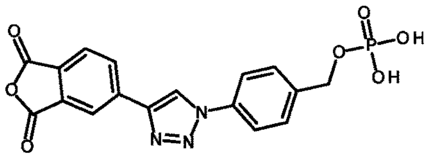
Figure 4E:
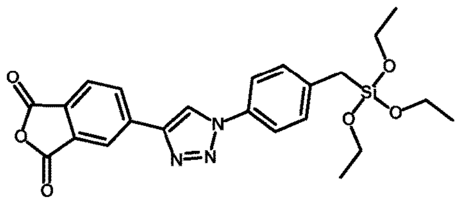
Figure 4E:
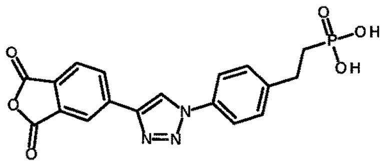
Figure 4E:
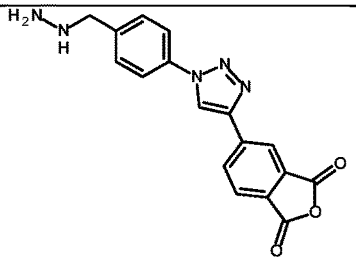
Figure 4E:
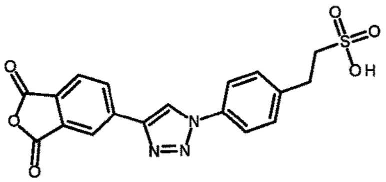
Figure 4E:
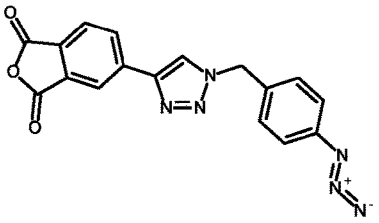
Figure 4E:
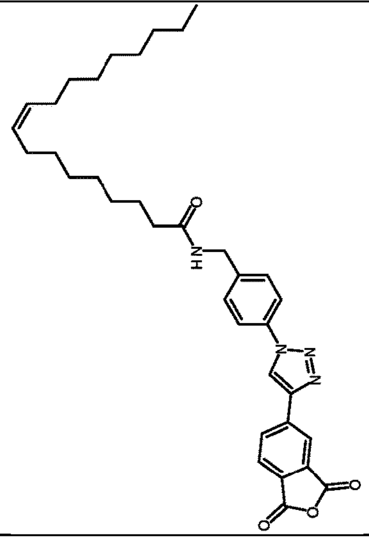
Figure 4F:
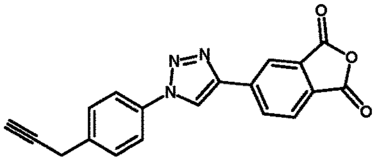
Figure 4F:
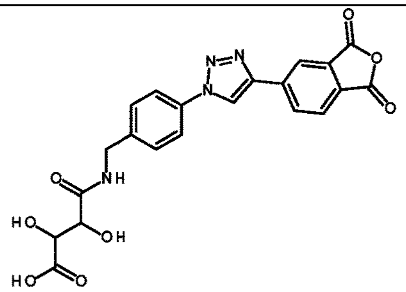
Figure 4F:
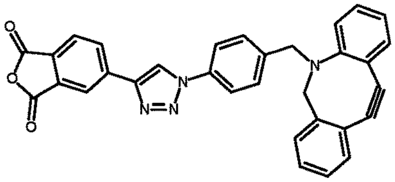
Figure 4F:
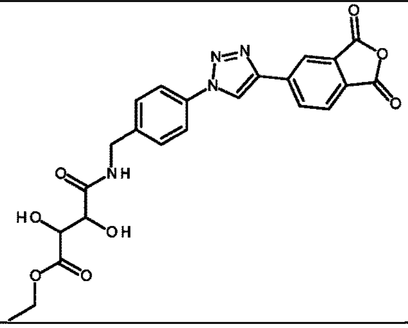
Figure 4F:
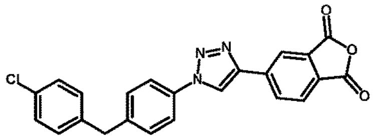
Figure 4F:
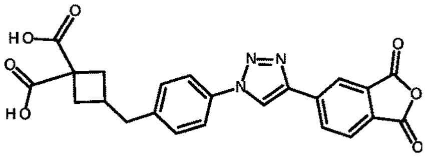
Figure 4F:
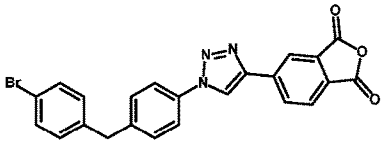
Figure 4F:
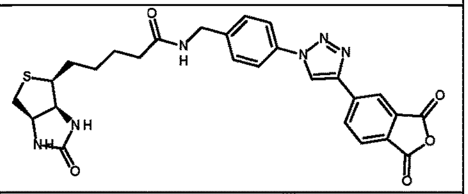
Figure 4F:
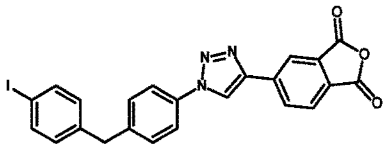
Figure 4F:
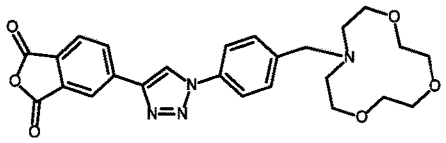
Figure 4F:
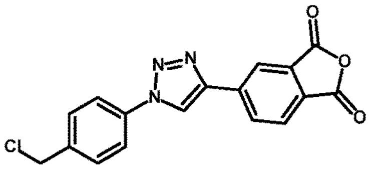
Figure 4F:
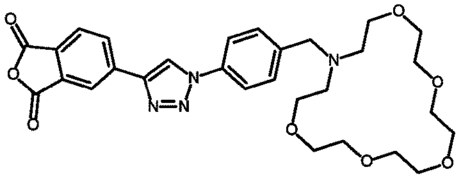
Figure 4G:
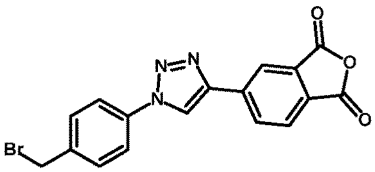
Figure 4G:
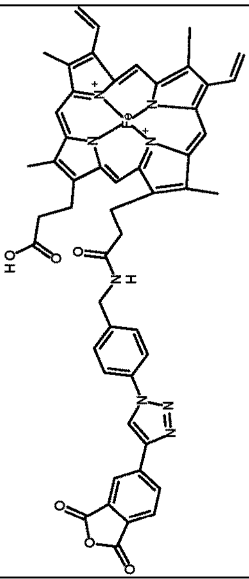
Figure 4G:
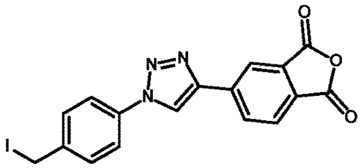
Figure 4G:
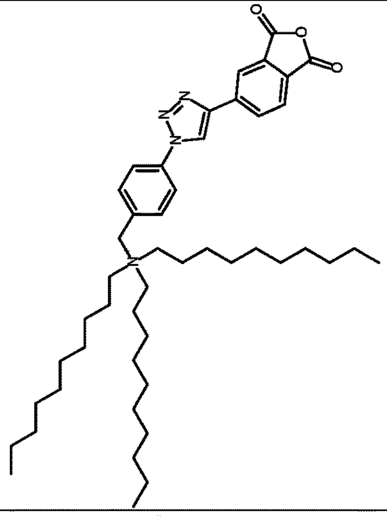
Figure 4G:
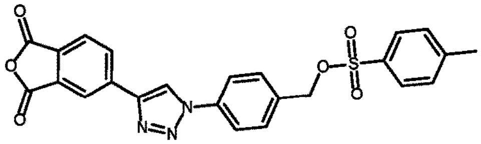
Figure 4G:
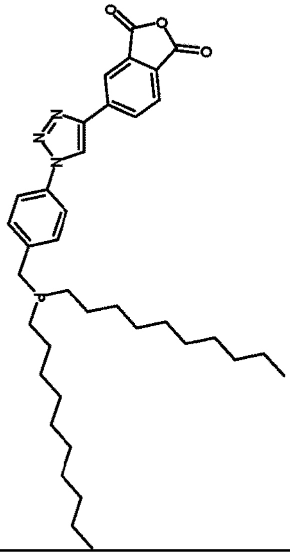
Figure 4H:
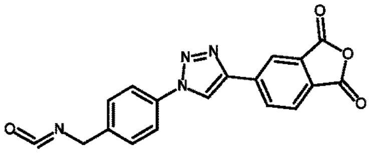
Figure 4H:
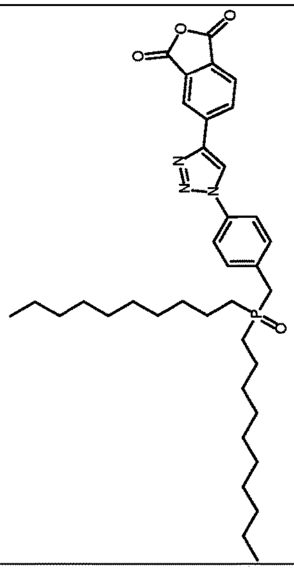
Figure 4H:
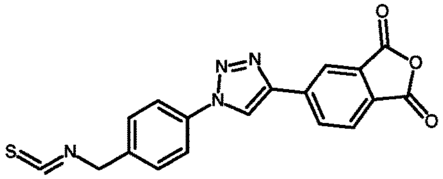
Figure 4H:
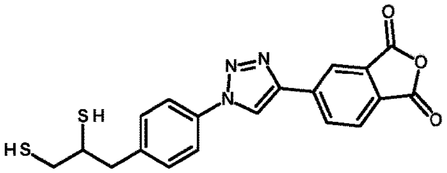
Figure 4H:
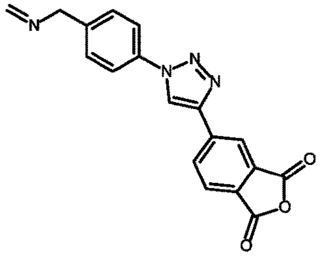
Figure 4H:
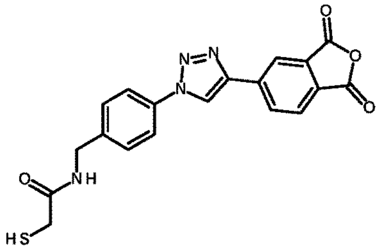
Figure 4H:
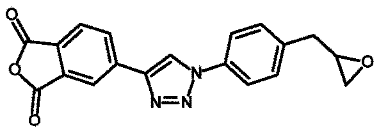
Figure 4H:
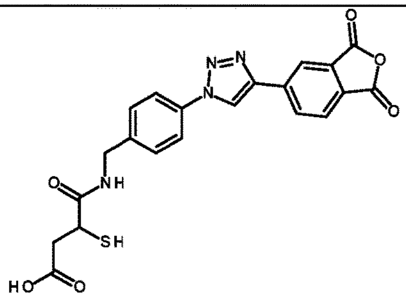
Figure 4H:
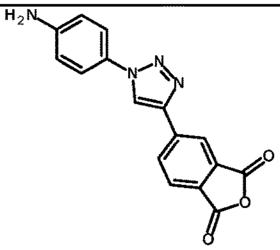
Figure 4H:
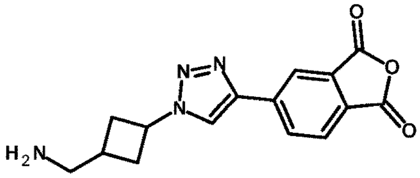
Figure 4I:
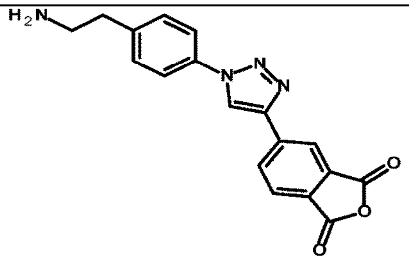
Figure 4I:
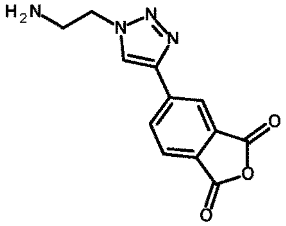
Figure 4I:
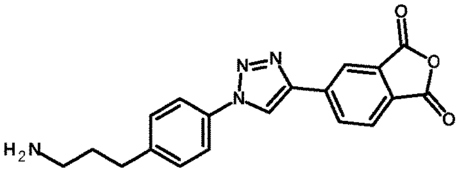
Figure 4I:
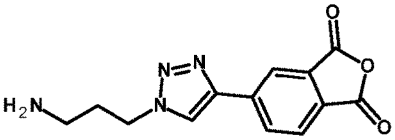
Figure 4I:
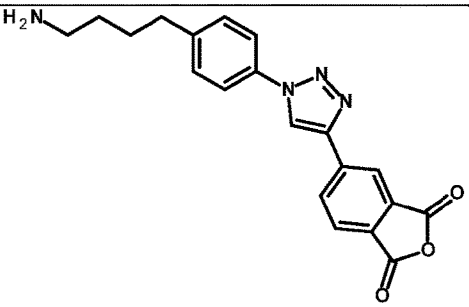
Figure 4I:
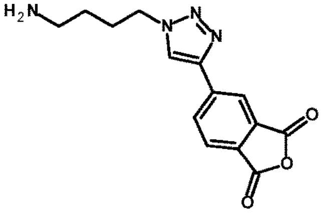
Figure 4I:
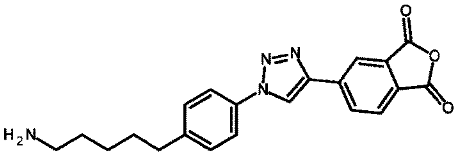
Figure 4I:
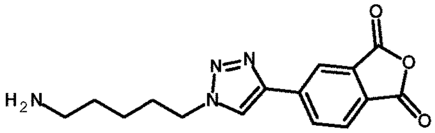
Figure 4I:
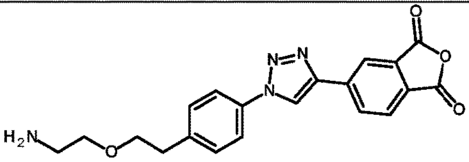
Figure 4I:
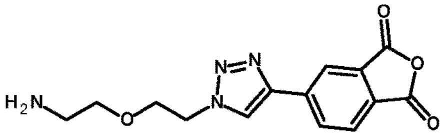
Figure 4I:
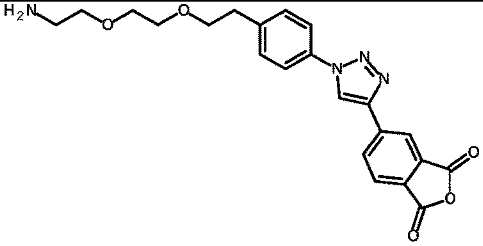
Figure 4I:
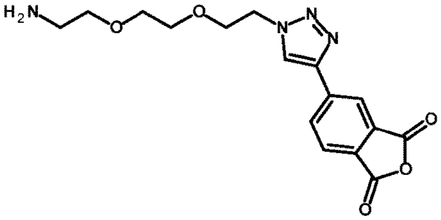
Figure 4J:
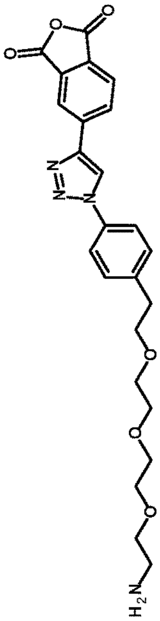
Figure 4J:
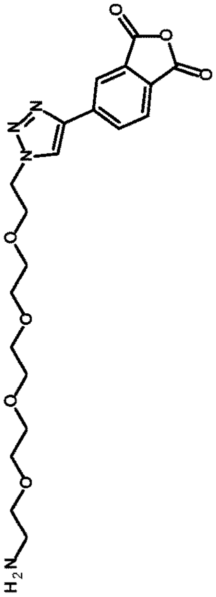
Figure 4J:
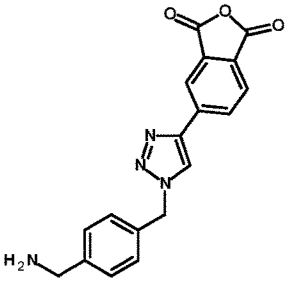
Figure 4J:
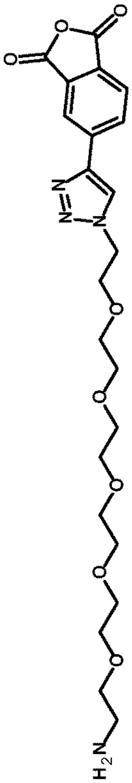
Figure 4K:
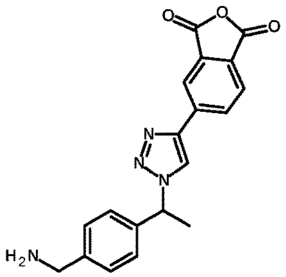
Figure 4K:
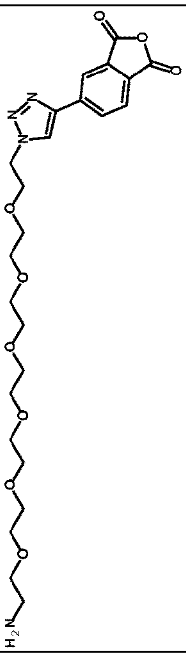
Figure 4K:
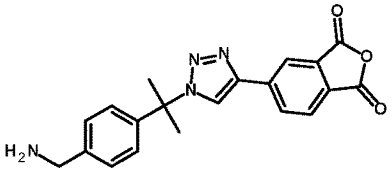
Figure 4K:
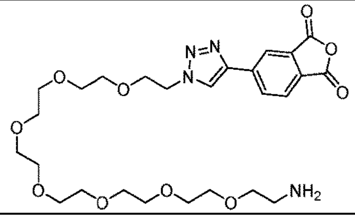
Figure 4K:
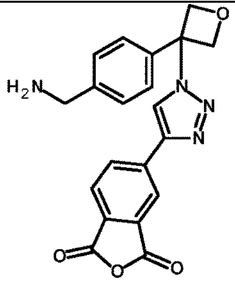
Figure 4K:
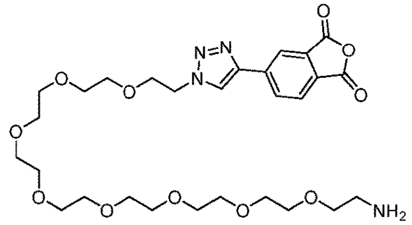
Figure 4K:
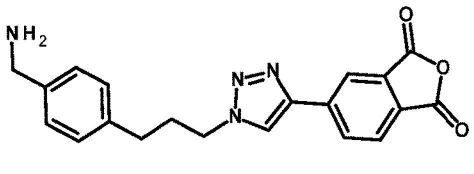
Figure 4K:
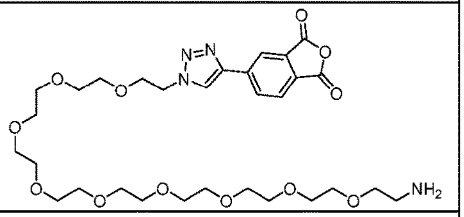
Figure 4K:
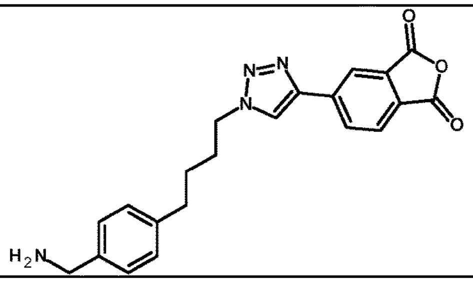
Figure 4K:
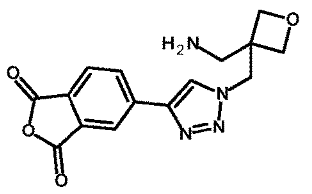
Figure 4L:
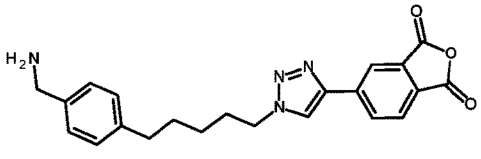
Figure 4L:
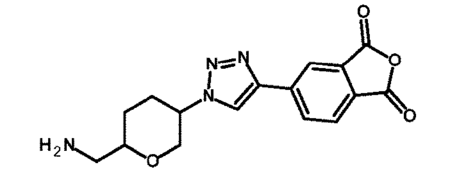
Figure 4L:
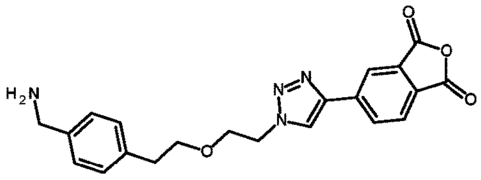
Figure 4L:
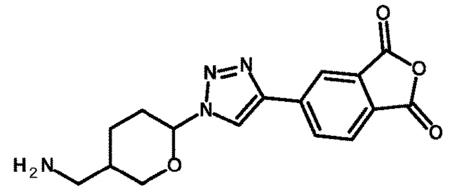
Figure 4L:
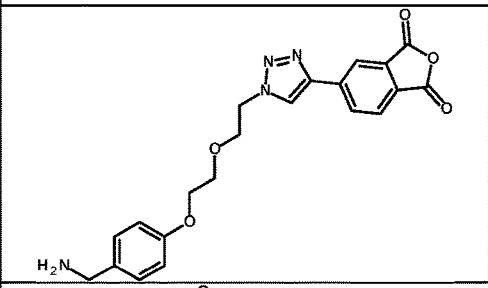
Figure 4L:
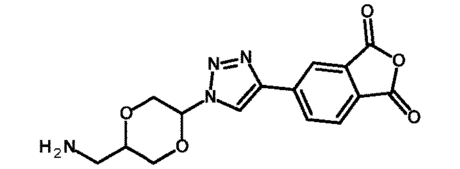
Figure 4L:
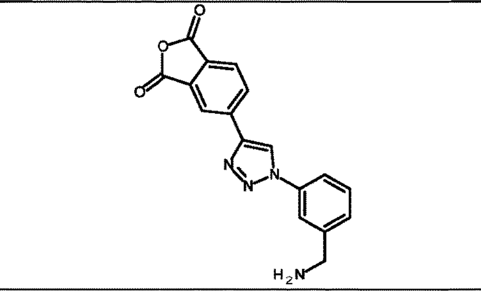
Figure 4L:
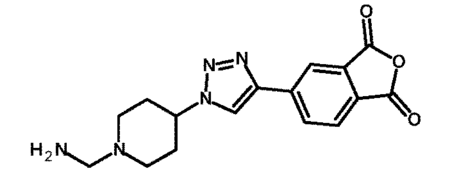
Figure 4L:
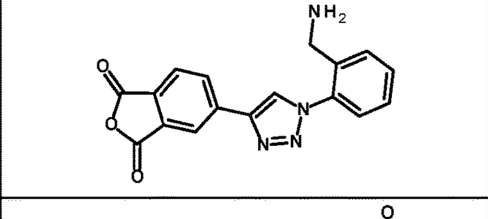
Figure 4L:
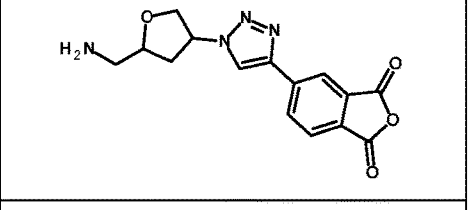
Figure 4L:
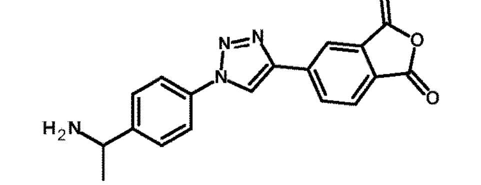
Figure 4L:
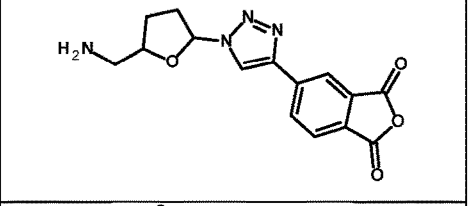
Figure 4L:
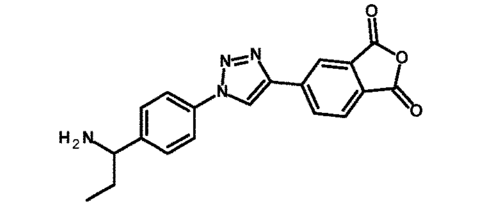
Figure 4L:
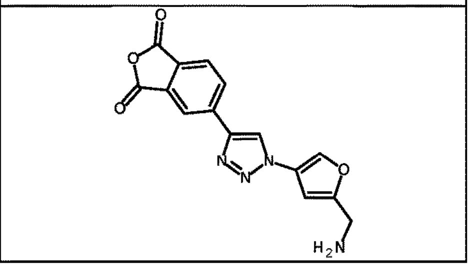
Figure 4M:
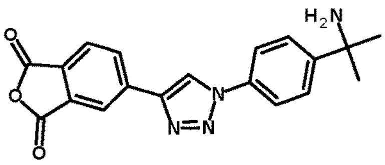
Figure 4M:
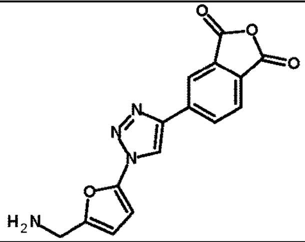
Figure 4M:
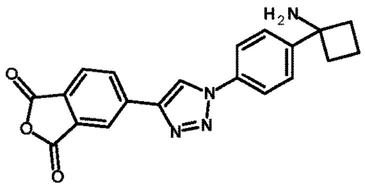
Figure 4M:
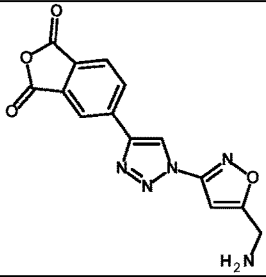
Figure 4M:
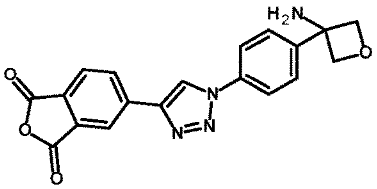
Figure 4M:
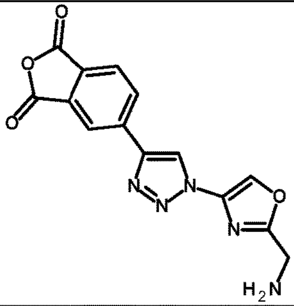
Figure 4M:
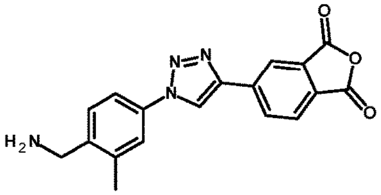
Figure 4M:
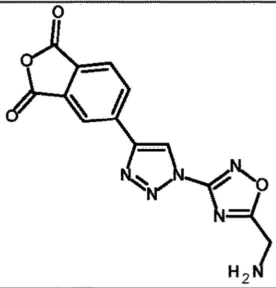
Figure 4M:
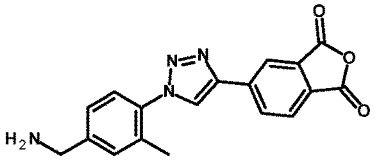
Figure 4M:
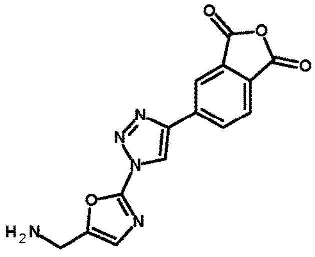
Figure 4M:
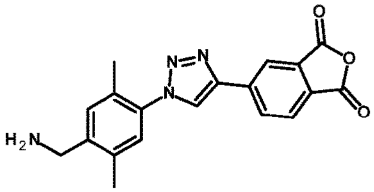
Figure 4M:
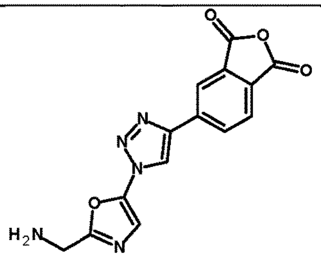
Figure 4N:
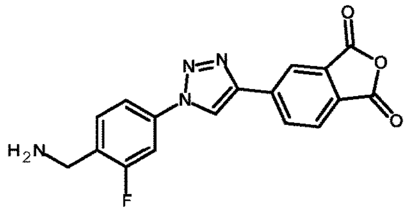
Figure 4N:
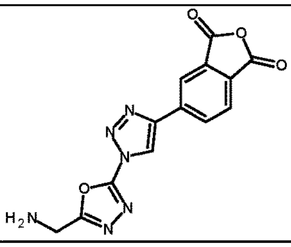
Figure 4N:
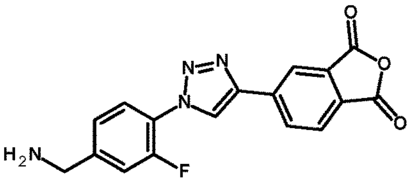
Figure 4N:
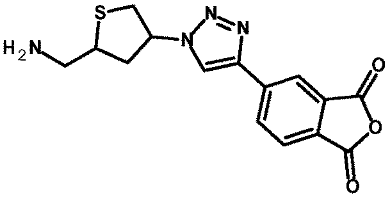
Figure 4N:
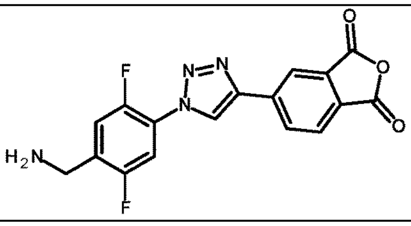
Figure 4N:
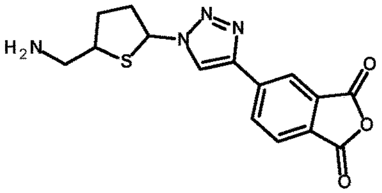
Figure 4N:
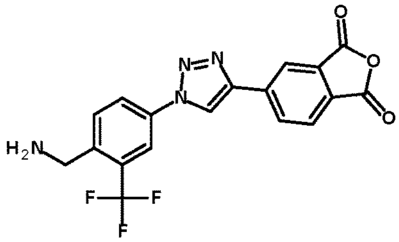
Figure 4N:
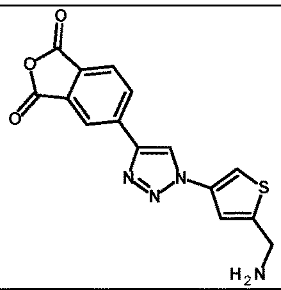
Figure 4N:
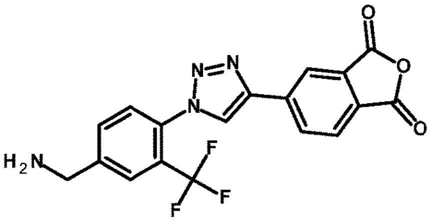
Figure 4N:
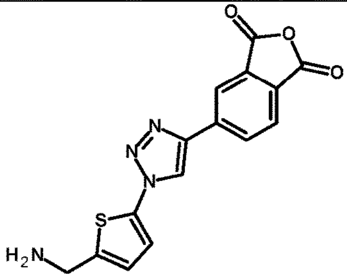
Figure 4N:
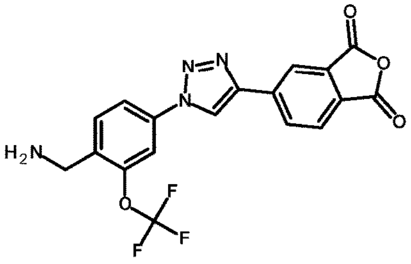
Figure 4N:
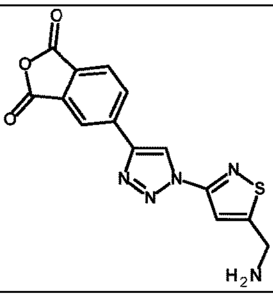
Figure 4O:
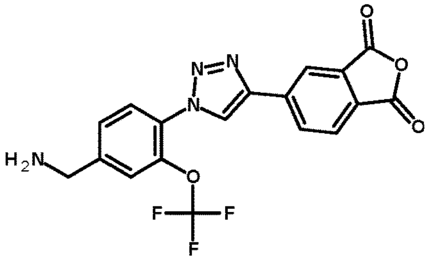
Figure 4O:
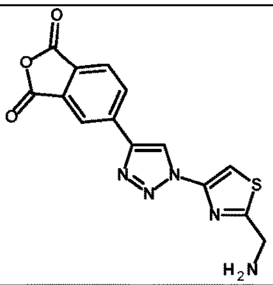
Figure 4O:
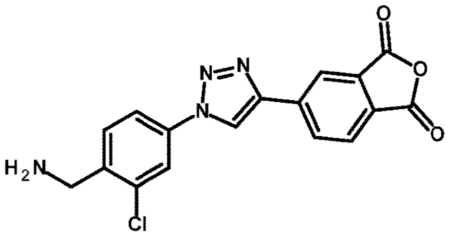
Figure 4O:
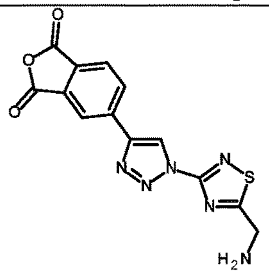
Figure 4O:
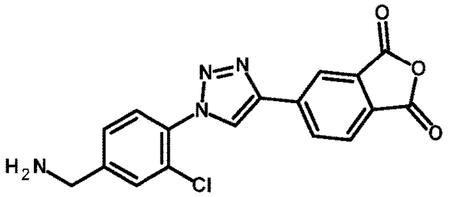
Figure 4O:
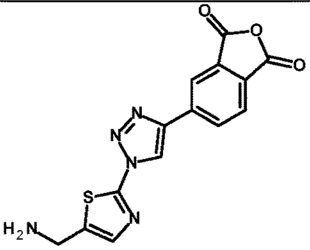
Figure 4O:
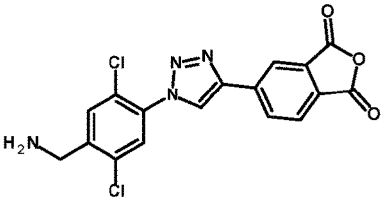
Figure 4O:
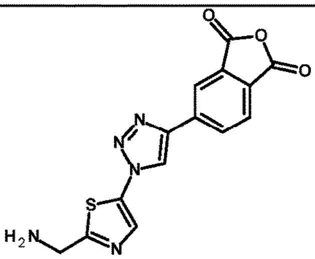
Figure 4O:
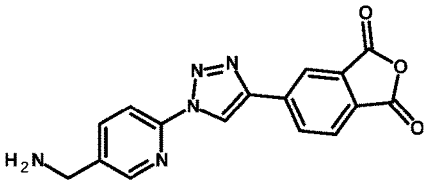
Figure 4O:
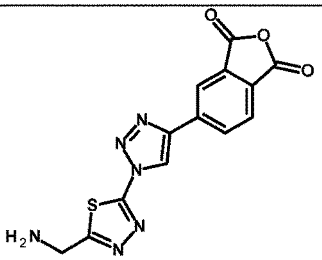
Figure 4O:
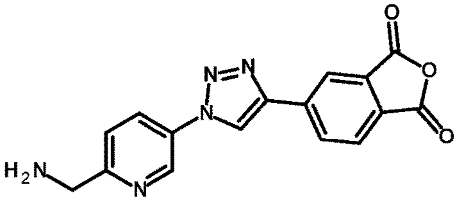
Figure 4O:
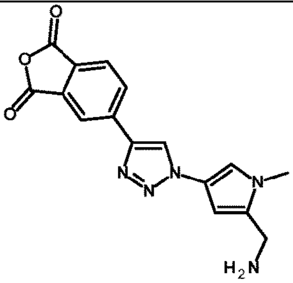
Figure 4P:
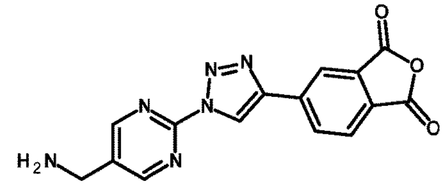
Figure 4P:
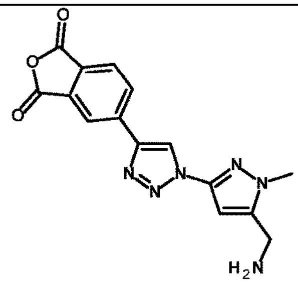
Figure 4P:
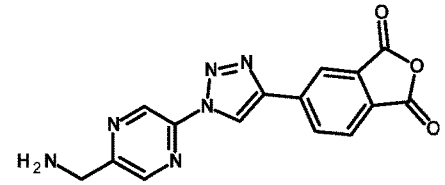
Figure 4P:
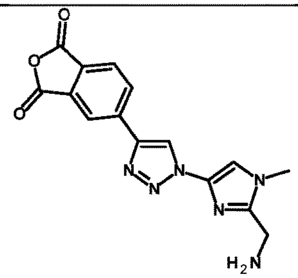
Figure 4P:
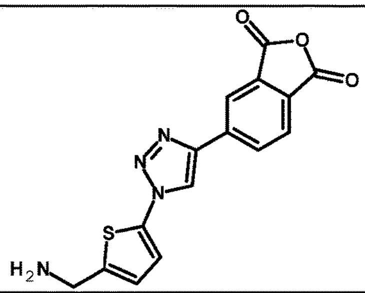
Figure 4P:
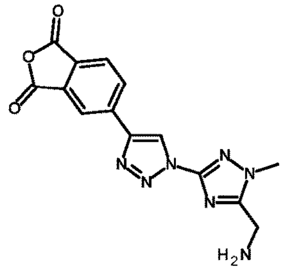
Figure 4P:
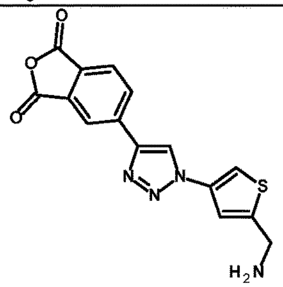
Figure 4P:
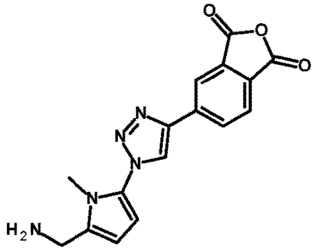
Figure 4P:
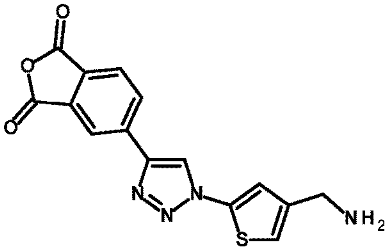
Figure 4P:
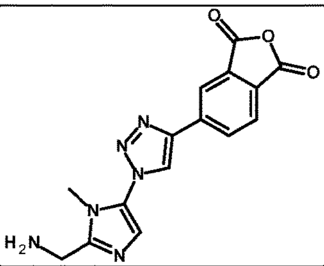
Figure 4P:
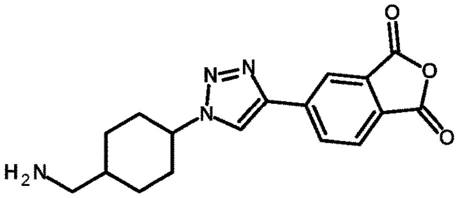
Figure 4P:
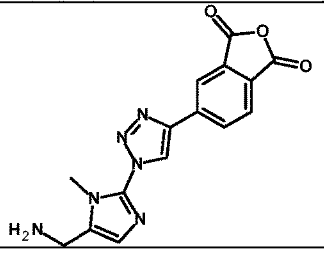
Figure 4Q:
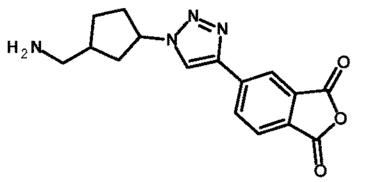
Figure 4Q:
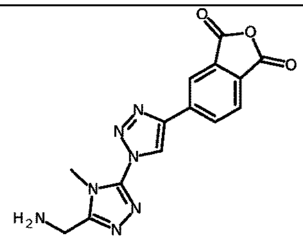
Figure 4Q:
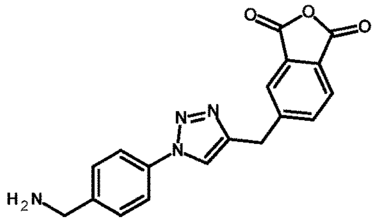
Figure 4Q:
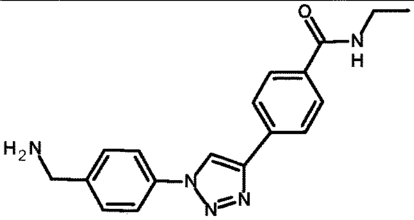
Figure 4Q:
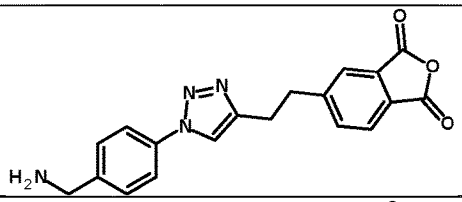
Figure 4Q:
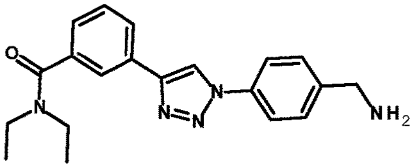
Figure 4Q:
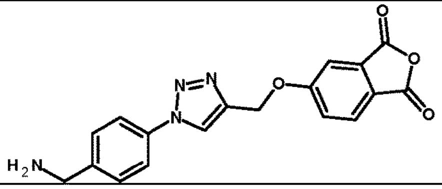
Figure 4Q:
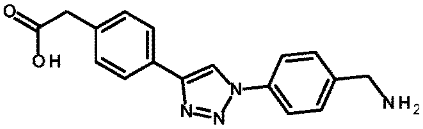
Figure 4Q:
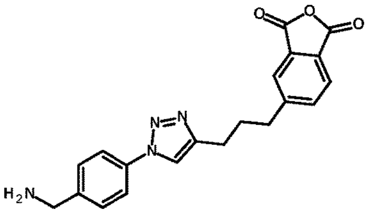
Figure 4Q:
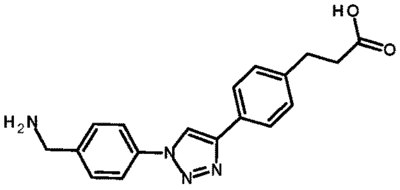
Figure 4Q:
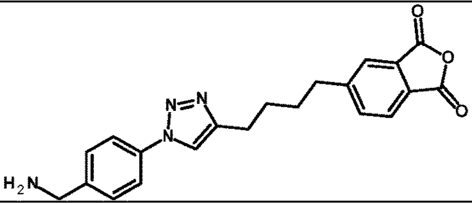
Figure 4Q:
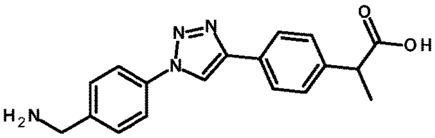
Figure 4Q:
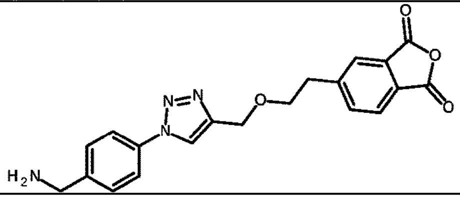
Figure 4Q:
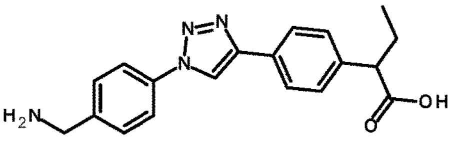
Figure 4R:
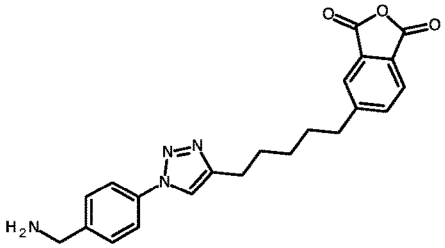
Figure 4R:
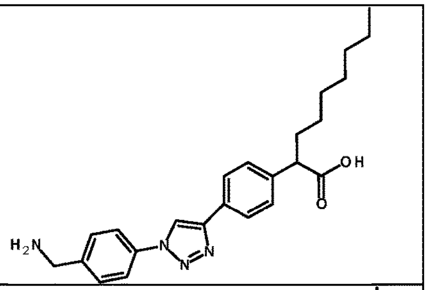
Figure 4R:
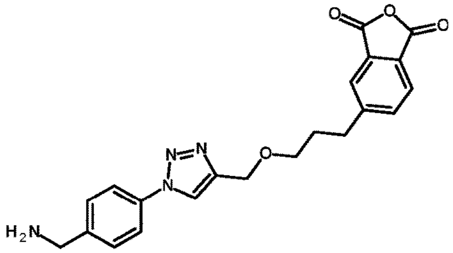
Figure 4R:
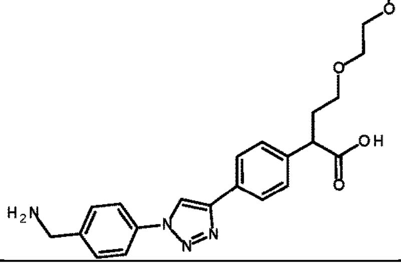
Figure 4R:
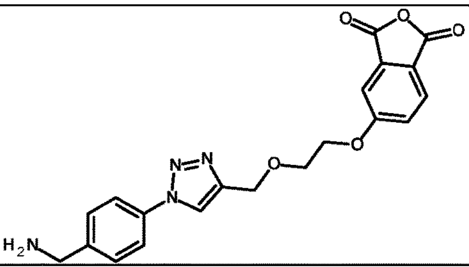
Figure 4R:
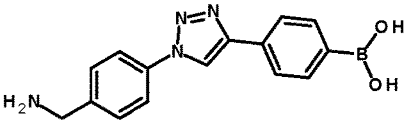
Figure 4R:
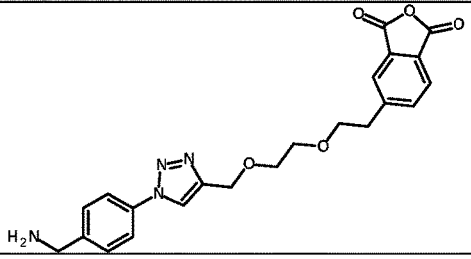
Figure 4R:
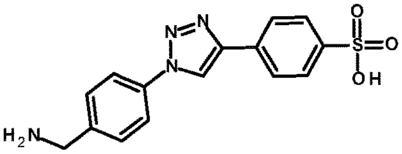
Figure 4R:
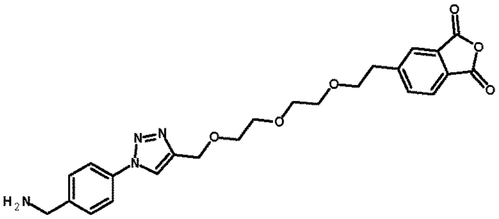
Figure 4R:
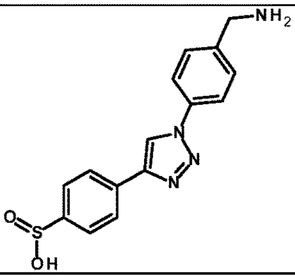
Figure 4R:
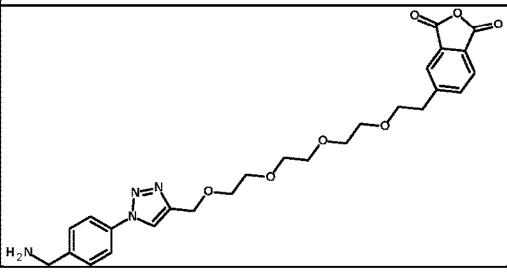
Figure 4R:
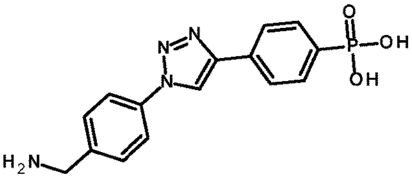
Figure 4S:
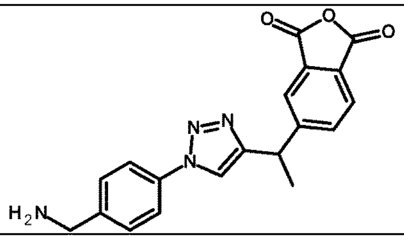
Figure 4S:
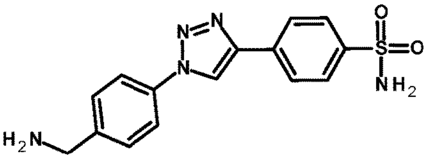
Figure 4S:
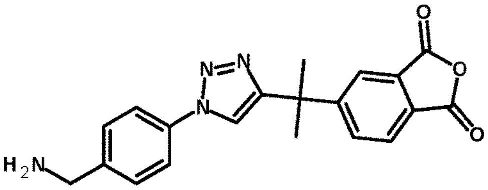
Figure 4S:
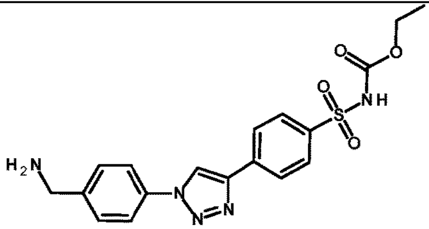
Figure 4S:
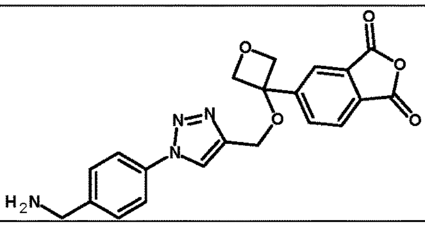
Figure 4S:
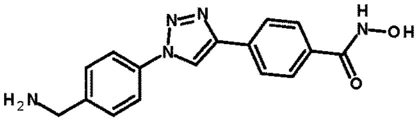
Figure 4S:
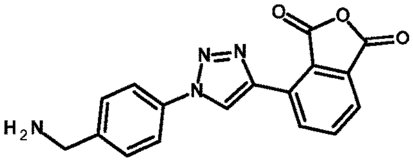
Figure 4S:
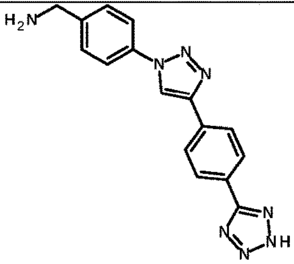
Figure 4S:
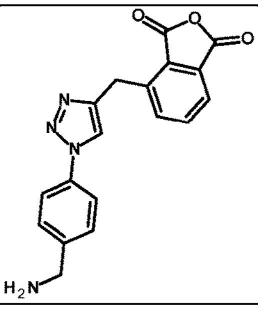
Figure 4S:
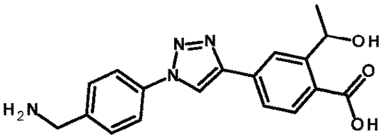
Figure 4S:
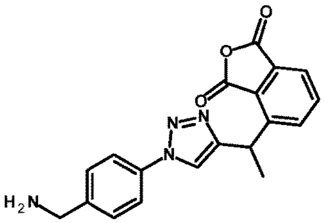
Figure 4S:
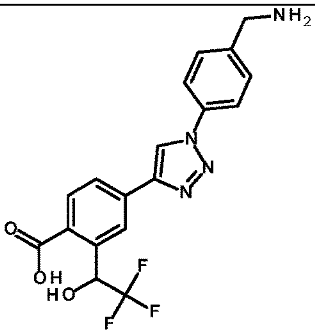
Figure 4T:
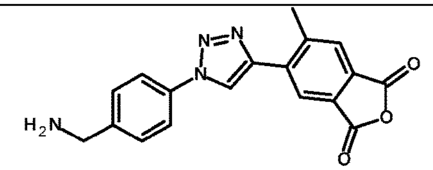
Figure 4T:
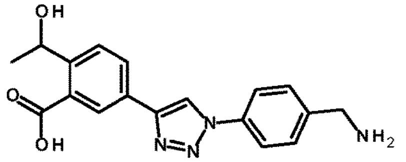
Figure 4T:
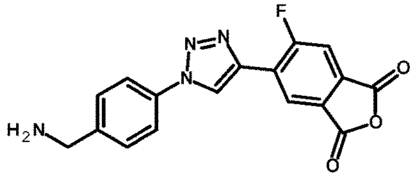
Figure 4T:
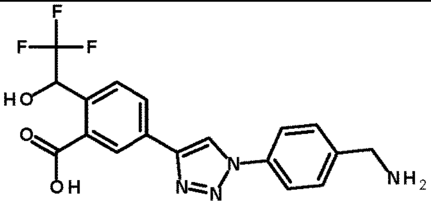
Figure 4T:
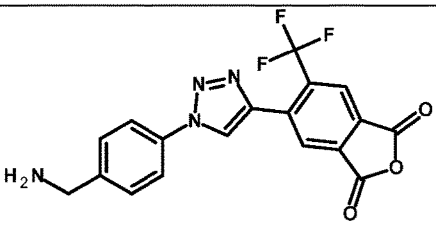
Figure 4T:
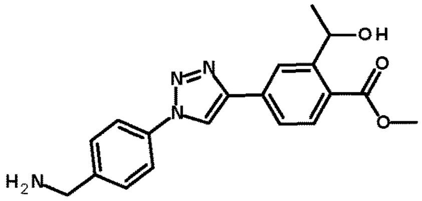
Figure 4T:
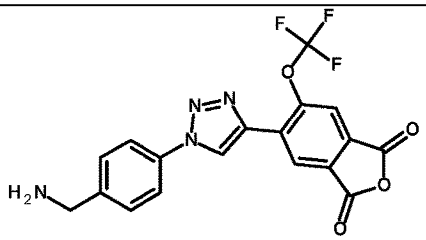
Figure 4T:
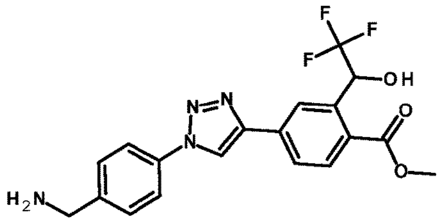
Figure 4T:
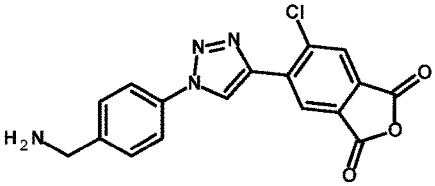
Figure 4T:
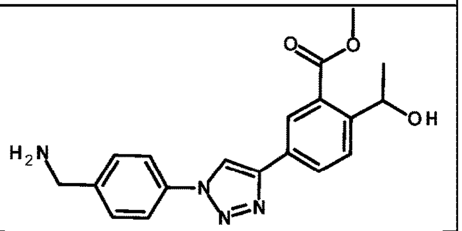
Figure 4T:
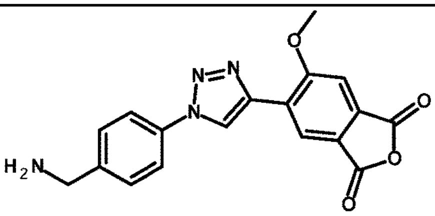
Figure 4T:
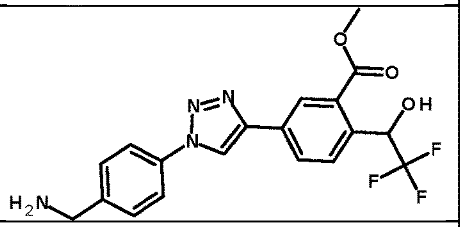
Figure 4T:
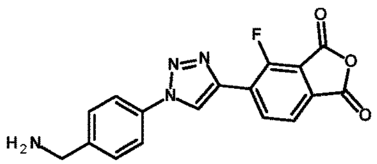
Figure 4T:
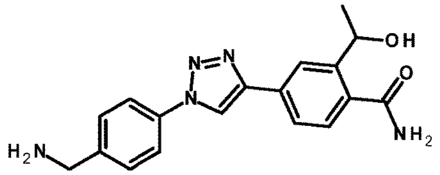
Figure 4U:
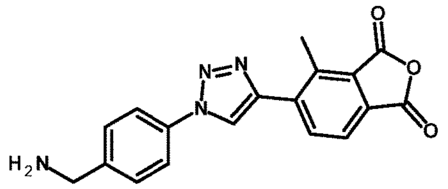
Figure 4U:
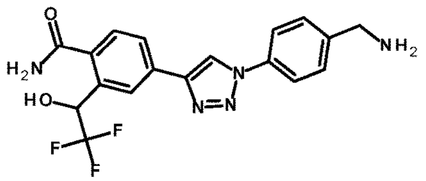
Figure 4U:
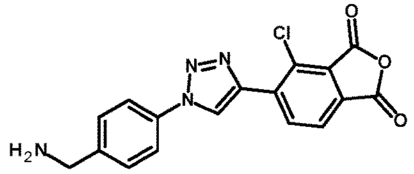
Figure 4U:
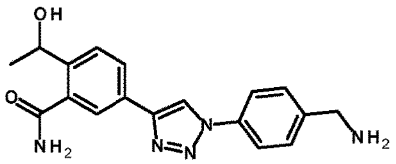
Figure 4U:
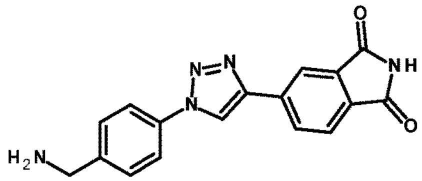
Figure 4U:
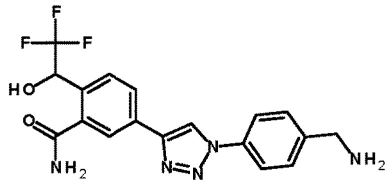
Figure 4U:
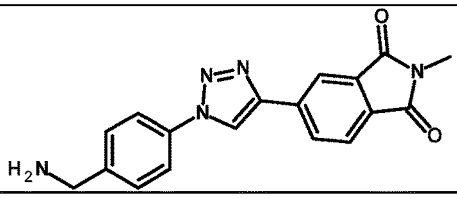
Figure 4U:
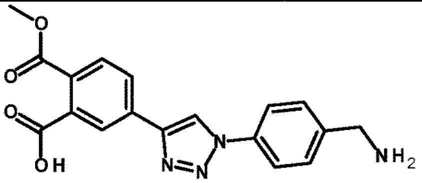
Figure 4U:
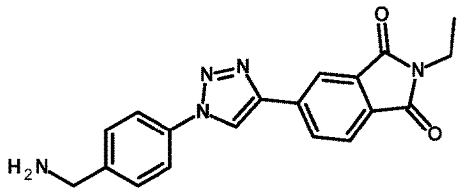
Figure 4U:
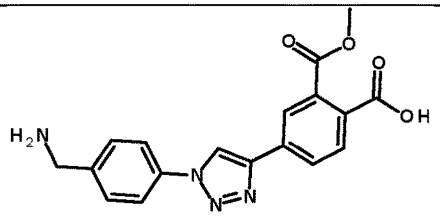
Figure 4U:
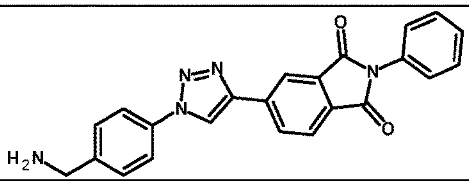
Figure 4U:
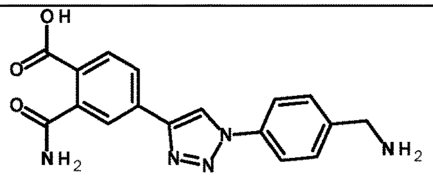
Figure 4U:
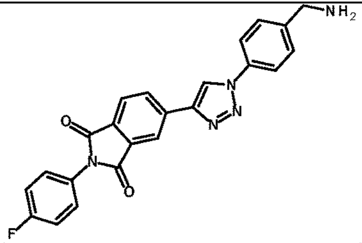
Figure 4U:
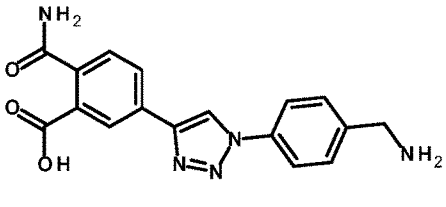
Figure 4U:
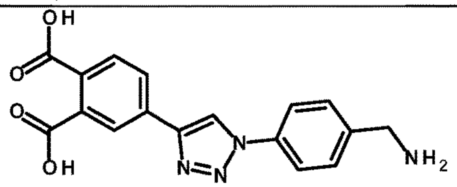
Figure 4U:
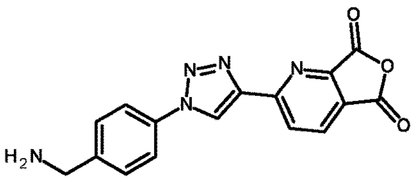
Figure 4V:
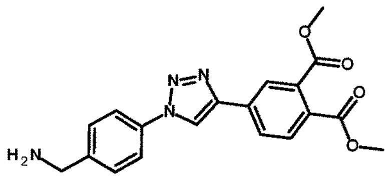
Figure 4V:
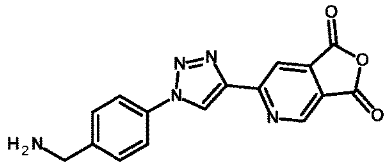
Figure 4V:
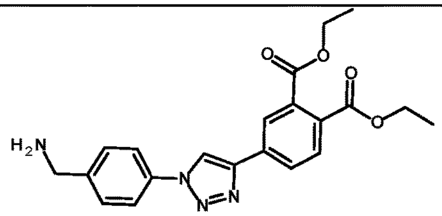
Figure 4V:
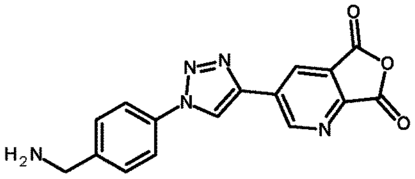
Figure 4V:
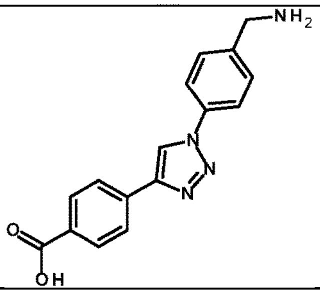
Figure 4V:
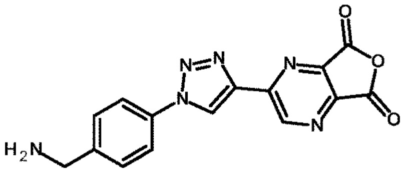
Figure 4V:
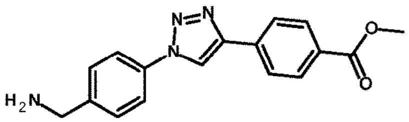
Figure 4V:
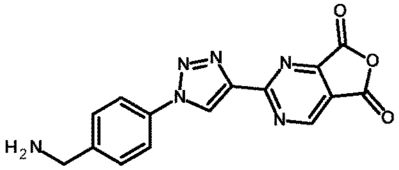
Figure 4V:
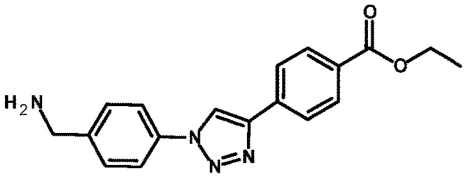
Figure 4V:
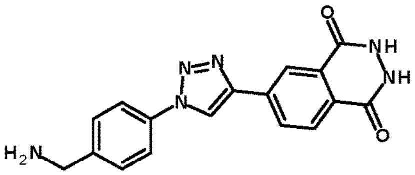
Figure 4V:
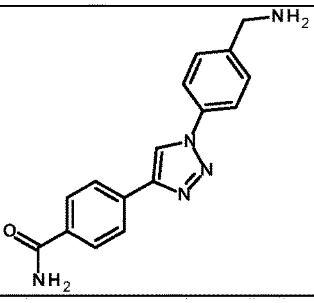
Figure 4V:
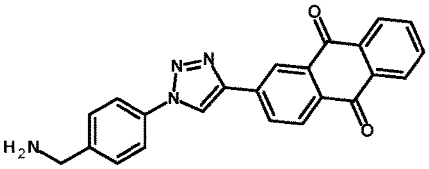
Figure 4V:
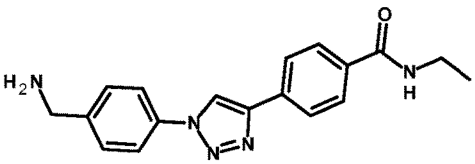
Figure 4V:
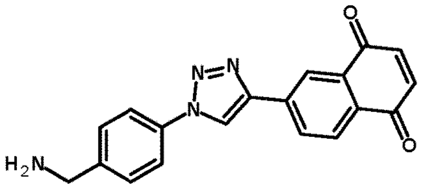
Figure 4W:
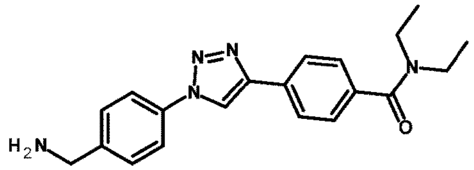
Figure 4W:
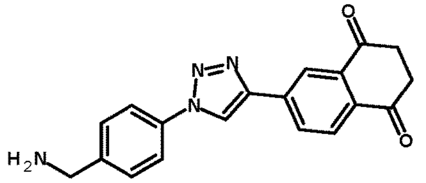
Figure 4W:
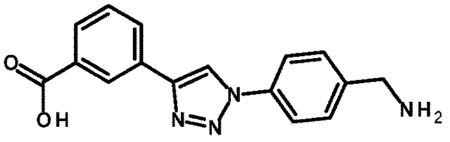
Figure 4W:
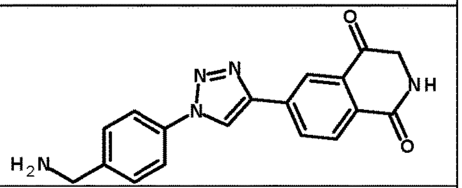
Figure 4W:
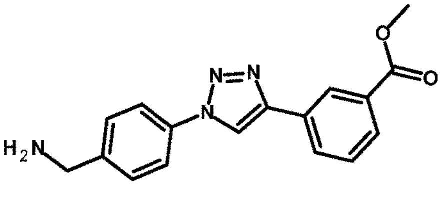
Figure 4W:
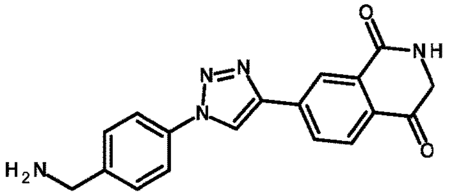
Figure 4W:
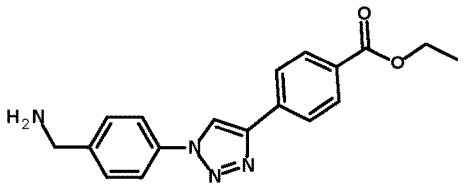
Figure 4W:
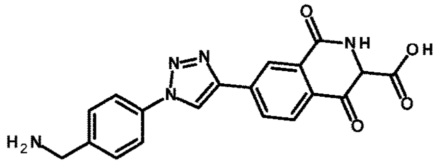
Figure 4W:
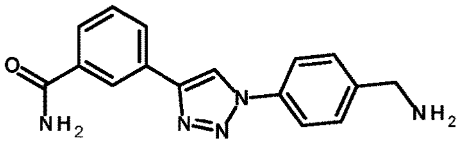
Figure 4W:
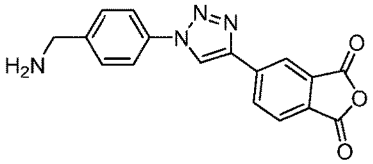
Figure 4W:
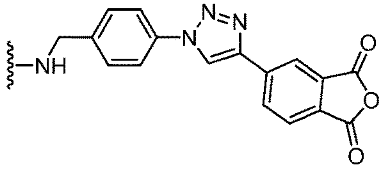
Figure 4W:
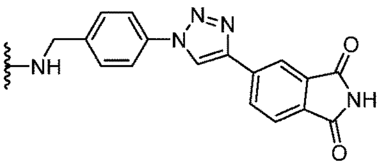
Figure 4W:
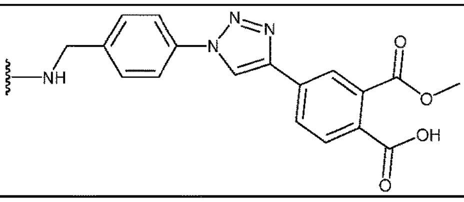
Figure 4W:
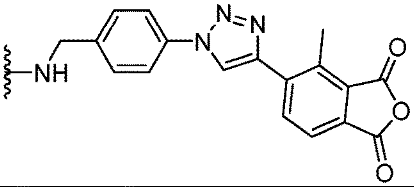
Figure 4X:
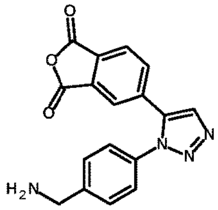
Figure 4X:
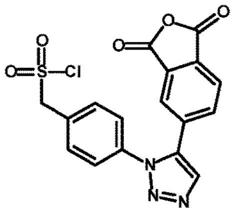
Figure 4X:
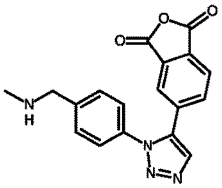
Figure 4X:
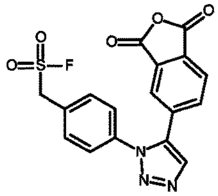
Figure 4X:
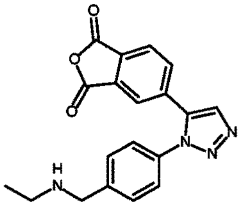
Figure 4X:
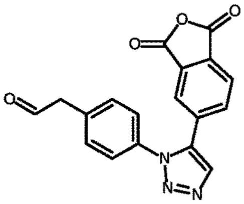
Figure 4X:
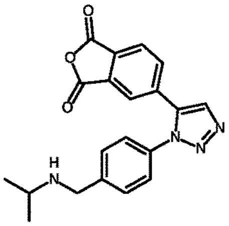
Figure 4X:
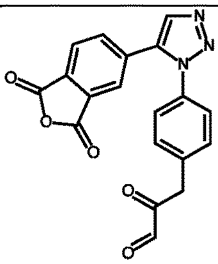
Figure 4X:
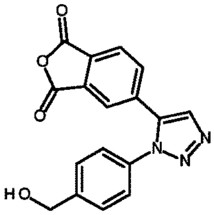
Figure 4X:
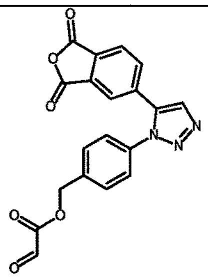
Figure 4X:
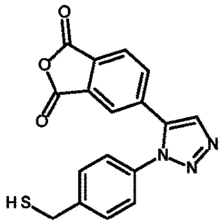
Figure 4X:
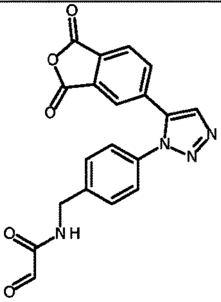
Figure 4Y:
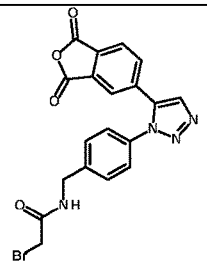
Figure 4Y:
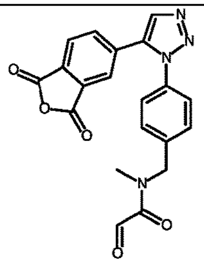
Figure 4Y:
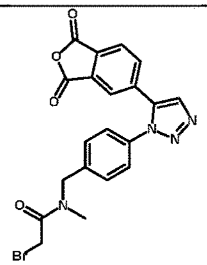
Figure 4Y:
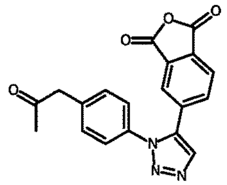
Figure 4Y:
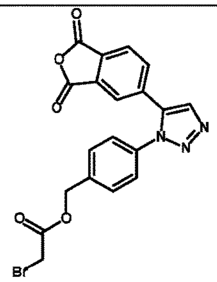
Figure 4Y:
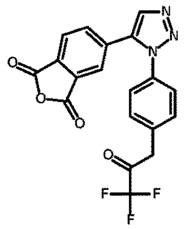
Figure 4Y:
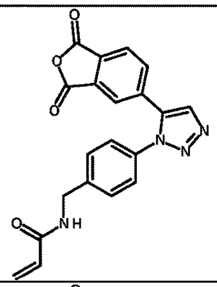
Figure 4Y:
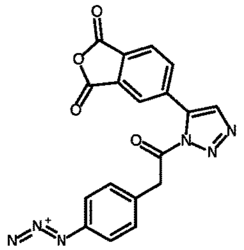
Figure 4Y:
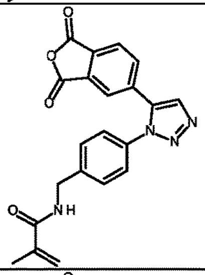
Figure 4Y:
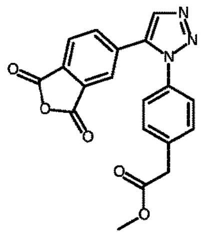
Figure 4Y:
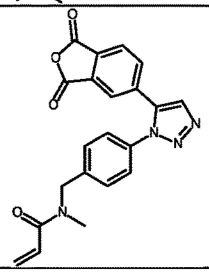
Figure 4Y:
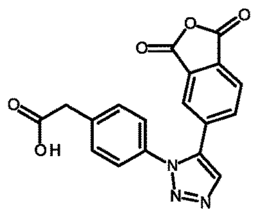
Figure 4Z:
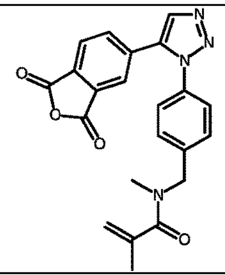
Figure 4Z:
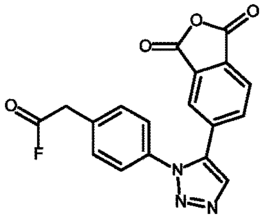
Figure 4Z:
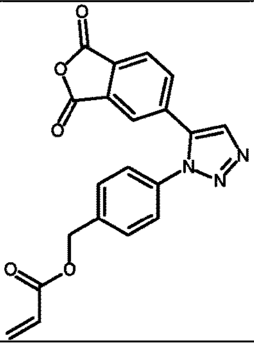
Figure 4Z:
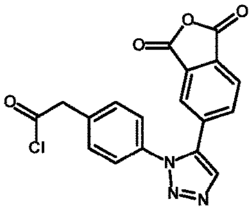
Figure 4Z:
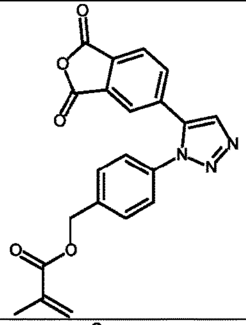
Figure 4Z:
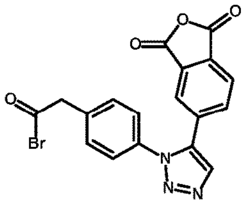
Figure 4Z:
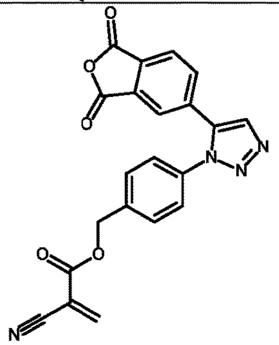
Figure 4Z:
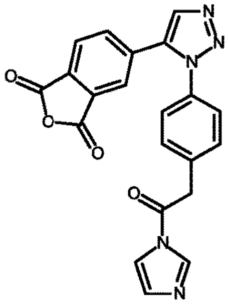
Figure 4Z:
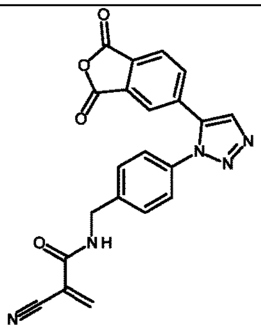
Figure 4Z:
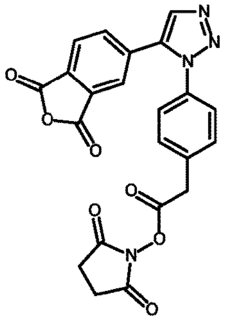
Figure 4A:
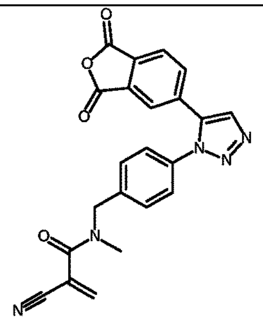
Figure 4A:
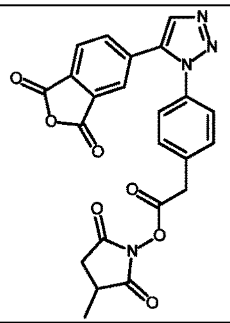
Figure 4A:
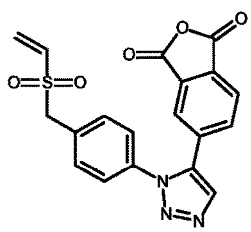
Figure 4A:
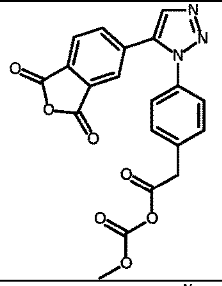
Figure 4A:
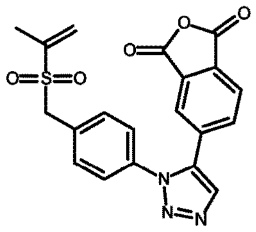
Figure 4A:
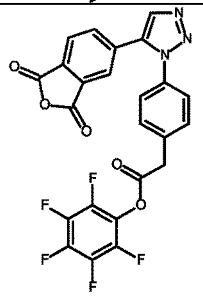
Figure 4A:
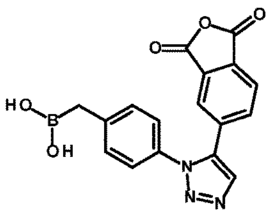
Figure 4A:
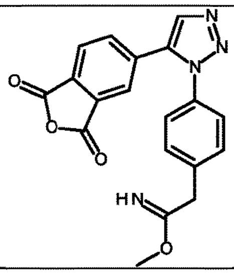
Figure 4A:
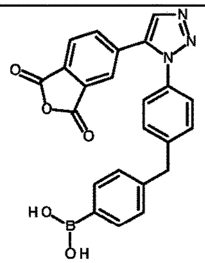
Figure 4A:
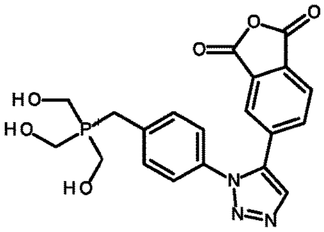
Figure 4A:
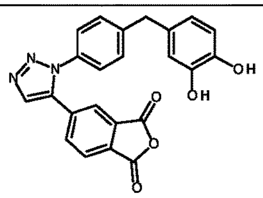
Figure 4A:
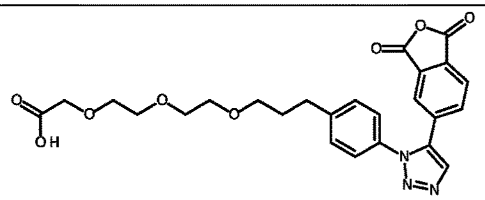
Figure 4B:
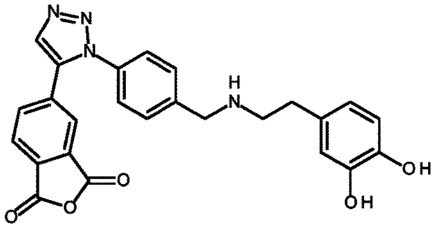
Figure 4B:
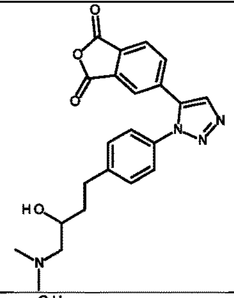
Figure 4B:
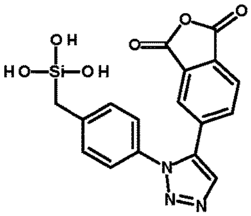
Figure 4B:
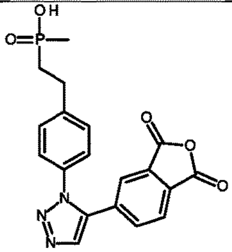
Figure 4B:
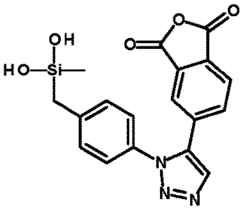
Figure 4B:
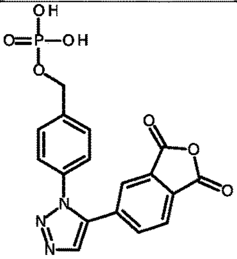
Figure 4B:
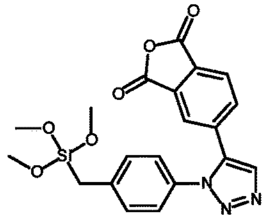
Figure 4B:
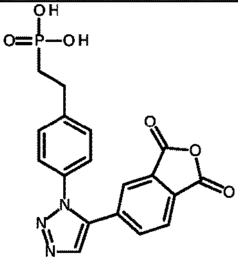
Figure 4B:
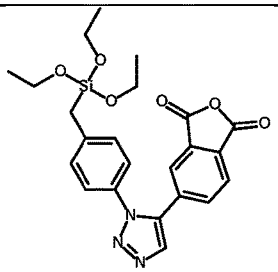
Figure 4B:
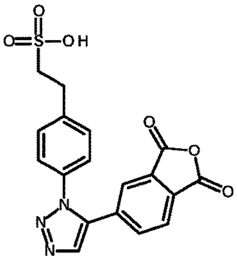
Figure 4B:
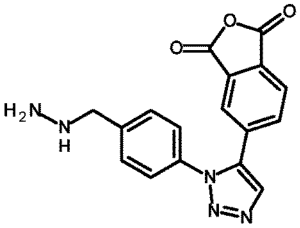
Figure 4B:
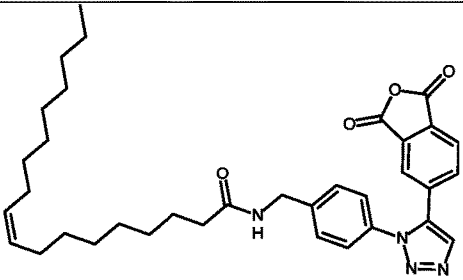
Figure 4C:
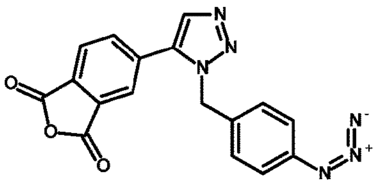
Figure 4C:
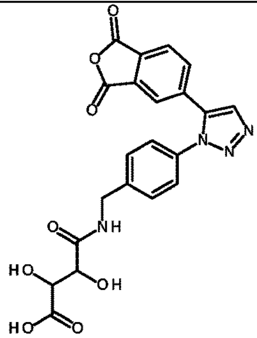
Figure 4C:
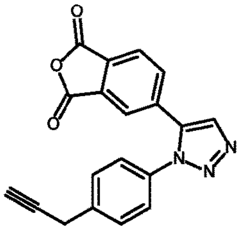
Figure 4C:
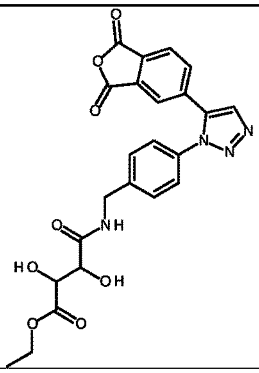
Figure 4C:
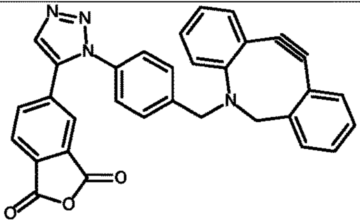
Figure 4C:
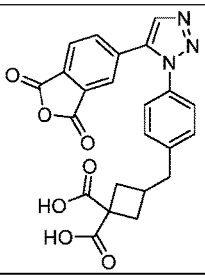
Figure 4C:
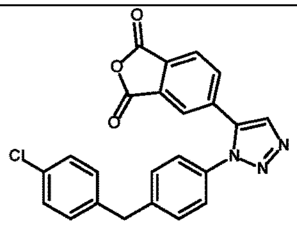
Figure 4C:
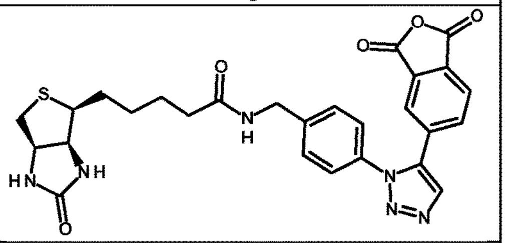
Figure 4C:
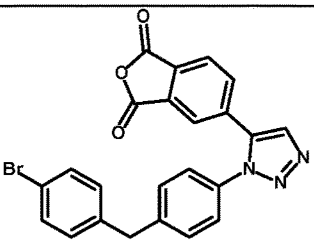
Figure 4C:
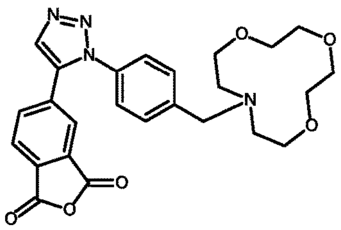
Figure 4D:
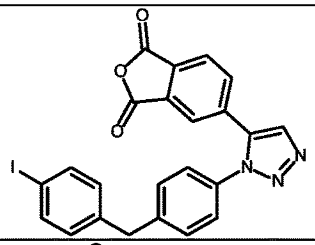
Figure 4D:
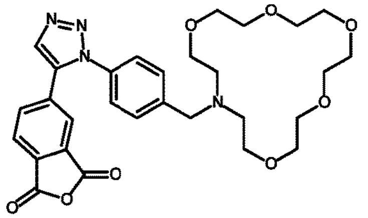
Figure 4D:
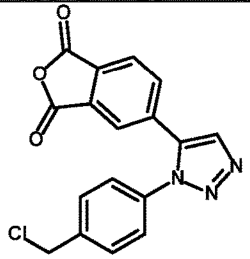
Figure 4D:
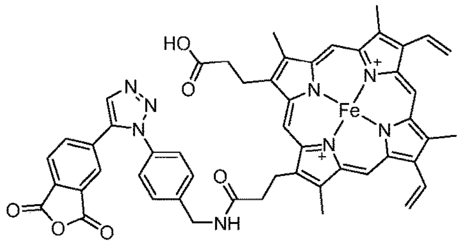
Figure 4D:
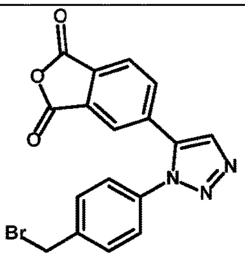
Figure 4D:
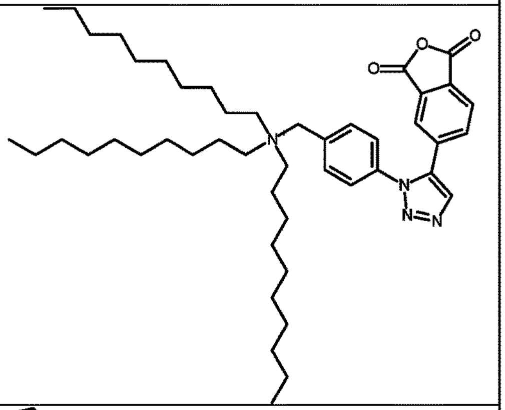
Figure 4D:
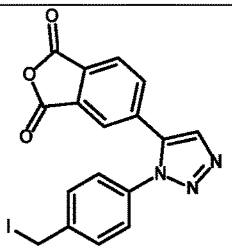
Figure 4D:
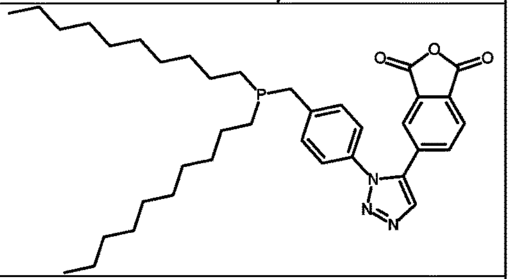
Figure 4D:
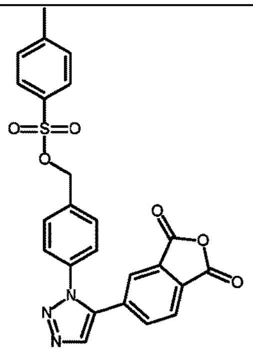
Figure 4D:
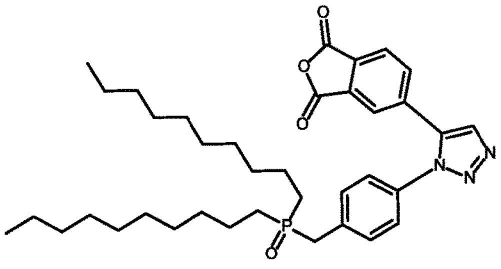
Figure 4E:
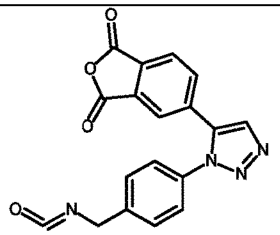
Figure 4E:
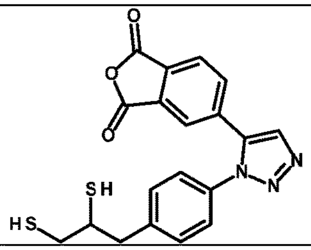
Figure 4E:
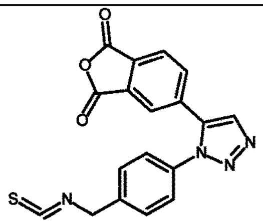
Figure 4E:
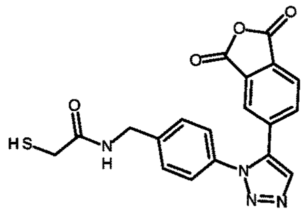
Figure 4E:
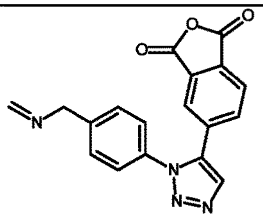
Figure 4E:
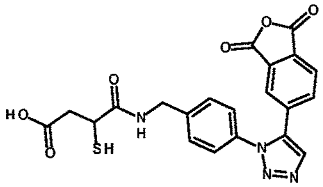
Figure 4E:
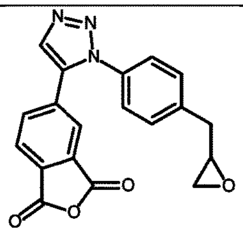
Figure 4E:
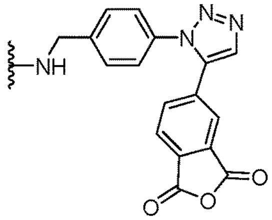
Figure 4E:
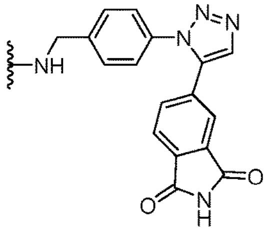
Figure 4E:
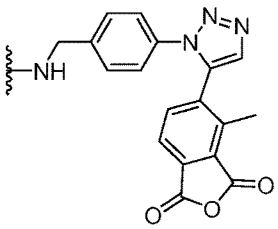
Figure 4E:
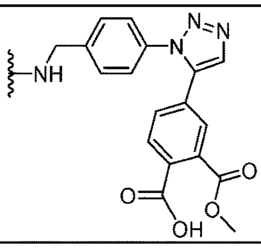
Figure 4F:
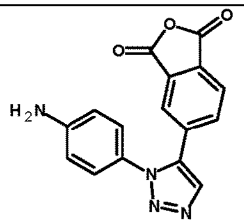
Figure 4F:
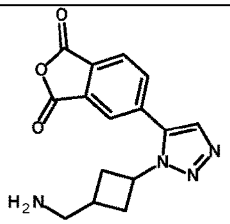
Figure 4F:
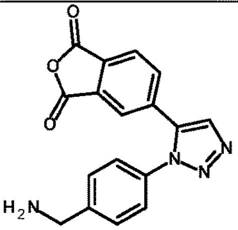
Figure 4F:
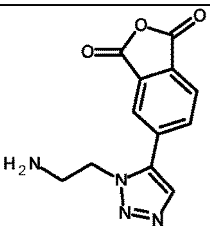
Figure 4F:
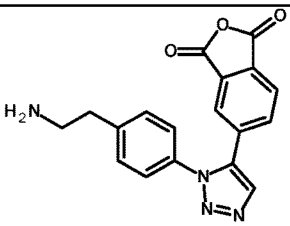
Figure 4F:
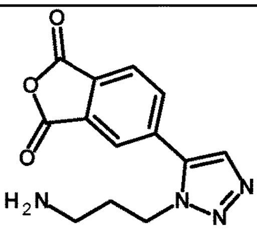
Figure 4F:
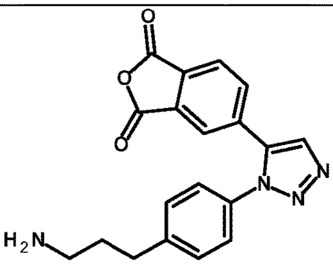
Figure 4F:
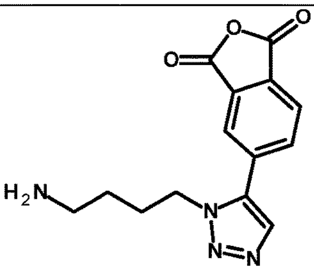
Figure 4F:
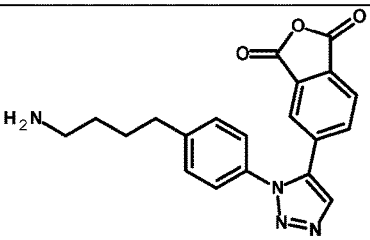
Figure 4F:
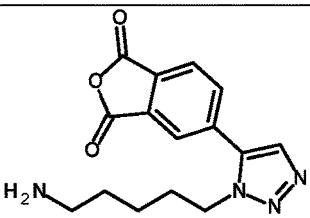
Figure 4F:
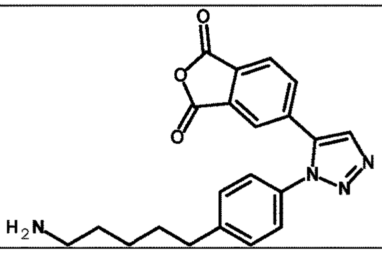
Figure 4F:
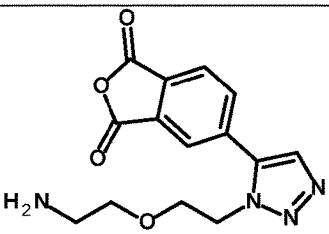
Figure 4G:
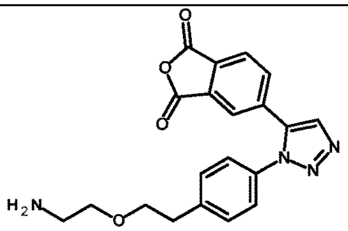
Figure 4G:
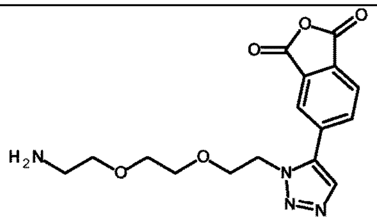
Figure 4G:
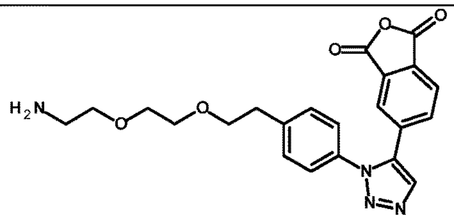
Figure 4G:
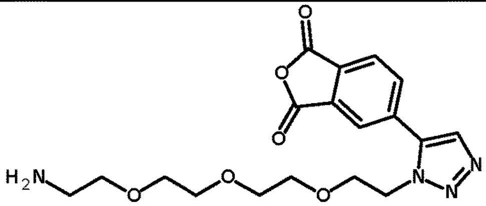
Figure 4G:
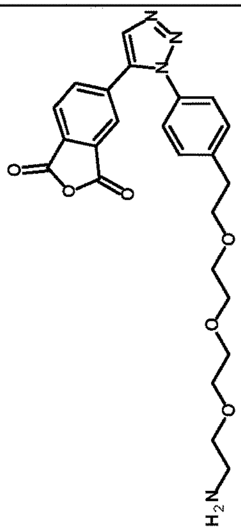
Figure 4G:
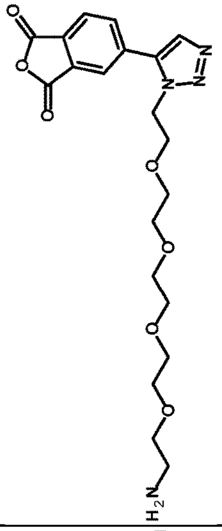
Figure 4G:
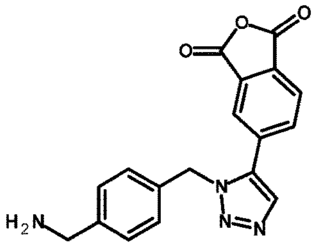
Figure 4G:
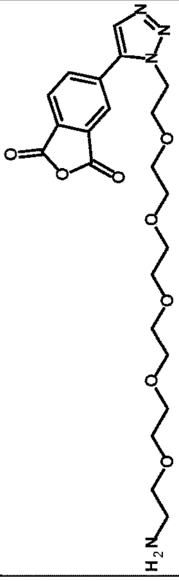
Figure 4H:
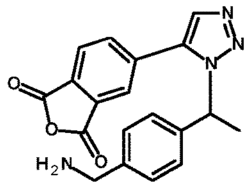
Figure 4H:
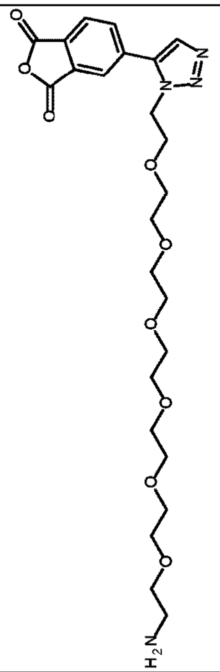
Figure 4H:
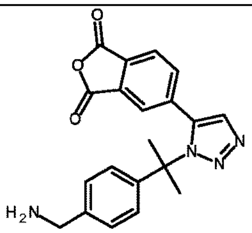
Figure 4H:
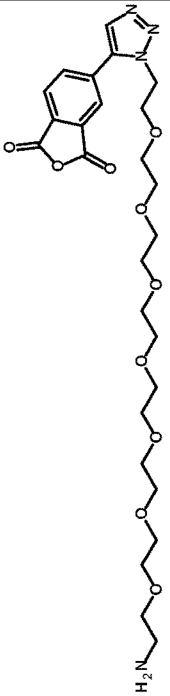
Figure 4H:
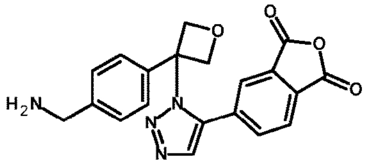
Figure 4H:
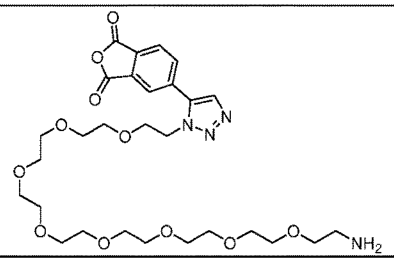
Figure 4I:
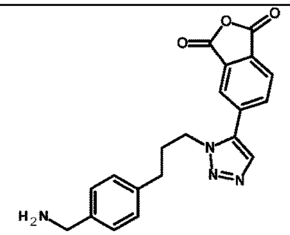
Figure 4I:
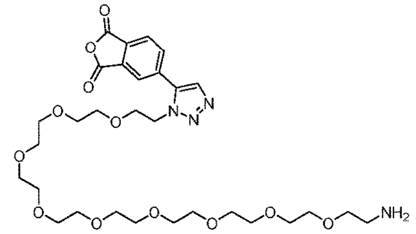
Figure 4I:
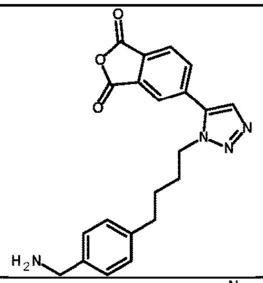
Figure 4I:
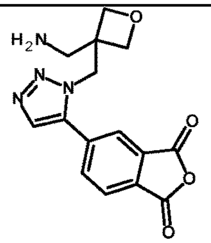
Figure 4I:
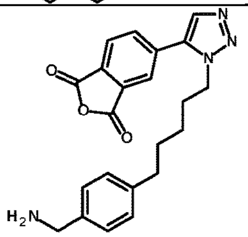
Figure 4I:
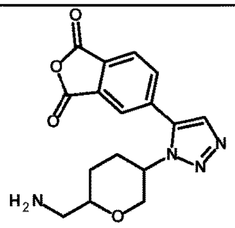
Figure 4I:
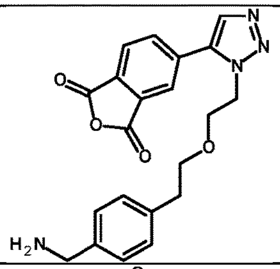
Figure 4I:
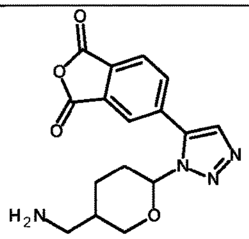
Figure 4I:
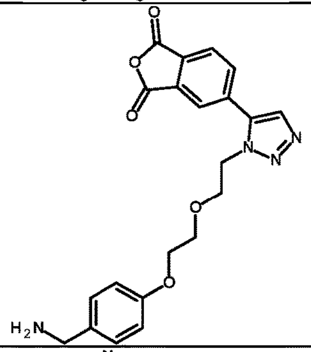
Figure 4I:
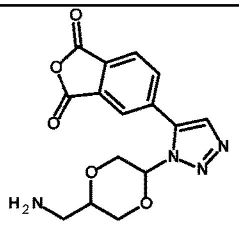
Figure 4I:
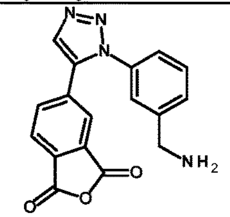
Figure 4I:
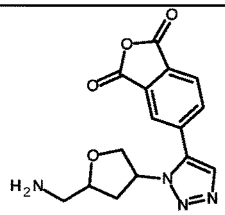
Figure 4J:
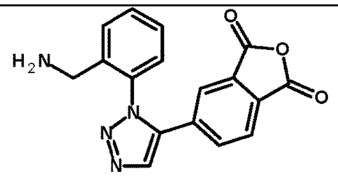
Figure 4J:
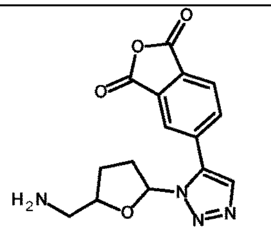
Figure 4J:
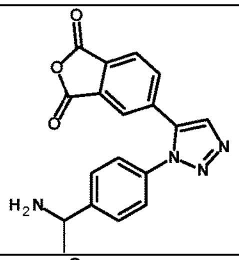
Figure 4J:
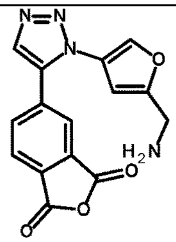
Figure 4J:
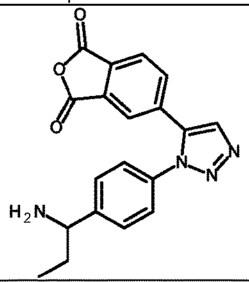
Figure 4J:
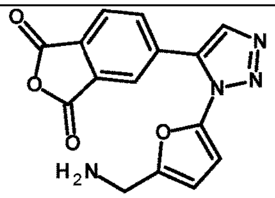
Figure 4J:
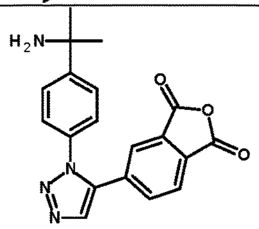
Figure 4J:
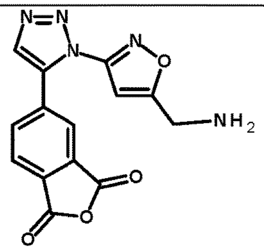
Figure 4J:
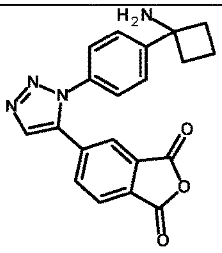
Figure 4J:
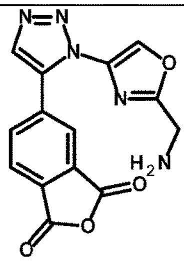
Figure 4J:
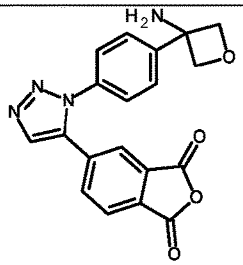
Figure 4J:
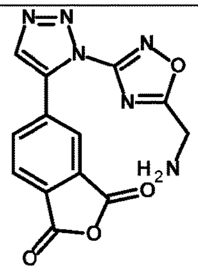
Figure 4K:
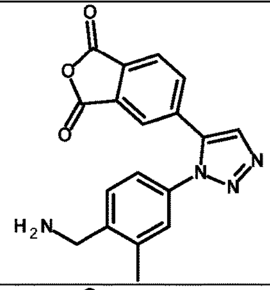
Figure 4K:
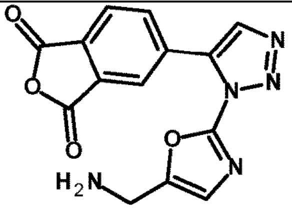
Figure 4K:
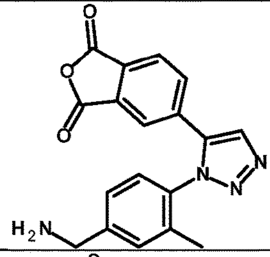
Figure 4K:
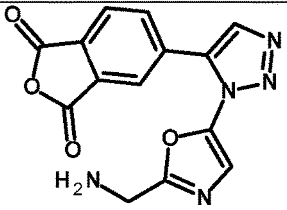
Figure 4K:
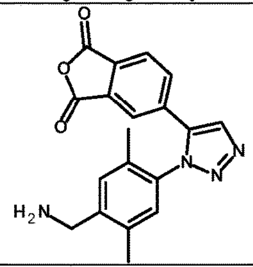
Figure 4K:
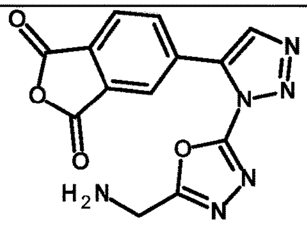
Figure 4K:
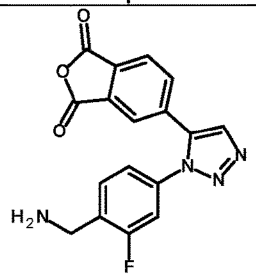
Figure 4K:
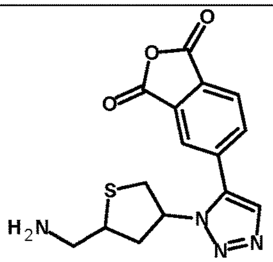
Figure 4K:
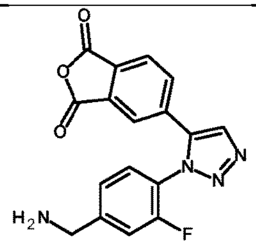
Figure 4K:
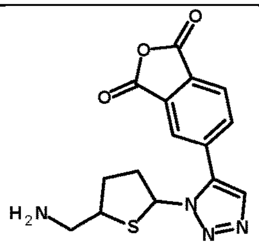
Figure 4K:
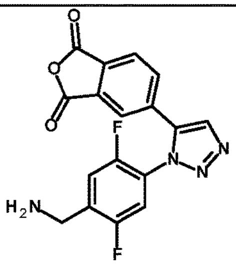
Figure 4K:
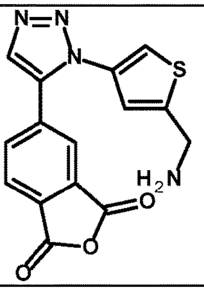
Figure 4L:
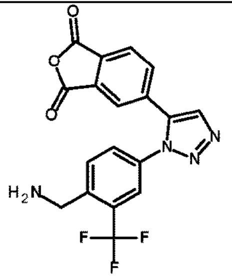
Figure 4L:
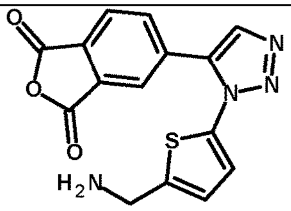
Figure 4L:
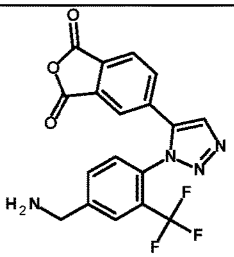
Figure 4L:
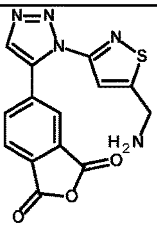
Figure 4L:
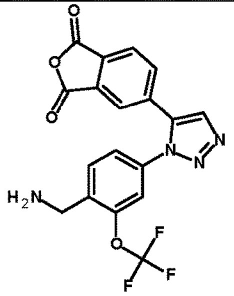
Figure 4L:
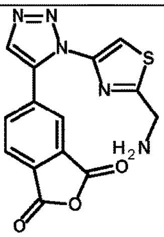
Figure 4L:
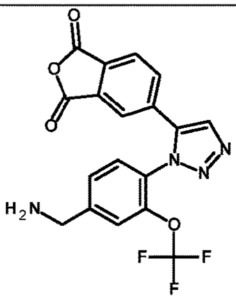
Figure 4L:
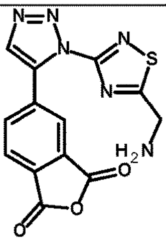
Figure 4L:
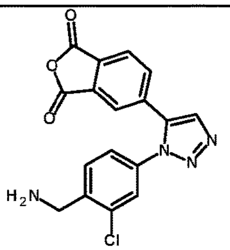
Figure 4L:
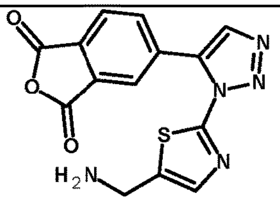
Figure 4L:
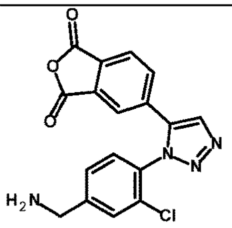
Figure 4L:
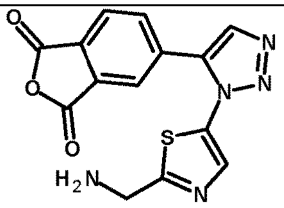
Figure 4M:
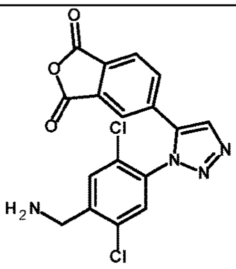
Figure 4M:
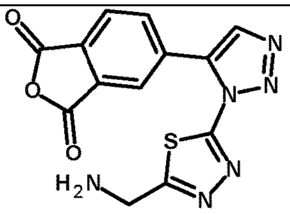
Figure 4M:
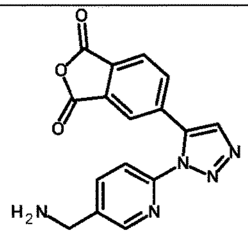
Figure 4M:
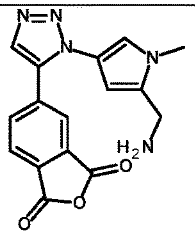
Figure 4M:
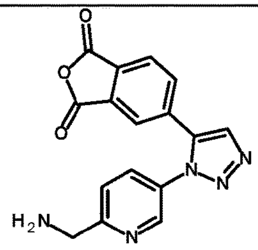
Figure 4M:
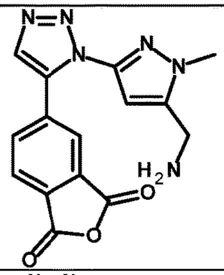
Figure 4M:
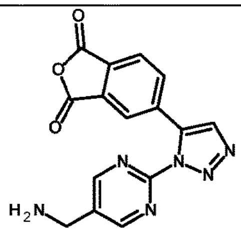
Figure 4M:
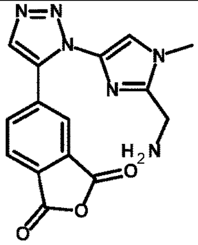
Figure 4M:
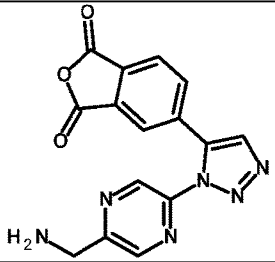
Figure 4M:
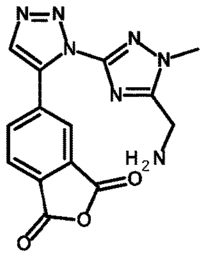
Figure 4M:
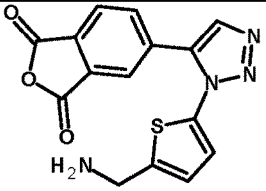
Figure 4M:
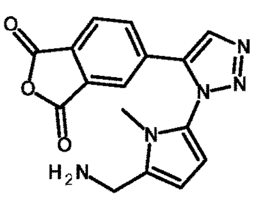
Figure 4N:
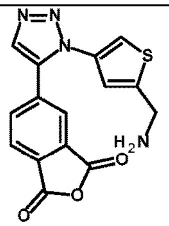
Figure 4N:
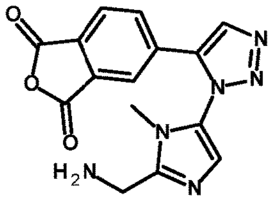
Figure 4N:
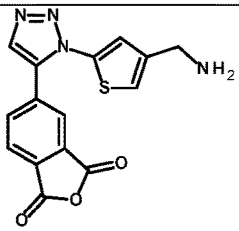
Figure 4N:
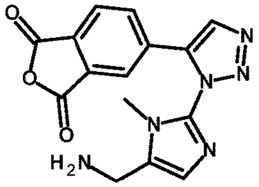
Figure 4N:
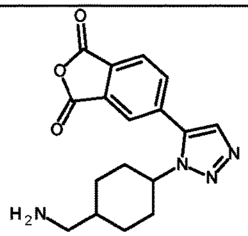
Figure 4N:
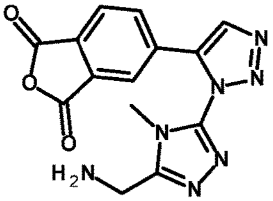
Figure 4N:
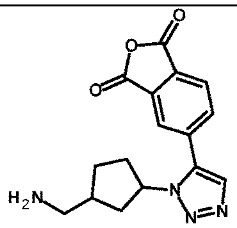
Figure 4N:
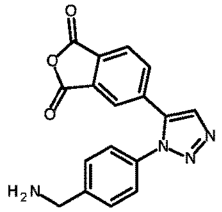
Figure 4N:
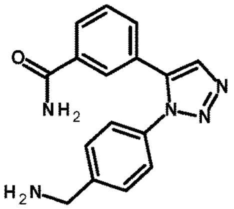
Figure 4N:
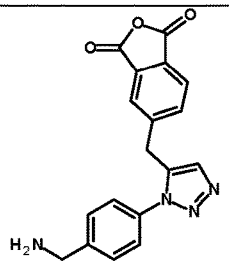
Figure 4N:
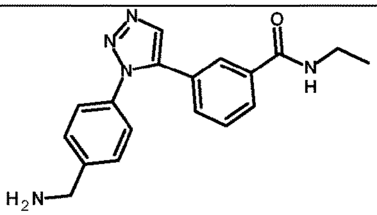
Figure 4O:
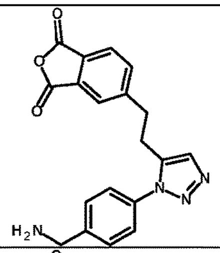
Figure 4O:
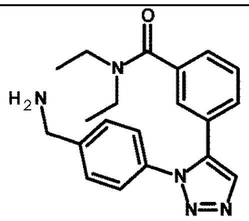
Figure 4O:
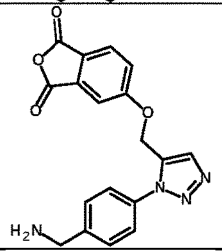
Figure 4O:
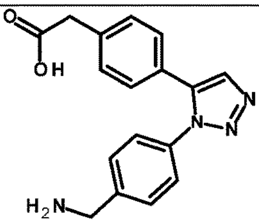
Figure 4O:
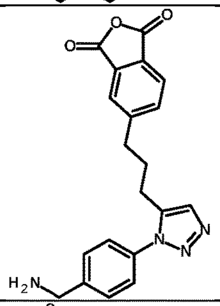
Figure 4O:
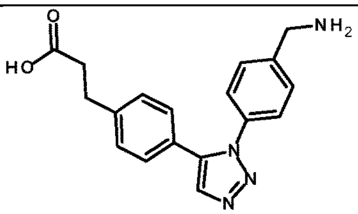
Figure 4O:
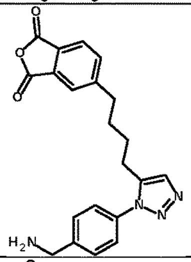
Figure 4O:
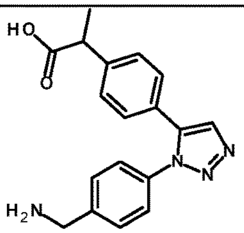
Figure 4O:
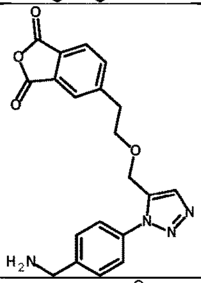
Figure 4O:
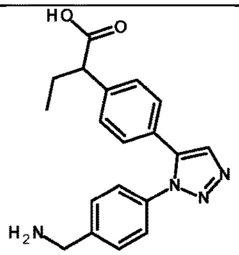
Figure 4O:
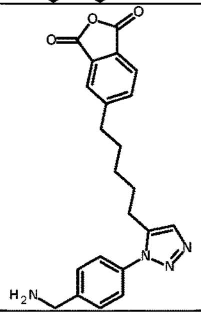
Figure 4O:
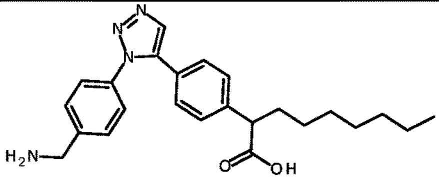
Figure 4P:
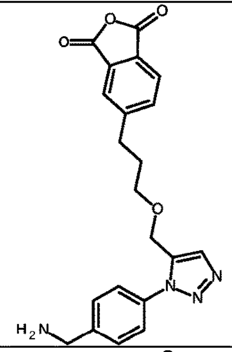
Figure 4P:
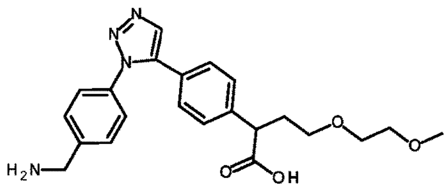
Figure 4P:
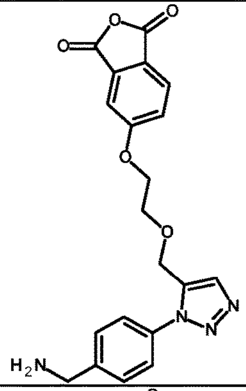
Figure 4P:
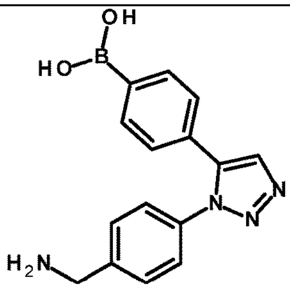
Figure 4P:
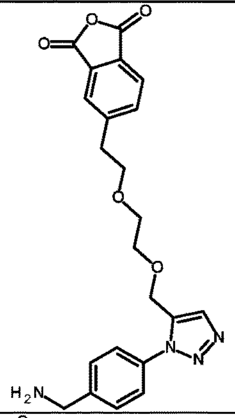
Figure 4P:
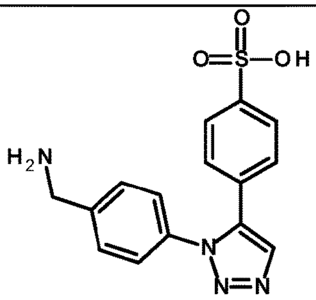
Figure 4P:
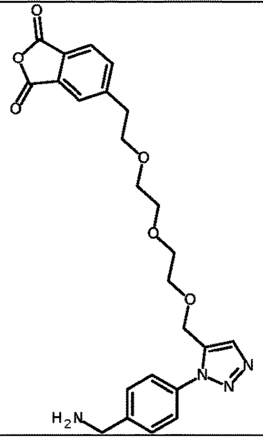
Figure 4P:
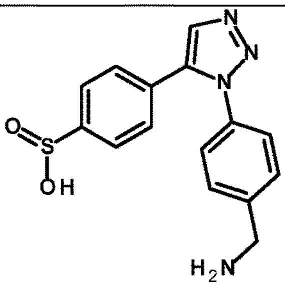
Figure 4Q:
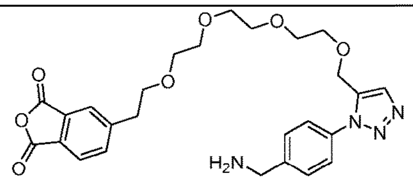
Figure 4Q:
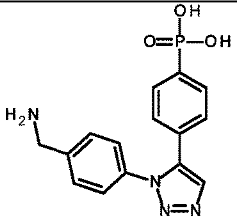
Figure 4Q:
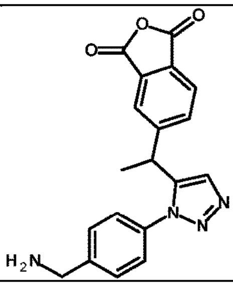
Figure 4Q:
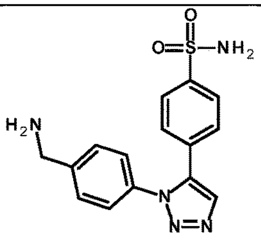
Figure 4Q:
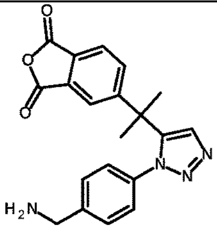
Figure 4Q:
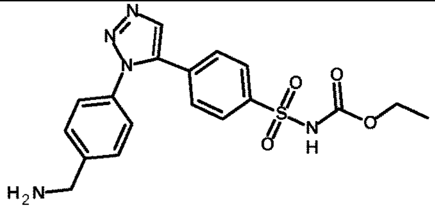
Figure 4Q:
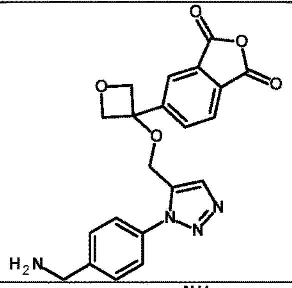
Figure 4Q:
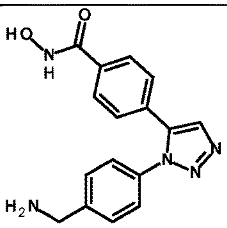
Figure 4Q:
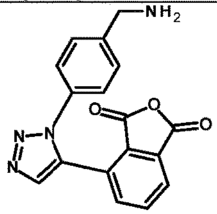
Figure 4Q:
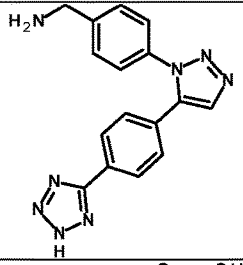
Figure 4Q:
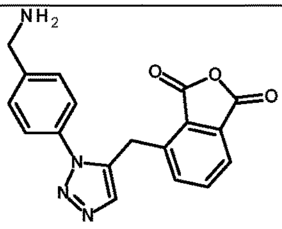
Figure 4Q:
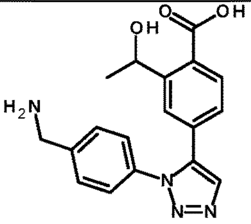
Figure 4R:
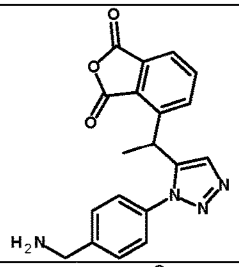
Figure 4R:
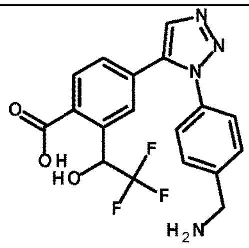
Figure 4R:
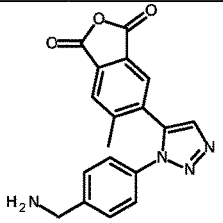
Figure 4R:
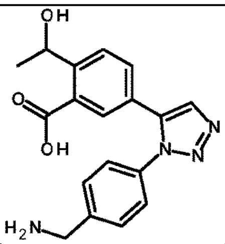
Figure 4R:
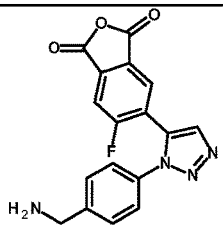
Figure 4R:
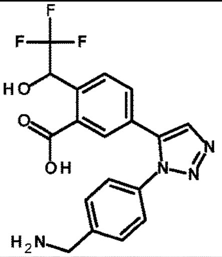
Figure 4R:
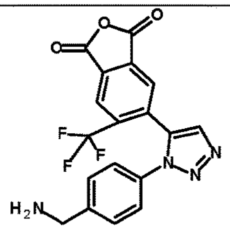
Figure 4R:
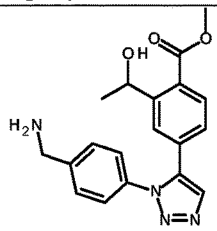
Figure 4R:
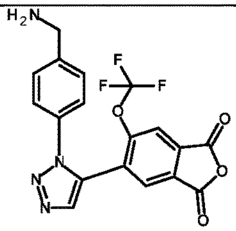
Figure 4R:
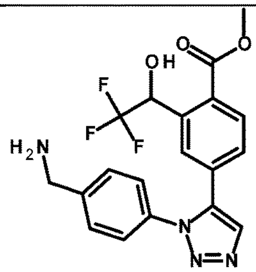
Figure 4R:
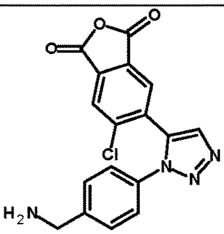
Figure 4R:
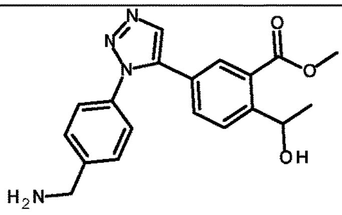
Figure 4S:
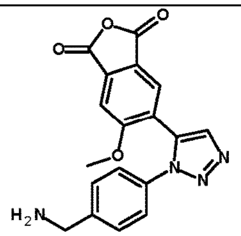
Figure 4S:
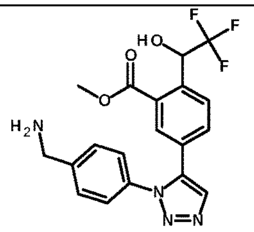
Figure 4S:
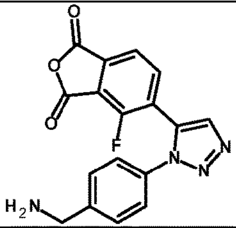
Figure 4S:
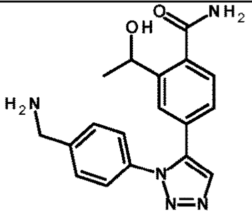
Figure 4S:
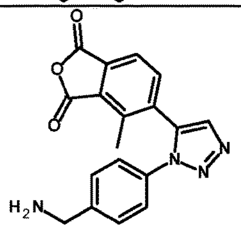
Figure 4S:
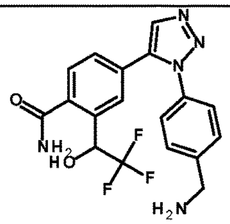
Figure 4S:
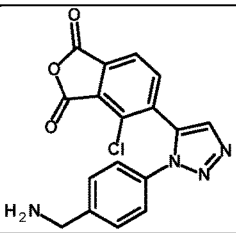
Figure 4S:
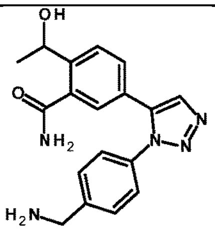
Figure 4S:
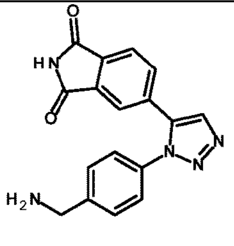
Figure 4S:
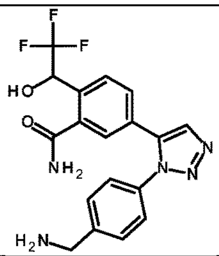
Figure 4S:
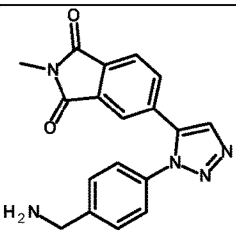
Figure 4S:
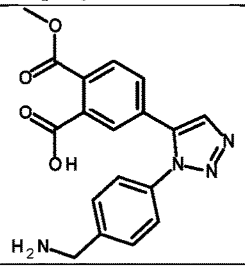
Figure 4T:
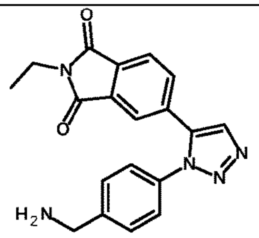
Figure 4T:
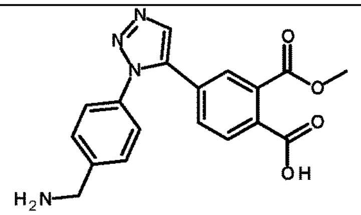
Figure 4T:
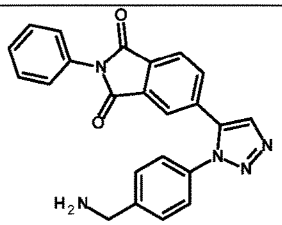
Figure 4T:
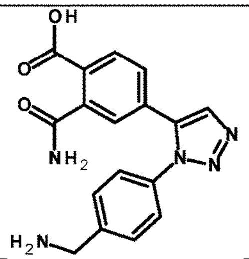
Figure 4T:
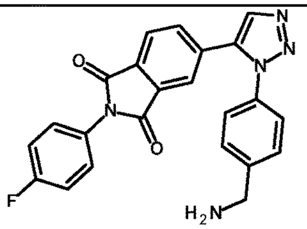
Figure 4T:
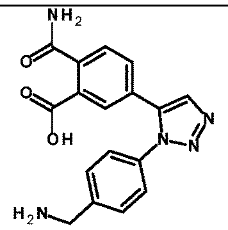
Figure 4T:
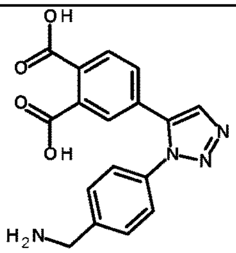
Figure 4T:
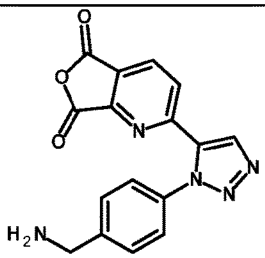
Figure 4T:
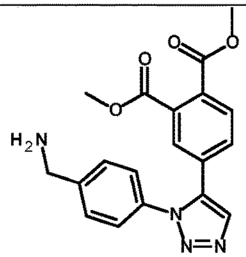
Figure 4T:
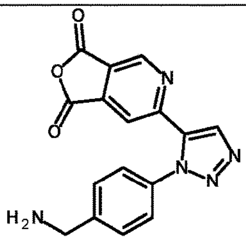
Figure 4T:
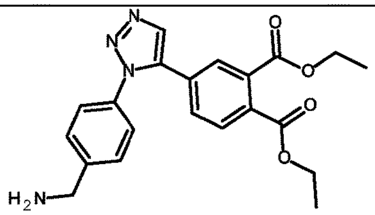
Figure 4T:
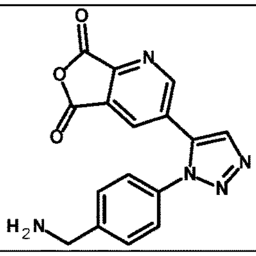
Figure 4U:
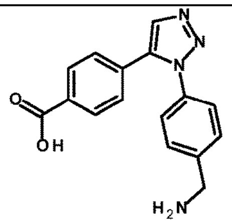
Figure 4U:
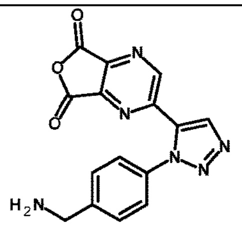
Figure 4U:
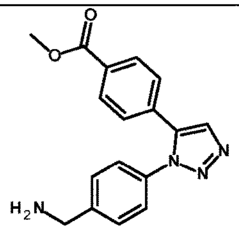
Figure 4U:
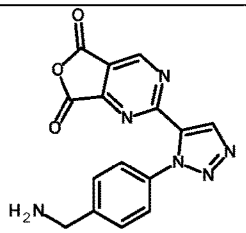
Figure 4U:
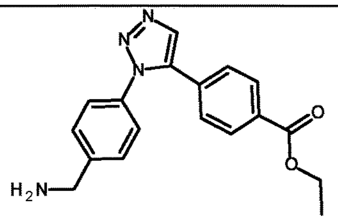
Figure 4U:
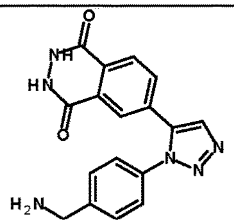
Figure 4U:
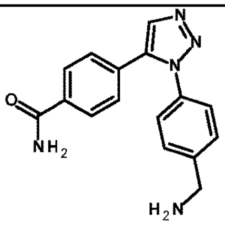
Figure 4U:
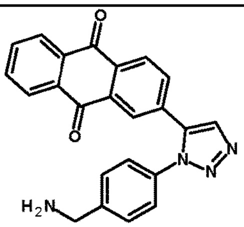
Figure 4U:
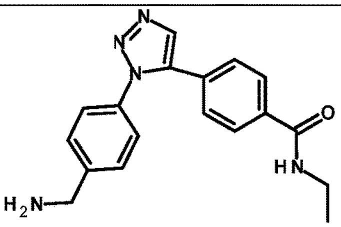
Figure 4U:
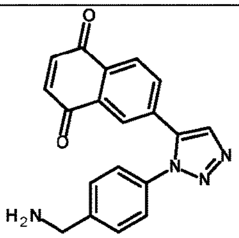
Figure 4U:
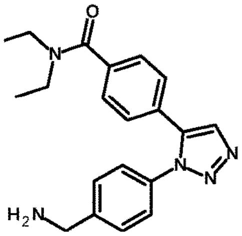
Figure 4U:
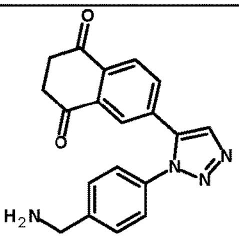
Figure 4V:
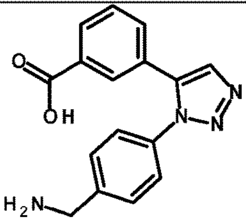
Figure 4V:
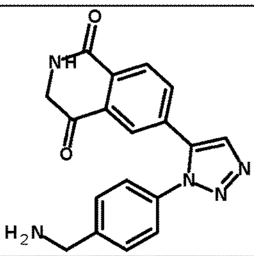
Figure 4V:
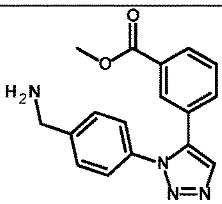
Figure 4V:
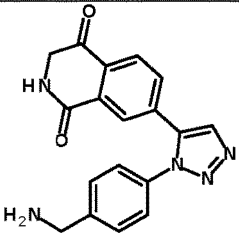
Figure 4V:
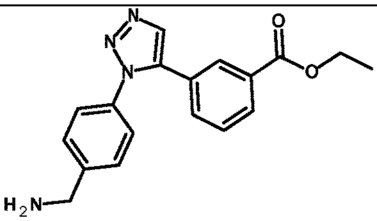
Figure 4V:
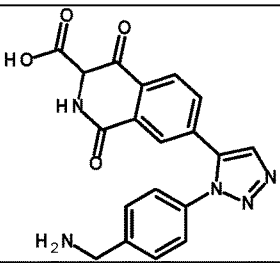
Figure 5A:
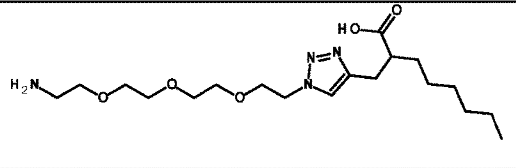
Figure 5A:
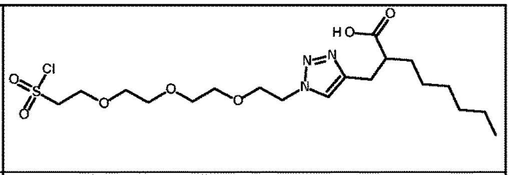
Figure 5A:
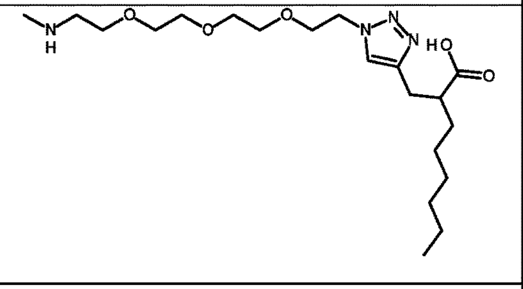
Figure 5A:
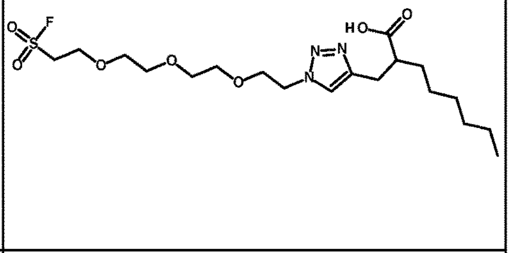
Figure 5A:
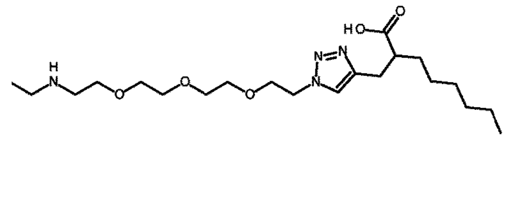
Figure 5A:
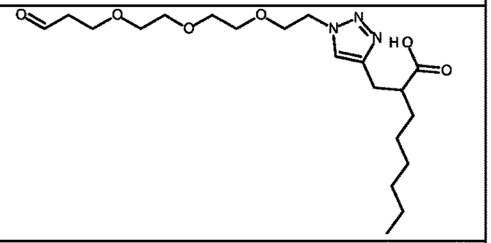
Figure 5A:
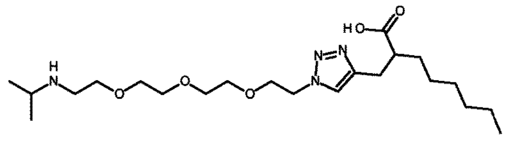
Figure 5A:
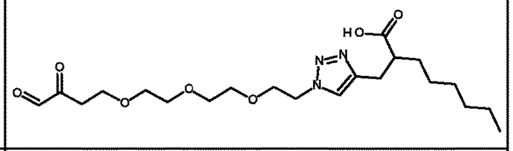
Figure 5A:
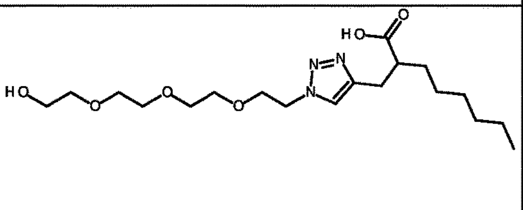
Figure 5A:
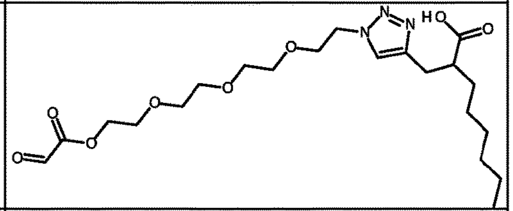
Figure 5A:
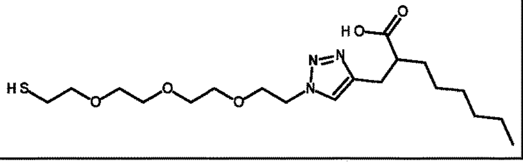
Figure 5A:
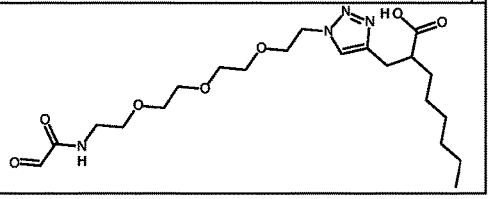
Figure 5B:
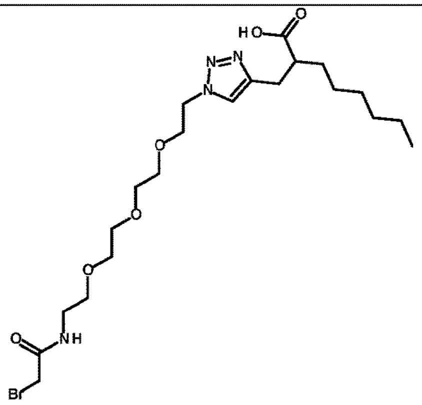
Figure 5B:
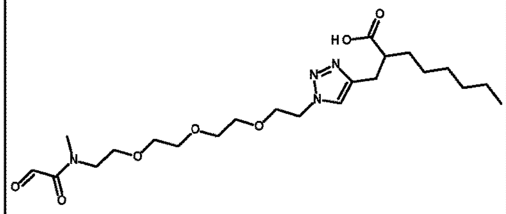
Figure 5B:
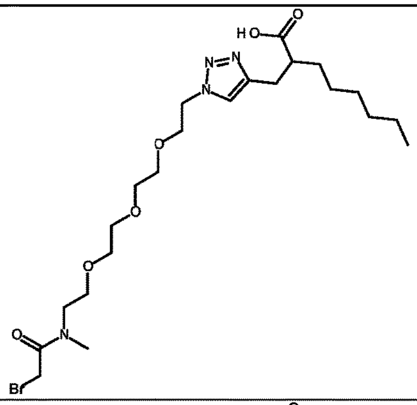
Figure 5B:
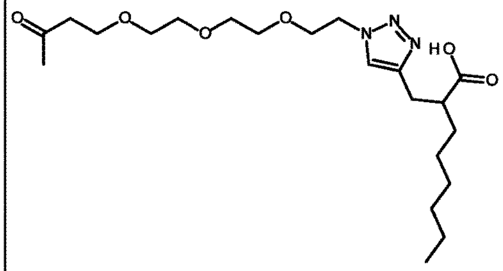
Figure 5B:
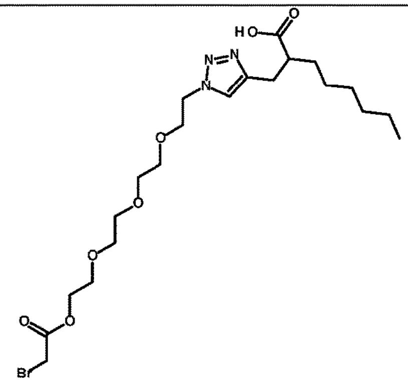
Figure 5B:
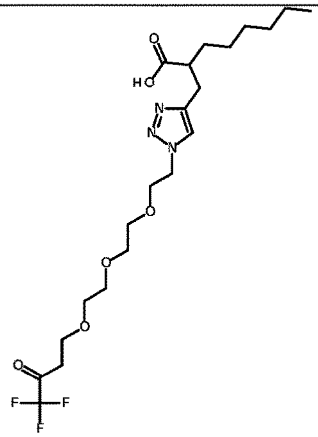
Figure 5C:
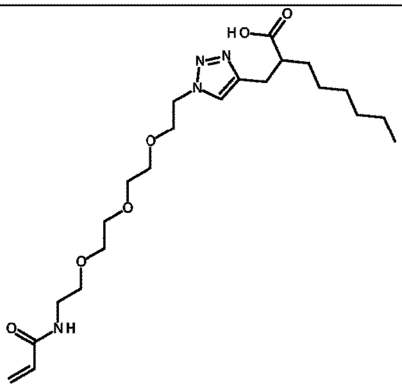
Figure 5C:
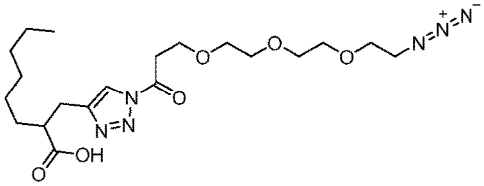
Figure 5C:
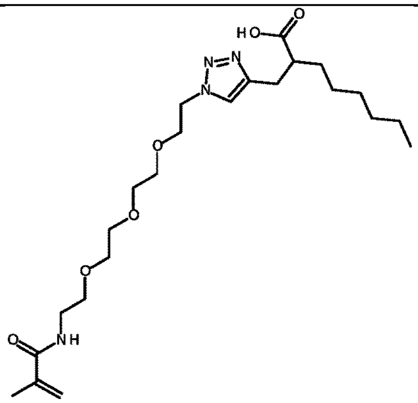
Figure 5C:
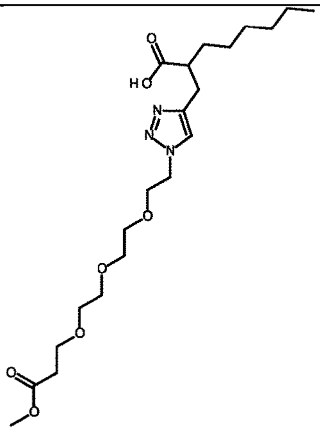
Figure 5C:
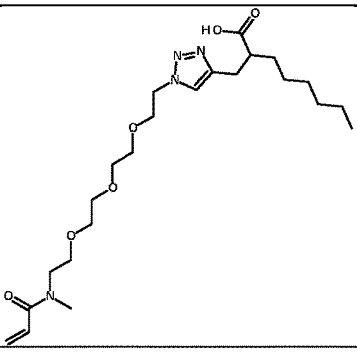
Figure 5C:
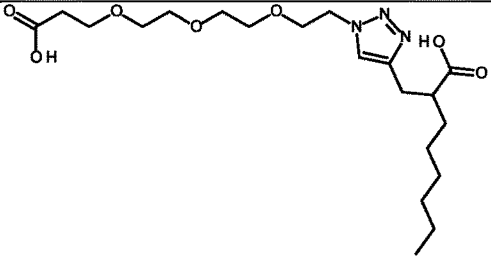
Figure 5D:
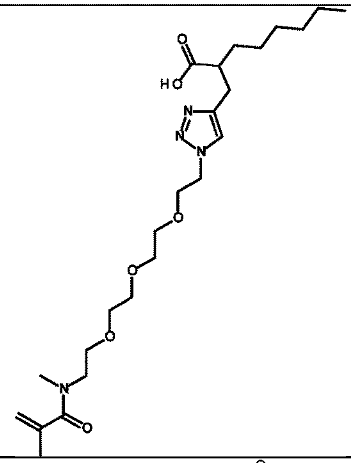
Figure 5D:
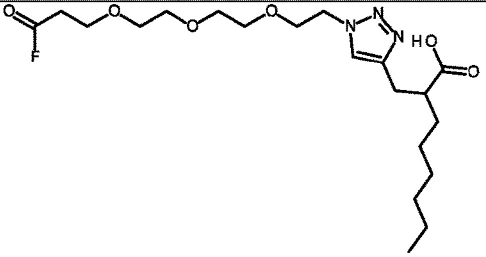
Figure 5D:
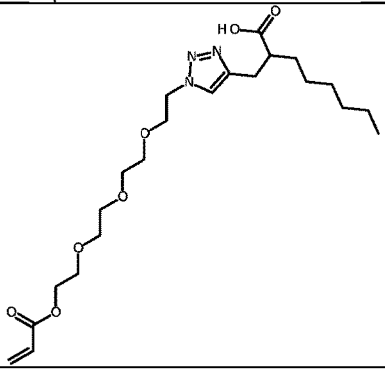
Figure 5D:
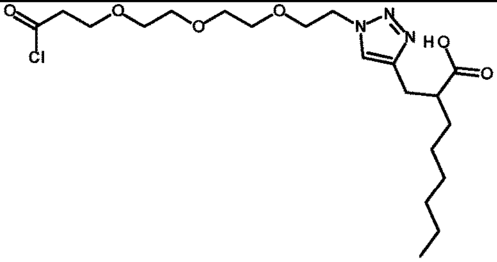
Figure 5D:
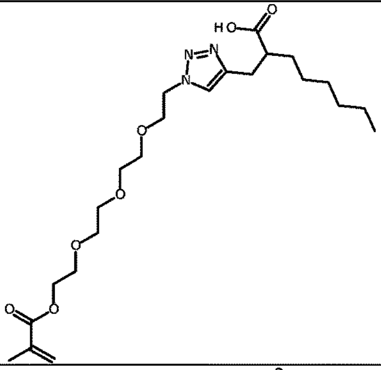
Figure 5D:
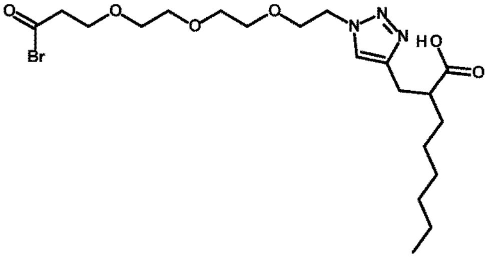
Figure 5D:
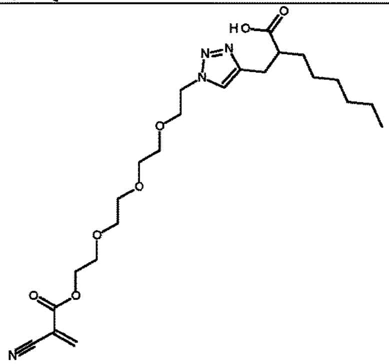
Figure 5D:
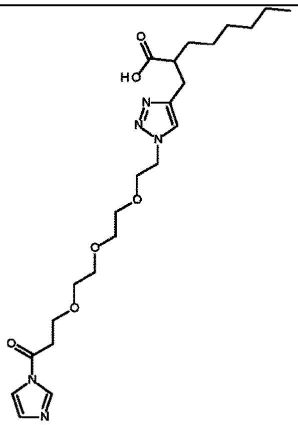
Figure 5E:
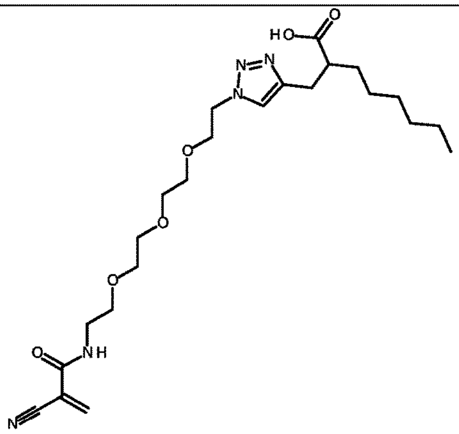
Figure 5E:
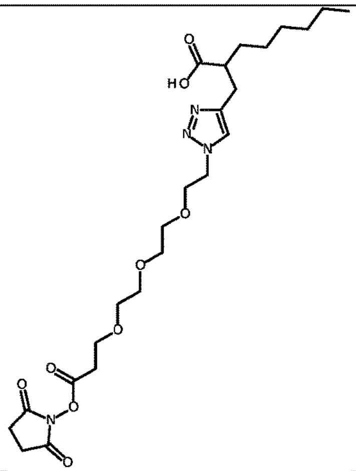
Figure 5E:
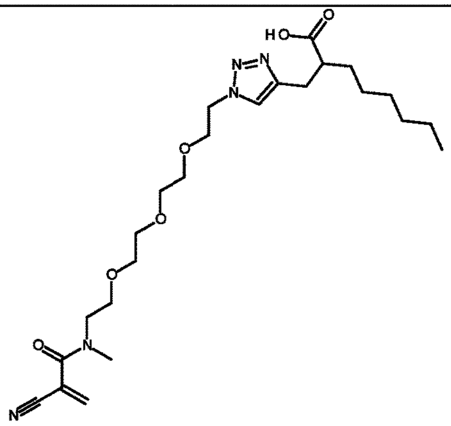
Figure 5E:
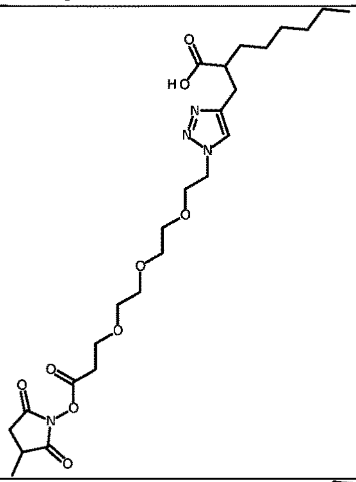
Figure 5E:
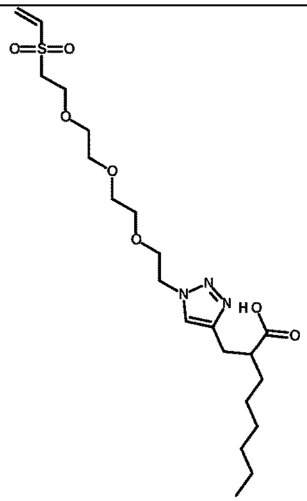
Figure 5E:
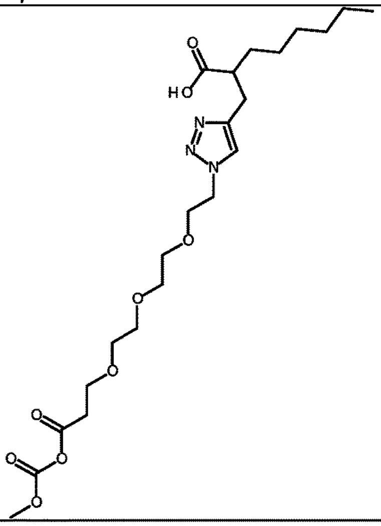
Figure 5F:
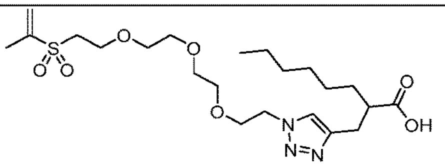
Figure 5F:
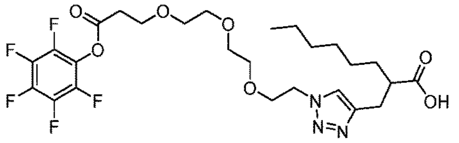
Figure 5F:
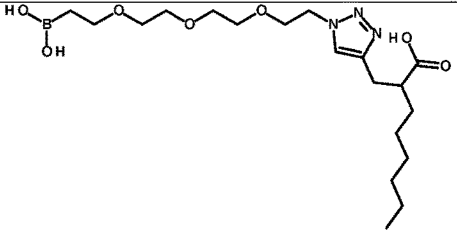
Figure 5F:
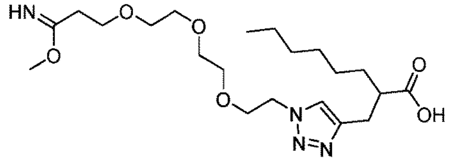
Figure 5F:
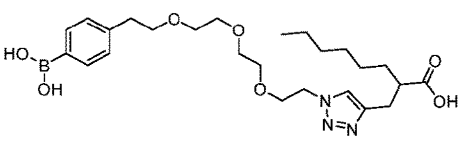
Figure 5F:
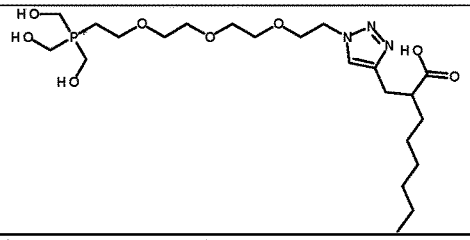
Figure 5F:
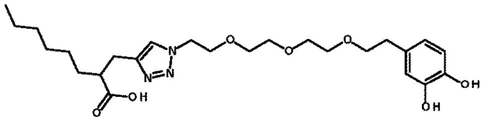
Figure 5F:
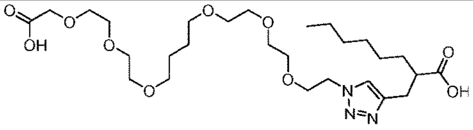
Figure 5F:
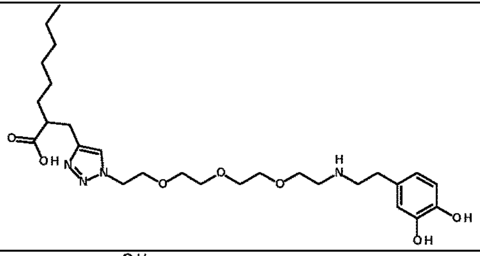
Figure 5F:
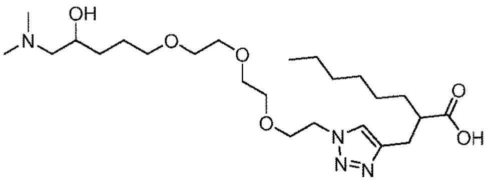
Figure 5F:
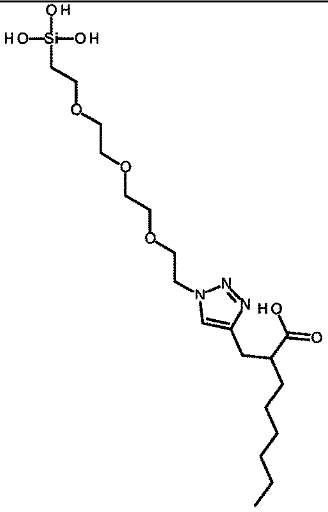
Figure 5F:
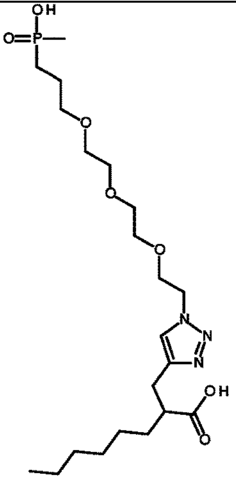
Figure 5G:
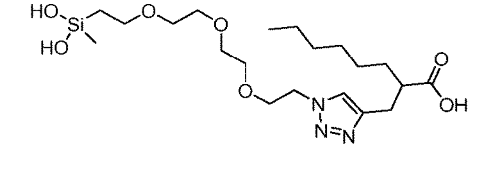
Figure 5G:
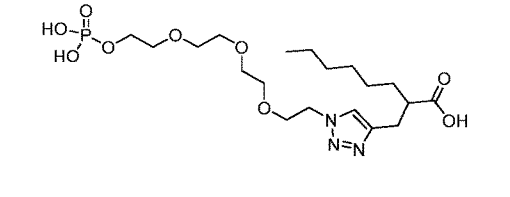
Figure 5G:
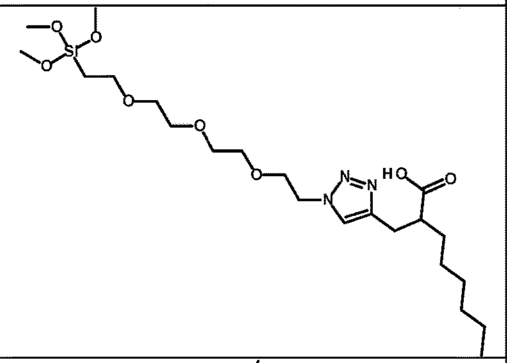
Figure 5G:
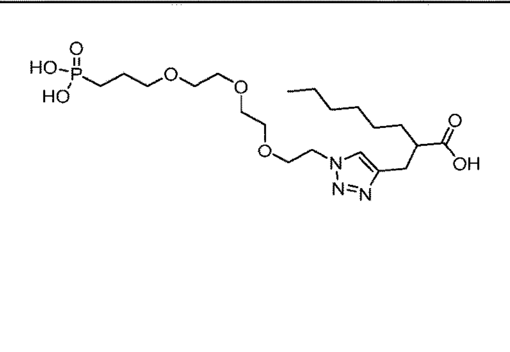
Figure 5G:
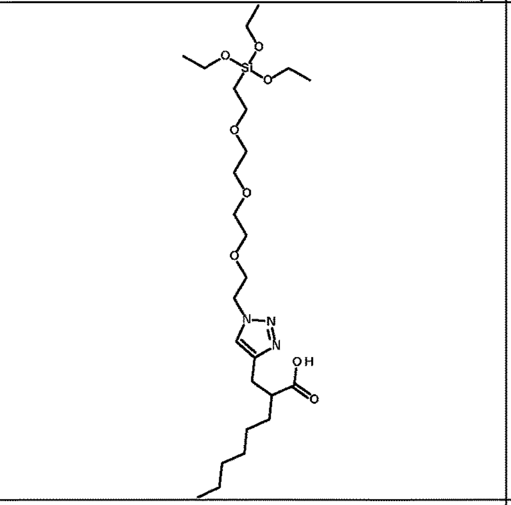
Figure 5G:
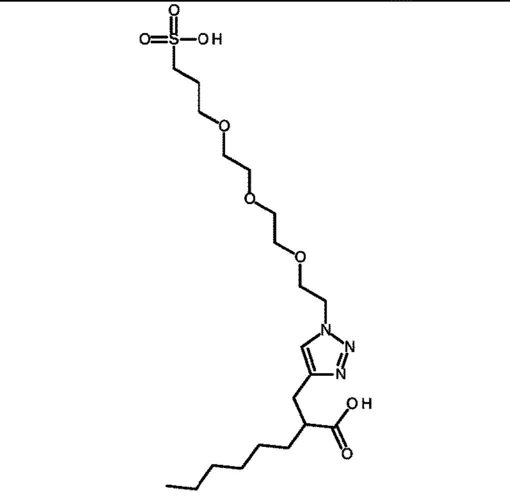
Figure 5G:
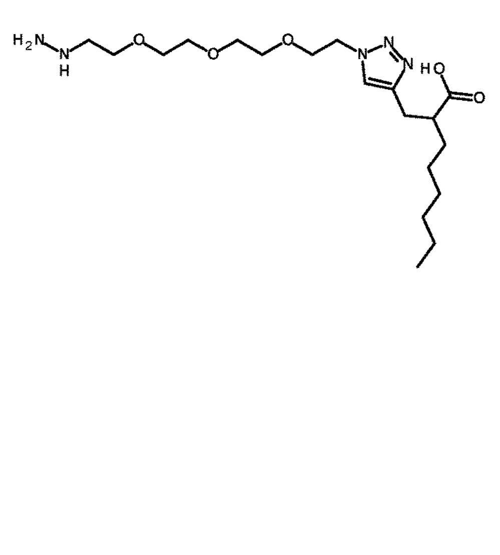
Figure 5G:
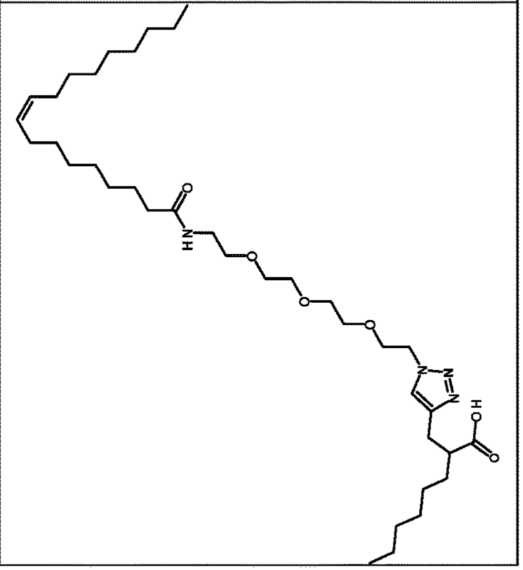
Figure 5H:
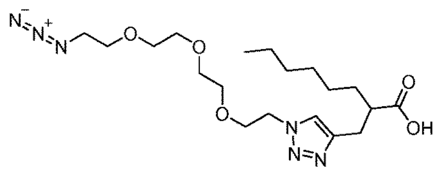
Figure 5H:
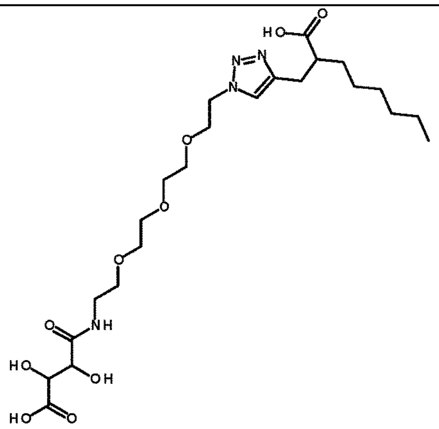
Figure 5H:
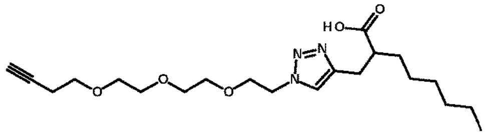
Figure 5H:
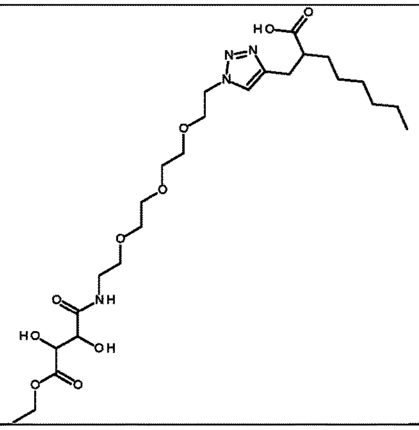
Figure 5H:
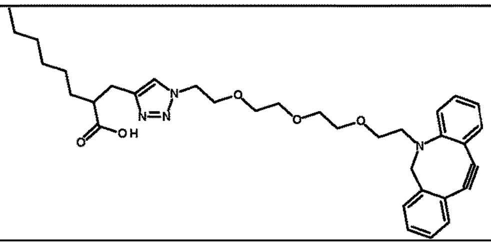
Figure 5H:
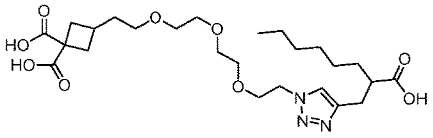
Figure 5H:
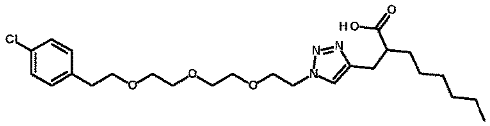
Figure 5H:
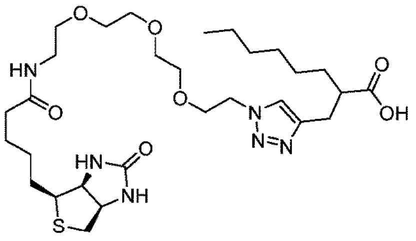
Figure 5I:
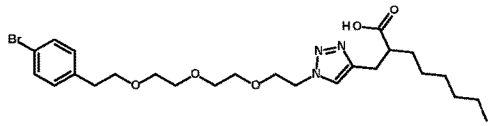
Figure 5I:
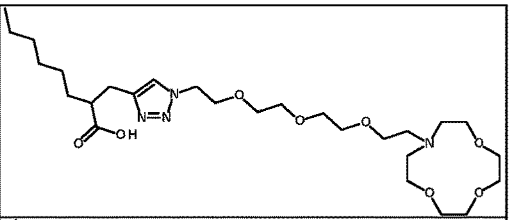
Figure 5I:
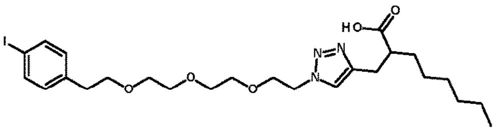
Figure 5I:
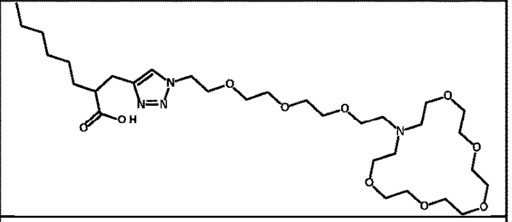
Figure 5I:
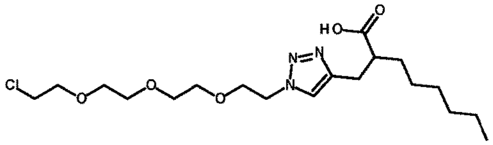
Figure 5I:
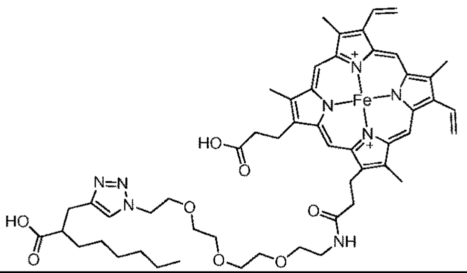
Figure 5I:
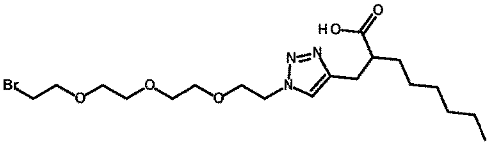
Figure 5I:
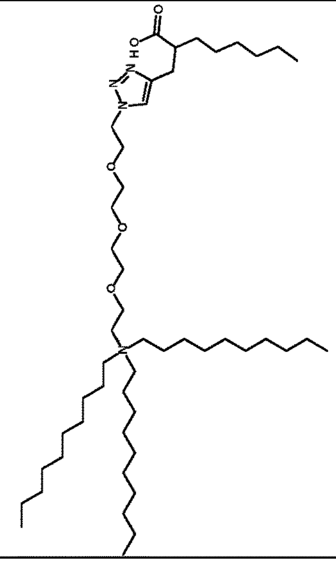
Figure 5J:
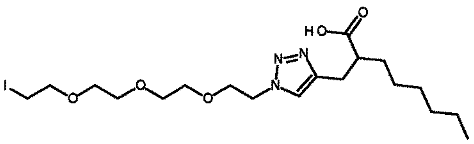
Figure 5J:
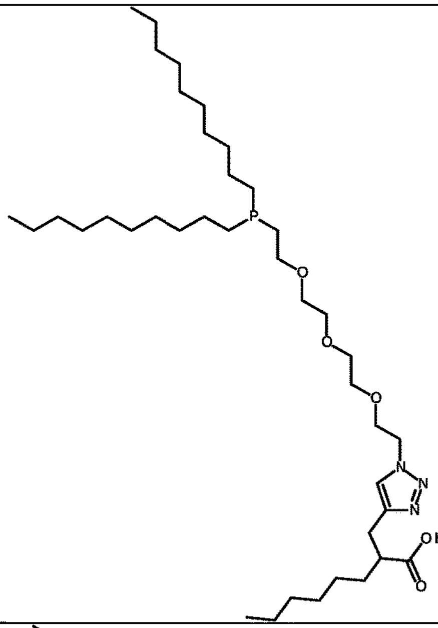
Figure 5J:
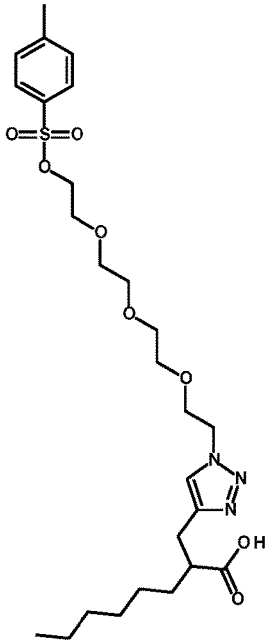
Figure 5J:
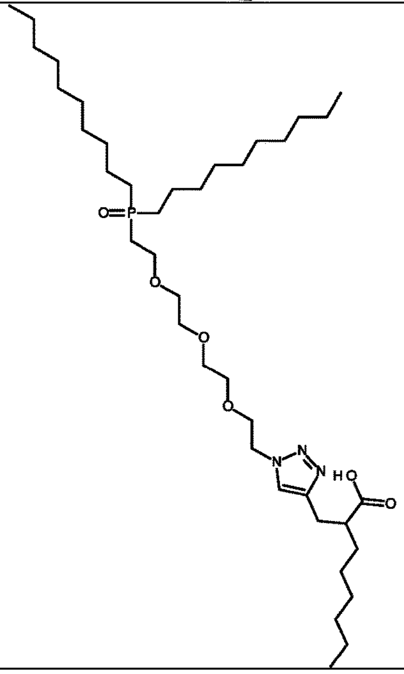
Figure 5J:
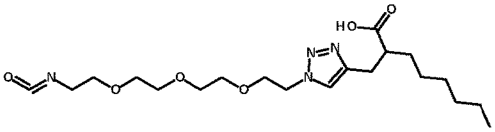
Figure 5J:
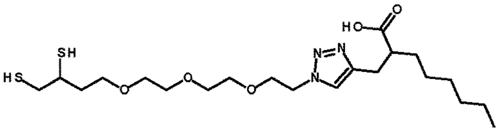
Figure 5K:
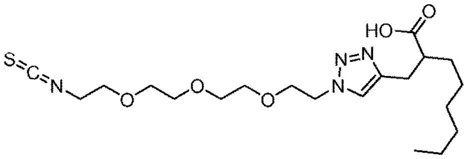
Figure 5K:
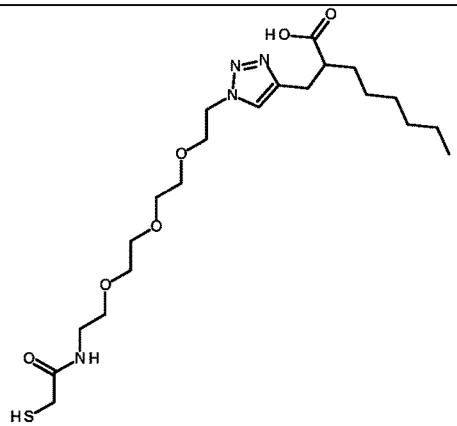
Figure 5K:
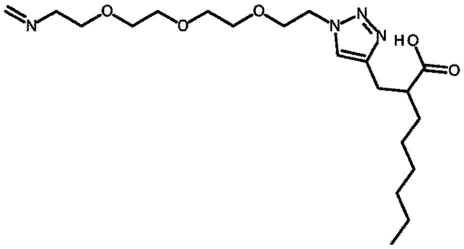
Figure 5K:
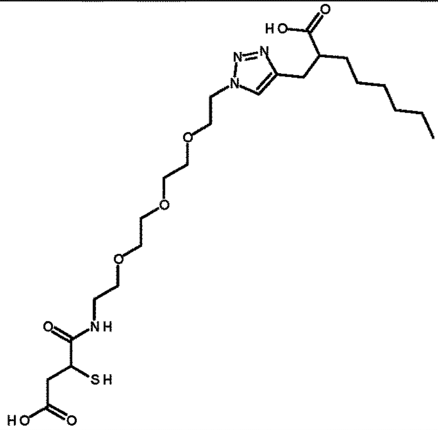
Figure 5K:
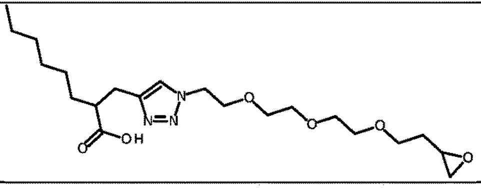
Figure 5K:
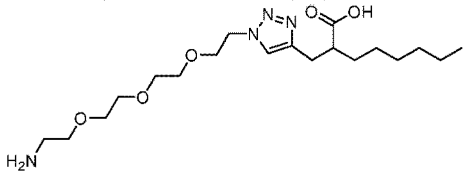
Figure 5K:
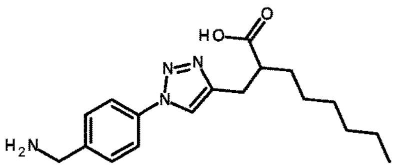
Figure 5K:
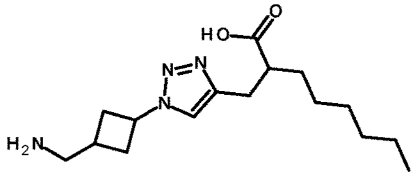
Figure 5K:
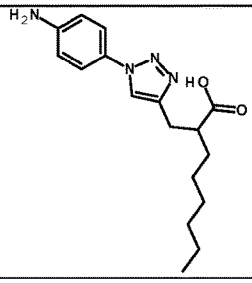
Figure 5K:
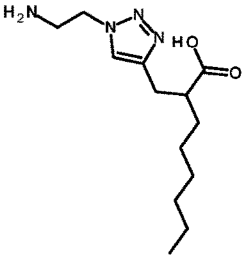
Figure 5L:
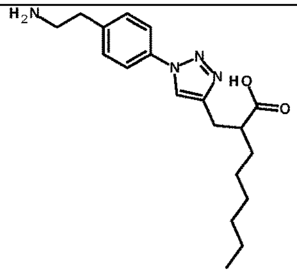
Figure 5L:
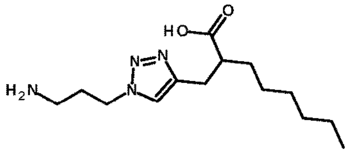
Figure 5L:
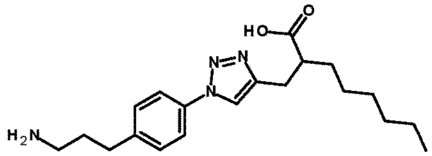
Figure 5L:
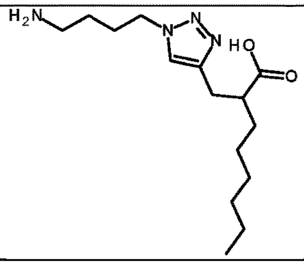
Figure 5L:
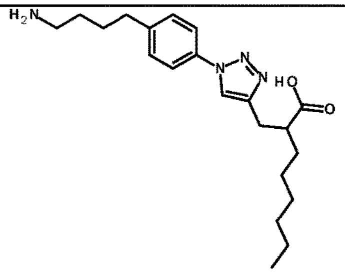
Figure 5L:
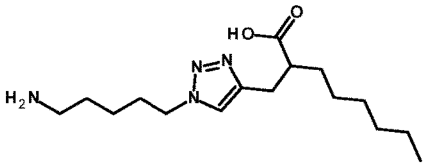
Figure 5L:
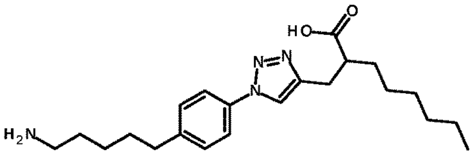
Figure 5L:
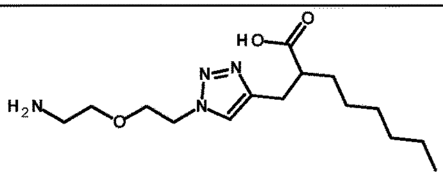
Figure 5L:
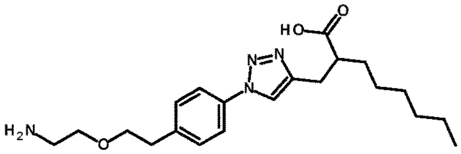
Figure 5L:
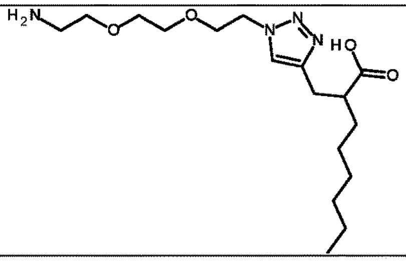
Figure 5L:
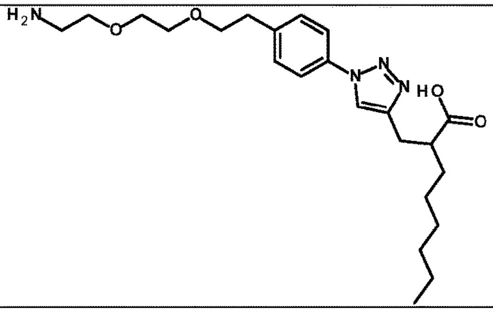
Figure 5L:
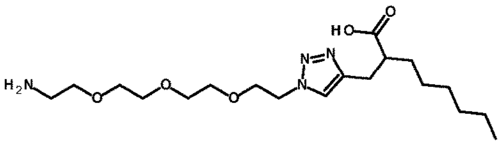
Figure 5M:
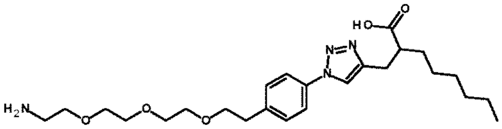
Figure 5M:
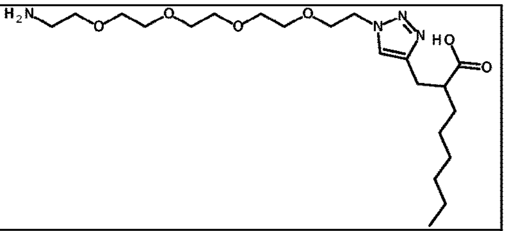
Figure 5M:
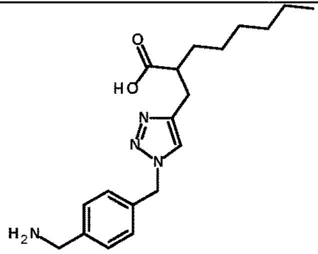
Figure 5M:
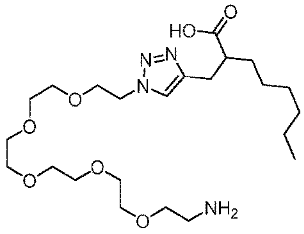
Figure 5M:
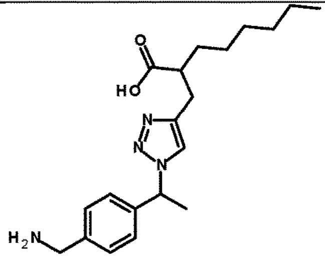
Figure 5M:
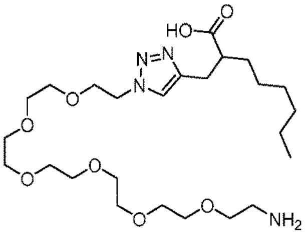
Figure 5M:
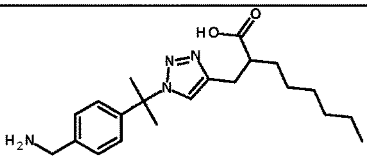
Figure 5M:
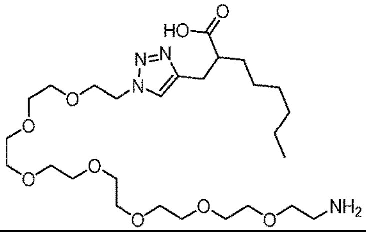
Figure 5M:
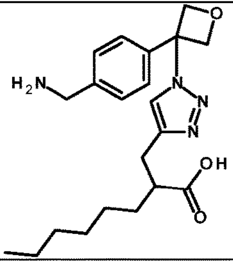
Figure 5M:
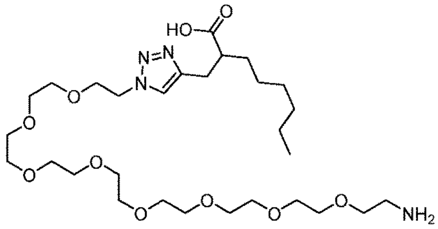
Figure 5M:
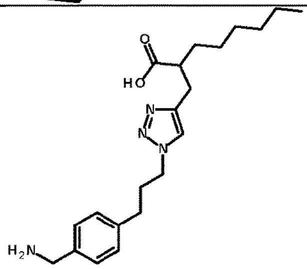
Figure 5M:
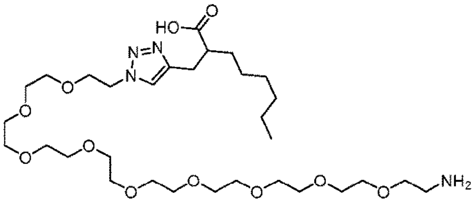
Figure 5N:
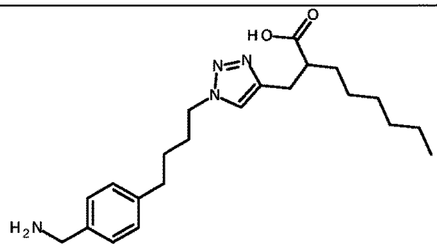
Figure 5N:
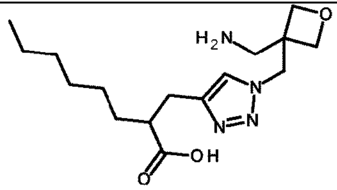
Figure 5N:
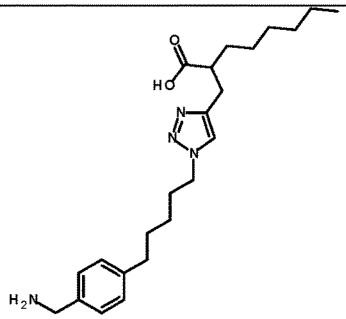
Figure 5N:
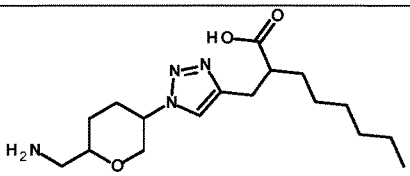
Figure 5N:
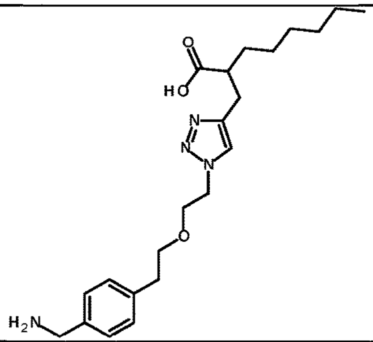
Figure 5N:
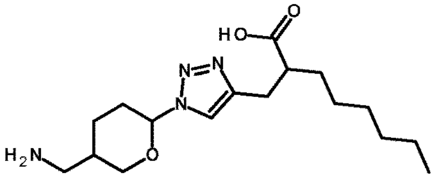
Figure 5N:
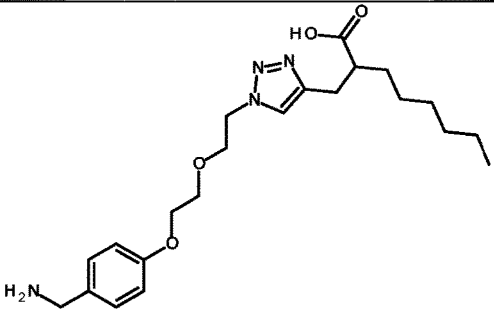
Figure 5N:
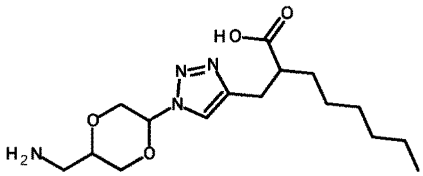
Figure 5N:
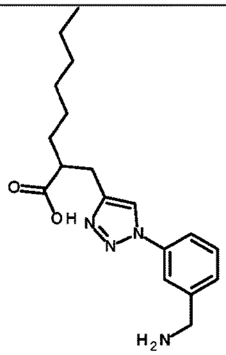
Figure 5N:
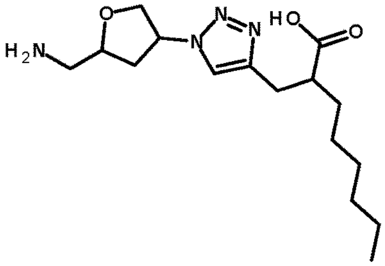
Figure 5O:
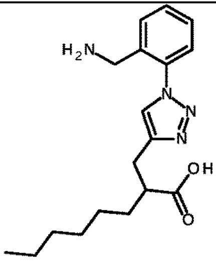
Figure 5O:
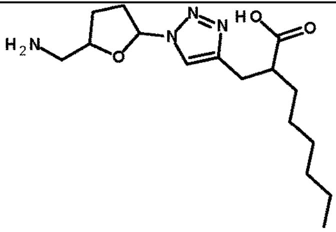
Figure 5O:
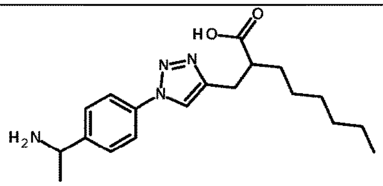
Figure 5O:
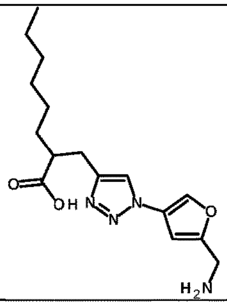
Figure 5O:
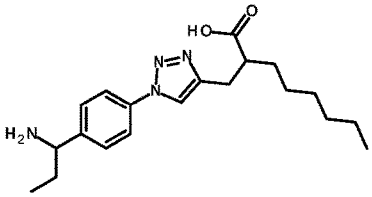
Figure 5O:
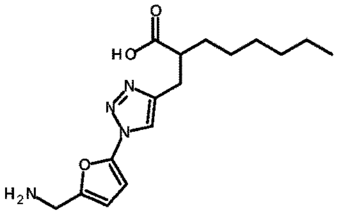
Figure 5O:
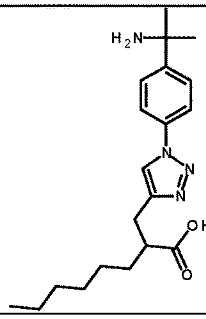
Figure 5O:
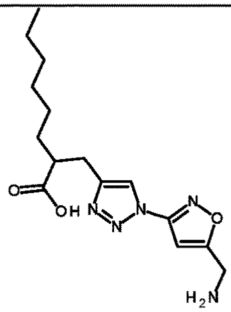
Figure 5O:
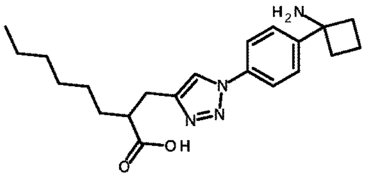
Figure 5O:
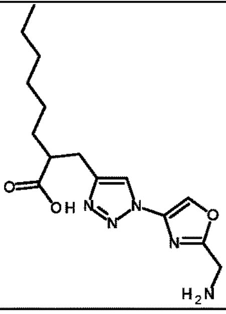
Figure 5P:
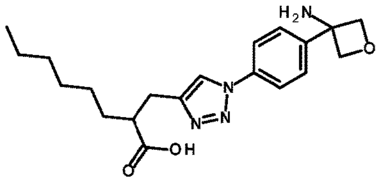
Figure 5P:
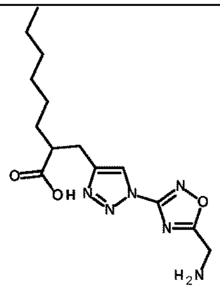
Figure 5P:
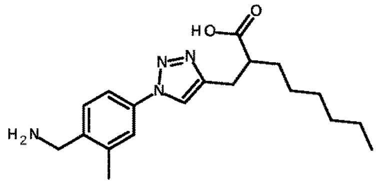
Figure 5P:
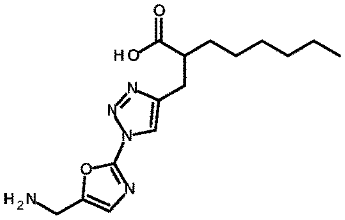
Figure 5P:
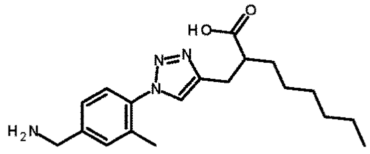
Figure 5P:
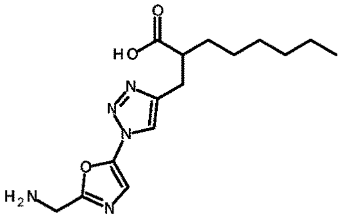
Figure 5P:
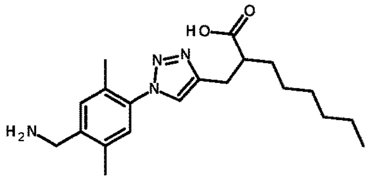
Figure 5P:
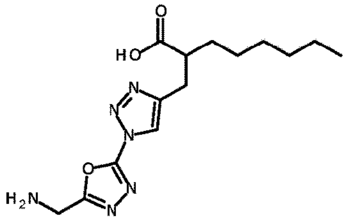
Figure 5P:
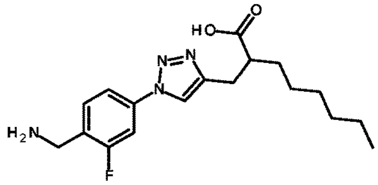
Figure 5P:
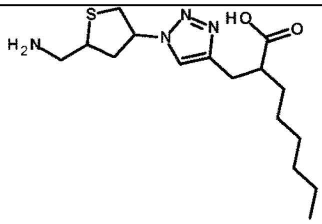
Figure 5P:
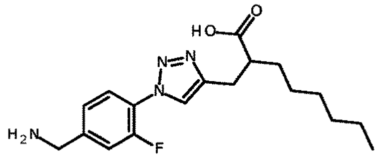
Figure 5P:
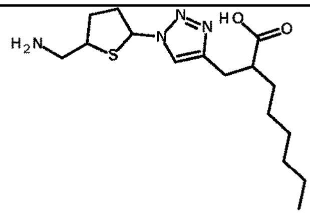
Figure 5Q:
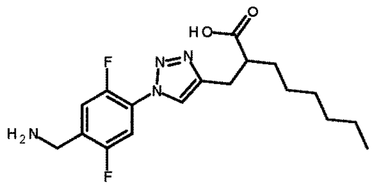
Figure 5Q:
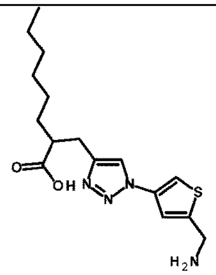
Figure 5Q:
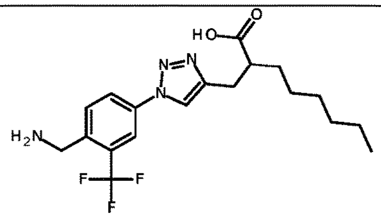
Figure 5Q:
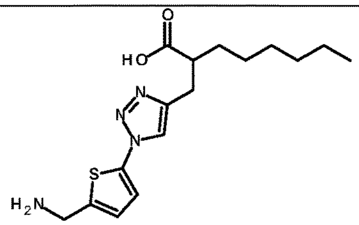
Figure 5Q:
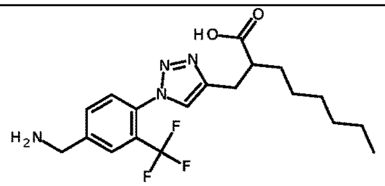
Figure 5Q:
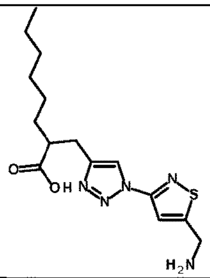
Figure 5Q:
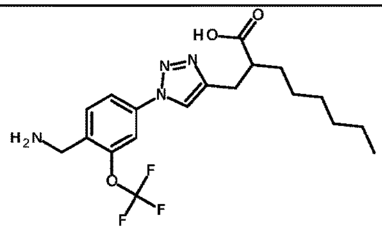
Figure 5Q:
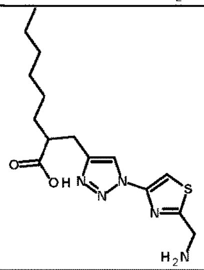
Figure 5Q:
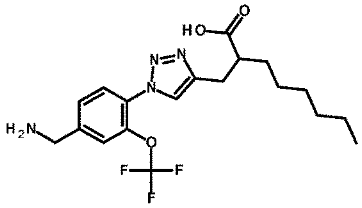
Figure 5Q:
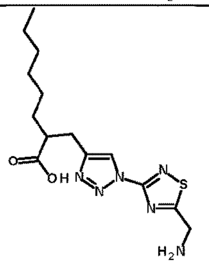
Figure 5Q:
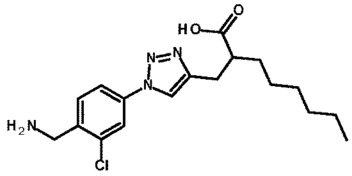
Figure 5Q:
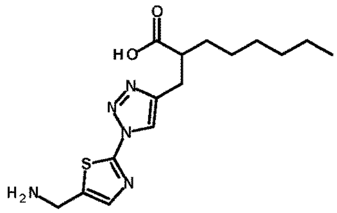
Figure 5R:
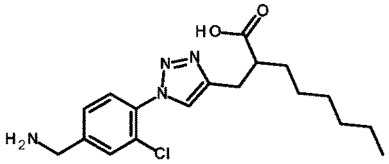
Figure 5R:
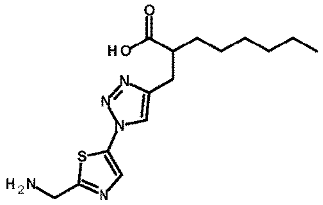
Figure 5R:
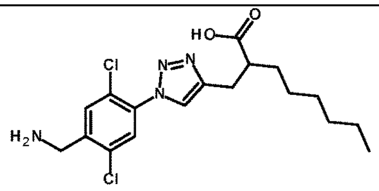
Figure 5R:
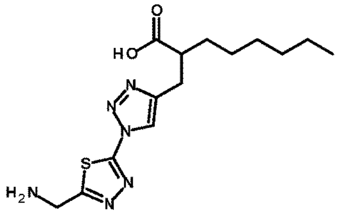
Figure 5R:
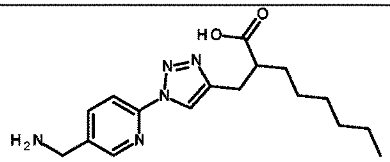
Figure 5R:
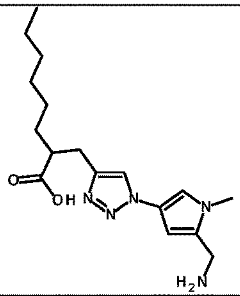
Figure 5R:
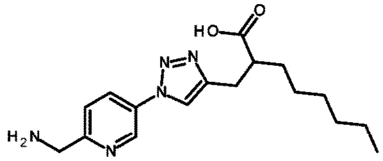
Figure 5R:
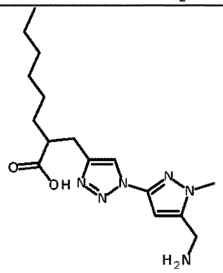
Figure 5R:
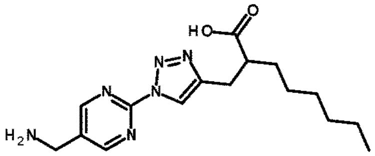
Figure 5R:
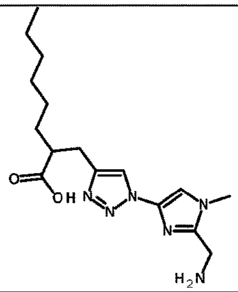
Figure 5R:
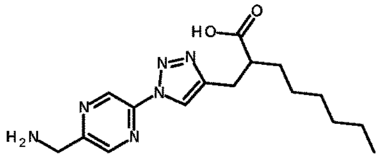
Figure 5R:
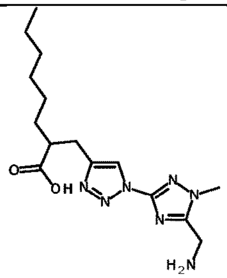
Figure 5S:
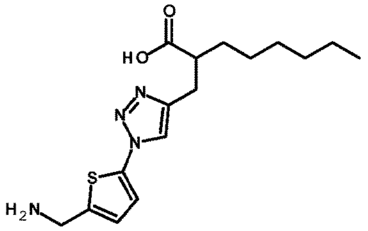
Figure 5S:
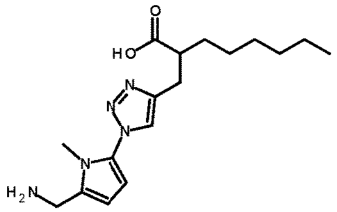
Figure 5S:
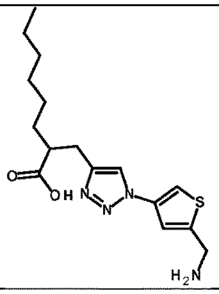
Figure 5S:
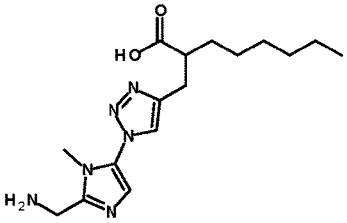
Figure 5S:
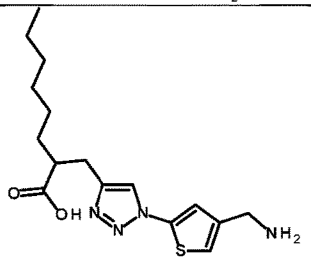
Figure 5S:
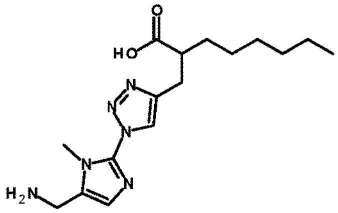
Figure 5S:
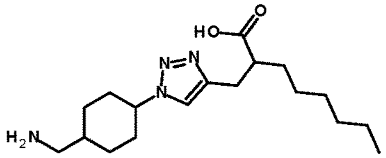
Figure 5S:
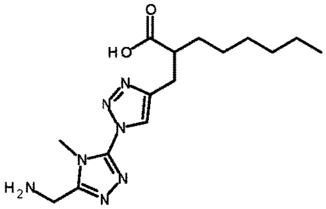
Figure 5S:
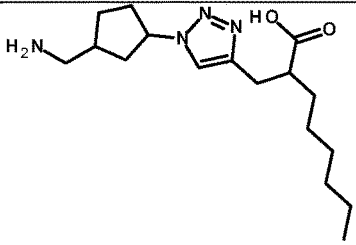
Figure 5S:
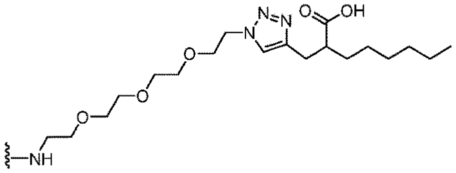
Figure 5S:
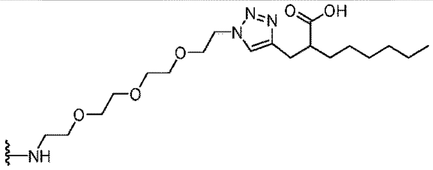
Figure 5S:
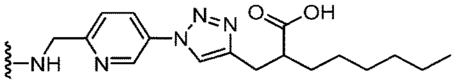
Figure 5S:
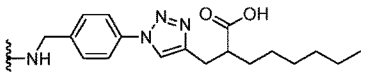
Figure 5S:
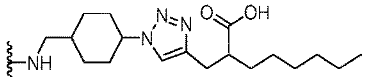
Figure 5T:
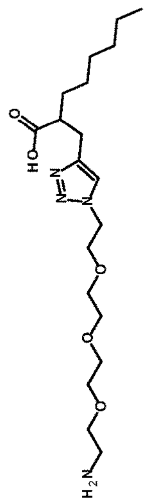
Figure 5T:
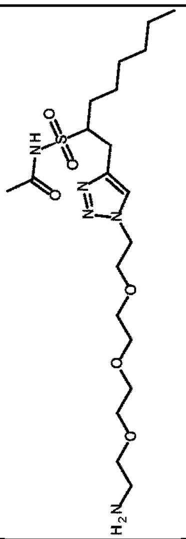
Figure 5T:
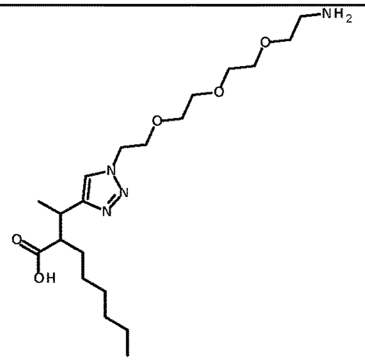
Figure 5T:
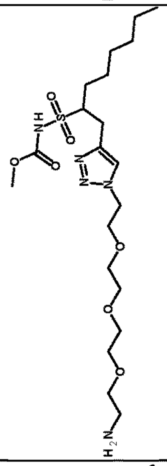
Figure 5T:
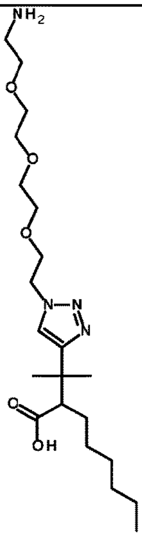
Figure 5T:
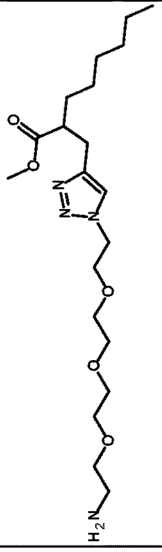
Figure 5U:
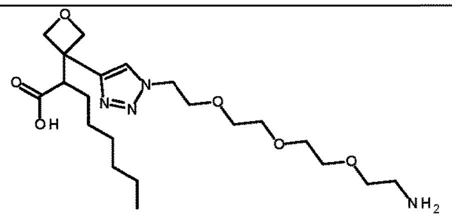
Figure 5U:
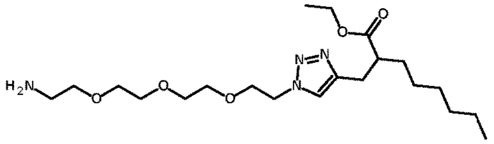
Figure 5U:
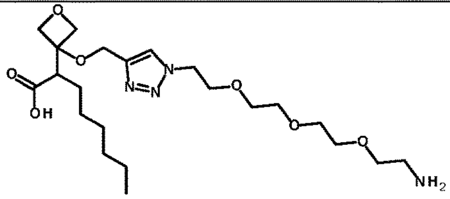
Figure 5U:
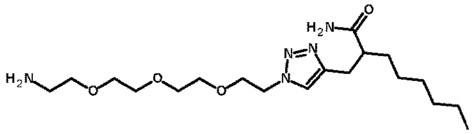
Figure 5U:
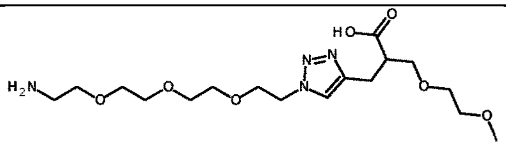
Figure 5U:
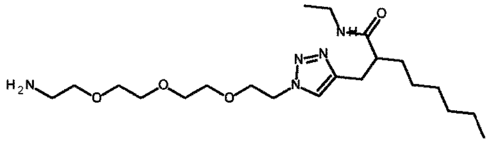
Figure 5U:
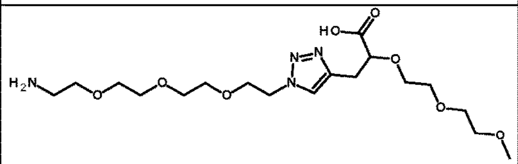
Figure 5U:
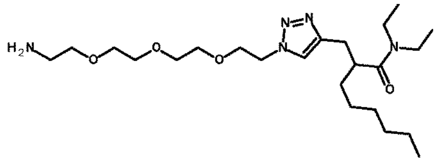
Figure 5U:
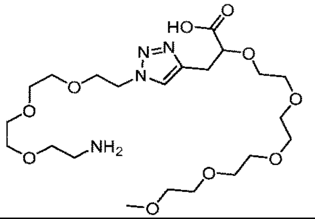
Figure 5U:
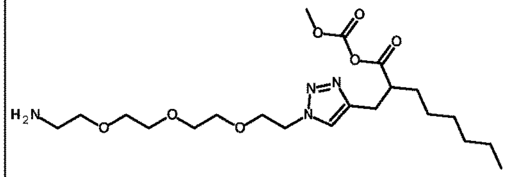
Figure 5U:
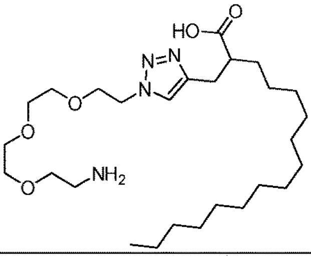
Figure 5U:
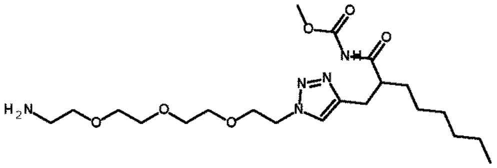
Figure 5V:
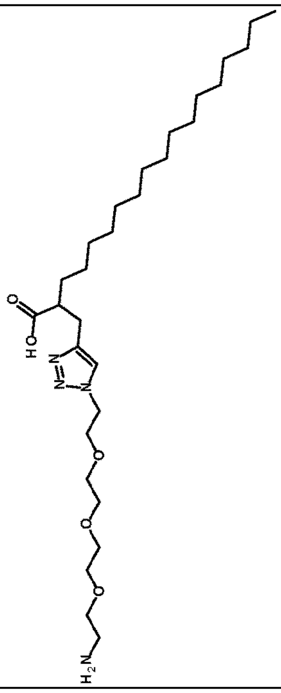
Figure 5V:
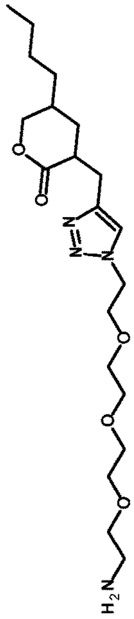
Figure 5V:
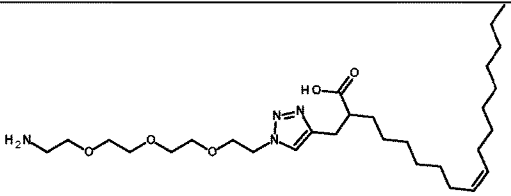
Figure 5V:
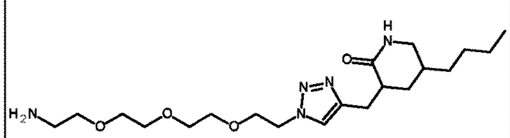
Figure 5V:
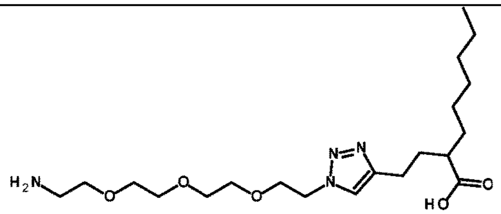
Figure 5V:
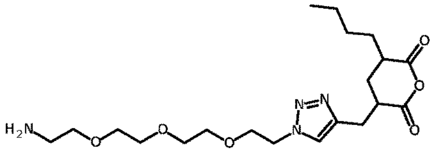
Figure 5V:
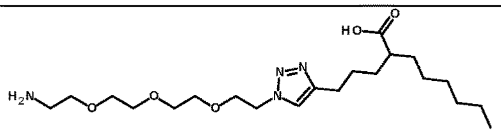
Figure 5V:
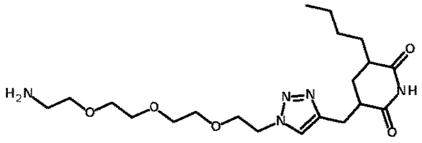
Figure 5V:
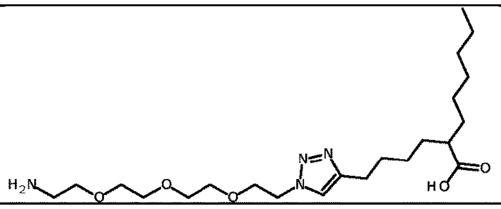
Figure 5V:
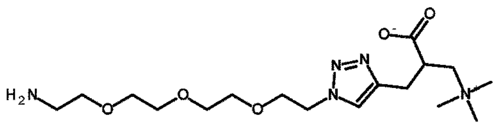
Figure 5W:
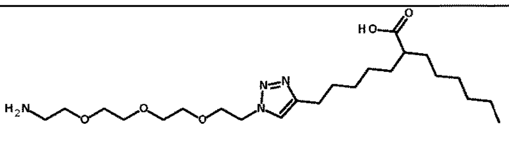
Figure 5W:
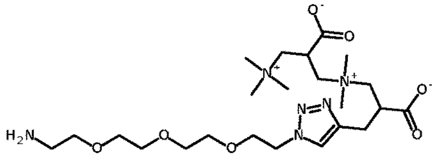
Figure 5W:
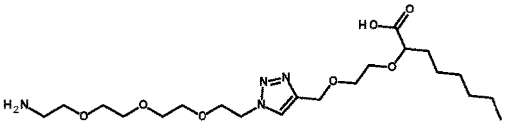
Figure 5W:
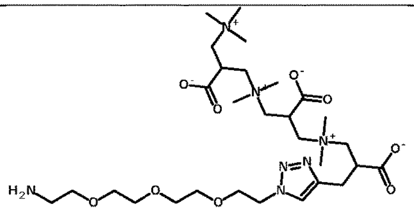
Figure 5W:
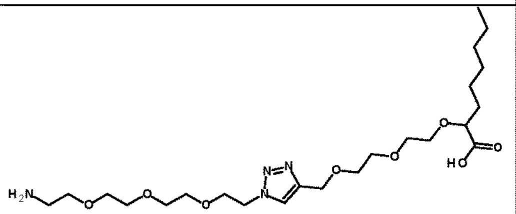
Figure 5W:
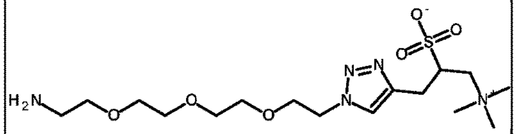
Figure 5W:
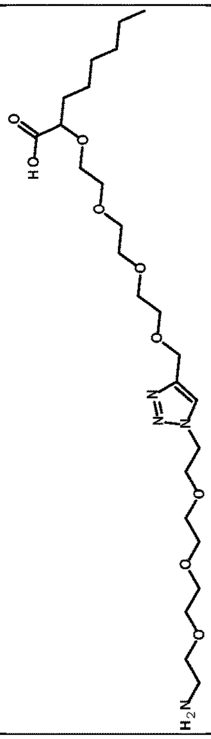
Figure 5W:
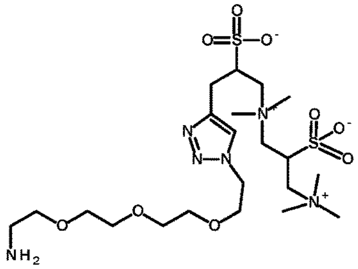
Figure 5X:
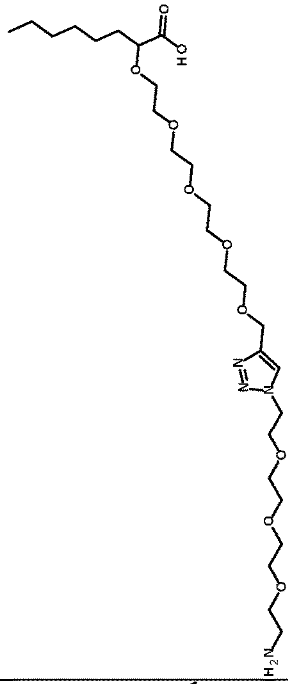
Figure 5X:
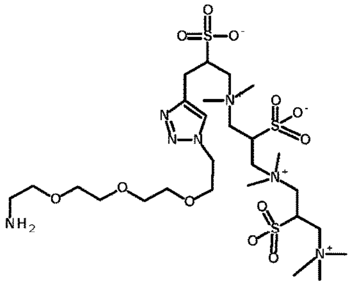
Figure 5X:
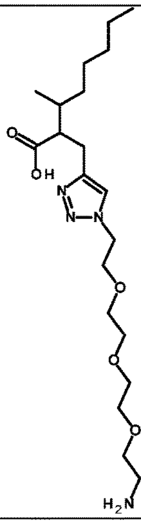
Figure 5X:
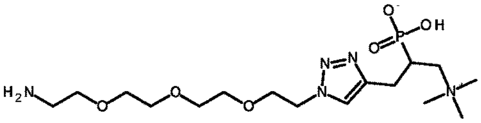
Figure 5X:
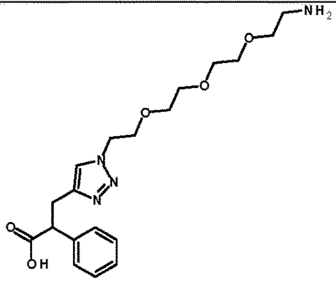
Figure 5X:
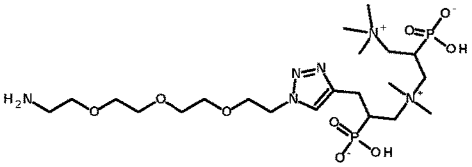
Figure 5Y:
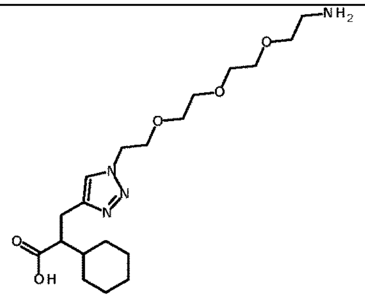
Figure 5Y:
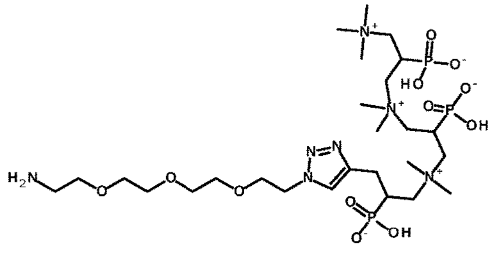
Figure 5Y:
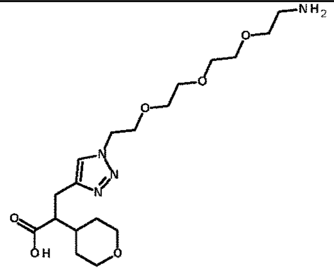
Figure 5Y:
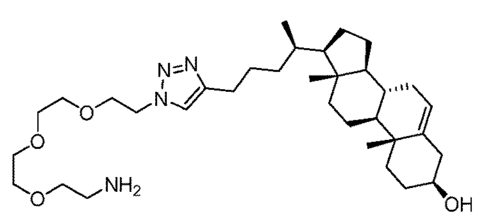
Figure 5Y:
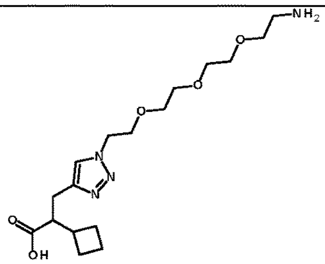
Figure 5Y:
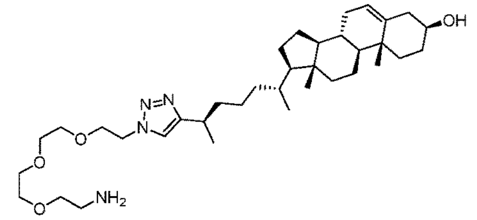
Figure 5Y:
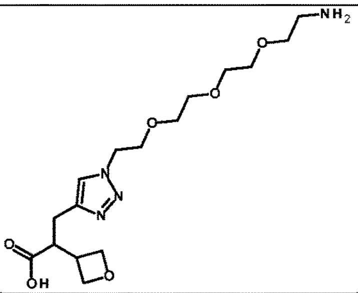
Figure 5Y:
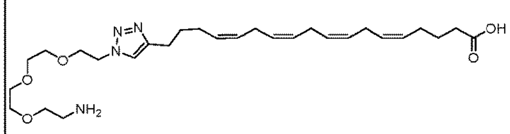
Figure 5Y:
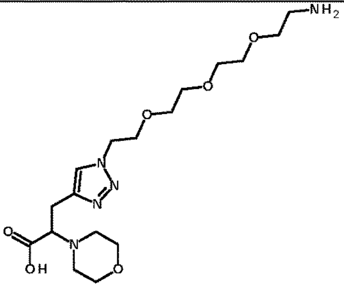
Figure 5Y:
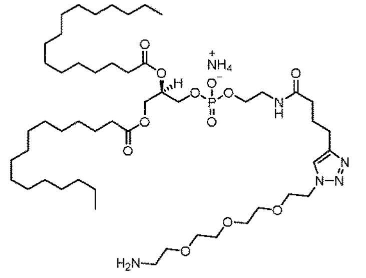
Figure 5Z:
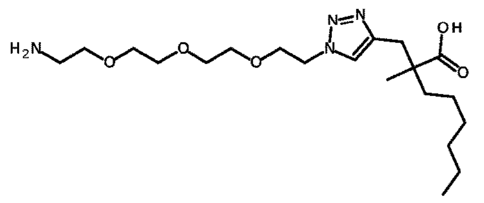
Figure 5Z:
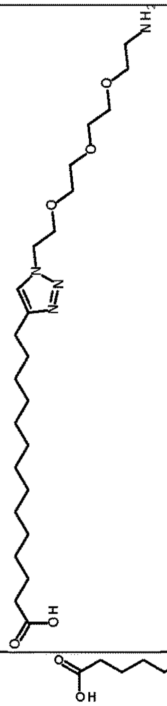
Figure 5Z:
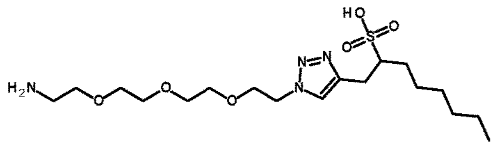
Figure 5Z:
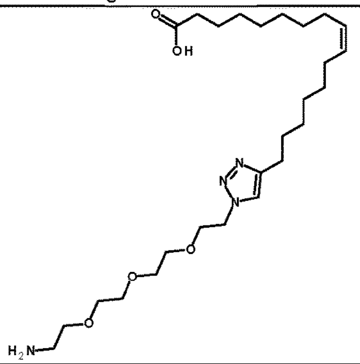
Figure 5Z:
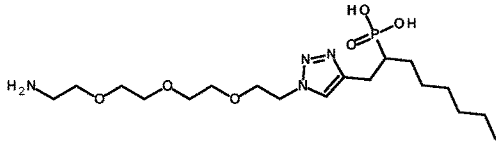
Figure 5Z:
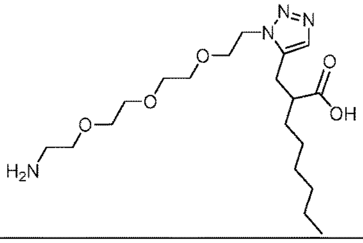
Figure 5Z:
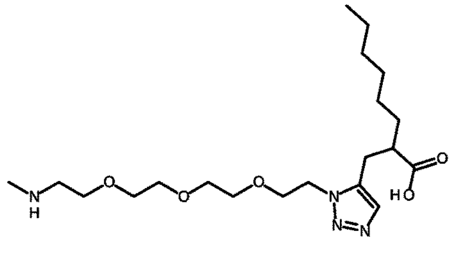
Figure 5Z:
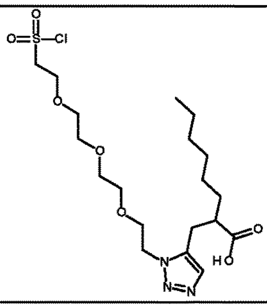
Figure 5A:
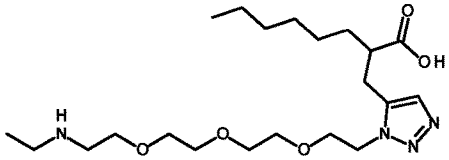
Figure 5A:
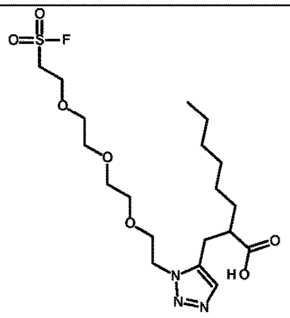
Figure 5A:
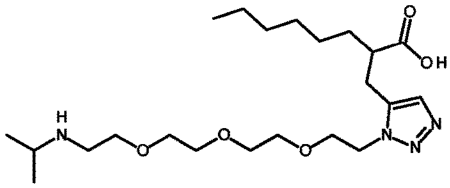
Figure 5A:
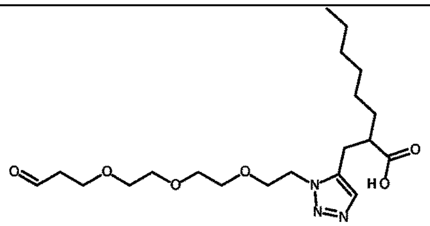
Figure 5A:
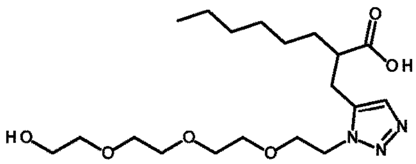
Figure 5A:
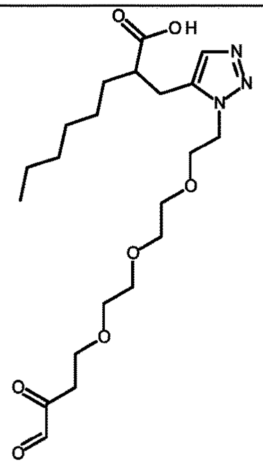
Figure 5A:
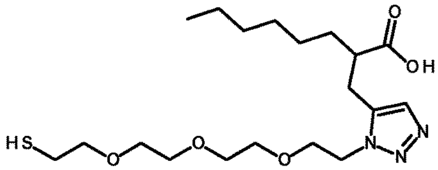
Figure 5A:
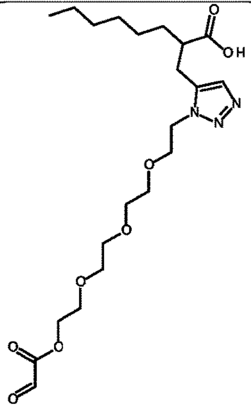
Figure 5B:
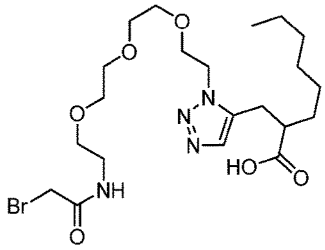
Figure 5B:
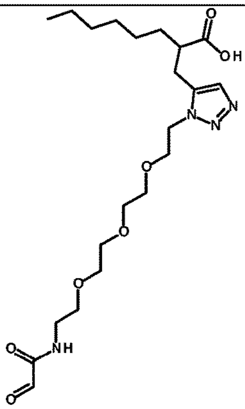
Figure 5B:
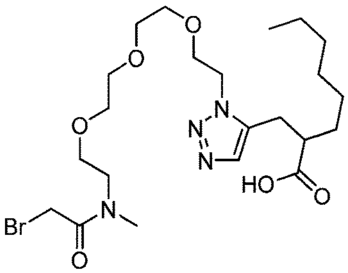
Figure 5B:
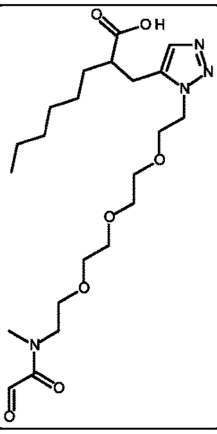
Figure 5B:
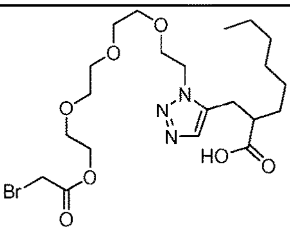
Figure 5B:
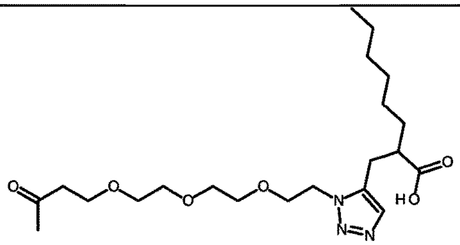
Figure 5B:
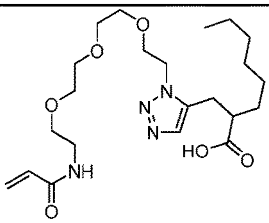
Figure 5B:
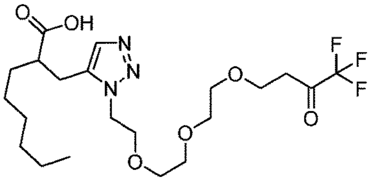
Figure 5C:
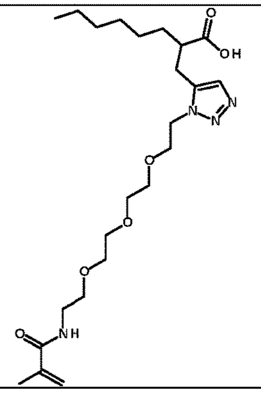
Figure 5C:
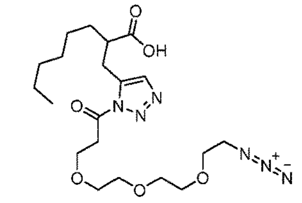
Figure 5C:
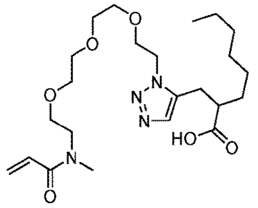
Figure 5C:
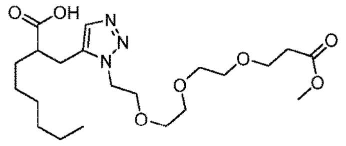
Figure 5C:
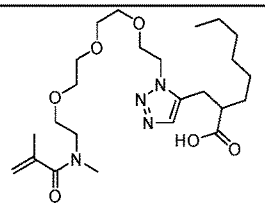
Figure 5C:
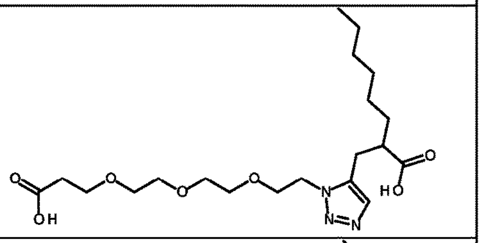
Figure 5C:
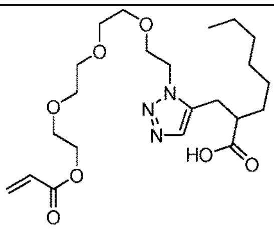
Figure 5C:
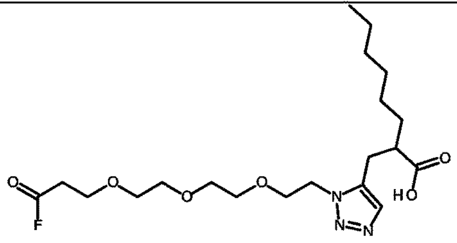
Figure 5C:
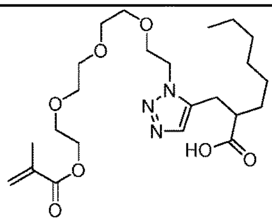
Figure 5C:
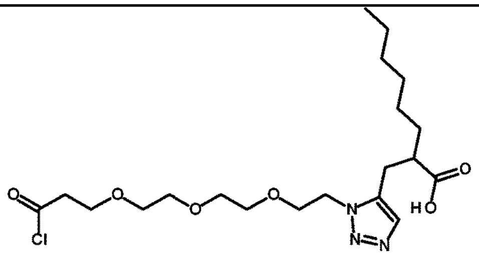
Figure 5D:
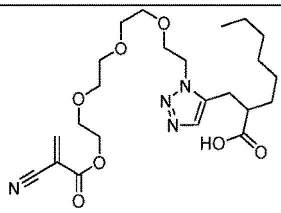
Figure 5D:
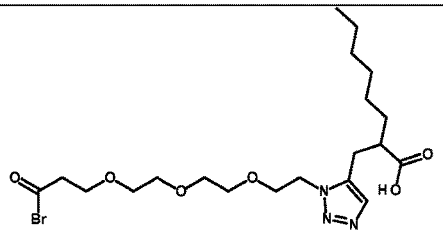
Figure 5D:
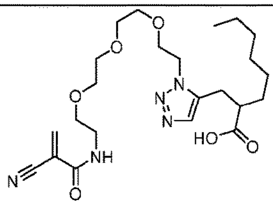
Figure 5D:
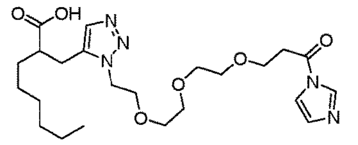
Figure 5D:
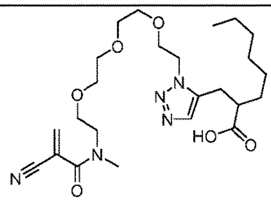
Figure 5D:
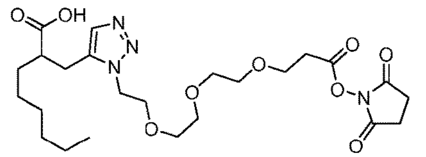
Figure 5D:
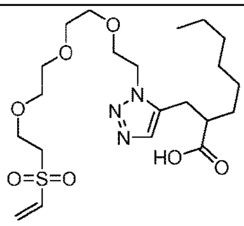
Figure 5D:
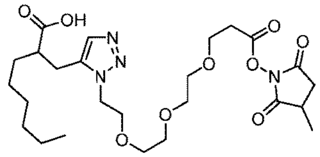
Figure 5D:
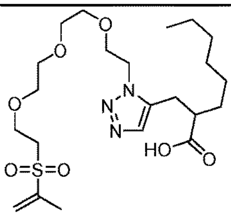
Figure 5D:
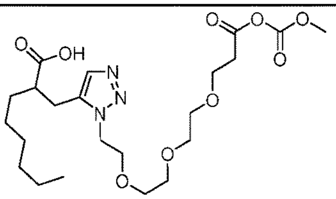
Figure 5D:
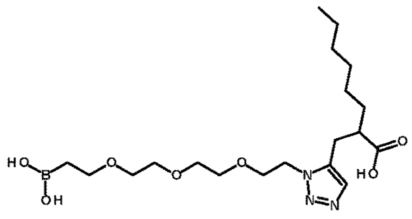
Figure 5D:
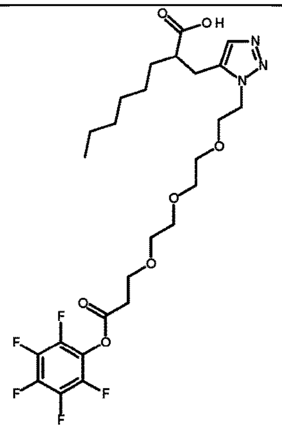
Figure 5E:
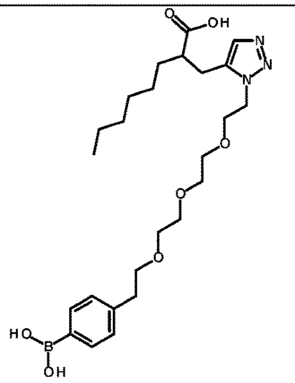
Figure 5E:
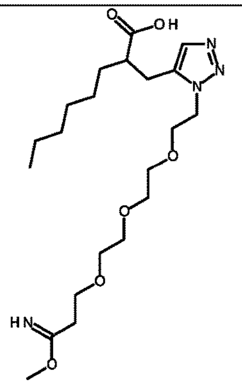
Figure 5E:
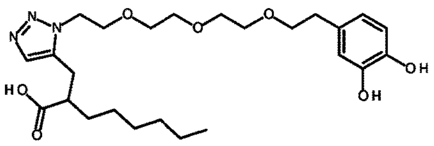
Figure 5E:
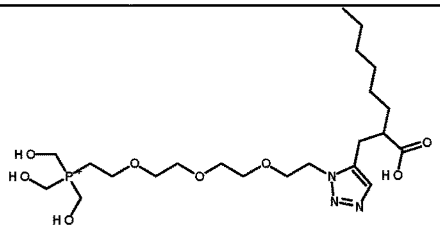
Figure 5E:
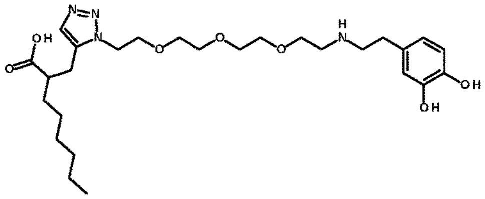
Figure 5E:
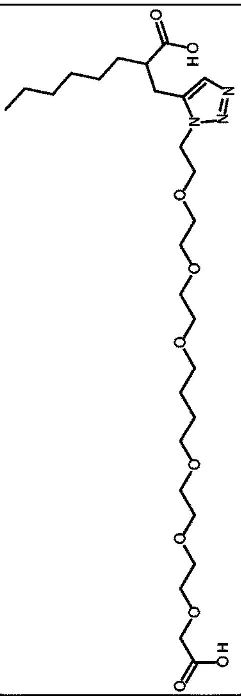
Figure 5E:
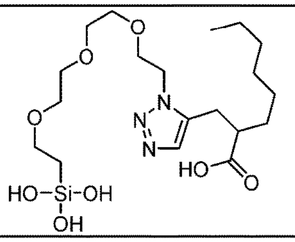
Figure 5E:
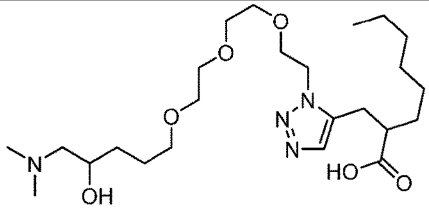
Figure 5F:
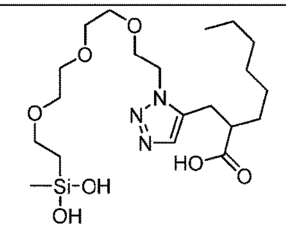
Figure 5F:
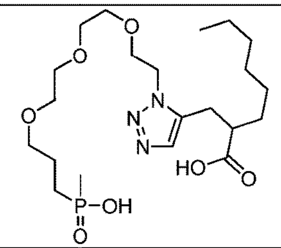
Figure 5F:
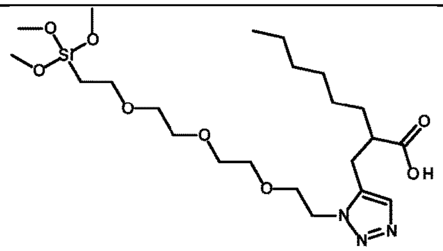
Figure 5F:
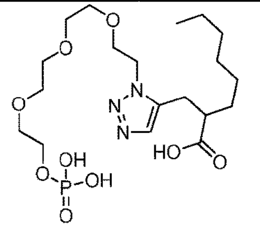
Figure 5F:
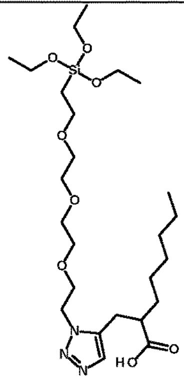
Figure 5F:
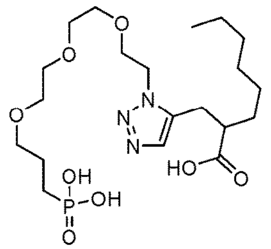
Figure 5F:
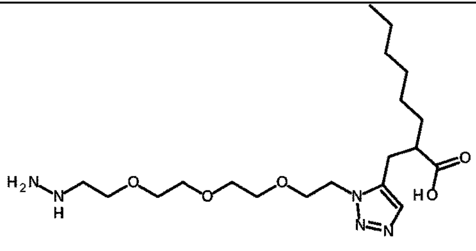
Figure 5F:
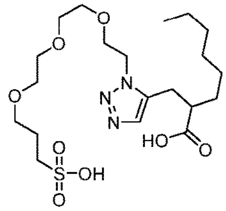
Figure 5F:
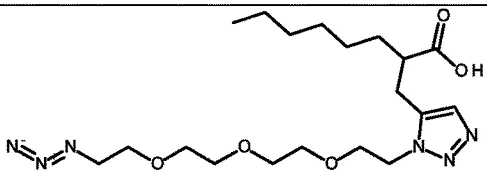
Figure 5F:
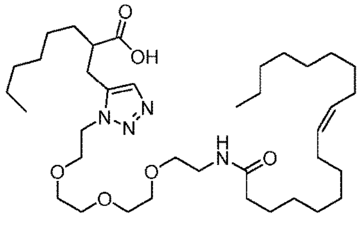
Figure 5F:
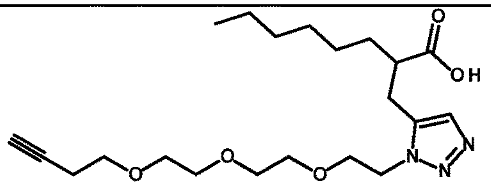
Figure 5F:
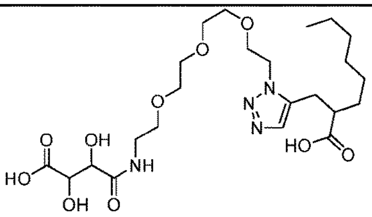
Figure 5G:
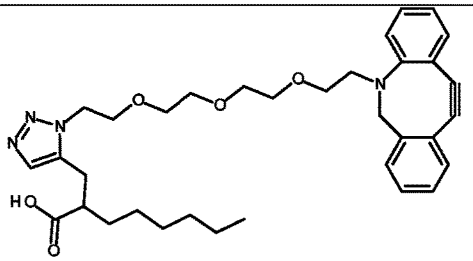
Figure 5G:
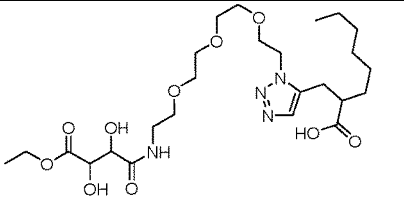
Figure 5G:
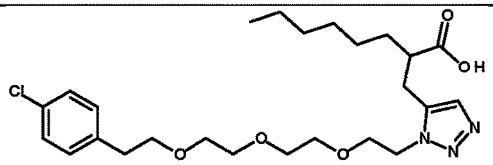
Figure 5G:
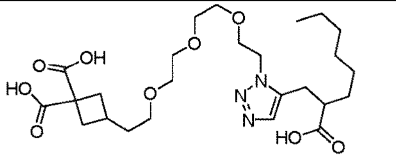
Figure 5G:
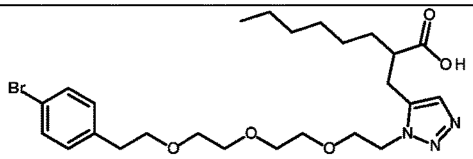
Figure 5G:
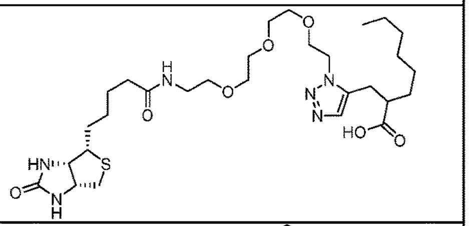
Figure 5G:
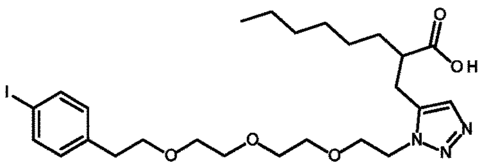
Figure 5G:
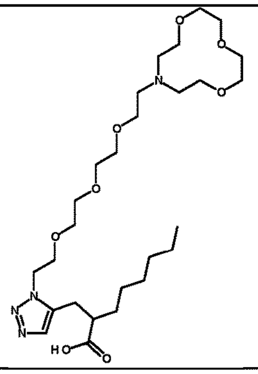
Figure 5G:
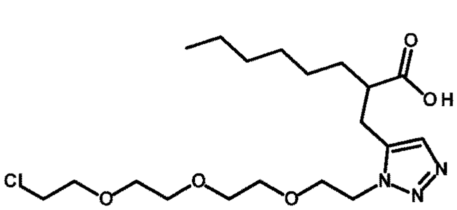
Figure 5G:
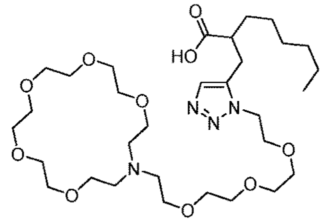
Figure 5H:
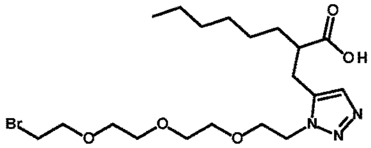
Figure 5H:
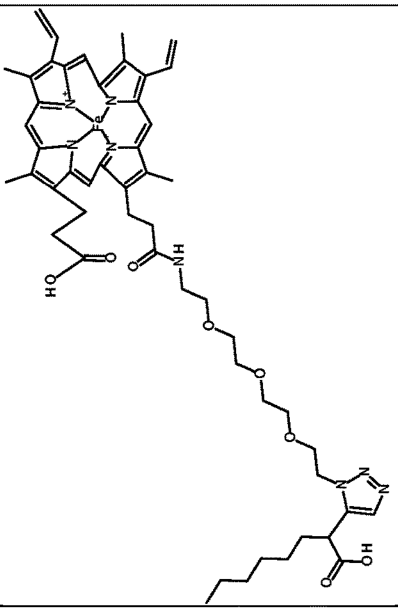
Figure 5H:
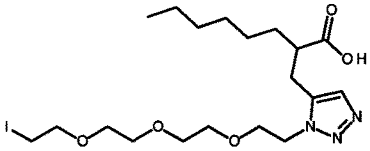
Figure 5H:
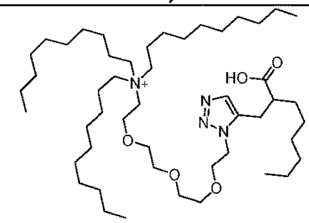
Figure 5H:
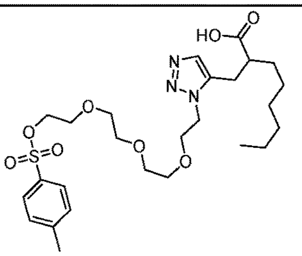
Figure 5H:
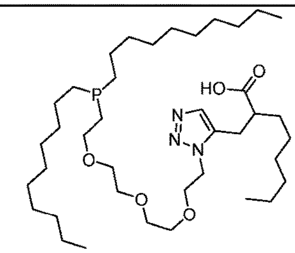
Figure 5H:
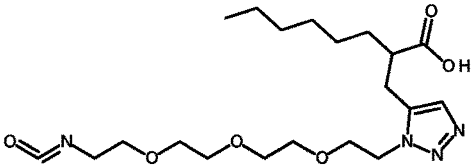
Figure 5H:
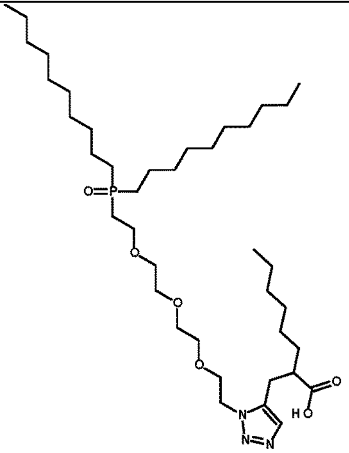
Figure 5I:
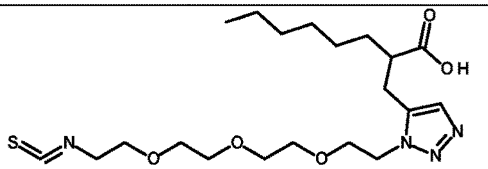
Figure 5I:
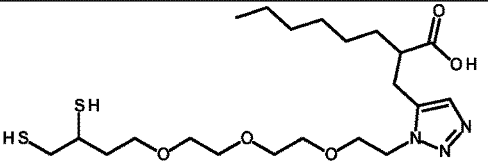
Figure 5I:
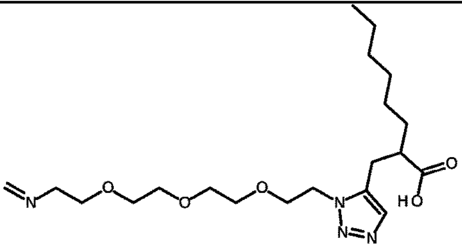
Figure 5I:
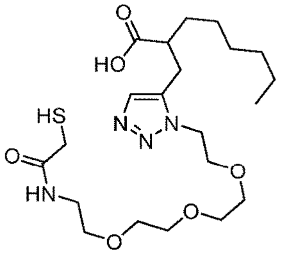
Figure 5I:
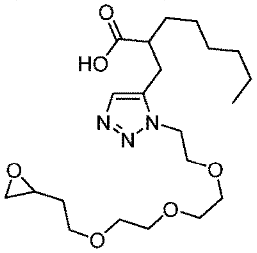
Figure 5I:
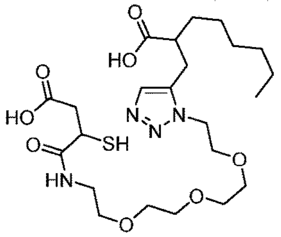
Figure 5I:
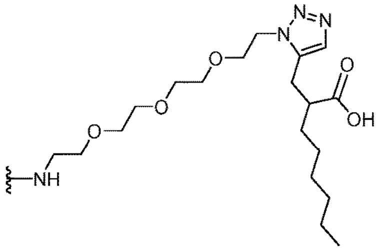
Figure 5I:
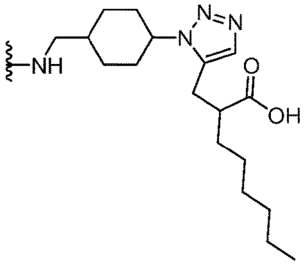
Figure 5I:
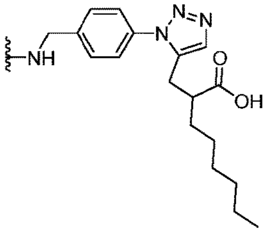
Figure 5I:
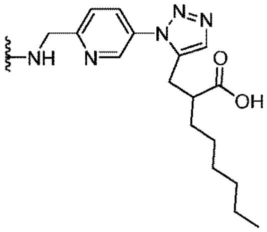
Figure 5J:
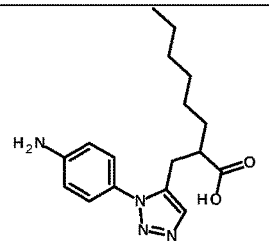
Figure 5J:
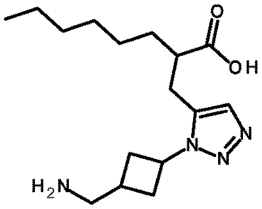
Figure 5J:
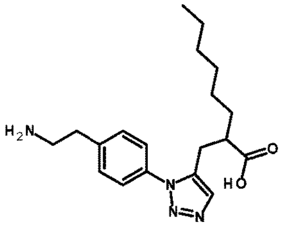
Figure 5J:
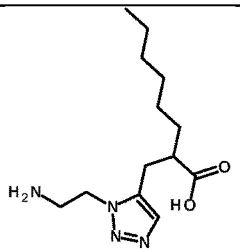
Figure 5J:
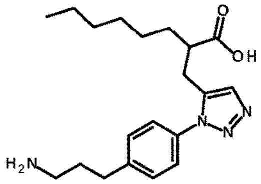
Figure 5J:
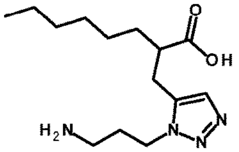
Figure 5J:
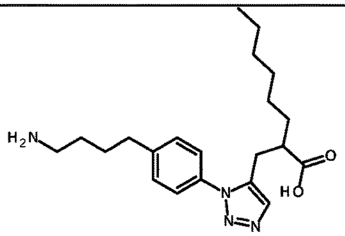
Figure 5J:
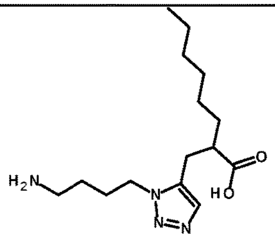
Figure 5J:
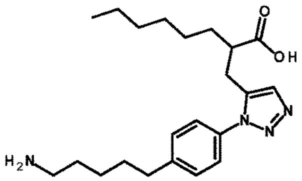
Figure 5J:
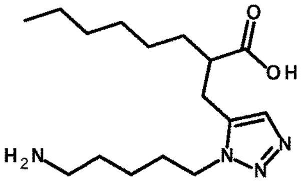
Figure 5J:
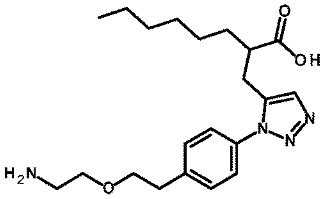
Figure 5J:
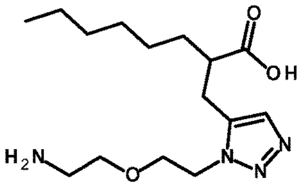
Figure 5K:
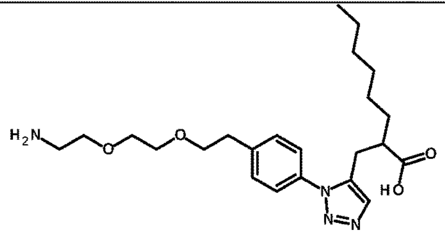
Figure 5K:
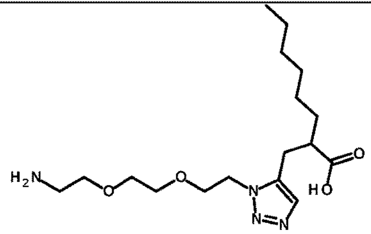
Figure 5K:
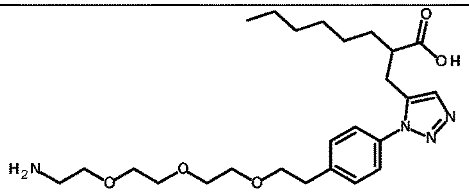
Figure 5K:
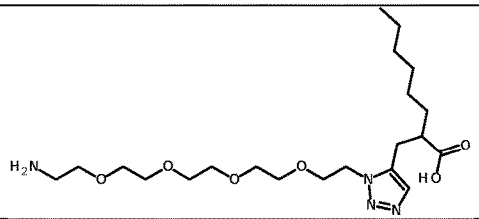
Figure 5K:
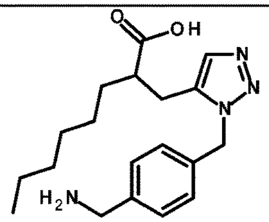
Figure 5K:
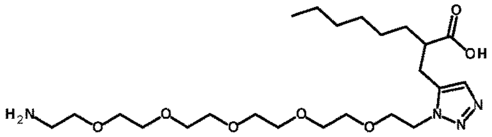
Figure 5K:
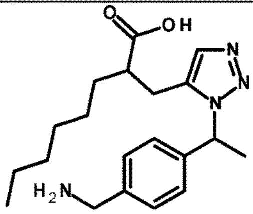
Figure 5K:
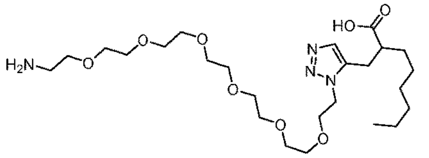
Figure 5K:
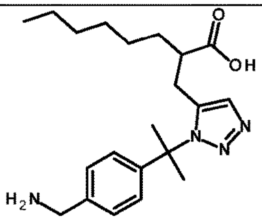
Figure 5K:
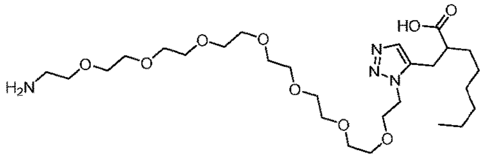
Figure 5K:
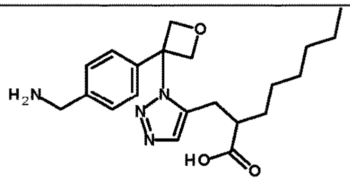
Figure 5K:
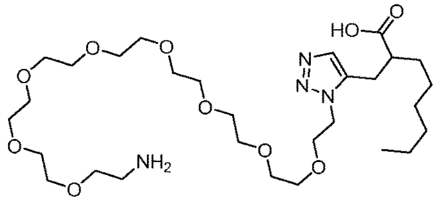
Figure 5L:
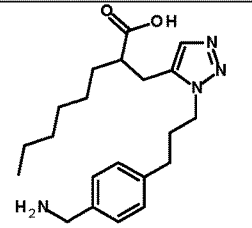
Figure 5L:
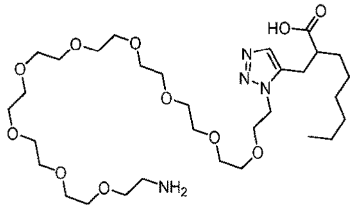
Figure 5L:
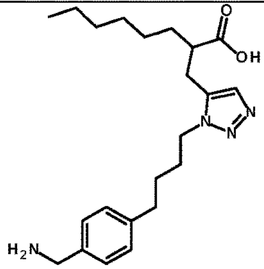
Figure 5L:
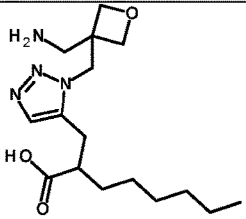
Figure 5L:
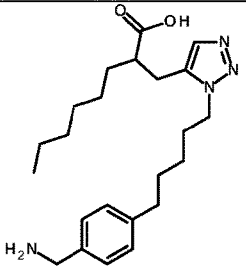
Figure 5L:
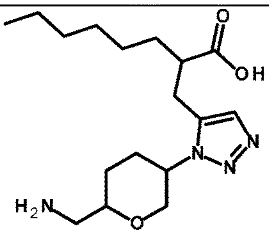
Figure 5L:
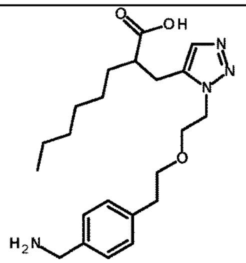
Figure 5L:
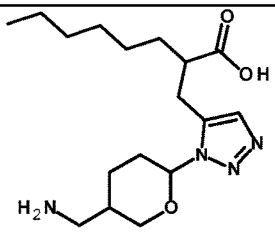
Figure 5L:
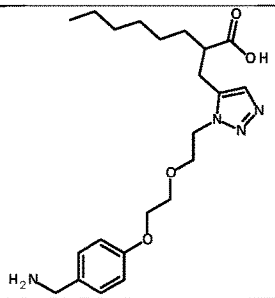
Figure 5L:
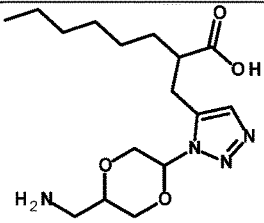
Figure 5L:
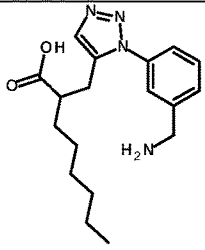
Figure 5L:
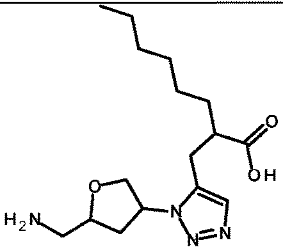
Figure 5M:
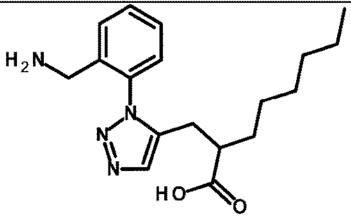
Figure 5M:
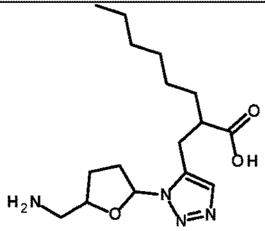
Figure 5M:
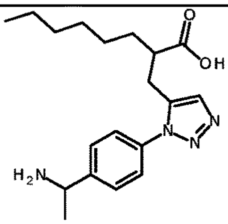
Figure 5M:
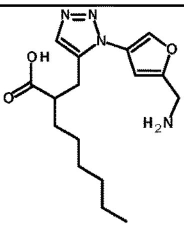
Figure 5M:
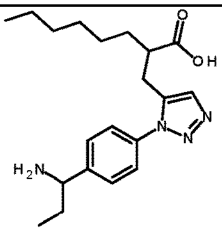
Figure 5M:
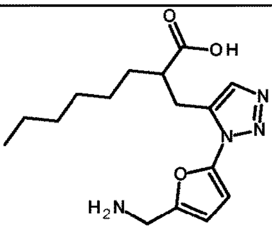
Figure 5M:
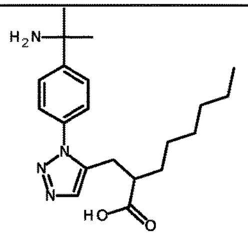
Figure 5M:
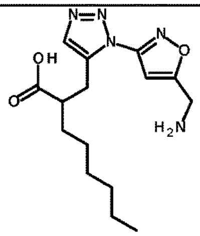
Figure 5M:
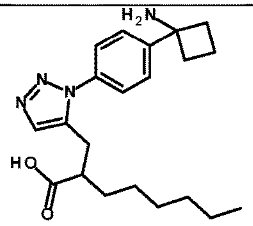
Figure 5M:
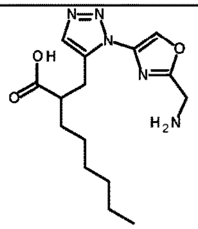
Figure 5M:
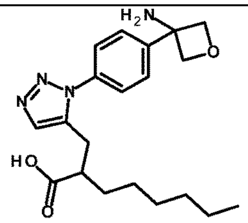
Figure 5M:
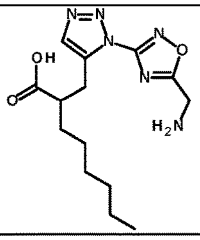
Figure 5N:
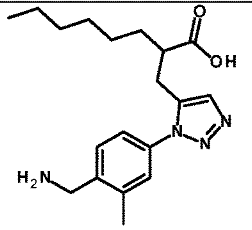
Figure 5N:
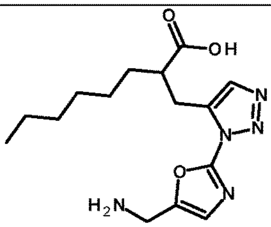
Figure 5N:
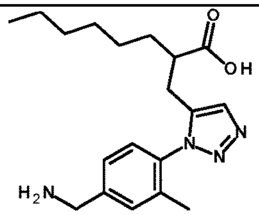
Figure 5N:
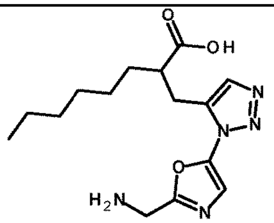
Figure 5N:
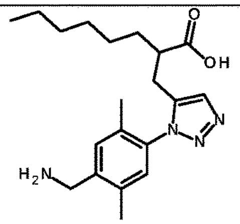
Figure 5N:
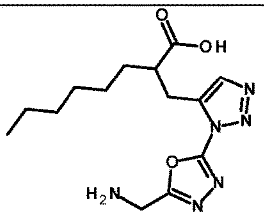
Figure 5N:
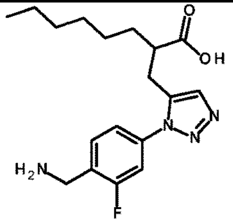
Figure 5N:
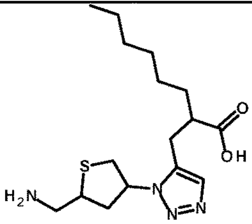
Figure 5N:
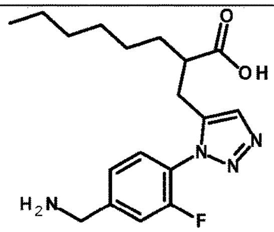
Figure 5N:
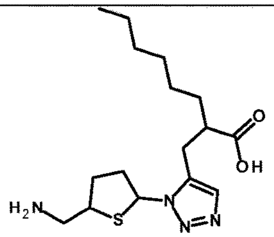
Figure 5N:
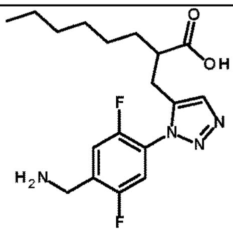
Figure 5N:
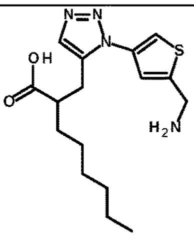
Figure 5O:
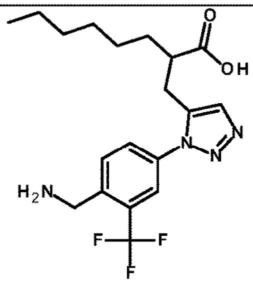
Figure 5O:
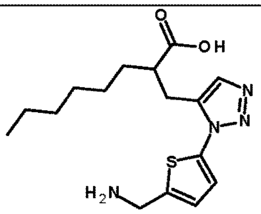
Figure 5O:
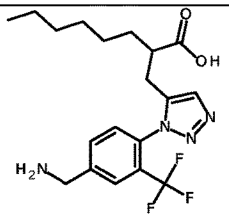
Figure 5O:
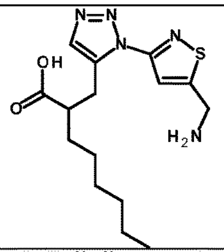
Figure 5O:
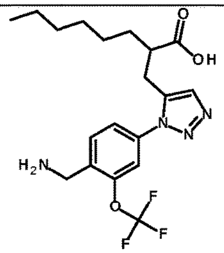
Figure 5O:
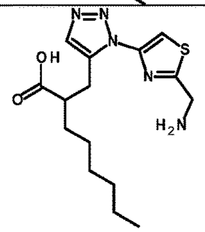
Figure 5O:
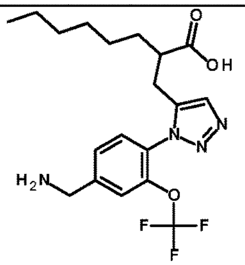
Figure 5O:
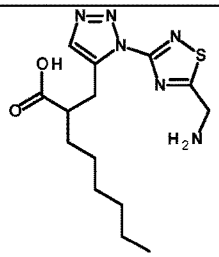
Figure 5O:
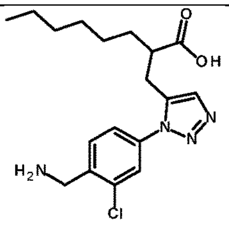
Figure 5O:
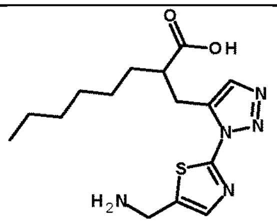
Figure 5O:
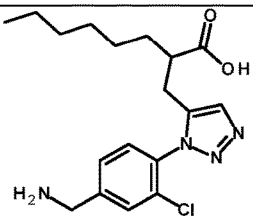
Figure 5O:
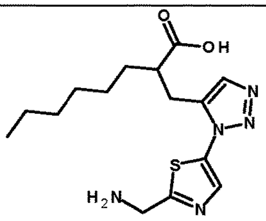
Figure 5P:
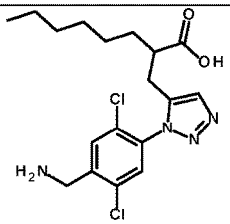
Figure 5P:
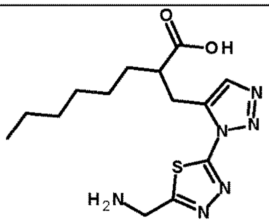
Figure 5P:
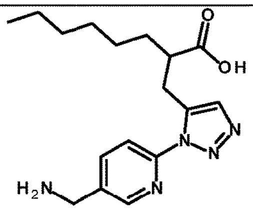
Figure 5P:
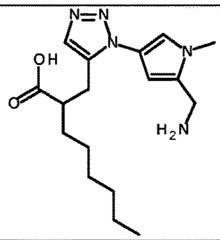
Figure 5P:
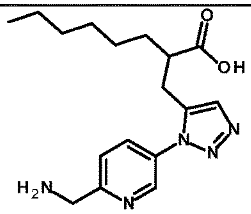
Figure 5P:
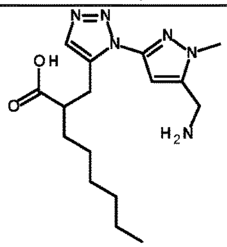
Figure 5P:
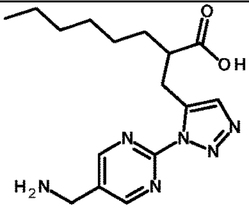
Figure 5P:
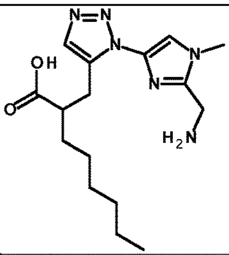
Figure 5P:
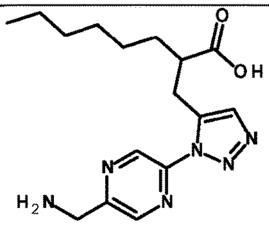
Figure 5P:
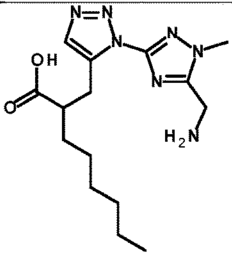
Figure 5P:
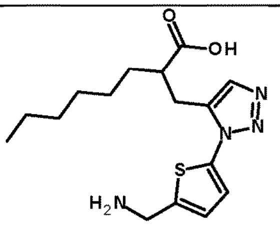
Figure 5P:
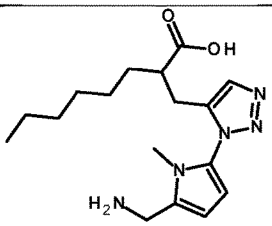
Figure 5Q:
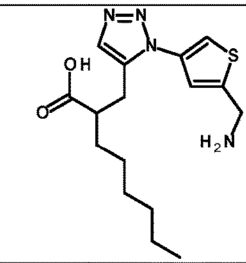
Figure 5Q:
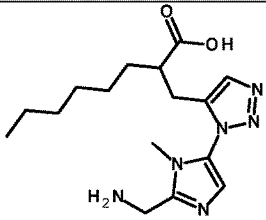
Figure 5Q:
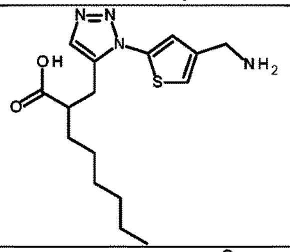
Figure 5Q:
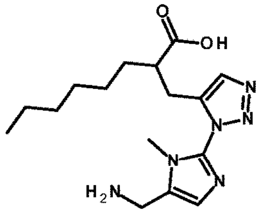
Figure 5Q:
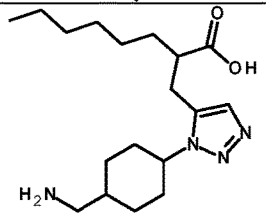
Figure 5Q:
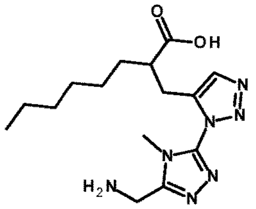
Figure 5Q:
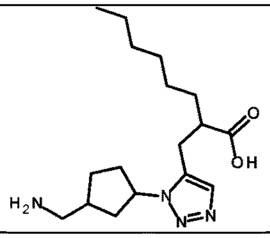
Figure 5Q:
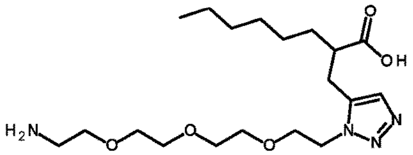
Figure 5Q:
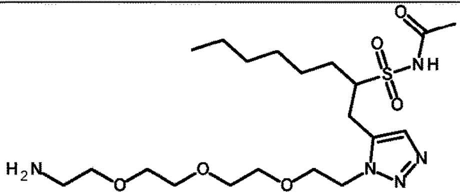
Figure 5Q:
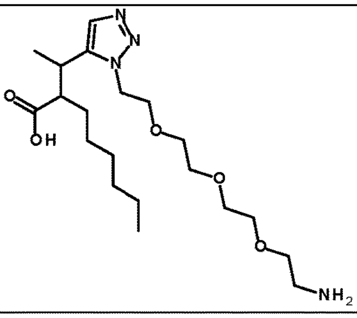
Figure 5Q:
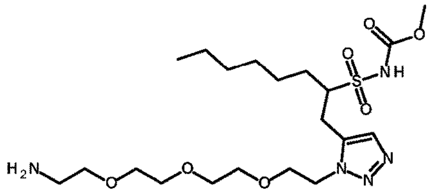
Figure 5R:
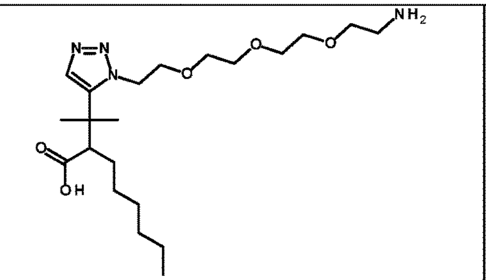
Figure 5R:
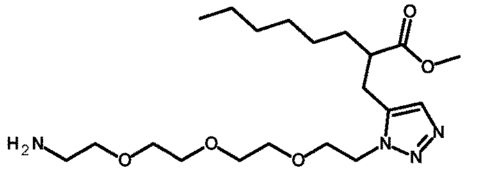
Figure 5R:
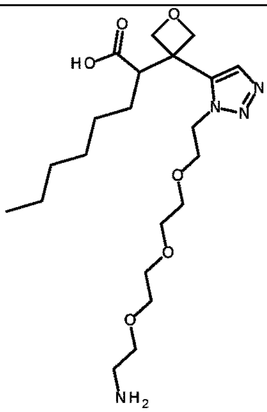
Figure 5R:
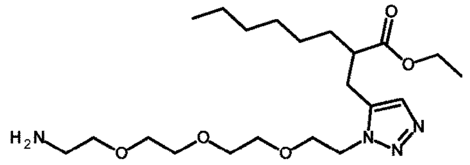
Figure 5R:
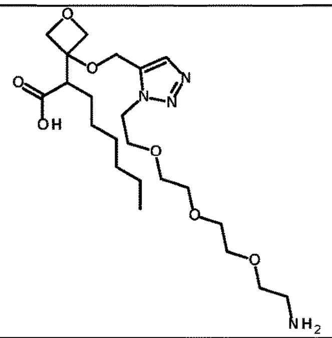
Figure 5R:
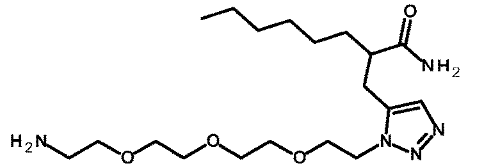
Figure 5R:
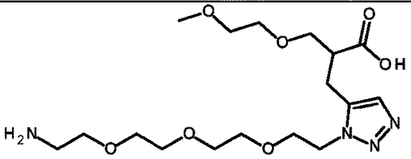
Figure 5R:
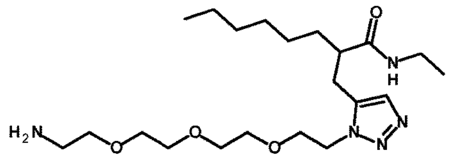
Figure 5R:
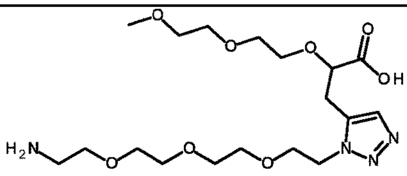
Figure 5R:
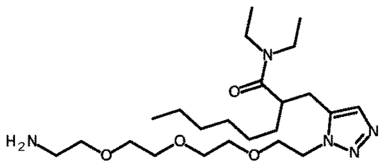
Figure 5S:
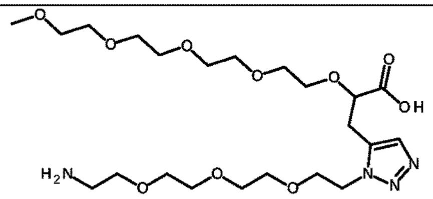
Figure 5S:
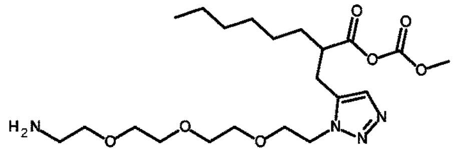
Figure 5S:
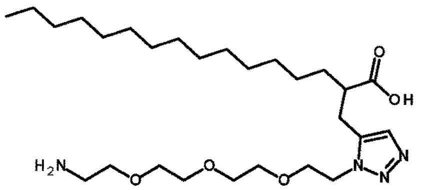
Figure 5S:
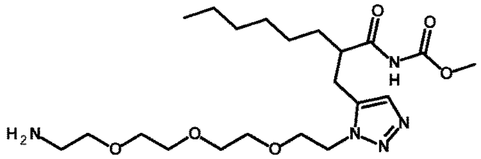
Figure 5S:
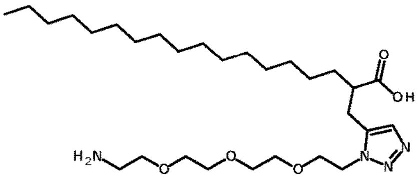
Figure 5S:
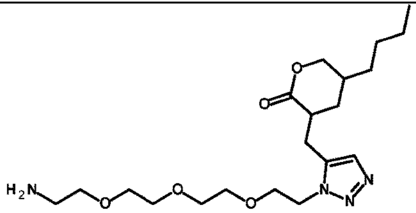
Figure 5S:
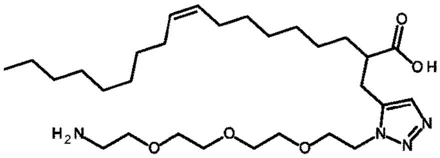
Figure 5S:
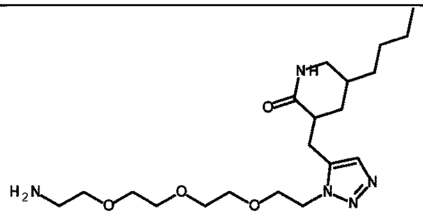
Figure 5S:
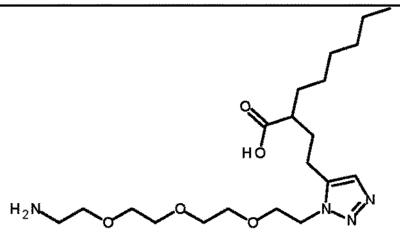
Figure 5S:
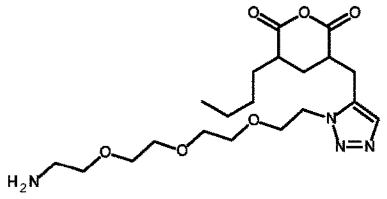
Figure 5S:
Figure 5S:
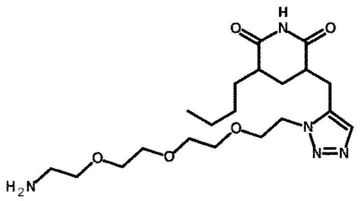
Figure 5T:
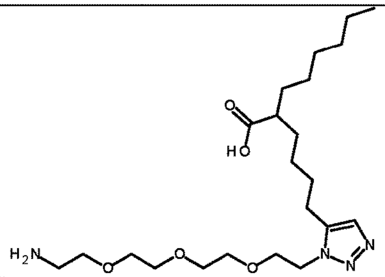
Figure 5T:
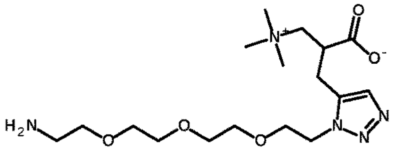
Figure 5T:
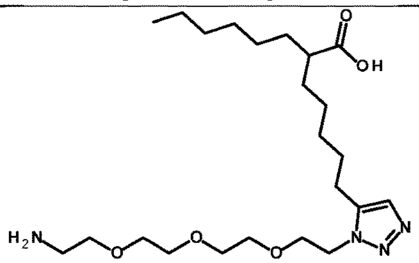
Figure 5T:
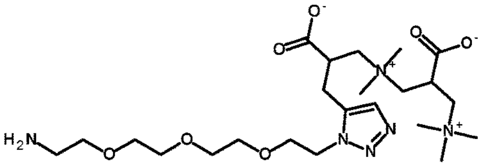
Figure 5T:
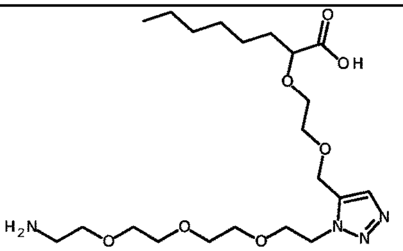
Figure 5T:
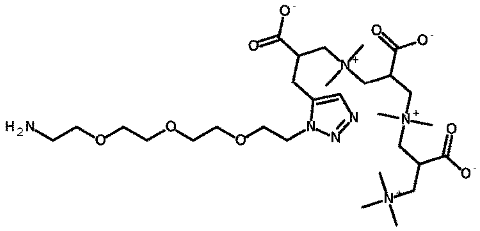
Figure 5T:
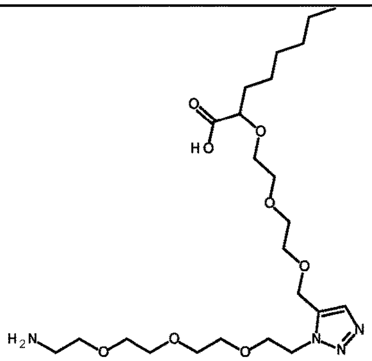
Figure 5T:
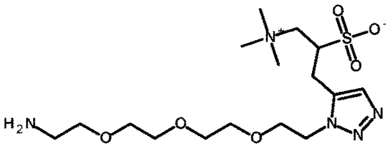
Figure 5T:
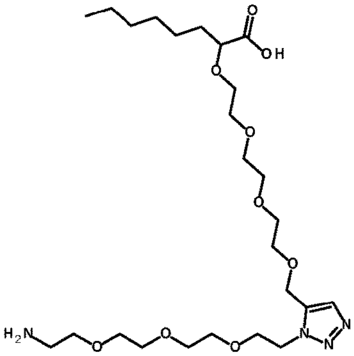
Figure 5T:
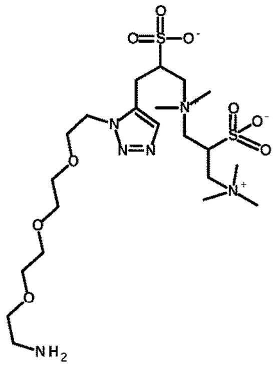
Figure 5U:
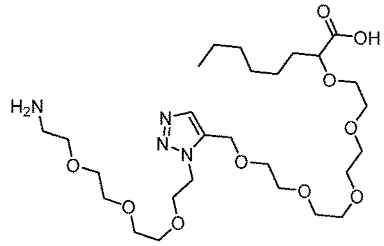
Figure 5U:
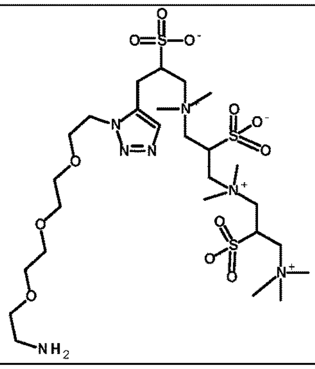
Figure 5U:
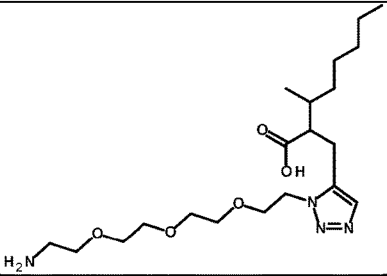
Figure 5U:
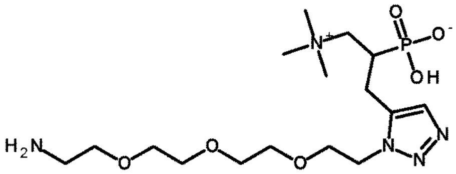
Figure 5U:
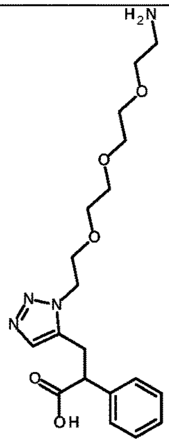
Figure 5U:
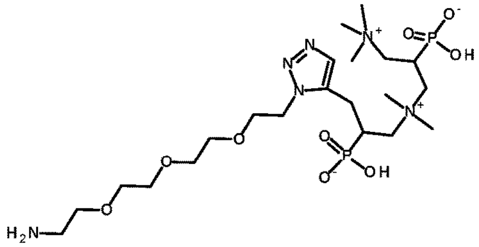
Figure 5U:
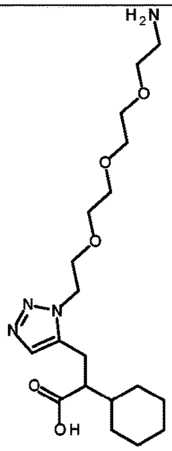
Figure 5U:
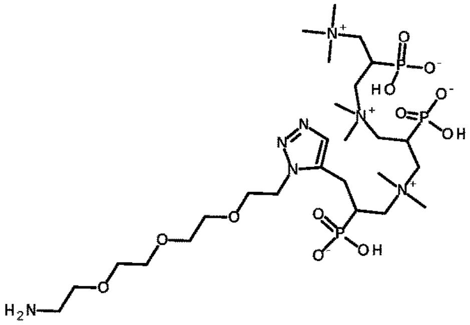
Figure 5V:
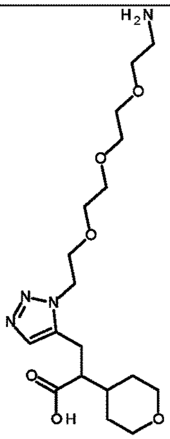
Figure 5V:
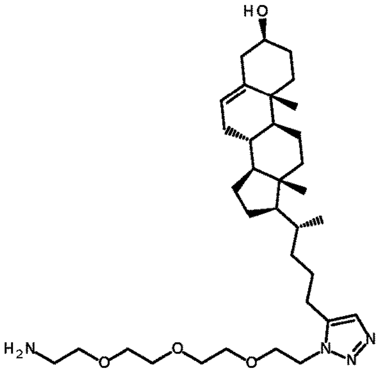
Figure 5V:
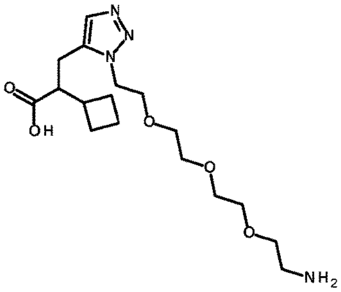
Figure 5V:
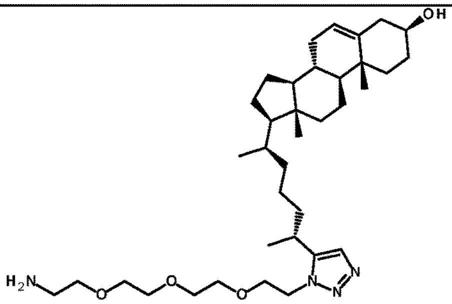
Figure 5V:
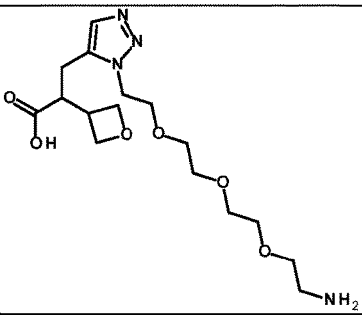
Figure 5V:
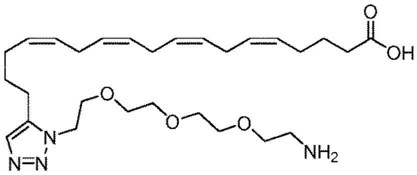
Figure 5V:
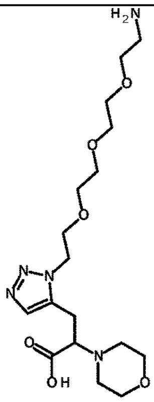
Figure 5V:
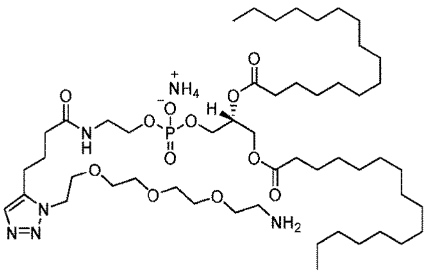
Figure 5W:
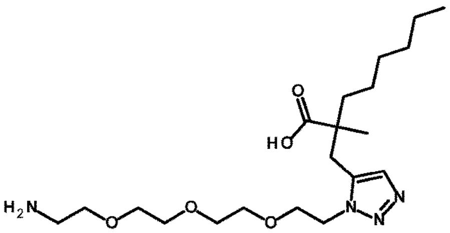
Figure 5W:
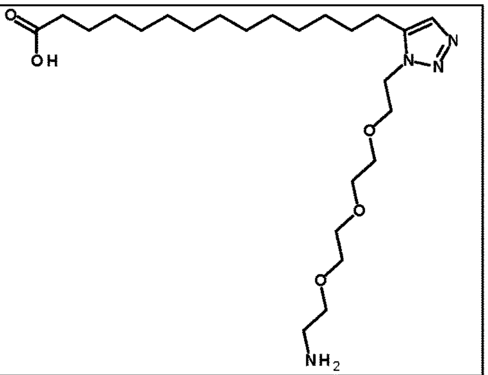
Figure 5W:
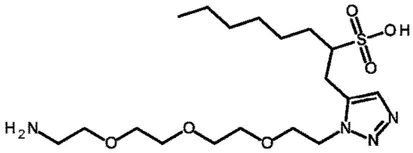
Figure 5W:
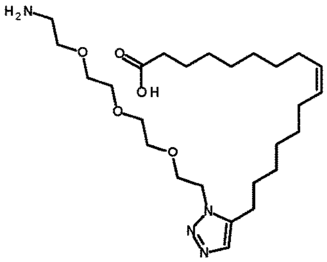
Figure 5W:
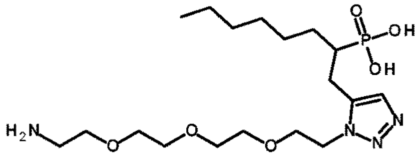

In some embodiments, a compound of Formula (I) is selected from a compound depicted in any one of FIGS. 1A-5WW or a pharmaceutically acceptable salt thereof.

In some embodiments, the compound of Formula (I) is a compound of Formula (II):

Formula (I-a)

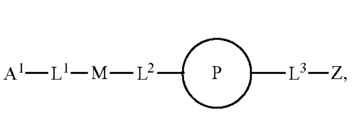

or a salt thereof, wherein A1 is hydrogen, alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, —$N(R^C)(R^D)$, —$N(R^C)C(O)R^B$, —$C(O)N(R^C)(R^D)$, —$N_3$, —NC, —CN, —NCO, —NCS, —$N(R^C)N(R^D)_2$, —NCN($R^C$), —C(═$N(R^C)(R^D)$)$OR^A$, —$SR^E$, —$S(O)_xR^E$, —OS$(O)_xR^E$, —$N(R^C)S(O)_xR^E$, —$S(O)_xN(R^C)(R^D)$, —$P(R^F)_y$, —$Si(OR^A)_3$, —$Si(R^G)(OR^A)_2$, —$B(OR^A)_2$, or a metal, wherein each alkyl, alkenyl, alkynyl, heteroalkyl, cycloalkyl, heterocyclyl, aryl, and heteroaryl is optionally substituted by one or more $R^1$; each of $L^1$ and $L^3$ is independently a bond, alkyl, or heteroalkyl, wherein each alkyl and heteroalkyl is optionally substituted by one or more $R^2$; $L^2$ is a bond; M is alkyl, heteroalkyl, cycloalkyl, heterocyclyl, aryl, or heteroaryl, each of which is optionally substituted by one or more $R^3$; P is heteroaryl optionally substituted by one or more $R^4$; Z is alkyl, alkenyl, alkynyl, heteroalkyl, cycloalkyl, heterocyclyl, aryl, or heteroaryl, each of which is optionally substituted by one or more $R^5$; each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$; or $R^C$ and $R^D$, taken together with the nitrogen atom to which they are attached, form a ring (e.g., a 5-7 membered ring), optionally substituted with one or more $R^6$; each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, $S(O)_xR^{E1}$, —OS$(O)_xR^{E1}$, —$N(R^{C1})S(O)_xR^{E1}$, —$S(O)_xN(R^{C1})(R^{D1})$, —$P(R^{F1})$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$; each $R^{A1}$, $R^{B1}$, Rei $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$; each $R^7$ is independently alkyl, alkenyl, alkynyl, heteroalkyl, halogen, cyano, oxo, hydroxyl, cycloalkyl, or heterocyclyl; x is 1 or 2; and y is 2, 3, or 4.

In some embodiments, A1 is alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, or —$N(R^C)(R^D)$. In some embodiments, A1 is alkyl, alkenyl, alkynyl, heteroalkyl, —$OR^A$, —$C(O)OR^A$, —$C(O)R^B$, —$OC(O)R^B$ or —$N(R^C)(R^D)$. In some embodiments, A1 is alkyl, $OR^A$, —$C(O)OR^A$, —$C(O)R^B$, —$OC(O)R^B$, or —$N(R^C)(R^D)$. In some embodiments, A1 is $N(R^C)(R^D)$. In some embodiments, A1 is $N(R^C)(R^D)$, and $R^C$ an $R^D$ is independently hydrogen or alkyl. In some embodiments, A1 is $NH_2$. In some embodiments, A1 is $NH_2$ or $NHC(O)C(CH_2)CH_3$.

In some embodiments, $L^1$ is a bond, alkyl, or heteroalkyl. In some embodiments, $L^1$ is alkyl. In some embodiments, $L^1$ is $C_1$-$C_6$ alkyl. In some embodiments, $L^1$ is —$CH_2$— or —$CH_2CH_2$—.

In some embodiments, $L^3$ is a bond, alkyl, or heteroalkyl. In some embodiments, $L^3$ is a bond. In some embodiments, $L^3$ is alkyl. In some embodiments, $L^3$ is $C_1$-$C_6$ alkyl. In some embodiments, $L^3$ is —$CH_2$—. In some embodiments, $L^3$ is heteroalkyl. In some embodiments, $L^3$ is $C_1$-$C_6$ heteroalkyl. In some embodiments, $L^3$ is —$CH_2O$—.

In some embodiments, M is heteroalkyl, aryl, or heteroaryl. In some embodiments, M is heteroalkyl. In some embodiments, M is (—$OCH_2CH_2$-)z, wherein z is an integer selected from 1 to 10. In some embodiments, M is —$OCH_2CH_2$—, (—$OCH_2CH_2$—$)_2$, (—$OCH_2CH_2$—$)_3$, or (—$OCH_2CH_2$—$)_4$. In some embodiments, M is (—$OCH_2CH_2$—$)_3$. In some embodiments, M is aryl. In some embodiments, M is phenyl. In some embodiments, M is unsubstituted phenyl.

In some embodiments, P is a tricyclic, bicyclic, or monocyclic heteroaryl. In some embodiments, P is a monocyclic heteroaryl. In some embodiments, P is a nitrogen-containing heteroaryl. In some embodiments, P is a monocyclic, nitrogen-containing heteroaryl. In some embodiments, P is a 5-membered heteroaryl. In some embodiments, P is a 5-membered nitrogen-containing heteroaryl. In some embodiments, P is tetrazolyl, imidazolyl, pyrazolyl, or triazolyl, pyrrolyl, oxazolyl, or thiazolyl. In some embodiments, P is tetrazolyl, imidazolyl, pyrazolyl, or triazolyl, or pyrrolyl. In some embodiments, P is triazolyl. In some embodiments, P is 1,2,3-triazolyl or 1,2,4-triazolyl. In some embodiments, P is 1,2,4-triazolyl.

In some embodiments, Z is alkyl, heteroalkyl, cycloalkyl, heterocyclyl, aryl, or heteroaryl. In some embodiments, Z is heterocyclyl. In some embodiments, Z is monocyclic or bicyclic heterocyclyl. In some embodiments, Z is an oxygen-containing heterocyclyl. In some embodiments, Z is a 6-membered heterocyclyl. In some embodiments, Z is a 6-membered oxygen-containing heterocyclyl. In some embodiments, Z is tetrahydropyranyl. In some embodiments, Z is a bicyclic oxygen-containing heterocyclyl. In some embodiments, Z is phthalic anhydridyl. In some embodiments, Z is a sulfur-containing heterocyclyl. In some embodiments, Z is a 6-membered sulfur-containing heterocyclyl. In some embodiments, Z is a 6-membered heterocyclyl containing a nitrogen atom and a sulfur atom. In some embodiments, Z is thiomorpholinyl-1,1-dioxidyl. In some embodiments, Z is oxetanyl, tetrahydrofuranyl, tetrahydropyranyl, thiomorpholinyl-1,1-dioxide, piperidinyl, piperazinyl, or pyrrolidinyl.

In some embodiments, Z is aryl. In some embodiments, Z is monocyclic aryl. In some embodiments, Z is phenyl. In some embodiments, Z is monosubstituted phenyl (e.g., with 1 $R^5$). In some embodiments, Z is monosubstituted phenyl, wherein the 1 $R^5$ is a nitrogen-containing group. In some embodiments, Z is monosubstituted phenyl, wherein the 1 $R^5$ is $NH_2$. In some embodiments, Z is monosubstituted phenyl, wherein the 1 $R^5$ is an oxygen-containing group. In some embodiments, Z is monosubstituted phenyl, wherein the 1 $R^5$ is an oxygen-containing heteroalkyl. In some embodiments, Z is monosubstituted phenyl, wherein the 1 $R^5$ is $OCH_3$. In some embodiments, Z is monosubstituted phenyl, wherein the 1 $R^5$ is in the ortho position. In some embodiments, Z is monosubstituted phenyl, wherein the 1 $R^5$ is in the meta position. In some embodiments, Z is monosubstituted phenyl, wherein the 1 $R^5$ is in the para position.

In some embodiments, Z is alkyl. In some embodiments, Z is $C_1$-$C_{12}$ alkyl. In some embodiments, Z is $C_1$-$C_{10}$ alkyl. In some embodiments, Z is $C_1$-$C_8$ alkyl. In some embodiments, Z is $C_1$-$C_8$ alkyl substituted with 1-5 $R^5$. In some embodiments, Z is $C_1$-$C_8$ alkyl substituted with 1 $R^5$. In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1})(R^{D1})$ In some embodiments, Z is $C_1$-$C_8$ alkyl substituted with 1 $R^5$, wherein $R^5$ is —$OR^{A1}$ or —$C(O)OR^{A1}$. In some embodiments, Z is $C_1$-$C_8$ alkyl substituted with 1 $R^5$, wherein $R^5$ is —OH or —C(O)OH.

Figure 6A:
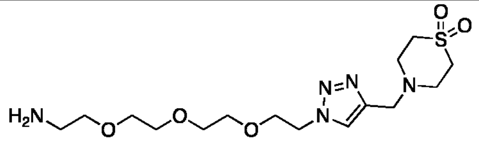
Figure 6A:
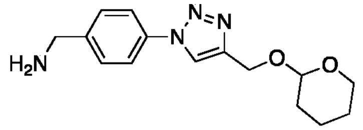
Figure 6A:
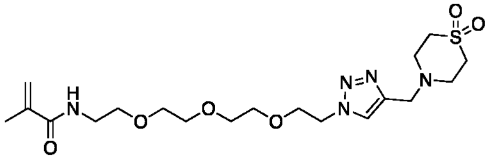
Figure 6A:
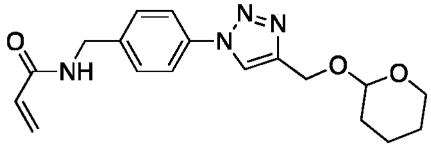
Figure 6A:
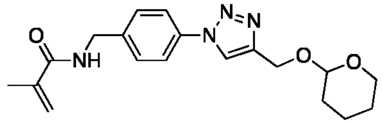
Figure 6A:
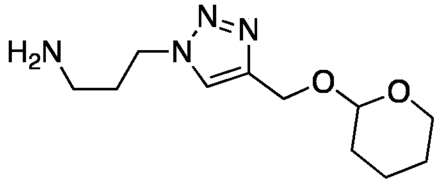
Figure 6A:
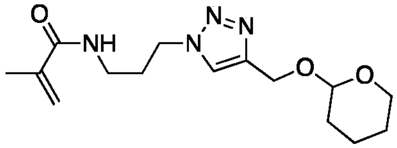
Figure 6A:
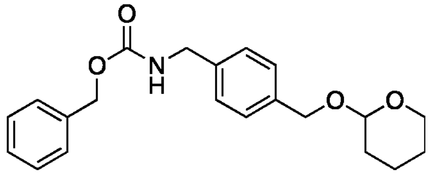
Figure 6A:
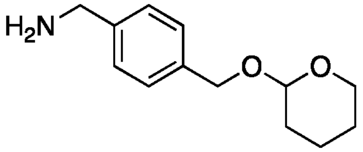
Figure 6B:
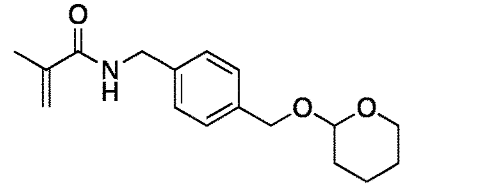
Figure 6B:
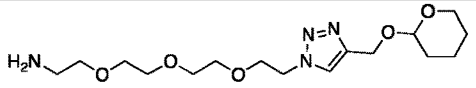
Figure 6B:
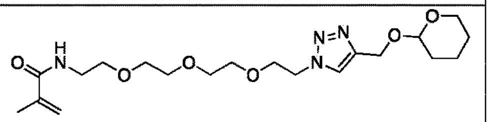
Figure 6B:
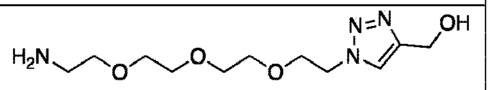
Figure 6B:
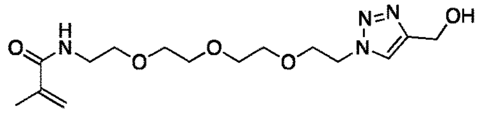
Figure 6B:
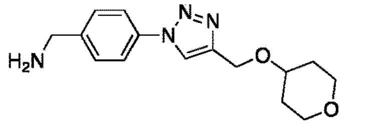
Figure 6B:
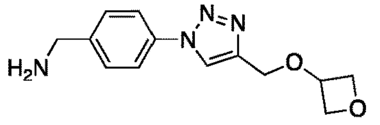
Figure 6B:
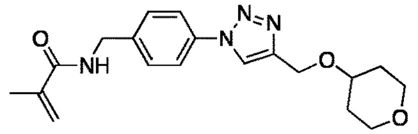
Figure 6B:
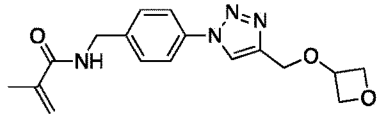
Figure 6B:
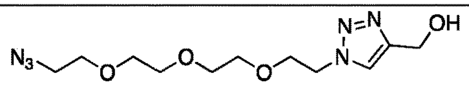
Figure 6B:
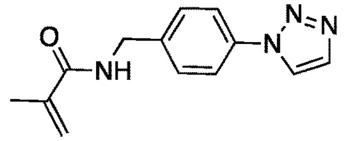
Figure 6B:
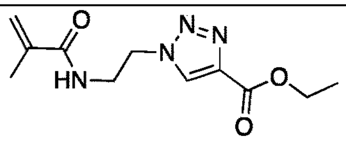
Figure 6C:
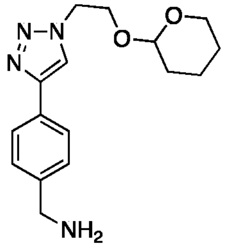
Figure 6C:
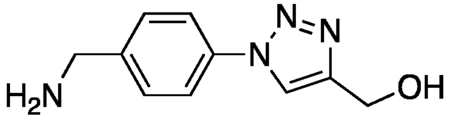
Figure 6C:
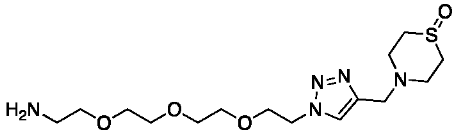
Figure 6C:
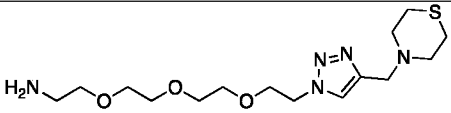
Figure 6C:
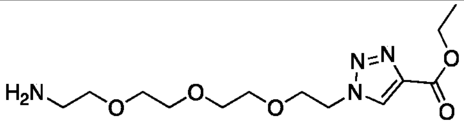
Figure 6C:
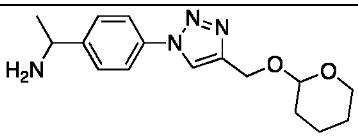
Figure 6C:
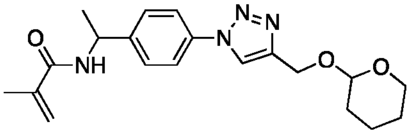
Figure 6C:
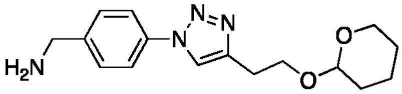
Figure 6C:
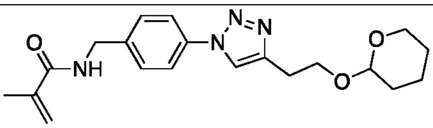
Figure 6C:
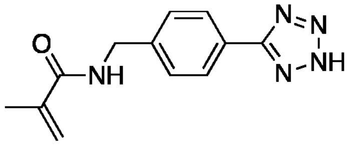
Figure 6D:
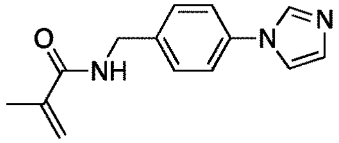
Figure 6D:
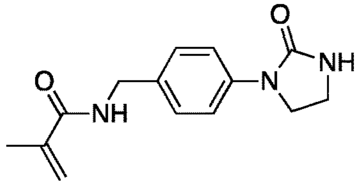
Figure 6D:
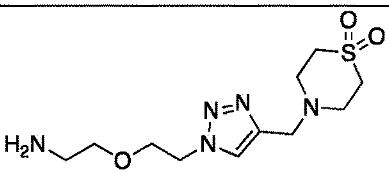
Figure 6D:
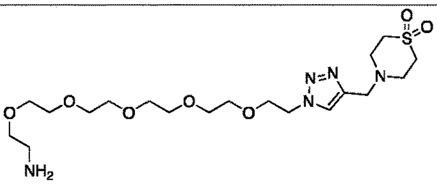
Figure 6D:
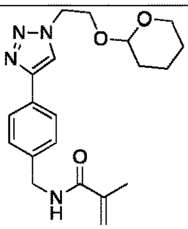
Figure 6D:
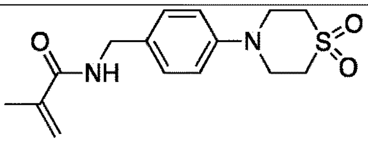
Figure 6D:
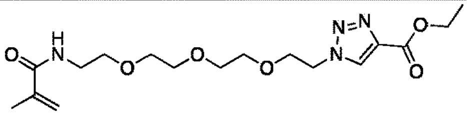
Figure 6D:
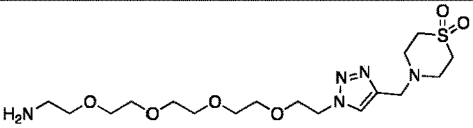
Figure 6D:
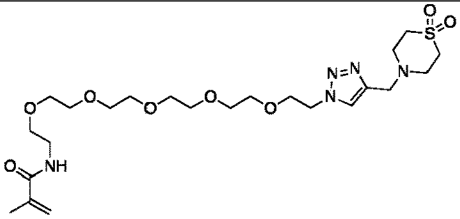
Figure 6E:
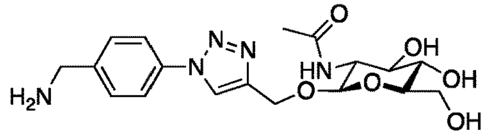
Figure 6E:
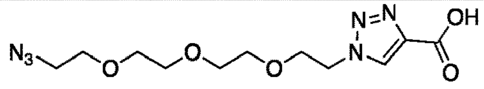
Figure 6E:
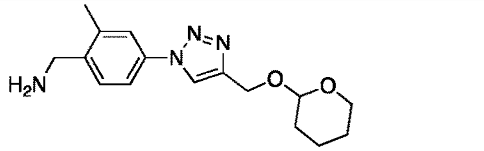
Figure 6E:
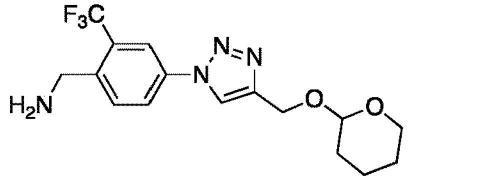
Figure 6E:
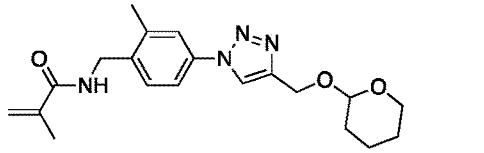
Figure 6E:
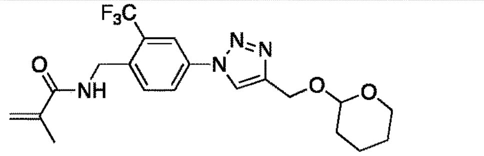
Figure 6E:
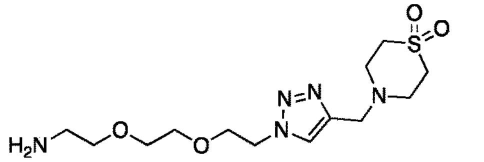
Figure 6E:
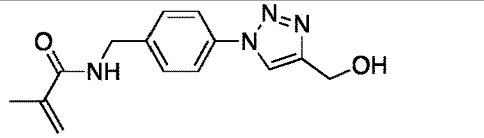
Figure 6E:
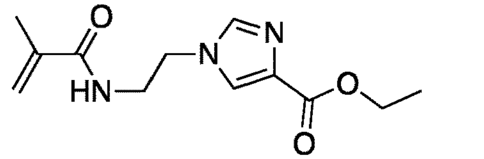
Figure 6E:
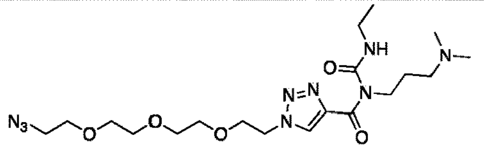
Figure 6F:
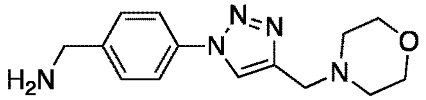
Figure 6F:
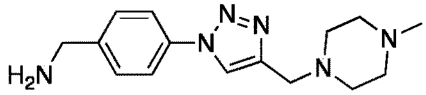
Figure 6F:
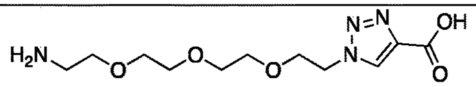
Figure 6F:
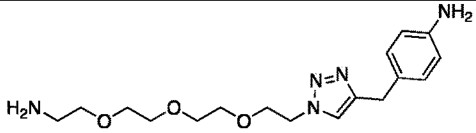
Figure 6F:
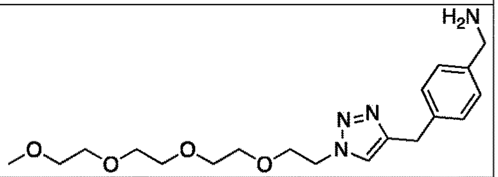
Figure 6F:
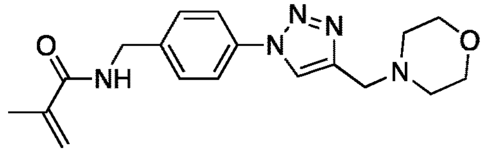
Figure 6F:
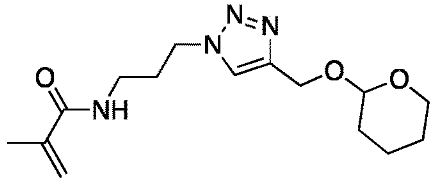
Figure 6F:
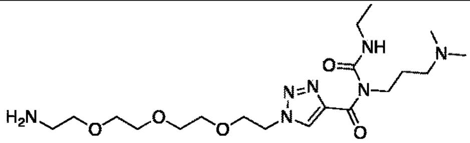
Figure 6F:
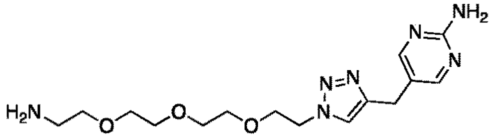
Figure 6F:
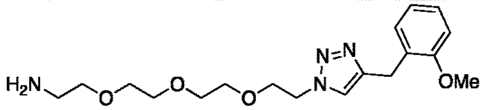
Figure 6F:
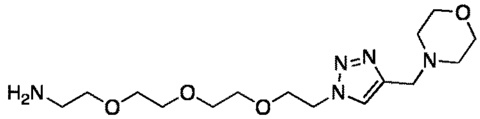
Figure 6G:
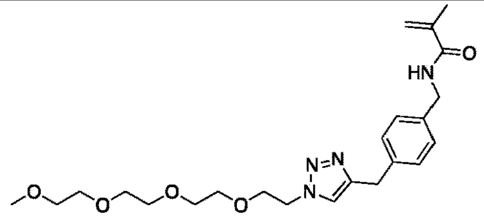
Figure 6G:
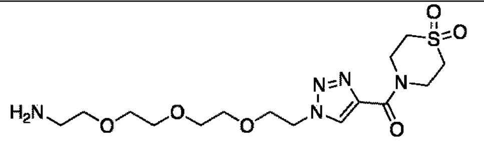
Figure 6G:
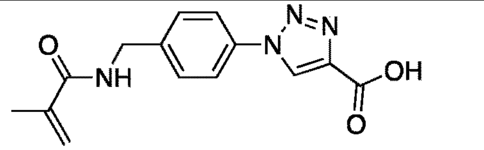
Figure 6G:
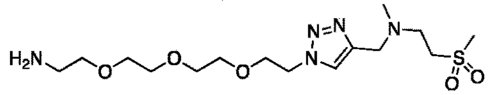
Figure 6G:
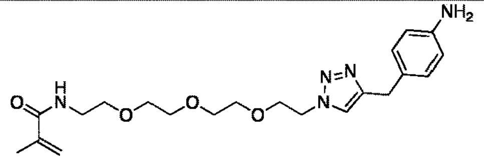
Figure 6G:
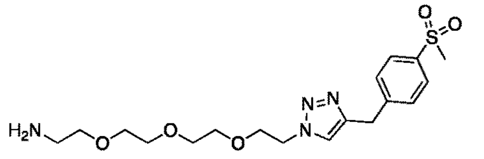
Figure 6G:
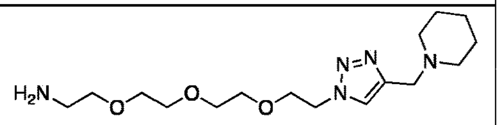
Figure 6G:
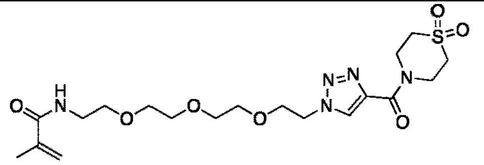
Figure 6G:
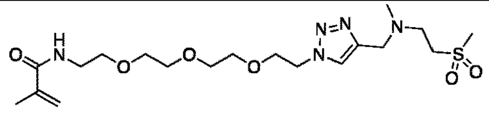
Figure 6G:
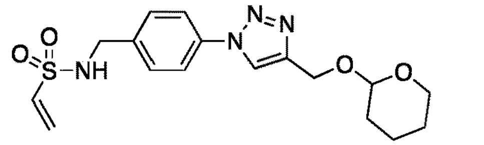
Figure 6H:
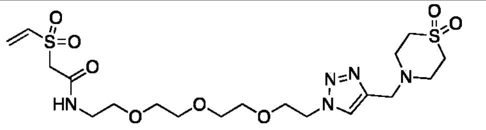
Figure 6H:
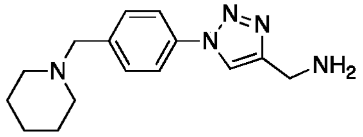
Figure 6H:
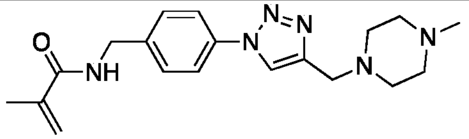
Figure 6H:
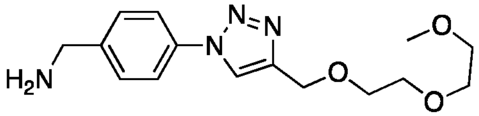
Figure 6H:
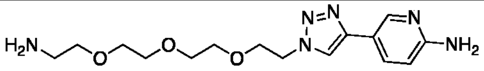
Figure 6H:
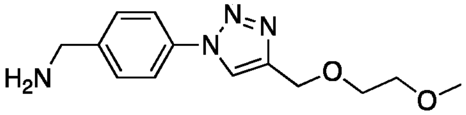
Figure 6H:
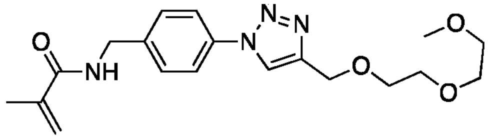
Figure 6H:
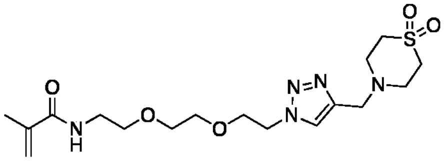
Figure 6H:
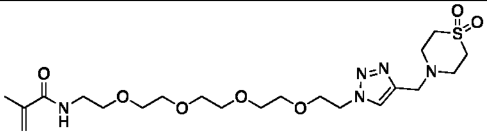
Figure 6H:
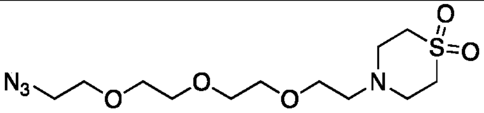
Figure 6H:
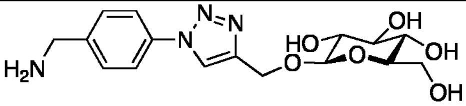
Figure 6I:
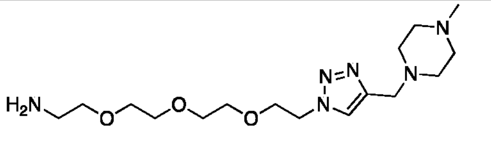
Figure 6I:
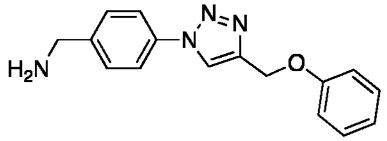
Figure 6I:
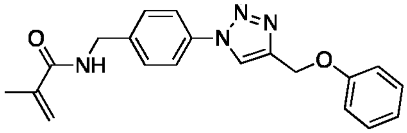
Figure 6I:
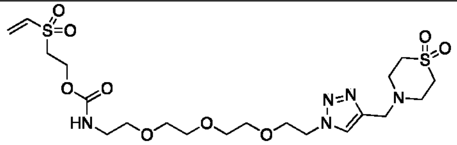
Figure 6I:
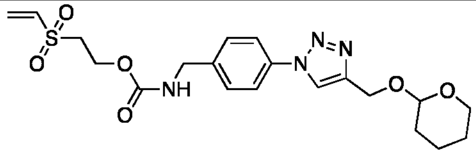
Figure 6I:
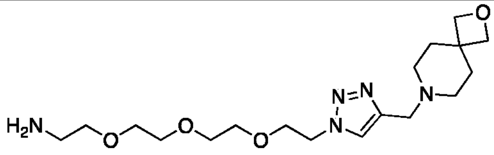
Figure 6I:
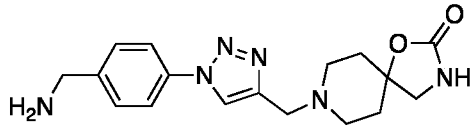
Figure 6I:
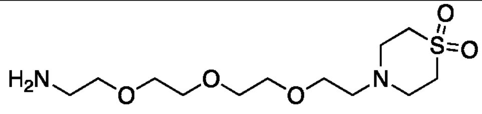
Figure 6I:
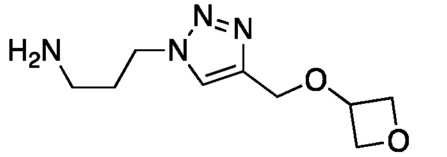
Figure 6I:
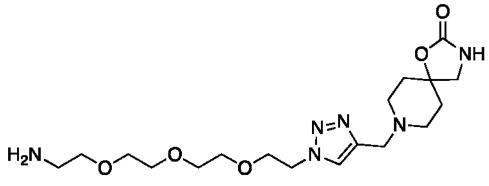
Figure 6J:
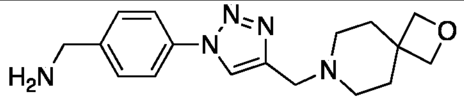
Figure 6J:
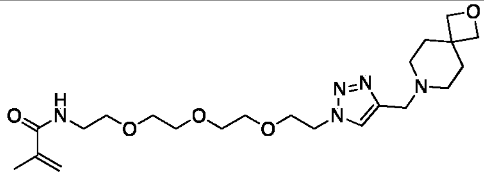
Figure 6J:
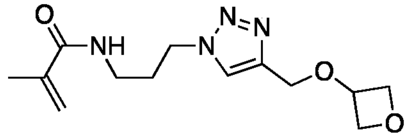
Figure 6J:
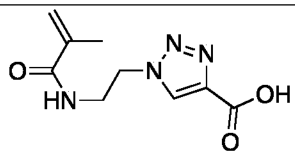
Figure 6J:
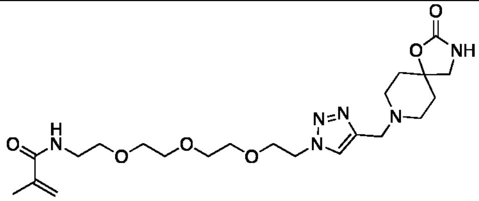
Figure 6J:
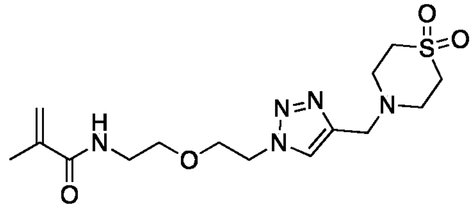
Figure 6J:
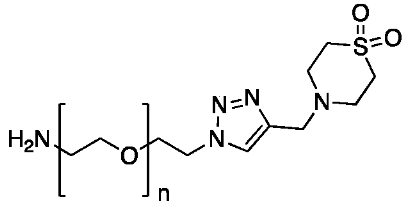
Figure 6J:
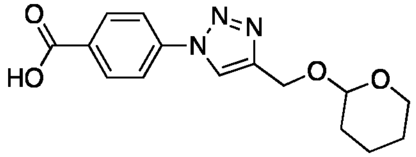
Figure 6J:
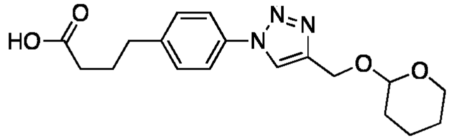
Figure 6K:
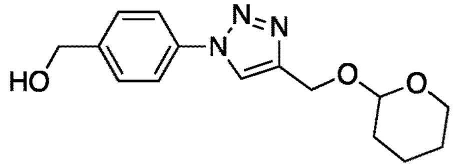
Figure 6K:
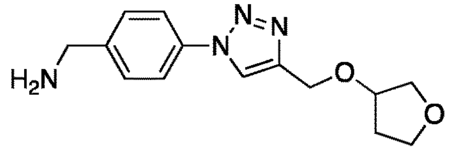
Figure 6K:
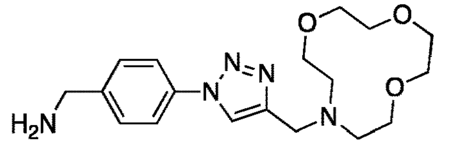
Figure 6K:
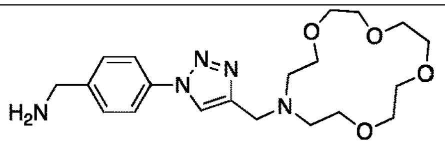
Figure 6K:
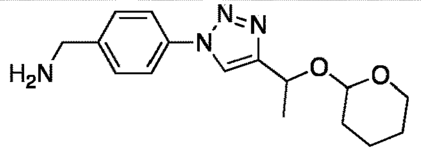
Figure 6K:
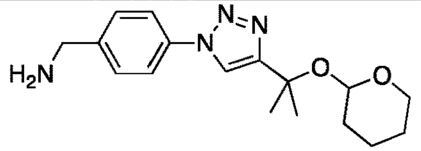
Figure 6K:
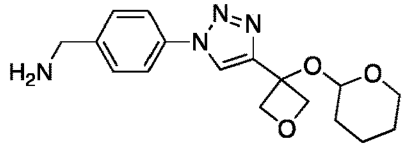
Figure 6K:
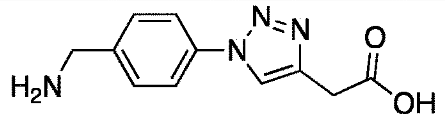
Figure 6K:
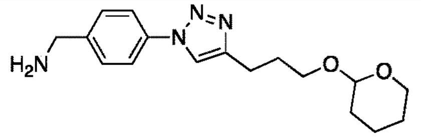
Figure 6K:
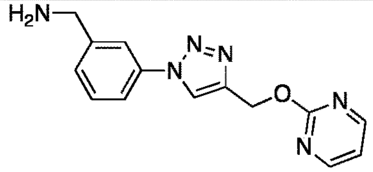
Figure 6L:
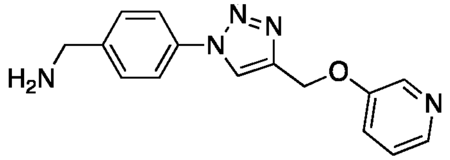
Figure 6L:
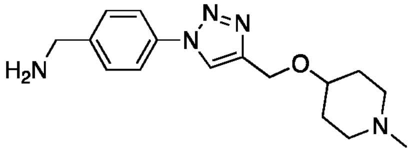
Figure 6L:
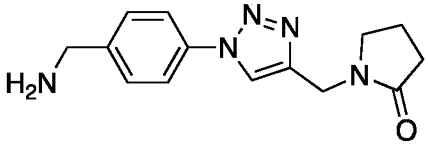
Figure 6L:
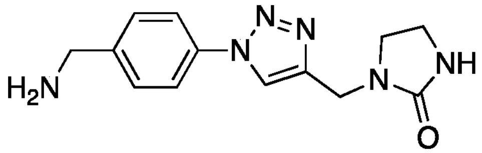
Figure 6L:
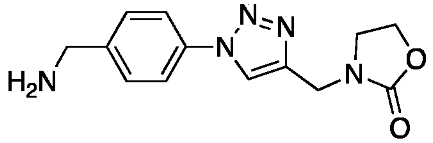
Figure 6L:
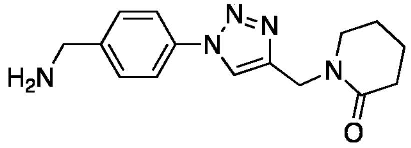
Figure 6L:
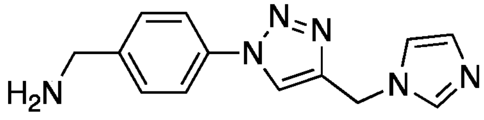
Figure 6L:
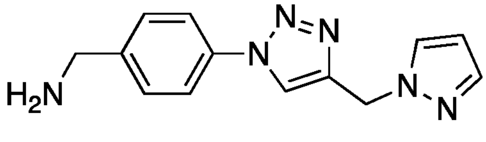
Figure 6L:
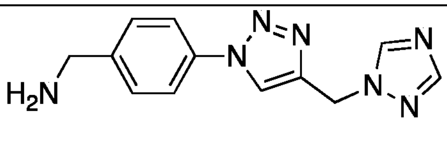
Figure 6L:
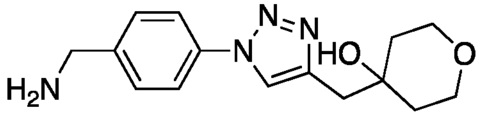
Figure 6M:
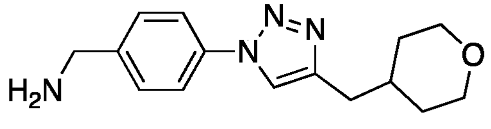
Figure 6M:
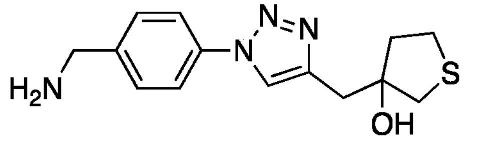
Figure 6M:
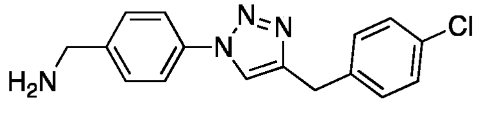
Figure 6M:
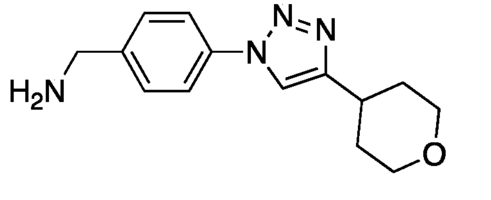
Figure 6M:
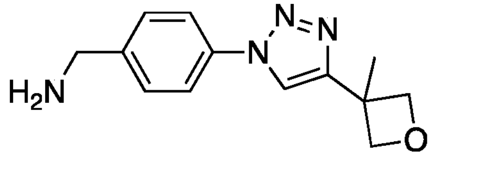
Figure 6M:
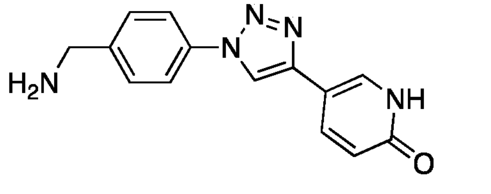
Figure 6M:
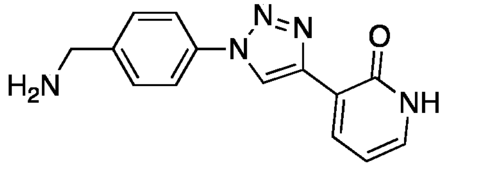
Figure 6M:
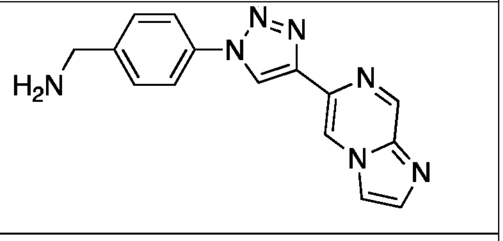
Figure 6M:
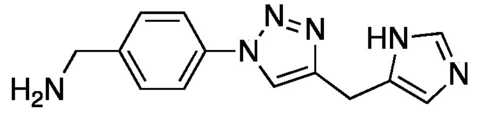
Figure 6N:
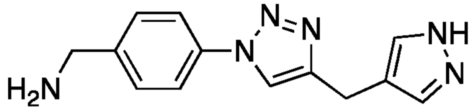
Figure 6N:
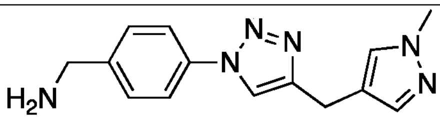
Figure 6N:
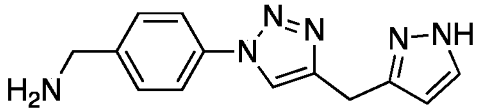
Figure 6N:
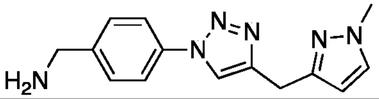
Figure 6N:
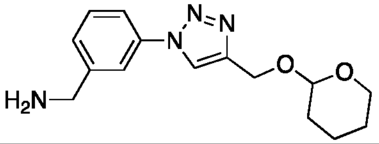
Figure 6N:
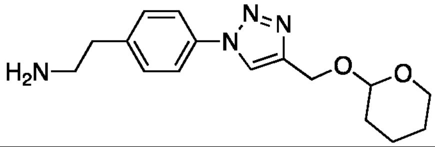
Figure 6N:
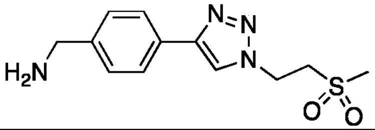
Figure 6N:
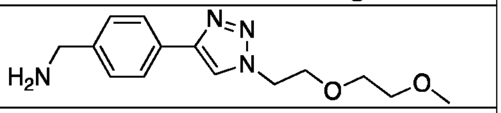
Figure 6N:
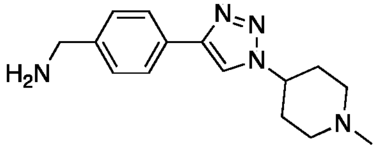
Figure 6N:
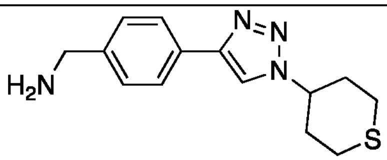
Figure 6N:
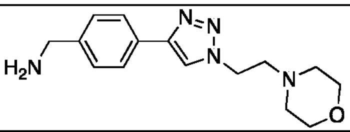
Figure 6N:
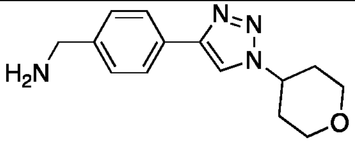
Figure 6O:
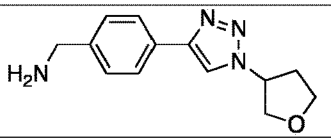
Figure 6O:
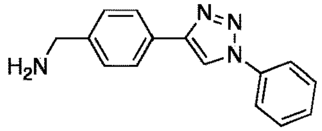
Figure 6O:
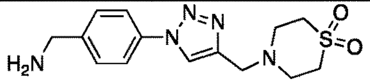
Figure 6O:
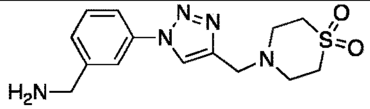
Figure 6O:
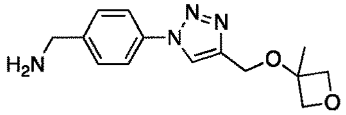
Figure 6O:
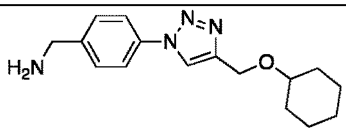
Figure 6O:
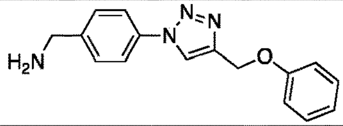
Figure 6O:
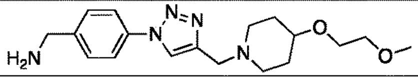
Figure 6O:
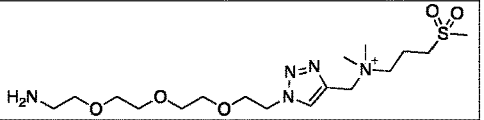
Figure 6O:
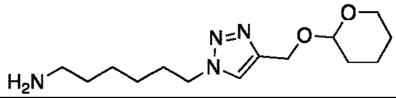
Figure 6O:
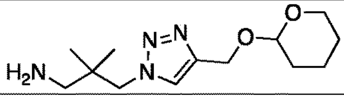
Figure 6O:
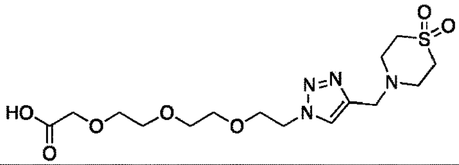
Figure 6O:
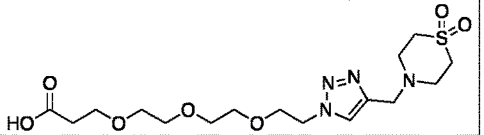
Figure 6O:
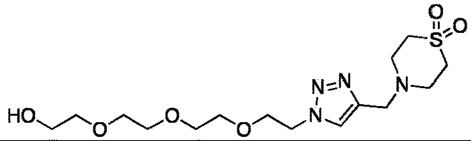
Figure 6P:
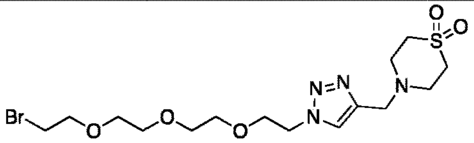
Figure 6P:
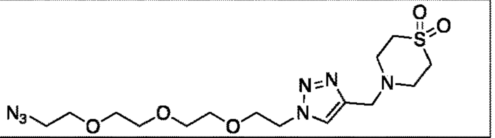
Figure 6P:
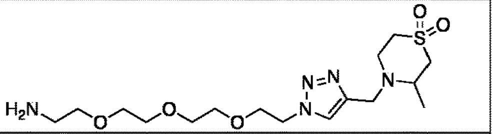
Figure 6P:
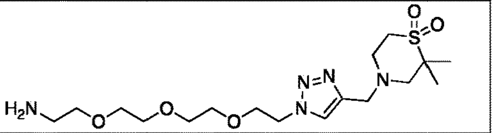
Figure 6P:
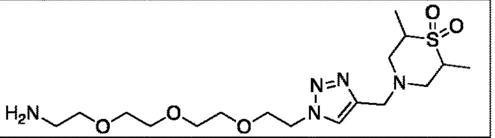
Figure 6P:
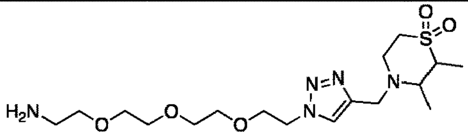
Figure 6P:
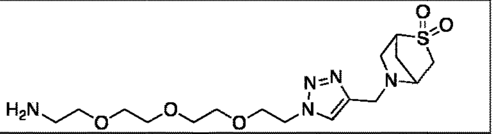
Figure 6P:
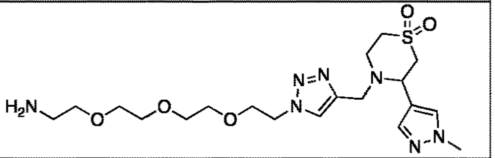
Figure 6P:
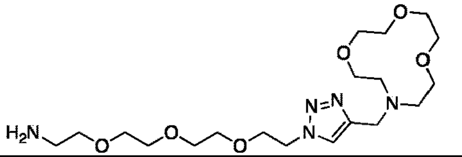
Figure 6P:
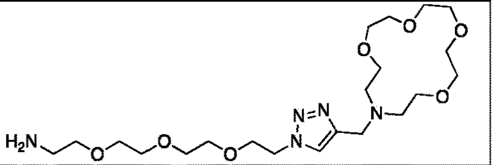
Figure 6P:
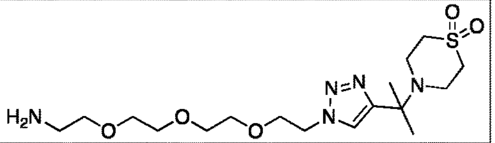
Figure 6P:
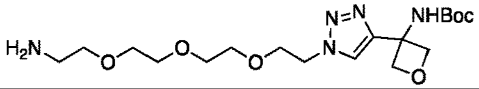
Figure 6Q:
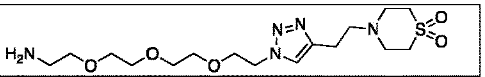
Figure 6Q:
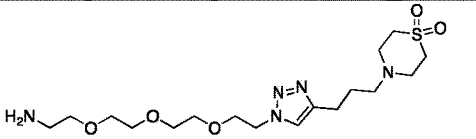
Figure 6Q:
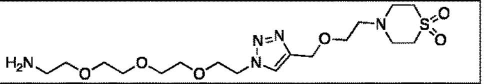
Figure 6Q:
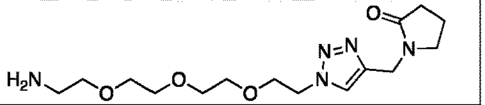
Figure 6Q:
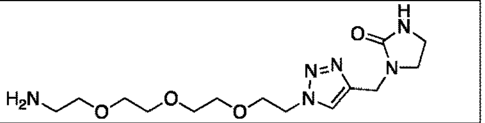
Figure 6Q:
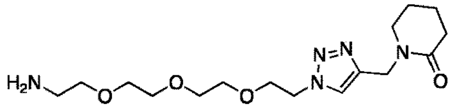
Figure 6Q:
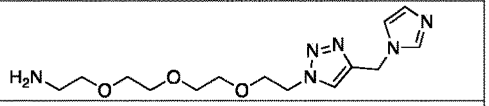
Figure 6Q:
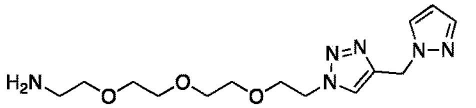
Figure 6Q:
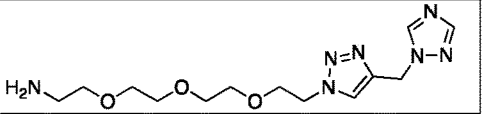
Figure 6Q:
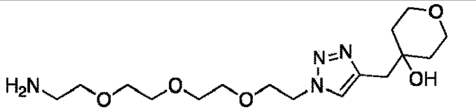
Figure 6Q:
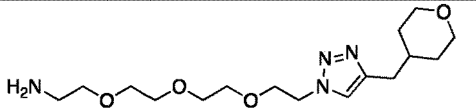
Figure 6Q:
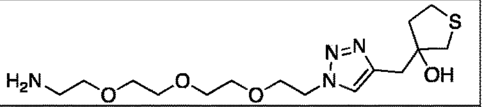
Figure 6Q:
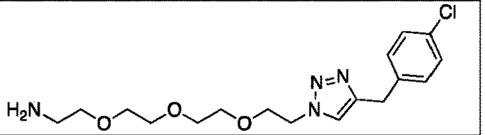
Figure 6Q:
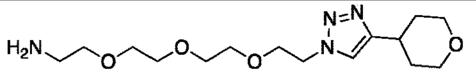
Figure 6Q:
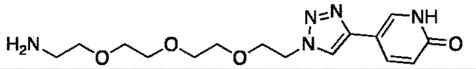
Figure 6Q:
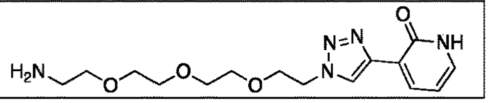
Figure 6R:
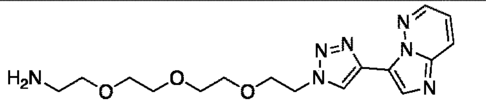
Figure 6R:
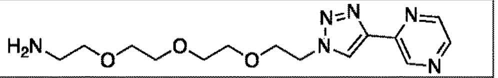
Figure 6R:
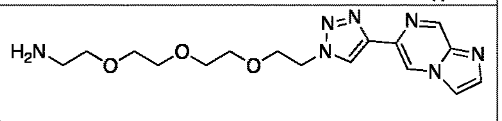
Figure 6R:
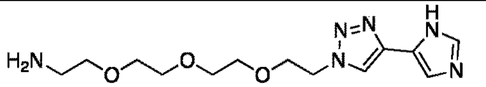
Figure 6R:
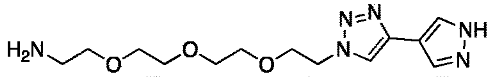
Figure 6R:
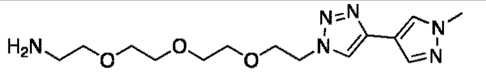
Figure 6R:
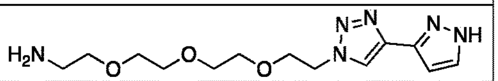
Figure 6R:
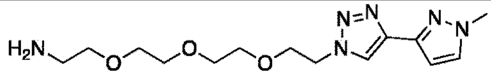
Figure 6R:
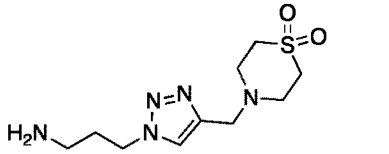
Figure 6R:
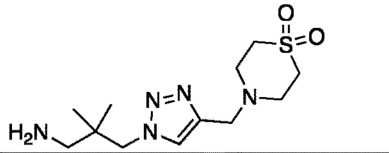
Figure 6R:
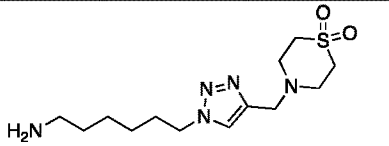
Figure 6R:
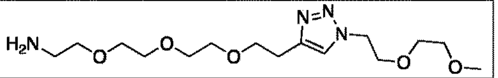
Figure 6R:
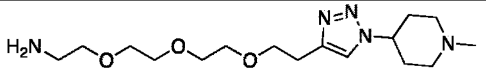
Figure 6R:
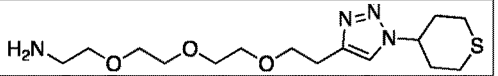
Figure 6R:
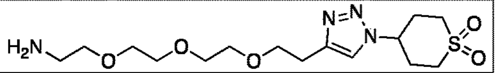
Figure 6R:
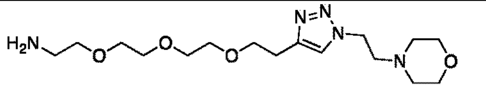
Figure 6R:
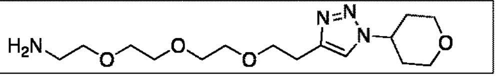
Figure 6S:
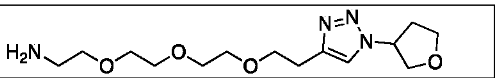
Figure 6S:
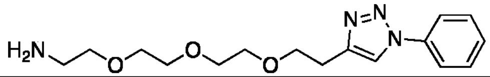
Figure 6S:
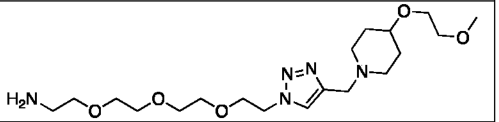
Figure 6S:
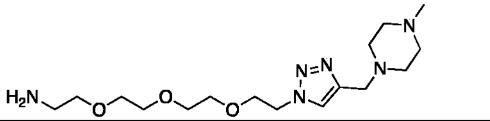
Figure 6S:
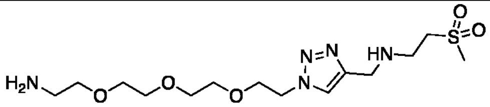
Figure 6S:
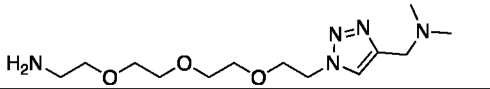
Figure 6S:
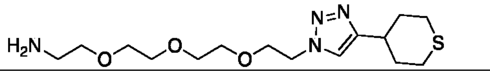
Figure 6S:
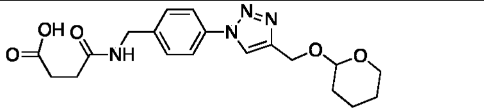
Figure 6S:
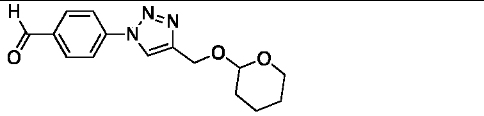
Figure 6S:
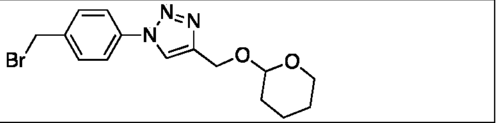
Figure 6S:
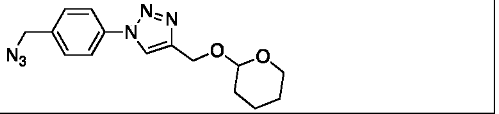
Figure 6S:
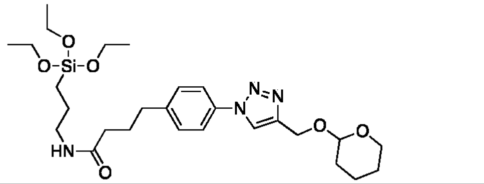
Figure 6S:
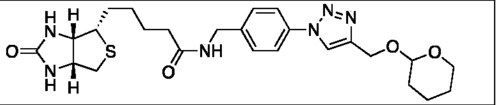
Figure 6S:
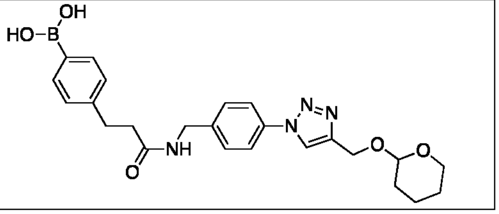
Figure 6T:
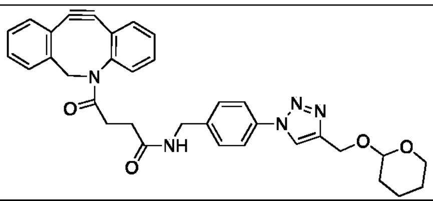
Figure 6T:
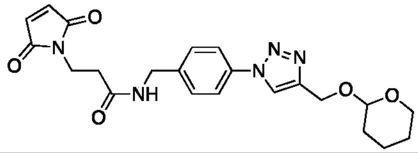
Figure 6T:
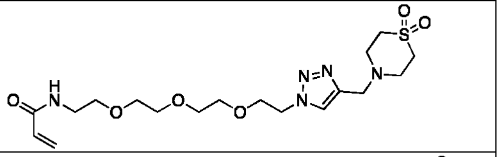
Figure 6T:
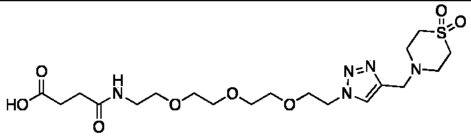
Figure 6T:
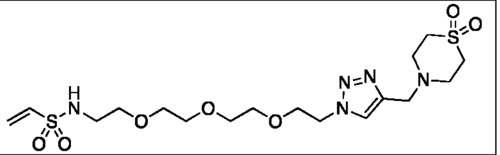
Figure 6T:
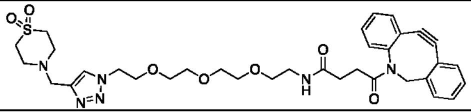
Figure 6T:
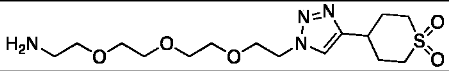
Figure 6T:
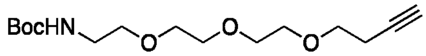
Figure 6T:
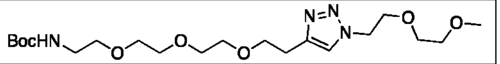
Figure 6T:
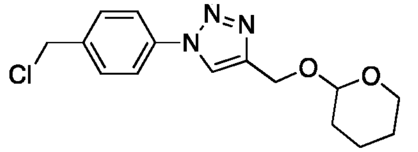
Figure 6T:
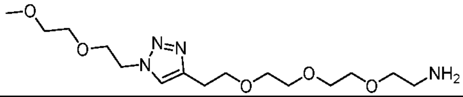
Figure 6T:
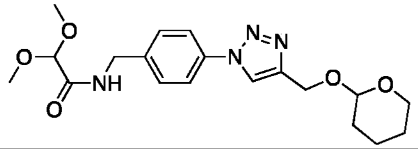
Figure 6T:
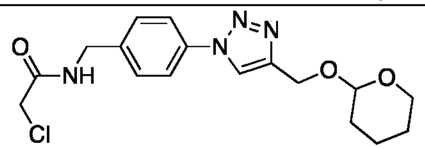
Figure 6U:
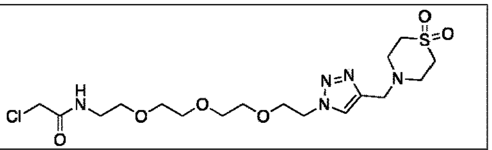
Figure 6U:
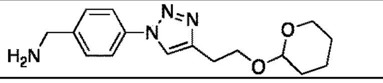
Figure 6U:
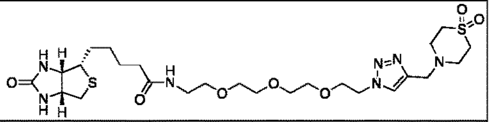
Figure 6U:
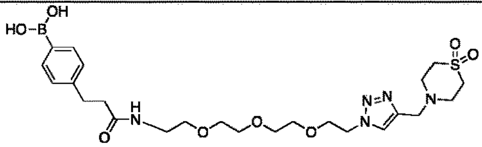
Figure 6U:
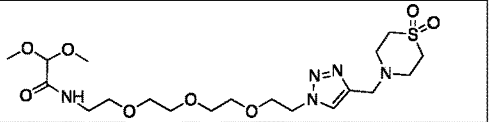
Figure 6U:
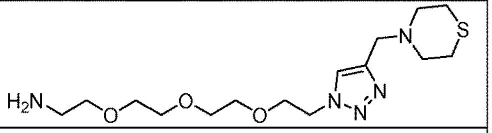
Figure 6U:
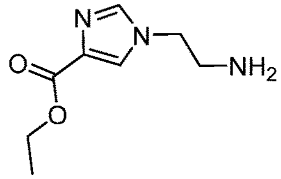
Figure 6U:
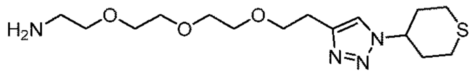
Figure 6U:
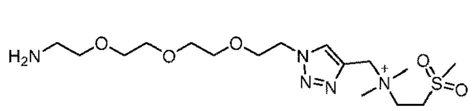
Figure 6U:
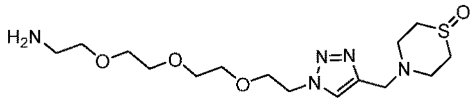
Figure 6V:
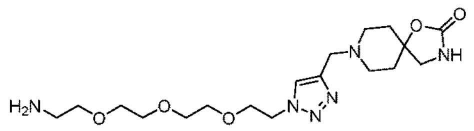
Figure 6V:
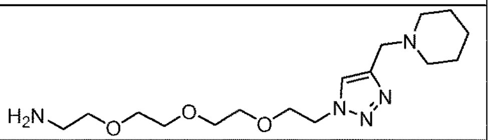
Figure 6V:
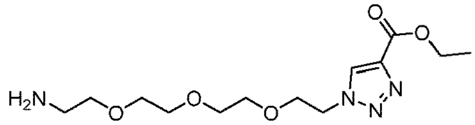
Figure 6V:
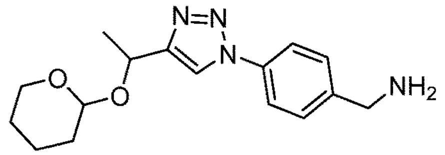
Figure 6V:
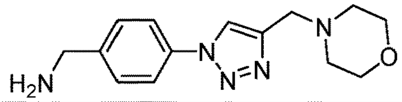
Figure 6V:
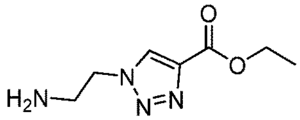
Figure 6V:
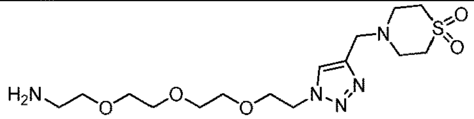
Figure 6V:
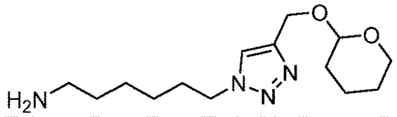
Figure 6V:
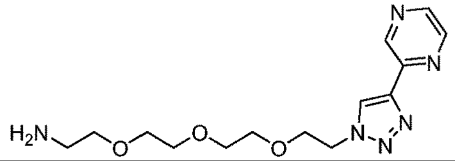
Figure 6V:
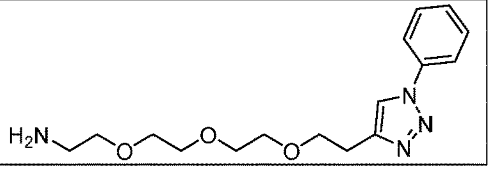
Figure 6W:
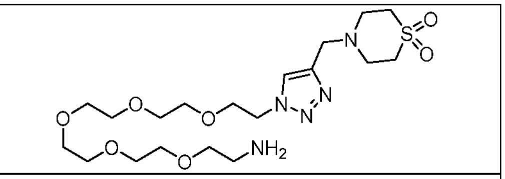
Figure 6W:
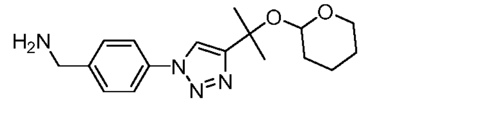
Figure 6W:
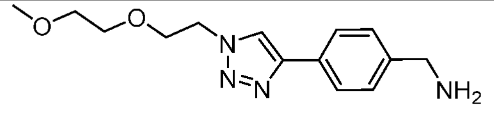
Figure 6W:
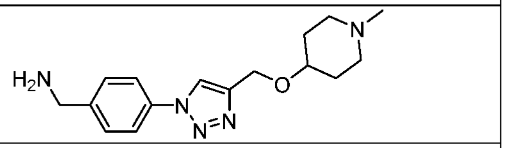
Figure 6W:
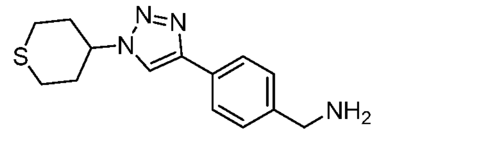
Figure 6W:
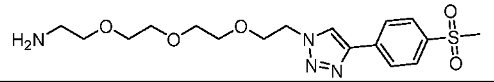
Figure 6W:
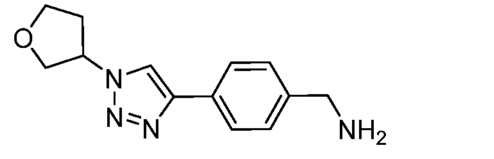
Figure 6W:
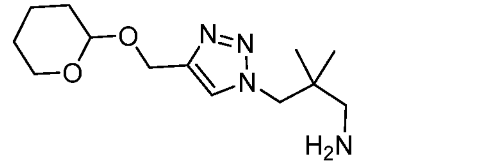
Figure 6W:
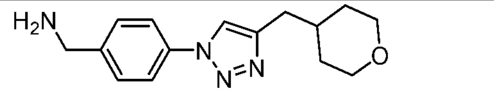
Figure 6W:
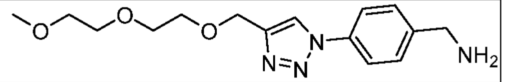
Figure 6W:
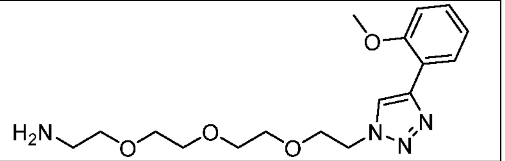
Figure 6W:
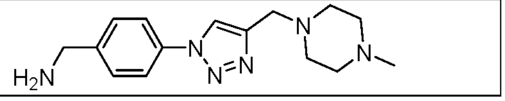
Figure 6X:
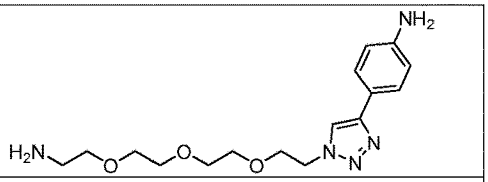
Figure 6X:
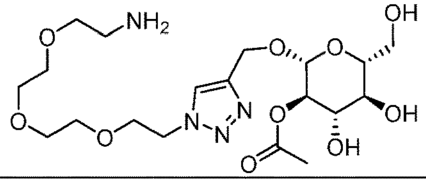
Figure 6X:
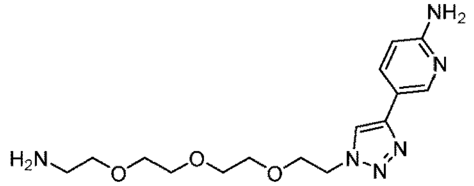
Figure 6X:
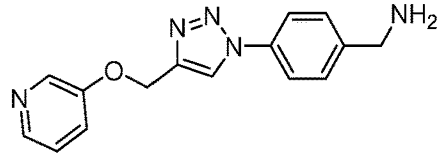
Figure 6X:
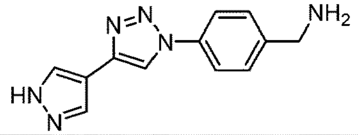
Figure 6X:
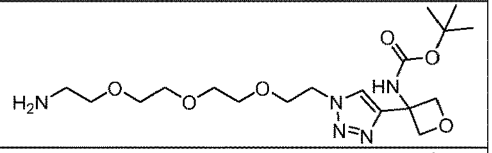
Figure 6X:
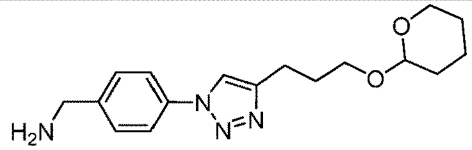
Figure 6X:
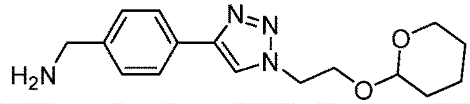
Figure 6X:
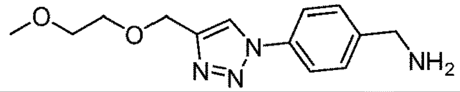
Figure 6X:
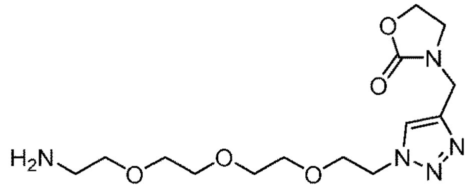
Figure 6Y:
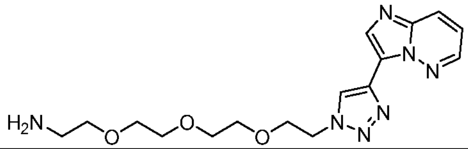
Figure 6Y:
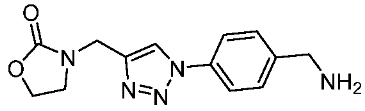
Figure 6Y:
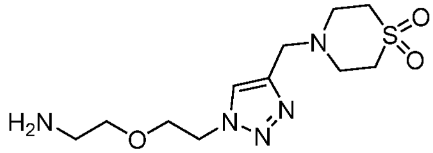
Figure 6Y:
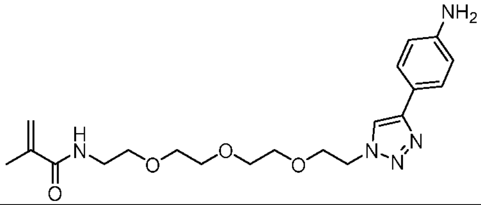
Figure 6Y:
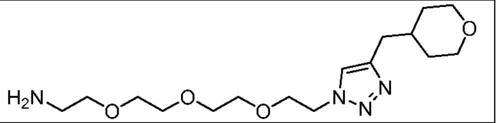
Figure 6Y:
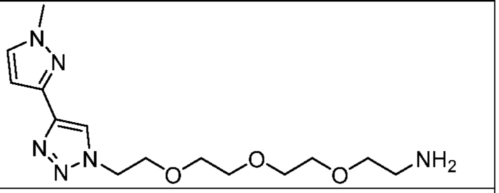
Figure 6Y:
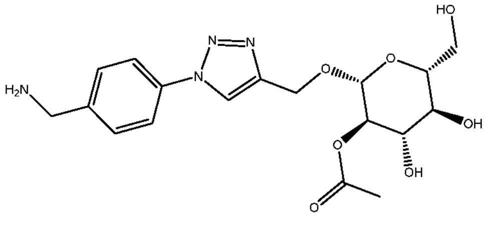
Figure 6Y:
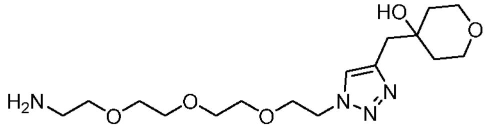
Figure 6Z:
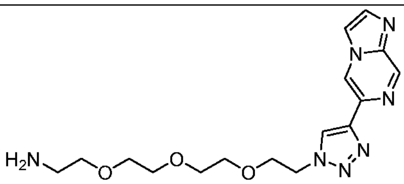
Figure 6Z:
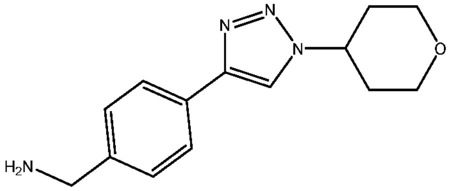
Figure 6Z:
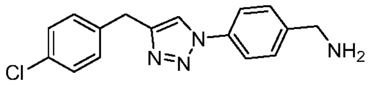
Figure 6Z:
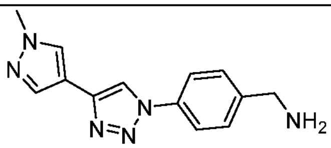
Figure 6Z:
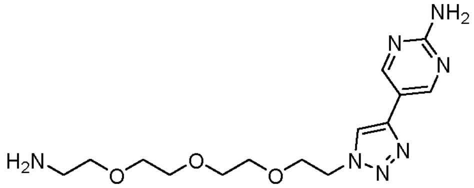
Figure 6Z:
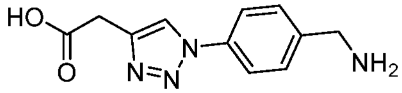
Figure 6Z:
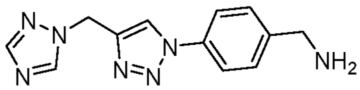
Figure 6A:
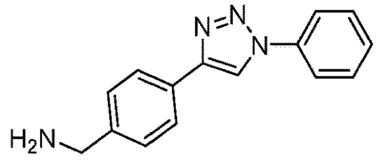
Figure 6A:
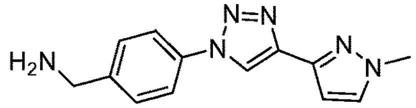
Figure 6A:
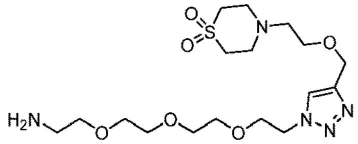
Figure 6A:
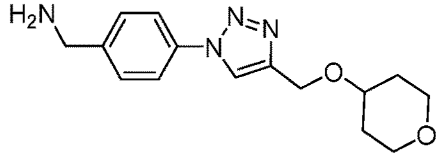
Figure 6A:
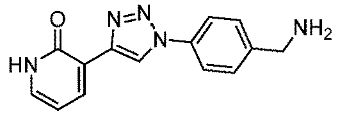
Figure 6A:
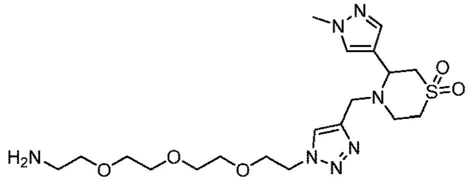
Figure 6A:
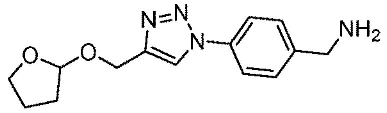
Figure 6A:
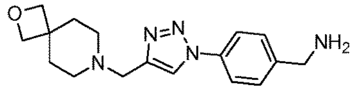
Figure 6A:
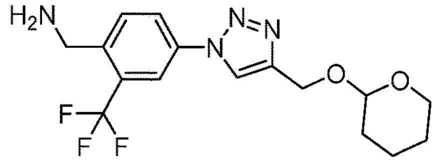
Figure 6B:
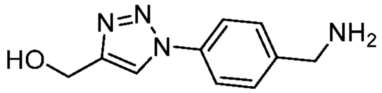
Figure 6B:
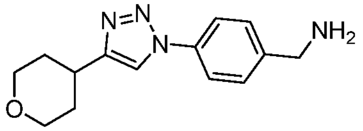
Figure 6B:
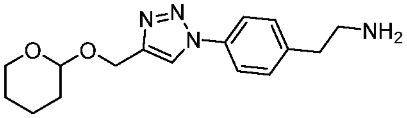
Figure 6B:
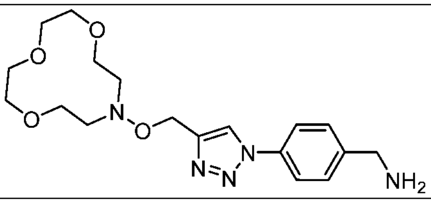
Figure 6B:
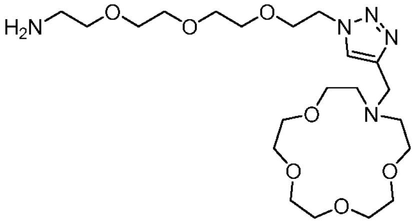
Figure 6B:
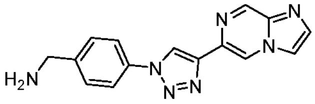
Figure 6B:
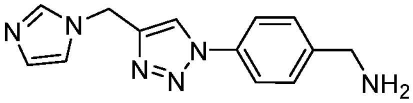
Figure 6B:
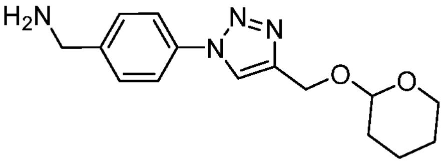
Figure 6B:
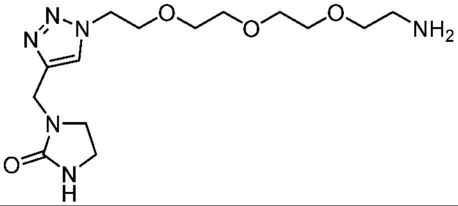
Figure 6C:
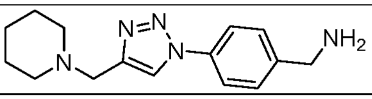
Figure 6C:
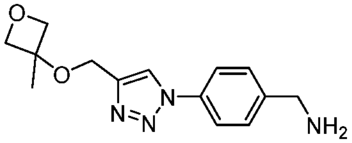
Figure 6C:
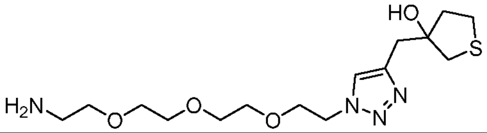
Figure 6C:
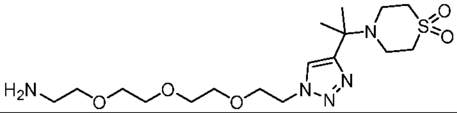
Figure 6C:
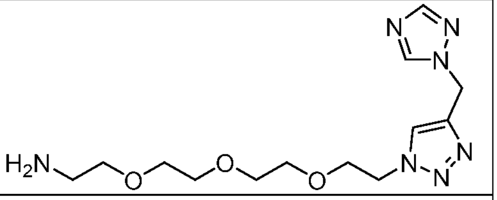
Figure 6C:
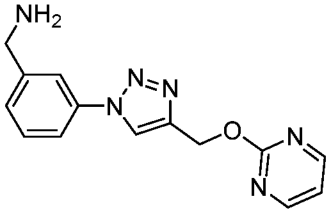
Figure 6C:
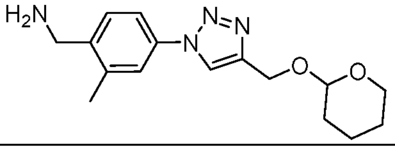
Figure 6C:
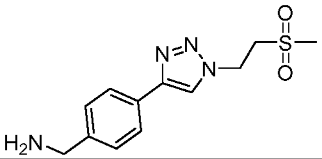
Figure 6C:
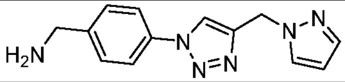
Figure 6C:
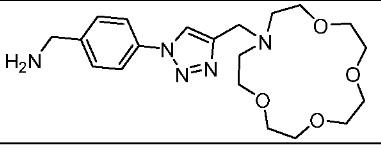
Figure 6C:
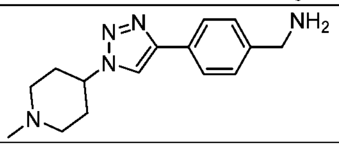
Figure 6D:
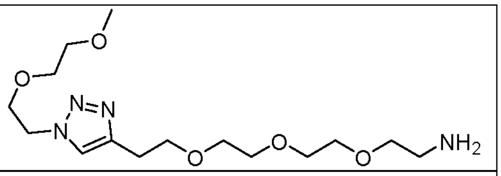
Figure 6D:
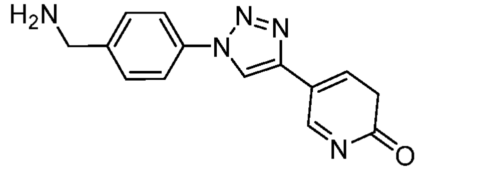
Figure 6D:
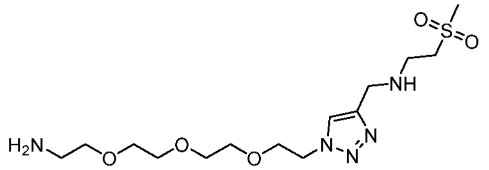
Figure 6D:
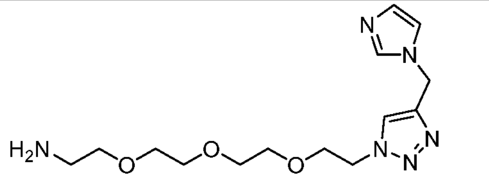
Figure 6D:
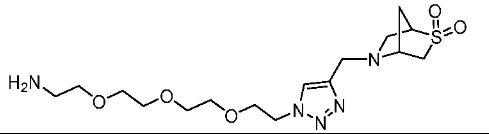
Figure 6D:
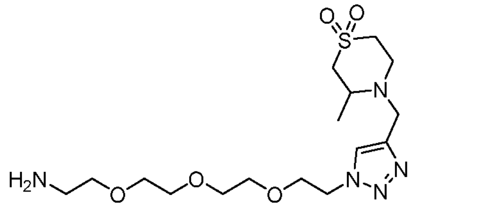
Figure 6D:
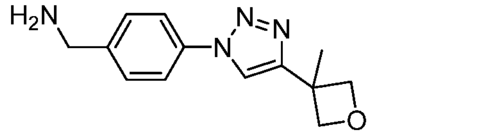
Figure 6D:
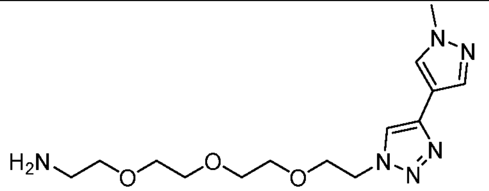
Figure 6D:
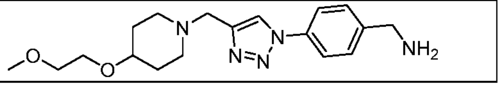
Figure 6E:
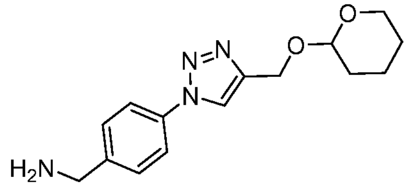
Figure 6E:
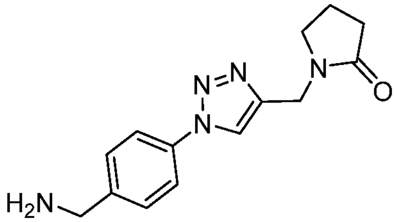
Figure 6E:
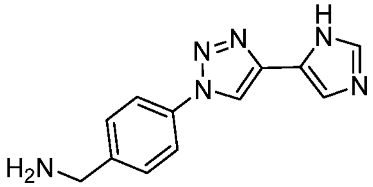
Figure 6E:
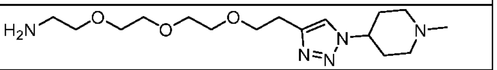
Figure 6E:
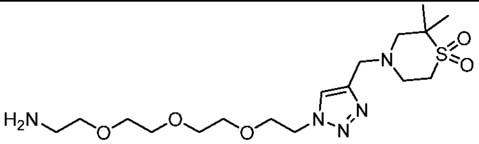
Figure 6E:
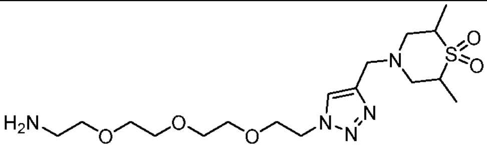
Figure 6E:
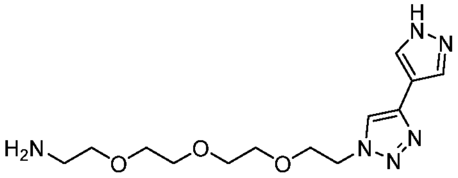
Figure 6E:
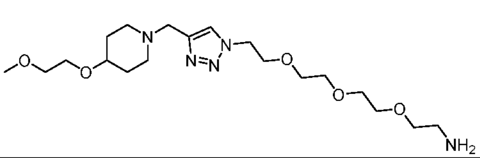
Figure 6E:
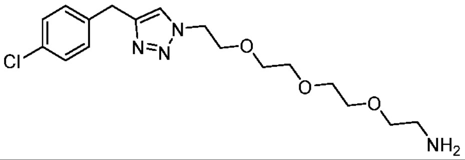
Figure 6F:
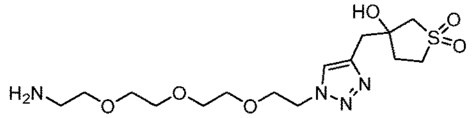
Figure 6F:
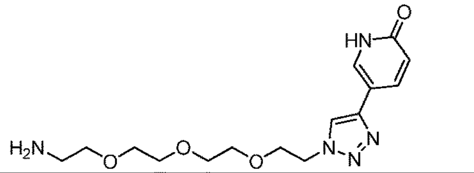
Figure 6F:
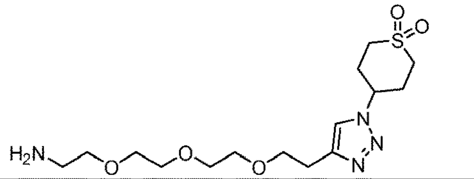
Figure 6F:
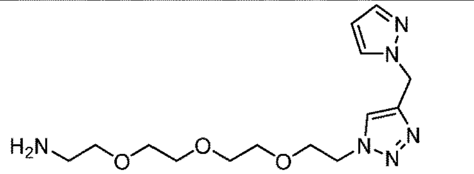
Figure 6F:
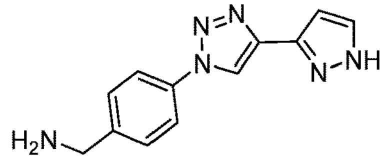
Figure 6F:
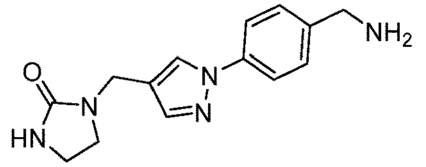
Figure 6F:
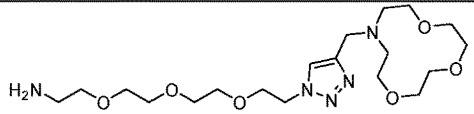
Figure 6F:
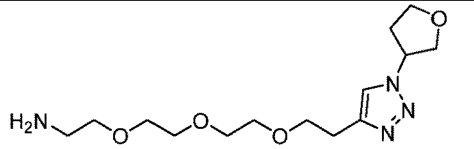
Figure 6F:
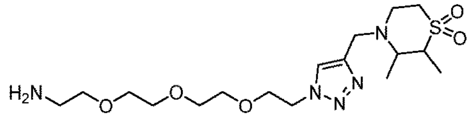
Figure 6G:
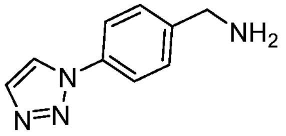
Figure 6G:
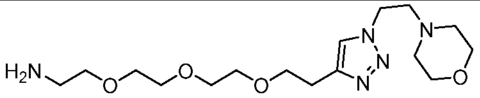
Figure 6G:
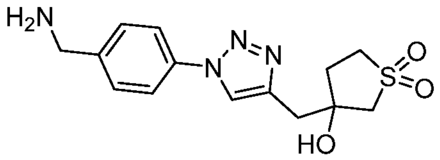
Figure 6G:
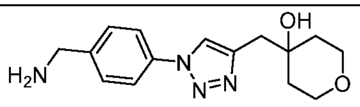
Figure 6G:
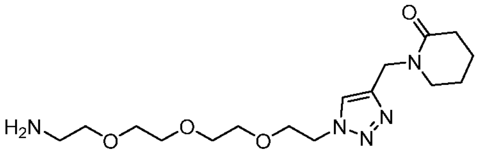
Figure 6G:
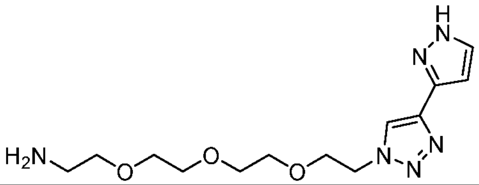
Figure 6G:
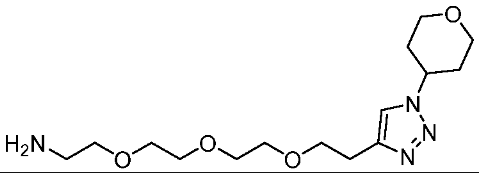
Figure 6G:
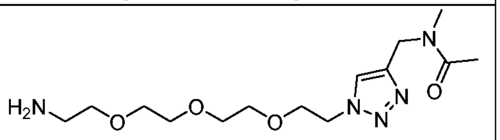
Figure 6G:
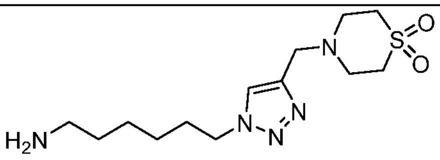
Figure 6H:
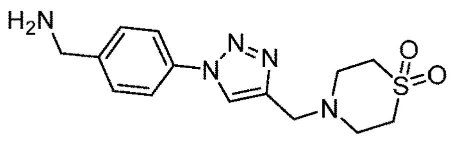
Figure 6H:
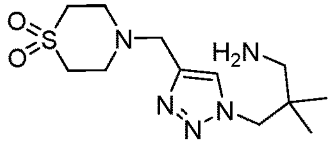
Figure 6H:
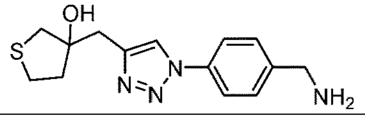
Figure 6H:
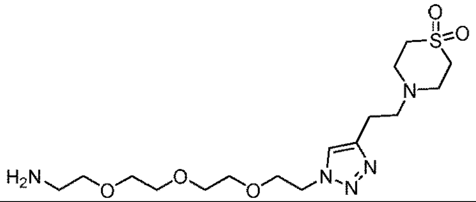
Figure 6H:
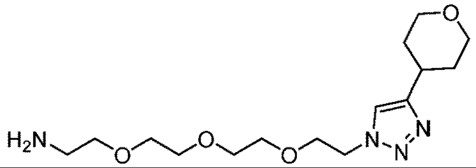
Figure 6H:
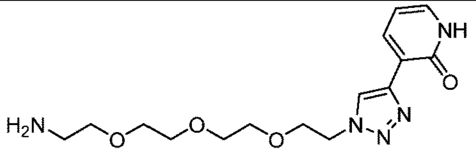
Figure 6H:
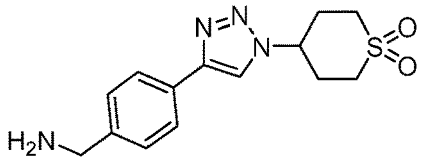
Figure 6H:
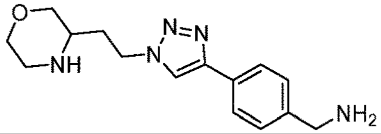
Figure 6H:
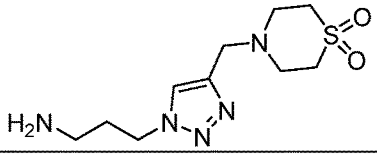
Figure 6H:
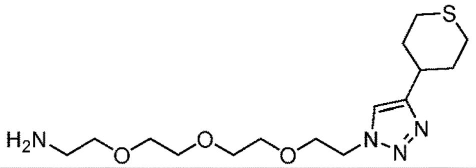
Figure 6I:
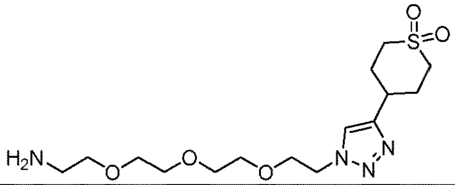
Figure 6I:
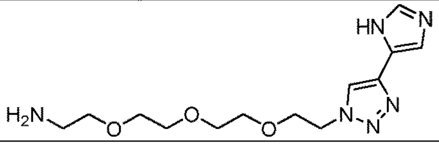
Figure 6I:
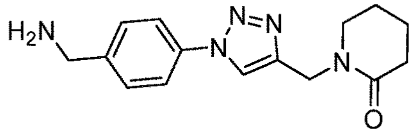
Figure 6I:
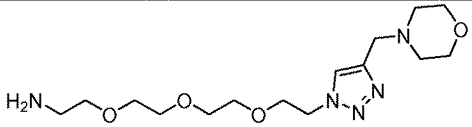
Figure 6I:
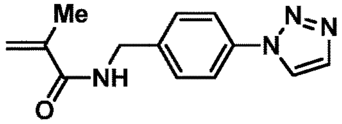
Figure 6I:
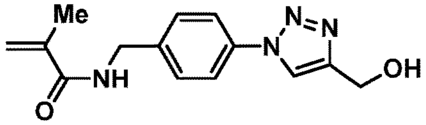
Figure 6I:
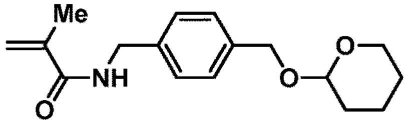
Figure 6I:
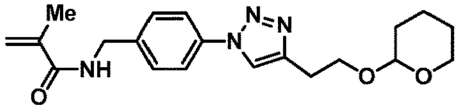
Figure 6I:
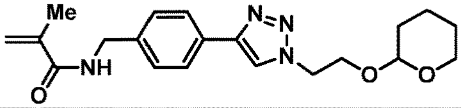
Figure 6I:
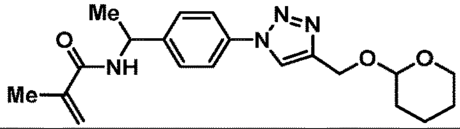
Figure 6I:
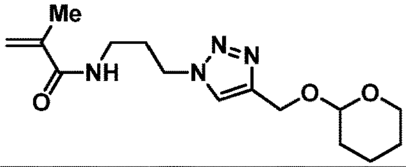
Figure 6I:
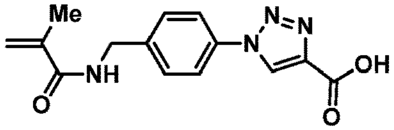
Figure 6J:
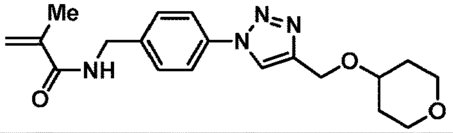
Figure 6J:
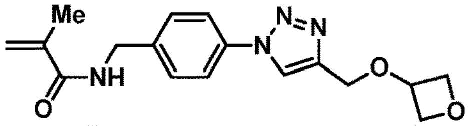
Figure 6J:
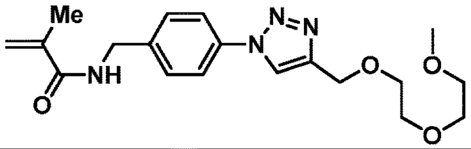
Figure 6J:
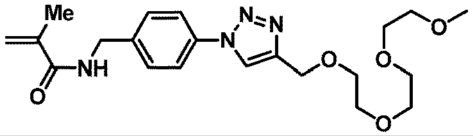
Figure 6J:
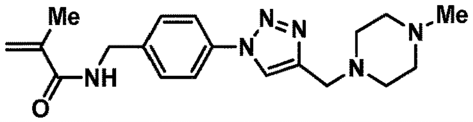
Figure 6J:
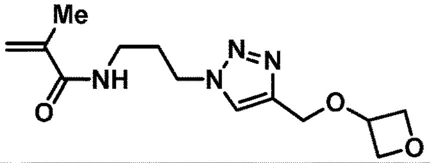
Figure 6J:
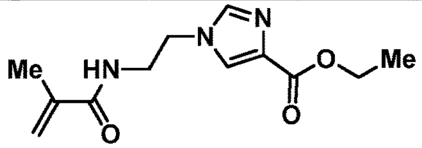
Figure 6J:
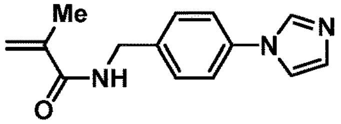
Figure 6J:
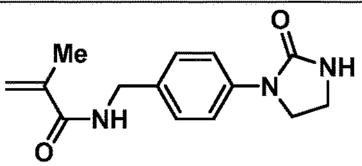
Figure 6J:
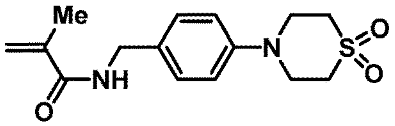
Figure 6J:
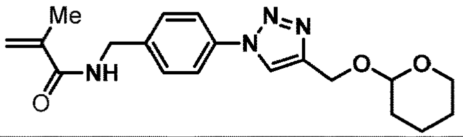
Figure 6J:
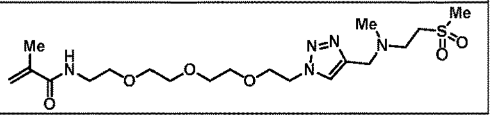
Figure 6K:
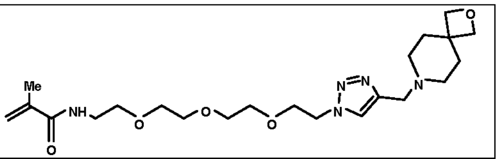
Figure 6K:
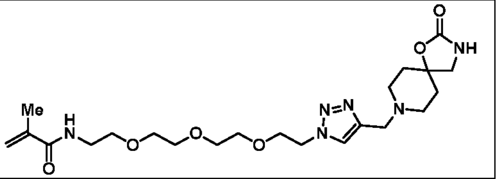
Figure 6K:
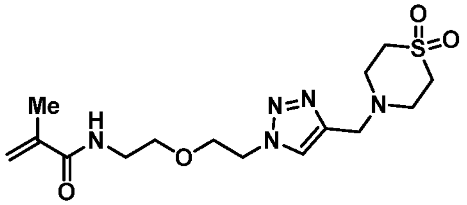
Figure 6K:
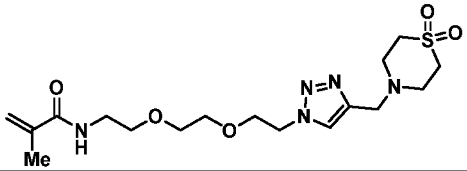
Figure 6K:
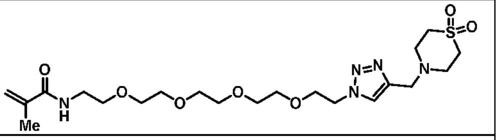
Figure 6K:
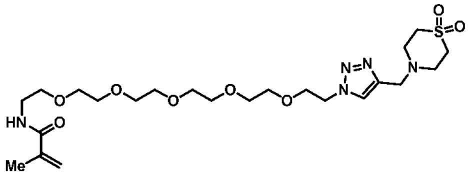

In some embodiments, a compound of Formula (II) is selected from a compound depicted in any one of FIGS. 1A-6KK or a pharmaceutically acceptable salt thereof. In some embodiments, a compound of Formula (II) is selected from a compound depicted in any one of FIGS. 1A-6KK and is associated with an implantable element (e.g., a device or material) described herein, e.g., though an attachment group (e.g., as described herein).

In some embodiments, the compound of Formula (II) is a compound of Formula (II-a):

Formula (II-a)

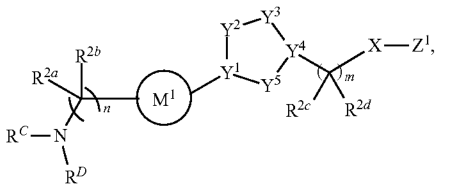

or a salt thereof, wherein Ring $M^1$ is cycloalkyl, heterocyclyl, aryl, or heteroaryl, each of which is optionally substituted with 1-5 $R^3$; each of $Y^1$ and $Y^4$ is independently C(R') or N; each of $Y^2$, $Y^3$, and $Y^5$ is independently C(R')(R"), $N(R^{10})$, S, or O, wherein only two of $Y^2$, $Y^3$, and $Y^5$ may be O or S; and wherein each of $Y^1$, $Y^2$, $Y^3$, $Y^4$, and $Y^5$ is linked with single bonds or double bonds to achieve appropriate valency; X is absent, $N(R^{10})(R^{11})$, O, or S; $Z^1$ is alkyl, alkenyl, alkynyl, heteroalkyl, cycloalkyl, heterocyclyl, aryl, or heteroaryl, each of which is optionally substituted by one or more $R^5$; each of R' and R" is independently hydrogen, alkyl, halogen, or cycloalkyl; or each of R' and R" are taken together to form an oxo group; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; or $R^C$ and $R^D$, taken together with the nitrogen atom to which they are attached, form a ring (e.g., a 5-7 membered ring), optionally substituted with 1-6 $R^6$; each of $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, heteroaryl; each of $R^{10}$ and $R^{11}$ is independently hydrogen, alkyl, alkenyl, alkynyl, heteroalkyl, halogen, —$C(O)R^{B1}$, —$N(R^{C1})C(O)R^{B1}$, —$C(O)N(R^{C1})$, $SR^{E1}$, $S(O)_x$, cycloalkyl, or heterocyclyl; each $R^{A1}$, $R^{B1}$, $R^{C1}$, $R^{D1}$ and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 0, 1, 2, 3, 4, 5, or 6; and x is 1 or 2.

In some embodiments, the compound of Formula (II) is a compound of Formula (II-b):

Formula (II-b)

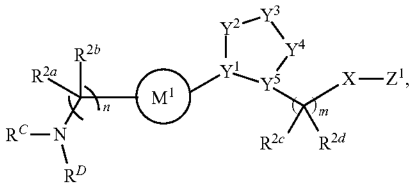

or a salt thereof, wherein Ring $M^1$ is cycloalkyl, heterocyclyl, aryl, or heteroaryl, each of which is optionally substituted with 1-5 $R^3$; each of $Y^1$ and $Y^4$ is independently C(R') or N; each of $Y^2$, $Y^3$, and $Y^5$ is independently C(R')(R"), $N(R^{10})$, S, or O, wherein only two of $Y^2$, $Y^3$, and $Y^5$ may be O or S; and wherein each of Y, $Y^2$, $Y^3$, $Y^4$, and $Y^5$ is linked with single bonds or double bonds to achieve appropriate valency; X is absent, $N(R^{10})(R^{11})$, O, or S; $Z^1$ is alkyl, alkenyl, alkynyl, heteroalkyl, cycloalkyl, heterocyclyl, aryl, or heteroaryl, each of which is optionally substituted by one or more $R^5$; each of R' and R" is independently hydrogen, alkyl, halogen, or cycloalkyl; or each of R' and R" are taken together to form an oxo group; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; or $R^C$ and $R^D$, taken together with the nitrogen atom to which they are attached, form a ring (e.g., a 5-7 membered ring), optionally substituted with 1-6 $R^6$; each of $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, heteroaryl; each of $R^{10}$ and $R^{11}$ is independently hydrogen, alkyl, alkenyl, alkynyl, heteroalkyl, halogen, —$C(O)R^{B1}$, —$N(R^{C1})C(O)R^{B1}$, —$C(O)N(R^{C1})$, $SR^{E1}$, $S(O)_x$, cycloalkyl, or heterocyclyl; each $R^{A1}$, $R^{B1}$, $R^{C1}$, $R^{D1}$ and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 0, 1, 2, 3, 4, 5, or 6; and x is 1 or 2.

In some embodiments, the compound of Formula (II) is a compound of Formula (II-c):

Formula (II-c)

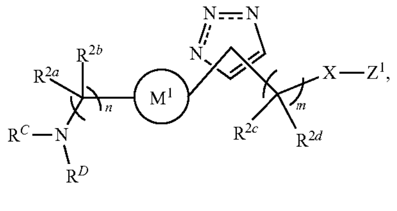

or a salt thereof, wherein Ring $M^1$ is cycloalkyl, heterocyclyl, aryl, or heteroaryl, each of which is optionally substituted with 1-5 $R^3$; $Z^1$ is alkyl, alkenyl, alkynyl, heteroalkyl, cycloalkyl, heterocyclyl, aryl, or heteroaryl, each of which is optionally substituted by one or more $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; or $R^C$ and $R^D$, taken together with the nitrogen atom to which they are attached, form a ring (e.g., a 5-7 membered ring), optionally substituted with 1-6 $R^6$; each of $R^3$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, cycloalkyl, heterocyclyl, aryl, heteroaryl; each of $R^{10}$ and $R^{11}$ is independently hydrogen, alkyl, alkenyl, alkynyl, heteroalkyl, halogen, —C(O)$R^{B1}$, —N($R^{C1}$)C(O)$R^{B1}$, —C(O)N($R^{C1}$), $SR^{E1}$, $S(O)_x$, cycloalkyl, or heterocyclyl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 0, 1, 2, 3, 4, 5, or 6; and x is 1 or 2.

In some embodiments, the compound of Formula (II) is a compound of Formula (II-d):

Formula (II-d)

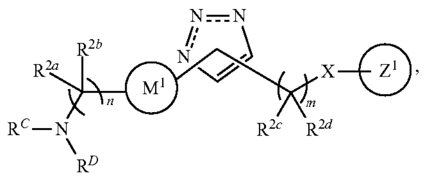

or a salt thereof, wherein Ring $M^1$ is cycloalkyl, heterocyclyl, aryl, or heteroaryl, each of which is optionally substituted with 1-5 $R^3$; Ring $Z^1$ is cycloalkyl, heterocyclyl, aryl or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; X is absent, N($R^{10}$)($R^{11}$), O, or S; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$) N($R^{C1}$)C(O)$R^{B1}$, —C(O)N($R^{C1}$), $SR^{E1}$, cycloalkyl, heterocyclyl, aryl, or heteroaryl; each of $R^1$ and $R^{11}$ is independently hydrogen, alkyl, alkenyl, alkynyl, heteroalkyl, —C(O)$OR^{A1}$, —C(O)$R^{B1}$, —OC(O)$R^{B1}$, —C(O)N($R^{C1}$), cycloalkyl, heterocyclyl, aryl, or heteroaryl; each $R^{A1}$, $R^{B1}$, $R^{C1}$, $R^{D1}$ and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 0, 1, 2, 3, 4, 5, or 6; and “ ” refers to a connection to a device or material (e.g., a device or material described herein).

In some embodiments, the compound of Formula (II) is a compound of Formula (II-e):

Formula (II-e)

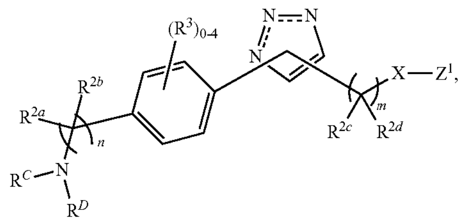

or a salt thereof, wherein $Z^1$ is alkyl, alkenyl, alkynyl, heteroalkyl, cycloalkyl, heterocyclyl, aryl, or heteroaryl, each of which is optionally substituted by one or more $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$, or $R^C$ and $R^D$, taken together with the nitrogen atom to which they are attached, form a ring (e.g., a 5-7 membered ring), optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, cycloalkyl, heterocyclyl, aryl, heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, —CN, oxo, hydroxyl, cycloalkyl, or heterocyclyl; and each m and n is independently 0, 1, 2, 3, 4, 5, or 6.

In some embodiments, $Z^1$ is alkyl or heteroalkyl. In some embodiments, $Z^1$ is heteroalkyl (e.g., $C_1$-$C_{12}$ heteroalkyl). In some embodiments, $Z^1$ is an oxygen-containing heteroalkyl or a nitrogen-containing heteroalkyl. In some embodiments, $Z^1$ is $(—OCH_2CH_2)_3OCH_3$, wherein z is an integer selected from 1 to 10 (e.g., z is 1, 2, 3, 4, 5, 6, 7, 8, 9, or 10). In some embodiments, $Z^1$ is $(—OCH_2CH_2)_3OCH_3$. In some embodiments, X is absent. In some embodiments, m is 1. In some embodiments, n is 1. In some embodiments, each of $R^{2a}$, $R^{2b}$, $R^{2c}$, and $R^{2d}$ is independently hydrogen. In some embodiments, one of $R^C$ and $R^D$ is independently hydrogen, alkyl, alkenyl, alkynyl, or heteroalkyl (e.g., C(O)C($C{=}CH_2$)$CH_3$). In some embodiments, one of $R^C$ and $R^D$ is independently hydrogen and the other of $R^C$ and $R^D$ is independently alkenyl (e.g., $C(O)C(C{=}CH_2)CH_3$). In some embodiments, each of $R^C$ and $R^D$ is independently hydrogen.

In some embodiments, the compound of Formula (II) is a compound of Formula (II-f):

(II-f)

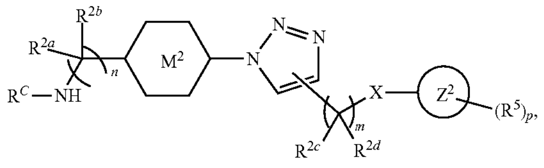

or a salt thereof, wherein Ring $M^2$ is aryl or heteroaryl, optionally substituted by one or more $R^3$; Ring $Z^2$ is cycloalkyl, heterocyclyl, aryl or heteroaryl; each of $R^{2a}$, $R^{2a}$, $R^{2c}$, and $R^{2d}$ is independently hydrogen, alkyl or heteroalkyl; or $R^{2a}$ and $R^{2b}$ or $R^{2c}$ and $R^{2d}$ are taken together to form an oxo group; X is absent, O, or S; each $R^3$ or $R^5$ is independently alkyl, heteroalkyl, halogen, oxo, $—OR^{A1}$, $—C(O)OR^{A1}$, or $—C(O)R^{B1}$; or two $R^5$ are taken together to form a 5-6 membered ring fused to Ring $Z^2$; each $R^{A1}$, $R^{B1}$, $R^{C1}$, $R^{D1}$ and $R^{E1}$ is independently hydrogen, alkyl, heteroalkyl; m and p are each independently 0, 1, 2, 3, 4, 5, or 6; and "∿∿" refers to a connection to a device or material (e.g., a device or material described herein).

In some embodiments, the compound of Formula (II) is a compound of Formula (II-g):

(II-g)

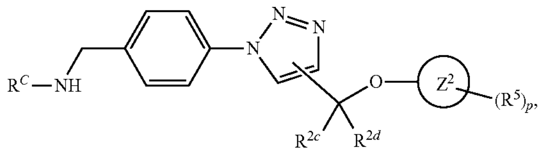

or a salt thereof, wherein Ring $Z^2$ is cycloalkyl, heterocyclyl, aryl or heteroaryl; each of $R^{2c}$ and $R^{2d}$ is independently hydrogen, alkyl, heteroalkyl; or $R^{2c}$ and $R^{2d}$ are taken together to form an oxo group; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each of $R^5$ is independently alkyl, heteroalkyl, halogen, oxo, $—OR^{A1}$, $—C(O)OR^{A1}$, or $—C(O)R^{B1}$; each $R^{A1}$ or $R^{B1}$ is independently hydrogen, alkyl, heteroalkyl; p is 0, 1, 2, 3, 4, 5, or 6; and "∿∿" refers to a connection to a device or material (e.g., a device or material described herein).

In some embodiments, the compound of Formula (II) is a compound of Formula (II-g-2):

Formula (II-g-2)

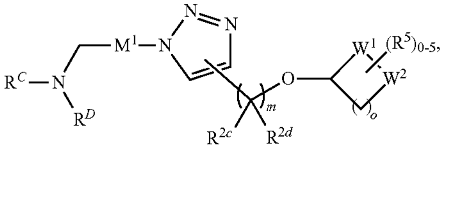

or a salt thereof, wherein $M^1$ is alkyl, alkenyl, alkynyl, optionally substituted by one or more $R^3$; each of $W^1$ and $W^2$ are independently C(R')(R"), $N(R^{20})$, or S(O)x; each of $R^{2c}$ and $R^{2d}$ is independently hydrogen, alkyl, or heteroalkyl; or $R^{2c}$ and $R^{2d}$ are taken together to form an oxo group; each $R^5$ is independently alkyl, heteroalkyl, halogen, cyano, azido, oxo, $—OR^{A1}$, $—C(O)OR^{A1}$, $—C(O)R^{B1}$, $—OC(O)R^{B1}$, $—N(R^{C1})(R^{D1})$, $—N(R^{C1})C(O)R^{B1}$, $—C(O)N(R^{C1})$, or $SR^{E1}$, cycloalkyl, heterocyclyl, aryl, heteroaryl; $R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$, or $R^C$ and $R^D$, taken together with the nitrogen atom to which they are attached, form a ring (e.g., a 5-7 membered ring), optionally substituted with 1-6 $R^6$; each of R' and R" is independently hydrogen, alkyl, alkenyl, halogen, cyano, or cycloalkyl; each $R^{20}$ is hydrogen, alkyl, or $—C(O)R^{B1}$; each $R^{A1}$, $R^{B1}$, $R^{C1}$, $R^{D1}$, and $R^{E1}$ is independently hydrogen, alkyl, or heteroalkyl; each m is independently 1, 2, 3, 4, 5, or 6; o is 1, 2, 3, 4 or 5; and x is 0, 1, or 2.

In some embodiments, one of $W^1$ and $W^2$ is independently O. In some embodiments, $W^1$ is O. In some embodiments, $W^2$ is O. In some embodiments, $W^1$ is C(R')(R") (e.g., CH2) and $W^2$ is O. In some embodiments, o is 1, 2, or 3. In some embodiments, m is 1. In some embodiments, Ring $M^2$ is alkyl (e.g., methyl, ethyl, or propyl). In some embodiments, each of $R^{2c}$ and $R^{2d}$ is independently hydrogen. In some embodiments, one of $R^C$ and $R^D$ is independently hydrogen, alkyl, alkenyl, alkynyl, or heteroalkyl (e.g., $C(O)C(C{=}CH_2)CH_3$). In some embodiments, one of $R^C$ and $R^D$ is independently hydrogen and the other of $R^C$ and $R^D$ is independently alkenyl (e.g., $C(O)C(C{=}CH_2)CH_3$).

In some embodiments, the compound of Formula (II) is a compound of Formula (II-h):

Formula (II-h)

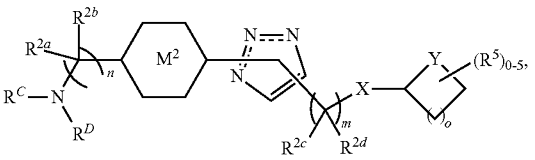

or a salt thereof, wherein Ring $M^2$ is aryl or heteroaryl, each of which is optionally substituted with 1-5 $R^4$; Y is O, S, or $N(R^{10})$ optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; X is absent, $N(R^{10})(R^{11})$, O, or S; $R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$, or $R^C$ and $R^D$, taken together with the nitrogen atom to which they are attached, form a ring (e.g., a 5-7 membered ring), optionally substituted with 1-6 $R^6$, or one or both of $R^C$ and $R^D$ is bound to an atom within L or M or one of the substituents of L or M to form a ring optionally substituted with 1-6 $R^6$; each $R^4$, $R^5$, $R^6$, $R^{10}$, and $R^{11}$ is independently alkyl, alkenyl, alkynyl, heteroalkyl, halogen, cyano, azido, oxo, $—OR^{A1}$, $—C(O)OR^{A1}$, $—C(O)R^{B1}$, $—OC(O)R^{B1}$, $—N(R^{C1})(R^{D1})$, —N($R^{C1}$)C(O)$R^{B1}$, —C(O)N($R^{C1}$), $SR^{E1}$, cycloalkyl, heterocyclyl, aryl, heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$, each $R^7$ is independently alkyl, alkenyl, alkynyl, heteroalkyl, halogen, —CN, oxo, hydroxyl, cycloalkyl, or heterocyclyl; each m and n is independently 1, 2, 3, 4, 5, or 6; and o is 1, 2, 3, 4 or 5.

In some embodiments, the compound of Formula (II) is a compound of Formula (II-i):

Formula (II-i)

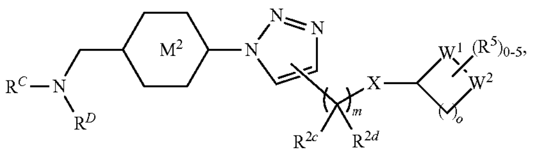

or a salt thereof, wherein Ring $M^2$ is aryl or heteroaryl; each of $W^1$ and $W^2$ are independently C(R')(R"), N($R^{20}$), or $S(O)_x$; each of $R^{2c}$ and $R^{2d}$ is independently hydrogen, alkyl, or heteroalkyl; or $R^{2c}$ and $R^{2d}$ are taken together to form an oxo group; each $R^5$ is independently alkyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), or $SR^{E1}$, cycloalkyl, heterocyclyl, aryl, heteroaryl; $R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$, or $R^C$ and $R^D$, taken together with the nitrogen atom to which they are attached, form a ring (e.g., a 5-7 membered ring), optionally substituted with 1-6 $R^6$; each of R' and R" is independently hydrogen, alkyl, alkenyl, halogen, cyano, or cycloalkyl; each $R^{20}$ is hydrogen, alkyl, or —C(O)$R^{B1}$; each $R^{A1}$, $R^{B1}$, $R^{C1}$, $R^{D1}$, and $R^{E1}$ is independently hydrogen, alkyl, heteroalkyl; each m is independently 1, 2, 3, 4, 5, or 6; o is 1, 2, 3, 4 or 5; and x is 0, 1, or 2.

In some embodiments, the compound of Formula (II) is a compound of Formula (II-i-2):

Formula (II-i-2)

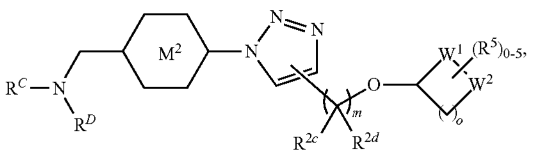

or a salt thereof, wherein Ring $M^2$ is aryl or heteroaryl; each of $W^1$ and $W^2$ are independently C(R')(R"), N($R^{20}$), or $S(O)_x$; each of $R^{2c}$ and $R^{2d}$ is independently hydrogen, alkyl, or heteroalkyl; or $R^{2c}$ and $R^{2d}$ are taken together to form an oxo group; each $R^5$ is independently alkyl, heteroalkyl, halogen, cyano, azido, oxo, —$OR^{A1}$, —C(O)$OR^{A1}$, —C(O)$R^{B1}$—OC(O)$R^{B1}$, —N($R^{C1}$)($R^{D1}$), —N($R^{C1}$)C(O)$R^{B1}$, —C(O)N($R^{C1}$), or $SR^{E1}$, cycloalkyl, heterocyclyl, aryl, heteroaryl; $R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$, or $R^C$ and $R^D$, taken together with the nitrogen atom to which they are attached, form a ring (e.g., a 5-7 membered ring), optionally substituted with 1-6 $R^6$; each of R' and R" is independently hydrogen, alkyl, alkenyl, halogen, cyano, or cycloalkyl; each $R^{20}$ is hydrogen, alkyl, or —C(O)$R^{B1}$; each $R^{A1}$, $R^{B1}$, $R^{C1}$, $R^{D1}$, and $R^{E1}$ is independently hydrogen, alkyl, heteroalkyl; each m is independently 1, 2, 3, 4, 5, or 6; o is 1, 2, 3, 4 or 5; and x is 0, 1, or 2.

In some embodiments, one of $W^1$ and $W^2$ is independently O. In some embodiments, $W^1$ is O. In some embodiments, $W^2$ is O. In some embodiments, $W^1$ is C(R')(R") (e.g., CH2) and $W^2$ is O. In some embodiments, o is 1, 2, or 3. In some embodiments, m is 1. In some embodiments, Ring $M^2$ is aryl (e.g., phenyl). In some embodiments, each of $R^{2c}$ and $R^{2d}$ is independently hydrogen. In some embodiments, one of $R^C$ and $R^D$ is independently hydrogen, alkyl, alkenyl, alkynyl, or heteroalkyl (e.g., $C(O)C(C{=}CH_2)CH_3$). In some embodiments, one of $R^C$ and $R^D$ is independently hydrogen and the other of $R^C$ and $R^D$ is independently alkenyl (e.g., $C(O)C(C{=}CH_2)CH_3$).

In some embodiments, the compound of Formula (II) is a compound of Formula (II-j):

Formula (I-j)

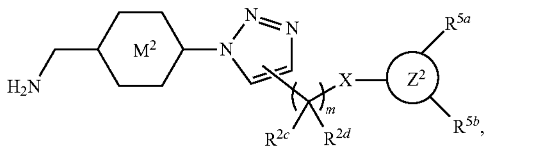

or a salt thereof, wherein Ring $M^2$ is aryl or heteroaryl; Ring $Z^2$ is aryl or heteroaryl; each of $R^{2c}$ and $R^{2d}$ is independently hydrogen, alkyl, or heteroalkyl; or $R^{2c}$ and $R^{2d}$ are taken together to form an oxo group; X is absent, O, or S; each of $R^{5a}$ and $R^{5b}$ is independently alkyl, heteroalkyl, halogen, oxo, —$OR^{A1}$, —C(O)$OR^{A1}$, or —C(O)$R^{B1}$; or $R^{5a}$ and $R^{5b}$ are taken together to form a 5-6 membered ring fused to Ring $Z^2$; each $R^{A1}$ and $R^{B1}$ is independently hydrogen, alkyl, heteroalkyl; and each m is independently 0, 1, 2, 3, 4, 5, or 6.

In some embodiments, the compound of Formula (II) is a compound of Formula (II-k):

Formula (II-k)

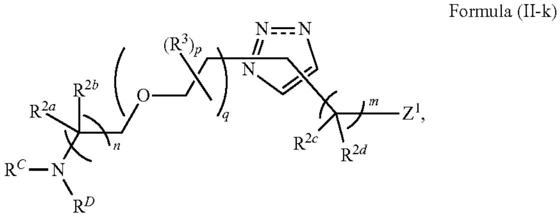

or a salt thereof, wherein $Z^1$ is alkyl, alkenyl, alkynyl, heteroalkyl, cycloalkyl, heterocyclyl, aryl, or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; or $R^C$ and $R^D$, taken together with the nitrogen atom to which they are attached, form a ring (e.g., a 5-7 membered ring), optionally substituted with 1-6 $R^6$; each of $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$—$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, —CN, oxo, hydroxyl, cycloalkyl, or heterocyclyl; m and n are each independently 0, 1, 2, 3, 4, 5, or 6; p is 0, 1, 2, 3, or 4; and q is an integer from 0 to 25.

In some embodiments, the compound of Formula (II) is a compound of Formula (II-l):

Formula (II-l)

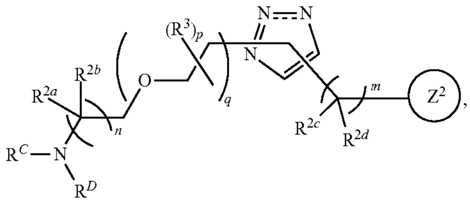
, or a salt thereof, wherein Ring $Z^2$ is heterocyclyl, aryl, or heteroaryl, optionally substituted with 1-5 $R^5$; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; $R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; or $R^C$ and $R^D$, taken together with the nitrogen atom to which they are attached, form a ring (e.g., a 5-7 membered ring), optionally substituted with 1-6 $R^6$; each of $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, —CN, oxo, hydroxyl, cycloalkyl, or heterocyclyl; m and n are each independently 0, 1, 2, 3, 4, 5, or 6; p is 0, 1, 2, 3, or 4; and q is an integer from 0 to 25.

In some embodiments, the compound of Formula (II) is a compound of Formula (II-m):

Formula (II-m)

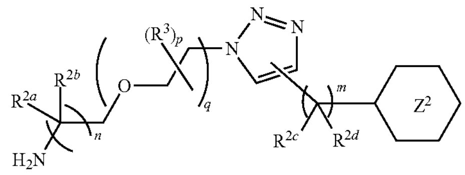
, or a salt thereof, wherein Ring $Z^2$ is heterocyclyl or heteroaryl, optionally substituted with 1-5 $R^5$; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each $R^3$ is independently alkyl, heteroalkyl, halogen, cyano, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; each $R^5$ is independently alkyl, heteroalkyl, halogen, cyano, oxo, —$OR^{A1}$, $C(O)OR^{A1}$ or —$C(O)R^{B1}$; each $R^{A1}$, $R^{B1}$, $R^{C1}$, $R^{D1}$, and $R^{E1}$ is independently hydrogen, alkyl, or heteroalkyl; each of m and n is independently 1, 2, or 3; each of p and q is independently 0, 1, 2, 3, or 4.

In some embodiments, for example, any one of the Formula described herein (e.g., a compound of Formulas (II-a), (II-b), (II-c), (II-d), (II-e), (II-f), (II-g), (II-h), (II-j), (II-k), (II-l), (II-m)), $Z^1$, Ring $Z^1$, or Ring $Z^2$ is heterocyclyl. In some embodiments, $Z^1$, Ring $Z^1$, or Ring $Z^2$ is a six-membered heterocyclyl, a five-membered heterocyclyl, or a four-membered heterocyclyl. In some embodiments, $Z^1$, Ring $Z^1$, or Ring $Z^2$ is an oxygen-containing heterocyclyl, a nitrogen-containing heterocyclyl, or a sulfur-containing heterocyclyl.

In some embodiments, $Z^1$, Ring $Z^1$, or Ring $Z^2$ is an oxygen-containing heterocyclyl. In some embodiments, $Z^1$, Ring $Z^1$, or Ring $Z^2$ is tetrahydropyranyl, dioxanyl, tetrahydrofuranyl, oxetanyl, or oxiranyl. In some embodiments, $Z^1$, Ring $Z^1$, or Ring $Z^2$ is selected from:

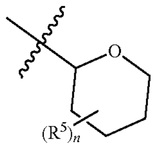
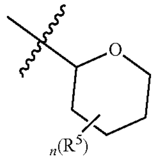
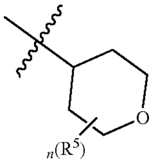
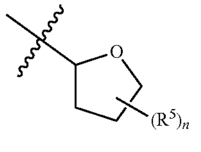
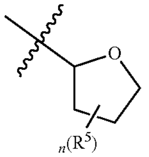
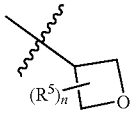
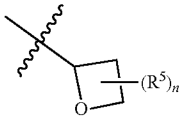
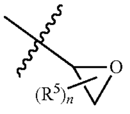
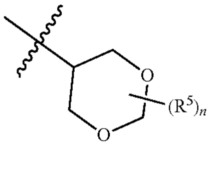
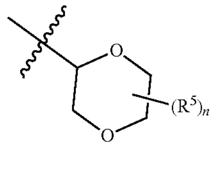

-continued

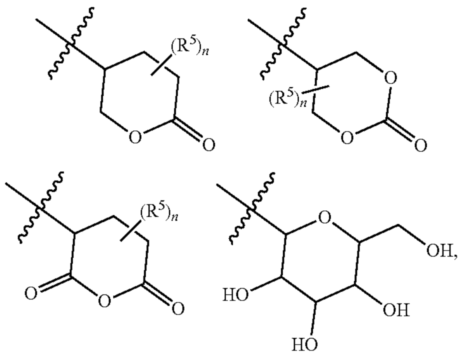

wherein n is an integer between 0 and 10.

In some embodiments, $Z^1$, Ring $Z^1$, or Ring $Z^2$ is a nitrogen-containing heterocyclyl. In some embodiments, $Z^1$, Ring $Z^1$, or Ring $Z^2$ is piperidinyl, piperazinyl, hexahydropyrimidinyl, pyrrolidinyl, imidazolidinyl, azetidinyl, or aziridinyl. In some embodiments, $Z^1$, Ring $Z^1$, or Ring $Z^2$ is selected from:

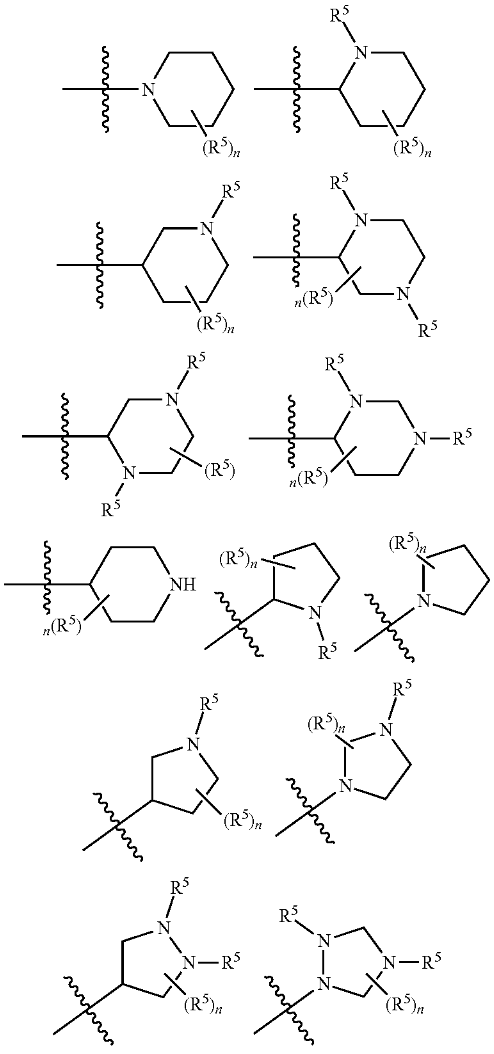

-continued

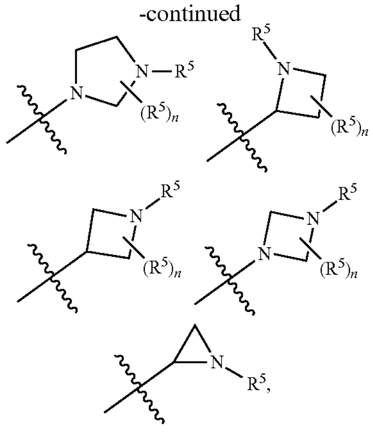

wherein n is an integer between 0 and 10.

In some embodiments, the compound of Formula (II) is a compound of Formula (II-n):

Formula (I-b-3)

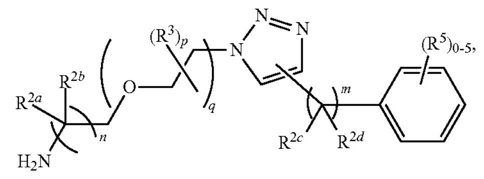

or a salt thereof, wherein each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each $R^3$ is independently alkyl, heteroalkyl, halogen, cyano, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; each $R^5$ is independently alkyl, heteroalkyl, halogen, cyano, —$OR^{A1}$, —$C(O)OR^{A1}$, or —$C(O)R^{B1}$; each $R^{A1}$, $R^{B1}$, $R^{C1}$, $R^{D1}$, and $R^{E1}$ is independently hydrogen, alkyl, or heteroalkyl; m and n are each independently 0, 1, 2, 3, 4, 5, or 6; p is 0, 1, 2, 3, or 4; and q is an integer from 0 to 25.

In some embodiments, the compound of Formula (II) is a compound of Formula (II-o):

Formula (II-o)

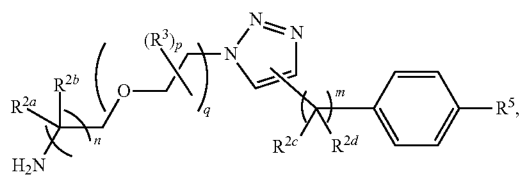

or a salt thereof, wherein each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each $R^3$ is independently alkyl, heteroalkyl, halogen, cyano, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; $R^5$ is alkyl, halogen, —$N(R^{C1})(R^{D1})$, —$N(R^{C1})C(O)R^{B1}$, —$C(O)N(R^{C1})$, or $SR^{E1}$; each $R^{A1}$, $R^{B1}$, $R^{C1}$, $R^{D1}$, and $R^{E1}$ is independently hydrogen, alkyl, or heteroalkyl; m and n are each independently 0, 1, 2, 3, 4, 5, or 6; p is 0, 1, 2, 3, or 4; and q is an integer from 0 to 25.

In some embodiments, the compound of Formula (II) is a compound of Formula (II-p):

Formula (II-p)

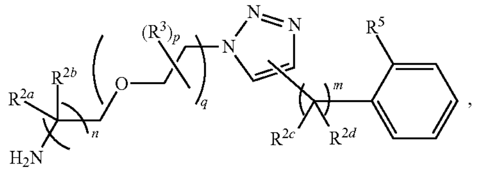

or a salt thereof, wherein each of $R^{2a}$, $R^{2b}$, $R^{2c}$, and $R^{2d}$ is independently hydrogen, alkyl, heteroalkyl, or halo, or $R^{2a}$ and $R^{2b}$ or $R^{2c}$ and $R^{2d}$ are taken together to form an oxo group; each $R^3$ is independently alkyl, heteroalkyl, halogen, cyano, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; $R^5$ is alkyl, heteroalkyl, halogen, cyano, —$OR^{A1}$, —$C(O)OR^{A1}$, or —$C(O)R^{B1}$; each $R^{A1}$, $R^{B1}$, $R^{C1}$, $R^{D1}$, and $R^{E1}$ is independently hydrogen, alkyl, or heteroalkyl; m and n are each independently 0, 1, 2, 3, 4, 5, or 6; p is 0, 1, 2, 3, or 4; and q is an integer from 0 to 25.

In some embodiments, the compound of Formula (II) is a compound of Formula (II-q):

Formula (II-q)

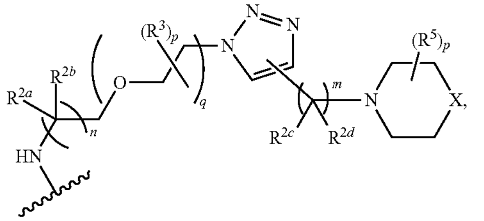

or a salt thereof, wherein X is C(R')(R"), N(R'), or $S(O)_x$; each of R' and R" is independently hydrogen, alkyl, halogen, or cycloalkyl; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each $R^3$ is independently alkyl, heteroalkyl, halogen, cyano, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; each $R^5$ is independently alkyl, heteroalkyl, halogen, cyano, —$OR^{A1}$, —$C(O)OR^{A1}$, —$C(O)R^{B1}$, —$N(R^{C1})(R^{D1})$, —$N(R^{C1})C(O)R^{B1}$, —$C(O)N(R^{C1})$, or $SR^{E1}$; each $R^{A1}$, $R^{B1}$, Rei, $R^{D1}$, and $R^{E1}$ is independently hydrogen, alkyl, or heteroalkyl; m, n, and o are each independently 0, 1, 2, 3, 4, 5, or 6; p is 0, 1, 2, 3, 4, or 5; q is an integer from 0 to 25; x is 0, 1, or 2; and " " refers to a connection to a device or material (e.g., a device or material described herein).

In some embodiments, X is N(R'), e.g., and R' is hydrogen or alkyl. In some embodiments, X is $S(O)_x$, e.g., and x is 0, 1, or 2. In some embodiments, X is not $S(O)_2$.

In some embodiments, the compound of Formula (II) is a compound of Formula (II-r):

Formula (II-r)

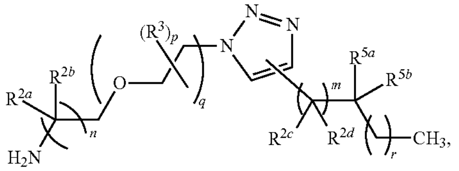

or a salt thereof, wherein each of $R^{2a}$, $R^{2b}$, $R^{2c}$, and $R^{2d}$ is independently hydrogen, alkyl, heteroalkyl, halo, cyano, nitro, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, or —$C(O)N(R^{C1})$; or $R^{2a}$ and $R^{2b}$ or $R^{2c}$ and $R^{2d}$ are taken together to form an oxo group; each $R^3$ is independently alkyl, heteroalkyl, halogen, cyano, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; each of $R^{5a}$ and 5b is independently alkyl, heteroalkyl, halogen, cyano, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; each $R^{A1}$, $R^{B1}$, $R^{C1}$, $R^{D1}$, and $R^{E1}$ is independently hydrogen, alkyl, or heteroalkyl; m and n are each independently 0, 1, 2, 3, 4, 5, or 6; p is 0, 1, 2, 3, or 4; q is an integer from 0 to 25; and r is an integer between 0 and 10.

In some embodiments, the compound of Formula (I) or Formula (II) (e.g., a compound of Formulas (II-a), (II-b), (II-c), (II-d), (II-e), (II-f), (II-g), (II-g-2), (II-h), (II-i), (II-i-2), (II-j), (II-k), (II-l), (II-m), (II-n), (II-o), (II-p), (II-q) or (II-r)) is selected from a compound depicted in any one of FIGS. 1A-6KK or a pharmaceutically acceptable salt thereof.

In some embodiments, the compound of Formula (I) or Formula (II) (e.g., a compound of Formulas (II-a), (II-b), (II-c), (II-d), (II-e), (II-f), (II-g), (II-g-2), (II-h), (II-i), (II-i-2), (II-j), (II-k), (II-l), (II-m), (II-n), (II-o), (II-p), (II-q) or (II-r)) is not a compound disclosed in any of WO2012/112982, WO2012/167223, WO2014/153126, WO2016/187225, WO2016/019391, WO2017/075630, WO 2017/075631, and US 2016-0030359.

In some embodiments, the compound of Formula (I) or Formula (II) (e.g., a compound of Formulas (II-a), (II-b), (II-c), (II-d), (II-e), (II-f), (II-g), (II-g-2), (II-h), (II-i), (II-i-2), (II-j), (II-k), (II-l), (II-m), (II-n), (II-o), (II-p), (II-q) or (II-r)) is not a compound selected from the following:

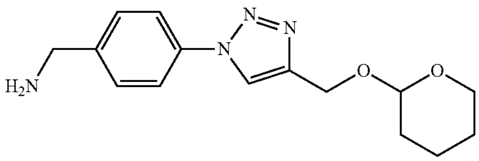

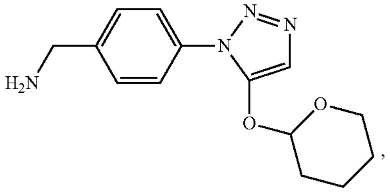

-continued

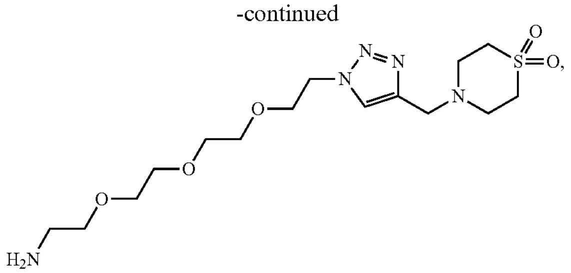

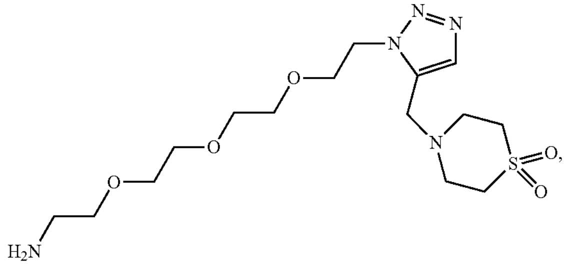

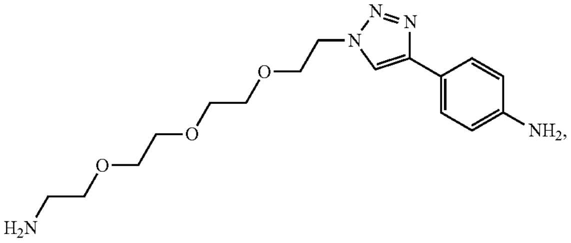

and

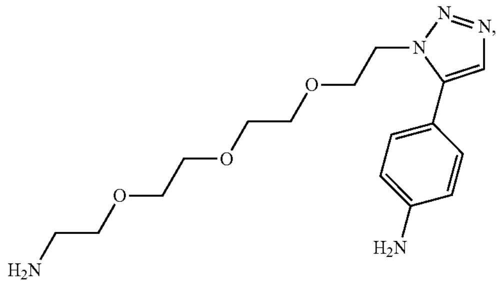

or a salt thereof.

In some embodiments, the compound of Formula (I) or Formula (II) (e.g., a compound of Formulas (II-a), (II-b), (II-c), (II-d), (II-e), (II-f), (II-g), (II-g-2), (II-h), (II-i), (II-i-2), (II-j), (II-k), (II-l), (II-m), (II-n), (II-o), (II-p), (II-q) or (II-r)) is not a compound selected from the following:

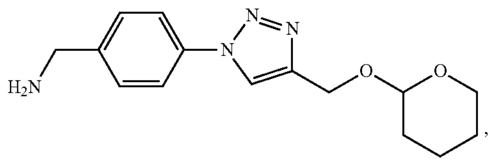

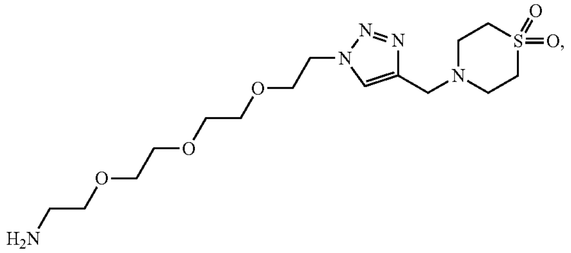

-continued and

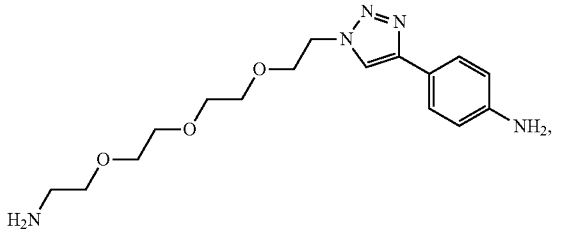

or a salt thereof.

In some embodiments, the compound of Formula (I) is a compound of Formula (III):

Formula (III)

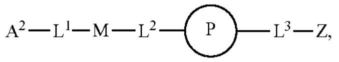

or a salt thereof, wherein A2 is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, —NCN—, —C(=N($R^C$)($R^D$))O—, —S—, —S$(O)_x$—, —OS$(O)_x$—, —N($R^C$)S$(O)_x$—, —S$(O)_x$N($R^C$)—, —P$(R^F)_y$—, —Si$(OR^A)_2$—, —Si($R^G$)($OR^A$)—, —B($OR^A$)—, or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted by one or more $R^1$; each of $L^1$ and $L^3$ is independently a bond, alkyl, or heteroalkyl, wherein each alkyl and heteroalkyl is optionally substituted by one or more $R^2$; $L^2$ is a bond; M is alkyl, heteroalkyl, cycloalkyl, heterocyclyl, aryl, or heteroaryl, each of which is optionally substituted by one or more $R^3$; P is heteroaryl optionally substituted by one or more $R^4$; Z is alkyl, alkenyl, alkynyl, heteroalkyl, cycloalkyl, heterocyclyl, aryl, or heteroaryl, each of which is optionally substituted by one or more $R^5$; each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$; or $R^C$ and $R^D$, taken together with the nitrogen atom to which they are attached, form a ring (e.g., a 5-7 membered ring), optionally substituted with one or more $R^6$; each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O) N($R^{C1}$) $SR^{E1}$, S$(O)_x R^{E1}$, —OS$(O)_x R^{E1}$, —N($R^{C1}$)S$(O)_x R^{E1}$, —S$(O)_x$N($R^{C1}$)($R^{D1}$), —P$(R^{F1})_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$; each $R^{A1}$, $R^{B1}$, Rei $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$; each $R^7$ is independently alkyl, alkenyl, alkynyl, heteroalkyl, halogen, cyano, oxo, hydroxyl, cycloalkyl, or heterocyclyl; x is 1 or 2; and y is 2, 3, or 4.

In some embodiments, A2 is alkyl, alkenyl, alkynyl, heteroalkyl, cycloalkyl, heterocyclyl, aryl, heteroaryl, —O—, —C(O)O—, —C(O)—, —OC(O)—, or —N($R^C$)—. In some embodiments, A2 is alkyl, alkenyl, alkynyl, heteroalkyl, —O—, —C(O)O—, —C(O)—, —OC(O—, or —N($R^C$)—. In some embodiments, A2 is alkyl, —O—, —C(O)O—, —C(O)—, —OC(O), or —N($R^C$)—. In some embodiments, A2 is —N($R^C$)—. In some embodiments, A2 is —N($R^C$)—, and $R^C$ an $R^D$ is independently hydrogen or alkyl. In some embodiments, A2 is —NH—. In some embodiments, A2 is NH— or NH(C(O)C($CH_3$)$CH_2$—.

In some embodiments, $L^1$ is a bond, alkyl, or heteroalkyl. In some embodiments, $L^1$ is alkyl. In some embodiments, $L^1$ is $C_1$-$C_6$ alkyl. In some embodiments, $L^1$ is —$CH_2$— or —$CH_2CH_2$—. In some embodiments, $L^1$ is substituted by $R^3$.

In some embodiments, $L^3$ is a bond, alkyl, or heteroalkyl. In some embodiments, $L^3$ is a bond. In some embodiments, $L^3$ is alkyl. In some embodiments, $L^3$ is $C_1$-$C_6$ alkyl. In some embodiments, $L^3$ is —$CH_2$—. In some embodiments, $L^3$ is heteroalkyl. In some embodiments, $L^3$ is $C_1$-$C_6$ heteroalkyl. In some embodiments, $L^3$ is —$CH_2O$—. In some embodiments, $L^3$ is substituted by $R^3$.

In some embodiments, M is alkyl, heteroalkyl, aryl, or heteroaryl. In some embodiments, M is alkyl (e.g., methyl, ethyl, propyl). In some embodiments, M is heteroalkyl, aryl, or heteroaryl. In some embodiments, M is heteroalkyl. In some embodiments, M is (—$OCH_2CH_2$-)z, wherein z is an integer selected from 1 to 10. In some embodiments, M is —$OCH_2CH_2$—, (—$OCH_2CH_2$-$)_2$, (—$OCH_2CH_2$-$)_3$, or (—$OCH_2CH_2$-$)_4$. In some embodiments, M is (—$OCH_2CH_2$-$)_3$. In some embodiments, M is aryl. In some embodiments, M is phenyl. In some embodiments, M is unsubstituted phenyl.

In some embodiments, P is a tricyclic, bicyclic, or monocyclic heteroaryl. In some embodiments, P is a monocyclic heteroaryl. In some embodiments, P is a nitrogen-containing heteroaryl. In some embodiments, P is a monocyclic, nitrogen-containing heteroaryl. In some embodiments, P is a 5-membered heteroaryl. In some embodiments, P is a 5-membered nitrogen-containing heteroaryl. In some embodiments, P is tetrazolyl, imidazolyl, pyrazolyl, or triazolyl, pyrrolyl, oxazolyl, or thiazolyl. In some embodiments, P is tetrazolyl, imidazolyl, pyrazolyl, or triazolyl, or pyrrolyl. In some embodiments, P is triazolyl. In some embodiments, P is 1,2,3-triazolyl.

In some embodiments, Z is alkyl, heteroalkyl, cycloalkyl, heterocyclyl, aryl, or heteroaryl. In some embodiments, Z is heterocyclyl. In some embodiments, Z is monocyclic or bicyclic heterocyclyl. In some embodiments, Z is an oxygen-containing heterocyclyl. In some embodiments, Z is a 6-membered heterocyclyl. In some embodiments, Z is a 6-membered oxygen-containing heterocyclyl. In some embodiments, Z is tetrahydropyranyl. In some embodiments, Z is a bicyclic oxygen-containing heterocyclyl. In some embodiments, Z is phthalic anhydridyl. In some embodiments, Z is a sulfur-containing heterocyclyl. In some embodiments, Z is a 6-membered sulfur-containing heterocyclyl. In some embodiments, Z is a 6-membered heterocyclyl containing a nitrogen atom and a sulfur atom. In some embodiments, Z is thiomorpholinyl-1,1-dioxidyl. In some embodiments, Z is oxetanyl, tetrahydrofuranyl, tetrahydropyranyl, thiomorpholinyl-1,1-dioxide, piperidinyl, piperazinyl, or pyrrolidinyl.

In some embodiments, Z is aryl. In some embodiments, Z is monocyclic aryl. In some embodiments, Z is phenyl. In some embodiments, Z is monosubstituted phenyl (e.g., with 1 $R^5$). In some embodiments, Z is monosubstituted phenyl, wherein the 1 $R^5$ is a nitrogen-containing group. In some embodiments, Z is monosubstituted phenyl, wherein the 1 $R^5$ is $NH_2$. In some embodiments, Z is monosubstituted phenyl, wherein the 1 $R^5$ is an oxygen-containing group. In some embodiments, Z is monosubstituted phenyl, wherein the 1 $R^5$ is an oxygen-containing heteroalkyl. In some embodiments, Z is monosubstituted phenyl, wherein the 1 $R^5$ is $OCH_3$. In some embodiments, Z is monosubstituted phenyl, wherein the 1 $R^5$ is in the ortho position. In some embodiments, Z is monosubstituted phenyl, wherein the 1 $R^5$ is in the meta position. In some embodiments, Z is monosubstituted phenyl, wherein the 1 $R^5$ is in the para position.

In some embodiments, Z is alkyl. In some embodiments, Z is $C_1$-$C_{12}$ alkyl. In some embodiments, Z is $C_1$-$C_{10}$ alkyl. In some embodiments, Z is $C_1$-$C_8$ alkyl. In some embodiments, Z is $C_1$-$C_8$ alkyl substituted with 1-5 $R^5$. In some embodiments, Z is $C_1$-$C_8$ alkyl substituted with 1 $R^5$. In some embodiments, Z is $C_1$-$C_8$ alkyl substituted with 1 $R^5$, wherein $R^5$ is alkyl, heteroalkyl, halogen, oxo, —$OR^{A1}$, —C(O)$OR^{A1}$, —C(O)$R^{B1}$, —OC(O)$R^{B1}$, or —N($R^{C1}$)($R^{D1}$) In some embodiments, Z is $C_1$-$C_8$ alkyl substituted with 1 $R^5$, wherein $R^5$ is —$OR^{A1}$ or —C(O)$OR^{A1}$. In some embodiments, Z is $C_1$-$C_8$ alkyl substituted with 1 $R^5$, wherein $R^5$ is —$OR^{A1}$ or —C(O)OH.

In some embodiments, the compound of Formula (III) is selected from any one of the compounds depicted in any one of FIGS. 1A-6KK or a pharmaceutically acceptable salt thereof.

In some embodiments, the compound of Formula (III) is a compound of Formula (III-a).

Formula (III-a)

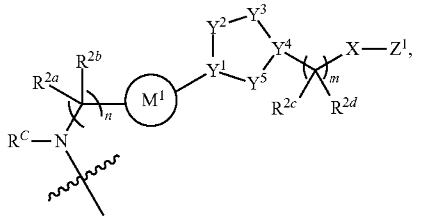

or a salt thereof, wherein Ring $M^1$ is cycloalkyl, heterocyclyl, aryl, or heteroaryl, each of which is optionally substituted with 1-5 $R^3$; each of $Y^1$ and $Y^4$ is independently C(R') or N; each of $Y^2$, $Y^3$, and $Y^5$ is independently C(R')(R''), N($R^{10}$), S, or O, wherein only two of $Y^2$, $Y^3$, and $Y^5$ may be O or S; and wherein each of $Y^1$, $Y^2$, $Y^3$, $Y^4$, and $Y^5$ is linked with single bonds or double bonds to achieve appropriate valency; X is absent, N($R^{10}$)($R^{11}$), O, or S; $Z^1$ is alkyl, alkenyl, alkynyl, heteroalkyl, cycloalkyl, heterocyclyl, aryl, or heteroaryl, each of which is optionally substituted by one or more $R^5$; each of R' and R'' is independently hydrogen, alkyl, halogen, or cycloalkyl; or each of R' and R'' are taken together to form an oxo group; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each of $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —C(O) $N(R^{C1})$, $SR^{E1}$, cycloalkyl, heterocyclyl, aryl, heteroaryl; each of $R^{10}$ and $R^{11}$ is independently hydrogen, alkyl, alkenyl, alkynyl, heteroalkyl, halogen, —$C(O)R^{B1}$, —$N(R^{C1})C(O)R^{B1}$, —$C(O)N(R^{C1})$, $SR^{E1}$, $S(O)_x$, cycloalkyl, or heterocyclyl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 0, 1, 2, 3, 4, 5, or 6; x is 1 or 2; and "∿∿" refers to a connection to a device or material (e.g., a device or material described herein).

In some embodiments, the compound of Formula (II) is a compound of Formula (III-b).

Formula (III-b)

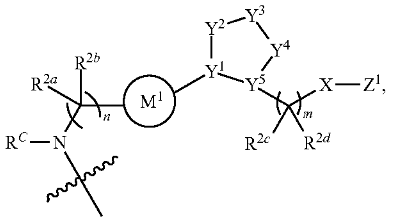

or a salt thereof, wherein Ring $M^1$ is cycloalkyl, heterocyclyl, aryl, or heteroaryl, each of which is optionally substituted with 1-5 $R^3$; each of $Y^1$ and $Y^4$ is independently C(R') or N; each of $Y^2$, $Y^3$, and $Y^5$ is independently C(R')(R"), $N(R^{10})$, S, or O, wherein only two of $Y^2$, $Y^3$, and $Y^5$ may be O or S; and wherein each of Y, $Y^2$, $Y^3$, $Y^4$, and $Y^5$ is linked with single bonds or double bonds to achieve appropriate valency; X is absent, $N(R^{10})(R^{11})$, O, or S; $Z^1$ is alkyl, alkenyl, alkynyl, heteroalkyl, cycloalkyl, heterocyclyl, aryl, or heteroaryl, each of which is optionally substituted by one or more $R^5$; each of R' and R" is independently hydrogen, alkyl, halogen, or cycloalkyl; or each of R' and R" are taken together to form an oxo group; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each of $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —C(O) $N(R^{C1})$, $SR^{E1}$, cycloalkyl, heterocyclyl, aryl, heteroaryl; each of $R^{10}$ and $R^{11}$ is independently hydrogen, alkyl, alkenyl, alkynyl, heteroalkyl, halogen, —$C(O)R^{B1}$, —$N(R^{C1})C(O)R^{B1}$, —$C(O)N(R^{C1})$, $SR^{E1}$, $S(O)_x$, cycloalkyl, or heterocyclyl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 0, 1, 2, 3, 4, 5, or 6;

x is 1 or 2; and "∿∿" refers to a connection to a device or material (e.g., a device or material described herein).

In some embodiments, the compound of Formula (III) is a compound of Formula (III-c).

Formula (III-c)

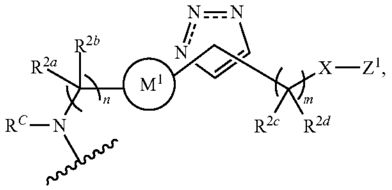

or a salt thereof, wherein Ring $M^1$ is cycloalkyl, heterocyclyl, aryl, or heteroaryl, each of which is optionally substituted with 1-5 $R^3$; $Z^1$ is alkyl, alkenyl, alkynyl, heteroalkyl, cycloalkyl, heterocyclyl, aryl, or heteroaryl, each of which is optionally substituted by one or more $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each of $R^3$, $R^5$, and $R^6$ is independently alkyl, alkenyl, alkynyl, heteroalkyl, halogen, cyano, azido, oxo, —$OR^{A1}$, —$C(O)OR^{A1}$, —C(O) $R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, heteroaryl; each of $R^{10}$ and $R^{11}$ is independently hydrogen, alkyl, alkenyl, alkynyl, heteroalkyl, halogen, —$C(O)R^{B1}$, —$N(R^{C1})C(O)R^{B1}$, —$C(O)N(R^{C1})$, $SR^{E1}$, $S(O)_x$, cycloalkyl, or heterocyclyl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 0, 1, 2, 3, 4, 5, or 6; x is 1 or 2; and "∿∿" refers to a connection to a device or material (e.g., a device or material described herein).

In some embodiments, the compound of Formula (III) is a compound of Formula (III-d).

Formula (III-d)

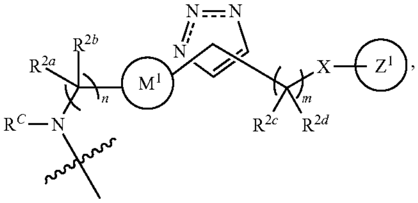

or a salt thereof, wherein Ring $M^1$ is cycloalkyl, heterocyclyl, aryl, or heteroaryl, each of which is optionally substituted with 1-5 $R^3$; Ring $Z^1$ is cycloalkyl, heterocyclyl, aryl or heteroaryl, optionally substituted with 1-5 $R^5$ each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; X is absent, $N(R^{10})(R^{11})$, O, or S; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, or heteroaryl; each of $R^{10}$ and $R^{11}$ is independently hydrogen, alkyl, alkenyl, alkynyl, heteroalkyl, —$C(O)OR^{A1}$, —$C(O)R^{B1}$, —$OC(O)R^{B1}$, —$C(O)N(R^{C1})$, cycloalkyl, heterocyclyl, aryl, or heteroaryl; each $R^{A1}$, $R^{B1}$, $R^{C1}$, $R^{D1}$ and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 0, 1, 2, 3, 4, 5, or 6; and “ ” refers to a connection to a device or material (e.g., a device or material described herein).

In some embodiments, the compound of Formula (III) is a compound of Formula (III-e):

Formula (III-e)

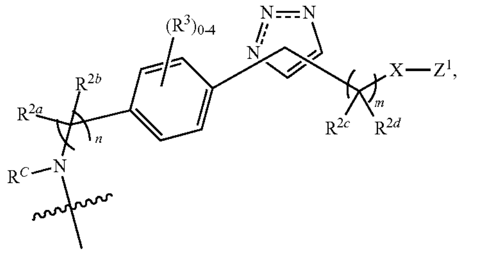

or a salt thereof, wherein $Z^1$ is alkyl, alkenyl, alkynyl, heteroalkyl, cycloalkyl, heterocyclyl, aryl, or heteroaryl, each of which is optionally substituted by one or more $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, —CN, oxo, hydroxyl, cycloalkyl, or heterocyclyl; each m and n is independently 0, 1, 2, 3, 4, 5, or 6; and “ ” refers to a connection to a device or material (e.g., a device or material described herein).

In some embodiments, $Z^1$ is alkyl or heteroalkyl. In some embodiments, $Z^1$ is heteroalkyl (e.g., $C_1$-$C_{12}$ heteroalkyl). In some embodiments, $Z^1$ is an oxygen-containing heteroalkyl or a nitrogen-containing heteroalkyl. In some embodiments, $Z^1$ is $(—OCH_2CH_2)_3OCH_3$, wherein z is an integer selected from 1 to 10 (e.g., z is 1, 2, 3, 4, 5, 6, 7, 8, 9, or 10). In some embodiments, $Z^1$ is $(—OCH_2CH_2)_3OCH_3$. In some embodiments, X is absent. In some embodiments, m is 1. In some embodiments, n is 1. In some embodiments, each of $R^{2a}$, $R^{2b}$, $R^{2c}$, and $R^{2d}$ is independently hydrogen. In some embodiments, $R^C$ is hydrogen, alkyl, alkenyl, alkynyl, or heteroalkyl (e.g., $C(O)C(C{=}CH_2)CH_3$). In some embodiments, $R^C$ is hydrogen. In some embodiments, $R^C$ is alkenyl (e.g., $C(O)C(C{=}CH_2)CH_3$).

In some embodiments, the compound of Formula (III) is a compound of Formula (III-f):

(III-f)

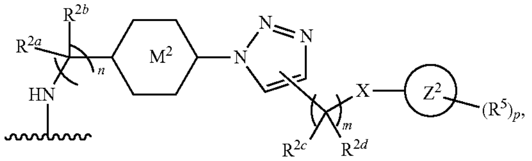

or a salt thereof, wherein Ring $M^2$ is aryl or heteroaryl, optionally substituted by one or more $R^3$; Ring $Z^2$ is cycloalkyl, heterocyclyl, aryl or heteroaryl; each of $R^{2a}$, $R^{2a}$, $R^{2c}$, and $R^{2d}$ is independently hydrogen, alkyl or heteroalkyl; or $R^{2a}$ and $R^{2b}$ or $R^{2c}$ and $R^{2d}$ are taken together to form an oxo group; X is absent, O, or S; each $R^3$ or $R^5$ is independently alkyl, heteroalkyl, halogen, oxo, —$OR^{A1}$, —$C(O)OR^{A1}$, or —$C(O)R^{B1}$; or two $R^5$ are taken together to form a 5-6 membered ring fused to Ring $Z^2$; each $R^{A1}$, $R^{B1}$, $R^{C1}$, $R^{D1}$ and $R^{E1}$ is independently hydrogen, alkyl, heteroalkyl; m and p are each independently 0, 1, 2, 3, 4, 5, or 6; and “ ” refers to a connection to a device or material (e.g., a device or material described herein).

In some embodiments, the compound of Formula (III) is a compound of Formula (III-g):

(III-g)

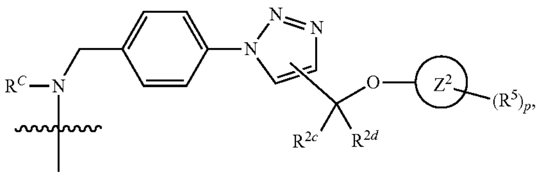

or a salt thereof, wherein Ring $Z^2$ is cycloalkyl, heterocyclyl, aryl or heteroaryl; each of $R^{2c}$ and $R^{2d}$ is independently hydrogen, alkyl, heteroalkyl; or $R^{2c}$ and $R^{2d}$ are taken together to form an oxo group; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each of $R^5$ is independently alkyl, heteroalkyl, halogen, oxo, —$OR^{A1}$, —$C(O)OR^{A1}$, or —$C(O)R^{B1}$; each $R^{A1}$ or $R^{B1}$ is independently hydrogen, alkyl, heteroalkyl; p is 0, 1, 2, 3, 4, 5, or 6; and “ ” refers to a connection to a device or material (e.g., a device or material described herein).

In some embodiments, the compound of Formula (III) is a compound of Formula (III-g-2):

Formula (III-g-2)

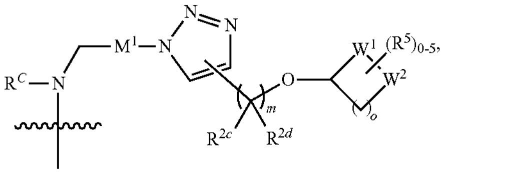

or a salt thereof, wherein $M^1$ is alkyl, alkenyl, alkynyl, optionally substituted by one or more $R^3$; each of $W^1$ and $W^2$ are independently C(R')(R''), $N(R^{20})$, or $S(O)_x$; each of $R^{2c}$ and $R^{2d}$ is independently hydrogen, alkyl, or heteroalkyl; or $R^{2c}$ and $R^{2d}$ are taken together to form an oxo group; each $R^5$ is independently alkyl, heteroalkyl, halogen, cyano, azido, oxo, $—OR^{A1}$, $—C(O)OR^{A1}$, $—C(O)R^{B1}$, $—OC(O)R^{B1}$, $—N(R^{C1})(R^{D1})$, $—N(R^{C1})C(O)R^{B1}$, $—C(O)N(R^{C1})$, or $SR^{E1}$, cycloalkyl, heterocyclyl, aryl, heteroaryl; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each of R' and R'' is independently hydrogen, alkyl, alkenyl, halogen, cyano, or cycloalkyl; each $R^{20}$ is hydrogen, alkyl, or $—C(O)R^{B1}$; each $R^{A1}$, $R^{B1}$, $R^{C1}$, $R^{D1}$, and $R^{E1}$ is independently hydrogen, alkyl, or heteroalkyl; each m is independently 1, 2, 3, 4, 5, or 6; o is 1, 2, 3, 4 or 5; and x is 0, 1, or 2.

In some embodiments, one of $W^1$ and $W^2$ is independently O. In some embodiments, $W^1$ is O. In some embodiments, $W^2$ is O. In some embodiments, $W^1$ is C(R')(R'') (e.g., CH2) and $W^2$ is O. In some embodiments, o is 1, 2, or 3. In some embodiments, m is 1. In some embodiments, Ring $M^2$ is alkyl (e.g., methyl, ethyl, or propyl). In some embodiments, each of $R^{2c}$ and $R^{2d}$ is independently hydrogen. In some embodiments, one of $R^C$ and $R^D$ is independently hydrogen, alkyl, alkenyl, alkynyl, or heteroalkyl (e.g., $C(O)C(C{=}CH_2)CH_3$). In some embodiments, one of $R^C$ and $R^D$ is independently hydrogen and the other of $R^C$ and $R^D$ is independently alkenyl (e.g., $C(O)C(C{=}CH_2)CH_3$).

In some embodiments, the compound of Formula (III) is a compound of Formula

Formula (III-h)

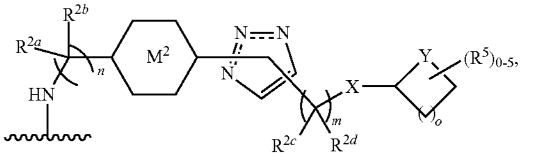

or a salt thereof, wherein Ring $M^2$ is aryl or heteroaryl, each of which is optionally substituted with 1-5 $R^4$; Y is O, S, or $N(R^{10})$ optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; X is absent, $N(R^{10})(R^{11})$, O, or S; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$, or $R^C$ is bound to an atom within L or M or one of the substituents of L or M to form a ring optionally substituted with 1-6 $R^6$; each $R^4$, $R^5$, $R^6$, $R^{10}$, and $R^{11}$ is independently alkyl, alkenyl, alkynyl, heteroalkyl, halogen, cyano, azido, oxo, $—OR^{A1}$, $—C(O)OR^{A1}$, $—C(O)R^{B1}$, $—OC(O)R^{B1}$, $—N(R^{C1})(R^{D1})$, $—N(R^{C1})C(O)R^{B1}$, $—C(O)N(R^{C1})$, $SR^{E1}$, cycloalkyl, heterocyclyl, aryl, heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$, each $R^7$ is independently alkyl, alkenyl, alkynyl, heteroalkyl, halogen, —CN, oxo, hydroxyl, cycloalkyl, or heterocyclyl; each m and n is independently 1, 2, 3, 4, 5, or 6; o is 1, 2, 3, 4 or 5; and "∿∿" refers to a connection to a device or material (e.g., a device or material described herein).

In some embodiments, the compound of Formula (III) is a compound of Formula (III-i):

Formula (III-i)

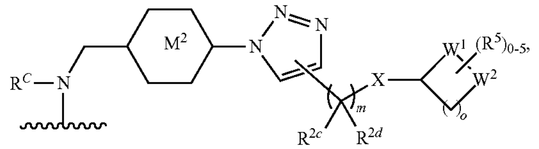

or a salt thereof, wherein Ring $M^2$ is aryl or heteroaryl; each of $W^1$ and $W^2$ are independently C(R')(R''), $N(R^{20})$, or S(O)x; each of $R^{2c}$ and $R^{2d}$ is independently hydrogen, alkyl, or heteroalkyl; or $R^{2c}$ and $R^{2d}$ are taken together to form an oxo group; each $R^5$ is independently alkyl, heteroalkyl, halogen, cyano, azido, oxo, $—OR^{A1}$, $—C(O)OR^{A1}$, $—C(O)R^{B1}—OC(O)R^{B1}$, $—N(R^{C1})(R^{D1})$, $—N(R^{C1})C(O)R^{B1}$, $—C(O)N(R^{C1})$, or $SR^{E1}$, cycloalkyl, heterocyclyl, aryl, heteroaryl; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each of R' and R'' is independently hydrogen, alkyl, alkenyl, halogen, cyano, or cycloalkyl; each $R^{20}$ is hydrogen, alkyl, or $—C(O)R^{B1}$; each $R^{A1}$, $R^{B1}$, $R^{C1}$, $R^{D1}$, and $R^{E1}$ is independently hydrogen, alkyl, heteroalkyl; each m is independently 1, 2, 3, 4, 5, or 6; o is 1, 2, 3, 4 or 5; and x is 0, 1, or 2.

In some embodiments, the compound of Formula (III) is a compound of Formula (III-i-2):

Formula (III-i-2)

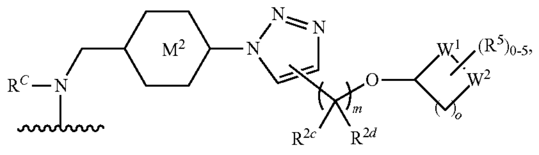

or a salt thereof, wherein Ring $M^2$ is aryl or heteroaryl; each of $W^1$ and $W^2$ are independently C(R')(R''), $N(R^{20})$, or S(O)x; each of $R^{2c}$ and $R^{2d}$ is independently hydrogen, alkyl, or heteroalkyl; or $R^{2c}$ and $R^{2d}$ are taken together to form an oxo group; each $R^5$ is independently alkyl, heteroalkyl, halogen, cyano, azido, oxo, $—OR^{A1}$, $—C(O)OR^{A1}$, $—C(O)R^{B1}$, $—OC(O)R^{B1}$, $—N(R^{C1})(R^{D1})$, $—N(R^{C1})C(O)R^{B1}$, $—C(O)N(R^{C1})$, or $SR^{E1}$, cycloalkyl, heterocyclyl, aryl, heteroaryl; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each of R' and R" is independently hydrogen, alkyl, alkenyl, halogen, cyano, or cycloalkyl; each $R^{20}$ is hydrogen, alkyl, or —C(O)$R^{B1}$; each $R^{A1}$, $R^{B1}$, $R^{C1}$, $R^{D1}$, and $R^{E1}$ is independently hydrogen, alkyl, heteroalkyl; each m is independently 1, 2, 3, 4, 5, or 6; o is 1, 2, 3, 4 or 5; and x is 0, 1, or 2.

In some embodiments, one of $W^1$ and $W^2$ is independently O. In some embodiments, $W^1$ is O. In some embodiments, $W^2$ is O. In some embodiments, $W^1$ is C(R')(R") (e.g., CH2) and $W^2$ is O. In some embodiments, o is 1, 2, or 3. In some embodiments, m is 1. In some embodiments, Ring $M^2$ is aryl (e.g., phenyl). In some embodiments, each of $R^{2c}$ and $R^{2d}$ is independently hydrogen. In some embodiments, one of $R^C$ and $R^D$ is independently hydrogen, alkyl, alkenyl, alkynyl, or heteroalkyl (e.g., $C(O)C(C{=}CH_2)CH_3$). In some embodiments, one of $R^C$ and $R^D$ is independently hydrogen and the other of $R^C$ and $R^D$ is independently alkenyl (e.g., $C(O)C(C{=}CH_2)CH_3$).

In some embodiments, the compound of Formula (III) is a compound of Formula (III-j):

Formula (III-j)

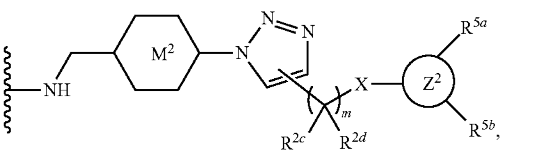

or a salt thereof, wherein Ring $M^2$ is aryl or heteroaryl; Ring $Z^2$ is aryl or heteroaryl; each of $R^{2c}$ and $R^{2d}$ is independently hydrogen, alkyl, or heteroalkyl; or $R^{2c}$ and $R^{2d}$ are taken together to form an oxo group; X is absent, O, or S; each of $R^{5a}$ and $R^{5b}$ is independently alkyl, heteroalkyl, halogen, oxo, —$OR^{A1}$, —C(O)$OR^{A1}$, or —C(O)$R^{B1}$; or $R^{5a}$ and $R^{5b}$ are taken together to form a 5-6 membered ring fused to Ring $Z^2$; each $R^{A1}$ and $R^{B1}$ is independently hydrogen, alkyl, heteroalkyl; each m is independently 0, 1, 2, 3, 4, 5, or 6; and "∿∿∿ " refers to a connection to a device or material (e.g., a device or material described herein).

In some embodiments, the compound of Formula (III) is a compound of Formula (III-k):

(III-k)

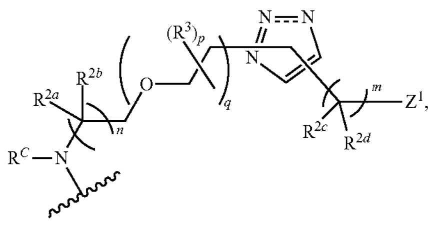

or a salt thereof, wherein $Z^1$ is alkyl, alkenyl, alkynyl, heteroalkyl, cycloalkyl, heterocyclyl, aryl, or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each of $R^3$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, cycloalkyl, heterocyclyl, aryl, heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; m and n are each independently 0, 1, 2, 3, 4, 5, or 6; p is 0, 1, 2, 3, or 4; q is an integer from 0 to 25; and "∿∿∿ " refers to a connection to a device or material (e.g., a device or material described herein).

In some embodiments, the compound of Formula (III) is a compound of Formula (III-l).

Formula (III-l)

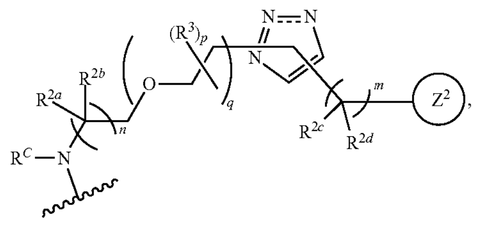

or a salt thereof, wherein Ring $Z^2$ is heterocyclyl, aryl, or heteroaryl, optionally substituted with 1-5 $R^5$; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each of $R^3$, $R^5$, and $R^6$ is independently alkyl, alkenyl, alkynyl, heteroalkyl, halogen, cyano, azido, oxo, —$OR^{A1}$, C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, cycloalkyl, heterocyclyl, aryl, heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, —CN, oxo, hydroxyl, cycloalkyl, or heterocyclyl; m and n are each independently 0, 1, 2, 3, 4, 5, or 6; p is 0, 1, 2, 3, or 4; q is an integer from 0 to 25; and "∿∿∿ " refers to a connection to a device or material (e.g., a device or material described herein).

In some embodiments, the compound of Formula (III) is a compound of Formula (III-m)

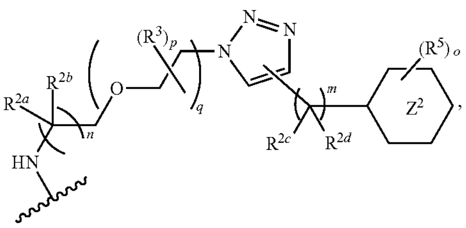

or a salt thereof, wherein Ring $Z^2$ is cycloalkyl, heterocyclyl, aryl, or heteroaryl; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each $R^3$ is independently alkyl, heteroalkyl, halogen, cyano, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; each $R^5$ is independently alkyl, heteroalkyl, halogen, cyano, —$OR^{A1}$, —$C(O)OR^{A1}$, —$C(O)R^{B1}$, —$N(R^{C1})(R^{D1})$, —$N(R^{C1})C(O)R^{B1}$, —$C(O)N(R^{C1})$, $SR^{E1}$; each $R^{A1}$, $R^{B1}$, $R^{C1}$, $R^{D1}$, and $R^{E1}$ is independently hydrogen, alkyl, or heteroalkyl; m, n, and o are each independently 0, 1, 2, 3, 4, 5, or 6; p is 0, 1, 2, 3, 4, or 5; q is an integer from 0 to 25; and "~~~~" refers to a connection to a device or material (e.g., a device or material described herein).

In some embodiments, for example, any one of the Formula described herein (e.g., a compound of Formulas (III-a), (III-b), (III-c), (III-d), (III-e), (III-f), (III-g), (III-h), (III-j), (III-k), (III-l), (III-m)), $Z^1$, Ring $Z^1$, or Ring $Z^2$ is heterocyclyl. In some embodiments, $Z^1$, Ring $Z^1$, or Ring $Z^2$ is a six-membered heterocyclyl, a five-membered heterocyclyl, or a four-membered heterocyclyl. In some embodiments, $Z^1$, Ring $Z^1$, or Ring $Z^2$ is an oxygen-containing heterocyclyl, a nitrogen-containing heterocyclyl, or a sulfur-containing heterocyclyl.

In some embodiments, $Z^1$, Ring $Z^1$, or Ring $Z^2$ is an oxygen-containing heterocyclyl. In some embodiments, $Z^1$, Ring $Z^1$, or Ring $Z^2$ is tetrahydropyranyl, dioxanyl, tetrahydrofuranyl, oxetanyl, or oxiranyl. In some embodiments, $Z^1$, Ring $Z^1$, or Ring $Z^2$ is selected from:

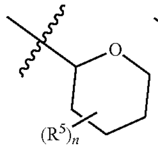 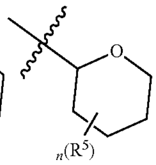 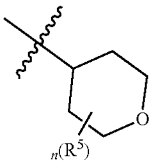

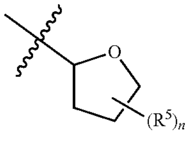 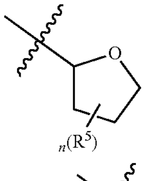 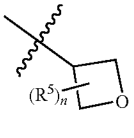

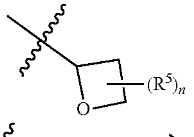 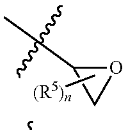

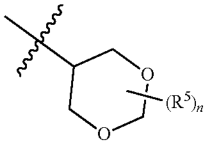 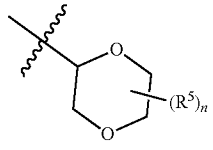

-continued

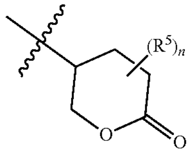 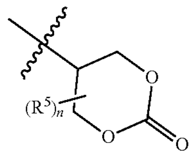

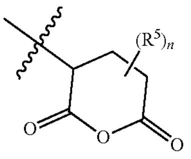 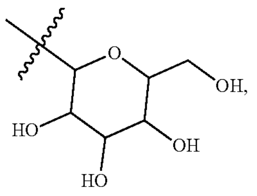

wherein n is an integer between 0 and 10.

In some embodiments, $Z^1$, Ring $Z^1$, or Ring $Z^2$ is a nitrogen-containing heterocyclyl. In some embodiments, $Z^1$, Ring $Z^1$, or Ring $Z^2$ is piperidinyl, piperazinyl, hexahydropyrimidinyl, pyrrolidinyl, imidazolidinyl, azetidinyl, or aziridinyl. In some embodiments, $Z^1$, Ring $Z^1$, or Ring $Z^2$ is selected from:

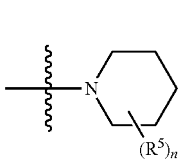 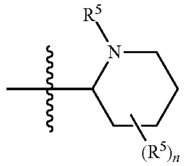

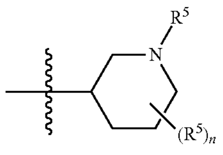 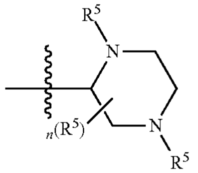

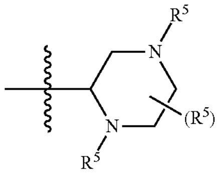 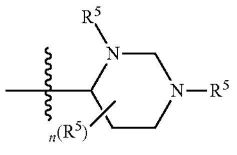

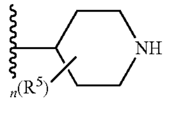 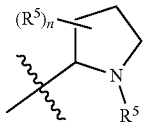 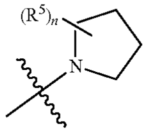

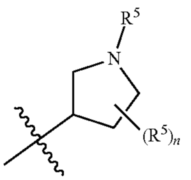 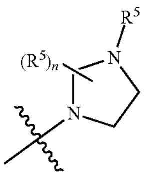

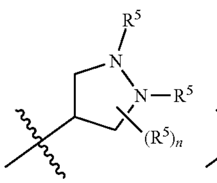 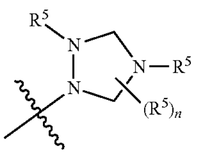

-continued

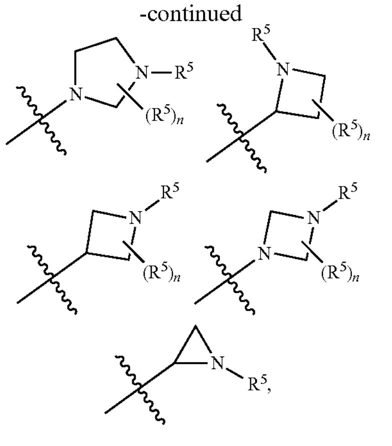

wherein n is an integer between 0 and 10.

In some embodiments, the compound of Formula (III) is a compound of Formula (III-n):

(III-n)

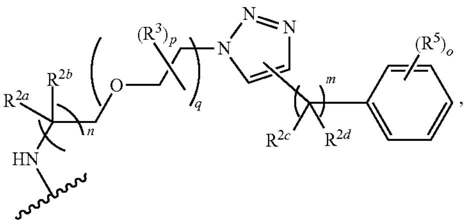

or a salt thereof, wherein each of $R^{2a}$, $R^{2b}$, $R^{2c}$ and $R^{2d}$ is independently hydrogen, alkyl, heteroalkyl, halo; or $R^{2a}$ and $R^{2b}$ or $R^{2c}$ and $R^{2d}$ are taken together to form an oxo group; each $R^3$ is independently alkyl, heteroalkyl, halogen, cyano, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$ or $SR^{E1}$; each $R^5$ is independently alkyl, heteroalkyl, halogen, cyano, —$OR^{A1}$, —$C(O)OR^{A1}$, —$C(O)R^{B1}$, —$N(R^{C1})(R^{D1})$, —$N(R^{C1})C(O)R^{B1}$, —$C(O)N(R^{C1})$, or $SR^{E1}$; each $R^{A1}$, $R^{B1}$, $R^{C1}$, $R^{D1}$, and $R^{E1}$ is independently hydrogen, alkyl, or heteroalkyl; m, n, and o are each independently 0, 1, 2, 3, 4, 5, or 6; p is 0, 1, 2, 3, 4, or 5; q is an integer from 0 to 25; and “ ” refers to a connection to a device or material (e.g., a device or material described herein).

In some embodiments, the compound of Formula (III) is a compound of Formula (III-o):

(III-o)

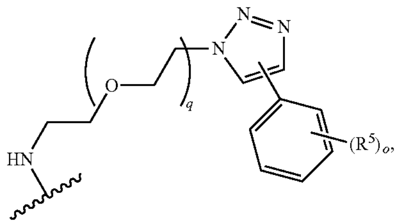

or a salt thereof, wherein each $R^5$ is independently alkyl, heteroalkyl, halogen, cyano, —$OR^{A1}$, —$C(O)OR^{A1}$, —$C(O)R^{B1}$, —$N(R^{C1})(R^{D1})$, —$N(R^{C1})C(O)R^{B1}$, —$C(O)N(R^{C1})$, or $SR^{E1}$; each $R^{A1}$, $R^{B1}$, $R^{C1}$, $R^{D1}$, and $R^{E1}$ is independently hydrogen, alkyl, or heteroalkyl; o is 0, 1, 2, 3, 4, 5, or 6; q is an integer from 0 to 25; and “ ” refers to a connection to a device or material (e.g., a device or material described herein).

In some embodiments, the compound of Formula (III) is a compound of Formula (III-p):

Formula (III-p)

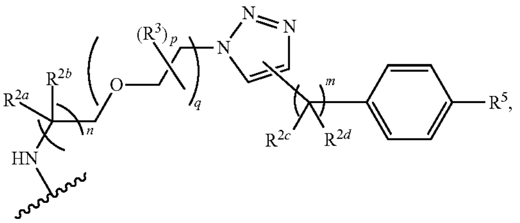

or a salt thereof, wherein each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each $R^3$ is independently alkyl, heteroalkyl, halogen, cyano, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; $R^5$ is alkyl, halogen, —$N(R^{C1})(R^{D1})$, —$N(R^{C1})C(O)R^{B1}$, —$C(O)N(R^{C1})$, or $SR^{E1}$; each $R^{A1}$, $R^{B1}$, $R^{C1}$, $R^{D1}$, and $R^{E1}$ is independently hydrogen, alkyl, or heteroalkyl; m and n are each independently 0, 1, 2, 3, 4, 5, or 6; p is 0, 1, 2, 3, or 4; q is an integer from 0 to 25; and “ ” refers to a connection to a device or material (e.g., a device or material described herein).

In some embodiments, the compound of Formula (III) is a compound of Formula (III-q):

Formula (III-q)

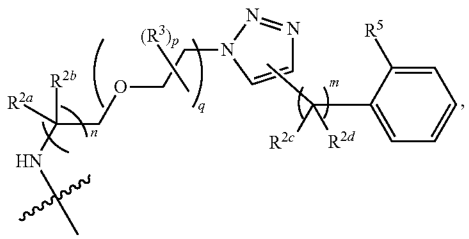

or a salt thereof, wherein each of $R^{2a}$, $R^{2b}$, $R^{2c}$, and $R^{2d}$ is independently hydrogen, alkyl, heteroalkyl, or halo, or $R^{2a}$ and $R^{2b}$ or $R^{2c}$ and $R^{2d}$ are taken together to form an oxo group; each $R^3$ is independently alkyl, heteroalkyl, halogen, cyano, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; $R^5$ is alkyl, heteroalkyl, halogen, cyano, —$OR^{A1}$, —$C(O)OR^{A1}$, or —$C(O)R^{B1}$; each $R^{A1}$, $R^{B1}$, $R^{C1}$, $R^{D1}$, and $R^{E1}$ is independently hydrogen, alkyl, or heteroalkyl; m and n are each independently 0, 1, 2, 3, 4, 5, or 6; p is 0, 1, 2, 3, or 4; q is an integer from 0 to 25; and “ ” refers to a connection to a device or material (e.g., a device or material described herein).

In some embodiments, the compound of Formula (III) is a compound of Formula (III-r):

Formula (III-r)

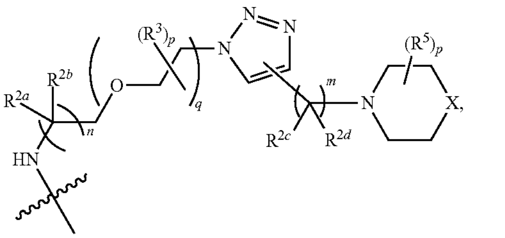

or a salt thereof, wherein X is C(R')(R"), N(R'), or $S(O)_x$; each of R' and R" is independently hydrogen, alkyl, halogen, or cycloalkyl; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each $R^3$ is independently alkyl, heteroalkyl, halogen, cyano, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; each $R^5$ is independently alkyl, heteroalkyl, halogen, cyano, —$OR^{A1}$, —$C(O)OR^{A1}$, —$C(O)R^{B1}$, —$N(R^{C1})(R^{D1})$, —$N(R^{C1})C(O)R^{B1}$, —$C(O)N(R^{C1})$, or $SR^{E1}$; each $R^{A1}$, $R^{B1}$, $R^{C1}$, $R^{D1}$, and $R^{E1}$ is independently hydrogen, alkyl, or heteroalkyl; m and n are each independently 0, 1, 2, 3, 4, 5, or 6; p is 0, 1, 2, 3, 4, or 5; q is an integer from 0 to 25; x is 0, 1, or 2; and "~" refers to a connection to a device or material (e.g., a device or material described herein).

In some embodiments, X is N(R'), e.g., and R' is hydrogen or alkyl. In some embodiments, X is $S(O)_x$, e.g., and x is 0, 1, or 2. In some embodiments, X is not $S(O)_2$.

In some embodiments, the compound of Formula (III) is a compound of Formula (III-s).

Formula (III-s)

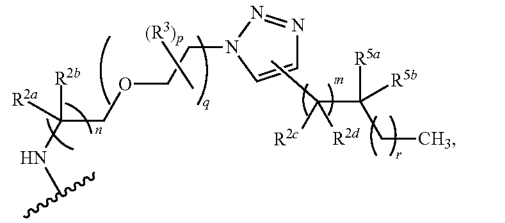

or a salt thereof, wherein each of $R^{2a}$, $R^{2b}$, $R^{2c}$, and $R^{2d}$ is independently hydrogen, alkyl, heteroalkyl, halo, cyano, nitro, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, or —$C(O)N(R^{C1})$; or $R^{2a}$ and $R^{2b}$ or $R^{2c}$ and $R^{2d}$ are taken together to form an oxo group; each $R^3$ is independently alkyl, heteroalkyl, halogen, cyano, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; each of $R^{5a}$ and 5b is independently alkyl, heteroalkyl, halogen, cyano, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, or $SR^{E1}$; each $R^{A1}$, $R^{B1}$, $R^{C1}$, $R^{D1}$, and $R^{E1}$ is independently hydrogen, alkyl, or heteroalkyl; m and n are each independently 0, 1, 2, 3, 4, 5, or 6; p is 0, 1, 2, 3, or 4; q is an integer from 0 to 25; r is an integer between 0 and 10; and "~" refers to a connection to an attachment group (e.g., an attachment group described herein) or a device material (e.g., a device or material described herein).

In some embodiments, the compound of Formula (I) or Formula (III) (e.g., a compound of Formulas (III-a), (III-b), (III-c), (III-d), (III-e), (III-f), (III-g), (III-g-2), (III-h), (III-i), (III-i-2), (III-j), (III-k), (III-l), (III-m), (III-n), (III-o), (III-p), (III-q), (III-r), or (II-s)) is selected from a compound depicted in any one of FIGS. 1-6 or a pharmaceutically acceptable salt thereof.

In some embodiments, the compound of Formula (I) or Formula (III) (e.g., a compound of Formulas (III-a), (III-b), (III-c), (III-d), (III-e), (III-f), (III-g), (III-g-2), (III-h), (III-i), (III-i-2), (III-j), (III-k), (III-l), (III-m), (III-n), (III-o), (III-p), (III-q), (III-r), or (II-s)) is not a compound disclosed in any of WO2012/112982, WO2012/167223, WO2014/153126, WO2016/187225, WO2016/019391, WO2017/075630, WO 2017/075631, and US 2016-0030359.

In some embodiments, the compound of Formula (I) or Formula (III) (e.g., a compound of Formulas (III-a), (III-b), (III-c), (III-d), (III-e), (III-f), (III-g), (III-g-2), (III-h), (III-i), (III-i-2), (III-j), (III-k), (III-l), (III-m), (III-n), (III-o), (III-p), (III-q), (III-r), or (II-s)) is not a compound selected from the following:

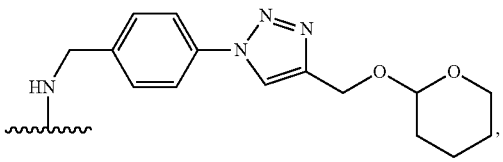

,

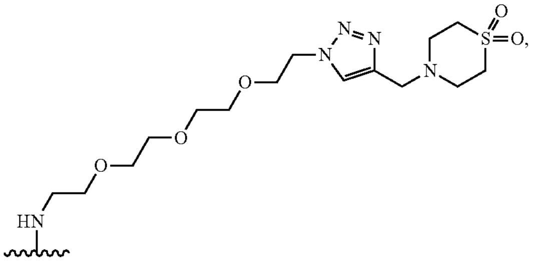

and

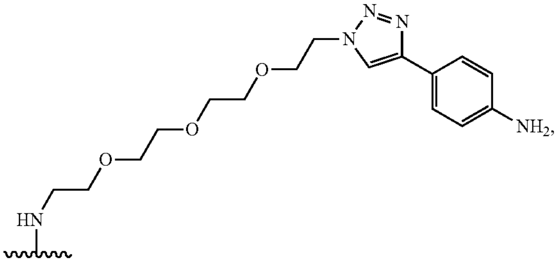

or a salt thereof.

In some embodiments, the compound of Formula (I) or Formula (III) (e.g., a compound of Formulas (III-a), (III-b), (III-c), (III-d), (III-e), (III-f), (III-g), (III-g-2), (III-h), (III-compound selected from the following:

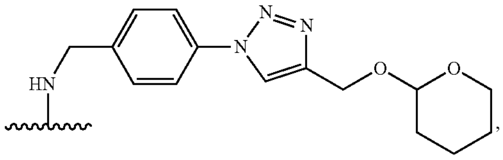

,

-continued

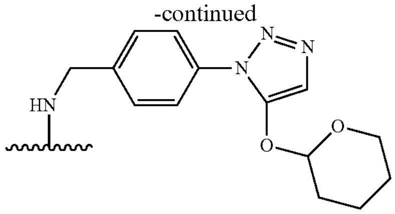

,

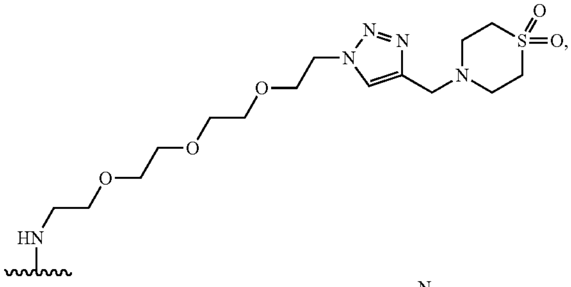

,

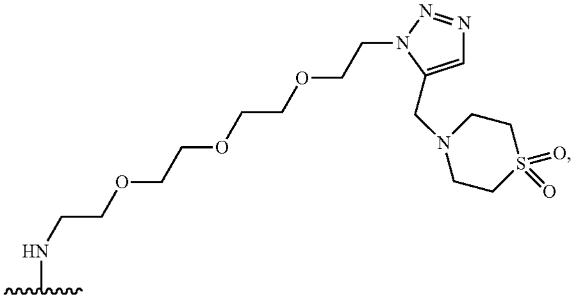

,

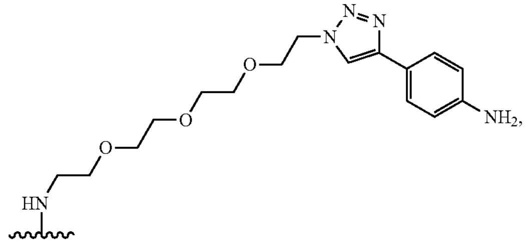

, and

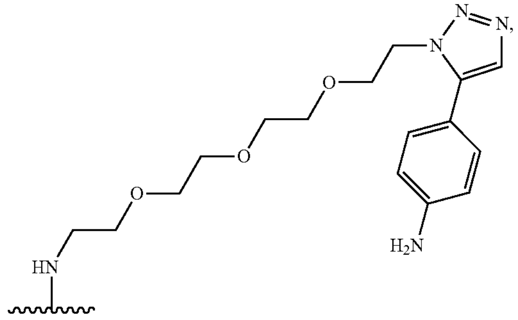

or a salt thereof.

In some embodiments, the compound of Formula (I) or Formula (III) (e.g., a compound of Formulas (III-a), (III-b), (III-c), (III-d), (III-e), (III-f), (III-g), (III-g-2), (III-h), (III-i), (III-i-2), (III-j), (III-k), (III-l), (III-m), (III-n), (III-o), (III-p), (III-q), (III-r), or (II-s)) is not bound to a polymer selected from alginate, carboxypolystyrene, polystyrene, glass, PDMS, or silicone.

Attachment Groups

The compounds, materials, and devices described herein may be connected through any attachment chemistry known in the art. A listing of exemplary attachment chemistries is outlined in *Bioconjugate Techniques* ($3^{rd}$ ed, Greg T. Hermanson, Waltham, MA: Elsevier, Inc, 2013), which is incorporated herein by reference in its entirety.

In some embodiments, a compound described herein (e.g., a compound of Formula (I) as described herein) is linked to a material or device through an amine. Amine linkages may be generated through an isothiocyanate, an isocyanate, an acyl azide, an NHS ester, a sulfonyl chloride, a tosylate ester, an aldehyde, a glyoxal, an epoxide, an oxirane, a carbonate, an arylating agent, an imidoester, a carbodiimide, an anhydride, a fluorophenyl ester, a hydromethyl phosphine derivative, via guanidination, or any derivative thereof, e.g., as described on pages 229-240 of *Bioconjugate Techniques* (Id).

In some embodiments, a compound described herein (e.g., a compound of Formula (I) as described herein) is linked to a material or device through a thiol. Exemplary thiol linkages may be prepared using a haloacetyl, an alkyl halide derivative, a maleimide, an aziridine, an acryloyl, an arylating agent, a thiol-disulfide exchange reagent, a vinyl sulfone reagent, a metal-thiol dative bond, native chemical ligation, metal modification (e.g., via cisplatin), or any derivative thereof, as described on pages 240-246 of *Bioconjugate Techniques* (Id).

In some embodiments, a compound described herein (e.g., a compound of Formula (I) as described herein) is linked to a material or device through a carboxylate. Exemplary carboxylate linkages may be prepared using a diazoalkane, a diazoacetyl, N,N'-carbonyl diimidazole, a carbodiimide, or any derivative thereof, as described on pages 246-248 of *Bioconjugate Techniques* (Id).

In some embodiments, a compound described herein (e.g., a compound of Formula (I) as described herein) is linked to a material or device through a hydroxyl group. Linkages generated through a hydroxyl group may be prepared via an epoxide, oxirane, N,N'-carbonyl diimidazole, N,N'-disuccinimidyl carbonate, N-hydroxysuccinimidyl chloroformate, periodate oxidation, enzymatic oxidation, an alkyl halogen, an isocyanate, or any derivative thereof, e.g., as described on pages 248-250 of *Bioconjugate Techniques* (Id).

In some embodiments, a compound described herein (e.g., a compound of Formula (I) as described herein) is linked to a material or device through an aldehyde or ketone. Exemplary linkages though an aldehyde or ketone may be generated via a hydrazine, a hydrazide, Schiff base formation, reductive amination, an aminooxy derivative, Mannich condensation, or any derivative thereof, e.g., as described on pages 251-252 of *Bioconjugate Techniques* (Id).

In some embodiments, a compound described herein (e.g., a compound of Formula (I) as described herein) is linked to a material or device through an active hydrogen reaction. Examples of such linkages may be generated through a diazonium derivative, Mannich condensation, iodination reactions, or any derivative thereof, e.g., as described on pages 252-253 of *Bioconjugate Techniques* (Id).

In some embodiments, a compound described herein (e.g., a compound of Formula (I) as described herein) is linked to a material or device through a photochemical reaction. Examples of such linkages may be generated through an aryl azide, halogenated aryl azide, benzophenone, anthraquinone, a diazo compound, diazo derivative, psoralen derivative, or any derivative thereof, e.g., as described on pages 253-256 of *Bioconjugate Techniques* (Id).

In some embodiments, a compound described herein (e.g., a compound of Formula (I) as described herein) is linked to a material or device through a cycloaddition reaction. Examples of such linkages may be generated through a Diels-Alder reaction, boronic acid derivative, click chemistry (e.g., Cu-promoted azide-alkyne [3+2] cycloaddition), or any derivative thereof, e.g., as described on pages 257-258 of *Bioconjugate Techniques* (Id).

In some embodiments, a compound described herein (e.g., a compound of Formula (I) as described herein) is linked to a material or device through the use of a cross-linker. Exemplary cross-linkers include zero-length cross-linkers, homobifunctional cross-linker, heterobifunctional cross-linkers, and trifunctional cross-linkers, e.g., as described on pages 259-339 of *Bioconjugate Techniques* (Id). In some embodiments, the cross-linker is a zero-length cross linker (e.g., carbodiimides (e.g., EDC, CMC, DCC, or DIC), Woodward's reagent K, N,N'carbonyl diimidazole, a Schiff base, or a derivative thereof). In some embodiments, the cross-linker is a homobifunctional cross-linker (e.g., a cross-linker comprising an NHS ester (e.g., DSP, DTSSP, DSS, $BS^3$, DST, sulfo-DST, BSOCOES, sulfo-BSOCOES, EGS, sulfo-EGS, DSG, or DSC), an imidoester (DMA, DMP, DMS, DTBP), a sulfhydryl reactive group (e.g., DPDPB, BMH), a difluorobenzene derivative (e.g., DFDNB, DFDNPS), a photoreactive group (e.g., BASED), an aldehyde (e.g., formaldehyde, glutaraldehyde), a bis-epoxide (1,4-butanediol diglycidyl ester), a hydrazide (e.g., adipic acid dihydrazide), a bis-diazonium, or a bis-alkylhalide), a bis-diazonium derivative (e.g., o-tolidine diazotized, bis-diazotized benzidine), a bis-alkylhalide, or a derivative thereof). In some embodiments, the cross-linker is a heterobifunctional cross-linker (e.g., amine-reactive and sulfhydryl-reactive cross-linkers (e.g., SPDP, LC-SPDP, suldo-LC-SPDP, SMPT, sulfo-LC-SMPT, SMCC, sulfo-SMCC, MBS, sulfo-MBS, SIAB, sulfo-SIAB, SMPB, sulfo-SMPB, GMBS, sulfo-GMBS, SBAP, SIA), carbonyl reactive and sulfhydryl reactive cross-linkers (e.g., MPBH, $M_2C_2H$, PDPH), amine reactive and photoreactive cross-linkers (e.g., NHS-ASA, sulfo-NHS-ASA, sulfo-NHS-LC-ASA, SASD, HSAB, sulfo-HSAB, SANPAH, sulfo-SANPAH, ANB-NOS, SAND, SADP, sulfo-SADP, sulfo-SAPB, SAED, sulfo-SAMCA, p-nitrophenyl diazopyruvate, PNP-DTP), sulfhydryl reactive and photoreactive cross-linkers (e.g., ASIB, APDP, benzophenone-4-iodoacetamide, benzophenone-4-maleimide), carbonyl-reactive and photoreactive cross-linkers (e.g., ABH), carboxylate-reactive and photoreactive cross-linkers (e.g., ASBA), arginine-reactive and photoreactive cross-linkers (e.g., APG), or a derivative thereof. In some embodiments, the cross-linker is a trifunctional cross-linker (e.g., 4-azido-2-nitrophenylbiocytin-4-nitrophenyl ester, sulfo-SBED, MTS-ATF-biotin, MTS-ATF-LC-biotin, a hydroxymethyl phosphine derivative, or tricepts reagent).

In some embodiments, a compound described herein (e.g., a compound of Formula (I) as described herein) is linked to a material or device through the use of a dendrimer or dendron. Exemplary dendrimers and dendrons include an amine-containing dendrimer, a dendrimer-chelate derivative, a dendrimer fluorescent quantum dot, or a derivative thereof, e.g., as described on pages 351-384 of *Bioconjugate Techniques* (Id).

In some embodiments, a compound described herein (e.g., a compound of Formula (I) as described herein) is linked to a material or device through the use of a cross-bridge or cleavable reagent system. Exemplary cross-bridges and cleavable reagent systems include a disulfide, an periodate-cleavable glycol, a dithionite-cleavable bond, a hydroxylamine-cleavable ester, a base labile sulfone, an acyl hydrazine-cleavable linker, a photocleavable linker, or a derivative thereof, e.g., as described on pages 387-392 of *Bioconjugate Techniques* (Id).

In some embodiments, a compound described herein (e.g., a compound of Formula (I) as described herein) is linked to a material or device through the use of a fluorescent probe, a streptavidin-biotin system, an avidin-biotin system, an isotope label, a silane, a microparticle, a nanoparticle, a chromatography support, a buckyball, a fullerene, a carbon nanotube, a biorthogonal reagent, a polyethylene glycol (e.g., or other synthetic polymer modification), a vaccine, an immunogen, an antibody, a liposome, an enzyme, a nucleic acid, an oligonucleotide, or a protein-protein interaction, or a derivative thereof, e.g., as described on pages 395-1014 of *Bioconjugate Techniques* (Id).

Additional examples of linkage chemistries envisaged by the present invention are described within Veiseh et al (2010) *Adv Drug Deliv Rev* 62:284-304; the entire contents of which is incorporated herein by reference.

Devices and Materials

In some aspects of the present invention, a compound (e.g., a compound of Formula (I)), or a composition comprising the same is entirely or partially disposed within an implantable element. The implantable element may comprise an enclosing element that encapsulates or coats a cell, in part or in whole. In an embodiment, an implantable element comprises an enclosing component that is formed, or could be formed, in situ on or surrounding a cell, e.g., a plurality of cells, e.g., a cluster of cells, or on a microcarrier, e.g., a bead, or a matrix comprising a cell or cells (referred to herein as an "in-situ encapsulated implantable element"). In an embodiment, an implantable element comprises an enclosing component that is preformed prior to combination with the enclosed cell, e.g., a plurality of cells, e.g., a cluster of cells, or a microcarrier, e.g., a bead or a matrix comprising a cell (referred to herein as device-based-implantable element, or DB-implantable element).

The implantable elements described herein include devices or materials, for example, devices or materials associated with a compound described herein (e.g., a compound of Formula (I)). In some embodiments, a device or material may be associated with a compound described in FIGS. 1A-6KK, or a pharmaceutically acceptable salt thereof. In some embodiments, a device or material may be covalently attached to a compound described in FIGS. 1A-6KK, or a pharmaceutically acceptable salt thereof, e.g., through an attachment group (e.g., an attachment group described herein). Any of the devices or materials described herein may be associated with any of the compounds described herein (e.g., a compound of Formula (I), or a compound described in FIGS. 1A-6KK).

Devices included herein include devices that are configured with a lumen, e.g., a lumen having one, two or more openings, e.g., tubular devices. A typical stent is an example of a device configured with a lumen and having two openings. Other examples include shunts.

Devices included herein include flexible devices, e.g., devices that are configured to conform to the shape of the body.

Devices included herein include devices comprising an element that stabilizes the location of the device, e.g., an adhesive, or fastener, e.g., a torque-based or friction based fastener, e.g., a screw or a pin.

Devices included herein include devices configured to monitor a substance, e.g., an exogenous substance, e.g., a therapeutic agent or toxin, or an endogenous body product, e.g., insulin. Such devices include diagnostic devices.

Devices included herein include devices configured to release a substance, e.g., an exogenous substance, e.g., a therapeutic agent. In some embodiments, the therapeutic agent is a compound described herein (e.g., a compound of Formula (I)) or a pharmaceutically acceptable salt thereof. In some embodiments, the therapeutic agent is a biological material. In some embodiments, the therapeutic agent is a cell, cell product, tissue, tissue product, protein, hormone, enzyme, antibody, antibody fragment, antigen, epitope, drug, vaccine, or any derivative thereof.

Devices herein include articulable devices that are configured to change conformation in response to a signal or movement of the body, e.g., an artificial joint, e.g., a knee, hip, or other artificial joint.

Exemplary devices of the present invention are outlined in greater detail below.

Stents

Devices included herein include stents or other devices that are configured to be placed partially or entirely in a lumen of the body. A vascular stent is a stent configured for disposition entirely, or partially, within a lumen of the vasculature, e.g., a coronary, urinary, biliary, venous, or coronary stent. Stents can be configured to have other properties, e.g., to be expandable, or to release or elute a substance, e.g., a therapeutic agent. Stents can be configured so as to affect the shape of adjacent tissue, e.g., to keep a passage open. Typically a stent can be made of metal, plastic, or a material described herein. Stents can be configured for use in coronary heart disease, carotid artery disease, high blood pressure, peripheral arterial disease, aneurysm, stroke, atherosclerosis, an aged subject (e.g., at least 60 years of age), or a subject undergoing coronary angioplasty. Exemplary stents include: coronary, aortic, drug-eluting, intracranial, pancreatic, carotid, iliac, renal, femoral, ureteral, bladder fetal, duodenal, biliary shunts. Shunts can comprise stainless steel, gold, titanium, cobalt-chromium alloy, tantalum alloy, nitinol, silicone, polyurethane, polyesters, polyorthoesters, polyanhydrides, or collagen.

Shunts

Devices included herein include shunts or other devices that are configured to connect to connect, and typically provide fluid connection with, a first part of the body, e.g., a first organ, and a second part of the body, or the exterior. A stunt can be configured to be permanent or temporary. Typically a shunt can be made of metal, plastic, or a material described herein. Shunts can be configured to have other properties, e.g., to be expandable, or to release or elute a substance, e.g., a therapeutic agent. Shunts can be configured for use in the eye, e.g., a glaucoma shunt, the CNS, e.g., the brain or spinal column, a cavity, e.g., the peritoneal cavity, or an organ. Shunts can be configured for use in the treatment of coronary heart disease, carotid artery disease, high blood pressure, peripheral arterial disease, aneurysm, stroke, atherosclerosis, or to treat a subject (e.g., at least 60 years of age), or a subject undergoing coronary angioplasty. Exemplary shunts include: peritoneal, endolymphatic, intracranial, and tympanostomy shunts.

Dressing

Devices included herein include dressings, e.g., bandages, or other devices that are configured to place a surface of the dressing in contact with a site on the body, e.g., a wound, e.g., a traumatic wound or surgical wound. Dressings can be configured for internal use, e.g., on the surface of an organ or cavity, or external use, e.g., on the skin. A dressing can be configured to be permanent or temporary. Typically a dressing can be made of metal, plastic, or a material described herein. Dressings can be configured to have any of a variety of properties, e.g., to promote healing, to promote coagulation, to release or elute a substance, e.g., a therapeutic agent. Dressings can be configured of flexible material, to promote contact with or adherence to a site on the body. In embodiments a dressing includes an element configured for contact with the site, e.g., a porous element, and an element configured to stabilize the position of the dressing, for example, an adhesive element.

Scaffoldings

Devices included herein include scaffoldings (also termed "scaffolds") that are configured to allow invasion of the device by tissue of the body. Scaffoldings can be configured as meshes, networks, or as porous. Typically a scaffolding will comprise an element or elements that provide dimensional stability. Scaffoldings can be configured to be permanent or temporary. Typically a scaffolding can be made of metal, plastic, or a material described herein. Scaffoldings can be configured to have any of a variety of properties, e.g., to promote growth, or growth or regeneration is a desired direction, or to release or elute a substance, e.g., a therapeutic agent. Scaffoldings can be configured of flexible material or nonflexible material. Scaffoldings include bone scaffoldings, for the promotion of growth of bone or surrounding tissues, e.g., configured for use in breaks, fractures, osteoporosis, or joint replacement.

Cochlear Implants

Devices included herein include cochlear implants. Cochlear implants can be configured to have any of a variety of properties, e.g., to promote growth or to release or elute a substance, e.g., a therapeutic agent.

Ocular Devices

Devices included herein include ocular devices that are configured for placement on the eye, in the eye, or in or on the tissues surrounding the eye. Such devices include eye mountable devices, e.g., contact lenses. Such devices also include intraocular devices, including intraocular lenses, e.g., phasic intraocular lenses, implantable lens (e.g., made of polymers), e.g., for cataract treatment/surgery, shunts, e.g., glaucoma shunts, or devices for the release of a substance, e.g., a therapeutic agent. Ocular devices can be configured to monitor a substance, e.g., a therapeutic agent or a bodily component, e.g., a biomarker, e.g., in tears. Ocular devices can be configured to be permanent or temporary. Typically an ocular device can be made of metal, plastic, or a material described herein. Ocular devices can be configured to release or elute a substance, e.g., a therapeutic agent.\

Articulable Devices

Devices herein include articulable devices that are configured to change conformation in response to a signal or movement of the body, e.g., an artificial joint, e.g., a knee, hip, or other artificial joint. Typically an articulable device will comprise an element or elements that provide dimensional stability. Typically an articulable device can be made of metal, plastic, or a material described herein. Articulable devices can be configured to have any of a variety of properties, e.g., to promote growth, or growth or regeneration is a desired direction, or to release or elute a substance, e.g., a therapeutic agent.

Soft Tissue Prosthetic Devices

Devices included herein include soft tissue prosthetic devices. Soft tissue prosthetic devices can be configured to have any of a variety of properties, e.g., to promote growth, or to release or elute a substance, e.g., a therapeutic agent.

Fasteners, e.g., Surgical Fasteners

Devices included herein include fasteners, e.g., surgical fasteners, e.g., flexible surgical fasteners, e.g., sutures, configured, e.g., to stabilize the position of a first part of the body with a second part of the body. Surgical fasteners also include non-flexible devices, e.g., staples. Surgical fasteners can be configured to be permanent or temporary. Surgical fasteners include ligature clips and tissue staples. Surgical fasteners can be configured to release or elute a substance, e.g., a therapeutic agent. Exemplary fasteners include fasteners for fixation of hard and soft tissue, cranioplasty plate, bone fixation, including staples and pins metallic and ceramics. Fasteners include those for fastening body portion can comprise bioabsorbable polymers, e.g., poly (p-dioxane), polylactide, polyglycolides, polycaprolactone, poly (orthoesters), trimethylene carbonate polymer, co-polymers and/or mixtures. Devices can be reinforced with fibers, e.g., of polymeric or ceramic materials. Exemplary sutures include: absorbable, non-absorbable, and recombinant. Sutures can comprise polyglycolic acid, poly (ethylene terephthalate), nitinol, stainless steel, silk, polyamide, polyester, polypropylene, poly(hydroxybutyrate), polydioxanone, or polytetrafluoroethylene.

Stabilization Devices

Devices included herein include stabilization devices, e.g., configured to hold a first part of the body immovable relative to a second part of the body, e.g., a pin, screw, plate, collar or cage. Such devices can be configured to stabilize a broken or fractured bone. Such devices can be made from metal, plastic or a material described herein.

Catheters

Devices included herein include catheters, e.g., balloon catheters, configured to promote opening of a lumen, typically a vascular lumen, e.g., a coronary vascular lumen. Catheters can be configured to be permanent or temporary. Typically a catheter can be made of metal, plastic, or a material described herein. Catheters can be configured to have any of a variety of properties, e.g., to promote healing, to be expandable, or to release or elute a substance, e.g., a therapeutic agent. Exemplary catheters include: hemodialysis, biliary, peritoneal, subclavian, suprapubic, ventricular, atrial, intravascular, subcutaneous catheters. They can comprise silicone rubber, nylon, polyurethane, polyethylene terephthalate (PET), latex, thermoplastic elastomers. Some catheters have a thin hydrophilic surface coating.

Ports

Devices included herein include ports or other devices that are configured to provide access to the body. A port can be configured to allow continuous, or intermittent connection to a reservoir containing a substance, e.g, a therapeutic agent. Ports can be configured to have other properties, e.g., to be closeable, or to release or elute a substance, e.g., a therapeutic agent. Ports can be configured so as to conform to the surface of the body. Typically a port can be made of metal, plastic, or a material described herein. Ports can be configured for use subjects having chronic illness or cancer.

Prostheses

Devices included herein include prostheses, e.g., an acetabular cup impaction plate, a prosthetic acetabular cup inserter or impactor, trapezometacarpal prosthesis, a spinal prose this, e.g., an intervertebral disc prosthesis. Prostheses can be configured to have other properties, e.g., to release or elute a substance, e.g., a therapeutic agent. Prostheses include those for the hip, ankle, breast, chin, mandibular, ear, elbow, esophageal, eye, keratoprosthesis, facial, finger, ligament, nose, penis, shoulder, testicle, tendon, toe, trachea, vascular, dental, or finger. They can comprise nylon, acrylics, polyester resins, polypropylene, polyethylene, polyurethane, silicone, fiber reinforcements (glass and carbon), aluminum, titanium, or steel.

Extracorporeal Devices

Devices included herein include extracorporeal devices, e.g., devices through which a tissue or fluid, e.g., blood or spinal fluid, is passed, including, e.g., renal dialysis device, port, and tubing, e.g., dialysis tubing. Extracorporeal devices can be configured to have other properties, e.g., to be closeable, or to release or elute a substance, e.g., a therapeutic agent.

Sensors

Devices included herein include those comprising a sensor. The sensor can sense or monitor a signal, e.g., chemical moiety, e.g., glucose, insulin, or a therapeutic agent, electromagnetic radiation, e.g., light, or electric current. The device can be configured to respond to the signal, e.g., by releasing a substance, e.g., a therapeutic agent. The device can be configured to respond to the signal, e.g., by producing a signal, which, e.g., can be received by a receiver, e.g., a receiver located inside or outside the body. The produced signal can be a chemical moiety, electromagnetic radiation, e.g., light, or electric current. Compounds described herein can minimize interference by immune responders, e.g., within the first 12, 24, 36, or 48 hours of implantation.

Orthopedic Devices and Implants

Devices included herein include orthopedic devices and implants, e.g., pins, rods, screws, and plates. Such devices can be configured for: bone replacement (e.g., hip, knee replacement), bone repair (e.g., repair of a fragmented bone, e.g., rib, vertebra, cranial bone, facial bone (e.g., nasal bone, maxillae, lacrimal bone, zygomatic bone, palatine bone, inferior nasal concha, vomer, mandible, hyoid bone), arm bone (e.g., clavicle, scapula, humerus, ulna, radius, carpal, metacarpal, phalange of hand), leg bone (e.g., hip bone, femur, patella (knee cap), tibia, fibula, foot bone, metatarsal, phalange of foot). The devices can be configured to have other properties, e.g., to be expandable, or to release or elute a substance, e.g., a therapeutic agent. The device can be made from of metal, plastic, or a material described herein. Also include are non-mechanical or non-rigid devices. Such devices include Synvisc-One® (hylan G-F 20), which is approved for treating pain in osteoarthritis (OA) of the knee (Hylan G-F 20 is an elastoviscous high molecular weight fluid comprising hylan A and hylan B polymers produced from chicken combs. Hylans are derivatives of hyaluronan (sodium hyaluronate). Hylan G-F 20 comprises hyaluronan that is chemically crosslinked.

Cosmetic or Reconstruction Surgical Devices

Devices included herein include cosmetic devices or devices used in reconstructive surgery, e.g., implants, e.g., breast implants, prostheses, e.g., nose prostheses, fillers, e.g., dermal fillers, (e.g., injectable dermal filler), e.g., comprising hyaluronic acid (HA), calcium hydroxyapatite (CaHA), poly-L-lactic acid, or polymethylmethacrylate (PMMA).

Encapsulated or Entrapped Cells or Tissues

Devices include encapsulated or entrapped cells or tissues, e.g., pancreatic islet cells or pancreatic tissue. The cells or tissue can be encapsulated or entrapped in a polymer.

Miscellaneous Implantable Devices

Devices included herein include, orthopedic fixation devices, dental implants, skin covering devices; dialysis media, and drug-delivery devices, and artificial or engineered organs, e.g., hearts. Other devices included herein include: silicon implants, drainage devices, e.g., bladder drainage devices, cell selection systems, adhesives, e.g., cement, clamp, clip, contraceptive devices, intrauterine devices, corneal implants, dermal implants, dental implants, ocular implants, intragastric implants, facial implants, penile implants, implants for control of incontinence, e.g., urine or fecal, defibrillators, dosimeters, electrodes, pumps, e.g., infusion pumps, filters, embolization devices, fastener, fillers, fixatives, grafts, hearing aids, cardio or heart-related devices, e.g., pacemakers and valves, batteries or power sources, hemostatic agents, incontinence devices, intervertebral body fusion devices, intraoral devices, lenses, meshes, needles, nervous system stimulators, patches, peritoneal access devices, plates, plugs, pressure monitoring devices, rings, transponders, hip implants, bone implants, or valves. Also included are devices used in one or more of: anesthesiology, cardiovascular, clinical chemistry, dental, ear, nose, throat, gastroenterology, urology, general hospital, hematology, immunology, microbiology, neurology, obstetrics/gynecology, ophthalmic, orthopedic, pathology, physical medicine, radiology, general or plastic surgery, and/or clinical toxicology. Devices include clips, e.g., anchor fascial, aneurysm, hemostatic, coronary artery bypass, ophthalmic tantalum, tubal occlusion, vascular, and marker radiographic clips. Clips can comprise titanium, titanium-aluminum alloy, or cobalt-chromium-nickel-molybdenum-iron alloy. Devices include defibrillators, which can comprise a battery, case, e.g., a titanium case, and flexible insulated wires or leads. Entire structures can be sealed in a polymeric envelope. Devices include implanted dosimeters, pressure monitoring devices, e.g., intra-abdominal, cranial and intra-aneurysm pressure monitoring devices. Devices include valves e.g., heart, pulmonary and ureterovesicle valves. Valves can comprise mechanical, synthetic and biological valves. Valves can be made of stainless steel, titanium, silicone, pyrolytic carbon. Polytetrafluoroethylene, polyethylene terephthalate, cow pericardium, or pig heart.

Devices include meshes, e.g., absorbable/non-absorbable, collagen, synthetic/non-synthetic meshes. Meshes can comprise: polyglycolic acid, polypropylene, polyethylene terephthalate, nonocryl (poliglecaprone 25), cellulose, macroporous polyester, poly-4-hydroxybutrate, polytetrafluoroethylene, biologics (human dermis, porcine dermis, porcine small intestine submucosa, bovine pericardium), or fibroin.

Devices for stimulation of the nervous system, e.g., the peripheral or central nervous system, e.g., the spinal-cord. Devices include the Medtronic Model 3998 Lead, or devices substantially similar in structure and or function. A lead can include polyurethane lead bodies joined to one silicone rubber paddle. A lead can have 2 parallel rows of 4 platinum iridium electrodes on the distal end. At the proximal end of each lead body are the lead contacts, which fit into a Medtronic in-line, four-conductor connector.

Devices include plates, e.g., for use with bone, e.g., cranioplasty or mandibular plates, made e.g., of titanium, titanium alloys, nitrogen stainless steel, or cobalt-chromium-tungsten-nickel alloy.

Devices include plugs, e.g., a plug, e.g., a biopsy plug, e.g., a lung biopsy plug, made e.g., of polyethylene glycol (PEG) hydrogel. Other plugs are configured for cerebrospinal fluid leakage (Dural), arteries (BioGlue), lung tissue (AeriSeal). Exemplary materials include polyethylene glycol ester and trilysine amine (Dural), bovine serum albumin and glutaraldehyde (BioGlue), or aminated polyvinyl alcohol and glutaraldehyde (AeriSeal).

Devices included herein include FDA class 1, 2, or 3 devices, e.g., devices that are unclassified or not classified, or classified as a humanitarian use device (HUD).

Non-Medical Devices

Devices included herein include non-medical devices. Such devices can be wearable or implantable. Such devices can be configured to work with a telecommunication device, e.g., a telephone or smartphone, contact lenses, devices that identify or transmit a signal correlated to the location of the subject, e.g., by GPS tracking, an RFI chip, devices for monitoring or optimizing body performance, e.g., implantable "Fitbit-type" device, e.g., that can provide information on one or more biomarkers, implantable device for military use, implantable devices for determining the health, or condition, of the subject, devices for tracking an animal, e.g., an agricultural animal, e.g., a horse, cow, pig or goat, a pet, e.g., dog, cat, etc, a wild animal, e.g., an endangered animal, or an implantable device to track a desired person (e.g., a prisoner).

Components of or Content of Devices

Devices included herein can contain, deliver or present a cellular component, e.g., a human cell, e.g., immune cell, e.g., T cell, NK cell, B cell, red blood cell; a tissue, an organ or artificial organ, or a cellular sensor.

Devices included herein can contain, an electronic component, e.g., a transmitter, receiver, transponder, microchip, power source, e.g., a battery (e.g., active device having its own power source).

Devices included herein can comprise a number of components or materials. Exemplary components or materials can be purely structural, therapeutic, or both. A device can comprise a biomolecule component, e.g., a carbohydrate, e.g., a polysaccharide, e.g., a marine polysaccharide, e.g., alginate, agar, agarose, carrageenans, cellulose and amylose, chitin and chitosan; cross-linked polysaccharides, e.g., cross-linked by diacrylates; or a polysaccharide or derivative/modification thereof described in, e.g., Laurienzo (2010), *Mar. Drugs.* 8.9:2435-65.

A device can include a protein or polypeptide, e.g an antibody, protein, enzyme, or growth factor. A device can include an active or inactive fragment of a protein or polypeptide. Enzymes include glucose oxidase (e.g., for glucose sensor), kinase, phosphatase, oxygenase, hydrogenase, reductase.

Devices can include a polymer (e.g., hydrogel, plastic) component. Exemplary polymers include polyethylene, polypropylene, polystyrene, polyester (e.g., PLA, PLG, or PGA, polyhydroxyalkanoates (PHAs), or other biosorbable plastic), polycarbonate, polyvinyl chloride (PVC), polyethersulfone (PES), polyacrylate (e.g., acrylic or PMMA), hydrogel (e.g., acrylic polymer or blend of acrylic and silicone polymers), polysulfone, polyetheretherketone, thermoplastic elastomers (TPE or TPU), thermoset elastomer (e.g., silicone (e.g., silicone elastomer)), poly-p-xylylene (Parylene), fluoropolymers (e.g., PTFE), and polyacrylics such as poly(acrylic acid) and/or poly(acrylamide), or mixtures thereof.

Exemplary polyethylenes include: ultra-low-density polyethylene (ULDPE) (e.g., with polymers with densities ranging from 0.890 to 0.905 $g/cm^3$, containing comonomer); very-low-density polyethylene (VLDPE) (e.g., with polymers with densities ranging from 0.905 to 0.915 $g/cm^3$, containing comonomer); linear low-density polyethylene (LLDPE) (e.g., with polymers with densities ranging from 0.915 to 0.935 $g/cm^3$, contains comonomer); low-density polyethylene (LDPE) (e.g., with polymers with densities ranging from about 0.915 to 0.935 $g/m^3$); Medium density polyethylene (MDPE) (e.g., with polymers with densities ranging from 0.926 to 0.940 $g/cm^3$, may or may not contain comonomer); high-density polyethylene (HDPE) (e.g., with polymers with densities ranging from 0.940 to 0.970 $g/cm^3$, may or may not contain comonomer).

Exemplary polypropylenes include: homopolymers, random copolymers (homophasic copolymers), and impact copolymers (heterophasic copolymers), e.g., as described in McKeen, *Handbook of Polymer Applications in Medicine and Medical Devices,* 3—Plastics Used in Medical Devices, (2014):21-53, which is incorporated herein by reference in its entirety.

Exemplary polystyrenes include: general purpose or crystal (PS or GPPS), high impact (HIPS), and syndiotactic (SPS).

Exemplary TPEs include: (i) TPA—polyamide TPE, comprising a block copolymer of alternating hard and soft segments with amide chemical linkages in the hard blocks and ether and/or ester linkages in the soft blocks; (ii) TPC—copolyester TPE, consisting of a block copolymer of alternating hard segments and soft segments, the chemical linkages in the main chain being ester and/or ether; (iii) TPO—olefinic TPE, consisting of a blend of a polyolefin and a conventional rubber, the rubber phase in the blend having little or no cross-linking; (iv) TPS—styrenic TPE, consisting of at least a triblock copolymer of styrene and a specific diene, where the two end blocks (hard blocks) are polystyrene and the internal block (soft block or blocks) is a polydiene or hydrogenated polydiene; (v) TPU-urethane TPE, consisting of a block copolymer of alternating hard and soft segments with urethane chemical linkages in the hard blocks and ether, ester or carbonate linkages or mixtures of them in the soft blocks; (vi) TPV—thermoplastic rubber vulcanizate consisting of a blend of a thermoplastic material and a conventional rubber in which the rubber has been cross-linked by the process of dynamic vulcanization during the blending and mixing step; and (vii) TPZ—unclassified TPE comprising any composition or structure other than those grouped in TPA, TPC, TPO, TPS, TPU, and TPV.

Devices can include linear, branched, or cross-linked polymers or polymers of selected molecular weight ranges, degree of polymerization, viscosity or melt flow rate. Branched polymers can include one or more of the following types: star polymers, comb polymers, brush polymers, dendronized polymers, ladders, and dendrimers. Linear polymers can include but are not limited to: polyethylene, polyvinyl chloride (PVC), Nylon 66, and polymethyl methacrylate (PMMA). Thermoresponsive polymers, e.g., gel (e.g., becomes a solid or liquid upon exposure to heat or a certain temperature) can also be used. Photocrosslinkable polymers, e.g., gel (e.g., becomes a solid upon photocrosslinking) can also be used.

Devices can include a polymeric component or material such as those described by ASTM International (e.g., in F451-08, F602-09(2015), F624-09(2015)e1, F639-09 (2015), F641-09(2014), F648-14, F665-09(2015), F702-10, F754-08(2015), F755-99(2011), F997-10, F1855-00(2011), F1925-09, F2026-16, F2038-00(2011), F2042-00(2011), F2313-10, F2565-13, F2579-10, F2695-12, F2759-11, F2820-12, F2848-16, F2902-12, F3087-15).

Devices can include a component or material for plastic and reconstructive surgery such as those described by ASTM International (e.g., in F881-94(2014), F1441-03 (2014), and F2051-00(2014)).

Devices can comprise non organic or metal components or materials, e.g., steel (e.g., stainless steel), titanium, other metal or alloy. Devices can include nonmetal components or materials, e.g., ceramic, or hydroxyapatite elements.

Devices can include components or materials that are made of a conductive material (e.g., gold, platinum, palladium, titanium, copper, aluminum, silver, metals, any combinations of these, etc.).

Devices can include a metallurgical component or metallurgical material such as those described by ASTM International (e.g., in F67-13, F75-12, F86-13, F90-14, F136-13, F138-13a, F139-12, F560-13e1, F562-13, F601-13, F620-11(2015), F621-12, F629-15, F688-14, F799-11, F899-12b, F961-14, F1058-08, F1091-12, F1108-14, F1295-11, F1314-13ae1, F1350-15, F1377-13, F1472-14, F1537-11, F1580-12, F1586-13e1, F1713-08(2013), F1813-13, F2005-05(2015), F2063-12, F2066-13e1, F2146-13, F2181-14, F2229-12, F2257-14, F2834-10(2016), F2527-16, F2581-12, F2633-13, F2885-11, F2886-10, F2895-15, F2989-13, F3046-13, or F3160-16).

Devices can include more than one component, e.g., more than one component disclosed herein, e.g., more than one of a metal, plastic, ceramic, composite, or hybrid material.

In metal-containing devices the amount of metal (e.g., by % weight, actual weight) can be: at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In plastic-containing devices the amount of plastic (e.g., by % weight, actual weight) can be: at least 5%, e.g., at least 5%, 10%, 20%, 30%, 40%, 50%, 60%, 70%, 80%, 90%, 95%, 99%, or more, w/w; or less than 20%, e.g., less than 20%, 15%, 10%, 5%, 1%, 0.5%, 0.1%, or less.

In ceramic-containing devices the amount of ceramic (e.g., by % weight, actual weight) can be: at least 5%, e.g., at least 5%, 10%, 20%, 30%, 40%, 50%, 60%, 70%, 80%, 90%, 95%, 99%, or more, w/w; or less than 20%, e.g., less than 20%, 15%, 10%, 5%, 1%, 0.5%, 0.1%, or less.

Features of Devices

Components or materials used in a device (or the entire device) can be optimized for one or more of: biocompatibility, e.g., it minimizes immune rejection or fibrosis; heat-resistance; elasticity; tensile strength; chemical resistance (e.g., resistance to oils, greases, disinfectants, bleaches, processing aids, or other chemicals used in the production, use, cleaning, sterilizing and disinfecting of the device); electrical properties; surface and volume conductivity or resistivity, dielectric strength; comparative tracking index; mechanical properties; shelf life, long term durability sterilization capability (e.g., capable of withstanding sterilization processes, such as steam, dry heat, ethylene oxide (EtO), electron beam, and/or gamma radiation, e.g., while maintaining the properties for the intended use of the device), e.g., thermal resistance to autoclave/steam conditions, hydrolytic stability for steam sterilization, chemical resistance to EtO, resistance to high-energy radiation (e.g., electron beam, UV, and gamma); or crystal structure.

A device can be assembled in vivo (e.g., injectable substance that forms a structured shape in vivo, e.g., at body temperature) or ex vivo.

A device can have nanodimensions, e.g., can comprise a nanoparticle, e.g., nanoparticle made of a polymer described herein, e.g., PLA. Nanoparticles can be chemically modified nanoparticles, e.g., modified to prevent uptake by macrophages and Kupfer cells (e.g., a process called opsonization); or to alter the circulation half-life of the nanoparticle. Nanoparticles can include iron nanoparticle (injectable) (e.g., Advanced Magnetics iron nanoparticles). Exemplary nanoparticles are described in Veiseh et al (2010) *Adv Drug Deliv Rev* 62:284-304, which is incorporated herein by reference in its entirety.

An device can be configured for implantation, or implanted, or disposed into the omentum of a subject, into the subcutaneous fat of a subject, intramuscularly in a subject. A device can be configured for implantation, or implanted, or disposed: on or in the skin; a mucosal surface, a body cavity, the peritoneal cavity; the CNS, e.g., the brain or spinal cord; an organ, e.g., the heart, liver, kidney, spleen, lung, lymphatic system, vasculature, the oral cavity, the nasal cavity, the teeth, the gums, the GI tract; bone; hip; fat tissue; muscle tissue; circulating blood; the eye (e.g., intraocular); breast, vagina; uterus, a joint, e.g., the knee or hip joint, or the spine.

A device can comprise an electrochemical sensor, e.g., an electrochemical sensor including a working electrode and a reference electrode. For example, an electrochemical sensor includes a working electrode and a reference electrode that reacts with an analyte to generate a sensor measurement related to a concentration of the analyte in a fluid to which the eye-mountable device is exposed. The device can comprise a window, e.g., of a transparent polymeric material having a concave surface and a convex surface a substrate, e.g., at least partially embedded in a transparent polymeric material A device can also comprise an electronics module including one or more of an antenna; and a controller electrically connected to the electrochemical sensor and the antenna, wherein the controller is configured to control the electrochemical sensor to obtain a sensor measurement related to a concentration of an analyte in a fluid to which the device, e.g., an the-mountable device is exposed and use the antenna to indicate the sensor measurement.

Devices may be used for varying periods of time including from a day or two, to more than 1, 2, 3, 4, or years. Devices can be configured for the duration of implantation, e.g., configured to resist fibrotic inactivation by fibrosis for all or part of the expected duration.

A device can be configured for limited exposure (e.g., less than 2 days, e.g., less than 2 days, 1 day, 24 hours, 20 hours, 16 hours, 12 hours, 10 hours, 8 hours, 6 hours, 5 hours, 4 hours, 3 hours, 2 hours, 1 hour or less).

A device can be configured for prolonged exposure (e.g., at least 2 days, 3 days, 4 days, 5 days, 6 days, 7 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more)

A device can be configured for permanent exposure (e.g., at least 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more).

A device may be coated with a compound described herein (e.g., a compound of Formula (I)) or a pharmaceutically acceptable salt thereof, or a material comprising a compound described herein (e.g., a compound of Formula (I)) or a pharmaceutically acceptable salt thereof. In an embodiment, the compound (e.g., the compound of Formula (I)) is disposed on a surface, e.g., an inner or outer surface, of the device. In an embodiment, the compound (e.g., the compound of Formula (I)) is distributed evenly across the surface. In an embodiment, the compound (e.g., the compound of Formula (I)) is distributed unevenly across the surface.

In some embodiments, a device is coated (e.g., covered, partially or in full), with a compound (e.g., the compound of Formula (I)) or a material comprising a compound (e.g., the compound of Formula (I)) or a pharmaceutically acceptable salt thereof. In some embodiments, a device is coated with a single layer of a compound (e.g., a compound of Formula (I)). In some embodiments, a device is coated with multiple layers of a compound (e.g., a compound of Formula (I)), e.g., at least 2 layers, 3 layers, 4 layers, 5 layers, 10 layers, 20 layers, 50 layers or more.

In an embodiment a first portion of the surface of the device comprises a compound (e.g., a compound of Formula (I)) that modulates, e.g., downregulates or upregulates, a biological function and a second portion of the device lacks the compound, or has substantially lower density of the compound.

In an embodiment a first portion of the surface of the device comprises a compound (e.g., a compound of Formula (I)) that modulates, e.g., down regulates, an immune response and a second portion of the surface comprises a second compound (e.g., a compound of Formula (I)), e.g., that upregulates the immune response, second portion of the device lacks the compound (e.g., the compound of Formula (I)), or has substantially lower density of the compound.

In some embodiments, a device is coated or chemically derivatized in a symmetrical manner with a compound (e.g., a compound of Formula (I)), or a material comprising a compound (e.g., a compound of Formula (I)), or a pharmaceutically acceptable salt thereof. In some embodiments, a device is coated or chemically derivatized in an asymmetrical manner with a compound (e.g., a compound of Formula (I)), or a material comprising a compound (e.g., a compound of Formula (I)), or a pharmaceutically acceptable salt thereof. For example, an exemplary device may be partially coated (e.g., at least about 5%, 10%, 15%, 20%, 25%, 30%, 35%, 40%, 45%, 50%, 55%, 60%, 65%, 70%, 75%, 80%, 85%, 90%, 95%, 99%, or 99.9% coated) with a compound (e.g., a compound of Formula (I)) or a material comprising a compound (e.g., a compound of Formula (I)) or a pharmaceutically acceptable salt thereof.

Exemplary devices coated or chemically derivatized with a compound (e.g., a compound of Formula (I)), or a material comprising a compound (e.g., a compound of Formula (I)), or a pharmaceutically acceptable salt thereof may be prepared using any method known in the art, such as through self-assembly (e.g., via block copolymers, adsorption (e.g., competitive adsorption), phase separation, microfabrication, or masking).

In some embodiments, the device comprises a surface exhibiting two or more distinct physicochemical properties (e.g., 3, 4, 5, 6, 7, 8, 9, 10, or more distinct physicochemical properties). In some embodiments, the device is or comprises Janus particle (e.g., a Janus nanoparticle). For example, one or more regions of the device (e.g., a Janus particle) may be hydrophobic, hydrophilic, or amphiphilic. An exemplary device may feature a Janus particle or property thereof as disclosed in Walther et al (2013) *Chem Rev* 113:5194-5261, which is incorporated herein by reference in its entirety.

In some embodiments, the coating or chemical derivatization of the surface of an exemplary device with a compound (e.g., a compound of Formula (I)), a material comprising a compound (e.g., a compound of Formula (I)), or a pharmaceutically acceptable salt thereof is described as the average number of attached compounds per given area, e.g., as a density. For example, the density of the coating or chemical derivatization of an exemplary device may be 0.01, 0.1, 0.5, 1, 5, 10, 15, 20, 50, 75, 100, 200, 400, 500, 750, 1,000, 2,500, or 5,000 compounds per square μm or square mm, e.g., on the surface or interior of said device.

In some embodiments, the device comprises a compound (e.g., a compound of Formula (I)) or a material comprising a compound (e.g., a compound of Formula (I)) or a pharmaceutically acceptable salt thereof comprising A1 (e.g., as described herein), and said compound or material is contained within the device. In some embodiments, the device comprising a compound of Formula (I) comprising A1 is non-covalently attached to the device, e.g., on the surface or in the interior of the device.

In some embodiments, the device comprises a compound of Formula (I) or a material comprising a compound of Formula (I) or a pharmaceutically acceptable salt thereof comprising A2, and, e.g., is covalently attached to the device. In an embodiment, A2 is attached directly to the device. In an embodiment, A2 is attached to the device by an attachment group (e.g., an attachment group described herein). In an embodiment the device is attached, e.g., covalently, to the attachment group, and A2 is attached, e.g., covalently to the attachment group.

A device comprising a compound of Formula (I) or a pharmaceutically acceptable salt thereof may have a reduced immune response (e.g., a marker of an immune response) compared to a device that does not comprise a compound of Formula (I) or a pharmaceutically acceptable salt thereof. A marker of immune response is one or more of: cathepsin activity in vivo as described in Example 7 or Example 9, or the level of a marker of immune response, e.g., TNF-α, IL-13, IL-6, G-CSF, GM-CSF, IL-4, CCL2, or CCL4, as measured, e.g., by ELISA. In some embodiments, a marker of immune response is the percentage of macrophage adhesion to a surface, e.g., in vitro, e.g., as described in Example 8. In some embodiments, a marker of immune response is the amount of adhered tissue to a disk, e.g., in vivo, e.g., placed in a subject (e.g., a mouse), as described in Example 10. In some embodiments, a device comprising a compound of Formula (I) or a pharmaceutically acceptable salt thereof has about a 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100% reduced immune response (e.g., a marker of an immune response) compared to a device that does not comprise a compound of Formula (I) or a pharmaceutically acceptable salt thereof. In some embodiments, the reduced immune response (e.g., a marker of an immune response) is measured after about 30 minutes, about 1 hour, about 6 hours, about 12 hours, about 1 day, about 2 days, about 3 days, about 4 days, about 1 week, about 2 weeks, about 1 month, about 2 months, about 3 months, about 6 months, or longer. In some embodiments, a device comprising a compound of Formula (I) is coated by the compound of Formula (I) or encapsulated a compound of Formula (I).

A device comprising a compound of Formula (I) or a pharmaceutically acceptable salt thereof may have an increased immune response (e.g., a marker of an immune response) compared to a device that does not comprise a compound of Formula (I) or a pharmaceutically acceptable salt thereof. A marker of immune response is one or more of: cathepsin activity in vivo as described in Example 7 or Example 9, or the level of a marker of immune response, e.g., TNF-α, IL-13, IL-6, G-CSF, GM-CSF, IL-4, CCL2, or CCL4, as measured, e.g., by ELISA. In some embodiments, a marker of immune response is the percentage of macrophage adhesion to a surface, e.g., in vitro, e.g., as described in Example 8. In some embodiments, a marker of immune response is the amount of adhered tissue to a disk, e.g., in vivo, placed in a subject (e.g., a mouse), as described in Example 10. In some embodiments, a device comprising a compound of Formula (I) or a pharmaceutically acceptable salt thereof has about a 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100%, or about 1000% increased immune response (e.g., a marker of an immune response) compared to a device that does not comprise a compound of Formula (I) or a pharmaceutically acceptable salt thereof. In some embodiments, the increased immune response (e.g., a marker of an immune response) is measured after about 30 minutes, about 1 hour, about 6 hours, about 12 hours, about 1 day, about 2 days, about 3 days, about 4 days, about 1 week, about 2 weeks, about 1 month, about 2 months, about 3 months, about 6 months, or longer. In some embodiments, a device comprising a compound of Formula (I) is coated by the compound of Formula (I) or encapsulated a compound of Formula (I).

A device may have a smooth surface, or may comprise a protuberance, depression, well, slit, or hole, or any combination thereof. Said protuberance, depression, well, slit or hole may be any size, e.g., from 10 μm to about 1 nm, about 5 μm to about 1 nm, about 2.5 μm to about 1 nm, 1 μm to about 1 nm, 500 nm to about 1 nm, or about 100 nm to about 1 nm. The smooth surface or protuberance, depression, well, slit, or hole, or any combination thereof, may be coated or chemically derivatized with a compound of Formula (I), a material comprising a compound of Formula (I), or a pharmaceutically acceptable salt thereof.

A device may take any suitable shape, such as a sphere, spheroid, ellipsoid, disk, cylinder, torus, cube, stadiumoid, cone, pyramid, triangle, rectangle, square, or rod, or may comprise a curved or flat section. Any shaped, curved, or flat device may be coated or chemically derivatized with a compound of Formula (I), a material comprising a compound of Formula (I), or a pharmaceutically acceptable salt thereof.

A device may exhibit a range of sizes or diameters. In some embodiments, a device has a mean diameter or size that is greater than 1 mm. In some embodiments, a device has a mean diameter or size that is greater than 1.5 mm, 2 mm, 3 mm, 4 mm, 5 mm, 6 mm, 7 mm, 8 mm, 9 mm, 10 mm, or greater.

In some embodiments, the device is not a device disclosed in any of WO2012/112982, WO2012/167223, WO2014/153126, WO2016/019391, US2012-0213708, US 2016-0030359, and US 2016-0030360.

In an embodiment, the device comprises a cell described herein. In an embodiment, the device comprises a cell, e.g., a recombinant cell or stem cell, which provides a substance, e.g., a therapeutic agent. Examples of therapeutic agents include cell products, tissue products, proteins, enzymes, antibodies, antigens, epitopes, drugs, and vaccines. In some embodiments, the therapeutic agent is a biological material.

In an embodiment, the device is a recombinant cell or stem cell that provides a substance. In an embodiment, the substance comprises a polypeptide. In an embodiment the cell is a human cell and the polypeptide is a human polypeptide. In an embodiment the cell is a non-human cell and the polypeptide is a human polypeptide. In an embodiment, the cell provides a substance that alleviates a disease, disorder, or condition (e.g., as described herein). In an embodiment the substance is insulin and the disorder is diabetes.

Additional Exemplary Devices

Devices included herein include devices described in, or substantially similar in terms of structure or function to devices described in, one or more of the following Google (Verily) patent documents: US20160117532A1, WO2016115018A1, U.S. Pat. Nos. 9,282,920B2, 9,289,123B2, 9,289,954B2, 9,295,403B1, 9,298,020B1, 9,307,901B1, 9,320,460B2, 9,326,710B1, 9,332,935B2, 9,366,570B1, 9,372,168B2, 9,398,868B1, 9,400,904B2, U.S. D75486151, U.S. D755786S1, WO2015191203A8, or WO2016115035A1.

Devices included herein include devices described in, or substantially similar in terms of structure or function to devices described in, one or more of the Establishment Labs patent documents US20150150675A1 or US20150282926A1.

Devices included herein include devices described in, or substantially similar in terms of structure or function to devices described in, one or more of the following Becton Dickinson patent documents: EP1003586B1, EP1005909B1, U.S. Pat. No. 9,095,849B2, EP101012B1, EP1011764B1, U.S. Pat. No. 7,972,578B2, EP1393764B1, EP1433705B1, U.S. Pat. No. 7,141,042B2, EP1064039B1, EP107197B2, US20140324088A1, EP1086718B1, EP1086719B1, U.S. Pat. Nos. 7,052,268B2, 9,364,606B2, 7,296,566B2, EP1095668B1, EP1099432B1, EP1102606B1, EP1106250B1, EP1106251B1, EP1107002B1, EP1110077B1, U.S. Pat. No. 7,691,088B2, EP1537885B1, EP1141672B1, U.S. Pat. No. 6,817,143B2, EP115587B1, EP1162463B1, EP1171185B1, EP1177802B1, EP1181891B1, EP1192996B1, EP1193499B1, EP1208862B1, EP121262B1, EP1215494B1, EP1724335B1, EP1253421B1, EP1281435B1, EP1282469B1, EP1284160B1, U.S. Pat. No. 6,969,375B2, EP1284785B1, EP1285674B1, EP1289588B1, U.S. Pat. No. 7,731,968B2, EP129029B1, U.S. Pat. No. 8,172,815B2, EP1299147B1, EP1301236B1, EP1301237B1, EP1305076B1, US20150011937A1, EP1579805B1, EP1320060B1, EP1327476B1, EP1327874B1, EP1329718B1, EP1331874B1, EP1338339B1, EP2070488B1, EP1845370B1, U.S. Pat. No. 6,918,891B2, EP1346740B1, EP1346742B1, U.S. Pat. Nos. 7,399,394B2, 8,459,257B2, EP1350531B1, U.S. Pat. No. 8,708,977B2, EP1352668B1, EP2783708B1, EP1356302B1, EP1360677B1, U.S. Pat. No. 7,578,805B2, EP1368081B1, EP1372772B1, EP1377327B1, EP1379299B1, EP1694391B1, EP13803B1, EP1383545B1, EP1391611B1, EP1391717B1, EP1394247B1, U.S. Pat. Nos. 7,186,235B2, 7,021,463B2, EP1401517B1, U.S. Pat. No. 8,808,321B2, EP1430834B1, US20150051582A1, U.S. Pat. No. 8,414,560B2, EP1436021B1, EP1438098B1, EP1439870B1, EP1440703B1, EP1447072B1, EP1449551B1, EP1449560B1, U.S. Pat. No. 9,314,787B2, EP1457228B1, EP1458760B1, EP1460932B1, EP1464351B1, U.S. Pat. No. 7,851,593B2, EP1472979B1, EP1473052B1, U.S. Pat. No. 9,259,538B2, EP1972919B1, EP1486584B1, EP1757240B1, EP1700615B1, EP1494124B1, EP1495133B1, EP1506413B1, EP1514919B1, EP1523359B1, EP1529489B1, EP1531896B1, U.S. Pat. No. 9,386,955B2, US20070299395A1, U.S. Pat. Nos. 7,967,010B2, 8,133,207B2, EP1994951B1, EP1558310B1, EP1693077B1, EP1575656B1, EP1579815B1, U.S. Pat. No. 8,603,040B2, EP1592346B1, EP1592443B1, EP1594559B1, U.S. Pat. Nos. 7,332,227B2, 8,632,740B2, 8,016,795B2, EP1684833B1, EP1691868B1, EP2191899B1, US20150018641A1, EP1697743B1, EP1715908B1, US20100305544A1, U.S. Pat. No. 8,357,107B2, EP173811B1, U.S. Pat. Nos. 9,380,975B2, 7,951,605B2, 8,221,441B2, 9,267,167B2, EP1773519B1, EP1773520B1, EP1785159B1, EP1786506B1, EP180702B1, EP1816947B1, US20140081238A1, EP184852B1, U.S. Pat. No. 7,879,607B2, 8,262,641B2, EP1868501B1, EP1879028B1, EP189152B1, EP1904124B1, EP1907527B1, U.S. Pat. No. 8,419,690B2, EP1933906B1, EP1951342B1, US20140328734A1, U.S. Pat. No. 8,816,022B2, EP2007450B1, U.S. Pat. No. 9,259,537B2, U.S. Pat. No. 8,715,248B2, US20150004629A1, EP2032993B1, U.S. Pat. No. 9,174,004B2, EP2037989B1, EP204109B1, EP2044402B1, EP2046418B1, EP2046422B1, EP2047159B1, EP2047161B1, EP2061529B1, EP2073883B1, EP2079386B1, U.S. Pat. No. 8,540,677B2, US20130190695A1, US20150100026A1, EP2083885B1, EP2083906B1, EP2089093B1, EP210343B1, EP2111547B1, EP2119464B1, U.S. Pat. No. 9,109,984B2, EP2129405B1, U.S. Pat. No. 8,764,710B2, EP2675420B1, US20150177152A1, EP2153865B1, US20150202378A1, EP2197522B1, U.S. Pat. Nos. 9,242,050B2, 9,259,553B2, EP2214754B1, EP2217308B1, EP2217927B1, EP222103B1, EP223002B1, EP2231247B1, EP2237038B1, U.S. Pat. No. 8,353,876B2, EP2245177B1, EP224650B1, EP2250281B1, EP2265306B1, U.S. Pat. No. 8,939,942B2, US20130018312A1, EP2271939B1, EP2282799B1, EP2291216B1, EP2324875B1, EP2527039B1, EP233376B1, U.S. Pat. No. 8,956,309B2, EP2355879B1, U.S. Pat. No. 9,278,193B2, EP2396055B1, U.S. RE45896E1, EP2398545B1, EP2403573B1, U.S. Pat. Nos. 9,381,136B2, 8,876,780B2, US20160051748A1, EP2420272B1, EP2424612B1, U.S. Pat. No. 9,011,389B2, EP2451343B1, US20160038067A1, US20140316375A1, EP2682057B1, EP2459256B1, EP2477687B1, EP250891B1, EP2781228B1, EP2544750B1, EP2566537B1, EP2566570B1, EP2571549B1, US20150208973A1, EP2595534B1, EP2595681B1, EP2598030B1, EP2611493B1, EP2613841B1, U.S. Pat. No. 9,101,719B2, EP263450B1, EP2645932B1, U.S. Pat. No. 9,333,146B2, EP2651490B1, EP2671606B1, U.S. Pat. No. 9,101,725B2, EP2683306B1, U.S. Pat. No. 9,266,651B2, US20150101957A1, US20150202368A1, US20150250949A1, EP2717947B1, EP2731665B1, EP2819633B1, EP2825500B1, EP282840B1, EP283663B1, EP284232B2, EP297252B1, EP300221B1, EP302625B2, EP310862B1, EP311011B1, EP314328B1, EP329041B1, EP334015B1, EP33528B1, EP335664B1, EP338418B1, EP345415B1, EP346732B1, EP347771B1, EP355637B1, EP378745B1, EP494333B1, EP385953B1, EP388463B1, U.S. Pat. No. 5,441,539A, EP42211B1, EP425319B1, EP459093B1, EP462255B1, EP464257B1, EP468430B1, EP475686B1, EP483618B1, EP485764B1, EP491547B1, U.S. Pat. No. 5,578,492A, EP49591B1, EP496200B1, EP498353B1, U.S. Pat. No. 6,900,030B2, EP518397B1, EP535810B1, EP547463B1, EP547482B1, EP553741B1, EP554841B1, EP554842B1, EP554995B1, U.S. Pat. No. 5,674,203A, EP556618B1, EP567029B1, EP567944B1, EP568207B1, EP573947B1, EP574908B1, EP575736B1, EP579414B1, EP579704B2, EP580094B1, EP585912B1, EP585914B1, EP586666B2, EP588122B1, EP595507B1, EP597584B1, EP603717B1, EP608985B1, EP60981B1, EP615765B1, EP615766B1, EP615767B1, EP621232B1, EP636343B1, U.S. Pat. No. 5,824,198A, EP666084B1, EP670481B1, EP696437B1, EP696460B1, EP696643B1, EP698397B1, EP702579B1, EP702973B1, EP705613B1, EP707860B1, EP719565B1, EP719566B1, EP722749B1, EP726451B1, EP737855B1, EP738517B1, EP744183B1, EP749762B1, EP761562B1, EP764450B1, EP765651B1, EP765653B1, EP77441B1, EP783344B1, EP783346B1, EP787824B1, EP787826B1, EP787827B1, EP787828B1, EP789092B1, EP806221B1, EP81202B1, EP812597B1, EP812602B1, EP815888B1, EP815889B1, EP815890B1, EP820779B1, EP820783B1, EP824922B1, EP827754B1, EP829248B1, EP829250B1, EP832659B1, EP832660B1, EP832665B1, EP832822B1, EP834553B1, EP866119B1, EP875757B1, EP888794B1, EP896826B1, EP896827B1, EP897708B1, EP902289B1, EP904763B1, EP915720B1, EP940182B1, EP940185B1, EP940186B1, EP940187B1, U.S. Pat. No. 6,638,256B2, EP941743B1, EP941767B1, EP970996B1, EP990412B1, EP990430B1, U.S. Pat. Nos. 8,277,408B2, 1,537,888A, 1,678,991A, 1,892,803A, 6,944,338B2, 6,864,071B2, 6,572,827B2, US20050267412A1, U.S. Pat. Nos. 7,182,734B2, 6,686,204B2, US20030053938A1, U.S. Pat. Nos. 8,425,864B2, 6,899,850B2, 6,730,059B2, US20030125677A1, US20030181861A1, U.S. Pat. No. 6,932,803B2, US20030187398A1, U.S. Pat. No. 7,785,485B2, US20030220587A1, US20030220618A1, US20030229316A1, U.S. Pat. Nos. 7,985,387B2, 7,169,132B2, US20070095424A1, US20040143226A1, US20050197629A1, US20040179971A1, US20040236287A1, WO2005034625A1, WO2005028639A2, WO2005044350A1, U.S. Pat. No. 7,101,351B2, US20050119627A1, U.S. Pat. No. 7,144,388B2, WO2005072798A1, U.S. Pat. No. 7,344,517B2, WO2005072800A1, WO2005016401A3, U.S. Pat. No. 7,896,837B2, US20050247666A1, US20060040311A1, U.S. Pat. No. 7,093,482B2, WO2006044865A3, U.S. Pat. No. 7,970,725B2, U.S. Pat. No. 8,815,574B2, U.S. Pat. No. 8,062,252B2, WO2007027204A3, WO2006115866A1, US20070019502A1, U.S. Pat. No. 7,537,581B2, U.S. Pat. Nos. 8,377,010B2, 7,717,882B2, US20160121526A9, US20160158521A1, US20130218129A1, US20070134719A1, U.S. Pat. No. 7,524,641B2, WO2007100776A3, WO2007095045A3, US20070224701A1, U.S. Pat. Nos. 8,062,261B2, 9,320,459B2, US20120058351A1, WO2008013684A3, WO2008014437A3, WO2008014440A3, WO2008014439A3, U.S. Pat. Nos. 8,822,208B2, 8,478,445B2, US20080082033A1, WO2008043069A3, U.S. Pat. No. 8,062,267B2, WO2008043015A3, U.S. Pat. Nos. 8,366,676B2, 8,062,266B2, 9,011,382B2, US20080221501A1, U.S. Pat. No. 7,540,858B2, US20080194986A1, U.S. Pat. Nos. 8,066,670B2, 8,337,483B2, US20080221396A1, US20080221500A1, U.S. Pat. No. 7,648,028B2, WO2008121829A1, US20080269690A1, WO2008131361A3, US20080277332A1, U.S. Pat. Nos. 8,377,040B2, 8,241,567B2, US20130289524A1, U.S. Pat. No. 8,772,047B2, US20090043225A1, US20090043242A1, U.S. Pat. No. 8,386,184B2, US20090088729A1, WO2009055595A1, US20090124997A1, U.S. Pat. Nos. 9,278,180B2, 7,901,383B2, 8,298,180B2, US20090238726A1, US20160196395A1, U.S. Pat. No. 8,162,902B2, US20160157767A1, U.S. Pat. Nos. 7,947,018B2, 8,366,684B2, 9,101,748B2, US20090287167A1, U.S. Pat. Nos. 8,038,647B2, 8,974,411B2, 8,172,813B2, 8,801,675B2, US20130237913A1, U.S. Pat. Nos. 8,905,975B2, 8,754,020B2, 8,568,358B2, 9,339,741B2, 8,412,300B2, 8,357,121B2, 8,337,461B2, 8,500,693B2, 8,357,125B2, US20140364805A1, U.S. Pat. Nos. 8,556,848B2, 9,364,828B2, 8,491,530B2, US20100292656A1, US20100294663A1, WO2010141290A1, U.S. Pat. No. 8,472,017B2, US20140114257A1, U.S. Pat. Nos. 8,821,455B2, 8,474,300B2, 8,038,657B2, 8,939,928B2, 7,908,155B2, 8,900,198B2, WO2011028279A1, U.S. Pat. No. 9,375,529B2, WO2011028374A1, US20150079144A1, U.S. Pat. Nos. 9,375,385B2, 8,993,644B2, US20110071492A1, US20110092917A1, U.S. Pat. Nos. 8,449,479B2, 8,936,578B2, U.S. Pat. No. 8,945,023B2, US20110174820A1, U.S. Pat. No. 8,871,527B2, US20110186537A1, US20150314080A1, US20150051552A1, U.S. Pat. No. 8,979,807B2, US20160038684A1, US20150265772A1, US20110276031A1, U.S. Pat. No. 8,924,036B2, US20110311416A1, U.S. Pat. No. 8,802,603B2, US20120016213A1, U.S. Pat. No. 9,314,201B2, US20120016318A1, U.S. Pat. No. 9,381,337B2, US20120029438A1, U.S. Pat. No. 9,044,554B2, US20120041394A1, US20150359960A1, US20150218354A1, U.S. Pat. No. 9,375,551B2, US20120070879A1, US20120100557A1, U.S. Pat. Nos. 9,220,842B2, 8,858,531B2, US20120150129A1, US20120157928A1, US20120175806A1, U.S. Pat. Nos. 9,017,291B2, 8,469,923B2, US20150135813A1, U.S. Pat. Nos. 9,283,321B2, 8,758,878B2, 9,259,554B2, 8,641,675B2, WO2012134513A1, US20120301910A1, US20120302966A1, US20140338171A1, US20130011851A1, U.S. Pat. No. 9,176,071B2, US20140276449A1, U.S. Pat. Nos. 9,126,012B2, 9,089,671B2, 9,155,864B2, US20160015867A1, U.S. Pat. No. 8,747,360B2, US20130150796A1, U.S. Pat. Nos. 8,790,667B2, 8,945,071B2, U.S. Pat. No. 9,155,863B2, US20130178759A1, U.S. Pat. No. 8,882,726B2, US20130183655A1, WO2013138809A3, WO2013151860A1, US20160136359A1, US20140378910A1, US20150141932A1, U.S. Pat. Nos. 9,068,565B2, 8,622,967B2, US20160206869A1, WO2013177034A1, US20160067365A1, US20150265735A1, US20130330739A1, WO2014004659A3, U.S. Pat. No. 9,132,238B2, WO2014022030A3, US20140011292A1, US20150305981A1, US20140030754A1, WO2015006340A1, US20140039408A1, US20160184527A1, US20140058336A1, US20140058353A1, U.S. Pat. Nos. 8,915,891B2, 9,272,088B2, US20140074033A1, U.S. Pat. No. 9,155,866B2, US20140081239A1, US20140088509A1, US20140088512A1, US20140088550A1, U.S. Pat. No. 9,358,344B2, US20140094776A1, US20140100522A1, US20140100544A1, US20140107613A1, US20150160116A1, U.S. Pat. No. 9,155,867B2, WO2014077831A1, WO2014081713A1, U.S. Pat. No. 9,265,895B2, U.S. Pat. No. 8,834,401B2, US20160101276A1, US20140170642A1, US20140171875A1, U.S. Pat. No. 8,764,706B2, US20160175198A1, US20140200154A1, US20140220552A1, US20140221934A1, U.S. Pat. No. 9,039,989B2, WO2014126862A1, WO2014126864A2, US20140228775A1, US20160199633A1, U.S. Pat. No. 8,974,414B2, WO2014137731A1, U.S. Pat. No. 9,327,095B2, WO2014138413A3, WO2014159619A1, US20140269160A1, US20140276219A1, U.S. Pat. No. 9,381,320B2, WO2014150665A3, US20140303568A1, U.S. Pat. Nos. 9,380,972B2, 9,366,616B2, US20140309552A1, US20140316337A1, US20140350485A1, U.S. Pat. Nos. 8,992,835B2, 9,347,933B2, WO2014176393A3, US20140324017A1, US20140343502A1, US20140343511A1, US20140343897A1, US20140358119A1, US20140364809A1, US20140374414A1, US20140379273A1, US20150005669A1, US20150010939A1, US20150025473A1, US20150025503A1, US20150033535A1, US20150034516A1, US20150038909A1, US20150038910A1, U.S. Pat. No. 9,078,983B2, US20150051583A1, US20150057612A1, US20150065991A1, US20150073384A1, US20150080799A1, US20150080800A1, US20150080807A1, WO2015042517A3, US20150100022A1, US20150105739A1, US20150105745A1, US20150118688A1, WO2015065700A1, WO2015069638A1, WO2015069789A1, WO2015069631A1, US20150126963A1, WO2015073384A1, WO2015084474A1, US20150165125A1, WO2015100028A1, US20150185225A1, US20150196715A1, WO2015112427A1, WO2015116816A1, WO2015116805A1, WO2015116794A1, US20150224028A1, WO2015126699A1, WO2015126700A3, US20160158520A1, US20150283372A1, US20150297195A1, WO2015167871A1, US20150297452A1, WO2015164413A1, WO2015164385A1, WO2015164365A1, US20150306307A1, US20150306318A1, WO2015164133A3, US20150306351A1, WO2015164134A3, US20150306369A1, US20150306370A1, US20150314071A1, US20150314074A1, US20150320639A1, US20150328370A1, US20150328412A1, US20150347714A1, US20160008517A1, US20160008569A1, US20160008579A1, US20160015305A1, US20160022179A1, US20160024419A1, US20160024549A1, US20160028821A1, US20160029977A1, US20160030683A1, US20160041167A1, US20160158435A1, US20160069781A1, WO2016040323A1, US20160073937A1, US20160074284A1, US20160074572A1, US20160074587A1, US20160075460A1, US20160081606A1, US20160082183A1, US20160089056A1, US20160089070A1, WO2016053726A1, WO2016060793A1, US20160101632A1, US20160101887A1, US20160129202A1, US20160136412A1, US20160136639A1, US20160143811A1, US20160158449A1, US20160151584A1, US20160158462A1, US20160158518A1, US20160206806A1, US20160209328A1, US20160213818A1, US20160213843A1, US20160213853A1, US20160213856A1, US20160213861A1, US20160213862A1, US20160213911A1, US20160216178A1, US20160216179A1, U.S. Pat. Nos. 2,179,839A, 2,376,436A, 2,547,099A, 2,550,053A, 2,605,763A, 2,635,601A, 2,642,064A, 2,645,223A, 2,653,602A, 2,687,727A, 2,722,931A, 3,045,673A, 3,368,783A, 3,394,702A, 3,444,620A, 3,456,487A, 3,456,488A, 3,469,572A, 3,469,750A, 3,485,236A, 3,485,265A, 3,492,396A, 3,494,352A, 3,505,843A, 3,512,666A, 3,522,132A, 3,541,233A, 3,572,660A, 3,695,445A, 3,587,562A, 3,602,272A, 3,609,768A, 3,626,928A, 3,629,999A, 3,638,481A, 3,689,839A, 3,704,705A, U.S. RE29559E1, 3,727,084A, 3,736,824A, 3,737,973A, 3,742,187A, 3,766,908A, 3,779,383A, 3,788,149A, 3,793,726A, 3,814,080A, 3,834,226A, 3,836,079A, 3,849,072A, 3,858,065A, 3,861,560A, 3,861,800A, 3,867,726A, 3,874,503A, 3,887,464A, 3,903,887A, 3,914,865A, 3,921,369A, 3,931,018A, 3,935,113A, 3,941,699A, 3,954,014A, 3,945,928A, 4,059,407A, 3,965,848A, 3,972,812A, 3,973,194A, 4,004,692A, 4,024,857A, 4,042,145A, 4,050,316A, 4,064,871A, 4,065,970A, 4,110,604A, 4,116,066A, 4,124,044A, 4,385,844A, 4,181,233A, 4,212,308A, 4,226,036A, 4,243,534A, 4,256,106A, 4,265,760A, 4,275,591A, 4,275,730A, 4,441,951A, 4,296,631A, 4,307,731A, 4,317,456A, 4,320,769A, 4,326,927A, 4,327,718A, 4,330,216A, 4,358,539A, 4,364,903A, 4,384,581A, 4,386,716A, 4,391,274A, 4,417,981A, 4,483,925A, 4,490,141A, 4,498,766A, 4,499,052A, 4,545,677A, 4,577,630A, 4,579,828A, 4,600,302A, 4,605,919A, 4,609,286A, 4,615,340A, 4,634,676A, 4,647,643A, 4,661,300A, 4,710,635A, 4,730,624A, 4,749,655A, 4,751,001A, 4,768,653A, 4,786,556A, 4,789,639A, 4,790,312A, 4,800,878A, 4,805,611A, 4,810,652A, 4,812,293A, 4,834,720A, 4,838,857A, 4,840,908A, 4,855,240A, 4,859,864A, 4,867,887A, 4,886,505A, 4,919,134A, 4,931,044A, 4,944,730A, 4,944,918A, 4,966,758A, 5,064,415A, 5,030,002A, 5,077,372A, 5,175,977A, 5,067,491A, 5,089,205A, 5,092,858A, 5,098,410A, 5,185,127A, 5,254,096A, 5,425,915A, 5,295,967A, 5,306,235A, 5,308,341A, 5,310,403A, 5,317,162A, 5,322,609A, 5,358,501A, 5,376,073A, 5,409,461A, 5,409,829A, 5,431,672A, 5,470,743A, 5,533,994A, 5,501,665A, 5,515,161A, 5,515,713A, 5,535,771A, 5,954,684A, 5,542,760A, 5,545,375A, 5,545,708A, 5,563,356A, 5,568,815A, 5,702,367A, 5,578,270A, 5,620,454A, 5,624,849A, 5,632,732A, 5,643,202A, 6,046,143A, 5,654,054A, 5,683,771A, 5,665,596A, 5,807,605A, 5,667,985A, 5,686,096A, 5,688,232A, 5,688,747A, 5,707,363A, 5,712,095A, 5,712,229A, WO1998013098A1, 5,725,831A, 5,735,810A, 5,738,647A, 5,746,727A, 5,952,069A, 5,766,154A, 5,950,986A, 5,780,294A, 5,783,439A, 5,788,863A, 5,792,097A, 5,795,748A, 5,797,867A, 5,797,889A, 5,798,273A, 5,800,410A, 5,817,509A, 6,146,374A, 5,820,621A, WO1999000153A1, 5,836,914A, 5,843,015A, 5,854,065A, 6,018,680A, 5,858,693A, 5,862,310A, 5,879,075A, 5,882,677A, 5,882,922A, 5,893,842A, 5,899,876A, 5,911,711A, 5,913,845A, 5,919,172A, 5,919,182A, 5,924,206A, 5,925,029A, 5,935,598A, 5,944,695A, 5,945,281A, 5,948,673A, 5,951,515A, 5,957,887A, 5,964,737A, 5,989,924A, 5,992,899A, 6,009,344A, 6,010,462A, 6,012,034A, 6,029,083A, 6,597,450B1, 6,054,188A, 6,057,165A, 6,077,259A, 6,508,966B1, WO2000041760A1, U.S. Pat. Nos. 6,090,078A, 6,090,093A, 6,107,777A, 6,110,427A, 6,120,481A, 6,132,684A, 6,162,398A, 6,171,261B1, 6,171,287B1, 6,762,206B2, 6,187,768B1, 6,190,367B1, 6,197,001B1, 6,210,375B1, 6,211,477B1, 6,213,994B1, 6,220,246B1, 6,425,884B1, 6,235,010B1, 6,245,044B1, 6,277,099B1, 6,280,400B1, 6,294,999B1, 6,325,764B1, 6,350,254B1, 6,358,475B1, 6,408,897B1, 6,409,528B1, 6,409,971B1, 6,427,875B1, 6,428,527B1, 6,432,663B1, 6,516,953B1, 6,527,019B2, 6,568,241B2, 6,571,540B1, 6,663,601B2, WO2002068849A8, 6,626,869B1, 6,953,448B2, 6,638,440B1, 6,642,047B2, 6,660,489B2, 6,666,359B2, 6,680,208B1, 6,709,857B2, 6,750,457B2, 7,390,312B2, 6,788,409B2, 6,792,662B2, 6,813,017B1, 6,826,949B1, 6,840,291B2, 6,922,576B2, 6,994,213B2, 7,008,406B2, 7,016,087B2, 7,182,277B2, 7,387,637B2, 7,044,125B2, 7,615,271B2, 7,198,855B2, 7,396,484B2, 7,444,005B2, 7,642,060B2, 7,643,134B2, 7,981,081B2, 7,682,344B2, 7,704,935B1, 7,713,250B2, 7,776,012B2, 7,787,197B2, 7,854,889B2, 7,981,079B2, 8,002,174B2, 8,003,329B2, 8,137,313B2, 8,240,468B2, 8,285,487B2, 9,205,205B2, 8,369,916B2, 8,389,290B2, 8,413,651B2, 8,417,381B2, 8,603,345B2, 8,709,033B2, 8,822,211B2, 8,858,582B2, 8,945,050B2, 9,056,182B2, 9,101,724B2, 9,220,851B2, 9,345,835B2, 9,365,814B2, 9,381,524B2, 9,399,120B2, 9,399,125B2, U.S. D38337551, U.S. D40807951, U.S. D42561851, U.S. D425983S1, U.S. D42598451, U.S. D43997651, U.S. D459803S1, U.S. D460180S1, U.S. D460181S1, U.S. D460182S1, U.S. D460551S1, U.S. D462761S1, U.S. D462762S1, U.S. D462763S1, U.S. D462764S1, U.S. D463024S1, U.S. D463025S1, U.S.

D465845S1, U.S. D483487S1, U.S. D532517S1, U.S. D538934S1, U.S. D569975S1, U.S. D592302S1, U.S. D601695S1, U.S. D604840S1, U.S. D604841S1, U.S. D611139S1, U.S. D613398S1, U.S. D647627S1, U.S. D627060S1, U.S. D640787S1, U.S. D655424S1, U.S. D676957S1, U.S. D680643S1, U.S. D684685S1, U.S. D684686S1, U.S. D685083S1, U.S. D685084S1, U.S. D687140S1, U.S. D687141S1, U.S. D687536S1, U.S. D688784S1, U.S. D688790S1, U.S. D688791S1, U.S. D688792S1, U.S. D688793S1, U.S. D696771S1, U.S. D696773S1, U.S. D703314S1, U.S. D740937S1, U.S. D751699S1, U.S. RE31915E1, U.S. RE38964E1, WO1992007245A1, WO1994017853A1, WO2000074772A1, WO1996009851A1, WO1996016690A1, WO1997007854A1, WO1997011741A1, WO1997011744A1, WO1997012644A1, WO1998022625A1, WO1998057689A1, WO1999012606A1, WO1999015221A1, WO1999016485A1, WO1999032168A1, WO2000015287A2, WO2000015289A1, WO2000018369A1, WO2000018465A1, WO2000024312A1, WO2000048663A1, WO2000062036A9, WO2000068270A1, WO2001038882A1, WO2002083216A1, WO2002083230A1, WO2002087494A2, WO2002097571A2, WO2003024511A8, WO2003044158A1, WO2003045973A2, WO2003095974A3, WO2004001404A1, WO2004032750A1, WO2004078232A3, WO2004078233A3, WO2004105840A1, WO2005016239A2, WO2005023328A3, WO2005033296A1, WO2005046701A1, WO2005074460A2, WO2005111086A2, WO2006053316A9, WO2006060710A2, WO2006079728A1, WO2006117692A1, WO2006127962A3, WO2006131832A1, WO2007025084A2, WO2007047328A1, WO2007078841A2, WO2007147862A1, WO2008097217A1, WO2008097979A3, WO2009030974A1, WO2009030975A1, WO2009030976A1, WO2009105062A1, WO2009123737A2, WO2009133153A1, WO2010035056A1, WO2010052517A1, WO2010077277A1, WO2010077278A1, WO2010085338A1, WO2010090734A1, WO2010106031A1, WO2010128406A1, WO2011008190A1, WO2011034516A1, WO2011034576A1, WO2011068542A1, WO2011069145A3, WO2011075099A1, WO2011075100A1, WO2011075102A1, WO2011075103A1, WO2011075104A1, WO2011075105A1, WO2011080543A1, WO2011094025A1, WO2012109310A3, WO2012125132A1, WO2012125133A1, WO2013109864A1, WO2013115730A1, WO2013116702A1, WO2013141814A1, WO2014085395A1, WO2014159928A1, WO2015061711A1, WO2015067548A1, WO2015069649A1, WO2015081337A3, WO2015085019A1, WO2015085031A4, WO2015126721A1, WO2015160420A1, WO2015164647A1, WO2015164648A1, WO2015164649A1, WO2015164650A1, WO2015164651A1, WO2015164653A1, WO2015164655A3, WO2015172037A1, WO2015181173A1, WO2016007438A1, WO2016014162A1, WO2016018189A1, WO2016019192A1, WO2016028684A1, WO2016032394A1, WO2016032967A1, WO2016040423A1, WO2016048878A1, WO2016050699A1, WO2016064916A1, WO2016090265A1, WO2016115372A1, or WO2016118915A1.

Devices included herein include an implantable described in, or substantially similar in terms of structure or function to devices described in, one or more EP1458760B1, U.S. Pat. No. 7,951,605B2, EP446450B1, WO2005034625A1, WO2007100776A2, US20080221501A1, US20080221500A1, US20080277332A1, U.S. Pat. No. 8,241,567B2, US20090043242A1, U.S. Pat. No. 8,939, 928B2, US20160213818A1, U.S. Pat. Nos. 4,834,720A, 6,077,259A, WO2003045973A2, or WO2007025084A2.

Devices included herein include devices described in, or substantially similar in terms of structure or function to devices described in, one or more of the following Medtronic patent documents: U.S. Pat. Nos. 3,737,579A, 3,788,329A, 3,844,292A, 3,855,996A, 3,888,261A, 3,901, 247A, 3,918,460A, 3,924,640A, 3,943,937A, 3,957,056A, 3,964,470A, 3,999,555A, 3,999,556A, 4,010,758A, 4,010, 760A, 4,024,875A, 4,044,775A, 4,066,086A, 4,106,512A, 4,119,103A, 4,135,518A, 4,146,036A, 4,207,903A, 4,209, 019A, 4,217,913A, 4,267,843A, 4,276,883A, 4,280,510A, 4,305,397A, 4,311,153A, 4,324,252A, 4,374,382A, 4,381, 786A, 4,384,585A, 4,401,120A, 4,402,323A, 4,481,950A, 4,485,813A, 4,531,523A, 4,548,209A, 4,556,063A, 4,595, 009A, 4,771,772A, 4,630,611A, 4,676,248A, 4,692,147A, 4,693,253A, 4,968,293A, 4,987,897A, 5,006,115A, 5,171, 228A, 5,080,096A, 5,088,488A, 5,104,755A, 5,107,833A, 5,115,818A, 5,117,824A, 5,354,319A, 5,133,422A, 5,168, 871A, 5,222,980A, 5,243,981A, 5,257,622A, 5,273,518A, 5,292,342A, 5,312,446A, 5,314,451A, 5,324,310A, 5,324, 315A, 5,328,465A, 5,331,966A, 5,354,318A, 5,360,437A, 5,369,364A, 5,370,668A, 5,383,909A, 5,383,922A, 5,391, 193A, 5,402,794A, 5,409,009A, 5,417,719A, 5,423,806A, 5,429,618A, 5,431,695A, 5,443,450A, 5,443,492A, 5,456, 698A, 5,464,435A, 5,782,891A, 5,476,501A, 5,486,200A, 5,527,348A, 5,535,097A, 5,540,729A, 5,540,731A, 5,540, 732A, 5,549,654A, 5,562,714A, 5,564,434A, 5,591,212A, 5,607,463A, 6,006,139A, 5,893,881A, 5,673,473A, 5,683, 432A, 5,683,446A, 5,817,137A, 5,712,462A, 5,713,858A, 5,716,391A, 5,725,561A, 6,617,142B2, 5,836,992A, 5,741, 310A, U.S. RE42934E1, 5,752,977A, 6,178,350B1, 5,931, 857A, 5,755,758A, 5,759,197A, 5,824,056A, 5,766,042A, 5,766,225A, 5,766,232A, 5,897,590A, 6,785,576B2, 5,776, 168A, 5,782,838A, 5,782,888A, 5,782,892A, 5,782,903A, 5,798,114A, 5,800,376A, 5,801,188A, 5,810,735A, 5,814, 079A, 5,814,083A, 5,814,089A, 5,817,133A, 5,866,851A, 5,819,740A, 6,090,503A, 5,824,029A, 5,832,932A, 5,833, 651A, 5,833,709A, 5,836,982A, 5,836,989A, 5,837,006A, 5,840,069A, 5,843,135A, 5,843,149A, 5,843,150A, 5,851, 217A, 5,851,221A, 5,871,513A, 6,146,743A, 5,861,013A, 5,861,019A, 5,865,842A, 6,031,710A, 5,869,078A, 5,871, 508A, 6,163,724A, 5,919,215A, 5,876,353A, 6,007,493A, 6,370,433B1, 5,893,883A, 5,895,733A, 5,897,577A, 5,897, 584A, 5,899,927A, 6,731,976B2, 5,904,708A, 5,910,156A, 5,916,237A, 5,919,209A, 5,919,216A, 5,919,221A, 6,343, 233B1, 5,941,906A, 5,942,276A, 5,944,745A, 5,948,004A, 5,954,755A, 5,954,756A, 5,955,218A, 5,957,861A, 5,968, 079A, 5,974,873A, 5,975,085A, 6,394,981B2, 6,214, 370B1, 5,980,973A, 6,437,076B1, 6,496,715B1, 5,993, 414A, 5,994,444A, 5,999,857A, 7,177,140B2, 6,006,135A, 6,006,137A, 6,009,350A, 6,305,381B1, 6,016,447A, 6,337, 997B1, 6,021,352A, 6,496,729B2, 6,234,973B1, 6,040, 082A, 6,044,297A, 6,216,038B1, 6,044,304A, 6,102,874A, 6,048,328A, 6,049,736A, 6,051,887A, 6,052,623A, 6,055,457A, 6,057,175A, 6,058,326A, 6,077,227A, 6,080,188A, 6,450,172B1, 6,091,986A, 6,094,597A, 6,099,479A, 6,099,559A, 6,106,454A, 6,106,477A, 6,112,119A, 6,381,493B1, 6,115,630A, 6,115,634A, 6,115,636A, 6,117,979A, 6,125,300A, 6,128,526A, 6,128,528A, 6,129,742A, 6,129,745A, 6,141,583A, 7,155,288B2, 6,152,885A, 6,152,898A, 6,154,675A, 6,155,267A, 6,159,240A, 6,159,253A, 6,577,896B2, 6,162,180A, 6,163,723A, 6,167,310A, 6,167,312A, 6,169,925B1, 6,171,252B1, 6,178,349B1, 6,189,536B1, 6,529,771B1, 6,209,764B1, 6,200,265B1, 6,201,993B1, 6,203,523B1, 7,231,253B2, 6,824,561B2, 6,542,350B1, 6,210,417B1, 6,216,537B1, 6,379,691B1, 6,223,081B1, 6,223,083B1, 6,228,050B1, 6,230,059B1, 6,236,882B1, 6,236,889B1, 6,238,367B1, 6,240,317B1, 6,249,703B1, 6,250,309B1, 6,263,237B1, 6,687,547B2, 6,549,811B2, 9,192,467B2, 6,266,566B1, 6,274,265B1, 6,280,433B1, 6,635,048B1, 6,292,697B1, 7,376,468B2, 6,293,922B1, 6,295,473B1, 6,309,411B1, 6,315,769B1, 6,317,625B1, 6,317,626B1, 8,463,382B2, 6,321,104B1, 6,699,187B2, 6,329,929B1, 6,330,477B1, 6,748,653B2, 6,334,871B1, 6,340,368B1, 6,347,245B1, 6,348,050B1, 6,351,675B1, 6,356,789B1, 6,360,750B1, 6,363,282B1, 6,374,140B1, 6,379,300B1, 7,076,303B2, 6,386,882B1, 6,389,315B1, 6,397,100B2, 6,399,144B2, 6,411,851B1, 6,415,181B1, 7,058,453B2, 6,421,564B1, 8,938,306B2, 6,434,426B1, 6,438,407B1, 6,438,408B1, 6,438,409B1, 6,438,420B1, 6,442,427B1, 6,442,430B1, 7,463,930B2, 6,443,891B1, 6,445,952B1, 6,449,508B1, 6,449,510B1, 6,453,195B1, 6,453,198B1, 6,456,875B1, 6,456,883B1, 6,456,887B1, 6,458,118B1, 6,463,329B1, 6,466,824B1, 6,470,212B1, 6,979,315B2, 6,477,420B1, 6,477,424B1, 6,480,744B2, 6,482,154B1, 6,482,177B1, 6,484,054B2, 6,485,464B1, 7,070,577B1, 6,496,730B1, 7,815,568B2, 6,498,951B1, 6,505,067B1, 6,505,077B1, 6,505,080B1, 6,508,771B1, 6,509,145B1, 6,510,345B1, 6,510,348B2, 6,512,949B1, 6,512,958B1, 7,369,892B2, 6,520,936B1, 6,522,915B1, 6,868,288B2, 6,537,268B1, 6,556,873B1, 6,561,975B1, 6,562,000B2, 6,650,937B2, 6,567,701B2, 6,889,084B2, 6,567,704B2, 6,572,542B1, 6,572,543B1, 6,572,583B1, 6,574,503B2, 6,574,511B2, 6,577,901B2, 8,562,591B2, 6,580,946B2, 6,580,947B1, 6,580,948B2, 6,582,418B1, 6,583,796B2, 6,584,352B2, 7,313,443B2, 6,589,187B1, 7,279,112B2, 6,592,571B1, 6,594,526B2, 6,595,927B2, 6,599,250B2, 8,641,674B2, 6,609,028B2, 6,613,079B1, 6,615,083B2, 6,622,046B2, 7,027,872B2, 6,626,867B1, 6,626,931B2, 6,629,931B1, 6,636,762B2, 7,934,508B2, 7,177,699B2, 6,645,176B1, 6,647,299B2, 6,648,823B2, 6,650,938B2, 6,650,941B2, 7,807,300B2, 6,650,944B2, 6,652,510B2, 9,314,628B2, 6,662,050B2, 6,663,609B2, 7,429,255B2, 6,696,318B2, 6,671,549B2, 6,714,806B2, 6,671,552B2, 6,675,044B2, 7,239,916B2, 6,963,482B2, 6,681,135B1, 6,690,959B2, 6,692,834B1, 6,695,790B2, 6,697,676B2, 6,699,200B2, 6,701,188B2, 7,226,586B2, 6,704,602B2, 6,704,604B2, 6,714,811B1, 6,719,689B2, 6,721,592B2, 6,721,599B2, 6,721,602B2, 6,725,866B2, 6,728,574B2, 6,728,576B2, 7,206,635B2, 6,733,476B2, 6,733,519B2, 6,738,667B2, 7,610,099B2, 6,738,671B2, 6,740,076B2, 7,434,312B2, 8,734,397B2, 6,743,831B2, 7,640,054B2, 6,745,076B2, 6,745,079B2, 6,746,426B1, 6,746,481B1, 6,748,260B2, 6,748,270B2, 6,749,581B2, 6,752,765B1, 6,754,527B2, 6,754,529B2, 6,754,532B1, 7,289,852B2, 6,754,536B2, 6,754,538B2, 6,760,615B2, 6,766,190B2, 6,770,729B2, 8,060,202B2, 6,772,006B2, 6,780,770B2, 6,782,290B2, 6,786,910B2, 7,335,530B2, 6,788,973B2, 6,792,308B2, 6,792,312B2, 7,082,330B2, 6,796,956B2, 6,799,072B2, 7,505,869B2, 6,799,991B2, 6,801,424B1, 6,804,552B2, 6,804,554B2, 7,181,505B2, 6,805,667B2, 6,807,048B1, 6,807,439B2, 6,812,217B2, 6,813,516B2, 6,813,518B2, 7,309,262B2, 6,819,544B1, 6,820,019B1, 6,823,209B2, 6,823,213B1, 8,002,700B2, 8,105,268B2, 6,836,682B2, 6,839,592B2, 7,641,705B2, 6,847,845B2, 8,170,681B2, 6,921,295B2, 6,855,456B2, 6,862,794B2, 6,865,419B2, 6,869,404B2, 6,871,098B2, 6,879,861B2, 6,881,516B2, 6,882,882B2, 6,882,883B2, 6,925,447B2, 6,883,241B2, 6,884,122B2, 6,885,889B2, 6,885,891B2, 6,887,207B2, 6,889,078B2, 6,892,094B2, 6,894,246B2, 6,895,275B2, 7,330,754B2, 6,898,463B2, 6,901,287B2, 6,901,289B2, 6,901,292B2, 8,639,338B2, 6,904,315B2, 6,909,920B2, 6,910,084B2, 6,920,677B2, 6,922,584B2, 6,922,592B2, 6,923,784B2, 8,133,435B2, 6,928,338B1, 7,486,184B2, 6,931,272B2, 6,931,279B2, 6,931,284B2, 7,274,966B2, 6,934,586B2, 6,934,589B2, 7,657,323B2, 6,937,891B2, 6,937,906B2, 6,941,332B2, 6,944,488B2, 6,944,489B2, 6,950,706B2, 6,951,664B2, 6,959,214B2, 6,961,448B2, 6,961,610B2, 6,963,780B2, 6,964,641B2, 6,966,322B2, 6,968,234B2, 7,744,560B2, 8,036,737B2, 6,978,178B2, 6,980,860B2, 6,980,863B2, 7,212,133B2, 6,985,776B2, 7,085,952B2, 6,991,961B2, 6,994,676B2, 6,996,437B2, 6,997,919B2, 6,999,816B2, 7,001,359B2, 7,499,260B2, 7,010,355B2, 7,139,613B2, 7,013,180B2, 7,014,610B2, 7,016,733B2, 7,023,359B2, 7,024,244B2, 7,024,246B2, 7,025,730B2, 7,947,378B2, 7,027,861B2, 7,027,862B2, 7,027,868B2, 7,584,002B2, 7,029,460B2, 7,031,771B2, 7,031,772B2, 7,035,078B1, 7,035,684B2, 8,538,527B2, 7,037,266B2, 7,039,810B1, 7,043,295B2, 7,045,279B1, 7,050,851B2, 7,058,450B2, 7,062,322B2, 7,064,168B2, 7,065,398B2, 7,066,891B2, 7,981,107B2, 7,068,491B1, 7,069,078B2, 7,072,725B2, 7,076,283B2, 7,130,677B2, 7,076,290B2, 7,076,298B2, 7,076,309B2, 7,076,520B2, 7,079,887B2, 7,079,895B2, 7,624,293B2, 7,082,327B2, 7,082,333B1, 7,082,334B2, 7,083,588B1, 7,085,604B2, 7,846,095B2, 7,089,049B2, 7,089,057B2, 7,517,337B2, 7,092,759B2, 7,092,765B2, 7,096,063B2, 7,096,067B2, 7,099,714B2, 7,107,093B2, 7,107,098B2, 8,920,432B2, 7,120,484B2, 7,122,026B2, 7,122,027B2, 7,123,122B2, 7,123,963B2, 7,123,964B2, 7,123,965B2, 7,774,066B2, 7,647,107B2, 7,127,299B2, 7,130,678B2, 7,130,681B2, 7,130,684B2, 7,130,685B2, 7,130,687B2, 7,130,699B2, 7,130,700B2, 7,133,718B2, 7,139,610B2, 7,142,921B2, 7,142,923B2, 7,917,206B2, 7,146,214B2, 7,603,177B2, 7,146,224B2, 7,146,225B2, 7,149,572B2, 7,826,896B2, 7,149,581B2, 7,151,914B2, 7,151,962B2, 7,200,434B2, 7,155,283B2, 7,158,827B2, 7,162,300B2, 7,162,307B2, 7,164,572B1, 7,164,948B2, 7,164,951B2, 7,167,074B2, 8,744,587B2, 7,167,747B2, 8,989,869B2, 7,175,024B2, 7,176,261B2, 7,179,238B2, 7,181,268B2, 7,181,272B2, 7,181,275B2, 7,181,283B2, 8,214,051B2, 7,184,831B2, 7,184,832B2, 7,184,837B2, 7,186,214B2, 7,187,535B1, 7,187,975B2, 7,187,978B2, 7,187,979B2, 7,190,993B2, 7,191,009B2, 7,191,015B2, 7,191,016B2, 7,192,399B2, 9,248,298B2, 7,203,551B2, 7,367,956B2, 8,027,728B2, 7,209,790B2, 7,210,966B2, 7,212,856B2, 8,666,497B2, 7,214,068B2, 7,218,964B2, 7,848,813B2, 7,218,968B2, 7,650,190B2, 7,224,576B2, 7,225,032B2, 7,853,328B2, 7,233,821B2, 7,233,825B2, 7,235,067B2, 7,236,834B2, 7,239,926B2, 7,239,927B2, 7,241,180B1, 7,248,918B2, 7,248,920B2, 7,248,924B2, 7,251,532B2, 7,853,323B2, 7,254,443B2, 7,257,445B2, 7,263,399B2, 7,264,611B2, 7,265,676B2, 7,266,412B2, 7,272,433B2, 7,277,757B2, 7,280,869B2, 7,783,354B2, 7,283,872B2, 8,116,876B2, 7,286,880B2, 7,286,881B2, 7,288,066B2, 7,777,153B2, 7,289,851B2, 7,289,855B2, 7,292,168B2, 7,292,888B2, 7,299,085B2, 7,300,463B2, 8,727, 988B2, 7,305,993B2, 7,711,435B2, 7,313,436B2, 8,688,221B2, 7,313,529B2, 7,315,759B2, 7,317,941B2, 7,317,946B2, 7,319,898B2, 7,319,899B2, 7,319,901B2, 9,138,537B2, 9,101,715B2, 7,324,949B2, 9,272,140B2, 7,328,070B2, 7,328,131B2, 8,792,982B2, 7,856,987B2, 9,065,145B2, 7,342,508B2, 7,953,494B2, 7,345,607B1, 7,695,859B2, 7,519,261B2, 7,765,088B2, 7,363,078B2, 7,363,087B2, 8,335,568B2, 7,367,951B2, 7,369,891B2, 7,371,228B2, 7,899,546B2, 7,377,940B2, 7,381,180B2, 7,381,215B2, 7,383,734B2, 8,354,881B2, 8,700,154B2, 7,386,351B2, 7,387,624B2, 7,389,146B2, 9,197,173B2, 7,392,082B2, 7,400,924B2, 8,831,737B2, 7,412,282B2, 7,537,493B2, 7,415,307B2, 7,429,938B1, 7,433,736B2, 7,437,194B2, 7,438,686B2, 7,442,183B2, 7,442,721B2, 7,457,658B2, 7,460,910B2, 7,463,917B2, 9,186,517B2, 7,463,934B2, 7,467,014B2, 7,470,233B2, 8,940,522B2, 7,474,247B1, 7,474,916B2, 7,474,920B2, 7,474,923B2, 7,477,943B2, 7,479,910B1, 7,483,748B2, 8,155,749B2, 8,337,431B2, 7,491,246B2, 7,493,159B2, 8,005,551B2, 7,496,403B2, 7,496,408B2, 7,496,409B2, 7,916,448B2, 7,856,269B2, 8,843,203B2, 7,505,816B2, 7,512,431B2, 8,880,184B2, 7,953,482B2, 7,515,961B2, 7,515,967B2, 7,519,409B2, 7,831,311B2, 7,519,433B2, 8,072,338B2, 7,524,331B2, 7,526,335B2, 7,526,339B2, 7,848,796B2, 7,526,341B2, 8,229,568B2, 8,233,994B2, 7,536,224B2, 7,537,245B2, 7,537,474B2, 7,539,004B2, 7,539,540B2, 7,539,545B2, 7,974,677B2, 7,542,799B2, 8,032,224B2, 7,546,166B2, 7,548,784B2, 7,551,960B2, 9,149,628B2, 7,556,886B2, 8,135,470B2, 7,559,900B2, 7,561,911B2, 7,561,913B2, 7,736,192B2, 7,563,231B2, 7,565,196B2, 7,697,994B2, 7,953,471B2, 8,792,971B2, 7,570,996B2, 8,706,253B2, 7,574,266B2, 8,523,773B2, 8,260,418B2, 7,578,828B2, 7,579,106B2, 7,582,068B2, 7,590,450B2, 8,401,649B2, 7,593,773B2, 7,593,777B2, 7,594,889B2, 8,280,478B2, 8,062,074B2, 7,976,534B2, 8,415,319B2, 7,606,615B2, 7,622,303B2, 7,610,083B2, 8,150,513B2, 7,613,512B2, 7,616,992B2, 7,616,995B2, 8,233,990B2, 7,620,446B2, 7,620,454B2, 7,623,053B2, 7,623,917B2, 8,355,783B2, 7,627,376B2, 7,632,234B2, 8,233,984B2, 7,641,992B2, 7,647,103B2, 7,647,111B2, 7,647,116B2, 7,647,121B2, 8,285,388B2, 7,653,437B2, 7,654,843B2, 7,657,300B2, 9,199,090B2, 7,657,325B2, 7,658,737B2, 8,275,444B2, 7,660,630B2, 8,792,986B2, 7,667,954B2, 7,668,597B2, 7,668,600B2, 7,672,715B2, 8,200,333B2, 7,672,731B2, 7,676,268B2, 7,678,101B2, 7,680,539B2, 7,680,540B2, 7,682,316B2, 7,684,171B2, 7,684,855B2, 9,393,408B2, 7,684,872B2, 7,685,005B2, 7,687,268B2, 7,691,400B2, 8,968,763B2, 8,818,489B2, 7,696,259B2, 7,697,972B2, 8,706,222B2, 7,699,832B2, 7,699,892B2, 7,706,869B2, 7,706,889B2, 8,131,370B2, 8,428,712B2, 7,713,656B2, 7,714,757B2, 7,715,906B2, 7,715,919B2, 8,758,242B2, 7,720,543B2, 8,825,175B2, 8,175,695B2, 7,725,177B2, 7,725,190B2, 7,729,754B2, 7,729,764B2, 8,050,763B2, 9,037,257B2, 7,729,783B2, 7,734,345B2, 7,734,346B2, 7,736,392B2, 7,738,948B2, 7,738,951B2, 7,738,960B2, 8,706,255B2, 7,742,816B2, 7,742,818B2, 7,742,822B2, 7,748,093B2, 8,939,737B2, 7,753,962B2, 8,340,769B2, 7,914,343B2, 8,417,346B2, 9,216,294B2, 9,173,678B2, 7,763,035B2, 7,763,827B2, 7,764,988B2, 7,764,989B2, 7,765,012B2, 7,766,826B2, 7,767,652B2, 8,332,031B2, 7,769,451B2, 7,769,458B2, 8,761,888B2, 9,125,607B2, 7,774,056B2, 8,738,148B2, 7,774,072B2, 8,332,038B2, 7,776,351B2, 8,777,851B2, 7,783,350B2, 7,783,355B2, 8,209,032B2, 7,785,264B2, 7,785,741B2, 7,787,944B2, 7,787,947B2, 7,790,461B2, 7,792,580B2, 7,792,584B2, 7,904,170B2, 9,393,416B2, 7,801,613B2, 7,801,623B2, 7,803,164B2, 7,805,189B2, 7,805,200B2, 8,151,801B2, 8,423,146B2, 7,811,600B2, 7,815,927B2, 7,818,059B2, 7,818,060B2, 7,818,180B2, 7,819,909B2, 7,824,805B2, 7,826,895B2, 7,831,303B2, 7,831,304B2, 7,831,312B2, 8,706,185B2, 7,835,793B2, 7,835,795B2, 7,837,743B2, 7,839,620B2, 7,840,276B2, 7,844,347B2, 8,025,644B2, 8,755,882B2, 7,848,808B2, 7,962,211B2, 7,850,615B2, 7,852,052B2, 8,731,656B2, 7,855,653B2, 7,858,107B2, 7,860,568B2, 8,485,979B2, 7,867,221B2, 8,774,915B2, 8,032,216B2, 7,869,876B2, 7,873,410B2, 7,873,418B2, 8,152,730B2, 7,875,008B2, 8,015,978B2, 7,879,495B2, 7,881,765B2, 7,881,770B2, 7,885,712B2, 7,890,162B2, 7,890,181B2, 7,904,179B2, 7,892,595B2, 7,892,840B2, 8,849,400B2, 8,620,416B2, 7,894,898B2, 7,894,899B2, 7,894,908B2, 7,896,813B2, 7,897,168B2, 8,498,705B2, 8,389,331B2, 7,904,153B2, 7,904,158B2, 7,904,168B2, 7,912,537B2, 8,494,648B2, 7,912,552B2, 7,913,015B2, 9,259,177B2, 8,346,355B2, 8,478,409B2, 7,917,228B2, 8,089,787B2, 7,925,322B2, 7,927,282B2, 7,927,326B2, 7,927,738B2, 7,928,818B2, 9,031,649B2, 7,930,026B2, 7,930,037B2, 7,930,039B2, 8,281,408B2, 7,931,643B2, 9,040,045B2, 9,072,832B2, 7,933,653B2, 7,933,658B2, 7,935,062B2, 7,935,705B2, 7,935,935B2, 8,554,315B2, 7,937,149B2, 8,521,286B2, 7,941,213B2, 7,941,225B2, 7,941,226B2, 8,920,389B2, 8,430,852B2, 7,949,391B2, 7,949,392B2, 7,949,404B2, 7,951,137B2, 7,953,488B2, 7,953,492B2, 7,955,385B2, 7,955,512B2, 7,983,755B2, 7,957,812B2, 9,259,587B2, 7,963,922B2, 8,131,369B2, 8,480,655B2, 7,972,273B2, 8,849,385B2, 8,527,039B2, 8,185,207B2, 7,984,717B2, 8,428,718B2, 7,988,635B2, 7,988,674B2, 7,991,456B2, 7,991,467B2, 7,991,471B2, 8,961,598B2, 7,996,070B2, 7,996,084B2, 8,000,532B2, 9,014,804B2, 8,352,030B2, 9,192,769B2, 9,108,063B2, 8,657,587B2, 8,048,152B2, 8,010,207B2, 8,012,127B2, 8,224,458B2, 8,539,956B2, 8,016,814B2, 8,016,859B2, 8,016,877B2, 8,019,420B2, 8,019,433B2, 8,019,437B2, 8,021,299B2, 8,021,421B2, 8,021,679B2, 8,473,053B2, 9,333,078B2, 8,032,221B2, 8,033,998B2, 8,036,749B2, 8,041,424B2, 8,041,427B2, 8,041,433B2, 8,046,063B2, 8,046,064B2, 8,046,072B2, 8,048,042B2, 8,048,409B2, 8,050,750B2, 8,050,751B2, 8,050,759B2, 8,050,771B2, 8,052,610B2, 8,551,113B2, 8,055,322B2, 8,700,143B2, 8,059,386B2, 8,059,628B2, 8,062,227B2, 8,064,999B2, 8,065,006B2, 8,065,007B2, 8,437,856B2, 8,280,521B2, 8,067,024B2, 8,068,903B2, 8,068,910B2, 8,068,917B2, 9,172,192B2, 8,781,585B2, 8,078,285B2, 8,233,977B2, 8,082,037B2, 8,083,730B2, 8,086,307B2, 8,086,323B2, 8,090,566B2, 8,095,225B2, 8,099,164B2, 8,099,170B2, 8,100,871B2, 8,457,750B2, 8,108,043B2, 8,108,044B2, 8,108,048B2, 8,112,159B2, 8,118,750B2, 8,121,691B2, 8,121,705B2, 8,126,539B2, 8,126,549B2, 8,127,582B2, 8,128,616B2, 8,679,518B2, 8,129,477B1, 9,042,982B2, 8,136,431B2, 8,137,687B2, 8,140,156B2, 8,630,717B2, 8,140,171B2, 8,141,556B2, 8,145,313B2, 8,594,801B2, 8,147,275B1, 8,147,898B2, 8,515,549B2, 8,155,742B2, 8,155,758B2, 9,393,115B2, 9,259,589B2, 8,160,707B2, 8,668,666B2, 8,622,998B2, 8,165,676B2, 8,165,691B2, 8,170,515B2, 8,170,636B2, 8,170,666B2, 8,172,760B2, 8,731,641B2, 8,175,706B2, 8,175,720B2, 8,182,830B2, 8,185,206B2, 8,187,181B2, 8,187,200B2, 8,190,251B2, 8,190,260B2, 9,192,763B2, 8,192,398B2, 8,192,418B2, 8,193,766B2, 8,195,294B2, 8,200,322B2, 8,200,329B2, 8,290,593B2, 8,204,593B2, 8,204,597B2, 8,676,337B2, 8,568,389B2, 9,179,860B2, 8,209,016B2, 8,209,018B2, 8,905,948B2, 8,211,028B2, 8,214,045B2, 8,214,156B2, 8,216,158B2, 8,219,196B2, 8,219,199B2, 8,219,200B2, 8,219,202B2, 8,219,204B2, 9,327,129B2, 8,219,207B2, 8,219,213B2, 8,221,354B2, 8,224,447B2, 8,229, 558B2, 8,229,559B2, 8,229,560B2, 8,229,567B2, 9,026, 223B2, 8,233,986B2, 8,236,341B2, 8,236,442B2, 8,753, 331B2, 8,241,619B2, 8,244,339B2, 8,244,355B2, 8,751, 001B2, 8,801,668B2, 8,825,160B2, 8,255,046B2, 8,256, 425B2, 8,260,412B2, 8,512,254B2, 8,660,643B2, 8,260, 422B2, 8,265,750B2, 8,265,769B2, 8,265,770B2, 8,265, 771B2, 8,271,072B2, 8,271,089B2, 8,275,432B2, 8,275, 435B2, 8,875,602B2, 8,278,871B2, 8,280,500B2, 8,280, 517B2, 8,282,625B2, 8,285,379B2, 8,287,520B2, 8,290, 557B2, 8,290,588B2, 8,292,842B2, 8,292,948B2, 8,295, 929B2, 8,295,933B2, 8,295,938B2, 8,630,719B2, 8,298, 153B2, 9,302,082B2, 8,298,564B2, 8,301,110B2, 8,301, 233B2, 8,301,265B2, 8,306,620B2, 8,306,624B2, 8,313, 762B2, 8,314,594B2, 9,008,789B2, 8,323,267B2, 8,326, 431B2, 8,328,867B2, 8,331,077B2, 8,332,011B2, 8,332, 032B2, 8,332,042B2, 8,332,045B2, 8,333,728B2, 8,813, 753B2, 8,340,750B2, 8,340,759B2, 8,340,783B2, 8,346, 190B2, 9,259,584B2, 8,348,909B2, 8,349,003B2, 8,352, 028B2, 8,352,034B2, 8,352,038B2, 8,352,039B2, 8,352, 043B2, 8,355,774B2, 8,359,094B2, 8,359,098B2, 8,362, 742B2, 8,364,272B2, 8,369,946B2, 8,369,965B2, 8,497, 133B1, 8,373,075B2, 8,374,686B2, 8,374,700B2, 8,380, 294B2, 8,380,295B2, 8,380,309B2, 8,401,648B2, 8,380, 320B2, 8,386,051B2, 8,386,053B2, 8,391,964B2, 8,391, 975B2, 8,391,978B2, 9,126,049B2, 8,395,880B2, 8,396, 543B2, 8,504,165B2, 8,396,565B2, 8,398,610B2, 8,401, 643B2, 8,718,770B2, 9,055,974B2, 8,406,893B2, 8,406, 901B2, 8,409,219B2, 8,412,351B2, 9,204,842B2, 8,419, 710B2, 8,888,699B2, 8,423,141B2, 9,265,650B2, 8,428, 697B2, 8,428,717B2, 9,020,594B2, 8,428,744B2, 8,430, 651B2, 8,433,396B2, 8,433,402B2, 8,433,408B2, 8,433, 409B2, 8,435,186B2, 8,436,251B2, 8,437,837B2, 8,437, 840B2, 8,437,850B2, 8,437,851B2, 8,755,901B2, 8,467, 882B2, 8,438,039B2, 8,442,627B2, 8,442,651B2, 8,444, 609B2, 8,445,008B2, 8,447,406B2, 8,447,408B2, 8,447, 413B2, 8,449,602B2, 8,706,218B2, 8,452,396B2, 8,452, 402B2, 8,452,414B2, 8,454,566B2, 8,461,681B2, 8,463, 393B2, 8,467,870B2, 8,473,056B2, 8,473,063B2, 8,475, 407B2, 8,478,400B2, 8,478,402B2, 8,478,424B2, 8,532, 790B2, 9,113,812B2, 8,483,813B2, 8,483,833B2, 9,259, 572B2, 8,489,164B2, 8,489,168B2, 8,489,189B2, 8,491, 547B2, 8,761,886B2, 8,497,804B2, 8,500,713B2, 8,504, 154B2, 8,504,156B2, 8,506,550B2, 8,509,893B2, 8,509, 909B2, 8,509,912B2, 8,512,286B2, 8,512,312B2, 8,512, 731B2, 8,513,120B2, 8,521,281B2, 8,525,027B2, 9,026, 206B2, 8,527,046B2, 8,527,059B2, 8,532,741B2, 8,532, 769B2, 8,532,775B2, 8,534,293B2, 8,535,280B2, 9,381, 084B2, 8,535,704B2, 8,538,538B2, 8,540,642B2, 8,541, 131B2, 8,543,214B2, 8,545,484B2, 8,548,543B2, 8,554, 314B2, 8,554,331B2, 8,555,891B2, 8,557,273B2, 8,560, 064B2, 8,565,865B2, 8,565,872B2, 8,568,474B2, 9,132, 268B2, 8,571,677B2, 8,571,678B2, 9,047,708B2, 8,578, 118B2, 8,579,786B2, 8,579,824B2, 8,579,965B2, 8,583, 221B1, 8,583,233B2, 8,588,915B2, 8,588,916B2, 8,588, 932B2, 8,588,935B2, 9,360,447B2, 8,593,816B2, 8,594, 775B2, 8,594,798B2, 8,597,042B2, 8,600,478B2, 8,606, 355B1, 8,608,481B2, 8,608,729B2, 8,774,918B2, 8,612, 021B2, 8,612,055B2, 8,612,167B2, 8,615,299B2, 8,617, 082B2, 8,620,449B2, 8,744,597B2, 9,364,646B2, 8,626, 287B2, 8,626,310B2, 9,079,014B2, 8,712,539B2, 9,247, 883B2, 9,168,371B2, 8,634,903B2, 8,634,911B2, 8,855, 780B2, 8,634,925B2, 8,634,926B2, 9,393,434B2, 8,639, 316B2, 8,639,323B2, 9,233,249B2, 8,639,328B2, 8,639, 335B2, 8,639,340B2, 8,639,341B2, 8,641,659B2, 8,644, 923B2, 9,089,704B2, 8,644,931B2, 8,644,932B2, 8,644, 936B2, 8,644,948B2, 8,995,949B2, 8,649,852B2, 8,660, 635B2, 8,660,662B2, 8,666,511B2, 9,008,779B2, 8,790, 295B1, 8,673,194B2, 8,673,339B2, 8,676,289B2, 8,676, 319B2, 8,676,320B2, 8,682,437B2, 8,688,200B2, 8,688, 201B2, 8,688,238B2, 8,691,258B2, 8,694,097B2, 8,694, 125B2, 8,694,128B2, 8,696,689B2, 8,700,155B2, 8,700, 157B2, 8,700,174B2, 8,706,181B2, 8,706,220B2, 8,706, 228B2, 8,706,229B2, 8,706,237B2, 8,708,934B2, 8,712, 509B2, 9,345,896B2, 9,174,059B2, 9,318,916B2, 8,717, 430B2, 8,718,762B2, 8,718,769B2, 8,720,276B2, 8,721, 587B2, 8,721,661B2, 8,725,263B2, 8,727,996B2, 8,730, 032B2, 8,731,663B2, 8,731,669B2, 8,738,121B2, 8,738, 132B1, 8,744,560B2, 9,072,914B2, 9,220,905B2, 8,744, 578B2, 8,996,123B2, 8,750,961B1, 8,750,976B2, 8,751, 000B2, 9,278,223B2, 8,751,009B2, 8,751,010B2, 8,755, 881B2, 8,758,365B2, 8,768,486B2, 8,774,909B2, 8,777, 850B2, 8,777,874B2, 8,777,932B2, 8,778,521B2, 8,781, 547B2, 8,781,582B2, 8,781,595B2, 8,784,478B2, 8,788, 028B2, 8,788,055B2, 8,795,260B2, 8,795,352B2, 8,798, 723B2, 8,798,750B2, 8,798,751B2, 8,798,759B2, 8,801, 706B2, 8,801,728B2, 8,805,496B2, 8,805,505B1, 8,805, 508B2, 8,805,518B2, 8,805,528B2, 8,805,537B1, 9,314, 612B2, 8,810,394B2, 8,814,798B2, 8,818,508B2, 8,818, 523B2, 8,823,382B2, 8,824,161B2, 9,079,040B2, 8,825, 180B2, 8,827,904B2, 8,827,913B2, 8,831,721B2, 8,831, 723B2, 8,834,392B2, 8,838,242B2, 8,838,251B2, 8,838, 254B2, 8,872,035B2, 8,842,893B2, 8,843,209B2, 9,061, 161B2, 8,855,755B2, 8,855,765B2, 8,855,777B2, 8,858, 619B2, 8,862,212B2, 8,862,451B2, 8,868,201B2, 9,089, 695B2, 8,871,238B2, 8,874,197B2, 8,874,237B2, 8,876, 727B2, 8,876,892B2, 8,880,186B2, 9,149,633B2, 8,900, 190B2, 8,884,779B2, 8,886,302B2, 8,886,311B2, 9,168, 379B2, 8,886,323B2, 8,887,619B2, 8,888,847B2, 8,890, 681B2, 8,891,847B2, 8,892,204B2, 8,892,214B2, 8,892, 217B2, 8,897,868B2, 8,903,473B2, 8,903,492B2, 8,903, 497B2, 9,216,286B2, 8,909,329B2, 8,909,351B2, 8,911, 427B2, 8,914,101B2, 8,916,004B2, 8,916,290B2, 8,918, 176B2, 8,918,187B2, 9,375,580B2, 8,923,976B2, 8,924, 023B2, 8,926,523B2, 9,132,217B2, 8,926,692B2, 8,929, 995B2, 8,934,973B2, 8,936,630B2, 8,938,292B2, 8,939, 905B2, 8,940,799B2, 8,942,795B2, 8,983,619B2, 8,942, 935B2, 8,945,145B2, 8,945,146B2, 8,945,451B2, 8,948, 868B2, 8,948,883B2, 8,954,008B2, 8,954,160B2, 8,954, 162B2, 8,958,870B2, 8,958,875B2, 8,961,505B2, 8,965, 506B2, 8,972,005B2, 8,974,524B2, 8,977,350B2, 8,979, 825B2, 8,983,606B2, 8,983,618B2, 8,983,620B2, 8,986, 371B2, 8,986,372B2, 8,989,840B2, 8,989,872B2, 8,989, 873B2, 8,990,924B2, 8,995,731B2, 8,996,111B2, 8,996, 113B2, 8,998,841B2, 8,998,929B2, 9,002,447B2, 9,002, 454B2, 9,220,911B2, 9,131,858B2, 9,008,744B2, 9,008, 773B2, 9,008,782B2, 9,008,788B2, 9,014,815B2, 9,259, 578B2, 9,020,610B2, 9,035,844B2, 9,037,237B2, 9,037, 240B2, 9,037,263B2, 9,042,983B2, 9,042,995B2, 9,272, 091B2, 9,056,153B2, 9,056,206B2, 9,061,146B2, 9,095, 715B2, 9,061,163B2, 9,061,373B2, 9,067,042B2, 9,072, 447B2, 9,248,288B2, 9,101,776B2, 9,077,030B2, 9,078, 781B2, 9,079,039B2, 9,084,901B2, 9,095,284B2, 9,095, 728B2, 9,099,720B2, 9,101,281B2, 9,106,004B2, 9,283, 381B2, 9,122,785B2, 9,123,107B2, 9,126,031B2, 9,132, 008B2, 9,132,274B2, 9,136,728B2, 9,138,574B2, 9,138, 576B2, 9,138,584B2, 9,144,681B2, 9,144,685B2, 9,149, 627B2, 9,149,635B2, 9,149,638B2, 9,155,897B2, 9,162, 072B2, 9,168,374B2, 9,168,376B2, 9,168,380B1, 9,168, 384B2, 9,174,055B2, 9,174,058B2, 9,179,984B2, 9,180, 303B2, 9,185,087B2, 9,185,489B2, 9,186,509B2, 9,186, 513B2, 9,186,519B2, 9,192,719B2, 9,192,738B2, 9,192, 758B2, 9,192,770B2, 9,199,078B1, 9,199,086B2, 9,205, 182B2, 9,205,252B2, 9,205,268B2, 9,209,824B2, 9,211, 252B2, 9,216,257B2, 9,216,293B2, 9,216,295B2, 9,216, 297B2, 9,220,890B2, 9,220,902B2, 9,220,906B2, 9,220,913B2, 9,227,069B2, 9,232,898B2, 9,238,135B2, 9,240,117B2, 9,242,086B2, 9,242,108B2, 9,242,109B2, 9,248,300B2, 9,252,415B2, 9,254,350B2, 9,254,392B2, 9,259,163B2, 9,259,312B2, 9,259,530B2, 9,259,571B2, 9,265,953B2, 9,265,954B2, 9,265,955B2, 9,270,134B2, 9,271,856B2, 9,272,147B2, 9,278,219B2, 9,278,220B2, 9,278,229B1, 9,283,382B2, 9,283,396B2, 9,289,145B2, 9,289,607B2, 9,289,612B1, 9,289,613B2, 9,295,826B2, 9,295,850B2, 9,301,698B2, 9,301,834B2, 9,302,043B2, 9,302,100B2, 9,314,205B2, 9,314,572B2, 9,320,470B2, 9,320,901B2, 9,320,905B2, 9,326,711B2, 9,326,854B2, 9,327,070B2, 9,327,117B2, 9,327,133B2, 9,339,197B2, 9,339,601B2, 9,339,657B2, 9,345,185B2, 9,345,892B2, 9,345,895B2, 9,348,974B2, 9,351,648B2, 9,352,125B2, 9,362,660B2, 9,362,774B2, 9,364,162B2, 9,370,654B2, 9,375,181B2, 9,375,440B2, 9,375,578B2, 9,381,039B2, 9,381,362B2, 9,381,366B2, 9,381,367B2, 9,386,927B2, 9,387,318B2, 9,387,330B2, 9,387,331B2, 9,393,404B2, 9,393,424B2, 9,393,432B2, 9,398,901B2, 9,399,091B2, 9,399,130B2, 9,399,140B2, 9,399,141B2, 9,399,143B2, 9,401,562B2, 9,401,894B2, U.S. D438204S1, U.S. D461560S1, U.S. D523144S1, U.S. RE32227E1, U.S. RE32361E1, U.S. RE45509E1, U.S. RE42682E1, U.S. RE43952E1, or U.S. RE44075E1.

Devices included herein include devices described in, or substantially similar in terms of structure or function to devices described in, a Novo Nordisk patent document.

Devices included herein include devices described in, or substantially similar in terms of structure or function to devices described in, a Johnson & Johnson patent document.

Devices included herein include devices described in, or substantially similar in terms of structure or function to devices described in, an Allergan patent document.

Devices included herein include devices, e.g., catheters, described in, or substantially similar in terms of structure or function to devices described in, one or more of the following patent documents: US20010000802A1, U.S. Pat. No. 6,481,440B2, US20140148805A1, U.S. Pat. Nos. 7,338,487B2, 7,189,222B2, 7,069,634B1, 6,549,811B2, US20010039419A1, US20030144731A1, US20050096701A1, US20020019629A1, U.S. Pat. Nos. 8,956,402B2, 6,572,645B2, US20050234432A1, US20040162601A1, U.S. Pat. Nos. 7,442,183B2, 6,659,981B2, WO2002058465A9, U.S. Pat. Nos. 6,785,576B2, 6,571,125B2, US20040073099A1, US20020138123A1, US20040230278A1, U.S. Pat. No. 6,697,676B2, US20050004611A1, US20140343549A1, U.S. Pat. Nos. 6,679,860B2, 7,909,794B2, U.S. Pat. No. 6,771,737B2, US20030045786A1, U.S. Pat. Nos. 6,799,991B2, 6,699,240B2, 7,337,011B2, U.S. Pat. No. 6,607,478B2, WO2003073942A3, WO2003047676A1, U.S. Pat. No. 7,065,394B2, US20080188796A1, U.S. Pat. Nos. 6,921,295B2, 7,029,460B2, US20040198864A1, U.S. Pat. No. 6,939,338B2, US20060084941A1, US20030216700A1, US20040033251A1, U.S. Pat. No. 6,923,788B2, US20040039437A1, U.S. Pat. No. 7,018,384B2, US20040047911A1, US20060160899A1, US20110046457A1, US20040067221A1, U.S. Pat. No. 7,044,932B2, US20040086543A1, US20040086569A1, US20070106201A1, U.S. Pat. Nos. 8,852,173B2, 7,189,215B2, US20040111150A1, US20040115273A1, US20040127978A1, U.S. Pat. Nos. 7,052,486B2, 7,715,919B2, US20070079836A1, U.S. Pat. Nos. 8,957,198B2, 7,001,421B2, US20120245533A1, U.S. Pat. No. 7,413,564B2, WO2004078248A1, US20040193107A1, U.S. Pat. Nos. 7,153,292B2, 7,162,309B2, 7,273,486B2, 7,163,555B2, 7,198,637B2, WO2004093933A1, U.S. Pat. Nos. 7,182,744B2, 8,940,522B2, 7,208,001B2, 7,238,182B2, US20060217698A1, US20040215181A1, US20040215213A1, U.S. Pat. Nos. 7,797,049B2, 8,246,602B2, 7,371,249B2, 6,989,027B2, US20040230176A1, US20040230182A1, U.S. Pat. No. 8,396,549B2, US20040230298A1, US20040236395A1, US20040236399A1, U.S. Pat. No. 6,953,425B2, US20040242990A1, US20040243022A1, US20040243214A1, US20040243224A1, U.S. Pat. No. 8,972,003B2, US20060009834A1, U.S. Pat. Nos. 7,115,179B2, 7,105,015B2, WO2004112655A1, WO2004112657A1, WO2005002658A1, U.S. Pat. Nos. 8,454,566B2, 7,387,626B2, 7,427,280B2, US20050019919A1, U.S. Pat. No. 7,875,008B2, US20050021128A1, US20060265140A1, WO2005011786A1, U.S. Pat. No. 7,041,080B2, US20060247603A1, U.S. Pat. No. 7,303,574B2, WO2006019634A1, U.S. Pat. No. 7,951,129B2, US20050043786A1, US20050049693A1, US20050049694A1, U.S. Pat. Nos. 7,818,040B2, 7,104,989B2, 7,156,843B2, US20050055078A1, WO2005094931A1, US20160074600A1, U.S. Pat. Nos. 7,208,008B2, 8,801,692B2, US20050079199A1, U.S. Pat. No. 7,022,116B2, US20090214612A1, U.S. Pat. Nos. 7,682,358B2, 6,994,718B2, U.S. Pat. Nos. 7,252,665B2, 7,517,337B2, US20050107819A1, U.S. Pat. No. 7,276,045B2, US20050118370A1, U.S. Pat. No. 8,883,716B2, US20050131344A1, US20050131446A1, US20050137683A1, WO2006036192A1, US20050143729A1, US20050143803A1, WO2005065537A1, U.S. Pat. No. 8,025,644B2, US20050149174A1, US20050152940A1, US20050152942A1, US20050152943A1, WO2005067820A2, US20050154451A1, US20050154452A1, US20050154455A1, U.S. Pat. Nos. 7,416,555B2, 7,657,323B2, 8,019,437B2, US20050182384A1, US20050182389A1, US20050182474A1, US20050187430A1, US20050197691A1, WO2005089674A1, US20110213328A1, WO2005089850A3, US20080039784A1, U.S. Pat. No. 8,794,437B2, US20050228490A1, U.S. Pat. No. 7,033,344B2, US20050245923A1, WO2005110542A1, U.S. Pat. No. 7,818,039B2, US20050256510A1, US20050256541A1, U.S. Pat. No. 8,048,149B2, US20050260157A1, U.S. Pat. No. 9,220,490B2, WO2005113058A1, US20050261762A1, U.S. Pat. No. 7,955,371B2, US20050267562A1, U.S. Pat. No. 8,706,260B2, US20050276863A1, U.S. Pat. Nos. 8,048,409B2, 7,331,948B2, 7,717,950B2, 8,388,671B2, US20100249897A1, U.S. Pat. No. 7,767,652B2, WO2006020230A2, U.S. Pat. No. 7,651,525B2, WO2006019712A1, WO2006023859A1, U.S. Pat. Nos. 7,815,597B2, 7,294,117B2, 7,819,841B2, US20060047265A1, US20060051392A1, US20130023814A1, U.S. Pat. No. 7,597,703B2, US20060062822A1, U.S. Pat. No. 7,867,269B2, US20060074396A1, US20060074477A1, WO2006041649A1, U.S. Pat. No. 7,283,878B2, US20060079951A1, US20060085012A1, U.S. Pat. No. 7,842,070B2, US20080051871A1, WO2006047378A2, WO2006047676A1, US20060095005A1, WO2006050396A3, U.S. Pat. No. 7,727,199B2, WO2006052521A3, US20060100492A1, US20060100689A1, US20060106420A1, US20060127158A1, U.S. Pat. No. 7,947,378B2, US20060129221A1, US20060135948A1, U.S. Pat. Nos.

7,575,590B2, 8,435,286B2, US20060167474A1, U.S. Pat. No. 8,979,801B2, US20110172606A1, WO2006083744A1, WO2006086161A1, U.S. Pat. No. 8,214,015B2, US20060184186A1, US20060184225A1, US20060184227A1, US20060184236A1, U.S. Pat. Nos. 7,537,245B2, 7,955,385B2, US20060210600A1, U.S. Pat. No. 7,653,432B2, US20060229561A1, U.S. Pat. Nos. 7,828,832B2, 7,771,464B2, US20060241342A1, U.S. Pat. Nos. 7,955,384B2, 7,909,810B2, 7,824,369B2, WO2006122045A1, US20060257445A1, U.S. Pat. No. 8,740,833B2, WO2006124353A3, U.S. Pat. Nos. 7,678, 101B2, 7,387,624B2, 7,427,288B2, US20060282161A1, US20060287702A1, US20060293698A1, U.S. Pat. No. 7,912,539B2, 8,057,466B2, WO2007112135A2, U.S. Pat. No. 9,345,858B2, WO2007018823A1, WO2007015876A1, U.S. Pat. No. 7,674,252B2, US20070043420A1, U.S. Pat. No. 7,473,272B2, U.S. Pat. No. 7,655,040B2, WO2007030266A2, U.S. Pat. Nos. 8,968,379B2, 8,206, 428B2, WO2008027665A1, US20070067020A1, U.S. Pat. No. 9,242,074B2, US20070078513A1, US20100152845A1, U.S. Pat. No. 7,749,262B2, US20070093869A1, US20070098703A1, U.S. Pat. No. 8,295,947B2, US20070100439A1, U.S. Pat. No. 8,298,210B2, U.S. Pat. No. 9,084,872B2, US20070123925A1, US20070123926A1, US20100241179A1, U.S. Pat. Nos. 8,333,728B2, 7,931, 646B2, 7,473,230B2, WO2008073695A2, US20070142779A1, US20110282264A1, WO2008124303A3, US20070142905A1, US20070161590A1, U.S. Pat. No. 9,078,781B2, WO2007111724A3, WO2007117726A2, US20070170623A1, U.S. Pat. No. 9,173,678B2, WO2007090074A1, US20070179496A1, U.S. Pat. No. 8,067,024B2, US20070208256A1, US20070208381A1, US20070208410A1, US20070219576A1, US20070225674A1, US20070225680A1, US20070225681A1, U.S. Pat. No. 7,955,512B2, WO2007112159A3, US20070231361A1, WO2007115152A3, WO2007115017A1, U.S. Pat. No. 7,625,403B2, WO2007117768A2, U.S. Pat. No. 7,955, 365B2, WO2007121055A1, US20070238979A1, WO2007121078A3, US20070239252A1, U.S. Pat. Nos. 7,524,331B2, 7,740,655B2, US20070239269A1, U.S. Pat. Nos. 7,591,848B2, 7,442,721B2, 8,066,760B2, WO2007121072A2, US20070244546A1, US20070244547A1, U.S. Pat. Nos. 8,454,683B2, 8,303, 569B2, 7,442,207B2, 8,551,161B2, US20070253994A1, US20070253995A1, US20070253998A1, WO2007127530A1, US20070255333A1, U.S. Pat. No. 9,084,901B2, US20070255396A1, U.S. Pat. No. 8,241, 619B2, US20110104234A1, WO2007133884A1, WO2007133883A3, US20070283969A1, US20070288000A1, US20080006554A1, U.S. Pat. No. 7,731,653B2, US20100174353A1, U.S. Pat. Nos. 8,152, 804B2, 7,811,304B2, 8,206,350B2, US20080039738A1, US20080039768A1, WO2008033632A1, U.S. Pat. No. 7,955,640B2, WO2008039917A2, US20140171791A1, US20100042039A1, U.S. Pat. No. 8,150,497B2, US20080097570A1, U.S. Pat. No. 8,945,089B2, US20080103476A1, U.S. Pat. No. 8,688,238B2, WO2008054441A1, US20080103573A1, US20080103575A1, WO2008054446A1, WO2008054444A1, US20080103578A1, US20080103580A1, U.S. Pat. Nos. 7,963,960B2, 7,682, 365B2, 8,298,564B2, US20080125744A1, US20140188149A1, US20080132982A1, WO2008070423A1, WO2008124222A1, U.S. Pat. No. 8,419,710B2, WO2008076653A1, WO2008079621A1, WO2008079557A1, U.S. Pat. Nos. 9,220,573B2, 8,473, 030B2, WO2008089133A1, US20080172119A1, WO2008094914A1, U.S. Pat. No. 7,682,388B2, 7,753, 962B2, 7,575,593B2, WO2008094936A3, WO2008106307A1, U.S. Pat. Nos. 8,273,402B2, 8,343, 181B2, WO2008112391A2, WO2008112390A2, U.S. Pat. Nos. 8,021,679B2, 8,871,238B2, 8,137,687B2, US20080233267A1, US20080234657A1, US20080234717A1, WO2008124306A2, U.S. Pat. No. 8,920,389B2, US20080245375A1, US20080249458A1, US20080249501A1, US20140058356A1, WO2008124309A1, US20080249618A1, US20110150966A1, US20080255507A1, U.S. Pat. No. 8,747,353B2, US20080255512A1, U.S. Pat. No. 7,879, 045B2, WO2008127875A1, U.S. Pat. No. 8,133,266B2, WO2008127888A2, WO2008130405A1, US20080262432A1, U.S. Pat. Nos. 7,833,218B2, 7,806, 917B2, WO2008130795A1, U.S. Pat. Nos. 8,010,177B2, 8,311,611B2, US20080269641A1, U.S. Pat. Nos. 8,945, 114B2, 8,814,856B2, US20080269869A1, US20080269876A1, WO2008137300A1, US20080289300A1, US20080305143A1, U.S. Pat. Nos. 8,328,867B2, 9,186,207B2, 8,852,620B2, 8,205,317B2, WO2009014916A2, US20090036799A1, US20090053208A1, US20090054836A1, WO2009032588A1, WO2009042338A1, WO2009048813A1, US20090118811A1, WO2009064603A1, WO2009064672A3, US20090132019A1, U.S. Pat. Nos. 8,016,880B2, 8,876, 774B2, 8,600,470B2, 8,070,720B2, 8,021,379B2, WO2009088783A3, U.S. Pat. No. 8,603,038B2, U.S. Pat. No. 7,766,860B2, WO2009097165A2, U.S. Pat. No. 9,364, 324B2, WO2009099682A2, WO2009099807A3, WO2009102591A1, US20090204104A1, US20090222088A1, U.S. Pat. No. 8,016,814B2, WO2009111126A1, US20090230167A1, WO2009117182A2, WO2009117183A1, US20090234227A1, US20090234282A1, U.S. Pat. No. 8,197,475B2, US20090238815A1, U.S. Pat. No. 8,066, 677B2, US20090240238A1, US20110295355A1, U.S. Pat. No. 8,052,738B2, US20090248034A1, U.S. Pat. No. 8,016, 842B2, US20150250986A1, US20090248139A1, US20140046424A1, US20090254105A1, US20090254113A1, US20090259174A1, U.S. Pat. No. 8,287,520B2, WO2009129276A2, US20090259285A1, US20090259290A1, US20090259293A1, US20090259296A1, US20090259299A1, US20090264771A1, US20150045811A1, U.S. Pat. Nos. 8,206,430B2, 8,374,680B2, U.S. Pat. No. 8,016,799B2, US20090264859A1, US20090264863A1, US20090264898A1, US20090264906A1, U.S. Pat. No. 8,292,885B2, US20090264985A1, WO2010039644A2, US20090270714A1, U.S. Pat. Nos. 7,947,012B2, 7,942, 852B2, 8,398,591B2, 8,002,763B2, 8,142,415B2, US20090270964A1, US20090270966A1, US20090270976A1, US20150018839A1, US20090276027A1, US20090297576A1, WO2009148856A2, U.S. Pat. No. 9,056,157B2, US20150174394A1, WO2008108901A8, US20100010393A1, U.S. Pat. No. 9,061,123B2, US20100022940A1, US20100022943A1, US20110301625A1, US20100030063A1, US20100030196A1, US20140088693A1, US20100036238A1, US20100036471A1, U.S. Pat. No. 8,002,826B2, US20130296880A1, U.S. Pat. No. 7,954, 688B2, WO2010028063A8, WO2010033355A1, WO2010039587A1, US20100106234A1,

US20150094651A1, WO2011050458A1, US20100114283A1, WO2010059391A1, WO2011008332A1, U.S. Pat. No. 8,021,330B2, WO2010059388A2, US20100125282A1, WO2010056518A3, WO2010059387A1, WO2010059479A2, US20100129414A1, US20100185083A1, US20100131001A1, WO2010059561A3, WO2010065306A1, U.S. Pat. Nos. 8,731,641B2, 8,177,802B2, WO2010068382A3, US20110155149A1, U.S. Pat. No. 8,158,187B2, WO2010080304A1, US20100168833A1, US20100179565A1, US20100179632A1, WO2010082985A3, U.S. Pat. Nos. 8,862,451B2, 8,182,460B2, US20100196437A1, U.S. Pat. No. 8,282,620B2, US20100198338A1, US20100204687A1, U.S. Pat. No. 8,644,907B2, US20130218151A1, U.S. Pat. Nos. 9,339,630B2, 8,740,930B2, US20100217371A1, WO2010098940A2, US20100222846A1, US20100226893A1, U.S. Pat. No. 8,784,800B2, US20100227799A1, US20100230392A1, US20100234934A1, U.S. Pat. No. 9,144,667B2, US20100241140A1, US20100241163A1, US20120078165A1, U.S. Pat. No. 8,460,238B2, US20100249898A1, U.S. Pat. Nos. 9,066,785B2, 9,220,886B2, US20120269897A1, US20100261737A1, U.S. Pat. Nos. 8,086,293B2, 8,929,969B2, US20130345662A1, U.S. Pat. No. 8,764,777B2, WO2010120415A3, U.S. Pat. Nos. 8,518,060B2, 8,864,786B2, U.S. Pat. Nos. 8,709,465B2, 8,610,531B2, 8,890,681B2, WO2010120425A3, US20100268191A1, U.S. Pat. No. 7,942,917B2, US20100268317A1, U.S. Pat. Nos. 8,183,221B2, 8,876,877B2, 8,790,295B1, 8,292,941B2, 8,622,998B2, 9,026,223B2, US20100280595A1, U.S. Pat. Nos. 8,585,690B2, 8,162,975B2, 8,052,737B2, US20160166380A1, U.S. Pat. No. 8,207,138B2, US20100305428A1, U.S. Pat. No. 8,606,369B2, US20100324643A1, U.S. Pat. Nos. 9,226,995B2, 8,290,572B2, US20150182669A1, US20110052666A1, U.S. Pat. Nos. 8,494,613B2, 8,801,706B2, 8,029,562B2, US20110066029A1, US20110066226A1, WO2011037801A1, WO2011047463A1, WO2011049802A1, U.S. Pat. Nos. 8,372,055B2, 8,372,054B2, US20150157402A1, US20110106131A1, US20110125241A1, U.S. RE45865E1, U.S. Pat. No. 8,805,533B2, US20150209513A1, US20110144637A1, U.S. Pat. Nos. 8,241,311B2, 8,795,260B2, 8,983,619B2, US20110160790A1, U.S. Pat. No. 8,182,830B2, WO2011084175A1, U.S. Pat. Nos. 8,986,293B2, 9,089,314B2, US20150094701A1, U.S. Pat. No. 9,211,091B2, US20110190692A1, US20160166306A1, US20130138097A1, US20110190763A1, U.S. Pat. No. 8,287,526B2, US20110202127A1, U.S. Pat. No. 8,475,523B2, US20160192984A1, US20110208075A1, WO2011106354A1, WO2011106532A1, US20140012253A1, U.S. Pat. No. 8,206,374B2, US20110245782A1, US20110245821A1, U.S. Pat. Nos. 8,628,513B2, 8,398,610B2, 8,636,811B2, U.S. Pat. No. 8,454,682B2, WO2011133469A1, US20130123913A1, U.S. Pat. Nos. 9,237,961B2, 8,377,083B2, 8,834,499B2, 9,326,870B2, WO2011136883A1, US20140039610A1, US20110264206A1, U.S. Pat. Nos. 9,067,042B2, 8,777,932B2, 9,072,516B2, US20110270385A1, U.S. Pat. Nos. 9,023,096B2, 9,387,077B2, 8,734,780B2, US20110301575A1, US20120010691A1, US20120016411A1, U.S. Pat. Nos. 8,543,190B2, 9,352,094B2, 8,298,209B2, 8,690,859B2, 8,753,330B2, 8,679,105B2, 8,672,930B2, US20120035601A1, US20140005770A1, US20120036720A1, US20150088249A1, US20120053514A1, US20120053571A1, U.S. Pat. No. 8,798,764B2, WO2012030437A1, U.S. Pat. No. 8,467,853B2, US20120078266A1, US20120087869A1, U.S. Pat. No. 9,345,530B2, US20150126997A1, US20120101434A1, U.S. Pat. Nos. 9,333,023B2, 8,584,849B2, US20120108953A1, US20120108954A1, US20160000563A1, U.S. Pat. No. 9,220,555B2, US20120109118A1, US20120109148A1, US20120109149A1, US20120109272A1, US20150224213A1, US20120116486A1, U.S. Pat. No. 8,565,898B2, US20160095654A1, U.S. Pat. No. 9,168,079B2, US20140180306A1, US20120172891A1, U.S. Pat. No. 9,179,860B2, US20120191080A1, US20120197234A1, US20120197366A1, U.S. Pat. No. 8,850,676B2, US20120220528A1, US20140148754A1, US20120226303A1, US20120232563A1, U.S. Pat. Nos. 8,831,741B2, 8,858,548B2, 8,292,842B2, 8,486,014B2, WO2012129646A1, U.S. Pat. No. 9,168,093B2, WO2012134704A9, US20150257774A1, US20120259314A1, US20120261290A1, U.S. Pat. No. 8,924,023B2, WO2012145080A1, US20120265164A1, U.S. Pat. Nos. 8,979,825B2, 9,055,974B2, 8,727,996B2, 8,845,588B2, 8,873,900B2, 8,622,934B2, US20120277155A1, US20120277544A1, US20120277717A1, U.S. Pat. No. 8,998,933B2, US20120283722A1, U.S. Pat. Nos. 8,401,643B2, 9,144,494B2, US20120323254A1, U.S. Pat. Nos. 8,571,626B2, 8,926,588B2, 8,500,716B2, US20130030406A1, US20130035636A1, U.S. Pat. Nos. 8,758,365B2, 9,364,637B2, US20140371845A1, WO2013048650A1, U.S. Pat. No. 9,278,176B2, WO2013059324A1, U.S. Pat. No. 8,545,484B2, US20130096537A1, WO2013066930A1, US20160051309A1, US20160206360A1, WO2013062745A3, US20130116737A1, U.S. Pat. No. 8,636,692B2, US20150374437A1, US20130144283A1, US20130165758A1, US20150045781A1, U.S. Pat. No. 9,168,080B2, U.S. Pat. No. 9,345,528B2, US20160074090A1, U.S. Pat. Nos. 8,968,233B2, 8,617,128B2, WO2013134733A3, U.S. Pat. No. 8,764,674B2, US20130253342A1, US20130253345A1, US20130253346A1, U.S. Pat. Nos. 9,295,547B2, 9,066,800B2, US20130261739A1, U.S. Pat. Nos. 9,044,248B2, 9,020,224B2, US20130288218A1, US20160166305A1, U.S. Pat. No. 9,216,050B2, US20130289678A1, US20130289682A1, U.S. Pat. No. 9,393,140B2, US20130289692A1, US20130289693A1, US20130289696A1, US20150025617A1, U.S. Pat. Nos. 9,095,350B2, 9,364,286B2, US20130296957A1, US20160066988A1, US20130331672A1, US20130331831A1, U.S. Pat. Nos. 8,951,296B2, 9,314,511B2, U.S. Pat. No. 9,345,538B2, US20150094804A1, WO2014018769A3, U.S. Pat. Nos. 9,271,856B2, 9,370,311B2, US20140052118A1, US20140058292A1, US20140058501A1, WO2014039333A1, US20160058522A1, US20150352316A1, US20140114215A1, US20150250981A1, U.S. Pat. No. 9,023,080B2, US20140114346A1, U.S. Pat. Nos. 9,056,002B2, 9,144,663B2, US20140128726A1, US20140128963A1, WO2014074462A3, U.S. Pat. Nos. 9,144,493B2, 9,289,607B2, US20140288546A1, WO2014081910A2, US20140142688A1, US20140148889A1, WO2014089366A3, U.S. Pat. Nos. 9,072,619B2, 9,149,198B2, 9,017,317B2, 9,008,752B2, 9,393,361B2, US20140171942A1, US20140180278A1, WO2014113864A1, U.S. Pat. No. 9,295,550B2, US20140214155A1, US20140215791A1, U.S. Pat. No.

9,393,112B2, US20140236091A1, US20140236287A1, WO2014133829A2, US20140249617A1, U.S. Pat. No. 9,038,822B2, US20140275993A1, US20140276416A1, US20140276417A1, U.S. Pat. Nos. 9,302,043B2, 9,352,125B2, US20140276709A1, U.S. Pat. No. 9,345,540B2, WO2014150595A1, WO2014160118A1, U.S. Pat. Nos. 9,179,974B2, 9,066,726B2, WO2014151273A1, US20140276904A1, WO2014151295A1, WO2014150989A1, WO2014160416A2, WO2014152131A1, US20140288501A1, US20140296736A1, US20140296973A1, US20140324064A1, US20140330248A1, US20140336162A1, US20150238253A1, U.S. Pat. No. 9,351,789B2, US20140370490A1, U.S. Pat. No. 9,326,854B2, US20150005767A1, U.S. Pat. Nos. 9,345,529B2, 9,237,948B2, US20150018940A1, US20150025621A1, US20150045787A1, US20150051594A1, US20160001063A1, U.S. Pat. Nos. 9,326,816B2, 9,339,332B2, WO2015047817A1, U.S. Pat. No. 9,138,578B2, US20150073515A1, US20150080844A1, US20150080926A1, US20150081011A1, WO2015048119A1, US20150088111A1, US20150105809A1, US20150112234A1, WO2015061493A1, WO2015061478A1, WO2015066617A9, US20150126986A1, US20150127043A1, WO2015073427A1, WO2015073423A1, US20150133850A1, U.S. Pat. No. 9,314,572B2, US20150133888A1, WO2015073477A3, WO2015073478A1, U.S. Pat. No. 9,050,439B1, US20150157382A1, US20150161347A1, US20160184560A1, WO2015108733A1, US20150196391A1, WO2015106335A1, US20150196783A1, US20150209104A1, US20150216580A1, US20150230851A1, US20150250524A1, WO2015134661A1, US20150257824A1, US20150257825A1, US20150265812A1, US20150272655A1, US20150297346A1, US20150305633A1, US20150305807A1, US20150305808A1, US20150306358A1, US20150320475A1, US20150327924A1, US20150342627A1, WO2015187479A1, US20150343655A1, US20150351853A1, US20160199003A1, US20150359487A1, US20150359589A1, WO2015195828A3, US20160058438A1, US20160022455A1, US20160038769A1, US20160051324A1, US20160058503A1, WO2016044020A1, US20160095535A1, WO2016061669A1, US20160114151A1, US20160120598A1, WO2016077099A1, US20160135879A1, US20160139399A1, US20160151156A1, WO2016094466A1, US20160166158A1, US20160166326A1, US20160206853A1, US20160220295A1, US20160220305A1, US20160220829A1, U.S. Pat. Nos. 3,659,588A, 3,815,611A, 3,996,926A, 3,902,501A, 3,938,506A, 4,350,155A, 4,509,947A, 4,708,145A, 4,727,877A, 4,771,772A, 4,917,666A, 5,376,074A, 4,953,551A, 5,078,723A, 5,893,840A, 5,104,404A, 5,115,811A, 5,125,895A, 5,273,546A, 5,158,547A, 5,168,873A, 5,224,491A, 5,180,372A, 5,190,058A, 5,192,297A, 5,246,014A, 5,257,622A, 5,267,958A, 5,271,898A, 5,279,561A, 5,284,480A, 5,295,959A, 5,304,122A, 5,313,967A, 5,318,525A, 5,328,465A, 5,410,797A, 5,344,439A, 5,350,361A, 5,352,236A, 5,357,978A, 5,667,521A, 5,383,922A, 5,388,590A, 5,873,842A, 5,397,304A, 5,405,339A, 5,405,376A, 5,409,458A, 5,409,469A, 5,417,707A, 5,423,806A, 5,425,710A, 6,016,809A, 5,441,504A, 5,445,148A, WO1996004034A1, U.S. Pat. Nos. 5,484,449A, 5,720,726A, 5,545,200A, 5,490,521A, 5,497,782A, 5,820,586A, 5,507,732A, 5,509,910A, 5,513,650A, 5,573,533A, 5,545,138A, 5,545,149A, 5,997,468A, 5,549,556A, 5,549,557A, 5,558,635A, 5,569,294A, 5,584,830A, 6,080,190A, 5,596,996A, 5,601,538A, 5,603,703A, 5,603,704A, 5,607,404A, 5,607,463A, 5,906,613A, 5,613,953A, 5,624,617A, 5,628,754A, 5,630,830A, 6,447,523B1, 5,643,207A, 5,643,209A, 6,923,828B1, 5,672,169A, 5,676,659A, 5,690,613A, 5,693,066A, 5,983,126A, 5,697,951A, 5,701,911A, 6,302,990B1, 5,702,818A, 5,832,932A, 5,713,858A, 5,713,867A, 5,978,702A, 5,833,624A, WO1998014120A1, U.S. Pat. Nos. 5,727,552A, 5,728,065A, 5,814,014A, 6,056,837A, 5,738,666A, 5,746,709A, WO1998033551A1, 5,749,852A, 5,749,921A, 5,752,930A, 5,752,937A, 5,964,971A, 6,356,790B1, 5,759,474A, 5,769,819A, 5,769,858A, 5,769,882A, WO1998036788A1, 5,779,699A, 5,782,798A, 5,792,104A, 5,811,043A, 5,799,384A, 6,491,719B1, 5,807,249A, 6,030,405A, 5,814,011A, 6,139,539A, 5,820,629A, 5,823,955A, 5,824,032A, 8,317,854B1, 6,203,568B1, 6,263,224B1, 5,827,225A, 5,827,242A, 5,827,272A, 5,833,651A, 5,836,990A, 6,338,725B1, 5,843,150A, 5,848,987A, 5,897,584A, 5,853,375A, 5,853,424A, 5,865,842A, 5,865,843A, 5,871,468A, 5,876,376A, 5,876,398A, 5,879,295A, 5,879,380A, 5,885,247A, 5,891,386A, 5,897,528A, 6,221,059B1, 5,899,927A, 5,899,934A, 6,199,262B1, 5,902,308A, 5,902,331A, 5,913,854A, 6,056,906A, 5,916,178A, 6,068,629A, 6,156,034A, 5,919,188A, 5,927,277A, 5,938,582A, 5,938,694A, 5,944,712A, 5,948,345A, 5,951,540A, 5,954,687A, 5,961,510A, 5,964,771A, 5,964,778A, 5,967,988A, 5,968,085A, 6,171,281B1, 5,975,085A, 5,980,927A, 5,984,963A, 5,992,211A, 6,110,144A, 5,994,444A, 5,997,563A, 6,002,955A, 6,004,261A, 6,004,289A, 6,223,087B1, 6,013,051A, 6,022,341A, 6,234,973B1, 6,027,462A, 6,027,474A, 6,221,063B1, 6,033,388A, 6,042,579A, 6,044,304A, 6,055,457A, 6,059,739A, 6,375,774B1, 7,785,345B2, 6,063,057A, 6,063,078A, 6,063,092A, 6,066,126A, 6,068,622A, 6,071,287A, 6,323,459B1, 6,077,223A, 6,078,832A, 6,641,609B2, 6,093,142A, 6,094,598A, 6,099,496A, 6,099,499A, 6,102,938A, 6,106,454A, 6,106,510A, 6,108,402A, 6,108,571A, 6,109,269A, 6,110,146A, 6,110,155A, 6,183,420B1, 6,115,622A, 6,119,029A, 6,120,480A, 6,126,652A, 6,128,520A, 6,263,237B1, 6,129,705A, 6,129,708A, 6,129,738A, 6,141,574A, 6,142,938A, 6,485,440B1, 6,152,885A, 6,152,914A, 6,544,247B1, 6,309,402B1, 6,161,029A, 6,165,198A, 6,176,242B1, 6,179,811B1, 6,179,856B1, 6,183,505B1, 7,001,358B2, 6,196,995B1, 6,198,966B1, 6,200,264B1, 6,200,305B1, 6,241,728B1, 6,210,396B1, 6,210,417B1, 6,213,988B1, 6,251,115B1, 6,217,526B1, 6,218,016B1, 6,223,081B1, 6,227,203B1, 6,228,052B1, 6,228,073B1, 6,231,564B1, 6,245,013B1, 6,852,261B2, U.S. RE39438E1, 6,251,084B1, 6,251,092B1, 6,273,850B1, 6,276,661B1, 6,280,413B1, 6,280,414B1, 6,379,346B1, 6,620,381B2, 6,283,944B1, 6,293,922B1, 6,301,507B1, 6,306,141B1, 6,733,519B2, 6,321,104B1, 6,539,265B2, 6,331,189B1, 6,338,709B1, 6,827,733B2, 6,355,057B1, 6,356,784B1, WO2003086521A1, U.S. Pat. No. 6,402,777B1, WO2002004062A3, WO2002062421A1, U.S. Pat. Nos. 6,415,823B1, 6,428,565B1, 6,458,118B1, 6,478,777B1, 6,488,701B1, 6,493,591B1, 6,496,561B1, 6,500,147B2, 6,511,507B2, 6,512,958B1, 6,520,916B1, 6,537,268B1, 6,540,727B2, 6,546,077B2, 6,547,813B2, WO2002049713B1, 6,554,802B1, 6,558,401B1, 6,562,000B2, 6,572,583B1, 6,579,305B1, 6,589,274B2, 6,591,472B1, 6,602,271B2, 6,607,496B1, 6,635,049B1, 6,663,609B2, 7,214,198B2, 6,669,647B2, 6,671,550B2, 6,676,699B2, 6,689,056B1, 7,226,586B2, 6,709,432B2, 6,725,

866B2, 6,918,928B2, 6,731,976B2, 6,736,827B1, 6,740,191B2, WO2005000388A1, 6,746,392B2, 6,746,426B1, 6,746,481B1, 6,749,581B2, 6,754,536B2, 6,756,449B2, 6,800,065B2, 6,823,217B2, 6,827,715B2, 6,849,073B2, 6,866,624B2, 6,871,085B2, 6,878,161B2, 6,890,340B2, 6,893,416B2, 6,905,477B2, 6,893,429B2, 6,901,287B2, 6,902,057B2, 6,908,439B2, 6,909,920B2, 6,918,929B2, 6,937,897B2, WO2004058341A3, 6,955,674B2, 6,966,890B2, 6,966,923B2, 6,974,448B2, 6,985,776B2, 6,986,785B2, 7,014,610B2, 7,027,876B2, 7,037,290B2, 7,043,295B2, 7,045,279B1, 7,056,325B1, 7,060,038B2, 7,070,577B1, 7,070,579B1, 7,082,335B2, 7,083,639B2, 7,103,418B2, 7,104,399B2, 7,105,031B2, 7,108,682B2, 7,142,919B2, 7,144,419B2, 7,163,552B2, 7,169,126B2, 7,169,160B1, 7,172,571B2, 7,184,839B2, 7,207,981B2, 7,218,964B2, 7,223,247B2, 8,348,884B2, 7,236,834B2, 7,254,443B2, 7,300,434B2, 7,344,543B2, 7,925,328B2, 7,316,661B2, 7,316,706B2, 7,316,711B2, 7,321,798B2, 7,328,057B2, 7,328,131B2, 7,344,515B2, 7,353,946B2, 8,083,753B2, 7,371,248B2, 7,377,931B2, 7,387,636B2, 7,387,645B2, 7,399,296B2, 7,457,658B2, 7,470,281B2, 7,500,986B2, 7,527,636B2, 8,162,941B2, 7,967,789B2, 7,604,644B2, 7,588,581B2, 7,794,454B2, 8,298,217B2, 7,657,325B2, 7,682,352B2, 7,682,390B2, 7,695,674B2, 7,729,764B2, 7,738,942B2, 8,679,104B2, 7,742,809B2, 7,744,645B2, 7,753,876B2, 7,765,014B2, 7,769,451B2, 7,801,622B2, 7,815,656B2, 7,835,778B2, 9,211,393B2, 8,313,457B2, 7,877,144B2, 7,901,396B2, 8,608,730B2, 7,912,554B2, 7,955,298B2, 7,974,710B2, 7,988,668B2, 8,007,469B2, 8,758,325B2, 8,048,042B2, 8,092,483B2, 8,100,871B2, 8,112,292B2, 8,128,616B2, 8,257,312B2, 8,268,418B2, 8,273,084B2, 8,298,218B2, 8,298,219B2, 8,346,373B2, 8,348,909B2, 8,747,460B2, 8,454,587B2, 8,388,628B2, 8,398,630B2, 8,403,866B2, 8,409,237B2, 8,414,489B2, 8,444,609B2, 8,465,469B2, 8,491,547B2, 8,500,688B2, 8,500,713B2, 8,509,916B2, 8,512,281B2, 8,512,312B2, 8,518,097B2, 8,579,963B2, 8,591,783B2, 8,617,152B2, 8,623,013B2, 8,647,336B2, 8,652,133B2, 8,668,704B2, 8,672,988B2, 8,696,689B2, 8,858,619B2, 8,734,484B2, 8,784,360B2, 8,845,615B2, 8,870,940B2, 8,892,197B2, 8,986,361B2, 8,992,515B2, 9,005,194B2, 9,023,040B2, 9,039,712B2, 9,192,738B2, 9,220,888B2, 9,226,689B2, 9,278,190B2, 9,375,440B2, 9,387,031B2, 9,387,035B2, 9,398,966B2, 9,399,115B2, 9,402,992B2, 9,406,129B2, U.S. D330078S1, U.S. D345419S1, U.S. D369857S1, U.S. RE37148E1, U.S. RE43750E1, WO1992008501A1, WO1992009331A1, WO1993005842A1, WO1994021325A2, WO1996033756A1, WO1997014466A1, WO1997021455A1, WO1997040883A1, WO1997046175A1, WO1997048439A1, WO1998025656A2, WO1998048896A1, WO1999001073A1, WO1999045993A1, WO1999048548A1, WO1999053994A1, WO2000001420A2, WO2000051660A1, WO2001034049A9, WO2001056633A2, WO2001076678A1, WO2001085227A2, WO2002015954A1, WO2002026140A1, WO2002047745A3, WO2002060505A2, WO2002083229A3, WO2002094334A1, WO2003020336A3, WO2003022180A1, WO2003028590A1, WO2003059429A3, WO2003068313A1, WO2003079936A9, WO2003082364A2, WO2003090642A1, WO2003090809A1, WO2003101523A1, WO2004000168A1, WO2004009147A1, WO2004026383A3, WO2004026387A1, WO2004030739A1, WO2004047684A1, WO2004047900A1, WO2004047913A1, WO2004067077A1, WO2004093730A2, WO2004096339A1, WO2005004968A1, WO2005007211A3, WO2005018697A2, WO2005018702A2, WO2005032650A1, WO2005062890A3, WO2005062942A3, WO2005079904A1, WO2005089866A1, WO2005112780A2, WO2005115521A1, WO2005120375A2, WO2006028824A1, WO2006028855A1, WO2006033816A1, WO2006096441A2, WO2006113828A2, WO2007079352A2, WO2007115158A3, WO2007117755A3, WO2007127709A2, WO2008008827A2, WO2008022021A2, WO2008048575A3, WO2008063759A2, WO2008086079A9, WO2008091515A2, WO2008106338A2, WO2008130354A1, WO2008130355A1, WO2008130361A1, WO2008134509A1, WO2008137351A1, WO2008137352A1, WO2008141321A1, WO2009029069A1, WO2009035449A1, WO2009070675A2, WO2010014420A1, WO2010059409A2, WO2010105081A1, WO2010144668A1, WO2011014364A1, WO2011025629A1, WO2011087804A2, WO2011123247A1, WO2011153210A1, WO2012015636A1, WO2012068268A2, WO2012103274A1, WO2012135224A9, WO2012145545A1, WO2012151048A3, WO2013040082A2, WO2013048725A3, WO2013085719A1, WO2013134541A3, WO2013151766A1, WO2015053934A1, WO2015061621A1, WO2015113027A3, WO2015126838A1, WO2015143372A3, WO2015164151A1, WO2016033543A1, WO2016075536A2, WO2016100806A1, or WO2016118426A1.

Devices included herein include devices, e.g., a sensor or implantable sensor, described in, or substantially similar in terms of structure or function to devices described in, one or more of the following patent documents: US20010000802A1, US20020183824A1, U.S. Pat. Nos. 7,016,721B2, 6,539,253B2, US20050234432A1, U.S. Pat. No. 7,442,183B2, US20040138721A1, US20060265140A1, US20020087146A1, U.S. Pat. Nos. 8,417,334B2, 6,571,125B2, 7,369,892B2, 6,901,292B2, 7,337,001B2, 7,239,916B2, 7,181,268B2, US20150057518A1, WO2003073942A3, U.S. Pat. Nos. 8,116,876B2, 6,959,214B2, WO2003051196A1, U.S. Pat. No. 7,018,336B2, US20140107581A1, U.S. Pat. Nos. 7,120,484B2, 7,153,265B2, 7,865,246B2, 7,247,138B2, US20040033251A1, US20040039437A1, US20040047911A1, U.S. Pat. Nos. 8,506,550B2, 7,912,525B2, US20040086569A1, US20040115273A1, WO2005061044A3, US20040127978A1, US20040133119A1, U.S. Pat. Nos. 7,149,572B2, 7,052,486B2, US20040138518A1, U.S. Pat. Nos. 9,072,832B2, 7,917,206B2, 7,715,919B2, US20090048584A1, WO2004073138A1, WO2004077650A2, U.S. Pat. Nos. 6,887,207B2, 7,035,684B2, 8,150,513B2, 6,885,889B2, 7,082,330B2, 7,248,918B2, 6,944,488B2, 8,216,177B2, 6,931,272B2, WO2004096342A2, WO2004098381A2, US20040230182A1, US20110203923A1, U.S. Pat. Nos. 7,620,454B2, 7,742,818B2, US20050004612A1, U.S. Pat. Nos. 9,272,140B2, 7,846,095B2, 7,092,759B2, 7,027,866B2, US20050027323A1, US20050043616A1, US20050048641A1, US20100056885A1, US20090203979A1, U.S. Pat. No. 8,086,323B2, US20160074600A1, U.S. Pat. Nos. 7,225,032B2, 7,515,967B2, 7,418,292B2, 7,330,754B2, 7,856,987B2, US20050096514A1, US20050096637A1, U.S. Pat. Nos. 8,777,852B2, 8,948,836B2, 7,846,137B2, 8,165,672B2, 7,930,024B2, 8,133,435B2, 8,103,357B2, WO2005072818A1, WO2005072819A1, U.S. Pat. Nos. 7,548,784B2, 8,000,807B2, 7,272,433B2, WO2005104989A2, US20050245794A1, US20050245840A1, US20070203531A9, U.S. Pat. Nos. 8,688,221B2, 9,237,865B2, US20060013802A1, WO2006050405A1, US20060019397A1, WO2006014759A1, WO2006014754A2, U.S. Pat. Nos. 8,055,322B2, 7,767,652B2, 7,815,597B2, 8,292,856B2, WO2006034372A1, U.S. Pat. Nos. 7,744,560B2, 7,283,878B2, 7,641,992B2, 7,682,745B2, 7,879,495B2, 8,768,446B2, US20060122863A1, U.S. Pat. No. 7,947,378B2, US20060173440A1, U.S. Pat. Nos. 9,192,763B2, 8,774,912B2, 8,903,492B2, 7,819,909B2, 7,623,923B2, 8,478,411B2, 7,933,653B2, 7,328,070B2, 8,831,737B2, 7,505,816B2, 7,647,121B2, 8,108,049B2, US20060265025A1, U.S. Pat. Nos. 8,057,466B2, 8,021,299B2, 8,761,888B2, US20070027495A1, U.S. Pat. No. 7,512,431B2, WO2007041113A1, US20070078493A1, U.S. Pat. No. 8,118,750B2, US20070096686A1, US20070100388A1, U.S. Pat. No. 8,285,388B2, US20070129769A1, U.S. Pat. Nos. 8,731,656B2, 9,101,715B2, 9,125,607B2, 8,548,591B2, US20070233238A1, U.S. Pat. No. 8,485,979B2, US20140249600A1, U.S. Pat. No. 8,072,338B2, WO2007130177A1, WO2007130167A1, U.S. Pat. Nos. 8,326,431B2, 8,135,470B2, 8,311,636B2, 9,205,264B2, US20080125838A1, WO2008022021A2, US20100145271A1, U.S. Pat. Nos. 8,308,661B2, 8,332,038B2, 8,335,568B2, WO2009032392A1, U.S. Pat. No. 8,352,030B2, US20080081958A1, WO2008048962A2, U.S. Pat. No. 8,688,238B2, US20080103543A1, WO2008054441A1, US20080103573A1, US20080103575A1, WO2008054446A1, WO2008054444A1, US20080103578A1, US20080103580A1, U.S. Pat. No. 7,774,072B2, US20100327887A1, U.S. Pat. Nos. 8,354,881B2, 8,920,389B2, 7,803,164B2, 7,976,534B2, US20080262580A1, U.S. Pat. Nos. 8,457,750B2, 8,204,597B2, 8,805,508B2, 8,295,933B2, 8,121,691B2, 8,538,523B2, 7,714,757B2, 8,535,280B2, US20120330380A1, U.S. Pat. Nos. 7,983,757B2, 8,751,001B2, 8,005,551B2, US20090137980A1, U.S. Pat. No. 8,216,134B2, US20090192450A1, U.S. Pat. No. 9,309,550B2, US20090198146A1, U.S. Pat. No. 7,913,015B2, U.S. Pat. Nos. 8,016,814B2, 8,588,932B2, 8,332,045B2, 8,095,225B2, 8,078,285B2, 8,849,424B2, 8,287,520B2, US20090264957A1, U.S. Pat. Nos. 8,135,479B2, 8,688,201B2, US20090270844A1, U.S. Pat. No. 8,831,721B2, US20090270949A1, US20150374991A1, U.S. Pat. Nos. 8,295,929B2, 8,280,500B2, US20150283386A1, U.S. Pat. Nos. 7,886,608B2, 9,326,711B2, US20090326350A1, U.S. Pat. Nos. 9,327,129B2, 8,708,934B2, US20130317568A1, US20100010585A1, U.S. Pat. Nos. 8,209,028B2, 8,260,418B2, US20100022856A1, WO2010014483A3, WO2010014959A3, US20100030043A1, US20140275899A1, US20100030063A1, U.S. Pat. Nos. 8,938,292B2, 8,273,032B2, 7,953,488B2, US20150230722A1, US20100047210A1, US20100057153A1, U.S. Pat. No. 8,175,706B2, US20100076519A1, US20150321015A1, U.S. Pat. No. 8,280,517B2, WO2010045169A1, WO2010053792A3, U.S. Pat. Nos. 8,195,280B2, 8,718,769B2, 8,062,227B2, WO2010056425A1, U.S. Pat. Nos. 8,611,996B2, 9,289,613B2, US20100114222A1, US20100114244A1, WO2010056401A1, US20100125194A1, WO2010059588A1, U.S. Pat. Nos. 8,818,489B2, 9,320,470B2, 8,160,834B2, 8,275,435B2, 9,370,654B2, US20100198284A1, U.S. Pat. No. 8,423,141B2, US20100198308A1, U.S. Pat. No. 8,050,763B2, US20100198311A1, US20100210954A1, US20100217135A1, U.S. Pat. Nos. 8,362,742B2, 8,200,333B2, US20100223020A1, US20100228135A1, US20140107567A1, U.S. Pat. Nos. 8,340,769B2, 8,271,089B2, 9,220,886B2, US20100274115A1, U.S. Pat. Nos. 8,790,295B1, 9,026,223B2, U.S. Pat. Nos. 8,622,998B2, 8,512,731B2, 8,391,964B2, 8,608,481B2, US20100324471A1, U.S. Pat. Nos. 8,172,760B2, 8,523,773B2, 8,140,156B2, US20110004124A1, U.S. Pat. Nos. 8,332,031B2, 8,086,307B2, 9,037,237B2, US20110066029A1, US20110077574A1, US20110077616A1, US20110082356A1, U.S. Pat. No. 8,271,072B2, US20110105921A1, U.S. Pat. Nos. 8,532,769B2, 8,204,593B2, US20110106205A1, US20110106212A1, US20110106228A1, US20110112422A1, U.S. Pat. Nos. 8,753,331B2, 8,936,630B2, 8,374,686B2, US20150209513A1, U.S. Pat. Nos. 8,660,628B2, 8,498,705B2, 8,983,619B2, WO2011090552A1, US20110160790A1, U.S. Pat. Nos. 8,152,730B2, 8,755,882B2, US20110190692A1, U.S. Pat. Nos. 8,504,165B2, 9,364,162B2, 9,272,147B2, US20110196451A1, U.S. Pat. Nos. 8,483,802B2, 9,216,297B2, 8,810,394B2, WO2011129909A3, US20110257907A1, U.S. Pat. Nos. 8,801,668B2, 8,465,436B2, US20110268248A1, U.S. Pat. Nos. 8,433,402B2, 8,364,272B2, US20110282225A1, US20110288388A1, U.S. Pat. No. 8,397,578B2, US20110301479A1, US20110301575A1, US20110319723A1, US20120004526A1, US20120029323A1, U.S. Pat. Nos. 8,882,710B2, 8,788,028B2, 9,333,365B2, US20120053514A1, U.S. Pat. No. 8,954,152B2, US20120097554A1, WO2012058141A1, US20120101393A1, WO2012058118A1, U.S. Pat. Nos. 9,204,842B2, 8,548,543B2, 8,489,164B2, 8,585,604B2, 9,095,284B2, 9,192,719B2, US20120109272A1, U.S. Pat. Nos. 8,706,253B2, 8,489,168B2, 8,792,982B2, US20150217118A1, US20120136413A1, U.S. Pat. No. 8,892,204B2, US20120158086A1, WO2012092180A1, U.S. Pat. No. 8,868,212B2, US20120172690A1, US20120172891A1, U.S. Pat. Nos. 8,386,051B2, 8,594,801B2, 8,808,532B2, US20120191153A1, US20120194191A1, WO2012102746A8, U.S. Pat. Nos. 8,700,174B2, 9,168,374B2, 9,332,928B2, 8,977,350B2, 8,639,316B2, 8,720,276B2, WO2012134704A9, U.S. Pat. Nos. 8,512,286B2, 8,568,389B2, 8,979,825B2, 8,892,207B2, US20120277606A1, US20120277717A1, US20120277815A1, U.S. Pat. Nos. 9,138,584B2, 9,008,744B2, 8,827,913B2, 9,339,657B2, 8,401,643B2, US20120296222A1, U.S. Pat. Nos. 8,617,082B2, 9,180,009B2, 9,259,163B2, 8,777,874B2, 8,512,254B2, 8,798,751B2, US20130018233A1, US20150360034A1, WO2013066930A1, US20130072786A1, US20130072998A1, U.S. Pat. Nos. 9,101,281B2, 8,939,905B2, US20160121107A1, US20130110008A1, US20130150921A1, U.S. Pat. Nos. 8,543,204B2, 9,131,858B2, US20130197348A1, US20150126833A1, US20130211205A1, US20130253309A1, US20130253342A1, US20130253343A1, U.S. Pat. No. 9,339,197B2, US20130253345A1, US20130253346A1, U.S. Pat. Nos. 9,220,906B2, 9,314,630B2, 9,132,217B2, US20130274830A1, WO2013158238A3, U.S. Pat. No. 8,926,523B2, US20130289384A1, US20130289638A1, WO2013177573A3, WO2013184235A1, US20130328572A1, US20140012115A1, U.S. Pat. Nos. 9,360,447B2, 9,351,648B2, US20160095546A1, U.S. Pat. No. 8,918,176B2, WO2014058611A1, US20140107502A1, U.S. Pat. No. 8,923,963B2, WO2014070473A1, US20140148656A1, U.S. Pat. No. 9,259,584B2, US20140163346A1, US20140163644A1, US20140243634A1, US20140285396A1, WO2016003667A1, US20140358135A1, US20140379039A1, U.S. Pat. No. 9,079,039B2, US20150051467A1, U.S. Pat. No. 9,209,824B2, US20150080977A1, U.S. Pat. No. 9,387,331B2, US20150101841A1, U.S. Pat. No. 9,185,087B2, US20150119662A1, WO2015077568A1, WO2015081221A1, WO2015094618A1, WO2015094576A2, US20150214604A1, WO2015119852A1, US20150250427A1, US20150297905A1, US20150306391A1, US20150306406A1, US20160023000A1, US20160030741A1, WO2016025406A1, U.S. Pat. No. 9,393,424B2, US20160113534A1, US20160113618A1, US20160121124A1, US20160144164A1, WO2016085850A3, US20160166326A1, US20160175584A1, WO2016106305A1, WO2016115059A1, US20160206250A1, US20160213265A1, US20160216768A1, U.S. Pat. Nos. 4,350,155A, 4,428,378A, 4,467,807A, 4,485,813A, 4,735,205A, 4,754,753A, 4,813,421A, 4,951,667A, 4,903,701A, 4,932,406A, 4,967,755A, 4,968,293A, 4,987,897A, 5,006,115A, 5,342,409A, 5,040,536A, 5,052,388A, WO1992004075A1, WO1992000779A1, U.S. Pat. Nos. 5,088,488A, 5,089,019A, 5,146,918A, 5,168,873A, 5,174,287A, 5,199,428A, 5,215,082A, 5,222,506A, 5,226,413A, 5,233,983A, 5,233,984A, 5,273,518A, 5,391,188A, 5,312,446A, 5,312,453A, 5,330,513A, 5,336,244A, 5,342,406A, 5,353,800A, 5,354,318A, WO1995003737A1, WO1995000201A1, U.S. Pat. Nos. 5,409,009A, 5,438,990A, 5,486,200A, 5,522,859A, 5,529,578A, WO1996026674A1, U.S. Pat. Nos. 5,540,731A, 5,540,732A, 5,549,654A, 5,554,177A, 5,562,711A, 5,564,434A, 5,593,431A, WO1997040884A1, U.S. Pat. Nos. 6,038,475A, 5,792,186A, 5,702,427A, 5,832,932A, 5,978,702A, 5,833,709A, 5,725,561A, 5,814,014A, 5,741,211A, 5,782,891A, 5,810,735A, 5,814,089A, 5,987,356A, 5,995,872A, WO1999020340A1, U.S. Pat. Nos. 6,327,503B1, 5,871,508A, 5,876,353A, 5,891,180A, 6,731,976B2, 5,919,209A, 5,919,221A, 5,944,745A, 5,957,861A, 5,957,957A, 6,412,490B1, 5,994,444A, WO2000024458A1, U.S. Pat. Nos. 6,337,997B1, 6,223,080B1, 6,234,973B1, 6,238,423B1, 6,042,579A, WO2000018317A2, 6,280,409B1, 6,048,328A, 6,058,326A, 6,058,331A, 6,073,048A, 6,077,227A, U.S. RE42934E1, 6,091,986A, 6,091,988A, 6,091,992A, 6,094,598A, 6,097,984A, 6,099,479A, 6,102,678A, 6,115,635A, WO2000038572A9, 6,126,611A, WO2000057781A1, U.S. Pat. Nos. 6,129,745A, 6,572,543B1, 6,134,470A, 6,141,590A, 6,152,885A, 6,155,267A, 7,191,018B2, 6,162,180A, 6,163,723A, 6,167,308A, 6,171,252B1, 6,178,349B1, 6,190,324B1, 6,198,966B1, 6,209,764B1, 6,878,135B1, 6,208,900B1, 6,542,350B1, 6,221,024B1, 6,223,081B1, 6,227,203B1, 6,236,882B1, 6,236,889B1, 6,263,237B1, 7,269,457B2, 6,274,265B1, 6,292,697B1, 6,295,473B1, 6,317,625B1, 6,317,626B1, 6,356,784B1, 6,374,140B1, 6,381,493B1, 6,408,205B1, 6,415,181B1, 6,423,029B1, 6,449,508B1, 6,458,118B1, 6,477,395B2, 6,477,420B1, 6,477,424B1, 6,480,744B2, 6,493,591B1, 6,505,077B1, 6,510,345B1, 6,512,939B1, 6,512,949B1, 6,567,705B1, 6,572,542B1, 6,580,946B2, 6,580,947B1, 7,279,112B2, 6,595,927B2, 6,599,250B2, 6,615,083B2, 6,635,049B1, 6,666,821B2, 6,671,550B2, 6,681,135B1, 7,493,159B2, 6,689,056B1, 6,695,790B2, 7,226,586B2, 6,714,811B1, 6,719,689B2, 6,731,984B2, 6,738,671B2, 6,740,076B2, 6,752,765B1, 6,754,532B1, 6,754,536B2, 6,766,183B2, 6,792,308B2, 6,823,213B1, 6,836,682B2, 6,839,592B2, 6,865,419B2, 6,869,404B2, 6,873,870B2, 6,882,882B2, 6,882,883B2, 6,885,891B2, 6,892,094B2, 6,909,920B2, 6,922,585B2, 6,922,592B2, 6,934,586B2, 6,937,906B2, 6,944,489B2, 6,961,448B2, 6,964,641B2, 6,980,860B2, 7,003,336B2, 7,024,244B2, 7,025,730B2, 7,031,772B2, 7,037,266B2, 7,044,920B2, 7,050,855B2, 7,058,450B2, WO2007035332A1, U.S. Pat. Nos. 7,069,078B2, 7,076,283B2, 7,082,327B2, 7,083,588B1, 7,092,765B2, 7,099,714B2, 7,122,027B2, 7,123,965B2, 7,130,681B2, 7,130,687B2, 7,130,700B2, 7,142,919B2, 7,149,581B2, 7,155,278B2, 7,524,292B2, WO2007035299A1, U.S. Pat. Nos. 7,164,948B2, 7,181,275B2, 7,181,284B2, 7,184,832B2, 7,192,399B2, 7,203,551B2, 7,218,968B2, 7,650,190B2, 7,853,328B2, 8,348,884B2, 7,233,821B2, 7,248,924B2, 7,254,451B2, 7,257,445B2, 7,283,872B2, 7,292,888B2, 7,315,759B2, 7,319,899B2, 7,328,131B2, 7,336,994B2, 7,342,508B2, 7,345,607B1, 7,367,951B2, 8,700,154B2, 7,433,736B2, 7,438,686B2, 7,470,233B2, WO2009042749A2, U.S. Pat. Nos. 7,474,920B2, 7,474,923B2, WO2009042012A1, 7,488,291B2, 7,515,961B2, 7,974,677B2, 7,559,900B2, 7,563,231B2, 7,953,471B2, 7,584,002B2, 7,593,777B2, 7,594,889B2, 7,623,053B2, 7,636,595B2, 7,647,106B2, 7,653,437B2, 7,657,300B2, 8,792,986B2, 7,672,715B2, 7,682,316B2, 7,684,872B2, 7,697,972B2, 7,729,764B2, 7,734,345B2, 7,738,948B2, 7,738,951B2, 7,785,264B2, 7,787,942B2, 7,787,947B2, 7,792,588B2, 7,835,784B2, 7,844,347B2, 7,848,808B2, 7,850,615B2, 7,855,653B2, 7,867,221B2, 7,873,410B2, 7,896,813B2, 7,904,168B2, 7,912,537B2, 7,927,282B2, 7,935,062B2, 7,935,935B2, 7,941,221B2, 7,963,922B2, 7,970,466B2, 7,972,273B2, 7,991,456B2, 7,991,467B2, 7,993,269B2, 7,996,070B2, 7,996,084B2, 8,000,532B2, 8,016,859B2, 8,033,998B2, 8,041,424B2, 8,046,064B2, 8,046,072B2, 8,050,759B2, 8,052,610B2, 8,073,541B2, 8,083,730B2, 8,099,164B2, 8,118,748B2, 8,141,556B2, 8,145,313B2, 8,155,758B2, 8,165,676B2, 8,170,636B2, 8,187,200B2, 8,200,329B2, 8,211,028B2, 8,224,447B2, 8,244,355B2, 8,244,379B2, 8,275,432B2, 8,290,557B2, 8,298,153B2, 8,301,233B2, 8,813,753B2, 8,340,750B2, 8,380,295B2, 8,706,202B2, 9,126,049B2, 8,394,463B1, 8,433,396B2, 8,433,408B2, 8,442,627B2, 8,452,402B2, 8,467,882B2, 8,478,375B2, 8,478,402B2, 8,489,189B2, 8,491,547B2, 8,540,642B2, 8,565,873B2, 8,579,824B2, 8,606,355B1, 8,620,424B2, 8,632,473B2, 8,639,323B2, 8,700,113B2, 8,694,097B2, 8,700,155B2, 8,738,131B2, 8,750,961B1, 8,750,976B2, 8,755,885B2, 8,777,850B2, 8,781,547B2, 8,798,723B2, 8,827,904B2, 8,855,755B2, 8,876,727B2, 8,886,302B2, 8,897,868B2, 8,983,606B2, 9,008,789B2, 9,042,983B2, 9,072,870B2, 9,132,268B2, 9,144,681B2, 9,149,638B2, 9,174,055B2, 9,186,509B2, WO2016064578A1, U.S. Pat. Nos. 9,301,698B2, 9,314,205B2, 9,327,117B2, 9,381,366B2, 9,399,076B2, 9,399,091B2, 9,399,139B2, 9,399,140B2, U.S. RE42226E1, U.S. RE42682E1, U.S. RE43952E1, WO1986000234A1, WO1991008781A1, WO1992011901A1, WO1993020889A1, WO1995032758A1, WO1999003532A3, WO1999021612A1, WO1999038438A1, WO2000024457A1, WO2001074968A3, WO2001083029A1, WO2002000297A2, WO2002060505A2, WO2002062215A3, WO2003063954A1, WO2003090616A1, WO2003090861A1, WO2003092494A1, WO2004012808A1, WO2004041354A1, WO2004041358A1, WO2004062486A2, WO2004069334A1, WO2004071291A3, WO2004084768A2, WO2004103469A1, WO2005009514A2, WO2005011490A1, WO2005018697A2, WO2005018702A2, WO2005018740A1, WO2005021089A1, WO2005021093A1, WO2005035052A1, WO2005044371A1, WO2005053793A1, WO2005089866A1, WO2005123178A2, WO2006060587A1, WO2006060704A9, WO2006060763A1, WO2006081374A1, WO2006081432A1, WO2006081453A2, WO2006083885A1, WO2006088576A2, WO2006104843A1, WO2006115777A1, WO2006115837A2, WO2007027506A2, WO2007035443A1, WO2007035445A1, WO2007038544A1, WO2007038646A1, WO2007065049A1, WO2007067883A3, WO2007076220A1, WO2007079288A1, WO2007079325A1, WO2007087551A1, WO2007090159A1, WO2007101229A1, WO2007118133A2, WO2007124194A2, WO2007127551A2, WO2007127606A1, WO2007127627A1, WO2008134178A1, WO2008013881A3, WO2008130801A1, WO2008055159A2, WO2008061135A2, WO2008076491A3, WO2008079664A1, WO2008094816A3, WO2008134603A2, WO2008144125A1, WO2009070675A2, WO2009114303A1, WO2009134478A1, WO2010005788A3, WO2010014053A1, WO2010014066A1, WO2010051153A1, WO2010051155A1, WO2010051156A1, WO2010051175A1, WO2010077330A1, WO2010144668A1, WO2011014322A1, WO2011053481A1, WO2011087581A3, WO2011126823A1, WO2012015948A1, WO2012016167A1, WO2012057865A1, WO2012135224A9, or WO2016100799A1.

Devices included herein include an implant, e.g., ocular implant, device described in, or substantially similar in terms of structure or function to devices described in, one or more of the following patent documents: US20040033251A1, US20040039437A1, US20040047911A1, US20040086569A1, US20040115273A1, US20040127978A1, U.S. Pat. No. 7,767,652B2, WO2007030266A2, U.S. Pat. Nos. 8,021,679B2, 8,137,687B2, US20100152831A1, U.S. Pat. Nos. 4,271,841A, 7,226,586B2, 7,160,264B2, WO2005018697A2, WO2005018702A2, WO2006060806A2, U.S. Pat. Nos. 7,482,783B2, 7,858,107B2, 8,021,299B2, 9,393,416B2, US20070276439A1, U.S. Pat. Nos. 8,332,038B2, 8,335,568B2, WO2011059948A1, U.S. Pat. No. 8,617,128B2, US20150265207A1, US20150306391A1, U.S. Pat. Nos. 6,923,784B2, 7,160,264B2, 8,313,762B2, U.S. Pat. No. 8,696,689B2, U.S. RE43952E1, WO1997040791A1, WO2005089647A1, or WO2007065049A1.

Devices described herein include devices, e.g., peritoneal implant, described in, or substantially similar in terms of structure or function to devices described in, one or more of the following patent documents: U.S. Pat. Nos. 7,247,138B2, 8,506,550B2, 7,418,292B2, WO2006020230A2, U.S. Pat. No. 9,125,607B2, US20120179015A1, US20100022940A1, WO2010078263A2, US20140148754A1, U.S. Pat. No. 9,320,842B2, WO2014121159A1, US20140220699A1, U.S. Pat. Nos. 6,461,329B1, 6,537,268B1, 6,731,976B2, WO2003020336A2, or WO2007047539A2.

Devices included herein include devices, e.g., a neural device, described in, or substantially similar in terms of structure or function to devices described in, one or more of the following patent documents: U.S. Pat. Nos. 6,484,059B2, 7,027,872B2, 6,690,959B2, 6,537,272B2, 7,442,183B2, US20040073099A1, U.S. Pat. No. 6,892,097B2, WO2002074386A1, U.S. Pat. No. 7,218,964B2, US20060206166A1, US20030045786A1, US20110087309A1, U.S. Pat. Nos. 7,187,978B2, 7,010,355B2, 7,006,872B2, US20030204206A1, U.S. Pat. No. 6,950,706B2, WO2003090853A1, US20090259278A1, WO2003090609A2, U.S. Pat. Nos. 7,805,189B2, 9,314,628B2, US20040067221A1, U.S. Pat. Nos. 6,950,709B2, 8,187,181B2, 7,976,465B2, 7,242,983B2, 8,594,798B2, US20040138518A1, 9,072,832B2, 7,917,206B2, 7,715,919B2, 8,579,786B2, WO2004073138A1, US20100063134A1, US20040193229A1, U.S. Pat. No. 7,130,684B2, US20040236381A1, US20040236382A1, U.S. Pat. Nos. 8,600,495B2, 7,107,104B2, 7,328,069B2, US20050019919A1, U.S. Pat. Nos. 7,616,998B2, 7,769,442B2, 7,330,754B2, US20090214612A1, U.S. Pat. No. 8,883,716B2, US20110213328A1, WO2006050405A1, WO2006020230A2, U.S. Pat. No. 7,815,597B2, WO2006041649A1, U.S. Pat. Nos. 7,641,992B2, 7,682,745B2, 7,879,495B2, 9,259,177B2, 8,761,868B2, 7,363,089B2, US20060161235A1, US20060167525A1, U.S. Pat. Nos. 7,421,297B2, 8,150,530B2, US20060257912A1, US20060264777A1, U.S. Pat. Nos. 8,021,299B2, 7,769,472B2, 7,822,482B2, 9,393,416B2, WO2007041113A1, US20140222101A1, U.S. Pat. Nos. 7,676,271B2, 8,423,146B2, US20160151633A1, U.S. Pat. Nos. 8,209,018B2, 8,190,251B2, 8,548,591B2, US20070249953A1, US20100292753A1, WO2007124192A1, U.S. Pat. No. 8,527,039B2, US20140249600A1, WO2007127073A2, US20070253994A1, US20070253997A1, U.S. Pat. Nos. 8,417,346B2, WO2007130167A1, 8,326,431B2, 8,219,202B2, 7,359,837B2, 7,764,989B2, 7,853,323B2, 8,355,789B2, US20140012131A1, WO2008054447A1, U.S. Pat. Nos. 8,380,311B2, 8,798,759B2, US20080269835A1, 8,219,207B2, US20150209578A1, U.S. Pat. Nos. 9,311,335B2, 9,149,628B2, WO2009139932A1, 8,280,478B2, 8,706,194B2, US20100047915A1, US20100114195A1, U.S. Pat. No. 8,386,053B2, US20100114283A1, US20100137926A1, U.S. Pat. No. 8,784,800B2, US20140107567A1, U.S. Pat. No. 8,183,221B2, US20100280335A1, U.S. Pat. No. 8,207,138B2, US20100305428A1, US20100324643A1, US20150100064A1, U.S. Pat. No. 8,958,870B2, U.S. Pat. No. 8,554,331B2, US20110098795A1, US20110123593A1, US20110125241A1, US20160192984A1, US20110208075A1, US20110257503A1, WO2011136870A1, U.S. Pat. Nos. 8,457,749B2, 8,401,670B2, 8,843,200B2, 8,447,406B2, 9,345,530B2, US20150126997A1, U.S. Pat. No. 8,583,254B2, US20150224213A1, U.S. Pat. No. 8,565,886B2, US20120116486A1, U.S. Pat. No. 8,457,750B2, US20160095654A1, U.S. Pat. No. 9,014,804B2, U.S. Pat. No. 8,781,583B2, WO2012134704A3, U.S. Pat. Nos. 9,173,609B2, 8,868,173B2, US20120277823A1, U.S. Pat. Nos. 9,008,414B2, 8,961,535B2, US20130116737A1, US20150374437A1, US20130144283A1, US20130218250A1, US20130282001A1, U.S. Pat. Nos. 8,751,009B2, 9,259,181B2, US20130289678A1, US20160066988A1, US20150133904A1, US20140058292A1, US20140114215A1, WO2014081910A2, US20140275993A1, U.S. Pat. No. 9,066,726B2, WO2014151295A1, US20140316402A1, U.S. Pat. Nos. 9,155,893B2, 9,211,413B2, US20140336162A1, US20150238253A1, US20150051594A1, US20150065945A1, U.S. Pat. Nos. 9,326,816B2, 9,339,332B2, WO2015047817A1, US20150073515A1, US20150080926A1, US20150088111A1, US20150111918A1, US20150112234A1, US20150119867A1, US20150133850A1, US20150196783A1, US20150306402A1, US20150320475A1, US20150327924A1, US20150356274A1, US20150359589A1, US20160038769A1, US20160074110A1, US20160095546A1, US20160114153A1, US20160121101A1, US20160143591A1, WO2016083460A1, US20160220305A1, U.S. Pat. No. 4,341,221A, WO1992004075A1, U.S. Pat. Nos. 5,265,608A, 5,282,468A, 5,121,754A, 5,143,067A, 5,342,409A, 5,458,629A, 5,643,330A, 5,913,882A, 5,711,316A, 5,978,702A, 5,733,322A, 5,814,014A, 5,752,979A, 5,782,891A, 5,800,474A, 5,801,188A, 6,146,743A, 5,865,843A, 6,031,710A, 6,337,997B1, 6,042,579A, WO1999055413A9, U.S. Pat. Nos. 6,094,598A, 6,128,537A, 6,178,349B1, 6,227,203B1, 6,251,115B1, 6,356,784B1, 6,374,140B1, 6,484,054B2, 6,561,975B1, 6,572,542B1, 6,804,554B2, 6,820,019B1, 6,855,456B2, 6,884,122B2, 6,909,918B2, 6,920,360B2, 6,937,906B2, 6,961,448B2, 6,968,234B2, 6,980,863B2, 7,066,891B2, 7,066,910B2, WO2007035332A1, U.S. Pat. Nos. 7,079,887B2, 7,089,057B2, 7,110,827B2, 7,130,687B2, 7,155,278B2, WO2007035299A1, U.S. Pat. Nos. 7,179,279B2, 7,191,015B2, 7,216,001B2, 7,650,190B2, 8,348,884B2, 7,292,888B2, 7,415,308B2, 7,515,961B2, 7,526,340B2, 7,594,889B2, 7,667,954B2, 7,672,733B2, 7,680,539B2, 7,684,855B2, 7,787,944B2, 7,813,809B2, 7,941,221B2, 7,949,391B2, 7,949,392B2, 8,078,280B2, 8,155,758B2, 8,336,553B2, 8,398,630B2, 8,543,214B2, 8,606,355B1, 8,623,066B2, 8,652,133B2, 8,718,763B2, 8,725,259B2, 8,761,890B2, 8,911,427B2, 8,974,436B2, 9,072,870B2, 9,095,698B2, 9,119,543B2, 9,144,681B2, 9,180,299B2, 9,202,114B2, 9,387,318B2, 9,393,404B2, 9,402,992B2, WO1991008016A1, WO2001052729A3, WO2002045566A2, WO2002059908A2, WO2003028804A1, WO2003035164A3, WO2003035172A1, WO2003059440A3, WO2003089047A1, WO2003090616A1, WO2004098381A3, WO2005011487A1, WO2006044406A1, WO2006044890A3, WO2006060806A2, WO2006104843A1, WO2006115837A2, WO2007027289A1, WO2007035443A1, WO2007035445A1, WO2007118133A2, WO2008008827A2, WO2008021157A1, WO2008033253A2, WO2008086079A9, WO2008133683A1, WO2008144125A1, WO2009129026A1, WO2009129163A2, WO2011002546A1, WO2012068268A2, WO2013134133A1, WO2014150595A1, or WO2016033543A1.

Devices described herein include devices described in, or substantially similar in terms of structure or function to devices described in, one or more of the following patent documents: U.S. Pat. Nos. 6,481,440B2, 7,632,306B2, US20050222688A1, U.S. Pat. Nos. 8,187,319B2, 6,607,478B2, 7,637,944B2, WO2003082150A1, U.S. Pat. Nos. 7,578,843B2, 8,029,564B2, US20040059318A1, U.S. Pat. Nos. 6,989,027B2, 7,637,943B2, 7,381,180B2, US20050096751A1, WO2005067821A1, WO2005067820A2, U.S. Pat. No. 9,259,312B2, US20050245957A1, US20050246037A1, WO2005113058A1, U.S. Pat. No. 9,192,467B2, US20100249897A1, U.S. Pat. No. 7,318,835B2, US20140052242A1, US20060111769A1, US20060184235A1, WO2006094146A3, U.S. Pat. No. 7,419,501B2, WO2007030266A2, U.S. Pat. No. 8,702,787B2, US20070100355A1, US20070208256A1, U.S. Pat. Nos. 7,955,380B2, 7,955,512B2, US20070225797A1, WO2007115017A1, U.S. Pat. Nos. 7,481,836B2, 9,331,328B2, 7,625,403B2, WO2007121041A2, U.S. Pat. Nos. 7,524,331B2, 7,740,655B2, US20070239269A1, U.S. Pat. No. 7,591,848B2, WO2007121072A3, US20070244545A1, US20070244546A1, US20110104234A1, U.S. Pat. Nos. 8,398,707B2, 7,963,960B2, 7,615,072B2, WO2008124222A1, US20080147173A1, U.S. Pat. Nos. 7,651,527B2, 8,473,030B2, US20080172119A1, U.S. Pat. No. 7,753,962B2, WO2008097763A1, WO2008106309A1, WO2008112391A2, WO2008112390A2, U.S. Pat. Nos. 8,021,679B2, 8,137,687B2, US20110150966A1, WO2008130795A1, U.S. Pat. No. 8,852,620B2, WO2009058671A3, U.S. Pat. Nos. 9,393,115B2, 9,364,324B2, US20090222088A1, U.S. Pat. Nos. 8,034,099B2, 7,976,875B2, US20090259284A1, US20090259285A1, US20090259290A1, US20090259296A1, US20090264976A1, US20090264993A1, US20090270965A1, US20090270971A1, U.S. Pat. No. 9,173,737B2, US20090294049A1, U.S. Pat. Nos. 9,149,357B2, 8,801,776B2, US20100131049A1, US20100152831A1, U.S. Pat. No. 8,158,187B2, US20120226348A1, U.S. Pat. Nos. 8,133,267B2, 9,301,863B2, 9,144,667B2, 8,052,741B2, 9,066,785B2, US20100256723A1, U.S. Pat. Nos. 9,060,891B2, 8,888,836B2, US20160000589A1, U.S. Pat. Nos. 8,419,782B2, 8,709,465B2, 7,942,917B2, US20100268317A1, US20120065725A1, U.S. Pat. Nos. 8,506,622B2, 8,540,764B2, 8,876,877B2, 8,052,737B2, 9,308,382B2, US20110040367A1, U.S. Pat. Nos. 8,377,115B2, U.S. RE45865E1, 9,060,857B2, US20110184505A1, U.S. Pat. Nos. 8,500,802B2, 8,292,948B2, US20110202127A1, U.S. Pat. No. 8,475,523B2, WO2011106354A1, WO2011106532A1, U.S. Pat. No. 9,072,603B2, US20110238168A1, US20140180401A1, U.S. Pat. Nos. 9,320,597B2, 8,926,692B2, WO2011129944A1, U.S. Pat. Nos. 8,491,650B2, 8,771,344B2, US20150173895A1, U.S. Pat. No. 8,986,372B2, US20140074227A1, US20110257721A1, WO2011133276A1, US20110257728A1, US20130282111A1, U.S. Pat. Nos. 9,333,078B2, 9,326,870B2, US20110264191A1, US20140100653A1, U.S. Pat. Nos. 9,173,738B2, 8,740,976B2, 8,876,892B2, US20140039610A1, US20140371848A1, U.S. Pat. No. 9,132,008B2, US20110264206A1, US20110264208A1, U.S. Pat. No. 8,333,800B2, US20110270379A1, U.S. Pat. No. 8,337,546B2, US20110270385A1, U.S. Pat. No. 9,023,096B2, US20110282438A1, U.S. Pat. Nos. 8,747,463B2, 9,387,071B2, 9,387,077B2, US20110301702A1, US20120022641A1, US20140005770A1, US20150088249A1, US20160038323A1, WO2012030598A3, US20130046378A1, U.S. Pat. No. 9,192,466B2, US20120103840A1, U.S. Pat. Nos. 8,677,601B2, 9,345,470B2, 8,622,934B2, WO2012145245A1, WO2012145240A1, U.S. Pat. Nos. 9,173,736B2, 9,370,423B2, 9,144,494B2, 8,511,244B2, US20140371845A1, WO2013048650A1, U.S. Pat. No. 9,254,190B2, WO2013085719A1, US20130204356A1, U.S. Pat. Nos. 9,393,136B2, 9,005,270B2, 9,295,547B2, 9,066,800B2, 9,023,098B2, WO2013151628A3, US20130268065A1, U.S. Pat. Nos. 9,301,839B2, 9,220,616B2, 8,920,485B2, 9,095,421B2, US20130282113A1, U.S. Pat. No. 9,393,140B2, US20130289692A1, US20130289700A1, US20130289701A1, US20130289702A1, US20150025617A1, US20150157445A1, US20130304196A1, US20130305800A1, US20140296973A1, U.S. Pat. No. 9,271,856B2, US20140031923A1, US20140039612A1, US20160089236A1, U.S. Pat. No. 8,974,524B2, US20140058501A1, WO2014039334A1, WO2014039333A1, U.S. Pat. No. 9,192,469B2, US20140081128A1, U.S. Pat. No. 8,961,593B2, US20140100652A1, US20140114345A1, U.S. Pat. Nos. 9,056,002B2, 9,144,663B2, US20160100940A1, US20150209143A1, US20140128726A1, US20140128963A1, WO2014074464A3, US20140135907A1, U.S. Pat. Nos. 9,072,602B2, 9,144,493B2, WO2014081564A3, U.S. Pat. No. 9,199,348B2, US20140148889A1, U.S. Pat. Nos. 8,986,371B2, 9,132,007B2, US20150289977A1, U.S. Pat. No. 9,055,999B2, US20140200660A1, US20140213889A1, U.S. Pat. No. 9,295,550B2, US20140214155A1, WO2015153755A3, U.S. Pat. No. 9,095,463B2, US20140236287A1, U.S. Pat. Nos. 9,101,473B2, 9,333,077B2, 9,232,994B2, US20150148898A1, US20140330368A1, U.S. Pat. No. 9,375,311B2, WO2014186235A1, U.S. Pat. No. 9,295,548B2, US20140358156A1, U.S. Pat. Nos. 9,326,854B2, 9,237,948B2, US20150018944A1, US20150025621A1, US20150025622A1, US20150039081A1, US20150081011A1, U.S. Pat. No. 9,387,074B2, US20150105857A1, US20150112430A1, US20150119692A1, US20150119974A1, US20150119980A1, US20150182333A1, US20150196391A1, US20150209140A1, US20150231387A1, US20150272731A1, U.S. Pat. No. 9,381,083B2, US20150297346A1, US20150305860A1, US20150305902A1, US20150313710A1, US20160199062A1, US20160113764A1, US20160051364A1, WO2016073189A1, WO2016089777A1, US20160206428A1, US20160213470A1, US20160220241A1, US20160220363A1, US20160220367A1, US20160220370A1, U.S. Pat. Nos. 4,339,831A, 4,458,693A, 4,450,710A, 4,605,406A, 4,808,180A, 4,816,029A, 4,886,062A, 4,935,030A, 4,969,458A, 5,032,128A, 5,037,377A, 5,246,451A, 5,271,898A, 5,279,612A, 5,653,745A, 5,314,467A, 5,449,384A, 5,716,401A, 6,004,346A, 5,607,463A, 5,674,279A, 5,749,921A, 5,834,051A, 5,755,772A, 5,755,773A, 5,766,240A, 6,656,214B1, 6,491,719B1, 6,843,803B2, 6,355,060B1, 6,203,568B1, 5,824,066A, 5,824,069A, 6,878,161B2, 5,906,619A, 6,645,244B2, 5,948,019A, 6,097,978A, 6,102,938A, 6,129,738A, 6,139,575A, 6,203,550B1, 6,218,016B1, U.S. RE39438E1, 6,270,524B1, 6,276,661B1, 6,733,519B2, 6,338,725B1, 6,347,632B1, 6,355,057B1, 6,361,557B1, 6,372,283B1, 7,018,400B2, 6,533,811B1, 6,669,647B2, 6,676,699B2, 6,863,684B2, 6,918,926B2, 6,921,407B2, U.S. RE42395E1, 7,022,134B1, 7,022,135B2, 8,105,377B2, 7,131,991B2, 7,503,930B2, 7,377,940B2, 7,974,677B2, 7,953,471B2, 7,655,036B2, 7,658,727B1, 7,682,390B2, 7,699,168B2, U.S. RE44075E1, 7,740,656B2, 7,840,253B2, 7,967,857B2, 7,972,377B2, 7,989,157B2, 7,993,395B2, 8,048,152B2, 8,048,042B2, 8,083,793B2, 8,137,398B2, 8,197,538B2, 8,211,169B2, 8,221,315B2, 8,273,118B2, 8,323,337B2, 8,454,684B2, 8,500,755B2, 8,506,620B2, 8,529,583B1, 8,565,872B2, 8,672,999B2, 8,696,743B2, 8,858,619B2, 8,734,484B2, 8,747,458B2, 8,778,010B2, 8,784,478B2, 8,870,940B2, 9,011,524B2, 9,011,528B2, 9,283,073B2, 9,402,719B2, WO1996007771A1, WO1997049353A1, WO2001064124A1, WO2003011184A8, WO2004084768A3, WO2005018490B1, WO2005042046A1, WO2006044679A1, WO2009029069A1, WO2009129020A3, WO2012083070A1, WO2014071236A1, WO2015073815A1, WO2016100799A1, or WO2016118522A1.

Devices included herein include devices described in, or substantially similar in terms of structure or function to devices described in, one or more of the following patent documents: U.S. Pat. No. 6,944,489B2, US20040033251A1, US20040039417A1, US20040039437A1, U.S. Pat. No. 7,018,384B2, US20040047911A1, U.S. Pat. No. 6,963,773B2, US20040086569A1, US20040115273A1, US20040127978A1, U.S. Pat. No. 8,454,566B2, US20050256510A1, U.S. Pat. Nos. 7,767,652B2, 8,740,833B2, WO2007030266A2, US20070078513A1, U.S. Pat. Nos. 8,333,728B2, 7,955,512B2, WO2007121055A1, U.S. Pat. Nos. 7,442,721B2, 8,241,619B2, US20080125838A1, US20100042039A1, U.S. Pat. Nos. 8,021,679B2, 8,137,687B2, US20080249458A1, U.S. Pat. Nos. 8,083,716B2, 7,763,007B2, WO2009117182A2, WO2009117183A1, US20090238815A1, US20100022940A1, U.S. Pat. No. 9,192,769B2, US20100152831A1, U.S. Pat. Nos. 8,158,187B2, 8,278,871B2, 8,709,465B2, US20100305428A1, U.S. Pat. Nos. 8,442,651B2, 9,061,115B2, US20160184563A1, US20140360598A1, U.S. Pat. Nos. 9,017,277B2, 8,467,872B2, 8,626,287B2, WO2013059324A1, U.S. Pat. Nos. 8,968,233B2, 9,056,171B2, 9,067,050B2, US20160166813A1, U.S. Pat. No. 8,831,749B2, US20150306382A1, US20150306383A1, US20160144168A1, WO2016115059A1, U.S. Pat. Nos. 3,718,142A, 3,911,929A, 3,968,802A, 4,333,470A, 4,406,286A, 4,476,868A, 4,813,952A, 5,135,467A, 5,562,714A, 5,755,773A, 5,800,376A, 6,102,938A, 6,292,701B1, 6,421,563B1, 6,731,976B2, 6,733,471B1, 6,932,827B2, 6,985,775B2, 7,014,610B2, 7,172,571B2, 7,224,560B2, 7,328,057B2, 7,582,068B2, 8,396,568B2, 8,412,351B2, 9,020,610B2, 9,084,583B2, WO2005018697A2, WO2005018702A2, WO2005030322A1, WO2005118014A3, WO2008022021A2, WO2008134634A1, WO2010126884A2, WO2011014399A1, or WO2015053934A1.

Devices included herein include devices, e.g., a filler, described in, or substantially similar in terms of structure or function to devices described in, one or more of the following patent documents: US20040006383A1, U.S. Pat. Nos. 8,187,319B2, 8,734,397B2, 7,018,384B2, US20040249430A1, U.S. Pat. Nos. 7,156,843B2, 7,879,270B2, US20050124781A1, WO2005065581A1, U.S. Pat. No. 7,108,549B2, US20060030911A1, US20060134357A1, WO2008073695A2, WO2008118579A1, U.S. Pat. Nos. 7,974,704B2, 8,831,748B2, 8,016,814B2, US20090259174A1, WO2010111211A2, U.S. Pat. No. 8,864,786B2, WO2010138386A3, WO2012075296A1, U.S. Pat. No. 8,353,952B2, US20160038212A1, U.S. Pat. No. 9,006,955B2, US20120197366A1, US20150258335A1, US20150306382A1, US20160030644A1, U.S. Pat. Nos.

4,360,573A, 4,611,395A, 4,695,519A, 5,115,818A, 5,347,708A, 5,810,867A, 6,221,059B1, 6,534,587B1, 6,347,632B1, 6,497,841B1, 6,911,036B2, 7,172,587B2, 7,177,140B2, 7,853,328B2, 7,323,142B2, 7,442,466B2, 7,740,656B2, 7,741,375B2, 7,875,697B2, 8,396,568B2, 8,663,225B2, WO2004103463A1, WO2007100995A2, WO2007130948A1, WO2008100840A1, WO2008103466A1, WO2008109020A3, WO2008115694A2, or WO2012148754A1.

Devices included herein include devices, e.g., a nanoparticulate device, described in, or substantially similar in terms of structure or function to devices described in, one or more of the following patent documents: US20040241089A1, US20050009074A1, US20050055078A1, U.S. Pat. No. 7,635,541B2, WO2007047692A2, U.S. Pat. No. 8,128,953B2, US20090198117A1, U.S. Pat. No. 8,016,814B2, US20100131051A1, US20100152832A1, US20100280595A1, U.S. Pat. No. 8,442,651B2, US20120067455A1, US20140052119A1, U.S. Pat. Nos. 8,084,841B2, 8,940,544B2, or WO2008008827A2.

Devices included herein include devices, e.g., an artificial organ, described in, or substantially similar in terms of structure or function to devices described in, one or more of the following patent documents: U.S. Pat. No. 4,987,897A or 8,108,048B2.

Devices included herein include devices, e.g., a device for dialysis, described in, or substantially similar in terms of structure or function to devices described in, one or more of the following patent documents: 8,086,323B2, 8,016,814B2, 8,229,560B2, US20140148754A1, U.S. Pat. Nos. 9,320,842B2, 9,017,277B2, US20160038666A1, US20130213890A1, US20130256227A1, WO2014121168A1, WO2014121159A1, U.S. Pat. No. 9,144,640B2, US20150114891A1, US20140220699A1, US20140326671A1, WO2015199864A4, WO2015081221A1, US20150359954A1, US20150250427A1, WO2015199766A1, WO2015199767A1, WO2015199768A1, US20160166748A1, US20160166751A1, US20160166752A1, US20160166753A1, U.S. Pat. Nos. 5,716,378A, 6,695,790B2, 7,153,473B2, 6,932,827B2, 9,399,090B2, U.S. D711543S1, U.S. D713042S1, U.S. D714455S1, U.S. D714456S1, U.S. D714945S1, U.S. D714946S1, U.S. D722081S1, or WO2007127834A2

Devices included herein include devices described in, or substantially similar in terms of structure or function to devices described in, one or more of the following Dexcom patent documents: US20150157248A1, US20160178558A1, US20160183856A1, US20110124992A1, US20080045824A1, WO2005112741A3, US20060015020A1, U.S. Pat. No. 8,277,713B2, US20150119666A1, U.S. Pat. No. 9,143,569B2, US20090242399A1, US20140378793A1, US20160083768A1, US20090299155A1, WO2009105337A3, US20100049024A1, U.S. Pat. No. 9,339,222B2, US20160101232A1, WO2010127169A3, US20160157766A1, US20160100807A1, U.S. Pat. No. 9,336,353B2, WO2012050926A3, US20160058353A1, US20150087942A1, US20140001042A1, US20160088428A1, US20160198986A1, WO2013022775A1, WO2013032940A1, U.S. Pat. No. 9,386,522B2, US20130245401A1, US20160106349A1, US20160078190A1, US20150090589A1, US20160066843A1, US20140128803A1, US20140088389A1, US20150366491A1, U.S. Pat. No. 9,258,350B2, US20160113556A1, US20150250429A1, WO2014074338A3, US20160183858A1, US20160073879A1, US20160081551A1, US20150366494A1, US20160183855A1, US20150025495A1, U.S. Pat. No. 9,375,065B2, WO2015066051A3, WO2015065922A1, US20160089066A1, WO2015073588A1, US20160066826A1, US20160120448A1, WO2015122964A1, US20150289821A1, US20150351670A1, US20160058380A1, US20160198988A1, WO2016057343A1, US20160183792A1, US20160193409A1, WO2016118635A1, U.S. Pat. Nos. 7,108,778B2, 7,530,950B2, 7,693,560B2, WO2005010518A1, WO2005012871A3, WO2007084130A1, WO2007097754A1, WO2007120129A1, WO2008041984A1, or WO2008105768A1.

Devices included herein include devices described in, or substantially similar in terms of structure or function to devices described in, one or more of the following Abbott patent documents: US20020019991A1, US20120239139A1, US20130190856A1, US20050143752A1, US20060057618A1, US20140221801A1, US20150265197A1, US20150112425A1, US20060235532A1, US20070083199A1, US20070112415A1, U.S. Pat. No. 8,588,881B2, US20070203491A1, US20070213829A1, US20110144736A1, WO2008005277A1, U.S. Pat. Nos. 8,029,558B2, 7,918,011B2, US20080065044A1, U.S. Pat. Nos. 8,652,043B2, 8,846,839B2, 8,121,857B2, 8,974,514B2, WO2008002667A3, U.S. Pat. No. 8,323,327B2, US20080287967A1, US20080319528A1, U.S. Pat. No. 8,382,817B2, US20090018662A1, US20100104506A1, U.S. Pat. No. 8,252,361B2, US20160000360A1, US20090054749A1, US20090076590A1, U.S. Pat. Nos. 7,956,100B2, 8,216,296B2, WO2009154646A1, US20090182379A1, US20150086603A1, US20140322294A1, US20090149945A1, U.S. Pat. No. 8,556,931B2, US20090157089A1, U.S. Pat. No. 9,272,376B2, US20140046156A1, U.S. Pat. Nos. 8,361,538B2, 8,211,489B2, US20090187215A1, WO2009114257A3, US20150267000A1, U.S. Pat. No. 8,377,116B2, US20130145729A1, US20090248130A1, U.S. Pat. Nos. 8,323,676B2, 9,375,445B2, US20090259118A1, U.S. Pat. No. 8,945,663B2, US20150174300A1, US20150025345A1, U.S. Pat. Nos. 8,343,529B2, 8,322,238B2, US20090304693A1, US20090311253A1, U.S. Pat. Nos. 8,562,131B2, 9,186,440B2, US20100040537A1, US20130004416A1, US20140135921A1, U.S. Pat. Nos. 7,896,704B2, 9,039,748B2, US20100074900A1, U.S. Pat. Nos. 8,092,822B2, 9,023,262B2, 8,974,517B2, 8,239,004B2, US20100196315A1, U.S. Pat. No. 8,465,544B2, US20140178454A1, US20100217211A1, US20110165063A1, US20100222875A1, US20100233079A1, US20140236068A1, US20100256680A1, WO2011050262A2, US20100266531A1, US20150216462A1, US20140193475A1, U.S. Pat. Nos. 8,389,646B2, 9,216,238B2, 8,000,763B2, 8,911,766B2, US20100331819A1, US20110004294A1, US20110004302A1, US20110021889A1, U.S. Pat. Nos. 8,119,704B2, 9,072,599B2, US20110034802A1, US20110044980A1, US20110046709A1, US20140100649A1, U.S. Pat. Nos. 9,011,532B2, 8,437,829B2, 8,304,498B2, US20110091372A1, US20110091463A1, US20110137243A1, US20110142761A1, US20110178096A1, US20110184258A1, U.S. Pat. No. 9,291,591B2, US20150024039A1, US20160030217A1, U.S. Pat. Nos. 8,521,318B2, 8,492,484B2, 8,747,738B2, US20110212094A1, US20140155986A1, US20110223176A1, US20110229548A1, US20110230959A1, US20150217009A1, U.S. Pat. No. 9,387,282B2, WO2011129917A1, U.S. Pat. No. 8,679,519B2, US20150317186A1, US20110257722A1, U.S. Pat. No. 8,524,148B2, US20110264103A1, US20160120669A1, U.S. Pat. No. 8,323,678B2, US20110280800A1, US20110282441A1, US20110288577A1, U.S. Pat. No. 8,241,353B2, US20110295356A1, US20110313510A1, U.S. Pat. No. 8,715,719B2, US20110311711A1, U.S. Pat. No. 8,632,841B2, US20110319738A1, US20110319985A1, US20120003291A1, U.S. Pat. No. 8,585,759B2, US20150157658A1, U.S. Pat. Nos. 8,323,799B2, 9,078,958B2, 8,524,132B2, 8,545,556B2, 9,278,026B2, 8,377,533B2, 9,156,949B2, US20120121684A1, US20120143327A1, WO2012121775A9, U.S. Pat. No. 9,336,423B2, US20120201746A1, WO2012109373A2, U.S. Pat. No. 9,320,595B2, US20140031919A1, U.S. Pat. No. 8,927,047B2, US20150083272A1, U.S. Pat. No. 9,051,065B2, US20120219696A1, U.S. Pat. No. 8,852,668B2, US20120258108A1, US20120259399A1, US20120263722A1, U.S. Pat. No. 8,630,810B2, US20120275996A1, U.S. Pat. No. 8,747,649B2, US20120290070A1, US20120296187A1, WO2012149410A3, US20120296426A1, US20120303114A1, U.S. Pat. Nos. 8,894,204B2, 8,821,958B2, US20120330404A1, U.S. Pat. No. 9,180,225B2, US20130005218A1, U.S. Pat. No. 8,734,891B2, US20150250627A1, U.S. Pat. Nos. 8,968,398B2, 9,039,760B2, WO2013043429A1, US20150182223A1, US20150105804A1, US20140079743A1, WO2013052184A1, US20130092298A1, US20130092299A1, U.S. Pat. No. 8,613,849B2, US20130092555A1, U.S. Pat. Nos. 8,617,379B2, 8,617,380B2, US20130096666A1, U.S. Pat. No. 8,790,393B2, US20150100010A1, US20130103138A1, US20130226283A1, U.S. Pat. No. 8,865,189B2, US20150045877A1, US20130129911A1, U.S. Pat. Nos. 8,999,369B2, 9,205,575B2, US20130138117A1, U.S. Pat. No. 9,393,619B2, US20160106585A1, U.S. Pat. Nos. 9,345,599B2, 8,840,678B2, 9,220,759B2, US20130230564A1, U.S. Pat. No. 9,144,487B2, US20130259921A1, US20160184121A1, US20130261723A1, US20160213501A1, U.S. Pat. Nos. 9,358,096B2, 8,871,236B2, 8,956,401B2, 8,864,818B2, US20140288628A1, US20130303496A1, U.S. Pat. Nos. 9,084,671B2, 9,358,325B2, US20130324676A1, U.S. Pat. Nos. 8,784,859B2, 9,339,592B2, 8,864,820B2, WO2014005068A1, U.S. Pat. Nos. 9,066,992B2, 8,876,890B2, US20150196693A1, US20140018903A1, U.S. Pat. No. 9,199,004B2, US20140025160A1, US20140033504A1, US20150182672A1, US20140081417A1, US20140052245A1, US20150374885A1, US20140081372A1, US20140079742A1, US20140081662A1, U.S. Pat. No. 8,758,801B2, WO2014062339A1, US20140107759A1, WO2014065885A1, U.S. Pat. Nos. 9,217,042B2, 9,060,923B2, 9,345,668B2, US20140147485A1, US20140147686A1, US20140154300A1, US20140163666A1, US20140163674A1, US20160045646A1, U.S. Pat. No. 9,067,002B2, US20140188208A1, U.S. Pat. No. 9,393,352B2, WO2014109822A3, US20140200655A1, US20140212476A1, U.S. Pat. No. 9,101,697B2, US20140228932A1, US20160000592A1, WO2014138377A1, WO2014143585A1, WO2014137787A1, U.S. Pat. No. 9,339,401B2, US20160095515A1, WO2014149451A1, US20140277077A1, US20140277331A1, US20140277343A1, WO2014149083A1, US20160157988A1, US20140294912A1, US20140309724A1, US20140324166A1, US20140330194A1, US20140335143A1, US20160158060A1, US20140336747A1, WO2014182696A3, US20140358217A1, US20140364935A1, US20160184491A1, US20140370073A1, US20140377325A1, US20140379064A1, US20150057743A1, US20150005601A1, US20150006109A1, U.S. Pat. Nos. 9,345,597B2, 9,364,350B2, US20150025338A1, US20150030652A1, US20150045882A1, US20150127082A1, US20150062529A1, WO2015187659A2, US20150073536A1, WO2015048158A1, US20150088241A1, U.S. Pat. No. 9,381,279B2, US20150119908A1, WO2015065967A1, US20150134048A1, US20150146758A1, US20150150989A1, US20150151030A1, U.S. Pat. No. 9,327,062B2, US20150174299A1, US20150174303A1, US20150196690A1, U.S. Pat. Nos. 9,375,304B2, 9,345,814B2, WO2015119976A1, US20150223740A1, WO2015134682A1, US20160076077A1, US20150305899A1, WO2015168087A3, US20150313735A1, US20150318101A1, US20150320549A1, US20150328375A1, U.S. Pat. No. 9,381,280B2, US20160030211A1, US20150366690A1, US20160022449A1, US20160038315A1, US20160045346A1, US20160074154A1, US20160128856A1, US20160158420A1, US20160184120A1, US20160184595A1, U.S. Pat. Nos. 2,513,014A, 3,620,216A, 3,748,209A, 5,700,671A, 6,349,740B1, 7,022,136B2, 7,087,083B2, 7,163,558B2, 7,491,218B2, 8,613,764B2, 7,335,227B2, 8,759,055B2, 7,569,655B2, 7,749,263B2, 7,763,271B1, 7,771,739B2, 8,282,679B2, 7,828,916B2, 7,833,544B2, 7,846,385B2, 7,862,830B2, 7,922,760B2, 7,927,621B2, 8,043,367B2, 7,964,210B2, 8,057,529B2, 8,062,350B2, 8,109,904B1, 8,128,688B2, 8,155,722B2, 8,165,651B2, 8,183,337B1, 8,202,528B2, 8,216,310B2, 8,219,175B2, 8,241,348B2, 8,241,653B1, 8,246,670B2, 8,262,723B2, 8,280,474B2, 8,337,739B2, 8,403,980B2, 8,373,090B2, 8,486,141B2, 8,500,786B2, 9,005,276B2, 8,562,669B2, 8,758,401B2, 8,579,956B2, 8,620,398B2, 8,636,884B2, 8,657,871B2, 8,673,334B2, 8,703,169B1, 8,746,882B2, 8,753,709B2, 8,765,162B2, 8,801,781B2, 8,808,723B2, 8,889,172B1, 9,056,155B1, 9,060,849B2, 9,101,698B2, 9,211,203B2, 9,248,121B2, 9,259,515B2, 9,375,331B2, 9,402,752B2, 9,408,727B2, 9,408,949B2, 9,408,952B2, WO1997041824A2, WO1998014977A1, WO2002033688B1, WO2002051810A2, WO2002068410A1, WO2004004602A1, WO2004010971A1, WO2005011539A3, WO2006019591A1, WO2006019659A1, WO2005011660A1, WO2005117728A1, WO2005118015A1, WO2005120277A1, WO2005120369A1, WO2006005116A1, WO2006026725A2, WO2006060765A2, WO2006101737A1, WO2006106268A3, WO2006133315A2, WO2006138690A3, WO2007035441A1, WO2007038076A1, WO2007062070A1, WO2007126606A3, WO2008088456A3, WO2007139668A3, WO2007142801A1, WO2007143063A3, WO2007146049A2, WO2007146231A2, WO2007146410A2, WO2007148012B1, WO2008002479A3, WO2008005317A1, WO2008005439A1, WO2008005530A1, WO2008008283A1, WO2008008334A3, WO2008008427A2, WO2009114326A3, WO2008008491A3, WO2008011048A2, WO2008011093A3, WO2008016667A3, WO2008033263A3, WO2008063287A2, WO2008079361A2, WO2008091747A1, WO2008100847A2, WO2008118257A1, WO2008121508A3, WO2008127271A2, WO2008137237A3, WO2008137649A3, WO2008147621A8, WO2008147645A1, WO2008150280A1, WO2008154111A3, WO2008157254A2, WO2008157339A3, WO2009005675A1, WO2009011850A2, WO2009020936A3, WO2009023618A3, WO2009040380A1, WO2009047352A1, WO2009058666A1, WO2009061848A2, WO2009062711A1, WO2009073569A2, WO2009080323A1, WO2009080325A1, WO2009148848A1, WO2009155206A3, WO2009155299A3, WO2009158290A3, WO2010014391A1, WO2010028087A2, WO2010066446A1, WO2010077949A1, WO2010091005A1, WO2010141897A3, WO2011017340A1, WO2011026130A1, WO2011044386A1, WO2011050979A1, WO2011116090A1, WO2011127141A1, WO2011140167A3, WO2011163478A2, WO2012006490A2, WO2012018790A2, WO2012027570A2, WO2014159743A1, WO2012082898A1, WO2012088290A2, WO2012158202A2, WO2013059624A1, WO2013078135A2, WO2014047483A1, WO2015038940A1, or WO2015119653A1.

Devices included herein include devices described in, or substantially similar in terms of structure or function to devices described in, one or more of the following Semprus patent documents: WO2009085096A3, US20140045398A1, U.S. Pat. No. 9,004,682B2, US20160146974A1, U.S. Pat. Nos. 9,000,063B2, 9,006,359B2, US20130158488A1, US20130158517A1, US20130158518A1, U.S. Pat. No. 8,870,372B2, US20130188124A1, US20140037967A1, U.S. Pat. No. 9,096,703B2, WO2011156590A4, or WO2015021123A1.

Devices included herein include devices described in, or substantially similar in terms of structure or function to devices described in, one or more of the following Teleflex patent documents: U.S. Pat. No. 6,435,056B2, US20020062708A1, U.S. Pat. Nos. 6,575,053B2, 6,634,252B2, 6,733,201B2, 6,571,658B2, US20030140723A1, U.S. Pat. No. 7,228,757B2, US20040168537A1, U.S. Pat. Nos. 6,965,817B2, 7,578,215B2, 7,335,070B2, US20050160859A1, U.S. Pat. Nos. 7,040,937B2, 7,574,937B2, 7,628,096B2, 7,644,727B2, US20060017334A1, U.S. Pat. No. 7,258,072B2, US20060083640A1, U.S. Pat. Nos. 7,128,626B2, 7,245,112B2, 7,597,552B2, 7,215,100B2, WO2006127275A3, U.S. Pat. No. 7,318,386B2, US20070055419A1, U.S. Pat. No. 8,062,010B2, US20070137367A1, U.S. Pat. Nos. 7,388,156B2, 7,400,138B2, US20070245848A1, U.S. Pat. Nos. 7,588,057B2, 7,587,958B2, US20080142349A1, US20080148890A1, US20080149469A1, US20080298788A1, U.S. Pat. Nos. 8,156,881B2, 8,252,081B2, 8,691,286B2, 8,747,911B2, 9,333,280B2, US20120052185A1, US20100234815A1, US20140336584A1, US20140025106A1, U.S. Pat. No. 8,612,072B2, US20130245651A1, US20120029561A1, US20150151025A1, US20130312741A1, U.S. Pat. No. 8,672,966B2, US20120258238A1, US20120184160A1, US20120244761A1, US20120266888A1, US20130030389A1, US20150209536A1, US20130184736A1, US20130218188A1, US20160151073A1, US20130261642A1, U.S. Pat. No. 9,333,536B2, US20140121515A1, US20150352329A1, US20140200554A1, WO2014113428A1, U.S. Pat. No. 9,208,429B2, WO2014124240A1, US20140228685A1, US20140251333A1, WO2014152837A1, US20140261420A1, US20150258230A1, WO2014152812A1, WO2014152807A8, US20140275958A1, WO2014152823A1, US20150051584A1, WO2014159985A1, US20140303554A1, US20150018850A1, US20150065954A1, US20150065992A1, US20150066080A1, US20150119906A1, WO2015069846A1, WO2015081201A1, US20150148800A1, WO2015089038A1, WO2015089034A1, US20150157801A1, US20150201920A1, US20150265777A1, US20160000311A1, US20160001032A1, US20160015423A1, US20160015863A1, US20160022916A1, US20160022962A1, US20160030692A1, US20160038621A1, US20160045217A1, US20160074055A1, US20160184542A1, US20160192829A1, US20160220795A1, US20160228148A1, U.S. Pat. Nos. 2,401,100A, 2,404,885A, 2,425,992A, 2,445,997A, 2,484,551A, 2,496,931A, 2,498,843A, 2,526,563A, 2,551,546A, 2,569,810A, 2,578,592A, 2,601,083A, 2,652,245A, 2,750,582A, 2,788,885A, 2,814,483A, 2,821,092A, 2,875,597A, 2,890,593A, 2,902,877A, 2,924,987A, 2,927,473A, 2,938,404A, 2,957,352A, 2,957,353A, 2,959,982A, 3,051,886A, 3,058,687A, 3,063,303A, 3,091,496A, 3,135,130A, 3,138,511A, 3,143,001A, 3,153,944A, 3,162,425A, 3,166,849A, 3,169,409A, 3,169,719A, 3,177,901A, 3,183,737A, 3,184,986A, 3,184,991A, 3,206,998A, 3,218,880A, 3,230,979A, 3,237,477A, 3,238,808A, 3,248,250A, 3,248,251A, 3,257,863A, 3,261,568A, 3,263,519A, 3,263,520A, 3,263,948A, 3,263,949A, 3,285,551A, 3,289,491A, 3,293,896A, 3,300,258A, 3,300,331A, 3,301,592A, 3,302,479A, 3,317,993A, 3,321,244A, 3,321,246A, 3,342,243A, 3,348,427A, 3,350,959A, 3,351,382A, 3,352,814A, 3,354,742A, 3,369,426A, 3,390,589A, 3,393,578A, 3,395,027A, 3,395,591A, 3,398,600A, 3,411,373A, 3,416,389A, 3,423,229A, 3,424,027A, 3,426,613A, 3,427,894A, 3,429,197A, 3,429,700A, 3,434,501A, 3,435,107A, 3,438,280A, 3,438,468A, 3,443,451A, 3,452,479A, 3,464,285A, 3,464,286A, 3,464,287A, 3,479,903A, 3,487,709A, 3,495,786A, 3,505,900A, 3,513,719A, 3,516,299A, 3,516,301A, 3,518,896A, 3,531,061A, 3,550,248A, 3,554,050A, 3,570,324A, 3,572,153A, 3,572,159A, 3,572,160A, 3,580,103A, 3,613,148A, 3,656,975A, 3,661,352A, 3,710,645A, 3,665,784A, 3,674,307A, 3,730,130A, 3,741,513A, 3,766,801A, 3,815,201A, 3,798,992A, 3,823,978A, 3,828,624A, 3,859,702A, 3,833,257A, 3,838,607A, 3,842,695A, 3,847,034A, 3,869,293A, 3,871,244A, 3,929,032A, 3,885,474A, 3,885,770A, 3,908,687A, 3,929,031A, 3,935,796A, 3,964,344A, 3,945,268A, 3,954,022A, 3,960,032A, 3,964,337A, 3,993,350A, 4,007,645A, 4,011,770A, 4,014,136A, 4,014,281A, 4,038,881A, 4,062,251A, 4,092,905A, 4,171,943A, 4,106,168A, 4,173,157A, 4,175,450A, 4,177,691A, 4,185,515A, 4,185,517A, 4,188,835A, 4,218,935A, 4,228,757A, 4,238,107A, 4,238,972A, 4,261,220A, 4,271,700A, 4,321,840A, 4,324,148A, 4,325,904A, 4,327,600A, 4,331,041A, 4,333,361A, 4,406,177A, 4,649,010A, 4,449,470A, 4,458,552A, 4,459,870A, 4,470,363A, 4,499, 785A, 4,503,730A, 4,509,387A, 4,517,765A, 4,519,294A, 4,535,260A, 4,547,239A, 4,572,053A, 4,581,953A, 4,590,819A, 4,606,237A, 4,610,180A, 4,625,579A, 4,642,032A, 4,657,024A, 4,669,494A, 4,841,806A, U.S. RE33043E1, 4,688,445A, 4,694,705A, 4,700,485A, 4,712,397A, 4,721,469A, 4,723,059A, 4,793,050A, 4,742,297A, 4,763,541A, 4,765,199A, 4,773,279A, 4,773,882A, 4,806,161A, 4,811,621A, 4,842,592A, 4,860,609A, 4,872,365A, 4,872,367A, 4,881,447A, 4,882,971A, 4,893,582A, 4,898,077A, 4,899,956A, 4,909,095A, 4,932,689A, 4,941,766A, 4,951,524A, 4,970,912A, 5,001,927A, 5,003,838A, 5,005,409A, 5,014,569A, 5,018,469A, 5,042,645A, 5,046,763A, 5,058,462A, 5,065,961A, 5,072,759A, 5,074,162A, 5,079,967A, 5,081,908A, 5,088,664A, 5,092,542A, 5,092,801A, 5,101,962A, 5,104,156A, 5,105,678A, 5,105,924A, 5,113,717A, 5,142,782A, 5,138,898A, 5,142,933A, 5,156,063A, 5,161,427A, 5,161,428A, 5,167,166A, U.S. RE37775E1, 5,171,172A, 5,280,733A, 5,186,417A, 5,192,476A, 5,199,320A, 5,199,321A, 5,211,193A, 5,213,527A, 5,216,919A, 5,218,881A, 5,220,832A, 5,230,257A, 5,239,890A, 5,241,879A, 5,253,543A, 5,261,293A, 5,265,495A, 5,272,934A, 5,275,531A, 5,317,935A, 5,435,052A, 5,342,321A, U.S. RE36342E1, 5,377,556A, 5,381,706A, 5,381,834A, 5,383,377A, 5,383,630A, 5,398,566A, 5,427,045A, 5,435,203A, 5,440,946A, U.S. RE36722E1, 5,477,745A, 5,481,871A, 5,493,934A, 5,509,750A, 5,531,134A, 5,533,419A, 5,546,827A, 5,547,069A, 5,555,769A, 5,560,259A, 5,570,611A, 5,570,612A, 5,575,180A, 5,664,462A, 5,579,662A, 5,582,074A, 5,596,908A, 5,605,074A, 5,613,405A, 5,613,406A, 5,613,524A, 5,615,583A, 5,615,584A, WO1998003840A1, U.S. Pat. Nos. 5,653,147A, U.S. RE39327E1, 6,257,280B1, 5,656,774A, 6,332,167B1, 5,678,456A, 5,682,796A, 5,682,797A, 5,682,798A, 5,685,199A, 6,298,748B1, 5,862,580A, 5,702,196A, 5,704,255A, 6,658,488B2, 5,724,858A, 5,724,907A, 5,728,121A, 5,737,973A, 5,752,414A, 5,802,930A, 5,836,212A, 5,853,202A, 5,857,386A, 5,860,303A, 6,082,625A, 5,898,308A, 6,185,806B1, 5,911,790A, 5,911,791A, 5,931,510A, 5,934,150A, 5,943,908A, 5,951,518A, 5,997,370A, 6,003,402A, 6,016,049A, 6,016,717A, 6,038,939A, 6,039,084A, 6,056,020A, 6,058,797A, 6,070,489A, 6,082,217A, 6,101,896A, 6,237,565B1, 6,308,395B1, 6,134,987A, 6,138,802A, 6,374,695B1, 6,158,299A, 6,209,417B1, 6,173,625B1, 6,179,081B1, 6,186,025B1, 6,189,408B1, 6,205,883B1, 6,209,418B1, 6,212,970B1, 6,216,555B1, 6,220,112B1, 6,220,222B1, 6,230,579B1, 6,231,476B1, 6,241,068B1, 6,244,107B1, 6,357,319B2, 6,263,859B1, 6,302,150B1, 6,314,831B2, 6,330,838B1, 6,662,677B2, 6,364,047B1, 6,382,045B1, 6,389,926B1, 6,393,934B1, 6,406,340B1, 6,450,801B1, 6,523,565B2, 6,557,821B2, 6,579,072B2, 6,612,200B1, 6,631,883B1, 6,948,528B2, 6,651,574B1, 6,658,706B2, 6,689,054B2, 6,695,868B2, 6,698,309B2, 6,718,845B2, 6,725,741B2, 7,128,627B2, 7,055,760B2, 7,025,026B2, 6,799,487B2, 6,811,141B2, 6,814,097B2, 6,817,978B2, 6,840,888B1, 6,845,965B2, 6,851,445B2, 7,059,347B2, 6,901,952B2, 6,955,103B2, 6,963,146B2, 7,021,854B2, 7,052,504B2, 7,109,851B2, 7,135,981B1, 7,137,347B2, 7,154,248B2, 7,156,125B2, 7,156,708B2, 7,228,859B2, 7,240,588B1, 7,261,689B2, 7,284,936B1, 7,290,465B2, 7,316,696B2, 7,316,699B2, 7,326,223B2, 7,364,482B1, 7,390,316B2, 7,560,905B2, 7,407,420B2, 7,421,772B2, 7,476,223B2, 7,497,183B2, 7,503,104B2, 7,562,602B2, 7,562,607B2, 7,585,304B2, 7,594,509B2, 7,672,759B1, 7,717,462B2, 7,722,418B2, 7,736,308B2, 8,000,851B2, 7,806,142B2, 8,011,260B2, 7,975,567B2, 8,007,330B2, 8,025,006B2, 8,028,510B2, 8,097,005B2, 8,298,252B2, 9,326,757B2, 9,326,784B2, 9,333,029B2, U.S. D33738451, U.S. D34408951, U.S. D350393S1, U.S. D508227S1, U.S. D51031051, U.S. D51031151, U.S. D51055651, U.S. D51055751, U.S. D510558S1, U.S. D51055951, U.S. D51236451, U.S. D54022751, U.S. D56275351, U.S. D56275451, U.S. D74041051, WO1999028672A1, WO2001064553A1, WO2003036142A1, WO2003045635A1, WO2004015313A3, WO2005005846A1, WO2005006921A1, WO2005078547A1, WO2006020650A1, WO2006078579A3, WO2006126984A3, WO2007019673A1, WO2007073501A3, WO2007108957A3, WO2007109108A3, WO2007127295A3, WO2008019019A3, WO2009004492A3, WO2010039828A1, WO2010136789A1, WO2011098914A1, WO2011107890A3, WO2011098922A3, WO2012066346A1, WO2013082301A1, WO2013109835A1, WO2015049582A1, WO2016018806A1, WO2016022789A1, WO2016022894A1, WO2016022897A1, WO2016025545A1, or WO2016126299A1.

Devices included herein include devices described in, or substantially similar in terms of structure or function to devices described in, one or more of the following Stryker patent documents: U.S. Pat. No. 1,667,102A, US20020127540A1, US20040138128A1, US20050080335A1, US20050107878A1, US20060058787A1, US20060293689A1, US20080109007A1, US20080109008A1, U.S. Pat. No. 7,557,078B1, US20090017430A1, US20090259240A1, US20100204798A1, US20100305714A1, US20110019884A1, US20110150943A1, US20110213379A1, US20110213406A1, US20110218560A1, US20110295308A1, US20110314602A1, US20120197302A1, US20120237568A1, U.S. Pat. No. 8,974,513B2, US20120277802A1, US20130013001A1, US20130211535A1, US20130220858A1, US20130225948A1, US20130226215A1, US20130231610A1, US20130238032A1, US20130264749A1, US20130304074A1, US20130317512A1, US20130325053A1, US20130331656A1, US20140012335A1, US20140031831A1, US20140039629A1, US20140051632A1, US20140067065A1, US20140088595A1, US20140114362A1, US20140121674A1, US20140162273A1, US20140200671A1, US20140222078A1, US20140249570A1, US20140257486A1, US20140277145A1, US20140277206A1, US20140277391A1, US20140336595A1, US20140342976A1, US20140343643A1, US20140364863A1, US20140371862A1, US20140378973A1, US20150025367A1, US20150032160A1, US20150045838A1, US20150057758A1, US20150073415A1, US20150080299A1, US20150088210A1, US20150100094A1, US20150112179A1, US20150133943A1, US20150133945A1, US20150142003A1, US20150142119A1, US20150148176A1, US20150150504A1, US20150164569A1, US20150164647A1, US20150182295A1, US20150201999A1, US20150202053A1, US20150216614A1, US20150230930A1, US20150265361A1, US20150297273A1, US20150342745A1, US20150342755A1, US20150352350A1, US20150374446A1, US20160000486A1, US20160008045A1, US20160015935A1, US20160045268A1, US20160058922A1, US20160074073A1, US20160074118A1, US20160095636A1, US20160113775A1, US20160135815A1, US20160144070A1, US20160158036A1, US20160174991A1, US20160175019A1, US20160199101A1, US20160199111A1, US20160199190A1, US20160199193A1, US20160213482A1, US20160220730A1, US20160220793A1, U.S. Pat. Nos. 3,308,491A, 3,955,567A, 4,509,516A, 4,817,629A, 4,919,667A, 5,268,622A, 5,584,838A, 5,741,254A, 5,879,306A, 5,910,816A, 5,961,524A, 6,004,327A, 6,102,957A, 6,019,766A, 6,129,764A, 6,620,168B1, 6,258,095B1, 6,280,475B1, 6,296,647B1, 6,375,683B1, 6,426,332B1, 6,504,079B2, 6,520,969B2, 6,547,791B1, 6,572,617B1, 6,579,320B1, 6,582,466B1, 6,582,468B1, 6,605,117B2, 6,641,261B2, 6,664,308B2, 6,673,115B2, 6,716,957B2, 6,729,726B2, 6,733,532B1, 684,008A, 6,908,485B2, 7,026,292B1, 7,077,847B2, 7,147,643B2, 7,156,874B2, 7,232,443B2, 7,311,710B2, 7,316,684B1, 7,347,130B2, 7,410,947B2, 7,491,221B2, 7,507,709B2, 7,549,994B2, 7,569,055B2, 7,637,929B2, 7,637,950B2, 7,648,508B2, 7,648,529B2, 7,682,361B2, 7,686,806B2, 7,686,837B2, 7,722,574B2, 7,766,917B2, 7,776,040B2, 7,799,062B2, 7,803,369B2, 7,890,179B2, 7,927,346B2, 8,007,448B2, 8,014,849B2, 8,016,852B2, 8,052,729B2, 8,057,480B2, 8,137,385B2, 8,142,485B2, 8,172,862B2, 8,173,149B2, 8,202,292B2, 8,226,660B2, 8,226,680B2, 8,226,691B2, 8,234,722B2, 8,241,345B2, 8,246,627B2, 8,262,607B2, 8,372,062B2, 8,308,751B2, 8,328,791B2, 8,377,062B2, 8,377,878B2, 8,403,938B2, 8,425,529B2, 8,444,661B2, 8,449,581B2, 8,483,434B2, 8,486,101B2, 8,486,104B2, 8,486,117B2, 8,506,615B2, 8,529,619B2, 8,540,759B2, 8,556,944B2, 8,560,083B2, 8,565,870B2, 8,603,091B2, 8,603,175B2, 8,617,173B2, 8,632,568B2, 8,672,940B2, 8,709,014B2, 8,728,134B2, 8,740,909B2, 8,740,952B2, 8,747,430B2, 8,748,378B2, 8,753,399B2, 8,814,920B2, 8,834,479B2, 8,840,666B2, 8,858,596B2, 8,864,802B2, 8,882,740B2, 8,894,660B2, 8,979,848B2, 9,002,451B2, 9,011,447B2, 9,011,668B2, 9,017,415B2, 9,034,020B2, 9,044,283B2, 9,060,874B2, 9,084,710B2, 9,089,378B2, 9,107,711B2, 9,119,938B2, 9,162,040B2, 9,186,189B2, 9,198,701B2, 9,198,703B2, 9,220,534B2, 9,232,948B2, 9,247,977B2, 9,265,541B2, 9,283,007B2, 9,314,250B2, 9,314,326B2, 9,320,554B2, 9,320,555B2, 9,320,630B2, 9,326,779B2, 9,333,013B2, 9,339,280B2, 9,339,315B2, 9,345,578B2, 9,351,775B2, 9,358,049B2, 9,358,053B2, 9,358,117B2, 9,381,085B2, 9,387,023B2, 9,402,661B2, 9,408,716B1, U.S. RE42377E1, U.S. RE43311E1, U.S. RE45676E1, WO1996022747A1, WO2000062717A1, WO2001062190A1, WO2003024316A3, WO2004004663A2, WO2005077403A1, WO2005084701A1, WO2005111069A2, WO2005115438A1, WO2006029406A3, WO2006063156A1, WO2006078656B1, WO2006090261A1, WO2007047629A2, WO2007118591A1, WO2007142818A2, WO2008036167A4, WO2008067455A2, WO2008080073A3, WO2008085289A1, WO2008122008A1, WO2011072128A1, WO2011097402A1, WO2013192431A1, WO2014091454A1, WO2014105873A1, WO2014137876A2, WO2014151577A1, WO2014159350A1, WO2015028100A1, WO2015042238A1, WO2015065969A1, WO2015102988A1, WO2015124171A1, WO2015157181A1, WO2015167997A1, WO2015168016A1, WO2015172842A1, WO2015184075A1, WO2016020014A1, WO2016039979A3, or WO2016069830A2.

In any and all aspects of the present invention, in some embodiments, the compound, composition, or implantable element (e.g., device or material) is a composition, or implantable element (e.g., device or material) other than a compound, composition, or implantable element (e.g., device or material) described in WO2012/112982, WO2012/167223, WO2014/153126, WO2016/187225, WO2016/019391, WO2017/075630, WO 2017/075631, and US 2016-0030359. In some embodiments, the compound of Formula (I) or device comprising the same is a compound or device other than a compound or device described in WO2012/112982, WO2012/167223, WO2014/153126, WO2016/187225, WO2016/019391, WO2017/075630, WO 2017/075631, and US 2016-0030359. In some embodiments, the device comprises a material other than a material described in WO2012/112982, WO2012/167223, WO2014/153126, WO2016/187225, WO2016/019391, WO2017/075630, WO 2017/075631, and US 2016-0030359. In some embodiments, the device is attached to a compound of Formula (I) through an attachment group other than an attachment group described in WO2012/112982, WO2012/167223, WO2014/153126, WO2016/187225, WO2016/019391, WO2017/075630, WO 2017/075631, and US 2016-0030359.

Cells and Other Components

The implantable elements described herein (e.g., devices and materials, e.g., associated with a compound, e.g., a compound of Formula (I)) may encapsulate or coat a cell or plurality of cells, entirely or at least in part. In an embodiment, the device comprises a cell. In some embodiments, the cell is an engineered cell or a non-engineered cell. In an embodiment, the cell is a naturally derived cell or a recombinant cell. In an embodiment, the cell is an autologous, allogeneic, or xenogeneic cell (these terms refer to the relationship between the cell and a subject to which the cell is administered). In an embodiment, the cell is an immortalized cell or is derived from an immortalized cell.

In an embodiment, the cell is a less differentiated cell, e.g., pluripotent cell, multipotent cell, a stem cell, an embryonic stem cell, a mesenchymal stem cell, an induced pluripotent stem cell, a reprogrammed cell, a reprogrammed stem cell, or a cell derived from reprogrammed stem cells. A less differentiated cell can be a naturally occurring cell, a less differentiated cell, or an induced less differentiated cell, e.g., respectively, a stem cell or an induced stem cell.

In an embodiment, the cell is derived from a naturally a derived source, xenotissue, allotissue, a cadaver, a cell line, or a primary cell.

In an embodiment, the cell type for use with a device or method described herein is selected based on the desired output (e.g., desired therapeutic effect).

In an embodiment, the device comprises a plurality of cells, e.g., more than 2, 3, 4, 5, 10, 15, 20, 25, 50, 75, 100, 150, 200, 250, 300, 400, 500, 600, 700, 800, 900, or 1,000 cells.

Types of cells for inclusion in the disclosed devices described herein include liver cells (e.g., hepatoblasts liver stellate cells, biliary cells, or hepatocytes), insulin producing cells (e.g., pancreatic islet cells, isolated pancreatic beta cells, or insulinoma cells), kidney cells, epidermal cells, epithelial cells, neural cells, including neurons and glial cells (e.g., astrocytes), ganglion cells, retinal pigment epithelial cells, adrenal medulla cells, lung cells, cardiac muscle cells, osteoblast cells, osteoclast cells, bone marrow cells, spleen cells, thymus cells, glandular cells, blood cells (e.g., T cells, B cells, macrophage lineage cells, lymphocytes, or monocytes), endocrine hormone-producing cells (e.g., parathyroid, thyroid, or adrenal cells), cells of intestinal origin and other cells acting primarily to synthesize and secret or to metabolize materials, endothelial cells (e.g., capillary endothelial cells), fibroblasts (e.g., dermal fibroblasts), myogenic cells, keratinocytes, smooth muscle cells, progenitor cells (e.g., bone marrow progenitor cells, adipose progenitor cells, hepatic precursor cells, endothelia progenitor cells, peripheral blood progenitor cells, or progenitor cells from muscle or skin), and marrow stromal cells (e.g., CHO cells, MDCK cells and PC12 cells).

In an embodiment, the cell is a retinal pigment epithelial (RPE) cell, or an RPE-like cell. An RPE-like cell refers to a cell having one or more of the following characteristics: a) it comprises a retinal pigment epithelial cell (RPE) or a cell derived therefrom, including a cell derived from a primary cell culture of RPE cells, a cell isolated directly (without long term culturing, e.g., less than 5 or 10 passages or rounds of cell division since isolation) from naturally occurring RPE cells, e.g., from a human or other mammal, a cell derived from a transformed, an immortalized, or a long term (e.g., more than 5 or 10 passages or rounds of cell division) RPE cell culture; b) a cell that has been obtained from a less differentiated cell, e.g., a cell developed, programmed, or reprogramed (e.g., in vitro) into an RPE cell or a cell that is, except for any genetic engineering, substantially similar to one or more of a naturally occurring RPE cell or a cell from a primary or long term culture of RPE cells (e.g., such an active cell can be derived from an IPS cell); or c) a cell that has one or more of the following properties: i) it expresses one or more of the biomarkers CRALBP, RPE-65, RLBP, BEST1, or αB-crystallin; ii) it does not express one or more of the biomarkers CRALBP, RPE-65, RLBP, BEST1, or αB-crystallin; iii) it is naturally found in the retina and forms a monolayer above the choroidal blood vessels in the Bruch's membrane; or iv) it is responsible for epithelial transport, light absorption, secretion, and immune modulation in the retina.

In an embodiment, the device comprises a cell, e.g., a recombinant cell, which provides a substance, e.g., a therapeutic agent. In an embodiment, the substance comprises a polypeptide. In an embodiment, the cell is a human cell and the polypeptide is a human polypeptide. In an embodiment, the cell is a non-human cell and the polypeptide is a human polypeptide. In an embodiment, the subject has a disorder, and the cell provides a substance that alleviates the disorder. In an embodiment, the disorder is diabetes and the substance is insulin.

In an embodiment, the method comprises, providing a compound of Formula (I) or a pharmaceutically acceptable salt thereof at a site which does not comprise an implanted cell or device, e.g., a joint. In an embodiment, the method comprises, providing a device comprising compound of Formula (I) or a pharmaceutically acceptable salt thereof at a site which does not comprise an implanted cell or device, e.g., a joint. In an embodiment, the method comprises, providing a device coated with a compound of Formula (I) or a pharmaceutically acceptable salt thereof at a site which does not comprise an implanted cell or device, e.g., a joint. In an embodiment, the method comprises, providing a device encapsulating a compound of Formula (I) or a pharmaceutically acceptable salt thereof at a site which does not comprise an implanted cell or device, e.g., a joint.

In another aspect, the invention features a method of making a compound (e.g., a compound of Formula (I)) or a pharmaceutically acceptable salt thereof.

In another aspect, the invention features a method of making a device comprising a compound (e.g., a compound of Formula (I)), wherein the method comprises associating a compound of Formula (I) with said device.

In an embodiment, the device is a device described herein. In some embodiments, the cell is a cell described herein.

In another aspect, the present invention features methods for modulating the efficiency or fidelity of a device, e.g., a device comprising a compound (e.g., a compound of Formula (I)), or a material or device comprising a compound (e.g., a compound of Formula (I)), or a pharmaceutically acceptable salt thereof. In some embodiments, the modulating comprises increasing or decreasing. In some embodiments, the method comprises increasing the long-term performance of a device comprising a compound (e.g., a compound of Formula (I)) or a pharmaceutically acceptable salt thereof. In some embodiments, the method comprises increasing the tolerability of a device comprising a compound (e.g., a compound of Formula (I)) or a pharmaceutically acceptable salt thereof. In some embodiments, the method comprises reducing the failure rate of a device comprising a compound (e.g., a compound of Formula (I)) or a pharmaceutically acceptable salt thereof.

In an embodiment, the method comprises, providing a compound (e.g., a compound of Formula (I)) or a pharmaceutically acceptable salt at the site of an implanted cell or device.

In an embodiment, the site comprises an exogenous entity, e.g., an implanted device, or cell, e.g., a device or material described in herein, comprising a compound of Formula (IO or a pharmaceutically acceptable salt thereof. In an embodiment providing comprises providing a device or cell, e.g., a device or cell described herein, to the subject.

In an embodiment the compound is provided at the time of implantation of the device or cell, e.g., associated with, e.g., covalently associated with the device or cell.

In an embodiment, the method comprises reducing an unwanted reaction to an implanted device or cell, e.g., reducing fibrosis or, inflammation at, or inactivation of, the implanted device or cell.

Methods of Treatment

The present invention features a compound described herein (e.g., a compound of Formula (I)), or a device or material comprising a compound (e.g., a compound of Formula (I)), or a pharmaceutically acceptable salt thereof, and methods of use thereof. In one aspect, the compounds, compositions, devices, materials, and methods may be used to treat a disease, disorder, or condition, e.g., as described herein.

In some embodiments, the disease, disorder, or condition affects a system of the body, e.g. the nervous system (e.g., peripheral nervous system (PNS) or central nervous system (CNS)), vascular system, skeletal system, respiratory system, endocrine system, lymph system, reproductive system, or gastrointestinal tract. In some embodiments, the disease, disorder, or condition affects a part of the body, e.g., blood, eye, brain, skin, lung, stomach, mouth, ear, leg, foot, hand, liver, heart, kidney, bone, pancreas, spleen, large intestine, small intestine, spinal cord, muscle, ovary, uterus, vagina, or penis.

Exemplary diseases, disorders, or conditions include neurodegenerative disease, cancer (e.g., cancer of the breast, brain, skin, liver, eye, lung, or other organ or tissue), autoimmune disease (e.g., diabetes, multiple sclerosis, lupus, occlusions, capsular contractions), or a liver disease (e.g., hepatitis B infection, hepatitis C infection, cirrhosis, or liver cancer). In some embodiments, the disease is diabetes (e.g., type 1 diabetes or type 2 diabetes). In some embodiments, the condition is fibrosis. In some embodiments, the condition is inflammation.

In certain embodiments, the disease, disorder, or condition is an inflammatory disease. All types of inflammatory diseases are contemplated as being within the scope of the invention. In certain embodiments, the inflammatory disease is an autoinflammatory disease. In some embodiments, the inflammatory disease is an autoimmune disease.

In some embodiments, the disease, disorder or condition is a neurodegenerative disease. Exemplary neurodegenerative diseases include Alzheimer's disease, Huntington's disease, Parkinson's disease (PD) amyotrophic lateral sclerosis (ALS), multiple sclerosis (MS) and cerebral palsy (CP), dentatorubro-pallidoluysian atrophy (DRPLA), neuronal intranuclear hyaline inclusion disease (NIHID), dementia with Lewy bodies, Down's syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Jakob-Creutzfeldt disease, Niemann-Pick disease type 3, progressive supranuclear palsy, subacute sclerosing panencephalitis, spinocerebellar ataxias, Pick's disease, and dentatorubral-pallidoluysian atrophy.

In some embodiments, the disease, disorder, or condition is an autoimmune disease, e.g., scleroderma, multiple sclerosis, lupus, or allergies.

In some embodiments, the disease is a liver disease, e.g., hepatitis B, hepatitis C, cirrhosis, NASH.

In some embodiments, the disease, disorder, or condition is cancer. Exemplary cancers include leukemia, lymphoma, melanoma, lung cancer, brain cancer (e.g., glioblastoma), sarcoma, pancreatic cancer, renal cancer, liver cancer, testicular cancer, prostate cancer, or uterine cancer.

In some embodiments, the disease, disorder, or condition is an orthopedic condition. Exemplary orthopedic conditions include osteoporosis, osteonecrosis, Paget's disease, or a fracture.

In some embodiments, the disease, disorder or condition is a lysosomal storage disease. Exemplary lysosomal storage diseases include Gaucher disease (e.g., Type I, Type II, Type III), Tay-Sachs disease, Fabry disease, Farber disease, Hurler syndrome, Hunter syndrome, lysosomal acid lipase deficiency, Niemann-Pick disease, Salla disease, Sanfilippo syndrome, multiple sulfatase deficiency, Maroteaux-Lamy syndrome, metachromatic leukodystrophy, Krabbe disease, Scheie syndrome, Hurler-Scheie syndrome, Sly syndrome, hyaluronidase deficiency, Pompe disease, Danon disease, gangliosidosis, or Morquio syndrome.

In some embodiments, the disease, disorder, or condition is a blood clotting disorder or a coagulation disorder. Exemplary blood clotting disorders or coagulation disorders include hemophilia (e.g., hemophilia A or hemophilia B), Von Willebrand disease, thrombocytopenia, uremia, Bernard-Soulier syndrome, Factor XII deficiency, vitamin K deficiency, or congenital afibrinogenimia.

In some embodiments, the disease, disorder, or condition is an amino acid metabolism disorder, e.g., phenylketonuria, tyrosinemia (e.g., Type 1 or Type 2), alkaptonuria, homocystinuria, hyperhomocysteinemia, maple syrup urine disease.

In some embodiments, the disease, disorder, or condition is a fatty acid metabolism disorder, e.g., hyperlipidemia, hypercholesterolemia, galactosemia.

In some embodiments, the disease, disorder, or condition is a purine or pyrimidine metabolism disorder, e.g., Lesch-Nyhan syndrome, The present invention additionally features methods for modulating an immune response in a subject comprising providing to a subject a compound of Formula (I), or a material or device comprising a compound of Formula (I), or a pharmaceutically acceptable salt thereof. In some embodiments, the modulating comprises an upregulation or downregulation of the immune response, or a component thereof in a subject, e.g., at a site in the subject, e.g., the site of an implanted cell or device.

In some embodiments, the method comprises providing a compound of Formula (I) in order to downregulate an immune response. In some embodiments, the method comprises providing a device comprising compound of Formula (I) in order to downregulate an immune response.

In some embodiments, the method comprises providing a compound of Formula (I) in order to upregulate an immune response. In some embodiments, the method comprises providing a device comprising a compound of Formula (I) in order to upregulate an immune response.

In some embodiments, the method comprises modulating inflammation in a subject (e.g., decreasing inflammation or increasing inflammation). In some embodiments, the method comprises modulating fibrosis in a subject (e.g., decreasing fibrosis or increasing fibrosis). In some embodiments, the method comprises modulating the level of a component of the immune system in a subject (e.g., increasing the level or decreasing the level of a component). Exemplary immune system components that may be modulated by a method described herein include T cells (e.g., an invasive T cell, a killer T cell, an effector T cell, a memory T cell, a gamma delta T cell, a helper T cell), B cells, antibodies, or other components.

In some embodiments, the method comprises the additional step of administering one or more additional pharmaceutical agents in combination with the compound described herein (e.g., the compound of Formula (I)) or a pharmaceutically acceptable salt thereof. Such additional pharmaceutical agents include, but are not limited to, anti-proliferative agents, anti-cancer agents, anti-diabetic agents, anti-inflammatory agents, immunosuppressant agents, and a pain-relieving agent.

Pharmaceutical Compositions and Administration

The present invention provides pharmaceutical compositions comprising a compound of Formula (I), or a pharmaceutically acceptable salt, solvate, hydrate, tautomer, stereoisomer, or isotopically labeled derivative thereof, as described herein, and optionally a pharmaceutically acceptable excipient. In certain embodiments, the compound of Formula (I) or a pharmaceutically acceptable salt, solvate, hydrate, tautomer, stereoisomer, or isotopically labeled derivative thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I) (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Compounds, compositions, and devices comprising said compounds and compositions administered or implanted orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

For ophthalmic use, provided compounds, compositions, and devices may be formulated as micronized suspensions or in an ointment such as petrolatum.

Pharmaceutically acceptable compositions of this invention may also be administered by nasal aerosol or inhalation.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form, e.g., single unit dosage form, for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

ENUMERATED EMBODIMENTS

1. A compound of Formula (I):

A-$L^1$-M-$L^2$-P-$L^3$-Z (I)

or a salt thereof, wherein:

A is selected from A1 or A2, wherein

A1 is hydrogen, alkyl, alkenyl, alkynyl, heteroalkyl, cycloalkyl, heterocyclyl, aryl, heteroaryl, —$OR^A$, —C(O)$OR^A$, —C(O)$R^B$, —OC(O)$R^B$, —N($R^C$)($R^D$), —N($R^C$)C(O)$R^B$, —C(O)N($R^C$)($R^D$), —$N_3$, —NC, —CN, —NCO, —NCS, —N($R^C$)N($R^D$)$_2$, —NCN$R^C$, —C(=N($R^C$)($R^D$))$OR^A$, —$SR^E$, —S(O)$_x R^E$, —OS(O)$_x R^E$, —N($R^C$)S(O)$_x R^E$, —S(O)$_x$N($R^C$)($R^D$), —P($R^F$)$_y$, —Si($OR^A$)$_3$, —Si($R^G$)($OR^A$)$_2$, —B($OR^A$)$_2$, or a metal, wherein each alkyl, alkenyl, alkynyl, heteroalkyl, cycloalkyl, heterocyclyl, aryl, heteroaryl is optionally substituted with one or more $R^1$;

A2 is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, —NCN—, —C(=N($R^C$)($R^D$))O—, —S—, —S(O)$_x$—, —OS(O)$_x$, —N($R^C$)S(O)$_x$—, —S(O)$_x$N($R^C$)—, —P($R^F$), —Si($OR^A$)$_2$—, —Si($R^G$)($OR^A$), —B($OR^A$), or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted by one or more $R^1$;

each $L^1$, $L^2$, and $L^3$ is independently a bond, alkyl, alkenyl, alkynyl, or heteroalkyl, wherein each alkyl, alkenyl, alkynyl, and heteroalkyl is optionally substituted by 1-5 $R^2$;

M is alkyl, alkenyl, alkynyl, heteroalkyl, cycloalkyl, heterocyclyl, aryl, or heteroaryl, each of which is optionally substituted by one or more $R^3$;

P is cycloalkyl, heterocyclyl, aryl, or heteroaryl, each of which is optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with one or more $R^6$, or $R^C$ and $R^D$, taken together with the nitrogen atom to which they are attached, form a ring (e.g., a 5-7 membered ring), optionally substituted with one or more $R^6$, each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, —S(O)$_x R^E$, —OS(O)$_x R^E$, —N($R^C$)S(O)$_x R^E$, —S(O)$_x$N($R^C$)($R^D$), —P($R^F$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

2. The compound of embodiment 1, wherein A is A1.

3. The compound of any one of the preceding embodiments, wherein A1 is hydrogen, alkyl, alkenyl, alkynyl, heteroalkyl, cycloalkyl, heterocyclyl, aryl, heteroaryl, —$OR^A$, —C(O)$OR^A$, —C(O)$R^B$, —OC(O)$R^B$, or —N($R^C$)($R^D$).

4. The compound of any one of the preceding embodiments, wherein A1 is —N($R^C$)($R^D$) (e.g., $NH_2$) or NHC(O)C($CH_2$)$CH_3$.

5. The compound of embodiment 1, wherein A is A2.

6. The compound of embodiment 5, wherein A2 is alkyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —Si($OR^A$)$_2$—, —Si($R^G$)($OR^A$)—, or —B($OR^A$)—.

7. The compound of any one of embodiments 5-6, wherein A2 is —N($R^C$)— (e.g., NH—) or NH(C(O)C($CH_3$)$CH_2$—.

8. The compound of any one of embodiments 5-7, wherein the compound comprises A2, and, e.g., is covalently attached to a device.

9. The compound of embodiment 8, wherein A2 is attached directly to the device.

10. The compound of any one of embodiments 8-9, wherein A2 is attached to the device by an attachment group.

11. The compound of any one of embodiments 9-10, wherein the device is attached, e.g., covalently, to the attachment group, and A2 is attached, e.g., covalently to the attachment group.

12. The compound of any one of the preceding embodiments, wherein each $L^1$, $L^2$, and $L^3$ is independently a bond, alkyl, or heteroalkyl.

13. The compound of any one of the preceding embodiments, wherein $L^1$ is a bond, alkyl, or heteroalkyl.

14. The compound of any one of the preceding embodiments, wherein $L^1$ is $C_1$-$C_6$ alkyl (e.g., —$CH_2$— or —$CH_2CH_2$—).

15. The compound of any one of the preceding embodiments, wherein $L^2$ is a bond.

16. The compound of any one of the preceding embodiments, wherein $L^3$ is a bond, alkyl, or heteroalkyl.

17. The compound of any one of the preceding embodiments, wherein $L^3$ is $C_1$-$C_6$ alkyl (e.g., —$CH_2$—) or heteroalkyl (e.g., —$CH_2$O—).

18. The compound of any one of the preceding embodiments, wherein M is alkyl, heteroalkyl, aryl, or heteroaryl.

19. The compound of any one of the preceding embodiments, wherein M is alkyl (e.g., methyl, ethyl, or propyl).

20. The compound of any one of the preceding embodiments, wherein M heteroalkyl, e.g., —$OCH_2CH_2$-)z, wherein z is an integer selected from 1 to 10.

21. The compound of any one of the preceding embodiments, wherein M is aryl (e.g., phenyl).

22. The compound of any one of the preceding embodiments, wherein P is a tricyclic, bicyclic, or monocyclic heteroaryl.

23. The compound of any one of the preceding embodiments, wherein P is a nitrogen-containing heteroaryl.

24. The compound of any one of the preceding embodiments, wherein P is a 5-membered nitrogen-containing heteroaryl (e.g., tetrazolyl, imidazolyl, pyrazolyl, or triazolyl, pyrrolyl, oxazolyl, or thiazolyl).

25. The compound of any one of the preceding embodiments, wherein P is triazolyl (e.g., 1,2,3-triazolyl or 1,2,4-triazolyl).

26. The compound of any one of the preceding embodiments, wherein P is selected from

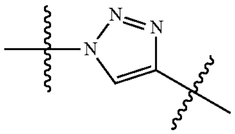

and

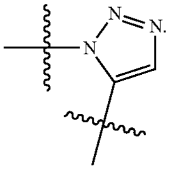

27. The compound of any one of the preceding embodiments, wherein Z is alkyl, heterocyclyl, or aryl, each of which is optionally substituted by one or more $R^5$.

28. The compound of any one of the preceding embodiments, wherein Z is heterocyclyl (e.g., 6-membered heterocyclyl).

29. The compound of embodiment 28, wherein Z is a nitrogen-containing heterocyclyl, an oxygen-containing heterocyclyl, or a sulfur-containing heterocyclyl (e.g., tetrahydropyranyl or thiomorpholinyl-1,1-dioxide).

30. The compound of any one of embodiments 1-27, wherein Z is aryl (e.g., phenyl).

31. The compound of embodiment 30, wherein Z is monosubstituted phenyl (e.g., with 1 $R^5$).

32. The compound of embodiment 31, wherein Z is monosubstituted phenyl, wherein the 1 $R^5$ an amine-containing group (e.g., $NH_2$).

33. The compound of embodiment 31, wherein Z is monosubstituted phenyl, wherein the 1 $R^5$ is an oxygen-containing group (e.g., $OCH_3$).

34. The compound of any one of embodiment 31-33, wherein the 1 $R^5$ is in the ortho position or the para position.

35. The compound of any one of embodiments 1-27, wherein Z is alkyl (e.g., $C_1$-$C_{12}$ alkyl).

36. The compound of embodiment 35, wherein Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1})(R^{D1})$.

37. The compound of embodiment 36, wherein Z is $C_1$-$C_8$ alkyl substituted with 1 $R^5$, wherein $R^5$ is —OH or —C(O)OH.

38. The compound of embodiment 1, wherein the compound is the compound of Formula (I) is a compound of Formula (II):

Formula (II)

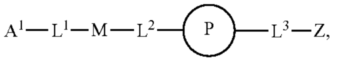

or a salt thereof, wherein

A1 is hydrogen, alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, —$N(R^C)(R^D)$, —$N(R^C)C(O)R^B$, —$C(O)N(R^C)(R^D)$, —$N_3$, —NC, —CN, —NCO, —NCS, —$N(R^C)N(R^D)_2$, —$NCN(R^C)$, —$C(=N(R^C)(R^D))OR^A$, —$SR^E$, —$S(O)_xR^E$, —$OS(O)_xR^E$, —$N(R^C)S(O)_xR^E$, —$S(O)_x$ $N(R^C)(R^D)$, —$P(R^F)$, —$Si(OR^A)_3$, —$Si(R^G)(OR^A)_2$, —$B(OR^A)_2$, or a metal, wherein each alkyl, alkenyl, alkynyl, heteroalkyl, cycloalkyl, heterocyclyl, aryl, and heteroaryl is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is alkyl, heteroalkyl, cycloalkyl, heterocyclyl, aryl, or heteroaryl, each of which is optionally substituted by one or more $R^3$;

P is heteroaryl optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, $S(O)_xR^{E1}$, —$OS(O)_xR^{E1}$, —$N(R^{C1})S(O)_xR^{E1}$, —$S(O)_xN(R^{C1})(R^{D1})$, —$P(R^F)_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$; each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

39. The compound of embodiment 1, wherein the compound of Formula (II) is a compound of Formula (II-c):

Formula (II-c)

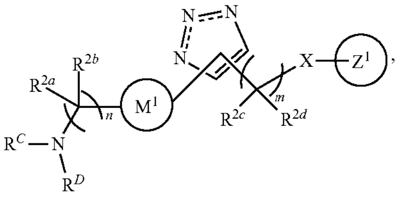

or a salt thereof, wherein

Ring $M^1$ is cycloalkyl, heterocyclyl, aryl, or heteroaryl, each of which is optionally substituted with 1-5 $R^3$;

Ring $Z^1$ is cycloalkyl, heterocyclyl, aryl, or heteroaryl, optionally substituted with 1-5 $R^5$;

each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl;

or $R^{2a}$ and $R^{2b}$ or $R^{2c}$ and $R^{2d}$ are taken together to form an oxo group;

X is absent, $N(R^{10})(R^{11})$, O, or S;

$R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$, or $R^C$ and $R^D$, taken together with the nitrogen atom to which they are attached, form a ring (e.g., a 5-7 membered ring), optionally substituted with 1-6 $R^6$, or one or both of $R^C$ and $R^D$ is bound to an atom within L or M or one of the substituents of L or M to form a ring optionally substituted with 1-6 $R^6$;

each $R^4$, $R^5$, and $R^6$ is independently alkyl, alkenyl, alkynyl, heteroalkyl, halogen, cyano, azido, oxo, $—OR^{A1}$, $—C(O)OR^{A1}$, $—C(O)R^{B1}$, $—OC(O)R^{B1}$, $—N(R^{C1})(R^{D1})$, $—N(R^{C1})C(O)R^{B1}$, $—C(O)N(R^{C1})$, $SR^{E1}$, cycloalkyl, heterocyclyl, aryl, heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$;

each of $R^{10}$ and $R^{11}$ is independently hydrogen, alkyl, alkenyl, alkynyl, heteroalkyl, $C(O)OR^{A1}$, $—C(O)R^{B1}$, $—C(O)N(R^{C1})$; each $R^7$ is independently alkyl, alkenyl, alkynyl, heteroalkyl, halogen, —CN, oxo, hydroxyl, cycloalkyl, or heterocyclyl;

and each m and n is independently 0, 1, 2, 3, 4, 5, or 6.

40. The compound of embodiment 1, wherein the compound of Formula (I) is a compound of Formula (II-k):

Formula (II-k)

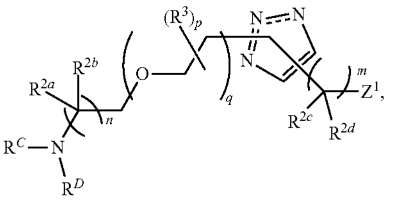

or a salt thereof, wherein $Z^1$ is alkyl, alkenyl, alkynyl, heteroalkyl, cycloalkyl, heterocyclyl, aryl, or heteroaryl, optionally substituted with 1-5 $R^5$;

each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group;

$R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; or $R^C$ and $R^D$, taken together with the nitrogen atom to which they are attached, form a ring (e.g., a 5-7 membered ring), optionally substituted with 1-6 $R^6$;

each of $R^3$, $R^5$, and $R^6$ is independently alkyl, alkenyl, alkynyl, heteroalkyl, halogen, cyano, azido, oxo, $—OR^{A1}$, $—C(O)OR^{A1}$, $—C(O)R^{B1}$, $—OC(O)R^{B1}$, $—N(R^{C1})(R^{D1})$, $—N(R^{C1})C(O)R^{B1}$, $—C(O)N(R^{C1})$, $SR^{E1}$, cycloalkyl, heterocyclyl, aryl, heteroaryl;

each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$;

each $R^7$ is independently alkyl, alkenyl, alkynyl, heteroalkyl, halogen, —CN, oxo, hydroxyl, cycloalkyl, or heterocyclyl;

m and n are each independently 0, 1, 2, 3, 4, 5, or 6; p is 0, 1, 2, 3, or 4; and q is an integer from 0 to 25.

41. The compound of embodiment 1, wherein the compound of Formula (I) is a compound of Formula (III):

Formula (III)

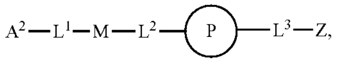

or a salt thereof, wherein

A2 is alkyl, alkenyl, alkynyl, heteroalkyl, cycloalkyl, heterocyclyl, aryl, heteroaryl, —O—, —C(O)O—, —C(O)—, —OC(O)—, $—N(R^C)—$, $—N(R^C)C(O)—$, $—C(O)N(R^C)—$, $—N(R^C)N(R^D)—$, —NCN—, $—C(=N(R^C)(R^D))O—$, —S—, $—S(O)_x—$, $—OS(O)_x$, $—N(R^C)S(O)_x—$, $—S(O)_xN(R^C)—$, $—P(R^F)$, $—Si(OR^A)_2—$, $—Si(R^G)(OR^A)—$, $—B(OR^A)$, or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond; M is alkyl, heteroalkyl, cycloalkyl, heterocyclyl, aryl, or heteroaryl, each of which is optionally substituted by one or more $R^3$;

P is heteroaryl optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$; or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, $S(O)_xR^{E1}$, —$OS(O)_xR^{E1}$, —$N(R^{C1})S(O)_xR^{E1}$, —$S(O)_xN(R^{C1})(R^{D1})$, —$P(R^{F1})_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

42. The compound of embodiment 41, wherein the compound of Formula (III) is a compound of Formula (III-c):

Formula (II-c)

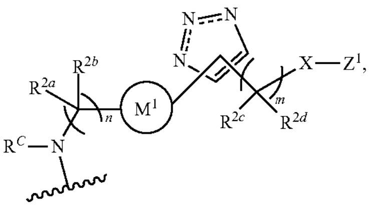

or a salt thereof, wherein

Ring $M^1$ is cycloalkyl, heterocyclyl, aryl, or heteroaryl, each of which is optionally substituted with 1-5 $R^3$;

$Z^1$ is alkyl, alkenyl, alkynyl, heteroalkyl, cycloalkyl, heterocyclyl, aryl, or heteroaryl, each of which is optionally substituted by one or more $R^5$;

each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl;

or $R^{2a}$ and $R^{2b}$ or $R^{2c}$ and $R^{2d}$ are taken together to form an oxo group;

$R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$;

each of $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, heteroaryl;

each of $R^{10}$ and $R^{11}$ is independently hydrogen, alkyl, alkenyl, alkynyl, heteroalkyl, halogen, —$C(O)R^{B1}$, —$N(R^{C1})C(O)R^{B1}$, —$C(O)N(R^{C1})$, $SR^{E1}$, $S(O)_x$, cycloalkyl, or heterocyclyl;

each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$;

each $R^7$ is independently alkyl, alkenyl, alkynyl, heteroalkyl, halogen, cyano, oxo, hydroxyl, cycloalkyl, or heterocyclyl;

each m and n is independently 0, 1, 2, 3, 4, 5, or 6;

x is 1 or 2; and

"∿∿∿" refers to a connection to a device or material (e.g., a device or material described herein).

43. The compound of embodiment 41, wherein the compound of Formula (III) is a compound of Formula (III-k):

(III-k)

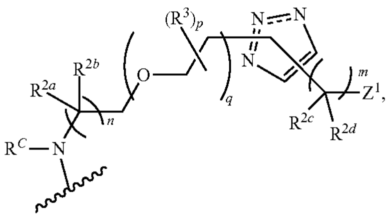

or a salt thereof, wherein:

$Z^1$ is alkyl, alkenyl, alkynyl, heteroalkyl, cycloalkyl, heterocyclyl, aryl, or heteroaryl, optionally substituted with 1-5 $R^5$;

each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl;

or $R^{2a}$ and $R^{2b}$ or $R^{2c}$ and $R^{2d}$ are taken together to form an oxo group;

$R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$;

each of $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, heteroaryl;

each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$;

each $R^7$ is independently alkyl, alkenyl, alkynyl, heteroalkyl, halogen, cyano, oxo, hydroxyl, cycloalkyl, or heterocyclyl;

m and n are each independently 0, 1, 2, 3, 4, 5, or 6;

p is 0, 1, 2, 3, or 4;

q is an integer from 0 to 25; and

"∿∿∿" refers to a connection to a device or material (e.g., a device or material described herein).

44. The compound of any one of the preceding embodiments, wherein the compound (e.g., the compound of Formula (I) or Formula (III)) is disposed on a surface, e.g., an inner or outer surface, of a device.
45. The compound of any one of the preceding embodiments, wherein the compound is selected from a compound depicted in any one of FIGS. 1A-6KK, or a pharmaceutically acceptable salt thereof.
46. The compound of any one of the preceding embodiments, wherein, when displayed on a substrate has the property of blocking the adhesion of macrophage to the substrate, e.g., as compared with a control, e.g., macrophage binding to fibronectin displayed on an otherwise similar substrate.
47. The compound of any one of the preceding embodiments, wherein in a macrophage assay, e.g., the assay described in Example 8, the compound has a percent cell adhesion score of less than 0, 5, 7, 10, 15, or 20%.
48. The compound of any one of the preceding embodiments, wherein the compound has the property of, when displayed on the surface of a substrate implanted into a subject or test animal, e.g., a mouse, inhibiting the association or interaction of a host tissue or a host cell with the substrate, e.g., as compared with a control, e.g., an otherwise similar substrate lacking the compound.
49. The compound of embodiment 48, wherein the substrate is implanted in a mouse in the assay described in Example 10.
50. The compound of any of embodiments 48-49, wherein host tissue or cell comprises adhered tissue (e.g., fibrotic tissue).
51. The compound of any of embodiments 48-50, wherein host tissue or cell comprises an immune cell.
52. The compound of any of embodiments 48-50, wherein host tissue or cell comprises a macrophage.
53. The compound of any embodiments 48-52, wherein the association, as compared with the control, is reduced by at least 10, 20, 30, 40, 50, 60, 70, 80, or 90%.
54. The compound of embodiment 53, wherein the reduction in association is measured in terms of weight of the associated tissue or cells, volume of the associated tissue or cells, percentage of the substrate coated, or number of associated cells.
55. The compound of any one of the preceding embodiments, wherein the compound has the property of when displayed on the surface of each of plurality of substrates implanted into a subject or test animal, e.g., a mouse, for a time sufficient for host tissue to associate with a control substrate (e.g., a substrate otherwise similar but lacking compound) at least one of the substrates is substantially free of host associated tissue, e.g., host fibrotic tissue.
56. The compound of claim 55, wherein the plurality of substrates are implanted in a mouse in the assay described in Example 10.
57. The compound of any of embodiments 55-56, wherein five substrates are implanted in a mouse.
58. The compound of any of embodiments 55-57, wherein five substrates are implanted in a mouse.
59. The compound of embodiment 55, wherein after being implanted for a time sufficient for host tissue to associate with the control substrate at least X of the substrates is substantially free of host associated tissue, e.g., host fibrotic tissue, wherein X=1, 2, 3, 4, or 5.
60. The compound of embodiment 59, wherein X=2.
61. The compound of embodiment 59, wherein X=3.
62. The compound of embodiment 59, wherein X=4.
63. The compound of embodiment 59, wherein X=5.
64. The compound of any one of the preceding embodiments, wherein, when displayed on a substrate the compound has the property of promoting the adhesion of macrophage to the substrate, e.g., as compared with a control, e.g., macrophage binding to PEG displayed on an otherwise similar substrate.
65. The compound of any one of the preceding embodiments, wherein in a macrophage assay, e.g., the assay described in Example 8, the compound has a percent cell adhesion score of more than 0, 5, 7, 10, 15, or 20%.
66. The compound of any one of the preceding embodiments, wherein the compound has the property of, when displayed on the surface of a substrate implanted into a subject or test animal, e.g., a mouse, increasing the association or interaction of a host tissue or a host cell with the substrate, e.g., as compared with a control, e.g., an otherwise similar substrate lacking the compound.
67. The compound of embodiment 66, wherein the substrate is implanted in a mouse in the assay described in Example 10.
68. The method of any of embodiments 66-67, wherein host tissue or cell comprises adhered tissue (e.g., fibrotic tissue).
69. The method of any of embodiments 66-68, wherein host tissue or cell comprises an immune cell.
70. The method of any of embodiments 66-69, wherein host tissue or cell comprises a macrophage.
71. The compound of any embodiments 66-70, wherein the association, as compared with the control, is increased by at least 10, 20, 30, 40, 50, 60, 70, 80, or 90%
72. The compound of embodiment 71, wherein the reduction in association is measured in terms of weight of the associated tissue or cells, volume of the associated tissue or cells, percentage of the substrate coated, or number of associated cells).
73. The compound of any one of the preceding embodiments, wherein the compound has the property of when displayed on the surface of each of plurality of substrates implanted into a subject or test animal, e.g., a mouse, for a time sufficient for host tissue to associate with a control substrate (e.g., a substrate otherwise similar but lacking compound) at least one, or all, of the substrates is substantially covered with host associated tissue, e.g., host fibrotic tissue.
74. The compound of embodiment 73, wherein the plurality of substrates are implanted in a mouse in the assay described in Example 10.
75. The compound of any of embodiments 73-74, wherein the plurality of substrates are implanted in a mouse in the assay described in Example 10.
76. The compound of any of embodiments 73-75, wherein five substrates are implanted in a mouse.
77. A pharmaceutical composition comprising a compound of any one of the preceding embodiments and a pharmaceutically acceptable excipient.
78. A method of treating a disease, disorder, or condition, or modulating an immune response in a subject, e.g., at a site in the subject, e.g., the site of an implanted cell or device, comprising providing to the subject, e.g., at the site, a compound of Formula (I):

$$A\text{-}L^1\text{-}M\text{-}L^2\text{-}P\text{-}L^3\text{-}Z \quad (I)$$

or a salt thereof, wherein:

A is selected from A1 or A2, wherein

A1 is hydrogen, alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, —$N(R^C)(R^D)$, —$N(R^C)C(O)R^B$, —$C(O)N(R^C)(R^D)$, —$N_3$, —NC, —CN, —NCO, —NCS, —$N(R^C)N(R^D)_2$, —$NCNR^C$, —$C(=N(R^C)(R^D))OR^A$, —$SR^E$, —$S(O)_x R^E$, —$OS(O)_xR^E$, —$N(R^C)S(O)_xR^E$, —$S(O)_xN(R^C)(R^D)$, —$P(R^F)_y$, —$Si(OR^A)_3$, —$Si(R^G)(OR^A)_2$, —$B(OR^A)_2$, or a metal, wherein each alkyl, alkenyl, alkynyl, heteroalkyl, cycloalkyl, heterocyclyl, aryl, heteroaryl is optionally substituted with one or more $R^1$;

A2 is alkyl, alkenyl, alkynyl, heteroalkyl, cycloalkyl, heterocyclyl, aryl, heteroaryl, —O—, —C(O)O—, —C(O)—, —OC(O)—, —$N(R^C)$—, —$N(R^C)C(O)$—, —$C(O)N(R^C)$—, —$N(R^C)N(R^D)$—, —NCN—, —$C(=N(R^C)(R^D))O$—, —S—, —$S(O)_x$—, —$OS(O)_x$, —$N(R^C)S(O)_x$—, —$S(O)_xN(R^C)$—, —$P(R^F)$, —$Si(OR^A)_2$—, —$Si(R^G)(OR^A)$, —$B(OR^A)$, or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted by one or more $R^1$;

each $L^1$, $L^2$, and $L^3$ is independently a bond, alkyl, alkenyl, alkynyl, or heteroalkyl, wherein each alkyl, alkenyl, alkynyl, and heteroalkyl is optionally substituted by 1-5 $R^2$;

M is alkyl, alkenyl, alkynyl, heteroalkyl, cycloalkyl, heterocyclyl, aryl, or heteroaryl, each of which is optionally substituted by one or more $R^3$;

P is cycloalkyl, heterocyclyl, aryl, or heteroaryl, each of which is optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with one or more $R^6$, or $R^C$ and $R^D$, taken together with the nitrogen atom to which they are attached, form a ring (e.g., a 5-7 membered ring), optionally substituted with one or more $R^6$, each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, —$S(O)_xR^E$, —$OS(O)_xR^E$, —$N(R^C)S(O)_xR^E$, —$S(O)_xN(R^C)(R^D)$, —$P(R^F)_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4, to thereby treat or modulate the immune response in the subject.

79. The method of claim 78, wherein providing comprises providing a device, e.g., a device described herein, to the subject.

80. The method of any one of embodiments 78-79, wherein providing comprises administering the compound, systemically, or locally.

81. The method of any one of embodiments 78-80, wherein the method comprises treating a subject, e.g., for a disorder or condition, e.g., a condition characterized by unwanted immune response.

82. The method of any one of embodiments 78-81, wherein the method comprises treating a subject, e.g., for a disorder or condition, e.g., a condition characterized by an inadequate immune response.

83. The method of any one of embodiments 78-82, wherein the method comprises providing a compound of Formula (I) or a pharmaceutically acceptable salt or composition thereof, e.g., to downregulate an immune response.

84. The method of any one of embodiments 78-83, wherein the method comprises providing a compound of Formula (I) or a pharmaceutically acceptable salt or composition thereof, e.g., to upregulate an immune response.

85. The method of any one of embodiments 78-84, wherein the method comprises reducing an unwanted reaction to an implanted device or cell, e.g., reducing fibrosis or, inflammation at, or inactivation of, the implanted device or cell.

86. The method of embodiment 85, wherein the device comprises a cell, e.g., a recombinant cell, which provides a substance, e.g., a therapeutic agent.

87. A device comprising a compound of Formula (I):

$$A\text{-}L^1\text{-}M\text{-}L^2\text{-}P\text{-}L^3 \quad (I)$$

or a salt thereof, wherein:

A is selected from A1 or A2, wherein

A1 is hydrogen, alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, —$N(R^C)(R^D)$, —$N(R^C)C(O)R^B$, —$C(O)N(R^C)(R^D)$, —$N_3$, —NC, —CN, —NCO, —NCS, —$N(R^C)N(R^D)_2$, —$NCNR^C$, —$C(=N(R^C)(R^D))OR^A$, —$SR^E$, —$S(O)_x R^E$, —$OS(O)_xR^E$, —$N(R^C)S(O)_xR^E$, —$S(O)_xN(R^C)(R^D)$, —$P(R^F)_y$, —$Si(OR^A)_3$, —$Si(R^G)(OR^A)_2$, —$B(OR^A)_2$, or a metal, wherein each alkyl, alkenyl, alkynyl, heteroalkyl, cycloalkyl, heterocyclyl, aryl, heteroaryl is optionally substituted with one or more $R^1$;

A2 is alkyl, alkenyl, alkynyl, heteroalkyl, cycloalkyl, heterocyclyl, aryl, heteroaryl, —O—, —C(O)O—, —C(O)—, —OC(O)—, —$N(R^C)$—, —$N(R^C)C(O)$—, —$C(O)N(R^C)$—, —$N(R^C)N(R^D)$—, —NCN—, —$C(=N(R^C)(R^D))O$—, —S—, —$S(O)_x$—, —$OS(O)_x$, —$N(R^C)S(O)_x$—, —$S(O)_xN(R^C)$—, —$P(R^F)$, —$Si(OR^A)_2$—, —$Si(R^G)(OR^A)$, —$B(OR^A)$, or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted by one or more $R^1$;

each $L^1$, $L^2$, and $L^3$ is independently a bond, alkyl, alkenyl, alkynyl, or heteroalkyl, wherein each alkyl, alkenyl, alkynyl, and heteroalkyl is optionally substituted by 1-5 $R^2$;

M is alkyl, alkenyl, alkynyl, heteroalkyl, cycloalkyl, heterocyclyl, aryl, or heteroaryl, each of which is optionally substituted by one or more $R^3$;

P is cycloalkyl, heterocyclyl, aryl, or heteroaryl, each of which is optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with one or more $R^6$, or $R^C$ and $R^D$, taken together with the nitrogen atom to which they are attached, form a ring (e.g., a 5-7 membered ring), optionally substituted with one or more $R^6$, each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, —$S(O)_xR^E$, —$OS(O)_xR^E$, —$N(R^C)S(O)_xR^E$, —$S(O)_xN(R^C)(R^D)$, —$P(R^F)_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

88. The device of embodiment 87, wherein the compound is disposed on a surface, e.g., an inner or outer surface, of the device.

89. The device of any one of embodiments 87-88, wherein the compound is distributed evenly across the surface.

90. The device of any one of embodiments 87-89, wherein the compound is distributed unevenly across the surface.

91. The device of embodiment 90, wherein the device is administered or provided to a subject for the treatment of a disease, disorder, or condition.

92. The device of embodiment 90, wherein a first portion of the surface of the device comprises a compound of Formula I that modulates, e.g., down regulates or upregulates, an immune response and a second portion of the device lacks the compound, or has substantially lower density of the compound.

93. The device of embodiment 90, wherein a first portion of the surface of the device comprises a compound of Formula I that modulates, e.g., down regulates, an immune response and a second portion of the surface comprises a second compound of Formula I, e.g., that upregulates the immune response, second portion of the device lacks the compound, or has substantially lower density of the compound.

94. The device of any one of embodiments 87-93, wherein the device comprises a cell, e.g., a recombinant cell, which provides a substance, e.g., a therapeutic agent.

95. The device of embodiment 94, wherein the substance comprises a polypeptide.

96. A method of making a device comprising Formula (I):

$$A\text{-}L^1\text{-}M\text{-}L^2\text{-}P\text{-}L^3\text{-}Z \quad (I)$$

or a salt thereof, wherein:

A is selected from A1 or A2, wherein

A1 is hydrogen, alkyl, alkenyl, alkynyl, heteroalkyl, cycloalkyl, heterocyclyl, aryl, heteroaryl, —$OR^A$, —$C(O)OR^A$, —$C(O)R^B$, —$OC(O)R^B$, —$N(R^C)(R^D)$, —$N(R^C)C(O)R^B$, —$C(O)N(R^C)(R^D)$, —$N_3$, —NC, —CN, —NCO, —NCS, —$N(R^C)N(R^D)_2$, —$NCNR^C$, —$C(=N(R^C)(R^D))OR^A$, —$SR^E$, —$S(O)_x R^E$, —$OS(O)_xR^E$, —$N(R^C)S(O)_xR^E$, —$S(O)_xN(R^C)(R^D)$, —$P(R^F)_y$, —$Si(OR^A)_3$, —$Si(R^G)(OR^A)_2$, —$B(OR^A)_2$, or a metal, wherein each alkyl, alkenyl, alkynyl, heteroalkyl, cycloalkyl, heterocyclyl, aryl, heteroaryl is optionally substituted with one or more $R^1$;

A2 is alkyl, alkenyl, alkynyl, heteroalkyl, cycloalkyl, heterocyclyl, aryl, heteroaryl, —O—, —C(O)O—, —C(O)—, —OC(O)—, —$N(R^C)$—, —$N(R^C)C(O)$—, —$C(O)N(R^C)$—, —$N(R^C)N(R^D)$—, —NCN—, —$C(=N(R^C)(R^D))O$—, —S—, —$S(O)_x$—, —$OS(O)_x$, —$N(R^C)S(O)_x$—, —$S(O)_xN(R^C)$—, —$P(R^F)$, —$Si(OR^A)_2$—, —$Si(R^G)(OR^A)$, —$B(OR^A)$, or a metal, wherein each alkyl, alkenyl, alkynyl, heteroalkyl, cycloalkyl, heterocyclyl, aryl, and heteroaryl is linked to an attachment group (e.g., an attachment group defined herein) and is optionally substituted by one or more $R^1$;

each $L^1$, $L^2$, and $L^3$ is independently a bond, alkyl, alkenyl, alkynyl, or heteroalkyl, wherein each alkyl, alkenyl, alkynyl, and heteroalkyl is optionally substituted by 1-5 $R^2$;

M is alkyl, alkenyl, alkynyl, heteroalkyl, cycloalkyl, heterocyclyl, aryl, or heteroaryl, each of which is optionally substituted by one or more $R^3$;

P is cycloalkyl, heterocyclyl, aryl, or heteroaryl, each of which is optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with one or more $R^6$, or $R^C$ and $R^D$, taken together with the nitrogen atom to which they are attached, form a ring (e.g., a 5-7 membered ring), optionally substituted with one or more $R^6$, each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, —$S(O)_xR^E$, —$OS(O)_xR^E$, —$N(R^C)S(O)_xR^E$, —$S(O)_xN(R^C)(R^D)$, —$P(R^F)_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4; wherein the compound of Formula (I) is associated with the device (e.g., through an attachment group).

EXAMPLES

In order that the invention described herein may be more fully understood, the following examples are set forth. The synthetic and biological examples described in this application are offered to illustrate the compounds, compositions, devices, and methods provided herein and are not to be construed in any way as limiting their scope.

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Exemplary compounds, compositions, devices, and materials of the invention may be prepared using any of the strategies described below.

Example 1: Huisgen Cycloaddition

Huisgen Cycloaddition to Afford 1,4-Substituted Triazoles

The copper-catalyzed Huisgen [3+2] cycloaddition was used to prepare triazole-based compounds and compositions, devices, and materials thereof. The scope and typical protocols have been the subject of many reviews (e.g., Meldal, M. and Tornoe, C. W. *Chem. Rev.* (2008) 108:2952-3015; Hein, J. E. and Fokin, V. V. *Chem. Soc. Rev.* (2010) 39(4):1302-1315; both of which are incorporated herein by reference).

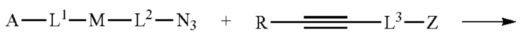

-continued

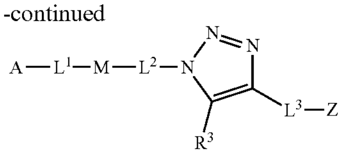

In the example shown above, the azide is the reactive moiety in the fragment containing the connective element A, while the alkyne is the reactive component of the pendant group Z. As depicted below, these functional handles can be exchanged to produce a structurally related triazole product. The preparation of these alternatives is similar, and do not require special considerations.

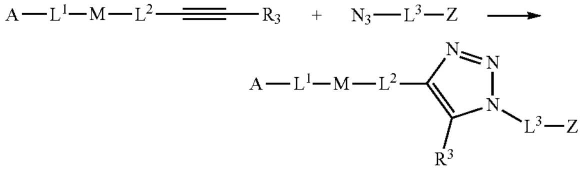

A typical Huisgen cycloaddition procedure starting with an iodide is outlined below. In some instances, iodides are transformed into azides during the course of the reaction for safety.

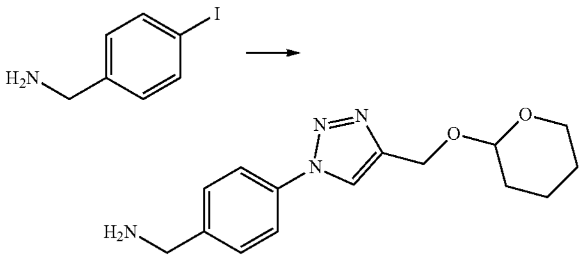

A solution of sodium azide (1.1 eq), sodium ascorbate, (0.1 eq) trans-N,N'-dimethylcyclohexane-1,2-diamine (0.25 eq), copper (I) iodide in methanol (1.0 M, limiting reagent) was degassed with bubbling nitrogen and treated with the acetylene (1 eq) and the aryl iodide (1.2 eq). This mixture was stirred at rt for 5 minutes, then warmed to 55° C. for 16 h. The reaction was then cooled to room temperature, filtered through a funnel, and the filter cake washed with methanol. The combined filtrates were concentrated and purified via flash chromatography on silica gel (120 g silica, gradient of 0 to 40% (3% aqueous ammonium hydroxide, 22% methanol, remainder dichloromethane) in dichloromethane to afford the desired target material.

A typical Huisgen cycloaddition procedure starting with an azide is outlined below.

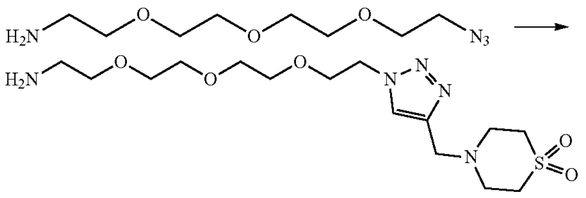

A solution of tris[(1-benzyl-1H-1,2,3-triazol-4-yl)methyl] amine (0.2 eq), triethylamine (0.5 eq), copper (I) iodide (0.06 eq) in methanol (0.4 M, limiting reagent) was treated with the acetylene (1.0 eq) and cooled to 0° C. The reaction was allowed to warm to room temperature over 30 minutes, then heated to 55° C. for 16h. The reaction was cooled to room temperature, concentrated, and purified with HPLC (C18 column, gradient of 0 to 100% (3% aqueous ammonium hydroxide, 22% methanol remainder dichloromethane) in dichloromethane to afford the desired target material.

Huisgen Cycloaddition to Afford 1,5-Substituted Triazoles

The Huisgen [3+2] cycloaddition was also performed with ruthenium catalysts to obtain 1,5-disubstituted products preferentially (e.g., as described in Zhang et al, *J. Am. Chem. Soc.,* 2005, 127, 15998-15999; Boren et al, *J. Am. Chem. Soc.,* 2008, 130, 8923-8930, each of which is incorporated herein by reference in its entirety).

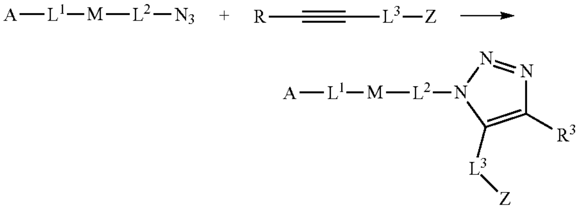

As described previously, the azide and alkyne groups may be exchanged to form similar triazoles as depicted below.

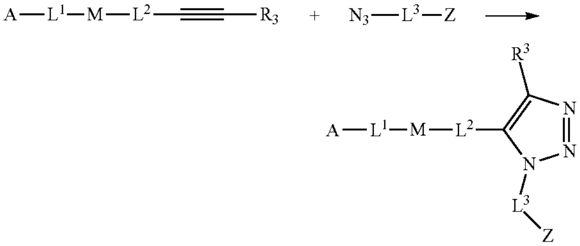

A typical procedure is described as follows: a solution of the alkyne (1 eq) and the azide (1 eq) in dioxane (0.8M) were added dropwise to a solution of pentamethylcyclo-pentadienylbis(triphenylphosphine) ruthenium(II) chloride (0.02 eq) in dioxane (0.16M). The vial was purged with nitrogen, sealed and the mixture heated to 60° C. for 12h. The resulting mixture was concentrated and purified via flash chromatography on silica gel to afford the requisite compound.

Example 2: Protocols for the Synthesis of Exemplary Compounds

General Protocol a for 1,3-Dipolar Cycloaddition

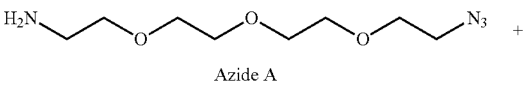

Azide A

-continued

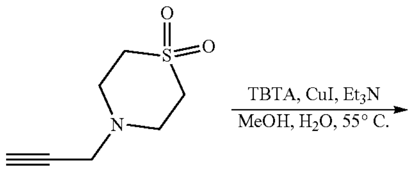

Alkyne B

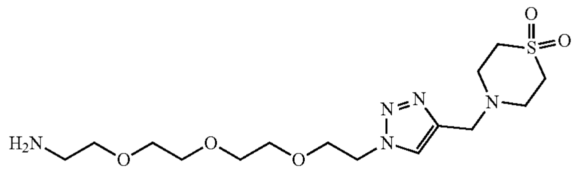

Compound 3037

To a solution of dimethyl-(2-methylsulfonylethyl)-prop-2-ynyl-ammonium (Alkyne B, 6.3 g, 28.86 mmol, 1 eq), TBTA (3.83 g, 7.22 mmol, 0.25 eq), copper iodide (550 mg, 2.89 mmol, 0.1 eq), and triethylamine (TEA, 1.01 mL, 7.22 mmol, 0.25 eq) in methanol (50 mL) and water (12 mL) were purged with a stream of nitrogen for 5 minutes and cooled with an ice bath. 2-[2-[2-(2-azidoethoxy)ethoxy] ethoxy]ethanamine (Azide A, 5.0 g, 28.86 mmol, 1 eq) was added and the mixture was stirred at room temperature for 5 minutes and then heated to 55° C. overnight. The reaction mixture was cooled to room temperature and filtered. The solvent was removed under reduced pressure and the residue was purified over silica gel to afford 4-((1-(2-(2-(2-(2-aminoethoxy)ethoxy)ethoxy)ethyl)-1H-1,2,3-triazol-4-yl) methyl)thiomorpholine 1,1-dioxide (Compound 3037, 8.0 g, 71%) as an oil. MS ESI $[M+H]^+$=392.2

A similar procedure was used to prepare the following compounds:

| Compound Number | $M^+$ + H Observed or 1H NMR Data |
|---|---|
| 3042 | 241.2 |
| 3047 | 359.2 |
| 3058 | 303.2 |
| 3060 | 376.2 |
| 3061 | 360.2 |
| 3070 | 304.1 |
| 3071 | 480.3 |
| 3075 | 436.2 |
| 3083 | 348.2 |
| 3090 | 336.2 |
| 3091 | 351.2 |
| 3095 | 338.2 |
| 3096 | 351.2 |
| 3097 | 344.2 |
| 3101 | 394.2 |
| 3103 | 399.1 |
| 3104 | 342.2 |
| 3112 | 337.2 |
| 3119 | 357.2 |
| 3124 | 406.2 ($M^+$ + Na) |
| 3127 | 213.1 |
| 3128 | 435.2 ($M^+$ + Na) |
| 3135 | $^1H$ NMR (500 Mz, $CDCl_3$) δ 7.70 (1H, s), 4.54 (2H, s), 3.86-3.49 (98H, m), 3.05-2.96 (4H, m) |

General Protocol B for 1,3-Dipolar Cycloaddition

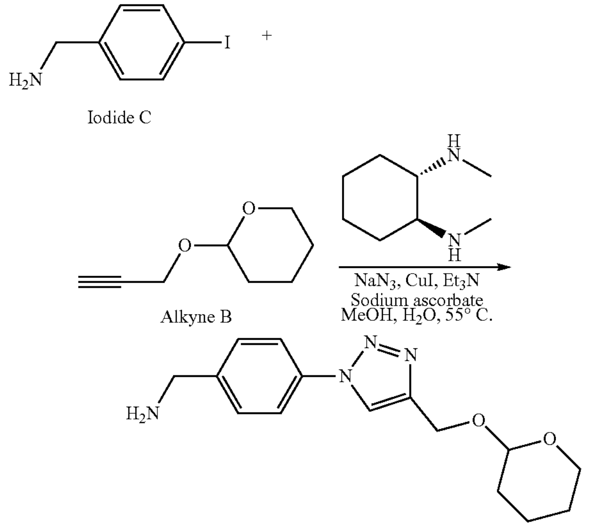

Iodide C

Alkyne B

Compound 3038

A mixture of (4-iodophenyl)methanamine (Iodide C, 5.0 g, 18.55 mmol, 1.0 eq), (1S,2S)—N1,N2-dimethylcyclohexane-1,2-diamine (0.59 mL, 3.71 mmol, 0.2 eq), sodium ascorbate (368 mg, 1.86 mmol, 0.1 eq), copper iodide (530 mg, 2.78 mmol, 0.15 eq), sodium azide (2.41 g, 37.1 mmol, 2.0 eq), $Et_3N$ (3.11 mL, 22.26 mmol, 1.2 eq) and 2-(prop-2-yn-1-yloxy)tetrahydro-2H-pyran (Alkyme B, 2.6 g, 18.55 mmol, 1.0 eq) in methanol (50 mL) and water (12 mL) were purged with nitrogen for 5 minutes and heated to 55° C. overnight. The reaction mixture was cooled to room temperature and filtered. The solvent was removed under reduced pressure and the residue was purified over silica gel to afford (4-(4-(((tetrahydro-2H-pyran-2-yl)oxy)methyl)-1H-1,2,3-triazol-1-yl)phenyl)methanamine (Compound 3038, 3.54 g, 66%) as a solid. MS ESI $[M+H]^+$=289.2.

A similar procedure was used to prepare the following compounds:

| Compound Number | $M^+$ + H Observed |
|---|---|
| 3051 | 289.2 |
| 3052 | 261.1 |
| 3063 | 303.2 |
| 3065 | 303.2 |
| 3077 | 408.1 |
| 3079 | 303.2 |
| 3080 | 357.1 |
| 3087 | 274.1 |
| 3088 | 287.2 |
| 3090 | 336.2 |
| 3091 | 351.2 |
| 3109 | 272.2 |
| 3111 | 307.2 |
| 3113 | 263.1 |
| 3120 | 281.1 |
| 3125 | 343.2 |
| 3129 | 314.2 |
| 3266 | 303.1 |

General Protocol for Amine Functionalization (General Procedure C)

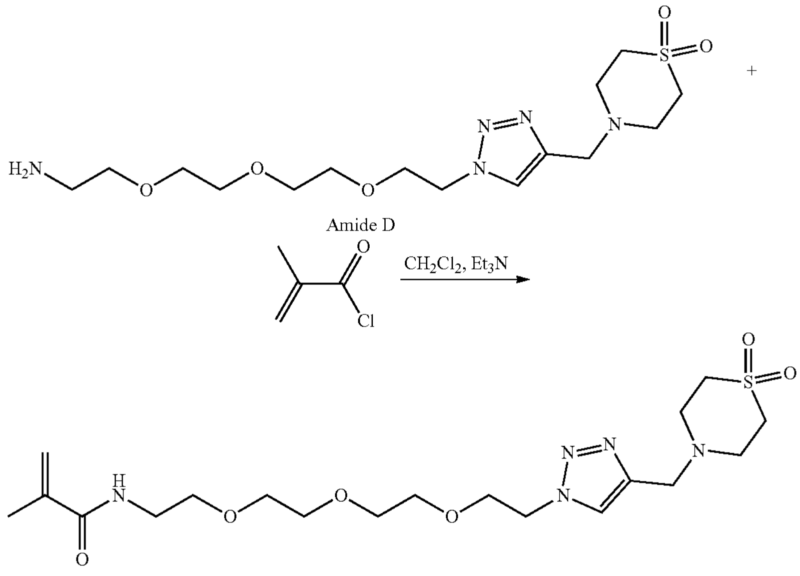

Amide D

Compound 3039

To a solution of 4-((1-(2-(2-(2-(2-aminoethoxy)ethoxy)ethoxy)ethyl)-1H-1,2,3-triazol-4-yl)methyl)thiomorpholine 1,1-dioxide (Amine D, 1 g, 2.55 mmol, 1 eq) and TEA (0.54 mL, 3.83 mmol, 1.5 eq) in $CH_2Cl_2$ (24 mL) was added drop wise methacryloyl chloride (0.37 mL, 3.83 mmol, 11.5 eq). The reaction was stirred for 12 hours at room temperature and concentrated under reduced pressure. The residue was purified by silica gel to afford N-(2-(2-(2-(2-(4-((1,1-dioxidothiomorpholino)methyl)-1H-1,2,3-triazol-1-yl)ethoxy)ethoxy)-ethoxy)ethyl)-methacrylamide (Compound 3039, 980 mg, 83% yield) as a solid. MS ESI $[M+H]^+$=460.2.

A similar procedure was used to prepare the following compounds:

| Compound Number | $M^+$ + H Observed |
|---|---|
| 3041 | 357.3 |
| 3043 | 309.4 |
| 3048 | 427.3 |
| 3049 | 297.2 ($M^+$ + Na) |
| 3053 | 357.2 |
| 3054 | 329.2 |
| 3056 | 243.1 |
| 3057 | 253.1 |
| 3064 | 371.3 |
| 3066 | 371.3 |
| 3067 | 244.1 |
| 3068 | 242.1 |
| 3069 | 260.1 |
| 3072 | 371.2 |
| 3073 | 326.1 (M + $NH4^+$) |
| 3074 | 385.2 |
| 3076 | 548.3 |
| 3081 | 371.2 |
| 3082 | 425.1 |
| 3092 | 342.2 |
| 3093 | 309.4 |
| 3098 | 419.2 |
| 3102 | 404.2 |
| 3105 | 474.2 |
| 3106 | 462.2 |
| 3110 | 355.2 |
| 3114 | 375.2 |
| 3115 | 416.2 |
| 3116 | 504.2 |
| 3121 | 349.1 |
| 3130 | 452.3 |
| 3131 | 281.1 |
| 3133 | 481.2 |
| 3134 | 372.1 |

Synthesis of Compound 3040

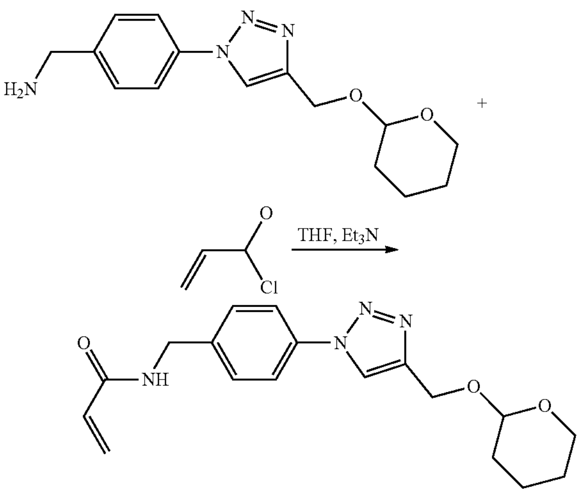

To a solution of (4-(4-(((tetrahydro-2H-pyran-2-yl)oxy) methyl)-1H-1,2,3-triazol-1-yl)phenyl)methanamine (2, 500 mg, 1.7 mmol, 1 eq) and TEA (351 mg, 3.5 mmol, 483 uL, 2 eq) in THE (10 mL) was added drop wise prop-2-enoyl chloride (126 mg, 1.4 mmol, 113 uL, 0.8 eq) at 0° C. After addition, the mixture was stirred at 25° C. for 12 h, at which point the desired product was observed by LCMS. The reaction mixture was concentrated under reduced pressure and the residue was purified by preparative HPLC to afford N-(4-(4-(((tetrahydro-2H-pyran-2-yl)oxy)methyl)-1H-1,2,3-triazol-1-yl)benzyl)acrylamide (Compound 3040, 280 mg, 818 umoL, 47% yield) as a solid. MS ESI $[M+H]^+$=343.1.

Synthesis of Compound 3044

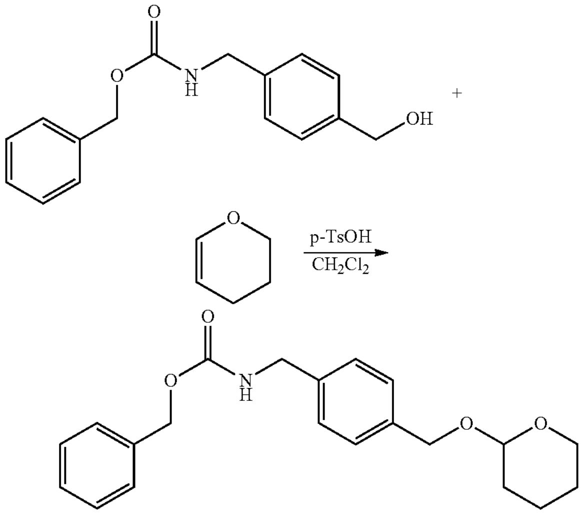

Benzyl (4-(hydroxymethyl)benzyl)carbamate (2.71 g, 10 mmol, 1 eq), 3,4-dihydro-2H-pyran (1.81 mL, 20 mmol, 2 eq), and p-toluenesulfonic acid monohydrate (285 mg, 1.5 mmol, 0.15 eq) in dichloromethane (100 mL) were stirred at room temperature overnight, at which point the desired product was observed by LCMS. The solvent was removed under reduced pressure and the crude product was purified by silica gel to afford benzyl (4-(((tetrahydro-2H-pyran-2-yl)oxy)methyl)benzyl)carbamate (Compound 3044, 2.4 g, 68%) as an oil. MS ESI $[M+H]^+$=356.2.

Synthesis of Compound 3045

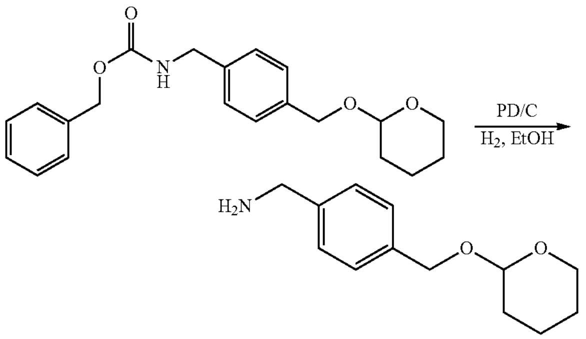

(4-(((tetrahydro-2H-pyran-2-yl)oxy)methyl)benzyl)carbamate (Compound 8, 1.5 g, 4.2 mmol, 1 eq) and palladium on carbon (160 mg, 10 wt. %) in EtOH were placed in a flask and briefly evacuated, and then hydrogen was added via a balloon and the mixture was stirred for 1 hour at room temperature. The solvent was removed under reduced pressure and the crude product was purified over silica gel to afford (4-(((tetrahydro-2H-pyran-2-yl)oxy)methyl)-phenyl) methanamine (Compound 3045, 890 mg, 95%) as a colorless oil. MS ESI $[M+H]^+$=460.2.

General Protocol for Deprotection (General Procedure D)

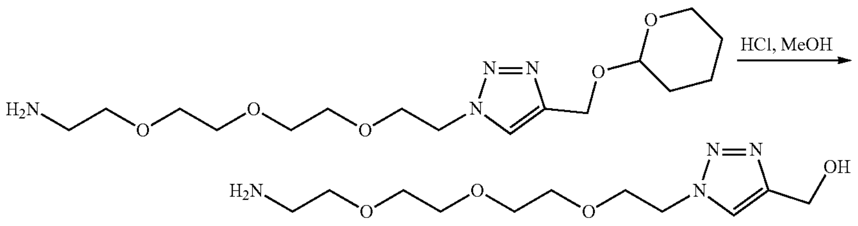

Compound 3049

2-(2-(2-(2-(4-(((tetrahydro-2H-pyran-2-yl)oxy)methyl)-1H-1,2,3-triazol-1-yl)ethoxy)ethoxy)ethoxy)ethan-1-amine (Compound 3047, 1.9 g, 5.3 mmol) was dissolved in HCl (1N in MeOH, 10 mL) and stirred for 90 minutes at room temperature. The solvent was removed under reduced pressure and the residue was purified on silica gel to afford (1-(2-(2-(2-(2-aminoethoxy)ethoxy)ethoxy)ethyl)-1H-1,2,3-triazol-4-yl)methanol (Compound 3049, 462 mg, 32%) as a colorless oil. MS ESI $[M+Na]^+$=297.2.

A similar procedure was used to prepare the following compounds:

| Compound Number | $M^+$ + H Observed |
|---|---|
| 3050 | 343.2 |
| 3059 | 205.1 |
| 3084 | 273.1 |

General Protocol for Alkyne Intermediate Synthesis (General Procedure E)

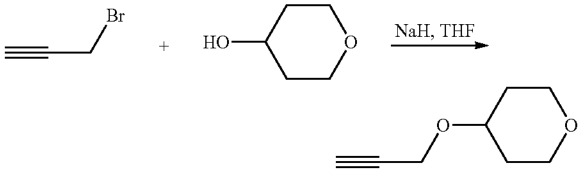

To a solution of tetrahydro-2H-pyran-4-ol (2.75 mL, 28.8 mmol, 1 eq) in THE (65 mL) was slowly added NaH (2.3 g, 60.0 mmol, 60% purity, 2 eq) at 0° C. After addition, the mixture was stirred at this temperature for 30 minutes and then 3-bromoprop-1-yne (2.6 mL, 28.8 mmol, 1.0 eq) was added in a drop wise fashion. The mixture was stirred for 12 h and allowed to warm to room temperature. TLC indicated one major new spot with lower polarity. The reaction mixture was quenched by addition ice water (100 mL), and then extracted with DCM (3×50 mL). The combined organic layer concentrated under reduced pressure and purified over silica gel to afford 4-(prop-2-yn-1-yloxy)tetrahydro-2H-pyran (Intermediate 15, 2.35 g) as an oil that was used directly in the coupling step.

A similar procedure was used to obtain the following alkyne intermediates:

| Intermediate Number | Structure | 1H-NMR Data |
|---|---|---|
| 17 | 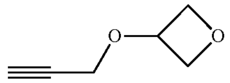 | $^1$H NMR (400 Mz, $CDCl_3$) δ 4.83-6.69 (5H, m), 4.16 (2H, d), 2.45 (1H, t) |
| 231 | 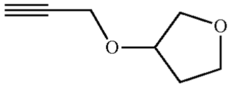 | |

Synthesis of Compound 3055

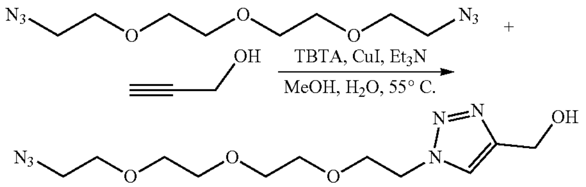

To a solution of prop-2-yn-1-ol (0.71 mL, 12.0 mmol, 1 eq), TBTA (1.59 g, 3.0 mmol, 0.25 eq), copper iodide (229 mg, 1.2 mmol, 0.1 eq), triethylamine (0.42 mL, 3.0 mmol, 0.25 eq) in methanol (50 mL) and water (6 mL) were purged with a stream of nitrogen for 5 minutes and cooled with an ice bath. 1-Azido-2-(2-(2-(2-azidoethoxy)ethoxy)ethoxy)ethane (5.86 g, 24.0 mmol, 1 eq) was added and the mixture was stirred at room temperature for 5 minutes and then heated to 55° C. for over night. The reaction mixture was cooled to room temperature and filtered through 413 filter paper. The solvent was removed under reduced pressure and the residue was purified over silica gel to afford (1-(2-(2-(2-(2-azidoethoxy)ethoxy)ethoxy)ethyl)-1H-1,2,3-triazol-4-yl)methanol (Compound 3055, 3.6 g, 64%) as a colorless oil. MS ESI $[M+H]^+$=301.2.

Synthesis of Compound 3062

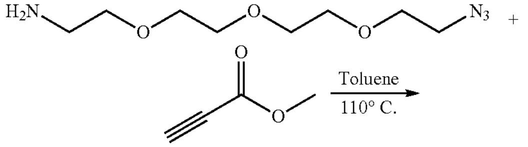

-continued

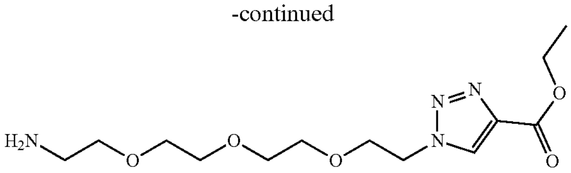

2-[2-[2-(2-azidoethoxy)ethoxy]ethoxy]ethanamine (0.79 mL, 4 mmol, 1 eq), ethyl propionate (0.81 mL, 8 mmol, 2 eq) and toluene (4 mL) were heated to 110° C. in a capped microwave tube (20 mL) for 30 minutes. The mixture was then allowed to warm to room temperature and purified over silica gel to afford: ethyl 1-(2-(2-(2-(2-aminoethoxy)ethoxy)ethoxy)ethyl)-1H-1,2,3-triazole-4-carboxylate (Compound 3062, 190 mg, 15%) as an oil. MS ESI $[M+H]^+$=317.2. $^1$H NMR (400 Mz, $CDCl_3$) δ 8.34 (1H, s), 4.63 (2H, t), 4.46 (2H, q), 3.92 (2H, t), 3.65 (8H, d), 3.53 (2H, t), 2.88 (2H, t), 1.44 (3H, t), 1.28 (2H, s br).

Synthesis of Compound 3078

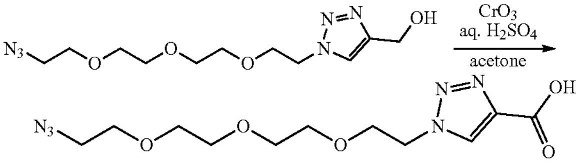

A solution of (1-(2-(2-(2-(2-azidoethoxy)ethoxy)ethoxy)ethyl)-1H-1,2,3-triazol-4-yl)methanol (Compound 3057, 0.5 g, 1.7 mmol, 1.0 eq) in acetone (16 mL) was cooled with an ice bath and Jones Reagent (2N, 4.2 mL, 8.3 mmol, 5.0 eq) was added in a dropwise fashion. The cooling bath was removed and the mixture was stirred at room temperature for 4 hours. The reaction mixture was filtered over a plug of Celite, concentrated and purified over silica gel to afford 1-(2-(2-(2-(2-azidoethoxy)ethoxy)ethoxy)ethyl)-1H-1,2,3-triazole-4-carboxylic acid (Compound 3078, 0.37 g, 71%) as a clear oil. MS ESI $[M+H]^+$=315.1.

Synthesis of Compound 3086

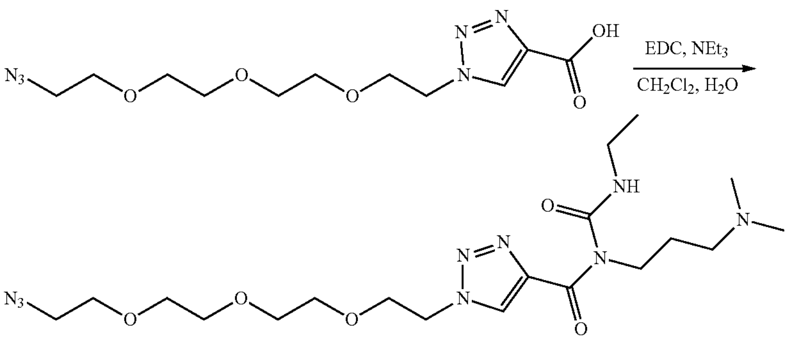

1-(2-(2-(2-(2-azidoethoxy)ethoxy)ethoxy)ethyl)-1H-1,2,3-triazole-4-carboxylic acid (Compound 3080, 0.5 g, 1.59 mmol, 1 eq), EDC (458 mg, 2.39 mmol, 1.5 eq) in $CH_2Cl_2$ (15 mL) were stirred at room temperature for 3 hours. The TLC showed consumption of the starting material. Water (1 mL) was added and the mixture was stirred over night at room temperature. The solvent was removed under reduced pressure and the crude product was purified over silica gel to afford: 1-(2-(2-(2-(2-azidoethoxy)ethoxy)ethoxy)ethyl)-N-(3-(dimethylamino)propyl)-N-(ethylcarbamoyl)-1H-1,2,3-triazole-4-carboxamide (Compound 3086, 317 mg, 42%) as a colorless oil. MS ESI $[M+H]^+$=470.2.

General Protocol for Azide Reductions (General Procedure F)

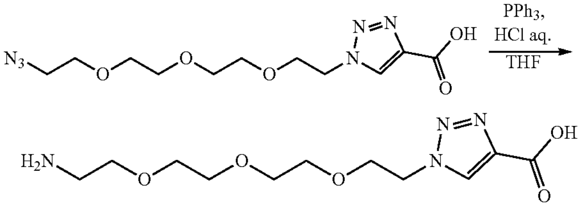

Compound 3089

1-(2-(2-(2-(2-azidoethoxy)ethoxy)ethoxy)ethyl)-1H-1,2,3-triazole-4-carboxylic acid (Compound 3080, 0.5 g, 1.59 mmol, 1 eq) was dissolved in THE (10 mL) and Triphenylphosphine (0.63 g, 2.39 mmol, 1.5 eq) was added. The mixture was stirred at room temperature for 12 hours. HCl (2N, 10 mL) was added and the mixture was stirred over night. The solvent was removed under reduced pressure and the mixture was purified by C18 reverse phase chromatography to afford 1-(2-(2-(2-(2-aminoethoxy)ethoxy)ethoxy)ethyl)-1H-1,2,3-triazole-4-carboxylic acid (Compound 3089, 0.2 g, 44%) as a colorless oil. MS ESI $[M+H]^+$=289.1

A similar procedure was used to prepare the following compounds:

| Compound Number | $M^+$ + H Observed |
|---|---|
| 3094 | 444.3 |
| 3126 | 311.2 |

Synthesis of Compound 3099

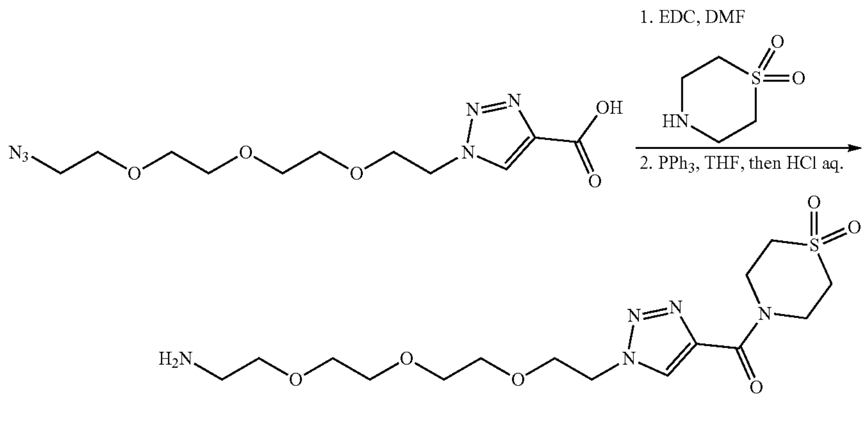

1-(2-(2-(2-(2-azidoethoxy)ethoxy)ethoxy)ethyl)-1H-1,2,3-triazole-4-carboxylic acid (Compound 3080, 0.94 g, 2.98 mmol, 1 eq) was dissolved in DMF (10 mL). N-ethyl-N-isopropyl-propan-2-amine (385 mg, 2.98 mmol, 1 eq), 1,4-thiazinane 1,1-dioxide (806 mg, 5.96 mmol, 2.0 eq) followed by [dimethylamino(triazolo[4,5-b]pyridin-3-yloxy)methylene]-dimethyl-ammonium;hexafluorophosphate (1.36 g, 3.58 mmol, 1.2 eq) were added and the mixture was stirred at room temperature overnight. The mixture was concentrated and flushed over silica gel to afford 1.74 g of an oil that was dissolved in THF (10 mL) and triphenylphosphine (1.55 g, 5.91 mmol) was added. The mixture was stirred overnight and HCl (2N, 5 mL) was added. The mixture was stirred at room temperature for 4 days, concentrated and purified over reversed phase C-18 silica gel to afford (1-(2-(2-(2-(2-aminoethoxy)ethoxy)ethoxy)ethyl)-1H-1,2,3-triazol-4-yl)(1,1-dioxidothiomorpholino)methanone (Compound 3099, 485 mg, 40%) as colorless oil. MS ESI $[M+H]^+$=406.1

Synthesis of Intermediate 66

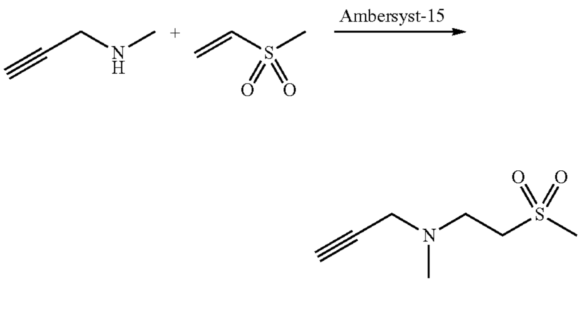

To a mixture of 1-methylsulfonylethylene (4.99 g, 47.03 mmol, 4.13 mL) and Amberlyst-15 ((30% w/w)), N-methylprop-2-yn-1-amine (2.6 g, 37.62 mmol) was added in a dropwise fashion. The mixture was stirred at room temperature for 12 hours. The catalyst was removed by filtration and the filtrate was concentrated under reduced pressure to afford: N-methyl-N-(2-(methylsulfonyl)ethyl)prop-2-yn-1-amine (Intermediate 66, 6.43 g, 98%) as an oil. MS ESI $[M+H]^+$=176.1.

Synthesis of Compound 3100

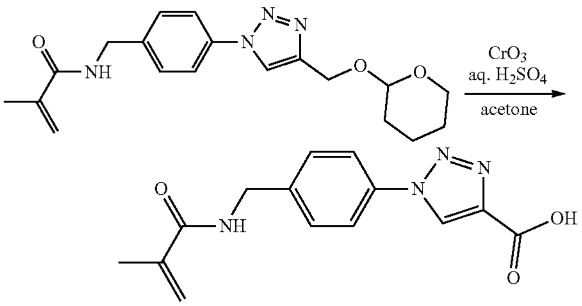

N-(4-(4-(((tetrahydro-2H-pyran-2-yl)oxy)methyl)-1H-1,2,3-triazol-1-yl)benzyl)methacrylamide (0.5 g, 1.4 mmol, 1.0 eq) was suspended in acetone (25 mL) and cooled with an ice bath. Jones Reagent (2N, 5 mL, 7.1 eq) was added in a dropwise fashion. The mixture was allowed to warm to room temperature and stirred for 5 hours before quenching by the addition of isopropanol. The suspension was filtered over a plug of Celite, concentrated under reduced pressure, and purified over silica gel to afford 1-(4-(methacrylamidomethyl) phenyl)-1H-1,2,3-triazole-4-carboxylic acid (Compound 3100, 160 mg, 40%) as a white solid. MS ESI $[M+H]^+$=287.1.

Synthesis of Intermediate 74

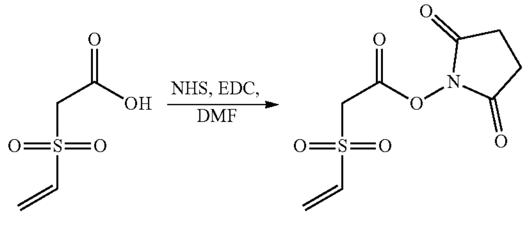

A mixture of 2-(vinylsulfonyl)acetic acid (1 g, 6.7 mmol, 1.0 eq), NHS (766 mg, 6.7 mmol, 1.0 eq), EDC (1.03 g, 6.7 mmol, 1.0 eq) in DMF (15 mL) was stirred over night at room temperature and concentrated under reduced pressure.

The residue was taken up in EtOAc (100 mL) and washed with water (4×50 mL). The solvent was then removed under reduced pressure to afford 2,5-dioxopyrrolidin-1-yl 2-(vinylsulfonyl)acetate (Intermediate 74, 493 mg) as yellow oil that was directly used in the next coupling step. MS ESI $[M+H]^+$=248.0

Synthesis of Compound 3107

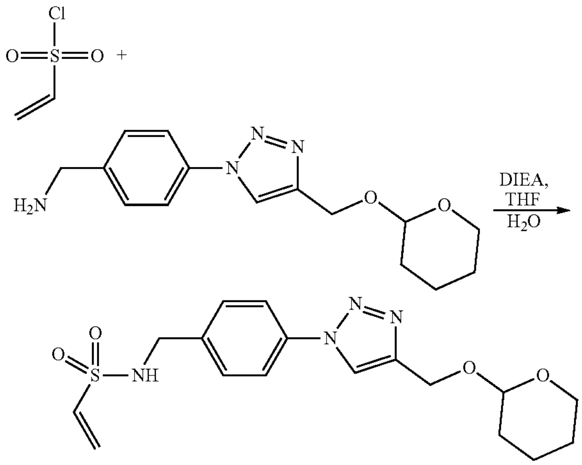

(4-(4-(((tetrahydro-2H-pyran-2-yl)oxy)methyl)-1H-1,2,3-triazol-1-yl)phenyl)methanamine (Compound 3038, 1.14 g, 3.95 mmol, 1.0 eq) was dissolved in water (10 mL) and THF (10 mL). DIEA (0.69 mL, 3.95 mmol, 1.0 eq) was added followed by ethenesulfonyl chloride (0.5 g, 3.95 mmol, 1.0 eq) and the mixture was stirred over night at room temperature. The solvent was removed under reduced pressure and the crude product was purified over silica gel to afford: N-(4-(4-(((tetrahydro-2H-pyran-2-yl)oxy)methyl)-1H-1,2,3-triazol-1-yl)benzyl)ethenesulfonamide (Compound 3107, 24 mg, 2%) as a colorless solid. MS ESI $[M+H]^+$=379.1

Synthesis of Compound 3108

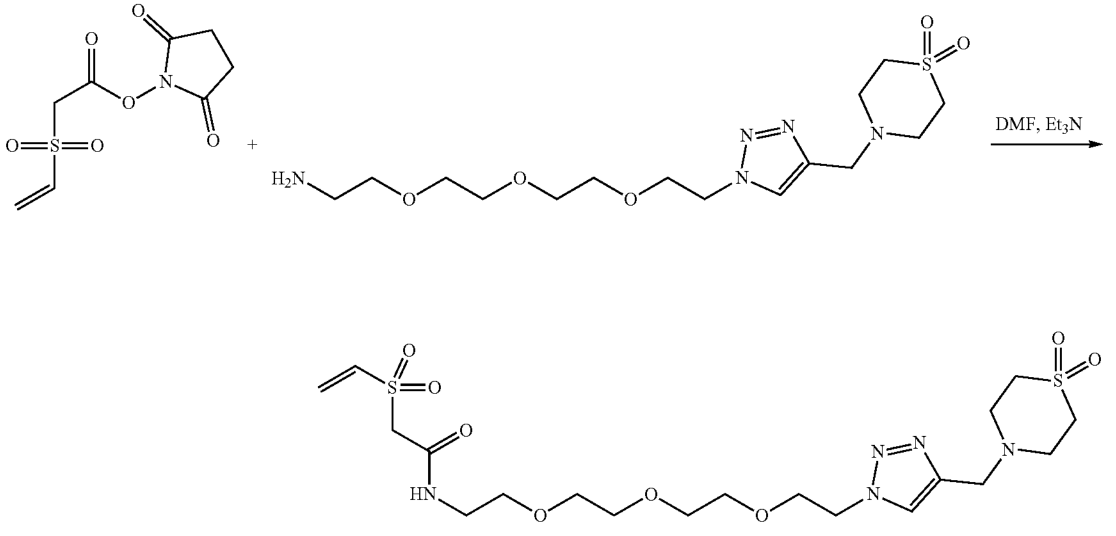

A mixture of 4-((1-(2-(2-(2-(2-aminoethoxy)ethoxy)ethoxy)ethyl)-1H-1,2,3-triazol-4-yl)methyl)thiomorpholine 1,1-dioxide (Compound 3037, 760 mg, 1.94 mmol, 1.0 eq), 2,5-dioxopyrrolidin-1-yl 2-(vinylsulfonyl)acetate (Intermediate 74, 480 mg, 1.94 mmol, 1.0 eq), and triethylamine (0.54 mL, 3.9 mmol, 2.0 eq) in DMF (15 mL) was stirred at room temperature over night and concentrated under reduced pressure. The crude product was purified over silica gel to afford: N-(2-(2-(2-(2-(4-((1,1-dioxidothiomorpholino)methyl)-1H-1,2,3-triazol-1-yl)ethoxy)ethoxy)ethoxy)ethyl)-2-(vinylsulfonyl)acetamide (Compound 3108, 90 mg) as a colorless oil. MS ESI $[M+H]^+$=524.2

Synthesis of Compound 3117

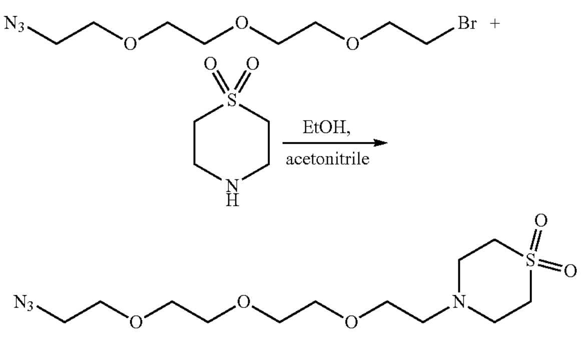

A mixture of 1-azido-2-(2-(2-(2-bromoethoxy)ethoxy)ethoxy)ethane (750 mg, 2.7 mmol, 1.0 eq), thiomorpholine 1,1-dioxide (720 mg, 5.3 mmol, 2.0 eq), ethanol (1 mL), and acetonitrile (2 mL) were heated to 120° C. for 2 h in a sealed microwave tube (20 mL). After being cooled to room temperature the solvent was removed under reduced pressure and the crude product was purified over silica gel to afford 4-(2-(2-(2-(2-azidoethoxy)ethoxy)ethoxy)ethyl)thiomorpholine 1,1-dioxide (Compound 3117, 752 mg, 84%) as an oil. MS ESI $[M+H]^+$=337.2. $^1H$ NMR (400 Mz, $CDCl_3$) δ 3.83-3.67 (8H, m), 3.65-3.63 (4H, m), 3.42 (2H, t), 3.14-3.11 (4H, m), 3.09-3.07 (4H, m), 2.80 (2H, t).

Synthesis of Compound 3118

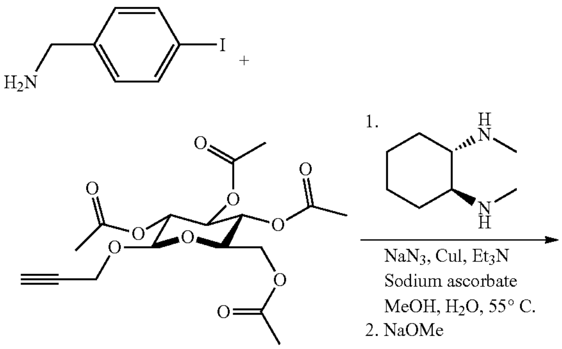

-continued

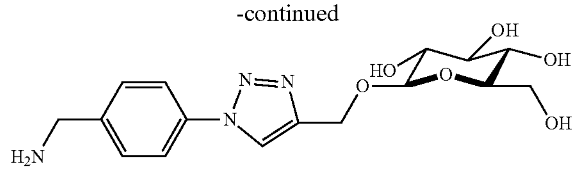

Compound 3118

A mixture of (4-iodophenyl)methanamine (4.0 g, 14.8 mmol, 1.0 eq), (1S,2S)—N1,N2-dimethylcyclohexane-1,2-diamine (0.46 mL, 3.0 mmol, 0.2 eq), sodium ascorbate (294 mg, 1.5 mmol, 0.1 eq), copper iodide (424 mg, 2.2 mmol, 0.15 eq), sodium azide (1.93 g, 29.7 mmol, 2.0 eq), $Et_3N$ (2.48 mL, 17.8 mmol, 1.2 eq) and (2R,3R,4S,5R,6R)-2-(acetoxymethyl)-6-(prop-2-yn-1-yloxy)tetrahydro-2H-pyran-3,4,5-triyl triacetate (5.73 g, 14.8 mmol, 1.0 eq) in methanol (36 mL) and water (9 mL) were purged with nitrogen for 5 minutes and heated to 55° C. overnight. The reaction mixture was cooled to room temperature and filtered through 413 filter paper. The solvent was removed under reduced pressure and the residue was purified over silica gel to afford a colorless oil, which was further purified to remove contaminants. The oil was dissolved in THE (5 mL), followed by addition of sodium methanolate (0.5N, 1 mL). The mixture was stirred at room temperature for 12 hours and neutralized by the addition of Amberlite IR 120 ($H^+$) ion exchange resin. The resin was removed by filtration and the mixture was concentrated under reduced pressure. The crude product was purified by reverse phase C18 silica gel to afford (2R,3R,4S,5S,6R)-2-((1-(4-(aminomethyl)phenyl)-1H-1,2,3-triazol-4-yl)methoxy)-6-(hydroxymethyl) tetrahydro-2H-pyran-3,4,5-triol (Compound 3118, 16 mg, <1%) as a colorless solid. MS ESI $[M+H]^+$=367.1.

General Protocol for SVEC Coupling (General Procedure G)

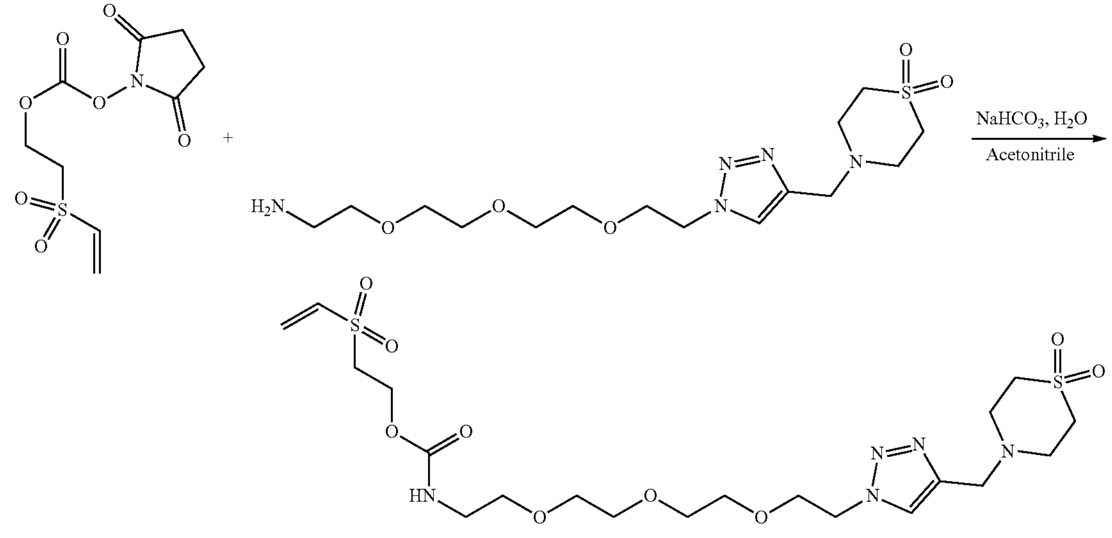

Compound 3122

4-((1-(2-(2-(2-(2-aminoethoxy)ethoxy)ethoxy)ethyl)-1H-1,2,3-triazol-4-yl)methyl)thiomorpholine 1,1-dioxide (Compound 3037, 0.65 g, 1.7 mmol, 1.0 eq) was added to a stirred solution of 2,5-dioxopyrrolidin-1-yl (2-(vinylsulfonyl)ethyl) carbonate (0.5 g, 1.8 mmol, 1.1 eq) in acetonitrile (10 mL). Water (10 mL) and sodium hydrogen carbonate (153 mg, 1.8 mmol, 1.1 eq) were added and the mixture was stirred for 1 hour at room temperature. The mixture was diluted with brine (15 mL) and extracted with dichloromethane (3×15 mL). The combined organic phases were filtered over cotton and concentrated under reduced pressure. The crude product was purified over silica gel to afford: 2-(vinylsulfonyl)ethyl (2-(2-(2-(2-(4-((1,1-dioxidothiomorpholino)methyl)-1H-1,2,3-triazol-1-yl)ethoxy)ethoxy)ethoxy)ethyl)carbamate (Compound 3122 738 mg, 80%) as a colorless oil. MS ESI $[M+H]^+$=554.2.

A similar procedure was used to prepare the following compound:

| Compound Number | $M^+$ + H Observed |
|---|---|
| 3123 | 451.1 |
| 3126 | 311.2 |

Synthesis of Compound 3132

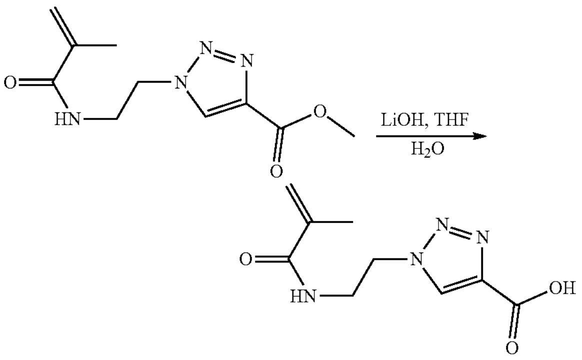

Ethyl 1-(2-methacrylamidoethyl)-1H-imidazole-4-carboxylate (0.2 g, 0.8 mmol, 1.0 eq) was dissolved in water (10 mL) and THE (10 mL). Lithium hydroxide (0.2 g, 8.4 mmol, 10 eq) was added and the mixture was stirred over night at room temperature. The solvent was removed under reduced pressure and the crude product was purified over silica gel to afford 1-(2-methacrylamidoethyl)-1H-1,2,3-triazole-4-carboxylic acid (Compound 3132). MS ESI $[M+H]^+$=224.1

General Protocol for 1,3 Dipolar Cycloaddition (General Procedure H)

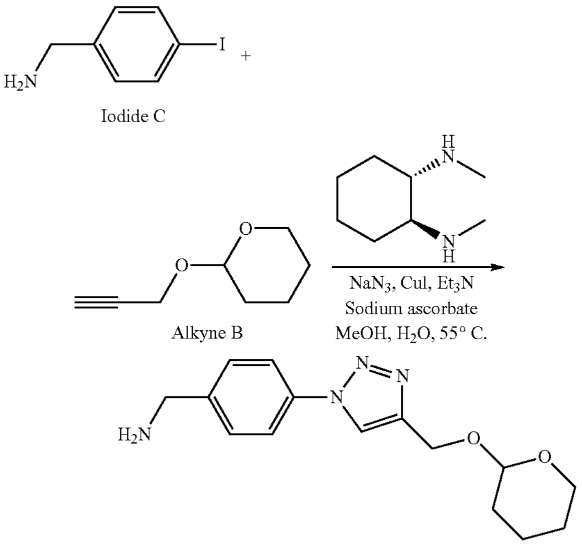

Iodide C

Alkyne B

Compound 3038

A mixture of (4-iodophenyl)methanamine (338 mg, 1.5 mmol), (1S,2S)—N1,N2-dimethylcyclohexane-1,2-diamine (41 mg, 290.0 umol, 46 uL), sodium ascorbate (29 mg, 145.0 umol), iodocopper (41 mg, 218 umol), azidosodium (189 mg, 2.9 mmol, 102 uL), $Et_3N$ (176 mg, 1.8 mmol, 243 uL)

and prop-2-ynoxycyclohexane (0.2 g, 1.5 mmol) in methanol (10 mL) and $H_2O$ (1 mL) was stirred at 55° C. for 12 h, at which point the desired product was observed by LCMS. Silica Bond Metal Scavenger was added to the mixture to remove the metal, and the reaction mixture was filtered and concentrated under reduced pressure to give a residue, which was purified by prep-HPLC (Column Waters Xbridge Prep (OBD C18 150*30 10u), Buffer A: water (0.05% ammonia hydroxide v/v); Buffer B: acetonitrile; 25% to 55% Buffer B over 12 minutes at 40 mL/min). Compound (4-(4-(((tetrahydro-2H-pyran-2-yl)oxy)methyl)-1H-1,2,3-triazol-1-yl)phenyl)methanamine (Compound 3038, 62 mg, 211.65 umol, 97.76%) was obtained as a white solid. MS ESI $[M+H]^+$=289.2.

A similar procedure was used to prepare the following compounds:

| Compound Number | $M^+$ + H Observed |
|---|---|
| 3136 | 304.1 |
| 3137 | 346.2 |
| 3138 | 290.1 |
| 3139 | 275.1 |
| 3140 | 362.2 |
| 3141 | 406.2 |
| 3142 | 303.1 |
| 3143 | 317.1 |
| 3144 | 331.1 |
| 3145 | 233.0 |
| 3146 | 317.1 |
| 3147 | 283.1 |
| 3148 | 282.1 |
| 3149 | 302.2 |
| 3150 | 272.1 |
| 3151 | 273.1 |
| 3152 | 274.1 |
| 3153 | 286.1 |
| 3154 | 255.1 |
| 3155 | 255.1 |
| 3156 | 256.1 |
| 3157 | 289.1 |
| 3158 | 273.1 |
| 3159 | 291.0 |
| 3160 | 299.0 |
| 3161 | 259.1 |
| 3162 | 245.1 |
| 3163 | 268.1 |
| 3164 | 268.1 |
| 3165 | 292.1 |
| 3166 | 241.1 |
| 3167 | 241.1 |
| 3168 | 255.1 |
| 3169 | 241.1 |
| 3170 | 255.1 |
| 3171 | 289.1 |
| 3172 | 303.1 |
| 3173 | 281.0 |
| 3174 | 277.1 |
| 3175 | 272.3 |
| 3176 | 275.1 |
| 3177 | 288.1 |
| 3178 | 259.1 |
| 3179 | 245.0 |
| 3180 | 251.1 |
| 3181 | 322.1 |
| 3182 | 322.1 |
| 3183 | 275.1 |
| 3184 | 287.1 |
| 3185 | 281.2 |
| 3186 | 346.2 |

General Protocol for 1,3 Dipolar Cycloaddition (General Procedure I)

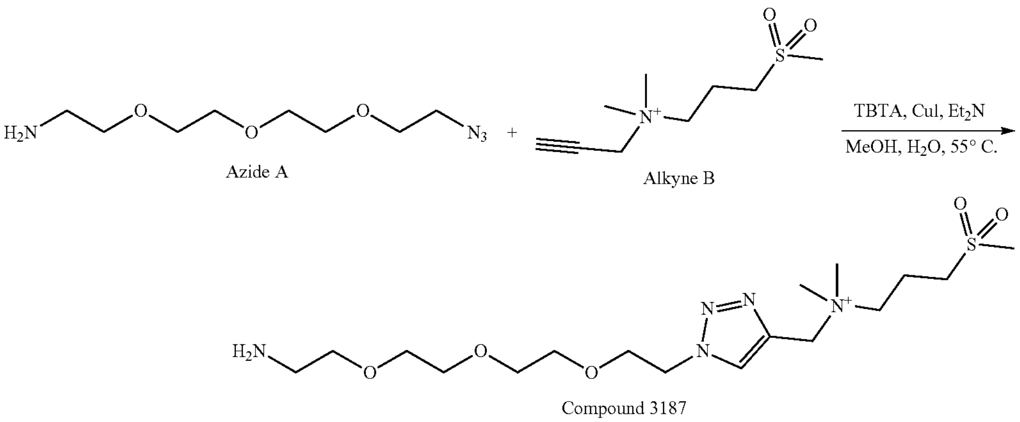

Azide A

Alkyne B

Compound 3187

To a solution of N,N-dimethyl-N-(3-(methylsulfonyl)propyl)prop-2-yn-1-aminium (Alkyne B, 400 mg, 2.1 mmol) and TBTA (245 mg, 462 umol) in methanol (5 mL) was added iodocopper (40 mg, 210 umol) and $Et_3N$ (53 mg, 526 umol, 73 uL). After addition, the mixture was stirred and 2-[2-[2-(2-azidoethoxy)ethoxy]ethoxy]ethanamine (Azide A, 459 mg, 2.1 mmol) was added dropwise at 25° C., and then the mixture was stirred at 55° C. for 12 h, at which point LCMS analysis showed formation of the desired product. Silica Bond Metal Scavenger was added to remove the metal, and the mixture was filtered and concentrated under reduced pressure to give a residue. The residue was purified by prep-HPLC (Column Waters Xbridge Prep (OBD C18 150*30 10u), Buffer A: water (0.04% $NH_3H_2O$ v/v); Buffer B: acetonitrile; 1% to 30% Buffer B over 12 minutes at 40 mL/min). Compound N-((1-(2-(2-(2-(2-aminoethoxy) ethoxy)-ethoxy)ethyl)-1H-1,2,3-triazol-4-yl)methyl)-N,N-dimethyl-3-(methylsulfonyl)propan-1-aminium (Compound 3187, 223.8 mg, 483 umol) was obtained as an oil. MS ESI $[M-CH_2]^+$=408.2.

A similar procedure was used to prepare the following compounds:

| Compound Number | $M^+$ + H Observed |
|---|---|
| 3188 | 283.2 |
| 3189 | 269.1 |
| 3190 | 407.1 |
| 3191 | 421.1 |
| 3192 | 393.1 |
| 3193 | 455.1 |
| 3194 | 418.2 |
| 3195 | 406.1 |
| 3196 | 420.3 |
| 3197 | 420.2 |
| 3198 | 420.2 |
| 3199 | 404.1 |
| 3200 | 472.2 |
| 3201 | 432.2 |
| 3202 | 476.3 |
| 3203 | 420.2 |
| 3204 | 416.2 |
| 3205 | 406.2 |
| 3206 | 420.2 |
| 3207 | 436.2 |
| 3208 | 342.3 |
| 3209 | 343.2 |

-continued

| Compound Number | $M^+$ + H Observed |
|---|---|
| 3210 | 356.2 |
| 3211 | 325.2 |
| 3212 | 325.2 |
| 3213 | 326.1 |
| 3214 | 359.2 |
| 3215 | 343.2 |
| 3216 | 361.2 |
| 3217 | 369.1 |
| 3218 | 329.2 |
| 3219 | 338.1 |
| 3220 | 338.1 |
| 3221 | 362.2 |
| 3222 | 323.1 |
| 3223 | 362.2 |
| 3224 | 311.1 |
| 3225 | 311.1 |
| 3226 | 325.2 |
| 3227 | 311.1 |
| 3228 | 325.1 |
| 3229 | 274.1 |
| 3230 | 302.1 |
| 3231 | 316.1 |
| 3240 | 416.2 |
| 3241 | 357.2 |
| 3242 | 380.3 |
| 3243 | 302.3 |
| 3244 | 345.1 |

Synthesis of Compound 3245

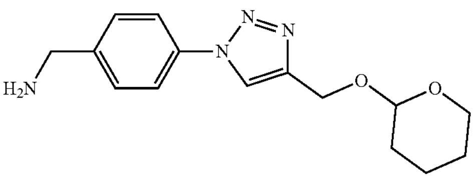

+

-continued

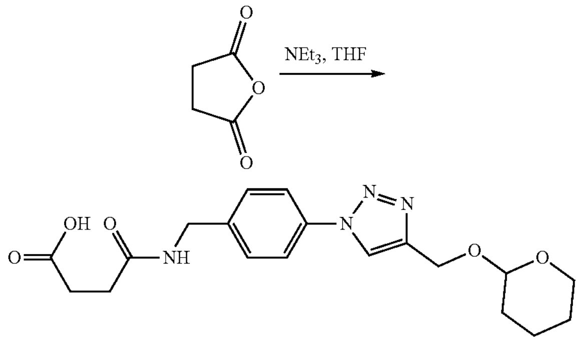

To a solution of (4-(4-(((tetrahydro-2H-pyran-2-yl)oxy)methyl)-1H-1,2,3-triazol-1-yl)phenyl)methanamine (Compound 3038, 500 mg, 1.7 mmol, 1 eq) and TEA (350 mg, 3.5 mmol, 482 uL, 2 eq) in THF (10 mL) was added dropwise tetrahydrofuran-2,5-dione (139 mg, 1.4 mmol, 0.8 eq) at 0° C. After addition, the mixture was stirred at 25° C. for 12 h. LCMS showed the reaction was completed and one main peak with the desired MS was detected. The reaction mixture was concentrated under reduced pressure to remove solvent. The residue was purified by prep-HPLC (Column Gemini 200*30 10, Buffer A: water (10 mM $NH_4HCO_3$ v/v); Buffer B: acetonitrile; 1% to 40% Buffer B over 12 minutes at 40 mL/min). Compound 4-oxo-4-[[4-[4-(tetrahydropyran-2-yloxymethyl)triazol-1-yl]phenyl]methylamino]butanoic acid (Compound 3245, 210 mg, 528 umol) was obtained as a white solid. MS ESI $[M^+-H]$=387.0.

Synthesis of Compound 3246

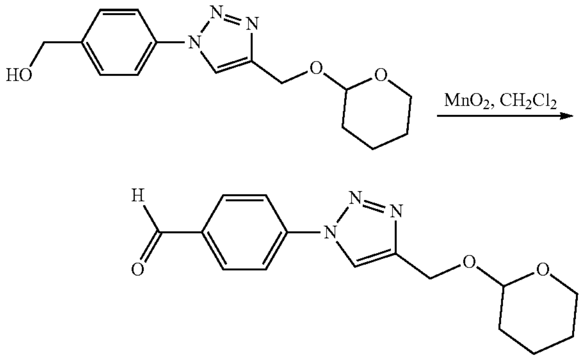

To a solution of [4-[4-(tetrahydropyran-2-yloxymethyl) triazol-1-yl]phenyl]methanol (1 g, 3.5 mmol, 1 eq) in DCM (20 mL) was added $MnO_2$ (1.50 g, 17.3 mmol, 5 eq). The mixture was stirred at 25° C. for 12 h under $N_2$ atmosphere. LCMS showed desired MS. The reaction mixture was filtered and concentrated under reduced pressure to give a residue. The residue was purified by prep-HPLC (Column Gemini 200*30 10, Buffer A: water (10 mM $NH_4HCO_3$ v/v); Buffer B: acetonitrile; 25% to 55% Buffer B over 12 minutes at 40 mL/min). Compound 4-[4-(tetrahydropyran-2-yloxymethyl) triazol-1-yl]benzaldehyde (Compound 3246, 177 mg, 611 umol) was obtained as a white solid. MS ESI $[M^+-H]$=288.1.

Synthesis of Compound 3247

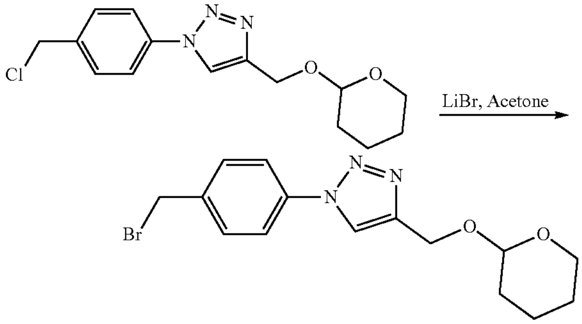

To a solution of 1-(4-(chloromethyl)phenyl)-4-(((tetrahydro-2H-pyran-2-yl)oxy)methyl)-1H-1,2,3-triazole (0.3 g, 975 umol) in Acetone (10 mL) was added LiBr (847 mg, 9.9 mmol, 245 uL). The mixture was stirred at 50° C. for 12 h under $N_2$ atmosphere. The reaction mixture was diluted with $H_2O$ (90 mL) and extracted with EtOAc (30 mL×3). The combined organic layers were washed with saturated brine (90 mL), dried over anhydrous $Na_2SO_4$, filtered and concentrated under reduced pressure to give a residue. The residue was purified by column chromatography ($SiO_2$, Petroleum ether/Ethyl acetate=20/1 to 1:1) to afford 1-(4-(bromomethyl)phenyl)-4-(((tetrahydro-2H-pyran-2-yl)oxy)methyl)-1H-1,2,3-triazole (Compound 3247, 0.26 g, 584 umol), which was obtained as a white solid. MS ESI $[M^+-H]$=352.0.

Synthesis of Compound 3248

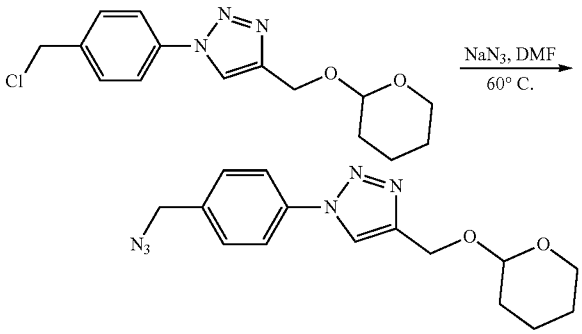

To a solution of 1-(4-(chloromethyl)phenyl)-4-(((tetrahydro-2H-pyran-2-yl)oxy)methyl)-1H-1,2,3-triazole (0.1 g, 325 umol) in DMF (10 mL) was added $NaN_3$ (211 mg, 3.3 mmol, 114 uL). The mixture was stirred at 60° C. for 12 h under $N_2$ atmosphere. TLC showed the reaction was completed. The reaction mixture was diluted with $H_2O$ (30 mL) and extracted with EtOAc (10 mL×3). The combined organic layers were washed with saturated brine (30 mL×1), dried over anhydrous $Na_2SO_4$, filtered and concentrated under reduced pressure to give a residue. The residue was purified by column chromatography ($SiO_2$, Petroleum ether/Ethyl acetate=20/1 to 1:1) to afford 1-(4-(azidomethyl)phenyl)-4-(((tetrahydro-2H-pyran-2-yl)oxy)methyl)-1H-1,2,3-triazole (Compound 3248, 0.1 g, 304 umol) as a white solid. MS ESI $[MH]^+$=315.1.0.

Synthesis of Compound 3249

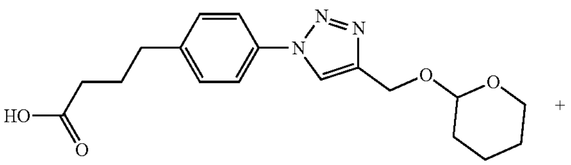

-continued

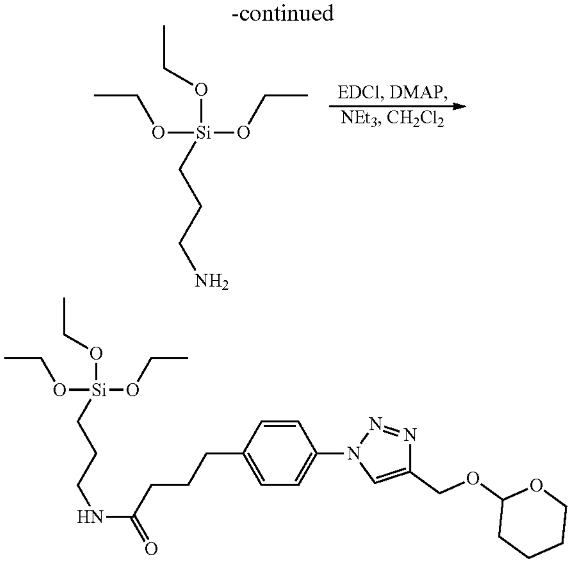

A mixture of 4-(4-(4-(((tetrahydro-2H-pyran-2-yl)oxy)methyl)-1H-1,2,3-triazol-1-yl)phenyl)butanoic acid (0.25 g, 724 umol, 1 eq), 3-triethoxysilylpropan-1-amine (160 mg, 724 umol, 1 eq), EDCI (167 mg, 869 umol, 1.2 eq), DMAP (2.7 mg, 22 umol, 0.03 eq) and TEA (88 mg, 869 umol, 121 uL, 1.2 eq) in DCM (10 mL) was stirred at 25° C. for 10 h. LCMS showed the reaction was completed and one main peak with desired MS was detected. The reaction mixture was extracted with H2O (20 mL) and DCM (20 mL×3). The combined organic layers were dried over $Na_2SO_4$, filtered and concentrated under reduced pressure to give a residue. The residue was purified by prep-HPLC (Column YMC-Actus Triart C18 100*30 mm*5 um, Buffer A: water (10 mM $NH_4HCO_3$ v/v); Buffer B: acetonitrile; 45% to 65% Buffer B over 12 minutes at 40 mL/min). Compound 4-(4-(4-(((tetrahydro-2H-pyran-2-yl)oxy)methyl)-1H-1,2,3-triazol-1-yl)phenyl)-N-(3-(triethoxysilyl)propyl)butanamide (Compound 3249, 55 mg, 93 umol) was obtained as a white solid. MS ESI $[M^+-OEt]^+$=503.3.

General Protocol for Amine Functionalization (General Procedure Q)

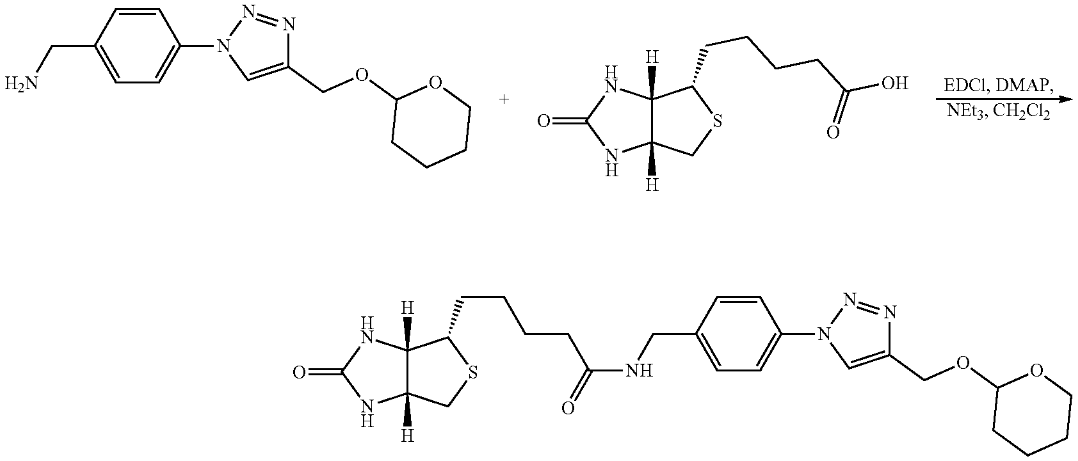

A mixture of 5-((3aS,4S,6aR)-2-oxohexahydro-1H-thieno[3,4-d]imidazol-4-yl)pentanoic acid (401 mg, 1.7 mmol, 1 eq), (4-(4-(((tetrahydro-2H-pyran-2-yl)oxy)methyl)-1H-1,2,3-triazol-1-yl)phenyl)methanamine (Compound 3038, 473 mg, 1.7 mmol, 1 eq), EDCI (377 mg, 2.0 mmol, 1.2 eq), DMAP (4 mg, 33 umol, 0.02 eq) and TEA (199 mg, 2.0 mmol, 274 uL, 1.2 eq) in DCM (20 mL) was stirred at 25° C. for 10 h, at which point the desired product was observed by LCMS. The reaction mixture was diluted with $H_2O$ (30 mL) and extracted with DCM (30 mL×3). The combined organic layers were dried over $Na_2SO_4$, filtered and concentrated under reduced pressure to give a residue. The residue was purified by prep-HPLC (Column Gemini 200*30 10, Buffer A: water (10 mM $NH_4HCO_3$ v/v); Buffer B: acetonitrile; 15% to 45% Buffer B over 12 minutes at 40 mL/min) to afford 5-((3aS,4S,6aR)-2-oxohexahydro-1H-thieno[3,4-d]imidazol-4-yl)-N-(4-(4-(((tetrahydro-2H-pyran-2-yl)oxy)methyl)-1H-1,2,3-triazol-1-yl)benzyl)pentanamide (Compound 3250, 184 mg, 331 umol) was obtained as a white solid. MS ESI $[M^+H]^+$=512.2.

A similar procedure was used to prepare the following compound:

| Compound Number | $M^+$ + H Observed |
|---|---|
| 3267 | 618.2 |

General Protocol for Amine Functionalization (General Procedure R)

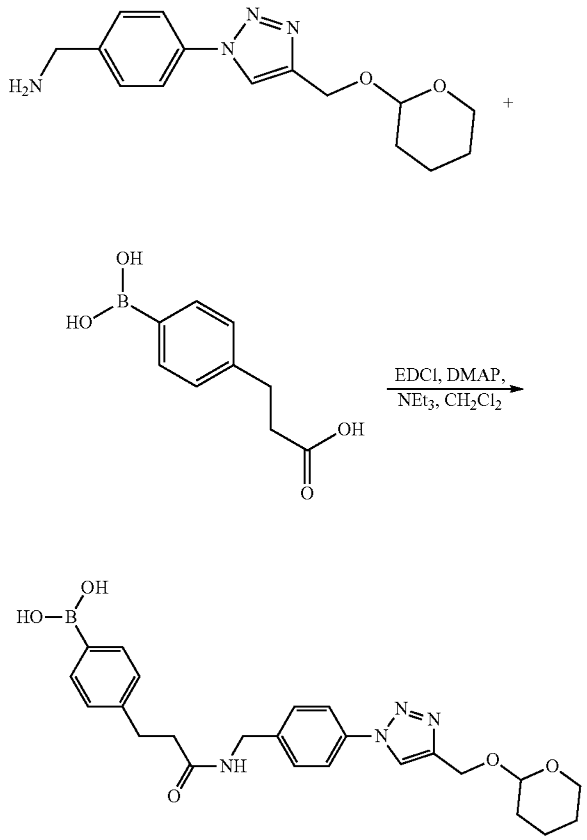

A mixture of (4-(4-(((tetrahydro-2H-pyran-2-yl)oxy)methyl)-1H-1,2,3-triazol-1-yl)phenyl)methanamine (Compound 3038, 0.5 g, 1.7 mmol, 1 eq), 3-(4-boronophenyl)propanoic acid (336 mg, 1.7 mmol, 1 eq), EDCI (399 mg, 2.1 mmol, 1.2 eq), DMAP (6 mg, 52 umol, 0.03 eq) and TEA (211 mg, 2.1 mmol, 290 uL, 1.2 eq) in DCM (20 mL) was stirred at 25° C. for 10 h. LCMS showed one main peak with desired MS was detected. The reaction mixture was extracted with $H_2O$ (20 mL) and DCM (30 mL×3). The combined organic layers were dried over $Na_2SO_4$, filtered and concentrated under reduced pressure to give a residue. The residue was purified by prep-HPLC (Column Gemini 200*30 10, Buffer A: water (10 mM $NH_4OH$ v/v); Buffer B: acetonitrile; 20% to 50% Buffer B over 12 minutes at 40 mL/min). Compound (4-(3-oxo-3-((4-(4-(((tetrahydro-2H-pyran-2-yl)oxy)methyl)-1H-1,2,3-triazol-1-yl)benzyl)amino)propyl)phenyl)boronic acid (Compound 3251, 215 mg, 461 umol) was obtained as a yellow solid. MS ESI $[MH]^+$=465.2.

A similar procedure was used to prepare the following compound:

| Compound Number | $M^+$ + H Observed |
|---|---|
| 3268 | 568.2 |

Synthesis of Compound 3252

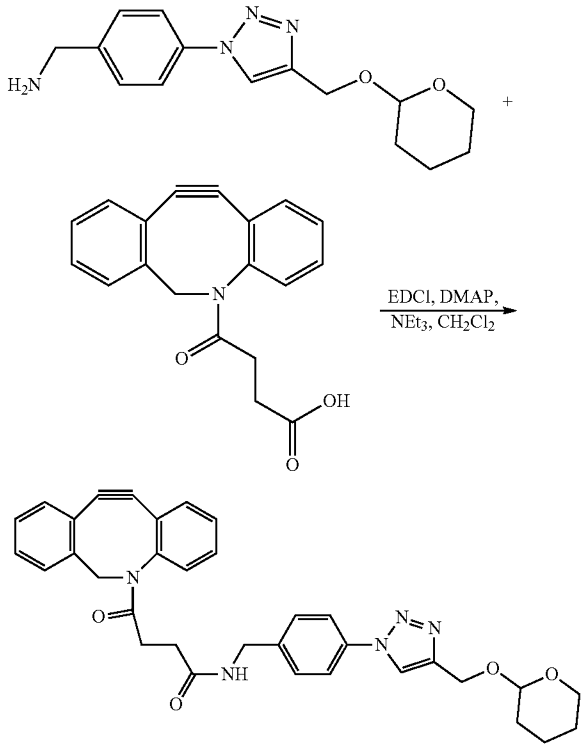

A mixture of (4-(4-(((tetrahydro-2H-pyran-2-yl)oxy)methyl)-1H-1,2,3-triazol-1-yl)phenyl)methanamine (Compound 3038, 385 mg, 1.3 mmol), 4-(11,12-didehydrodibenzo[b,f]azocin-5(6H)-yl)-4-oxobutanoic acid (364 mg, 1.3 mmol), 3-(ethyliminomethyleneamino)-N,N-dimethyl-propan-1-amine; hydrochloride (290 mg, 1.5 mmol), N,N-dimethylpyridin-4-amine (8 mg, 63 umol) and N,N-diethylethanamine (153 mg, 1.5 mmol, 211 uL) in DCM (15 mL) was stirred at 25° C. for 12 h, at which point the desired product was observed by LCMS. The reaction mixture was filtered and concentrated under reduced pressure to give a residue, which was purified by prep-HPLC (Column Gemini 200*30 10, Buffer A: water (10 mM $NH_4HCO_3$ v/v); Buffer B: acetonitrile; 45%-65% Buffer B over 12 minutes at 40 mL/min). 4-(11,12-didehydrodibenzo[b,f]azocin-5(6H)-yl)-N-(4-(4-(((tetrahydro-2H-pyran-2-yl)oxy)methyl)-1H-1,2,3-triazol-1-yl)benzyl)-4-oxobutanamide (Compound 3252, 87 mg, 131 umol) was obtained as a white solid. MS ESI $[MH]^+$=576.3.

Synthesis of Compound 3253

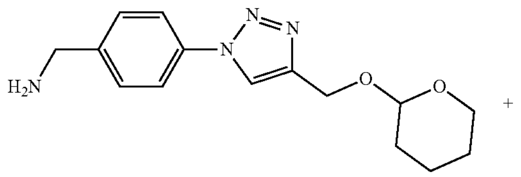

-continued

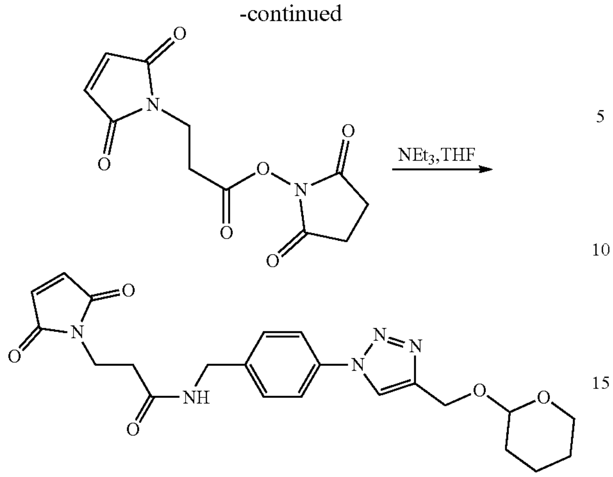

Compound 3252

A mixture of (4-(4-(((tetrahydro-2H-pyran-2-yl)oxy)methyl)-1H-1,2,3-triazol-1-yl)phenyl)methanamine (Compound 3038, 260 mg, 902 umol), 2,5-dioxopyrrolidin-1-yl 3-(2,5-dioxo-2,5-dihydro-1H-pyrrol-1-yl)propanoate (240 mg, 902 umol) and N,N-diethylethanamine (183 mg, 1.8 mmol, 251 uL) in THF (10 mL) was stirred at 25° C. for 12 h, at which point the desired product was observed by LCMS. The reaction mixture was concentrated under reduced pressure to remove solvent and gave a residue, which was purified by column chromatography ($SiO_2$, Petroleum ether/Ethyl acetate=5:1 to 0:1) and prep-TLC ($SiO_2$, EtOAc). 3-(2,5-dioxo-2,5-dihydro-1H-pyrrol-1-yl)-N-(4-(4-(((tetrahydro-2H-pyran-2-yl)oxy)methyl)-1H-1,2,3-triazol-1-yl)benzyl)propanamide (Compound 3253, 61 mg, 134 umol) was obtained as a solid. MS ESI $[M+H]^+$=440.2.

General Procedure for Amine Functionalization (General Procedure K)

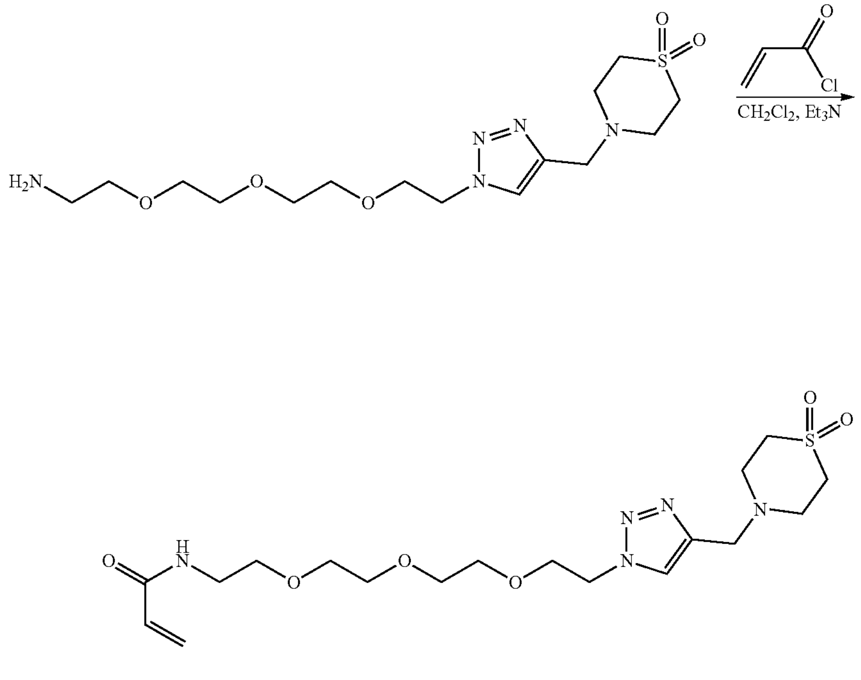

To a solution of 4-((1-(2-(2-(2-(2-aminoethoxy)ethoxy)ethoxy)ethyl)-1H-1,2,3-triazol-4-yl)methyl)thiomorpholine 1,1-dioxide (Compound 3037, 350 mg, 894 umol) in DCM (2 mL) and TEA (271 mg, 2.7 mmol, 374 uL) was added prop-2-enoyl chloride (65 mg, 715 umol) at 0° C. The mixture was stirred at 25° C. for 12 h. LCMS showed a peak with desired MS. The reaction mixture was concentrated under reduced pressure to remove solvent. The residue was purified by prep-HPLC (Column Gemini 200*30 10, Buffer A: water (10 mM $NH_4HCO_3$ v/v); Buffer B: acetonitrile; 45%-65% Buffer B over 12 minutes at 40 mL/min). N-(2-(2-(2-(2-(4-((1,1-dioxidothiomorpholino)methyl)-1H-1,2,3-triazol-1-yl)ethoxy)ethoxy)ethoxy)ethyl)acrylamide (Compound 3254, 150 mg, 337 umol) was obtained as an oil. MS ESI $[M+H]^+$=446.2.

A similar procedure was used to prepare the following compounds:

| Compound Number | $M^+$ + H Observed |
|---|---|
| 3255 | 492.2 |
| 3256 | 482.1 |

Synthesis of Compound 3257

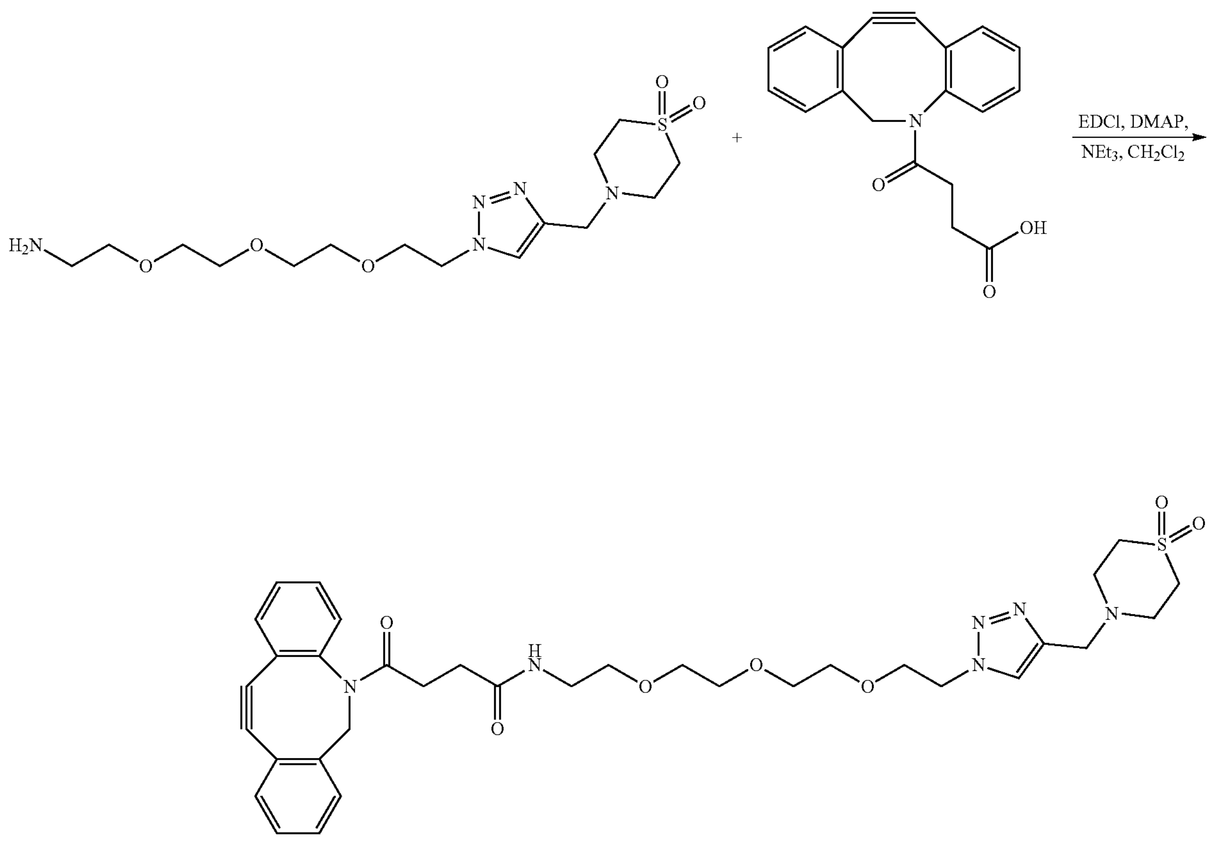

To a solution of 4-((1-(2-(2-(2-(2-aminoethoxy)ethoxy) ethoxy)ethyl)-1H-1,2,3-triazol-4-yl)methyl)thiomorpholine 1,1-dioxide (Compound, 0.3 g, 766 umol) in DCM (10 mL) was added 3-(ethyliminomethyleneamino)-N,N-dimethyl-propan-1-amine;hydrochloride (176 mg, 920 umol), DMAP (5 mg, 38 umol), TEA (93 mg, 920 umol, 128 uL) and 4-(11,12-didehydrodibenzo[b,f]azocin-5(6H)-yl)-4-oxobutanoic acid (234 mg, 766 umol). The mixture was stirred at 25° C. for 12 h under $N_2$ atmosphere. The reaction mixture was filtered and concentrated under reduced pressure to give a residue. The residue was purified by prep-HPLC (Column: Waters Xbridge Prep OBD C18 150*30 10; Buffer A: water (10 mM $NH_4HCO_3$ v/v); Buffer B: acetonitrile; 25%-50% Buffer B over 12 minutes at 40 mL/min). Compound N-(2-(2-(2-(2-(4-((1,1-dioxidothiomorpholino)-methyl)-1H-1,2,3-triazol-1-yl)ethoxy)ethoxy)ethoxy)-ethyl)-4-oxo-4-(11,12-didehydrodibenzo[b,f]azocin-5(6H)-yl)butanamide (Compound 3257, 110 mg, 152 umol) was obtained as a colorless oil. MS ESI $[M^+H]^+$=679.2.

Synthesis of Compound 3258

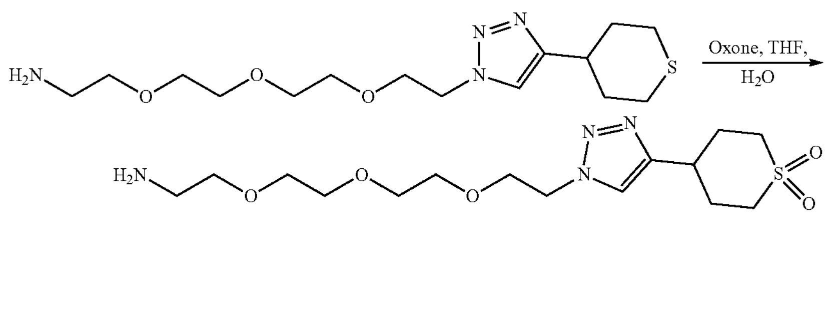

To the solution of 2-(2-(2-(2-(4-(tetrahydro-2H-thiopyran-4-yl)-1H-1,2,3-triazol-1-yl)ethoxy)ethoxy) ethoxy) ethan-1-amine (0.1 g, 290 umol) in $H_2O$ (5 mL) and THE (5 mL) was added Oxone (50 mg, 290 umol), then the mixture was stirred at 25° C. for 1 h. TLC showed the reaction was completed, and solvent was removed under reduced pressure. The residue was purified by prep-HPLC (Column: Waters Xbridge Prep OBD C18 150*30 10; Buffer A: water (10 mM $NH_4HCO_3$ v/v); Buffer B: acetonitrile; 1%-30% Buffer B over 12 minutes at 40 mL/min). 4-(1-(2-(2-(2-(2-aminoethoxy)ethoxy)ethoxy)ethyl)-1H-1,2,3-triazol-4-yl) tetrahydro-2H-thiopyran 1,1-dioxide (Compound 3258, 36 mg, 93 umol) was obtained as yellow oil. MS ESI $[M^+H]^+$= 377.1.

General Protocol for Compound 3262 (General Procedure L)

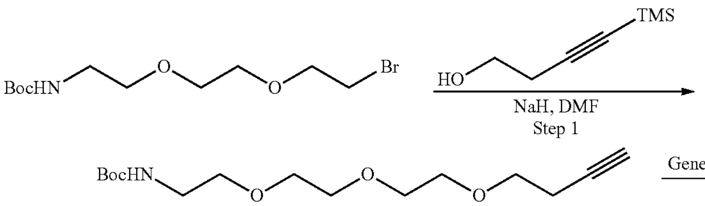

Compound 3259

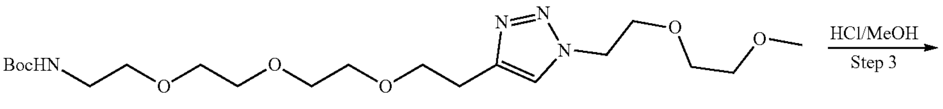

Compound 3260

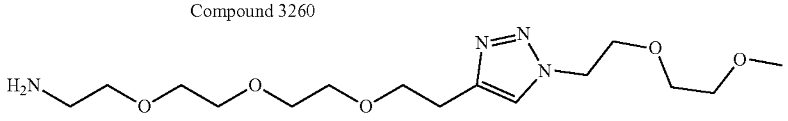

Compound 3262

Step 1

4-(Trimethysilyl)but-3-yn-1-ol (2.28 g, 16 mmol) in DMF (50 mL) was added NaH (736 mg, 18.4 mmol, 60% purity) at 0° C. and stirred at 0° C. for 15 min. Then tert-butyl (2-(2-(2-bromoethoxy)ethoxy)ethyl)carbamate (5 g, 16 mmol) was added and the mixture was stirred at 29° C. for 12 h. TLC indicated complete conversion. The reaction mixture was diluted with $H_2O$ (100 mL) and extracted with EtOAc (100 mL×2). The combined organic layers were washed with saturated brines (100 mL×2), dried over $Na_2SO_4$, filtered and concentrated under reduced pressure to give a residue. The residue was purified by column chromatography ($SiO_2$, Petroleum ether/Ethyl acetate=20/1 to 2:1) to yield Compound 3259, tert-butyl (2-(2-(2-(but-3-yn-1-yloxy)ethoxy)ethoxy)ethyl)carbamate (2.6 g, 8.6 mmol) as a colorless oil. $^1H$ NMR (400 Mz, $CDCl_3$) δ 3.66-3.61 (10H, m), 3.55 (2H, t), 3.33-3.31 (2H, m), 2.49 (2H, td), 1.44 (9H, s).

Step 2

General procedure A was carried out to obtain tert-butyl (2-(2-(2-(2-(1-(2-(2-methoxyethoxy)ethyl)-1H-1,2,3-triazol-4-yl)ethoxy)ethoxy)ethoxy)ethyl)carbamate (Compound 3260).

Step 3

The solution of tert-butyl (2-(2-(2-(2-(1-(2-(2-methoxyethoxy)ethyl)-1H-1,2,3-triazol-4-yl)ethoxy)ethoxy) ethoxy) ethyl)carbamate (Compound 3260, 120 mg, 269 umol) in HCl/MeOH (15 mL, ~4 N) was stirred at 25° C. for 5 h. TLC showed the reaction was completed. The solvent was removed and $NH_3 \cdot H_2O$ was added to the mixture to change the pH of the solution to 7-8. The residue was purified by prep-HPLC (Column: Waters Xbridge Prep OBD C18 150*30 10; Buffer A: water (10 mM $NH_4HCO_3$ v/v); Buffer B: acetonitrile; 1%-20% Buffer B over 11 minutes at 40 mL/min) to afford Compound 3262, 2-(2-(2-(2-(1-(2-(2-methoxyethoxy)ethyl)-1H-1,2,3-triazol-4-yl)ethoxy) ethoxy)ethoxy)ethan-1-amine (45 mg, 129 umol) as an oil.

A similar procedure was used to prepare the following compounds:

| Compound Number | $M^+$ + H Observed |
|---|---|
| 3232 | 347.2 |
| 3233 | 342.3 |
| 3234 | 345.1 |
| 3235 | 377.1 |
| 3236 | 358.2 |
| 3237 | 329.2 |
| 3238 | 315.1 |
| 3239 | 321.2 |

Synthesis of Compound 3261

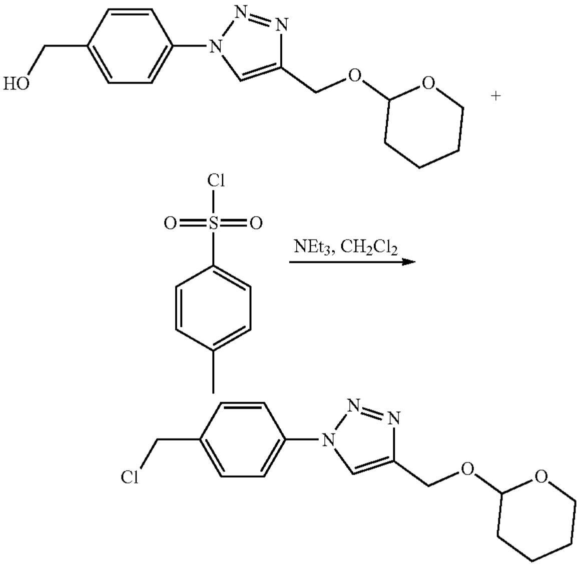

To a solution of (4-(4-(((tetrahydro-2H-pyran-2-yl)oxy) methyl)-1H-1,2,3-triazol-1-yl)phenyl)methanol (3 g, 10.4 mmol) in DCM (50 mL) was added TEA (1.57 g, 15.6 mmol, 2.2 mL). The mixture was stirred at 0° C. for 2 h under $N_2$ atmosphere. A solution of 4-methylbenzenesulfonyl chloride (2.37 g, 12.4 mmol) in DCM (50 mL) was added dropwise to the solution at 0° C., then the mixture was stirred at 25° C. for 10 h under $N_2$ atmosphere. TLC indicated the reaction was completed. The reaction mixture was diluted with $H_2O$ (90 mL) and extracted with DCM (30 mL×3), and the combined organic layers were washed with saturated brine (90 mL), dried over anhydrous $Na_2SO_4$, filtered and concentrated under reduced pressure to give a residue. The residue was purified by column chromatography ($SiO_2$, Petroleum ether/Ethyl acetate=20/1 to 1:1) to afford Compound 3261, 1-(4-(chloromethyl)phenyl)-4-(((tetrahydro-2H-pyran-2-yl)oxy)methyl)-1H-1,2,3-triazole (1.58 g, 4.9 mmol) as a solid. MS ESI $[M^+H]^+$=308.1.

General Protocol for Amine Functionalization (General Procedure O)

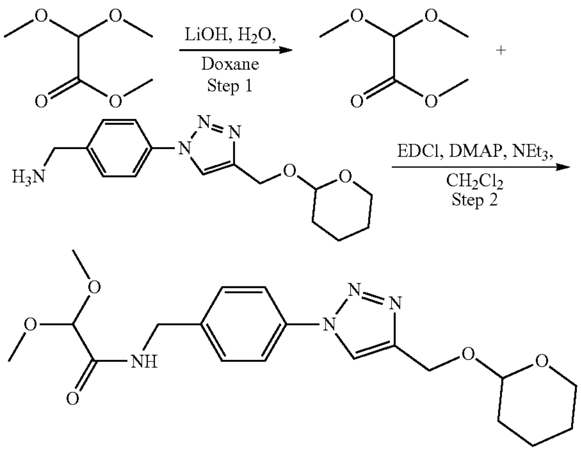

Step 1

To a solution of methyl 2,2-dimethoxyacetate (8.7 g, 64.9 mmol, 7.98 mL, 1 eq) in dioxane (50 mL) and $H_2O$ (50 mL) was added $LiOH·H_2O$ (3.27 g, 77.8 mmol, 1.2 eq) at 0° C. After addition, the mixture was stirred at this temperature for 1 h, and then the resulting mixture was stirred at 20° C. for 10 h. TLC indicated that one new spot formed. The reaction mixture was diluted with NaOH aqueous solution (1 M, 80 mL), and extracted with petroleum ether (80 mL×3). The combined aqueous layers were acidified with HCl (6 M) aqueous solution to pH=1, and then extracted with ethyl acetate (80 mL for 3 times). The combined organic layers were dried over $Na_2SO_4$, filtered and concentrated under reduced pressure to give 3.54 g of a colorless oil, which was used directly in the next step.

Step 2

A mixture of (4-(4-(((tetrahydro-2H-pyran-2-yl)oxy) methyl)-1H-1,2,3-triazol-1-yl)phenyl)methanamine (Compound 3038, 1 g, 3.5 mmol, 1 eq), 2,2-dimethoxyacetic acid (416 mg, 3.5 mmol, 1 eq), EDCI (798 mg, 4.2 mmol, 1.2 eq), DMAP (8 mg, 69 umol, 0.02 eq) and TEA (421 mg, 4.2 mmol, 579 uL, 1.2 eq) in DCM (20 mL) was stirred at 25° C. for 10 h. The reaction mixture was mixed with $H_2O$ (20 mL) and DCM (20 mL×3). The organic layer was dried over $Na_2SO_4$, filtered and concentrated under reduced pressure to give a residue. The residue was purified by prep-HPLC (Column Gemini 200*30 10, Buffer A: water (10 mM $NH_4HCO_3$ v/v); Buffer B: acetonitrile; 15-45% Buffer B over 20 minutes at 40 mL/min). Compound 2,2-dimethoxy-N-(4-(4-(((tetrahydro-2H-pyran-2-yl)oxy)methyl)-1H-1,2,3-triazol-1-yl)benzyl)acetamide (Compound 3263, 523 mg, 1.3 mmol) was obtained as white solid. MS ESI $[M^+H]^+$=391.2.

Synthesis of Compound 3264

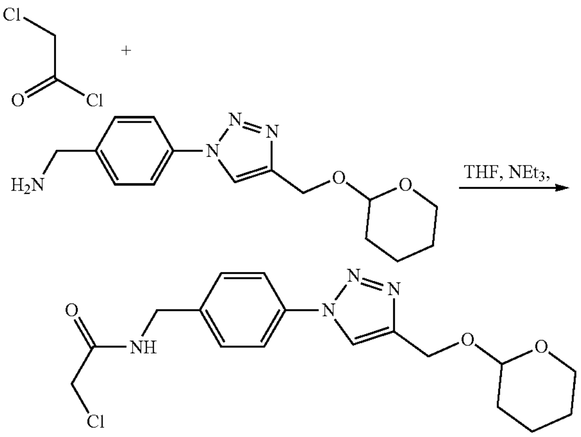

To a solution of (4-(4-(((tetrahydro-2H-pyran-2-yl)oxy) methyl)-1H-1,2,3-triazol-1-yl)phenyl)methanamine (Compound 3038, 400 mg, 1.4 mmol) and TEA (281 mg, 2.8 mmol, 387 uL) in THF (15 mL) was added dropwise 2-chloroacetyl chloride (125 mg, 1.1 mmol, 88 uL) at 0° C. After addition, the mixture was stirred at 25° C. for 12 h. The reaction mixture was filtered and purified by column chromatography ($SiO_2$, Petroleum ether:Ethyl acetate=4:1 to 2:1). Compound 2-chloro-N-(4-(4-(((tetrahydro-2H-pyran-2-yl)oxy)methyl)-1H-1,2,3-triazol-1-yl)benzyl)acetamide (Compound 3264, 200 mg, 506 umol) was obtained as a solid. MS ESI $[M^+H]^+$=365.1.

Synthesis of Compound 3265

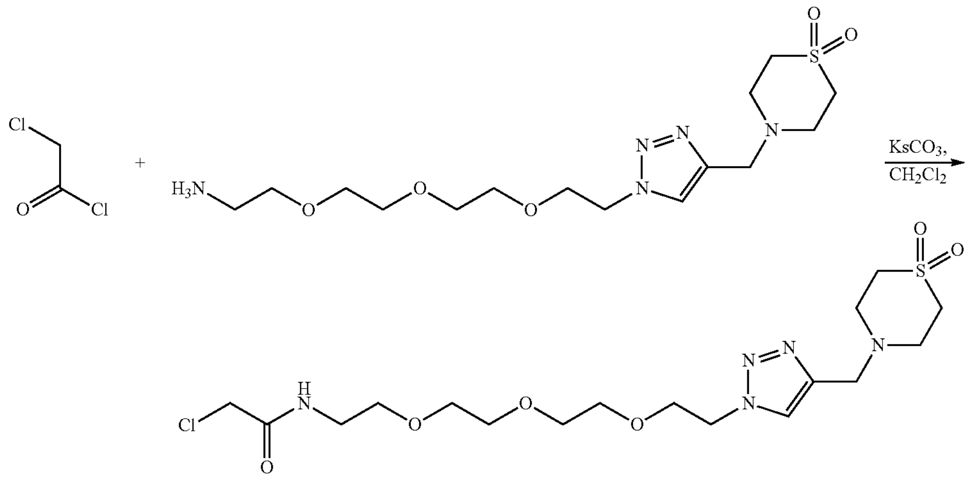

To a solution of 4-((1-(2-(2-(2-(2-aminoethoxy)ethoxy)ethoxy)ethyl)-1H-1,2,3-triazol-4-yl)methyl)thiomorpholine 1,1-dioxide (Compound 3037, 0.2 g, 511 umol) in DCM (5 mL) was added $K_2CO_3$ (212 mg, 1.53 mmol). The mixture was stirred at 0° C. and 2-chloroacetyl chloride was added (87 mg, 766 umol, 61 uL). The mixture was stirred at 25° C. for 12 h under $N_2$ atmosphere, and filtered and concentrated under reduced pressure to give a residue. The residue was purified by prep-HPLC (Column Waters Xbridge Prep OBD C18 150*30, 10, Buffer A: water (10 mM $NH_4HCO_3$ v/v); Buffer B: acetonitrile; 1%-50% Buffer B over 12 minutes at 40 mL/min). 2-chloro-N-(2-(2-(2-(2-(4-((1,1-dioxidothiomorpholino)methyl)-1H-1,2,3-triazol-1-yl)ethoxy)ethoxy)ethoxy)ethyl)acetamide (Compound 3265, 67 mg, 131 umol) was obtained as an oil. MS ESI $[M^{+}H]^{+}$=468.1.

General Protocol for Secondary Amine Functionalization (General Procedure M)

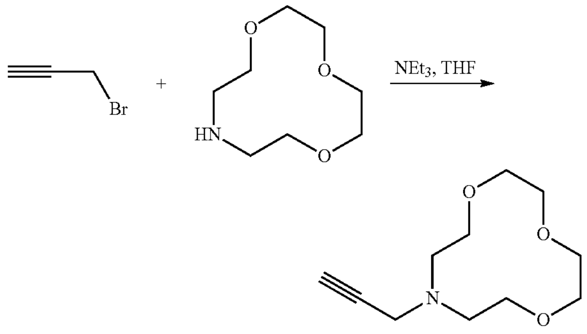

To a solution of 1,4,7-trioxa-10-azacyclododecane (1.05 g, 6.0 mmol, 1 eq) and TEA (606 mg, 6.0 mmol, 834 uL, 1 eq) in THE (30 mL) was added dropwise 3-bromoprop-1-yne (713 mg, 6.0 mmol, 517 uL, 1 eq). The mixture was stirred at 25° C. for 10 h, at which point LCMS analysis showed formation of the desired product. The reaction mixture was mixed with $H_2O$ (50 mL) and extracted with EtOAc (50 mL×7), and the organic phases were separated, dried over $Na_2SO_4$, filtered and concentrated under reduced pressure to give a residue, which 1H NMR analysis indicated was the desired compound 10-prop-2-ynyl-1,4,7-trioxa-10-azacyclododecane (Intermediate 237, 1.17 g, 5.5 mmol), isolated as an oil.

A similar procedure was used to prepare the following compound:

| Intermediate Number | Structure |
|---|---|
| 238 | 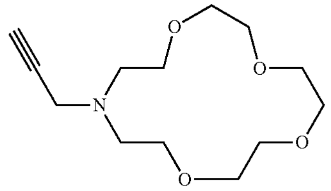 [SMILES: C#CCN1CCOCCOCCOCCOCC1] |

General Protocol for Hydroxyl Functionalization (General Procedure N)

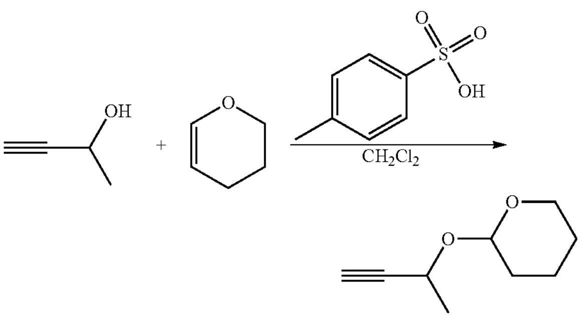

To a solution of but-3-yn-2-ol (10 g, 142.67 mmol, 11.19 mL, 1 eq) in DCM (100 mL) was added 3,4-dihydro-2H-pyran (12.00 g, 142.67 mmol, 13.04 mL, 1 eq) and PTSA-$H_2O$ (245.69 mg, 1.43 mmol, 0.01 eq). The mixture was stirred at 20° C. for 10 h, and the reaction mixture was concentrated under reduced pressure to remove solvent to give a residue. The residue was purified by column chromatography ($SiO_2$, Petroleum ether/Ethyl acetate=1:0). Compound 2-(but-3-yn-2-yloxy)tetrahydro-2H-pyran (Intermediate 239, 8.12 g, 52.66 mmol) was obtained as an oil.

A similar procedure was used to prepare the following compounds:

| Intermediate Number | Structure |
|---|---|
| 240 | 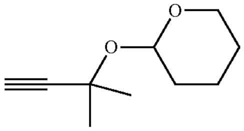 |
| 241 | 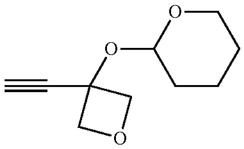 |
| 242 | 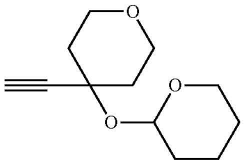 |
| 243 | 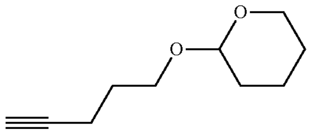 |

Synthesis of Intermediate 244

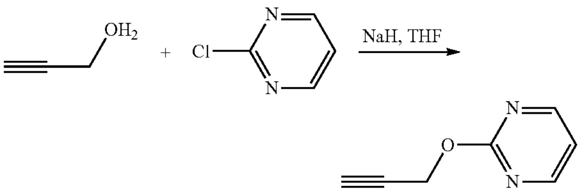

To a solution of prop-2-yn-1-ol (4.89 g, 87.31 mmol, 5.16 mL, 2 eq) in THE (100 mL) was slowly added NaH (2.44 g, 61.12 mmol, 60% purity, 1.4 eq) at 0° C. After addition, the mixture was stirred at this temperature for 1 h, and then 2-chloropyrimidine (5 g, 43.66 mmol, 1 eq) was added dropwise at 20° C. The resulting mixture was stirred at 60° C. for 10 h. The reaction mixture was quenched by addition ice water (100 mL), and then extracted with EtOAc (80 mL×3). The combined organic layers were dried over $Na_2SO_4$, filtered and concentrated under reduced pressure to give a residue. Compound 2-(prop-2-yn-1-yloxy)pyrimidine (Intermediate 244, 6.02 g) was obtained as brown oil.

General Protocol for Hydroxyl Functionalization (General Procedure O)

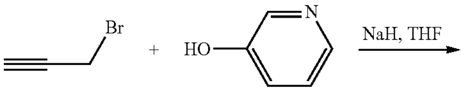

-continued

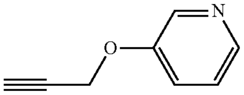

To a solution of pyridin-3-ol (10 g, 105.15 mmol, 1 eq) in DMF (100 mL) was slowly added NaH (4.21 g, 105.15 mmol, 60% purity, 1 eq) at 0° C. After the addition, the mixture was stirred at 0° C. for 1 h and then 3-bromoprop-1-yne (15.01 g, 126.18 mmol, 10.88 mL, 1.2 eq) was added drop wise at 20° C. The resulting mixture was stirred at 20° C. for 10 h. The reaction mixture was quenched by addition ice water (100 mL), and then extracted with EtOAc (20 mL×3). The combined organic layers were dried over $Na_2SO_4$, filtered and concentrated under reduced pressure to give a residue. The residue was purified by column chromatography (SiO2, Petroleum ether/Ethyl acetate=10:1) to afford Intermediate 245, 3-(prop-2-yn-1-yloxy)pyridine (2.50 g, 18.78 mmol) as an oil.

A similar procedure was used to prepare the following compounds:

| Intermediate Number | Structure |
|---|---|
| 246 | 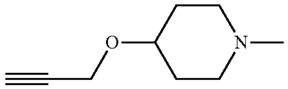 |
| 247 | 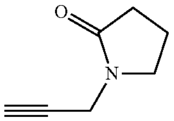 |
| 248 | 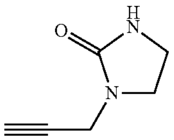 |
| 249 | 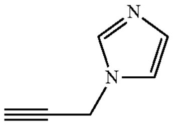 |
| 250 | 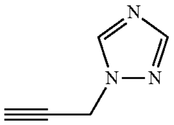 |

Synthesis of Intermediate 251

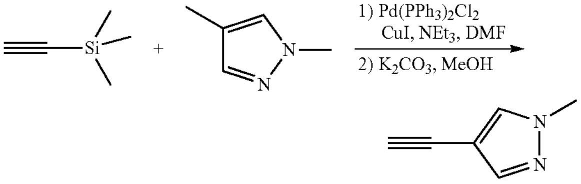

To a solution of 4-iodo-1-methyl-pyrazole (5 g, 24.04 mmol, 1 eq) in DMF (50 mL) and TEA (50 mL), ethynyl (trimethyl)silane (2.36 g, 24.04 mmol, 3.33 mL, 1 eq), $Pd(PPh_3)_2Cl_2$ (1.69 g, 2.40 mmol, 0.1 eq) and CuI (457.84 mg, 2.40 mmol, 0.1 eq) were added. The mixture was stirred at 25° C. for 12 h under $N_2$ atmosphere. Then the reaction mixture was filtered and concentrated under reduced pressure to give a residue, which was taken up in MeOH (50 mL). $K_2CO_3$ (4.98 g, 36.06 mmol, 1.5 eq) was added, and the mixture was stirred at 25° C. for 12 h under $N_2$ atmosphere. The reaction mixture was diluted with $H_2O$ (100 mL) and extracted with EtOAc (60 mL×3). The combined organic layers were washed with saturated brine (100 mL), dried over anhydrous $Na_2SO_4$, filtered and concentrated under reduced pressure to give a residue. The residue was purified by column chromatography ($SiO_2$, Petroleum ether/Ethyl acetate=20/1 to 0:1). 4-ethynyl-1-methyl-1H-pyrazole (Intermediate 251, 1.5 g, 14.13 mmol) was obtained as an oil.

Synthesis of Intermediate 252

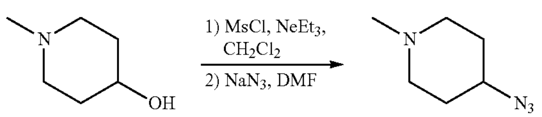

1-Methylpiperidin-4-ol (2.0 g, 17.4 mmol) in DCM (20 mL) was cooled to 0° C. Then to the solution was added TEA (2.28 g, 22.6 mmol, 3.15 mL), followed by methanesulfonyl chloride (2.19 g, 19.1 mmol, 1.48 mL). The mixture was stirred at 0° C. for 1.5 h. The reaction mixture was quenched by addition $H_2O$ (50 mL) at 0° C., and then extracted with DCM (50 mL×3). The combined organic layers were washed with saturated brines (100 mL×2), dried over $Na_2SO_4$, filtered and concentrated under reduced pressure to give a 1.6 g of a yellow oil that was dissolved in N,N-dimethylformamide (20 mL). Azidosodium (807.31 mg, 12.42 mmol, 436.38 uL) was added and the mixture was degassed and purged with $N_2$ for 3 times. The mixture was stirred at 65° C. for 12 h under $N_2$ atmosphere. The reaction mixture was quenched by addition $H_2O$ (80 mL) at 0° C., and then extracted with DCM (100 mL×2). The combined organic layers were washed with saturated brine (150 mL×2), dried over $Na_2SO_4$, filtered and concentrated under reduced pressure to give a residue: 4-azido-1-methylpiperidine (Intermediate 252, 0.8 g) as a an oil.

Synthesis of Intermediate 253

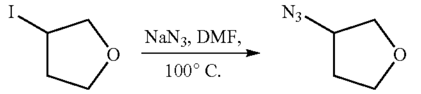

A solution of 3-iodotetrahydrofuran (2 g, 10.10 mmol) and sodium azide (984.90 mg, 15.15 mmol, 532 uL) in DMF (20 mL) was stirred at 100° C. for 15 h under $N_2$. The reaction mixture was filtered, and the filtrate was diluted with water (30 mL). Then the solution was extracted with DCM (15 mL×5). The combined organic layers were washed with brine (30 mL), dried over $Na_2SO_4$, filtered and concentrated under reduced pressure to give crude 3-azido-tetrahydrofuran (Intermediate 253, 1.1 g, 9.72 mmol) was obtained as a liquid.

Synthesis of Intermediate 254

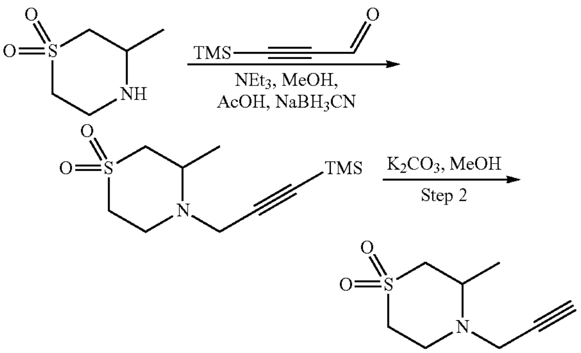

Step 1

To the solution of 3-methylthiomorpholine 1,1-dioxide (0.3 g, 1.62 mmol) in methanol (10 mL) were added N,N-diethylethanamine (163.50 mg, 1.62 mmol, 225 uL) and 3-(trimethylsilyl)propiolaldehyde (244.74 mg, 1.94 mmol, 285 uL). After the addition, HOAc was added to adjust the pH of the solution to 5-6. The mixture was stirred at 25° C. for 0.5 h, and then sodium cyanoborohydride (152 mg, 2.42 mmol) was added to the mixture at 10° C. After the addition, the mixture was stirred at 25° C. for 2 h. The solvent was removed and the crude product was purified by chromatography on silica gel (Petroleum ether:Ethyl acetate=20:1-1:1) to yield 3-methyl-4-(3-(trimethylsilyl) prop-2-yn-1-yl)thiomorpholine 1,1-dioxide (0.2 g, 771 umol) as a solid.

Step 2

To the solution of 3-methyl-4-(3-(trimethylsilyl)prop-2-yn-1-yl)thiomorpholine 1,1-dioxide (0.2 g, 770.89 umol) in methanol (10 mL) was added $K_2CO_3$ (213.08 mg, 1.54 mmol). Then the mixture was stirred at 25° C. for 2 h, at which point TLC showed the reaction was completed. The solvent was removed to yield 3-methyl-4-(prop-2-yn-1-yl) thiomorpholine 1,1-dioxide (Intermediate 254, 0.2 g, crude) as a solid which was used in further coupling reactions.

General Protocol for Secondary Amine Functionalization

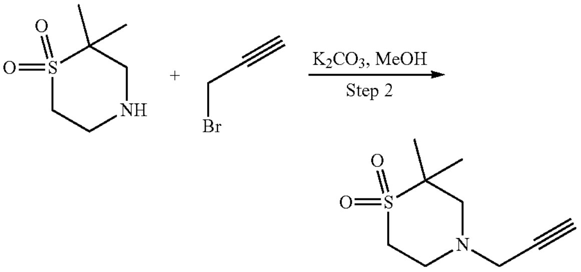

To the solution of 2,2-dimethylthiomorpholine 1,1-dioxide (50 mg, 306 umol) and triethylamine (62 mg, 613 umol, 85 uL) in THE (5 mL) was added 3-bromoprop-1-yne (55 mg, 459 umol). The mixture was stirred at 25° C. for 16 h. The solvent was removed under reduced pressure and the residue was purified by chromatography on silica gel (Petroleum ether:Ethyl acetate=10:1-1:1). 2,2-dimethyl-4-(prop-2-yn-1-yl)thiomorpholine 1,1-dioxide (Intermediate 255, 5 mg, 25 umol) was obtained as a solid. $^1H$ NMR (400 Mz, $CDCl_3$) δ 3.40 (2H, d), 3.12-3.04 (4H, m), 2.78 (2H, s), 2.32-2.30 (1H, m), 1.44 (6H, s).

A similar procedure was used to prepare the following compounds:

| Intermediate Number | Structure |
| --- | --- |
| 256 | 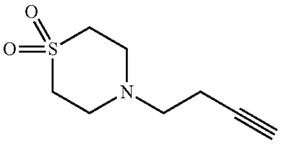 |
| 257 | 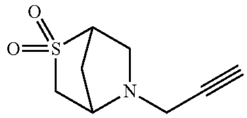 |
| 258 | 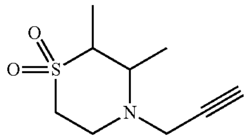 |
| 259 | 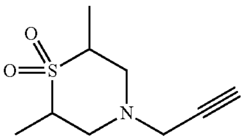 |

Synthesis of Intermediate 260

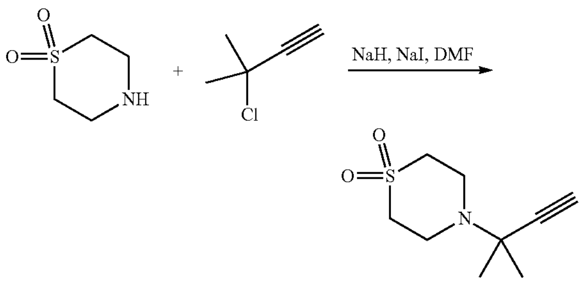

To a solution of thiomorpholine 1,1-dioxide (5 g, 36.99 mmol, 1 eq) in DMF (100 mL) was added NaH (1.78 g, 44.38 mmol, 60% purity, 1.2 eq). The mixture was stirred at 0° C. for 1 h. Then 3-chloro-3-methyl-but-1-yne (5.69 g, 55.48 mmol, 6.23 mL, 1.5 eq) and NaI (554.39 mg, 3.70 mmol, 0.1 eq) were added and the mixture was stirred at 25° C. for 4 h under $N_2$ atmosphere. The reaction mixture was quenched by addition $H_2O$ (5 mL) at 0° C., and then diluted with $H_2O$ (100 mL) and extracted with EtOAc (50 mL×3). The combined organic layers were washed with saturated brine (100 mL), dried over anhydrous $Na_2SO_4$, filtered and concentrated under reduced pressure to give a residue. The residue was purified by column chromatography (SiO2, Petroleum ether/Ethyl acetate=20/1 to 0:1). Compound 4-(2-methylbut-3-yn-2-yl)thiomorpholine 1,1-dioxide (Intermediate 260, 3.5 g) was obtained as a solid.

General Protocol for Hydroxyl Functionalization (General Procedure P)

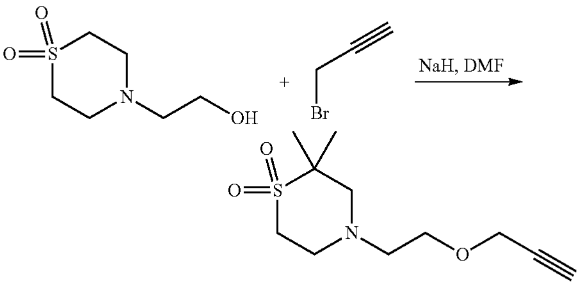

To a solution of 4-(2-hydroxyethyl)thiomorpholine 1,1-dioxide (1.5 g, 8.37 mmol, 1 eq) in DMF (20 mL) was added slowly NaH (368 mg, 9.2 mmol, 60% purity, 1.1 eq) at 0° C. After addition, the mixture was stirred at this temperature for 1 h, and then 3-bromoprop-1-yne (1.29 g, 10.88 mmol, 937 uL, 1.3 eq) was added dropwise at 25° C. The resulting mixture was stirred at 25° C. for 10 h. The reaction mixture was quenched by addition $H_2O$ (20 mL), and then extracted with EtOAc (20 mL×3). The combined organic layers were washed with saturated NaCl (10 mL), dried over $Na_2SO_4$, filtered and concentrated under reduced pressure to give a residue. Compound 2,2-dimethyl-4-(2-(prop-2-yn-1-yloxy)ethyl)thiomorpholine 1,1-dioxide (Intermediate 261, 1.32 g, 6.1 mmol) was obtained as a solid.

A similar procedure was used to prepare the following compounds:

| Intermediate Number | Structure |
| --- | --- |
| 262 | 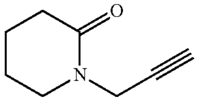 |
| 263 | 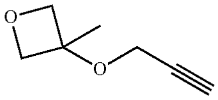 |
| 264 | 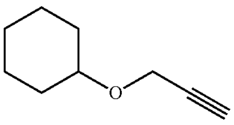 |

Synthesis of Intermediate 265

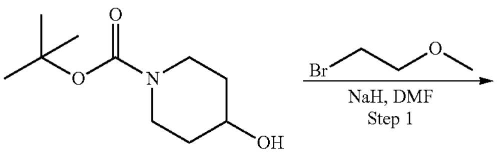

-continued

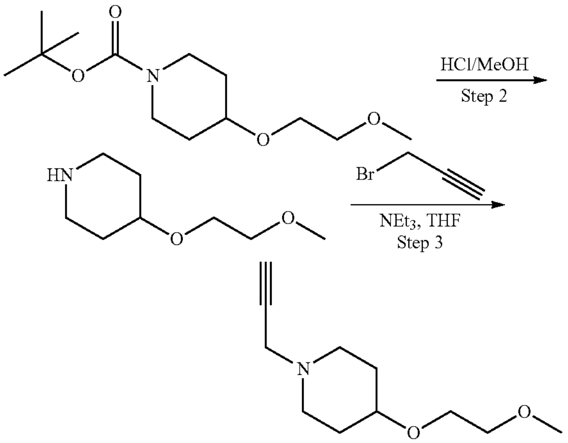

Step 1

To a stirred solution of sodium hydride (1.99 g, 49.69 mmol, 60% purity) in THE (20 mL) was added dropwise tert-butyl 4-hydroxypiperidine-1-carboxylate (5 g, 24.84 mmol) in THE (30 mL) under $N_2$ atmosphere at 0° C. After stirring 0.5 h, 1-bromo-2-methoxy-ethane (5.18 g, 37.26 mmol, 3.50 mL) was added to the mixture. The reaction mixture was slowly allowed to attain to 25° C. and stirred for 12 h. The reaction mixture was quenched by addition of saturated $NH_4Cl$ solution. The solution was extracted with EtOAc (100 mL×3). The combined organic phases were washed with brine, dried over $Na_2SO_4$ and concentrated under reduced pressure to give the crude product. The crude product was purified by column chromatography ($SiO_2$, Petroleum ether/Ethyl acetate=10:1 to 8:1) to afford tert-butyl4-(2-methoxyethoxy)piperidine-1-carboxylate (2.6 g, 10 mmol) was obtained as colorless oil.

Step 2

A mixture of tert-butyl 4-(2-methoxyethoxy)piperidine-1-carboxylate (0.5 g, 1.93 mmol) in HCl/MeOH (20 mL, 4N) was stirred at 25° C. for 0.5 h. The reaction mixture was concentrated under reduced pressure to give the product. Compound 4-(2-methoxyethoxy)piperidine (0.3 g, 1.9 mmol) was obtained as an oil. $^1H$ NMR (400 Mz, $D_3COD$) δ 7.17-7.05 (1H, m), 3.64-3.57 (4H, m), 3.49 (3H, d), 3.31-3.24 (3H, m), 3.06-3.01 (2H, m), 1.96-1.92 (2H, m), 1.86-1.81 (2H, m).

Step 3

To a solution of 4-(2-methoxyethoxy)piperidine (0.3 g, 1.9 mmol) in THE (10 mL) was added N,N-diethylethanamine (229 mg, 2.3 mmol, 315 uL). After addition, the mixture was stirred and 3-bromoprop-1-yne (269 mg, 2.3 mmol) was added dropwise. The resulting mixture was stirred at 25° C. for 12 h. The reaction mixture was filtered and concentrated under reduced pressure to give a residue. 1H NMR analysis indicated the residue was the desired product and compound 4-(2-methoxyethoxy)-1-prop-2-yn-1-yl-piperidine (Intermediate 265, 200 mg, 1.0 mmol) was obtained as an oil. $^1H$ NMR (400 Mz, $CDCl_3$) δ 3.62-3.60 (2H, m), 3.56-3.54 (2H, m), 3.40 (3H, s), 3.39-3.31 (3H, m), 2.83-2.80 (2H, m), 2.38-2.34 (2H, m), 2.26-2.24 (1H, m), 1.98-1.94 (2H, m), 1.69-1.66 (2H, m).

Synthesis of Intermediate 266

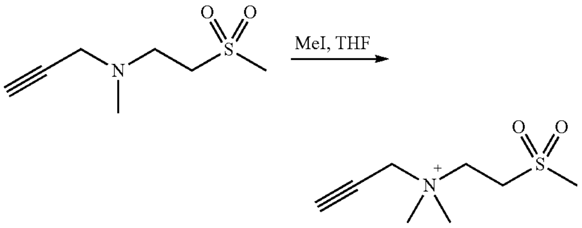

To a solution of N-methyl-N-(2-(methylsulfonyl)ethyl)prop-2-yn-1-amine (439 mg, 2.5 mmol) in THE (15 mL) was added iodomethane (1.42 g, 10.0 mmol, 624 uL). The mixture was stirred at 25° C. for 5 h. The reaction mixture was filtered and collected filter residue for detection. Compound N,N-dimethyl-N-(2-(methylsulfonyl)ethyl)prop-2-yn-1-aminium (266, 400 mg, 2.1 mmol) was obtained as a white solid. $^1H$ NMR (400 Mz, $D_2O$) δ 4.33 (2H, s), 4.00-3.93 (4H, m), 3.25 (6H, s), 3.20 (3H, s), 2.92 (1H, s).

Synthesis of Intermediate 267

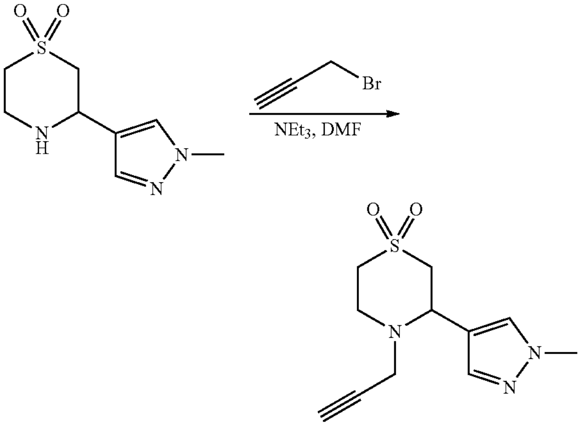

To a solution of 3-(1-methyl-1H-pyrazol-4-yl)thiomorpholine 1,1-dioxide (100 mg, 465 umol), triethylamime (129 uL, 929 umol) in DMF (3 mL) was added 3-bromoprop-1-yne (83 mg, 697 umol). The mixture was stirred at 25° C. for 16 h. Water (5 mL) was added and the mixture was extracted with EtOAc (3×5 mL). The combined organic layers were dried over $NaSO_4$, filtered, and concentrated under reduced pressure to afford: 3-(1-methyl-1H-pyrazol-4-yl)-4-(prop-2-yn-1-yl)thiomorpholine 1,1-dioxide (Intermediate 267, 50 mg, 197 umol) was obtained as an oil. MS ESI $[M^{+}H]^{+}$= 253.9.

Example 3: Conjugation of Exemplary Compounds to Alginate

In one exemplary embodiment, exemplary compounds can be attached to a polymer. In this example, the polymer (alginate) contains reactive carboxylic acid groups. Any of the components capable of coupling to a carboxylic acid, such as an amine described herein, may be an appropriate partner for this coupling reaction.

The alginate polymer is dissolved in water (30 mL/gram polymer) and treated with 2-chloro-4,6-dimethoxy-1,3,5-triazine (0.5 eq) and N-methylmorpholine (1 eq). To this mixture is added a solution of the amine of interest in acetonitrile (0.3M). The reaction is then warmed to 55° C. for 16h, then cooled to room temperature and carefully concentrated via rotary evaporation, then dissolved in water. The mixture is filtered through a bed of cyano-modified silica gel (Silicycle) and the filter cake is washed with water. The resulting solution is then dialyzed (10,000 MWCO membrane) against water for 24 hours, where the water is replace twice. The resulting solution is concentrated via lyophilization to afford the functionalized polymer.

Example 4: Conjugation of Exemplary Compounds to NHS-Modified Plates

Exemplary compounds of the invention were prepared at a concentration of 0.1M in a 0.1M bicarbonate buffer (pH 8.2) containing 25% v/v DMSO. Control solutions of 0.1M PEG750-amine and 0.01% fibronectin were prepared in 0.1M bicarbonate buffer (pH 8.2).

Each small molecule amine solution (100 μL) was pipetted into eight wells of an NHS-activated 96 well plate and incubated 2 hours at room temperature. Each plate consisted of two lanes spiked with the two control solutions and ten lanes spiked with test molecule solutions. The test wells were rinsed once with 200 μL 0.1M bicarbonate buffer (pH 8.2) containing 25% v/v DMSO followed by three washes with 200 μL Hyclone™ water. The control wells were rinsed with 0.1M bicarbonate buffer (pH 8.2) followed by three 200 μL Hyclone™ water washes. Plates were dried at room temperature in a sterile hood and stored at 4-8° C. until use.

Example 5: Conjugation of Exemplary Compounds to Silicone Disks

Disks (5 mm) were cut from a medical grade silicone sheet (1 mm thick) using a biopsy punch. Disks were rinsed several times with HyClone water to remove particulates and then cleaned by sonication: 10 minutes each in 200 proof ethanol, acetone, and hexane. Cleaned disks were dried overnight under vacuum. Small molecule methacrylamides were screened for their solubility at 0.2M in blends of DMSO and toluene. Fresh solutions of the appropriate DMSO/toluene blend (typically 5-15 v/v % DMSO) were prepared the day of the reaction and degassed with nitrogen prior to use. The methacrylamide was added and vortexed or sonicated to achieve a clear 0.2M working solution. The surface of clean PDMS disks were activated by air plasma treatment (<300 mtorr, 30W, 1 minute per side). After the second treatment, the disks were immediately removed from the reactor and transferred to the working solution for a one-hour reaction with mild agitation. Post-reaction, the disks were washed 3×10 minutes in methanol, 3×10 minutes in 200 proof ethanol, and then dried overnight under vacuum. Disks were sterilized by dipping into 70% ethanol and drying in sterile vials in a sterile hood. Disks were stored at room temperature prior to use.

Example 6: Conjugation of Exemplary Compounds onto a Surface Via Plasma Treatment The compounds described in this disclosure can be attached to surfaces with a variety of methods. In this example, an acrylate derivative is attached to a polymer surface via plasma treatment. The polymeric material or device may be treated with plasma for 1 minute of each side (Harrick Plasma Cleaner) and immediately dropped into a solution of the methacryl compound in 5% DMSO in toluene (0.2M overall). The reaction can be stirred or shaken (as appropriate) for 1h. The materials will be filtered out of the solution and washed with methanol (3×), ethanol (3×) and dried under vacuum.

Example 7. In Vitro Assay of Exemplary Compounds: Cathepsin Activity

Efficacy and/or toxicity of the compounds, materials, and devices disclosed herein, may be investigated using an in vitro cathepsin activity assay as described in Vegas et al (2016) *Nat Biotechnol* 34(3):666. Briefly, recombinant mouse Cathepsin B (rmCathepsin B, R&D System) may be diluted to 10 uM in activation buffer (25 mM MES, 5 mM DTT, pH 5.0), and incubated at rt for 15 minutes to activate, then diluted further in assay buffer (25 mM MES, pH 5.0) and transferred to the wells of a 96-well plate to a final concentration of 0.1 uM. The substrate (e.g., Prosense 750 Fast (PerkinElmer) and barium chloride) can be diluted in assay buffer and transferred into the wells of the plate containing the Cathepsin B, such that the final concentration of the substrate may be 0.5 uM and barium chloride 20 mM. Fluorescence measurements may then be recorded after a 2 hour incubation at rt using appropriate excitation and emission wavelengths of the substrate. Other cathepsins, such as Cathepsin L, may be used in this assay.

Example 8: In Vitro Assay of Exemplary Compounds: Macrophage Adhesion

Macrophage cell lines were plated onto 96 well plates, 50000 cells per well, and incubated at 37 degrees Celsius for one hour. Plates were then placed at a 45-degree angle and washed by applying fluid shear 5 times. Non-adherent and adherent cells were then separated and treated with a Cell titer-glo kit to quantify the number of live cells. Live cells were detected using luminescence-based plate reader measurements. The resulting cell adhesion values for each small molecule amine was averaged across the eight wells and standard deviations calculated. The average cell adhesion value for each small molecule was normalized relative to the averages for the two controls on each plate: PEG750=0, Fibronectin (FN)=100. Small molecule normalized value=(SM-PEG750)/(FN-PEG750). Results are expressed as a percentage of cells adhered on the plates. % Percent adherent cells=(Luminescence of adhered cells)/(Luminescence of adhered+non-adhered cells). Data represents mean+/− standard error of the mean and are summarized in Table 1 below. In this table, "A" represents a cell adhesion value of <0% to about 10%; "B" represents a cell adhesion value of 10% to about 50%; and "C" represents a cell adhesion value of 50% to 100%.

TABLE 1

| Compound Number | Assay Results |
|---|---|
| 3271 | A |
| 3243 | A |
| 3096 | A |
| 3272 | A |
| 3124 | A |
| 3083 | A |

TABLE 1-continued

| Compound Number | Assay Results |
| --- | --- |
| 3184 | A |
| 3037 | A |
| 3111 | A |
| 3127 | A |
| 3112 | A |
| PEG750 | A |
| 3273 | A |
| 3274 | A |
| 3275 | A |
| 3276 | A |
| 3277 | A |
| 3278 | A |
| 3279 | A |
| 3405 | A |
| 3280 | A |
| 3281 | A |
| 3282 | A |
| 3283 | A |
| 3284 | A |
| 3285 | A |
| 3286 | A |
| 3287 | A |
| 3288 | A |
| 3290 | A |
| 3052 | A |
| 3292 | A |
| 3293 | A |
| 3294 | A |
| 3295 | A |
| 3296 | A |
| 3297 | A |
| 3298 | A |
| 3299 | A |
| 3300 | A |
| 3301 | A |
| 3302 | A |
| 3303 | A |
| 3304 | A |
| 3305 | A |
| 3306 | A |
| 3307 | A |
| 3308 | A |
| 3309 | B |
| 3310 | B |
| 3311 | B |
| 3312 | B |
| 3313 | B |
| 3315 | B |
| 3316 | B |
| 3317 | B |
| 3318 | B |
| 3319 | B |
| 3320 | B |
| 3321 | B |
| 3322 | B |
| 3323 | B |
| 3324 | B |
| 3325 | B |
| 3326 | B |
| 3327 | B |
| 3328 | B |
| 3329 | B |
| 3330 | B |
| 3331 | B |
| 3332 | B |
| 3333 | B |
| 3334 | B |
| 3335 | B |
| 3336 | B |
| 3337 | B |
| 3338 | B |
| 3339 | B |
| 3340 | B |
| 3341 | B |
| 3342 | B |
| 3343 | B |
| 3344 | B |
| 3345 | B |

TABLE 1-continued

| Compound Number | Assay Results |
| --- | --- |
| 3346 | B |
| 3347 | B |
| 3348 | B |
| 3349 | B |
| 3350 | B |
| 3351 | B |
| 3352 | B |
| 3353 | B |
| 3354 | B |
| 3355 | B |
| 3356 | B |
| 3357 | B |
| 3358 | B |
| 3359 | B |
| 3360 | B |
| 3361 | B |
| 3362 | B |
| 3363 | B |
| 3364 | B |
| 3365 | B |
| 3366 | B |
| 3367 | B |
| 3368 | B |
| 3369 | B |
| 3370 | C |
| 3371 | C |
| 3372 | C |
| 3373 | C |
| 3374 | C |
| 3375 | C |
| 3376 | C |
| 3377 | C |
| 3378 | C |
| 3379 | C |
| 3380 | C |
| 3381 | C |
| 3382 | C |
| 3383 | C |
| 3384 | C |
| 3385 | C |
| 3386 | C |
| 3387 | C |
| 3388 | C |
| 3389 | C |
| 3390 | C |
| 3391 | C |
| 3392 | C |
| 3393 | C |
| 3394 | C |
| 3395 | C |
| 3396 | C |
| 3397 | C |
| 3398 | C |
| 3399 | C |
| 3400 | C |
| 3401 | C |
| 3402 | C |
| 3403 | C |
| 3040 | C |
| Fibronectin | C |

Example 9. In Vivo Assay of Exemplary Compounds: Cathepsin Activity

In order to determine the efficacy and/or toxicity of the compounds, materials, and devices disclosed herein, an in vivo fluorescent assay will be used as described in Vegas et al (2016) *Nat Biotechnol* 34(3):666. In general, young mice (e.g., 8-12 week old female SKH1 mice) will be administered, injected, or implanted with the compound, material, or device of interest. The mice may be fed an AIN-93G purified rodent diet to minimize fluorescent background after administration, injection, or implantation. Six days later, ProSense-680 (VisEn Medical, 2-5 nm) will be dissolved in sterile PBS and injected into the tail vein of each mouse. At day 7, the mice will be analyzed by fluorescence imaging to determine the level of cathepsin activity, which correlates to the modulation of the inflammatory response in the site of interest. The inflammatory response may also be assessed by detecting and measuring a suite of cytokines, such as TNF-α, IL-13, IL-6, G-CSF, GM-CSF, IL-4, CCL2, and CCL4, which are known mediators of the foreign body response and fibrosis.

Example 10. In Vivo Assay of Exemplary Compounds: Disk Implantation 5 mm silicone disks that were chemically modified as described in Example X were implanted into the intraperitoneal (IP) space of $C_{57}$BL/6J mice according to the procedure below.

Preparation: Mice were prepared for surgery by being placed under anesthesia under a continuous flow of 1-4% isofluorane with oxygen at 0.5 L/min. Preoperatively, all mice received a 0.05-0.1 mg/kg of body weight dose of buprenorphine subcutaneously as a pre-surgical analgesic, along with 0.5 ml of 0.9% saline subcutaneously to prevent dehydration. A shaver with size #40 clipper blade was used to remove hair to reveal an area of about 2 cm×2 cm on ventral midline of the animal abdomen. The entire shaved area was aseptically prepared with a minimum of 3 cycles of scrubbing with povidine (in an outward centrifugal direction from the center of the incision site when possible), followed by rinsing with 70% alcohol. A final skin paint with povidine was also applied. The surgical site was draped with sterile disposable paper to exclude surrounding hair from touching the surgical site, after disinfection of table top surface with 70% ethanol. Personnel used proper PPE, gowning, surgical masks, and surgical gloves.

Surgical procedure: A sharp surgical blade or scissor was used to cut a 0.5-0.75 mm midline incision through the skin and the linea alba into the abdomen of the subject mice. The surgeon attempted to keep the incision as small as possible. Flat sterile forceps were used to transfer one silicone disk into the peritoneal cavity of each mouse. The abdominal muscle was closed by suturing with 5-0 Ethicon black silk or PDS-absorbable 5.0-6.0 monofilament absorbable thread, and the external skin layer was closed using wound clips. Blood and tissue debris were removed from the surgical instruments between procedures and the instruments were also re-sterilized between animal using a hot bead sterilizer. After the surgery, the animals were put back in the cage on a heat pad or under a heat lamp and monitored until they came out of anesthesia.

Intraoperative care: Animals were kept warm using Deltaphase isothermal pad. The animal's eyes were hydrated with sterile ophthalmic ointment during the period of surgery. Care was taken to avoid wetting the surgical site excessively to avoid hypothermia. Respiratory rate and character were monitored continuously. If vital signs are indicative of extreme pain and distress, the animal was euthanized in a carbon dioxide chamber followed by cervical dislocation.

Fourteen days post-implantation, the disks were retrieved and the number of disks containing adhered tissue was counted. The results of this assay are summarized in Table 2 below. In this table, "A" corresponds with a value of 0-1 disks containing adhered tissue; "B" corresponds with a value of 2-3 disks containing adhered tissue; and "C" corresponds with a value of 4-5 disks containing adhered tissue.

TABLE 2

| Compound Number | Assay Results |
|---|---|
| 3406 | B |
| 3407 | B |
| 3408 | B |
| 3409 | B |
| 3410 | B |
| 3411 | B |
| 3412 | B |
| 3413 | C |
| 3414 | C |
| 3415 | B |
| 3416 | A |
| 3417 | C |
| 3418 | A |
| 3419 | A |
| 3420 | B |
| 3421 | C |
| 3422 | C |
| 3423 | B |
| 3425 | B |
| 3426 | B |
| 3427 | C |
| 3428 | B |
| 3429 | B |
| 3430 | B |
| 3431 | C |
| 3424 | A |

EQUIVALENTS AND SCOPE

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present invention, as defined in the following claims.

The invention claimed is:

1. A compound of Formula (II-c):

Formula (II-c)

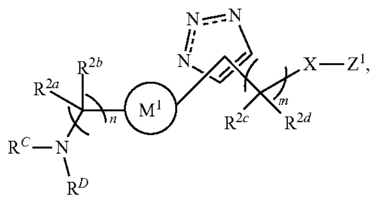

or a salt thereof, wherein:

Ring $M^1$ is phenyl optionally substituted with 1-4 $R^3$;

$Z^1$ is $C_2$-$C_{12}$ heteroalkyl, cycloalkyl, heterocyclyl, or heteroaryl, each of which is optionally substituted by one or more $R^5$;

X is absent or O;

each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl;

or $R^{2a}$ and $R^{2b}$ or $R^{2c}$ and $R^{2d}$ are taken together to form an oxo group;

$R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$;

or $R^C$ and $R^D$, taken together with the nitrogen atom to which they are attached, form a ring, optionally substituted with 1-6 $R^6$;

each of $R^3$, $R^5$, and $R^6$ is independently alkyl, alkenyl, alkynyl, heteroalkyl, halogen, cyano, azido, oxo, cycloalkyl, heterocyclyl, aryl, or heteroaryl;

m is 0, 1, 2, 3, 4, 5, or 6;

n is 1, 2, 3, 4, 5, or 6;

wherein the triazolyl ring is

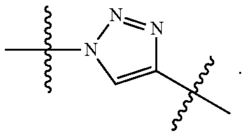 [SMILES: *c1cn(*)nn1]

and, wherein the compound is not

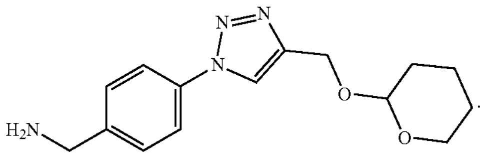 [SMILES: NCc1ccc(-n2cc(COC3CCCCO3)nn2)cc1]

2. The compound of claim 1, wherein each of $R^{2a}$, $R^{2b}$, $R^{2c}$, and $R^{2d}$ is independently hydrogen or alkyl or one of $R^{2a}$ and $R^{2b}$ or $R^{2e}$ and $R^{2d}$ are taken together to form an oxo group.

3. The compound of claim 2, wherein each of $R^{2a}$, $R^{2b}$, $R^{2c}$, and $R^{2d}$ is independently hydrogen.

4. The compound of claim 1, wherein each of m and n is 1.

5. The compound of claim 1, wherein $Z^1$ is heterocyclyl.

6. The compound of claim 5, wherein $Z^1$ is a nitrogen-containing heterocyclyl, an oxygen-containing heterocyclyl, or a sulfur-containing heterocyclyl.

7. The compound of claim 1, wherein the compound is disposed on a surface of a device.

8. The compound of claim 1, wherein the compound is selected from

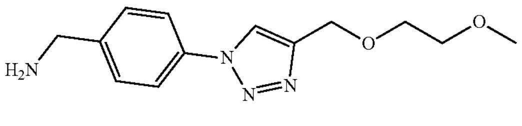

-continued

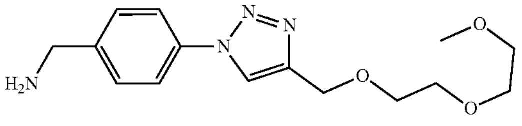

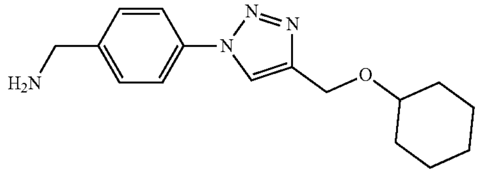

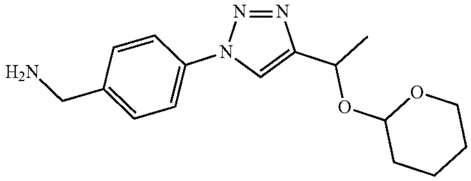

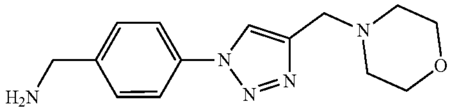

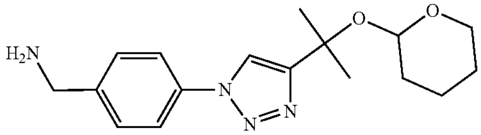

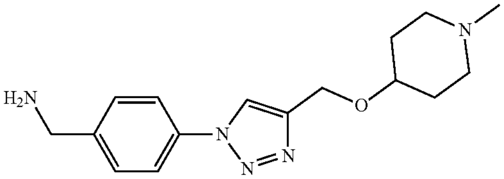

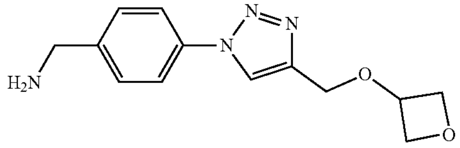

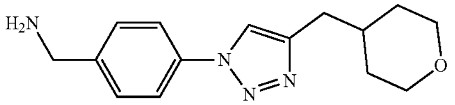

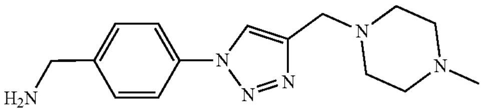

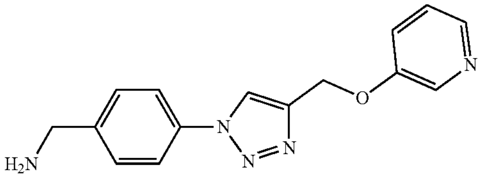

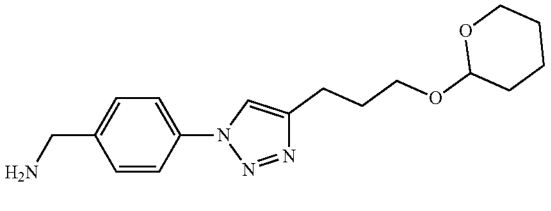

-continued

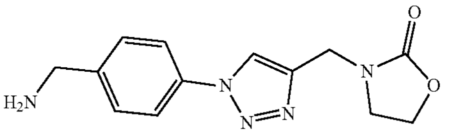

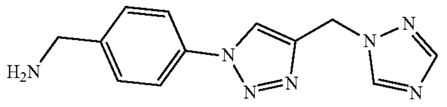

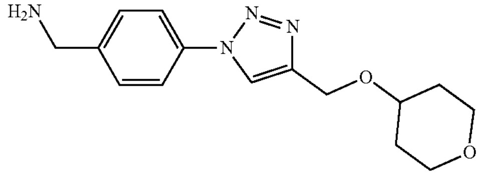

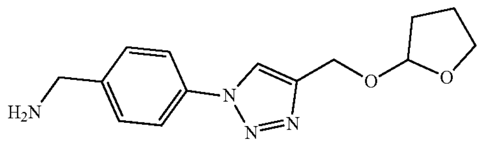

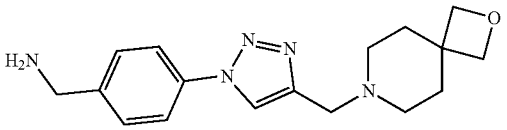

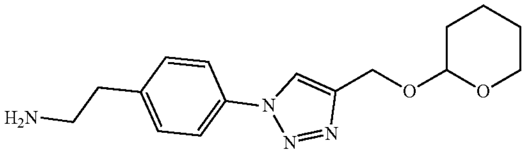

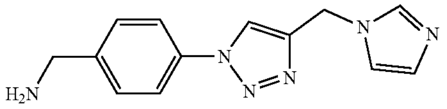

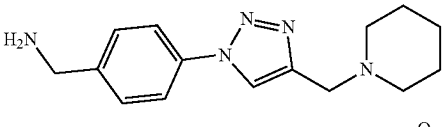

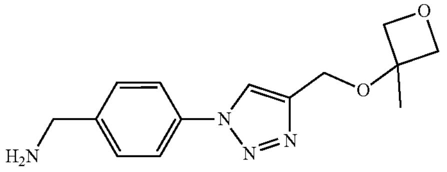

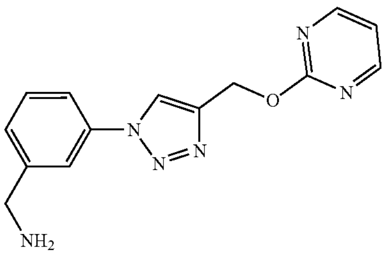

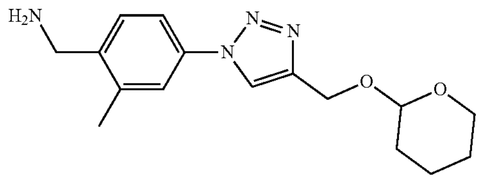

-continued

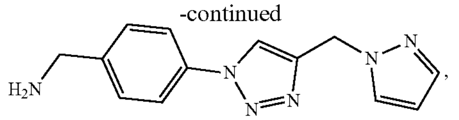

or a pharmaceutically acceptable salt thereof.

9. A pharmaceutical composition comprising a compound of Formula (II-c):

Formula (II-c)

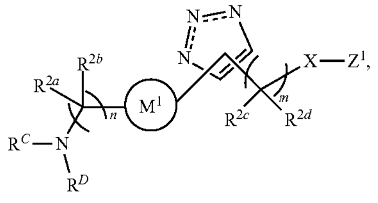

or a salt thereof, wherein:

Ring $M^1$ is phenyl optionally substituted with 1-4 $R^3$;

$Z^1$ is $C_2$-$C_{12}$heteroalkyl, cycloalkyl, heterocyclyl, or heteroaryl, each of which is optionally substituted by one or more $R^5$;

X is absent or O;

each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl;

or $R^{2a}$ and $R^{2b}$ or $R^{2c}$ and $R^{2d}$ are taken together to form an oxo group;

$R^C$ and $R^D$ are independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$;

or $R^C$ and $R^D$, taken together with the nitrogen atom to which they are attached, form a ring, optionally substituted with 1-6 $R^6$;

each of $R^3$, $R^5$, and $R^6$ is independently alkyl, alkenyl, alkynyl, heteroalkyl, halogen, cyano, azido, oxo, cycloalkyl, heterocyclyl, aryl, or heteroaryl;

m is 0, 1, 2, 3, 4, 5, or 6;

n is 1, 2, 3, 4, 5, or 6;

the triazolyl ring is

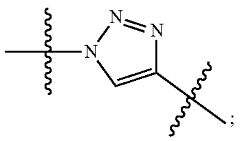 [SMILES: *c1cn(*)nn1]

and, wherein the compound is not

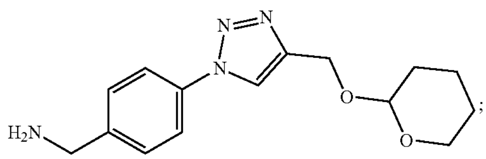 [SMILES: NCc1ccc(-n2cc(COC3CCCCO3)nn2)cc1]

and a pharmaceutically acceptable excipient.

10. The compound of claim 1, wherein X is absent.

11. The compound of claim 6, wherein $Z^1$ is oxetanyl, tetrahydrofuranyl, tetrahydropyranyl, thiomorpholinyl-1,1-dioxide, piperidinyl, piperazinyl, or pyrrolidinyl.

12. The compound of claim 11, wherein $Z^1$ is tetrahydropyranyl.

* * * * *